US012384828B2

(12) United States Patent
Pentecost et al.

(10) Patent No.: US 12,384,828 B2
(45) Date of Patent: Aug. 12, 2025

(54) ENGINEERED EXTRACELLULAR VESICLES COMPRISING FUSION PROTEINS

(71) Applicant: DIADEM BIOTHERAPEUTICS, INC., Torrance, CA (US)

(72) Inventors: Mickey Pentecost, West Hollywood, CA (US); Wojciech Bartkowski, La Crescenta (CA)

(73) Assignee: Diadem Biotherapeutics, Inc., Torrance, CA (US)

( * ) Notice: Subject to any disclaimer, the term of this patent is extended or adjusted under 35 U.S.C. 154(b) by 67 days.

(21) Appl. No.: 18/056,029

(22) Filed: Nov. 16, 2022

(65) Prior Publication Data

US 2023/0312678 A1 Oct. 5, 2023

Related U.S. Application Data

(60) Division of application No. 17/377,550, filed on Jul. 16, 2021, now Pat. No. 11,578,116, which is a continuation of application No. PCT/US2021/016949, filed on Feb. 5, 2021.

(60) Provisional application No. 62/970,374, filed on Feb. 5, 2020.

(51) Int. Cl.

| | |
|---|---|
| ***C07K 14/705*** | (2006.01) |
| ***A61K 35/17*** | (2025.01) |
| ***A61K 47/54*** | (2017.01) |
| ***A61K 47/58*** | (2017.01) |
| ***A61K 47/62*** | (2017.01) |
| ***A61K 47/69*** | (2017.01) |
| ***A61P 27/02*** | (2006.01) |
| ***A61P 37/06*** | (2006.01) |
| ***C07K 14/75*** | (2006.01) |
| ***C12N 9/14*** | (2006.01) |
| *A61K 38/00* | (2006.01) |

(52) U.S. Cl.

CPC ........ *C07K 14/70532* (2013.01); *A61K 35/17* (2013.01); *A61K 47/544* (2017.08); *A61K 47/605* (2017.08); *A61K 47/62* (2017.08); *A61K 47/69* (2017.08); *A61K 47/6901* (2017.08); *A61K 47/6911* (2017.08); *A61K 47/6917* (2017.08); *A61P 27/02* (2018.01); *A61P 37/06* (2018.01); *C07K 14/705* (2013.01); *C07K 14/70521* (2013.01); *C07K 14/7056* (2013.01); *C07K 14/70596* (2013.01); *C07K 14/75* (2013.01); *C12N 9/14* (2013.01); *A61K 38/00* (2013.01); *C07K 14/70503* (2013.01); *C07K 2319/01* (2013.01); *C07K 2319/02* (2013.01); *C07K 2319/035* (2013.01); *C07K 2319/055* (2013.01); *C07K 2319/30* (2013.01); *C07K 2319/74* (2013.01); *C07K 2319/75* (2013.01); *C07K 2319/912* (2013.01); *C07K 2319/915* (2013.01); *C12Y 304/24081* (2013.01)

(58) Field of Classification Search

CPC ........ C07K 14/70532; C07K 14/70521; C07K 14/70596; C07K 2319/035; C07K 2319/055; C07K 2319/30; C07K 2319/75; C07K 2319/92; C07K 2319/915; A61K 47/6917; A61K 38/00; C12Y 304/24081

See application file for complete search history.

(56) References Cited

U.S. PATENT DOCUMENTS

| | | | |
|---|---|---|---|
| 3,773,919 | A | 11/1973 | Boswell et al. |
| 4,186,183 | A | 1/1980 | Alving et al. |
| 4,217,344 | A | 8/1980 | Handjani et al. |
| 4,235,871 | A | 11/1980 | Papahadjopoulos et al. |
| 4,261,975 | A | 4/1981 | Fullerton et al. |
| 4,485,054 | A | 11/1984 | Mezei et al. |

(Continued)

FOREIGN PATENT DOCUMENTS

| | | | |
|---|---|---|---|
| CA | 3073162 | A1 | 2/2019 |
| EP | 0264166 | B1 | 8/1996 |

(Continued)

OTHER PUBLICATIONS

Audagnotto M and Dal Pararo M. (2017) Computational and Structural Biotechnology Journal 15:307-319. (doi.org/10.1016/j.csbj 2017.03.004).*

(Continued)

*Primary Examiner* — Robert S Landsman

(74) *Attorney, Agent, or Firm* — WILSON SONSINI GOODRICH & ROSATI

(57) ABSTRACT

Described herein are compositions and techniques related to generation and therapeutic application of artificial synapses. Artificial synapses are engineered extracellular vesicles, including exosomes, which incorporate sticky binders on their surface to anchor signaling domains against biological targets, such as receptors. These engineered additives can be organized in genetic vector constructs, expressed in mammalian cells, wherein the sticky binders attach to extracellular vesicles such as exosomes, thereby presenting their joined signaling domains which are rapidly taken up by recipient cells. Artificial synapses adopt the hallmark biophysical and biochemical features of extracellular vesicles, allowing for rapid deployment and scale-up. Importantly, this strategy can allow for kinetically favorable signal generation and signal propagation. This includes, for example, increasing density of agonist presentation to support receptor clustering—an onerous barrier for traditional receptor targeting strategies.

23 Claims, 102 Drawing Sheets

Specification includes a Sequence Listing.

(56) References Cited

U.S. PATENT DOCUMENTS

| | | | | |
|---|---|---|---|---|
| 4,501,728 | A | 2/1985 | Geho et al. | |
| 4,774,085 | A | 9/1988 | Fidler | |
| 4,816,567 | A | 3/1989 | Cabilly et al. | |
| 4,837,028 | A | 6/1989 | Allen | |
| 4,873,316 | A | 10/1989 | Meade et al. | |
| 4,897,355 | A | 1/1990 | Eppstein et al. | |
| 4,946,787 | A | 8/1990 | Eppstein et al. | |
| 5,049,386 | A | 9/1991 | Eppstein et al. | |
| 5,585,089 | A | 12/1996 | Queen et al. | |
| 5,693,780 | A | 12/1997 | Newman et al. | |
| 7,704,964 | B2 | 4/2010 | Delcayre et al. | |
| 9,546,371 | B2 | 1/2017 | Mamoun et al. | |
| 9,611,481 | B2 | 4/2017 | Mamoun | |
| 10,195,290 | B1 | 2/2019 | Dooley et al. | |
| 10,370,663 | B2 | 8/2019 | Lotvall et al. | |
| 10,617,768 | B2 | 4/2020 | Lu et al. | |
| 10,695,443 | B2 | 6/2020 | Lotvall et al. | |
| 10,723,782 | B2 | 7/2020 | Lewis et al. | |
| 11,260,076 | B2 | 3/2022 | Copik | |
| 11,578,116 | B2 | 2/2023 | Pentecost et al. | |
| 11,746,138 | B2 | 9/2023 | Pentecost et al. | |
| 11,851,470 | B2 * | 12/2023 | Riazifar | C07K 14/70521 |
| 2016/0137716 | A1 | 5/2016 | El Andaloussi et al. | |
| 2017/0087087 | A1 | 3/2017 | Leonard et al. | |
| 2017/0258938 | A1 | 9/2017 | Lotvall et al. | |
| 2017/0333479 | A1 | 11/2017 | Copik et al. | |
| 2018/0015182 | A1 | 1/2018 | Lu et al. | |
| 2018/0117117 | A1 | 5/2018 | Choi et al. | |
| 2018/0135056 | A1 | 5/2018 | Lotvall et al. | |
| 2018/0236104 | A1 | 8/2018 | Lotvall et al. | |
| 2019/0015333 | A1 | 1/2019 | Lu et al. | |
| 2019/0060483 | A1 | 2/2019 | Dooley et al. | |
| 2019/0117792 | A1 | 4/2019 | Dooley et al. | |
| 2019/0151456 | A1 | 5/2019 | McConnell et al. | |
| 2019/0167810 | A1 | 6/2019 | Hean et al. | |
| 2019/0202892 | A1 | 7/2019 | Lewis et al. | |
| 2019/0224331 | A1 | 7/2019 | Wiklander | |
| 2019/0290585 | A1 | 9/2019 | Wiklander | |
| 2019/0388347 | A1 | 12/2019 | Wiklander et al. | |
| 2020/0054686 | A1 | 2/2020 | Rodriguez-Borlado et al. | |
| 2020/0062813 | A1 | 2/2020 | Nordin et al. | |
| 2020/0109183 | A1 | 4/2020 | Wiklander et al. | |
| 2020/0155703 | A1 | 5/2020 | Lotvall et al. | |
| 2020/0163998 | A1 | 5/2020 | Park et al. | |
| 2020/0206360 | A1 | 7/2020 | Choi et al. | |
| 2020/0207833 | A1 | 7/2020 | El Andaloussi et al. | |
| 2020/0222556 | A1 | 7/2020 | Dooley et al. | |
| 2020/0347112 | A1 | 11/2020 | McConnell et al. | |
| 2020/0407419 | A1 | 12/2020 | Lewis et al. | |
| 2021/0030850 | A1 | 2/2021 | Leonard et al. | |
| 2021/0371497 | A1 | 12/2021 | Pentecost et al. | |
| 2021/0379198 | A1 | 12/2021 | Pentecost et al. | |
| 2022/0411481 | A1 | 12/2022 | Pentecost et al. | |

FOREIGN PATENT DOCUMENTS

| | | | |
|---|---|---|---|
| JP | 2021508691 | A | 3/2021 |
| JP | 2021515570 | A | 6/2021 |
| JP | 2021532736 | A | 12/2021 |
| WO | WO-9116024 | A1 | 10/1991 |
| WO | WO-9117424 | A1 | 11/1991 |
| WO | WO-9614057 | A1 | 5/1996 |
| WO | 2017081082 | A2 | 5/2017 |
| WO | 2018015535 | A1 | 1/2018 |
| WO | 2018129207 | A1 | 7/2018 |
| WO | 2019027847 | A1 | 2/2019 |
| WO | WO-2019035057 | A2 | 2/2019 |
| WO | 2019178334 | A1 | 9/2019 |
| WO | WO-2019236082 | A1 | 12/2019 |
| WO | 2020154746 | A1 | 7/2020 |
| WO | 2020257710 | A1 | 12/2020 |
| WO | 2021159016 | A1 | 8/2021 |

OTHER PUBLICATIONS

Geneovese S, et al. (2009) Phytochemistry. 70:1082-1091. (doi: 10.1016/j.phytochem.2009.06.016).*

Clarke CF and Allan CM. (Jun. 25, 2015) Nature. 522:427.*

Resh MD. (Jul. 2016) Prog Lipid Res. 63:120-131. (doi:10.1016/j.plipres.2016.05.002).*

Trinh R, et al. (2004) Molecular Immunology. 40:717-722. (doi: 10.1016/j.molimm.2003.08.006).*

Certified Copy of U.S. Appl. No. 62/864,566, filed Jun. 21, 2019, 6 pages.

Certified Copy of U.S. Appl. No. 62/875,001, filed Jul. 17, 2019, 9 pages.

Riazifar et al., Stem Cell Extracellular Vesicles: Extended Messages of Regeneration; Annu Rev Pharmacol Toxicol., 2017, 57:125-154.

Riazifar et al., Stem Cell-Derived Exosomes as Nanotherapeutics for Autoimmune and Neurodegenerative Disorders, ACS Nano. 2019, 13(6):6670-6688.

Yáñez-Mó, et al., Biological properties of extracellular vesicles and their physiological functions, J Extracell Vesicles, 2015(4):27066. Published May 14, 2015. doi:10.3402/jev.v4.27066.

Yadid et al., Endothelial extracellular vesicles contain protective proteins and rescue ischemia-reperfusion injury in a human heart-on-chip, 2020, Science Translation Medicine 12, 17 pages.

de Abreu et al., Native and bioengineered extracellular vesicles for cardiovascular therapeutics, Nature Reviews Cardiology, 2020, 17(11), 685-697.

Zhang et al., Characterization of Protein Profiling and mRNA Expression of LLC Exosomes, 2019, Protein J 38:586-597 (2019).

Zha et al., Extracellular vesicles: An overview of biogenesis, function, and role in breast cancer, Tumor Biology, 2017, pp. 1-7.

Tan et al., Thrombin stimulated platelet-derived exosomes inhibit platelet-derived growth factor receptor-beta expression in vascular smooth muscle cells, Cellular Physiology and Biochemistry, 2016, 38:2348-2365.

Kalluri et al., The biology, function, and biomedical applications of exosomes, Science 2020, 367, 17 pages.

Resh, Fatty acylation of proteins: new insights into membrane targeting of myristoylated and palmitoylated proteins, Biochimica et Biophysica Acta (BBA)—Molecular Cell Research, 1999, vol. 1451, Issue 1, pp. 1-17, doi.org/10.1016/S0167-4889(99)00075-0.

Alberts et al., Membrane Proteins, Molecular Biology of the Cell, 2020, 4th edition, New York: Garland Science, 2002, 16 pages, https://www.ncbi.nlm.nih.gov/books/NBK26878/.

Apolloni et. al., H-ras but Not K-ras Traffics to the Plasma Membrane through the Exocytic Pathway, Molecular and Cellular Biology, Apr. 2000, 20 (7) 2475-2487, DOI: 10.1128/MCB.20.7.2475-2487.2000.

Dawaliby et. al., Phosphatidylethanolamine Is a Key Regulator of Membrane Fluidity in Eukaryotic Cells, Membrane Biology, 2016, vol. 291(7), 10 pages, doi.org/10.1074/jbc.M115.706523.

Deschenes, Protein Palmitoylation, Encyclopedia of Biological Chemistry (Second Edition), Academic Press, 2013, pp. 645-647, ISBN 9780123786319, https://doi.org/10.1016/B978-0-12-378630-2.00022-0.

Palsuledesai et al., Protein Prenylation: Enzymes, Therapeutics, and Biotechnology Applications, ACS Chemical Biology 2015 10 (1), 51-62, DOI: 10.1021/cb500791f.

Hung et al., Stabilization of exosome-targeting peptides via engineered glycosylation, J Biol Chem, Mar. 27, 2015;290(13):8166-72, doi: 10.1074/jbc.M114.621383.

O'Shea et al., Peptide 'Velcro': design of a heterodimeric coiled coil, Curr Biol. Oct. 1, 1993;3(10):658-67. doi: 10.1016/0960-9822(93)90063-t. PMID: 15335856.

Udenwobele, et al., Myristoylation: An Important Protein Modification in the Immune Response, Frontiers in Immunology, vol. 8, 2017, DOI=10.3389/fimmu.2017.00751.

Kinoshita, Biosynthesis and biology of mammalian GPI-anchored proteins Open Biol. 2020, 16 pages, 10190290, http://doi.org/10.1098/rsob.190290.

Chen et al., Fusion protein linkers: property, design and functionality, Adv Drug Deliv Rev. 2013, 65(10):1357-1369 doi:10.1016/j.addr.2012.09.039.

(56) References Cited

OTHER PUBLICATIONS

Müller et al., Protein fusions to coiled-coil domains, Methods Enzymol. 2000; 328:261-82. doi: 10.1016/s0076-6879(00)28402-4. PMID: 11075350.
Whitford et al., Exosome manufacturing status, Future Med Chem. May 2019; 11(10):1225-1236. doi: 10.4155/mc-2018-0417. PMID: 31280675.
Patel et al., Towards rationally designed biomanufacturing of therapeutic extracellular vesicles: impact of the bioproduction microenvironment, Biotechnol Adv. Dec. 2018; 36(8):2051-2059. doi: 10.1016/j.biotechadv.2018.09.001. Epub Sep. 12, 2018. PMID: 30218694; PMCID: PMC6250573.
Ng et al., Bioprocess decision support tool for scalable manufacture of extracellular vesicles, Biotechnol Bioeng. Feb. 2019; 116(2):307-319. doi: 10.1002/bit.26809. Epub Nov. 8, 2018. PMID: 30063243; PMCID: PMC6322973.
Paganini et al., Scalable Production and Isolation of Extracellular Vesicles: Available Sources and Lessons from Current Industrial Bioprocesses, Biotechnol J. Oct. 2019; 14 (10):e1800528. doi: 10.1002/biot.201800528. Epub Jul. 8, 2019. PMID: 31140717.
Zhang et al., Exosome: A Review of Its Classification, Isolation Techniques, Storage, Diagnostic and Targeted Therapy Applications, Int J Nanomedicine, Sep. 22, 2020;15:6917-6934. doi: 10.2147/IJN.S264498. PMID: 33061359; PMCID: PMC7519827.
Kluszczyńska et al., Methods for the Determination of the Purity of Exosomes, Curr Pharm Des. 2019; 25(42):4464-4485. doi: 10.2174/1381612825666191206162712. PMID: 31808383.
Nolan et al. Analysis of Individual Extracellular Vesicles by Flow Cytometry, Methods Mol Biol. 2018; 1678:79-92. doi: 10.1007/978-1-4939-7346-0_5. PMID: 29071676.
Doyle et al., Overview of Extracellular Vesicles, Their Origin, Composition, Purpose, and Methods for Exosome Isolation and Analysis, Cells, Jul. 15, 2019; 8(7):727. doi: 10.3390/cells8070727. PMID: 31311206; PMCID: PMC6678302.
Pugholm et al., Antibody-Based Assays for Phenotyping of Extracellular Vesicles, Biomed Res Int. 2015; 2015:524817. doi: 10.1155/2015/524817. Epub Dec. 3, 2015. PMID: 26770974; PMCID: PMC4681819.
Shao et al., New Technologies for Analysis of Extracellular Vesicles, Chem Rev. Feb. 28, 2018; 118(4):1917-1950. doi: 10.1021/acs.chemrev.7b00534. Epub Jan. 31, 2018. PMID: 29384376; PMCID: PMC6029891.
Elshaer et al., Adipose stem cells and their paracrine factors are therapeutic for early retinal complications of diabetes In the Ins2Akita mouse, Stem Cell Research & Therapy, 2018, 9:322, 18 pages.
Jha et al., TSG-6 in conditioned media from adipose mesenchymal stem cells protects against visual deficits in mild traumatic brain injury model through neurovascular modulation, Stem Cell Research & Therapy, 2019, 10:318, 15 pages.
Jha et al., Concentrated conditioned media from adipose tissue erived mesenchymal stem cells mitigates visual deficits and retinal inflammation following mild traumatic brain injury, International Journal of Molecular Sciences, 2018. 19:1-22.
ISR and WO for PCT/US2021/016949 dated Jul. 22, 2021, 12 pages.
Andreu et al., Tetraspanins in Extracellular Vesicle Formation and Function, Frontiers in Immunology, 2014, vol. 5 (442), pp. 1-12.
Armstrong et al., Re-Engineering Extracellular Vesicles as Smart Nanoscale Therapeutics, ACS Nano, 2017, vol. 11(1), pp. 69-83.
"Engineered", Lexico, available online at https://www.lexico.com/en/definition/engineered, 4 pages (accessed on Mar. 7, 2022) (Year: 2022).
"Homology", Encyclopedia Britannica, available online at www.britannica.com/science/homology-evolution, 3 pages at p. 1, 1st paragraph (accessed on Mar. 8, 2022) (Year: 2022).
Kanduc et al., Homology, Similarity and Identity in Peptide Epitope Immunodefinition, Journal of Peptide Science, 2012, vol. 18, pp. 487-494.
Pearson et al., An Introduction to Sequence Similarity ("Homology") Searching, Curr Protoc Bioinformatics, 2013, 9 pages.
Samudrala et al., Difference between Homology, Identity and Similarity, available on line at http://www.bio.net/mm/proteins/1998-July/006538.html, 1 page (1998) (Year: 1998).
Yang et al., Engineering of Fc Fragments with Optimized Physicochemical Properties Implying Improvement of Clinical Potentials for Fc-Based Therapeutics, Frontiers in Immunology, 2018, vol. 8, 14 pages.
Barile et al., Exosomes: Therapy delivery tools and biomarkers of diseases Pharmacology and Therapeutics, 2017, 174:63-78 (http://dx.doi.org/10/1016/j.pharmthera.2017-02-020).
Ferguson et al., Exosomes as therapeutics: the implications of molecular composition and exosomal heterogeneity (2016) Journal of Controlled Release. 228:179-190 (http://dx.doi.org/10/1016/j.conrel.2016.02.037).
Murphy, et al., Extracellular vesicle-based therapeutics: natural versus engineered targeting and trafficking (2019) Experimental & Molecular Medicine. 51:32 (https://doi.org/10/1038/s12276-019-0223-5).
Liu et al., Design strategies and application progress of therapeutic exosomes (2019) Theranostics. 9(4):1015-1028 (doi: 10.7150/thno.30853).
Supp ESR for 21750784.7 dated Apr. 3, 2024, 11 pages.
ISR/WO for PCT/US2024/010433 dated Apr. 17, 2024, 15 pages.
Umeda et al., Structural insights into tetraspanin CD9 function,, supplemental information, Nat. Commun. 11:11 (2020).
Umeda et al., Structural insights into tetraspanin CD9 function, Nat. Commun. 11:152 (2020).
UniProt Accession No. A0A024RB05, 5 pages (2014).
Yang et al., Extracellular vesicles as a platform for membrane-associated therapeutic protein delivery, J. Extracellular Vesicles 2018, 7:15.
Adjei, Akwete, and Garren, Julie. Pulmonary delivery of peptide drugs: effect of particle size on bioavailability of leuprolide acetate in healthy male volunteers. Pharmaceutical Research 7(6):565-569 (1990).
Ahmad, Imran, and Allen, Theresa M. Antibody-mediated specific binding and cytotoxicity of liposome-entrapped doxorubicin to lung cancer cells in vitro. Cancer Research 52(17):4817-4820 (1992).
Allen, Loyd V. et al. Remington: The Science and Practice of Pharmacy, 22nd Edition. Pharmaceutical Press (2012).
Anderson, Paula J. et al. Effect of cystic fibrosis on inhaled aerosol boluses. 1-3. Am Rev Respir Dis 140(5):1317-1324 (1989).
Banerji, Julian. et al. A lymphocyte-specific cellular enhancer is located downstream of the joining region in immunoglobulin heavy chain genes. Cell 33(3):729-740 (1983).
Behr, Jean-Paul. Gene transfer with synthetic cationic amphiphiles: prospects for gene therapy. Bioconjugate Chemistry 5(5):382-389 (1994).
Bird, Robert E. et al. Single-chain Antigen-binding Proteins. Science 242(4877):423-426 (1988).
Blaese, M. et al. Vectors in cancer therapy: how will they deliver? Cancer Gene Therapy 2(4):291-297 (1995).
Brinkmann, Ulrich et al. The making of bispecific antibodies. MAbs 9(2):182-212 (2017).
Byrne, G. W., and Ruddle, F. H. Multiplex gene regulation: a two-tiered approach to transgene regulation in transgenic mice. Proceedings of the National Academy of Sciences 86(14):5473-5477 (1989).
Byron, Peter R. Determinants of drug and polypeptide bioavailability from aerosols delivered to the lung. Advanced Drug Delivery Reviews 5(1-2):107-132 (1990).
Calame, Kathryn, and Eaton, Suzanne. Transcriptional controlling elements in the immunoglobulin and T cell receptor loci. Advances in Immunology 43:235-275 (1988).
Camper, Sally A., and Tilghman, Shirley M. Postnatal repression of the alpha-fetoprotein gene is enhancer independent. Genes and Development 3(4):537-546 (1989).
Chothia, Cyrus et al. Canonical Structures for the Hypervariable Regions of Immunoglobulins. Journal of Molecular Biology 196(4):901-917 (1987).
Chothia, Cyrus et al. Conformations of Immunoglobulin Hypervariable Regions. Nature 342(6252):877-883 (1989).

(56) References Cited

OTHER PUBLICATIONS

Crystal, Ronald G. Transfer of genes to humans: early lessons and obstacles to success. Science 270(5235):404-410 (1995).
Damms, Bob; et al. The cost of delivering drugs without needles. Bio/Technology 13.12: 1438-1440. (1995).
Dordunoo, S. K. et al. Preformulation studies on solid dispersions containing triamterene or temazepam in polyethylene glycols or Gelucire 44/14 for liquid filling of hard gelatin capsules. Drug Development and Industrial Pharmacy 17(12):1685-1713 (1991).
Edlund, Thomas. et al. Cell-specific expression of the rat insulin gene: evidence for role of two distinct 5' flanking elements. Science 230(4728):912-916 (1985).
French, Donna L. et al. The influence of formulation on emission, deaggregation and deposition of dry powders for inhalation. Journal of Aerosol Science 27(5):769-783 (1996).
Gao, X, and HUANG, Long-bin. Cationic liposome-mediated gene transfer. Gene Therapy 2(10):710-722 (1995).
Goh, Wei Jiang. et al. Bioinspired cell-derived nanovesicles versus exosomes as drug delivery systems: a cost-effective alternative. Scientific Reports 7(1):14322, 1-10 (2017).
Gonda, Igor. Aerosols for delivery of therapeutic and diagnostic agents to the respiratory tract. Critical Reviews in Therapeutic Drug Carrier Systems 6(4):273-313 (1990).
Greenfield, Edward A. Antibodies, A Laboratory Manual. Second Edition. Cold Spring Harbor Press (2013).
Holliger, Philipp et al. "Diabodies": Small Bivalent and Bispecific Antibody Fragments. Proceedings of the National Academy of Sciences of the United States of America 90(14):6444-6448 (1993).
Hornyak, Gabor L. et al. Introduction to Nanoscience and Nanotechnology. CRC Press (2008).
Huston, James S. et al. Protein Engineering of Antibody Binding Sites: Recovery of Specific Activity in an Anti-digoxin Single-chain Fv Analogue Produced in *Escherichia coli*. PNAS USA 85(16):5879-5883 (1988).
Kabat, Elvin A. et al. Sequences of proteins of immunological interest. 5th Edition. Public Health Service, National Institutes of Health, Bethesda MD (1991).
Kaufman, Randal J. et al. Translational efficiency of polycistronic mRNAs and their utilization to express heterologous genes in mammalian cells. The EMBO Journal 6(1):187-193 (1987).
Kessel, Michael, and Peter Gruss. Murine developmental control genes. Science 249(4967):374-379 (1990).
Kobayashi, Shinzo et al. Pulmonary delivery of salmon calcitonin dry powders containing absorption enhancers in rats. Pharmaceutical Research 13(1):80-83 (1996).
Kohler, G., and Milstein, C. Derivation of specific antibody-producing tissue culture and tumor lines by cell fusion. European Journal of Immunology 6(7):511-519 (1976).
Kontermann, Roland, and Dubel, Stefan. Antibody Engineering. Springer Verlag (2001).
Lanzavecchia, Antonio, and Scheidegger, D. The use of hybrid hybridomas to target human cytotoxic T lymphocytes. European journal of immunology 17(1):105-111 (1987).
Lasic, D.D. Liposomes: From Physics to Applications. Elsevier (1993).
Morrison, Sherie L. et al. Chimeric Human Antibody Molecules: Mouse Antigen-Binding Domains With Human Constant Region Domains. PNAS USA 81(21):6851-6855 (1984).
New, R C C. Liposomes. A practical approach, IRL Press (1990).
Niven, Ralph W. et al. The pulmonary absorption of aerosolized and intratracheally instilled rhG-CSF and monoPEGylated rhG-CSF. Pharmaceutical Research 12(9):1343-1349 (1995).
Osol, Arthur. Remington's Pharmaceutical Sciences, 16th Edition. Mack Publishing Company (1980).
Patton, J. S. et al. Bioavailability of pulmonary delivered peptides and proteins: alpha-interferon, calcitonins and parathyroid hormones. Journal of Controlled Release 28(1-3):79-85 (1994).
Patton, John S, and Platz, Robert M. (D) Routes of delivery: Case studies:(2) Pulmonary delivery of peptides and proteins for systemic action. Advanced Drug Delivery Reviews 8(2-3): 179-196 (1992).
PCT/US2021/016949 International Preliminary Report on Patentability dated Aug. 18, 2022.
Pinkert, Carl A. et al. An albumin enhancer located 10 kb upstream functions along with its promoter to direct efficient, liver-specific expression in transgenic mice. Genes and Development 1(3):268-276 (1987).
Poljak, Roberto J. Production and Structure of Diabodies. Structure 2(12): 1121-1123 (1994).
Queen, Cary, and Baltimore, David. Immunoglobulin gene transcription is activated by downstream sequence elements. Cell 33(3):741-748 (1983).
Remy, Jean-Serge et al. Gene transfer with a series of lipophilic DNA-binding molecules. Bioconjugate Chemistry 5(6):647-654 (1994).
Riechmann, Lutz et al. Reshaping Human Antibodies for Therapy. Nature 332(6162):323-327 (1988).
Rudt, S., and R. H. Muller. In vitro phagocytosis assay of nano-and microparticles by chemiluminescence. I. Effect of analytical parameters, particle size and particle concentration. Journal of Controlled Release 22(3):263-271 (1992).
Sambrook, Joseph, and Green, Michael R. Molecular Cloning: A Laboratory Manual, 4th edition. Cold Spring Harbor Laboratory Press (2012).
Sambrook, Joseph et al. Molecular Cloning: A Laboratory Manual, 2nd Edition. Cold Spring Harbor Laboratory Press (1989).
Seed, Brian. An LFA-3 cDNA encodes a phospholipid-linked membrane protein homologous to its receptor CD2. Nature 329(6142):840-842 (1987).
Sheen, Pai-Chang et al. Bioavailability of a poorly water-soluble drug from tablet and solid dispersion in humans. Journal of Pharmaceutical Sciences 80(7):712-714 (1991).
Singleton, Paul, and Sainsbury, Diana. Dictionary of Microbiology and Molecular Biology, 3rd Edition revised. John wiley and Sons (2006).
Singleton, Paul. Dictionary of DNA and Genome Technology, Third Edition. Wiley-Blackwell (2012).
Smith, Michael B. March's Advanced Organic Chemistry, Reactions, Mechanisms, and Structure. 7th Edition. John Wiley and Sons (2013).
Sonnhammer, Erik LL. et al. A hidden Markov model for predicting transmembrane helices in protein sequences. International Conference on Intelligent Systems for Molecular Biology 6:175-182 (1998).
Tabata, Yasuhiko, and Ikada, Yoshito. Macrophage phagocytosis of biodegradable microspheres composed of L-lactic acid/glycolic acid homo-and copolymers. Journal of Biomedical Materials Research 22(10):837-858 (1988).
Tan, Lina et al. Recent advances of exosomes in immune modulation and autoimmune diseases. Autoimmunity 49(6):357-365 (2016).
Tansey, Ian P. The challenges in the development of metered dose inhalation aerosols using ozone-friendly propellants. Spray Technol and Market 4:26-29 (1994).
Timsina, M. P. et al. Drug delivery to the respiratory tract using dry powder inhalers. International Journal of Pharmaceutics 101(1-2):1-13 (1994).
Visser, J. An Invited Review: Van der Waals and other cohesive forces affecting powder fluidization. Powder Technology 58(1):1-10 (1989).
Wall, Doris A. Pulmonary absorption of peptides and proteins. Drug Delivery 2(1):1-20 (1995).
Winkler, Johannes. Oligonucleotide conjugates for therapeutic applications. Therapeutic Delivery 4(7):791-809 (2013).
Winoto, Astar, and Baltimore, David. A novel, inducible and T cell-specific enhancer located at the 3' end of the T cell receptor alpha locus. The EMBO Journal 8(3):729-733 (1989).
Zanen, Pieter et al. The optimal particle size for parasympathicolytic aerosols in mild asthmatics. International Journal of Pharmaceutics 114(1):111-115 (1995).
Zapata, Gerardo et al. Engineering Linear F(ab')2 Fragments for Efficient Production in *Escherichia coli* and Enhanced Antiproliferative Activity. Protein Engineering 8(10):1057-1062 (1995).

(56) References Cited

OTHER PUBLICATIONS

Zha, Quan Bin et al. Extracellular vesicles: An overview of biogenesis, function, and role in breast cancer. Tumor Biology 39(2):1-7 (2017).

* cited by examiner

Phosphatidylserine binding: Lactadherin (MFGE8) C1C2

>NM_005928.4 Homo sapiens milk fat globule-EGF factor 8 protein (MFGE8), transcript variant 1, mRNA
AGAACCCCGCGGGGTCTGAGCAGCCCAGCGTGCCCATTCCAGCGCCCGCGTCCCCGCAGCATGCCGCGCCCCCGCCTGCTGGCCGCGCTGTGCGGCGCGCTGCTCTG
CGCCCCCAGCCTCCTCGTCGCCCTGGATATCTGTTCCAAAAACCCCTGCCACAACGGTGGTTTATGCGAGGAGATTTCCCAAGAAGTGCGAGGAGATGTCTTCCCCTC
GTACACCTGCACGTGCCTTAAGGGCTACGCGGGCAACCACTGTGAGACGAAATGTGTCGAGCCACTGGGCCTGGAGAATGGGAACATTGCCAACTCACAGATCGCC
GCCTCGTCTGTGCGTGTGACCTTCTTGGGTTTGCAGCATTGGGTCCCGGAGCTGGCCCGCCTGAACCGCGCAGGCATGGTCAATGCCTGGACACCCAGCAGCAATG
ACGATAACCCCTGGATCCAGGTGAACCTGCTGCGGAGGATGTGGGTAACAGGTGTGGTGACGCAGGGTGCCAGCCGCTTGGCCAGTCATGAGTACCTGAAGGCC
TTCAAGGTGGCCTACAGCCTTAATGGACACGAATTCGATTTCATCCATGATGTTAATAAAAAACACAAGGAGTTTGTGGGTAACTGGAACAAAAACGCGGTGCAT
GTCAACCTGTTTGAGACCCCTGTGGAGGCTCAGTACGTGAGATTGTACCCCACGAGCTGCCACACGGCCTGCACTCTGCGCTTTGAGCTACTGGGCTGTGAGCTGA
ACGGATGCGCCAATCCCCTGGGCCTGAAGAATAACAGCATCCCTGACAAGCAGATCACGGCCTCCAGCAGCTACAAGACCTGGGGCTTGCATCTCTTCAGCTGGAA
CCCCTCCTATGCACGGCTGGACAAGCAGGGCAACTTCAACGCCTGGGTTGCGGGGAGCTACGGTAACGATCAGTGGCTGCAGGTGGACCTGGGCTCCTCGAAGGA
GGTGACAGGCATCATCACCCAGGGGGCCCGTAACTTTGGCTCTGTCCAGTTTGTGGCATCCTACAAGGTTGCCTACAGTAATGACAGTGCGAACTGGACTGAGTAC
CAGGACCCCAGGACTGGCAGCAGTAAGATCTTCCCTGGCAACTGGGACAACCACTCCCACAAGAAGAACTTGTTTGAGACGCCCATCCTGGCTCGCTATGTGCGCA
TCCTGCCTGTAGCCTGGCACAACCGCATCGCCCTGCGCCTGGAGCTGCTGGGCTGTTAGTGGCCACCTGCCACCCCCAGGTCTTCCTGCTTTCCATGGCCCGCTGCC
TCTTGGCTTCTCAGCCCCTTTAAATCACCATAGGGCTGGGGACTGGGGAAGGGGAGGGTGTTCAGAGGCAGCACCACCACACAGTCACCCCTCCCTCCCTCTTTCCCA
CCCTCCACCTCTCACGGGCCCTGCCCCAGCCCCTAAGCCCCGTCCCCTAACCCCCAGTCCTCACTGTCCTGTTTTCTTAGGCACTGAGGGATCTGAGTAGGTCTGGGAT
GGACAGGAAAGGGCAAAGTAGGGCGTGTGGTTTCCCTGCCCCTGTCCGGACCGCCGATCCCAGGTGCGTGTGTCTCTGTCTCTCCTAGCCCCTCTCTCACACATCACA
TTCCCATGGTGGCCTCAAGAAAGGCCCGGAAGCGCCAGGCTGGAGATAACAGCCTCTTGCCCGTCGGCCCTGCGTCGGCCCTGGGGTACCATGTGGCCACAACTGCT
GTGGCCCCCTGTCCCCAAGACACTTCCCCTTGTCTCCCTGGTTGCCTCTCTTGCCCCTTGTCCTGAAGCCCAGCGACACAGAAGGGGGTGGGGCGGGTCTATGGGGA
GAAAGGGAGCGAGGTCAGAGGAGGGCATGGGTTGGCAGGGTGGGCGTTTGGGGCCCTCTATGCTGGCTTTTCACCCCAGAGGACACAGGCAGCTTCCAAAATATA
TTTATCTTCTTCACGGGAA >NP_005919.2 lactadherin isoform a preproprotein [Homo sapiens]
MPRPRLLAALCGALLCAPSLLVALDICSKNPCHNGGLCEEISQEVRGDVFPSYTCTCLKGYAGNHCETKCVEPLGLENGNIANSQIAASSVRVTFLGLQHWVPELARLNRAG
MVNAWTPSSNDDNPWIQVNLLRRMWVTGVVTQGASRLASHEYLKAFKVAYSLNGHEFDFIHDVNKKHKEFVGNWNKNAVHVNLFETPVEAQYVRLYPTSCHTACT
LRFELLGCELNGCANPLGLKNNSIPDKQITASSSYKTWGLHLFSWNPSYARLDKQGNFNAWVAGSYGNDQWLQVDLGSSKEVTGIITQGARNFGSVQFVASYKVAYSN
DSANWTEYQDPRTGSSKIFPGNWDNHSHKKNLFETPILARYVRILPVAWHNRIALRLELLGC

*FIG. 2A*

Lipid binding: CD55 (DAF) Glycosylphosphatidylinositol (GPI) Anchor

>NM_000574.5 Homo sapiens CD55 molecule (Cromer blood group) (CD55), transcript variant 1, mRNA
CTGCTTACTGCAACTCGCTCCGGCCGCTGGGCGTAGCTGCGACTCGGCGGAGTCCCGGCGGCGCGTCCTTGTTCTAACCCGGCGCGCCATGACCGTCGCGCGGCCGAGCG
TGCCCGCGGCGCTGCCCCTCCTCGGGGAGCTGCCCCGGCTGCTGCTGCTGGTGCTGTTGTGCCTGCCGGCCGTGTGGGGTGACTGTGGCCTTCCCCCAGATGTACCTAATG
CCCAGCCAGCTTTGGAAGGCCGTACAAGTTTTCCCGAGGATACTGTAATAACGTACAAATGTGAAGAAAGCTTTGTGAAAATTCCTGGCGAGAAGGACTCAGTGATCTGCC
TTAAGGGCAGTCAATGGTCAGATATTGAAGAGTTCTGCAATCGTAGCTGCGAGGTGCCAACAAGGCTAAATTCTGCATCCCTCAAACAGCCTTATATCACTCAGAATTATTT
TCCAGTCGGTACTGTTGTGGAATATGAGTGCCGTCCAGGTTACAGAAGAGAACCTTCTCTATCACCAAAACTAACTTGCCTTCAGAATTTAAAATGGTCCACAGCAGTCGAA
TTTTGTAAAAAGAAATCATGCCCTAATCCGGGAGAAATACGAAATGGTCAGATTGATGTACCAGGTGGCATATTATTTGGTGCAACCATCTCCTTCTCATGTAACACAGGGT
ACAAATTATTTGGCTCGACTTCTAGTTTTTGTCTTATTTCAGGCAGCTCTGTCCAGTGGAGTGACCCGTTGCCAGAGTGCAGAGAAATTTATTGTCCAGCACCACCACAAATT
GACAATGGAATAATTCAAGGGGAACGTGACCATTATGGATATAGACAGTCTGTAACGTATGCATGTAATAAAGGATTCACCATGATTGGAGAGCACTCTATTTATTGTACT
GTGAATAATGATGAAGGAGAGTGGAGTGGCCCACCACCTGAATGCAGAGGAAAATCTCTAACTTCCAAGGTCCCACCAACAGTTCAGAAACCTACCACAGTAAATGTTCCA
ACTACAGAAGTCTCACCAACTTCTCAGAAAACCACCACAAAAACCACCACACCAAATGCTCAAGCAACACGGAGTACACCTGTTTCCAGGACAACCAAGCATTTTCATGAAA
CAACCCCAAATAAAGGAAGTGGAACCACTTCAGGTACTACCCGTCTTCTATCTGGGCACACGTGTTTCACGTTGACAGGTTTGCTTGGGACGCTAGTAACCATGGGCTTG
CTGACTTAGCCAAAGAAGAGTTAAGAAGAAAATACACACAAGTATACAGACTGTTCCTAGTTTCTTAGACTTATCTGCATATTGGATAAAATAAATGCAATTGTGCTCTTCA
TTTAGGATGCTTTCATTGTCTTTAAGATGTGTTAGGAATGTCAACAGAGCAAGGAGAAAAAAGGCAGTCCTGGAATCACATTCTTAGCACACCTACACCTCTTGAAAATAGA
ACAACTTGCAGAATTGAGAGTGATTCCTTTCCTAAAAGTGTAAGAAAGCATAGAGATTTGTTCGTATTTAGAATGGGATCACGAGGAAAAGAGAAGGAAAGTGATTTTTTT
CCACAAGATCTGTAATGTTATTTCCACTTATAAAGGAAATAAAAAATGAAAAACATTATTTGGATATCAAAAGCAAATAAAAACCCAATTCAGTCTCTTCTAAGCAAAATTGC
TAAAGAGAGATGAACCACATTATAAAGTAATCTTTGGCTGTAAGGCATTTTCATCTTTCCTTCGGGTTGGCAAAATATTTTAAAGGTAAAACATGCTGGTGAACCAGGGGTG
TTGATGGTGATAAGGGAGGAATATAGAATGAAAGACTGAATCTTCCTTTGTTGCACAAATAGAGTTTGGAAAAAGCCTGTGAAAGGTGTCTTCTTTGACTTAATGTCTTTAA
AAGTATCCAGAGATACTACAATATTAACATAAGAAAAGATTATATATTATTTCTGAATCGAGATGTCCATAGTCAAATTTGTAAATCTTATTCTTTTGTAATATTTATTTATATT
TATTTATGACAGTGAACATTCTGATTTTACATGTAAAACAAGAAAAGTTGAAGAAGATATGTGAAGAAAAATGTATTTTTCCTAAATAGAAATAAATGATCCCATTTTTTGGT
ATCATGTAGTATGTGAAATTTATTCTTAAACGTGACTACTTTATTTCTAAATAAGAAATTCCCTACCTGCTTCCTACAAGCAGTTCAGAATGCCATGCCTTGGTTGTCCTAGTG
TGAATAATTTTCAGCTACTTTAAAATTATATTGTACTTTCTCAAGCATGTCATATCCTTTCCTATTAGAGTATCTATATTACTTGTTACTGATTTACCTGAAGGCAATCTGATTA
ATTTCTAGGTTTTTACCATATTCTTGTCATCTTGCCAATTACATTTTAAGTGTTAGACTAGACTAAGATGTACTAGTTGTATAGAATATAACTAGA
TTTATTATGGCAATGTTTATTTTGTCATTTTGCTTCATCTGTTTTGTTGTTGAAGTACTTTAAATTTCATACGTTCATGGCATTTCACTGTAAAGACTTTAATGTGTATTTCTTAA
AATAAAACTTTTTTTCCTCCTTAA >NP_000565.1 complement decay-accelerating factor isoform 1 preproprotein [Homo sapiens]
MTVARPSVPAALPLLGELPRLLLLVLLCLPAVWGDCGLPPDVPNAQPALEGRTSFPEDTVITYKCEESFVKIPGEKDSVICLKGSQWSDIEEFCNRSCEVPTRLNSASLKQPYITQNYFP
VGTVVEYECRPGYRREPSLSPKLTCLQNLKWSTAVEFCKKKSCPNPGEIRNGQIDVPGGILFGATISFSCNTGYKLFGSTSSFCLISGSSVQWSDPLPECREIYCPAPPQIDNGIIQGERD
HYGYRQSVTYACNKGFTMIGEHSIYCTVNNDEGEWSGPPPECRGKSLTSKVPPTVQKPTTVNVPTTEVSPTSQKTTTKTTTPNAQATRSTPVSRTTKHFHETTPNKGSGTTSGTTRL
LSGHTCFTLTGLLGTLVTMGLLT

*FIG. 2B*

Fc Linker

>KY053479.1 Synthetic construct Fc-adiponectin gene, complete cds
ATGTACAGGATGCAACTCCTGTCTTGCATTGCACTAAGTCTTGCACTTGTCACGAACTCGATATCGGCCA
TGGTTAGATCTGACAAAACTCACACATGCCCACCGTGCCCAGCACCTGAACTCCTGGGGGGACCGTCAGTCTTCCTCTTCCCCCCAAAACCCAAGGACACCCTCATGA
TCTCCCGGACCCCTGAGGTCACATGCGTGGTGGTGGACGTGAGCCACGAAGACCCTGAGGTCAAGTTCAACTGGTACGTGGACGGCGTGGAGGTGCATAATGCCA
AGACAAAGCCGCGGGAGGAGCAGTACAACAGCACGTACCGTGTGGTCAGCGTCCTCACCGTCCTGCACCAGGACTGGCTGAATGGCAAGGAGTACAAGTGCAAG
GTCTCCAACAAAGCCCTCCCAGCCCCCATCGAGAAAACCATCTCCAAAGCCAAAGGGCAGCCCCGAGAACCACAGGTGTACACCCTGCCCCCATCCCGGGAGGAGA
TGACCAAGAACCAGGTCAGCCTGACCTGCCTGGTCAAAGGCTTCTATCCCAGCGACATCGCCGTGGAGTGGGAGAGCAATGGGCAGCCGGAGAACAACTACAAGA
CCACGCCTCCCGTGCTGGACTCCGACGGCTCCTTCTTCCTCTACAGCAAGCTCACCGTGGACAAGAGCAGGTGGCAGCAGGGGAACGTCTTCTCATGCTCCGTGATG
CACGAGGCTCTGCACAACCACTACACGCAGAAGAGCCTCTCCCTGTCTCCGGGTAAAGCCAGCGGAAGTGGCGGAGGAGGCGGTCCTGGAGAAGGTGCCTATGTAT
ACCGCTCAGCATTCAGTGTGGGATTGGAGACTTACGTTACTATCCCCAACATGCCCATTCGCTTTACCAAGATCTTCTACAATCAGCAAAACCACTATGATGGCTCCACT
GGTAAATTCCACTGCAACATTCCTGGGCTGTACTACTTTGCCTACCACATCACAGTCTATATGAAGGATGTGAAGGTCAGCCTCTTCAAGAAGGACAAGGCTATGCTCT
TCACCTATGATCAGTACCAGGAAAATAATGTGGACCAGGCCTCCGGCTCTGTGCTCCTGCATCTGGAGGTGGGCGACCAAGTCTGGCTCCAGGTGTATGGGGAAGGA
GAGCGTAATGGACTCTATGCTGATAATGACAATGACTCCACCTTCACAGGCTTTCTTCTCTACCATGACACCAACTCTAGAAAGCTTCCTGGAGAAGGTGCCTATGTATA
CCGCTCAGCATTCAGTGTGGGATTGGAGACTTACGTTACTATCCCCAACATGCCCATTCGCTTTACCAAGATCTTCTACAATCAGCAAAACCACTATGATGGCTCCACTG
GTAAATTCCACTGCAACATTCCTGGGCTGTACTACTTTGCCTACCACATCACAGTCTATATGAAGGATGTGAAGGTCAGCCTCTTCAAGAAGGACAAGGCTATGCTCTT
CACCTATGATCAGTACCAGGAAAATAATGTGGACCAGGCCTCCGGCTCTGTGCTCCTGCATCTGGAGGTGGGCGACCAAGTCTGGCTCCAGGTGTATGGGGAAGGAG
AGCGTAATGGACTCTATGCTGATAATGACAATGACTCCACCTTCACAGGCTTTCTTCTCTACCATGACACCAACACTAGTCCTGGAGAAGGTGCCTATGTATACCGCTCA
GCATTCAGTGTGGGATTGGAGACTTACGTTACTATCCCCAACATGCCCATTCGCTTTACCAAGATCTTCTACAATCAGCAAAACCACTATGATGGCTCCACTGGTAAATT
CCACTGCAACATTCCTGGGCTGTACTACTTTGCCTACCACATCACAGTCTATATGAAGGATGTGAAGGTCAGCCTCTTCAAGAAGGACAAGGCTATGCTCTTCACCTAT
GATCAGTACCAGGAAAATAATGTGGACCAGGCCTCCGGCTCTGTGCTCCTGCATCTGGAGGTGGGCGACCAAGTCTGGCTCCAGGTGTATGGGGAAGGAGAGCGTA
ATGGACTCTATGCTGATAATGACAATGACTCCACCTTCACAGGCTTTCTTCTCTACCATGACACCAACTAA >Fc Translation
DKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALP
APIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQK
SLSLSPGK

*FIG. 3*

Human PD-L1 extracellular domains

>NM_014143.4 Homo sapiens CD274 molecule (CD274), transcript variant 1, mRNA

AGTTCTGCGCAGCTTCCCGAGGCTCCGCACCAGCCGCGCTTCTGTCCGCCTGCAGGGCATTCCAGAAAGATGAGGATATTTGCTGTCTTTATATTCATGACCTACTGGCATTTGCTGAACGCATTTAC
TGTCACGGTTCCCAAGGACCTATATGTGGTAGAGTATGGTAGCAATATGACAATTGAATGCAAATTCCCAGTAGAAAAACAATTAGACCTGGCTGCACTAATTGTCTATTGGGAAATGGAGGAT
AAGAACATTATTCAATTTGTGCATGGAGAGGAAGACCTGAAGGTTCAGCATAGTAGCTACAGACAGAGGGCCCGGCTGTTGAAGGACCAGCTCTCCCTGGGAAATGCTGCACTTCAGATCACA
GATGTGAAATTGCAGGATGCAGGGGTGTACCGCTGCATGATCAGCTATGGTGGTGCCGACTACAAGCGAATTACTGTGAAAGTCAATGCCCCATACAACAAAATCAACCAAAGAATTTTGGTTG
TGGATCCAGTCACCTCTGAACATGAACTGACATGTCAGGCTGAGGGCTACCCCAAGGCCGAAGTCATCTGGACAAGCAGTGACCATCAAGTCCTGAGTGGTAAGACCACCACCACCAATTCCAA
GAGAGAGGAGAAGCTTTTCAATGTGACCAGCACACTGAGAATCAACACAACAACTAATGAGATTTTCTACTGCACTTTTAGGAGATTAGATCCTGAGGAAAACCATACAGCTGAATTGGTCATC
CCAGAACTACCTCTGGCACATCCTCCAAATGAAAGGACTCACTTGGTAATTCTGGGAGCCATCTTATTATGCCTTGGTGTAGCACTGACATTCATCTTCCGTTTAAGAAAAGGGAGAATGATGGA
TGTGAAAAAATGTGGCATCCAAGATACAAACTCAAAGAAGCAAAGTGATACACATTTGGAGGAGACGTAATCCAGCATTGGAACTTCTGATCTTCAAGCAGGGATTCTCAACCTGTGGTTTAGGG
GTTCATCGGGGCTGAGCGTGACAAGAGGAAGGAATGGGCCCGTGGGATGCAGGCAATGTGGGACTTAAAAGGCCCAAGCACTGAAAATGGAACCTGGCGAAAGCAGAGGAGGAGAATGAAGAA
AGATGGAGTCAAACAGGGAGCCTGGAGGGAGACCTTGATACTTTCAAATGCCTGAGGGGCTCATCGACGCCTGTGACAGGGAGAAAGGATACTTCTGAACAAGGAGCCTCCAAGCAAATCATCCAT
TGCTCATCCTAGGAAGACGGGTTGAGAATCCCTAATTTGAGGGTCAGTTCCTGCAGAAGTGCCCTTTGCCTCCACTCAATGCCTCAATTTGTTTTCTGCATGACTGAGAGTCTCAGTGTTGGAACGGGA
CAGTATTTATGTATGAGTTTTTCCTATTTATTTTGAGTCTGTGAGGTCTTCTTGTCATGTGAGTGTGGTTGTGAATGATTTCTTTTGAAGATATATTGTAGTAGATGTTACAATTTTGTCGCCAAACTAAA
CTTGCTGCTTAATGATTTGCTCACATCTAGTAAAACATGGAGTATTTGTAAGGTGCTTGGTCTCCTCTATAACTACAAGTATACATTGGAAGCATAAAGATCAAACCGTTGGTTGCATAGGATGTCACCT
TTATTTAACCCATTAATACTCTGGTTGACCTAATCTTATTCTCAGACCTCAAGTGTCTGTGCAGTATCTGTTCCATTTAAATATCAGCTTTACAATTATGTGGTAGCCTACACACATAATCTCATTTCATCG
CTGTAACCACCCTGTTGTGATAACCACTATTATTTTACCCATCGTACAGCTGAGGAAGCAAACAGATTAAGTAACTTGCCCAAACCAGTAAATAGCAGACCTCAGACTGCCACCCACTGTCCTTTTATAA
TACAATTTACAGCTATATTTTACTTTAAGCAATTCTTTTATTCAAAAACCATTTATTAAGTGCCCTTGCAATATCAATCGCTGTGCCAGGCATTGAATCTACAGATGTGAGCAAGACAAAGTACCTGTCCT
CAAGGAGCTCATAGTATAATGAGGAGATTAACAAGAAAATGTATTATTACAATTTAGTCCAGTGTCATAGCATAAGGATGATGCGAGGGGAAAACCCGAGCAGTGTTGCCAAGAGGAGGAAATAGG
CCAATGTGGTCTGGGACGGTTGGATATACTTAAACATCTTAATAATCAGAGTAATTTTCATTTACAAAGAGAGGTCGGTACTTAAAATAACCCTGAAAAATAACACTGGAATTCCTTTTCTAGCATTAT
ATTTATTCCTGATTTGCCTTTGCCATATAATCTAATGCTTGTTTATATAGTGTCTGGTATTGTTTAACAGTTCTGTCTTTTCTATTTAAATGCCACTAAATTTTAAATTCATACCTTTCCATGATTCAAAATTC
AAAAGATCCCATGGGAGATGGTTGGAAAATCTCCACTTCATCCTCCAAGCCATTCAAGTTTCCTTTCCAGAAGCAACTGCTACTGCCTTTCATTCATATGTTCTTCTAAAGATAGTCTACATTTGGAAAT
GTATGTTAAAAGCACGTATTTTTAAAATTTTTTTCCTAAATAGTAACACATTGTATGTCTGCTGTGTACTTTGCTATTTTTATTTATTTTAGTGTTTCTTATATAGCAGATGGAATGAATTTGAAGTTCCCA
GGGCTGAGGATCCATGCCTTCTTTGTTTCTAAGTTATCTTTCCCATAGCTTTTCATTATCTTTCATATGATCCAGTATATGTTAAATATGTCCTACATATACATTTAGACAACCACCATTTGTTAAGTATTT
GCTCTAGGACAGAGTTTGGATTTGTTTATGTTTGCTCAAAAGGAGACCCATGGGCTCTCCAGGGTGCACTGAGTCAATCTAGTCCTAAAAAGCAATCTTATTATTAACTCTGTATGACAGAATCATGTC
TGGAACTTTTGTTTTCTGCTTTCTGTCAAGTATAAACTTCACTTTGATGCTGTACTTGCAAAATCACATTTTCTTTCTGGAAATTCCGGCAGTGTACCTTGACTGCTAGCTACCCTGTGCCAGAAAAGCCT
CATTCGTTGTGCTTGAACCCTTGAATGCCACCAGCTGTCATCACTACACAGCCCTCCTAAGAGGCTTCCTGGAGGTTTCGAGATTCAGATGCCCTGGGAGATCCCAGAGTTTCCTTTCCCTCTTGGCCAT
ATTCTGGTGTCAATGACAAGGAGTACCTTGGCTTTGCCACATGTCAAGGCTGAAGAAACAGTGTCTCCAACAGAGCTCCTTGTGTTATCTGTTTGTACATGTGCATTTGTACAGTAATTGGTGTGACAG
TGTTCTTTGTGTGAATTACAGGCAAGAATTGTGGCTGAGCAAGGCACATAGTCTACTCAGTCTATTCCTAAGTCCTAACTCCTCCTTGTGGTGTTGGATTTGTAAGGCACTTTATCCCTTTTGTCTCATGT
TTCATCGTAAATGGCATAGGCAGAGATGATACCTAATTCTGCATTTGATTGTCACTTTTTGTACCTGCATTAATTTAATAAAATATTCTTATTTATTTTGTTACTTGGTACACCAGCATGTCCATTTTCTTG
TTTATTTTGTGTTTAATAAAATGTTCAGTTTAACATCCCA

>NP_054862.1 programmed cell death 1 ligand 1 isoform a precursor [Homo sapiens]

**MRIFAVFIFMTYWHLLNAFTVTVPKDLYVVEYGSNMTIECKFPVEKQLDLAALIVYWEMEDKNIIQFVHGEEDLKVQHSSYRQRARLLKDQLSLGNAALQITDVKLQDAGVYRCMISYGGADYKRITVKV
NAPYNKINQRILVVDPVTSEHELTCQAEGYPKAEVIWTSSDHQVLSGKTTTTNSKREEKLFNVTSTLRINTTTNEIFYCTFRRLDPEENHTAELVIPELPLAHPPNERTHLVILGAILLCLGVALTFIFRLRKGRM
MDVKKCGIQDTNSKKQSDTHLEET**

*FIG. 4A*

Human PD-L2 extracellular domains

>NM_025239.4 Homo sapiens programmed cell death 1 ligand 2 (PDCD1LG2), mRNA
ACTCTCATGTTACGGCAAACCTTAAGCTGAATGAACAACTTTTCTTCTCTTGAATATATCTTAACGCCAAATTTTGAGTGCTTTTTTGTTACCCATCCTCATATGTCCCAGCTA
GAAAGAATCCTGGGTTGGAGCTACTGCATGTTGATTGTTTTGTTTTTCCTTTTGGCTGTTCATTTTGGTGGCTACTATAAGGAAATCTAACACAAACAGCAACTGTTTTTTG
TTGTTTACTTTTGCATCTTTACTTGTGGAGCTGTGGCAAGTCCTCATATCAAATACAGAACATGATCTTCCTCCTGCTAATGTTGAGCCTGGAATTGCAGCTTCACCAGATA
GCAGCTTTATTCACAGTGACAGTCCCTAAGGAACTGTACATAATAGAGCATGGCAGCAATGTGACCCTGGAATGCAACTTTGACACTGGAAGTCATGTGAACCTTGGA
GCAATAACAGCCAGTTTGCAAAAGGTGGAAAATGATACATCCCCACACCGTGAAAGAGCCACTTTGCTGGAGGAGCAGCTGCCCCTAGGGAAGGCCTCGTTCCACAT
ACCTCAAGTCCAAGTGAGGGACGAAGGACAGTACCAATGCATAATCATCTATGGGGTCGCCTGGGACTACAAGTACCTGACTCTGAAAGTCAAAGCTTCCTACAGGA
AAATAAACACTCACATCCTAAAGGTTCCAGAAACAGATGAGGTAGAGCTCACCTGCCAGGCTACAGGTTATCCTCTGGCAGAAGTATCCTGGCCAAACGTCAGCGTTC
CTGCCAACACCAGCCACTCCAGGACCCCTGAAGGCCTCTACCAGGTCACCAGTGTTCTGCGCCTAAAGCCACCCCCTGGCAGAAACTTCAGCTGTGTGTTCTGGAATAC
TCACGTGAGGGAACTTACTTTGGCCAGCATTGACCTTCAAAGTCAGATGGAACCCAGGACCCATCCAACTTGGCTGCTTCACATTTTCATCCCCTTCTGCATCATTGCTT
TCATTTTCATAGCCACAGTGATAGCCCTAAGAAAACAACTCTGTCAAAAGCTGTATTCTTCAAAAGACACAACAAAAAGACCTGTCACCACAACAAAGAGGGAAGTGA
ACAGTGCTATCTGAACCTGTGGTCTTGGGAGCCAGGGTGACCTGATATGACATCTAAAGAAGCTTCTGGACTCTGAACAAGAATTCGGTGGCCTGCAGAGCTTGCCATTT
GCACTTTTCAAATGCCTTTGGATGACCCAGCACTTTAATCTGAAACCTGCAACAAGACTAGCCAACACCTGGCCATGAAACTTGCCCCTTCACTGATCTGGACTCACCTCTG
GAGCCTATGGCTTTAAGCAAGCACTACTGCACTTTACAGAATTACCCCACTGGATCCTGGACCCACAGAATTCCTTCAGGATCCTTCTTGCTGCCAGACTGAAAGCAAAAG
GAATTATTTCCCCTCAAGTTTTCTAAGTGATTTCCAAAAGCAGAGGTGTGTGGAAATTTCCAGTAACAGAAACAGATGGGTTGCCAATAGAGTTATTTTTTATCTATAGCTT
CCTCTGGGTACTAGAAGAGGCTATTGAGACTATGAGCTCACAGACAGGGCTTCGCACAAACTCAAATCATAATTGACATGTTTTATGGATTACTGGAATCTTGATAGCAT
AATGAAGTTGTTCTAATTAACAGAGAGCATTTAAATATACACTAAGTGCACAAATTGTGGAGTAAAGTCATCAAGCTCTGTTTTTGAGGTCTAAGTCACAAAGCATTTGTT
TTAACCTGTAATGGCACCATGTTTAATGGTGGTTTTTTTTTTGAACTACATCTTTCCTTTAAAAATTATTGGTTTCTTTTTATTTGTTTTTACCTTAGAAATCAATTATATACAG
TCAAAAATATTTGATATGCTCATACGTTGTATCTGCAGCAATTTCAGATAAGTAGCTAAAATGGCCAAAGCCCCAAACTAAGCCTCCTTTTCTGGCCCTCAATATGACTTTA
AATTTGACTTTTCAGTGCCTCAGTTTGCACATCTGTAATACAGCAATGCTAAGTAGTCAAGGCCTTTGATAATTGGCACTATGGAAATCCTGCAAGATCCCACTACATATGT
GTGGAGCAGAAGGGTAACTCGGCTACAGTAACAGCTTAATTTTGTTAAATTTGTTCTTTATACTGGAGCCATGAAGCTCAGAGCATTAGCTGACCCTTGAACTATTCAAAT
GGGCACATTAGCTAGTATAACAGACTTACATAGGTGGGCCTAAAGCAAGCTCCTTAACTGAGCAAAATTTGGGGCTTATGAGAATGAAAGGGTGTGAAATTGACTAACA
GACAAATCATACATCTCAGTTTCTCAATTCTCATGTAAATCAGAGAATGCCTTTAAAGAATAAAACTCAATTGTTATTCTTCAACGTTCTTTATATATTCTACTTTTGGGTA >NP_079515.2 programmed cell death 1 ligand 2 precursor [Homo sapiens]
MIFLLLMLSLELQLHQIAALFTVTVPKELYIIEHGSNVTLECNFDTGSHVNLGAITASLQKVENDTSPHRERATLLEEQLPLGKASFHIPQVQVRDEGQYQCIIIYGVAWDYKYLTL
KVKASYRKINTHILKVPETDEVELTCQATGYPLAEVSWPNVSVPANTSHSRTPEGLYQVTSVLRLKPPPGRNFSCVFWNTHVRELTLASIDLQSQMEPRTHPTWLLHIFIPFCII
AFIFIATVIALRKQLCQKLYSSKDTTKRPVTTTKREVNSAI

*FIG. 4B*

Human CTLA-4 (CD152) extracellular domains

>NM_005214.5 Homo sapiens cytotoxic T-lymphocyte associated protein 4 (CTLA4), transcript variant 1, mRNA
GCTTTCTATTCAAGTGCCTTCTGTGTGTGCACATGTGTAATACATATCTGGGATCAAAGCTATCTATATAAAGTCCTTGATTCTGTGTGGGTTCAAACACATTTCAAAGCTT
CAGGATCCTGAAAGGTTTTGCTCTACTTCCTGAAGACCTGAACACCGCTCCCATAAAGCCATGGCTTGCCTTGGATTTCAGCGGCACAAGGCTCAGCTGAACCTGGCTA
CCAGGACCTGGCCCTGCACTCTCCTGTTTTTTCTTCTCTTCATCCCTGTCTTCTGCAAAGCAATGCACGTGGCCCAGCCTGCTGTGGTACTGGCCAGCAGCCGAGGCATC
GCCAGCTTTGTGTGTGAGTATGCATCTCCAGGCAAAGCCACTGAGGTCCGGGTGACAGTGCTTCGGCAGGCTGACAGCCAGGTGACTGAAGTCTGTGCGGCAACCTA
CATGATGGGGAATGAGTTGACCTTCCTAGATGATTCCATCTGCACGGGCACCTCCAGTGGAAATCAAGTGAACCTCACTATCCAAGGACTGAGGGCCATGGACACGG
GACTCTACATCTGCAAGGTGGAGCTCATGTACCCACCGCCATACTACCTGGGCATAGGCAACGGAACCCAGATTTATGTAATTGATCCAGAACCGTGCCCAGATTCTG
ACTTCCTCCTCTGGATCCTTGCAGCAGTTAGTTCGGGGTTGTTTTTTTATAGCTTTCTCCTCACAGCTGTTTCTTTGAGCAAAATGCTAAAGAAAAGAAGCCCTCTTACA
ACAGGGGTCTATGTGAAAATGCCCCCAACAGAGCCAGAATGTGAAAAGCAATTTCAGCCTTATTTTATTCCCATCAATTGAGAAACCATTATGAAGAAGAGAGTCCAT
ATTTCAATTTCCAAGAGCTGAGGCAATTCTAACTTTTTTGCTATCCAGCTATTTTTATTTGTTTGTGCATTTGGGGGGAATTCATCTCTCTTTAATATAAAGTTGGATGCGG
AACCCAAATTACGTGTACTACAATTTAAAGCAAAGGAGTAGAAAGACAGAGCTGGGATGTTTCTGTCACATCAGCTCCACTTTCAGTGAAAGCATCACTTGGGATTAATA
TGGGGATGCAGCATTATGATGTGGGTCAAGGAATTAAGTTAGGGAATGGCACAGCCCAAAGAAGGAAAAGGCAGGGAGCGAGGGAGAAGACTATATTGTACACACC
TTATATTTACGTATGAGACGTTTATAGCCGAAATGATCTTTTCAAGTTAAATTTTATGCCTTTTATTTCTTAAACAAATGTATGATTACATCAAGGCTTCAAAAATACTCACA
TGGCTATGTTTTAGCCAGTGATGCTAAAGGTTGTATTGCATATATACATATATATATATATATATATATATATATATATATATATATATATATATATATATTTTAATTTGA
TAGTATTGTGCATAGAGCCACGTATGTTTTTGTGTATTTGTTAATGGTTTGAATATAAACACTATATGGCAGTGTCTTTCCACCTTGGGTCCCAGGGAAGTTTTGTGGAGG
AGCTCAGGACACTAATACACCAGGTAGAACACAAGGTCATTTGCTAACTAGCTTGGAAACTGGATGAGGTCATAGCAGTGCTTGATTGCGTGGAATTGTGCTGAGTTGG
TGTTGACATGTGCTTTGGGGCTTTTACACCAGTTCCTTTCAATGGTTTGCAAGGAAGCCACAGCTGGTGGTATCTGAGTTGACTTGACAGAACACTGTCTTGAAGACAAT
GGCTTACTCCAGGAGACCCACAGGTATGACCTTCTAGGAAGCTCCAGTTCGATGGGCCCAATTCTTACAAACATGTGGTTAATGCCATGGACAGAAGAAGGCAGCAGGT
GGCAGAATGGGGTGCATGAAGGTTTCTGAAAATTAACACTGCTTGTGTTTTTAACTCAATATTTTCCATGAAAATGCAACAACATGTATAATATTTTTAATTAAATAAAAA
TCTGTGGTGGTCGTTTTCCGGA >NP_005205.2 cytotoxic T-lymphocyte protein 4 isoform CTLA4-TM precursor [Homo sapiens]
MACLGFQRHKAQLNLATRTWPCTLLFFLLFIPVFCKAMHVAQPAVVLASSRGIASFVCEYASPGKATEVRVTVLRQADSQVTEVCAATYMMGNELTFLDDSICTGTSSGNQ
VNLTIQGLRAMDTGLYICKVELMYPPPYYLGIGNGTQIYVIDPEPCPDSDFLLWILAAVSSGLFFYSFLLTAVSLSKMLKKRSPLTTGVYVKMPPTEPECEKQFQPYFIPIN

*FIG. 4C* hCTLA4-Fc-*GPI*

ATGGCTTGCCTTGGATTTCAGCGGCACAAGGCTCAGCTGAACCTGGCTACCAGGACCTGGCCCTGCACTCTCCTGTTTTTCTTCTCTTCATCCCT
GTCTTCTGCAAAGCAATGCACGTGGCCCAGCCTGCTGTGGTACTGGCCAGCAGCCGAGGCATCGCCAGCTTTGTGTGTGAGTATGCATCTCCAG
GCAAAGCCACTGAGGTCCGGGTGACAGTGCTTCGGCAGGCTGACAGCCAGGTGACTGAAGTCTGTGCGGCAACCTACATGATGGGGAATGAG
TTGACCTTCCTAGATGATTCCATCTGCACGGGCACCTCCAGTGGAAATCAAGTGAACCTCACTATCCAAGGACTGAGGGCCATGGACACGGGAC
TCTACATCTGCAAGGTGGAGCTCATGTACCCACCGCCATACTACCTGGGCATAGGCAACGGAACCCAGATTTATGTAATTGATCCAGAACCGTGC
CCAGATTCTGACATCGATGACAAAACTCACACATGCCCACCGTGCCCAGCACCTGAACTCCTGGGGGGACCGTCAGTCTTCCTCTTCCCCCCAAA
ACCCAAGGACACCCTCATGATCTCCCGGACCCCTGAGGTCACATGCGTGGTGGTGGACGTGAGCCACGAAGACCCTGAGGTCAAGTTCAACTGG
TACGTGGACGGCGTGGAGGTGCATAATGCCAAGACAAAGCCGCGGGAGGAGCAGTACAACAGCACGTACCGTGTGGTCAGCGTCCTCACCGTC
CTGCACCAGGACTGGCTGAATGGCAAGGAGTACAAGTGCAAGGTCTCCAACAAAGCCCTCCCAGCCCCCATCGAGAAAACCATCTCCAAAGCCA
AAGGGCAGCCCCGAGAACCACAGGTGTACACCCTGCCCCCATCCCGGGAGGAGATGACCAAGAACCAGGTCAGCCTGACCTGCCTGGTCAAAG
GCTTCTATCCCAGCGACATCGCCGTGGAGTGGGAGAGCAATGGGCAGCCGGAGAACAACTACAAGACCACGCCTCCCGTGCTGGACTCCGACG
GCTCCTTCTTCCTCTACAGCAAGCTCACCGTGGACAAGAGCAGGTGGCAGCAGGGGAACGTCTTCTCATGCTCCGTGATGCACGAGGCTCTGCAC
AACCACTACACGCAGAAGAGCCTCTCCCTGTCTCCGGGTAAAATCGAT*CCAAATAAAGGAAGTGGAACCACTTCAGGTACTACCCGTCTTCTATCT*
*GGGCACACGTGTTTCACGTTGACAGGTTTGCTTGGGACGCTAGTAACCATGGGCTTGCTGACTTAG*

MACLGFQRHKAQLNLATRTWPCTLLFFLLFIPVFCKAMHVAQPAVVLASSRGIASFV
CEYASPGKATEVRVTVLRQADSQVTEVCAATYMMGNELTFLDDSICTGTSSGNQVNL
TIQGLRAMDTGLYICKVELMYPPPYYLGIGNGTQIYVIDPEPCPDSDIDDKTHTCPP
CPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQ
PREPQVYTLPPSREEMTKNQVSLTCLVKGFYPSDIAVEWESNGQPENNYKTTPPVLD
SDGSFFLYSKLTVDKSRWQQGNVFSCSVMHEALHNHYTQKSLSLSPGKID*PNKGSGT*
*TSGTTRLLSGHTCFTLTGLLGTLVTMGLLT*

*FIG. 5C* hPDL1-*GPI*-P2A-hHVEM-*GPI*

ATGAGGATATTTGCTGTCTTTATATTCATGACCTACTGGCATTTGCTGAACGCATTTACTGTCACGGTTCCCAAGGACCTATATGTGGTAGAGTATGGTAG
CAATATGACAATTGAATGCAAATTCCCAGTAGAAAAACAATTAGACCTGGCTGCACTAATTGTCTATTGGGAAATGGAGGATAAGAACATTATTCAATTTG
TGCATGGAGAGGAAGACCTGAAGGTTCAGCATAGTAGCTACAGACAGAGGGCCCGGCTGTTGAAGGACCAGCTCTCCCTGGGAAATGCTGCACTTCAGATC
ACAGATGTGAAATTGCAGGATGCAGGGGTGTACCGCTGCATGATCAGCTATGGTGGTGCCGACTACAAGCGAATTACTGTGAAAGTCAATGCCCCATACAA
CAAAATCAACCAAAGAATTTTGGTTGTGGATCCAGTCACCTCTGAACATGAACTGACATGTCAGGCTGAGGGCTACCCCAAGGCCGAAGTCATCTGGACAA
GCAGTGACCATCAAGTCCTGAGTGGTAAGACCACCACCACCAATTCCAAGAGAGAGGAGAAGCTTTTCAATGTGACCAGCACACTGAGAATCAACACAACA
ACTAATGAGATTTTCTACTGCACTTTTAGGAGATTAGATCCTGAGGAAAACCATACAGCTGAATTGGTCATCCCAGAACTACCTCTGGCACATCCTCCAAA
TGAAAGG*CCAAATAAAGGAAGTGGAACCACTTCAGGTACTACCCGTCTTCTATCTGGGCACACGTGTTTCACGTTGACAGGTTTGCTTGGGACGCTAGTAA*
*CCATGGGCTTGCTGACT*GGAAGCGGAGCTACTAACTTCAGCCTGCTGAAGCAGGCTGGCGACGTGGAGGAGAACCCTGGACCTATGGAGCCTCCTGGAGAC
TGGGGGCCTCCTCCCTGGAGATCCACCCCCAAAACCGACGTCTTGAGGCTGGTGCTGTATCTCACCTTCCTGGGAGCCCCCTGCTACGCCCCAGCTCTGCC
GTCCTGCAAGGAGGACGAGTACCCAGTGGGCTCCGAGTGCTGCCCCAAGTGCAGTCCAGGTTATCGTGTGAAGGAGGCCTGCGGGGAGCTGACGGGCACAG
TGTGTGAACCCTGCCCTCCAGGCACCTACATTGCCCACCTCAATGGCCTAAGCAAGTGTCTGCAGTGCCAAATGTGTGACCCAGCCATGGGCCTGCGCGCG
AGCCGGAACTGCTCCAGGACAGAGAACGCCGTGTGTGGCTGCAGCCCAGGCCACTTCTGCATCGTCCAGGACGGGGACCACTGCGCCGCGTGCCGCGCTTA
CGCCACCTCCAGCCCGGGCCAGAGGGTGCAGAAGGGAGGCACCGAGAGTCAGGACACCCTGTGTCAGAACTGCCCCCCGGGGACCTTCTCTCCCAATGGGA
CCCTGGAGGAATGTCAGCACCAGACCAAGTGCAGCTGGCTGGTGACGAAGGCCGGAGCTGGGACCAGCAGCTCCCACTGGGTA*CCAAATAAAGGAAGTGGA*
*ACCACTTCAGGTACTACCCGTCTTCTATCTGGGCACACGTGTTTCACGTTGACAGGTTTGCTTGGGACGCTAGTAACCATGGGCTTGCTGACTTAG*

MRIFAVFIFMTYWHLLNAFTVTVPKDLYVVEYGSNMTIECKFPVEKQLDLAALIVYWEMEDKNIIQFVHGEEDLKVQHSSYRQRARLLKDQLSLGNAALQI
TDVKLQDAGVYRCMISYGGADYKRITVKVNAPYNKINQRILVVDPVTSEHELTCQAEGYPKAEVIWTSSDHQVLSGKTTTTNSKREEKLFNVTSTLRINTT
TNEIFYCTFRRLDPEENHTAELVIPELPLAHPPNER*PNKGSGTTSGTTRLLSGHTCFTLTGLLGTLVTMGLLT*GSGATNFSLLKQAGDVEENPGPMEPPGD
WGPPPWRSTPKTDVLRLVLYLTFLGAPCYAPALPSCKEDEYPVGSECCPKCSPGYRVKEACGELTGTVCEPCPPGTYIAHLNGLSKCLQCQMCDPAMGLRA
SRNCSRTENAVCGCSPGHFCIVQDGDHCAACRAYATSSPGQRVQKGGTESQDTLCQNCPPGTFSPNGTLEECQHQTKCSWLVTKAGAGTSSSHWV*PNKGSG*
*TTSGTTRLLSGHTCFTLTGLLGTLVTMGLLT*

*FIG. 5D* hPDL1-*GPI*-P2A-FGL1-*GPI*

ATGAGGATATTTGCTGTCTTTATATTCATGACCTACTGGCATTTGCTGAACGCATTTACTGTCACGGTTCCCAAGGACCTATATGTGGTAGAGTATGGTAGC
AATATGACAATTGAATGCAAATTCCCAGTAGAAAAACAATTAGACCTGGCTGCACTAATTGTCTATTGGGAAATGGAGGATAAGAACATTATTCAATTTGTG
CATGGAGAGGAAGACCTGAAGGTTCAGCATAGTAGCTACAGACAGAGGGCCCGGCTGTTGAAGGACCAGCTCTCCCTGGGAAATGCTGCACTTCAGATCACA
GATGTGAAATTGCAGGATGCAGGGGTGTACCGCTGCATGATCAGCTATGGTGGTGCCGACTACAAGCGAATTACTGTGAAAGTCAATGCCCCATACAACAAA
ATCAACCAAAGAATTTTGGTTGTGGATCCAGTCACCTCTGAACATGAACTGACATGTCAGGCTGAGGGCTACCCCAAGGCCGAAGTCATCTGGACAAGCAGT
GACCATCAAGTCCTGAGTGGTAAGACCACCACCACCAATTCCAAGAGAGAGGAGAAGCTTTTCAATGTGACCAGCACACTGAGAATCAACACAACAACTAAT
GAGATTTTCTACTGCACTTTTAGGAGATTAGATCCTGAGGAAAACCATACAGCTGAATTGGTCATCCCAGAACTACCTCTGGCACATCCTCCAAATGAAAGG
*CCAAATAAAGGAAGTGGAACCACTTCAGGTACTACCCGTCTTCTATCTGGGCACACGTGTTTCACGTTGACAGGTTTGCTTGGGACGCTAGTAACCATGGGC*
*TTGCTGACT*GGAAGCGGAGCTACTAACTTCAGCCTGCTGAAGCAGGCTGGCGACGTGGAGGAGAACCCTGGACCTATGGCAAAGGTGTTCAGTTTCATCCTT
GTTACCACCGCTCTGACAATGGGCAGGGAAATTTCGGCGCTCGAGGACTGTGCCCAGGAGCAGATGCGGCTCAGAGCCCAGGTGCGCCTGCTTGAGACCCGG
GTCAAACAGCAACAGGTCAAGATCAAGCAGCTTTTGCAGGAGAATGAAGTCCAGTTCCTTGATAAAGGAGATGAGAATACTGTCATTGATCTTGGAAGCAAG
AGGCAGTATGCAGATTGTTCAGAGATTTTCAATGATGGGTATAAGCTCAGTGGATTTTACAAAATCAAACCTCTCCAGAGCCCAGCAGAATTTTCTGTTTAT
TGTGACATGTCCGATGGAGGAGGATGGACTGTAATTCAGAGACGATCTGATGGCAGTGAAAACTTTAACAGAGGATGGAAAGACTATGAAAATGGCTTTGGA
AATTTTGTCCAAAAACATGGTGAATATTGGCTGGGCAATAAAAATCTTCACTTCTTGACCACTCAAGAAGACTACACTTTAAAAATCGACCTTGCAGATTTT
GAAAAAAATAGCCGTTATGCACAATATAAGAATTTCAAAGTTGGAGATGAAAAGAATTTCTACGAGTTGAATATTGGGGAATATTCTGGAACAGCTGGAGAT
TCCCTTGCGGGGAATTTTCATCCTGAGGTGCAGTGGTGGGCTAGTCACCAAAGAATGAAATTCAGCACGTGGGACAGAGATCATGACAACTATGAAGGGAAC
TGCGCAGAAGAAGATCAGTCTGGCTGGTGGTTTAACAGGTGTCACTCTGCAAACCTGAATGGTGTATACTACAGCGGCCCCTACACGGCTAAAACAGACAAT
GGGATTGTCTGGTACACCTGGCATGGGTGGTGGTATTCTCTGAAATCTGTGGTTATGAAAATTAGGCCAAATGATTTTATTCCAAATGTAATT*CCAAATAAA*
*GGAAGTGGAACCACTTCAGGTACTACCCGTCTTCTATCTGGGCACACGTGTTTCACGTTGACAGGTTTGCTTGGGACGCTAGTAACCATGGGCTTGCTGACT*
*TAG*

MRIFAVFIFMTYWHLLNAFTVTVPKDLYVVEYGSNMTIECKFPVEKQLDLAALIVYWEMEDKNIIQFVHGEEDLKVQHSSYRQRARLLKDQLSLGNAALQIT
DVKLQDAGVYRCMISYGGADYKRITVKVNAPYNKINQRILVVDPVTSEHELTCQAEGYPKAEVIWTSSDHQVLSGKTTTTNSKREEKLFNVTSTLRINTTTN
EIFYCTFRRLDPEENHTAELVIPELPLAHPPNER*PNKGSGTTSGTTRLLSGHTCFTLTGLLGTLVTMGLLT*GSGATNFSLLKQAGDVEENPGPMAKVFSFIL
VTTALTMGREISALEDCAQEQMRLRAQVRLLETRVKQQQVKIKQLLQENEVQFLDKGDENTVIDLGSKRQYADCSEIFNDGYKLSGFYKIKPLQSPAEFSVY
CDMSDGGGWTVIQRRSDGSENFNRGWKDYENGFGNFVQKHGEYWLGNKNLHFLTTQEDYTLKIDLADFEKNSRYAQYKNFKVGDEKNFYELNIGEYSGTAGD
SLAGNFHPEVQWWASHQRMKFSTWDRDHDNYEGNCAEEDQSGWWFNRCHSANLNGVYYSGPYTAKTDNGIVWYTWHGWWYSLKSVVMKIRPNDFIPNVI*PNK*
*GSGTTSGTTRLLSGHTCFTLTGLLGTLVTMGLLT*

*FIG. 5E* hPDL1-*GPI*

ATGAGGATATTTGCTGTCTTTATATTCATGACCTACTGGCATTTGCTGAACGCATTTACTGTCACGGTTCCCAAGGACCTATATGTGGTAGAG
TATGGTAGCAATATGACAATTGAATGCAAATTCCCAGTAGAAAAACAATTAGACCTGGCTGCACTAATTGTCTATTGGGAAATGGAGGATAAG
AACATTATTCAATTTGTGCATGGAGAGGAAGACCTGAAGGTTCAGCATAGTAGCTACAGACAGAGGGCCCGGCTGTTGAAGGACCAGCTCTCC
CTGGGAAATGCTGCACTTCAGATCACAGATGTGAAATTGCAGGATGCAGGGGTGTACCGCTGCATGATCAGCTATGGTGGTGCCGACTACAAG
CGAATTACTGTGAAAGTCAATGCCCCATACAACAAAATCAACCAAAGAATTTTGGTTGTGGATCCAGTCACCTCTGAACATGAACTGACATGT
CAGGCTGAGGGCTACCCCAAGGCCGAAGTCATCTGGACAAGCAGTGACCATCAAGTCCTGAGTGGTAAGACCACCACCACCAATTCCAAGAGA
GAGGAGAAGCTTTTCAATGTGACCAGCACACTGAGAATCAACACAACAACTAATGAGATTTTCTACTGCACTTTTAGGAGATTAGATCCTGAG
GAAAACCATACAGCTGAATTGGTCATCCCAGAACTACCTCTGGCACATCCTCCAAATGAAAGG*CCAAATAAAGGAAGTGGAACCACTTCAGGT*
*ACTACCCGTCTTCTATCTGGGCACACGTGTTTCACGTTGACAGGTTTGCTTGGGACGCTAGTAACCATGGGCTTGCTGACTTAG*

MRIFAVFIFMTYWHLLNAFTVTVPKDLYVVEYGSNMTIECKFPVEKQLDLAALIVYWEMEDKNIIQFVHGEEDLKVQHSSYRQRARLLKDQLS
LGNAALQITDVKLQDAGVYRCMISYGGADYKRITVKVNAPYNKINQRILVVDPVTSEHELTCQAEGYPKAEVIWTSSDHQVLSGKTTTTNSKR
EEKLFNVTSTLRINTTTNEIFYCTFRRLDPEENHTAELVIPELPLAHPPNER*PNKGSGTTSGTTRLLSGHTCFTLTGLLGTLVTMGLLT*

*FIG. 5F* hPDL1-Fc-*GPI*

ATGAGGATATTTGCTGTCTTTATATTCATGACCTACTGGCATTTGCTGAACGCATTTACTGTCACGGTTCCCAAGGACCTATATGTGGTAGAGTATGGTAG
CAATATGACAATTGAATGCAAATTCCCAGTAGAAAAACAATTAGACCTGGCTGCACTAATTGTCTATTGGGAAATGGAGGATAAGAACATTATTCAATTTG
TGCATGGAGAGGAAGACCTGAAGGTTCAGCATAGTAGCTACAGACAGAGGGCCCGGCTGTTGAAGGACCAGCTCTCCCTGGGAAATGCTGCACTTCAGATC
ACAGATGTGAAATTGCAGGATGCAGGGGTGTACCGCTGCATGATCAGCTATGGTGGTGCCGACTACAAGCGAATTACTGTGAAAGTCAATGCCCCATACAA
CAAAATCAACCAAAGAATTTTGGTTGTGGATCCAGTCACCTCTGAACATGAACTGACATGTCAGGCTGAGGGCTACCCCAAGGCCGAAGTCATCTGGACAA
GCAGTGACCATCAAGTCCTGAGTGGTAAGACCACCACCACCAATTCCAAGAGAGAGGAGAAGCTTTTCAATGTGACCAGCACACTGAGAATCAACACAACA
ACTAATGAGATTTTCTACTGCACTTTTAGGAGATTAGATCCTGAGGAAAACCATACAGCTGAATTGGTCATCCCAGAACTACCTCTGGCACATCCTCCAAA
TGAAAGGATCGATGACAAAACTCACACATGCCCACCGTGCCCAGCACCTGAACTCCTGGGGGGACCGTCAGTCTTCCTCTTCCCCCCAAAACCCAAGGACA
CCCTCATGATCTCCCGGACCCCTGAGGTCACATGCGTGGTGGTGGACGTGAGCCACGAAGACCCTGAGGTCAAGTTCAACTGGTACGTGGACGGCGTGGAG
GTGCATAATGCCAAGACAAAGCCGCGGGAGGAGCAGTACAACAGCACGTACCGTGTGGTCAGCGTCCTCACCGTCCTGCACCAGGACTGGCTGAATGGCAA
GGAGTACAAGTGCAAGGTCTCCAACAAAGCCCTCCCAGCCCCCATCGAGAAAACCATCTCCAAAGCCAAAGGGCAGCCCCGAGAACCACAGGTGTACACCC
TGCCCCCATCCCGGGAGGAGATGACCAAGAACCAGGTCAGCCTGACCTGCCTGGTCAAAGGCTTCTATCCCAGCGACATCGCCGTGGAGTGGGAGAGCAAT
GGGCAGCCGGAGAACAACTACAAGACCACGCCTCCCGTGCTGGACTCCGACGGCTCCTTCTTCCTCTACAGCAAGCTCACCGTGGACAAGAGCAGGTGGCA
GCAGGGGAACGTCTTCTCATGCTCCGTGATGCACGAGGCTCTGCACAACCACTACACGCAGAAGAGCCTCTCCCTGTCTCCGGGTAAAATCGAT*CCAAATA*
*AAGGAAGTGGAACCACTTCAGGTACTACCCGTCTTCTATCTGGGCACACGTGTTTCACGTTGACAGGTTTGCTTGGGACGCTAGTAACCATGGGCTTGCTG*
*ACTTAG*

MRIFAVFIFMTYWHLLNAFTVTVPKDLYVVEYGSNMTIECKFPVEKQLDLAALIVYWEMEDKNIIQFVHGEEDLKVQHSSYRQRARLLKDQLSLGNAALQI
TDVKLQDAGVYRCMISYGGADYKRITVKVNAPYNKINQRILVVDPVTSEHELTCQAEGYPKAEVIWTSSDHQVLSGKTTTTNSKREEKLFNVTSTLRINTT
TNEIFYCTFRRLDPEENHTAELVIPELPLAHPPNERIDDKTHTCPPCPAPELLGGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESN
GQPENNYKTTPPVLDSDGSFFLYSKLTVDKSRWQQGNVFSCSVMHEALHNHYTQKSLSLSPGKID*PNKGSGTTSGTTRLLSGHTCFTLTGLLGTLVTMGLL*
*T*

*FIG. 5G* hPDL2-Fc-*GPI*

ATGATCTTCCTCCTGCTAATGTTGAGCCTGGAATTGCAGCTTCACCAGATAGCAGCTTTATTCACAGTGACAGTCCCTAAGGAACTGTACATAATAGAGCAT
GGCAGCAATGTGACCCTGGAATGCAACTTTGACACTGGAAGTCATGTGAACCTTGGAGCAATAACAGCCAGTTTGCAAAAGGTGGAAAATGATACATCCCCA
CACCGTGAAAGAGCCACTTTGCTGGAGGAGCAGCTGCCCCTAGGGAAGGCCTCGTTCCACATACCTCAAGTCCAAGTGAGGGACGAAGGACAGTACCAATGC
ATAATCATCTATGGGGTCGCCTGGGACTACAAGTACCTGACTCTGAAAGTCAAAGCTTCCTACAGGAAAATAAACACTCACATCCTAAAGGTTCCAGAAACA
GATGAGGTAGAGCTCACCTGCCAGGCTACAGGTTATCCTCTGGCAGAAGTATCCTGGCCAAACGTCAGCGTTCCTGCCAACACCAGCCACTCCAGGACCCCT
GAAGGCCTCTACCAGGTCACCAGTGTTCTGCGCCTAAAGCCACCCCCTGGCAGAAACTTCAGCTGTGTGTTCTGGAATACTCACGTGAGGGAACTTACTTTG
GCCAGCATTGACCTTCAAAGTCAGATGGAACCCAGGACCCATCCAACTATCGATGACAAAACTCACACATGCCCACCGTGCCCAGCACCTGAACTCCTGGGG
GGACCGTCAGTCTTCCTCTTCCCCCCAAAACCCAAGGACACCCTCATGATCTCCCGGACCCCTGAGGTCACATGCGTGGTGGTGGACGTGAGCCACGAAGAC
CCTGAGGTCAAGTTCAACTGGTACGTGGACGGCGTGGAGGTGCATAATGCCAAGACAAAGCCGCGGGAGGAGCAGTACAACAGCACGTACCGTGTGGTCAGC
GTCCTCACCGTCCTGCACCAGGACTGGCTGAATGGCAAGGAGTACAAGTGCAAGGTCTCCAACAAAGCCCTCCCAGCCCCCATCGAGAAAACCATCTCCAAA
GCCAAAGGGCAGCCCCGAGAACCACAGGTGTACACCCTGCCCCCATCCCGGGAGGAGATGACCAAGAACCAGGTCAGCCTGACCTGCCTGGTCAAAGGCTTC
TATCCCAGCGACATCGCCGTGGAGTGGGAGAGCAATGGGCAGCCGGAGAACAACTACAAGACCACGCCTCCCGTGCTGGACTCCGACGGCTCCTTCTTCCTC
TACAGCAAGCTCACCGTGGACAAGAGCAGGTGGCAGCAGGGGAACGTCTTCTCATGCTCCGTGATGCACGAGGCTCTGCACAACCACTACACGCAGAAGAGC
CTCTCCCTGTCTCCGGGTAAAATCGAT*CCAAATAAAGGAAGTGGAACCACTTCAGGTACTACCCGTCTTCTATCTGGGCACACGTGTTTCACGTTGACAGGT*
*TTGCTTGGGACGCTAGTAACCATGGGCTTGCTGACTTAG*

MIFLLLMLSLELQLHQIAALFTVTVPKELYIIEHGSNVTLECNFDTGSHVNLGAITASLQKVENDTSPHRERATLLEEQLPLGKASFHIPQVQVRDEGQYQC
IIIYGVAWDYKYLTLKVKASYRKINTHILKVPETDEVELTCQATGYPLAEVSWPNVSVPANTSHSRTPEGLYQVTSVLRLKPPPGRNFSCVFWNTHVRELTL
ASIDLQSQMEPRTHPTIDDKTHTCPPCPAPELLGGPSVFLFPPKPKDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFL
YSKLTVDKSRWQQGNVFSCSVMHEALHNHYTQKSLSLSPGKID*PNKGSGTTSGTTRLLSGHTCFTLTGLLGTLVTMGLLT*

*FIG. 5H* hPDL1-*C1C2*

ATGAGGATATTTGCTGTCTTTATATTCATGACCTACTGGCATTTGCTGAACGCATTTACTGTCACGGTTCCCAAGGACCTATATGTGGTAGAGTATGGTAG
CAATATGACAATTGAATGCAAATTCCCAGTAGAAAAACAATTAGACCTGGCTGCACTAATTGTCTATTGGGAAATGGAGGATAAGAACATTATTCAATTTG
TGCATGGAGAGGAAGACCTGAAGGTTCAGCATAGTAGCTACAGACAGAGGGCCCGGCTGTTGAAGGACCAGCTCTCCCTGGGAAATGCTGCACTTCAGATC
ACAGATGTGAAATTGCAGGATGCAGGGGTGTACCGCTGCATGATCAGCTATGGTGGTGCCGACTACAAGCGAATTACTGTGAAAGTCAATGCCCCATACAA
CAAAATCAACCAAAGAATTTTGGTTGTGGATCCAGTCACCTCTGAACATGAACTGACATGTCAGGCTGAGGGCTACCCCAAGGCCGAAGTCATCTGGACAA
GCAGTGACCATCAAGTCCTGAGTGGTAAGACCACCACCACCAATTCCAAGAGAGAGGAGAAGCTTTTCAATGTGACCAGCACACTGAGAATCAACACAACA
ACTAATGAGATTTTCTACTGCACTTTTAGGAGATTAGATCCTGAGGAAAACCATACAGCTGAATTGGTCATCCCAGAACTACCTCTGGCACATCCTCCAAA
TGAAAGGATCGAT*GTCGAGCCACTGGGCATGGAGAATGGGAACATTGCCAACTCACAGATCGCCGCCTCATCTGTGCGTGTGACCTTCTTGGGTTTGCAGC*
*ATTGGGTCCCGGAGCTGGCCCGCCTGAACCGCGCAGGCATGGTCAATGCCTGGACACCCAGCAGCAATGACGATAACCCCTGGATCCAGGTGAACCTGCTG*
*CGGAGGATGTGGGTAACAGGTGTGGTGACGCAGGGTGCCAGCCGCTTGGCCAGTCATGAGTACCTGAAGGCCTTCAAGGTGGCCTACAGCCTTAATGGACA*
*CGAATTCGATTTCATCCATGATGTTAATAAAAAACACAAGGAGTTTGTGGGTAACTGGAACAAAAACGCGGTGCATGTCAACCTGTTTGAGACCCCTGTGG*
*AGGCTCAGTACGTGAGATTGTACCCCACGAGCTGCCACACGGCCTGCACTCTGCGCTTTGAGCTACTGGGCTGTGAGCTGAACGGATGCGCCAATCCCCTG*
*GGCCTGAAGAATAACAGCATCCCTGACAAGCAGATCACGGCCTCCAGCAGCTACAAGACCTGGGGCTTGCATCTCTTCAGCTGGAACCCCTCCTATGCACG*
*GCTGGACAAGCAGGGCAACTTCAACGCCTGGGTTGCGGGGAGCTACGGTAACGATCAGTGGCTGCAGATCTTCCCTGGCAACTGGGACAACCACTCCCACA*
*AGAAGAACTTGTTTGAGACGCCCATCCTGGCTCGCTATGTGCGCATCCTGCCTGTAGCCTGGCACAACCGCATCGCCCTGCGCCTGGAGCTGCTGGGCTGT*
*TAG*

MRIFAVFIFMTYWHLLNAFTVTVPKDLYVVEYGSNMTIECKFPVEKQLDLAALIVYWEMEDKNIIQFVHGEEDLKVQHSSYRQRARLLKDQLSLGNAALQI
TDVKLQDAGVYRCMISYGGADYKRITVKVNAPYNKINQRILVVDPVTSEHELTCQAEGYPKAEVIWTSSDHQVLSGKTTTTNSKREEKLFNVTSTLRINTT
TNEIFYCTFRRLDPEENHTAELVIPELPLAHPPNERID*VEPLGMENGNIANSQIAASSVRVTFLGLQHWVPELARLNRAGMVNAWTPSSNDDNPWIQVNLL*
*RRMWVTGVVTQGASRLASHEYLKAFKVAYSLNGHEFDFIHDVNKKHKEFVGNWNKNAVHVNLFETPVEAQYVRLYPTSCHTACTLRFELLGCELNGCANPL*
*GLKNNSIPDKQITASSSYKTWGLHLFSWNPSYARLDKQGNFNAWVAGSYGNDQWLQIFPGNWDNHSHKKNLFETPILARYVRILPVAWHNRIALRLELLGC*

*FIG. 5I* hPDL2-*C1C2*

ATGATCTTCCTCCTGCTAATGTTGAGCCTGGAATTGCAGCTTCACCAGATAGCAGCTTTATTCACAGTGACAGTCCCTAAGGAACTGTACATAATAGAGCA
TGGCAGCAATGTGACCCTGGAATGCAACTTTGACACTGGAAGTCATGTGAACCTTGGAGCAATAACAGCCAGTTTGCAAAAGGTGGAAAATGATACATCCC
CACACCGTGAAAGAGCCACTTTGCTGGAGGAGCAGCTGCCCCTAGGGAAGGCCTCGTTCCACATACCTCAAGTCCAAGTGAGGGACGAAGGACAGTACCAA
TGCATAATCATCTATGGGGTCGCCTGGGACTACAAGTACCTGACTCTGAAAGTCAAAGCTTCCTACAGGAAAATAAACACTCACATCCTAAAGGTTCCAGA
AACAGATGAGGTAGAGCTCACCTGCCAGGCTACAGGTTATCCTCTGGCAGAAGTATCCTGGCCAAACGTCAGCGTTCCTGCCAACACCAGCCACTCCAGGA
CCCCTGAAGGCCTCTACCAGGTCACCAGTGTTCTGCGCCTAAAGCCACCCCCTGGCAGAAACTTCAGCTGTGTGTTCTGGAATACTCACGTGAGGGAACTT
ACTTTGGCCAGCATTGACCTTCAAAGTCAGATGGAACCCAGGACCCATCCAACTATCGAT*GTCGAGCCACTGGGCATGGAGAATGGGAACATTGCCAACTC*
*ACAGATCGCCGCCTCATCTGTGCGTGTGACCTTCTTGGGTTTGCAGCATTGGGTCCCGGAGCTGGCCCGCCTGAACCGCGCAGGCATGGTCAATGCCTGGA*
*CACCCAGCAGCAATGACGATAACCCCTGGATCCAGGTGAACCTGCTGCGGAGGATGTGGGTAACAGGTGTGGTGACGCAGGGTGCCAGCCGCTTGGCCAGT*
*CATGAGTACCTGAAGGCCTTCAAGGTGGCCTACAGCCTTAATGGACACGAATTCGATTTCATCCATGATGTTAATAAAAAACACAAGGAGTTTGTGGGTAA*
*CTGGAACAAAAACGCGGTGCATGTCAACCTGTTTGAGACCCCTGTGGAGGCTCAGTACGTGAGATTGTACCCCACGAGCTGCCACACGGCCTGCACTCTGC*
*GCTTTGAGCTACTGGGCTGTGAGCTGAACGGATGCGCCAATCCCCTGGGCCTGAAGAATAACAGCATCCCTGACAAGCAGATCACGGCCTCCAGCAGCTAC*
*AAGACCTGGGGCTTGCATCTCTTCAGCTGGAACCCCTCCTATGCACGGCTGGACAAGCAGGGCAACTTCAACGCCTGGGTTGCGGGGAGCTACGGTAACGA*
*TCAGTGGCTGCAGATCTTCCCTGGCAACTGGGACAACCACTCCCACAAGAAGAACTTGTTTGAGACGCCCATCCTGGCTCGCTATGTGCGCATCCTGCCTG*
*TAGCCTGGCACAACCGCATCGCCCTGCGCCTGGAGCTGCTGGGCTGTTAG*

MIFLLLMLSLELQLHQIAALFTVTVPKELYIIEHGSNVTLECNFDTGSHVNLGAITASLQKVENDTSPHRERATLLEEQLPLGKASFHIPQVQVRDEGQYQ
CIIIYGVAWDYKYLTLKVKASYRKINTHILKVPETDEVELTCQATGYPLAEVSWPNVSVPANTSHSRTPEGLYQVTSVLRLKPPPGRNFSCVFWNTHVREL
TLASIDLQSQMEPRTHPTI*DVEPLGMENGNIANSQIAASSVRVTFLGLQHWVPELARLNRAGMVNAWTPSSNDDNPWIQVNLLRRMWVTGVVTQGASRLAS*
*HEYLKAFKVAYSLNGHEFDFIHDVNKKHKEFVGNWNKNAVHVNLFETPVEAQYVRLYPTSCHTACTLRFELLGCELNGCANPLGLKNNSIPDKQITASSSY*
*KTWGLHLFSWNPSYARLDKQGNFNAWVAGSYGNDQWLQIFPGNWDNHSHKKNLFETPILARYVRILPVAWHNRIALRLELLGC*

*FIG. 5J*

*4F2*-h41BBL

*ATGAGCCAGGACACCGAGGTGGATATGAAGGAGGTGGAGCTGAATGAGTTAGAGCCCGAGAAGCAGCCGATGAACGCGGCGTCTGGGGCGGCCATGTCCCTG*
*GCGGGAGCCGAGAAGAATGGTCTGGTGAAGATCAAGGTGGCGGAAGACGAGGCGGAGGCGGCAGCCGCGGCTAAGTTCACGGGCCTGTCCAAGGAGGAGCTG*
*CTGAAGGTGGCAGGCAGCCCCGGCTGGGTACGCACCCGCTGGGCACTGCTGCTGCTCTTCTGGCTCGGCTGGCTCGGCATGCTTGCTGGTGCCGTGGTCATA*
*ATCGTG*GCCTGCCCCTGGGCCGTGTCCGGGGCTCGCGCCTCGCCCGGCTCCGCGGCCAGCCCGAGACTCCGCGAGGGTCCCGAGCTTTCGCCCGACGATCCC
GCCGGCCTCTTGGACCTGCGGCAGGGCATGTTTGCGCAGCTGGTGGCCCAAAATGTTCTGCTGATCGATGGGCCCCTGAGCTGGTACAGTGACCCAGGCCTG
GCAGGCGTGTCCCTGACGGGGGGCCTGAGCTACAAAGAGGACACGAAGGAGCTGGTGGTGGCCAAGGCTGGAGTCTACTATGTCTTCTTTCAACTAGAGCTG
CGGCGCGTGGTGGCCGGCGAGGGCTCAGGCTCCGTTTCACTTGCGCTGCACCTGCAGCCACTGCGCTCTGCTGCTGGGGCCGCCGCCCTGGCTTTGACCGTG
GACCTGCCACCCGCCTCCTCCGAGGCTCGGAACTCGGCCTTCGGTTTCCAGGGCCGCTTGCTGCACCTGAGTGCCGGCCAGCGCCTGGGCGTCCATCTTCAC
ACTGAGGCCAGGGCACGCCATGCCTGGCAGCTTACCCAGGGCGCCACAGTCTTGGGACTCTTCCGGGTGACCCCCGAAATCCCAGCCGGACTCCCTTCACCG
AGGTCGGAATAA

*MSQDTEVDMKEVELNELEPEKQPMNAASGAAMSLAGAEKNGLVKIKVAEDEAEAAAAAKFTGLSKEELLKVAGSPGWVRTRWALLLLFWLGWLGMLAGAVVI*
*IV*ACPWAVSGARASPGSAASPRLREGPELSPDDPAGLLDLRQGMFAQLVAQNVLLIDGPLSWYSDPGLAGVSLTGGLSYKEDTKELVVAKAGVYYVFFQLEL
RRVVAGEGSGSVSLALHLQPLRSAAGAAALALTVDLPPASSEARNSAFGFQGRLLHLSAGQRLGVHLHTEARARHAWQLTQGATVLGLFRVTPEIPAGLPSP
RSE

*FIG. 5K* hPDL1-4Fc-*GPI*

ATGAGGATATTTGCTGTCTTTATATTCATGACCTACTGGCATTTGCTGAACGCATTTACTGTCACGGTTCCCAAGGACCTATATGTGGTAGAGTATGGTAG
CAATATGACAATTGAATGCAAATTCCCAGTAGAAAAACAATTAGACCTGGCTGCACTAATTGTCTATTGGGAAATGGAGGATAAGAACATTATTCAATTTG
TGCATGGAGAGGAAGACCTGAAGGTTCAGCATAGTAGCTACAGACAGAGGGCCCGGCTGTTGAAGGACCAGCTCTCCCTGGGAAATGCTGCACTTCAGATC
ACAGATGTGAAATTGCAGGATGCAGGGGTGTACCGCTGCATGATCAGCTATGGTGGTGCCGACTACAAGCGAATTACTGTGAAAGTCAATGCCCCATACAA
CAAAATCAACCAAAGAATTTTGGTTGTGGATCCAGTCACCTCTGAACATGAACTGACATGTCAGGCTGAGGGCTACCCCAAGGCCGAAGTCATCTGGACAA
GCAGTGACCATCAAGTCCTGAGTGGTAAGACCACCACCACCAATTCCAAGAGAGAGGAGAAGCTTTTCAATGTGACCAGCACACTGAGAATCAACACAACA
ACTAATGAGATTTTCTACTGCACTTTTAGGAGATTAGATCCTGAGGAAAACCATACAGCTGAATTGGTCATCCCAGAACTACCTCTGGCACATCCTCCAAA
TGAAAGGGAGTCCAAATATGGTCCCCCATGCCCATCATGCCCAGCACCTGAGTTCCTGGGGGGACCATCAGTCTTCCTGTTCCCCCCAAAACCCAAGGACA
CTCTCATGATCTCCCGGACCCCTGAGGTCACGTGCGTGGTGGTGGACGTGAGCCAGGAAGACCCCGAGGTCCAGTTCAACTGGTACGTGGATGGCGTGGAG
GTGCATAATGCCAAGACAAAGCCGCGGGAGGAGCAGTTCAACAGCACGTACCGTGTGGTCAGGGTCCTCACCGTCCTGCACCAGGACTGGCTGAACGGTAA
GGAGTACAAGTGCAAGGTCTCCAACAAAGGCCTCCCGTCCTCCATCGAGAAAACCATCTCCAAAGCCAAAGGGCAGCCCCGAGAGCCACAGGTGTACACCC
TGCCCCCATCCCAGGAGGAGATGACCAAGAACCAGGTCAGCCTGACCTGCCTGGTCAAAGGCTTCTACCCCAGCGACATCGCCGTGGAGTGGGAGAGCAAT
GGGCAGCCGGAGGACAACTACAAGACCACGCCTCCCGTGCTGGACTCCGACGGCTCCTTCTTCCTCTACAGCAGGCTAACCGTGGACAAGAGCAGGTGGCA
GGAGGGGAATGTCTTCTCATGCTCCGTGATGCATGAGGCTCTGCACAACCACTACACACAGAAGAGCCTCTCCCTGTCTCCGGGTAAA*CCAAATAAAGGAA*
*GTGGAACCACTTCAGGTACTACCCGTCTTCTATCTGGGCACACGTGTTTCACGTTGACAGGTTTGCTTGGGACGCTAGTAACCATGGGCTTGCTGACTTAG*

MRIFAVFIFMTYWHLLNAFTVTVPKDLYVVEYGSNMTIECKFPVEKQLDLAALIVYWEMEDKNIIQFVHGEEDLKVQHSSYRQRARLLKDQLSLGNAALQI
TDVKLQDAGVYRCMISYGGADYKRITVKVNAPYNKINQRILVVDPVTSEHELTCQAEGYPKAEVIWTSSDHQVLSGKTTTTNSKREEKLFNVTSTLRINTT
TNEIFYCTFRRLDPEENHTAELVIPELPLAHPPNERESKYGPPCPSCPAPEFLGGPSVFLFPPKPKDTLMISRTPEVTCVVVDVSQEDPEVQFNWYVDGVE
VHNAKTKPREEQFNSTYRVVRVLTVLHQDWLNGKEYKCKVSNKGLPSSIEKTISKAKGQPREPQVYTLPPSQEEMTKNQVSLTCLVKGFYPSDIAVEWESN
GQPEDNYKTTPPVLDSDGSFFLYSRLTVDKSRWQEGNVFSCSVMHEALHNHYTQKSLSLSPGK*PNKGSGTTSGTTRLLSGHTCFTLTGLLGTLVTMGLLT*

*FIG. 5L*

*Myr*-NanoLuc Luciferase

*ATGGGTTGCTGTTTCTCCAAGACC*GGCTCGAGCGGCGTCTTCACACTCGAAGATTTCGTTGGGGACTGGCGACAGACAGCCGGCTACAACC
TGGACCAAGTCCTTGAACAGGGAGGTGTGTCCAGTTTGTTTCAGAATCTCGGGGTGTCCGTAACTCCGATCCAAAGGATTGTCCTGAGCGG
TGAAAATGGGCTGAAGATCGACATCCATGTCATCATCCCGTATGAAGGTCTGAGCGGCGACCAAATGGGCCAGATCGAAAAAATTTTTAAG
GTGGTGTACCCTGTGGATGATCATCACTTTAAGGTGATCCTGCACTATGGCACACTGGTAATCGACGGGGTTACGCCGAACATGATCGACT
ATTTCGGACGGCCGTATGAAGGCATCGCCGTGTTCGACGGCAAAAAGATCACTGTAACAGGGACCCTGTGGAACGGCAACAAAATTATCGA
CGAGCGCCTGATCAACCCCGACGGCTCCCTGCTGTTCCGAGTAACCATCAACGGAGTGACCGGCTGGCGGCTGTGCGAACGCATTCTGGCG
TAA

*MGCCFSKT*GSSGVFTLEDFVGDWRQTAGYNLDQVLEQGGVSSLFQNLGVSVTPIQRIVLSGENGLKIDIHVIIPYEGLSGDQMGQIEKIFK
VVYPVDDHHFKVILHYGTLVIDGVTPNMIDYFGRPYEGIAVFDGKKITVTGTLWNGNKIIDERLINPDGSLLFRVTINGVTGWRLCERILA

*FIG. 5M*

*Myr*-mScarlet

*ATGGGTTGCTGTTTCTCCAAGACC*GGCTCGAGCGGCGTGAGCAAGGGCGAGGCAGTGATCAAGGAGTTCATGCGGTTCAAGGTGCACATGGAG
GGCTCCATGAACGGCCACGAGTTCGAGATCGAGGGCGAGGGCGAGGGCCGCCCCTACGAGGGCACCCAGACCGCCAAGCTGAAGGTGACCAAG
GGTGGCCCCCTGCCCTTCTCCTGGGACATCCTGTCCCCTCAGTTCATGTACGGCTCCAGGGCCTTCACCAAGCACCCCGCCGACATCCCCGAC
TACTATAAGCAGTCCTTCCCCGAGGGCTTCAAGTGGGAGCGCGTGATGAACTTCGAGGACGGCGGCGCCGTGACCGTGACCCAGGACACCTCC
CTGGAGGACGGCACCCTGATCTACAAGGTGAAGCTCCGCGGCACCAACTTCCCTCCTGACGGCCCCGTAATGCAGAAGAAGACAATGGGCTGG
GAAGCGTCCACCGAGCGGTTGTACCCCGAGGACGGCGTGCTGAAGGGCGACATTAAGATGGCCCTGCGCCTGAAGGACGGCGGCCGCTACCTG
GCGGACTTCAAGACCACCTACAAGGCCAAGAAGCCCGTGCAGATGCCCGGCGCCTACAACGTCGACCGCAAGTTGGACATCACCTCCCACAAC
GAGGACTACACCGTGGTGGAACAGTACGAACGCTCCGAGGGCCGCCACTCCACCGGCGGCATGGACGAGCTGTACAAG

*MGCCFSKT*GSSGVSKGEAVIKEFMRFKVHMEGSMNGHEFEIEGEGEGRPYEGTQTAKLKVTKGGPLPFSWDILSPQFMYGSRAFTKHPADIPD
YYKQSFPEGFKWERVMNFEDGGAVTVTQDTSLEDGTLIYKVKLRGTNFPPDGPVMQKKTMGWEASTERLYPEDGVLKGDIKMALRLKDGGRYL
ADFKTTYKAKKPVQMPGAYNVDRKLDITSHNEDYTVVEQYERSEGRHSTGGMDELYK

*FIG. 5N* hSecPDL1-*GPI*

ATGAGGATATTTGCTGTCTTTATATTCATGACCTACTGGCATTTGCTGAACGCATTTACTGTCACGGTTCCCAAGGACCTATATGTGGTAGAGTATGGTAGC
AATATGACAATTGAATGCAAATTCCCAGTAGAAAAACAATTAGACCTGGCTGCACTAATTGTCTATTGGGAAATGGAGGATAAGAACATTATTCAATTTGTG
CATGGAGAGGAAGACCTGAAGGTTCAGCATAGTAGCTACAGACAGAGGGCCCGGCTGTTGAAGGACCAGCTCTCCCTGGGAAATGCTGCACTTCAGATCACA
GATGTGAAATTGCAGGATGCAGGGGTGTACCGCTGCATGATCAGCTATGGTGGTGCCGACTACAAGCGAATTACTGTGAAAGTCAATGCCCCATACAACAAA
ATCAACCAAAGAATTTTGGTTGTGGATCCAGTCACCTCTGAACATGAACTGACATGTCAGGCTGAGGGCTACCCCAAGGCCGAAGTCATCTGGACAAGCAGT
GACCATCAAGTCCTGAGTGGTAAGACCACCACCACCAATTCCAAGAGAGAGGAGAAGCTTTTCAATGTGACCAGCACACTGAGAATCAACACAACAACTAAT
GAGATTTTCTACTGCACTTTTAGGAGATTAGATCCTGAGGAAAACCATACAGCTGAATTGGTCATCCCAGGTAATATTCTGAATGTGTCCATTAAAATATGT
CTAACACTGTCCCCTAGCACC_CCAAATAAAGGAAGTGGAACCACTTCAGGTACTACCCGTCTTCTATCTGGGCACACGTGTTTCACGTTGACAGGTTTGCTT_
_GGGACGCTAGTAACCATGGGCTTGCTGACTTAG_

MRIFAVFIFMTYWHLLNAFTVTVPKDLYVVEYGSNMTIECKFPVEKQLDLAALIVYWEMEDKNIIQFVHGEEDLKVQHSSYRQRARLLKDQLSLGNAALQIT
DVKLQDAGVYRCMISYGGADYKRITVKVNAPYNKINQRILVVDPVTSEHELTCQAEGYPKAEVIWTSSDHQVLSGKTTTTNSKREEKLFNVTSTLRINTTTN
EIFYCTFRRLDPEENHTAELVIPGNILNVSIKICLTLSPST_PNKGSGTTSGTTRLLSGHTCFTLTGLLGTLVTMGLLT_

*FIG. 5O*

*Tfr2*-h41BBL

*ATGGAGCGGCTTTGGGGTCTATTCCAGAGAGCGCAACAACTGTCCCCAAGATCCTCTCAGACCGTCTACCAGCGTGTGGAAGGCCCCCGGAAAGGGCACCTGG*
*AGGAGGAAGAGGAAGACGGGGAGGAGGGGGCGGAGACATTGGCCCACTTCTGCCCCATGGAGCTGAGGGGCCCTGAGCCCCTGGGCTCTAGACCCAGGCAGCC*
*AAACCTCATTCCCTGGGCGGCAGCAGGACGGAGGGCTGCCCCCTACCTGGTCCTGACGGCCCTGCTGATCTTCACTGGGGCCTTCCTACTGGGCTACGTCGCC*
*TTCCGAGGGTCC* *GCCTGCCCCTGGGCCGTGTCCGGGGCTCGCGCCTCGCCCGGCTCCGCGGCCAGCCCGAGACTCCGCGAGGGTCCCGAGCTTTCGCCCGACG*
*ATCCCGCCGGCCTCTTGGACCTGCGGCAGGGCATGTTTGCGCAGCTGGTGGCCCAAAATGTTCTGCTGATCGATGGGCCCCTGAGCTGGTACAGTGACCCAGG*
*CCTGGCAGGCGTGTCCCTGACGGGGGGCCTGAGCTACAAAGAGGACACGAAGGAGCTGGTGGTGGCCAAGGCTGGAGTCTACTATGTCTTCTTTCAACTAGAG*
*CTGCGGCGCGTGGTGGCCGGCGAGGGCTCAGGCTCCGTTTCACTTGCGCTGCACCTGCAGCCACTGCGCTCTGCTGCTGGGGCCGCCGCCCTGGCTTTGACCG*
*TGGACCTGCCACCCGCCTCCTCCGAGGCTCGGAACTCGGCCTTCGGTTTCCAGGGCCGCTTGCTGCACCTGAGTGCCGGCCAGCGCCTGGGCGTCCATCTTCA*
*CACTGAGGCCAGGGCACGCCATGCCTGGCAGCTTACCCAGGGCGCCACAGTCTTGGGACTCTTCCGGGTGACCCCCGAAATCCCAGCCGGACTCCCTTCACCG*
*AGGTCGGAATAA*

*MERLWGLFQRAQQLSPRSSQTVYQRVEGPRKGHLEEEEEDGEEGAETLAHFCPMELRGPEPLGSRPRQPNLIPWAAAGRRAAPYLVLTALLIFTGAFLLGYVA*
*FRGS* ACPWAVSGARASPGSAASPRLRGPELSPDDPAGLLDLRQGMFAQLVAQNVLLIDGPLSWYSDPGLAGVSLTGGLSYKEDTKELVVAKAGVYYVFFQLEL
RRVVAGEGSGSVSLALHLQPLRSAAGAAALALTVDLPPASSEARNSAFGFQGRLLHLSAGQRLGVHLHTEARARHAWQLTQGATVLGLFRVTPEIPAGLPSPR
SE

*FIG. 5P*

*CD9tm3*-h41BBL

*ATGGGCTGCTGCGGGGCTGTGCAGGAGTCCCAGTGCATGCTGGGACTGTTCTTCGGCTTCCTCTTGGTGATATTCGCCATTGAAATAGCT*
*GCGGCCATCTGGGGATATTCCCACAAGGATGAG*GCCTGCCCCTGGGCCGTGTCCGGGGCTCGCGCCTCGCCCGGCTCCGCGGCCAGCCCG
AGACTCCGCGAGGGTCCCGAGCTTTCGCCCGACGATCCCGCCGGCCTCTTGGACCTGCGGCAGGGCATGTTTGCGCAGCTGGTGGCCCAA
AATGTTCTGCTGATCGATGGGCCCCTGAGCTGGTACAGTGACCCAGGCCTGGCAGGCGTGTCCCTGACGGGGGGCCTGAGCTACAAAGAG
GACACGAAGGAGCTGGTGGTGGCCAAGGCTGGAGTCTACTATGTCTTCTTTCAACTAGAGCTGCGGCGCGTGGTGGCCGGCGAGGGCTCA
GGCTCCGTTTCACTTGCGCTGCACCTGCAGCCACTGCGCTCTGCTGCTGGGGCCGCCGCCCTGGCTTTGACCGTGGACCTGCCACCCGCC
TCCTCCGAGGCTCGGAACTCGGCCTTCGGTTTCCAGGGCCGCTTGCTGCACCTGAGTGCCGGCCAGCGCCTGGGCGTCCATCTTCACACT
GAGGCCAGGGCACGCCATGCCTGGCAGCTTACCCAGGGCGCCACAGTCTTGGGACTCTTCCGGGTGACCCCCGAAATCCCAGCCGGACTC
CCTTCACCGAGGTCGGAATAA

*MGCCGAVQESQCMLGLFFGFLLVIFAIEIAAAIWGYSHKDE*ACPWAVSGARASPGSAASPRLREGPELSPDDPAGLLDLRQGMFAQLVAQ
NVLLIDGPLSWYSDPGLAGVSLTGGLSYKEDTKELVVAKAGVYYVFFQLELRRVVAGEGSGSVSLALHLQPLRSAAGAAALALTVDLPPA
SSEARNSAFGFQGRLLHLSAGQRLGVHLHTEARARHAWQLTQGATVLGLFRVTPEIPAGLPSPRSE

*FIG. 5Q*

*Myr/Palm-4F2*-h41BBL

*ATGGGTTGCTGTTTCTCCAAGACC*GGCTCGAGCGGC*AGCCAGGACACCGAGGTGGATATGAAGGAGGTGGAGCTGAATGAGTTAGAGCCCGAGAAGCAGCCGA*
*TGAACGCGGCGTCTGGGGCGGCCATGTCCCTGGCGGGAGCCGAGAAGAATGGTCTGGTGAAGATCAAGGTGGCGGAAGACGAGGCGGAGGCGGCAGCCGCGGC*
*TAAGTTCACGGGCCTGTCCAAGGAGGAGCTGCTGAAGGTGGCAGGCAGCCCCGGCTGGGTACGCACCCGCTGGGCACTGCTGCTGCTCTTCTGGCTCGGCTGG*
*CTCGGCATGCTTGCTGGTGCCGTGGTCATAATCGTG*GCCTGCCCCTGGGCCGTGTCCGGGGCTCGCGCCTCGCCCGGCTCCGCGGCCAGCCCGAGACTCCGCG
AGGGTCCCGAGCTTTCGCCCGACGATCCCGCCGGCCTCTTGGACCTGCGGCAGGGCATGTTTGCGCAGCTGGTGGCCCAAAATGTTCTGCTGATCGATGGGCC
CCTGAGCTGGTACAGTGACCCAGGCCTGGCAGGCGTGTCCCTGACGGGGGGCCTGAGCTACAAAGAGGACACGAAGGAGCTGGTGGTGGCCAAGGCTGGAGTC
TACTATGTCTTCTTTCAACTAGAGCTGCGGCGCGTGGTGGCCGGCGAGGGCTCAGGCTCCGTTTCACTTGCGCTGCACCTGCAGCCACTGCGCTCTGCTGCTG
GGGCCGCCGCCCTGGCTTTGACCGTGGACCTGCCACCCGCCTCCTCCGAGGCTCGGAACTCGGCCTTCGGTTTCCAGGGCCGCTTGCTGCACCTGAGTGCCGG
CCAGCGCCTGGGCGTCCATCTTCACACTGAGGCCAGGGCACGCCATGCCTGGCAGCTTACCCAGGGCGCCACAGTCTTGGGACTCTTCCGGGTGACCCCCGAA
ATCCCAGCCGGACTCCCTTCACCGAGGTCGGAATAA

*MGCCFSKT*GSSG*SQDTEVDMKEVELNELEPEKQPMNAASGAAMSLAGAEKNGLVKIKVAEDEAEAAAAAKFTGLSKEELLKVAGSPGWVRTRWALLLLFWLGW*
*LGMLAGAVVIIV*ACPWAVSGARASPGSAASPRLREGPELSPDDPAGLLDLRQGMFAQLVAQNVLLIDGPLSWYSDPGLAGVSLTGGLSYKEDTKELVVAKAGV
YYVFFQLELRRVVAGEGSGSVSLALHLQPLRSAAGAAALALTVDLPPASSEARNSAFGFQGRLLHLSAGQRLGVHLHTEARARHAWQLTQGATVLGLFRVTPE
IPAGLPSPRSE

*FIG. 5R*

*Myr/Palm*-Link-41BBL

*ATGGGTTGCTGTTTCTCCAAGACC*GGCTCGAGCGGCTGGGCCCTGGTCGCGGGGCTGCTGCTGCTGCTGCTGCTCGCTGCCGCCTGCGCCGTCTTCCTCGCC
TGCCCCTGGGCCGTGTCCGGGGCTCGCGCCTCGCCCGGCTCCGCGGCCAGCCCGAGACTCCGCGAGGGTCCCGAGCTTTCGCCCGACGATCCCGCCGGCCTC
TTGGACCTGCGGCAGGGCATGTTTGCGCAGCTGGTGGCCCAAAATGTTCTGCTGATCGATGGGCCCCTGAGCTGGTACAGTGACCCAGGCCTGGCAGGCGTG
TCCCTGACGGGGGGCCTGAGCTACAAAGAGGACACGAAGGAGCTGGTGGTGGCCAAGGCTGGAGTCTACTATGTCTTCTTTCAACTAGAGCTGCGGCGCGTG
GTGGCCGGCGAGGGCTCAGGCTCCGTTTCACTTGCGCTGCACCTGCAGCCACTGCGCTCTGCTGCTGGGGCCGCCGCCCTGGCTTTGACCGTGGACCTGCCA
CCCGCCTCCTCCGAGGCTCGGAACTCGGCCTTCGGTTTCCAGGGCCGCTTGCTGCACCTGAGTGCCGGCCAGCGCCTGGGCGTCCATCTTCACACTGAGGCC
AGGGCACGCCATGCCTGGCAGCTTACCCAGGGCGCCACAGTCTTGGGACTCTTCCGGGTGACCCCCGAAATCCCAGCCGGACTCCCTTCACCGAGGTCGGAA
TAA

*MGCCFSKT*GSSG*WALVAGLLLLLLLAAACAVFLACPWAVSGARASPGSAASPRLREGPELSPDDPAGLLDLRQGMFAQLVAQNVLLIDGPLSWYSDPGLAGV*
*SLTGGLSYKEDTKELVVAKAGVYYVFFQLELRRVVAGEGSGSVSLALHLQPLRSAAGAAALALTVDLPPASSEARNSAFGFQGRLLHLSAGQRLGVHLHTEA*
*RARHAWQLTQGATVLGLFRVTPEIPAGLPSPRSE*

*FIG. 5S* hPDL1-Link-*GPI*

ATGAGGATATTTGCTGTCTTTATATTCATGACCTACTGGCATTTGCTGAACGCATTTACTGTCACGGTTCCCAAGGACCTATATGTGGTAGA
GTATGGTAGCAATATGACAATTGAATGCAAATTCCCAGTAGAAAAACAATTAGACCTGGCTGCACTAATTGTCTATTGGGAAATGGAGGATA
AGAACATTATTCAATTTGTGCATGGAGAGGAAGACCTGAAGGTTCAGCATAGTAGCTACAGACAGAGGGCCCGGCTGTTGAAGGACCAGCTC
TCCCTGGGAAATGCTGCACTTCAGATCACAGATGTGAAATTGCAGGATGCAGGGGTGTACCGCTGCATGATCAGCTATGGTGGTGCCGACTA
CAAGCGAATTACTGTGAAAGTCAATGCCCCATACAACAAAATCAACCAAAGAATTTTGGTTGTGGATCCAGTCACCTCTGAACATGAACTGA
CATGTCAGGCTGAGGGCTACCCCAAGGCCGAAGTCATCTGGACAAGCAGTGACCATCAAGTCCTGAGTGGTAAGACCACCACCACCAATTCC
AAGAGAGAGGAGAAGCTTTTCAATGTGACCAGCACACTGAGAATCAACACAACAACTAATGAGATTTTCTACTGCACTTTTAGGAGATTAGA
TCCTGAGGAAAACCATACAGCTGAATTGGGCTCGAGCGGC*CCAAATAAAGGAAGTGGAACCACTTCAGGTACTACCCGTCTTCTATCTGGGC*
*ACACGTGTTTCACGTTGACAGGTTTGCTTGGGACGCTAGTAACCATGGGCTTGCTGACTTAG*

MRIFAVFIFMTYWHLLNAFTVTVPKDLYVVEYGSNMTIECKFPVEKQLDLAALIVYWEMEDKNIIQFVHGEEDLKVQHSSYRQRARLLKDQL
SLGNAALQITDVKLQDAGVYRCMISYGGADYKRITVKVNAPYNKINQRILVVDPVTSEHELTCQAEGYPKAEVIWTSSDHQVLSGKTTTTNS
KREEKLFNVTSTLRINTTTNEIFYCTFRRLDPEENHTAELGSSG*PNKGSGTTSGTTRLLSGHTCFTLTGLLGTLVTMGLLT*

*FIG. 5T* hSecPDL1-*CD9tm2*

ATGAGGATATTTGCTGTCTTTATATTCATGACCTACTGGCATTTGCTGAACGCATTTACTGTCACGGTTCCCAAGGACCTATATGTGGTAGAGTATGGTA
GCAATATGACAATTGAATGCAAATTCCCAGTAGAAAAACAATTAGACCTGGCTGCACTAATTGTCTATTGGGAAATGGAGGATAAGAACATTATTCAATT
TGTGCATGGAGAGGAAGACCTGAAGGTTCAGCATAGTAGCTACAGACAGAGGGCCCGGCTGTTGAAGGACCAGCTCTCCCTGGGAAATGCTGCACTTCAG
ATCACAGATGTGAAATTGCAGGATGCAGGGGTGTACCGCTGCATGATCAGCTATGGTGGTGCCGACTACAAGCGAATTACTGTGAAAGTCAATGCCCCAT
ACAACAAAATCAACCAAAGAATTTTGGTTGTGGATCCAGTCACCTCTGAACATGAACTGACATGTCAGGCTGAGGGCTACCCCAAGGCCGAAGTCATCTG
GACAAGCAGTGACCATCAAGTCCTGAGTGGTAAGACCACCACCACCAATTCCAAGAGAGAGGAGAAGCTTTTCAATGTGACCAGCACACTGAGAATCAAC
ACAACAACTAATGAGATTTTCTACTGCACTTTTAGGAGATTAGATCCTGAGGAAAACCATACAGCTGAATTGGTCATCCCAGGTAATATTCTGAATGTGT
CCATTAAAATATGTCTAACACTGTCCCCTAGCACC*TTCTACACAGGAGTCTATATTCTGATCGGAGCCGGCGCCCTCATGATGCTGGTGGGCTTCCTGGG*
*CTGCTGCGGGGCTGTGCAGGAGTCCCAGTGCTAG*

MRIFAVFIFMTYWHLLNAFTVTVPKDLYVVEYGSNMTIECKFPVEKQLDLAALIVYWEMEDKNIIQFVHGEEDLKVQHSSYRQRARLLKDQLSLGNAALQ
ITDVKLQDAGVYRCMISYGGADYKRITVKVNAPYNKINQRILVVDPVTSEHELTCQAEGYPKAEVIWTSSDHQVLSGKTTTTNSKREEKLFNVTSTLRIN
TTTNEIFYCTFRRLDPEENHTAELVIPGNILNVSIKICLTLSPST*FYTGVYILIGAGALMMLVGFLGCCGAVQESQC*

*FIG. 5U* hSecPDL1-*CD9tm2*-*KRAS*

ATGAGGATATTTGCTGTCTTTATATTCATGACCTACTGGCATTTGCTGAACGCATTTACTGTCACGGTTCCCAAGGACCTATATGTGGTAGAGTATGGTAGC
AATATGACAATTGAATGCAAATTCCCAGTAGAAAAACAATTAGACCTGGCTGCACTAATTGTCTATTGGGAAATGGAGGATAAGAACATTATTCAATTTGTG
CATGGAGAGGAAGACCTGAAGGTTCAGCATAGTAGCTACAGACAGAGGGCCCGGCTGTTGAAGGACCAGCTCTCCCTGGGAAATGCTGCACTTCAGATCACA
GATGTGAAATTGCAGGATGCAGGGGTGTACCGCTGCATGATCAGCTATGGTGGTGCCGACTACAAGCGAATTACTGTGAAAGTCAATGCCCCATACAACAAA
ATCAACCAAAGAATTTTGGTTGTGGATCCAGTCACCTCTGAACATGAACTGACATGTCAGGCTGAGGGCTACCCCAAGGCCGAAGTCATCTGGACAAGCAGT
GACCATCAAGTCCTGAGTGGTAAGACCACCACCACCAATTCCAAGAGAGAGGAGAAGCTTTTCAATGTGACCAGCACACTGAGAATCAACACAACAACTAAT
GAGATTTTCTACTGCACTTTTAGGAGATTAGATCCTGAGGAAAACCATACAGCTGAATTGGTCATCCCAGGTAATATTCTGAATGTGTCCATTAAAATATGT
CTAACACTGTCCCCTAGCACC*TTCTACACAGGAGTCTATATTCTGATCGGAGCCGGCGCCCTCATGATGCTGGTGGGCTTCCTGGGCTGCTGCGGGGCTGTG*
*CAGGAGTCCCAGTGCAAAAAGAAGAAAAAGAAGTCAAAGACAAAGTGTGTAATTATGTAA*

MRIFAVFIFMTYWHLLNAFTVTVPKDLYVVEYGSNMTIECKFPVEKQLDLAALIVYWEMEDKNIIQFVHGEEDLKVQHSSYRQRARLLKDQLSLGNAALQIT
DVKLQDAGVYRCMISYGGADYKRITVKVNAPYNKINQRILVVDPVTSEHELTCQAEGYPKAEVIWTSSDHQVLSGKTTTTNSKREEKLFNVTSTLRINTTTN
EIFYCTFRRLDPEENHTAELVIPGNILNVSIKICLTLSPST*FYTGVYILIGAGALMMLVGFLGCCGAVQESQCKKKKKKSKTKCVIM*

*FIG. 5V* hSecPDL1-*CD9tm4*

ATGAGGATATTTGCTGTCTTTATATTCATGACCTACTGGCATTTGCTGAACGCATTTACTGTCACGGTTCCCAAGGACCTATATGTGGTAGAGTATGGTAG
CAATATGACAATTGAATGCAAATTCCCAGTAGAAAAACAATTAGACCTGGCTGCACTAATTGTCTATTGGGAAATGGAGGATAAGAACATTATTCAATTTG
TGCATGGAGAGGAAGACCTGAAGGTTCAGCATAGTAGCTACAGACAGAGGGCCCGGCTGTTGAAGGACCAGCTCTCCCTGGGAAATGCTGCACTTCAGATC
ACAGATGTGAAATTGCAGGATGCAGGGGTGTACCGCTGCATGATCAGCTATGGTGGTGCCGACTACAAGCGAATTACTGTGAAAGTCAATGCCCCATACAA
CAAAATCAACCAAAGAATTTTGGTTGTGGATCCAGTCACCTCTGAACATGAACTGACATGTCAGGCTGAGGGCTACCCCAAGGCCGAAGTCATCTGGACAA
GCAGTGACCATCAAGTCCTGAGTGGTAAGACCACCACCACCAATTCCAAGAGAGAGGAGAAGCTTTTCAATGTGACCAGCACACTGAGAATCAACACAACA
ACTAATGAGATTTTCTACTGCACTTTTAGGAGATTAGATCCTGAGGAAAACCATACAGCTGAATTGGTCATCCCAGGTAATATTCTGAATGTGTCCATTAA
AATATGTCTAACACTGTCCCCTAGCACC*ATCGGCGCAGTGGGCATCGGCATTGCCGTGGTCATGATATTTGGCATGATCTTCAGTATGATCTTGTGCTGTG*
*CTATCCGCAGGAACCGCGAGATGGTCTAG*

MRIFAVFIFMTYWHLLNAFTVTVPKDLYVVEYGSNMTIECKFPVEKQLDLAALIVYWEMEDKNIIQFVHGEEDLKVQHSSYRQRARLLKDQLSLGNAALQI
TDVKLQDAGVYRCMISYGGADYKRITVKVNAPYNKINQRILVVDPVTSEHELTCQAEGYPKAEVIWTSSDHQVLSGKTTTTNSKREEKLFNVTSTLRINTT
TNEIFYCTFRRLDPEENHTAELVIPGNILNVSIKICLTLSPST*IGAVGIGIAVVMIFGMIFSMILCCAIRRNREMV*

*FIG. 5W* hSecPDL1-*CD81*

ATGAGGATATTTGCTGTCTTTATATTCATGACCTACTGGCATTTGCTGAACGCATTTACTGTCACGGTTCCCAAGGACCTATATGTGGTAGAGTATGGTAGCAATAT
GACAATTGAATGCAAATTCCCAGTAGAAAAACAATTAGACCTGGCTGCACTAATTGTCTATTGGGAAATGGAGGATAAGAACATTATTCAATTTGTGCATGGAGAGG
AAGACCTGAAGGTTCAGCATAGTAGCTACAGACAGAGGGCCCGGCTGTTGAAGGACCAGCTCTCCCTGGGAAATGCTGCACTTCAGATCACAGATGTGAAATTGCAG
GATGCAGGGGTGTACCGCTGCATGATCAGCTATGGTGGTGCCGACTACAAGCGAATTACTGTGAAAGTCAATGCCCCATACAACAAAATCAACCAAAGAATTTTGGT
TGTGGATCCAGTCACCTCTGAACATGAACTGACATGTCAGGCTGAGGGCTACCCCAAGGCCGAAGTCATCTGGACAAGCAGTGACCATCAAGTCCTGAGTGGTAAGA
CCACCACCACCAATTCCAAGAGAGAGGAGAAGCTTTTCAATGTGACCAGCACACTGAGAATCAACACAACAACTAATGAGATTTTCTACTGCACTTTTAGGAGATTA
GATCCTGAGGAAAACCATACAGCTGAATTGGTCATCCCAGGTAATATTCTGAATGTGTCCATTAAAATATGTCTAACACTGTCCCCTAGCACC*CTGTACCTCATCGG*
*CATTGCTGCCATCGTGGTCGCTGTGATCATGATCTTCGAGATGATCCTGAGCATGGTGCTGTGCTGTGGCATCCGGAACAGCTCCGTGTACTGA*

MRIFAVFIFMTYWHLLNAFTVTVPKDLYVVEYGSNMTIECKFPVEKQLDLAALIVYWEMEDKNIIQFVHGEEDLKVQHSSYRQRARLLKDQLSLGNAALQITDVKLQ
DAGVYRCMISYGGADYKRITVKVNAPYNKINQRILVVDPVTSEHELTCQAEGYPKAEVIWTSSDHQVLSGKTTTTNSKREEKLFNVTSTLRINTTTNEIFYCTFRRL
DPEENHTAELVIPGNILNVSIKICLTLSPST*LYLIGIAAIVVAVIMIFEMILSMVLCCGIRNSSVY*

*FIG. 5X* hCD200-Fc-GPI

ATGGAGAGGCTGGTGATCAGGATGCCCTTCTCTCATCTGTCTACCTACAGCCTGGTTTGGGTCATGGCAGCAGTGGTGCTGTGCACAGCACAAGTGCAAGTGGTGAC
CCAGGATGAAAGAGAGCAGCTGTACACACCTGCTTCCTTAAAATGCTCTCTGCAAAATGCCCAGGAAGCCCTCATTGTGACATGGCAGAAAAAGAAAGCTGTAAGCC
CAGAAAACATGGTCACCTTCAGCGAGAACCATGGGGTGGTGATCCAGCCTGCCTATAAGGACAAGATAAACATTACCCAGCTGGGACTCCAAAACTCAACCATCACC
TTCTGGAATATCACCCTGGAGGATGAAGGGTGTTACATGTGTCTCTTCAATACCTTTGGTTTTGGGAAGATCTCAGGAACGGCCTGCCTCACCGTCTATGTACAGCC
CATAGTATCCCTTCACTACAAATTCTCTGAAGACCACCTAAATATCACTTGCTCTGCCACTGCCCGCCCAGCCCCCATGGTCTTCTGGAAGGTCCCTCGGTCAGGGA
TTGAAAATAGTACAGTGACTCTGTCTCACCCAAATGGGACCACGTCTGTTACCAGCATCCTCCATATCAAAGACCCTAAGAATCAGGTGGGGAAGGAGGTGATCTGC
CAGGTGCTGCACCTGGGGACTGTGACCGACTTTAAGCAAACCGTCAACAAAGGCATCGATGACAAAACTCACACATGCCCACCGTGCCCAGCACCTGAACTCCTGGG
GGGACCGTCAGTCTTCCTCTTCCCCCCAAAACCCAAGGACACCCTCATGATCTCCCGGACCCCTGAGGTCACATGCGTGGTGGTGGACGTGAGCCACGAAGACCCTG
AGGTCAAGTTCAACTGGTACGTGGACGGCGTGGAGGTGCATAATGCCAAGACAAAGCCGCGGGAGGAGCAGTACAACAGCACGTACCGTGTGGTCAGCGTCCTCACC
GTCCTGCACCAGGACTGGCTGAATGGCAAGGAGTACAAGTGCAAGGTCTCCAACAAAGCCCTCCCAGCCCCCATCGAGAAAACCATCTCCAAAGCCAAAGGGCAGCC
CCGAGAACCACAGGTGTACACCCTGCCCCCATCCCGGGAGGAGATGACCAAGAACCAGGTCAGCCTGACCTGCCTGGTCAAAGGCTTCTATCCCAGCGACATCGCCG
TGGAGTGGGAGAGCAATGGGCAGCCGGAGAACAACTACAAGACCACGCCTCCCGTGCTGGACTCCGACGGCTCCTTCTTCCTCTACAGCAAGCTCACCGTGGACAAG
AGCAGGTGGCAGCAGGGGAACGTCTTCTCATGCTCCGTGATGCACGAGGCTCTGCACAACCACTACACGCAGAAGAGCCTCTCCCTGTCTCCGGGTAAAATCGATCC
AAATAAAGGAAGTGGAACCACTTCAGGTACTACCCGTCTTCTATCTGGGCACACGTGTTTCACGTTGACAGGTTTGCTTGGGACGCTAGTAACCATGGGCTTGCTGA
CTTAG

MERLVIRMPFSHLSTYSLVWVMAAVVLCTAQVQVVTQDEREQLYTPASLKCSLQNAQEALIVTWQKKKAVSPENMVTFSENHGVVIQPAYKDKINITQLGLQNSTIT
FWNITLEDEGCYMCLFNTFGFGKISGTACLTVYVQPIVSLHYKFSEDHLNITCSATARPAPMVFWKVPRSGIENSTVTLSHPNGTTSVTSILHIKDPKNQVGKEVIC
QVLHLGTVTDFKQTVNKGIDDKTHTCPPCPAPELLGGPSVFLFPPKPKDTLMISRTPEVTCVVVDVSHEDPEVKFNWYVDGVEVHNAKTKPREEQYNSTYRVVSVLT
VLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDK
SRWQQGNVFSCSVMHEALHNHYTQKSLSLSPGKIDPNKGSGTTSGTTRLLSGHTCFTLTGLLGTLVTMGLLT

FIG. 5Y hFGL1-*GPI*

ATGGCAAAGGTGTTCAGTTTCATCCTTGTTACCACCGCTCTGACAATGGGCAGGGAAATTTCGGCGCTCGAGGACTGTGCCCAGGAGCAGATGCGGCTCA
GAGCCCAGGTGCGCCTGCTTGAGACCCGGGTCAAACAGCAACAGGTCAAGATCAAGCAGCTTTTGCAGGAGAATGAAGTCCAGTTCCTTGATAAAGGAGA
TGAGAATACTGTCATTGATCTTGGAAGCAAGAGGCAGTATGCAGATTGTTCAGAGATTTTCAATGATGGGTATAAGCTCAGTGGATTTTACAAAATCAAA
CCTCTCCAGAGCCCAGCAGAATTTTCTGTTTATTGTGACATGTCCGATGGAGGAGGATGGACTGTAATTCAGAGACGATCTGATGGCAGTGAAAACTTTA
ACAGAGGATGGAAAGACTATGAAAATGGCTTTGGAAATTTTGTCCAAAAACATGGTGAATATTGGCTGGGCAATAAAAATCTTCACTTCTTGACCACTCA
AGAAGACTACACTTTAAAAATCGACCTTGCAGATTTTGAAAAAAATAGCCGTTATGCACAATATAAGAATTTCAAAGTTGGAGATGAAAAGAATTTCTAC
GAGTTGAATATTGGGGAATATTCTGGAACAGCTGGAGATTCCCTTGCGGGGAATTTTCATCCTGAGGTGCAGTGGTGGCTAGTCACCAAAGAATGAAAT
TCAGCACGTGGGACAGAGATCATGACAACTATGAAGGGAACTGCGCAGAAGAAGATCAGTCTGGCTGGTGGTTTAACAGGTGTCACTCTGCAAACCTGAA
TGGTGTATACTACAGCGGCCCCTACACGGCTAAAACAGACAATGGGATTGTCTGGTACACCTGGCATGGGTGGTGGTATTCTCTGAAATCTGTGGTTATG
AAAATTAGGCCAAATGATTTTATTCCAAATGTAATT*CCAAATAAAGGAAGTGGAACCACTTCAGGTACTACCCGTCTTCTATCTGGGCACACGTGTTTCA*
*CGTTGACAGGTTTGCTTGGGACGCTAGTAACCATGGGCTTGCTGACTTAG*

MAKVFSFILVTTALTMGREISALEDCAQEQMRLRAQVRLLETRVKQQQVKIKQLLQENEVQFLDKGDENTVIDLGSKRQYADCSEIFNDGYKLSGFYKIK
PLQSPAEFSVYCDMSDGGGWTVIQRRSDGSENFNRGWKDYENGFGNFVQKHGEYWLGNKNLHFLTTQEDYTLKIDLADFEKNSRYAQYKNFKVGDEKNFY
ELNIGEYSGTAGDSLAGNFHPEVQWWASHQRMKFSTWDRDHDNYEGNCAEEDQSGWWFNRCHSANLNGVYYSGPYTAKTDNGIVWYTWHGWWYSLKSVVM
KIRPNDFIPNVI*PNKGSGTTSGTTRLLSGHTCFTLTGLLGTLVTMGLLT*

*FIG. 5Z* hGal9-Fc-GPI

ATGGCCTTCAGCGGTTCCCAGGCTCCCTACCTGAGTCCAGCTGTCCCCTTTTCTGGGACTATTCAAGGAGGTCTCCAGGACGGACTTCAGATCACTGTCAATGGGACC
GTTCTCAGCTCCAGTGGAACCAGGTTTGCTGTGAACTTTCAGACTGGCTTCAGTGGAAATGACATTGCCTTCCACTTCAACCCTCGGTTTGAAGATGGAGGGTACGTG
GTGTGCAACACGAGGCAGAACGGAAGCTGGGGGCCCGAGGAGAGGAAGACACACATGCCTTTCCAGAAGGGGATGCCCTTTGACCTCTGCTTCCTGGTGCAGAGCTCA
GATTTCAAGGTGATGGTGAACGGGATCCTCTTCGTGCAGTACTTCCACCGCGTGCCCTTCCACCGTGTGGACACCATCTCCGTCAATGGCTCTGTGCAGCTGTCCTAC
ATCAGCTTCCAGAACCCCCGCACAGTCCCTGTTCAGCCTGCCTTCTCCACGGTGCCGTTCTCCCAGCCTGTCTGTTTCCCACCCAGGCCCAGGGGGCGCAGACAAAAA
CCTCCCGGCGTGTGGCCTGCCAACCCGGCTCCCATTACCCAGACAGTCATCCACACAGTGCAGAGCGCCCCTGGACAGATGTTCTCTACTCCCGCCATCCCACCTATG
ATGTACCCCCACCCCGCCTATCCGATGCCTTTCATCACCACCATTCTGGGAGGGCTGTACCCATCCAAGTCCATCCTCCTGTCAGGCACTGTCCTGCCCAGTGCTCAG
AGGTTCCACATCAACCTGTGCTCTGGGAACCACATCGCCTTCCACCTGAACCCCCGTTTTGATGAGAATGCTGTGGTCCGCAACACCCAGATCGACAACTCCTGGGGG
TCTGAGGAGCGAAGTCTGCCCCGAAAAATGCCCTTCGTCCGTGGCCAGAGCTTCTCAGTGTGGATCTTGTGTGAAGCTCACTGCCTCAAGGTGGCCGTGGATGGTCAG
CACCTGTTTGAATACTACCATCGCCTGAGGAACCTGCCCACCATCAACAGACTGGAAGTGGGGGGCGACATCCAGCTGACCCATGTGCAGACAATCGATGACAAAACT
CACACATGCCCACCGTGCCCAGCACCTGAACTCCTGGGGGGACCGTCAGTCTTCCTCTTCCCCCCAAAACCCAAGGACACCCTCATGATCTCCCGGACCCCTGAGGTC
ACATGCGTGGTGGTGGACGTGAGCCACGAAGACCCTGAGGTCAAGTTCAACTGGTACGTGGACGGCGTGGAGGTGCATAATGCCAAGACAAAGCCGCGGGAGGAGCAG
TACAACAGCACGTACCGTGTGGTCAGCGTCCTCACCGTCCTGCACCAGGACTGGCTGAATGGCAAGGAGTACAAGTGCAAGGTCTCCAACAAAGCCCTCCCAGCCCCC
ATCGAGAAAACCATCTCCAAAGCCAAAGGGCAGCCCCGAGAACCACAGGTGTACACCCTGCCCCCATCCCGGGAGGAGATGACCAAGAACCAGGTCAGCCTGACCTGC
CTGGTCAAAGGCTTCTATCCCAGCGACATCGCCGTGGAGTGGGAGAGCAATGGGCAGCCGGAGAACAACTACAAGACCACGCCTCCCGTGCTGGACTCCGACGGCTCC
TTCTTCCTCTACAGCAAGCTCACCGTGGACAAGAGCAGGTGGCAGCAGGGGAACGTCTTCTCATGCTCCGTGATGCACGAGGCTCTGCACAACCACTACACGCAGAAG
AGCCTCTCCCTGTCTCCGGGTAAAATCGATCCAAATAAAGGAAGTGGAACCACTTCAGGTACTACCCGTCTTCTATCTGGGCACACGTGTTTCACGTTGACAGGTTTG
CTTGGGACGCTAGTAACCATGGGCTTGCTGACTTAG

MAFSGSQAPYLSPAVPFSGTIQGGLQDGLQITVNGTVLSSSGTRFAVNFQTGFSGNDIAFHFNPRFEDGGYVVCNTRQNGSWGPEERKTHMPFQKGMPFDLCFLVQSS
DFKVMVNGILFVQYFHRVPFHRVDTISVNGSVQLSYISFQNPRTVPVQPAFSTVPFSQPVCFPPRPRGRRQKPPGVWPANPAPITQTVIHTVQSAPGQMFSTPAIPPM
MYPHPAYPMPFITTILGGLYPSKSILLSGTVLPSAQRFHINLCSGNHIAFHLNPRFDENAVVRNTQIDNSWGSEERSLPRKMPFVRGQSFSVWILCEAHCLKVAVDGQ
HLFEYYHRLRNLPTINRLEVGGDIQLTHVQTIDDKTHTCPPCPAPELLGGPSVFLFPPKPKDTLMISRTPEVTCVVVDVSHEDPEVKFNWYVDGVEVHNAKTKPREEQ
YNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGS
FFLYSKLTVDKSRWQQGNVFSCSVMHEALHNHYTQKSLSLSPGKIDPNKGSGTTSGTTRLLSGHTCFTLTGLLGTLVTMGLLT

FIG. 5AA hCD200-*GPI*

ATGGAGAGGCTGGTGATCAGGATGCCCTTCTCTCATCTGTCTACCTACAGCCTGGTTTGGGTCATGGCAGCAGTGGTGCTGTGCACAGCACAAGTGCAAGT
GGTGACCCAGGATGAAAGAGAGCAGCTGTACACACCTGCTTCCTTAAAATGCTCTCTGCAAAATGCCCAGGAAGCCCTCATTGTGACATGGCAGAAAAAGA
AAGCTGTAAGCCCAGAAAACATGGTCACCTTCAGCGAGAACCATGGGGTGGTGATCCAGCCTGCCTATAAGGACAAGATAAACATTACCCAGCTGGGACTC
CAAAACTCAACCATCACCTTCTGGAATATCACCCTGGAGGATGAAGGGTGTTACATGTGTCTCTTCAATACCTTTGGTTTTGGGAAGATCTCAGGAACGGC
CTGCCTCACCGTCTATGTACAGCCCATAGTATCCCTTCACTACAAATTCTCTGAAGACCACCTAAATATCACTTGCTCTGCCACTGCCCGCCCAGCCCCCA
TGGTCTTCTGGAAGGTCCCTCGGTCAGGGATTGAAAATAGTACAGTGACTCTGTCTCACCCAAATGGGACCACGTCTGTTACCAGCATCCTCCATATCAAA
GACCCTAAGAATCAGGTGGGGAAGGAGGTGATCTGCCAGGTGCTGCACCTGGGGACTGTGACCGACTTTAAGCAAACCGTCAACAAAGGC*CCAAATAAAGG*
*AAGTGGAACCACTTCAGGTACTACCCGTCTTCTATCTGGGCACACGTGTTTCACGTTGACAGGTTTGCTTGGGACGCTAGTAACCATGGGCTTGCTGACTT*
*AG*

MERLVIRMPFSHLSTYSLVWVMAAVVLCTAQVQVVTQDEREQLYTPASLKCSLQNAQEALIVTWQKKKAVSPENMVTFSENHGVVIQPAYKDKINITQLGL
QNSTITFWNITLEDEGCYMCLFNTFGFGKISGTACLTVYVQPIVSLHYKFSEDHLNITCSATARPAPMVFWKVPRSGIENSTVTLSHPNGTTSVTSILHIK
DPKNQVGKEVICQVLHLGTVTDFKQTVNKG*PNKGSGTTSGTTRLLSGHTCFTLTGLLGTLVTMGLLT*

*FIG. 5BB* hGal9-*GPI*

ATGGCCTTCAGCGGTTCCCAGGCTCCCTACCTGAGTCCAGCTGTCCCCTTTTCTGGGACTATTCAAGGAGGTCTCCAGGACGGACTTCAGATCACTGTCAATGGGACC
GTTCTCAGCTCCAGTGGAACCAGGTTTGCTGTGAACTTTCAGACTGGCTTCAGTGGAAATGACATTGCCTTCCACTTCAACCCTCGGTTTGAAGATGGAGGGTACGTG
GTGTGCAACACGAGGCAGAACGGAAGCTGGGGGCCCGAGGAGAGGAAGACACACATGCCTTTCCAGAAGGGGATGCCCTTTGACCTCTGCTTCCTGGTGCAGAGCTCA
GATTTCAAGGTGATGGTGAACGGGATCCTCTTCGTGCAGTACTTCCACCGCGTGCCCTTCCACCGTGTGGACACCATCTCCGTCAATGGCTCTGTGCAGCTGTCCTAC
ATCAGCTTCCAGAACCCCCGCACAGTCCCTGTTCAGCCTGCCTTCTCCACGGTGCCGTTCTCCCAGCCTGTCTGTTTCCCACCCAGGCCCAGGGGGCGCAGACAAAAA
CCTCCCGGCGTGTGGCCTGCCAACCCGGCTCCCATTACCCAGACAGTCATCCACACAGTGCAGAGCGCCCCTGGACAGATGTTCTCTACTCCCGCCATCCCACCTATG
ATGTACCCCCACCCCGCCTATCCGATGCCTTTCATCACCACCATTCTGGGAGGGCTGTACCCATCCAAGTCCATCCTCCTGTCAGGCACTGTCCTGCCCAGTGCTCAG
AGGTTCCACATCAACCTGTGCTCTGGGAACCACATCGCCTTCCACCTGAACCCCCGTTTTGATGAGAATGCTGTGGTCCGCAACACCCAGATCGACAACTCCTGGGGG
TCTGAGGAGCGAAGTCTGCCCCGAAAAATGCCCTTCGTCCGTGGCCAGAGCTTCTCAGTGTGGATCTTGTGTGAAGCTCACTGCCTCAAGGTGGCCGTGGATGGTCAG
CACCTGTTTGAATACTACCATCGCCTGAGGAACCTGCCCACCATCAACAGACTGGAAGTGGGGGGCGACATCCAGCTGACCCATGTGCAGACA*CCAAATAAAGGAAGT*
*GGAACCACTTCAGGTACTACCCGTCTTCTATCTGGGCACACGTGTTTCACGTTGACAGGTTTGCTTGGGACGCTAGTAACCATGGGCTTGCTGACTTAG*

MAFSGSQAPYLSPAVPFSGTIQGGLQDGLQITVNGTVLSSSGTRFAVNFQTGFSGNDIAFHFNPRFEDGGYVVCNTRQNGSWGPEERKTHMPFQKGMPFDLCFLVQSS
DFKVMVNGILFVQYFHRVPFHRVDTISVNGSVQLSYISFQNPRTVPVQPAFSTVPFSQPVCFPPRPRGRRQKPPGVWPANPAPITQTVIHTVQSAPGQMFSTPAIPPM
MYPHPAYPMPFITTILGGLYPSKSILLSGTVLPSAQRFHINLCSGNHIAFHLNPRFDENAVVRNTQIDNSWGSEERSLPRKMPFVRGQSFSVWILCEAHCLKVAVDGQ
HLFEYYHRLRNLPTINRLEVGGDIQLTHVQT*PNKGSGTTSGTTRLLSGHTCFTLTGLLGTLVTMGLLT*

*FIG. 5CC* hHVEM-*GPI*

*ATGGAGCCTCCTGGAGACTGGGGGCCTCCTCCCTGGAGATCCACCCCCAAAACCGACGTCTTGAGGCTGGTGCTGTATCTCACCTTCCTGGG*
*AGCCCCCTGCTACGCCCCAGCTCTGCCGTCCTGCAAGGAGGACGAGTACCCAGTGGGCTCCGAGTGCTGCCCCAAGTGCAGTCCAGGTTATC*
*GTGTGAAGGAGGCCTGCGGGGAGCTGACGGGCACAGTGTGTGAACCCTGCCCTCCAGGCACCTACATTGCCCACCTCAATGGCCTAAGCAAG*
*TGTCTGCAGTGCCAAATGTGTGACCCAGCCATGGGCCTGCGCGCGAGCCGGAACTGCTCCAGGACAGAGAACGCCGTGTGTGGCTGCAGCCC*
*AGGCCACTTCTGCATCGTCCAGGACGGGGACCACTGCGCCGCGTGCCGCGCTTACGCCACCTCCAGCCCGGGCCAGAGGGTGCAGAAGGGAG*
*GCACCGAGAGTCAGGACACCCTGTGTCAGAACTGCCCCCCGGGGACCTTCTCTCCCAATGGGACCCTGGAGGAATGTCAGCACCAGACCAAG*
*TGCAGCTGGCTGGTGACGAAGGCCGGAGCTGGGACCAGCAGCTCCCACTGGGTA*\ *CCAAATAAAGGAAGTGGAACCACTTCAGGTACTACCCG*
*TCTTCTATCTGGGCACACGTGTTTCACGTTGACAGGTTTGCTTGGGACGCTAGTAACCATGGGCTTGCTGACTTAG*

MEPPGDWGPPPWRSTPKTDVLRLVLYLTFLGAPCYAPALPSCKEDEYPVGSECCPKCSPGYRVKEACGELTGTVCEPCPPGTYIAHLNGLSK
CLQCQMCDPAMGLRASRNCSRTENAVCGCSPGHFCIVQDGDHCAACRAYATSSPGQRVQKGGTESQDTLCQNCPPGTFSPNGTLEECQHQTK
CSWLVTKAGAGTSSSHWV*PNKGSGTTSGTTRLLSGHTCFTLTGLLGTLVTMGLLT*

*FIG. 5DD* hPDL2-*GPI*

ATGATCTTCCTCCTGCTAATGTTGAGCCTGGAATTGCAGCTTCACCAGATAGCAGCTTTATTCACAGTGACAGTCCCTAAGGAACTGTACATAA
TAGAGCATGGCAGCAATGTGACCCTGGAATGCAACTTTGACACTGGAAGTCATGTGAACCTTGGAGCAATAACAGCCAGTTTGCAAAAGGTGGA
AAATGATACATCCCCACACCGTGAAAGAGCCACTTTGCTGGAGGAGCAGCTGCCCCTAGGGAAGGCCTCGTTCCACATACCTCAAGTCCAAGTG
AGGGACGAAGGACAGTACCAATGCATAATCATCTATGGGGTCGCCTGGGACTACAAGTACCTGACTCTGAAAGTCAAAGCTTCCTACAGGAAAA
TAAACACTCACATCCTAAAGGTTCCAGAAACAGATGAGGTAGAGCTCACCTGCCAGGCTACAGGTTATCCTCTGGCAGAAGTATCCTGGCCAAA
CGTCAGCGTTCCTGCCAACACCAGCCACTCCAGGACCCCTGAAGGCCTCTACCAGGTCACCAGTGTTCTGCGCCTAAAGCCACCCCCTGGCAGA
AACTTCAGCTGTGTGTTCTGGAATACTCACGTGAGGGAACTTACTTTGGCCAGCATTGACCTTCAAAGTCAGATGGAACCCAGGACCCATCCAA
CT*CCAAATAAAGGAAGTGGAACCACTTCAGGTACTACCCGTCTTCTATCTGGGCACACGTGTTTCACGTTGACAGGTTTGCTTGGGACGCTAGT*
*AACCATGGGCTTGCTGACTTAG*

MIFLLLMLSLELQLHQIAALFTVTVPKELYIIEHGSNVTLECNFDTGSHVNLGAITASLQKVENDTSPHRERATLLEEQLPLGKASFHIPQVQV
RDEGQYQCIIIYGVAWDYKYLTLKVKASYRKINTHILKVPETDEVELTCQATGYPLAEVSWPNVSVPANTSHSRTPEGLYQVTSVLRLKPPPGR
NFSCVFWNTHVRELTLASIDLQSQMEPRTHPT*PNKGSGTTSGTTRLLSGHTCFTLTGLLGTLVTMGLLT*

*FIG. 5EE* hTSG6-*GPI*

ATGATCATCTTAATTTACTTATTTCTCTTGCTATGGGAAGACACTCAAGGATGGGGATTCAAGGATGGAATTTTTCATAACTCCATATGGC
TTGAACGAGCAGCCGGTGTGTACCACAGAGAAGCACGGTCTGGCAAATACAAGCTCACCTACGCAGAAGCTAAGGCGGTGTGTGAATTTGA
AGGCGGCCATCTCGCAACTTACAAGCAGCTAGAGGCAGCCAGAAAAATTGGATTTCATGTCTGTGCTGCTGGATGGATGGCTAAGGGCAGA
GTTGGATACCCCATTGTGAAGCCAGGGCCCAACTGTGGATTTGGAAAAACTGGCATTATTGATTATGGAATCCGTCTCAATAGGAGTGAAA
GATGGGATGCCTATTGCTACAACCCACACGCAAAGGAGTGTGGTGGCGTCTTTACAGATCCAAAGCAAATTTTTAAATCTCCAGGCTTCCC
AAATGAGTACGAAGATAACCAAATCTGCTACTGGCACATTAGACTCAAGTATGGTCAGCGTATTCACCTGAGTTTTTTAGATTTTGACCTT
GAAGATGACCCAGGTTGCTTGGCTGATTATGTTGAAATATATGACAGTTACGATGATGTCCATGGCTTTGTGGGAAGATACTGTGGAGATG
AGCTTCCAGATGACATCATCAGTACAGGAAATGTCATGACCTTGAAGTTTCTAAGTGATGCTTCAGTGACAGCTGGAGGTTTCCAAATCAA
ATATGTTGCAATGGATCCTGTATCCAAATCCAGTCAAGGAAAAAATACAAGTACTACTTCTACTGGAAATAAAAACTTTTTAGCTGGAAGA
TTTAGCCACTTAATCGAT*CCAAATAAAGGAAGTGGAACCACTTCAGGTACTACCCGTCTTCTATCTGGGCACACGTGTTTCACGTTGACAG*
*GTTTGCTTGGGACGCTAGTAACCATGGGCTTGCTGACTTAG*

MIILIYLFLLLWEDTQGWGFKDGIFHNSIWLERAAGVYHREARSGKYKLTYAEAKAVCEFEGGHLATYKQLEAARKIGFHVCAAGWMAKGR
VGYPIVKPGPNCGFGKTGIIDYGIRLNRSERWDAYCYNPHAKECGGVFTDPKQIFKSPGFPNEYEDNQICYWHIRLKYGQRIHLSFLDFDL
EDDPGCLADYVEIYDSYDDVHGFVGRYCGDELPDDIISTGNVMTLKFLSDASVTAGGFQIKYVAMDPVSKSSQGKNTSTTSTGNKNFLAGR
FSHLID*PNKGSGTTSGTTRLLSGHTCFTLTGLLGTLVTMGLLT*

*FIG. 5FF* hHVEM-Fc-*GPI*

ATGGAGCCTCCTGGAGACTGGGGGCCTCCTCCCTGGAGATCCACCCCCAAAACCGACGTCTTGAGGCTGGTGCTGTATCTCACCTTCCTGGGAGCCCCCTGCTACGCC
CCAGCTCTGCCGTCCTGCAAGGAGGACGAGTACCCAGTGGGCTCCGAGTGCTGCCCCAAGTGCAGTCCAGGTTATCGTGTGAAGGAGGCCTGCGGGGAGCTGACGGGC
ACAGTGTGTGAACCCTGCCCTCCAGGCACCTACATTGCCCACCTCAATGGCCTAAGCAAGTGTCTGCAGTGCCAAATGTGTGACCCAGCCATGGGCCTGCGCGCGAGC
CGGAACTGCTCCAGGACAGAGAACGCCGTGTGTGGCTGCAGCCCAGGCCACTTCTGCATCGTCCAGGACGGGGACCACTGCGCCGCGTGCCGCGCTTACGCCACCTCC
AGCCCGGGCCAGAGGGTGCAGAAGGGAGGCACCGAGAGTCAGGACACCCTGTGTCAGAACTGCCCCCCGGGGACCTTCTCTCCCAATGGGACCCTGGAGGAATGTCAG
CACCAGACCAAGTGCAGCTGGCTGGTGACGAAGGCCGGAGCTGGGACCAGCAGCTCCCACTGGGTAATCGATGACAAAACTCACACATGCCCACCGTGCCCAGCACCT
GAACTCCTGGGGGGACCGTCAGTCTTCCTCTTCCCCCCAAAACCCAAGGACACCCTCATGATCTCCCGGACCCCTGAGGTCACATGCGTGGTGGTGGACGTGAGCCAC
GAAGACCCTGAGGTCAAGTTCAACTGGTACGTGGACGGCGTGGAGGTGCATAATGCCAAGACAAAGCCGCGGGAGGAGCAGTACAACAGCACGTACCGTGTGGTCAGC
GTCCTCACCGTCCTGCACCAGGACTGGCTGAATGGCAAGGAGTACAAGTGCAAGGTCTCCAACAAAGCCCTCCCAGCCCCCATCGAGAAAACCATCTCCAAAGCCAAA
GGGCAGCCCCGAGAACCACAGGTGTACACCCTGCCCCCATCCCGGGAGGAGATGACCAAGAACCAGGTCAGCCTGACCTGCCTGGTCAAAGGCTTCTATCCCAGCGAC
ATCGCCGTGGAGTGGGAGAGCAATGGGCAGCCGGAGAACAACTACAAGACCACGCCTCCCGTGCTGGACTCCGACGGCTCCTTCTTCCTCTACAGCAAGCTCACCGTG
GACAAGAGCAGGTGGCAGCAGGGGAACGTCTTCTCATGCTCCGTGATGCACGAGGCTCTGCACAACCACTACACGCAGAAGAGCCTCTCCCTGTCTCCGGGTAAAATC
GAT*CCAAATAAAGGAAGTGGAACCACTTCAGGTACTACCCGTCTTCTATCTGGGCACACGTGTTTCACGTTGACAGGTTTGCTTGGGACGCTAGTAACCATGGGCTTG*
*CTGACTTAG*

MEPPGDWGPPPWRSTPKTDVLRLVLYLTFLGAPCYAPALPSCKEDEYPVGSECCPKCSPGYRVKEACGELTGTVCEPCPPGTYIAHLNGLSKCLQCQMCDPAMGLRAS
RNCSRTENAVCGCSPGHFCIVQDGDHCAACRAYATSSPGQRVQKGGTESQDTLCQNCPPGTFSPNGTLEECQHQTKCSWLVTKAGAGTSSSHWVIDDKTHTCPPCPAP
ELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAK
GQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGKI
D*PNKGSGTTSGTTRLLSGHTCFTLTGLLGTLVTMGLLT*

*FIG. 5GG* mCTLA4-Fc-*GPI*

ATGGCTTGTCTTGGACTCCGGAGGTACAAAGCTCAACTGCAGCTGCCTTCTAGGACTTGGCCTTTTGTAGCCCTGCTCACTCTTCTTTTCATCCCAGTCTTC
TCTGAAGCCATACAGGTGACCCAACCTTCAGTGGTGTTGGCTAGCAGCCATGGTGTCGCCAGCTTTCCATGTGAATATTCACCATCACACAACACTGATGAG
GTCCGGGTGACTGTGCTGCGGCAGACAAATGACCAAATGACTGAGGTCTGTGCCACGACATTCACAGAGAAGAATACAGTGGGCTTCCTAGATTACCCCTTC
TGCAGTGGTACCTTTAATGAAAGCAGAGTGAACCTCACCATCCAAGGACTGAGAGCTGTTGACACGGGACTGTACCTCTGCAAGGTGGAACTCATGTACCCA
CCGCCATACTTTGTGGGCATGGGCAACGGGACGCAGATTTATGTCATTGATCCAGAACCATGCCCGGATTCTGAATCGATGACAAAACTCACACATGCCCAC
CGTGCCCAGCACCTGAACTCCTGGGGGGACCGTCAGTCTTCCTCTTCCCCCCAAAACCCAAGGACACCCTCATGATCTCCCGGACCCCTGAGGTCACATGCG
TGGTGGTGGACGTGAGCCACGAAGACCCTGAGGTCAAGTTCAACTGGTACGTGGACGGCGTGGAGGTGCATAATGCCAAGACAAAGCCGCGGGAGGAGCAGT
ACAACAGCACGTACCGTGTGGTCAGCGTCCTCACCGTCCTGCACCAGGACTGGCTGAATGGCAAGGAGTACAAGTGCAAGGTCTCCAACAAAGCCCTCCCAG
CCCCCATCGAGAAAACCATCTCCAAAGCCAAAGGGCAGCCCCGAGAACCACAGGTGTACACCCTGCCCCCATCCCGGGAGGAGATGACCAAGAACCAGGTCA
GCCTGACCTGCCTGGTCAAAGGCTTCTATCCCAGCGACATCGCCGTGGAGTGGGAGAGCAATGGGCAGCCGGAGAACAACTACAAGACCACGCCTCCCGTGC
TGGACTCCGACGGCTCCTTCTTCCTCTACAGCAAGCTCACCGTGGACAAGAGCAGGTGGCAGCAGGGGAACGTCTTCTCATGCTCCGTGATGCACGAGGCTC
TGCACAACCACTACACGCAGAAGAGCCTCTCCCTGTCTCCGGGTAAAATCGAT*CCAAATAAAGGAAGTGGAACCACTTCAGGTACTACCCGTCTTCTATCTG*
*GGCACACGTGTTTCACGTTGACAGGTTTGCTTGGGACGCTAGTAACCATGGGCTTGCTGACTTAG*

MACLGLRRYKAQLQLPSRTWPFVALLTLLFIPVFSEAIQVTQPSVVLASSHGVASFPCEYSPSHNTDEVRVTVLRQTNDQMTEVCATTFTEKNTVGFLDYPF
CSGTFNESRVNLTIQGLRAVDTGLYLCKVELMYPPPYFVGMGNGTQIYVIDPEPCPDSDIDDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQV
SLTCLVKGFYPSDIAVEWESNGQPENNYKTTPPVLDSDGSFFLYSKLTVDKSRWQQGNVFSCSVMHEALHNHYTQKSLSLSPGKID*PNKGSGTTSGTTRLLS*
*GHTCFTLTGLLGTLVTMGLLT*

FIG. 5HH mPDL1-*C1C2*

ATGAGGATATTTGCTGGCATTATATTCACAGCCTGCTGTCACTTGCTACGGGCGTTTACTATCACGGCTCCAAAGGACTTGTACGTGGTGGAGTATGGCAGC
AACGTCACGATGGAGTGCAGATTCCCTGTAGAACGGGAGCTGGACCTGCTTGCGTTAGTGGTGTACTGGGAAAAGGAAGATGAGCAAGTGATTCAGTTTGTG
GCAGGAGAGGAGGACCTTAAGCCTCAGCACAGCAACTTCAGGGGGAGAGCCTCGCTGCCAAAGGACCAGCTTTTGAAGGGAAATGCTGCCCTTCAGATCACA
GACGTCAAGCTGCAGGACGCAGGCGTTTACTGCTGCATAATCAGCTACGGTGGTGCGGACTACAAGCGAATCACGCTGAAAGTCAATGCCCCATACCGCAAA
ATCAACCAGAGAATTTCCGTGGATCCAGCCACTTCTGAGCATGAACTAATATGTCAGGCCGAGGGTTATCCAGAAGCTGAGGTAATCTGGACAAACAGTGAC
CACCAACCCGTGAGTGGGAAGAGAAGTGTCACCACTTCCCGGACAGAGGGGATGCTTCTCAATGTGACCAGCAGTCTGAGGGTCAACGCCACAGCGAATGAT
GTTTTCTACTGTACGTTTTGGAGATCACAGCCAGGGCAAAACCACACAGCGGAGCTGATCATCCCAGAACTGCCTGCAACACATCCTCCACAGAACAGGACT
ATCGAT*GTCGAGCCACTGGGCATGGAGAATGGGAACATTGCCAACTCACAGATCGCCGCCTCATCTGTGCGTGTGACCTTCTTGGGTTTGCAGCATTGGGTC*
*CCGGAGCTGGCCCGCCTGAACCGCGCAGGCATGGTCAATGCCTGGACACCCAGCAGCAATGACGATAACCCCTGGATCCAGGTGAACCTGCTGCGGAGGATG*
*TGGGTAACAGGTGTGGTGACGCAGGGTGCCAGCCGCTTGGCCAGTCATGAGTACCTGAAGGCCTTCAAGGTGGCCTACAGCCTTAATGGACACGAATTCGAT*
*TTCATCCATGATGTTAATAAAAAACACAAGGAGTTTGTGGGTAACTGGAACAAAAACGCGGTGCATGTCAACCTGTTTGAGACCCCTGTGGAGGCTCAGTAC*
*GTGAGATTGTACCCCACGAGCTGCCACACGGCCTGCACTCTGCGCTTTGAGCTACTGGGCTGTGAGCTGAACGGATGCGCCAATCCCCTGGGCCTGAAGAAT*
*AACAGCATCCCTGACAAGCAGATCACGGCCTCCAGCAGCTACAAGACCTGGGGCTTGCATCTCTTCAGCTGGAACCCCTCCTATGCACGGCTGGACAAGCAG*
*GGCAACTTCAACGCCTGGGTTGCGGGGAGCTACGGTAACGATCAGTGGCTGCAGATCTTCCCTGGCAACTGGGACAACCACTCCCACAAGAAGAACTTGTTT*
*GAGACGCCCATCCTGGCTCGCTATGTGCGCATCCTGCCTGTAGCCTGGCACAACCGCATCGCCCTGCGCCTGGAGCTGCTGGGCTGTTAG*

MRIFAGIIFTACCHLLRAFTITAPKDLYVVEYGSNVTMECRFPVERELDLLALVVYWEKEDEQVIQFVAGEEDLKPQHSNFRGRASLPKDQLLKGNAALQIT
DVKLQDAGVYCCIISYGGADYKRITLKVNAPYRKINQRISVDPATSEHELICQAEGYPEAEVIWTNSDHQPVSGKRSVTTSRTEGMLLNVTSSLRVNATAND
VFYCTFWRSQPGQNHTAELIIPELPATHPPQNRTID*VEPLGMENGNIANSQIAASSVRVTFLGLQHWVPELARLNRAGMVNAWTPSSNDDNPWIQVNLLRRM*
*WVTGVVTQGASRLASHEYLKAFKVAYSLNGHEFDFIHDVNKKHKEFVGNWNKNAVHVNLFETPVEAQYVRLYPTSCHTACTLRFELLGCELNGCANPLGLKN*
*NSIPDKQITASSSYKTWGLHLFSWNPSYARLDKQGNFNAWVAGSYGNDQWLQIFPGNWDNHSHKKNLFETPILARYVRILPVAWHNRIALRLELLGC*

*FIG. 5II* mPDL1-Fc-*GPI*

ATGAGGATATTTGCTGGCATTATATTCACAGCCTGCTGTCACTTGCTACGGGCGTTTACTATCACGGCTCCAAAGGACTTGTACGTGGTGGAGTATGGCAGC
AACGTCACGATGGAGTGCAGATTCCCTGTAGAACGGGAGCTGGACCTGCTTGCGTTAGTGGTGTACTGGGAAAAGGAAGATGAGCAAGTGATTCAGTTTGTG
GCAGGAGAGGAGGACCTTAAGCCTCAGCACAGCAACTTCAGGGGGAGAGCCTCGCTGCCAAAGGACCAGCTTTTGAAGGGAAATGCTGCCCTTCAGATCACA
GACGTCAAGCTGCAGGACGCAGGCGTTTACTGCTGCATAATCAGCTACGGTGGTGCGGACTACAAGCGAATCACGCTGAAAGTCAATGCCCCATACCGCAAA
ATCAACCAGAGAATTTCCGTGGATCCAGCCACTTCTGAGCATGAACTAATATGTCAGGCCGAGGGTTATCCAGAAGCTGAGGTAATCTGGACAAACAGTGAC
CACCAACCCGTGAGTGGGAAGAGAAGTGTCACCACTTCCCGGACAGAGGGGATGCTTCTCAATGTGACCAGCAGTCTGAGGGTCAACGCCACAGCGAATGAT
GTTTTCTACTGTACGTTTTGGAGATCACAGCCAGGGCAAAACCACACAGCGGAGCTGATCATCCCAGAACTGCCTGCAACACATCCTCCACAGAACAGGACT
ATCGATGACAAAACTCACACATGCCCACCGTGCCCAGCACCTGAACTCCTGGGGGGACCGTCAGTCTTCCTCTTCCCCCCAAAACCCAAGGACACCCTCATG
ATCTCCCGGACCCCTGAGGTCACATGCGTGGTGGTGGACGTGAGCCACGAAGACCCTGAGGTCAAGTTCAACTGGTACGTGGACGGCGTGGAGGTGCATAAT
GCCAAGACAAAGCCGCGGGAGGAGCAGTACAACAGCACGTACCGTGTGGTCAGCGTCCTCACCGTCCTGCACCAGGACTGGCTGAATGGCAAGGAGTACAAG
TGCAAGGTCTCCAACAAAGCCCTCCCAGCCCCCATCGAGAAAACCATCTCCAAAGCCAAAGGGCAGCCCCGAGAACCACAGGTGTACACCCTGCCCCCATCC
CGGGAGGAGATGACCAAGAACCAGGTCAGCCTGACCTGCCTGGTCAAAGGCTTCTATCCCAGCGACATCGCCGTGGAGTGGGAGAGCAATGGGCAGCCGGAG
AACAACTACAAGACCACGCCTCCCGTGCTGGACTCCGACGGCTCCTTCTTCCTCTACAGCAAGCTCACCGTGGACAAGAGCAGGTGGCAGCAGGGGAACGTC
TTCTCATGCTCCGTGATGCACGAGGCTCTGCACAACCACTACACGCAGAAGAGCCTCTCCCTGTCTCCGGGTAAAATCGAT*CCAAATAAAGGAAGTGGAACC*
*ACTTCAGGTACTACCCGTCTTCTATCTGGGCACACGTGTTTCACGTTGACAGGTTTGCTTGGGACGCTAGTAACCATGGGCTTGCTGACTTAG*

MRIFAGIIFTACCHLLRAFTITAPKDLYVVEYGSNVTMECRFPVERELDLLALVVYWEKEDEQVIQFVAGEEDLKPQHSNFRGRASLPKDQLLKGNAALQIT
DVKLQDAGVYCCIISYGGADYKRITLKVNAPYRKINQRISVDPATSEHELICQAEGYPEAEVIWTNSDHQPVSGKRSVTTSRTEGMLLNVTSSLRVNATAND
VFYCTFWRSQPGQNHTAELIIPELPATHPPQNRTIDDKTHTCPPCPAPELLGGPSVFLFPPKPKDTLMISRTPEVTCVVVDVSHEDPEVKFNWYVDGVEVHN
AKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGKID*PNKGSGTTSGTTRLLSGHTCFTLTGLLGTLVTMGLLT*

*FIG. 5JJ* mPDL1-*GPI*

ATGAGGATATTTGCTGGCATTATATTCACAGCCTGCTGTCACTTGCTACGGGCGTTTACTATCACGGCTCCAAAGGACTTGTACGTGGTGGA
GTATGGCAGCAACGTCACGATGGAGTGCAGATTCCCTGTAGAACGGGAGCTGGACCTGCTTGCGTTAGTGGTGTACTGGGAAAAGGAAGATG
AGCAAGTGATTCAGTTTGTGGCAGGAGAGGAGGACCTTAAGCCTCAGCACAGCAACTTCAGGGGGAGAGCCTCGCTGCCAAAGGACCAGCTT
TTGAAGGGAAATGCTGCCCTTCAGATCACAGACGTCAAGCTGCAGGACGCAGGCGTTTACTGCTGCATAATCAGCTACGGTGGTGCGGACTA
CAAGCGAATCACGCTGAAAGTCAATGCCCCATACCGCAAAATCAACCAGAGAATTTCCGTGGATCCAGCCACTTCTGAGCATGAACTAATAT
GTCAGGCCGAGGGTTATCCAGAAGCTGAGGTAATCTGGACAAACAGTGACCACCAACCCGTGAGTGGGAAGAGAAGTGTCACCACTTCCCGG
ACAGAGGGGATGCTTCTCAATGTGACCAGCAGTCTGAGGGTCAACGCCACAGCGAATGATGTTTTCTACTGTACGTTTTGGAGATCACAGCC
AGGGCAAAACCACACAGCGGAGCTGATCATCCCAGAACTGCCTGCAACACATCCTCCACAGAACAGGACT*CCAAATAAAGGAAGTGGAACCA*
*CTTCAGGTACTACCCGTCTTCTATCTGGGCACACGTGTTTCACGTTGACAGGTTTGCTTGGGACGCTAGTAACCATGGGCTTGCTGACTTAG*

MRIFAGIIFTACCHLLRAFTITAPKDLYVVEYGSNVTMECRFPVERELDLLALVVYWEKEDEQVIQFVAGEEDLKPQHSNFRGRASLPKDQL
LKGNAALQITDVKLQDAGVYCCIISYGGADYKRITLKVNAPYRKINQRISVDPATSEHELICQAEGYPEAEVIWTNSDHQPVSGKRSVTTSR
TEGMLLNVTSSLRVNATANDVFYCTFWRSQPGQNHTAELIIPELPATHPPQNRT*PNKGSGTTSGTTRLLSGHTCFTLTGLLGTLVTMGLLT*

*FIG. 5KK* mPDL2-*C1C2*

ATGCTGCTCCTGCTGCCGATACTGAACCTGAGCTTACAACTTCATCCTGTAGCAGCTTTATTCACCGTGACAGCCCCTAAAGAAGTGTACACCGTAGACGTC
GGCAGCAGTGTGAGCCTGGAGTGCGATTTTGACCGCAGAGAATGCACTGAACTGGAAGGGATAAGAGCCAGTTTGCAGAAGGTAGAAAATGATACGTCTCTG
CAAAGTGAAAGAGCCACCCTGCTGGAGGAGCAGCTGCCCCTGGGAAAGGCTTTGTTCCACATCCCTAGTGTCCAAGTGAGAGATTCCGGGCAGTACCGTTGC
CTGGTCATCTGCGGGGCCGCCTGGGACTACAAGTACCTGACGGTGAAAGTCAAAGCTTCTTACATGAGGATAGACACTAGGATCCTGGAGGTTCCAGGTACA
GGGGAGGTGCAGCTTACCTGCCAGGCTAGAGGTTATCCCCTAGCAGAAGTGTCCTGGCAAAATGTCAGTGTTCCTGCCAACACCAGCCACATCAGGACCCCC
GAAGGCCTCTACCAGGTCACCAGTGTTCTGCGCCTCAAGCCTCAGCCTAGCAGAAACTTCAGCTGCATGTTCTGGAATGCTCACATGAAGGAGCTGACTTCA
GCCATCATTGACCCTCTGAGTCGGATGGAACCCAAAGTCCCCAGAACGATCGAT*GTCGAGCCACTGGGCATGGAGAATGGGAACATTGCCAACTCACAGATC*
*GCCGCCTCATCTGTGCGTGTGACCTTCTTGGGTTTGCAGCATTGGGTCCCGGAGCTGGCCCGCCTGAACCGCGCAGGCATGGTCAATGCCTGGACACCCAGC*
*AGCAATGACGATAACCCCTGGATCCAGGTGAACCTGCTGCGGAGGATGTGGGTAACAGGTGTGGTGACGCAGGGTGCCAGCCGCTTGGCCAGTCATGAGTAC*
*CTGAAGGCCTTCAAGGTGGCCTACAGCCTTAATGGACACGAATTCGATTTCATCCATGATGTTAATAAAAAACACAAGGAGTTTGTGGGTAACTGGAACAAA*
*AACGCGGTGCATGTCAACCTGTTTGAGACCCCTGTGGAGGCTCAGTACGTGAGATTGTACCCCACGAGCTGCCACACGGCCTGCACTCTGCGCTTTGAGCTA*
*CTGGGCTGTGAGCTGAACGGATGCGCCAATCCCCTGGGCCTGAAGAATAACAGCATCCCTGACAAGCAGATCACGGCCTCCAGCAGCTACAAGACCTGGGGC*
*TTGCATCTCTTCAGCTGGAACCCCTCCTATGCACGGCTGGACAAGCAGGGCAACTTCAACGCCTGGGTTGCGGGGAGCTACGGTAACGATCAGTGGCTGCAG*
*ATCTTCCCTGGCAACTGGGACAACCACTCCCACAAGAAGAACTTGTTTGAGACGCCCATCCTGGCTCGCTATGTGCGCATCCTGCCTGTAGCCTGGCACAAC*
*CGCATCGCCCTGCGCCTGGAGCTGCTGGGCTGTTAG*

MLLLLPILNLSLQLHPVAALFTVTAPKEVYTVDVGSSVSLECDFDRRECTELEGIRASLQKVENDTSLQSERATLLEEQLPLGKALFHIPSVQVRDSGQYRC
LVICGAAWDYKYLTVKVKASYMRIDTRILEVPGTGEVQLTCQARGYPLAEVSWQNVSVPANTSHIRTPEGLYQVTSVLRLKPQPSRNFSCMFWNAHMKELTS
AIIDPLSRMEPKVPRT*IDVEPLGMENGNIANSQIAASSVRVTFLGLQHWVPELARLNRAGMVNAWTPSSNDDNPWIQVNLLRRMWVTGVVTQGASRLASHEY*
*LKAFKVAYSLNGHEFDFIHDVNKKHKEFVGNWNKNAVHVNLFETPVEAQYVRLYPTSCHTACTLRFELLGCELNGCANPLGLKNNSIPDKQITASSSYKTWG*
*LHLFSWNPSYARLDKQGNFNAWVAGSYGNDQWLQIFPGNWDNHSHKKNLFETPILARYVRILPVAWHNRIALRLELLGC*

*FIG. 5LL* mPDL2-Fc-*GPI*

**ATGCTGCTCCTGCTGCCGATACTGAACCTGAGCTTACAACTTCATCCTGTAGCAGCTTTATTCACCGTGACAGCCCCTAAAGAAGTGTACACCGTAGACGTCGGCAG
CAGTGTGAGCCTGGAGTGCGATTTTGACCGCAGAGAATGCACTGAACTGGAAGGGATAAGAGCCAGTTTGCAGAAGGTAGAAAATGATACGTCTCTGCAAAGTGAAA
GAGCCACCCTGCTGGAGGAGCAGCTGCCCCTGGGAAAGGCTTTGTTCCACATCCCTAGTGTCCAAGTGAGAGATTCCGGGCAGTACCGTTGCCTGGTCATCTGCGGG
GCCGCCTGGGACTACAAGTACCTGACGGTGAAAGTCAAAGCTTCTTACATGAGGATAGACACTAGGATCCTGGAGGTTCCAGGTACAGGGGAGGTGCAGCTTACCTG
CCAGGCTAGAGGTTATCCCCTAGCAGAAGTGTCCTGGCAAAATGTCAGTGTTCCTGCCAACACCAGCCACATCAGGACCCCCGAAGGCCTCTACCAGGTCACCAGTG
TTCTGCGCCTCAAGCCTCAGCCTAGCAGAAACTTCAGCTGCATGTTCTGGAATGCTCACATGAAGGAGCTGACTTCAGCCATCATTGACCCTCTGAGTCGGATGGAA
CCCAAAGTCCCCAGAACG**ATCGATGACAAAACTCACACATGCCCACCGTGCCCAGCACCTGAACTCCTGGGGGGACCGTCAGTCTTCCTCTTCCCCCCAAAACCCAA
GGACACCCTCATGATCTCCCGGACCCCTGAGGTCACATGCGTGGTGGTGGACGTGAGCCACGAAGACCCTGAGGTCAAGTTCAACTGGTACGTGGACGGCGTGGAGG
TGCATAATGCCAAGACAAAGCCGCGGGAGGAGCAGTACAACAGCACGTACCGTGTGGTCAGCGTCCTCACCGTCCTGCACCAGGACTGGCTGAATGGCAAGGAGTAC
AAGTGCAAGGTCTCCAACAAAGCCCTCCCAGCCCCCATCGAGAAAACCATCTCCAAAGCCAAAGGGCAGCCCCGAGAACCACAGGTGTACACCCTGCCCCCATCCCG
GGAGGAGATGACCAAGAACCAGGTCAGCCTGACCTGCCTGGTCAAAGGCTTCTATCCCAGCGACATCGCCGTGGAGTGGGAGAGCAATGGGCAGCCGGAGAACAACT
ACAAGACCACGCCTCCCGTGCTGGACTCCGACGGCTCCTTCTTCCTCTACAGCAAGCTCACCGTGGACAAGAGCAGGTGGCAGCAGGGGAACGTCTTCTCATGCTCC
GTGATGCACGAGGCTCTGCACAACCACTACACGCAGAAGAGCCTCTCCCTGTCTCCGGGTAAAATCGAT*CCAAATAAAGGAAGTGGAACCACTTCAGGTACTACCCG
TCTTCTATCTGGGCACACGTGTTTCACGTTGACAGGTTTGCTTGGGACGCTAGTAACCATGGGCTTGCTGACTTAG*

**MLLLLPILNLSLQLHPVAALFTVTAPKEVYTVDVGSSVSLECDFDRRECTELEGIRASLQKVENDTSLQSERATLLEEQLPLGKALFHIPSVQVRDSGQYRCLVICG
AAWDYKYLTVKVKASYMRIDTRILEVPGTGEVQLTCQARGYPLAEVSWQNVSVPANTSHIRTPEGLYQVTSVLRLKPQPSRNFSCMFWNAHMKELTSAIIDPLSRME
PKVPRT**IDDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCS
VMHEALHNHYTQKSLSLSPGKID*PNKGSGTTSGTTRLLSGHTCFTLTGLLGTLVTMGLLT*

*FIG. 5MM* mPDL1-mFc-*GPI*

ATGAGGATATTTGCTGGCATTATATTCACAGCCTGCTGTCACTTGCTACGGGCGTTTACTATCACGGCTCCAAAGGACTTGTACGTGGTGGAGTATGGCAGC
AACGTCACGATGGAGTGCAGATTCCCTGTAGAACGGGAGCTGGACCTGCTTGCGTTAGTGGTGTACTGGGAAAAGGAAGATGAGCAAGTGATTCAGTTTGTG
GCAGGAGAGGAGGACCTTAAGCCTCAGCACAGCAACTTCAGGGGGAGAGCCTCGCTGCCAAAGGACCAGCTTTTGAAGGGAAATGCTGCCCTTCAGATCACA
GACGTCAAGCTGCAGGACGCAGGCGTTTACTGCTGCATAATCAGCTACGGTGGTGCGGACTACAAGCGAATCACGCTGAAAGTCAATGCCCCATACCGCAAA
ATCAACCAGAGAATTTCCGTGGATCCAGCCACTTCTGAGCATGAACTAATATGTCAGGCCGAGGGTTATCCAGAAGCTGAGGTAATCTGGACAAACAGTGAC
CACCAACCCGTGAGTGGGAAGAGAAGTGTCACCACTTCCCGGACAGAGGGGATGCTTCTCAATGTGACCAGCAGTCTGAGGGTCAACGCCACAGCGAATGAT
GTTTTCTACTGTACGTTTTGGAGATCACAGCCAGGGCAAAACCACACAGCGGAGCTGATCATCCCAGAACTGCCTGCAACACATCCTCCACAGAACAGGACT
GGTTGTAAGCCTTGCATATGTACAGTCCCAGAAGTATCATCTGTCTTCATCTTCCCCCCAAAGCCCAAGGATGTGCTCACCATTACTCTGACTCCTAAGGTC
ACGTGTGTTGTGGTAGACATCAGCAAGGATGATCCCGAGGTCCAGTTCAGCTGGTTTGTAGATGATGTGGAGGTGCACACAGCTCAGACGCAACCCCGGGAG
GAGCAGTTCAACAGCACTTTCCGCTCAGTCAGTGAACTTCCCATCATGCACCAGGACTGGCTCAATGGCAAGGAGTTCAAATGCAGGGTCAACAGTGCAGCT
TTCCCTGCCCCCATCGAGAAAACCATCTCCAAAACCAAAGGCAGACCGAAGGCTCCACAGGTGTACACCATTCCACCTCCCAAGGAGCAGATGGCCAAGGAT
AAAGTCAGTCTGACCTGCATGATAACAGACTTCTTCCCTGAAGACATTACTGTGGAGTGGCAGTGGAATGGGCAGCCAGCGGAGAACTACAAGAACACTCAG
CCCATCATGGACACAGATGGCTCTTACTTCGTCTACAGCAAGCTCAATGTGCAGAAGAGCAACTGGGAGGCAGGAAATACTTTCACCTGCTCTGTGTTACAT
GAGGGCCTGCACAACCACCATACTGAGAAGAGCCTCTCCCACTCTCCTGGTAAA*CCAAATAAAGGAAGTGGAACCACTTCAGGTACTACCCGTCTTCTATCT*
*GGGCACACGTGTTTCACGTTGACAGGTTTGCTTGGGACGCTAGTAACCATGGGCTTGCTGACTTAG*

MRIFAGIIFTACCHLLRAFTITAPKDLYVVEYGSNVTMECRFPVERELDLLALVVYWEKEDEQVIQFVAGEEDLKPQHSNFRGRASLPKDQLLKGNAALQIT
DVKLQDAGVYCCIISYGGADYKRITLKVNAPYRKINQRISVDPATSEHELICQAEGYPEAEVIWTNSDHQPVSGKRSVTTSRTEGMLLNVTSSLRVNATAND
VFYCTFWRSQPGQNHTAELIIPELPATHPPQNRTGCKPCICTVPEVSSVFIFPPKPKDVLTITLTPKVTCVVVDISKDDPEVQFSWFVDDVEVHTAQTQPRE
EQFNSTFRSVSELPIMHQDWLNGKEFKCRVNSAAFPAPIEKTISKTKGRPKAPQVYTIPPPKEQMAKDKVSLTCMITDFFPEDITVEWQWNGQPAENYKNTQ
PIMDTDGSYFVYSKLNVQKSNWEAGNTFTCSVLHEGLHNHHTEKSLSHSPGK*PNKGSGTTSGTTRLLSGHTCFTLTGLLGTLVTMGLLT*

*FIG. 5NN* mPDL2-*GPI*

ATGCTGCTCCTGCTGCCGATACTGAACCTGAGCTTACAACTTCATCCTGTAGCAGCTTTATTCACCGTGACAGCCCCTAAAGAAGTGTACACCGTAGACG
TCGGCAGCAGTGTGAGCCTGGAGTGCGATTTTGACCGCAGAGAATGCACTGAACTGGAAGGGATAAGAGCCAGTTTGCAGAAGGTAGAAAATGATACGTC
TCTGCAAAGTGAAAGAGCCACCCTGCTGGAGGAGCAGCTGCCCCTGGGAAAGGCTTTGTTCCACATCCCTAGTGTCCAAGTGAGAGATTCCGGGCAGTAC
CGTTGCCTGGTCATCTGCGGGGCCGCCTGGGACTACAAGTACCTGACGGTGAAAGTCAAAGCTTCTTACATGAGGATAGACACTAGGATCCTGGAGGTTC
CAGGTACAGGGGAGGTGCAGCTTACCTGCCAGGCTAGAGGTTATCCCCTAGCAGAAGTGTCCTGGCAAAATGTCAGTGTTCCTGCCAACACCAGCCACAT
CAGGACCCCCGAAGGCCTCTACCAGGTCACCAGTGTTCTGCGCCTCAAGCCTCAGCCTAGCAGAAACTTCAGCTGCATGTTCTGGAATGCTCACATGAAG
GAGCTGACTTCAGCCATCATTGACCCTCTGAGTCGGATGGAACCCAAAGTCCCCAGAACG*CCAAATAAAGGAAGTGGAACCACTTCAGGTACTACCCGTC*
*TTCTATCTGGGCACACGTGTTTCACGTTGACAGGTTTGCTTGGGACGCTAGTAACCATGGGCTTGCTGACTTAG*

MLLLLPILNLSLQLHPVAALFTVTAPKEVYTVDVGSSVSLECDFDRRECTELEGIRASLQKVENDTSLQSERATLLEEQLPLGKALFHIPSVQVRDSGQY
RCLVICGAAWDYKYLTVKVKASYMRIDTRILEVPGTGEVQLTCQARGYPLAEVSWQNVSVPANTSHIRTPEGLYQVTSVLRLKPQPSRNFSCMFWNAHMK
ELTSAIIDPLSRMEPKVPRT*PNKGSGTTSGTTRLLSGHTCFTLTGLLGTLVTMGLLT*

*FIG. 5OO* mPDL1-*GPI*-P2A-mHVEM-*GPI*

ATGAGGATATTTGCTGGCATTATATTCACAGCCTGCTGTCACTTGCTACGGGCGTTTACTATCACGGCTCCAAAGGACTTGTACGTGGTGGAGTATGGCAGCAACGTC
ACGATGGAGTGCAGATTCCCTGTAGAACGGGAGCTGGACCTGCTTGCGTTAGTGGTGTACTGGGAAAAGGAAGATGAGCAAGTGATTCAGTTTGTGGCAGGAGAGGAG
GACCTTAAGCCTCAGCACAGCAACTTCAGGGGGAGAGCCTCGCTGCCAAAGGACCAGCTTTTGAAGGGAAATGCTGCCCTTCAGATCACAGACGTCAAGCTGCAGGAC
GCAGGCGTTTACTGCTGCATAATCAGCTACGGTGGTGCGGACTACAAGCGAATCACGCTGAAAGTCAATGCCCCATACCGCAAAATCAACCAGAGAATTTCCGTGGAT
CCAGCCACTTCTGAGCATGAACTAATATGTCAGGCCGAGGGTTATCCAGAAGCTGAGGTAATCTGGACAAACAGTGACCACCAACCCGTGAGTGGGAAGAGAAGTGTC
ACCACTTCCCGGACAGAGGGGATGCTTCTCAATGTGACCAGCAGTCTGAGGGTCAACGCCACAGCGAATGATGTTTTCTACTGTACGTTTTGGAGATCACAGCCAGGG
CAAAACCACACAGCGGAGCTGATCATCCCAGAACTGCCTGCAACACATCCTCCACAGAACAGGACT*CCAAATAAAGGAAGTGGAACCACTTCAGGTACTACCCGTCTT*
*CTATCTGGGCACACGTGTTTCACGTTGACAGGTTTGCTTGGGACGCTAGTAACCATGGGCTTGCTGACT*GGAAGCGGAGCTACTAACTTCAGCCTGCTGAAGCAGGCT
GGCGACGTGGAGGAGAACCCTGGACCTATGGAACCTCTCCCAGGATGGGGGTCGGCACCCTGGAGCCAGGCCCCTACAGACAACACCTTCAGGCTGGTGCCTTGTGTC
TTCCTTTTGAACTTGCTGCAGCGCATCTCTGCCCAGCCCTCATGCAGACAGGAGGAGTTCCTTGTGGGAGACGAGTGCTGCCCCATGTGCAACCCAGGTTACCATGTG
AAGCAGGTCTGCAGTGAGCATACAGGCACAGTGTGTGCCCCCTGTCCCCCACAGACATATACCGCCCATGCAAATGGCCTGAGCAAGTGTCTGCCCTGCGGAGTCTGT
GATCCAGACATGGGCCTGCTGACCTGGCAGGAGTGCTCCAGCTGGAAGGACACTGTGTGCAGATGCATCCCAGGCTACTTCTGTGAGAACCAGGATGGGAGCCACTGT
TCCACATGCTTGCAGCACACCACCTGCCCTCCAGGGCAGAGGGTAGAGAAGAGAGGGACTCACGACCAGGACACTGTATGTGCTGACTGCCTAACAGGGACCTTCTCA
CTTGGAGGGACTCAGGAGGAATGCCTGCCCTGGACCAACTGCAGTGCATTTCAACAGGAAGTAAGACGTGGGACCAACAGCACAGACACCACCTGCTCCTCCCAG*CCA*
*AATAAAGGAAGTGGAACCACTTCAGGTACTACCCGTCTTCTATCTGGGCACACGTGTTTCACGTTGACAGGTTTGCTTGGGACGCTAGTAACCATGGGCTTGCTGACT*
*TAG*

MRIFAGIIFTACCHLLRAFTITAPKDLYVVEYGSNVTMECRFPVERELDLLALVVYWEKEDEQVIQFVAGEEDLKPQHSNFRGRASLPKDQLLKGNAALQITDVKLQD
AGVYCCIISYGGADYKRITLKVNAPYRKINQRISVDPATSEHELICQAEGYPEAEVIWTNSDHQPVSGKRSVTTSRTEGMLLNVTSSLRVNATANDVFYCTFWRSQPG
QNHTAELIIPELPATHPPQNRT*PNKGSGTTSGTTRLLSGHTCFTLTGLLGTLVTMGLLT*GSGATNFSLLKQAGDVEENPGPMEPLPGWGSAPWSQAPTDNTFRLVPCV
FLLNLLQRISAQPSCRQEEFLVGDECCPMCNPGYHVKQVCSEHTGTVCAPCPPQTYTAHANGLSKCLPCGVCDPDMGLLTWQECSSWKDTVCRCIPGYFCENQDGSHC
STCLQHTTCPPGQRVEKRGTHDQDTVCADCLTGTFSLGGTQEECLPWTNCSAFQQEVRRGTNSTDTTCSSQ*PNKGSGTTSGTTRLLSGHTCFTLTGLLGTLVTMGLLT*

FIG. 5PP hPDL1-*ADAM10*

ATGAGGATATTTGCTGTCTTTATATTCATGACCTACTGGCATTTGCTGAACGCATTTACTGTCACGGTTCCCAAGGACCTATATGTGGTAGAGTATGGTAGC
AATATGACAATTGAATGCAAATTCCCAGTAGAAAAACAATTAGACCTGGCTGCACTAATTGTCTATTGGGAAATGGAGGATAAGAACATTATTCAATTTGTG
CATGGAGAGGAAGACCTGAAGGTTCAGCATAGTAGCTACAGACAGAGGGCCCGGCTGTTGAAGGACCAGCTCTCCCTGGGAAATGCTGCACTTCAGATCACA
GATGTGAAATTGCAGGATGCAGGGGTGTACCGCTGCATGATCAGCTATGGTGGTGCCGACTACAAGCGAATTACTGTGAAAGTCAATGCCCCATACAACAAA
ATCAACCAAAGAATTTTGGTTGTGGATCCAGTCACCTCTGAACATGAACTGACATGTCAGGCTGAGGGCTACCCCAAGGCCGAAGTCATCTGGACAAGCAGT
GACCATCAAGTCCTGAGTGGTAAGACCACCACCACCAATTCCAAGAGAGAGGAGAAGCTTTTCAATGTGACCAGCACACTGAGAATCAACACAACAACTAAT
GAGATTTTCTACTGCACTTTTAGGAGATTAGATCCTGAGGAAAACCATACAGCTGAATTGGTCATCCCAGAACTACCTCTGGCACATCCTCCAAATGAAAGG
*TGTGGAAATGGAATGGTAGAACAAGGTGAAGAATGTGATTGTGGCTATAGTGACCAGTGTAAAGATGAATGCTGCTTCGATGCAAATCAACCAGAGGGAAGA*
*AAATGCAAACTGAAACCTGGGAAACAGTGCAGTCCAAGTCAAGGTCCTTGTTGTACAGCACAGTGTGCATTCAAGTCAAAGTCTGAGAAGTGTCGGGATGAT*
*TCAGACTGTGCAAGGGAAGGAATATGTAATGGCTTCACAGCTCTCTGCCCAGCATCTGACCCTAAACCAAACTTCACAGACTGTAATAGGCATACACAAGTG*
*TGCATTAATGGGCAATGTGCAGGTTCTATCTGTGAGAAATATGGCTTAGAGGAGTGTACGTGTGCCAGTTCTGATGGCAAAGATGATAAAGAATTATGCCAT*
*GTATGCTGTATGAAGAAAATGGACCCATCAACTTGTGCCAGTACAGGGTCTGTGCAGTGGAGTAGGCACTTCAGTGGTCGAACCATCACCCTGCAACCTGGA*
*TCCCCTTGCAACGATTTTAGAGGTTACTGTGATGTTTTCATGCGGTGCAGATTAGTAGATGCTGATGGTCCTCTAGCTAGGCTTAAAAAAGCAATTTTTAGT*
*CCAGAGCTCTATGAAAACATTGCTGAATGGATTGTGGCTCATTGGTGGGCAGTATTACTTATGGGAATTGCTCTGATCATGCTAATGGCTGGATTTATTAAG*
*ATATGCAGTGTTCATACTCCAAGTAGTAATCCAAAGTTGCCTCCTCCTAAACCACTTCCAGGCACTTTAAAGAGGAGGAGACCTCCACAGCCCATTCAGCAA*
*CCCCAGCGTCAGCGGCCCCGAGAGAGTTATCAAATGGGACACATGAGACGCTAA*

MRIFAVFIFMTYWHLLNAFTVTVPKDLYVVEYGSNMTIECKFPVEKQLDLAALIVYWEMEDKNIIQFVHGEEDLKVQHSSYRQRARLLKDQLSLGNAALQIT
DVKLQDAGVYRCMISYGGADYKRITVKVNAPYNKINQRILVVDPVTSEHELTCQAEGYPKAEVIWTSSDHQVLSGKTTTTNSKREEKLFNVTSTLRINTTTN
EIFYCTFRRLDPEENHTAELVIPELPLAHPPNER*CGNGMVEQGEECDCGYSDQCKDECCFDANQPEGRKCKLKPGKQCSPSQGPCCTAQCAFKSKSEKCRDD*
*SDCAREGICNGFTALCPASDPKPNFTDCNRHTQVCINGQCAGSICEKYGLEECTCASSDGKDDKELCHVCCMKKMDPSTCASTGSVQWSRHFSGRTITLQPG*
*SPCNDFRGYCDVFMRCRLVDADGPLARLKKAIFSPELYENIAEWIVAHWWAVLLMGIALIMLMAGFIKICSVHTPSSNPKLPPPKPLPGTLKRRRPPQPIQQ*
*PQRQRPRESYQMGHMRR*

*FIG. 5QQ* hPDL1-4Fc-*CD9tm2*

ATGAGGATATTTGCTGTCTTTATATTCATGACCTACTGGCATTTGCTGAACGCATTTACTGTCACGGTTCCCAAGGACCTATATGTGGTAGAGTATGGTAGCAATAT
GACAATTGAATGCAAATTCCCAGTAGAAAAACAATTAGACCTGGCTGCACTAATTGTCTATTGGGAAATGGAGGATAAGAACATTATTCAATTTGTGCATGGAGAGG
AAGACCTGAAGGTTCAGCATAGTAGCTACAGACAGAGGGCCCGGCTGTTGAAGGACCAGCTCTCCCTGGGAAATGCTGCACTTCAGATCACAGATGTGAAATTGCAG
GATGCAGGGGTGTACCGCTGCATGATCAGCTATGGTGGTGCCGACTACAAGCGAATTACTGTGAAAGTCAATGCCCCATACAACAAAATCAACCAAAGAATTTTGGT
TGTGGATCCAGTCACCTCTGAACATGAACTGACATGTCAGGCTGAGGGCTACCCCAAGGCCGAAGTCATCTGGACAAGCAGTGACCATCAAGTCCTGAGTGGTAAGA
CCACCACCACCAATTCCAAGAGAGAGGAGAAGCTTTTCAATGTGACCAGCACACTGAGAATCAACACAACAACTAATGAGATTTTCTACTGCACTTTTAGGAGATTA
GATCCTGAGGAAAACCATACAGCTGAATTGGTCATCCCAGAACTACCTCTGGCACATCCTCCAAATGAAAGGGAGTCCAAATATGGTCCCCCATGCCCATCATGCCC
AGCACCTGAGTTCCTGGGGGGACCATCAGTCTTCCTGTTCCCCCCAAAACCCAAGGACACTCTCATGATCTCCCGGACCCCTGAGGTCACGTGCGTGGTGGTGGACG
TGAGCCAGGAAGACCCCGAGGTCCAGTTCAACTGGTACGTGGATGGCGTGGAGGTGCATAATGCCAAGACAAAGCCGCGGGAGGAGCAGTTCAACAGCACGTACCGT
GTGGTCAGGGTCCTCACCGTCCTGCACCAGGACTGGCTGAACGGTAAGGAGTACAAGTGCAAGGTCTCCAACAAAGGCCTCCCGTCCTCCATCGAGAAAACCATCTC
CAAAGCCAAAGGGCAGCCCCGAGAGCCACAGGTGTACACCCTGCCCCCATCCCAGGAGGAGATGACCAAGAACCAGGTCAGCCTGACCTGCCTGGTCAAAGGCTTCT
ACCCCAGCGACATCGCCGTGGAGTGGGAGAGCAATGGGCAGCCGGAGGACAACTACAAGACCACGCCTCCCGTGCTGGACTCCGACGGCTCCTTCTTCCTCTACAGC
AGGCTAACCGTGGACAAGAGCAGGTGGCAGGAGGGGAATGTCTTCTCATGCTCCGTGATGCATGAGGCTCTGCACAACCACTACACACAGAAGAGCCTCTCCCTGTC
TCCGGGTAAA*TTCTACACAGGAGTCTATATTCTGATCGGAGCCGGCGCCCTCATGATGCTGGTGGGCTTCCTGGGCTGCTGCGGGGCTGTGCAGGAGTCCCAGTGC*

MRIFAVFIFMTYWHLLNAFTVTVPKDLYVVEYGSNMTIECKFPVEKQLDLAALIVYWEMEDKNIIQFVHGEEDLKVQHSSYRQRARLLKDQLSLGNAALQITDVKLQ
DAGVYRCMISYGGADYKRITVKVNAPYNKINQRILVVDPVTSEHELTCQAEGYPKAEVIWTSSDHQVLSGKTTTTNSKREEKLFNVTSTLRINTTTNEIFYCTFRRL
DPEENHTAELVIPELPLAHPPNERESKYGPPCPSCPAPEFLGGPSVFLFPPKPKDTLMISRTPEVTCVVVDVSQEDPEVQFNWYVDGVEVHNAKTKPREEQFNSTYR
VVRVLTVLHQDWLNGKEYKCKVSNKGLPSSIEKTISKAKGQPREPQVYTLPPSQEEMTKNQVSLTCLVKGFYPSDIAVEWESNGQPEDNYKTTPPVLDSDGSFFLYS
RLTVDKSRWQEGNVFSCSVMHEALHNHYTQKSLSLSPGK*FYTGVYILIGAGALMMLVGFLGCCGAVQESQCVIM*

*FIG. 5RR* hPDL1-4Fc-*CD9tm2-KRAS*

ATGAGGATATTTGCTGTCTTTATATTCATGACCTACTGGCATTTGCTGAACGCATTTACTGTCACGGTTCCCAAGGACCTATATGTGGTAGAGTATGGTAGCAATAT
GACAATTGAATGCAAATTCCCAGTAGAAAAACAATTAGACCTGGCTGCACTAATTGTCTATTGGGAAATGGAGGATAAGAACATTATTCAATTTGTGCATGGAGAGG
AAGACCTGAAGGTTCAGCATAGTAGCTACAGACAGAGGGCCCGGCTGTTGAAGGACCAGCTCTCCCTGGGAAATGCTGCACTTCAGATCACAGATGTGAAATTGCAG
GATGCAGGGGTGTACCGCTGCATGATCAGCTATGGTGGTGCCGACTACAAGCGAATTACTGTGAAAGTCAATGCCCCATACAACAAAATCAACCAAAGAATTTTGGT
TGTGGATCCAGTCACCTCTGAACATGAACTGACATGTCAGGCTGAGGGCTACCCCAAGGCCGAAGTCATCTGGACAAGCAGTGACCATCAAGTCCTGAGTGGTAAGA
CCACCACCACCAATTCCAAGAGAGAGGAGAAGCTTTTCAATGTGACCAGCACACTGAGAATCAACACAACAACTAATGAGATTTTCTACTGCACTTTTAGGAGATTA
GATCCTGAGGAAAACCATACAGCTGAATTGGTCATCCCAGAACTACCTCTGGCACATCCTCCAAATGAAAGGGAGTCCAAATATGGTCCCCCATGCCCATCATGCCC
AGCACCTGAGTTCCTGGGGGGACCATCAGTCTTCCTGTTCCCCCCAAAACCCAAGGACACTCTCATGATCTCCCGGACCCCTGAGGTCACGTGCGTGGTGGTGGACG
TGAGCCAGGAAGACCCCGAGGTCCAGTTCAACTGGTACGTGGATGGCGTGGAGGTGCATAATGCCAAGACAAAGCCGCGGGAGGAGCAGTTCAACAGCACGTACCGT
GTGGTCAGGGTCCTCACCGTCCTGCACCAGGACTGGCTGAACGGTAAGGAGTACAAGTGCAAGGTCTCCAACAAAGGCCTCCCGTCCTCCATCGAGAAAACCATCTC
CAAAGCCAAAGGGCAGCCCCGAGAGCCACAGGTGTACACCCTGCCCCCATCCCAGGAGGAGATGACCAAGAACCAGGTCAGCCTGACCTGCCTGGTCAAAGGCTTCT
ACCCCAGCGACATCGCCGTGGAGTGGGAGAGCAATGGGCAGCCGGAGGACAACTACAAGACCACGCCTCCCGTGCTGGACTCCGACGGCTCCTTCTTCCTCTACAGC
AGGCTAACCGTGGACAAGAGCAGGTGGCAGGAGGGGAATGTCTTCTCATGCTCCGTGATGCATGAGGCTCTGCACAACCACTACACACAGAAGAGCCTCTCCCTGTC
TCCGGGTAAA*TTCTACACAGGAGTCTATATTCTGATCGGAGCCGGCGCCCTCATGATGCTGGTGGGCTTCCTGGGCTGCTGCGGGGCTGTGCAGGAGTCCCAGTGCA*
*AAAAGAAGAAAAAGAAGAAGAAGACAAAGTGTGTAATTATGTAA*

MRIFAVFIFMTYWHLLNAFTVTVPKDLYVVEYGSNMTIECKFPVEKQLDLAALIVYWEMEDKNIIQFVHGEEDLKVQHSSYRQRARLLKDQLSLGNAALQITDVKLQ
DAGVYRCMISYGGADYKRITVKVNAPYNKINQRILVVDPVTSEHELTCQAEGYPKAEVIWTSSDHQVLSGKTTTTNSKREEKLFNVTSTLRINTTTNEIFYCTFRRL
DPEENHTAELVIPELPLAHPPNERESKYGPPCPSCPAPEFLGGPSVFLFPPKPKDTLMISRTPEVTCVVVDVSQEDPEVQFNWYVDGVEVHNAKTKPREEQFNSTYR
VVRVLTVLHQDWLNGKEYKCKVSNKGLPSSIEKTISKAKGQPREPQVYTLPPSQEEMTKNQVSLTCLVKGFYPSDIAVEWESNGQPEDNYKTTPPVLDSDGSFFLYS
RLTVDKSRWQEGNVFSCSVMHEALHNHYTQKSLSLSPGK*FYTGVYILIGAGALMMLVGFLGCCGAVQESQCKKKKKKKTKCVIM*

*FIG. 5SS* hPDL1-Fc-*CD9tm2*

ATGAGGATATTTGCTGTCTTTATATTCATGACCTACTGGCATTTGCTGAACGCATTTACTGTCACGGTTCCCAAGGACCTATATGTGGTAGAGTATGGTAGC
AATATGACAATTGAATGCAAATTCCCAGTAGAAAAACAATTAGACCTGGCTGCACTAATTGTCTATTGGGAAATGGAGGATAAGAACATTATTCAATTTGTG
CATGGAGAGGAAGACCTGAAGGTTCAGCATAGTAGCTACAGACAGAGGGCCCGGCTGTTGAAGGACCAGCTCTCCCTGGGAAATGCTGCACTTCAGATCACA
GATGTGAAATTGCAGGATGCAGGGGTGTACCGCTGCATGATCAGCTATGGTGGTGCCGACTACAAGCGAATTACTGTGAAAGTCAATGCCCCATACAACAAA
ATCAACCAAAGAATTTTGGTTGTGGATCCAGTCACCTCTGAACATGAACTGACATGTCAGGCTGAGGGCTACCCCAAGGCCGAAGTCATCTGGACAAGCAGT
GACCATCAAGTCCTGAGTGGTAAGACCACCACCACCAATTCCAAGAGAGAGGAGAAGCTTTTCAATGTGACCAGCACACTGAGAATCAACACAACAACTAAT
GAGATTTTCTACTGCACTTTTAGGAGATTAGATCCTGAGGAAAACCATACAGCTGAATTGGTCATCCCAGAACTACCTCTGGCACATCCTCCAAATGAAAGG
ATCGATGACAAAACTCACACATGCCCACCGTGCCCAGCACCTGAACTCCTGGGGGGACCGTCAGTCTTCCTCTTCCCCCCAAAACCCAAGGACACCCTCATG
ATCTCCCGGACCCCTGAGGTCACATGCGTGGTGGTGGACGTGAGCCACGAAGACCCTGAGGTCAAGTTCAACTGGTACGTGGACGGCGTGGAGGTGCATAAT
GCCAAGACAAAGCCGCGGGAGGAGCAGTACAACAGCACGTACCGTGTGGTCAGCGTCCTCACCGTCCTGCACCAGGACTGGCTGAATGGCAAGGAGTACAAG
TGCAAGGTCTCCAACAAAGCCCTCCCAGCCCCCATCGAGAAAACCATCTCCAAAGCCAAAGGGCAGCCCCGAGAACCACAGGTGTACACCCTGCCCCCATCC
CGGGAGGAGATGACCAAGAACCAGGTCAGCCTGACCTGCCTGGTCAAAGGCTTCTATCCCAGCGACATCGCCGTGGAGTGGGAGAGCAATGGGCAGCCGGAG
AACAACTACAAGACCACGCCTCCCGTGCTGGACTCCGACGGCTCCTTCTTCCTCTACAGCAAGCTCACCGTGGACAAGAGCAGGTGGCAGCAGGGGAACGTC
TTCTCATGCTCCGTGATGCACGAGGCTCTGCACAACCACTACACGCAGAAGAGCCTCTCCCTGTCTCCGGGTAAAATCGAT*TTCTACACAGGAGTCTATATT*
*CTGATCGGAGCCGGCGCCCTCATGATGCTGGTGGGCTTCCTGGGCTGCTGCGGGGCTGTGCAGGAGTCCCAGTGCGTAATTATGTAA*

MRIFAVFIFMTYWHLLNAFTVTVPKDLYVVEYGSNMTIECKFPVEKQLDLAALIVYWEMEDKNIIQFVHGEEDLKVQHSSYRQRARLLKDQLSLGNAALQIT
DVKLQDAGVYRCMISYGGADYKRITVKVNAPYNKINQRILVVDPVTSEHELTCQAEGYPKAEVIWTSSDHQVLSGKTTTTNSKREEKLFNVTSTLRINTTTN
EIFYCTFRRLDPEENHTAELVIPELPLAHPPNERIDDKTHTCPPCPAPELLGGPSVFLFPPKPKDTLMISRTPEVTCVVVDVSHEDPEVKFNWYVDGVEVHN
AKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPE
NNYKTTPPVLDSDGSFFLYSKLTVDKSRWQQGNVFSCSVMHEALHNHYTQKSLSLSPGKID*FYTGVYILIGAGALMMLVGFLGCCGAVQESQCVIM*

*FIG. 5TT* hPDL1-Fc-*CD9tm2*-*KRAS*

ATGAGGATATTTGCTGTCTTTATATTCATGACCTACTGGCATTTGCTGAACGCATTTACTGTCACGGTTCCCAAGGACCTATATGTGGTAGAGTATGGT
AGCAATATGACAATTGAATGCAAATTCCCAGTAGAAAAACAATTAGACCTGGCTGCACTAATTGTCTATTGGGAAATGGAGGATAAGAACATTATTCAA
TTTGTGCATGGAGAGGAAGACCTGAAGGTTCAGCATAGTAGCTACAGACAGAGGGCCCGGCTGTTGAAGGACCAGCTCTCCCTGGGAAATGCTGCACTT
CAGATCACAGATGTGAAATTGCAGGATGCAGGGGTGTACCGCTGCATGATCAGCTATGGTGGTGCCGACTACAAGCGAATTACTGTGAAAGTCAATGCC
CCATACAACAAAATCAACCAAAGAATTTTGGTTGTGGATCCAGTCACCTCTGAACATGAACTGACATGTCAGGCTGAGGGCTACCCCAAGGCCGAAGTC
ATCTGGACAAGCAGTGACCATCAAGTCCTGAGTGGTAAGACCACCACCACCAATTCCAAGAGAGAGGAGAAGCTTTTCAATGTGACCAGCACACTGAGA
ATCAACACAACAACTAATGAGATTTTCTACTGCACTTTTAGGAGATTAGATCCTGAGGAAAACCATACAGCTGAATTGGTCATCCCAGAACTACCTCTG
GCACATCCTCCAAATGAAAGGATCGATGACAAAACTCACACATGCCCACCGTGCCCAGCACCTGAACTCCTGGGGGGACCGTCAGTCTTCCTCTTCCCC
CCAAAACCCAAGGACACCCTCATGATCTCCCGGACCCCTGAGGTCACATGCGTGGTGGTGGACGTGAGCCACGAAGACCCTGAGGTCAAGTTCAACTGG
TACGTGGACGGCGTGGAGGTGCATAATGCCAAGACAAAGCCGCGGGAGGAGCAGTACAACAGCACGTACCGTGTGGTCAGCGTCCTCACCGTCCTGCAC
CAGGACTGGCTGAATGGCAAGGAGTACAAGTGCAAGGTCTCCAACAAAGCCCTCCCAGCCCCCATCGAGAAAACCATCTCCAAAGCCAAAGGGCAGCCC
CGAGAACCACAGGTGTACACCCTGCCCCCATCCCGGGAGGAGATGACCAAGAACCAGGTCAGCCTGACCTGCCTGGTCAAAGGCTTCTATCCCAGCGAC
ATCGCCGTGGAGTGGGAGAGCAATGGGCAGCCGGAGAACAACTACAAGACCACGCCTCCCGTGCTGGACTCCGACGGCTCCTTCTTCCTCTACAGCAAG
CTCACCGTGGACAAGAGCAGGTGGCAGCAGGGGAACGTCTTCTCATGCTCCGTGATGCACGAGGCTCTGCACAACCACTACACGCAGAAGAGCCTCTCC
CTGTCTCCGGGTAAAATCGAT*TTCTACACAGGAGTCTATATTCTGATCGGAGCCGGCGCCCTCATGATGCTGGTGGGCTTCCTGGGCTGCTGCGGGGCT*
*GTGCAGGAGTCCCAGTGCAAAAAGAAGAAAAAGAAGAAGAAGACAAAGTGTGTAATTATGTAA*

MRIFAVFIFMTYWHLLNAFTVTVPKDLYVVEYGSNMTIECKFPVEKQLDLAALIVYWEMEDKNIIQFVHGEEDLKVQHSSYRQRARLLKDQLSLGNAAL
QITDVKLQDAGVYRCMISYGGADYKRITVKVNAPYNKINQRILVVDPVTSEHELTCQAEGYPKAEVIWTSSDHQVLSGKTTTTNSKREEKLFNVTSTLR
INTTTNEIFYCTFRRLDPEENHTAELVIPELPLAHPPNERIDDKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSD
IAVEWESNGQPENNYKTTPPVLDSDGSFFLYSKLTVDKSRWQQGNVFSCSVMHEALHNHYTQKSLSLSPGKID*FYTGVYILIGAGALMMLVGFLGCCGA*
*VQESQCKKKKKKKKTKCVIM*

*FIG. 5UU* mPDL1-mFc-*CD9tm2*

ATGAGGATATTTGCTGGCATTATATTCACAGCCTGCTGTCACTTGCTACGGGCGTTTACTATCACGGCTCCAAAGGACTTGTACGTGGTGGAGTATGGCAG
CAACGTCACGATGGAGTGCAGATTCCCTGTAGAACGGGAGCTGGACCTGCTTGCGTTAGTGGTGTACTGGGAAAAGGAAGATGAGCAAGTGATTCAGTTTG
TGGCAGGAGAGGAGGACCTTAAGCCTCAGCACAGCAACTTCAGGGGGAGAGCCTCGCTGCCAAAGGACCAGCTTTTGAAGGGAAATGCTGCCCTTCAGATC
ACAGACGTCAAGCTGCAGGACGCAGGCGTTTACTGCTGCATAATCAGCTACGGTGGTGCGGACTACAAGCGAATCACGCTGAAAGTCAATGCCCCATACCG
CAAAATCAACCAGAGAATTTCCGTGGATCCAGCCACTTCTGAGCATGAACTAATATGTCAGGCCGAGGGTTATCCAGAAGCTGAGGTAATCTGGACAAACA
GTGACCACCAACCCGTGAGTGGGAAGAGAAGTGTCACCACTTCCCGGACAGAGGGGATGCTTCTCAATGTGACCAGCAGTCTGAGGGTCAACGCCACAGCG
AATGATGTTTTCTACTGTACGTTTTGGAGATCACAGCCAGGGCAAAACCACACAGCGGAGCTGATCATCCCAGAACTGCCTGCAACACATCCTCCACAGAA
CAGGACTGGTTGTAAGCCTTGCATATGTACAGTCCCAGAAGTATCATCTGTCTTCATCTTCCCCCCAAAGCCCAAGGATGTGCTCACCATTACTCTGACTC
CTAAGGTCACGTGTGTTGTGGTAGACATCAGCAAGGATGATCCCGAGGTCCAGTTCAGCTGGTTTGTAGATGATGTGGAGGTGCACACAGCTCAGACGCAA
CCCCGGGAGGAGCAGTTCAACAGCACTTTCCGCTCAGTCAGTGAACTTCCCATCATGCACCAGGACTGGCTCAATGGCAAGGAGTTCAAATGCAGGGTCAA
CAGTGCAGCTTTCCCTGCCCCCATCGAGAAAACCATCTCCAAAACCAAAGGCAGACCGAAGGCTCCACAGGTGTACACCATTCCACCTCCCAAGGAGCAGA
TGGCCAAGGATAAAGTCAGTCTGACCTGCATGATAACAGACTTCTTCCCTGAAGACATTACTGTGGAGTGGCAGTGGAATGGGCAGCCAGCGGAGAACTAC
AAGAACACTCAGCCCATCATGGACACAGATGGCTCTTACTTCGTCTACAGCAAGCTCAATGTGCAGAAGAGCAACTGGGAGGCAGGAAATACTTTCACCTG
CTCTGTGTTACATGAGGGCCTGCACAACCACCATACTGAGAAGAGCCTCTCCCACTCTCCTGGTAAA*TTCTACACAGGAGTCTATATTCTGATCGGAGCCG*
*GCGCCCTCATGATGCTGGTGGGCTTCCTGGGCTGCTGCGGGGCTGTGCAGGAGTCCCAGTGCGTAATTATGTAA*

MRIFAGIIFTACCHLLRAFTITAPKDLYVVEYGSNVTMECRFPVERELDLLALVVYWEKEDEQVIQFVAGEEDLKPQHSNFRGRASLPKDQLLKGNAALQI
TDVKLQDAGVYCCIISYGGADYKRITLKVNAPYRKINQRISVDPATSEHELICQAEGYPEAEVIWTNSDHQPVSGKRSVTTSRTEGMLLNVTSSLRVNATA
NDVFYCTFWRSQPGQNHTAELIIPELPATHPPQNRTGCKPCICTVPEVSSVFIFPPKPKDVLTITLTPKVTCVVVDISKDDPEVQFSWFVDDVEVHTAQTQ
PREEQFNSTFRSVSELPIMHQDWLNGKEFKCRVNSAAFPAPIEKTISKTKGRPKAPQVYTIPPPKEQMAKDKVSLTCMITDFFPEDITVEWQWNGQPAENY
KNTQPIMDTDGSYFVYSKLNVQKSNWEAGNTFTCSVLHEGLHNHHTEKSLSHSPGK*FYTGVYILIGAGALMMLVGFLGCCGAVQESQCVIM*

*FIG. 5VV* mPDL1-mFc-*CD9tm2*-*KRAS*

ATGAGGATATTTGCTGGCATTATATTCACAGCCTGCTGTCACTTGCTACGGGCGTTTACTATCACGGCTCCAAAGGACTTGTACGTGGTGGAGTATGGCAGC
AACGTCACGATGGAGTGCAGATTCCCTGTAGAACGGGAGCTGGACCTGCTTGCGTTAGTGGTGTACTGGGAAAAGGAAGATGAGCAAGTGATTCAGTTTGTG
GCAGGAGAGGAGGACCTTAAGCCTCAGCACAGCAACTTCAGGGGGAGAGCCTCGCTGCCAAAGGACCAGCTTTTGAAGGGAAATGCTGCCCTTCAGATCACA
GACGTCAAGCTGCAGGACGCAGGCGTTTACTGCTGCATAATCAGCTACGGTGGTGCGGACTACAAGCGAATCACGCTGAAAGTCAATGCCCCATACCGCAAA
ATCAACCAGAGAATTTCCGTGGATCCAGCCACTTCTGAGCATGAACTAATATGTCAGGCCGAGGGTTATCCAGAAGCTGAGGTAATCTGGACAAACAGTGAC
CACCAACCCGTGAGTGGGAAGAGAAGTGTCACCACTTCCCGGACAGAGGGGATGCTTCTCAATGTGACCAGCAGTCTGAGGGTCAACGCCACAGCGAATGAT
GTTTTCTACTGTACGTTTTGGAGATCACAGCCAGGGCAAAACCACACAGCGGAGCTGATCATCCCAGAACTGCCTGCAACACATCCTCCACAGAACAGGACT
GGTTGTAAGCCTTGCATATGTACAGTCCCAGAAGTATCATCTGTCTTCATCTTCCCCCCAAAGCCCAAGGATGTGCTCACCATTACTCTGACTCCTAAGGTC
ACGTGTGTTGTGGTAGACATCAGCAAGGATGATCCCGAGGTCCAGTTCAGCTGGTTTGTAGATGATGTGGAGGTGCACACAGCTCAGACGCAACCCCGGGAG
GAGCAGTTCAACAGCACTTTCCGCTCAGTCAGTGAACTTCCCATCATGCACCAGGACTGGCTCAATGGCAAGGAGTTCAAATGCAGGGTCAACAGTGCAGCT
TTCCCTGCCCCCATCGAGAAAACCATCTCCAAAACCAAAGGCAGACCGAAGGCTCCACAGGTGTACACCATTCCACCTCCCAAGGAGCAGATGGCCAAGGAT
AAAGTCAGTCTGACCTGCATGATAACAGACTTCTTCCCTGAAGACATTACTGTGGAGTGGCAGTGGAATGGGCAGCCAGCGGAGAACTACAAGAACACTCAG
CCCATCATGGACACAGATGGCTCTTACTTCGTCTACAGCAAGCTCAATGTGCAGAAGAGCAACTGGGAGGCAGGAAATACTTTCACCTGCTCTGTGTTACAT
GAGGGCCTGCACAACCACCATACTGAGAAGAGCCTCTCCCACTCTCCTGGTAAA*TTCTACACAGGAGTCTATATTCTGATCGGAGCCGGCGCCCTCATGATG*
*CTGGTGGGCTTCCTGGGCTGCTGCGGGGCTGTGCAGGAGTCCCAGTGCAAAAAGAAGAAAAAGAAGAAGAAGACAAAGTGTGTAATTATGTAA*

MRIFAGIIFTACCHLLRAFTITAPKDLYVVEYGSNVTMECRFPVERELDLLALVVYWEKEDEQVIQFVAGEEDLKPQHSNFRGRASLPKDQLLKGNAALQIT
DVKLQDAGVYCCIISYGGADYKRITLKVNAPYRKINQRISVDPATSEHELICQAEGYPEAEVIWTNSDHQPVSGKRSVTTSRTEGMLLNVTSSLRVNATAND
VFYCTFWRSQPGQNHTAELIIPELPATHPPQNRTGCKPCICTVPEVSSVFIFPPKPKDVLTITLTPKVTCVVVDISKDDPEVQFSWFVDDVEVHTAQTQPRE
EQFNSTFRSVSELPIMHQDWLNGKEFKCRVNSAAFPAPIEKTISKTKGRPKAPQVYTIPPPKEQMAKDKVSLTCMITDFFPEDITVEWQWNGQPAENYKNTQ
PIMDTDGSYFVYSKLNVQKSNWEAGNTFTCSVLHEGLHNHHTEKSLSHSPGK*FYTGVYILIGAGALMMLVGFLGCCGAVQESQCKKKKKKKKTKCVIM*

*FIG. 5WW*

EAU Dosing Test Articles

| | Unmodified Exosomes (IVT) | mPD-L1-Fc-GPI Exosomes 1X (IVT) | mPD-L1-Fc-GPI Exosomes 10X (IVT) | mPD-L1 Exosomes (IV) |
|---|---|---|---|---|
| Dose | 2 μl | 2 μl | 2 μl | 5ml/kg |
| Total protein concentration | 40 μg/ml | 40 μg/ml | 400 μg/ml | 40 μg/ml |
| Total protein administered | 80 ng /eye | 80 ng /eye | 800 ng /eye | 50 μg/ animal (~200 μg/kg) |
| Exosome concentration | $5.7x10^{10}$/ml | $2.34x10^{10}$/ml | $2.34x10^{11}$/ml | $2.34x10^{10}$/ml |
| Total exosomes administered | $4.7x10^7$ | $4.7x10^7$ | $4.7x10^8$ | $2.93x10^{10}$ |

EAU Dosing Schedule

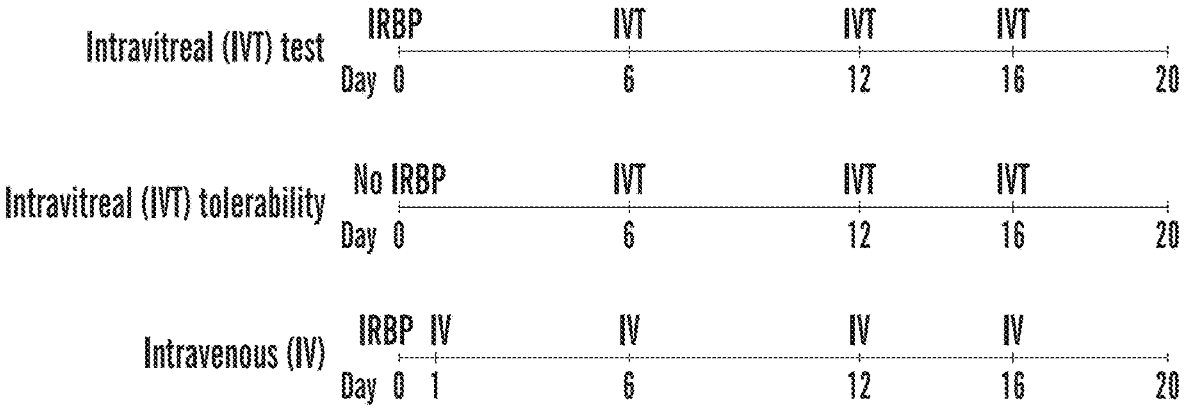

*FIG. 13A*

Type II Membrane Protein Constructs

Multiple Protein Display

Comparative Proteomics

| | Cell number | Glucose | Lactate | mPD-L1 ng/ml |
|---|---|---|---|---|
| Day 0 | 10,000 | 26.85492802 | 0 | NA |
| Day 1 | 1.11E+04 | 22.86821705 | 0 | 7.33 |
| Day 2 | 5.43E+04 | 21.20708749 | 2.775310835 | |
| Day 2 Post | 5.43E+04 | 23.97563677 | 0 | 9.61 |
| Day 3 | 5.34E+04 | 18.99224806 | 5.994671403 | |
| Day 3 Post | 5.34E+04 | 24.58471761 | 0 | 15.77 |
| Day 4 | 5.60E+04 | 18.16168328 | 3.663410302 | 19.05 |
| Day 5 | 7.51E+04 | 15.94684385 | 10.32415631 | 44.89 |

Tetraspanin characterization of exosomes internally loaded with NanoLuc Luciferase Proposed mechanism of PD-1 clustering agonism

ENGINEERED EXTRACELLULAR VESICLES COMPRISING FUSION PROTEINS

CROSS-REFERENCE TO RELATED APPLICATIONS

This application is a division of U.S. application Ser. No. 17/377,550, filed Jul. 16, 2021, now U.S. Pat. No. 11,578,116, which is a continuation of International Application No. PCT/US2021/016949, filed Feb. 5, 2021, which designated the U.S., and also claims the benefit of priority under 35 U.S.C. § 119(e) of U.S. Provisional Application No. 62/970,374, filed Feb. 5, 2020, the contents of each of which are incorporated herein by reference in their entirety.

SEQUENCE LISTING

The instant application contains a Sequence Listing which has been submitted electronically in XML format and is hereby incorporated by reference in its entirety. Said XML copy, created on Nov. 9, 2022, is named 085172_000001USD1_ST.26.xml and is 724,326 bytes in size.

FIELD OF THE INVENTION

This invention relates to the generation of artificial synapses or extracellular vesicles, including features of extracellular vesicles engineered to deliver signaling, for therapeutic use, including treatment of immune diseases and cancer.

BACKGROUND

Extracellular vesicles (EVs) play a critical role in intercellular communication by transferring microRNAs, lipids, and proteins to neighboring cells. The delivery of encapsulated molecules within EVs is a highly promising strategy as a therapeutic platform in many contexts, exploiting the unique biophysical and biochemical characteristics of extracellular vesicles (EVs). However, there remains a great need in the art for a flexible and dynamic platform, where specific biological signals can be reliably targeted without off-target effects and that provide a robust cellular response to achieve a therapeutic effect, such as modulating inflammation.

SUMMARY

The compositions and methods provided herein are based, in part, on the discovery that extracellular vesicles can be used to express engineered fusion polypeptides that can modulate biological signal generation. These engineered vesicles, also termed artificial synapses, adopt the hallmark biophysical and biochemical features of extracellular vesicles, but are further engineered with vesicle targeting domains (e.g., sticky binders) and signaling domains, optionally joined by a linker with specific functions. The fusion polypeptides provided herein are designed and produced as nucleic acid constructs (e.g., vectors) and expressed in cells, such as mammalian cells. In particular, the vesicle targeting domain of each fusion polypeptide anchors the polypeptide to the extracellular vesicle lipid membrane, thereby presenting the signaling domain(s) of the polypeptide. The signaling domains on or within the vesicle membrane can make contact with recipient cells via target polypeptides (e.g., receptors on the extracellular surface of the recipient cell). Importantly, this strategy can allow for kinetically favorable signal generation and signal propagation. This includes, for example, increasing density of agonist presentation to support receptor clustering of a target receptor located on a target cell—an onerous barrier for traditional receptor targeting strategies.

This strategy was applied to alter immune checkpoint signaling, by engineering artificial synapses through genetic constructs with lipid binding glycosylphosphatidylinositol (GPI) sticky binders joined with programmed death-ligand 1 (PD-L1) signaling domain, e.g., human programmed death-ligand 1 (hPD-L1), expressed in cells and capable of attachment to exosomes. Isolation, purification, and analysis of artificial synapses revealed a high density of signaling domains of the hPD-L1-GPI fusion polypeptide. The hPD-L1 artificial synapse exosomes further demonstrated enhanced agonist signaling than soluble PD-L1 ligand alone, supporting receptor clustering on a target cell. When applied to a model of experimental autoimmune uveoretinitis (EAU), a statistically significant reduction in EAU symptoms was observed.

Thus, in one aspect, provided herein is an engineered extracellular vesicle or artificial vesicle comprising: at least one fusion polypeptide comprising: at least one protein of interest (POI) domain; and at least one vesicle targeting domain. In some embodiments of any of the aspects, the engineered extracellular vesicle is an exosome. In some embodiments, of any of the aspects, the fusion protein further comprises at least one linker. In some embodiments of any of the aspects, the POI domain can substantially bind to a target polypeptide.

In another aspect, provided herein is an engineered extracellular vesicle comprising: at least one fusion polypeptide comprising:

(i) at least one protein of interest (POI) domain or a fragment thereof; and (ii) at least one vesicle targeting domain, wherein the POI domain is in an extracellular position relative to a lipid membrane of the extracellular vesicle.

In another aspect, provided herein is an engineered extracellular vesicle comprising:

(a) a first fusion polypeptide comprising:

(i) at least one protein of interest (POI) domain or a fragment thereof; and (ii) at least one vesicle targeting domain, wherein the at least one POI domain is in an extracellular position relative to a lipid membrane of the extracellular vesicle, (b) a second fusion polypeptide comprising:

(i) at least one protein of interest (POI) domain or a fragment thereof; and (ii) at least one vesicle targeting domain, wherein the POI domain is in an extracellular position relative to a lipid membrane of the extracellular vesicle, and wherein the at least one vesicle targeting domain is within a lipid membrane of the extracellular vesicle.

In another aspect, provided herein is an extracellular vesicle composition comprising: a plurality of artificial synapses, wherein each artificial synapse comprises (i) an extracellular vesicle; (ii) one or more sticky binders; and (iii) one or more signaling domains.

In another aspect, provided herein is a composition comprising a plurality of the engineered extracellular vesicles provided herein.

In another aspect, provided herein is a composition comprising two or more of the engineered extracellular vesicles provided herein.

In another aspect, provided herein is a composition comprising three or more of the engineered extracellular vesicles provided herein.

In another aspect, provided herein is a method of producing the engineered extracellular vesicle or the compositions provided herein, comprising:

(a) providing a population of cells expressing a vector construct encoding one or more sticky binder and one or more signaling domains; and (b) isolating a plurality of artificial synapses from the population of cells.

In another aspect, provided herein is a method of producing the engineered extracellular vesicle or the compositions provided herein, comprising:

(a) providing a population of cells expressing a vector construct encoding one or more sticky binder and one or more signaling domains; and (b) isolating a plurality of artificial synapses from the population of cells; and (c) purifying the plurality of artificial synapses from the population of cells.

In another aspect, provided herein is a method of modulating inflammation in a subject, the method comprising:

administering a composition comprising a plurality of engineered extracellular vesicles to a subject in need thereof, wherein the engineered extracellular vesicles comprise at least one fusion polypeptide comprising:

(i) at least one protein of interest (POI) domain or a fragment thereof; and (ii) at least one vesicle targeting domain.

In another aspect, provided herein is a use of a composition or engineered extracellular vesicle provided herein for the treatment of an inflammatory disease or condition.

In another aspect, provided herein is a use of a composition or engineered extracellular vesicle provided herein for the treatment of an autoimmune disease or condition.

In another aspect, provided herein is a use of a composition or engineered extracellular vesicle provided herein for the treatment of cancer.

In one embodiment of any of the aspects, the engineered extracellular vesicle is an exosome.

In another embodiment of any of the aspects, the protein of interest (POI) domain or a fragment thereof is a N-terminal domain of the fusion polypeptide. In another embodiment of any of the aspects, the POI domain is selected from the group consisting of: Table 1. In another embodiment of any of the aspects, the POI domain is PD-L1 or a fragment thereof. In another embodiment of any of the aspects, the POI domain is PD-L2 or a fragment thereof. In another embodiment of any of the aspects, the POI domain is FGL1 or a fragment thereof. In another embodiment of any of the aspects, the POI domain is 4-1BBL or a fragment thereof. In another embodiment of any of the aspects, the POI domain is CTLA-4 or a fragment thereof. In another embodiment of any of the aspects, the protein of interest (POI) domain is HVEM or a fragment thereof.

In another embodiment of any of the aspects, the vesicle targeting domain is a C-terminal domain of the fusion polypeptide. In another embodiment of any of the aspects, the vesicle targeting domain is in a luminal position relative to the lipid membrane of the extracellular vesicle. In another embodiment of any of the aspects, the vesicle targeting domain in an exterior position relative to the lipid membrane of the extracellular vesicle. In another embodiment of any of the aspects, the vesicle targeting domain is selected from the group consisting of: Table 3. In another embodiment of any of the aspects, the vesicle targeting domain is selected from the group consisting of: a Glycosylphosphatidylinositol (GPI) anchor, a fatty acylation site, and a prenylation site. In another embodiment of any of the aspects, the vesicle targeting domain is C1C2. In another embodiment of any of the aspects, the vesicle targeting domain is a GPI anchor.

In another embodiment of any of the aspects, the fusion polypeptide comprises at least two POI domains and/or at least two exosome targeting domains.

In another embodiment of any of the aspects, the POI domain substantially binds to one or more of a target polypeptide. In another embodiment of any of the aspects, the target polypeptide is selected from the group consisting of: Table 2.

In another embodiment of any of the aspects, the fusion polypeptide further comprises a peptide linker. In another embodiment of any of the aspects, the fusion polypeptide further comprises a fragment crystallizable region (Fc) domain. In another embodiment of any of the aspects, the linker is in an exterior position relative to the lipid membrane of the extracellular vesicle. In another embodiment of any of the aspects, the linker is a transmembrane linker. In another embodiment of any of the aspects, the linker is in a luminal position relative to the lipid membrane of the extracellular vesicle.

In another embodiment of any of the aspects, the engineered extracellular vesicle does not comprise an endogenous POI polypeptide.

In another embodiment of any of the aspects, the composition further comprises a pharmaceutically acceptable carrier.

In another embodiment of any of the aspects, the one or more sticky binders or the vesicle targeting domain is selected from the group consisting of: a GPI anchor, a fatty acylation site, and a prenylation site.

In another embodiment of any of the aspects, the signaling domain or the protein of interest comprises one or more of: PD-L1, PD-L2, CTLA-4 (CD152), 4-1BBL (CD137L), HVEM (CD270), FGL1, OX-2 (CD200), Galectin-9, PVR (CD155), Nectin-2 (CD112) isoform alpha, Nectin-2 (CD112) isoform beta, Nectin-2 (CD112) isoform delta, IL-10, TSG-6, B7-H3 (CD276), B7-H4 (VTCN1), B7-H5 (VISTA), B7-H7 (HHLA2), BTNL1, VSIG8, VSIG3 (IGSF11), VSIG4, TIM-3 (HAVCR2), TIM-4 (TIMD4), CEACAM1, BTN3A1, BTN3A2, BTN2A1, BTNL8, BTN2A2, BTN1A1, TIGIT, CD27L (CD70), CD30L (CD153), GITRL, CD40L (CD154), LIGHT (CD258), TL1, CD80, CD86, LFA-3 (CD58), SLAM (CD150), CD40, CD28, CD28H, CD2, LFA-3 (CD58), CD48, CD226, DR3, DcR3, FasL, TIM-1 (CD365), PD-1, or active fragment thereof.

In another embodiment of any of the aspects, the isolating is via size exclusion chromatography. In another embodiment of any of the aspects, the purifying is via multimodal chromatography. In another embodiment of any of the aspects, the method further comprises performing an assay for POI binding to a target polypeptide.

In another embodiment of any of the aspects, the vector construct further encodes a promoter. In another embodiment of any of the aspects, the promoter is a tissue-specific promoter or an inducible promotor.

In one embodiment of any of the aspects, the method further comprises selecting a subject that has or is suspected of having an autoimmune disease or an inflammatory disease or condition. In another embodiment of any of the aspects, the inflammatory disease and/or condition is acute.

In another embodiment of any of the aspects, the inflammatory related disease and/or condition is chronic.

In another embodiment of any of the aspects, administering the composition provided herein comprises injection, topical administration, or inhalation.

A BRIEF DESCRIPTION OF THE DRAWINGS

FIG. 1 shows construct representation of fusion polypeptides for labeling an exosome surface with Type I membrane proteins.

FIG. 2A shows nucleic acid and translated protein sequences of full-length Phosphatidylserine binding: Lactadherin (MFGE8) C1C2. Underlined nucleic acid sequence highlights the sequence translated to the C1C2 protein. Bold and underlined text highlights the C1C2 domain used to anchor signaling domains of interest (i.e., PD-L1 extracellular domain) onto the surface of the Inventors' artificial synapses. FIG. 2B shows nucleic acid and translated protein sequences of full length CD55 (DAF) Glycosylphosphatidylinositol (GPI) anchor. Bold and underlined text highlights the GPI anchor domain used to anchor signaling domains of interest (i.e., PD-L1 extracellular domain) onto the surface of the Inventors' artificial synapses engineered from exosomes. FIGS. 2A-2B disclose SEQ ID NOS: 199-200, and 196-197, respectively, in order of appearance.

FIG. 3 demonstrates the nucleic acid and translated protein sequence for the Fc linker used in genetically engineered constructs is shown in bold and underlined. FIG. 3 discloses SEQ ID NOS: 219-220, respectively, in order of appearance.

FIG. 4A demonstrates nucleic acid and translated protein sequence of human PD-L1 (CD274). Bold and underlined sequence highlights the PD-L1 extracellular domain used in the Inventors' artificial synapses engineered from exosomes. FIG. 4B demonstrates nucleic acid and protein sequence of human PD-L2. Bold and underlined sequence highlights the PD-L2 extracellular domain used in the Inventors' artificial synapses engineered from exosomes. FIG. 4C shows mRNA and protein sequence of human CTLA-4 (CD152). Bold and underlined sequence highlights the CTLA-4 extracellular domain used in the Inventors' artificial synapses. FIGS. 4A-4C disclose SEQ ID NOS: 1-2, 5-6, and 9-10, respectively, in order of appearance.

FIG. 5A shows an exemplary embodiment of pcDNA5-FRT cloning vector with a gene sequence coding for a fusion polypeptide inserted into a multiple cloning site. FIG. 5B shows an exemplary embodiment of the Gateway® destination vector pEF5-FRT-V5-DEST with a gene sequence coding for a fusion polypeptide inserted into a multiple cloning site. The vectors were used for constitutive high-level expression of fusion polypeptide described herein in mammalian cells. FIG. 5C shows the nucleic acid and protein sequence for the hCTLA4-Fc-GPI fusion polypeptide wherein the text for the signaling domain is bolded, Fc linker is underlined, and sticky binder is italicized. FIG. 5D shows the nucleic acid and protein sequence for the hPDL1-GPI-P2A-hHVEM-GPI fusion polypeptide wherein the text for the signaling domain hPDL1 and hHVEM are bolded, P2A sequence is underlined, and sticky binder GPI is italicized. With P2A included, a self-cleaving peptide sequence, artificial synapses with this feature will have both hPDL1-GPI and hHVEM-GPI loaded onto the surface. FIG. 5E shows the nucleic acid and protein sequence for the hPDL1-GPI-P2A-hFGL1-GPI fusion polypeptide wherein the text for the signaling domain hPDL1 and hFGL1 are bolded, P2A sequence is underlined, and sticky binder GPI is italicized. With P2A included, a self-cleaving peptide sequence, artificial synapses with this feature will have both hPDL1-GPI and FGL1-GPI loaded onto the surface. FIG. 5F shows the nucleic acid and protein sequence for the hPDL1-GPI fusion polypeptide wherein the text for the signaling domain hPDL1 is bolded and sticky binder GPI is italicized. FIG. 5G shows the nucleic acid and protein sequence for the hPDL1-Fc-GPI fusion polypeptide wherein the text for the signaling domain hPDL1 is bolded, Fc is underlined, and sticky binder GPI is italicized. FIG. 5H shows the nucleic acid and protein sequence for the hPDL2-Fc-GPI fusion polypeptide wherein the text for the signaling domain hPDL2 is bolded, Fc is underlined, and sticky binder GPI is italicized. FIG. 5I shows the nucleic acid and protein sequence for the hPDL1-C1C2 fusion polypeptide wherein the text for the signaling domain hPDL1 is bolded and sticky binder C1C2 is italicized. FIG. 5J shows the nucleic acid and protein sequence for the hPDL2-C1C2 fusion polypeptide wherein the text for the signaling domain hPDL2 is bolded and sticky binder C1C2 is italicized. FIG. 5K shows the nucleic acid and protein sequence for the 4F2-h41BBL fusion polypeptide wherein the text for the signaling domain h41BBL is bolded and sticky binder 4F2 is italicized. FIG. 5L shows the nucleic acid and protein sequence for the hPDL1-4Fc-GPI fusion polypeptide wherein the text for the signaling domain hPDL1 is bolded, 4Fc is underlined, and sticky binder GPI is italicized. FIG. 5M shows the nucleic acid and protein sequence for the Myr-NanoLuc® Luciferase fusion polypeptide wherein the text for the signaling domain NanoLuc® Luciferase is bolded, and sticky binder Myr is italicized. FIG. 5N shows the nucleic acid and protein sequence for the Myr-mScarlet fusion polypeptide wherein the text for the signaling domain mScarlet is bolded, and sticky binder Myr is italicized. FIG. 5O shows the nucleic acid and protein sequence for the secreted isoform of hPDL1 (SecPDL1) fusion polypeptide hSecPDL1-GPI wherein the text for the signaling domain hSecPDL1 is bolded and sticky binder GPI is italicized. FIG. 5P shows the nucleic acid and protein sequence for the Tfr2-h41BBL fusion polypeptide wherein the text for the signaling domain h41BBL is bolded and sticky binder Tfr2 is italicized. FIG. 5Q shows the nucleic acid and protein sequence for the CD9tm3-h41BBL fusion polypeptide wherein the text for the signaling domain h41BBL is bolded and sticky binder CD9tm3 is italicized. FIG. 5R shows the nucleic acid and protein sequence for the Myr/Palm-4F2-h41BBL fusion polypeptide wherein the text for the signaling domain h41BBL is bolded, sticky binder Myr/Palm is underlined, and sticky binder 4F2 is italicized. FIG. 5S shows the nucleic acid and protein sequence for the Myr/Palm-Link-h41BBL fusion polypeptide wherein the text for the signaling domain h41BBL is bolded, sticky binder Myr/Palm is italicized and underlined, and sticky binder Link (in this embodiment a GSSG linker (SEQ ID NO: 319)) is in regular text (not underlined and not italicized). FIG. 5T shows the nucleic acid and protein sequence for the hPDL1-Link-GPI fusion polypeptide wherein the text for the signaling domain hPDL1 is bolded, Link is underlined (in this embodiment a GSSG linker (SEQ ID NO: 319)), and sticky binder GPI is italicized. FIG. 5U shows the nucleic acid and protein sequence for the secreted isoform of hPDL1 (SecPDL1) fusion polypeptide hSecPDL1-CD9tm2 wherein the text for the signaling domain hSecPDL1 is bolded and sticky binder CD9tm2 is italicized. FIG. 5V shows the nucleic acid and protein sequence for the secreted isoform of hPDL1 (SecPDL1) fusion polypeptide hSecPDL1-CD9tm2-KRAS wherein the text for the signaling domain hSecPDL1 is bolded, sticky binder CD9tm2 is italicized, and sticky binder KRAS is italicized and underlined. FIG. 5W shows the nucleic acid and protein sequence for the secreted isoform of hPDL1 (SecPDL1) fusion polypeptide hSecPDL1-CD9tm4 wherein the text for the signaling domain hSecPDL1 is bolded and sticky binder CD9tm4 is italicized. FIG. 5X shows the nucleic acid and protein sequence for the secreted isoform of hPDL1 (SecPDL1) fusion polypeptide hSecPDL1-CD81 wherein the text for the signaling domain hSecPDL1 is bolded and sticky binder CD81 is italicized. FIG. 5Y shows the nucleic acid and protein sequence for the hCD200-Fc-GPI fusion polypeptide wherein the text for the signaling domain hCD200 is bolded, Fc is underlined, and sticky binder GPI is italicized, a spacer sequence domain (regular text, not underlined and not italicized) separates hCD200 sequence from the Fc domain, a spacer sequence domain (regular text, not underlined and not italicized) separates Fc sequence from the GPI. FIG. 5Z shows the nucleic acid and protein sequence for the hFGL1-GPI fusion polypeptide wherein the text for the signaling domain hFGL1 is bolded, and sticky binder GPI is italicized. FIG. 5AA shows the nucleic acid and protein sequence for the hGal9-Fc-GPI fusion polypeptide wherein the text for the signaling domain hGal9 is bolded, Fc is underlined, and sticky binder GPI is italicized. FIG. 5BB shows the nucleic acid and protein sequence for the hCD200-GPI fusion polypeptide wherein the text for the signaling domain hCD200 is bolded, and sticky binder GPI is italicized. FIG. 5CC shows the nucleic acid and protein sequence for the hGal9-GPI fusion polypeptide wherein the text for the signaling domain hGal9 is bolded, and sticky binder GPI is italicized. FIG. 5DD shows the nucleic acid and protein sequence for the hHVEM-GPI fusion polypeptide wherein the text for the signaling domain hHVEM is bolded, and sticky binder GPI is italicized. FIG. 5EE shows the nucleic acid and protein sequence for the hPDL2-GPI fusion polypeptide wherein the text for the signaling domain hPDL2 is bolded, and sticky binder GPI is italicized. FIG. 5FF shows the nucleic acid and protein sequence for the hTSG6-GPI fusion polypeptide wherein the text for the signaling domain hTSG6 is bolded, and sticky binder GPI is italicized. FIG. 5GG shows the nucleic acid and protein sequence for the hHVEM-Fc-GPI fusion polypeptide wherein the text for the signaling domain hHVEM is bolded, Fc is underlined, and sticky binder GPI is italicized. FIG. 5HH shows the nucleic acid and protein sequence for the mCTLA4-Fc-GPI fusion polypeptide wherein the text for the signaling domain mCTLA4 is bolded, Fc is underlined, and sticky binder GPI is italicized. FIG. 5II shows the nucleic acid and protein sequence for the mPDL1-C1C2 fusion polypeptide wherein the text for the signaling domain mPDL1 is bolded and sticky binder C1C2 is italicized. FIG. 5JJ shows the nucleic acid and protein sequence for the mPDL1-Fc-GPI fusion polypeptide wherein the text for the signaling domain mPDL1 is bolded, Fc is underlined, and sticky binder GPI is italicized. FIG. 5KK shows the nucleic acid and protein sequence for the mPDL1-GPI fusion polypeptide wherein the text for the signaling domain mPDL1 is bolded and sticky binder GPI is italicized. FIG. 5LL shows the nucleic acid and protein sequence for the mPDL2-C1C2 fusion polypeptide wherein the text for the signaling domain mPDL2 is bolded and sticky binder C1C2 is italicized. FIG. 5MM shows the nucleic acid and protein sequence for the mPDL2-Fc-GPI fusion polypeptide wherein the text for the signaling domain mPDL2 is bolded, Fc is underlined, and sticky binder GPI is italicized. FIG. 5NN shows the nucleic acid and protein sequence for the mPDL1-mFc-GPI fusion polypeptide wherein the text for the signaling domain mPDL2 is bolded, mFc is underlined, and sticky binder GPI is italicized. FIG. 5OO shows the nucleic acid and protein sequence for the mPDL2-GPI fusion polypeptide wherein the text for the signaling domain mPDL2 is bolded and sticky binder GPI is italicized. FIG. 5PP shows the nucleic acid and protein sequence for the mPDL1-GPI-P2A-mHVEM-GPI fusion polypeptide wherein the text for the signaling domain mPDL1 and mHVEM are bolded, P2A sequence is underlined, and sticky binder GPI is italicized. With P2A included, a self-cleaving peptide sequence, artificial synapses with this feature will have both mPDL1-GPI and mHVEM-GPI loaded onto the surface. FIG. 5QQ shows the nucleic acid and protein sequence for the hPDL1-ADAM10 fusion polypeptide wherein the text for the signaling domain mPDL1 is bolded and sticky binder ADAM10 is italicized. FIG. 5RR shows the nucleic acid and protein sequence for the hPDL1-4Fc-CD9tm2 fusion polypeptide wherein the text for the signaling domain hPDL1 is bolded, 4Fc is underlined, and sticky binder CD9tm2 is italicized. FIG. 5SS shows the nucleic acid and protein sequence for the fusion polypeptide hPDL1-4Fc-CD9tm2-KRAS wherein the text for the signaling domain hPDL1 is bolded, sticky binder 4Fc is underlined, sticky binder CD9tm2 is italicized, and sticky binder KRAS is italicized and underlined. FIG. 5TT shows the nucleic acid and protein sequence for the hPDL1-Fc-CD9tm2 fusion polypeptide wherein the text for the signaling domain hPDL1 is bolded, Fc is underlined, and sticky binder CD9tm2 is italicized. FIG. 5UU shows the nucleic acid and protein sequence for the fusion polypeptide hPDL1-Fc-CD9tm2-KRAS wherein the text for the signaling domain hPDL1 is bolded, sticky binder Fc is underlined, sticky binder CD9tm2 is italicized, and sticky binder KRAS is italicized and underlined. FIG. 5VV shows the nucleic acid and protein sequence for the mPDL1-mFc-CD9tm2 fusion polypeptide wherein the text for the signaling domain mouse PDL1 (mPDL1) is bolded, mouse mFc (mFc) is underlined, and sticky binder CD9tm2 is italicized. FIG. 5WW shows the nucleic acid and protein sequence for the fusion polypeptide mPDL1-mFc-CD9tm2-KRAS wherein the text for the signaling domain mPDL1 is bolded, sticky binder mFc is underlined, sticky binder CD9tm2 is italicized, and sticky binder KRAS is italicized and underlined. Wherein mPDL1 and mFc are mouse PDL1 and mouse Fc, respectively. FIGS. 5C-5WW disclose SEQ ID NOS: 223-224, 283-284, 239-240, 225-226, 229-230, 233-234, 227-228, 231-232, 235-238, 243-244, 241-242, 245-282, and 285-316, respectively, in order of appearance.

FIG. 6 shows hPD-L1-Fc-GPI artificial synapse purification via a multimodal resin marketed for exosome purification. Large MW artificial synapses elute in the first fraction as shown by the high hPD-L1 concentration and artificial synapse quantity (2.26E9 synapses/ml) in elution 1. Clean in place (CIP) fractions show bound and eliminated proteins from the Inventors' artificial synapse elution.

FIG. 7 shows hPDL1-Fc-GPI exosome purification via size exclusion chromatography using a resin marketed for exosome purification. Artificial synapses engineered from exosomes eluted from via a multimodal resin may be further purified via size exclusion chromatography using a resin marketed for exosome purification as shown here. Using a size exclusion chromatography, artificial synapses elute in fractions 7-9. Total protein (determined by Qubit™) and hPD-L1 ng/ml (determined by ELISA) of each fraction is shown in the graph. Bars show exosome number per ml (i.e., 1E10 exosomes/ml etc.). Fractions 7-9 contain >99% purified artificial synapses. Fractions 7-9 are pooled and may be concentrated using a filtration device, for example a 10K MWCO Amicon® centrifugal filter. Final purified product may be filtered through a low protein binding filter, for example a 0.2 μm or 0.45 μm PES filter.

FIG. 8 shows hPD-L1 Expression on exosomes, quantity and hPD-L1 concentration was determined in size exclusion chromatography fractions 7-9. Knowing the molecular weight of engineered hPD-L1, the Inventors can determine the number of hPD-L1 molecules per exosome to be approximately between 12 and 40 hPD-L1/exosome. This value is consistent between different purification runs and constructs.

FIG. 9 shows the purification of hPD-L2-Fc-GPI artificial synapses engineered from exosomes via multimodal resin marketed for exosome purification. This graph shows Abs 280 of fractions and quantity of hPDL2 in indicated fractions. Exosomes eluted in Elution 1. Clean in place (CIP) fractions show bound and eliminated proteins from the Inventors' artificial synapse elution.

FIG. 10 shows purification of hPD-L2-Fc-GPI labeled exosomes via size exclusion column as shown here using size exclusion resin marketed for exosome purification. Fractions containing large molecular weight exosomes (Fractions 7-9) showed high hPD-L2 concentration indicating that the purified exosomes contain hPD-L2-Fc-GPI. Total protein (determined by Qubit™) and hPD-L1 ng/ml (determined by ELISA) of each fraction is shown in the graph. Lower molecular weight unbound hPD-L2-Fc-GPI eluted at later fractions.

FIG. 11 shows hCTLA4-Fc-GPI exosome purification via size exclusion column as shown here using size exclusion resin marketed for exosome purification. Using size exclusion chromatography, exosomes elute in fractions 7-9. Total protein (determined by Qubit™) and hCTLA4 ng/ml (determined by ELISA) of each fraction is shown in the graph. Fractions 7-9 are pooled and contain >99% purified exosomes. Pooled exosome fractions may then be concentrated using a filtration device, for example a 10K MWCO Amicon® centrifugal filter. Final purified product may be filtered through a low protein binding filter, for example a 0.2 μm or 0.45 μm PES filter. Knowing the molecular weight of engineered hCTLA-4, the Inventors can determine the number of hCTLA-4 molecules per exosome to be approximately 233 hCTLA-4/exosome.

FIG. 12A shows PD-1 Signaling Bioassay Method. The Inventors established a method to validate that PD-L1 and PD-L2 artificial synapses engineered from exosomes can bind to cells expressing PD-1 ligand. To perform this validation method, the Inventors modified the PathHunter® PD-1 Signaling Bioassay from DISCOVERX® Briefly, the PathHunter® PD-1 Signaling Bioassay relies on the well-established PathHunter® Enzyme Fragment Complementation (EFC) technology to interrogate receptor activity. EFC consists of a split-galactosidase (β-gal) enzyme: the Enzyme Donor (ED) and Enzyme Acceptor (EA) fragments which independently have no β-gal activity. However, when forced to complement they form an active β-gal enzyme that will hydrolyze substrate to produce a chemiluminescent signal. The PathHunter® PD-1 Signaling Bioassay consists of human cells engineered to stably express an ED-tagged PD-1 receptor, while EA is fused to the phosphotyrosine-binding SH2 domain of the intracellular signaling protein, SHP1. Ligand or antibody-induced activation of the receptor results in phosphorylation of the receptor's cytosolic tail. Ligand engagement, through addition of ligand-presenting artificial synapses engineered from exosomes, results in phosphorylation of PD-1, leading to the recruitment of SHP1-EA. This forces complementation of the EFC components to create an active β-gal enzyme. This active enzyme hydrolyzes substrate to create chemiluminescence as a measure of receptor activity. Addition of an antagonist (e.g., antibody to PD-L1) blocks PD-1 signaling, and will prevent complementation, resulting in a loss of signal. FIG. 12B shows that the Inventors obtained approximately 10,000× higher increase in Relative Light Units (RLU) in Jurkat signaling cells treated with PD-L1 or PD-L2 labeled artificial synapses when compared to soluble PD-L1-Fc or PD-L2-Fc ligand, respectively. Meaning, it took 10,000× less μg/ml of PD-L1 or PD-L2 on artificial synapses than solubilized PD-L1-Fc or PD-L2 ligand to achieve the same RLU signaling. Shown is a dose-response curve for the PD-L1 and PD-L2 artificial synapses engineered from exosomes vs soluble PD-L1 and PD-L2 signaling bioassay.

FIG. 13A-13C shows experimental EAU outline Test Agent A—unmodified exosomes, Test Agent B—mPDL1-Fc-GPI artificial synapses engineered from exosomes 40 μg/ml, Test Agent C—mPDL1-Fc-GPI artificial synapses engineered from exosomes 400 μg/ml, IRBP-interphotoreceptor retinoid-binding protein (IRBP) peptide, BID-Bis in die (2× daily) p.o.—Per os (orally) (FIG. 13B) EAU symptoms appear at day 6. 1st intravitreal injection and 2nd intravenous injections are performed on Day 6. There is a statistically significant initial reduction in EAU in mouse PD-L1 (mPD-L1) artificial synapses engineered from exosomes treated rats via either the intravitreal and intravenous delivery modes. 2nd intravitreal and 3rd intravenous injections are performed on Day 12. There appears to be a more rapid rate of resolution in the 1× intravitreal and intravenous groups. (FIG. 13C) Weight of rats was monitored throughout the study. 3rd intravitreal and 4th intravenous injections are performed on Day 16. There does not appear to be any significant change in EAU in any of the test groups. The aforementioned results provide proof of principle of successfully treating an autoimmune condition (i.e., EAU) with human cell derived artificial synapses with PD-L1.

FIG. 14 shows 2 types of ligands displayed on the exosome surface (Type I and Type II membrane proteins). Type I membrane proteins wherein the N-Terminus is on the luminal (interior) side of the exosome membrane and the C-Terminus is on the exterior of the exosome.

Type II membrane proteins wherein the N-Terminus is on the exterior while the C-Terminus is on the interior.

FIG. 15 shows a schematic representation of several embodiments of Type I membrane protein constructs, which include but are not limited to: PD-L1, PD-L2, FGL1, OX40L. FIG. 15 discloses "GSSG link" as SEQ ID NO: 319.

FIG. 16 shows a schematic representation of several embodiments of the surface of an extracellular vesicle engineered with a Type I membrane protein of interest (POI) with a variable membrane anchor. Vesicle targeting sequences such as select sequences from 4F2 (CD98), ADAM10, CD298, TFR2, transmembrane portions of CD9, MARCKS, KRAS, and GPI from CD55. Proteins engineered to include a targeting sequence domain may include one or more linkers between the sticky binder and signaling domain (e.g., an Fc linker or a bond sequence wherein the bond sequence may be dimerization or multimerization sequence).

Figure 19:
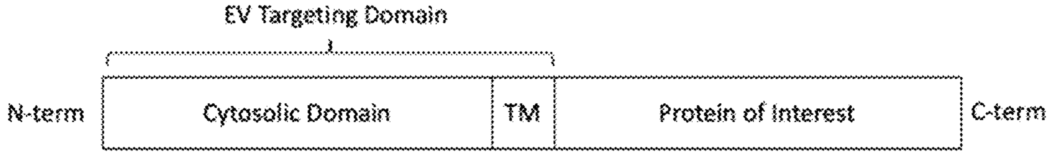

FIG. 19 demonstrates a construct design for labeling an exosome surface with Type II membrane proteins.

Figure 20:

FIG. 20 shows a schematic representation of a construct design for labeling an exosome surface with multiple POI domains operably linked by a cleavable (e.g., P2A) linker.

Figure 21:
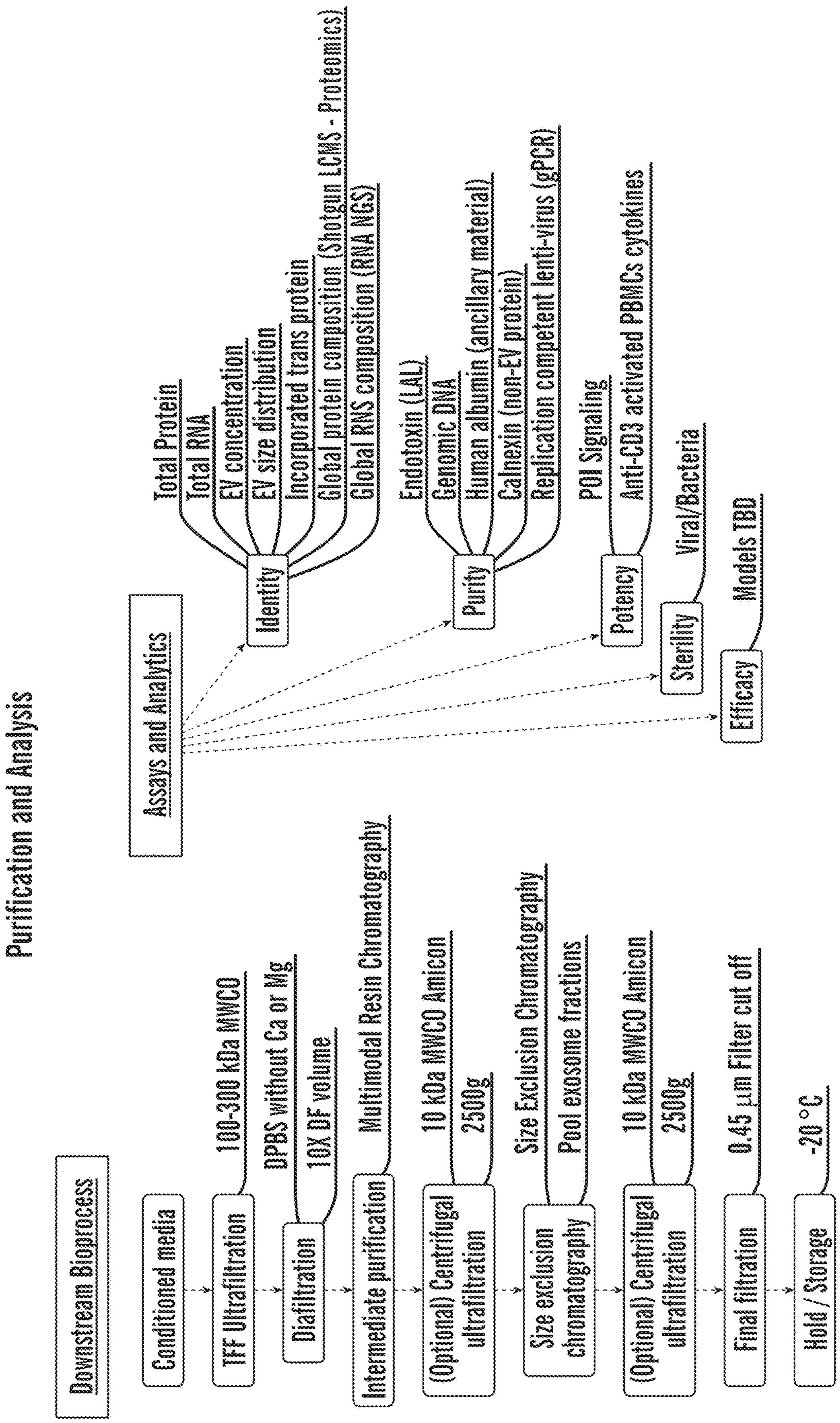

FIG. 21 shows a flow chart of purification and analytical processes provided herein.

Figure 22:
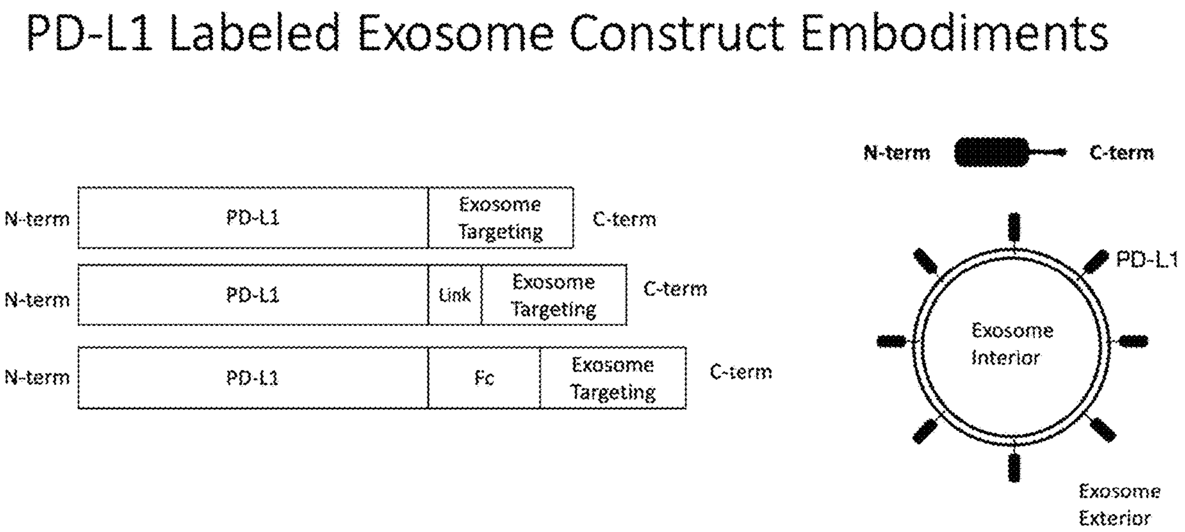

FIG. 22 shows a PD-L1 labeled exosome constructs.

Figure 23:
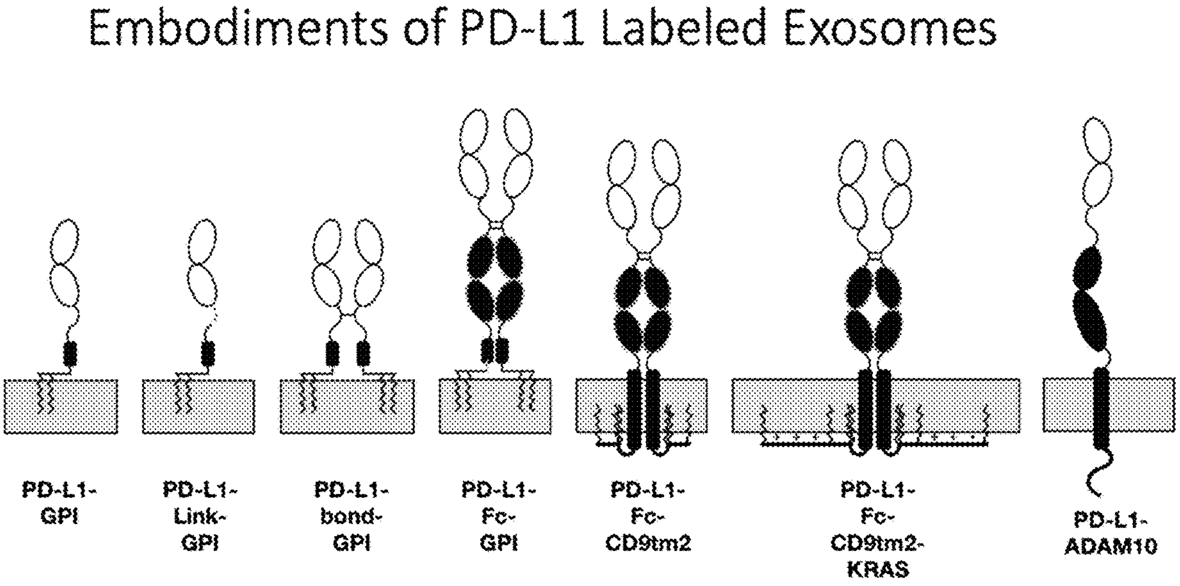

FIG. 23 shows several embodiments of the surface of an exosome engineered with PD-L1. The PD-L1 can be the membrane-bound PD-L1 isotype or secreted PD-L1 (SecPD-L1).

Figure 24:
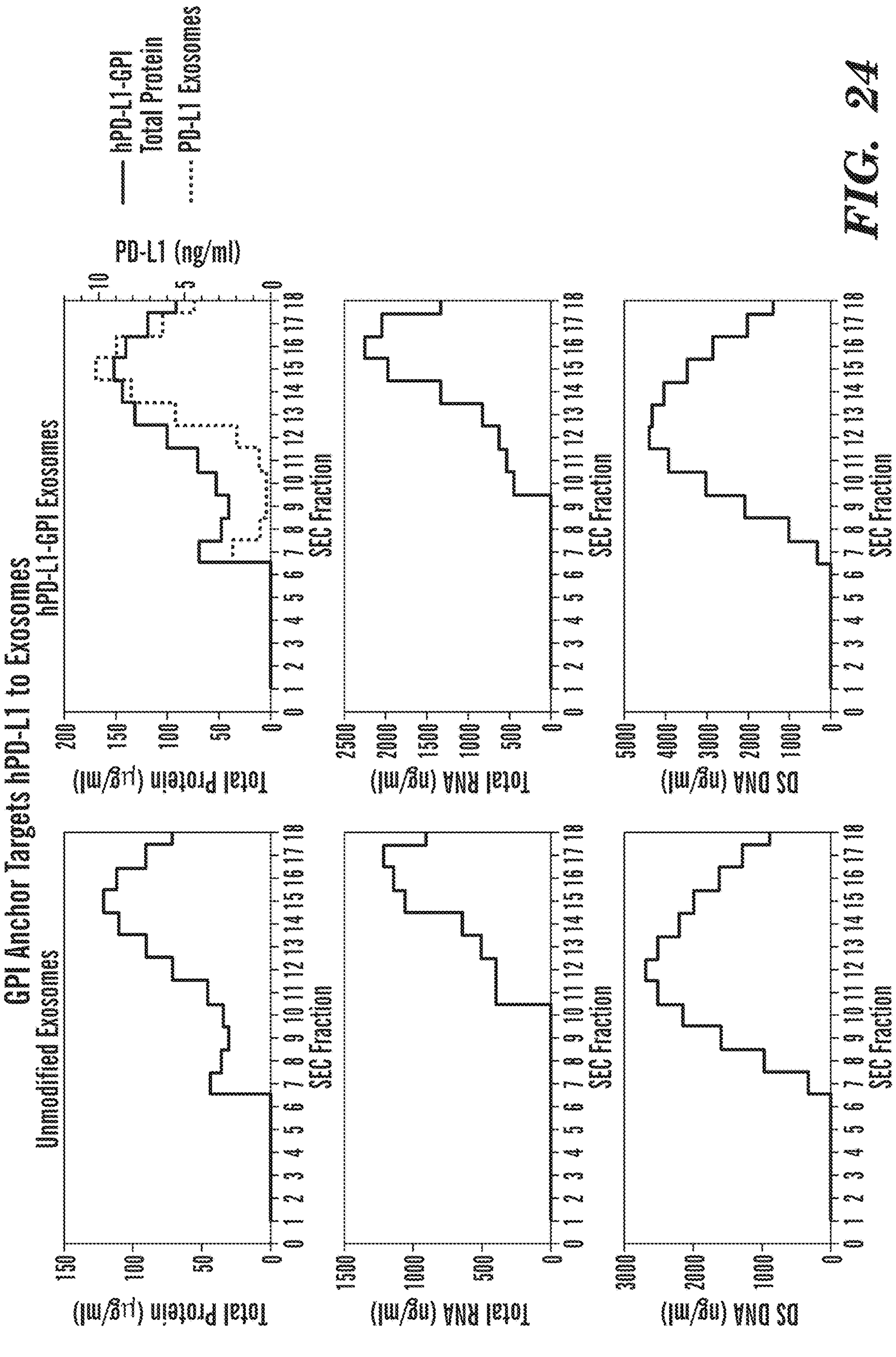
Figure 24:
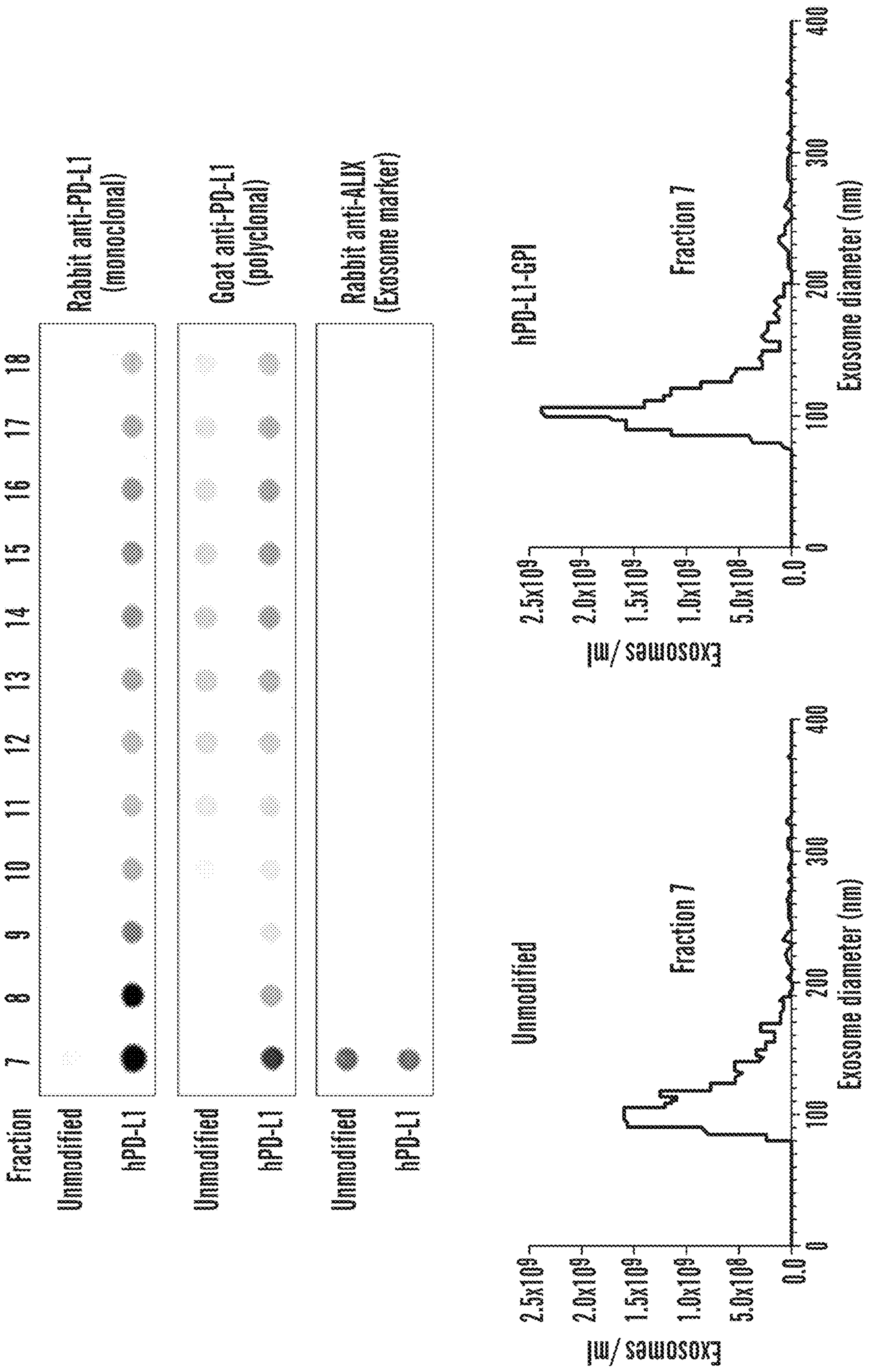

FIG. 24 demonstrates size exclusion chromatography for purifying human PD-L1-GPI (no Fc) exosomes. Left panel: Protein, RNA and DNA measurements in SEC fractions are shown. Invitrogen Qubit™ fluorometric assays were used to measure biomolecules from unmodified concentrated cell media SEC fractions or hPD-L1-Exo-Tag concentrated cell media SEC fractions. PD-L1 was measured using an R&D systems PD-L1 ELISA kit. Right panel shows dot-blot immunoblot analysis of SEC fractions. A 96-well dot blot apparatus was used to immobilize 50 μl of each SEC fraction onto PVDF. Right bottom figures: Exosome size and concentration was measured in fraction 7 by tunable resistive pulse sensing (TRPS).

Figure 25:
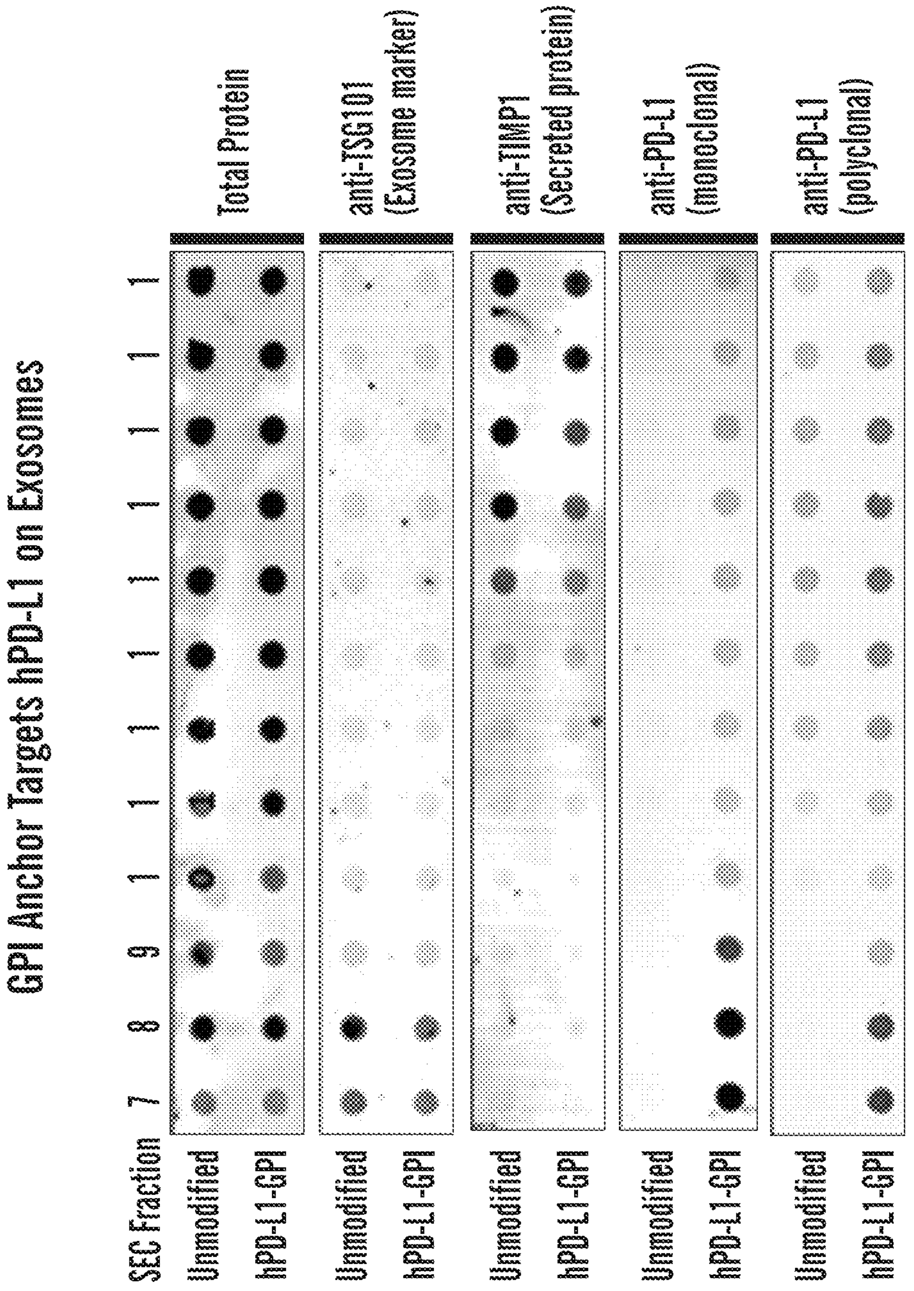
Figure 25:
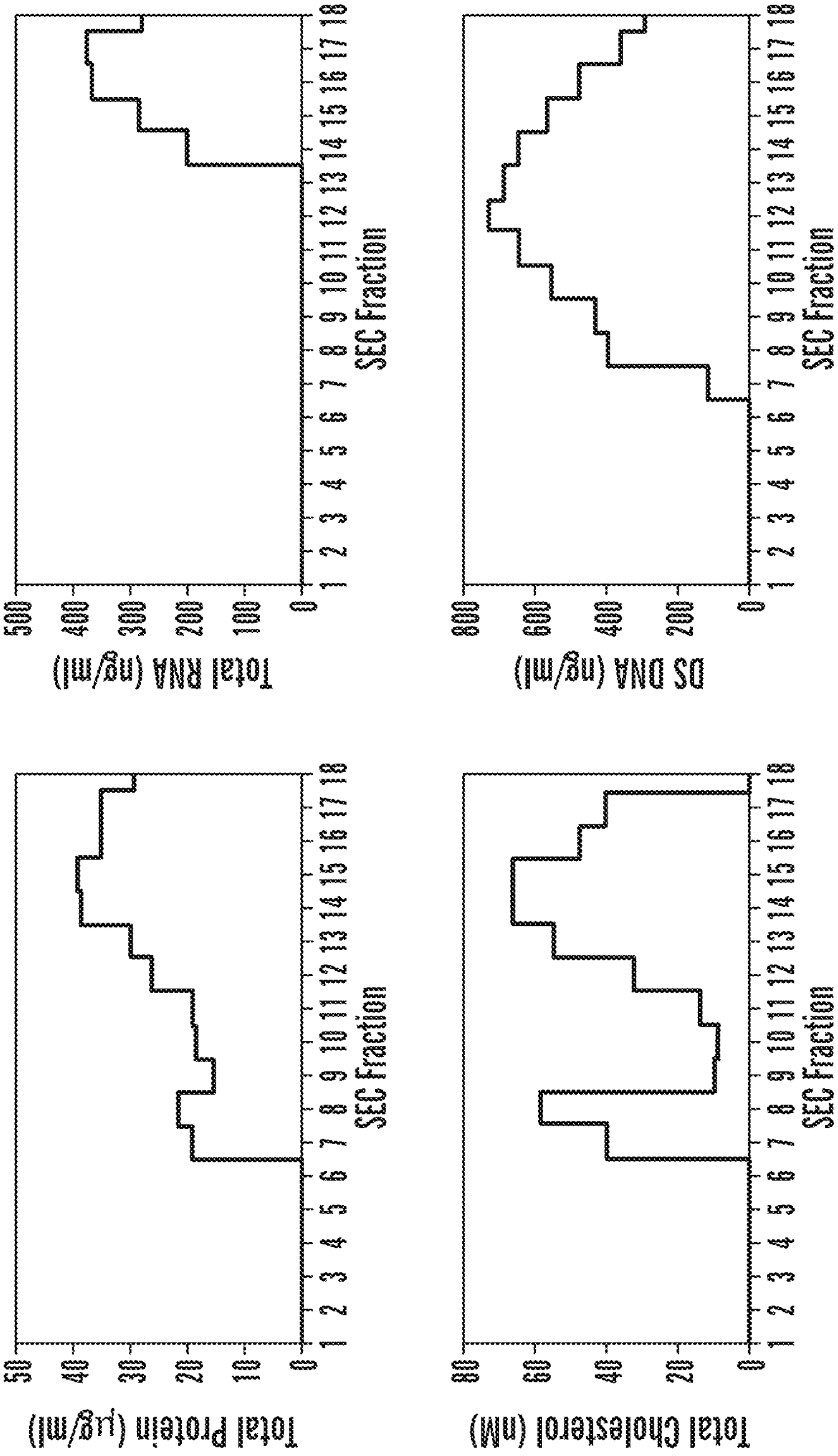
Figure 25:
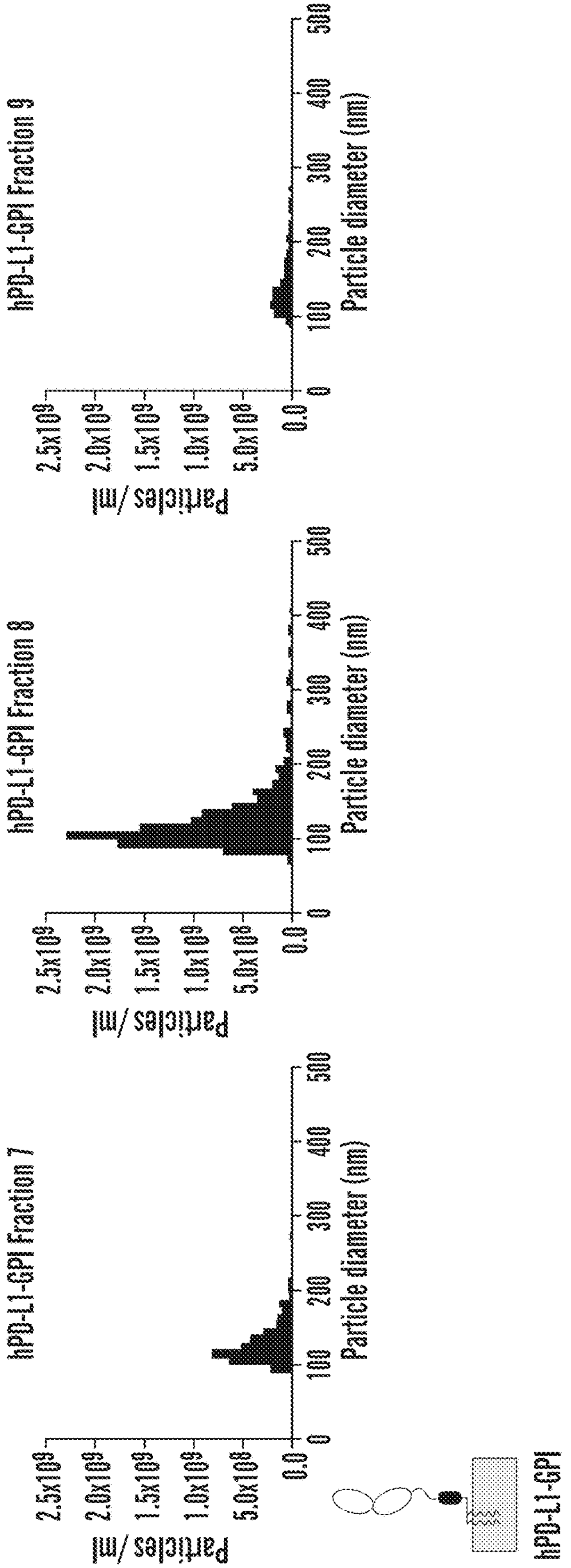

FIG. 25 demonstrates that GPI anchors hPD-L1 on exosomes.

Figure 26:
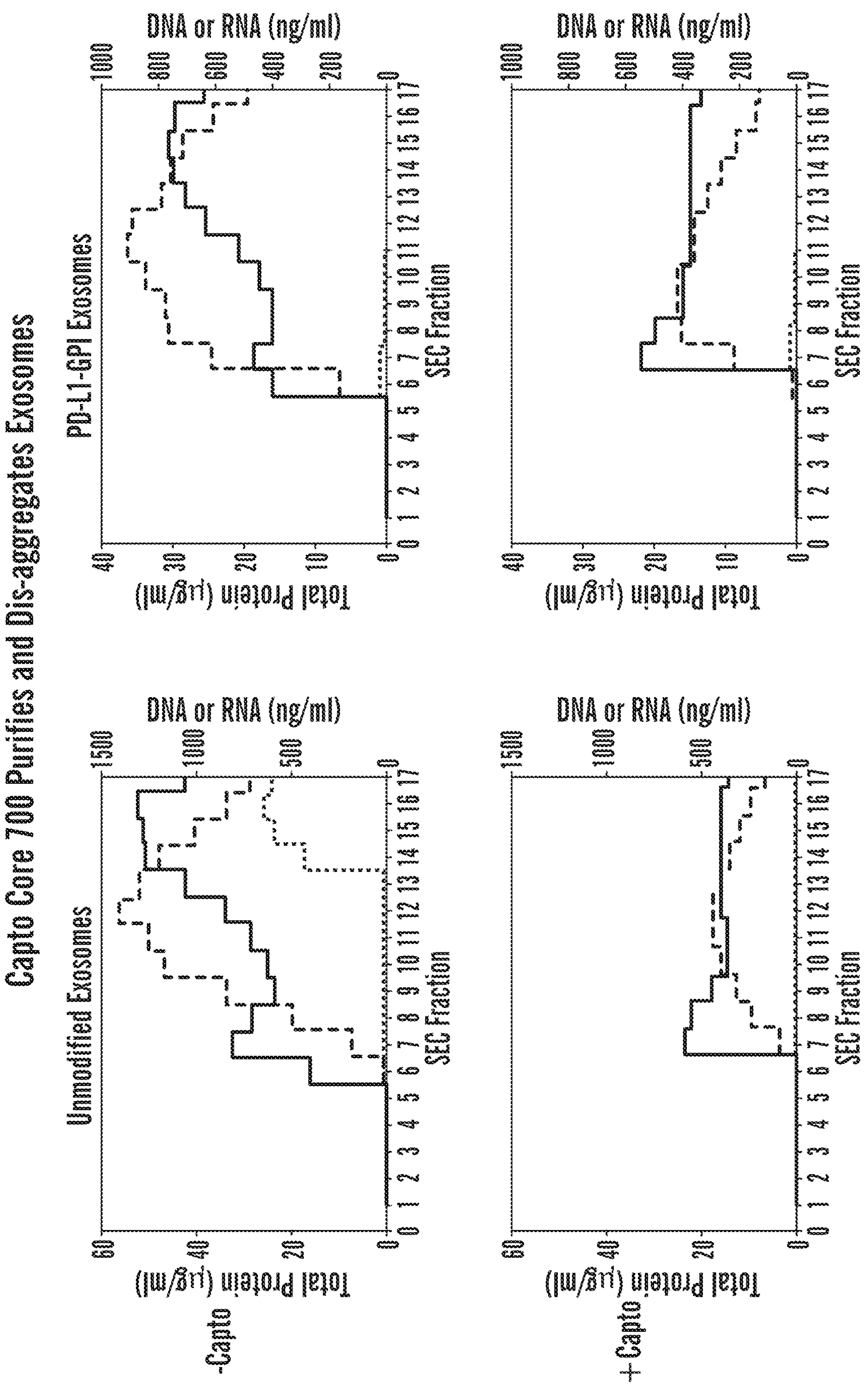
Figure 26:
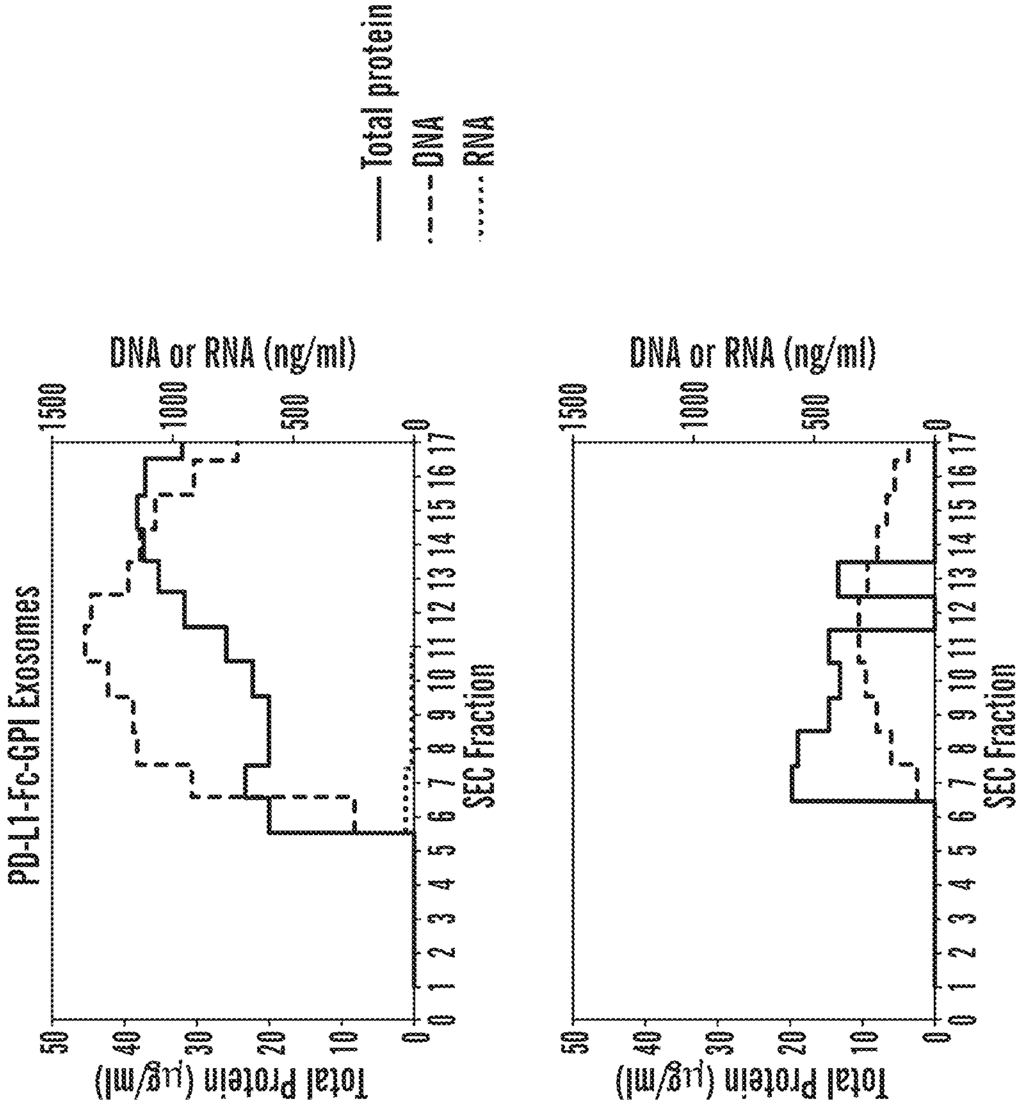
Figure 26:
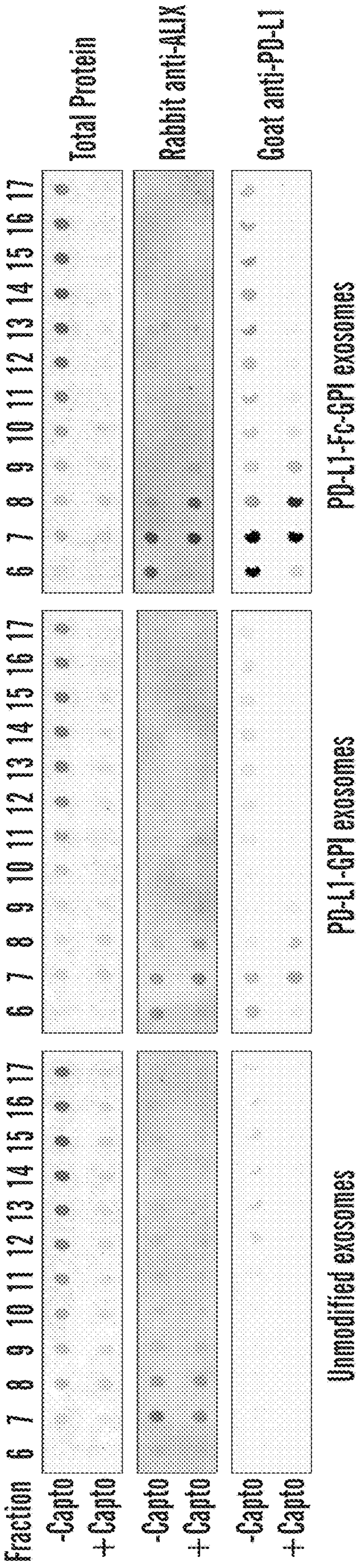

FIG. 26 demonstrates that a multimodal resin marketed for exosome purification purifies and disaggregates exosomes.

Figure 27:
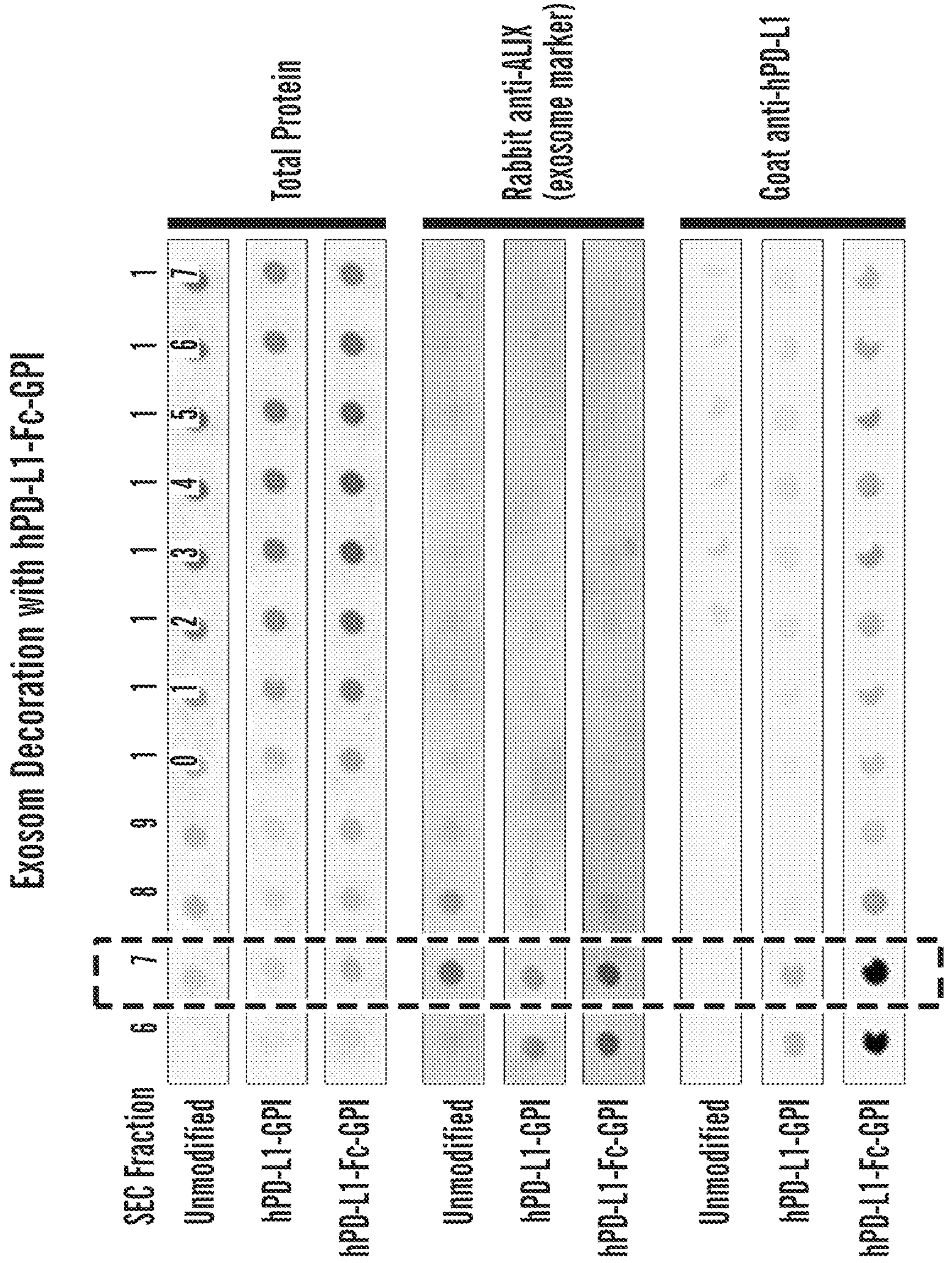
Figure 27:
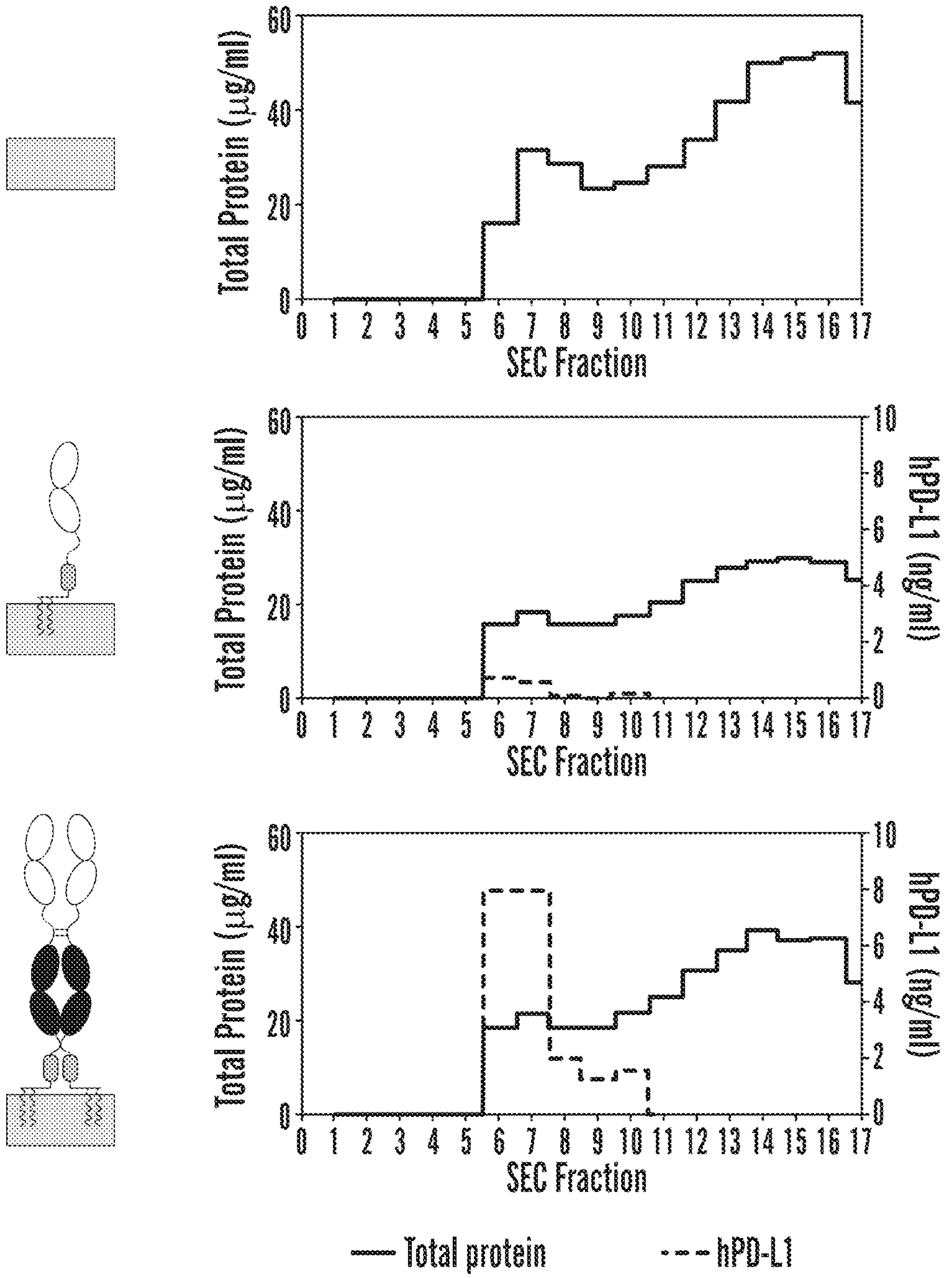

FIG. 27 shows the exosome decoration with hPD-L1-Fc-GPI.

Figure 28A:
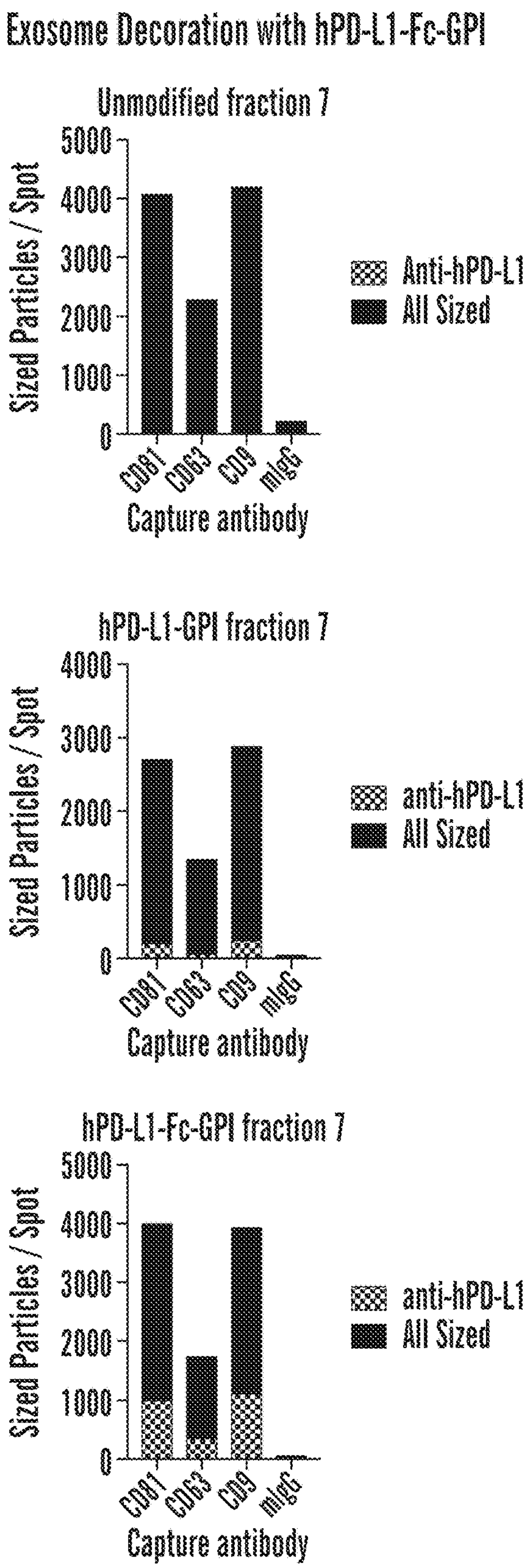
Figure 28A:
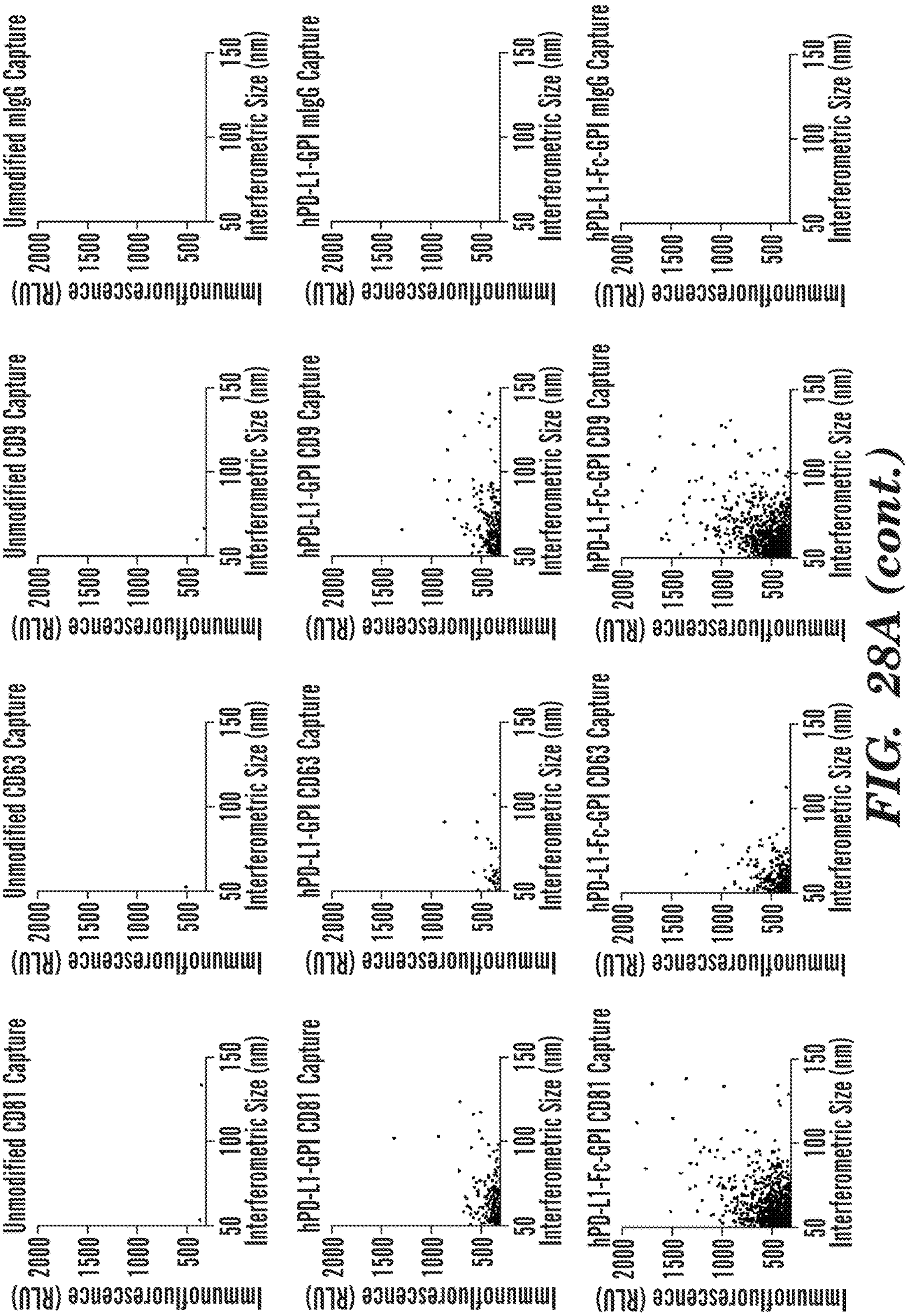
Figure 28B:
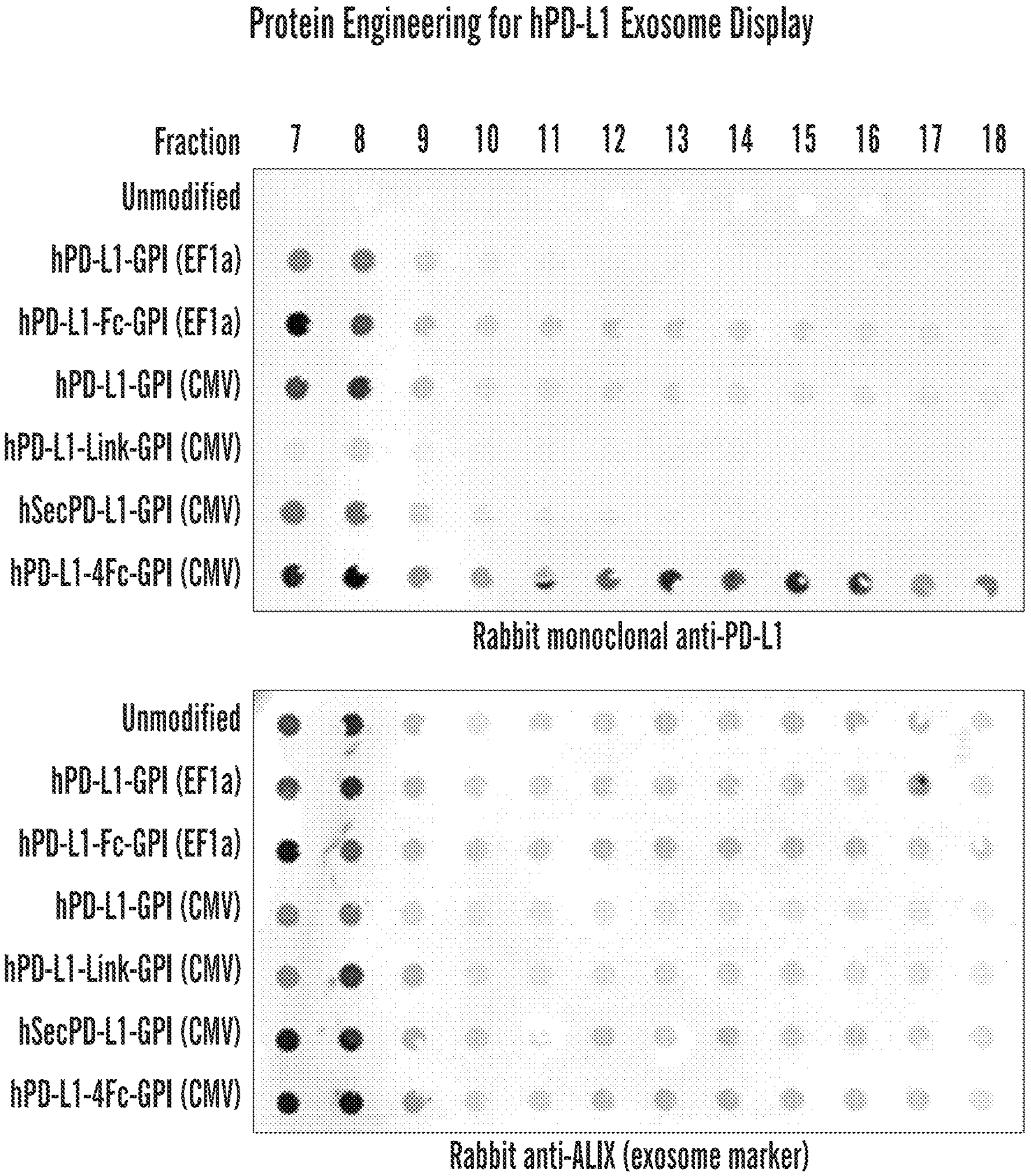
Figure 28B:
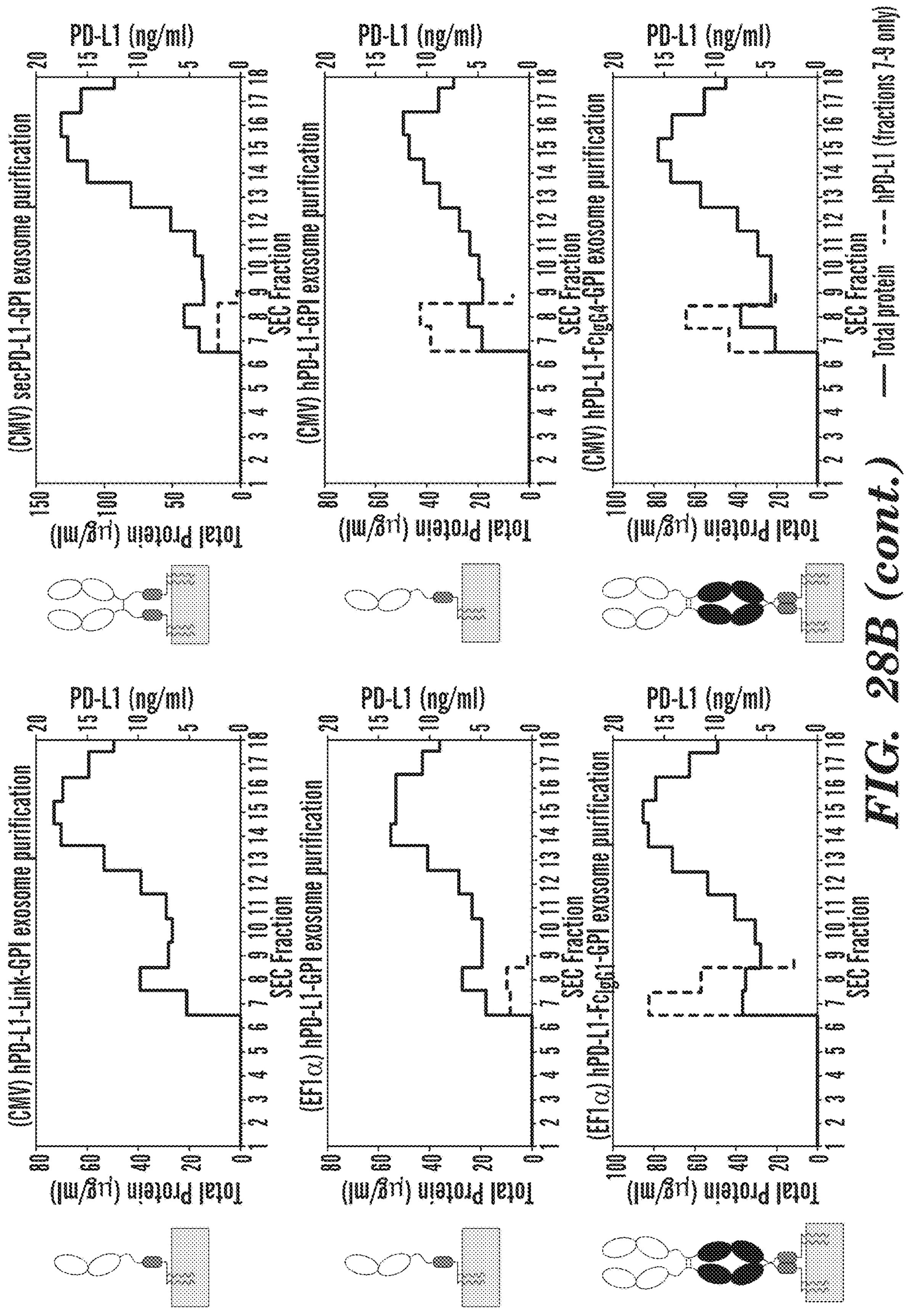

FIG. 28A shows the exosome decoration with hPD-L1-Fc-GPI. Fraction 7 contained the purified hPD-L1-Fc-GPI vesicles. FIG. 28B shows size exclusion chromatography (SEC) purification results of various embodiments of human PD-L1 displayed on the surface of extracellular vesicles.

Figure 29:
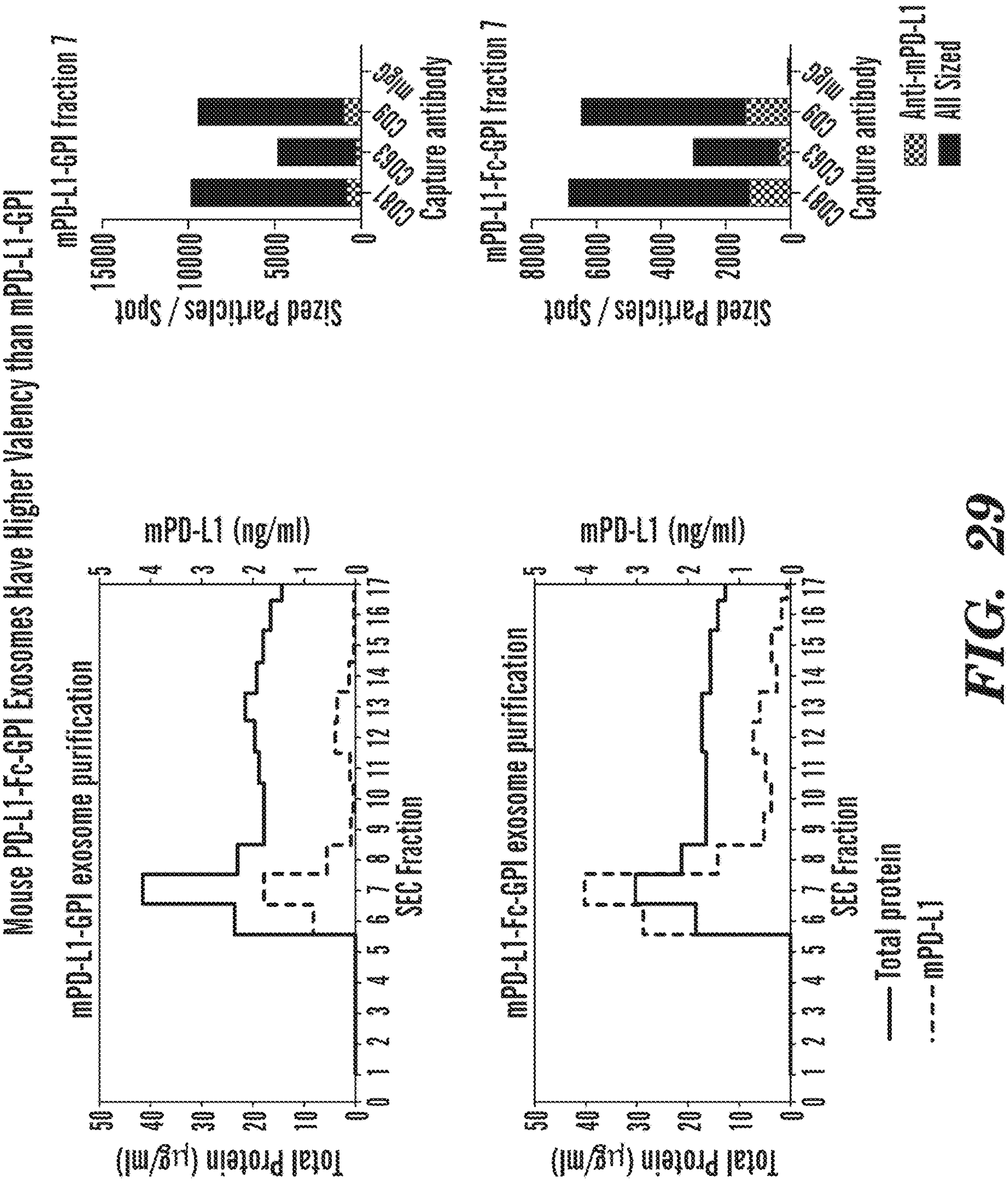
Figure 29:
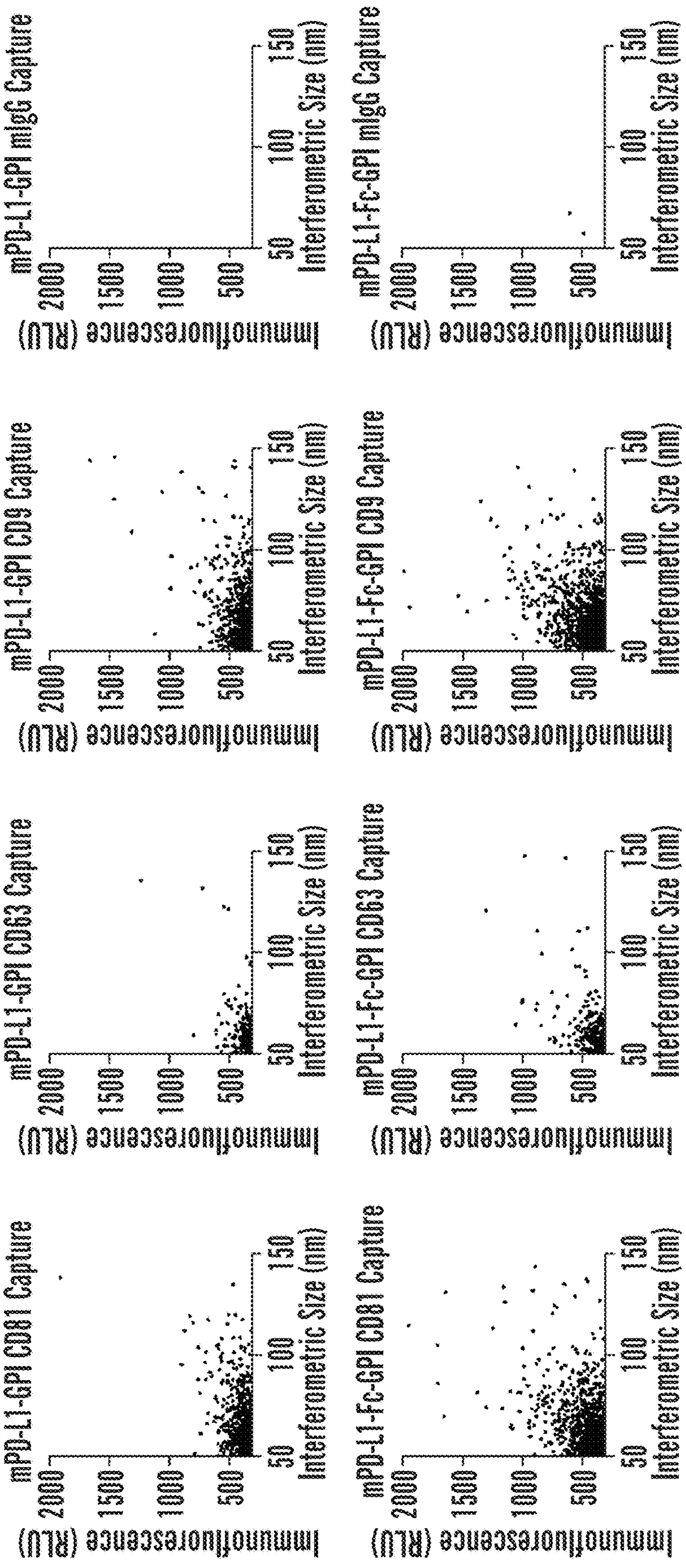

FIG. 29 shows that mouse PD-L1-Fc-GPI exosomes have higher valency than mPD-L1-GPI.

Figure 30A:
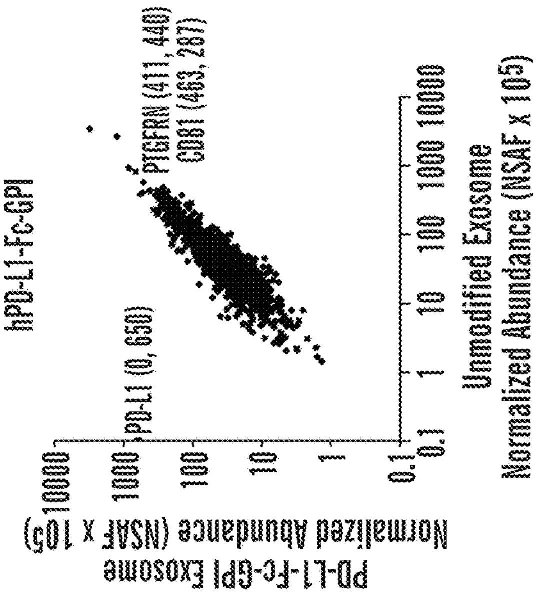
Figure 30B:
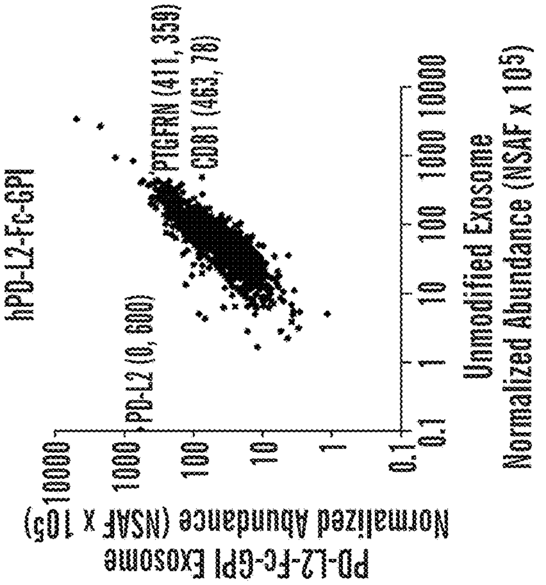
Figure 30C:
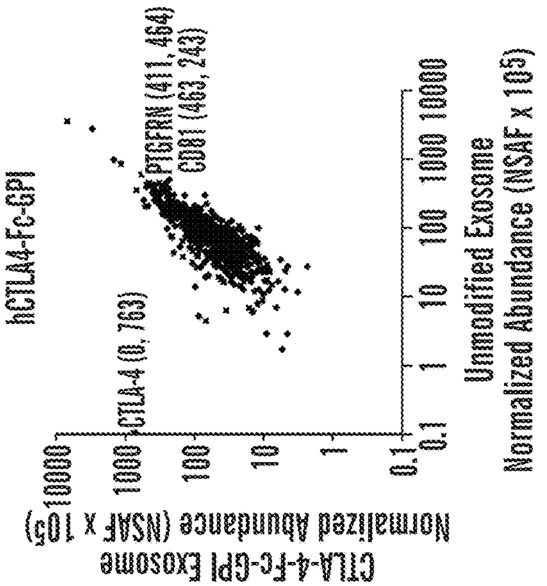

FIG. 30A-30C demonstrates comparison proteomics of transprotein expression and shows that surface labeling on the engineered extracellular vesicles provided herein do not affect the relative expression of native and associated exosome proteins. FIG. 30A shows hPD-L1-Fc-GPI. FIG. 30B shows hPD-L2-FcGPI. FIG. 30C shows hCTLA4-Fc-GPI.

Figure 31:
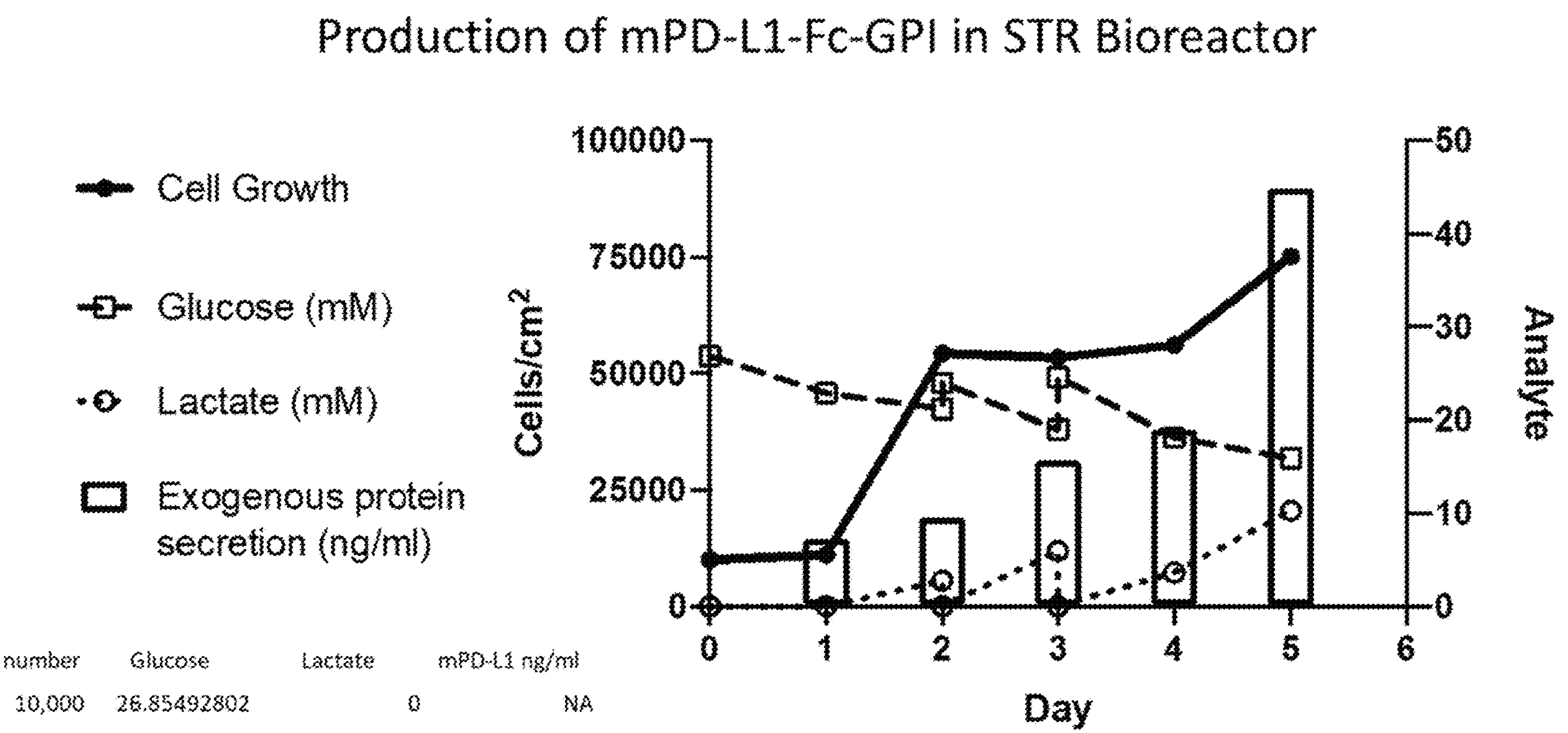

FIG. 31 shows production of mPD-L1-Fc-GPI in STR Bioreactor.

Figure 32:
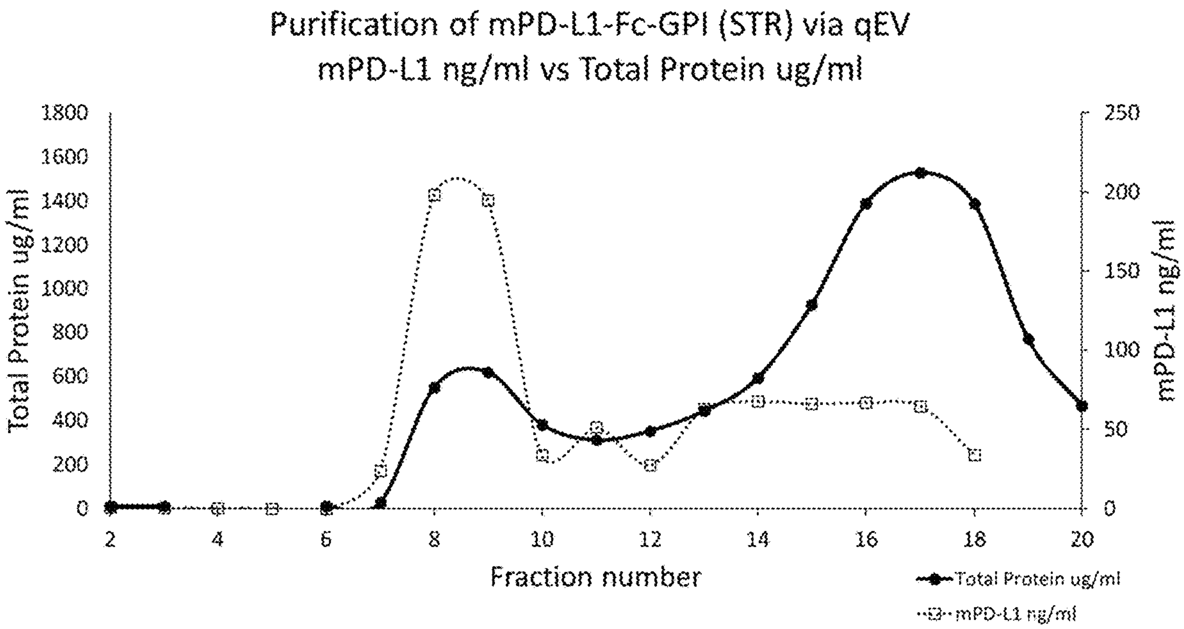

FIG. 32 shows purification of mPD-L1-Fc-GPI (STR) via SEC. Graph shows mPD-L1 ng/ml vs Total Protein μg/ml.

Figure 33:
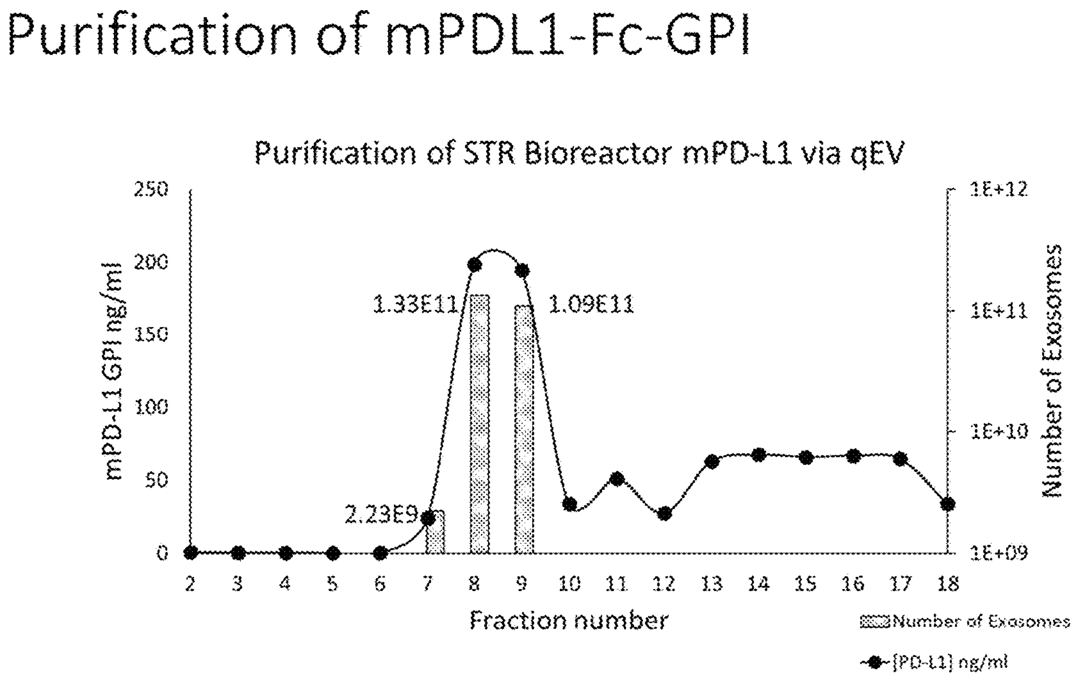

FIG. 33 shows purification mPDL1-Fc-GPI (STR bioreactor).

Figure 34:
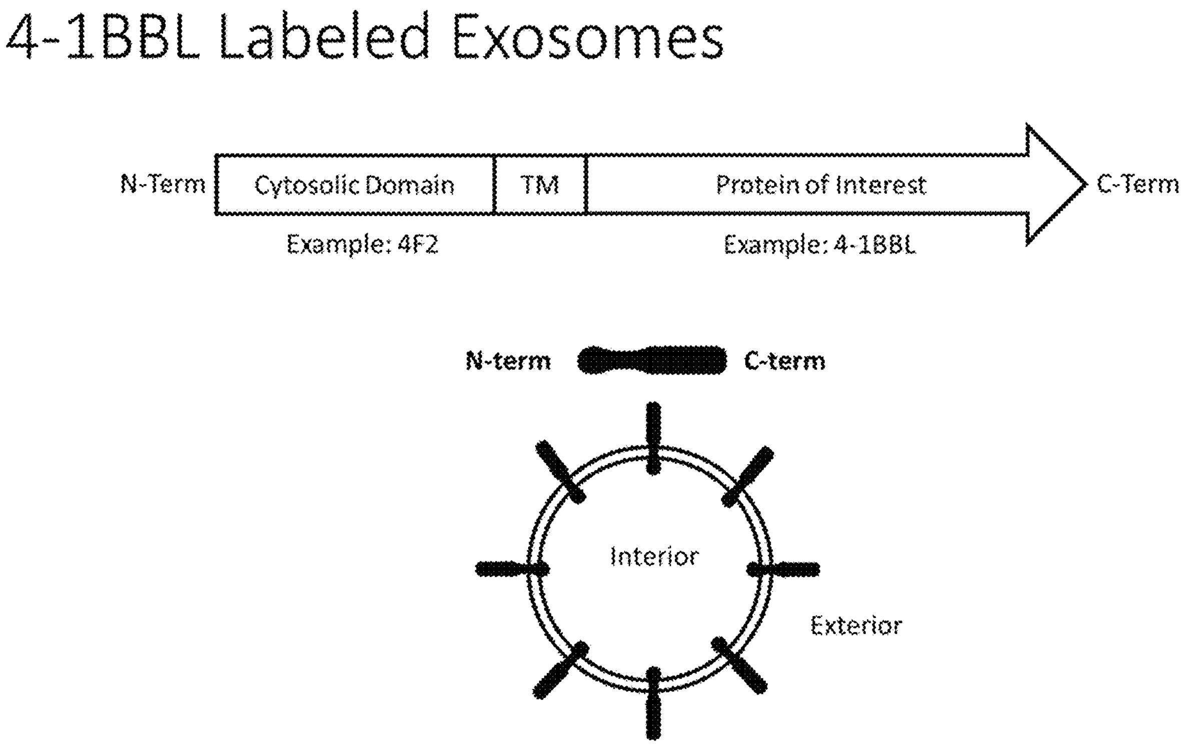

FIG. 34 shows a schematic representation of the 4-1BBL labeled exosomes. Top: Vector map showing the N-terminal cystolic domain, a transmembrane (TM) domain, and the POI domain at the C-terminus. Bottom: An embodiment of an engineered EV with a type-II membrane display of the fusion protein.

Figure 35:
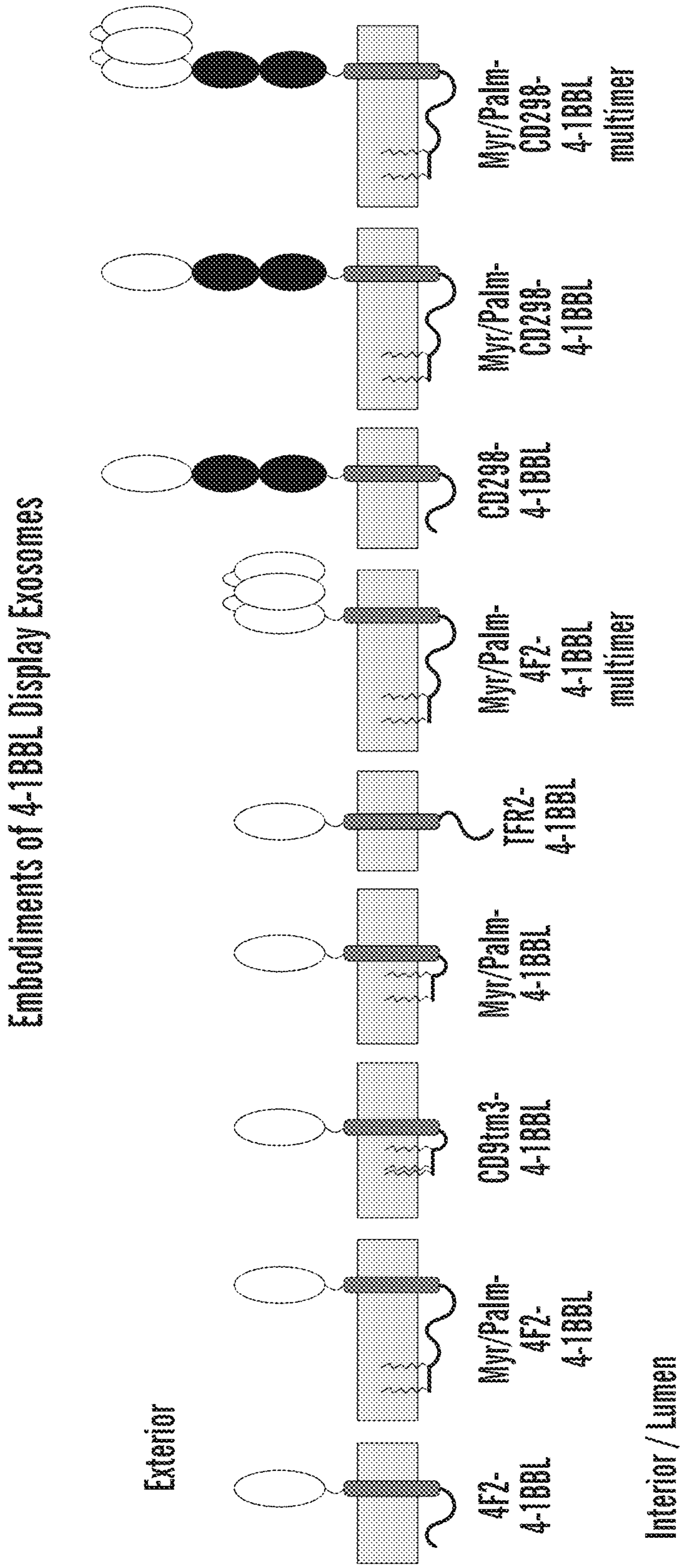

FIG. 35 shows embodiments of a 4-1BBL display exosome.

Figure 36A:
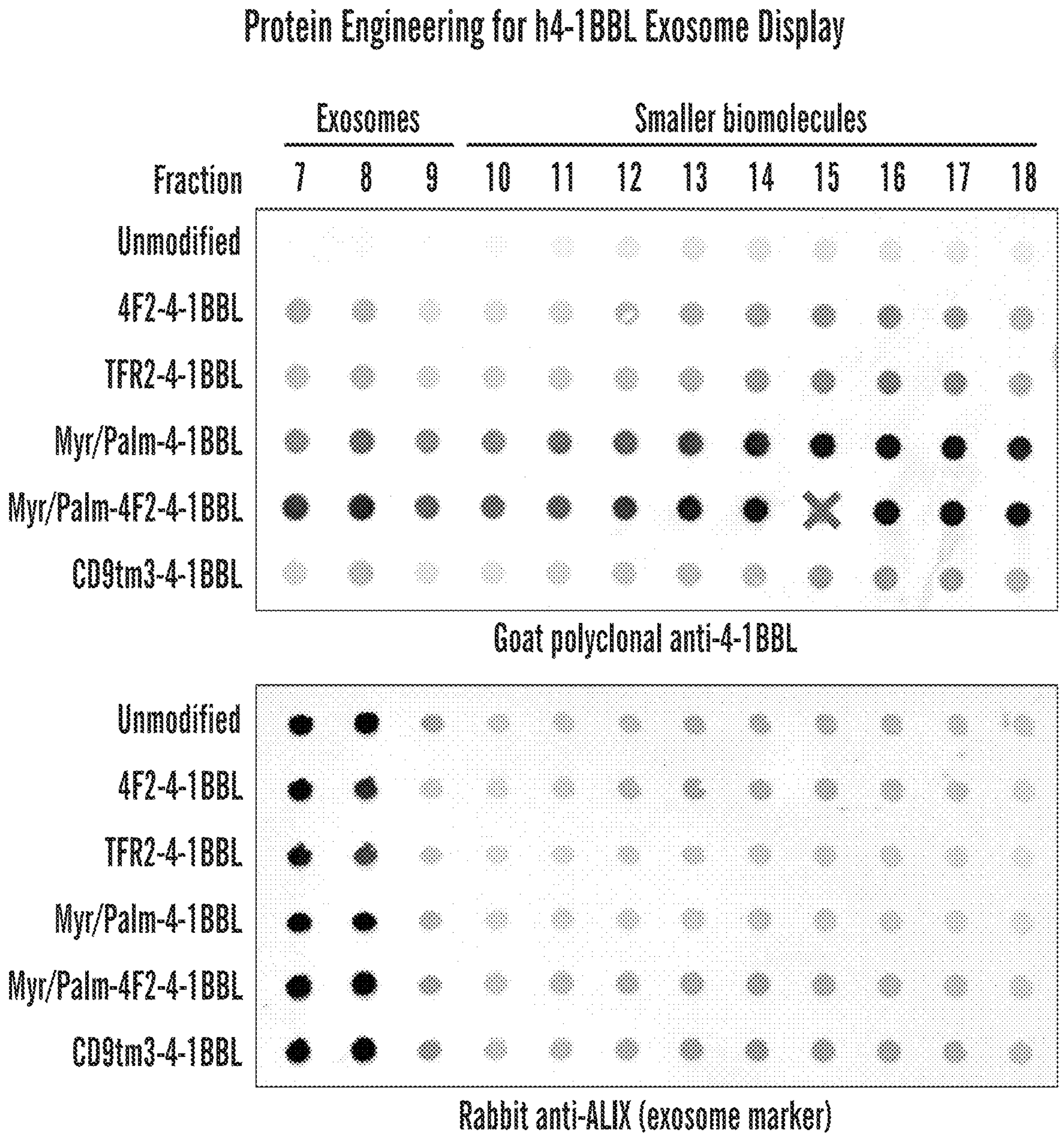
Figure 36A:
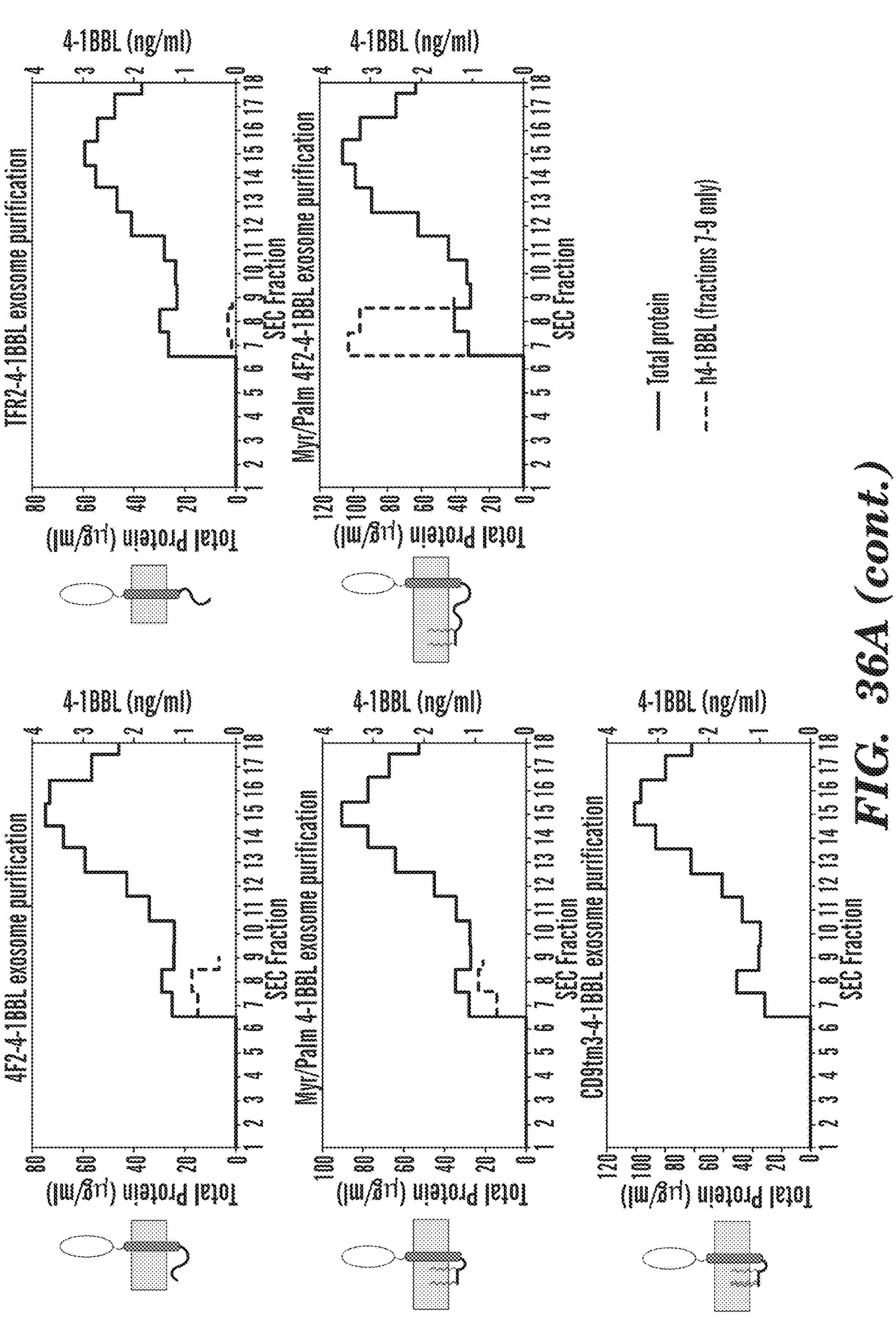
Figure 36B:
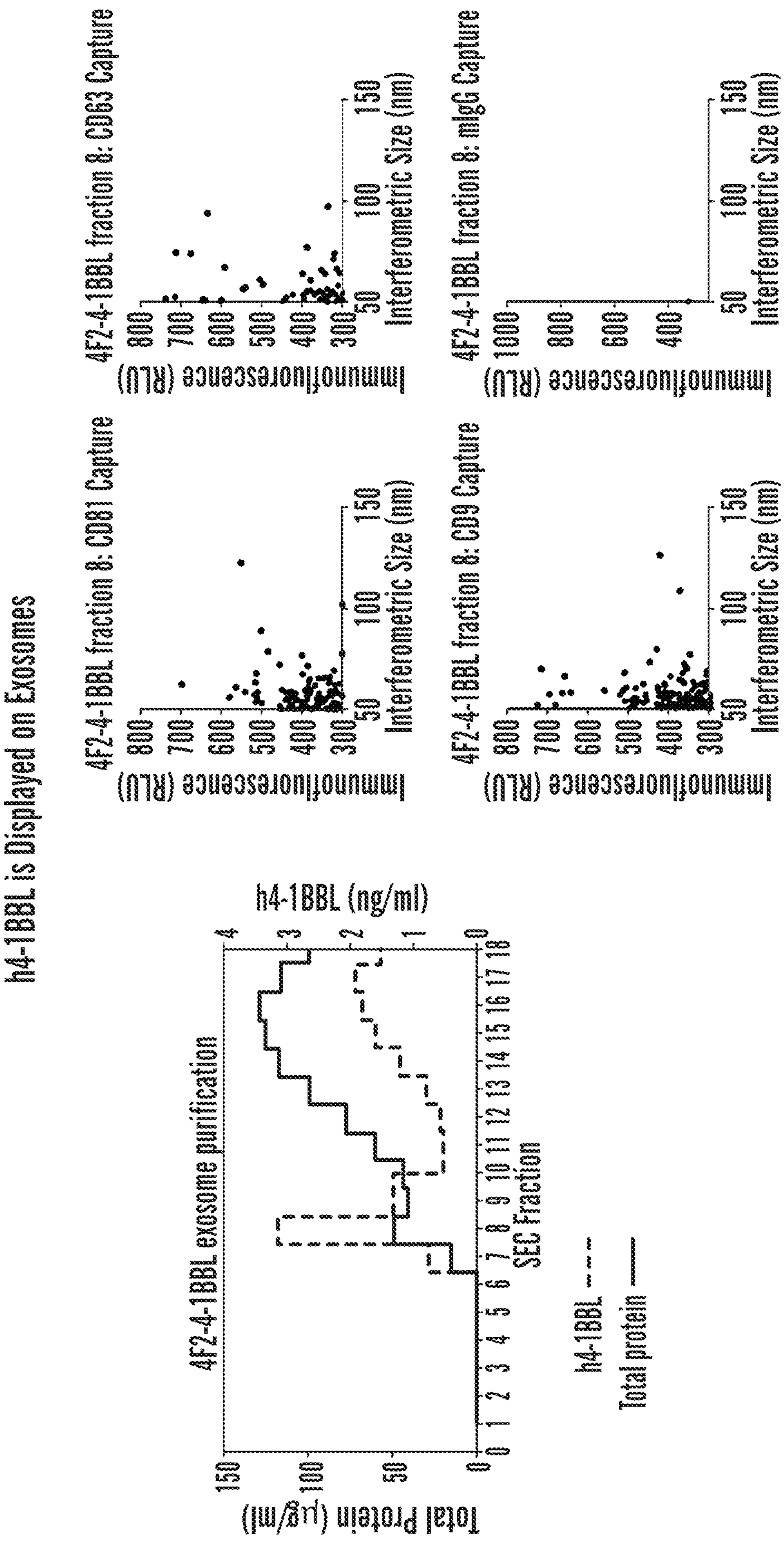

FIG. 36A-36B show the protein engineering and purification of 4F2-4-1BBL labeled exosomes. FIG. 36B confirms that h4-1BBL is displayed on the engineered exosomes.

Figure 37:
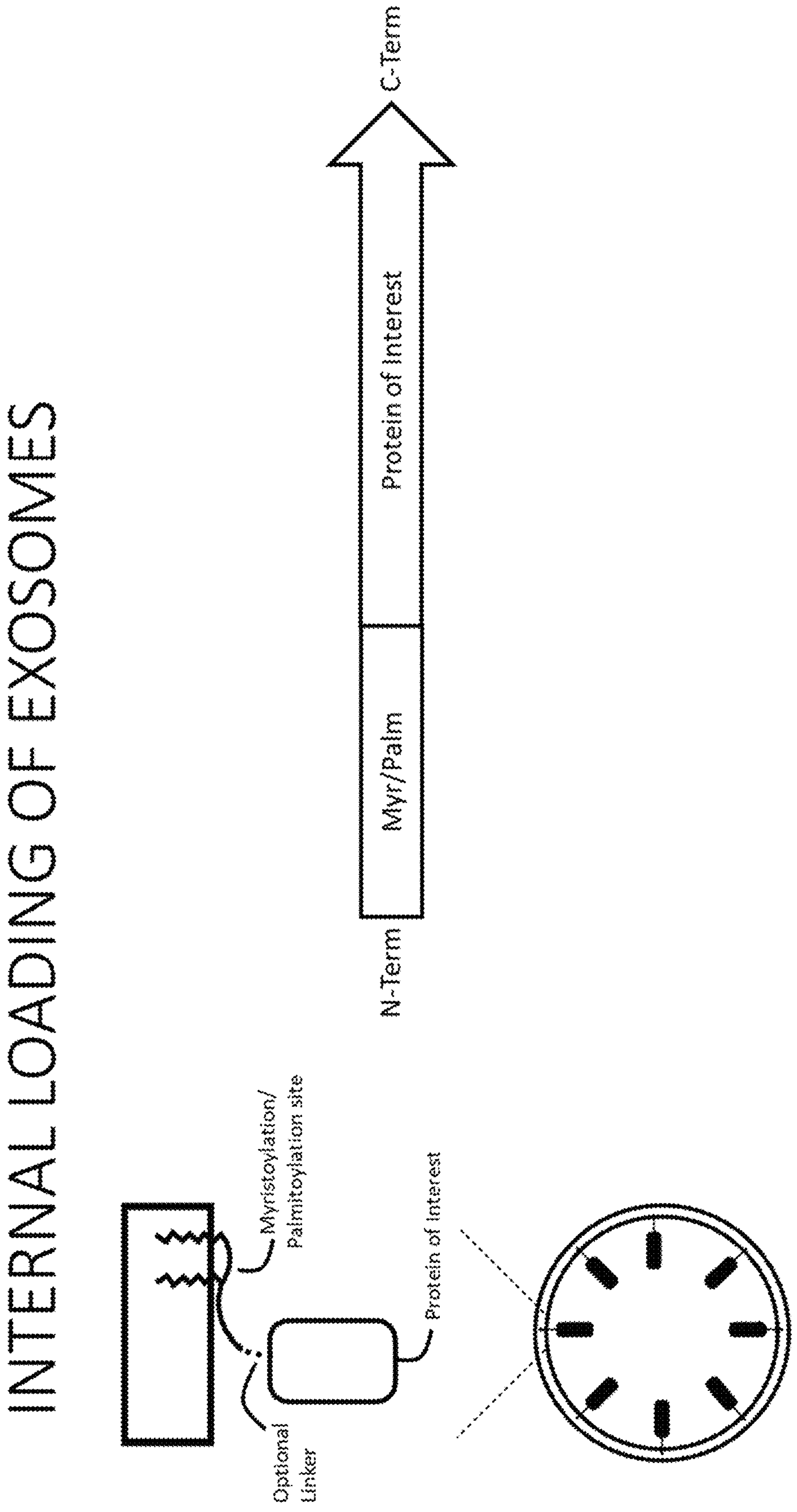

FIG. 37 shows internal fusion protein loading of exosomes.

Figure 38:
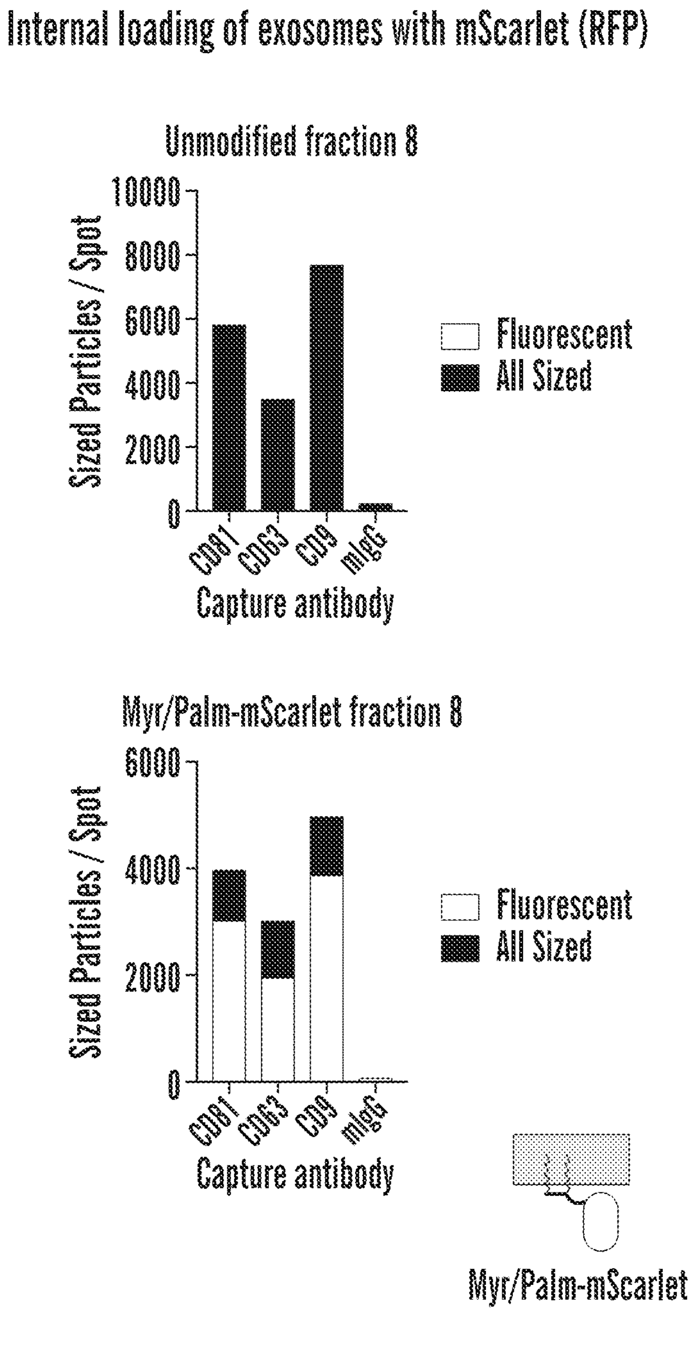
Figure 38:
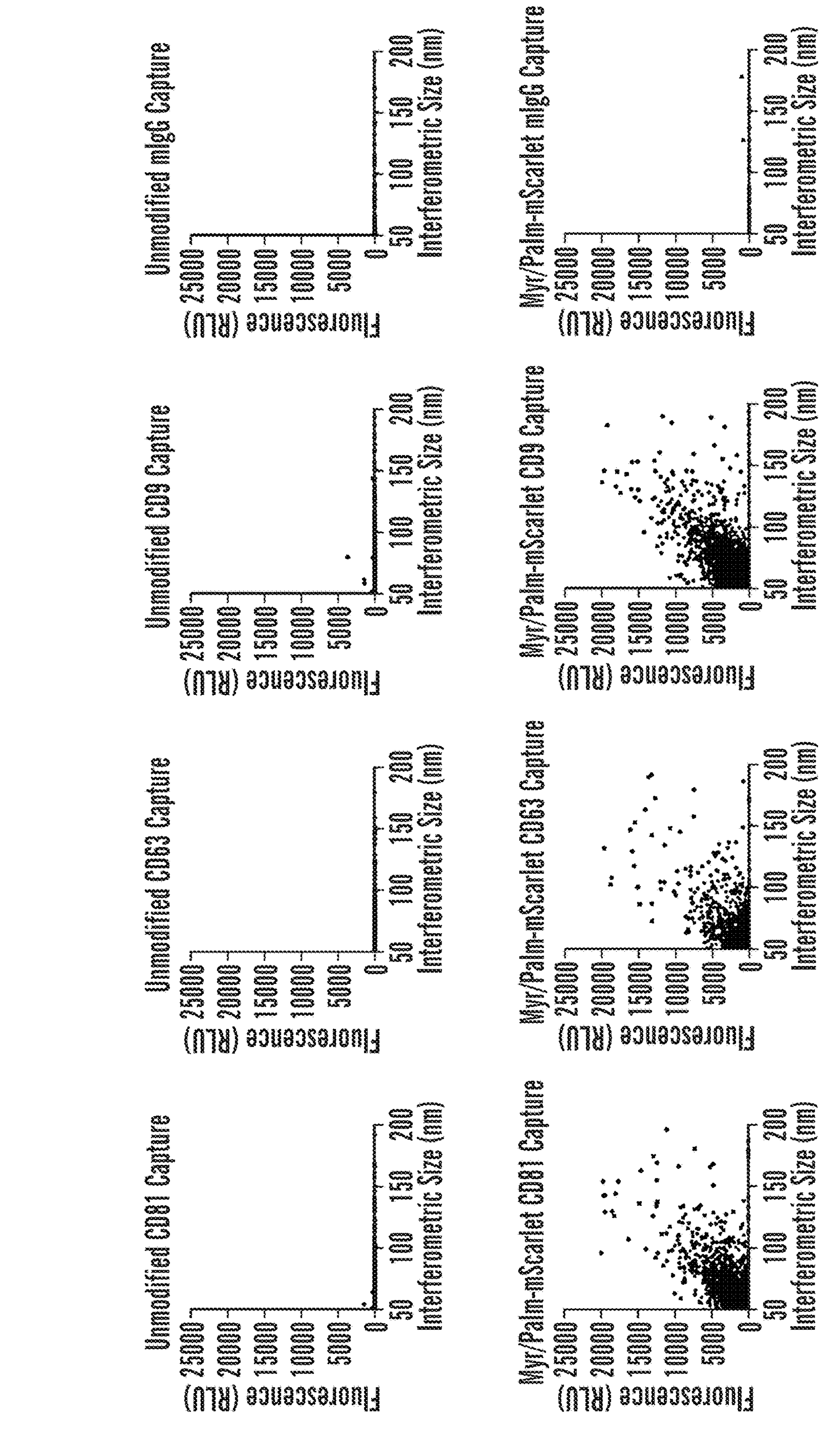

FIG. 38 shows internal loading of exosomes with mScarlet (RFP).

Figure 39A:
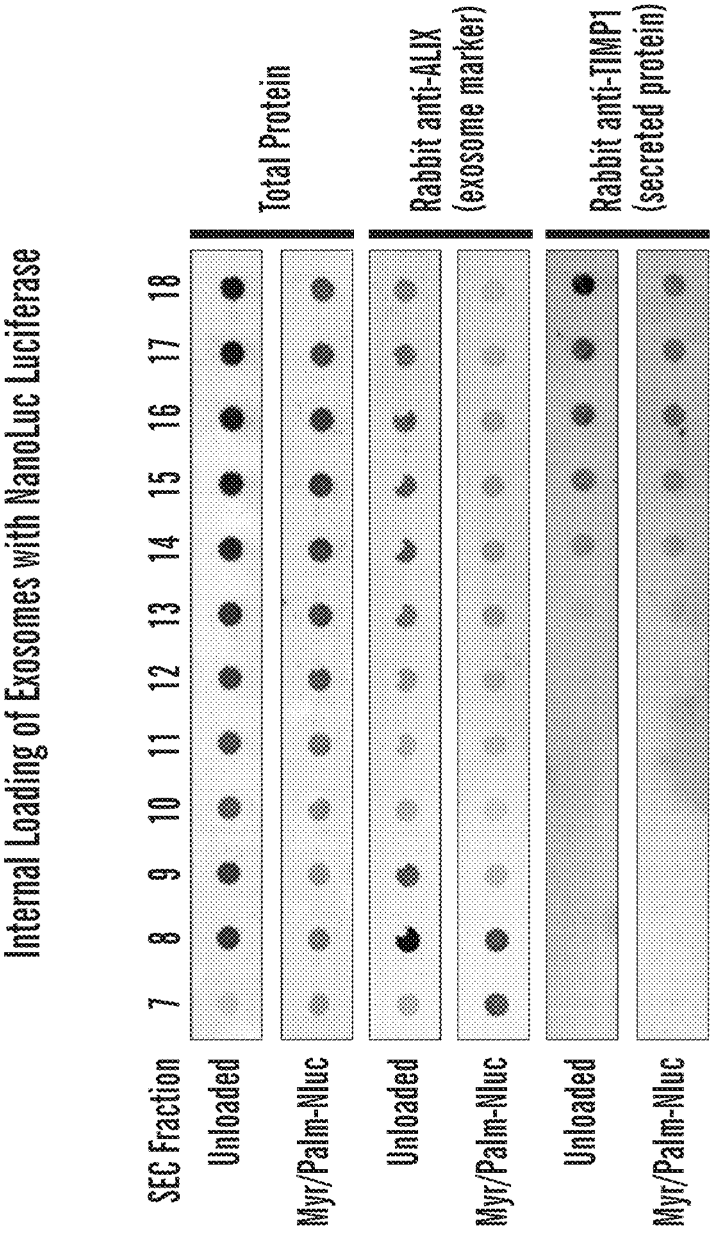
Figure 39A:
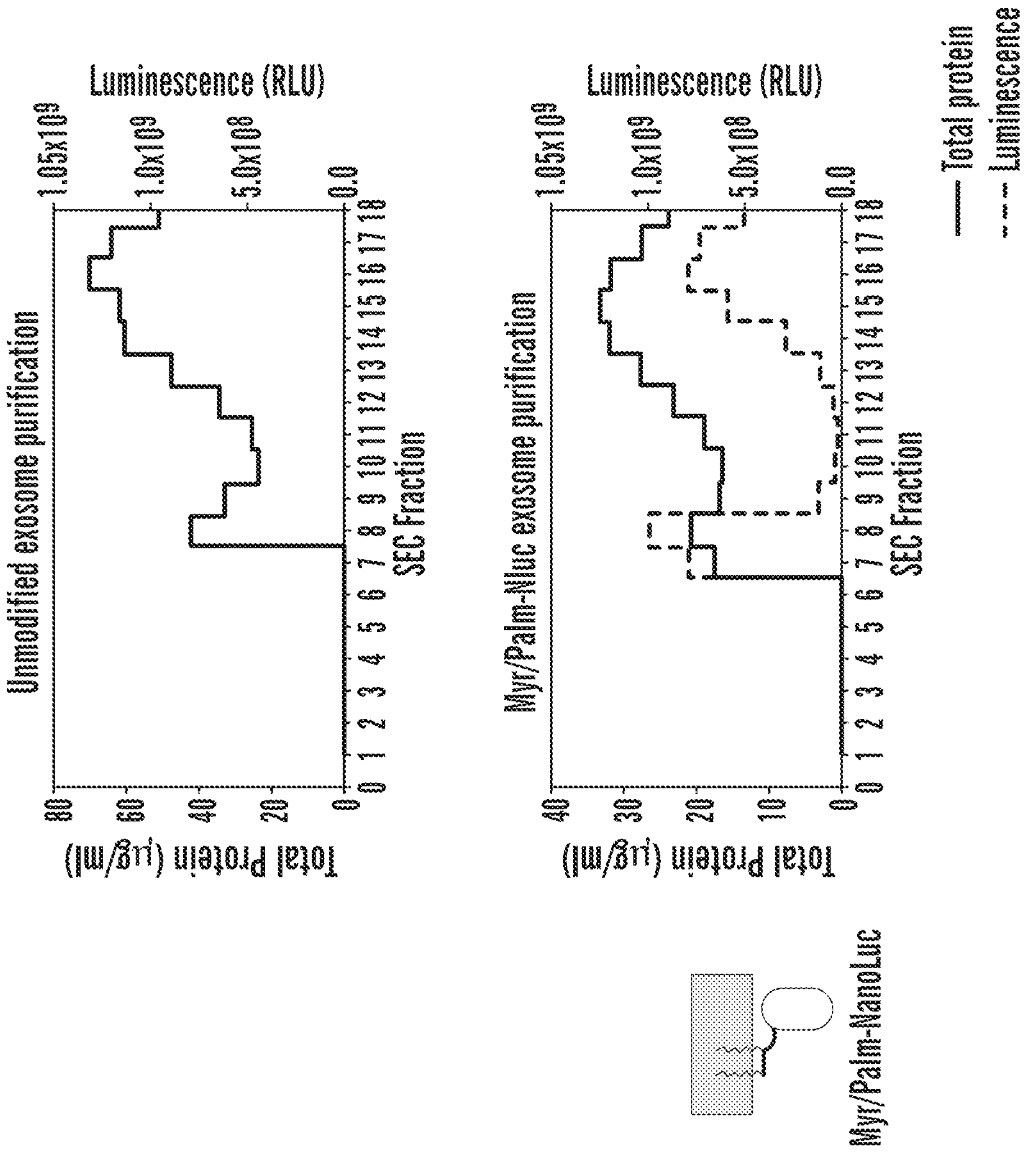
Figure 39B:
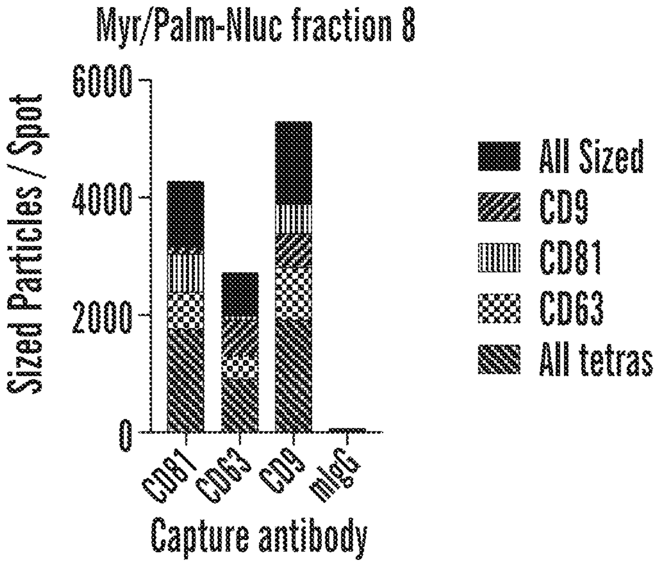

FIG. 39A shows internal loading of exosomes with NanoLuc® luciferase. FIG. 39B shows tetraspanin characterization of exosomes internally loaded with NanoLuc® luciferase.

Figure 40A:
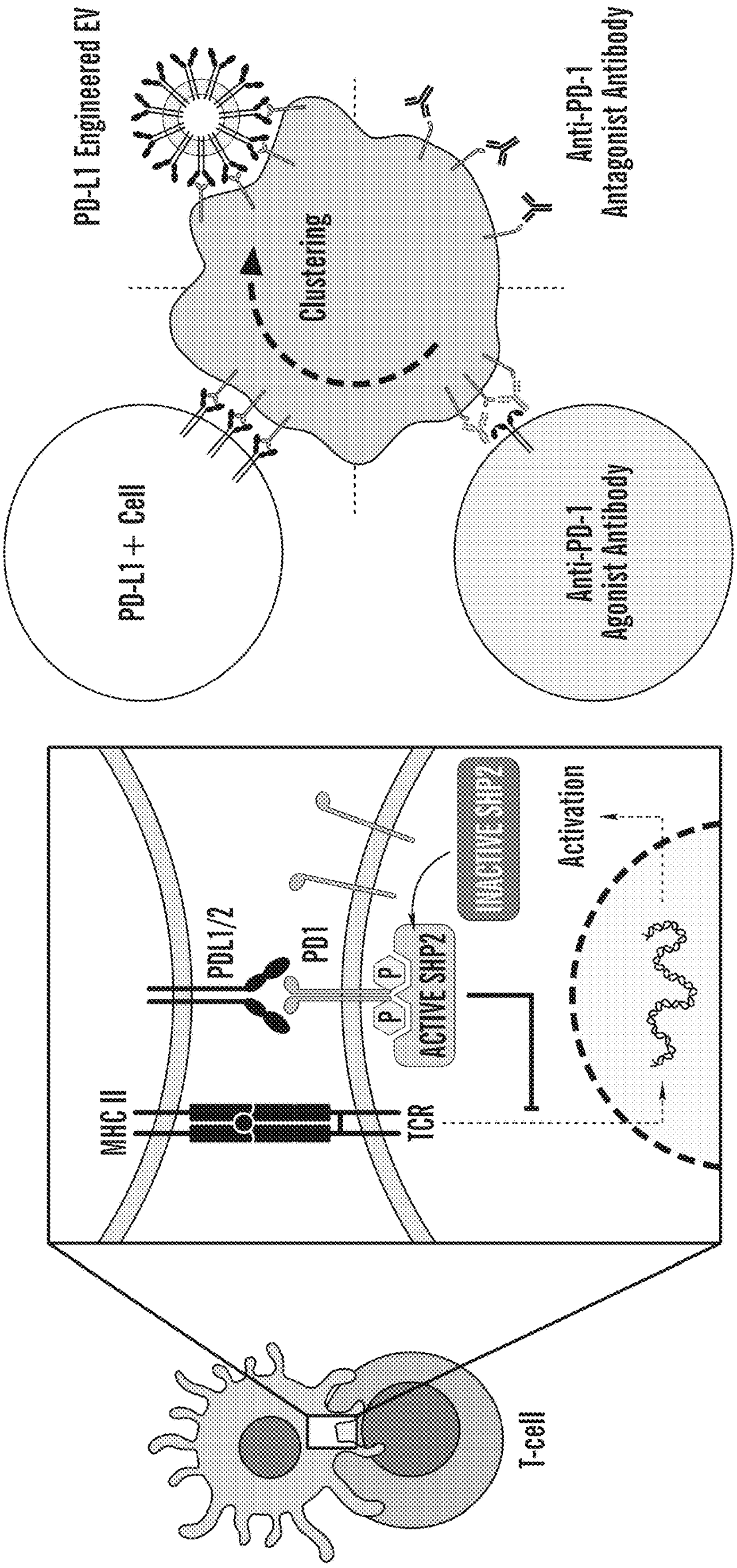

FIG. 40A shows the mechanism of PD-L1 engineered extracellular vesicles induce membrane clustering and receptor agonism on a target cell. An exemplary model of proposed mechanism of extracellular vesicles with a Type I membrane protein signaling domain (PD-L1) promoting receptor clustering on a target cell, wherein receptor clustering promotes increased potency of signal transduction of the target receptor. Antagonist antibodies function well at blocking receptors. Antibodies are poor agonist modalities due to their general inability to cluster receptors. Ligands on a membrane surface are potent agonists, however the cost and cold chain logistics of cell therapies makes commercialization difficult and expensive. Extracellular vesicles engineered with Type I membrane protein are able to induce receptor clustering of target receptors and initiate and propagate a potent signal response on a target cell.

Figure 40B:
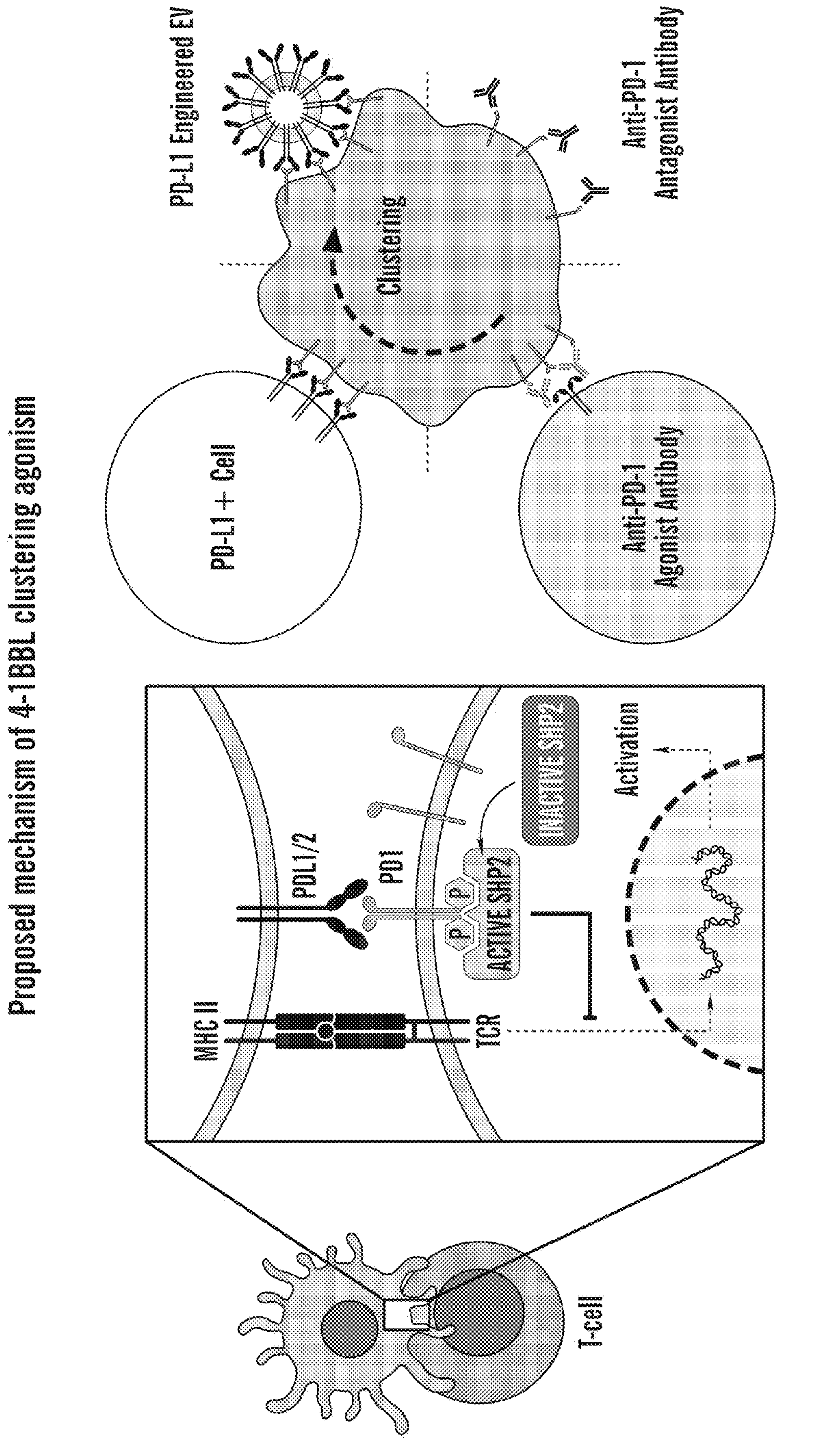

FIG. 40B shows the mechanism of 4-1BBL engineered extracellular vesicles induce membrane clustering and receptor agonism on a target cell. An exemplary model of proposed mechanism of extracellular vesicles with a Type II membrane protein signaling domain (4-1BBL) promoting receptor clustering on a target cell, wherein receptor clustering promotes increased potency of signal transduction of the target receptor. Soluble ligands are often poor agonist modalities due to their general inability to cluster receptors. Ligands displayed on a membrane surface are potent agonists, however the cost and cold chain logistics of cell therapies makes commercialization difficult and expensive. Extracellular vesicles engineered with Type II membrane protein are able to induce receptor clustering of target receptors and initiate and propagate a potent signal response on a target cell.

DETAILED DESCRIPTION

The compositions and methods provided herein are based, in part, on the discovery that engineered extracellular vesicles (e.g., exosomes) expressing an engineered fusion protein (e.g., PD-L1) reduces inflammation in an animal model of experimental autoimmune uveoretinitis (EAU), an autoimmune disorder. The compositions and methods provided herein are further based, in part, on the discovery that engineered extracellular vesicles produce enhanced signaling compared to an equal quantity of recombinant ligand. Since some cellular receptors, (e.g., PD-1) require clustering or super-clustering to promote a signaling response, it stands to reason that extracellular vesicles engineered to express ligands on their surface wherein the ligands may engage target receptors on target cells and promote clustering of said target receptors thereby promoting a signal response on said target cell.

In one aspect, provided herein is an engineered extracellular vesicle comprising: at least one fusion polypeptide comprising: at least one protein of interest (POI) domain; and at least one vesicle targeting domain. In some embodiments of any of the aspects, the engineered extracellular vesicle is an exosome. In some embodiments, of any of the aspects, the fusion protein further comprises at least one linker. In some embodiments of any of the aspects, the POI domain can substantially bind to a target polypeptide. In some embodiments of any of the aspects provided herein, the engineered extracellular vesicle is an artificial synapse.

Generally, the extracellular vesicles (e.g., exosomes) provided herein are produced by contacting a population of cells with a nucleic acid construct encoding the fusion proteins provided herein and isolating a plurality of extracellular vesicles. The extracellular vesicles can then be purified by methods provided herein and are formulated for therapeutic use, including but not limited to, for the treatment of autoimmune diseases, cancer, or modulating inflammation in a subject.

The compositions and methods provided herein are specifically designed to exploit the membrane trafficking mechanisms of extracellular vesicles and rely on the hallmark biophysical and biochemical properties of extracellular vesicles, such as exosomes. The vesicles/artificial synapses provided herein are specifically engineered to induce/agonize and propagate biological signaling via a target polypeptide (e.g., by activating a receptor or enzyme or agonizing said receptor or enzyme). Alternatively, the engineered extracellular vesicles provided herein can act as cellular decoys or to reduce or antagonize biological signaling, e.g., by blocking an endogenous ligand from binding to a target cellular receptor and preventing activation of the receptor.

Engineering of the extracellular vesicles provided herein extends these capabilities significantly by incorporating sticky binders attaching to extracellular vesicles such as exosomes, further coupled with signaling domains of choice. For example, attachment of sticky binders to exosomes, along with their linked signaling domains, allows for receptor clustering for biological signal induction/agonism and propagation not otherwise possible. In this aspect, the aforementioned design achieves the aim of an engineered extracellular vesicle by inducing the desired biological signaling in a target recipient cell.

Various aspects and embodiments of the compositions and methods are provided herein in detail below.

Engineered Extracellular Vesicle (EV) Compositions

The compositions provided herein comprises at least one extracellular vesicle (also termed artificial synapse or abbrv: EV), wherein the extracellular vesicle comprises at least one fusion polypeptide or a plurality of fusion polypeptides comprising: at least one vesicle targeting domain (e.g., sticky binders); and at least one protein of interest domain or a fragment thereof (also termed signaling domains).

Extracellular vesicles (EVs) are lipid particles that are released from various cell types that function to transfer "cargo" such as nucleic acids and proteins to other cells. EVs are not able to replicate but serve as cell messengers. EV-mediated signals can be transmitted by all the different biomolecule categories-protein, lipids, nucleic acids and sugars—and the unique package of this information provides both protection and the option of simultaneous delivery of multiple different messengers even to sites remote to the vesicular origin. See, e.g., Yáñez-Mó M, Siljander P R, Andreu Z, et al. Biological properties of extracellular vesicles and their physiological functions. J Extracell Vesicles. 2015; 4:27066. Published 2015 May 14. doi: 10.3402/jev.v4.27066, which is incorporated herein by reference in its entirety. Furthermore, there is an increasing amount of evidence that shows that EVs can modulate a milieu of cellular signaling processes. See, e.g., Yadid et al. *Science Translation Medicine* (2020); Cerqueira de Abreu et al. *Nature Reviews Cardiology* (2020); Zhang W. et al. *Protein J.* (2019); Zha Q B et al. *Tumor Biology*. February 2017; Tan et al. (2016) Recent advances of exosomes in immune modulation and autoimmune diseases, *Autoimmunity,* 49:6, 357-365; Kalluri R, LeBleu V S. et al. The biology, function, and biomedical applications of exosomes. Science. 2020 Feb. 7; 367(6478); which is incorporated herein by reference in its entirety.

There are various types of extracellular vesicles that are named for their site of origin in a cell, size, and structural and/or functional properties. In some embodiments of any of the aspects provided herein, the extracellular vesicle is an exosome, ectosome, macrovesicle, microparticle, apoptotic body, vesicular organelle, oncosome, exosphere, exomeres, or cell derived nanovesicle (CDN) ((e.g., by genesis via grating or shearing cells), liposomes or the like known by one of ordinary skill in the art. In various embodiments, the extracellular vesicle comprises a phospholipid bilayer with an exterior phospholipid layer and an interior phospholipid layer, wherein the exterior phospholipid layer has an external surface and an internal surface, wherein the interior phospholipid layer has an internal surface and an external surface, and the internal surface of the exterior phospholipid layer faces the internal surface of the interior phospholipid layer, and the phospholipid bilayer encloses an internal space, wherein the external surface of the interior phospholipid layer faces the internal space and wherein the external surface of the exterior phospholipid layer faces an extracellular environment, and the external surface of the inner phospholipid layer is the internal surface of the extracellular vesicle.

In various embodiments, the extracellular vesicles range in size from 30 nanometers (nm) to 300 nm. In various embodiments, the plurality of EVs range in size from about 30 nm to about 150 nm. In various embodiments, the plurality of EVs or artificial synapses includes one or more artificial synapses that are about 10 nm to about 250 nm in diameter, including those about 10 nm to about 15 nm, about 15 nm to about 20 nm, about 20 nm to about 25 nm, about 25 nm to about 30 nm, about 30 nm to about 35 nm, about 35 nm to about 40 nm, about 40 nm to about 50 nm, about 50 nm to about 60 nm3 about 60 nm to about 70 nm, about 70 nm to about 80 nm, about 80 nm to about 90 nm, about 90 nm to about 95 nm, about 95 nm to about 100 nm, about 100 nm to about 105 nm, about 105 nm to about 110 nm, about 110 nm to about 115 nm, about 115 nm to about 120 nm, about 120 nm to about 125 nm, about 125 nm to about 130 nm, about 130 nm to about 135 nm, about 135 nm to about 140 nm, about 140 nm to about 145 nm, about 145 nm to about 150 nm, about 150 to about 200 nm, about 200 nm to about 250 nm, about 250 nm or more.

In some embodiments of any of the aspects provided herein, the EV is an exosome. Exosomes are membrane-bound EVs that are produced in the endosomal compartment of most eukaryotic cells. As used herein, the term "exosome" refers to a species of extracellular vesicle between about 20 nm to about 400 μm in diameter, e.g, about 30 nm-200 nm in diameter by inward invagination of a portion of a membrane of an endosome (for example an early or late endosome), wherein the endosome is within a cell comprising a plasma membrane, and the exosome is released from the cell upon fusion of another portion of the endosome membrane with the plasma membrane. An exosome may refer to a species of extracellular vesicle between 20 nm-400 μM in diameter, more preferably 30 nm-200 nm in diameter, that originates by budding of a portion of a plasma membrane from a cell wherein the budded portion of the plasma membrane is released to the extracellular environment.

The EVs (e.g., exosomes or cell derived vesicles) provided herein may comprise cargo, for example, peptides, proteins, nucleic acids, lipids, metabolites, carbohydrates, biomolecules, small molecules, large molecules, vesicles, organelles, or fragments thereof. Exosome cargo may be located within the internal space of the exosome. EV cargo may be membrane bound spanning one or both layers of the exosome phospholipid bilayer (for example a transmembrane protein). EV cargo may be in contact with the exterior or interior surface of the exosome, for example through a covalent bond or a non-covalent bond. The phospholipid bilayer of the EV or exosome provided herein may comprise one or more transmembrane proteins, wherein a portion of the one or more transmembrane membrane proteins is located within the internal space of the exosome. The phospholipid bilayer of the EV or exosome provided herein may comprise one or more transmembrane proteins, wherein a portion of the one or more transmembrane membrane proteins traverses the EV phospholipid bilayer. The phospholipid bilayer of the EV may comprise one or more transmembrane proteins, wherein the one or more transmembrane membrane proteins comprises a domain on the exterior of the exosome.

In some embodiments of any of the aspects, the extracellular vesicles or exosomes provided herein endogenously express CD81+, CD82+, CD37+, CD63+, CD9+, CD151+, CD105+, or any combination thereof. In various embodiments, the plurality of artificial synapses includes one or more artificial synapses expressing a biomarker. In certain embodiments, the biomarkers are tetraspanins. In other embodiments, the tetraspanins are one or more selected from the group including CD63, CD81, CD82, CD53, CD151, and CD37. In other embodiments, the artificial synapses express one or more lipid raft associated proteins (e.g., glycosylphosphatidylinositol-anchored proteins and flotillin), cholesterol, sphingolipids such as sphingomyelin, and/or hexosylceramides.

In other embodiments, the biological protein is related to exosome formation and packaging of cytosolic proteins, e.g., Hsp70, Hsp90, 14-3-3 epsilon, PKM2, GW182 and AGO2. In certain embodiments, the artificial synapses express CD63, HSP70, CD105 or combinations thereof. In other embodiments, the artificial synapses do not express CD9 or CD81, or express neither. For example, plurality of artificial synapses can include one or more artificial synapses that are CD63+, HSP+, CD105+, CD9−, and CD81−.

The EVs provided herein are specifically engineered to express fusion polypeptides that elicit biological signaling via a target cell. In some embodiments, the fusion polypeptide is overexpressed to elicit a biological response on a target cell or target polypeptide. The engineered EV comprises at least one fusion polypeptide and can comprise a plurality of the same or different fusion polypeptides provided herein. The fusion polypeptides provided herein comprise a protein of interest domain, also termed the signaling domain.

The fusion polypeptides provided herein can comprise one or more of a protein of interest domain, such that expression of said fusion polypeptide is permitted and that the number of POI domains does not impede protein expression or folding. Furthermore, the EVs provided herein can express more than one fusion protein (e.g., encoded by multiple different nucleic acid constructs). One of skill in the art can appreciate that an engineered EV can include one or more combinations of different signaling domains and/or vesicle targeting domains, or that one can use a plurality of engineered EVs, each including one or more vesicle targeting domains and one or more signaling domains.

In some embodiments, the EVs provided herein comprise one or more, two or more, three or more, four or more, five or more, six or more, seven or more, eight or more, nine or more, or ten or more fusion proteins. The fusion proteins can be encoded by the same vector or separate vectors. In some embodiments of any of the aspects, the engineered extracellular vesicle comprises at least two POI domains and/or at least two vesicle targeting domains.

In some embodiments, the fusion polypeptide comprises one or more, two or more, three or more, four or more, five or more, or six or more POI domains on the same polypeptide or nucleic acid construct encoding said polypeptide. For example, the fusion polypeptides provided herein can express a fusion polypeptide encoding one or more, two or more, three or more, four or more, five or more, or six or more signaling domains. In another example, the fusion polypeptides provided herein can express a fusion polypeptide encoding an immune checkpoint protein or a protein involved in immune or cell synapse or any combination or fragment thereof.

In some embodiments, the EV comprises one or more, two or more, three or more, four or more, five or more, or six or more fusion polypeptides on the same EV. For example, EVs comprising one or more, two or more, three or more, four or more, five or more, or six or more fusion polypeptides wherein the fusion polypeptides encode a signaling domain. In another example, EVs comprising one or more, two or more, three or more, four or more, five or more, or six or more fusion polypeptides wherein the fusion polypeptides encode for one or more immune checkpoint proteins or proteins involved in immune or cell synapse, or any combination or fragment thereof.

In various embodiments, the signaling domain is a protein or peptide of interest, or a fragment thereof. In various embodiments, the protein of interest (signaling domain) is an immune checkpoint protein. The terms "immune checkpoint protein" or "protein involved in immune or cell synapse" can include but are not limited to adenosine A2A receptor (A2AR), Galectin 9, fibrinogen-like protein 1 (FGL-1), platelet endothelial adhesion factor-1 (PECAM-1), tumor necrosis factor gene 6 protein (TSG-6), Stabilin-1 (STAB-1) also known as Clever-1, Neuropilin 1 (NRP1), Neuropilin 2 (NRP2), semaphorin-3A (SEMA3A), semaphorin-3F (SEMA3F), repulsive guidance molecule B (RGMB) also known as DRG11, T-cell immunoglobulin and mucin domain 3 (TIM-3), T cell immunoreceptor with Ig and ITIM domains (TIGIT), human leukocyte antigen (HLA) class I, HLA class II, high mobility group protein B1 (HMGB1), phosphatidylserine, carcinoembryonic antigen-related cell adhesion molecule 1 (CEACAM-1), T-cell receptor (TCR), Src homology 2 domain-containing protein tyrosine phosphatase 1 (SHP-1), SHP-2, F-Box protein 38 (FBXO38), signaling lymphocytic activation molecule (SLAM)-associated protein (SAP) also known as SH2D1A, B7RP1, indoleamine 2,3-dioxygenase (IDO), NADH oxidase 2 (NOX2), tumor necrosis factor receptor (TNFR) superfamily member 18 (TNFRSF18) (also known as activation inducible TNFR family receptor (AITR), glucocorticoid-induced TNFR related (GITR) protein, and CD357), B7-H4 also known as V-set domain containing T-cell activator inhibitor (VTCN1), B7-H5 (also known as V-domain Ig suppressor of T-cell activation (VISTA), platelet receptor Gi24, and stress induced secreted protein 1 (SISP1), B7-H6 (also known as NCR3LG1), B7-H7 (also known as human endogenous retrovirus-H (HERV-H) long terminal repeat-associating protein 2 (HHLA2), apelin receptor (APLNR), interferon gamma (IFN y) receptor, programmed cell death-1 (PD-1), Protein Wnt-5a (WNT5A), serine/threonine-protein kinase PAK4, interleukin 6 (IL-6), interleukin-10 (IL-10), NKG2 family of C-type lectin receptors (for example NKG2A, B, C, D, E, F and H), ligands of NKG2 family, killer cell immunoglobulin-like receptors, CD-2, cluster of differentiation 4 (CD4), CD8, CD27, CD27 ligand (CD27L, also known as CD70), CD28, CD28H (also known as transmembrane and immunoglobulin domain containing 2 (TMIGD2) and Ig containing and proline-rich receptor-1 (IGPR1)), CD39, CD40, CD44, integrin associated protein (CD47), carcinoembryonic antigen related cell adhesion molecule 1 (CEACAM1 also known as CD66a), CD73, B7-1 (also known as CD80), B7-2 (also known as CD86), CD94, CD96, immunoglobulin superfamily member 2 (IGSF2) also known as CD101, nectin cell adhesion molecule 2 (NECTIN2) (also known as herpesvirus entry mediator B (HVEB), poliovirus receptor related 2 (PRR2, PVRL2 and PVRR2) and CD112), poliovirus receptor related immunoglobulin domain containing protein (PVIRG) also known as CD112R, CD122 (also known as IL5RB and P70-75), OX40 (also known as tumor necrosis factor receptor superfamily member 4 (TNFRSF4) and CD134), OX40 ligand (OX40L), 4-1BB (also known as CD137), CD134 (also known as 4-1BB ligand (4-1BBL) and as tumor necrosis factor ligand superfamily member 9 (TNFSF9) and CD137L), cytotoxic T-lymphocyte-associated protein 4 (CTLA-4) also known as CD152, CD154 (also known as CD40L), poliovirus receptor (PVR) also known as CD155, killer-cell immunoglobulin-like receptors (KIRs) (for example but not limited to CD158 family, CD158a, CD158g, CD158h, KIR2DL1, KIR2DS1, KIRDS3, and KIR2DS5), CD160, signal-regulatory protein alpha (SIRPα) also known as CD172a, OX-2 also known as CD200, CD200R, lymphocyte-activation gene 3 (LAG-3) also known as CD223, CD226, OX40L also known as CD252, herpes virus entry mediator (HVEM) also known as tumor necrosis factor receptor superfamily member 14 (TNFRSF14) and CD270, B- and T-lymphocyte attenuator (BTLA) also known as CD272, programmed cell death ligand-2 (PD-L2) (also known as B7-DC, PDCDILG2, and CD273), programmed cell death-ligand 1 (PD-L1) (also known as B7-H1 and CD274), B7-H2 (also known as inducible T-cell co-stimulator ligand (ICOSLG), B7RP1, and CD275), B7-H3 also known as CD276, inducible T-cell co-stimulator (ICOS) also known as CD278, programed cell death protein 1 (PD-1) also known as CD279, leukocyte-associated Ig-like receptor-1 (LAIR-1) also known as CD305, collagen family of proteins (for example but not limited to collagen I, collagen II, collagen III alpha 1, collagen IV, collagen XXIII alpha 1, collagen XXV alpha 1), sialic acid-binding immunoglobulin-type lectin 7 (SIGLEC7) also known as CD328, sialic acid-binding immunoglobulin-type lectin 7 (SIGLEC9) also known as CD329, natural cytotoxicity triggering receptor 3 (NKp30) also known as CD337, or any isoform, fragment, variation thereof, or a ligand to the aforementioned proteins thereof, or the like known by one of ordinary skill in the art. All variants are encompassed by the present invention.

In some embodiments of any of the aspects provided herein, the protein of interest domain (POI domain) comprises a polypeptide or a fragment thereof or a nucleic acid encoding said polypeptide or fragment thereof selected from the group consisting of: Table 1 (below). Non-limiting examples of nucleic acid sequences that encode the POI domains provided herein are also provided in

TABLE 1

Type I Proteins of Interest Amino Acid Sequence

| Protein of Interest | Transcript Sequence (SEQ ID NO:)<br>Amino Acid Sequence (SEQ ID NO:) |
|---|---|
| Human Programmed death-ligand 1 (PD-L1) | >NM_014143.4 *Homo sapiens* CD274 molecule (CD274), transcript variant 1, mRNA<br>AGTTCTGCGCAGCTTCCCGAGGCTCCGCACCAGCCGCGCTTCTGTCCGCCTGCAGGG<br>CATTCCAGAAAGATGAGGATATTTGCTGTCTTTATATTCATGACCTACTGGCATTTG<br>CTGAACGCATTTACTGTCACGGTTCCCAAGGACCTATATGTGGTAGAGTATGGTAGC<br>AATATGACAATTGAATGCAAATTCCCAGTAGAAAAACAATTAGACCTGGCTGCACTA<br>ATTGTCTATTGGGAAATGGAGGATAAGAACATTATTCAATTTGTGCATGGAGAGGAA<br>GACCTGAAGGTTCAGCATAGTAGCTACAGACAGAGGGCCCGGCTGTTGAAGGACCAG<br>CTCTCCCTGGGAAATGCTGCACTTCAGATCACAGATGTGAAATTGCAGGATGCAGGG<br>GTGTACCGCTGCATGATCAGCTATGGTGGTGCCGACTACAAGCGAATTACTGTGAAA<br>GTCAATGCCCCATACAACAAAATCAACCAAAGAATTTTGGTTGTGGATCCAGTCACC<br>TCTGAACATGAACTGACATGTCAGGCTGAGGGCTACCCCAAGGCCGAAGTCATCTGG<br>ACAAGCAGTGACCATCAAGTCCTGAGTGGTAAGACCACCACCACCAATTCCAAGAGA<br>GAGGAGAAGCTTTTCAATGTGACCAGCACACTGAGAATCAACACAACAACTAATGAG<br>ATTTTCTACTGCACTTTTAGGAGATTAGATCCTGAGGAAAACCATACAGCTGAATTG<br>GTCATCCCAGAACTACCTCTGGCACATCCTCCAAATGAAAGGACTCACTTGGTAATT<br>CTGGGAGCCATCTTATTATGCCTTGGTGTAGCACTGACATTCATCTTCCGTTTAAGA<br>AAAGGGAGAATGATGGATGTGAAAAAATGTGGCATCCAAGATACAAACTCAAAGAAG<br>CAAAGTGATACACATTTGGAGGAGACGTAATCCAGCATTGGAACTTCTGATCTTCAA<br>GCAGGGATTCTCAACCTGTGGTTTAGGGGTTCATCGGGGCTGAGCGTGACAAGAGGA<br>AGGAATGGGCCCGTGGGATGCAGGCAATGTGGGACTTAAAAGGCCCAAGCACTGAAA<br>ATGGAACCTGGCGAAAGCAGAGGAGGAGAATGAAGAAAGATGGAGTCAAACAGGGAG<br>CCTGGAGGGAGACCTTGATACTTTCAAATGCCTGAGGGGCTCATCGACGCCTGTGAC<br>AGGGAGAAAGGATACTTCTGAACAAGGAGCCTCCAAGCAAATCATCCATTGCTCATC<br>CTAGGAAGACGGGTTGAGAATCCCTAATTTGAGGGTCAGTTCCTGCAGAAGTGCCCT<br>TTGCCTCCACTCAATGCCTCAATTTGTTTTCTGCATGACTGAGAGTCTCAGTGTTGG<br>AACGGGACAGTATTTATGTATGAGTTTTTCCTATTTATTTTGAGTCTGTGAGGTCTT<br>CTTGTCATGTGAGTGTGGTTGTGAATGATTTCTTTTGAAGATATATTGTAGTAGATG<br>TTACAATTTTGTCGCCAAACTAAACTTGCTGCTTAATGATTTGCTCACATCTAGTAA<br>AACATGGAGTATTTGTAAGGTGCTTGGTCTCCTCTATAACTACAAGTATACATTGGA<br>AGCATAAAGATCAAACCGTTGGTTGCATAGGATGTCACCTTTATTTAACCCATTAAT<br>ACTCTGGTTGACCTAATCTTATTCTCAGACCTCAAGTGTCTGTGCAGTATCTGTTCC |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| | ATTTAAATATCAGCTTTACAATTATGTGGTAGCCTACACACATAATCTCATTTCATC<br>GCTGTAACCACCCTGTTGTGATAACCACTATTATTTTACCCATCGTACAGCTGAGGA<br>AGCAAACAGATTAAGTAACTTGCCCAAACCAGTAAATAGCAGACCTCAGACTGCCAC<br>CCACTGTCCTTTTATAATACAATTTACAGCTATATTTTACTTTAAGCAATTCTTTTA<br>TTCAAAAACCATTTATTAAGTGCCCTTGCAATATCAATCGCTGTGCCAGGCATTGAA<br>TCTACAGATGTGAGCAAGACAAAGTACCTGTCCTCAAGGAGCTCATAGTATAATGAG<br>GAGATTAACAAGAAAATGTATTATTACAATTTAGTCCAGTGTCATAGCATAAGGATG<br>ATGCGAGGGGAAAACCCGAGCAGTGTTGCCAAGAGGAGGAAATAGGCCAATGTGGTC<br>TGGGACGGTTGGATATACTTAAACATCTTAATAATCAGAGTAATTTTCATTTACAAA<br>GAGAGGTCGGTACTTAAAATAACCCTGAAAAATAACACTGGAATTCCTTTTCTAGCA<br>TTATATTTATTCCTGATTTGCCTTTGCCATATAATCTAATGCTTGTTTATATAGTGT<br>CTGGTATTGTTTAACAGTTCTGTCTTTTCTATTTAAATGCCACTAAATTTTAAATTC<br>ATACCTTTCCATGATTCAAAATTCAAAAGATCCCATGGGAGATGGTTGGAAAATCTC<br>CACTTCATCCTCCAAGCCATTCAAGTTTCCTTTCCAGAAGCAACTGCTACTGCCTTT<br>CATTCATATGTTCTTCTAAAGATAGTCTACATTTGGAAATGTATGTTAAAAGCACGT<br>ATTTTTAAAATTTTTTTCCTAAATAGTAACACATTGTATGTCTGCTGTGTACTTTGC<br>TATTTTTATTTATTTTAGTGTTTCTTATATAGCAGATGGAATGAATTTGAAGTTCCC<br>AGGGCTGAGGATCCATGCCTTCTTTGTTTCTAAGTTATCTTTCCCATAGCTTTTCAT<br>TATCTTTCATATGATCCAGTATATGTTAAATATGTCCTACATATACATTTAGACAAC<br>CACCATTTGTTAAGTATTTGCTCTAGGACAGAGTTTGGATTTGTTTATGTTTGCTCA<br>AAAGGAGACCCATGGGCTCTCCAGGGTGCACTGAGTCAATCTAGTCCTAAAAAGCAA<br>TCTTATTATTAACTCTGTATGACAGAATCATGTCTGGAACTTTTGTTTTCTGCTTTC<br>TGTCAAGTATAAACTTCACTTTGATGCTGTACTTGCAAAATCACATTTTCTTTCTGG<br>AAATTCCGGCAGTGTACCTTGACTGCTAGCTACCCTGTGCCAGAAAAGCCTCATTCG<br>TTGTGCTTGAACCCTTGAATGCCACCAGCTGTCATCACTACACAGCCCTCCTAAGAG<br>GCTTCCTGGAGGTTTCGAGATTCAGATGCCCTGGGAGATCCCAGAGTTTCCTTTCCC<br>TCTTGGCCATATTCTGGTGTCAATGACAAGGAGTACCTTGGCTTTGCCACATGTCAA<br>GGCTGAAGAAACAGTGTCTCCAACAGAGCTCCTTGTGTTATCTGTTTGTACATGTGC<br>ATTTGTACAGTAATTGGTGTGACAGTGTTCTTTGTGTGAATTACAGGCAAGAATTGT<br>GGCTGAGCAAGGCACATAGTCTACTCAGTCTATTCCTAAGTCCTAACTCCTCCTTGT<br>GGTGTTGGATTTGTAAGGCACTTTATCCCTTTTGTCTCATGTTTCATCGTAAATGGC<br>ATAGGCAGAGATGATACCTAATTCTGCATTTGATTGTCACTTTTTGTACCTGCATTA<br>ATTTAATAAAATATTCTTATTTATTTTGTTACTTGGTACACCAGCATGTCCATTTTC<br>TTGTTTATTTTGTGTTTAATAAAATGTTCAGTTTAACATCCCA (SEQ ID NO:<br>1) |
| | >NP_054862.1 programmed cell death 1 ligand 1 isoform a<br>precursor [*Homo sapiens*]<br>MRIFAVFIFMTYWHLLNAFTVTVPKDLYVVEYGSNMTIECKFPVEKQLDLAALIVYW<br>EMEDKNIIQFVHGEEDLKVQHSSYRQRARLLKDQLSLGNAALQITDVKLQDAGVYRC<br>MISYGGADYKRITVKVNAPYNKINQRILVVDPVTSEHELTCQAEGYPKAEVIWTSSD<br>HQVLSGKTTTTNSKREEKLFNVTSTLRINTTTNEIFYCTFRRLDPEENHTAELVIPE<br>LPLAHPPNERTHLVILGAILLCLGVALTFIFRLRKGRMMDVKKCGIQDTNSKKQSDT<br>HLEET (SEQ ID NO: 2) |
| Mouse PD-L1 | >NM_021893.3 *Mus musculus* CD274 antigen (Cd274), mRNA<br>GAAATCGTGGTCCCCAAGCCTCATGCCAGGCTGCACTTGCACGTCGCGGGCCAGTCT<br>CCTCGCCTGCAGATAGTTCCCAAAACATGAGGATATTTGCTGGCATTATATTCACAG<br>CCTGCTGTCACTTGCTACGGGCGTTTACTATCACGGCTCCAAAGGACTTGTACGTGG<br>TGGAGTATGGCAGCAACGTCACGATGGAGTGCAGATTCCCTGTAGAACGGGAGCTGG<br>ACCTGCTTGCGTTAGTGGTGTACTGGGAAAAGGAAGATGAGCAAGTGATTCAGTTTG<br>TGGCAGGAGAGGAGGACCTTAAGCCTCAGCACAGCAACTTCAGGGGGAGAGCCTCGC<br>TGCCAAAGGACCAGCTTTTGAAGGGAAATGCTGCCCTTCAGATCACAGACGTCAAGC<br>TGCAGGACGCAGGCGTTTACTGCTGCATAATCAGCTACGGTGGTGCGGACTACAAGC<br>GAATCACGCTGAAAGTCAATGCCCCATACCGCAAAATCAACCAGAGAATTTCCGTGG<br>ATCCAGCCACTTCTGAGCATGAACTAATATGTCAGGCCGAGGGTTATCCAGAAGCTG<br>AGGTAATCTGGACAAACAGTGACCACCAACCCGTGAGTGGGAAGAGAAGTGTCACCA<br>CTTCCCGGACAGAGGGGATGCTTCTCAATGTGACCAGCAGTCTGAGGGTCAACGCCA<br>CAGCGAATGATGTTTTCTACTGTACGTTTTGGAGATCACAGCCAGGGCAAAACCACA<br>CAGCGGAGCTGATCATCCCAGAACTGCCTGCAACACATCCTCCACAGAACAGGACTC<br>ACTGGGTGCTTCTGGGATCCATCCTGTTGTTCCTCATTGTAGTGTCCACGGTCCTCC<br>TCTTCTTGAGAAAACAAGTGAGAATGCTAGATGTGGAGAAATGTGGCGTTGAAGATA<br>CAAGCTCAAAAAACCGAAATGATACACAATTCGAGGAGACGTAAGCAGTGTTGAACC<br>CTCTGATCGTCGATTGGCAGCTTGTGGTCTGTGAAAGAAAGGGCCCATGGGACATGA<br>GTCCAAAGACTCAAGATGGAACCTGAGGGAGAGAACCAAGAAAGTGTTGGGAGAGGA<br>GCCTGGAACAACGGACATTTTTTCCAGGGAGACACTGCTAAGCAAGTTGCCCATCAG<br>TCGTCTTGGGAAATGGATTGAGGGTTCCTGGCTTAGCAGCTGGTCCTTGCACAGTGA<br>CCTTTTCCTCTGCTCAGTGCCGGGATGAGAGATGGAGTCATGAGTGTTGAAGAATAA<br>GTGCCTTCTATTTATTTTGAGTCTGTGTGTTCTCACTTTGGGCATGTAATTATGACT<br>GGTGAATTCTGACGACATGATAGATCTTAAGATGTAGTCACCAAACTCAACTGCTGC<br>TTAGCATCCTCCGTAACTACTGATACAAGCAGGGAACACAGAGGTCACCTGCTTGGT<br>TTGACAGGCTCTTGCTGTCTGACTCAAATAATCTTTATTTTTCAGTCCTCAAGGCTC<br>TTCGATAGCAGTTGTTCTGTATCAGCCTTATAGGTGTCAGGTATAGCACTCAACATC<br>TCATCTCATTACAATAGCAACCCTCATCACCATAGCAACAGCTAACCTCTGTTATCC<br>TCACTTCATAGCCAGGAAGCTGAGCGACTAAGTCACTTGCCCACAGAGTATCAGCTC |

TABLE 1-continued

| Type I Proteins of Interest Amino Acid Sequence | |
|---|---|
| Protein of Interest | Transcript Sequence (SEQ ID NO:) Amino Acid Sequence (SEQ ID NO:) |
| | TCAGATTTCTGTTCTTCAGCCACTGTCCTTTCAGGATAGAATTTGTCGTTAAGAAAT TAATTTAAAAACTGATTATTGAGTAGCATTGTATATCAATCACAACATGCCTTGTGC ACTGTGCTGGCCTCTGAGCATAAAGATGTACGCCGGAGTACCGGTCGGACATGTTTA TGTGTGTTAAATACTCAGAGAAATGTTCATTAACAAGGAGCTTGCATTTTAGAGACA CTGGAAAGTAACTCCAGTTCATTGTCTAGCATTACATTTACCTCATTTGCTATCCTT GCCATACAGTCTCTTGTTCTCCATGAAGTGTCATGAATCTTGTTGAATAGTTCTTTT ATTTTTTAAATGTTTCTATTTAAATGATATTGACATCTGAGGCGATAGCTCAGTTGG TAAAACCCTTTCCTCACAAGTGTGAAACCCTGAGTCTTATCCCTAGAACCCACATAA AAAACAGTTGCGTATGTTTGTGCATGCTTTTGATCCCAGCACTAGGGAGGCAGAGGC AGGCAGATCCTGAGCTCTCATTGACCACCCAGCCTAGCCTACATGGTTAGCTCCAGG CCTACAGGAGCTGGCAGAGCCTGAAAAACGATGCCTAGACACACACACACACACACA CACACACACACACACACACACACCATGTACTCATAGACCTAAGTGCACCCTCCTA CACATGCACACACATACAATTCAAACACAAATCAACAGGGAATTGTCTCAGAATGGT CCCCAAGACAAAGAAGAAGAAAAACACCAAACCAGCTCTATTCCCTCAGCCTATCCT CTCTACTCCTTCCTAGAAGCAACTACTATTGTTTTTGTATATAAATTTACCCAACGA CAGTTAATATGTAGAATATATATTAAAGTGTCTGTCAATATATATTATCTCTTTCTT TCTTTCTTCCTTTCTTTCTTTCTTTCTTTCTTTCTTTCTTTCTTTCTTTCTTTCTTT CTTCCTTCCTTCCTTCCTTCCTTCCTTCCTTCCTTCCTTTCTTTCTTTCTTTCTTTT TTTCTGTCTATCTGTACCTAAATGGTTGCTCACTATGCATTTTCTGTGCTCTTCGCC CTTTTTATTTAATGTATGGATATTTATGCTGCTTCCAGAATGGATCTAAAGCTCTTT GTTTCTAGGTTTTCTCCCCCATCCTTCTAGGCATCTCTCACACTGTCTAGGCCAGAC ACCATGTCTGCTGCCTGAATCTGTAGACACCATTTATAAAGCACGTACTCACCGAGT TTGTATTTGGCTTGTTCTGTGTCTGATTAAAGGGAGACCATGAGTCCCCAGGGTACA CTGAGTTACCCCAGTACCAAGGGGGAGCCTTGTTTGTGTCTCCATGGCAGAAGCAGG CCTGGAGCCATTTTGGTTTCTTCCTTGACTTCTCTCAAACACAGACGCCTCACTTGC TCATTACAGGTTCTCCTTTGGGAATGTCAGCATTGCTCCTTGACTGCTGGCTGCCCT GGAAGGAGCCCATTAGCTCTGTGTGAGCCCTTGACAGCTACTGCCTCTCCTTACCAC AGGGGCCTCTAAGATACTGTTACCTAGAGGTCTTGAGGATCTGTGTTCTCTGGGGGG AGGAAAGGAGGAGGAACCCAGAACTTTCTTACAGTTTTCCTTGTTCTGTCACATGTC AAGACTGAAGGAACAGGCTGGGCTACGTAGTGAGATCCTGTCTCAAAGGAAAGACGA GCATAGCCGAACCCCCGGTGGAACCCCCTCTGTTACCTGTTCACACAAGCTTATTGA TGAGTCTCATGTTAATGTCTTGTTTGTATGAAGTTTAAGAAAATATCGGGTTGGGCA ACACATTCTATTTATTCATTTTATTTGAAATCTTAATGCCATCTCATGGTGTTGGAT TGGTGTGGCACTTTATTCTTTTGTGTTGTGTATAACCATAAATTTTATTTTGCATCA GATTGTCAATGTATTGCATTAATTTAATAAATATTTTTATTTATTAAAAAAAAAAAA AAAAA (SEQ ID NO: 3) |
| | >NP_068693.1 programmed cell death 1 ligand 1 precursor [*Mus musculus*] MRIFAGIIFTACCHLLRAFTITAPKDLYVVEYGSNVTMECRFPVERELDLLALVVYW EKEDEQVIQFVAGEEDLKPQHSNFRGRASLPKDQLLKGNAALQITDVKLQDAGVYCC IISYGGADYKRITLKVNAPYRKINQRISVDPATSEHELICQAEGYPEAEVIWTNSDH QPVSGKRSVTTSRTEGMLLNVTSSLRVNATANDVFYCTFWRSQPGQNHTAELIIPEL PATHPPQNRTHWVLLGSILLFLIVVSTVLLFLRKQVRMLDVEKCGVEDTSSKNRNDT QFEET (SEQ ID NO: 4) |
| Human PD-L2 | >NM_025239.4 *Homo sapiens* programmed cell death 1 ligand 2 (PCD1LG2), mRNA ACTCTCATGTTACGGCAAACCTTAAGCTGAATGAACAACTTTTCTTCTCTTGAATAT ATCTTAACGCCAAATTTTGAGTGCTTTTTTGTTACCCATCCTCATATGTCCCAGCTA GAAAGAATCCTGGGTTGGAGCTACTGCATGTTGATTGTTTTGTTTTTCCTTTTGGCT GTTCATTTTGGTGGCTACTATAAGGAAATCTAACACAAACAGCAACTGTTTTTTGTT GTTTACTTTTGCATCTTTACTTGTGGAGCTGTGGCAAGTCCTCATATCAAATACAGA ACATGATCTTCCTCCTGCTAATGTTGAGCCTGGAATTGCAGCTTCACCAGATAGCAG CTTTATTCACAGTGACAGTCCCTAAGGAACTGTACATAATAGAGCATGGCAGCAATG TGACCCTGGAATGCAACTTTGACACTGGAAGTCATGTGAACCTTGGAGCAATAACAG CCAGTTTGCAAAAGGTGGAAAATGATACATCCCCACACCGTGAAAGAGCCACTTTGC TGGAGGAGCAGCTGCCCCTAGGGAAGGCCTCGTTCCACATACCTCAAGTCCAAGTGA GGGACGAAGGACAGTACCAATGCATAATCATCTATGGGGTCGCCTGGGACTACAAGT ACCTGACTCTGAAAGTCAAAGCTTCCTACAGGAAAATAAACACTCACATCCTAAAGG TTCCAGAAACAGATGAGGTAGAGCTCACCTGCCAGGCTACAGGTTATCCTCTGGCAG AAGTATCCTGGCCAAACGTCAGCGTTCCTGCCAACACCAGCCACTCCAGGACCCCTG AAGGCCTCTACCAGGTCACCAGTGTTCTGCGCCTAAAGCCACCCCCTGGCAGAAACT TCAGCTGTGTGTTCTGGAATACTCACGTGAGGGAACTTACTTTGGCCAGCATTGACC TTCAAAGTCAGATGGAACCCAGGACCCATCCAACTTGGCTGCTTCACATTTTCATCC CCTTCTGCATCATTGCTTTCATTTTCATAGCCACAGTGATAGCCCTAAGAAAACAAC TCTGTCAAAAGCTGTATTCTTCAAAAGACACAACAAAAAGACCTGTCACCACAACAA AGAGGGAAGTGAACAGTGCTATCTGAACCTGTGGTCTTGGGAGCCAGGGTGACCTGA TATGACATCTAAAGAAGCTTCTGGACTCTGAACAAGAATTCGGTGGCCTGCAGAGCT TGCCATTTGCACTTTTCAAATGCCTTTGGATGACCCAGCACTTTAATCTGAAACCTG CAACAAGACTAGCCAACACCTGGCCATGAAACTTGCCCCTTCACTGATCTGGACTCA CCTCTGGAGCCTATGGCTTTAAGCAAGCACTACTGCACTTTACAGAATTACCCCACT GGATCCTGGACCCACAGAATTCCTTCAGGATCCTTCTTGCTGCCAGACTGAAAGCAA AAGGAATTATTTCCCCTCAAGTTTTCTAAGTGATTTCCAAAAGCAGAGGTGTGTGGA AATTTCCAGTAACAGAAACAGATGGGTTGCCAATAGAGTTATTTTTTATCTATAGCT |

TABLE 1-continued

Type I Proteins of Interest Amino Acid Sequence

| Protein of Interest | Transcript Sequence (SEQ ID NO:)<br>Amino Acid Sequence (SEQ ID NO:) |
|---|---|
| | TCCTCTGGGTACTAGAAGAGGCTATTGAGACTATGAGCTCACAGACAGGGCTTCGCA<br>CAAACTCAAATCATAATTGACATGTTTTATGGATTACTGGAATCTTGATAGCATAAT<br>GAAGTTGTTCTAATTAACAGAGAGCATTTAAATATACACTAAGTGCACAAATTGTGG<br>AGTAAAGTCATCAAGCTCTGTTTTTGAGGTCTAAGTCACAAAGCATTTGTTTTAACC<br>TGTAATGGCACCATGTTTAATGGTGGTTTTTTTTTTGAACTACATCTTTCCTTTAAA<br>AATTATTGGTTTCTTTTTATTTGTTTTTACCTTAGAAATCAATTATATACAGTCAAA<br>AATATTTGATATGCTCATACGTTGTATCTGCAGCAATTTCAGATAAGTAGCTAAAAT<br>GGCCAAAGCCCCAAACTAAGCCTCCTTTTCTGGCCCTCAATATGACTTTAAATTTGA<br>CTTTTCAGTGCCTCAGTTTGCACATCTGTAATACAGCAATGCTAAGTAGTCAAGGCC<br>TTTGATAATTGGCACTATGGAAATCCTGCAAGATCCCACTACATATGTGTGGAGCAG<br>AAGGGTAACTCGGCTACAGTAACAGCTTAATTTTGTTAAATTTGTTCTTTATACTGG<br>AGCCATGAAGCTCAGAGCATTAGCTGACCCTTGAACTATTCAAATGGGCACATTAGC<br>TAGTATAACAGACTTACATAGGTGGGCCTAAAGCAAGCTCCTTAACTGAGCAAAATT<br>TGGGGCTTATGAGAATGAAAGGGTGTGAAATTGACTAACAGACAAATCATACATCTC<br>AGTTTCTCAATTCTCATGTAAATCAGAGAATGCCTTTAAAGAATAAAACTCAATTGT<br>TATTCTTCAACGTTCTTTATATATTCTACTTTTGGGTA (SEQ ID NO: 5)<br><br>>NP_079515.2 programmed cell death 1 ligand 2 precursor<br>[*Homo sapiens*]<br>MIFLLLMLSLELQLHQIAALFTVTVPKELYIIEHGSNVTLECNFDTGSHVNLGAITA<br>SLQKVENDTSPHRERATLLEEQLPLGKASFHIPQVQVRDEGQYQCIIIYGVAWDYKY<br>LTLKVKASYRKINTHILKVPETDEVELTCQATGYPLAEVSWPNVSVPANTSHSRTPE<br>GLYQVTSVLRLKPPPGRNFSCVFWNTHVRELTLASIDLQSQMEPRTHPTWLLHIFIP<br>FCIIAFIFIATVIALRKQLCQKLYSSKDTTKRPVTTTKREVNSAI (SEQ ID NO:<br>6) |
| Mouse PD-L2 | >NM_021396.2 *Mus musculus* programmed cell death 1 ligand<br>2 (Pdcd1lg2), mRNA<br>GACCACATCATTTTTGTTCCCTTTGTTGGATATATCCTAATGTCAAATGTGGCATAT<br>CTTTGTTGTCTCCTTCTGTCTCCCAACTAGAGAGAACACACTTACGGCTCCTGTCCC<br>GGGCAGGTTTGGTTGTCGGTGTGATTGGCTTCCAGGGAACCTGATACAAGGAGCAAC<br>TGTGTGCTGCCTTTTCTGTGTCTTTGCTTGAGGAGCTGTGCTGGGTGCTGATATTGA<br>CACAGACCATGCTGCTCCTGCTGCCGATACTGAACCTGAGCTTACAACTTCATCCTG<br>TAGCAGCTTTATTCACCGTGACAGCCCCTAAAGAAGTGTACACCGTAGACGTCGGCA<br>GCAGTGTGAGCCTGGAGTGCGATTTTGACCGCAGAGAATGCACTGAACTGGAAGGGA<br>TAAGAGCCAGTTTGCAGAAGGTAGAAAATGATACGTCTCTGCAAAGTGAAAGAGCCA<br>CCCTGCTGGAGGAGCAGCTGCCCCTGGGAAAGGCTTTGTTCCACATCCCTAGTGTCC<br>AAGTGAGAGATTCCGGGCAGTACCGTTGCCTGGTCATCTGCGGGGCCGCCTGGGACT<br>ACAAGTACCTGACGGTGAAAGTCAAAGCTTCTTACATGAGGATAGACACTAGGATCC<br>TGGAGGTTCCAGGTACAGGGGAGGTGCAGCTTACCTGCCAGGCTAGAGGTTATCCCC<br>TAGCAGAAGTGTCCTGGCAAAATGTCAGTGTTCCTGCCAACACCAGCCACATCAGGA<br>CCCCCGAAGGCCTCTACCAGGTCACCAGTGTTCTGCGCCTCAAGCCTCAGCCTAGCA<br>GAAACTTCAGCTGCATGTTCTGGAATGCTCACATGAAGGAGCTGACTTCAGCCATCA<br>TTGACCCTCTGAGTCGGATGGAACCCAAAGTCCCCAGAACGTGGCCACTTCATGTTT<br>TCATCCCGGCCTGCACCATCGCTTTGATCTTCCTGGCCATAGTGATAATCCAGAGAA<br>AGAGGATCTAGGGGAAGCTGTATTACGGAAGAAGATCTGGACCTGCGGTCTTGGGAG<br>TTGGAAGGATCTGATGGGAAACCCTCAAGAGACTTCTGGACTCAAAGTGAGAATCTT<br>GCAGGACCTGCCATTTGCACTTTTGAACCCTTTGGACGGTGACCCAGGGCTCCGAAG<br>AGGAGCTTGTAAGACTGACAATCTTCCCTCTGTCTCAAGACTCTCTGAACAGCAAGA<br>CCCCAATGGCACTTTAGACTTACCCCTGGGATCCTGGACCCCAGTGAGGGCCTAAGG<br>CTCCTAATGACTTTCAGGGTGAGAACAAAAGGAATTGCTCTCCGCCCCACCCCCACC<br>TCCTGCTTTCCGCAGGGAGACATGGAAATTCCCAGTTACTAAAATAGATTGTCAATA<br>GAGTTATTTATAGCCCTCATTTCCTCCGGGGACTTGGAAGCTTCAGACAGGGTTTTT<br>CATAAACAAAGTCATAACTGATGTGTTTTACAGCATCCTAGAATCCTGGCAGCCTCT<br>GAAGTTCTAATTAACTGGAAGCATTTAAGCAACACGTTAAGTACCCCCACTGTGGTA<br>TTTGTTTCTACTTTTCTGTTTTTAAAGTGTGAGTCACAAGGTAATTGTTGTAACCTG<br>TGATATCACTGTTTCTTGTGTCTCTTCTTTCAACTACATCTTTTAAAACAAAACGGT<br>GTGGGGTTTGGTTGTTTTGGTGGTAGTGGTAGTGTTTCTCAGTGGTATCTCCTTAAG<br>AAAAAAAATCATCATGCCAGTGAATTGTTTCTTCAGCCATTTCAGATGGGAAGCTGG<br>AATAGCCTGTCCCCCAAGCTAAGCCTTCTTCCCTAGCTTTCTGCGTGATTTTACATT<br>GAGCATTCCTGTTGCTTTGTTTCTATAACTGTAATGTGGTGATGTCATTGTTAGGGC<br>ACTTGAGGGTGGGCGTTCTGGAAGTCCTTTCAGGTTAGTGTTTGGGGGCAGGGTTGC<br>TCAGAATACATAAAGGTGCTAACTTAAACTGCAGCCATGGAGCTCAGTGAATTCACT<br>AACCTTCGGGCTGTCCAAATGTGCACATTAGCTACTGTGACCCCTGTAGGTTAGGGA<br>GCCTGAAGCCAGCTCTTTACCTGGTGTTTAGACTCAGCAGAATTTGGAGTCAATGGG<br>ACCAAATGGTTGTGAAATTAAGATTTGAAGTGTGCATCTTATTTTATCACCATCTGC<br>CCAACAAAACTTCAGAAAATGCCTTTGAAGCACAAAAATGTAATCGTTTATGTGAAA<br>TCTCTGAGTTGCATTTAGATGCCCATTGCAGCAAGGTGGCTCTCTCACAGATTCCAC<br>ACCTTAGCCTAAGATACCAGACAGCAGGACAGAGAGAAAAGTCCTTCCTGGTGTGCA<br>AACTTCCTTACACTGGACCTCGCCTCTCAGGTGTGTGATTGGTAGGCCAAATCCCGA<br>TAGCCAATCGGTGTTGGGTGCTTTGTCTGCTCTACTGGGAGTCCAGTGGTACAATGG<br>ATTCTGGCAAAATGCTGCCATCTTGGCCCTCGCTGGGCTGCTTTCTAGGATATTCAT<br>AGAGAAAGGGCCGTCCAGATCCAGTATCCTAAAATCCTGAGAGGAGAATATAAGTTA<br>GTGTGTCTCACTATAACTATCTCTATGATCGGTCACATTACTATCTAACAGTTACCA<br>AATACTATATGCCTAATACTGGTAAGCATTTTATACACACCATTGGATTGAATCCTC |

TABLE 1-continued

| Type I Proteins of Interest Amino Acid Sequence | |
| --- | --- |
| Protein of Interest | Transcript Sequence (SEQ ID NO:)<br>Amino Acid Sequence (SEQ ID NO:) |
| | TCAAAATCCTCAAAAAGGAAGTTATTAATACCTCCATAGGCAAGGAGCCCAGAACCC<br>AGAGAGGTCAGGCAGTCTAGTTATAGATGCCTGCTTTGTTTAGAAGTGAACAAGAGC<br>ATCAAATTATTAATGTGCCCTGGTTATTAATGCGCCCTGGTTACCTGCTGGATGGAA<br>CATCAAGGTGGACTTTTGGCAGTTGCATACACCCAGAGGTATTTTGGCTATTCACGG<br>ATTAATTTCACACGAAGTGTTTCAGAGACATGTGTAGGGGAAGTCCGGGTTCAGGGG<br>GCCTAAGATTCAAACTCTAGCTTAGCTACGTCTGACCTCCCTAAGCACTAACTTACT<br>ATCAAAAGAATGAGCAGTAAAAGAATGGTGTTTACTGCCTGCCTTTATCAGGCAGTG<br>AACGTGCAGCGGGCAACGAATGCTTGATAAGTGTGTGTCAGTGTGAAGTCCCATGTA<br>CCAGCCGCTGTCCCCACTGCAAAAGCAGCAGAGCGCTCAGACATCATCAGCTGATTT<br>ACCAGCAGCAGATTTCTTCTTCTAGTCCCATCCCTGAAGAAGCTTCCAGCCTAGGTA<br>CATTGCATGGGCTTTGTGCTCCAGGAGTTCCTACACAGCCCTCAACTTCAACACAGG<br>CAAAGTGCTTACTGATCCTCATGTATCTTACAGGGTCCCCTCTACCCACAATACCTC<br>ATTGCTGGAACTTCAAATCTTCCTGAATAAAAGCTTGCCCGTGGTTTAATTA (SEQ ID NO: 7) |
| | >NP_067371.1 programmed cell death 1 ligand 2 precursor [*Mus musculus*]<br>MLLLLPILNLSLQLHPVAALFTVTAPKEVYTVDVGSSVSLECDFDRRECTELEGIRA<br>SLQKVENDTSLQSERATLLEEQLPLGKALFHIPSVQVRDSGQYRCLVICGAAWDYKY<br>LTVKVKASYMRIDTRILEVPGTGEVQLTCQARGYPLAEVSWQNVSVPANTSHIRTPE<br>GLYQVTSVLRLKPQPSRNFSCMFWNAHMKELTSAIIDPLSRMEPKVPRTWPLHVFIP<br>ACTIALIFLAIVIIQRKRI (SEQ ID NO: 8) |
| Human CTLA-4 (CD152) | >NM_005214.5 *Homo sapiens* cytotoxic T-lymphocyte associated protein 4 (CTLA4), transcript variant 1, mRNA<br>GCTTTCTATTCAAGTGCCTTCTGTGTGCACATGTGTAATACATATCTGGGATCAA<br>AGCTATCTATATAAAGTCCTTGATTCTGTGTGGGTTCAAACACATTTCAAAGCTTCA<br>GGATCCTGAAAGGTTTTGCTCTACTTCCTGAAGACCTGAACACCGCTCCCATAAAGC<br>CATGGCTTGCCTTGGATTTCAGCGGCACAAGGCTCAGCTGAACCTGGCTACCAGGAC<br>CTGGCCCTGCACTCTCCTGTTTTTTCTTCTCTTCATCCCTGTCTTCTGCAAAGCAAT<br>GCACGTGGCCCAGCCTGCTGTGGTACTGGCCAGCAGCCGAGGCATCGCCAGCTTTGT<br>GTGTGAGTATGCATCTCCAGGCAAAGCCACTGAGGTCCGGGTGACAGTGCTTCGGCA<br>GGCTGACAGCCAGGTGACTGAAGTCTGTGCGGCAACCTACATGATGGGGAATGAGTT<br>GACCTTCCTAGATGATTCCATCTGCACGGGCACCTCCAGTGGAAATCAAGTGAACCT<br>CACTATCCAAGGACTGAGGGCCATGGACACGGGACTCTACATCTGCAAGGTGGAGCT<br>CATGTACCCACCGCCATACTACCTGGGCATAGGCAACGGAACCCAGATTTATGTAAT<br>TGATCCAGAACCGTGCCCAGATTCTGACTTCCTCCTCTGGATCCTTGCAGCAGTTAG<br>TTCGGGGTTGTTTTTTTATAGCTTTCTCCTCACAGCTGTTTCTTTGAGCAAAATGCT<br>AAAGAAAAGAAGCCCTCTTACAACAGGGGTCTATGTGAAAATGCCCCCAACAGAGCC<br>AGAATGTGAAAAGCAATTTCAGCCTTATTTTATTCCCATCAATTGAGAAACCATTAT<br>GAAGAAGAGAGTCCATATTTCAATTTCCAAGAGCTGAGGCAATTCTAACTTTTTTGC<br>TATCCAGCTATTTTTATTTGTTTGTGCATTTGGGGGGAATTCATCTCTCTTTAATAT<br>AAAGTTGGATGCGGAACCCAAATTACGTGTACTACAATTTAAAGCAAAGGAGTAGAA<br>AGACAGAGCTGGGATGTTTCTGTCACATCAGCTCCACTTTCAGTGAAAGCATCACTT<br>GGGATTAATATGGGGATGCAGCATTATGATGTGGGTCAAGGAATTAAGTTAGGGAAT<br>GGCACAGCCCAAAGAAGGAAAAGGCAGGGAGCGAGGGAGAAGACTATATTGTACACA<br>CCTTATATTTACGTATGAGACGTTTATAGCCGAAATGATCTTTTCAAGTTAAATTTT<br>ATGCCTTTTATTTCTTAAACAAATGTATGATTACATCAAGGCTTCAAAAATACTCAC<br>ATGGCTATGTTTTAGCCAGTGATGCTAAAGGTTGTATTGCATATATACATATATATA<br>TATATATATATATATATATATATATATATATATATATATATATATATTTTAATTTGA<br>TAGTATTGTGCATAGAGCCACGTATGTTTTTGTGTATTTGTTAATGGTTTGAATATA<br>AACACTATATGGCAGTGTCTTTCCACCTTGGGTCCCAGGGAAGTTTTGTGGAGGAGC<br>TCAGGACACTAATACACCAGGTAGAACACAAGGTCATTTGCTAACTAGCTTGGAAAC<br>TGGATGAGGTCATAGCAGTGCTTGATTGCGTGGAATTGTGCTGAGTTGGTGTTGACA<br>TGTGCTTTGGGGCTTTTACACCAGTTCCTTTCAATGGTTTGCAAGGAAGCCACAGCT<br>GGTGGTATCTGAGTTGACTTGACAGAACACTGTCTTGAAGACAATGGCTTACTCCAG<br>GAGACCCACAGGTATGACCTTCTAGGAAGCTCCAGTTCGATGGGCCCAATTCTTACA<br>AACATGTGGTTAATGCCATGGACAGAAGAAGGCAGCAGGTGGCAGAATGGGGTGCAT<br>GAAGGTTTCTGAAAATTAACACTGCTTGTGTTTTTAACTCAATATTTTCCATGAAAA<br>TGCAACAACATGTATAATATTTTTAATTAAATAAAAATCTGTGGTGGTCGTTTTCCG<br>GA (SEQ ID NO: 9) |
| | >NP_005205.2 cytotoxic T-lymphocyte protein 4 isoform CTLA4-TM precursor [*Homo sapiens*]<br>MACLGFQRHKAQLNLATRTWPCTLLFFLLFIPVFCKAMHVAQPAVVLASSRGIASFV<br>CEYASPGKATEVRVTVLRQADSQVTEVCAATYMMGNELTFLDDSICTGTSSGNQVNL<br>TIQGLRAMDTGLYICKVELMYPPPYYLGIGNGTQIYVIDPEPCPDSDFLLWILAAVS<br>SGLFFYSFLLTAVSLSKMLKKRSPLTTGVYVKMPPTEPECEKQFQPYFIPIN (SEQ ID NO: 10) |
| Mouse CTLA-4 (CD152) | >NM_009843.4 *Mus musculus* cytotoxic T-lymphocyte-associated protein 4 (Ctla4), transcript variant 1, mRNA<br>CTACACATATGTAGCACGTACCTTGGATCAAAGCTGTCTATATAAAGTCCCCGAGTC<br>TGTGTGGGTTCAAACACATCTCAAGGCTTCTGGATCCTGTTGGGTTTTACTCTGCTC<br>CCTGAGGACCTCAGCACATTTGCCCCCCAGCCATGGCTTGTCTTGGACTCCGGAGGT |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| | ACAAAGCTCAACTGCAGCTGCCTTCTAGGACTTGGCCTTTTGTAGCCCTGCTCACTC<br>TTCTTTTCATCCCAGTCTTCTCTGAAGCCATACAGGTGACCCAACCTTCAGTGGTGT<br>TGGCTAGCAGCCATGGTGTCGCCAGCTTTCCATGTGAATATTCACCATCACACAACA<br>CTGATGAGGTCCGGGTGACTGTGCTGCGGCAGACAAATGACCAAATGACTGAGGTCT<br>GTGCCACGACATTCACAGAGAAGAATACAGTGGGCTTCCTAGATTACCCCTTCTGCA<br>GTGGTACCTTTAATGAAAGCAGAGTGAACCTCACCATCCAAGGACTGAGAGCTGTTG<br>ACACGGGACTGTACCTCTGCAAGGTGGAACTCATGTACCCACCGCCATACTTTGTGG<br>GCATGGGCAACGGGACGCAGATTTATGTCATTGATCCAGAACCATGCCCGGATTCTG<br>ACTTCCTCCTTTGGATCCTTGTCGCAGTTAGCTTGGGGTTGTTTTTTTACAGTTTCC<br>TGGTCACTGCTGTTTCTTTGAGCAAGATGCTAAAGAAAAGAAGTCCTCTTACAACAG<br>GGGTCTATGTGAAAATGCCCCCAACAGAGCCAGAATGTGAAAAGCAATTTCAGCCTT<br>ATTTTATTCCCATCAACTGAAAGGCCGTTTATGAAGAAGAAGGAGCATACTTCAGTC<br>TCTAAAAGCTGAGGCAATTTCAACTTTCCTTTTCTCTCCAGCTATTTTTACCTGTTT<br>GTATATTTTAAGGAGAGTATGCCTCTCTTTAATAGAAAGCTGGATGCAAAATTCCAA<br>TTAAGCATACTACAATTTAAAGCTAAGGAGCATGAACAGAGAGCTGGGATATTTCTG<br>TTGTGTCAGAACCATTTTACTAAAAGCATCACTTGGAAGCAGCATAAGGATATAGCA<br>TTATGGTGTGGGGTCAAGGGAACATTAGGGAATGGCACAGCCCAAAGAAAGGAAGGG<br>GGTGAAGGAAGAGATTATATTGTACACATCTTGTATTTACCTGAGAGATGTTTATGA<br>CTTAAATAATTTTTAAATTTTTCATGCTGTTATTTTCTTTAACAATGTATAATTACA<br>CGAAGGTTTAAACATTTATTCACAGAGCTATGTGACATAGCCAGTGGTTCCAAAGGT<br>TGTAGTGTTCCAAGATGTATTTTTAAGTAATATTGTACATGGGTGTTTCATGTGCTG<br>TTGTGTATTTGCTGGTGGTTTGAATATAAACACTATGTATCAGTGTCGTCCCACAGT<br>GGGTCCTGGGGAGGTTTGGCTGGGGAGCTTAGGACACTAATCCATCAGGTTGGACTC<br>GAGGTCCTGCACCAACTGGCTTGGAAACTAGATGAGGCTGTCACAGGGCTCAGTTGC<br>ATAAACCGATGGTGATGGAGTGTAAACTGGGTCTTTACACTCATTTTATTTTTTGTT<br>TCTGCTTTTGTTTTCTTCAATGATTTGCAAGGAAACCAAAAGCTGGCAGTGTTTGTA<br>TGAACCTGACAGAACACTGTCTTCAAGGAAATGCCTCATTCCTGAGACCAGTAGGTT<br>TGTTTTTTTAGGAAGTTCCAATACTAGGACCCCCTACAAGTACTATGGCTCCTCGAA<br>AACACAAAGTTAATGCCACAGGAAGCAGCAGATGGTAGGATGGGATGCACAAGAGTT<br>CCTGAAAACTAACACTGTTAGTGTTTTTTTTTTAACTCAATATTTTCCATGAAAATG<br>CAACCACATGTATAATATTTTTAATTAAATAAAAGTTTCTTGTGATTGTTTT (SEQ<br>ID NO: 11) |
| | >NP_033973.2 cytotoxic T-lymphocyte protein 4 isoform 1<br>precursor [*Mus musculus*]<br>MACLGLRRYKAQLQLPSRTWPFVALLTLLFIPVFSEAIQVTQPSVVLASSHGVASFP<br>CEYSPSHNTDEVRVTVLRQTNDQMTEVCATTFTEKNTVGFLDYPFCSGTFNESRVNL<br>TIQGLRAVDTGLYLCKVELMYPPPYFVGMGNGTQIYVIDPEPCPDSDFLLWILVAVS<br>LGLFFYSFLVTAVSLSKMLKKRSPLTTGVYVKMPPTEPECEKQFQPYFIPIN (SEQ<br>ID NO: 12) |
| Human 4-1BBL (CD137L) | >NM_003811.4 *Homo sapiens* TNF superfamily member 9<br>(TNFSF9), mRNA<br>AGTCTCTCGTCATGGAATACGCCTCTGACGCTTCACTGGACCCCGAAGCCCCGTGGC<br>CTCCCGCGCCCCGCGCTCGCGCCTGCCGCGTACTGCCTTGGGCCCTGGTCGCGGGGC<br>TGCTGCTGCTGCTGCTGCTCGCTGCCGCCTGCGCCGTCTTCCTCGCCTGCCCCTGGG<br>CCGTGTCCGGGGCTCGCGCCTCGCCCGGCTCCGCGGCCAGCCCGAGACTCCGCGAGG<br>GTCCCGAGCTTTCGCCCGACGATCCCGCCGGCCTCTTGGACCTGCGGCAGGGCATGT<br>TTGCGCAGCTGGTGGCCCAAAATGTTCTGCTGATCGATGGGCCCCTGAGCTGGTACA<br>GTGACCCAGGCCTGGCAGGCGTGTCCCTGACGGGGGGCCTGAGCTACAAAGAGGACA<br>CGAAGGAGCTGGTGGTGGCCAAGGCTGGAGTCTACTATGTCTTCTTTCAACTAGAGC<br>TGCGGCGCGTGGTGGCCGGCGAGGGCTCAGGCTCCGTTTCACTTGCGCTGCACCTGC<br>AGCCACTGCGCTCTGCTGCTGGGGCCGCCGCCCTGGCTTTGACCGTGGACCTGCCAC<br>CCGCCTCCTCCGAGGCTCGGAACTCGGCCTTCGGTTTCCAGGGCCGCTTGCTGCACC<br>TGAGTGCCGGCCAGCGCCTGGGCGTCCATCTTCACACTGAGGCCAGGGCACGCCATG<br>CCTGGCAGCTTACCCAGGGCGCCACAGTCTTGGGACTCTTCCGGGTGACCCCCGAAA<br>TCCCAGCCGGACTCCCTTCACCGAGGTCGGAATAACGTCCAGCCTGGGTGCAGCCCA<br>CCTGGACAGAGTCCGAATCCTACTCCATCCTTCATGGAGACCCCTGGTGCTGGGTCC<br>CTGCTGCTTTCTCTACCTCAAGGGGCTTGGCAGGGGTCCCTGCTGCTGACCTCCCCT<br>TGAGGACCCTCCTCACCCACTCCTTCCCCAAGTTGGACCTTGATATTTATTCTGAGC<br>CTGAGCTCAGATAATATATTATATATATTATATATATATATATATTTCTATTTAAAG<br>AGGATCCTGAGTTTGTGAATGGACTTTTTTAGAGGAGTTGTTTTGGGGGGGGGGGGG<br>TCTTCGACATTGCCGAGGCTGGTCTTGAACTCCTGGACTTAGACGATCCTCCTGCCT<br>CAGCCTCCCAAGCAACTGGGATTCATCCTTTCTATTAATTCATTGTACTTATTTGCT<br>TATTTGTGTGTATTGAGCATCTGTAATGTGCCAGCATTGTGCCCAGGCTAGGGGGCT<br>ATAGAAACATCTAGAAATAGACTGAAAGAAAATCTGAGTTATGGTAATACGTGAGGA<br>ATTTAAAGACTCATCCCCAGCCTCCACCTCCTGTGTGATACTTGGGGGCTAGCTTTT<br>TTCTTTCTTTCTTTTTTTTGAGATGGTCTTGTTCTGTCAACCAGGCTAGAATGCAGC<br>GGTGCAATCATGAGTCAATGCAGCCTCCAGCCTCGACCTCCCGAGGCTCAGGTGATC<br>CTCCCATCTCAGCCTCTCGAGTAGCTGGGACCACAGTTGTGTGCCACCACACTTGGC<br>TAACTTTTTAATTTTTTTGCGGAGACGGTATTGCTATGTTGCCAAGGTTGTTTACAT<br>GCCAGTACAATTTATAATAAACACTCATTTTTCCTCCC (SEQ ID NO: 13) |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| | >NP_003802.1 tumor necrosis factor ligand superfamily member 9 [*Homo sapiens*]<br>MEYASDASLDPEAPWPPAPRARACRVLPWALVAGLLLLLLLAAACAVFLACPWAVSG<br>ARASPGSAASPRLREGPELSPDDPAGLLDLRQGMFAQLVAQNVLLIDGPLSWYSDPG<br>LAGVSLTGGLSYKEDTKELVVAKAGVYYVFFQLELRRVVAGEGSGSVSLALHLQPLR<br>SAAGAAALALTVDLPPASSEARNSAFGFQGRLLHLSAGQRLGVHLHTEARARHAWQL<br>TQGATVLGLFRVTPEIPAGLPSPRSE (SEQ ID NO: 14) |
| Mouse 4-1BBL (CD137L) | >NM_009404.3 *Mus musculus* tumor necrosis factor (ligand) superfamily, member 9 (Tnfsf9), mRNA<br>ATAAAGCACGGGCACTGGCGGGAGACGTGCACTGACCGACCGTGGTAATGGACCAGC<br>ACACACTTGATGTGGAGGATACCGCGGATGCCAGACATCCAGCAGGTACTTCGTGCC<br>CCTCGGATGCGGCGCTCCTCAGAGATACCGGGCTCCTCGCGGACGCTGCGCTCCTCT<br>CAGATACTGTGCGCCCCACAAATGCCGCGCTCCCCACGGATGCTGCCTACCCTGCGG<br>TTAATGTTCGGGATCGCGAGGCCGCGTGGCCGCCTGCACTGAACTTCTGTTCCCGCC<br>ACCCAAAGCTCTATGGCCTAGTCGCTTTGGTTTTGCTGCTTCTGATCGCCGCCTGTG<br>TTCCTATCTTCACCCGCACCGAGCCTCGGCCAGCGCTCACAATCACCACCTCGCCCA<br>ACCTGGGTACCCGAGAGAATAATGCAGACCAGGTCACCCCTGTTTCCCACATTGGCT<br>GCCCCAACACTACACAACAGGGCTCTCCTGTGTTCGCCAAGCTACTGGCTAAAAACC<br>AAGCATCGTTGTGCAATACAACTCTGAACTGGCACAGCCAAGATGGAGCTGGGAGCT<br>CATACCTATCTCAAGGTCTGAGGTACGAAGAAGACAAAAAGGAGTTGGTGGTAGACA<br>GTCCCGGGCTCTACTACGTATTTTTGGAACTGAAGCTCAGTCCAACATTCACAAACA<br>CAGGCCACAAGGTGCAGGGCTGGGTCTCTCTTGTTTTGCAAGCAAAGCCTCAGGTAG<br>ATGACTTTGACAACTTGGCCCTGACAGTGGAACTGTTCCCTTGCTCCATGGAGAACA<br>AGTTAGTGGACCGTTCCTGGAGTCAACTGTTGCTCCTGAAGGCTGGCCACCGCCTCA<br>GTGTGGGTCTGAGGGCTTATCTGCATGGAGCCCAGGATGCATACAGAGACTGGGAGC<br>TGTCTTATCCCAACACCACCAGCTTTGGACTCTTTCTTGTGAAACCCGACAACCCAT<br>GGGAATGAGAACTATCCTTCTTGTGACTCCTAGTTGCTAAGTCCTCAAGCTGCTATG<br>TTTTATGGGGTCTGAGCAGGGGTCCCTTCCATGACTTTCTCTTGTCTTTAACTGGAC<br>TTGGTATTTATTCTGAGCATAGCTCAGACAAGACTTTATATAATTCACTAGATAGCA<br>TTAGTAAACTGCTGGGCAGCTGCTAGATAAAAAAAAATTTCTAAATCAAAGTTTATA<br>TTTATATTAATATATAAAAATAAATGTGTTTGT (SEQ ID NO: 15) |
| | >NP_033430.1 tumor necrosis factor ligand superfamily member 9 [*Mus musculus*]<br>MDQHTLDVEDTADARHPAGTSCPSDAALLRDTGLLADAALLSDTVRPTNAALPTDAA<br>YPAVNVRDREAAWPPALNFCSRHPKLYGLVALVLLLLIAACVPIFTRTEPRPALTIT<br>TSPNLGTRENNADQVTPVSHIGCPNTTQQGSPVFAKLLAKNQASLCNTTLNWHSQDG<br>AGSSYLSQGLRYEEDKKELVVDSPGLYYVFLELKLSPTFTNTGHKVQGWVSLVLQAK<br>PQVDDFDNLALTVELFPCSMENKLVDRSWSQLLLLKAGHRLSVGLRAYLHGAQDAYR<br>DWELSYPNTTSFGLFLVKPDNPWE (SEQ ID NO: 16) |
| Human HVEM (CD270) | >NM_003820.4 *Homo sapiens* TNF receptor superfamily member 14 (TNFRSF14), transcript variant 1, DNA<br>ATACCGGCCCTTCCCCTCGGCTTTGCCTGGACAGCTCCTGCCTCCCGCAGGGCCCAC<br>CTGTGTCCCCCAGCGCCGCTCCACCCAGCAGGCCTGAGCCCCTCTCTGCTGCCAGAC<br>ACCCCCTGCTGCCCACTCTCCTGCTGCTCGGGTTCTGAGGCACAGCTTGTCACACCG<br>AGGCGGATTCTCTTTCTCTTTCTCTTTCTCTTCTGGCCCACAGCCGCAGCAATGGCG<br>CTGAGTTCCTCTGCTGGAGTTCATCCTGCTAGCTGGGTTCCCGAGCTGCCGGTCTGA<br>GCCTGAGGCATGGAGCCTCCTGGAGACTGGGGGCCTCCTCCCTGGAGATCCACCCCC<br>AAAACCGACGTCTTGAGGCTGGTGCTGTATCTCACCTTCCTGGGAGCCCCCTGCTAC<br>GCCCCAGCTCTGCCGTCCTGCAAGGAGGACGAGTACCCAGTGGGCTCCGAGTGCTGC<br>CCCAAGTGCAGTCCAGGTTATCGTGTGAAGGAGGCCTGCGGGGAGCTGACGGGCACA<br>GTGTGTGAACCCTGCCCTCCAGGCACCTACATTGCCCACCTCAATGGCCTAAGCAAG<br>TGTCTGCAGTGCCAAATGTGTGACCCAGCCATGGGCCTGCGCGCGAGCCGGAACTGC<br>TCCAGGACAGAGAACGCCGTGTGTGGCTGCAGCCCAGGCCACTTCTGCATCGTCCAG<br>GACGGGGACCACTGCGCCGCGTGCCGCGCTTACGCCACCTCCAGCCCGGGCCAGAGG<br>GTGCAGAAGGGAGGCACCGAGAGTCAGGACACCCTGTGTCAGAACTGCCCCCCGGGG<br>ACCTTCTCTCCCAATGGGACCCTGGAGGAATGTCAGCACCAGACCAAGTGCAGCTGG<br>CTGGTGACGAAGGCCGGAGCTGGGACCAGCAGCTCCCACTGGGTATGGTGGTTTCTC<br>TCAGGGAGCCTCGTCATCGTCATTGTTTGCTCCACAGTTGGCCTAATCATATGTGTG<br>AAAAGAAGAAAGCCAAGGGGTGATGTAGTCAAGGTGATCGTCTCCGTCCAGCGGAAA<br>AGACAGGAGGCAGAAGGTGAGGCCACAGTCATTGAGGCCCTGCAGGCCCCTCCGGAC<br>GTCACCACGGTGGCCGTGGAGGAGACAATACCCTCATTCACGGGGAGGAGCCCAAAC<br>CACTGACCCACAGACTCTGCACCCCGACGCCAGAGATACCTGGAGCGACGGCTGCTG<br>AAAGAGGCTGTCCACCTGGCGGAACCACCGGAGCCCGGAGGCTTGGGGGCTCCGCCC<br>TGGGCTGGCTTCCGTCTCCTCCAGTGGAGGGAGAGGTGGGGCCCCTGCTGGGGTAGA<br>GCTGGGGACGCCACGTGCCATTCCCATGGGCCAGTGAGGGCCTGGGGCCTCTGTTCT<br>GCTGTGGCCTGAGCTCCCCAGAGTCCTGAGGAGGAGCGCCAGTTGCCCCTCGCTCAC<br>AGACCACACACCCAGCCCTCCTGGGCCAGCCCAGAGGGCCCTTCAGACCCCAGCTGT |

TABLE 1-continued

Type I Proteins of Interest Amino Acid Sequence

| Protein of Interest | Transcript Sequence (SEQ ID NO:)<br>Amino Acid Sequence (SEQ ID NO:) |
|---|---|
| | CTGCGCGTCTGACTCTTGTGGCCTCAGCAGGACAGGCCCCGGGCACTGCCTCACAGC<br>CAAGGCTGGACTGGGTTGGCTGCAGTGTGGTGTTTAGTGGATACCACATCGGAAGTG<br>ATTTTCTAAATTGGATTTGAATTCGGCTCCTGTTTTCTATTTGTCATGAAACAGTGT<br>ATTTGGGGAGATGCTGTGGGAGGATGTAAATATCTTGTTTCTCCTCAAA (SEQ ID NO: 17) |
| | >NP_003811.2 tumor necrosis factor receptor superfamily member 14 isoform 1 precursor [*Homo sapiens*]<br>MEPPGDWGPPPWRSTPKTDVLRLVLYLTFLGAPCYAPALPSCKEDEYPVGSECCPKC<br>SPGYRVKEACGELTGTVCEPCPPGTYIAHLNGLSKCLQCQMCDPAMGLRASRNCSRT<br>ENAVCGCSPGHFCIVQDGDHCAACRAYATSSPGQRVQKGGTESQDTLCQNCPPGTFS<br>PNGTLEECQHQTKCSWLVTKAGAGTSSSHWVWWFLSGSLVIVIVCSTVGLIICVKRR<br>KPRGDVVKVIVSVQRKRQEAEGEATVIEALQAPPDVTTVAVEETIPSFTGRSPNH<br>(SEQ ID NO: 18) |
| Mouse HVEM (CD270) | >NM_178931.2 *Mus musculus* tumor necrosis factor receptor superfamily, member 14 (herpesvirus entry mediator) (Tnfrsf14), mRNA<br>GCTCTTGGCCTGAAGTTTCTTGATCAAGAAAATGGAACCTCTCCCAGGATGGGGGTC<br>GGCACCCTGGAGCCAGGCCCCTACAGACAACACCTTCAGGCTGGTGCCTTGTGTCTT<br>CCTTTTGAACTTGCTGCAGCGCATCTCTGCCCAGCCCTCATGCAGACAGGAGGAGTT<br>CCTTGTGGGAGACGAGTGCTGCCCCATGTGCAACCCAGGTTACCATGTGAAGCAGGT<br>CTGCAGTGAGCATACAGGCACAGTGTGTGCCCCCTGTCCCCCACAGACATATACCGC<br>CCATGCAAATGGCCTGAGCAAGTGTCTGCCCTGCGGAGTCTGTGATCCAGACATGGG<br>CCTGCTGACCTGGCAGGAGTGCTCCAGCTGGAAGGACACTGTGTGCAGATGCATCCC<br>AGGCTACTTCTGTGAGAACCAGGATGGGAGCCACTGTTCCACATGCTTGCAGCACAC<br>CACCTGCCCTCCAGGGCAGAGGGTAGAGAAGAGAGGGACTCACGACCAGGACACTGT<br>ATGTGCTGACTGCCTAACAGGGACCTTCTCACTTGGAGGGACTCAGGAGGAATGCCT<br>GCCCTGGACCAACTGCAGTGCATTTCAACAGGAAGTAAGACGTGGGACCAACAGCAC<br>AGACACCACCTGCTCCTCCCAGGTCGTCTACTACGTTGTGTCCATCCTTTTGCCACT<br>TGTGATAGTGGGAGCTGGGATAGCTGGATTCCTCATCTGCACGCGAAGACACCTGCA<br>CACCAGCTCAGTGGCCAAGGAGCTGGAGCCTTTCCAGGAACAACAGGAGAACACCAT<br>CAGGTTTCCAGTCACCGAGGTTGGGTTTGCTGAGACCGAGGAGGAGACAGCCTCCAA<br>CTGAACAAATTCTGGGTGACAAGACACCGAGGAGACGT (SEQ ID NO: 19) |
| | >NP_849262.1 tumor necrosis factor receptor superfamily member 14 precursor [*Mus musculus*]<br>MEPLPGWGSAPWSQAPTDNTFRLVPCVFLLNLLQRISAQPSCRQEEFLVGDECCPMC<br>NPGYHVKQVCSEHTGTVCAPCPPQTYTAHANGLSKCLPCGVCDPDMGLLTWQECSSW<br>KDTVCRCIPGYFCENQDGSHCSTCLQHTTCPPGQRVEKRGTHDQDTVCADCLTGTFS<br>LGGTQEECLPWTNCSAFQQEVRRGTNSTDTTCSSQVVYYVVSILLPLVIVGAGIAGF<br>LICTRRHLHTSSVAKELEPFQEQQENTIRFPVTEVGFAETEEETASN (SEQ ID NO: 20) |
| Human FGL1 | >NM_004467.4 *Homo sapiens* fibrinogen like 1 (FGL1), transcript variant 1, mRNA<br>AATGCAGTTACAGGATCCTGGGAAGCAGAGTGTCTGGATGGAACCTGAGCTGGGTCT<br>CTGACTCACTTCTGACTTTAGTTTTTCAAGGGGGAACATGGCAAAGGTGTTCAGTT<br>TCATCCTTGTTACCACCGCTCTGACAATGGGCAGGGAAATTTCGGCGCTCGAGGACT<br>GTGCCCAGGAGCAGATGCGGCTCAGAGCCCAGGTGCGCCTGCTTGAGACCCGGGTCA<br>AACAGCAACAGGTCAAGATCAAGCAGCTTTTGCAGGAGAATGAAGTCCAGTTCCTTG<br>ATAAAGGAGATGAGAATACTGTCATTGATCTTGGAAGCAAGAGGCAGTATGCAGATT<br>GTTCAGAGATTTTCAATGATGGGTATAAGCTCAGTGGATTTTACAAAATCAAACCTC<br>TCCAGAGCCCAGCAGAATTTTCTGTTTATTGTGACATGTCCGATGGAGGAGGATGGA<br>CTGTAATTCAGAGACGATCTGATGGCAGTGAAAACTTTAACAGAGGATGGAAAGACT<br>ATGAAAATGGCTTTGGAAATTTTGTCCAAAAACATGGTGAATATTGGCTGGGCAATA<br>AAAATCTTCACTTCTTGACCACTCAAGAAGACTACACTTTAAAAATCGACCTTGCAG<br>ATTTTGAAAAAAATAGCCGTTATGCACAATATAAGAATTTCAAAGTTGGAGATGAAA<br>AGAATTTCTACGAGTTGAATATTGGGGAATATTCTGGAACAGCTGGAGATTCCCTTG<br>CGGGGAATTTTCATCCTGAGGTGCAGTGGTGGGCTAGTCACCAAAGAATGAAATTCA<br>GCACGTGGGACAGAGATCATGACAACTATGAAGGGAACTGCGCAGAAGAAGATCAGT<br>CTGGCTGGTGGTTTAACAGGTGTCACTCTGCAAACCTGAATGGTGTATACTACAGCG<br>GCCCCTACACGGCTAAAACAGACAATGGGATTGTCTGGTACACCTGGCATGGGTGGT<br>GGTATTCTCTGAAATCTGTGGTTATGAAAATTAGGCCAAATGATTTTATTCCAAATG<br>TAATTTAATTGCTGCTGTTGGGCTTTCGTTTCTGCAATTCAGCTTTGTTTAAAGTGA<br>TTTGAAAAATACTCATTCTGAACATATCCATGCGCAATCATGATAACTGTTGTGAGT<br>AGTGCTTTTCATTCTTCTCACTTGCCTTTGTTACTTAATGTGCTTTCAGTACAGCAG<br>ATATGCAATATTCACCAAATAAATGTAGACTGTGTTAATA (SEQ ID NO: 21) |
| | >NP_004458.3 fibrinogen-like protein 1 precursor [*Homo sapiens*]<br>MAKVFSFILVTTALTMGREISALEDCAQEQMRLRAQVRLLETRVKQQQVKIKQLLQE<br>NEVQFLDKGDENTVIDLGSKRQYADCSEIFNDGYKLSGFYKIKPLQSPAEFSVYCDM<br>SDGGGWTVIQRRSDGSENFNRGWKDYENGFGNFVQKHGEYWLGNKNLHFLTTQEDYT<br>LKIDLADFEKNSRYAQYKNFKVGDEKNFYELNIGEYSGTAGDSLAGNFHPEVQWWAS |

TABLE 1-continued

Type I Proteins of Interest Amino Acid Sequence

| Protein of Interest | Transcript Sequence (SEQ ID NO:)<br>Amino Acid Sequence (SEQ ID NO:) |
|---|---|
| | HQRMKFSTWDRDHDNYEGNCAEEDQSGWWFNRCHSANLNGVYYSGPYTAKTDNGIVW<br>YTWHGWWYSLKSVVMKIRPNDFIPNVI (SEQ ID NO: 22) |
| Mouse FGL1 | >NM_145594.2 *Mus musculus* fibrinogen-like protein 1 (Fgl1), mRNA<br>GTTAGAAGTTCCTGGGAGGCTCTGTGTGGATGGACTGAGCCTAGCTAAGTCCTGATT<br>CATTTTGACTTGAGTTCTCTCAGTGGGAAGAATGGGAAAGATTTACAGCTTCGTCCT<br>GGTCGCCATTGCTCTGATGATGGGAAGGGAAGGTTGGGCCCTCGAGAGTGAGAACTG<br>CTTGCGGGAGCAGGTGAGGCTCAGGGCTCAGGTGCACCAGCTTGAGACCCGGGTCAA<br>ACAACAACAGACCATGATTGCACAGCTCTTGCATGAGAAGGAAGTCCAGTTTCTGGA<br>TAAAGGATCGGAGAACAGTTTCATTGACCTTGGAGGCAAGAAGCAGTATGCAGATTG<br>TTCAGAGATTTACAATGACGGATTTAAGCAGAGTGGATTTTACAAAATCAAACCTCT<br>TCAGAGCCTGGCAGAATTCTCTGTTTATTGTGACATGTCTGATGGAGGGGGATGGAC<br>TGTAATTCAGAGACGATCTGATGGCAGTGAGAACTTTAACAGGGGTTGGAATGACTA<br>TGAAAATGGCTTTGGAAACTTTGTCCAAAACAATGGCGAATACTGGCTGGGTAACAA<br>AAACATTAACTTGCTAACTATTCAAGGAGACTACACTTTAAAAATCGACCTGACAGA<br>TTTTGAGAAAAACAGCAGCTTCGCACAATACCAAAGTTTTAAAGTTGGTGATAAAAA<br>GTCTTTTTATGAACTAAATATTGGAGAATATTCTGGCACAGCTGGAGATTCCCTGTC<br>AGGAACTTTTCATCCTGAAGTACAGTGGTGGGCTAGTCACCAAAGGATGAAGTTCAG<br>CACGTGGGACAGAGATAACGACAATTACCAAGGAAACTGTGCTGAGGAAGAGCAGTC<br>TGGCTGGTGGTTTAACAGGTGTCACTCTGCAAACCTGAACGGTGTTTACTACCGTGG<br>TTCCTACAGGGCAGAAACGGATAATGGTGTTGTGTGGTACACCTGGCATGGGTGGTG<br>GTATTCCTTGAAATCTGTGGTTATGAAAATTAGGCCAAGTGATTTTATTCCAAATAT<br>TATTTAGTTGCCCTCATTGGGATCTCCTTTCTGTAATTCATCTTGGTTTACTTGAAA<br>ATAAATATTTGAAAAAGATATAATTCTGAATAACACA (SEQ ID NO: 23)<br><br>>NP_663569.2 fibrinogen-like protein 1 precursor [*Mus musculus*]<br>MGKIYSFVLVAIALMMGREGWALESENCLREQVRLRAQVHQLETRVKQQQTMIAQLL<br>HEKEVQFLDKGSENSFIDLGGKKQYADCSEIYNDGFKQSGFYKIKPLQSLAEFSVYC<br>DMSDGGGWTVIQRRSDGSENFNRGWNDYENGFGNFVQNNGEYWLGNKNINLLTIQGD<br>YTLKIDLTDFEKNSSFAQYQSFKVGDKKSFYELNIGEYSGTAGDSLSGTFHPEVQWW<br>ASHQRMKFSTWDRDNDNYQGNCAEEEQSGWWFNRCHSANLNGVYYRGSYRAETDNGV<br>VWYTWHGWWYSLKSVVMKIRPSDFIPNII (SEQ ID NO: 24) |
| Human OX-2 (CD200) | >NM_005944.7 *Homo sapiens* CD200 molecule (CD200), transcript variant 1, mRNA<br>AGAGCTCCAGGCGCACATCCGCAGTCAGCCACCTCGCGCGCGCCTCCAGGAGCAAGG<br>ATGGAGAGGCTGGTGATCAGGATGCCCTTCTCTCATCTGTCTACCTACAGCCTGGTT<br>TGGGTCATGGCAGCAGTGGTGCTGTGCACAGCACAAGTGCAAGTGGTGACCCAGGAT<br>GAAAGAGAGCAGCTGTACACACCTGCTTCCTTAAAATGCTCTCTGCAAAATGCCCAG<br>GAAGCCCTCATTGTGACATGGCAGAAAAAGAAAGCTGTAAGCCCAGAAAACATGGTC<br>ACCTTCAGCGAGAACCATGGGGTGGTGATCCAGCCTGCCTATAAGGACAAGATAAAC<br>ATTACCCAGCTGGGACTCCAAAACTCAACCATCACCTTCTGGAATATCACCCTGGAG<br>GATGAAGGGTGTTACATGTGTCTCTTCAATACCTTTGGTTTTGGGAAGATCTCAGGA<br>ACGGCCTGCCTCACCGTCTATGTACAGCCCATAGTATCCCTTCACTACAAATTCTCT<br>GAAGACCACCTAAATATCACTTGCTCTGCCACTGCCCGCCCAGCCCCCATGGTCTTC<br>TGGAAGGTCCCTCGGTCAGGGATTGAAAATAGTACAGTGACTCTGTCTCACCCAAAT<br>GGGACCACGTCTGTTACCAGCATCCTCCATATCAAAGACCCTAAGAATCAGGTGGGG<br>AAGGAGGTGATCTGCCAGGTGCTGCACCTGGGGACTGTGACCGACTTTAAGCAAACC<br>GTCAACAAAGGCTATTGGTTTTCAGTTCCGCTATTGCTAAGCATTGTTTCCCTGGTA<br>ATTCTTCTCGTCCTAATCTCAATCTTACTGTACTGGAAACGTCACCGGAATCAGGAC<br>CGAGAGCCCTAAATAAGTCACACAGCACCCTGAAAGTGATTCCCTGGTCTACTTGAA<br>TTTGACACAAGAGAAAAGCAGGAGGAAAAGGGGCCATTCTCCAAAGGACCTGAAAGA<br>GCAAAAGAGGTGGGAGCGAAAGCCTTAAGGATCCCACGACTTTTTACTGCCATCTGA<br>GCTACTCAGTGTTTGAATCCCAAGAGGAAGTCAGTTTACCTCTCAGGTCTGTTGTAG<br>GACTTGATTTTGTAAAGCAATGCCATGTTATGTGGTTGAAAGGGCACTGGACTTAGT<br>TAGTATCAGGAGCACTGAGCTCACAGACTGACTTGGGCTCCTACTGGTGGGGACCTC<br>TGTTAGTCACTTTACCTCATCCAAAGTATAAAGGAATTGGACCAAATAATTTACCAC<br>ATAGCTCTAAAACTTAATTTAAAATGTAATTCCAGAAAAAAAAAGGGAATAAGCAAA<br>GGGGGAAGAATTGAAAGAGAGAGAGAAGAAAGAATACAGAGAGCTTACCTTTTGCCT<br>TTCTGTTGATGTTACATCTCTTCTTCCTATGTTCTTAGGTCTATGAGTCTGTTTCCC<br>CATCATTTGGTATCTAGTCCAGTTCCTGCTTACTGCTTTGCTAATAGCTGGCCTTGC<br>TAGAATCCTTGGTTTCACTGCTGTTCTTCATGTGCTTCTATGAGATTTACTCCAACA<br>CAAATAGGACTGAATTTATTGTGAAGTAACATTGGCAATCTTAACTTATTCATTTAA<br>CTTATTTTTATAGCTAGATAAATATTGTTAGTCTTAGACAATAGCTCACATTTTTTG<br>AGAAGCATGCCCTCCCTGTCCATTTGTCTTATAACATGACCCAGCCCTATTTTACGT<br>CATTCTAAATTCAGCCTCATATAATGAAAATACATTATGAAAACAGATGTTTAGGAG<br>ATTTCCTGTATAGCAGTCAGCCAATTCATATGCTTTGTCTCTGCTGGCTTCTTTTTC<br>CATGCGTTAACTTTTCCCAATAGCAGAGGAGGCAAATATGAGCATACAATCCCTTTG<br>TTCTAAAGATATTGTTCCAGCTAGTGGAATGATGTTGAATCTTTAATAACCATAATT<br>AGTTGCTTTTTCAGTATCTTCTGCTTTGTCTGTGTCTATCCAGTGGCCTAGGAATTA<br>AAGTGTAAGTTGTTTTCGCTGTTAAATTGGATATTTATATATATATATAGCAAGATT<br>TTCATGTGTTATTTAATTCTGTATTGTTTCTTATATTTGTAGTAAAATATTGAACAA<br>TTAAAAGTGTTGACTCCAAA (SEQ ID NO: 25) |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| | >NP_005935.4 OX-2 membrane glycoprotein isoform a precursor [*Homo sapiens*]<br>MERLVIRMPFSHLSTYSLVWVMAAVVLCTAQVQVVTQDEREQLYTPASLKCSLQNAQ<br>EALIVTWQKKKAVSPENMVTFSENHGVVIQPAYKDKINITQLGLQNSTITFWNITLE<br>DEGCYMCLFNTFGFGKISGTACLTVYVQPIVSLHYKFSEDHLNITCSATARPAPMVF<br>WKVPRSGIENSTVTLSHPNGTTSVTSILHIKDPKNQVGKEVICQVLHLGTVTDFKQT<br>VNKGYWFSVPLLLSIVSLVILLVLISILLYWKRHRNQDREP (SEQ ID NO: 26) |
| Mouse OX-2 (CD200) | >NM_010818.3 *Mus musculus* CD200 antigen (Cd200), transcript variant 1, mRNA<br>GGGCGTGGTTGGTTGGTCGTCTCTTCCTCCACACTAGAGGAGCTGTAGAGTCTGCCT<br>GTGCAGTGGAGGGGGCTCTCTCTACGGCGAATAGTAGTGTCCCTGCTCACAGGTGTT<br>GCGGAGATATCCTCCATCGTGGAAGAGCTCAGACCCCGAGAAGCTGGTGTCTAGCTG<br>CGGCCCAGAGCAAGGATGGGCAGTCTGGTATTCAGGAGACCTTTCTGCCATCTCTCC<br>ACCTACAGCCTGATTTGGGGCATGGCAGCAGTAGCGCTGAGCACAGCTCAAGTGGAA<br>GTGGTGACCCAGGATGAAAGAAAGGCGCTGCACACAACTGCATCCTTACGATGTTCT<br>CTAAAAACATCCCAGGAACCCTTGATTGTGACATGGCAGAAAAAGAAAGCCGTGAGC<br>CCAGAAAACATGGTCACCTACAGCAAAACCCATGGGGTTGTAATCCAGCCTGCCTAC<br>AAAGACAGGATAAATGTCACAGAGCTGGGACTCTGGAACTCAAGCATCACCTTCTGG<br>AACACAACATTGGAAGATGAGGGCTGCTACATGTGTCTCTTCAACACGTTTGGTTCT<br>CAGAAGGTCTCAGGAACAGCTTGCCTTACCCTCTATGTACAGCCCATAGTACACCTT<br>CACTACAACTATTTTGAAGACCACCTAAACATCACTTGCTCTGCGACTGCCCGTCCA<br>GCCCCTGCCATCTCCTGGAAGGGTACTGGGACAGGAATTGAGAATAGTACCGAGAGT<br>CACTTCCATTCAAATGGGACTACATCTGTCACCAGCATCCTCCGGGTCAAAGACCCC<br>AAAACTCAAGTTGGGAAGGAAGTGATCTGCCAGGTTTTATACCTGGGGAATGTGATT<br>GACTACAAGCAGAGTCTGGACAAAGGATTTTGGTTTTCAGTTCCACTGTTGCTAAGC<br>ATTGTTTCTCTGGTAATTCTTCTGATCTTGATCTCCATCTTACTATACTGGAAACGT<br>CACCGAAATCAGGAGCGGGGTGAATCATCACAGGGGATGCAAAGAATGAAATAAGAG<br>CTCTAAAGAAATTATACAGAACCCTGAACGTGTTTCCCTGGTCTACTTGAATCTGAT<br>GTGAAAGAAAAGCAGGAGGGAAAAGGCCATTCTCCATAGGACCTAAGGAGAGCAAAA<br>GACCAGACACGAGCCTGTGAGGGATTTGACTTTTTGCTGTTGTCCCAGGTCCTCGGT<br>GTTTGCATTCCAAGAGGAAGTCGAGTGCCTCGGGTCTGTTGTAGGACTTGATTTTTT<br>TTTTTTTTGTAGAGCAATGCAGTGCCATGCTGTTAGAAAGGCTCCAGACTTAGAACC<br>ACCAGTGCCAAGCCAGCTCTCAGACCGACTAGGGCTCCCATCGGAGGAACAAATCGT<br>AGTCAACTTACCTCACAGAGCTCTCTGGTCCTTACACAAAGTAGAAAGGAGTGGGAC<br>CAGAAAATTGGCCATGTCTGAAATCTGATGGAATTTTTAGGAAGAAAACTGAAGAAT<br>AAGCAAAAGAAGAAAGAACACAGAAGGGTCCAAAGAGCTTCTGAGAGTACCTTTTGC<br>CTTTCTGTTGGTGTCCCAGCTCTGGTTTTGTTCTTAGGTCCGCCAGTGTGTTTCCCT<br>GTTGTTTGAGTATCTAGTTGACTACCTGCTACTGTTCTGCTGATGGTTGGCCTTGCT<br>AGAATCCCTGACTCCCCTGCCGTTCTCTATGTGCTTCTATGAGGGTTACTATGATGA<br>AAATAGAGCAGAAGATAGTGTGAAGTAACATTGGCAACTGTAATGTGTCCATTTAAC<br>TTATTTTTATAGCACTTAGGCAATATTGTTAGTCTTAGTGAGTAGTTCACATCTTTA<br>CAAAAGCATGCTCTCCCTATCCATTGGGCCCACAATAACACTCTCTTTGAGGCCATT<br>CTGAATCCTGTCTCGTGTAATGATAATATATTATGAAAACAGATACTTTAAGAATTT<br>CCTGTACAGCAGTCAGTTGTTTATTCTCTCTCTCTCTCTCTCTCTCTCTCTCCCTCC<br>CCCACCCCAGCTTCTTTTTCTGTGACTTTGTTTTTCATAAAGAGAAGGCATCTCCTG<br>AATACAATCGCTTTGTTCTGAAGACATCGTGAACTATTAATTCTTAACCCTTTGACA<br>AAACTAGTGAAGTTGTTTTCTGTATCTTTTGCTTCATCTGTCTTTATAGAGTGACCT<br>AGGAATTCAAGTGTAAGTTGTTTCCATTGTTGAACTGGATATTTATATACTTGGTAT<br>GCTTTTCACGTGTTATTTAATTCTGTATAATTTCCTATATTTGTATTAAAATATTGA<br>GCAATTAAAAGTGTCAACTAAATATTTGATGTGGCATTCCCTTGAGAAATATAGAAA<br>TAAAGAATAAAAAAAAAAAAAAAAAAA (SEQ ID NO: 27)<br><br>>NP_034948.3 OX-2 membrane glycoprotein isoform 1 precursor [*Mus musculus*]<br>MGSLVFRRPFCHLSTYSLIWGMAAVALSTAQVEVVTQDERKALHTTASLRCSLKTSQ<br>EPLIVTWQKKKAVSPENMVTYSKTHGVVIQPAYKDRINVTELGLWNSSITFWNTTLE<br>DEGCYMCLENTFGSQKVSGTACLTLYVQPIVHLHYNYFEDHLNITCSATARPAPAIS<br>WKGTGTGIENSTESHFHSNGTTSVTSILRVKDPKTQVGKEVICQVLYLGNVIDYKQS<br>LDKGFWFSVPLLLSIVSLVILLILISILLYWKRHRNQERGESSQGMQRMK (SEQ ID NO: 28) |
| Human Galectin-9 | >NM_009587.3 *Homo sapiens* galectin 9 (LGALS9), transcript variant 1, mRNA<br>CTTTGTTAAGTCGTTCCCTCTACAAAGGACTTCCTAGTGGGTGTGAAAGGCAGCGGT<br>GGCCACAGAGGCGGCGGAGAGATGGCCTTCAGCGGTTCCCAGGCTCCCTACCTGAGT<br>CCAGCTGTCCCCTTTTCTGGGACTATTCAAGGAGGTCTCCAGGACGGACTTCAGATC<br>ACTGTCAATGGGACCGTTCTCAGCTCCAGTGGAACCAGGTTTGCTGTGAACTTTCAG<br>ACTGGCTTCAGTGGAAATGACATTGCCTTCCACTTCAACCCTCGGTTTGAAGATGGA<br>GGGTACGTGGTGTGCAACACGAGGCAGAACGGAAGCTGGGGGCCCGAGGAGAGGAAG<br>ACACACATGCCTTTCCAGAAGGGGATGCCCTTTGACCTCTGCTTCCTGGTGCAGAGC<br>TCAGATTTCAAGGTGATGGTGAACGGGATCCTCTTCGTGCAGTACTTCCACCGCGTG<br>CCCTTCCACCGTGTGGACACCATCTCCGTCAATGGCTCTGTGCAGCTGTCCTACATC<br>AGCTTCCAGAACCCCCGCACAGTCCCTGTTCAGCCTGCCTTCTCCACGGTGCCGTTC |

TABLE 1-continued

Type I Proteins of Interest Amino Acid Sequence

| Protein of Interest | Transcript Sequence (SEQ ID NO:)<br>Amino Acid Sequence (SEQ ID NO:) |
|---|---|
| | TCCCAGCCTGTCTGTTTCCCACCCAGGCCCAGGGGGCGCAGACAAAAACCTCCCGGC<br>GTGTGGCCTGCCAACCCGGCTCCCATTACCCAGACAGTCATCCACACAGTGCAGAGC<br>GCCCCTGGACAGATGTTCTCTACTCCCGCCATCCCACCTATGATGTACCCCCACCCC<br>GCCTATCCGATGCCTTTCATCACCACCATTCTGGGAGGGCTGTACCCATCCAAGTCC<br>ATCCTCCTGTCAGGCACTGTCCTGCCCAGTGCTCAGAGGTTCCACATCAACCTGTGC<br>TCTGGGAACCACATCGCCTTCCACCTGAACCCCCGTTTTGATGAGAATGCTGTGGTC<br>CGCAACACCCAGATCGACAACTCCTGGGGGTCTGAGGAGCGAAGTCTGCCCCGAAAA<br>ATGCCCTTCGTCCGTGGCCAGAGCTTCTCAGTGTGGATCTTGTGTGAAGCTCACTGC<br>CTCAAGGTGGCCGTGGATGGTCAGCACCTGTTTGAATACTACCATCGCCTGAGGAAC<br>CTGCCCACCATCAACAGACTGGAAGTGGGGGGCGACATCCAGCTGACCCATGTGCAG<br>ACATAGGCGGCTTCCTGGCCCTGGGGCCGGGGGCTGGGGTGTGGGGCAGTCTGGGTC<br>CTCTCATCATCCCCACTTCCCAGGCCCAGCCTTTCCAACCCTGCCTGGGATCTGGGC<br>TTTAATGCAGAGGCCATGTCCTTGTCTGGTCCTGCTTCTGGCTACAGCCACCCTGGA<br>ACGGAGAAGGCAGCTGACGGGGATTGCCTTCCTCAGCCGCAGCAGCACCTGGGGCTC<br>CAGCTGCTGGAATCCTACCATCCCAGGAGGCAGGCACAGCCAGGGAGAGGGGAGGAG<br>TGGGCAGTGAAGATGAAGCCCCATGCTCAGTCCCCTCCCATCCCCCACGCAGCTCCA<br>CCCCAGTCCCAAGCCACCAGCTGTCTGCTCCTGGTGGGAGGTGGCCTCCTCAGCCCC<br>TCCTCTCTGACCTTTAACCTCACTCTCACCTTGCACCGTGCACCAACCCTTCACCCC<br>TCCTGGAAAGCAGGCCTGATGGCTTCCCACTGGCCTCCACCACCTGACCAGAGTGTT<br>CTCTTCAGAGGACTGGCTCCTTTCCCAGTGTCCTTAAAATAAAGAAATGAAAATGCT<br>TGTTGGCACATTCA (SEQ ID NO: 29)<br><br>>NP_033665.1 galectin-9 isoform long [*Homo sapiens*]<br>MAFSGSQAPYLSPAVPFSGTIQGGLQDGLQITVNGTVLSSSGTRFAVNFQTGFSGND<br>IAFHFNPRFEDGGYVVCNTRQNGSWGPEERKTHMPFQKGMPFDLCFLVQSSDFKVMV<br>NGILFVQYFHRVPFHRVDTISVNGSVQLSYISFQNPRTVPVQPAFSTVPFSQPVCFP<br>PRPRGRRQKPPGVWPANPAPITQTVIHTVQSAPGQMFSTPAIPPMMYPHPAYPMPFI<br>TTILGGLYPSKSILLSGTVLPSAQRFHINLCSGNHIAFHLNPRFDENAVVRNTQIDN<br>SWGSEERSLPRKMPFVRGQSFSVWILCEAHCLKVAVDGQHLFEYYHRLRNLPTINRL<br>EVGGDIQLTHVQT (SEQ ID NO: 30) |
| Mouse Galectin-9 | >NM_010708.2 *Mus musculus* lectin, galactose binding, soluble 9 (Lgals9), transcript variant 1, mRNA<br>GCCAAATAGCTGTGGTTTCTGTTTCCTAGCTCAGCCCTGCCCTGCGCAGAGTTCTGT<br>CGTCCACCATCGAGTGAGGAAGAGAGCATTGGTTCCCCTGAGATAGAAGAGATGGCT<br>CTCTTCAGTGCCCAGTCTCCATACATTAACCCGATCATCCCCTTTACTGGACCAATC<br>CAAGGAGGGCTGCAGGAGGGACTTCAGGTGACCCTCCAGGGGACTACCAAGAGTTTT<br>GCACAAAGGTTTGTGGTGAACTTTCAGAACAGCTTCAATGGAAATGACATTGCCTTC<br>CACTTCAACCCCCGGTTTGAGGAAGGAGGGTATGTGGTTTGCAACACGAAGCAGAAC<br>GGACAGTGGGGTCCTGAGGAGAGAAAGATGCAGATGCCCTTCCAGAAGGGGATGCCC<br>TTTGAGCTTTGCTTCCTGGTGCAGAGGTCAGAGTTCAAGGTGATGGTGAACAAGAAA<br>TTCTTTGTGCAGTACCAACACCGCGTACCCTACCACCTCGTGGACACCATCGCTGTC<br>TCCGGCTGCTTGAAGCTGTCCTTTATCACCTTCCAGAACTCTGCAGCCCCTGTCCAG<br>CATGTCTTCTCCACAGTGCAGTTCTCTCAGCCAGTCCAGTTCCCACGGACCCCTAAG<br>GGGCGCAAACAGAAAACTCAGAACTTTCGTCCTGCCCACCAGGCACCCATGGCTCAA<br>ACTACCATCCATATGGTTCACAGCACCCCTGGACAGATGTTCTCTACTCCTGGAATC<br>CCTCCTGTGGTGTACCCCACCCCAGCCTATACCATACCTTTCTACACCCCCATTCCA<br>AATGGGCTTTACCCGTCCAAGTCCATCATGATATCAGGCAATGTCTTGCCAGATGCT<br>ACGAGGTTCCATATCAACCTTCGCTGTGGAGGTGACATTGCTTTCCACCTGAACCCC<br>CGTTTCAATGAGAATGCTGTTGTCCGAAACACTCAGATCAACAACTCCTGGGGGCAG<br>GAAGAGCGAAGTCTGCTTGGGAGGATGCCCTTCAGTCGAGGCCAGAGCTTCTCGGTG<br>TGGATCATATGTGAAGGTCACTGCTTCAAGGTAGCTGTGAATGGTCAACACATGTGT<br>GAATATTACCACCGCCTGAAGAACTTGCAGGATATCAACACTCTAGAAGTGGCGGGT<br>GATATCCAGCTGACCCACGTGCAGACATAGGCAAGGTCTCTGGCCTAGGGATAAGGG<br>CTGGAGCACTCTGCCTGTGTCTTATCTTTCCCCTGTCTCAGCCCTGGCACCATCAGA<br>AGAGATCATCACTTATAGGAATTCCAGGAAGGTGAAATTCCCAATTGACTCCCTCCA<br>CAAAGGGGGTTTTCTAGGCTGTGTGGCACATGGCTGTCAGCCCATAGTCTGAGCCAT<br>TGCCCCCAAGCTAGCTATATACTGAGGGAAGTGACCCTCCTGGGTTTGCTCAGATCT<br>CTGATCGTTCCCCCCTCTGTGGCCCTTTTCTTTCACCCCTCCAGGAGAGCCACCCTG<br>ATATCATCCCACTGGCCTCCAACTGACCCACAATGTCCACAGTAACTTTCCCCCATT<br>CTCACCCAGTATCCATAAAATAAAGAAATAATATTGCTTGTCTACAC (SEQ ID NO: 31)<br><br>>NP_034838.2 galectin-9 isoform 1 [*Mus musculus*]<br>MALFSAQSPYINPIIPFTGPIQGGLQEGLQVTLQGTTKSFAQRFVVNFQNSFNGNDI<br>AFHFNPRFEEGGYVVCNTKQNGQWGPEERKMQMPFQKGMPFELCFLVQRSEFKVMVN<br>KKFFVQYQHRVPYHLVDTIAVSGCLKLSFITFQNSAAPVQHVFSTVQFSQPVQFPRT<br>PKGRKQKTQNFRPAHQAPMAQTTIHMVHSTPGQMFSTPGIPPVVYPTPAYTIPFYTP<br>IPNGLYPSKSIMISGNVLPDATRFHINLRCGGDIAFHLNPRFNENAVVRNTQINNSW<br>GQEERSLLGRMPFSRGQSFSVWIICEGHCFKVAVNGQHMCEYYHRLKNLQDINTLEV<br>AGDIQLTHVQT (SEQ ID NO: 32) |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| Human PVR (CD155) | >NM_006505.5 *Homo sapiens* PVR cell adhesion molecule (PVR), transcript variant 1, mRNA<br>AGTCACTTGTCTGGAGCTTGAAGAAGTGGGTATTCCCCTTCCCACCCCAGGCACTGG<br>AGGAGCGGCCCCCCGGGGATTCCAGGACCTGAGCTCCGGGAGCTGGACTCGCAGCGA<br>CCGCGGCAGAGCGAGCGGGCGCCGGGAAGCGAGGAGACGCCCGCGGGAGGCCCAGCT<br>GCTCGGAGCAACTGGCATGGCCCGAGCCATGGCCGCCGCGTGGCCGCTGCTGCTGGT<br>GGCGCTACTGGTGCTGTCCTGGCCACCCCCAGGAACCGGGGACGTCGTCGTGCAGGC<br>GCCCACCCAGGTGCCCGGCTTCTTGGGCGACTCCGTGACGCTGCCCTGCTACCTACA<br>GGTGCCCAACATGGAGGTGACGCATGTGTCACAGCTGACTTGGGCGCGGCATGGTGA<br>ATCTGGCAGCATGGCCGTCTTCCACCAAACGCAGGGCCCCAGCTATTCGGAGTCCAA<br>ACGGCTGGAATTCGTGGCAGCCAGACTGGGCGCGGAGCTGCGGAATGCCTCGCTGAG<br>GATGTTCGGGTTGCGCGTAGAGGATGAAGGCAACTACACCTGCCTGTTCGTCACGTT<br>CCCGCAGGGCAGCAGGAGCGTGGATATCTGGCTCCGAGTGCTTGCCAAGCCCCAGAA<br>CACAGCTGAGGTTCAGAAGGTCCAGCTCACTGGAGAGCCAGTGCCCATGGCCCGCTG<br>CGTCTCCACAGGGGGTCGCCCGCCAGCCCAAATCACCTGGCACTCAGACCTGGGCGG<br>GATGCCCAATACGAGCCAGGTGCCAGGGTTCCTGTCTGGCACAGTCACTGTCACCAG<br>CCTCTGGATATTGGTGCCCTCAAGCCAGGTGGACGGCAAGAATGTGACCTGCAAGGT<br>GGAGCACGAGAGCTTTGAGAAGCCTCAGCTGCTGACTGTGAACCTCACCGTGTACTA<br>CCCCCCAGAGGTATCCATCTCTGGCTATGATAACAACTGGTACCTTGGCCAGAATGA<br>GGCCACCCTGACCTGCGATGCTCGCAGCAACCCAGAGCCCACAGGCTATAATTGGAG<br>CACGACCATGGGTCCCCTGCCACCCTTTGCTGTGGCCCAGGGCGCCCAGCTCCTGAT<br>CCGTCCTGTGGACAAACCAATCAACACAACTTTAATCTGCAACGTCACCAATGCCCT<br>AGGAGCTCGCCAGGCAGAACTGACCGTCCAGGTCAAAGAGGGACCTCCCAGTGAGCA<br>CTCAGGCATGTCCCGTAACGCCATCATCTTCCTGGTTCTGGGAATCCTGGTTTTTCT<br>GATCCTGCTGGGGATCGGGATTTATTTCTATTGGTCCAAATGTTCCCGTGAGGTCCT<br>TTGGCACTGTCATCTGTGTCCCTCGAGTACAGAGCATGCCAGCGCCTCAGCTAATGG<br>GCATGTCTCCTATTCAGCTGTGAGCAGAGAGAACAGCTCTTCCCAGGATCCACAGAC<br>AGAGGGCACAAGGTGACAGCGTCGGGACTGAGAGGGGAGAGAGACTGGAGCTGGCAA<br>GGACGTGGGCCTCCAGAGTTGGACCCGACCCCAATGGATGAAGACCCCCTCCAAAGA<br>GACCAGCCTCCCTCCCTGTGCCAGACCTCAAAACGACGGGGGCAGGTGCAAGTTCAT<br>AGGTCTCCAAGACCACCCTCCTTTCATTTGCTAGAAGGACTCACTAGACTCAGGAAA<br>GCTGTTAGGCTCACAGTTACAGTTTATTACAGTAAAAGGACAGAGATTAAGATCAGC<br>AAAGGGAGGAGGTGCACAGCACACGTTCCACGACAGATGAGGCGACGGCTTCCATCT<br>GCCCTCTCCCAGTGGAGCCATATAGGCAGCACCTGATTCTCACAGCAACATGTGACA<br>ACATGCAAGAAGTACTGCCAATACTGCCAACCAGAGCAGCTCACTCGAGATCTTTGT<br>GTCCAGAGTTTTTTGTTTGTCTTGAGACAGGGTCTGGCTCTGTTGGCAGACTAGAGT<br>ACAGTGGTGAGATCACAGTTCATTGCAGCCTTGACTTCTCAACGCCAAGTCATCCTC<br>CCACCTCAGCCTCCTGAGTAGCTATGACTACAGGTATGTGCCACCACGTCTGGCTAA<br>TCTTTTTATTATTTGTAAAGTCGAGGTTTCCCTGTGTTGCCCAGGCTGGTCTTGAAC<br>TCTTGGCTCCAAGTGATACTTCTGCCTTGGCCTCCCAAAGTGCTGAATTAAGCAGCT<br>CACCATCCACACGGCTGACCTCATACATCAAGCCAATACCGTGTGGCCCAAGACCCC<br>CACCATAAATCACATCATTAGCATGAACCACCCAGAGTGGCCCAAGACTCCAAGATC<br>AGCTACCAGGCAGGATATTCCAAGGGCTTAGAGATGAATGCCCAGGAGCTGAGGATA<br>AAGGGCCCGATCTTTCTTTGGGCAAGGTTAAGCCTTTACTGCATAGCAGACCACACA<br>GAAGGGTGTGGGCCACCAGAGAATTTTGGTAAAAATTTGGCCTCTGGCCTTGAGCTT<br>CTAAATCTCTGTATCCGTCAGATCTCTGTGGTTACAAGAAACAGCCACTGACCCTGG<br>TCACCAGAGGCTGCAATTCAGGCCGCAAGCAGCTGCCTGGGGGGTGTCCAAGGAGCA<br>GAGAAAACTACTAGATGTGAACTTGAAGAAGGTTGTCAGCTGCAGCCACTTTCTGCC<br>AGCATCTGCAGCCACTTTCTGCCAGCATCTGCAGCCAGCAAGCTGGGACTGGCAGGA<br>AATAACCCACAAAAGAAGCAAATGCAATTTCCAACACAAGGGGGAAGGGATGCAGGG<br>GGAGGCAGCGCTGCAGTTGCTCAGGACACGCTCCTATAGGACCAAGATGGATGCGAC<br>CCAAGACCCAGGAGGCCCAGCTGCTCAGTGCAACTGACAAGTTAAAAAGGTCTATGA<br>TCTTGAGGGCAGACAGCAGAATTCCTCTTATAAAGAAAACTGTTTGGGAAAATACGT<br>TGAGGGAGAGAAGACCTTGGGCCAAGATGCTAAATGGGAATGCAAAGCTTGAGCTGC<br>TCTGCAAGAGAAAATAAGCAGGACAGAGGATTTGCTCTGGACAGAGATGGAAGAGCC<br>GGGAACAGAGAAGTGTGGGGAAGAGATAGGAACCAGCAGGATGGCAGGGGCAAAGGG<br>CTCAAGGGTGAGGAGGCCAGTGGGACCCCACAGAGTTGGGGAGATAAAGGAACATTG<br>GTTGCTTTGGTGGCACGTAAGCTCCTTGTCTGTCTCCAGCACCCAGAATCTCATTAA<br>AGCTTATTTATTGTACCTCCAGCGGCTGTGTGCAATGGGGTCTTTTGTGGAAATCAA<br>GGAGCAGACAGGTTTCATGTGTACTGTCACCACGTGGGATGGAACCAGAGGCATGGA<br>AGCAAGACGCTAAATGAAGAGGGCCATAAGGGCTGGGATTCCCAGGCACCTTAGGAA<br>CAGCTTGTCTTTTTTTTTTTCCTCTCCAAAAAAAATGTTTAAGGGACGGTGTCTCCT<br>GTCACCCAGGCTGGAGTGCAATGGCACGATCATAGCTCATTGCAGCCTCTAACTCCG<br>GGGCTCAAGCAATCCTCCCACCTCAGCCTACCAAGTAGCTGTGACCACAGCTGCCCC<br>TCACCATGCTAAGCTAATTTTTTTAATTAGATAGTACATAAACGTCCCAAAATTAGA<br>AGATAAAAAGACATGAGGGATCCATTCTAATTTGTGTTTGGAGTGTAATGGTCCAGC<br>TCCATTCTTCTGCACATGGATATCCAGTTTTACACAACACTGTGAATGTAATGAATG<br>CCACTGAATCATACACTCAAAAATAGCTAAAATGGCAAATTGTCTGTTATCTCTTTT<br>TAACCACCATTTTTGAAAATTAATTATACCAAAAAACCATTGAATAGTGCACTTTAT<br>TTATTTATTTATTTGTTTATTTATTTATTTATTTTAGAAATAAGAGTCTCACTTTGT<br>TGCCCAGGCTGGAGTGCAGTGGCGTGATCATGGCTCATTGCAGCCTCGACCTGCTGG<br>GCTCGGGCTATCCTTCCATCTCAGCCTCCCGAGTAGCTGGGACTATAGGTGGGCGCC<br>ACCCCACCTGGCTAAATCTCTTTTTAACTTTTGTAGAGATAGGCATCTCGCTATGTT<br>GCCTAGGCTGGGCTGGAACTCCTGGGCTCAAGTGCTCCTCCTGCCTTGGCCTCCCAA |

TABLE 1-continued

Type I Proteins of Interest Amino Acid Sequence

| Protein of Interest | Transcript Sequence (SEQ ID NO:)<br>Amino Acid Sequence (SEQ ID NO:) |
|---|---|
| | AGCGCTAGGATTACAGATGTGAGCCACCGCGCCCACCCTGAACCTTACTTTTTTTGC<br>TCAGTTTCTGGTAATTCAGAGAATGCCTCCTGAGTTGTTCTACACCCACCTCATATT<br>CCATGGGAGGGCTGTACAGGGCTTTTTTAACGAGGCCTCTAAGGACAGGCATTTGTA<br>TCCTTTCCAGCCTTTCACTATTACAATGTTGTAGTGAATAACTTTACACACTGTCAT<br>TTATTTTACTTTTTTTTTTTTTTATTTTAGAGAAAGGAATCTTGCCATCTTGCCCAG<br>GCTGGTCTCAAATTCCTGGGCCCAAACAATCCTCCCGCCTTGGCCTCCTAAAGTACT<br>GGGATTTATAGGCATAAGCCACCGTGCCTGGCCAATGCACACTGTCATTTAGCTCAT<br>GTTAACACCTGAGTGTAGGACACACTCCTGGAGGTGGAATTGCTGGGCCAAAGAGTA<br>TGTTTCTTGTCATTGTGATAGATATTGACAAATGAACCCTCACAGAAGTTGTGCTGA<br>GTTCTGTTCCCACCAGCGACGTAGGCGATGACCTTTTTCTGGAGGGAGGGGGCATCC<br>TTGGAGTCCACAGAGCCAGGAATGGAGAGTGGGCCCAGAATTTTGGTATAGGTGTTG<br>TATAAACTTATAGTAAGGTTAAGAAAACCGCAACTATCCTTATCAGAGACTTGGCGG<br>GGGGCAGGGTATGATGGAGATCATAAGGAGGCTAAAACACTCCACACCCTCCCTCTG<br>CATTGCTCCTGCACGGGAGTCGGGAATCTTTTCAGGTTGATACGATCTCACCTTGAG<br>GAGCTGTGAGGTCCCAGAAGCCTCTGGGTTGCAGATTGCTTGGGGTGAAAATGTCTG<br>TGCTACTGAAATCTAACTTTTTACAAAAAATTACGGGCTGGGCGCAGTGGCTCACGC<br>CTGTAATCCCAGCACTTTGGGAGGCTGCAGCGGGTGGATCACTTGAGGTAAGGAGTT<br>CAAGACCAGACCATAGTGAAACCGTGTCTCTACAAAAAAAATTAGCCAGGTGTGGTG<br>GTGCATGCTTGTAATCCCAGCTACTCAGAAGGCTGAGGTGGGAGAATCCCTTGAACC<br>CGGGAAGTGGAGGCTGGAGTAAACCATGATCGAGTTACTGCACTCCAGCCTGGGTGA<br>CAAGAGTGAGACTCTGTCTCCAAAAAAAAAAAAAAAAAAAAAAAAAAACTGGATTGCCT<br>GGCTCTACTCCGGGCACAGCATGCAGGCCCAGTTCTGCTGCTCTGCTGTTTGTTCTG<br>CTTTCCTCCACATATTGGCATCACCCTCTGGTGCCAAGATGGCTGCTGCATTCCAGG<br>CATCACATCCAGACTCAGACCCAGAGAAGCTGCCCATCCCTACCTGGGTGAGCCTTT<br>GTAGGAACGAGAAACCGCATCCAGCAGCAGAAACCTCACCCAGCAGCGTCTTTTCCG<br>GTCTCATTCACCAGCGCCGCCCACCGCTCAACCAATCCCTGGCCAAAAGAATGGGAC<br>CGCCTGGAAGGCTGGACCAAACAGGACCTGCCCTCTGGGGCTGGGGAGAGGCCCAGA<br>TGAAGGCTGCAGGACAGGATGGACTCCTAGACCTCTGTTACCAGCAGTGACTACCTC<br>TGTCTGGGTGGTTGGAACATGTTTGAATTTTATTCTAAGTACTGTCTACAAGTTCTG<br>CAATAAACCTTGACTCTTCTTTTAATAATGCAAAA (SEQ ID NO: 33)<br><br>>NP_006496.4 poliovirus receptor isoform alpha precursor<br>[*Homo sapiens*]<br>MARAMAAAWPLLLVALLVLSWPPPGTGDVVVQAPTQVPGFLGDSVTLPCYLQVPNME<br>VTHVSQLTWARHGESGSMAVFHQTQGPSYSESKRLEFVAARLGAELRNASLRMFGLR<br>VEDEGNYTCLFVTFPQGSRSVDIWLRVLAKPQNTAEVQKVQLTGEPVPMARCVSTGG<br>RPPAQITWHSDLGGMPNTSQVPGFLSGTVTVTSLWILVPSSQVDGKNVTCKVEHESF<br>EKPQLLTVNLTVYYPPEVSISGYDNNWYLGQNEATLTCDARSNPEPTGYNWSTTMGP<br>LPPFAVAQGAQLLIRPVDKPINTTLICNVTNALGARQAELTVQVKEGPPSEHSGMSR<br>NAIIFLVLGILVFLILLGIGIYFYWSKCSREVLWHCHLCPSSTEHASASANGHVSYS<br>AVSRENSSSQDPQTEGTR (SEQ ID NO: 34) |
| Mouse PVR (CD155) | >NM_027514.2 *Mus musculus* poliovirus receptor (Pvr), mRNA<br>AGGCGGCACCCGCTTAGCTGAGATTCCAGCACTTGACTTCAGGGTTTCGGAGAGATA<br>AGGCGCTTGGCCGTTACTAACTGGACTACAAAGAGCTGGATCGGACCGGAACCACAT<br>GGCTCAACTCGCCCGAGCCACCCGCTCCCCGCTGTCATGGCTGCTGCTGCTGTTCTG<br>CTATGCACTCCGGAAAGCGGGTGGGGATATACGTGTGCTGGTGCCCTACAATTCGAC<br>AGGCGTCTTGGGAGGGTCGACCACCTTGCACTGTAGTCTGACTTCTAATGAGAATGT<br>GACTATCACTCAAATAACCTGGATGAAGAAGGATTCAGGTGGATCCCACGCTCTTGT<br>GGCTGTCTTCCACCCCAAGAAGGGGCCCAACATCAAAGAGCCAGAGAGGGTGAAATT<br>CTTGGCTGCCCAACAGGATCTGAGGAACGCATCTCTGGCCATCTCGAACTTAAGTGT<br>AGAAGACGAAGGCATCTATGAATGTCAGATTGCCACATTCCCCAGAGGCAGTAGAAG<br>CACCAATGCCTGGCTGAAGGTGCAAGCCCGACCTAAGAACACTGCAGAGGCCCTGGA<br>GCCCTCTCCCACCTTGATACTGCAGGATGTGGCTAAATGCATCTCTGCCAATGGTCA<br>CCCTCCTGGACGAATCTCTTGGCCCTCGAATGTGAATGGAAGTCACCGTGAAATGAA<br>GGAACCAGGGTCCCAGCCGGGCACCACCACAGTTACCAGCTACCTCTCCATGGTACC<br>TTCTCGCCAGGCAGACGGCAAGAACATCACCTGCACGGTGGAGCATGAAAGCTTACA<br>GGAGCTGGACCAGCTGCTGGTGACCCTTTCCCAACCCTATCCACCTGAAAACGTGTC<br>CATCTCTGGCTATGACGGCAACTGGTATGTTGGCCTCACTAACTTGACCCTGACCTG<br>TGAAGCTCACAGCAAACCAGCGCCTGACATGGCTGGATATAACTGGAGCACGAACAC<br>GGGTGACTTTCCCAACTCTGTTAAGCGCCAGGGCAATATGCTTCTAATCTCCACCGT<br>AGAGGATGGTCTCAATAACACGGTCATTGTGTGCGAAGTCACCAATGCCCTAGGGTC<br>TGGGCAGGGCCAAGTGCACATCATTGTTAAAGAGAAACCTGAGAATATGCAGCAAAA<br>TACAAGATTACACCTAGGCTACATCTTTCTTATCGTCTTTGTCCTCGCTGTAGTCAT<br>CATCATCGCAGCACTATACACTATACGAAGATGCAGGCATGGTCGTGCTCTGCAGTC<br>CAATCCCTCAGAGAGGGAGAACGTCCAGTATTCATCTGTGAACGGCGACTGTAGACT<br>GAACATGGAGCCAAACAGCACAAGGTGACGGTGCTGGGTAGACAGAACTAAGGAACT<br>TGAAGGCATAGCAACTGGAACCCTACTCTCATAAATGAAGAAGCCTCCAGAGAGACT<br>GGCTGCTCAGTGTGATGAGCATAGCAAGTTTGGGGGGTCTCCCAGGATGCTGCCGAA<br>TTCCACGTTGTCAAAAGGACCCATGGAGGCCAGTGTGTTGGCTCACTCTTGACATCT<br>CAGCAAGCTGGGGGGGGGGGGGGAGCATAAAGCAAGGTTGAGTCTAGCTTGGGCTA<br>TAGAGCAAAGCCCTGTCCATACACAAACAAGCTAAGGGGCTTTGAGACGGTCAGAAA<br>CTGAAGTCTTGCTTTGGGTAAGGTAAATCCTCTACCGCATGTATGTGCTAGACTTGA<br>AAGACTTCCACACAGACCTCTTTATAAGTTGACTCCATTGGGGCTATCCCCTCCTCT<br>CTGGACAAGGTCTCTGTATGTAGCCAAGGCTAGGCTCAAACTCACAGAGATATGTCT |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| | GCTTCTACCTCCCCAGTGCTAGAGTTGAAAGTATTTGTGCCACTGCACTTTTCTAGG<br>TCTTCTTTTAATGAAGTAAAGTATATATTTATAAAAAGCTATTTAGTTATATATATA<br>TATATTTTTGAGACTATTTCATAGAGCCCAAGCTAACCTCAAACTTACTATGTAGCC<br>AAGAGTGATGGTAAACTAATTTATTTTAATTTATTTGTCTTCAATTTTAACCATCAC<br>CCAACCCCTGCTCCCTTCCATATCTTCTTTCAATCCATTTCATTGTCTTTTTCTTCC<br>CAGACACTATTCTGACTTACGTCTCCATTACAAACATTTTATTGAACTACATAAAAA<br>TGTGTGAACCACAAAAAAAAAATGTATTTGTCAAAATTGTAGTTGTCTTTCTGAGGC<br>TGACCTGAGTTCTCTGATACCATTCTCTCCAGTTGTATCCAGTTTCCTGTAAACAAT<br>GTGACTTTGTTTTTCTCAGTAGCTAAAACATCCCAATTATGTGAGTGTACACTTTCT<br>TTACTCATTCCTCTGTGGGCCACCAGCTGGGTTGGTTCCATATCTGAGCTATTGTGC<br>ATGGAATTGTCTCTGTGGTGGGTTTAGTAAACTCCCAGGAATGCCTGTACATGTTTG<br>TAGAGGCCAGAAGAAGGCACAAAATCTTGAGCCAGGCTTACATGCACTTGTGAGTAG<br>CCCCACATAGGTGCTAAGAACCCAGTTCAGGTCCTCTGCTGTGGGATGGTGGGCTGT<br>GCACAGAAAGCCTGGTCCCGGTCTAGCAAAGGTCTGGAACTCCGGAGCCGGTGGGCT<br>GTGATTTACACCAGCATGGGATGGAAGGAGTTGGACCTCGCCTCCTGGGCACCTGGC<br>TCCTGTCACATAGCTACAGCCTCCCACAGCCCCCCTATAGGGAGGTATGCAGCATCA<br>ATCACATAGTAGCTGCACTAAGCCCTCCCACATGCAAATAAGGTTTCCCCAAACTCT<br>CAGTCCAAGCCAATGAAAAGTACCTGCTGTCAAACCCTAAATCATCCCCAAAACTCT<br>GTAAGTCCTATCAGGGAATAAAATGTGTGTGAAAACTAAAAAAAAAAAAAAA (SEQ ID NO: 35)<br><br>>NP_081790.1 poliovirus receptor precursor [*Mus musculus*]<br>MAQLARATRSPLSWLLLLFCYALRKAGGDIRVLVPYNSTGVLGGSTTLHCSLTSNEN<br>VTITQITWMKKDSGGSHALVAVFHPKKGPNIKEPERVKFLAAQQDLRNASLAISNLS<br>VEDEGIYECQIATFPRGSRSTNAWLKVQARPKNTAEALEPSPTLILQDVAKCISANG<br>HPPGRISWPSNVNGSHREMKEPGSQPGTTTVTSYLSMVPSRQADGKNITCTVEHESL<br>QELDQLLVTLSQPYPPENVSISGYDGNWYVGLTNLTLTCEAHSKPAPDMAGYNWSTN<br>TGDFPNSVKRQGNMLLISTVEDGLNNTVIVCEVTNALGSGQGQVHIIVKEKPENMQQ<br>NTRLHLGYIFLIVFVLAVVIIIAALYTIRRCRHGRALQSNPSERENVQYSSVNGDCR<br>LNMEPNSTR (SEQ ID NO: 36) |
| Human Nectin-2 (CD112) isoform alpha | >NM_002856.3 *Homo sapiens* nectin cell adhesion molecule 2 (NECTIN2), transcript variant alpha, mRNA<br>GTGACGTCAGCGGGTTCGAACCGCCGGAGCTGAGCGAGAGGCCGGGGGTGCCGAGCC<br>GGGCGGGGAGAGCTGGGCCGGGAGAGCAGAACAGGGAGGCTAGAGCGCAGCGGGAAC<br>CGGCCCGGAGCCGGAGCCGGAGCCCCACAGGCACCTACTAAACCGCCCAGCCGATCG<br>GCCCCCACAGAGTGGCCCGCGGGCCTCCGGCCGGGCCCAGTCCCCTCCCGGGCCCTC<br>CATGGCCCGGGCCGCTGCCCTCCTGCCGTCGAGATCGCCGCCGACGCCGCTGCTGTG<br>GCCGCTGCTGCTGCTGCTGCTCCTGGAAACCGGAGCCCAGGATGTGCGAGTTCAAGT<br>GCTACCCGAGGTGCGAGGCCAGCTCGGGGGCACCGTGGAGCTGCCGTGCCACCTGCT<br>GCCACCTGTTCCTGGACTGTACATCTCCCTGGTGACCTGGCAGCGCCCAGATGCACC<br>TGCGAACCACCAGAATGTGGCCGCCTTCCACCCTAAGATGGGTCCCAGCTTCCCCAG<br>CCCGAAGCCTGGCAGCGAGCGGCTGTCCTTCGTCTCTGCCAAGCAGAGCACTGGGCA<br>AGACACAGAGGCAGAGCTCCAGGACGCCACGCTGGCCCTCCACGGGCTCACGGTGGA<br>GGACGAGGGCAACTACACTTGCGAGTTTGCCACCTTCCCCAAGGGGTCCGTCCGAGG<br>GATGACCTGGCTCAGAGTCATAGCCAAGCCCAAGAACCAAGCTGAGGCCCAGAAGGT<br>CACGTTCAGCCAGGACCCTACGACAGTGGCCCTCTGCATCTCCAAAGAGGGCCGCCC<br>ACCTGCCCGGATCTCCTGGCTCTCATCCCTGGACTGGGAAGCCAAAGAGACTCAGGT<br>GTCAGGGACCCTGGCCGGAACTGTCACTGTCACCAGCCGCTTCACCTTGGTGCCCTC<br>GGGCCGAGCAGATGGTGTCACGGTCACCTGCAAAGTGGAGCATGAGAGCTTCGAGGA<br>ACCAGCCCTGATACCTGTGACCCTCTCTGTACGCTACCCTCCTGAAGTGTCCATCTC<br>CGGCTATGATGACAACTGGTACCTCGGCCGTACTGATGCCACCCTGAGCTGTGACGT<br>CCGCAGCAACCCAGAGCCCACGGGCTATGACTGGAGCACGACCTCAGGCACCTTCCC<br>GACCTCCGCAGTGGCCCAGGGCTCCCAGCTGGTCATCCACGCAGTGGACAGTCTGTT<br>CAATACCACCTTCGTCTGCACAGTCACCAATGCCGTGGGCATGGGCCGCGCTGAGCA<br>GGTCATCTTTGTCCGAGAAACCCCCAGGGCCTCGCCCCGAGATGTGGGCCCGCTGGT<br>GTGGGGGGCCGTGGGGGGGACACTGCTGGTGCTGCTGCTTCTGGCTGGGGGGTCCTT<br>GGCCTTCATCCTGCTGAGGGTGAGGAGGAGGAGGAAGAGCCCTGGAGGAGCAGGAGG<br>AGGAGCCAGTGGCGACGGGGGATTCTACGATCCGAAAGCTCAGGTGTTGGGAAATGG<br>GGACCCCGTCTTCTGGACACCAGTAGTCCCTGGTCCCATGGAACCAGATGGCAAGGA<br>TGAGGAGGAGGAGGAGGAGGAAGAGAAGGCAGAGAAAGGCCTCATGTTGCCTCCACC<br>CCCAGCACTCGAGGATGACATGGAGTCCCAGCTGGACGGCTCCCTCATCTCACGGCG<br>GGCAGTTTATGTGTGACCTGGACACAGACAGAGACAGAGCCAGGCCCGGCCCTCCCG<br>CCCCCGACCTGACCACGCCGGCCTAGGGTTCCAGACTGGTTGGACTTGTTCGTCTGG<br>ACGACACTGGAGTGGAACACTGCCTCCCACTTTCTTGGGACTTGGAGGGAGGTGGAA<br>CAGCACACTGGACTTCTCCCGTCTCTAGGGCTGCATGGGGAGCCCGGGGAGCTGAGT<br>AGTGGGGATCCAGAGAGGACCCCCGCCCCCAGAGACTTGGTTTTGGCTCCAGCCTTC<br>CCCTGGCCCCGTGACACTCAGGAGTTAATAAATGCCTTGGAGGAAAACA (SEQ ID NO: 37)<br><br>>NP_002847.1 nectin-2 isoform alpha precursor [*Homo sapiens*]<br>MARAAALLPSRSPPTPLLWPLLLLLLLETGAQDVRVQVLPEVRGQLGGTVELPCHLL<br>PPVPGLYISLVTWQRPDAPANHQNVAAFHPKMGPSFPSPKPGSERLSFVSAKQSTGQ<br>DTEAELQDATLALHGLTVEDEGNYTCEFATFPKGSVRGMTWLRVIAKPKNQAEAQKV |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| | TFSQDPTTVALCISKEGRPPARISWLSSLDWEAKETQVSGTLAGTVTVTSRFTLVPS<br>GRADGVTVTCKVEHESFEEPALIPVTLSVRYPPEVSISGYDDNWYLGRTDATLSCDV<br>RSNPEPTGYDWSTTSGTFPTSAVAQGSQLVIHAVDSLFNTTFVCTVTNAVGMGRAEQ<br>VIFVRETPRASPRDVGPLVWGAVGGTLLVLLLLAGGSLAFILLRVRRRRKSPGGAGG<br>GASGDGGFYDPKAQVLGNGDPVFWTPVVPGPMEPDGKDEEEEEEEEKAEKGLMLPPP<br>PALEDDMESQLDGSLISRRAVYV (SEQ ID NO: 38) |
| Mouse Nectin-2 (CD112) isoform alpha | >NM_001159724.1 *Mus musculus* nectin cell adhesion molecule 2 (Nectin2), transcript variant 2, mRNA<br>GAGCCCTAGGATCGGCTTGGCGAAGAGGGGCGGGGCCTGTGACGTCATGAGTCCGGC<br>CCGCTGGAGCTAAGCGAGGGGCCGGGGGGCGCGGATCCTGAGAGCCAGGCGAGGGAA<br>AGCTGGGCCGAACGAACTGATCCGGGGAGCCGTGAGCGGCGGAAGCCGGCCTGGAGC<br>CGGACACTTCAGACCCCTGACTGCCCTCCCAGCCGATCGGTACACGAAGAGTGGTCC<br>CTAGGCACCCCCTGCCCGGGCCCAGTCCCTCCCCGGGCCCCCCATGGCCCGGGCCGC<br>AGTCCTCCCGCCGTCCAGATTGTCACCGACGCTGCCGTTGTTGCCGCTGCTACTGCT<br>CCTGCTTCAGGAAACAGGAGCCCAAGATGTGCGGGTACGAGTGCTTCCCGAGGTCCG<br>GGGCCGCTTGGGAGGCACCGTGGAGTTACCGTGCCACCTGCTCCCACCCACGACGGA<br>GCGCGTCTCTCAGGTGACCTGGCAGCGCCTGGATGGCACAGTTGTGGCTGCTTTCCA<br>CCCATCCTTCGGAGTGGATTTCCCCAACTCTCAGTTCAGCAAGGACCGTCTGTCCTT<br>TGTCAGAGCGAGACCAGAAACAAACGCAGACCTGCGGGATGCCACACTGGCCTTCCG<br>GGGACTGAGGGTAGAGGACGAGGGCAATTACACCTGCGAGTTTGCCACGTTTCCCAA<br>CGGTACCCGCAGGGGGGTGACCTGGCTCAGAGTCATAGCCCAGCCTGAGAACCACGC<br>TGAAGCCCAGGAGGTCACAATTGGCCCCCAGTCGGTGGCTGTAGCCCGCTGTGTCTC<br>CACTGGGGGCCGCCCCCCTGCCCGAATCACCTGGATCTCATCTCTGGGTGGAGAGGC<br>CAAAGATACTCAGGAGCCAGGGATACAGGCTGGCACCGTCACTATCATCAGCCGATA<br>CTCCTTGGTGCCCGTGGGCCGAGCGGATGGCGTCAAGGTCACGTGTAGAGTGGAACA<br>CGAGAGCTTCGAAGAGCCGATCCTGCTGCCAGTGACCCTCTCTGTGCGCTACCCTCC<br>AGAAGTATCCATCTCCGGCTATGATGACAACTGGTACCTTGGCCGCAGTGAGGCCAT<br>ACTGACCTGTGATGTACGAAGCAACCCAGAGCCCACAGACTATGACTGGAGCACGAC<br>CTCGGGCGTCTTCCCAGCCTCTGCAGTGGCCCAGGGCTCTCAGCTGCTTGTCCACTC<br>TGTGGATCGAATGGTCAACACTACCTTCATCTGTACAGCCACCAACGCTGTGGGGAC<br>AGGCCGTGCTGAGCAGGTCATCCTGGTGCGAGACACCCCCCAGGCCTCCCGAGATGT<br>GGGTCCGCTGGTGTGGGGGGCCGTGGGGGGAACATTGCTGGTGCTACTCCTGGCTGG<br>GGGGTTCCTGGCCTTGATCCTGCTGAGGGGGAGGAGGAGGCGGAAGAGCCCTGGAGG<br>AGGAGGAAATGATGGCGACAGAGGATCCTACGATCCAAAGACTCAGGTGTTTGGGAA<br>CGGGGGTCCTGTCTTCTGGAGGTCAGCATCCCCTGAGCCCATGAGGCCAGATGGCAG<br>GGAGGAAGATGAGGAGGAGGAGGAAGAAATGAAGGCAGAGGAAGGTCTCATGCTACC<br>TCCACACGAGTCACCTAAGGACGACATGGAGTCCCATCTGGATGGCTCCCTCATCTC<br>TCGGCGGGCAGTTTACGTGTGACCCTACGATATAGACACTGGACACATGGAAACACC<br>AAGTTCCACCCTCACTGCCAACCACACCAATGCCAGCCAGCAACGATGGCTAGGGAC<br>CGGTTGGACTGGTTCTTCTGGGGCACACTGGAGTTGGAAGGGCACCGCCCCTGCTTT<br>CAGGATAGAGGACAAGTGGAACCACACAGACTCCTATCTTTAGGGCCTCATGGAGTA<br>GGGGACCCCAGGAGCGCCATGGTGCACACTCAGGACTCCTCAGAGCTTGCTTTCGGC<br>CCCAGCCTAGCCCTGGCCCCGAAACACTCAGGAGCTAATAAATGCCTTGTCGGAAAA<br>AAAAAAAAAAAAA (SEQ ID NO: 39)<br><br>>NP_001153196.1 nectin-2 isoform 2 precursor [Mus *musculus*]<br>MARAAVLPPSRLSPTLPLLPLLLLLLQETGAQDVRVRVLPEVRGRLGGTVELPCHLL<br>PPTTERVSQVTWQRLDGTVVAAFHPSFGVDFPNSQFSKDRLSFVRARPETNADLRDA<br>TLAFRGLRVEDEGNYTCEFATFPNGTRRGVTWLRVIAQPENHAEAQEVTIGPQSVAV<br>ARCVSTGGRPPARITWISSLGGEAKDTQEPGIQAGTVTIISRYSLVPVGRADGVKVT<br>CRVEHESFEEPILLPVTLSVRYPPEVSISGYDDNWYLGRSEAILTCDVRSNPEPTDY<br>DWSTTSGVFPASAVAQGSQLLVHSVDRMVNTTFICTATNAVGTGRAEQVILVRDTPQ<br>ASRDVGPLVWGAVGGTLLVLLLAGGFLALILLRGRRRRKSPGGGGNDGDRGSYDPKT<br>QVFGNGGPVFWRSASPEPMRPDGREEDEEEEEMKAEEGLMLPPHESPKDDMESHLD<br>GSLISRRAVYV (SEQ ID NO: 40) |
| Human Nectin-2 (CD112) isoform delta | >NM_001042724.2 *Homo sapiens* nectin cell adhesion molecule 2 (NECTIN2), transcript variant delta, mRNA<br>GTGACGTCAGCGGGTTCGAACCGCCGGAGCTGAGCGAGAGGCCGGGGGTGCCGAGCC<br>GGGCGGGGAGAGCTGGGCCGGGAGAGCAGAACAGGGAGGCTAGAGCGCAGCGGGAAC<br>CGGCCCGGAGCCGGAGCCGGAGCCCCACAGGCACCTACTAAACCGCCCAGCCGATCG<br>GCCCCCACAGAGTGGCCCGCGGGCCTCCGGCCGGGCCCAGTCCCCTCCCGGGCCCTC<br>CATGGCCCGGGCCGCTGCCCTCCTGCCGTCGAGATCGCCGCCGACGCCGCTGCTGTG<br>GCCGCTGCTGCTGCTGCTGCTCCTGGAAACCGGAGCCCAGGATGTGCGAGTTCAAGT<br>GCTACCCGAGGTGCGAGGCCAGCTCGGGGGCACCGTGGAGCTGCCGTGCCACCTGCT<br>GCCACCTGTTCCTGGACTGTACATCTCCCTGGTGACCTGGCAGCGCCCAGATGCACC<br>TGCGAACCACCAGAATGTGGCCGCCTTCCACCCTAAGATGGGTCCCAGCTTCCCCAG<br>CCCGAAGCCTGGCAGCGAGCGGCTGTCCTTCGTCTCTGCCAAGCAGAGCACTGGGCA<br>AGACACACAGAGGCAGAGCTCCAGGACGCCACGCTGGCCCTCCACGGGCTCACGGTGGA<br>GGACGAGGGCAACTACACTTGCGAGTTTGCCACCTTCCCCAAGGGGTCCGTCCGAGG<br>GATGACCTGGCTCAGAGTCATAGCCAAGCCCAAGAACCAAGCTGAGGCCCAGAAGGT<br>CACGTTCAGCCAGGACCCTACGACAGTGGCCCTCTGCATCTCCAAAGAGGGCCGCCC<br>ACCTGCCCGGATCTCCTGGCTCTCATCCCTGGACTGGGAAGCCAAAGAGACTCAGGT |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| | GTCAGGGACCCTGGCCGGAACTGTCACTGTCACCAGCCGCTTCACCTTGGTGCCCTC<br>GGGCCGAGCAGATGGTGTCACGGTCACCTGCAAAGTGGAGCATGAGAGCTTCGAGGA<br>ACCAGCCCTGATACCTGTGACCCTCTCTGTACGCTACCCTCCTGAAGTGTCCATCTC<br>CGGCTATGATGACAACTGGTACCTCGGCCGTACTGATGCCACCCTGAGCTGTGACGT<br>CCGCAGCAACCCAGAGCCCACGGGCTATGACTGGAGCACGACCTCAGGCACCTTCCC<br>GACCTCCGCAGTGGCCCAGGGCTCCCAGCTGGTCATCCACGCAGTGGACAGTCTGTT<br>CAATACCACCTTCGTCTGCACAGTCACCAATGCCGTGGGCATGGGCCGCGCTGAGCA<br>GGTCATCTTTGTCCGAGAGACCCCCAACACAGCAGGCGCAGGGGCCACAGGCGGCAT<br>CATCGGGGGCATCATCGCCGCCATCATTGCTACTGCTGTGGCTGCCACGGGCATCCT<br>TATCTGCCGGCAGCAGCGGAAGGAGCAGACGCTGCAGGGGGCAGAGGAGGACGAAGA<br>CCTGGAGGGACCTCCCTCCTACAAGCCACCGACCCCAAAAGCGAAGCTGGAGGCACA<br>GGAGATGCCCTCCCAGCTCTTCACTCTGGGGGCCTCGGAGCACAGCCCACTCAAGAC<br>CCCCTACTTTGATGCTGGCGCCTCATGCACTGAGCAGGAAATGCCTCGATACCATGA<br>GCTGCCCACCTTGGAAGAACGGTCAGGACCCTTGCACCCTGGAGCCACAAGCCTGGG<br>GTCCCCCATCCCGGTGCCTCCAGGGCCACCTGCTGTGGAAGACGTTTCCCTGGATCT<br>AGAGGATGAGGAGGGGGAGGAGGAGGAAGAGTATCTGGACAAGATCAACCCCATCTA<br>TGATGCTCTGTCCTATAGCAGCCCCTCTGATTCCTACCAGGGCAAAGGCTTTGTCAT<br>GTCCCGGGCCATGTATGTGTGAGCTGCCATGCGCCTGGCGTCTCACATCTCACCTGT<br>TGATCCCTTAGCTTTCTTGCCAAGGATCTAGTGCCCCCTGACCTCTGGCCAGGCCAC<br>TGTCAGTTAACACATATGCATTCCATTTGTGATGTCTACCTTGGTGGCTCCACTATG<br>ACCCCTAACCCATGAGCCCAGAGAAATTCACCGTGATAATGGAATCCTGGCAACCTT<br>ATCTCATGAGGCAGGAGGTGGGGAAGGTGCTTCTGCACAACCTCTGATCCCAAGGAC<br>TCCTCTCCCAGACTGTGACCTTAGACCATACCTCTCACCCCCCAATGCCTCGACTCC<br>CCCAAAATCACAAAGAAGACCCTAGACCTATAATTTGTCTTCAGGTAGTAAATTCCC<br>AATAGGTCTGCTGGAGTGGGCGCTGAGGGCTCCCTGCTGCTCAGACCTGAGCCCTCC<br>AGGCAGCAGGGTCCCACTTACCCCCTCCCCACCCTGTTCCCCAAAGGTGGGAAAGAG<br>GGGATTCCCCAGCCCAAGGCAGGGTTTTCCCAGCACCCTCCTGTAAGCAGAAGTCTC<br>AGGGTCCAGACCCTTCCCTGAGCCCCCACCCCCACCCCAATTCCTGCCTACCAAGCA<br>AGCAGCCCCAGCCTAGGGTCAGACAGGGTGAGCCTCATACAGACTGTGCCTTGATGG<br>CCCCAGCCTTGGGAGAAGAATTTACTGTTAACCTGGAAGACTACTGAATCATTTTAC<br>CCTTGCCCAGTGGAATAGGACCTAAACATCCCCCTTCCGGGGAAAGTGGGTCATCTG<br>AATTGGGGGTAGCAATTGATACTGTTTTGTAAACTACATTTCCTACAAAATATGAAT<br>TTATACTTTGA (SEQ ID NO: 41)<br><br>>NP_001036189.1 nectin-2 isoform delta precursor [*Homo sapiens*]<br>MARAAALLPSRSPPTPLLWPLLLLLLLETGAQDVRVQVLPEVRGQLGGTVELPCHLL<br>PPVPGLYISLVTWQRPDAPANHQNVAAFHPKMGPSFPSPKPGSERLSFVSAKQSTGQ<br>DTEAELQDATLALHGLTVEDEGNYTCEFATFPKGSVRGMTWLRVIAKPKNQAEAQKV<br>TFSQDPTTVALCISKEGRPPARISWLSSLDWEAKETQVSGTLAGTVTVTSRFTLVPS<br>GRADGVTVTCKVEHESFEEPALIPVTLSVRYPPEVSISGYDDNWYLGRTDATLSCDV<br>RSNPEPTGYDWSTTSGTFPTSAVAQGSQLVIHAVDSLFNTTFVCTVTNAVGMGRAEQ<br>VIFVRETPNTAGAGATGGIIGGIIAAIIATAVAATGILICRQQRKEQTLQGAEEDED<br>LEGPPSYKPPTPKAKLEAQEMPSQLFTLGASEHSPLKTPYFDAGASCTEQEMPRYHE<br>LPTLEERSGPLHPGATSLGSPIPVPPGPPAVEDVSLDLEDEEGEEEEEYLDKINPIY<br>DALSYSSPSDSYQGKGFVMSRAMYV (SEQ ID NO: 42) |
| Mouse Nectin-2 (CD112) isoform beta | >NM_008990.3 *Mus musculus* nectin cell adhesion molecule 2 (Nectin2), transcript variant 1, mRNA<br>GAGCCCTAGGATCGGCTTGGCGAAGAGGGGCGGGGCCTGTGACGTCATGAGTCCGGC<br>CCGCTGGAGCTAAGCGAGGGGCCGGGGGGCGCGGATCCTGAGAGCCAGGCGAGGGAA<br>AGCTGGGCCGAACGAACTGATCCGGGGAGCCGTGAGCGGCGGAAGCCGGCCTGGAGC<br>CGGACACTTCAGACCCCTGACTGCCCTCCCAGCCGATCGGTACACGAAGAGTGGTCC<br>CTAGGCACCCCCTGCCCGGGCCCAGTCCCTCCCCGGGCCCCCCATGGCCCGGGCCGC<br>AGTCCTCCCGCCGTCCAGATTGTCACCGACGCTGCCGTTGTTGCCGCTGCTACTGCT<br>CCTGCTTCAGGAAACAGGAGCCCAAGATGTGCGGGTACGAGTGCTTCCCGAGGTCCG<br>GGGCCGCTTGGGAGGCACCGTGGAGTTACCGTGCCACCTGCTCCCACCCACGACGGA<br>GCGCGTCTCTCAGGTGACCTGGCAGCGCCTGGATGGCACAGTTGTGGCTGCTTTCCA<br>CCCATCCTTCGGAGTGGATTTCCCCAACTCTCAGTTCAGCAAGGACCGTCTGTCCTT<br>TGTCAGAGCGAGACCAGAAACAAACGCAGACCTGCGGGATGCCACACTGGCCTTCCG<br>GGGACTGAGGGTAGAGGACGAGGGCAATTACACCTGCGAGTTTGCCACGTTTCCCAA<br>CGGTACCCGCAGGGGGGTGACCTGGCTCAGAGTCATAGCCCAGCCTGAGAACCACGC<br>TGAAGCCCAGGAGGTCACAATTGGCCCCCAGTCGGTGGCTGTAGCCCGCTGTGTCTC<br>CACTGGGGGCCGCCCCCCTGCCCGAATCACCTGGATCTCATCTCTGGGTGGAGAGGC<br>CAAAGATACTCAGGAGCCAGGGATACAGGCTGGCACCGTCACTATCATCAGCCGATA<br>CTCCTTGGTGCCCGTGGGCCGAGCGGATGGCGTCAAGGTCACGTGTAGAGTGGAACA<br>CGAGAGCTTCGAAGAGCCGATCCTGCTGCCAGTGACCCTCTCTGTGCGCTACCCTCC<br>AGAAGTATCCATCTCCGGCTATGATGACAACTGGTACCTTGGCCGCAGTGAGGCCAT<br>ACTGACCTGTGATGTACGAAGCAACCCAGAGCCCACAGACTATGACTGGAGCACGAC<br>CTCGGGCGTCTTCCCAGCCTCTGCAGTGGCCCAGGGCTCTCAGCTGCTTGTCCACTC<br>TGTGGATCGAATGGTCAACACTACCTTCATCTGTACAGCCACCAACGCTGTGGGGAC<br>AGGCCGTGCTGAGCAGGTCATCCTGGTGCGAGAGTCACCCAGCACAGCAGGAGCAGG<br>GGCCACTGGTGGCATCATTGGAGGTATTATCGCTGCCATCATCGCCACCGCAGTGGC<br>TGGCACAGGCATCCTCATCTGCCGACAACAGCGGAAGGAGCAGAGGCTTCAAGCTGC<br>GGATGAGGAAGAAGAACTGGAAGGACCTCCCTCCTATAAACCACCCACCCCGAAGGC |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| | CAAGCTGGAGGAACCAGAGATGCCCTCTCAACTCTTCACCTTGGGGGCCTCAGAGCA<br>CAGCCCAGTGAAGACGCCATACTTTGATGCTGGTGTCTCTTGTGCTGATCAGGAGAT<br>GCCTCGGTATCACGAGCTGCCCACTCTGGAAGAGCGGTCAGGGCCCCTGCTGTTGGG<br>GGCTACAGGCCTGGGACCTTCTCTTCTGGTGCCTCCAGGACCCAATGTTGTGGAGGG<br>GGTTTCCCTGAGTCTCGAAGATGAGGAGGAAGATGATGAGGAGGAAGACTTCCTGGA<br>TAAAATCAACCCTATTTATGATGCCCTGTCCTACCCCAGCCCCTCTGACTCCTACCA<br>GAGCAAAGACTTTTTTGTGTCACGGGCCATGTATGTGTGAGGGAGGCACAGGGGCTC<br>TGACGTCTCACCTTTCACCCTTGACCCATGAGCTTTCCACCAGTAATCTAGGACACT<br>CTGACTTCCAGGCAGACCAGGGACAACTATCACCCATTGCAATCCACCTGTGACTTC<br>TTAGTGACTCCACCATGACGTCCAATCTATGATGTCTGAGGCAGGCAAACCTGCACA<br>ACTGGAAACCTGGAGATTTTTATCTCCCTTGGCAGGGAGCTCACCATATCCTTCTGC<br>ACCACCTGTGACCCCCCCCCCCCCCCAAGGACTCCTAAGACTACGACCCTTTGACC<br>ATGCCACTCAGTATCTCAAGAACCCTTAAAGTCCCAAAGGAATCGGACCTTGCACTT<br>GTCCTCAGGCAATAGAGTCCAACAGATATGCAAGAACGGGATCAGGGGCTCCCTGTT<br>GCTCAGACCTGAGCCCTCCAGGCAGCAGAAGCTCACCTGATCCCTCCCCACCCTGCT<br>CCCCAAAGGTGAAAAGGAGAGGATTCCCCAATGTAAGGTAGGACCTCCCCATCTCCA<br>CCTACTCCTGCAGGCAGGAATCTCAGGTTTCTCACACCCTCTCCTCAGCACCCAGGT<br>TCCTGTCTCCAGAGCATGAATTCCAGGTCCAATGCTAGAGGGGAGAACCTAATGCAA<br>GTGTGCCTTGCCACCCCAAGTTTGGGAGACTCTGCTCTTATCCTGAGGACTACTGAA<br>TTCTTTTAACCCCTACCCAGTGAGATGAGAACTACATATCCCTCTTTAGGGGATGGT<br>GTGTGTATGTGTGTGTGATGGAGAATCTGGGCATCTGGGTTGGGAATTTTATTTTGT<br>AAGCATTTCCTACATAATATGAGTTTCTACTTTGATAAAGTCTTGTGTTTTCTGTG<br>(SEQ ID NO: 43)<br><br>>NP_033016.3 nectin-2 isoform 1 precursor [*Mus musculus*]<br>MARAAVLPPSRLSPTLPLLPLLLLLLQETGAQDVRVRVLPEVRGRLGGTVELPCHLL<br>PPTTERVSQVTWQRLDGTVVAAFHPSFGVDFPNSQFSKDRLSFVRARPETNADLRDA<br>TLAFRGLRVEDEGNYTCEFATFPNGTRRGVTWLRVIAQPENHAEAQEVTIGPQSVAV<br>ARCVSTGGRPPARITWISSLGGEAKDTQEPGIQAGTVTIISRYSLVPVGRADGVKVT<br>CRVEHESFEEPILLPVTLSVRYPPEVSISGYDDNWYLGRSEAILTCDVRSNPEPTDY<br>DWSTTSGVFPASAVAQGSQLLVHSVDRMVNTTFICTATNAVGTGRAEQVILVRESPS<br>TAGAGATGGIIGGIIAAIIATAVAGTGILICRQQRKEQRLQAADEEEELEGPPSYKP<br>PTPKAKLEEPEMPSQLFTLGASEHSPVKTPYFDAGVSCADQEMPRYHELPTLEERSG<br>PLLLGATGLGPSLLVPPGPNVVEGVSLSLEDEEEDDEEEDFLDKINPIYDALSYPSP<br>SDSYQSKDFFVSRAMYV (SEQ ID NO: 44) |
| Human IL-10 | >NM_000572.3 *Homo sapiens* interleukin 10 (IL10),<br>transcript variant 1, mRNA<br>ACACATCAGGGGCTTGCTCTTGCAAAACCAAACCACAAGACAGACTTGCAAAAGAAG<br>GCATGCACAGCTCAGCACTGCTCTGTTGCCTGGTCCTCCTGACTGGGGTGAGGGCCA<br>GCCCAGGCCAGGGCACCCAGTCTGAGAACAGCTGCACCCACTTCCCAGGCAACCTGC<br>CTAACATGCTTCGAGATCTCCGAGATGCCTTCAGCAGAGTGAAGACTTTCTTTCAAA<br>TGAAGGATCAGCTGGACAACTTGTTGTTAAAGGAGTCCTTGCTGGAGGACTTTAAGG<br>GTTACCTGGGTTGCCAAGCCTTGTCTGAGATGATCCAGTTTTACCTGGAGGAGGTGA<br>TGCCCCAAGCTGAGAACCAAGACCCAGACATCAAGGCGCATGTGAACTCCCTGGGGG<br>AGAACCTGAAGACCCTCAGGCTGAGGCTACGGCGCTGTCATCGATTTCTTCCCTGTG<br>AAAACAAGAGCAAGGCCGTGGAGCAGGTGAAGAATGCCTTTAATAAGCTCCAAGAGA<br>AAGGCATCTACAAAGCCATGAGTGAGTTTGACATCTTCATCAACTACATAGAAGCCT<br>ACATGACAATGAAGATACGAAACTGAGACATCAGGGTGGCGACTCTATAGACTCTAG<br>GACATAAATTAGAGGTCTCCAAAATCGGATCTGGGGCTCTGGGATAGCTGACCCAGC<br>CCCTTGAGAAACCTTATTGTACCTCTCTTATAGAATATTTATTACCTCTGATACCTC<br>AACCCCCATTTCTATTTATTTACTGAGCTTCTCTGTGAACGATTTAGAAAGAAGCCC<br>AATATTATAATTTTTTTCAATATTTATTATTTTCACCTGTTTTTAAGCTGTTTCCAT<br>AGGGTGACACACTATGGTATTTGAGTGTTTTAAGATAAATTATAAGTTACATAAGGG<br>AGGAAAAAAAATGTTCTTTGGGGAGCCAACAGAAGCTTCCATTCCAAGCCTGACCAC<br>GCTTTCTAGCTGTTGAGCTGTTTTCCCTGACCTCCCTCTAATTTATCTTGTCTCTGG<br>GCTTGGGGCTTCCTAACTGCTACAAATACTCTTAGGAAGAGAAACCAGGGAGCCCCT<br>TTGATGATTAATTCACCTTCCAGTGTCTCGGAGGGATTCCCCTAACCTCATTCCCCA<br>ACCACTTCATTCTTGAAAGCTGTGGCCAGCTTGTTATTTATAACAACCTAAATTTGG<br>TTCTAGGCCGGGCGCGGTGGCTCACGCCTGTAATCCCAGCACTTTGGGAGGCTGAGG<br>CGGGTGGATCACTTGAGGTCAGGAGTTCCTAACCAGCCTGGTCAACATGGTGAAACC<br>CCGTCTCTACTAAAAATACAAAAATTAGCCGGGCATGGTGGCGCGCACCTGTAATCC<br>CAGCTACTTGGGAGGCTGAGGCAAGAGAATTGCTTGAACCCAGGAGATGGAAGTTGC<br>AGTGAGCTGATATCATGCCCCTGTACTCCAGCCTGGGTGACAGAGCAAGACTCTGTC<br>TCAAAAAATAAAAATAAAAATAAATTTGGTTCTAATAGAACTCAGTTTTAACTAGAA<br>TTTATTCAATTCCTCTGGGAATGTTACATTGTTTGTCTGTCTTCATAGCAGATTTTA<br>ATTTTGAATAAATAAATGTATCTTATTCACATCA (SEQ ID NO: 45)<br><br>>NP_000563.1 inter1eukin-10 isoform 1 precursor [*Homo sapiens*]<br>MHSSALLCCLVLLTGVRASPGQGTQSENSCTHFPGNLPNMLRDLRDAFSRVKTFFQM<br>KDQLDNLLLKESLLEDFKGYLGCQALSEMIQFYLEEVMPQAENQDPDIKAHVNSLGE<br>NLKTLRLRLRRCHRFLPCENKSKAVEQVKNAFNKLQEKGIYKAMSEFDIFINYIEAY<br>MTMKIRN (SEQ ID NO: 46) |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| Mouse IL-10 | >NM_010548.2 *Mus musculus* interleukin 10 (Il10), mRNA<br>ACATTTAGAGACTTGCTCTTGCACTACCAAAGCCACAAGGCAGCCTTGCAGAAAAGA<br>GAGCTCCATCATGCCTGGCTCAGCACTGCTATGCTGCCTGCTCTTACTGACTGGCAT<br>GAGGATCAGCAGGGGCCAGTACAGCCGGGAAGACAATAACTGCACCCACTTCCCAGT<br>CGGCCAGAGCCACATGCTCCTAGAGCTGCGGACTGCCTTCAGCCAGGTGAAGACTTT<br>CTTTCAAACAAAGGACCAGCTGGACAACATACTGCTAACCGACTCCTTAATGCAGGA<br>CTTTAAGGGTTACTTGGGTTGCCAAGCCTTATCGGAAATGATCCAGTTTTACCTGGT<br>AGAAGTGATGCCCCAGGCAGAGAAGCATGGCCCAGAAATCAAGGAGCATTTGAATTC<br>CCTGGGTGAGAAGCTGAAGACCCTCAGGATGCGGCTGAGGCGCTGTCATCGATTTCT<br>CCCCTGTGAAAATAAGAGCAAGGCAGTGGAGCAGGTGAAGAGTGATTTTAATAAGCT<br>CCAAGACCAAGGTGTCTACAAGGCCATGAATGAATTTGACATCTTCATCAACTGCAT<br>AGAAGCATACATGATGATCAAAATGAAAAGCTAAAACACCTGCAGTGTGTATTGAGT<br>CTGCTGGACTCCAGGACCTAGACAGAGCTCTCTAAATCTGATCCAGGGATCTTAGCT<br>AACGGAAACAACTCCTTGGAAAACCTCGTTTGTACCTCTCTCCGAAATATTTATTAC<br>CTCTGATACCTCAGTTCCCATTCTATTTATTCACTGAGCTTCTCTGTGAACTATTTA<br>GAAAGAAGCCCAATATTATAATTTTACAGTATTTATTATTTTTAACCTGTGTTTAAG<br>CTGTTTCCATTGGGGACACTTTATAGTATTTAAAGGGAGATTATATTATATGATGGG<br>AGGGGTTCTTCCTTGGGAAGCAATTGAAGCTTCTATTCTAAGGCTGGCCACACTTGA<br>GAGCTGCAGGGCCCTTTGCTATGGTGTCCTTTCAATTGCTCTCATCCCTGAGTTCAG<br>AGCTCCTAAGAGAGTTGTGAAGAAACTCATGGGTCTTGGGAAGAGAAACCAGGGAGA<br>TCCTTTGATGATCATTCCTGCAGCAGCTCAGAGGGTTCCCCTACTGTCATCCCCCAG<br>CCGCTTCATCCCTGAAAACTGTGGCCAGTTTGTTATTTATAACCACCTAAAATTAGT<br>TCTAATAGAACTCATTTTTAACTAGAAGTAATGCAATTCCTCTGGGAATGGTGTATT<br>GTTTGTCTGCCTTTGTAGCAGACTCTAATTTTGAATAAATGGATCTTATTCG (SEQ<br>ID NO: 47)<br><br>>NP_034678.1 interleukin-10 precursor [*Mus musculus*]<br>MPGSALLCCLLLLTGMRISRGQYSREDNNCTHFPVGQSHMLLELRTAFSQVKTFFQT<br>KDQLDNILLTDSLMQDFKGYLGCQALSEMIQFYLVEVMPQAEKHGPEIKEHLNSLGE<br>KLKTLRMRLRRCHRFLPCENKSKAVEQVKSDFNKLQDQGVYKAMNEFDIFINCIEAY<br>MMIKMKS (SEQ ID NO: 48) |
| Human TSG-6 | >NM_007115.3 *Homo sapiens* TNF alpha induced protein 6<br>(TNFAIP6), mRNA<br>AGTCACATTTCAGCCACTGCTCTGAGAATTTGTGAGCAGCCCCTAACAGGCTGTTAC<br>TTCACTACAACTGACGATATGATCATCTTAATTTACTTATTTCTCTTGCTATGGGAA<br>GACACTCAAGGATGGGGATTCAAGGATGGAATTTTTCATAACTCCATATGGCTTGAA<br>CGAGCAGCCGGTGTGTACCACAGAGAAGCACGGTCTGGCAAATACAAGCTCACCTAC<br>GCAGAAGCTAAGGCGGTGTGTGAATTTGAAGGCGGCCATCTCGCAACTTACAAGCAG<br>CTAGAGGCAGCCAGAAAAATTGGATTTCATGTCTGTGCTGCTGGATGGATGGCTAAG<br>GGCAGAGTTGGATACCCCATTGTGAAGCCAGGGCCCAACTGTGGATTTGGAAAAACT<br>GGCATTATTGATTATGGAATCCGTCTCAATAGGAGTGAAAGATGGGATGCCTATTGC<br>TACAACCCACACGCAAAGGAGTGTGGTGGCGTCTTTACAGATCCAAAGCAAATTTTT<br>AAATCTCCAGGCTTCCCAAATGAGTACGAAGATAACCAAATCTGCTACTGGCACATT<br>AGACTCAAGTATGGTCAGCGTATTCACCTGAGTTTTTTAGATTTTGACCTTGAAGAT<br>GACCCAGGTTGCTTGGCTGATTATGTTGAAATATATGACAGTTACGATGATGTCCAT<br>GGCTTTGTGGGAAGATACTGTGGAGATGAGCTTCCAGATGACATCATCAGTACAGGA<br>AATGTCATGACCTTGAAGTTTCTAAGTGATGCTTCAGTGACAGCTGGAGGTTTCCAA<br>ATCAAATATGTTGCAATGGATCCTGTATCCAAATCCAGTCAAGGAAAAAATACAAGT<br>ACTACTTCTACTGGAAATAAAAACTTTTTAGCTGGAAGATTTAGCCACTTATAAAAA<br>AAAAAAAAAGGATGATCAAAACACACAGTGTTTATGTTGGAATCTTTTGGAACTCCT<br>TTGATCTCACTGTTATTATTAACATTTATTTATTATTTTTCTAAATGTGAAAGCAAT<br>ACATAATTTAGGGAAAATTGGAAAATATAGGAAACTTTAAACGAGAAAATGAAACCT<br>CTCATAATCCCACTGCATAGAAATAACAAGCGTTAACATTTTCATATTTTTTTCTTT<br>CAGTCATTTTTCTATTTGTGGTATATGTATATATGTACCTATATGTATTTGCATTTG<br>AAATTTTGGAATCCTGCTCTATGTACAGTTTTGTATTATACTTTTTAAATCTTGAAC<br>TTTATAAACATTTTCTGAAATCATTGATTATTCTACAAAAACATGATTTTAAACAGC<br>TGTAAAATATTCTATGATATGAATGTTTTATGCATTATTTAAGCCTGTCTCTATTGT<br>TGGAATTTCAGGTCATTTTCATAAATATTGTTGCAATAAATATCCTTGAACACACAA<br>AAAAAAAAAAAAA (SEQ ID NO: 49)<br><br>>NP_009046.2 tumor necrosis factor-inducible gene 6<br>protein precursor [*Homo sapiens*]<br>MIILIYLFLLLWEDTQGWGFKDGIFHNSIWLERAAGVYHREARSGKYKLTYAEAKAV<br>CEFEGGHLATYKQLEAARKIGFHVCAAGWMAKGRVGYPIVKPGPNCGFGKTGIIDYG<br>IRLNRSERWDAYCYNPHAKECGGVFTDPKQIFKSPGFPNEYEDNQICYWHIRLKYGQ<br>RIHLSFLDFDLEDDPGCLADYVEIYDSYDDVHGFVGRYCGDELPDDIISTGNVMTLK<br>FLSDASVTAGGFQIKYVAMDPVSKSSQGKNTSTTSTGNKNFLAGRFSHL (SEQ ID<br>NO: 50) |
| Mouse TSG-6 | >NM_009398.2 *Mus musculus* tumor necrosis factor alpha<br>induced protein 6 (Tnfaip6), mRNA<br>CCGCTGCTCTGAGAATTTCGTGTGGGCAGCCCCGACATTGTAACCGGCTCTGCAACC<br>GAAGAGATGGTCGTCCTCCTTTGCTTATGCGTCTTGCTGTGGGAAGAGGCTCACGGA<br>TGGGGATTCAAGAACGGGATCTTTCATAACTCCATATGGCTTGAACAAGCAGCGGGC |

TABLE 1-continued

Type I Proteins of Interest Amino Acid Sequence

| Protein of Interest | Transcript Sequence (SEQ ID NO:)<br>Amino Acid Sequence (SEQ ID NO:) |
|---|---|
| | GTATACCACAGAGAAGCTCGGGCTGGCAGATACAAGCTCACCTACGCCGAAGCCAAG<br>GCCGTATGTGAATTTGAAGGTGGTCGTCTCGCAACCTACAAGCAGCTAGAGGCAGCC<br>AGAAAAATTGGATTCCATGTCTGTGCTGCTGGATGGATGGCCAAGGGTAGAGTCGGA<br>TACCCCATTGTGAAACCTGGGCCCAACTGTGGATTTGGGAAAACGGGTATCATCGAT<br>TATGGAATCCGGCTCAACAGGAGTGAGCGATGGGATGCCTATTGCTACAACCCACAT<br>GCAAAGGAGTGTGGTGGTGTCTTCACAGATCCGAAGCGAATTTTTAAATCCCCGGGC<br>TTCCCAAATGAGTACGATGACAACCAGGTCTGCTACTGGCACATTCGGCTCAAGTAC<br>GGTCAGCGAATTCACCTGAGCTTTTTGGACTTTGACCTTGAACATGATCCAGGCTGC<br>TTGGCTGACTATGTAGAAATCTATGACAGTTATGATGACGTCCACGGCTTTGTAGGA<br>AGATACTGTGGTGATGAACTTCCAGAAGACATCATTAGCACAGGAAATGTCATGACC<br>TTGAAGTTTCTGAGTGATGCATCCGTCACGGCTGGAGGCTTCCAGATTAAATACGTC<br>ACAGTGGATCCTGCATCTAAATCCAGTCAAGCCAAAAATACAAGTACTACTGGAAAT<br>AAGAAGTTCTTACCTGGAAGGTTTAGCCATCTATAAAAAATTTTTTTAAAAATGTT<br>CAAAACATCCAGTACAATATTTATATTTGTTTTTGTTGTTGTTGTTGGTTTTTTTTT<br>TTTTATTTTGTTTTGTTTTGTTTTTTTGAGACGGGGTTTCTCTGTATAGCCTTGGCT<br>GTCCTGGAACTCACTTTGAAGACCAGGCTGGCCTCGAACTCAGAAATCCACCTGCCT<br>CCGCCTACCAAGTGCTGGGATTAAAGGCGTCCACCACCACCGCCCGGCTTCAATATT<br>TATATTTGTAGCTCTTGGACCTCGTTTGTTCTCTTTTGTATTTTTATTATTAACATG<br>TATTTATTATTTTTCCAAATGTGAAAGCCATATGTAATTATGTGGAAAATTGACAAA<br>TAAATACAGAGAACTTCAAATGAGTTTTTTTTTTAAATCTCATAATTGTACTACACA<br>GAAATAACTAATGTTAAAGTTTTTAAATGTTTGTCTTTCATTCATTTTTCTACTTGT<br>AGTATATGTACATATGTAACTCTATGATTTGCGTTTGAATTTTGGCATTCTGCCTTT<br>TGTAACCTGATATTTTTAACCTTGACATTGTATAGCTCAAGCACTTCCCAAGATCTC<br>TGAGTTTTCTACAAAATGGGACTTTGTAAATATGATTGTTCCCTGCTTTATTTAAGC<br>TGAATTTATATTAGGATTTAAGGTTGTTTTCATAAATATTGCTGTAATAAATACTTT<br>TGGAT (SEQ ID NO: 51) |
| | >NP_033424.1 tumor necrosis factor-inducible gene 6 protein precursor [*Mus musculus*]<br>MVVLLCLCVLLWEEAHGWGFKNGIFHNSIWLEQAAGVYHREARAGRYKLTYAEAKV<br>CEFEGGRLATYKQLEAARKIGFHVCAAGWMAKGRVGYPIVKPGPNCGFGKTGIIDYG<br>IRLNRSERWDAYCYNPHAKECGGVFTDPKRIFKSPGFPNEYDDNQVCYWHIRLKYGQ<br>RIHLSFLDFDLEHDPGCLADYVEIYDSYDDVHGFVGRYCGDELPEDIISTGNVMTLK<br>FLSDASVTAGGFQIKYVTVDPASKSSQAKNTSTTGNKKFLPGRFSHL (SEQ ID NO: 52) |
| Human B7-H3 (CD276) | >NM_001024736.2 *Homo sapiens* CD276 molecule (CD276), transcript variant 1, mRNA<br>ATTCGGGCCGGGCCTCGCTGCGGCGGCGACTGAGCCAGGCTGGGCCGCGTCCCTGAG<br>TCCCAGAGTCGGCGCGGCGCGGCAGGGGCAGCCTTCCACCACGGGGAGCCCAGCTGT<br>CAGCCGCCTCACAGGAAGATGCTGCGTCGGCGGGGCAGCCCTGGCATGGGTGTGCAT<br>GTGGGTGCAGCCCTGGGAGCACTGTGGTTCTGCCTCACAGGAGCCCTGGAGGTCCAG<br>GTCCCTGAAGACCCAGTGGTGGCACTGGTGGGCACCGATGCCACCCTGTGCTGCTCC<br>TTCTCCCCTGAGCCTGGCTTCAGCCTGGCACAGCTCAACCTCATCTGGCAGCTGACA<br>GATACCAAACAGCTGGTGCACAGCTTTGCTGAGGGCCAGGACCAGGGCAGCGCCTAT<br>GCCAACCGCACGGCCCTCTTCCCGGACCTGCTGGCACAGGGCAACGCATCCCTGAGG<br>CTGCAGCGCGTGCGTGTGGCGGACGAGGGCAGCTTCACCTGCTTCGTGAGCATCCGG<br>GATTTCGGCAGCGCTGCCGTCAGCCTGCAGGTGGCCGCTCCCTACTCGAAGCCCAGC<br>ATGACCCTGGAGCCCAACAAGGACCTGCGGCCAGGGGACACGGTGACCATCACGTGC<br>TCCAGCTACCAGGGCTACCCTGAGGCTGAGGTGTTCTGGCAGGATGGGCAGGGTGTG<br>CCCCTGACTGGCAACGTGACCACGTCGCAGATGGCCAACGAGCAGGGCTTGTTTGAT<br>GTGCACAGCATCCTGCGGGTGGTGCTGGGTGCAAATGGCACCTACAGCTGCCTGGTG<br>CGCAACCCCGTGCTGCAGCAGGATGCGCACAGCTCTGTCACCATCACACCCCAGAGA<br>AGCCCCACAGGAGCCGTGGAGGTCCAGGTCCCTGAGGACCCGGTGGTGGCCCTAGTG<br>GGCACCGATGCCACCCTGCGCTGCTCCTTCTCCCCCGAGCCTGGCTTCAGCCTGGCA<br>CAGCTCAACCTCATCTGGCAGCTGACAGACACCAAACAGCTGGTGCACAGTTTCACC<br>GAAGGCCGGGACCAGGGCAGCGCCTATGCCAACCGCACGGCCCTCTTCCCGGACCTG<br>CTGGCACAAGGCAATGCATCCCTGAGGCTGCAGCGCGTGCGTGTGGCGGACGAGGGC<br>AGCTTCACCTGCTTCGTGAGCATCCGGGATTTCGGCAGCGCTGCCGTCAGCCTGCAG<br>GTGGCCGCTCCCTACTCGAAGCCCAGCATGACCCTGGAGCCCAACAAGGACCTGCGG<br>CCAGGGGACACGGTGACCATCACGTGCTCCAGCTACCGGGGCTACCCTGAGGCTGAG<br>GTGTTCTGGCAGGATGGGCAGGGTGTGCCCCTGACTGGCAACGTGACCACGTCGCAG<br>ATGGCCAACGAGCAGGGCTTGTTTGATGTGCACAGCGTCCTGCGGGTGGTGCTGGGT<br>GCGAATGGCACCTACAGCTGCCTGGTGCGCAACCCCGTGCTGCAGCAGGATGCGCAC<br>GGCTCTGTCACCATCACAGGGCAGCCTATGACATTCCCCCCAGAGGCCCTGTGGGTG<br>ACCGTGGGGCTGTCTGTCTGTCTCATTGCACTGCTGGTGGCCCTGGCTTTCGTGTGC<br>TGGAGAAAGATCAAACAGAGCTGTGAGGAGGAGAATGCAGGAGCTGAGGACCAGGAT<br>GGGGAGGGAGAAGGCTCCAAGACAGCCCTGCAGCCTCTGAAACACTCTGACAGCAAA<br>GAAGATGATGGACAAGAAATAGCCTGACCATGAGGACCAGGGAGCTGCTACCCCTCC<br>CTACAGCTCCTACCCTCTGGCTGCAATGGGGCTGCACTGTGAGCCCTGCCCCCAACA<br>GATGCATCCTGCTCTGACAGGTGGGCTCCTTCTCCAAAGGATGCGATACACAGACCA<br>CTGTGCAGCCTTATTTCTCCAATGGACATGATTCCCAAGTCATCCTGCTGCCTTTTT<br>TCTTATAGACACAATGAACAGACCACCCACAACCTTAGTTCTCTAAGTCATCCTGCC<br>TGCTGCCTTATTTCACAGTACATACATTTCTTAGGGACACAGTACACTGACCACATC<br>ACCACCCTCTTCTTCCAGTGCTGCGTGGACCATCTGGCTGCCTTTTTTCTCCAAAAG |

TABLE 1-continued

Type I Proteins of Interest Amino Acid Sequence

| Protein of Interest | Transcript Sequence (SEQ ID NO:)<br>Amino Acid Sequence (SEQ ID NO:) |
|---|---|
| | ATGCAATATTCAGACTGACTGACCCCCTGCCTTATTTCACCAAAGACACGATGCATA<br>GTCACCCCGGCCTTGTTTCTCCAATGGCCGTGATACACTAGTGATCATGTTCAGCCC<br>TGCTTCCACCTGCATAGAATCTTTTCTTCTCAGACAGGGACAGTGCGGCCTCAACAT<br>CTCCTGGAGTCTAGAAGCTGTTTCCTTTCCCCTCCTTCCTCCTCTTGCTCTAGCCTT<br>AATACTGGCCTTTTCCCTCCCTGCCCCAAGTGAAGACAGGGCACTCTGCGCCCACCA<br>CATGCACAGCTGTGCATGGAGACCTGCAGGTGCACGTGCTGGAACACGTGTGGTTCC<br>CCCCTGGCCCAGCCTCCTCTGCAGTGCCCCTCTCCCCTGCCCATCCTCCCCACGGAA<br>GCATGTGCTGGTCACACTGGTTCTCCAGGGGTCTGTGATGGGGCCCCTGGGGGTCAG<br>CTTCTGTCCCTCTGCCTTCTCACCTCTTTGTTCCTTTCTTTTCATGTATCCATTCAG<br>TTGATGTTTATTGAGCAACTACAGATGTCAGCACTGTGTTAGGTGCTGGGGGCCCTG<br>CGTGGGAAGATAAAGTTCCTCCCTCAAGGACTCCCCATCCAGCTGGGAGACAGACAA<br>CTAACTACACTGCACCCTGCGGTTTGCAGGGGGCTCCTGCCTGGCTCCCTGCTCCAC<br>ACCTCCTCTGTGGCTCAAGGCTTCCTGGATACCTCACCCCCATCCCACCCATAATTC<br>TTACCCAGAGCATGGGGTTGGGGCGGAAACCTGGAGAGAGGGACATAGCCCCTCGCC<br>ACGGCTAGAGAATCTGGTGGTGTCCAAAATGTCTGTCCAGGTGTGGGCAGGTGGGCA<br>GGCACCAAGGCCCTCTGGACCTTTCATAGCAGCAGAAAAGGCAGAGCCTGGGGCAGG<br>GCAGGGCCAGGAATGCTTTGGGGACACCGAGGGGACTGCCCCCCACCCCCACCATGG<br>TGCTATTCTGGGGCTGGGGCAGTCTTTTCCTGGCTTGCCTCTGGCCAGCTCCTGGCC<br>TCTGGTAGAGTGAGACTTCAGACGTTCTGATGCCTTCCGGATGTCATCTCTCCCTGC<br>CCCAGGAATGGAAGATGTGAGGACTTCTAATTTAAATGTGGGACTCGGAGGGATTTT<br>GTAAACTGGGGGTATATTTTGGGGAAAATAAATGTCTTTGTAAAAA (SEQ ID<br>NO: 53)<br><br>>NP_001019907.1 CD276 antigen isoform a precursor [*Homo<br>sapiens*]<br>MLRRRGSPGMGVHVGAALGALWFCLTGALEVQVPEDPVVALVGTDATLCCSFSPEPG<br>FSLAQLNLIWQLTDTKQLVHSFAEGQDQGSAYANRTALFPDLLAQGNASLRLQRVRV<br>ADEGSFTCFVSIRDFGSAAVSLQVAAPYSKPSMTLEPNKDLRPGDTVTITCSSYQGY<br>PEAEVFWQDGQGVPLTGNVTTSQMANEQGLFDVHSILRVVLGANGTYSCLVRNPVLQ<br>QDAHSSVTITPQRSPTGAVEVQVPEDPVVALVGTDATLRCSFSPEPGFSLAQLNLIW<br>QLTDTKQLVHSFTEGRDQGSAYANRTALFPDLLAQGNASLRLQRVRVADEGSFTCFV<br>SIRDFGSAAVSLQVAAPYSKPSMTLEPNKDLRPGDTVTITCSSYRGYPEAEVFWQDG<br>QGVPLTGNVTTSQMANEQGLFDVHSVLRVVLGANGTYSCLVRNPVLQQDAHGSVTIT<br>GQPMTFPPEALWVTVGLSVCLIALLVALAFVCWRKIKQSCEEENAGAEDQDGEGEGS<br>KTALQPLKHSDSKEDDGQEIA (SEQ ID NO: 54) |
| Mouse B7-H3 (CD276) | >NM_133983.4 *Mus musculus* CD276 antigen (Cd276), mRNA<br>CGGCGCGGCGCGCCAAAGTGACCTGGTACAGCCTGGACCCCAAGCTCATCGGCTTTG<br>TCTGGCTGGCCGCCTGGCCTCTTCCCACTTGGATTTGGATGATCCTGAGGCCTTTGG<br>AGGAACTTCGAGACAAAGGCCCCTCTTCCTCTTCCACGGGCAGGAGCAGCCATTCGC<br>CACGGAGAGCCCAGCTGTCAGCTGTCTCACAGGAAGATGCTTCGAGGATGGGGTGGC<br>CCCAGTGTGGGTGTGTGTGTGCGCACAGCACTGGGGGTGCTGTGCCTCTGCCTCACA<br>GGAGCTGTGGAAGTCCAGGTCTCTGAAGACCCCGTGGTGGCCCTGGTGGACACGGAT<br>GCCACCCTACGCTGCTCCTTTTCCCCAGAGCCTGGCTTCAGTCTGGCACAGCTCAAC<br>CTCATCTGGCAGCTGACAGACACCAAACAGCTGGTGCACAGCTTCACGGAGGGCCGG<br>GACCAAGGCAGTGCCTACTCCAACCGCACAGCGCTCTTCCCTGACCTGTTGGTGCAA<br>GGCAATGCGTCCTTGAGGCTGCAGCGCGTCCGAGTAACCGACGAGGGCAGCTACACC<br>TGCTTTGTGAGCATCCAGGACTTTGACAGCGCTGCTGTTAGCCTGCAGGTGGCCGCC<br>CCCTACTCGAAGCCCAGCATGACCCTGGAGCCCAACAAGGACCTACGTCCAGGGAAC<br>ATGGTGACCATCACGTGCTCTAGCTACCAGGGCTATCCGGAGGCCGAGGTGTTCTGG<br>AAGGATGGACAGGGAGTGCCCTTGACTGGCAATGTGACCACATCCCAGATGGCCAAC<br>GAGCGGGGCTTGTTCGATGTTCACAGCGTGCTGAGGGTGGTGCTGGGTGCTAACGGC<br>ACCTACAGCTGCCTGGTACGCAACCCGGTGTTGCAGCAAGATGCTCACGGCTCAGTC<br>ACCATCACAGGGCAGCCCCTGACATTCCCCCCTGAGGCTCTGTGGGTAACCGTGGGG<br>CTCTCTGTCTGTCTTGTGGTACTACTGGTGGCCCTGGCTTTCGTGTGCTGGAGAAAG<br>ATCAAGCAGAGCTGCGAGGAGGAGAATGCAGGTGCCGAGGACCAGGATGGAGATGGA<br>GAAGGATCCAAGACAGCTCTACGGCCTCTGAAACCCTCTGAAAACAAAGAAGATGAC<br>GGACAAGAAATTGCTTGATTGGGAGCTGCTGCCCTTCCCAGGTGGGGGGCCCACCCT<br>CTGGCAGTGTTGAGCTTCAATGCGAGCCCTTCCCCCAACGAATGGGTTTGTCCCACA<br>GATCTACCCGTTCGTCAAAGGACGTGGTCCATAGACCACCCACAGCCTTACTTTTCC<br>AATGGACTTAATTCCCATCATCCTGCAGCCTCATTTCTCCAGTGACACGATACACGA<br>ACCATCCTGCGGCCTTATTTCCCACGGACACGACACAAAGATGTCCCTCCTCGGTGT<br>TCCTCCAGAGTCGTCTGGTGGCCTTGTGATACGGCGTGAACCTTCTTCCTTCTGCCT<br>TACGTCTAATGGACACACACGCACCACCCCCACACCCTTGCTCCTCCAAAGCCATGC<br>AGACTGTGTAACTGCTATTATTCTCCAAGGGGCATCCTGTGCAGATGAAACCCTGCT<br>TTATTTCCCTGAAGACAGCTGCACAGTGACCTCTTAGTTCTTGCTCCCATGGCCCTG<br>ATGTATCCTAGTTACCAGCCCTCAACCTCAGTTCTGAGGGTGGGATCCCATCGCTCA<br>GCAAGGCTTCATCCTGACCTCCCTGCCCTGATCTGATCTGGCCCTGGCTTTTGTTGT<br>CTCGCTCCCTGACTAAGTGAGATGGGGCACTCTCCCGCCCCCGCCCCCCCCAGGTCA<br>CAGATACCTACCTGCAGCTGTGCGTGCTGGATCACGCACATACTTGCCTTGCATGGT<br>CTCCTGGCTGCCCTGGGCTGTGCCTGTTCTTCCATAGGAAGCAAGTTCTTGTCTCCC<br>TGGTTCTCAGGGCCCCTCAGGGGCTCAGCCTTCAGCCCTGTGCTTCCCCATGTTGGG<br>AATCTTTGTTACCTTTTTCTTCTTTGTAAATTAACATCTGATAACAACCACAGGGTC<br>CAATGGGACTTTCACAGACCTGCCAGCTAGATAAATAATGACAACAGAAGTTTATTA<br>ATATTTTAAGACTTAGGCCTTTTGCTGGGCAGCCTCCCAACTATTCTATCCTGACTA |

TABLE 1-continued

Type I Proteins of Interest Amino Acid Sequence

| Protein of Interest | Transcript Sequence (SEQ ID NO:)<br>Amino Acid Sequence (SEQ ID NO:) |
|---|---|
| | ATCCTGGCACTATGTCCCACCACATGGCCAGGTCTACCTCTCTGCTCCACTCTCCAT<br>CCACCTCCATGTCTGCCAGCAAATCTCCCGTGATTCAGTTCTTCTCCCAGAGTCCCT<br>ATCTCTGCCCAGAAGTACCATCTTCGACTTCCTGCCCAACTATTGGCCGTCAGCTCT<br>TCATTAAAGCCGATCAGATGTAATTCTAGATTGCCTTAGGCAGGTGAGGAAGAAACA<br>AGTATTTGTAAAATATGAGACCAGCAATGGGCCATAGAAATAACAGCACCAGATCCT<br>GCCAGCATTTAGCCCTCTGTTGGTACAAAATTAACAATTGAATATACAGAGACCTAC<br>TTCCAGAGTGTACCCCAACAACAGGCGTGAGCATGGTGCTGGGTACTAGGGTCCTGC<br>TGGAAAATCAGAGACCTTACCTACAGCTGGGACATGACCTTGCTTCCGACTTACCCA<br>CCACTTCTGGATACCTCACCCTCAGCCCACACTATCCCTGGCCTAGGGCCCAGGGTA<br>GAGCCAGAAACATGGAGAAAGCATGGCCCCTTGCCGTACCTGGAGAACTGGGTATTT<br>TCCAGAGTCTTTATAGATGTGGACTGGAAGGCAGGTGGCCACAGCCGTGCAGACCTG<br>GGTCAGGTCAGAAACCTATGCCATGCTGGGACCTACTCAACAGCAGAAGCATGAAGA<br>GGGCCTGAGGACAAGAAAGGCCTTCTTACCATGGTGCTATTCTGGAGCTGGGATATA<br>TACCTGGCTTGTCTCTGACTGCCCTGGCTTCTGGCAGAACTTCTGATGTCCTCCTGA<br>AGGCCTCTCTCCCACCCCAGTACCTGAGAACCTGAGGATAATTTAAACATGGGACTC<br>TGGCCAGCACCTGGGAGAGACAGGTAGATCTCTGATTTTTGACTCAGCCTGGTCTAT<br>CGAGTGAGTTCCAGGACATCTGGGGCTACACAGAGAAACCATCTTAAAGACTAAAAA<br>TAATAAACATGAGACTGTAAACTGGGTGTATTTTGGGAGAAATAAATGTCTTTTTCT<br>TTCAA (SEQ ID NO: 55) |
| | >NP_598744.1 CD276 antigen precursor [*Mus musculus*]<br>MLRGWGGPSVGVCVRTALGVLCLCLTGAVEVQVSEDPVVALVDTDATLRCSFSPEPG<br>FSLAQLNLIWQLTDTKQLVHSFTEGRDQGSAYSNRTALFPDLLVQGNASLRLQRVRV<br>TDEGSYTCFVSIQDFDSAAVSLQVAAPYSKPSMTLEPNKDLRPGNMVTITCSSYQGY<br>PEAEVFWKDGQGVPLTGNVTTSQMANERGLFDVHSVLRVVLGANGTYSCLVRNPVLQ<br>QDAHGSVTITGQPLTFPPEALWVTVGLSVCLVVLLVALAFVCWRKIKQSCEEENAGA<br>EDQDGDGEGSKTALRPLKPSENKEDDGQEIA (SEQ ID NO: 56) |
| Human B7-H4 (VTCN1) | >NM_024626.4 *Homo sapiens* V-set domain containing T cell activation inhibitor 1 (VTCN1), transcript variant 1, mRNA<br>GTGAGTCACCAAGGAAGGCAGCGGCAGCTCCACTCAGCCAGTACCCAGATACGCTGG<br>GAACCTTCCCCAGCCATGGCTTCCCTGGGGCAGATCCTCTTCTGGAGCATAATTAGC<br>ATCATCATTATTCTGGCTGGAGCAATTGCACTCATCATTGGCTTTGGTATTTCAGGG<br>AGACACTCCATCACAGTCACTACTGTCGCCTCAGCTGGGAACATTGGGGAGGATGGA<br>ATCCTGAGCTGCACTTTTGAACCTGACATCAAACTTTCTGATATCGTGATACAATGG<br>CTGAAGGAAGGTGTTTTAGGCTTGGTCCATGAGTTCAAAGAAGGCAAAGATGAGCTG<br>TCGGAGCAGGATGAAATGTTCAGAGGCCGGACAGCAGTGTTTGCTGATCAAGTGATA<br>GTTGGCAATGCCTCTTTGCGGCTGAAAAACGTGCAACTCACAGATGCTGGCACCTAC<br>AAATGTTATATCATCACTTCTAAAGGCAAGGGGAATGCTAACCTTGAGTATAAAACT<br>GGAGCCTTCAGCATGCCGGAAGTGAATGTGGACTATAATGCCAGCTCAGAGACCTTG<br>CGGTGTGAGGCTCCCCGATGGTTCCCCCAGCCCACAGTGGTCTGGGCATCCCAAGTT<br>GACCAGGGAGCCAACTTCTCGGAAGTCTCCAATACCAGCTTTGAGCTGAACTCTGAG<br>AATGTGACCATGAAGGTTGTGTCTGTGCTCTACAATGTTACGATCAACAACACATAC<br>TCCTGTATGATTGAAAATGACATTGCCAAAGCAACAGGGGATATCAAAGTGACAGAA<br>TCGGAGATCAAAAGGCGGAGTCACCTACAGCTGCTAAACTCAAAGGCTTCTCTGTGT<br>GTCTCTTCTTTCTTTGCCATCAGCTGGGCACTTCTGCCTCTCAGCCCTTACCTGATG<br>CTAAAATAATGTGCCTCGGCCACAAAAAAGCATGCAAAGTCATTGTTACAACAGGGA<br>TCTACAGAACTATTTCACCACCAGATATGACCTAGTTTTATATTTCTGGGAGGAAAT<br>GAATTCATATCTAGAAGTCTGGAGTGAGCAAACAAGAGCAAGAAACAAAAAGAAGCC<br>AAAAGCAGAAGGCTCCAATATGAACAAGATAAATCTATCTTCAAAGACATATTAGAA<br>GTTGGGAAAATAATTCATGTGAACTAGACAAGTGTGTTAAGAGTGATAAGTAAAATG<br>CACGTGGAGACAAGTGCATCCCCAGATCTCAGGGACCTCCCCCTGCCTGTCACCTGG<br>GGAGTGAGAGGACAGGATAGTGCATGTTCTTTGTCTCTGAATTTTTAGTTATATGTG<br>CTGTAATGTTGCTCTGAGGAAGCCCCTGGAAAGTCTATCCCAACATATCCACATCTT<br>ATATTCCACAAATTAAGCTGTAGTATGTACCCTAAGACGCTGCTAATTGACTGCCAC<br>TTCGCAACTCAGGGGCGGCTGCATTTTAGTAATGGGTCAAATGATTCACTTTTTATG<br>ATGCTTCCAAAGGTGCCTTGGCTTCTCTTCCCAACTGACAAATGCCAAAGTTGAGAA<br>AAATGATCATAATTTTAGCATAAACAGAGCAGTCGGCGACACCGATTTTATAAATAA<br>ACTGAGCACCTTCTTTTTAAACAAACAAATGCGGGTTTATTTCTCAGATGATGTTCA<br>TCCGTGAATGGTCCAGGGAAGGACCTTTCACCTTGTCTATATGGCATTATGTCATCA<br>CAAGCTCTGAGGCTTCTCCTTTCCATCCTGCGTGGACAGCTAAGACCTCAGTTTTCA<br>ATAGCATCTAGAGCAGTGGGACTCAGCTGGGGTGATTTCGCCCCCCATCTCCGGGGG<br>AATGTCTGAAGACAATTTTGGTTACCTCAATGAGGGAGTGGAGGAGGATACAGTGCT<br>ACTACCAACTAGTGGATAGAGGCCAGGGATGCTGCTCAACCTCCTACCATGTACAGG<br>ACGTCTCCCCATTACAACTACCCAATCCGAAGTGTCAACTGTGTCAGGGCTAAGAAA<br>CCCTGGTTTTGAGTAGAAAAGGGCCTGGAAAGAGGGGAGCCAACAAATCTGTCTGCT<br>TCCTCACATTAGTCATTGGCAAATAAGCATTCTGTCTCTTTGGCTGCTGCCTCAGCA<br>CAGAGAGCCAGAACTCTATCGGGCACCAGGATAACATCTCTCAGTGAACAGAGTTGA<br>CAAGGCCTATGGGAAATGCCTGATGGGATTATCTTCAGCTTGTTGAGCTTCTAAGTT<br>TCTTTCCCTTCATTCTACCCTGCAAGCCAAGTTCTGTAAGAGAAATGCCTGAGTTCT<br>AGCTCAGGTTTTCTTACTCTGAATTTAGATCTCCAGACCCTGCCTGGCCACAATTCA<br>AATTAAGGCAACAAACATATACCTTCCATGAAGCACACACAGACTTTTGAAAGCAAG<br>GACAATGACTGCTTGAATTGAGGCCTTGAGGAATGAAGCTTTGAAGGAAAAGAATAC<br>TTTGTTTCCAGCCCCCTTCCCACACTCTTCATGTGTTAACCACTGCCTTCCTGGACC |

TABLE 1-continued

Type I Proteins of Interest Amino Acid Sequence

| Protein of Interest | Transcript Sequence (SEQ ID NO:)<br>Amino Acid Sequence (SEQ ID NO:) |
|---|---|
| | TTGGAGCCACGGTGACTGTATTACATGTTGTTATAGAAAACTGATTTTAGAGTTCTG<br>ATCGTTCAAGAGAATGATTAAATATACATTTCCTACACCA (SEQ ID NO: 57)<br><br>>NP_078902.2 V-set domain-containing T-cell activation inhibitor 1 isoform 1 precursor [*Homo sapiens*]<br>MASLGQILFWSIISIIIILAGAIALIIGFGISGRHSITVTTVASAGNIGEDGILSCT<br>FEPDIKLSDIVIQWLKEGVLGLVHEFKEGKDELSEQDEMFRGRTAVFADQVIVGNAS<br>LRLKNVQLTDAGTYKCYIITSKGKGNANLEYKTGAFSMPEVNVDYNASSETLRCEAP<br>RWFPQPTVVWASQVDQGANFSEVSNTSFELNSENVTMKVVSVLYNVTINNTYSCMIE<br>NDIAKATGDIKVTESEIKRRSHLQLLNSKASLCVSSFFAISWALLPLSPYLMLK<br>(SEQ ID NO: 58) |
| Mouse B7-H4 (VTCN1) | >NM_178594.3 *Mus musculus* V-set domain containing T cell activation inhibitor 1 (Vtcn1), mRNA<br>GTGAGTCACAACACCCAGGAGGGCAGCAGCAGGCAGGCAGCTCCACTCACCAAAATC<br>TGGCCCCACACACAGCAGGACTGTGGGAAGGAACTCCCTCTCCATGGCTTCCTTGGG<br>GCAGATCATCTTTTGGAGTATTATTAACATCATCATCATCCTGGCTGGGGCCATCGC<br>ACTCATCATTGGCTTTGGCATTTCAGGCAAGCACTTCATCACGGTCACGACCTTCAC<br>CTCAGCTGGAAACATTGGAGAGGACGGGACCCTGAGCTGCACTTTTGAACCTGACAT<br>CAAACTCAACGGCATCGTCATCCAGTGGCTGAAAGAAGGCATCAAAGGTTTGGTCCA<br>CGAGTTCAAAGAAGGCAAAGACGACCTCTCACAGCAGCATGAGATGTTCAGAGGCCG<br>CACAGCAGTGTTTGCTGATCAGGTGGTAGTTGGCAATGCTTCCCTGAGACTGAAAAA<br>CGTGCAGCTCACGGATGCTGGCACCTACACATGTTACATCCGCACCTCAAAAGGCAA<br>AGGGAATGCAAACCTTGAGTATAAGACCGGAGCCTTCAGTATGCCAGAGATAAATGT<br>GGACTATAATGCCAGTTCAGAGAGTTTACGCTGCGAGGCTCCTCGGTGGTTCCCCCA<br>GCCCACAGTGGCCTGGGCATCTCAAGTCGACCAAGGAGCCAATTTCTCAGAAGTCTC<br>CAACACCAGCTTTGAGTTGAACTCTGAGAATGTGACCATGAAGGTCGTATCTGTGCT<br>CTACAATGTCACAATCAACAACACATACTCCTGTATGATTGAAAACGACATTGCCAA<br>AGCCACCGGGGACATCAAAGTGACAGATTCAGAGGTCAAAAGGCGAAGTCAGCTGCA<br>GTTGCTGAACTCTGGGCCTTCCCCGTGTGTTTTTTCTTCTGCCTTTGTGGCTGGCTG<br>GGCACTCCTATCTCTCTCCTGTTGCCTGATGCTAAGATGAGGGGCCCTGGCTACACA<br>AAAGCATGCAACGTTGCTGGTCCAACAGAATCCCGGAGAACTACAGAAATATTTTCC<br>TCAAGACATGACCTAGTTTTATATTTCTAGAAGAAGATGAAATCATGTCTAGAAGTC<br>TGGAGAGAGCAGACAGGAACAAGATGTGGAAGGAAAACAAAAGTAACCCACAGACAC<br>CCCCGATCGGAACAAGATGGACCTAGAAAATAATTCAACCAAACTAGAGTATACTAA<br>GTGTGCTGTTACAATGTGTGTAGGGTAGGTGTCCTCCCACATCTCAGGGGCCTCCCC<br>TGGTCCACCAGCTCCTGAGTTAGGATGGGCTGTTATGATGTCACTCTGAAGGTTCCT<br>GGATGGTTCCTACTGCCATATACTCATTTTATATTCAGCACATTAAACCATAGTGAA<br>TGCTATGAAAAGCTGCTAATCAGCTGCCACTCCGAGATTCGGAGGTGGCAACGTCTG<br>AGTGACAGGTCCAGTGATTCGCTTCTCCTTAGGATGCTTTTACAAGCTCTTTGGCGT<br>CTCCTCCCACCTGGCAAATGCCAAATGCATAGGGGAGGGTGATCATCATTCTAGGGC<br>AAACAAAATAGTTGAGGGATGCTGATTTCCCAAATCATCCGAATCACTTCTCCCTTG<br>AGCAAACAAGCGCCCTGTTATTTCTCAAATGCTGCTTTGTGAATCAGTCCAGGGCAA<br>GGCGCTCTCCTCATCCCGCTATGTGGCCTTAAGTCATCGTAAGGTTTGAAGTTTCTA<br>CTTTCGATCCTGCATGGAGAGCTATAATCTCAGCTCCCCCGCCCCCCCCACACACAC<br>CTCTGCACACACACCCCCCCCCAACACTGGGAGTAAACCAGGATGATGTCCGTCTTC<br>TCATTCCCCATGTGACCGTTGGCAGTGTAGAGAGACTGATTGTCACAGCTAAAGGAA<br>GAGGGACAACAGGGTCACTGGTGTCTACAGAGATTATATTCTACGTGTCTCACTGAA<br>TTTACACAACTCCAAGTGCCAACCACATCAAGGTCAGGAAATCCTGAACTGGAATAA<br>GAAAGACCCAGAAGATGAATGTGAACAGATCCATTTGCTTCCCGACAGTGGGCACAG<br>ACTTCAGTCTCTGGCTACTGTTCCAAGACCCAGGGCTCTGCAATTGTGTGACATCCT<br>TCAGTGAACCCACATGGGAAATTCTCCATGGAATTATCTTCAGCCCACTGTACTTCT<br>GAATCCCTCTTCCTTCCTTCTGTGCCACACAGCAAGTCTGGCTTAAATGCTGCCTGA<br>TCTCCATTTCAAGTTTTCTGCCTCTGGATTTTTAGATCTCAAGACCATGGACGAAAC<br>ATCAGTTACAGCAACAAAAGTGAATTTTCCGTGCAGAGACTTCTAGGGGTTCTGTTT<br>GTTTTCAGGGTGCTAGAGATCACACTCAGATGCTCATATATGTTAGGTAAATGTTCT<br>CCCACTGAGTTACAGCCCAGCTCACACAGAGACTTCTAAAAGAAAATACGGCCATGC<br>TCTTTGAAATGGAGCATTGAGGGATGAAGTTTGGATGGCGAAGAAAACTTCTCACCA<br>GCTCTCTCCCCACATTCGTGCCAAGCACTGCCTCCCTAGACTTCGGGTCACCATATC<br>TGTACTACGTTTTGATACAGAAGGCTCGAGACCATTCAAGAGAATTATTTAGTACAC<br>(SEQ ID NO: 59)<br><br>>NP_848709.2 V-set domain containing T-cell activation inhibitor 1 precursor [*Mus musculus*]<br>MASLGQIIFWSIINIIIILAGAIALIIGFGISGKHFITVTTFTSAGNIGEDGTLSCT<br>FEPDIKLNGIVIQWLKEGIKGLVHEFKEGKDDLSQQHEMFRGRTAVFADQVVVGNAS<br>LRLKNVQLTDAGTYTCYIRTSKGKGNANLEYKTGAFSMPEINVDYNASSESLRCEAP<br>RWFPQPTVAWASQVDQGANFSEVSNTSFELNSENVTMKVVSVLYNVTINNTYSCMIE<br>NDIAKATGDIKVTDSEVKRRSQLQLLNSGPSPCVFSSAFVAGWALLSLSCCLMLR<br>(SEQ ID NO: 60) |
| Human B7-H5 (VISTA) | >NM_022153.2 *Homo sapiens* V-set immunoregulatory receptor (VSIR), mRNA<br>AGTCGCGGGAGGCTTCCCCGCGCCGGCCGCGTCCCGCCCGCTCCCCGGCACCAGAAG<br>TTCCTCTGCGCGTCCGACGGCGACATGGGCGTCCCCACGGCCCTGGAGGCCGGCAGC |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| | TGGCGCTGGGGATCCCTGCTCTTCGCTCTCTTCCTGGCTGCGTCCCTAGGTCCGGTG<br>GCAGCCTTCAAGGTCGCCACGCCGTATTCCCTGTATGTCTGTCCCGAGGGGCAGAAC<br>GTCACCCTCACCTGCAGGCTCTTGGGCCCTGTGGACAAAGGGCACGATGTGACCTTC<br>TACAAGACGTGGTACCGCAGCTCGAGGGGCGAGGTGCAGACCTGCTCAGAGCGCCGG<br>CCCATCCGCAACCTCACGTTCCAGGACCTTCACCTGCACCATGGAGGCCACCAGGCT<br>GCCAACACCAGCCACGACCTGGCTCAGCGCCACGGGCTGGAGTCGGCCTCCGACCAC<br>CATGGCAACTTCTCCATCACCATGCGCAACCTGACCCTGCTGGATAGCGGCCTCTAC<br>TGCTGCCTGGTGGTGGAGATCAGGCACCACCACTCGGAGCACAGGGTCCATGGTGCC<br>ATGGAGCTGCAGGTGCAGACAGGCAAAGATGCACCATCCAACTGTGTGGTGTACCCA<br>TCCTCCTCCCAGGATAGTGAAAACATCACGGCTGCAGCCCTGGCTACGGGTGCCTGC<br>ATCGTAGGAATCCTCTGCCTCCCCCTCATCCTGCTCCTGGTCTACAAGCAAAGGCAG<br>GCAGCCTCCAACCGCCGTGCCCAGGAGCTGGTGCGGATGGACAGCAACATTCAAGGG<br>ATTGAAAACCCCGGCTTTGAAGCCTCACCACCTGCCCAGGGGATACCCGAGGCCAAA<br>GTCAGGCACCCCCTGTCCTATGTGGCCCAGCGGCAGCCTTCTGAGTCTGGGCGGCAT<br>CTGCTTTCGGAGCCCAGCACCCCCCTGTCTCCTCCAGGCCCCGGAGACGTCTTCTTC<br>CCATCCCTGGACCCTGTCCCTGACTCTCCAAACTTTGAGGTCATCTAGCCCAGCTGG<br>GGGACAGTGGGCTGTTGTGGCTGGGTCTGGGGCAGGTGCATTTGAGCCAGGGCTGGC<br>TCTGTGAGTGGCCTCCTTGGCCTCGGCCCTGGTTCCCTCCCTCCTGCTCTGGGCTCA<br>GATACTGTGACATCCCAGAAGCCCAGCCCCTCAACCCCTCTGGATGCTACATGGGGA<br>TGCTGGACGGCTCAGCCCCTGTTCCAAGGATTTTGGGGTGCTGAGATTCTCCCCTAG<br>AGACCTGAAATTCACCAGCTACAGATGCCAAATGACTTACATCTTAAGAAGTCTCAG<br>AACGTCCAGCCCTTCAGCAGCTCTCGTTCTGAGACATGAGCCTTGGGATGTGGCAGC<br>ATCAGTGGGACAAGATGGACACTGGGCCACCCTCCCAGGCACCAGACACAGGGCACG<br>GTGGAGAGACTTCTCCCCCGTGGCCGCCTTGGCTCCCCCGTTTTGCCCGAGGCTGCT<br>CTTCTGTCAGACTTCCTCTTTGTACCACAGTGGCTCTGGGGCCAGGCCTGCCTGCCC<br>ACTGGCCATCGCCACCTTCCCCAGCTGCCTCCTACCAGCAGTTTCTCTGAAGATCTG<br>TCAACAGGTTAAGTCAATCTGGGGCTTCCACTGCCTGCATTCCAGTCCCCAGAGCTT<br>GGTGGTCCCGAAACGGGAAGTACATATTGGGGCATGGTGGCCTCCGTGAGCAAATGG<br>TGTCTTGGGCAATCTGAGGCCAGGACAGATGTTGCCCCACCCACTGGAGATGGTGCT<br>GAGGGAGGTGGGTGGGGCCTTCTGGGAAGGTGAGTGGAGAGGGGCACCTGCCCCCCG<br>CCCTCCCCATCCCCTACTCCCACTGCTCAGCGCGGGCCATTGCAAGGGTGCCACACA<br>ATGTCTTGTCCACCCTGGGACACTTCTGAGTATGAAGCGGGATGCTATTAAAAACTA<br>CATGGGGAAACAGGTGCAAACCCTGGAGATGGATTGTAAGAGCCAGTTTAAATCTGC<br>ACTCTGCTGCTCCTCCCCCACCCCCACCTTCCACTCCATACAATCTGGGCCTGGTGG<br>AGTCTTCGCTTCAGAGCCATTCGGCCAGGTGCGGGTGATGTTCCCATCTCCTGCTTG<br>TGGGCATGCCCTGGCTTTGTTTTTATACACATAGGCAAGGTGAGTCCTCTGTGGAAT<br>TGTGATTGAAGGATTTTAAAGCAGGGGAGGAGAGTAGGGGGCATCTCTGTACACTCT<br>GGGGGTAAAACAGGGAAGGCAGTGCCTGAGCATGGGGACAGGTGAGGTGGGGCTGGG<br>CAGACCCCCTGTAGCGTTTAGCAGGATGGGGGCCCCAGGTACTGTGGAGAGCATAGT<br>CCAGCCTGGGCATTTGTCTCCTAGCAGCCTACACTGGCTCTGCTGAGCTGGGCCTGG<br>GTGCTGAAAGCCAGGATTTGGGGCTAGGCGGGAAGATGTTCGCCCAATTGCTTGGGG<br>GGTTGGGGGGATGGAAAAGGGGAGCACCTCTAGGCTGCCTGGCAGCAGTGAGCCCTG<br>GGCCTGTGGCTACAGCCAGGGAACCCCACCTGGACACATGGCCCTGCTTCTAAGCCC<br>CCCAGTTAGGCCCAAAGGAATGGTCCACTGAGGGCCTCCTGCTCTGCCTGGGCTGGG<br>CCAGGGGCTTTGAGGAGAGGGTAAACATAGGCCCGGAGATGGGGCTGACACCTCGAG<br>TGGCCAGAATATGCCCAAACCCCGGCTTCTCCCTTGTCCCTAGGCAGAGGGGGGTCC<br>CTTCTTTTGTTCCCTCTGGTCACCACAATGCTTGATGCCAGCTGCCATAGGAAGAGG<br>GTGCTGGCTGGCCATGGTGGCACACACCTGTCCTCCCAGCACTTTGCAGGGCTGAGG<br>TGGAAGGACCGCTTAAGCCCAGGTGTTCAAGGCTGCTGTGAGCTGTGTTCGAGCCAC<br>TACACTCCAGCCTGGGGACGGAGCAAAACTTTGCCTCAAAACAAATTTTAAAAAGAA<br>AGAAAGAAGGAAAGAGGGTATGTTTTTCACAATTCATGGGGGCCTGCATGGCAGGAG<br>TGGGGACAGGACACCTGCTGTTCCTGGAGTCGAAGGACAAGCCCACAGCCCAGATTC<br>CGGTTCTCCCAACTCAGGAAGAGCATGCCCTGCCCTCTGGGGAGGCTGGCCTGGCCC<br>CAGCCCTCAGCTGCTGACCTTGAGGCAGAGACAACTTCTAAGAATTTGGCTGCCAGA<br>CCCCAGGCCTGGCTGCTGCTGTGTGGAGAGGGAGGCGGCCCGCAGCAGAACAGCCAC<br>CGCACTTCCTCCTCAGCTTCCTCTGGTGCGGCCCTGCCCTCTCTTCTCTGGACCCTT<br>TTACAACTGAACGCATCTGGGCTTCGTGGTTTCCTGTTTTCAGCGAAATTTACTCTG<br>AGCTCCCAGTTCCATCTTCATCCATGGCCACAGGCCCTGCCTACAACGCACTAGGGA<br>CGTCCCTCCCTGCTGCTGCTGGGGAGGGGCAGGCTGCTGGAGCCGCCCTCTGAGTTG<br>CCCGGGATGGTAGTGCCTCTGATGCCAGCCCTGGTGGCTGTGGGCTGGGGTGCATGG<br>GAGAGCTGGGTGCGAGAACATGGCGCCTCCAGGGGGCGGGAGGAGCACTAGGGGCTG<br>GGGCAGGAGGCTCCTGGAGCGCTGGATTCGTGGCACAGTCTGAGGCCCTGAGAGGGA<br>AATCCATGCTTTTAAGAACTAATTCATTGTTAGGAGATCAATCAGGAATTAGGGGCC<br>ATCTTACCTATCTCCTGACATTCACAGTTTAATAGAGACTTCCTGCCTTTATTCCCT<br>CCCAGGGAGAGGCTGAAGGAATGGAATTGAAAGCACCATTTGGAGGGTTTTGCTGAC<br>ACAGCGGGGACTGCTCAGCACTCCCTAAAAACACACCATGGAGGCCACTGGTGACTG<br>CTGGTGGGCAGGCTGGCCCTGCCTGGGGGAGTCCGTGGCGATGGGCGCTGGGGTGGA<br>GGTGCAGGAGCCCCAGGACCTGCTTTTCAAAAGACTTCTGCCTGACCAGAGCTCCCA<br>CTACATGCAGTGGCCCAGGGCAGAGGGGCTGATACATGGCCTTTTTCAGGGGGTGCT<br>CCTCGCGGGGTGGACTTGGGAGTGTGCAGTGGGACAGGGGGCTGCAGGGGTCCTGCC<br>ACCACCGAGCACCAACTTGGCCCCTGGGGTCCTGCCTCATGAATGAGGCCTTCCCCA<br>GGGCTGGCCTGACTGTGCTGGGGGCTGGGTTAACGTTTTCTCAGGGAACCACAATGC<br>ACGAAAGAGGAACTGGGGTTGCTAACCAGGATGCTGGGAACAAAGGCCTCTTGAAGC<br>CCAGCCACAGCCCAGCTGAGCATGAGGCCCAGCCCATAGACGGCACAGGCCACCTGG<br>CCCATTCCCTGGGCATTCCCTGCTTTGCATTGCTGCTTCTCTTCACCCCATGGAGGC |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| | TATGTCACCCTAACTATCCTGGAATGTGTTGAGAGGGATTCTGAATGATCAATATAG<br>CTTGGTGAGACAGTGCCGAGATAGATAGCCATGTCTGCCTTGGGCACGGGAGAGGGA<br>AGTGGCAGCATGCATGCTGTTTCTTGGCCTTTTCTGTTAGAATACTTGGTGCTTTCC<br>AACACACTTTCACATGTGTTGTAACTTGTTTGATCCACCCCCTTCCCTGAAAATCCT<br>GGGAGGTTTTATTGCTGCCATTTAACACAGAGGGCAATAGAGGTTCTGAAAGGTCTG<br>TGTCTTGTCAAAACAAGTAAACGGTGGAACTACGACTAAA (SEQ ID NO: 61) |
| | >NP_071436.1 V-type immunoglobulin domain-containing suppressor of T-cell activation precursor [*Homo sapiens*]<br>MGVPTALEAGSWRWGSLLFALFLAASLGPVAAFKVATPYSLYVCPEGQNVTLTCRLL<br>GPVDKGHDVTFYKTWYRSSRGEVQTCSERRPIRNLTFQDLHLHHGGHQAANTSHDLA<br>QRHGLESASDHHGNFSITMRNLTLLDSGLYCCLVVEIRHHHSEHRVHGAMELQVQTG<br>KDAPSNCVVYPSSSQDSENITAAALATGACIVGILCLPLILLLVYKQRQAASNRRAQ<br>ELVRMDSNIQGIENPGFEASPPAQGIPEAKVRHPLSYVAQRQPSESGRHLLSEPSTP<br>LSPPGPGDVFFPSLDPVPDSPNFEVI (SEQ ID NO: 62) |
| Mouse B7-H5 (VISTA) | >NM_028732.4 *Mus musculus* V-set immunoregulatory receptor (Vsir), transcript variant 1, mRNA<br>GGGGGCGCTGCTGGGCGGGGAGCTTGCTCGGCCGCCTGCCTCGCCTTGGGCTCAGCA<br>TTCACTCTAGCGAGCGAGCGGCGTGTACAGCCGGCTCCCTGGGCTCCTGGAGTCCCG<br>CTTGCTCCAAGCGCACTCCAGCAGTCTCTTTCTGCTCTTGCCCGGCTCGACGGCGAC<br>ATGGGTGTCCCCGCGGTCCCAGAGGCCAGCAGCCCGCGCTGGGGAACCCTGCTCCTT<br>GCTATTTTCCTGGCTGCATCCAGAGGTCTGGTAGCAGCCTTCAAGGTCACCACTCCA<br>TATTCTCTCTATGTGTGTCCCGAGGGACAGAATGCCACCCTCACCTGCAGGATTCTG<br>GGCCCCGTGTCCAAAGGGCACGATGTGACCATCTACAAGACGTGGTACCTCAGCTCA<br>CGAGGCGAGGTCCAGATGTGCAAAGAACACCGGCCCATACGCAACTTCACATTGCAG<br>CACCTTCAGCACCACGGAAGCCACCTGAAAGCCAACGCCAGCCATGACCAGCCCCAG<br>AAGCATGGGCTAGAGCTAGCTTCTGACCACCACGGTAACTTCTCTATCACCCTGCGC<br>AATGTGACCCCAAGGGACAGCGGCCTCTACTGCTGTCTAGTGATAGAATTAAAAAAC<br>CACCACCCAGAACAACGGTTCTACGGGTCCATGGAGCTACAGGTACAGGCAGGCAAA<br>GGCTCGGGGTCCACATGCATGGCGTCTAATGAGCAGGACAGTGACAGCATCACGGCT<br>GCGGCCCTGGCCACCGGCGCCTGCATCGTGGGAATCCTCTGCCTCCCCCTTATCCTG<br>CTGCTGGTCTATAAGCAGAGACAGGTGGCCTCTCACCGCCGTGCCCAGGAGTTGGTG<br>AGGATGGACAGCAGCAACACCCAAGGAATCGAAAACCCAGGCTTCGAGACCACTCCA<br>CCCTTCCAGGGGATGCCTGAGGCCAAGACCAGGCCGCCACTGTCCTATGTGGCCCAG<br>CGGCAACCTTCGGAGTCAGGACGGTACCTGCTCTCTGACCCCAGCACACCTCTGTCG<br>CCTCCAGGCCCTGGGGACGTCTTTTTCCCATCCCTAGATCCAGTCCCTGACTCCCCT<br>AACTCTGAAGCCATCTAAACCAGCTGGGGAACCATGAACCATGGTACCTGGGTCAGG<br>GATATGTGCACTTGATCTATGGCTGGCCCTTGGACAGTCTTTTAGGCACTGACTCCA<br>GCTTCCTTGCTCCTGCTCTGAGCCTAGACTCTGCTTTTACAAGATGCACAGACCCTC<br>CCCTATCTCTTTCAGACGCTACTTGGGGGGCAGGGAGAAGATGTTGGATTGCTCATT<br>GCTGTTCTCAAGATCTTGGGATGCTGAGTTCTCCCTAGAGACTTGACTTCGACAGCC<br>ACAGATGTCAGATGACCTGCATCCTATGAACGTCCGGCTTGGCAAGAGCCTTTCTTC<br>ATGGAAACCAGTAGCCCGGAGGGGATGAGGTAGGCACCTTGCCACCCTCCCGGGAGA<br>GAGACACAAGATGTGAGAGACTCCTGCTCACTGTGGGGGTGTGGCTGGCCTGCTTGT<br>TTGCCTGAGGATGCTCCTCTGTTGGACTGACTCTATCCCCCTGGATTCTGGAGCTTG<br>GCTGGCCTATGTCCCACCAGAGGAGCATCTCAGCAGCCTTCCACCAGCAACCTGAGG<br>GCCTGCCAGCTTCGTGGCTCTGGGCTCTCATTACCTGTATGGCCGTCCACAGAGCTC<br>AGTGGCCAGAGGCTTTGAAACAGGAAGTACATGTCAGGTTCAGGAACCACTGTGAGC<br>TCATTAGTGTCTTGAGCAATGTGAGGCCTGGACCAGTGGACACGGAGGGAGGGTGGC<br>GAGAGGATGATGGGGATGATGAGGGGAACACGCTCCCTTCCTGTCCTTGTCATCCAC<br>CACTACCACTATTCAGTGTGGAGCAGTGGCAAAGGTGACCGACCTCCACAATGTCCT<br>AGTGATGCTGGACCATTTCTAAGTGTGAAAGAGATGCTATTAAAAACAGTATGTGGC<br>AATGGCTGCCAACAGCTGAGTGGACTGGAGGCACTGGCTTTAAGGCCCTGGAGGTGC<br>AGGGCCCGGTATGGGGATAGGGATGGGAGTTTCAGTGAGGGCCTAGGGATCACTCCG<br>CTTCTGACCACTCTTCTTCTGAGCCTCACCTCAGGGTGACCTTCAGGCACACAGAAG<br>AGCTTGCCCCTGGTCCGATACTACTCTTGGCTCTCATCTCCAGGGTTTGGCATGACC<br>TGGGCACACAGGGGGAGTCTTCAGAAAGGATTTTAAAGCATGAAAAGAAAGGGTAGT<br>TCTTGTGAGGTAGGGATGGGCAGCTGATGTTTGAGAGTGAGGAGGGATACGGCTGGG<br>CAGATCACTCTCCAGTCTCTAGAGGGAAAGTAGCTCTAAGTCTGGGAGAGCAGCAGC<br>CCAGTGGTACCATATGTCTTCTTGCAGCTTCCACTGGCTGGGCTGAACTGGGCATGG<br>GTAGGAAAGCTCCTGTTOTGGGCCTGCAGCCAGGGAGAACCCCATTCATTCCCTGAG<br>GACAGATGGGTGGGGAGAGAAGAGAGAGTTTCAGGCCGGGAAGCAGCAATAAGCTAT<br>CTGCTGGGGACCCAGACAAGTTGTCTGATGAGGTCCAAGATGTGGGATGCCAGTTAT<br>ACCTGGGGCTTGGGGATCCTTAGAGGCTTTGTATCATCATCATAGGAGTGTCGGGGT<br>GGCCAGGGCATCAAAGCCATGACCCCTGTTTTATCCTCAGGGTCCACTCTTCTGCAC<br>CATCCATTGCTCTAGATCTATGCAGTTACTATAGACAGAATGTGTTGTTCTGTTTGG<br>CTTTGGGGATAATGGCCTGGCGAACTGCCAGCTGTTCAGTGGCAGGGCTGTGAGGCC<br>AGTCAAAGACTAGAACCCACAGACCAGCTGAACGATGAGTATAGCCTGTCCCCTGGG<br>GGAGCCTGACCTGTCTCCAGCCCTAAGCTTCAGACCTCACCACTCAGATGACTTCTA<br>AGAATTTGCCTGTGGGGACCCCTGCATGGCTGCAGCTCCGTGGAAAGGAGAGGAGGC<br>CCCCAGCAGAAGAACCACTCGCTTCCTGCCCAGCTTCCTCCTGTAGGGCTCTAAGTC<br>TCTTCTTCTTGGGACCCTGCAAGCAAAGGCATGTCAGCTTGGTGGTTTCCTGTTTTG<br>GGTGAAGTTTTGTGTGGTCCGGGTTCTGTCTACATCCATGAACTTGGGTGCTACCAC<br>CTTGCTGCTGCTGTAGAGACAGCTGCAGGATCTTAGGGTGGAAAATGGAGGTGCCCT |

TABLE 1-continued

Type I Proteins of Interest Amino Acid Sequence

| Protein of Interest | Transcript Sequence (SEQ ID NO:)<br>Amino Acid Sequence (SEQ ID NO:) |
|---|---|
| | GAGGTGCTAGCCCTTGGGGCAAAAGATGGGGTGGCAATGAGACACAGTGGGGAACTG<br>AGTTCCCCAAGAGGAGGGAGGAGCCCTGTAGCCTCAAGGGCCATATTGGGTTCCTGG<br>TACCAGCAAAAGCCTAGAGAGCGAAGTCTGTATTTTGAGGAGGTAATTGATCCTTAC<br>GGAATCCATCAGAAATTTGGAGCGGGTGCTTTATCTATCTCTGGAGGGTCTCTACCT<br>ATCTCCGATGAAGCTCTCCCTGGGCCTGGGATGGGAGAAACCAGGAGGAAAGGTGTC<br>TGATAAAGCAGGGGCTTCTTGACAAGCCAAAGGGCCACTGGTAGCTGTTGTGGACCG<br>AGCTGACCCTGCTGAAGTATTGTAGTGTGCCTTGGACCAACTTCTCAAAAGAGCAAC<br>CCCGGGGCTACCCTACTTCTGCCAGGAAGAGGCGGAGAAGGGGCTGAGAGGCCTGGA<br>AGGGGCTAGCTCCTTCTTTGAGAACTGCTCCCCGGAGGACTTGGAGGAGGCGGCTAG<br>GCTACGGGCTGCTGAGGGCCCTTTGTCTTTCCTAACCTGGGCACTGTTAGGATGCTC<br>CCTCCTGGAAAAGGCTTTCCTGGGTGTGAGCTAGAGCAGTGTCCATGCCAGCGCTGA<br>ACCTGCCATGGTGGGAGCTGAACTAAAAATTTCTCAGGGAACTAAAATAGGCAAAAG<br>AGGAACTGGGGGAGGAGGGTGCCAGGCAGGATGGGGGGAAGGGAGGGCAGTGCAAAA<br>GTCTCTTGAAACACAGACAGCCCAGCTGAGTGCCAGTCCCAGATCACAGAGAATACG<br>GCTCATCTGGCTCATGTTCTGCATGCTTGCTGCTTTACCCTGGCACTTTCCTTCTCC<br>ACCATGAGTGCGAGTCCTGGGAGTCCTGGGAGGGTGAGGATTAATGCCAGCCTGGGG<br>AGCAGATAGCTGACAGAGTCCTTGGGTAACTGGCTTGAACCAGGACCTCAGGATTCC<br>ACTCTGGGGATCTAGCTTTGTCTGGGCCAGTGAAGATCTCTATAATGGCATTATTGC<br>CAGGGGATAAACATTTCACTGGGTTCTGATCTGTTGGGTGTGGCTTCCTGGAAAATA<br>TGGTGAGAGGAATTCTGCTAAGGATACAGTTGATAAGAAAGTTCTGAGATTGATTAG<br>TAATGCCTGCCTTGGACTCAGGAAGGGAAGTGGCAGTATGAATGCCATGTCTTAATC<br>ATTTTGGTTAAAATATGCTTCCCAAAAGATTTCCACGTGTGTTCTTGTTTATTTGAC<br>ATCTGTCTCCATATCAGTCTTGAAAGCCTTTCTGTGTGTATATATATATGATGTTTGCG<br>TGTATATATGTTTTTGTGTGTGCATATGGAAGTCAGAAATCACTGGGTGTCTTCCTC<br>CATTCCTTTGCAATGTATGTTTTTTTTTTTTTTTACGATTTATTTACTATATGAATGT<br>TTTGCCTGAATACATGCATAGGTGTCACGTACATGCCTGCTGGAACGCTTGGAACTG<br>GAGTTACAGGTGGCTATGAGCTACAGTGTGAGCACTGGGAATCAAACCTGGGTCTTC<br>TGCAAGAGCAACAAATTAAAAGTCAGCTCTTAACTACTTGAGCTATTTTTCCAACTC<br>C (SEQ ID NO: 63)<br><br>>NP_083008.1 V-type immunoglobulin domain-containing suppressor of T-cell activation isoform 1 precursor [*Mus musculus*]<br>MGVPAVPEASSPRWGTLLLAIFLAASRGLVAAFKVTTPYSLYVCPEGQNATLTCRIL<br>GPVSKGHDVTIYKTWYLSSRGEVQMCKEHRPIRNFTLQHLQHHGSHLKANASHDQPQ<br>KHGLELASDHHGNFSITLRNVTPRDSGLYCCLVIELKNHHPEQRFYGSMELQVQAGK<br>GSGSTCMASNEQDSDSITAAALATGACIVGILCLPLILLLVYKQRQVASHRRAQELV<br>RMDSSNTQGIENPGFETTPPFQGMPEAKTRPPLSYVAQRQPSESGRYLLSDPSTPLS<br>PPGPGDVFFPSLDPVPDSPNSEAI (SEQ ID NO: 64) |
| Human B7-H7 (HHLA2) | >NM_007072.4 *Homo sapiens* HERV-H LTR-associating 2 (HHLA2), transcript variant 1, mRNA<br>AGTTCTCTTCAAGTCATGTAATCGACTTTTTTGAATTAGTTTTCAGTTTCATTTTGT<br>TTTCCCTAATTCAAGTTGGGAACACTTCATTTTCCCCAATTCAAGTTGGGAACACTT<br>CCTTGGTATTTCCTTGCTACATGGACTTTAGCAAATGCTACTTTACTCTCCTTCCAG<br>CTACTCAGGAGGCTGAGGCAGGAGAATCGCTTGAACCCGGGAGGCGGAGGTTACAGT<br>GAGCCTTTTCCTAGTTTTACTGTTGGAAGCCTAACTCACAGGAGAGATTATGCAATA<br>CAGTCCTGAAGTCAAGGGAGGAGAGCATGTAGGAGAATACTAACCCTGCACAGATTG<br>TGATGGTGATGTGGAATATACTAAAGCCTAGAACGCACCTCCTCTGCATGACTAATA<br>TGTTCTGCACAAGACATGAAGGCACAGACAGCACTGTCTTTCTTCCTCATTCTCATA<br>ACATCTCTGAGTGGATCTCAAGGCATATTCCCTTTGGCTTTCTTCATTTATGTTCCT<br>ATGAATGAACAAATCGTCATTGGAAGACTTGATGAAGATATAATTCTCCCTTCTTCA<br>TTTGAGAGGGGATCCGAAGTCGTAATACACTGGAAGTATCAAGATAGCTATAAGGTT<br>CACAGTTACTACAAAGGCAGTGACCATTTGGAAAGCCAAGATCCCAGATATGCAAAC<br>AGGACATCCCTTTTCTATAATGAGATTCAAAATGGGAATGCGTCGCTATTTTTCAGA<br>AGAGTAAGCCTTCTGGACGAAGGAATTTACACCTGCTATGTAGGAACAGCAATTCAA<br>GTGATTACAAACAAAGTGGTGCTAAAGGTGGGAGTTTTTCTCACACCCGTGATGAAG<br>TATGAAAAGAGGAACACAAACAGCTTCTTAATATGCAGCGTGTTAAGTGTTTATCCT<br>CGTCCAATTATCACGTGGAAAATGGACAACACACCTATCTCTGAAAACAACATGGAA<br>GAAACAGGGTCTTTGGATTCTTTTTCTATTAACAGCCCACTGAATATTACAGGATCA<br>AATTCATCTTATGAATGTACAATTGAAAATTCACTGCTGAAGCAAACATGGACAGGG<br>CGCTGGACGATGAAAGATGGCCTTCATAAAATGCAAAGTGAACACGTTTCACTCTCA<br>TGTCAACCTGTAAATGATTATTTTTCACCAAACCAAGACTTCAAAGTTACTTGGTCC<br>AGAATGAAAAGTGGGACTTTCTCTGTCCTGGCTTACTATCTGAGCTCCTCACAAAAT<br>ACAATTATCAATGAATCCCGATTCTCATGGAACAAAGAGCTGATAAACCAGAGTGAC<br>TTCTCTATGAATTTGATGGATCTTAATCTTTCAGACAGTGGGGAATATTTATGCAAT<br>ATTTCTTCGGATGAATATACTTTACTTACCATCCACACAGTGCATGTAGAACCGAGC<br>CAAGAAACAGCTTCCCATAACAAAGGCTTATGGATTTTGGTGCCCTCTGCGATTTTG<br>GCAGCTTTTCTGCTGATTTGGAGCGTAAAATGTTGCAGAGCCCAGCTAGAAGCCAGG<br>AGGAGCAGACACCCTGCTGATGGAGCCCAACAAGAAAGATGTTGTGTCCCTCCTGGT<br>GAGCGCTGTCCCAGTGCACCCGATAATGGCGAAGAAAATGTGCCTCTTTCAGGAAAA<br>GTATAGGAAATGAGAGAAGACTGTGACAACTCATGACCTGCATCCTTAATATCCAGT<br>GACTTCATCTCCCCTTTCTTCACCACAATTCCAGGCAATGGCCTGTCGGAGCAGACA<br>ATTCTACCACTGCAAAGAGTTGTAACCATTTTCTGGTATCACATTTATTTTTCAAGA<br>CATACTTTTCAAGACATCATTCACTGACCCACTACCTGCATTGAGTATAAATGCCTG |

TABLE 1-continued

| Type I Proteins of Interest Amino Acid Sequence | |
|---|---|
| Protein of Interest | Transcript Sequence (SEQ ID NO:) Amino Acid Sequence (SEQ ID NO:) |
| | GATGTTAAGGATTCCAATTTAACTTTGAAAAGAACTGTCTCATTCATTTACATTTCT GTTACAGTCAGCCCAGGAGGTTACAGTGAGCTCTCCACTAAGAATCTGGAAGAAATG CATCACTAGGGGTTGATTCCCAATCTGATCAACTGATAATGGGTGAGAGAGCAGGTA AGAGCCAAAGTCACCTTAGTGGAAAGGTTAAAAACCAGAGCCTGGAAACCAAGATGA TTGATTTGACAAGGTATTTTAGTCTAGTTTTATATGAACGGTTGTATCAGGGTAACC AACTCGATTTGGGATGAATCTTAGGGCACCAAAGACTAAGACAGTATCTTTAAGATT GCTAGGGAAAAGGGCCCTATGTGTCAGGCCTCTGAGCCCAAGCCAAGCATCGCATCC CCTGTGATTTGCACGTATACATCCAGATGGCCTAAAGTAACTGAAGATCCACAAAAG AAGTAAAAATAGCCTTAACTGATGACATTCCACCATTGTGATTTGTTCCTGCCCCAC CCTAACTGATCAATGTACTTTGTAATCTCCCCCACCCTTAAGAAGGTACTTTGTAAT CTTCCCCCACCCTTAAGAAGGTTCTTTGTAATTCTCCCCACCCTTGAGAATGTACTTT GTGAGATCCACCCTGCCCACAAAACATTGCTCTTAACTTCACCGCCTAACCCAAAAC CTATAAGAACTAATGATAATCCATCACCCTTCGCTGACTCTCTTTTCGGACTCAGCC CACCTGCACCCAGGTGAAATAAACAGCTTTATTGCTCACACAAA (SEQ ID NO: 65) |
| | >NP_009003.1 HERV-H LTR-associating protein 2 isoform a precursor [*Homo sapiens*] MKAQTALSFFLILITSLSGSQGIFPLAFFIYVPMNEQIVIGRLDEDIILPSSFERGS EVVIHWKYQDSYKVHSYYKGSDHLESQDPRYANRTSLFYNEIQNGNASLFFRRVSLL DEGIYTCYVGTAIQVITNKVVLKVGVFLTPVMKYEKRNTNSFLICSVLSVYPRPIIT WKMDNTPISENNMEETGSLDSFSINSPLNITGSNSSYECTIENSLLKQTWTGRWTMK DGLHKMQSEHVSLSCQPVNDYFSPNQDFKVTWSRMKSGTFSVLAYYLSSSQNTIINE SRFSWNKELINQSDFSMNLMDLNLSDSGEYLCNISSDEYTLLTIHTVHVEPSQETAS HNKGLWILVPSAILAAFLLIWSVKCCRAQLEARRSRHPADGAQQERCCVPPGERCPS APDNGEENVPLSGKV (SEQ ID NO: 66 |
| Mouse BTNL1 | >NM_001111094.1 *Mus musculus* butyrophilin-like 1 (Btnl1), mRNA ACCCTTAAATAAGAGCTGAAGATGGCTGCAGCTTTCTCCTAGACTCCTCCAGGAGAA ACTCTAAAGCCAGAGCCTGGGGGCAGCATTGTGTGTCCACCTTGCCACTGAGAACAT CTACGGAAATTGGACACTCTGGCCCCAGCATCCACACGCTTGACTGTTGGCCACAGT AACACAGGTGTGGATGGTCCCCAGAGCCAGGGTCCAGGAGTGCACTGAGGATCCCTG GGGCTTCAAGGAACCCACAGCTCTGTCCAGACGGGAATTTTTTTCCTGAGAACTTTC ACCTGTTGCCCTCCTATGGTGAACCTGGACTTGACCTTCCACTCTGATGATGAAGGG CTCCCCCTCCGTCCCTCCAGCTGGTTGTCTCCTCCCTCTGCTCCTCCTGCTGTTTAC CGGAGTCTCTGGAGAAGTGTCTTGGTTTTCTGTGAAGGGACCAGCTGAGCCCATCAC TGTCCTGCTGGGGACTGAAGCCACCCTGCCCTGCCAGCTGTCTCCTGAACAGAGTGC AGCTCGCATGCACATCCGATGGTACCGTGCCCAGCCCACCCCTGCTGTGCTGGTGTT CCACAACGGACAGGAGCAGGGAGAGGTGCAGATGCCGGAATACAGGGGCAGGACCCA GATGGTGAGACAAGCCATTGACATGGGAAGTGTGGCTCTGCAGATACAGCAGGTCCA GGCCTCTGATGATGGCCTGTACCACTGTCAGTTTACAGATGGCTTCACCTCCCAAGA GGTCTCCATGGAGCTTCGAGTCATAGGTTTAGGCTCTGCCCCTCTTGTTCACATGAC AGGACCTGAGAATGATGGGATCCGAGTGTTGTGCTCCTCAAGTGGCTGGTTCCCAAA ACCCAAAGTGCAATGGAGAGACACCTCCGGGAACATGCTACTGTCCTCCTCTGAGTT GCAGACCCAAGACAGAGAGAAGGGCTCTTCCAGGTGGAAGTGTCTCTTTTGGTCACAGA TAGAGCTATTGGCAATGTGATCTGCTCCATCCAAAATCCCATGTATGACCAGGAGAA ATCGAAGGCCATCCTCCTCCCAGAGCCCTTCTTCCCCAAGACGTGTCCATGGAAAGT AGCCCTGGTTTGTTCTGTCCTCATACTATTGGTCCTGCTCGGTGGGATCAGCCTTGG AATCTGGAAAGAACATCAAGTCAAAAGGAGAGAAATTAAAAAATGGTCAAAGGAACA TGAAGAAATGCTTCTGTTGAAGAAGGGGACAAAATCTGTACTGAAGATCAGAGATGA CCTCCAGGCCGACCTAGATCGGAGGAAGGCGCTGTACAAAGAAGACTGGAAGAAGGC CTTGCTGTACCCTGACTGGAGGAAGGAGCTGTTCCAGGAGGCTCCTGTGAGGATAAA TTATGAAATGCCTGACCAGGACAAGACAGACTCAAGGACAGAAGAGAACAGAGGTGA GGAGACTGTCAGCAGCTCACAAGTAGACCACAACCTCATCACACTCTCCCAGGAAGG CTTCATGTTGGGAAGATACTACTGGGAGGTGGATGTCAAGGACACAGAGGAGTGGAC ACTAGGAGTTTATGAGCTGTGCACTCAGGATGCATCACTTACAGACCCCTTGAGGAA ATTCAGAGTCCTGGAAAAAGAATGGAGATGGATACAGGGCTCTTGACTTCTGTTCCCA AAACATTAATTCGGAAGAACCTCTGCAACTGAAGACACGTCCGCTGAAGATCGCCAT CTTCTTGGATCAGGAAGACAATGACCTCTCTTTCTACAACATGACCGATGAGACACA CATCTTTTCCTTTGCCCAGGTCCCTTTCTTGGGATCACCCTATCCTTACTTCACACG TAATTCCATGGGGCTCTCTGCAACAGCACAGCCCTAAGTGATGTGCACAGGGAATTC AATGGGTGGGTGCTGCAGCGTGCTACCCGTAAGGCCCTCTTAGGCAGGCACAGGGGG CCTCTGACCAAGAGGCCTCTTAACCTGAGACTCCATGAGCCTCGGGGATCAGATCCT GGACAAGATTCTCGGACCATCTGTGTCGTGCATGGTGTTATAGTTATTAATAGCCTT CCTTCTTTTGACAAAAATGTGTTTAATCATTCCTAAGATAAATGAATCCATGGCTTT CTGA (SEQ ID NO: 67) |
| | >NP_001104564.1 butyrophilin-like protein 1 precursor [*Mus musculus*] MMKGSPSVPPAGCLLPLLLLLFTGVSGEVSWFSVKGPAEPITVLLGTEATLPCQLSP EQSAARMHIRWYRAQPTPAVLVFHNGQEQGEVQMPEYRGRTQMVRQAIDMGSVALQI QQVQASDDGLYHCQFTDGFTSQEVSMELRVIGLGSAPLVHMTGPENDGIRVLCSSSG WFPKPKVQWRDTSGNMLLSSSELQTQDREGLFQVEVSLLVTDRAIGNVICSIQNPMY DQEKSKAILLPEPFFPKTCPWKVALVCSVLILLVLLGGISLGIWKEHQVKRREIKKW |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| | SKEHEEMLLLKKGTKSVLKIRDDLQADLDRRKALYKEDWKKALLYPDWRKELFQEAPVRINYEMPDQDKTDSRTEENRGEETVSSSQVDHNLITLSQEGFMLGRYYWEVDVKDTEEWTLGVYELCTQDASLTDPLRKFRVLEKNGDGYRALDFCSQNINSEEPLQLKTRPLKIAIFLDQEDNDLSFYNMTDETHIFSFAQVPFLGSPYPYFTRNSMGLSATAQP (SEQ ID NO: 68) |
| Human VSIG8 | >NM_001013661.1 *Homo sapiens* V-set and immunoglobulin domain containing 8 (VSIG8), mRNA ACTCATTGCACCTTCCTGCCACCCCAGGCAGTGTCTGGGCCCTCAGCTCCCCCTCCCTCCACCTACCCCCTCACACCCACCACTACGACCCCACGGGATACCCAGCCCAGACGGAGGAAACACCGAGCCTAGAGACATGAGAGTTGGAGGAGCATTCCACCTTCTACTCGTGTGCCTGAGCCCAGCACTGCTGTCTGCTGTGCGGATCAACGGGGATGGACAGGAGGTCCTGTACCTGGCAGAAGGTGATAATGTGAGGCTGGGCTGCCCCTACGTCCTGGACCCTGAGGACTATGGTCCCAATGGGCTGGACATCGAGTGGATGCAGGTCAACTCAGACCCCGCCCACCACCGAGAGAACGTGTTCCTTAGTTACCAGGACAAGAGGATCAACCATGGCAGCCTTCCCCATCTGCAGCAGAGGGTCCGCTTTGCAGCCTCAGACCCAAGCCAGTACGATGCCTCCATCAACCTCATGAACCTGCAGGTATCTGATACAGCCACTTATGAGTGCCGGGTGAAGAAGACCACCATGGCCACCCGGAAGGTCATTGTCACTGTCCAAGCACGACCTGCAGTGCCCATGTGCTGGACAGAGGGCCACATGACATATGGCAACGATGTGGTGCTGAAGTGCTATGCCAGTGGGGGCTCCCAGCCCCTCTCCTACAAGTGGGCCAAGATCAGTGGGCACCATTACCCCTATCGAGCTGGGTCTTACACCTCCCAGCACAGCTACCACTCAGAGCTGTCCTACCAGGAGTCCTTCCACAGCTCCATAAACCAAGGCCTGAACAATGGGGACCTGGTGTTGAAGGATATCTCCAGAGCAGATGATGGGCTGTATCAGTGCACAGTGGCCAACAACGTGGGCTACAGTGTTTGTGTGGTGGAGGTGAAGGTCTCAGACTCCCGGCGTATAGGCGTGATCATCGGCATCGTCCTGGGCTCTCTGCTCGCGCTGGGCTGCCTGGCCGTAGGCATCTGGGGGCTCGTCTGCTGCTGCTGCGGGGGCTCCGGGGCTGGCGGCGCCCGCGGTGCCTTCGGCTACGGCAACGGCGGCGGGGTCGGCGGAGGGGCCTGCGGCGACTTGGCTAGTGAGATCAGAGAGGACGCCGTGGCGCCCGGGTGCAAGGCCAGCGGGCGCGGCAGCCGCGTCACCCACCTCCTGGGGTACCCGACGCAGAACGTCAGCCGCTCCCTGCGCCGCAAGTACGCGCCTCCCCCCTGCGGCGGCCCCGAGGACGTGGCCCTGGCGCCCTGCACCGCCGCCGCCGCCTGCGAAGCGGGCCCCTCCCCGGTCTACGTCAAGGTCAAGAGCGCGGAGCCGGCTGACTGCGCCGAGGGGCCGGTGCAGTGCAAGAACGGCCTCTTGGTGTGAGCGCGCGCGCCGGGCCGGGCTGCGCCCCAGCCAGGAGGAGGGCGCGGGGCTCTCTGTCTGCAGCTGGGGACACGTCGGGGCTGGGGACGACCTCGCTCGCCCCAGGCTGCCAGGCGGCTGGGGGTGAAGGCATTTCCCTAAGGAAATGCGTAGGGAGGCAGAGCCTCCTCCCCAAAAGTGGGAAGGGGCGGGCGAGGGCGGAGGAAGGCGATCCTGAGCCTTCTCCGCACCCCCGGGACCGAAGGCTTGGGGGAGAGGGAGGGAGGAGGAGGCTGAGTGTCCTAGAGCGGCTGAGGCCGGAGGCCTGGTGTCCCCAGCCTAAGCAGAGGGCCCCGGGGGCCGGGTGGGTGGGGGTCTGTCTGGACGAATTGTTCTGTGTGTGAGGTCTGAGCTCTGAGGCAGCAGTGTTAGCACAATAAAGAAACATTGAGACGTGA (SEQ ID NO: 69) |
| | >NP_001013683.1 V-set and immunoglobulin domain-containing protein 8 precursor [*Homo sapiens*] MRVGGAFHLLLVCLSPALLSAVRINGDGQEVLYLAEGDNVRLGCPYVLDPEDYGPNGLDIEWMQVNSDPAHHRENVFLSYQDKRINHGSLPHLQQRVRFAASDPSQYDASINLMNLQVSDTATYECRVKKTTMATRKVIVTVQARPAVPMCWTEGHMTYGNDVVLKCYASGGSQPLSYKWAKISGHHYPYRAGSYTSQHSYHSELSYQESFHSSINQGLNNGDLVLKDISRADDGLYQCTVANNVGYSVCVVEVKVSDSRRIGVIIGIVLGSLLALGCLAVGIWGLVCCCCGGSGAGGARGAFGYGNGGGVGGGACGDLASEIREDAVAPGCKASGRGSRVTHLLGYPTQNVSRSLRRKYAPPPCGGPEDVALAPCTAAAACEAGPSPVYVKVKSAEPADCAEGPVQCKNGLLV (SEQ ID NO: 70) |
| Mouse VSIG8 | >NM_177723.4 *Mus musculus* V-set and immunoglobulin domain containing 8 (Vsig8), transcript variant 1, mRNA ACTCATTGCATCTTCCTGCCACCCCGGGCAGTGTCTGGGCCCTCCGCTCCCCCTCCCTCCACCTGCCCCTTCCACCCACCACCACCAGCCCACTGGAGCCCAGCTCAGGCGGAGGAAAGACCAAGCCTAGAGACATGGGAGTTCGAGGAGCACTCCATCTTCTACTTGTGTGCCTGAGCCCAGCACTGTTGTCTGCTGTAAGGATCAACGGGGATGGCCAGGAGGTCATGTACCTGGCAGAAGGTGACAATGTGAGGCTAGGCTGTCCCTACCTCCTGGATCCTGAGGATTTGGGTACCAACAGTCTGGACATTGAGTGGATGCAAGTCAACTCAGAGCCCTCACACAGGGAGAATGTTTTTCTTACTTATCAAGACAAGAGGATAGGTCATGGCAACCTCCCCCATCTGCAGCAGAGGGTCCGCTTTGCAGCCTCAGACCCCAGCCAGTACGATGCCTCCATCAACCTCATGAACCTGCAGGTATCTGACACAGCAACCTATGAGTGCCGGGTGAAGAAGACCACCATGGCCACCAGGAAGGTCATTGTCACTGTCCAAGCACGTCCTGCGGTGCCCATGTGTTGGACGGAAGGCCACATGTCAAAGGGCAACGATGTGGTGCTGAAGTGCTTTGCCAACGGAGGCTCTCAGCCCCTCTCCTACAAGTGGGCCAAGATCAGTGGGCACAGTCACCCCTACCGAGCTGGGGCTTACCACTCACAGCACAGCTTCCACTCTGAGCTTTCTTACCAAGAGTCATTCCACAGCACCATCAACCAAGGCCTGGGCAACGGAGACCTGCTGTTGAAGGGCATCAACGCAGACGACGATGGGCTGTATCAGTGCACAGTGGCCAACCATGTGGGCTACAGCGTCTGTGTGGTAGAGGTGAAAGTCTCAGACTCCCAGCGAGTAGGCATGATCGTTGGAGCAGTGCTGGGCTCTTTGCTCATGCTGGCCTGCCTGGCACTAGGCATCTGGGGGCTCATCTGCTGCTGCTGCGGAGGCGGCGGGGCCGGTGGTGCCCGAGGTGCCTTCGGCTACGGGGTCGGCGGCGGGGTCGGCGGAGGGGCCTGCGGCGACTTGGCTAGTGAGATCAGAGTGGACGCCGAGGCGCCCGGGTGTAAGGCCAGCGGGC |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| | GCGGCAGCCGCGTCACCCACCTCCTGGGGTACCCGACGCAGAACGTCAGCCGCTCCC<br>TGCGCCGCAAGTACGCGCCTCCGCCCTGCGGCGGCCCCGAGGACGTGGCCCTAGTGC<br>CCCGCACCGCCTCCGCCTCCTGCGAAGCGGGTCCCTCCCCCGTCTACATCAAGGTCA<br>AGAGCGCGGAGCCGGCCGACTGCGCCGACTGTGCCCAGGTCGAGCAGCGCTCGTGCA<br>AGGACGGCCTCTTAGTGTGAGCGCACAGCACCGGGCTGCGCCCCGGCTGGGAGGTGG<br>TTCGGGGGCTCTCTGCCCGCAGCTGGGGACAGGTTCGGGCCAGCAGACCTGGCTCTC<br>TCATTGGCCACCTAGCGGTGGTAAGGAAATTTCCCTCTGAGAAGCCAAGCCGGGCAG<br>ACCCTCCTCCCCTGTAGTGGAGGAGAGGCGGGGGAGACAGAAAACAGTTCAGAGCT<br>CTCCCTCACCCCTGGTTTCCAGGGAGAGGAAGGGAGAGGAGAGCTGTCGGTATCCCA<br>GAACCGCAGAGGTACAACCCAGATGTCCCCAGCCAAGGCGAGGGCCCCCCAGCCCTG<br>GGTAGGTGGATGTCAGGGCTGAATTGCTCTGTGTGTGAGATCTGAGCTCCAAGGCAA<br>CAGTGTTAGCACAATAAAGAAACTTAAAGACTGAAAAAAAAAAAAAA (SEQ ID<br>NO: 71)<br><br>>NP_808391.2 V-set and immunoglobulin domain-containing<br>protein 8 precursor [*Mus musculus*]<br>MGVRGALHLLLVCLSPALLSAVRINGDGQEVMYLAEGDNVRLGCPYLLDPEDLGTNS<br>LDIEWMQVNSEPSHRENVFLTYQDKRIGHGNLPHLQQRVRFAASDPSQYDASINLMN<br>LQVSDTATYECRVKKTTMATRKVIVTVQARPAVPMCWTEGHMSKGNDVVLKCFANGG<br>SQPLSYKWAKISGHSHPYRAGAYHSQHSFHSELSYQESFHSTINQGLGNGDLLLKGI<br>NADDDGLYQCTVANHVGYSVCVVEVKVSDSQRVGMIVGAVLGSLLMLACLALGIWGL<br>ICCCCGGGGAGGARGAFGYGVGGGVGGGACGDLASEIRVDAEAPGCKASGRGSRVTH<br>LLGYPTQNVSRSLRRKYAPPPCGGPEDVALVPRTASASCEAGPSPVYIKVKSAEPAD<br>CADCAQVEQRSCKDGLLV (SEQ ID NO: 72) |
| Human VSIG3<br>(ISF11) | >NM_001015887.3 *Homo sapiens* immunoglobulin superfamily<br>member 11 (IGSF11), transcript variant 2, mRNA<br>AGTCCTGGGGCAGGGCTGGGTGGCACGGCTGGCGAGCCCGGAACGCCTCTGGTCACA<br>GCTCAGCGTCCGCGGAGCCGGGCGGCGCTGCAGCTGCACTTGGCTCGTCTGTGGGTC<br>TGACAGTCCCAGCTCTGCGCGGGGAACAGCGGCCCGGCGCTGGGTGTGGGAGGACCA<br>GGCTGCCCCAAGAGCGCGGAGACTCACGCCCGCTCCTCTCCTGTTGCGACCGGGAGC<br>CGGGTAGGAGGCAGGCGCGCTCCCTGCGGCCCCGGGATGACTTCTCAGCGTTCCCCT<br>CTGGCGCCTTTGCTGCTCCTCTCTCTGCACGGTGTTGCAGCATCCCTGGAAGTGTCA<br>GAGAGCCCTGGGAGTATCCAGGTGGCCCGGGGTCAGCCAGCAGTCCTGCCCTGCACT<br>TTCACTACCAGCGCTGCCCTCATTAACCTCAATGTCATTTGGATGGTCACTCCTCTC<br>TCCAATGCCAACCAACCTGAACAGGTCATCCTGTATCAGGGTGGACAGATGTTTGAT<br>GGTGCCCCCCGGTTCCACGGTAGGGTAGGATTTACAGGCACCATGCCAGCTACCAAT<br>GTCTCTATCTTCATTAATAACACTCAGTTATCAGACACTGGCACCTACCAGTGCCTG<br>GTCAACAACCTTCCAGACATAGGGGGCAGGAACATTGGGGTCACCGGTCTCACAGTG<br>TTAGTTCCCCCTTCTGCCCCACACTGCCAAATCCAAGGATCCCAGGATATTGGCAGC<br>GATGTCATCCTGCTCTGTAGCTCAGAGGAAGGCATTCCTCGACCAACTTACCTTTGG<br>GAGAAGTTAGACAATACCCTCAAACTACCTCCAACAGCTACTCAGGACCAGGTCCAG<br>GGAACAGTCACCATCCGGAACATCAGTGCCCTGTCTTCAGGTTTGTACCAGTGCGTG<br>GCTTCTAATGCTATTGGAACCAGCACCTGTCTTCTGGATCTCCAGGTTATTTCACCC<br>CAGCCCAGGAACATTGGACTAATAGCTGGAGCCATTGGCACTGGTGCAGTTATTATC<br>ATTTTTTGCATTGCACTAATTTTAGGGGCATTCTTTTACTGGAGAAGCAAAAATAAA<br>GAGGAGGAAGAAGAAGAAATTCCTAATGAAATAAGAGAGGATGATCTTCCACCCAAG<br>TGTTCTTCTGCCAAAGCATTTCACACTGAGATTTCCTCCTCGGACAACAACACACTA<br>ACCTCTTCCAATGCCTACAACAGTCGATACTGGAGCAACAATCCAAAAGTTCATAGA<br>AACACAGAGTCAGTCAGCCACTTCAGTGACTTGGGCCAATCTTTCTCTTTCCACTCA<br>GGCAATGCCAACATACCATCCATTTATGCTAATGGGACCCATCTGGTCCCGGGTCAA<br>CATAAGACTCTGGTAGTGACAGCCAACAGAGGGTCATCACCACAGGTGATGTCCAGG<br>AGCAATGGCTCAGTCAGTAGGAAGCCTCGGCCTCCACACACTCATTCCTACACCATC<br>AGCCACGCAACACTGGAACGAATTGGTGCAGTACCTGTCATGGTACCAGCCCAGAGT<br>CGGGCCGGGTCCTTGGTATAGGACATGAGGAAATGTTGTGTTCAGAAATGAATAAAT<br>GGAATGCCCTCATACAAGGGGGAGGGTGGGGTGGGGAGTGCTGGGAAAGAAACACTT<br>CCTTATAATTATATTAGTAAAATGCACAAAGAAGAAGGCAGTGCTGTTACTTGGCCA<br>CTAAGATGTGTAAAATGGACTGAAATGCTCCATCATGAAGACTTGCTTCCCCACCAA<br>AGATGTCCTGGGATTCTGCTGGATCTCAAAGATGTGCCAAGCCAAGGAAAAAGATAC<br>AAGAGCAGAATAGTACTTAAAATCCAAACTGCCGCCCAGATGGGCTTGTTCTTCATG<br>CCTAACTTAATAATTTTTAAGAGATTAAAGTGCCAGATGGAGTTTAAATATTGAAAT<br>TATTTTAAAAGGTAGGTGTCTTTAAGAAAATAACAAGCAACCCTGTGATATGTTCCG<br>TCTCTCCCAATTCCCTCGTTATATAGAGGGCTTAATGGTATAAATGGTTAATATTGG<br>TCCCAACAGGGCTGACTCTTCTATCATATAATCAAAACTTTTTACATGAGCAAAATT<br>CAGTAAGAAATGGGGGAAGACAAAGGAAACGTCTTTGAGAAGCCCCTTCATATTTAT<br>TTATTTATCTCTTCCTGAACCATGAATTTCATATGTGGAATATTGCTATATTGACAG<br>ATTCTTGCCTGTCTGTGTTATTCTAGGATCTGTTACAGGTCCATGGCAATTACTGTT<br>TATTTTTTCCTGGAAAAATATTTTTTTATAAAAGGCTTTTTTTTTTTTTTAAATACA<br>TGAGAGGCATTGGGCTAAGAAAGAAAAGACTGTTGTATAATACCTTGTTCAATGGTT<br>GTATTTAGTGAGCTCATAGAGGTCCATCATATCATGACCGAGCTAGGTTGTGTGGGC<br>AGGAAGGTAGGGCTAAGGGGTTGTAGCCTTGCTGGGCAGCCTCTCAGAGCAAGGTTG<br>TTCAGATCTCCCTTGCTATTACAGTAGGTTACTATTAATGAGGGCAGCACCTGATGC<br>CTTTTGTACTGAGGTATGTAACTTTCTCCTTATTTGACAAGTAGAAGTTAACTTACT<br>TGTCAGGGAGGGCAGACGTTTTTTTGTTCTGTTTCGTTTTTCAAAATAATGCTTTTT<br>GCAAAAGAGGTAAGACTGAGACTAAAGGTGTTATCTTCTGGTGTGCTCCTGGAAGTG |

TABLE 1-continued

| Protein of Interest | Transcript Sequence (SEQ ID NO:)<br>Amino Acid Sequence (SEQ ID NO:) |
|---|---|
| | Type I Proteins of Interest Amino Acid Sequence |
| | TCTACCCTACATTTGTGTCAGCTCAGGGTTGCAGTGTTGCCCAGATGCATTTTACAT<br>CACTGTAAAGAGATTACTTTTGTGGTTACTACCTGGCTTGGCTGGCCTTGCGGTTCA<br>CCAGATTAATTTACAAACTCCCCCACTTTATTTTGTGCTATGTAGATCTGGCCATAC<br>TTGCATTAGTGACTGTCTTGCCTTAACCACACTTAAGCAACCCACAAATTTCTTCTC<br>AGATTTGTTTCCTAGATTACTTATGATACTCATCCCATGTCTCAATAAGAGTGTCTT<br>TTCTTTCTGGATGTGTTCTCTTACTCCCTCTTACCACCATACTTTTTGCTCTCTTCT<br>CCTGCAAGCGTAGTCTTCACAGGGAGTGGCTTCCTGACATTTTTTTCAGTTATGTGA<br>ATGAATGGAAACCAACAGCTGCTGCAAACACTGTTTTTCCAAGAAGGCTACACTCAG<br>AACCTAACCATTGCCAACCATTTCAGTATTGATAAAAAGCTGAATTTACTTTAGCAT<br>TACTTATTTTTTTTTCCATTTGATGGTTCTTACTTTGTAAAAATTTAAATAAATGAA<br>TGTCTATACTTTTTATAAAGAAAAGTGAAAATACCATGACACTGAAAAGATGATGCT<br>ATCAGATGCTGTTTAGAAAGCATTTATCTTGCATTTCTTTATTCTTTCTAATTATCT<br>AAAATTCAATAAAATTTTATTCATATAAAATAAGTTGTCATTAATTATCAATACTAA<br>CGAGTATGTCATTTTAAAACTTAGTATTCTCTTTAATGTTACAAGA (SEQ ID NO: 73)<br><br>>NP_001015887.1 immunoglobulin superfamily member 11 isoform b precursor [*Homo sapiens*]<br>MTSQRSPLAPLLLLSLHGVAASLEVSESPGSIQVARGQPAVLPCTFTTSAALINLNV<br>IWMVTPLSNANQPEQVILYQGGQMFDGAPRFHGRVGFTGTMPATNVSIFINNTQLSD<br>TGTYQCLVNNLPDIGGRNIGVTGLTVLVPPSAPHCQIQGSQDIGSDVILLCSSEEGI<br>PRPTYLWEKLDNTLKLPPTATQDQVQGTVTIRNISALSSGLYQCVASNAIGTSTCLL<br>DLQVISPQPRNIGLIAGAIGTGAVIIIFCIALILGAFFYWRSKNKEEEEEEIPNEIR<br>EDDLPPKCSSAKAFHTEISSSDNNTLTSSNAYNSRYWSNNPKVHRNTESVSHFSDLG<br>QSFSFHSGNANIPSIYANGTHLVPGQHKTLVVTANRGSSPQVMSRSNGSVSRKPRPP<br>HTHSYTISHATLERIGAVPVMVPAQSRAGSLV (SEQ ID NO: 74) |
| Mouse VSIG3 (IGSF11) | >NM_170599.2 *Mus musculus* immunoglobulin superfamily, member 11 (Igsf11), mRNA<br>CGGCTGGTGGTGGCCGCGGCGGCCGGCGAGCCCGGGACGCCCGAGCCTGCCCCGAGC<br>CTCGGCGGAGCGGAGTGGCCTCGGCGCTCCCGTGTCCCGCTTGGTCCCACGCTGCAC<br>CCCGCCGCCCAGGAGCCCGGCGGACGGCGGCTCCCCCGGCGGCTCCGGCATGACTCG<br>GCGGCGCTCCGCTCCGGCGTCCTGGCTGCTCGTGTCGCTGCTCGGTGTCGCAACATC<br>CCTGGAAGTGTCCGAGAGCCCAGGCAGTGTCCAGGTGGCCCGGGGCCAGACAGCAGT<br>CCTGCCCTGCGCCTTCTCCACCAGTGCTGCCCTCCTGAACCTCAATGTCATTTGGAT<br>GGTCATTCCCCTCTCCAATGCAAACCAGCCCGAACAGGTCATTCTTTATCAGGGTGG<br>ACAAATGTTTGACGGCGCCCTCCGGTTCCACGGGAGGGTAGGATTTACCGGCACCAT<br>GCCTGCTACCAATGTCTCGATCTTCATCAATAACACACAGCTGTCAGATACGGGCAC<br>GTACCAGTGCTTGGTGAATAACCTTCCAGACAGAGGGGGCAGAAACATCGGGGTCAC<br>TGGCCTCACAGTGTTAGTCCCCCCTTCTGCTCCACAATGCCAAATCCAAGGATCCCA<br>GGACCTCGGCAGTGACGTCATCCTTCTGTGTAGTTCAGAGGAAGGCATCCCTCGGCC<br>CACGTACCTTTGGGAGAAGTTAGATAATACGCTCAAGCTACCTCCAACAGCCACTCA<br>GGACCAGGTCCAGGGAACAGTCACCATCCGGAATATCAGTGCCCTCTCTTCCGGTCT<br>GTACCAGTGTGTGGCTTCTAATGCCATCGGGACCAGCACCTGTCTGCTGGACCTCCA<br>GGTTATCTCACCCCAGCCCCGGAGCGTTGGAGTAATAGCCGGAGCGGTTGGCACCGG<br>TGCTGTTCTTATCGTCATCTGCCTTGCACTAATTTCAGGGGCGTTCTTTTACTGGAG<br>AAGCAAAAACAAAGAGGAGGAGGAGGAAGAAATTCCTAATGAAATCAGAGAGGATGA<br>TCTTCCCCCTAAATGCTCTTCTGCCAAAGCCTTCCACACGGAGATATCCTCCTCAGA<br>AAATAACACGCTGACCTCTTCCAATACCTACAACAGTCGATACTGGAACAACAATCC<br>AAAACCCCATAGAAACACAGAGTCTTTCAACCACTTCAGTGACTTACGCCAGTCTTT<br>CTCTGGCAATGCAGTTATCCCATCAATCTATGCAAATGGGAACCATCTGGTTTTGGG<br>TCCACATAAGACTCTGGTAGTTACAGCCAACAGAGGGTCATCACCTCAGGTCTTGCC<br>CAGGAACAATGGTTCAGTCAGCAGGAAGCCTTGGCCTCAACACACTCATTCCTACAC<br>AGTAAGCCAAATGACCCTGGAGCGCATCGGTGCAGTGCCTGTCATGGTGCCTGCCCA<br>GAGTCGAGCAGGGTCCCTGGTATAGGATGACTGAGGAAACCATGTTCAGAAGAGAAT<br>AAATGGACCGCCTTCAGGCAAGGGGGGAGCACTGCCTTCAGGCAAGGGGGGAGCACT<br>GCCTTCAGGCAAGAGGGAGAGTGGGATGGGTGAGTGCTGAAAAATAAACTTTTGTTA<br>CGATTCCATTAGCAAAAAGCACAAAGAGGAGGCGTGTGTGAAGTGGCCTGGGGTTGT<br>TCCATAATGAAGACTCAAGAAGACTGTTTCCCCACCACAGATGTCCTGAGATTCAGT<br>TAAAACGAAACATGCTGCATCTCCAGAGATGTGCCAAGCCAAGGAGAATGCTAGAAG<br>CAGAGTAAAGCTTACCCCCCAAACTGTGGTCCAGCTGGACCCCTTCTTTAATTCTTG<br>CCTAACTTAATTATTTTCAGGACCCTTCAAGTGCCAGGTGGAATTTACATAATGAAA<br>TTATTTTTTAAAAATAGGTGTCCTTAGGGAGAGAAAACAGGAGCAAGCTCATGGTCT<br>GGCCTAGTCTCCCTCTCCCACTCCTTCTGATGACACTAGCAATGCATTCCATCTGAC<br>CTGACTTTATCATAGAGGCAAAATTGTTCAGAACACTGGCTGGAGATGGGGAGAAAT<br>AAGGAAACTTCTTGTGAACACCCTACACACACACACACACACACACACACACACACA<br>CACACACACACACACACACACACACACACACATTTATTTACCTCCTCCTGAACCATGAA<br>TCGTATTGGTGATTTTGCTATATTGACAGATTCTCATCTGTTACACTCTAGGATCTC<br>TCACAGGTCTGTGGCAATTACTGTTCATGATTTCCTGAAAAAATATTTTTTTAAAAG<br>AAAACTATTTTTTTTAAATACTAGAGAGACAGTGGACTAGGAAAGCGAGAACTTGCC<br>GCCTTGTCTAGTGACTGTATTCAATGACTGAACAGAGGCCCCCCCCACCATACAAGA<br>GTTTTAGGTGATTGAGTGGGTGGAACCAGCTGGAGCCAGGTGGGAGGGGCCTTTACA<br>TTGCCAGCAGGGCCCCAAAGAATTGAGATTGTGTATGGCAACCGTTAATGAGGACAG<br>CGCCTGATGCCTTTTGTACCGAGGAAGATAATTGCCTCTTGTTTGACAAGTAGAGTT<br>TAGTAGGTTATTACAAAAAGGGCAAGAGTTGTTTTGGTTTTGTTTCTTTCAAAATAA |

TABLE 1-continued

| Type I Proteins of Interest Amino Acid Sequence | |
|---|---|
| Protein of Interest | Transcript Sequence (SEQ ID NO:) Amino Acid Sequence (SEQ ID NO:) |
| | TTTTTTTTCAAAAGAATAACAAGGGTTAGGCAAATGGGGGACCTTCCTGTGTGCTCT TGGGGGTCTGCTCAGCATCTGGAAATTTGGGTGTGCGATTTTCCCTGAACACATTGC ATACCAGTGTAAAAAGACTCTGCCTCCCCCCTTTTTGGCTTTTTTACTGGGCTTGGC TGGCCTTGCAGTTTACCAGATTCATTTACAGACTCTCTGCTCTGTATGGCGCCGCCT GCCATGTCTGTCTTGGTGACTATCCTGCCTTAATCACTTTGCTTTAGGGCAACTCAT GGTGATCTCTTCCAAGATCTGTTTTTAAATTGTTTGGACTACTTGAGCCACAACTCT CAGAGGACATTCCTTTTTTTTTTTTTTTTTTTTTTTCTCCTTTCTTCCATTGCTTTGTC CCTCTTCCCCTGTGCTTCCTGCCTTCTTTCCCTGTCCCATGGGCACAGTCCTCACAG GGAGTGGCCTCCTCTCTCCAGTGATGTAAGTGAATGGAAGCCATCACTGGCTGCACA TACCTTTTTCAAAAGGGACACTCGGGAAGTCACTGCTGTGACCGTTTCGATGTTGAT AAGAAGGTGAATTTACTGTAGTGTTACCACCTTCTCCCCACTTGATGGTTCTTGACT TTGTAAAAATTTAAATAAATGAATGTCTATACTTTTTAAGGAAAAGAGAAAATACCA TGTCACAGAAAAGGTGAAACTATTAGATGCTGTTTAGAAAGCATTTATCTTGCATTT CTTTATTCTTTCTAATTACCTAAAATTCAATAAAAGTTTATTCATATAAAAAAAAAA AAAAAAAAA (SEQ ID NO: 75)<br><br>>NP_733548.2 immunoglobulin superfamily member 11 precursor [*Mus musculus*] MTRRRSAPASWLLVSLLGVATSLEVSESPGSVQVARGQTAVLPCAFSTSAALLNLNV IWMVIPLSNANQPEQVILYQGGQMFDGALRFHGRVGFTGTMPATNVSIFINNTQLSD TGTYQCLVNNLPDRGGRNIGVTGLTVLVPPSAPQCQIQGSQDLGSDVILLCSSEEGI PRPTYLWEKLDNTLKLPPTATQDQVQGTVTIRNISALSSGLYQCVASNAIGTSTCLL DLQVISPQPRSVGVIAGAVGTGAVLIVICLALISGAFFYWRSKNKEEEEEEIPNEIR EDDLPPKCSSAKAFHTEISSSENNTLTSSNTYNSRYWNNNPKPHRNTESFNHFSDLR QSFSGNAVIPSIYANGNHLVLGPHKTLVVTANRGSSPQVLPRNNGSVSRKPWPQHTH SYTVSQMTLERIGAVPVMVPAQSRAGSLV (SEQ ID NO: 76) |
| Human VSIG4 | >NM_007268.3 *Homo sapiens* V-set and immunoglobulin domain containing 4 (VSIG4), transcript variant 1, mRNA ACAGACGCTGGCGGCCACCAGAAGTTTGAGCCTCTTTGGTAGCAGGAGGCTGGAAGA AAGGACAGAAGTAGCTCTGGCTGTGATGGGGATCTTACTGGGCCTGCTACTCCTGGG GCACCTAACAGTGGACACTTATGGCCGTCCCATCCTGGAAGTGCCAGAGAGTGTAAC AGGACCTTGGAAAGGGGATGTGAATCTTCCCTGCACCTATGACCCCCTGCAAGGCTA CACCCAAGTCTTGGTGAAGTGGCTGGTACAACGTGGCTCAGACCCTGTCACCATCTT TCTACGTGACTCTTCTGGAGACCATATCCAGCAGGCAAAGTACCAGGGCCGCCTGCA TGTGAGCCACAAGGTTCCAGGAGATGTATCCCTCCAATTGAGCACCCTGGAGATGGA TGACCGGAGCCACTACACGTGTGAAGTCACCTGGCAGACTCCTGATGGCAACCAAGT CGTGAGAGATAAGATTACTGAGCTCCGTGTCCAGAAACTCTCTGTCTCCAAGCCCAC AGTGACAACTGGCAGCGGTTATGGCTTCACGGTGCCCCAGGGAATGAGGATTAGCCT TCAATGCCAGGCTCGGGGTTCTCCTCCCATCAGTTATATTTGGTATAAGCAACAGAC TAATAACCAGGAACCCATCAAAGTAGCAACCCTAAGTACCTTACTCTTCAAGCCTGC GGTGATAGCCGACTCAGGCTCCTATTTCTGCACTGCCAAGGGCCAGGTTGGCTCTGA GCAGCACAGCGACATTGTGAAGTTTGTGGTCAAAGACTCCTCAAAGCTACTCAAGAC CAAGACTGAGGCACCTACAACCATGACATACCCCTTGAAAGCAACATCTACAGTGAA GCAGTCCTGGGACTGGACCACTGACATGGATGGCTACCTTGGAGAGACCAGTGCTGG GCCAGGAAAGAGCCTGCCTGTCTTTGCCATCATCCTCATCATCTCCTTGTGCTGTAT GGTGGTTTTTACCATGGCCTATATCATGCTCTGTCGGAAGACATCCCAACAAGAGCA TGTCTACGAAGCAGCCAGGGCACATGCCAGAGAGGCCAACGACTCTGGAGAAACCAT GAGGGTGGCCATCTTCGCAAGTGGCTGCTCCAGTGATGAGCCAACTTCCCAGAATCT GGGCAACAACTACTCTGATGAGCCCTGCATAGGACAGGAGTACCAGATCATCGCCCA GATCAATGGCAACTACGCCCGCCTGCTGGACACAGTTCCTCTGGATTATGAGTTTCT GGCCACTGAGGGCAAAAGTGTCTGTTAAAAATGCCCCATTAGGCCAGGATCTGCTGA CATAATTGCCTAGTCAGTCCTTGCCTTCTGCATGGCCTTCTTCCCTGCTACCTCTCT TCCTGGATAGCCCAAAGTGTCCGCCTACCAACACTGGAGCCGCTGGGAGTCACTGGC TTTGCCCTGGAATTTGCCAGATGCATCTCAAGTAAGCCAGCTGCTGGATTTGGCTCT GGGCCCTTCTAGTATCTCTGCCGGGGGCTTCTGGTACTCCTCTCTAAATACCAGAGG GAAGATGCCCATAGCACTAGGACTTGGTCATCATGCCTACAGACACTATTCAACTTT GGCATCTTGCCACCAGAAGACCCGAGGGAGGCTCAGCTCTGCCAGCTCAGAGGACCA GCTATATCCAGGATCATTTCTCTTTCTTCAGGGCCAGACAGCTTTTAATTGAAATTG TTATTTCACAGGCCAGGGTTCAGTTCTGCTCCTCCACTATAAGTCTAATGTTCTGAC TCTCTCCTGGTGCTCAATAAATATCTAATCATAACAGCAA (SEQ ID NO: 77)<br><br>>NP_009199.1 V-set and immunoglobulin domain-containing protein 4 isoform 1 precursor [*Homo sapiens*] MGILLGLLLLGHLTVDTYGRPILEVPESVTGPWKGDVNLPCTYDPLQGYTQVLVKWL VQRGSDPVTIFLRDSSGDHIQQAKYQGRLHVSHKVPGDVSLQLSTLEMDDRSHYTCE VTWQTPDGNQVVRDKITELRVQKLSVSKPTVTTGSGYGFTVPQGMRISLQCQARGSP PISYIWYKQQTNNQEPIKVATLSTLLFKPAVIADSGSYFCTAKGQVGSEQHSDIVKF VVKDSSKLLKTKTEAPTTMTYPLKATSTVKQSWDWTTDMDGYLGETSAGPGKSLPVF AIILIISLCCMVVFTMAYIMLCRKTSQQEHVYEAARAHAREANDSGETMRVAIFASG CSSDEPTSQNLGNNYSDEPCIGQEYQIIAQINGNYARLLDTVPLDYEFLATEGKSVC (SEQ ID NO: 78) |

TABLE 1-continued

Type I Proteins of Interest Amino Acid Sequence

| Protein of Interest | Transcript Sequence (SEQ ID NO:)<br>Amino Acid Sequence (SEQ ID NO:) |
|---|---|
| Mouse VSIG4 | >NM_177789.5 *Mus musculus* V-set and immunoglobulin domain containing 4 (Vsig4), mRNA<br>AGCTACCAGCACTTCCAGGTTCTTCAGCAGCAAGAGGATGGAAGGATGAATAGAAGT<br>AGCTTCAAATAGGATGGAGATCTCATCAGGCTTGCTGTTCCTGGGCCACCTAATAGT<br>GCTCACCTATGGCCACCCCACCCTAAAAACACCTGAGAGTGTGACAGGGACCTGGAA<br>AGGAGATGTGAAGATTCAGTGCATCTATGATCCCCTGAGAGGCTACAGGCAAGTTTT<br>GGTGAAATGGCTGGTAAGACACGGCTCTGACTCCGTCACCATCTTCCTACGTGACTC<br>CACTGGAGACCATATCCAGCAGGCAAAGTACAGAGGCCGCCTGAAAGTGAGCCACAA<br>AGTTCCAGGAGATGTGTCCCTCCAAATAAATACCCTGCAGATGGATGACAGGAATCA<br>CTATACATGTGAGGTCACCTGGCAGACTCCTGATGGAAACCAAGTAATAAGAGATAA<br>GATCATTGAGCTCCGTGTTCGGAAATATAATCCACCTAGAATCAATACTGAAGCACC<br>TACAACCCTGCACTCCTCTTTGGAAGCAACAACTATAATGAGTTCAACCTCTGACTT<br>GACCACTAATGGGACTGGAAAACTTGAGGAGACCATTGCTGGTTCAGGGAGGAACCT<br>GCCAATCTTTGCCATAATCTTCATCATCTCCCTTTGCTGCATAGTAGCTGTCACCAT<br>ACCTTATATCTTGTTCCGCTGCAGGACATTCCAACAAGAGTATGTCTATGGAGTGAG<br>CAGGGTGTTTGCCAGGAAGACAAGCAACTCTGAAGAAACCACAAGGGTGACTACCAT<br>CGCAACTGATGAACCAGATTCCCAGGCTCTGATTAGTGACTACTCTGATGATCCTTG<br>CCTCAGCCAGGAGTACCAAATAACCATCAGATCAACAATGTCTATTCCTGCCTGCTG<br>AACACAGTTTCCAGAAACTAAGAAGTTCTTGCTACTGAAGAAAATAACATCTGCTAA<br>AATGCCCCTACTAAGTCAAGGTCTACTGGCGTAATTACCTGTTACTTATTTACTACT<br>TGCCTTCAACATAGCTTTCTCCCTGGCTTCCTTTCTTCTTAGACAACCTAAAGTATC<br>TATCTAGTCTGCCAATTCTGGGGCCATTGAGAAATCCTGGGTTTGGCTAAGAATATA<br>CTACATGCACCTCAAGAAATCTAGCTTCTGGGCTTCACCCAGAACAATTTTCTTCCT<br>AGGGCCTTCACAACTCTTCTCCAAACAGCAGAGAAATTCCATAGCAGTAGAGGTTCT<br>TTATCATGCCTCCAGACAGCGTGAGTCTCAGTCCTACAAACTCAGACAAGCACATGG<br>GTCTAGGATTACTCCTCTTTCTCTAGGGCCAGATGACTTTTAATTGATATTACTATT<br>GCTACATTATGAATCTAATGCACATGTATTCTTTTGTTGTTAATAAATGTTTAATCA<br>TGACATCAA(SEQ ID NO: 79)<br><br>>NP_808457.1 V-set and immunoglobulin domain-containing protein 4 precursor [*Mus musculus*]<br>MEISSGLLFLGHLIVLTYGHPTLKTPESVTGTWKGDVKIQCIYDPLRGYRQVLVKWL<br>VRHGSDSVTIFLRDSTGDHIQQAKYRGRLKVSHKVPGDVSLQINTLQMDDRNHYTCE<br>VTWQTPDGNQVIRDKIIELRVRKYNPPRINTEAPTTLHSSLEATTIMSSTSDLTTNG<br>TGKLEETIAGSGRNLPIFAIIFIISLCCIVAVTIPYILFRCRTFQQEYVYGVSRVFA<br>RKTSNSEETTRVTTIATDEPDSQALISDYSDDPCLSQEYQITIRSTMSIPAC (SEQ ID NO: 80) |
| Human Tim-3 (HAVCR2) | >NM_032782.5 *Homo sapiens* hepatitis A virus cellular receptor 2 (HAVCR2), mRNA<br>ATTTGGAGAGTTAAAACTGTGCCTAACAGAGGTGTCCTCTGACTTTTCTTCTGCAAG<br>CTCCATGTTTTCACATCTTCCCTTTGACTGTGTCCTGCTGCTGCTGCTGCTACTACT<br>TACAAGGTCCTCAGAAGTGGAATACAGAGCGGAGGTCGGTCAGAATGCCTATCTGCC<br>CTGCTTCTACACCCCAGCCGCCCCAGGGAACCTCGTGCCCGTCTGCTGGGGCAAAGG<br>AGCCTGTCCTGTGTTTGAATGTGGCAACGTGGTGCTCAGGACTGATGAAAGGGATGT<br>GAATTATTGGACATCCAGATACTGGCTAAATGGGGATTTCCGCAAAGGAGATGTGTC<br>CCTGACCATAGAGAATGTGACTCTAGCAGACAGTGGGATCTACTGCTGCCGGATCCA<br>AATCCCAGGCATAATGAATGATGAAAAATTTAACCTGAAGTTGGTCATCAAACCAGC<br>CAAGGTCACCCCTGCACCGACTCGGCAGAGAGACTTCACTGCAGCCTTTCCAAGGAT<br>GCTTACCACCAGGGGACATGGCCCAGCAGAGACACAGACACTGGGGAGCCTCCCTGA<br>TATAAATCTAACACAAATATCCACATTGGCCAATGAGTTACGGGACTCTAGATTGGC<br>CAATGACTTACGGGACTCTGGAGCAACCATCAGAATAGGCATCTACATCGGAGCAGG<br>GATCTGTGCTGGGCTGGCTCTGGCTCTTATCTTCGGCGCTTTAATTTTCAAATGGTA<br>TTCTCATAGCAAAGAGAAGATACAGAATTTAAGCCTCATCTCTTTGGCCAACCTCCC<br>TCCCTCAGGATTGGCAAATGCAGTAGCAGAGGGAATTCGCTCAGAAGAAAACATCTA<br>TACCATTGAAGAGAACGTATATGAAGTGGAGGAGCCCAATGAGTATTATTGCTATGT<br>CAGCAGCAGGCAGCAACCCTCACAACCTTTGGGTTGTCGCTTTGCAATGCCATAGAT<br>CCAACCACCTTATTTTTGAGCTTGGTGTTTTGTCTTTTTCAGAAACTATGAGCTGTG<br>TCACCTGACTGGTTTTGGAGGTTCTGTCCACTGCTATGGAGCAGAGTTTTCCCATTT<br>TCAGAAGATAATGACTCACATGGGAATTGAACTGGGACCTGCACTGAACTTAAACAG<br>GCATGTCATTGCCTCTGTATTTAAGCCAACAGAGTTACCCAACCCAGAGACTGTTAA<br>TCATGGATGTTAGAGCTCAAACGGGCTTTTATATACACTAGGAATTCTTGACGTGGG<br>GTCTCTGGAGCTCCAGGAAATTCGGGCACATCATATGTCCATGAAACTTCAGATAAA<br>CTAGGGAAAACTGGGTGCTGAGGTGAAAGCATAACTTTTTTGGCACAGAAAGTCTAA<br>AGGGGCCACTGATTTTCAAAGAGATCTGTGATCCCTTTTTGTTTTTTGTTTTTGAGA<br>TGGAGTCTTGCTCTGTTGCCCAGGCTGGAGTGCAATGGCACAATCTCGGCTCACTGC<br>AAGCTCCGCCTCCTGGGTTCAAGCGATTCTCCTGCCTCAGCCTCCTGAGTGGCTGGG<br>ATTACAGGCATGCACCACCATGCCCAGCTAATTTGTTGTATTTTTAGTAGAGACAGG<br>GTTTCACCATGTTGGCCAGTGTGGTCTCAAACTCCTGACCTCATGATTTGCCTGCCT<br>CGGCCTCCCAAAGCACTGGGATTACAGGCGTGAGCCACCACATCCAGCCAGTGATCC<br>TTAAAAGATTAAGAGATGACTGGACCAGGTCTACCTTGATCTTGAAGATTCCCTTGG<br>AATGTTGAGATTTAGGCTTATTTGAGCACTGCCTGCCCAACTGTCAGTGCCAGTGCA<br>TAGCCCTTCTTTTGTCTCCCTTATGAAGACTGCCCTGCAGGGCTGAGATGTGGCAGG<br>AGCTCCCAGGGAAAAACGAAGTGCATTTGATTGGTGTGTATTGGCCAAGTTTTGCTT |

TABLE 1-continued

Type I Proteins of Interest Amino Acid Sequence

| Protein of Interest | Transcript Sequence (SEQ ID NO:)<br>Amino Acid Sequence (SEQ ID NO:) |
|---|---|
| | GTTGTGTGCTTGAAAGAAAATATCTCTGACCAACTTCTGTATTCGTGGACCAAACTG<br>AAGCTATATTTTTCACAGAAGAAGAAGCAGTGACGGGGACACAAATTCTGTTGCCTG<br>GTGGAAAGAAGGCAAAGGCCTTCAGCAATCTATATTACCAGCGCTGGATCCTTTGAC<br>AGAGAGTGGTCCCTAAACTTAAATTTCAAGACGGTATAGGCTTGATCTGTCTTGCTT<br>ATTGTTGCCCCCTGCGCCTAGCACAATTCTGACACACAATTGGAACTTACTAAAAAT<br>TTTTTTTTACTGTT (SEQ ID NO: 81)<br><br>>NP_116171.3 hepatitis A virus cellular receptor 2 precursor [*Homo sapiens*]<br>MFSHLPFDCVLLLLLLLLTRSSEVEYRAEVGQNAYLPCFYTPAAPGNLVPVCWGKGA<br>CPVFECGNVVLRTDERDVNYWTSRYWLNGDFRKGDVSLTIENVTLADSGIYCCRIQI<br>PGIMNDEKFNLKLVIKPAKVTPAPTRQRDFTAAFPRMLTTRGHGPAETQTLGSLPDI<br>NLTQISTLANELRDSRLANDLRDSGATIRIGIYIGAGICAGLALALIFGALIFKWYS<br>HSKEKIQNLSLISLANLPPSGLANAVAEGIRSEENIYTIEENVYEVEEPNEYYCYVS<br>SRQQPSQPLGCRFAMP (SEQ ID NO: 82) |
| Mouse Tim-3 (HAVCR2) | >NM_134250.2 *Mus musculus* hepatitis A virus cellular receptor 2 (Havcr2), mRNA<br>ACCATTTTAACCGAGGAGCTAAAGCTATCCCTACACAGAGCTGTCCTTGGATTTCCC<br>CTGCCAAGTACTCATGTTTTCAGGTCTTACCCTCAACTGTGTCCTGCTGCTGCTGCA<br>ACTACTACTTGCAAGGTCATTGGAAAATGCTTATGTGTTTGAGGTTGGTAAGAATGC<br>CTATCTGCCCTGCAGTTACACTCTATCTACACCTGGGGCACTTGTGCCTATGTGCTG<br>GGGCAAGGGATTCTGTCCTTGGTCACAGTGTACCAACGAGTTGCTCAGAACTGATGA<br>AAGAAATGTGACATATCAGAAATCCAGCAGATACCAGCTAAAGGGCGATCTCAACAA<br>AGGAGACGTGTCTCTGATCATAAAGAATGTGACTCTGGATGACCATGGGACCTACTG<br>CTGCAGGATACAGTTCCCTGGTCTTATGAATGATAAAAAATTAGAACTGAAATTAGA<br>CATCAAAGCAGCCAAGGTCACTCCAGCTCAGACTGCCCATGGGGACTCTACTACAGC<br>TTCTCCAAGAACCCTAACCACGGAGAGAAATGGTTCAGAGACACAGACACTGGTGAC<br>CCTCCATAATAACAATGGAACAAAAATTTCCACATGGGCTGATGAAATTAAGGACTC<br>TGGAGAAACGATCAGAACTGCTATCCACATTGGAGTGGGAGTCTCTGCTGGGTTGAC<br>CCTGGCACTTATCATTGGTGTCTTAATCCTTAAATGGTATTCCTGTAAGAAAAAGAA<br>GTTATCGAGTTTGAGCCTTATTACACTGGCCAACTTGCCTCCAGGAGGGTTGGCAAA<br>TGCAGGAGCAGTCAGGATTCGCTCTGAGGAAAATATCTACACCATCGAGGAGAACGT<br>ATATGAAGTGGAGAATTCAAATGAGTACTACTGCTACGTCAACAGCCAGCAGCCATC<br>CTGACCGCCTCTGGACTGCCACTTTTAAAGGCTCGCCTTCATTTCTGACTTTGGTAT<br>TTCCCTTTTTGAAAACTATGTGATATGTCACTTGGCAACCTCATTGGAGGTTCTGAC<br>CACAGCCACTGAGAAAAGAGTTCCAGTTTTCTGGGGATAATTAACTCACAAGGGGAT<br>TCGACTGTAACTCATGCTACATTGAAATGCTCCATTTTATCCCTGAGTTTCAGGGAT<br>CGGATCTCCCACTCCAGAGACTTCAATCATGCGTGTTGAAGCTCACTCGTGCTTTCA<br>TACATTAGGAATGGTTAGTGTGATGTCTTTGAGACATAGAGGTTTGTGGTATATCTG<br>CAAAGCTCCTGAACAGGTAGGGGGAATAAAGGGCTAAGATAGGAAGGTGAGGTTCTT<br>TGTTGATGTTGAAAATCTAAAGAAGTTGGTAGCTTTTCTAGAGATTTCTGACCTTGA<br>AAGATTAAGAAAAAGCCAGGTGGCATATGCTTAACACTATATAACTTGGGAACCTTA<br>GGCAGGAGGGTGATAAGTTCAAGGTCAGCCAGGGCTATGCTGGTAAGACTGTCTCAA<br>AATCCAAAGACGAAAATAAACATAGAGACAGCAGGAGGCTGGAGATGAGGCTCGGAC<br>AGTGAGGTGCATTTTGTACAAGCACGAGGAATCTATATTTGATCGTAGACCCCACAT<br>GAAAAAGCTAGGCCTGGTAGAGCATGCTTGTAGACTCAAGAGATGGAGAGGTAAAGG<br>CACAACAGATCCCCGGGGCTTGCGTGCAGTCAGCTTAGCCTAGGTGCTGAGTTCCAA<br>GTCCACAAGAGTCCCTGTCTCAAAGTAAGATGGACTGAGTATCTGGCGAATGTCCAT<br>GGGGGTTGTCCTCTGCTCTCAGAAGAGACATGCACATGAACCTGCACACACACACAC<br>ACACACACACACACACACACACACACACACACACACACACATGAAATGAAGGTTC<br>TCTCTGTGCCTGCTACCTCTCTATAACATGTATCTCTACAGGACTCTCCTCTGCCTC<br>TGTTAAGACATGAGTGGGAGCATGGCAGAGCAGTCCAGTAATTAATTCCAGCACTCA<br>GAAGGCTGGAGCAGAAGCGTGGAGAGTTCAGGAGCACTGTGCCCAACACTGCCAGAC<br>TCTTCTTACAGAAGAAAAAGGTTACCCGCAAGCAGCCTGCTGTCTGTAAAAGGAAAC<br>CCTGCGAAAGGCAAACTTTGACTGTTGTGTGCTCAAGGGGAACTGACTCAGACAACT<br>TCTCCATTCCTGGAGGAAACTGGAGCTGTTTCTGACAGAAGAACAACCGGTGACTGG<br>GACATACGAAGGCAGAGCTCTTGCAGCAATCTATATAGTCAGCAAAATATTCTTTGG<br>GAGGACAGTCGTCACCAAATTGATTTCCAAGCCGGTGGACCTCAGTTTCATCTGGCT<br>TACAGCTGCCTGCCCAGTGCCCTTGATCTGTGCTGGCTCCCATCTATAACAGAATCA<br>AATTAAATAGACCCCGAGTGAAAATATTAAGTGAGCAGAAAGGTAGCTTTGTTCAAA<br>GATTTTTTTGCATTGGGGAGCAACTGTGTACATCAGAGGACATCTGTTAGTGAGGAC<br>ACCAAAACCTGTGGTACCGTTTTTTCATGTATGAATTTTGTTGTTTAGGTTGCTTCT<br>AGCTAGCTGTGGAGGTCCTGGCTTTCTTAGGTGGGTATGGAAGGGAGACCATCTAAC<br>AAAATCCATTAGAGATAACAGCTCTCATGCAGAAGGGAAAACTAATCTCAAATGTTT<br>TAAAGTAATAAAACTGTACTGGCAAAGTACTTTGAGCATATTTAAA (SEQ ID NO: 83)<br><br>>NP_599011.2 hepatitis A virus cellular receptor 2 homolog precursor [*Mus musculus*]<br>MFSGLTLNCVLLLLQLLLARSLENAYVFEVGKNAYLPCSYTLSTPGALVPMCWGKGF<br>CPWSQCTNELLRTDERNVTYQKSSRYQLKGDLNKGDVSLIIKNVTLDDHGTYCCRIQ<br>FPGLMNDKKLELKLDIKAAKVTPAQTAHGDSTTASPRTLTTERNGSETQTLVTLHNN |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| | NGTKISTWADEIKDSGETIRTAIHIGVGVSAGLTLALIIGVLILKWYSCKKKKLSSL<br>SLITLANLPPGGLANAGAVRIRSEENIYTIEENVYEVENSNEYYCYVNSQQPS<br>(SEQ ID NO: 84) |
| Human Tim-4<br>(TIMD4) | >NM_138379.3 *Homo sapiens* T cell immunoglobulin and mucin<br>domain containing 4 (TIMD4), transcript variant 1, mRNA<br>AGACTCCTGGGTCCGGTCAACCGTCAAAATGTCCAAAGAACCTCTCATTCTCTGGCT<br>GATGATTGAGTTTTGGTGGCTTTACCTGACACCAGTCACTTCAGAGACTGTTGTGAC<br>GGAGGTTTTGGGTCACCGGGTGACTTTGCCCTGTCTGTACTCATCCTGGTCTCACAA<br>CAGCAACAGCATGTGCTGGGGGAAAGACCAGTGCCCCTACTCCGGTTGCAAGGAGGC<br>GCTCATCCGCACTGATGGAATGAGGGTGACCTCAAGAAAGTCAGCAAAATATAGACT<br>TCAGGGGACTATCCCGAGAGGTGATGTCTCCTTGACCATCTTAAACCCCAGTGAAAG<br>TGACAGCGGTGTGTACTGCTGCCGCATAGAAGTGCCTGGCTGGTTCAACGATGTAAA<br>GATAAACGTGCGCCTGAATCTACAGAGAGCCTCAACAACCACGCACAGAACAGCAAC<br>CACCACCACACGCAGAACAACAACAACAAGCCCCACCACCACCCGACAAATGACAAC<br>AACCCCAGCTGCACTTCCAACAACAGTCGTGACCACACCCGATCTCACAACCGGAAC<br>ACCACTCCAGATGACAACCATTGCCGTCTTCACAACAGCAAACACGTGCCTTTCACT<br>AACCCCAAGCACCCTTCCGGAGGAAGCCACAGGTCTTCTGACTCCCGAGCCTTCTAA<br>GGAAGGGCCCATCCTCACTGCAGAATCAGAAACTGTCCTCCCCAGTGATTCCTGGAG<br>TAGTGTTGAGTCTACTTCTGCTGACACTGTCCTGCTGACATCCAAAGAGTCCAAAGT<br>TTGGGATCTCCCATCAACATCCCACGTGTCAATGTGGAAAACGAGTGATTCTGTGTC<br>TTCTCCTCAGCCTGGAGCATCTGATACAGCAGTTCCTGAGCAGAACAAAACAACAAA<br>AACAGGACAGATGGATGGAATACCCATGTCAATGAAGAATGAAATGCCCATCTCCCA<br>ACTACTGATGATCATCGCCCCCTCCTTGGGATTTGTGCTCTTCGCATTGTTTGTGGC<br>GTTTCTCCTGAGAGGGAAACTCATGGAAACCTATTGTTCGCAGAAACACACAAGGCT<br>AGACTACATTGGAGATAGTAAAAATGTCCTCAATGACGTGCAGCATGGAAGGGAAGA<br>CGAAGACGGCCTTTTTACCCTCTAACAACGCAGTAGCATGTTAGATTGAGGATGGGG<br>GCATGACACTCCAGTGTCAAAATAAGTCTTAGTAGATTTCCTTGTTTCATAAAAAAG<br>ACTCACTTATTCCATGGATGTCATTGATCCAGGCTTGCTTTAGTTTCATGAATGAAG<br>GGTACTTTAGAGACCACAA (SEQ ID NO: 85)<br><br>>NP_612388.2 T-cell immunoglobulin and mucin domain-<br>containing protein 4 isoform 1 precursor [*Homo sapiens*]<br>MSKEPLILWLMIEFWWLYLTPVTSETVVTEVLGHRVTLPCLYSSWSHNSNSMCWGKD<br>QCPYSGCKEALIRTDGMRVTSRKSAKYRLQGTIPRGDVSLTILNPSESDSGVYCCRI<br>EVPGWFNDVKINVRLNLQRASTTTHRTATTTTRRTTTTSPTTTRQMTTTPAALPTTV<br>VTTPDLTTGTPLQMTTIAVFTTANTCLSLTPSTLPEEATGLLTPEPSKEGPILTAES<br>ETVLPSDSWSSVESTSADTVLLTSKESKVWDLPSTSHVSMWKTSDSVSSPQPGASDT<br>AVPEQNKTTKTGQMDGIPMSMKNEMPISQLLMIIAPSLGFVLFALFVAFLLRGKLME<br>TYCSQKHTRLDYIGDSKNVLNDVQHGREDEDGLFTL (SEQ ID NO: 86) |
| Mouse Tim-4<br>(TIMD4) | >NM_178759.4 *Mus musculus* T cell immunoglobulin and mucin<br>domain containing 4 (Timd4), mRNA<br>AGATCCTATCAAAATGTCCAAGGGGCTTCTCCTCCTCTGGCTGGTGACGGAGCTCTG<br>GTGGCTTTATCTGACACCAGCTGCCTCAGAGGATACAATAATAGGGTTTTTGGGCCA<br>GCCGGTGACTTTGCCTTGTCATTACCTCTCGTGGTCCCAGAGCCGCAACAGTATGTG<br>CTGGGGCAAAGGTTCATGTCCCAATTCCAAGTGCAATGCAGAGCTTCTCCGTACAGA<br>TGGAACAAGAATCATCTCCAGGAAGTCAACAAAATATACACTTTTGGGGAAGGTCCA<br>GTTTGGTGAAGTGTCCTTGACCATCTCAAACACCAATCGAGGTGACAGTGGGGTGTA<br>CTGCTGCCGTATAGAGGTGCCTGGCTGGTTCAATGATGTCAAGAAGAATGTGCGCTT<br>GGAGCTGAGGAGAGCCACAACAACCAAAAAACCAACAACAACCACCCGGCCAACCAC<br>CACCCCTTATGTGACCACCACCACCCCAGAGCTGCTTCCAACAACAGTCATGACCAC<br>ATCTGTTCTCCCAACCACCACACCACCCCAGACACTAGCCACCACTGCCTTCAGTAC<br>AGCAGTGACCACGTGCCCCTCAACAACACCTGGCTCCTTCTCACAAGAAACCACAAA<br>AGGGTCCGCCTTCACTACAGAATCAGAAACTCTGCCTGCATCCAATCACTCTCAAAG<br>AAGCATGATGACCATATCTACAGACATAGCCGTACTCAGGCCCACAGGCTCTAACCC<br>TGGGATTCTCCCATCCACTTCACAGCTGACGACACAGAAAACAACATTAACAACAAG<br>TGAGTCTTTGCAGAAGACAACTAAATCACATCAGATCAACAGCAGACAGACCATCTT<br>GATCATTGCCTGCTGTGTGGGATTTGTGCTAATGGTGTTATTGTTTCTGGCGTTTCT<br>CCTTCGAGGGAAAGTCACAGGAGCCAACTGTTTGCAGAGACACAAGAGGCCAGACAA<br>CACTGAAGATAGTGACAGCGTCCTCAATGACATGTCACACGGGAGGGATGATGAAGA<br>CGGGATCTTCACTCTCTGACTCACCATCTTTATTTAGGATTAAGGATAGGGAATGGC<br>ACTTGAATTGTCAAAATAAGTTTGGGGACATTGTAATTTCCGTTTAAAGTCTCACTC<br>TGTTTACTGATGCTGTGGGTCCTGTCTGGTTGTATCTTCCCACATGAAGGTGCTTTA<br>GAGACACATTTTCCCTGCCTCGTGCCTTAGTCCTCTTTGTTGTTTTGTGGCTAGGTG<br>ACTTTTCACACTGGGCTTGAACACTGTCAGTGATGGTGAAATCCTTGCCACAGCTTT<br>GGGAGTCTCTTGCAGTCTCCCAGCAGTAGAGGGAGTTAGAAATATCCAGAGGGGAAA<br>AAAAAATCTCTCTTTTCAGACAGTATCTGCTTTATTGGTGGTAGCTGAACTTCATTT<br>ATACAGAGCTCCTTTAACCTGTCTGTCTTCTTCTTGGTATCTAAGCTGCCTTTTGTT<br>TTTGTTTTTGTTTTTGTTTTTATGATATTAACTTCTTTTCACATTCAAGTTTCTTTA<br>AAGTTGACTATAGTGCCTTCTGAACTCTTGCAGAGAGTTTGGATTTTGGAAGCTGCC<br>AGGTACCCATCACAGCAGGGGTGCCAGTGACAAGGATGGTGTACAAATGAAACACTG<br>AAGCTATCCAAATAAATTCCTCTAAGTGTAATTCATTTTACTGCAGCACAGGAAGAA<br>CAAATTTGTCTTACAACTTTAATAATTAGTACCATTATGAACCCTAGGAGAGAAATA<br>AGAGCAAATACCTGTTGAATAAATGAATGTAAGAAAATGTGTGTCTGAGCAAGAATA |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| | CTCTGTCTGGCTACTATGGGAAGCTAGCTAGATCTGAAAGACATTCTCAGACTATCC<br>TCATGTTCAAGGCATTAAAGGAATAAGCCTCCAGCCCCTAACCTTAGGAGAATTCTG<br>CAGTCAAGTGAGGAGTTTTTAAAACAGGAATCTCTAGGTTCCAGTCCTCTAGCTATT<br>CTTTTATGCTTAGTCCAGGTAATGAGTTGAACATCCAAGTATTTTTTAAGGACCCAA<br>AGAAATGCAACCAGAGCTATTACCAGAATTTTGGAGTGGTCCTCCTAGAGTTGCCGC<br>ATGTTGCTGGGAAAATTGGGGTCTTAGAGTTCTTAGTCTACTTAATAAAAGAATTTT<br>AAAAAATGG (SEQ ID NO: 87) |
| | >NP_848874.3 T-cell immunoglobulin and mucin domain-containing protein 4 precursor [*Mus musculus*]<br>MSKGLLLLWLVTELWWLYLTPAASEDTIIGFLGQPVTLPCHYLSWSQSRNSMC<br>WGKGSCPNSKCNAELLRTDGTRIISRKSTKYTLLGKVQFGEVSLTISNTNRGD<br>SGVYCCRIEVPGWFNDVKKNVRLELRRATTTKKPTTTTRPTTTPYVTTTTPEL<br>LPTTVMTTSVLPTTTPPQTLATTAFSTAVTTCPSTTPGSFSQETTKGSAFTTE<br>SETLPASNHSQRSMMTISTDIAVLRPTGSNPGILPSTSQLTTQKTTLTTSESL<br>QKTTKSHQINSRQTILIIACCVGFVLMVLLFLAFLLRGKVTGANCLQRHKRPD<br>NTEDSDSVLNDMSHGRDDEDGIFTL (SEQ ID NO: 88) |
| Human CEACAM1 | >NM_001712.5 *Homo sapiens* CEA cell adhesion molecule 1 (CEACAM1), transcript variant 1, mRNA<br>AGCACAGAGAGTGGAAAACAGCAGAGGTGACAGAGCAGCCGTGCTCGAAGCGT<br>TCCTGGAGCCCAAGCTCTCCTCCACAGGTGAAGACAGGGCCAGCAGGAGACAC<br>CATGGGGCACCTCTCAGCCCCACTTCACAGAGTGCGTGTACCCTGGCAGGGGC<br>TTCTGCTCACAGCCTCACTTCTAACCTTCTGGAACCCGCCCACCACTGCCCAG<br>CTCACTACTGAATCCATGCCATTCAATGTTGCAGAGGGGAAGGAGGTTCTTCT<br>CCTTGTCCACAATCTGCCCCAGCAACTTTTTGGCTACAGCTGGTACAAAGGGG<br>AAAGAGTGGATGGCAACCGTCAAATTGTAGGATATGCAATAGGAACTCAACAA<br>GCTACCCCAGGGCCCGCAAACAGCGGTCGAGAGACAATATACCCCAATGCATC<br>CCTGCTGATCCAGAACGTCACCCAGAATGACACAGGATTCTACACCCTACAAG<br>TCATAAAGTCAGATCTTGTGAATGAAGAAGCAACTGGACAGTTCCATGTATAC<br>CCGGAGCTGCCCAAGCCCTCCATCTCCAGCAACAACTCCAACCCTGTGGAGGA<br>CAAGGATGCTGTGGCCTTCACCTGTGAACCTGAGACTCAGGACACAACCTACC<br>TGTGGTGGATAAACAATCAGAGCCTCCCGGTCAGTCCCAGGCTGCAGCTGTCC<br>AATGGCAACAGGACCCTCACTCTACTCAGTGTCACAAGGAATGACACAGGACC<br>CTATGAGTGTGAAATACAGAACCCAGTGAGTGCGAACCGCAGTGACCCAGTCA<br>CCTTGAATGTCACCTATGGCCCGGACACCCCCACCATTTCCCCTTCAGACACC<br>TATTACCGTCCAGGGGCAAACCTCAGCCTCTCCTGCTATGCAGCCTCTAACCC<br>ACCTGCACAGTACTCCTGGCTTATCAATGGAACATTCCAGCAAAGCACACAAG<br>AGCTCTTTATCCCTAACATCACTGTGAATAATAGTGGATCCTATACCTGCCAC<br>GCCAATAACTCAGTCACTGGCTGCAACAGGACCACAGTCAAGACGATCATAGT<br>CACTGAGCTAAGTCCAGTAGTAGCAAAGCCCCAAATCAAAGCCAGCAAGACCA<br>CAGTCACAGGAGATAAGGACTCTGTGAACCTGACCTGCTCCACAAATGACACT<br>GGAATCTCCATCCGTTGGTTCTTCAAAAACCAGAGTCTCCCGTCCTCGGAGAG<br>GATGAAGCTGTCCCAGGGCAACACCACCCTCAGCATAAACCCTGTCAAGAGGG<br>AGGATGCTGGGACGTATTGGTGTGAGGTCTTCAACCCAATCAGTAAGAACCAA<br>AGCGACCCCATCATGCTGAACGTAAACTATAATGCTCTACCACAAGAAAATGG<br>CCTCTCACCTGGGGCCATTGCTGGCATTGTGATTGGAGTAGTGGCCCTGGTTG<br>CTCTGATAGCAGTAGCCCTGGCATGTTTTCTGCATTTCGGGAAGACCGGCAGG<br>GCAAGCGACCAGCGTGATCTCACAGAGCACAAACCCTCAGTCTCCAACCACAC<br>TCAGGACCACTCCAATGACCCACCTAACAAGATGAATGAAGTTACTTATTCTA<br>CCCTGAACTTTGAAGCCCAGCAACCCACACAACCAACTTCAGCCTCCCCATCC<br>CTAACAGCCACAGAAATAATTTATTCAGAAGTAAAAAAGCAGTAATGAAACCT<br>GTCCTGCTCACTGCAGTGCTGATGTATTTCAAGTCTCTCACCCTCATCACTAG<br>GAGATTCCTTTCCCCTGTAGGGGTAGAGGGGTGGGGACAGAAACAACTTTCTC<br>CTACTCTTCCTTCCTAATAGGCATCTCCAGGCTGCCTGGTCACTGCCCCTCTC<br>TCAGTGTCAATAGATGAAAGTACATTGGGAGTCTGTAGGAAACCCAACCTTCT<br>TGTCATTGAAATTTGGCAAAGCTGACTTTGGGAAAGAGGGACCAGAACTTCCC<br>CTCCCTTCCCCTTTTCCCAACCTGGACTTGTTTTAAACTTGCCTGTTCAGAGC<br>ACTCATTCCTTCCCACCCCCAGTCCTGTCCTATCACTCTAATTCGGATTTGCC<br>ATAGCCTTGAGGTTATGTCCTTTTCCATTAAGTACATGTGCCAGGAAACAAGA<br>GAGAGAGAAAGTAAAGGCAGTAATGCCTTCTCCTATTTCTCCAAAGCCTTGTG<br>TGAACTCACCAAACACAAGAAAATCAAATATATAACCAATAGTGAAATGCCAC<br>ACCTTTGTCCACTGTCAGGGTTGTCTACCTGTAGGATCAGGGTCTAAGCACCT<br>TGGTGCTTAGCTAGAATACCACCTAATCCTTCTGGCAAGCCTGTCTTCAGAGA<br>ACCCACTAGAAGCAACTAGGAAAATCACTTGCCAAAATCCAAGGCAATTCCTG<br>ATGGAAAATGCAAAAGCACATATATGTTTTAATATCTTTATGGGCTCTGTTCA<br>AGGCAGTGCTGAGAGGGAGGGGTTATAGCTTCAGGAGGGAACCAGCTTCTGAT<br>AAACACAATCTGCTAGGAACTTGGGAAAGGAATCAGAGAGCTGCCCTTCAGCG<br>ATTATTTAAATTATTGTTAAAGAATACACAATTTGGGGTATTGGGATTTTTCT<br>CCTTTTCTCTGAGACATTCCACCATTTTAATTTTTGTAACTGCTTATTTATGT<br>GAAAAGGGTTATTTTTACTTAGCTTAGCTATGTCAGCCAATCCGATTGCCTTA<br>GGTGAAAGAAACCACCGAAATCCCTCAGGTCCCTTGGTCAGGAGCCTCTCAAG<br>ATTTTTTTTGTCAGAGGCTCCAAATAGAAAATAAGAAAAGGTTTTCTTCATTC<br>ATGGCTAGAGCTAGATTTAACTCAGTTTCTAGGCACCTCAGACCAATCATCAA<br>CTACCATTCTATTCCATGTTTGCACCTGTGCATTTTCTGTTTGCCCCCATTCA |

TABLE 1-continued

Type I Proteins of Interest Amino Acid Sequence

| Protein of Interest | Transcript Sequence (SEQ ID NO:)<br>Amino Acid Sequence (SEQ ID NO:) |
|---|---|
| | CTTTGTCAGGAAACCTTGGCCTCTGCTAAGGTGTATTTGGTCCTTGAGAAGTG<br>GGAGCACCCTACAGGGACACTATCACTCATGCTGGTGGCATTGTTTACAGCTA<br>GAAAGCTGCACTGGTGCTAATGCCCCTTGGGGAAATGGGGCTGTGAGGAGGAG<br>GATTATAACTTAGGCCTAGCCTCTTTTAACAGCCTCTGAAATTTATCTTTTCT<br>TCTATGGGGTCTATAAATGTATCTTATAATAAAAAGGAAGGACAGGAGGAAGA<br>CAGGCAAATGTACTTCTCACCCAGTCTTCTACACAGATGGAATCTCTTTGGGG<br>CTAAGAGAAAGGTTTTATTCTATATTGCTTACCTGATCTCATGTTAGGCCTAA<br>GAGGCTTTCTCCAGGAGGATTAGCTTGGAGTTCTCTATACTCAGGTACCTCTT<br>TCAGGGTTTTCTAACCCTGACACGGACTGTGCATACTTTCCCTCATCCATGCT<br>GTGCTGTGTTATTTAATTTTTCCTGGCTAAGATCATGTCTGAATTATGTATGA<br>AAATTATTCTATGTTTTTATAATAAAAATAATATATCAGACATCGA (SEQ<br>ID NO: 89)<br><br>>NP_001703.2 carcinoembryonic antigen-related cell<br>adhesion molecule 1 isoform 1 precursor [*Homo*<br>*sapiens*]<br>MGHLSAPLHRVRVPWQGLLLTASLLTFWNPPTTAQLTTESMPFNVAEGKEVLL<br>LVHNLPQQLFGYSWYKGERVDGNRQIVGYAIGTQQATPGPANSGRETIYPNAS<br>LLIQNVTQNDTGFYTLQVIKSDLVNEEATGQFHVYPELPKPSISSNNSNPVED<br>KDAVAFTCEPETQDTTYLWWINNQSLPVSPRLQLSNGNRTLTLLSVTRNDTGP<br>YECEIQNPVSANRSDPVTLNVTYGPDTPTISPSDTYYRPGANLSLSCYAASNP<br>PAQYSWLINGTFQQSTQELFIPNITVNNSGSYTCHANNSVTGCNRTTVKTIIV<br>TELSPVVAKPQIKASKTTVTGDKDSVNLTCSTNDTGISIRWFFKNQSLPSSER<br>MKLSQGNTTLSINPVKREDAGTYWCEVFNPISKNQSDPIMLNVNYNALPQENG<br>LSPGAIAGIVIGVVALVALIAVALACFLHFGKTGRASDQRDLTEHKPSVSNHT<br>QDHSNDPPNKMNEVTYSTLNFEAQQPTQPTSASPSLTATEIIYSEVKKQ<br>(SEQ ID NO: 90) |
| Mouse CEACAM1 | >NM_001039185.1 *Mus musculus* carcinoembryonic<br>antigen-related cell adhesion molecule 1 (Ceacam1),<br>transcript variant 1, mRNA<br>AAAGCTCCTTTAAGAAAAGCAGGGCAGATATCAGGGCAGCCTGGCTTAGCAGT<br>AGTGTTGGAGAAGAAGCTAGCAGGCAGGCAGCAGAGACATGGAGCTGGCCTCA<br>GCACATCTCCACAAAGGGCAGGTTCCCTGGGGAGGACTACTGCTCACAGCCTC<br>ACTTTTAGCCTCCTGGAGCCCTGCCACCACTGCTGAAGTCACCATTGAGGCTG<br>TGCCGCCCCAGGTTGCTGAAGACAACAATGTTCTTCTACTTGTTCACAATCTG<br>CCCCTGGCGCTTGGAGCCTTTGCCTGGTACAAGGGAAACACTACGGCTATAGA<br>CAAAGAAATTGCACGATTTGTACCAAATAGTAATATGAATTTCACGGGGCAAG<br>CATACAGCGGCAGAGAGATAATATACAGCAATGGATCCCTGCTCTTCCAAATG<br>ATCACCATGAAGGATATGGGAGTCTACACACTAGATATGACAGATGAAAACTA<br>TCGTCGTACTCAGGCGACTGTGCGATTTCATGTACACCCCATATTATTAAAGC<br>CCAACATCACAAGCAACAACTCCAATCCCGTGGAGGGTGACGACTCCGTATCA<br>TTAACCTGTGACTCTTACACTGACCCTGATAATATAAACTACCTGTGGAGCAG<br>AAATGGTGAAAGCCTTTCAGAAGGTGACAGGCTGAAGCTGTCTGAGGGCAACA<br>GGACTCTCACTTTACTCAATGTCACGAGGAATGACACAGGACCCTATGTGTGT<br>GAAACCCGGAATCCAGTGAGTGTCAACCGAAGTGACCCATTCAGCCTGAACAT<br>TATCTATGGTCCGGACACCCCGATTATATCCCCCTCAGATATTTATTTGCATC<br>CAGGGTCAAACCTCAACCTCTCCTGCCATGCAGCCTCTAACCCACCTGCACAG<br>TACTTTTGGCTTATCAATGAGAAGCCCCATGCATCCTCCCAAGAGCTCTTTAT<br>CCCCAACATCACTACTAATAATAGCGGAACCTATACCTGCTTCGTCAATAACT<br>CTGTCACTGGCCTCAGTAGGACCACAGTCAAGAACATTACAGTCCTTGAGCCA<br>GTGACTCAGCCCTTCCTCCAAGTCACCAACACCACAGTCAAAGAACTAGACTC<br>TGTGACCCTGACCTGCTTGTCGAATGACATTGGAGCCAACATCCAGTGGCTCT<br>TCAATAGCCAGAGTCTTCAGCTCACAGAGAGAATGACACTCTCCCAGAACAAC<br>AGCATCCTCAGAATAGACCCTATTAAGAGGGAAGATGCCGGCGAGTATCAGTG<br>TGAAATCTCGAATCCAGTCAGCGTCAGGAGGAGCAACTCAATCAAGCTGGACA<br>TAATATTTGACCCAACACAAGGAGGCCTCTCAGATGGCGCCATTGCTGGCATC<br>GTGATTGGAGTTGTGGCTGGGGTGGCTCTAATAGCAGGGCTGGCATATTTCCT<br>CTATTCCAGGAAGTCTGGCGGGGGAAGTGACCAGCGAGATCTCACAGAGCACA<br>AACCCTCAGCCTCCAACCACAATCTGGCTCCTTCTGACAACTCTCCTAACAAG<br>GTGGATGACGTCGCATACACTGTCCTGAACTTCAATTCCCAGCAACCCAACCG<br>GCCAACTTCAGCCCCTTCTTCTCCAAGAGCCACAGAAACAGTTTATTCAGAAG<br>TAAAAAAGAAGTGAGCATAATCTGTCCGTCTGTCCTGCTGGCTGCACCAGTGA<br>TGCATTCCCGGATTCTGTTCCTCACTGGAGGGTCTCAGCACACACACACACGT<br>ACACATGCGCGCGCGCACACACACACACACACACACACACACACACTTACACA<br>CACACTCATGCATTCACTCTATTGACTCCTTCAGTGTCTATAGAAGAAAAGGT<br>GGATCCTGGAGCCTACAGAAAACTCAACCCTTCTAGGCTTTCAAATTTGGCTG<br>AGAGTGAGGTATCAAAATTTCTCACCCTTTCACTTTCCTGACCCAGATTGTTG<br>AAAATTGACCTATTCAGAGCACCTTCATTCCCCTCCCAACTCCAAGTCCTGCC<br>CTATCAGAGTCTGACTTGAATTTCCATAAACCTTGGAGGTCACCTAAGTGCTT<br>ACGCCAAACAAAACAAAACAAAACAAAACAAAACAAAACAAAACAAAACAAAA<br>CAAACCAGAAGCAGGAAATGGCCAGTCCCATATCTTTAAAGGCTGATTGGAAG<br>CCACCATACATGAGAAGATCAAACCTCCATGGGCAATCTACACACCCGACAAC<br>TGTCATGCTTACCCATCTGGGACATTCGAGTCTCTGAACCTTGTGCCCTCACG<br>CCTGAGCCCTTCTCTGAGCCTTTCTCCAGAAAATCCACTCACAGCAACTAGAG |

TABLE 1-continued

| Type I Proteins of Interest Amino Acid Sequence | |
|---|---|
| Protein of Interest | Transcript Sequence (SEQ ID NO:) Amino Acid Sequence (SEQ ID NO:) |
| | AGGCTCTTTGTCAGCAACTCCAAGCAAACTGCTAGGCAGGATTCAGAAGAAAA GACAGCATCTCTAACATCCACCAGGAAGGTGCCCAGAAAAGCAGAGCTGGTGA CTTTGGACTGACAGACATCTGGAGTGTGAAAAAGCAGCACAGAGCTAACCTTC GGAGAGTGTTGAAATTATTTGAAAAGAAGCCATATTTGGAGGTATTGGAGTTT TCCTCTTTCTGAGACAATCCACTATTTGAAAATTGTAGCTACTGAATTGCCTC TCAGTATGCGAGCTGATCACTTTGCCTTAGGGCCACTAGATTTCTGTCTCCCT TAGCCCCTCAAGCCCTTTTGATCATGAGTTCCAAACCAAAAATAAATAAATGA ACAGTGAGGCAGTCCCTTGCAGTACCACTGTCATGGGTCAGGCTAAGCCTCCT GCTTTTCTGAATTAGTCAAGAAAAGCCTTGGTTTCCCTTTTTCCATCTCTTTA TCTTGTCTTTCAGATACTGGCCAGAGCCTGGACACTCTTCCTCTGAGATCTCC AGCTTCTCTGCCTTCTTGTGTTTCTTTTAAACTCTAACAAAAACTGTTCTCAC CTTCAAAAAATAAAATAATAACAAGCTTTCCACATCCCCACCAAAGAGGGACC CAGCTAGGTTTCTGGAAACCCAGCACCAGCCTCCAGCTGCCCTTCTGCAGTGT TTCTGCCTCTGTTTCCCTTTCGTTTTGACTTTTTTCCTTCTTTTGAGACAGAG TTCCAGCATGGAGCCTGTGCAGGTTTCAATCCCACAGTAACACCTTCTGCAGC ACCCCACCTGCTCAGACTGCAGCCCTGGCCACCAGGCCTGGCTACCTGGACAT TCTGTCTGCCCTGCACTCTCAGGAAACCTTGGCCTCTGCTACTGTCTGTTTGG CTCATTCAAAGTGTGTCCTTAAAGGAATGCAGTCACCCATGCCAGAGGCAGTG TTTACAGCCTGGAATGCTCTGCACTTCCAGTGGACCAGTGCTCCACCGGAAGT GGGCTGTTAGCAGGGTCCTCTCACCTGGCCCTGGCCTTTCTGTAGCCTTGAAT CCTGCCTTCCCCCACCAGGGCACCAGGGATGAGTGCAGCAGCAGGAGGAGAGGC AAACAGTCACCTCAGGAACCTTCTGAGCTAAGGCACACCCTCTGTGCCTGTCA AGCAAAGGTTGTATTGGATATCAAGTGTTTGGTCTCACGCCAAGCCAACAGGC TTTGGAGAGAATTAATTAGTTCTCCTACTCAGGGATTTCTTTCAGTCCTAACA CAGCCTGTGTATATTTTGCTTCACCCACGCAATGCTGGATTATTTAATTTTGC CCGGCTTAAGACAAATCTGAGTTACTTGTAAATTTGCTCTATGTTCATAATAA AAATGTATTATATATCACTGATAGCA (SEQ ID NO: 91) |
| | >NP_001034274.1 carcinoembryonic antigen-related cell adhesion molecule 1 isoform 1 precursor [*Mus musculus*] MELASAHLHKGQVPWGGLLLTASLLASWSPATTAEVTIEAVPPQVAEDNNVLL LVHNLPLALGAFAWYKGNTTAIDKEIARFVPNSNMNFTGQAYSGREIIYSNGS LLFQMITMKDMGVYTLDMTDENYRRTQATVRFHVHPILLKPNITSNNSNPVEG DDSVSLTCDSYTDPDNINYLWSRNGESLSEGDRLKLSEGNRTLTLLNVTRNDT GPYVCETRNPVSVNRSDPFSLNIIYGPDTPIISPSDIYLHPGSNLNLSCHAAS NPPAQYFWLINEKPHASSQELFIPNITTNNSGTYTCFVNNSVTGLSRTTVKNI TVLEPVTQPFLQVTNTTVKELDSVTLTCLSNDIGANIQWLENSQSLQLTERMT LSQNNSILRIDPIKREDAGEYQCEISNPVSVRRSNSIKLDIIFDPTQGGLSDG AIAGIVIGVVAGVALIAGLAYFLYSRKSGGGSDQRDLTEHKPSASNHNLAPSD NSPNKVDDVAYTVLNFNSQQPNRPTSAPSSPRATETVYSEVKKK (SEQ ID NO: 92) |
| Human BTN3A1 | >NM_007048.6 *Homo sapiens* butyrophilin subfamily 3 member A1 (BTN3A1), transcript variant 1, mRNA ATTCCTCACGATGACCCGACAGTCTCTGCTTTCTTTTTCCTTTCTTCCAGAAG GAGATTTAACCATAGTAGAAAGAATGGAGAACTATTAACTGCCTTTCTTCTGT GGGCTGTGATTTTCAGAGGGGAATGCTAAGAGGTGATTTTCAATGTTGGGACT CAAAGGTGAAGACACTGAAGGACAGAATTTTTGGCAGAGGAAAGATCTTCTTC GGTCACCATACTTGAGTTAGCTCTAGGGAAGTGGAGGTTTCCATTTGGAATTC TATAGCTTCTTCCAGGTCATAGTGTCTGCCCCCCACCTTCCAGTATCTCCTGA TATGCAGCATGAATGAAAATGGCAAGTTTCCTGGCCTTCCTTCTGCTCAACTT TCGTGTCTGCCTCCTTTTGCTTCAGCTGCTCATGCCTCACTCAGCTCAGTTTT CTGTGCTTGGACCCTCTGGGCCCATCCTGGCCATGGTGGGTGAAGACGCTGAT CTGCCCTGTCACCTGTTCCCGACCATGAGTGCAGAGACCATGGAGCTGAAGTG GGTGAGTTCCAGCCTAAGGCAGGTGGTGAACGTGTATGCAGATGGAAAGGAAG TGGAAGACAGGCAGAGTGCACCGTATCGAGGGAGAACTTCGATTCTGCGGGAT GGCATCACTGCAGGGAAGGCTGCTCTCCGAATACACAACGTCACAGCCTCTGA CAGTGGAAAGTACTTGTGTTATTTCCAAGATGGTGACTTCTATGAAAAAGCCC TGGTGGAGCTGAAGGTTGCAGCACTGGGTTCTGATCTTCACGTTGATGTGAAG GGTTACAAGGATGGAGGGATCCATCTGGAGTGCAGGTCCACTGGCTGGTACCC CCAACCCCAAATACAGTGGAGCAACAACAAGGGAGAGAACATCCCGACTGTGG AAGCACCTGTGGTTGCAGACGGAGTGGGCCTGTATGCAGTAGCAGCATCTGTG ATCATGAGAGGCAGCTCTGGGGAGGGTGTATCCTGTACCATCAGAAGTTCCCT CCTCGGCCTGGAAAAGACAGCCAGCATTTCCATCGCAGACCCCTTCTTCAGGA GCGCCCAGAGGTGGATCGCCGCCCTGGCAGGGACCCTGCCTGTCTTGCTGCTG CTTCTTGGGGGAGCCGGTTACTTCCTGTGGCAACAGCAGGAGGAAAAAAAGAC TCAGTTCAGAAAGAAAAAGAGAGAGCAAGAGTTGAGAGAAATGGCATGGAGCA CAATGAAGCAAGAACAAAGCACAAGAGTGAAGCTCCTGGAGGAACTCAGATGG AGAAGTATCCAGTATGCATCTCGGGGAGAGAGACATTCAGCCTATAATGAATG GAAAAAGGCCCTCTTCAAGCCTGCGGATGTGATTCTGGATCCAAAAACAGCAA ACCCCATCCTCCTTGTTTCTGAGGACCAGAGGAGTGTGCAGCGTGCCAAGGAG CCCCAGGATCTGCCAGACAACCCTGAGAGATTTAATTGGCATTATTGTGTTCT CGGCTGTGAGAGCTTCATATCAGGGAGACATTACTGGGAGGTGGAGGTAGGGG ACAGGAAAGAGTGGCATATAGGGGTGTGCAGTAAGAATGTGCAGAGAAAAGGC |

TABLE 1-continued

| Type I Proteins of Interest Amino Acid Sequence | |
|---|---|
| Protein of Interest | Transcript Sequence (SEQ ID NO:) Amino Acid Sequence (SEQ ID NO:) |
| | TGGGTCAAAATGACACCTGAGAATGGATTCTGGACTATGGGGCTGACTGATGG GAATAAGTATCGGACTCTAACTGAGCCCAGAACCAACCTGAAACTTCCTAAGC CCCCTAAGAAAGTGGGGGTCTTCCTGGACTATGAGACTGGAGATATCTCATTC TACAATGCTGTGGATGGATCGCATATTCATACTTTCCTGGACGTCTCCTTCTC TGAGGCTCTATATCCTGTTTTCAGAATTTTGACCTTGGAGCCCACGGCCCTGA CTATTTGTCCAGCGTGAAAAGAAGAAGAGAGTTCCTCCAATTCTGACCGAGTG CTGATCATTCCCTAGAGACACCAGTAACCCCGGGCTTAGCTAACGAAAGTGGG GAGCCTCAGGCTGAAGTAACTTTTCTCTGCTTCTCCCTGCCCAGCTCAGAGCT GAGGGCCTCCCCCTCCACAGCAACCAATCACAACCATAAAGCTACAAGCACGC ACTGAAGCACTTTACTGATACTCATTCAATTATTCATATGACAGTTGTTTGAG TTTGGTACCATCTTATTTTCCCCTTATACAGATAAGGAAACTGGGGTGCAGAA AAGTGAATTGACTACAAAGTAGACATGACTAGTTAACAACACAGCTGGGATCT AAACAGCAATAACTAACATTAATGGAGAACTTAAAATGCTCTGAGTGCTGTGT TATGAGCTTTGGTGGATGTCACTCCTTTAATCCTCGCAACACCCTGTCGGGTA GTCTCATTTAGCAAGTATGGAAGTTGAGGCAGGGCAACATTAAGCAACTTACA TAACTCATGCAGTAATTTCTGCAGTTGGGAGATGTTCAGCTTCAGTCCCCGGC CCTATGGCCGTTCTTTTCCACCCTGTTTCTTCCCCCATAGGAAGAACCCACCT GTAGCCCTGAGGTTCTTTTCCCAGGATGGCTCCAGGATAAGGATCACTGTAGG TGGTTGTGGAGTTGACACCCCTGTTGACTCCTTCCCAGCTGATTGTCAGAGCC TTAGACCCAGCACGCCTTGGATTAGCTCTGCAGAGTGTCTTGGTTGAGAGAAT AACCTCACCGTACCCACATGACACGTGATTTGGAAAGAGACTAGAGGCCACAC TTGATAAATCATGGGGAACAGATGTGTTCCACCCAACAAATGTGATAAGTGAT CATGCAGCCAGAGCCAGCCTTCCTTCAATCAAGGTTTCCAGGCAGAGCAAATA CCCTAGAGATTCTCTGTGATATAGGAAATTTGGATGAAGGGAGCTAGAAGAAA TACAGGGATTTTTTTTTTTTTTTTTAAGATGGAGTCTTACTCTGTTGCTAGGCTG GAGTGCAGTGGTGCGATCTCAGCTCCCTGCAACCTCCACCTCCTGGGTTCAAA CAATTCTCCTGCCTCAGCCTCCCGAGTACTGGGAATATAGGTGCACGCCACCA CACCCAACAAATTTTTGTACTTTTAGTACAGATGAGGGTTCACTATGTTGGCC AGGATGGTCTCGATCTCTTGACCTCATGATCCACCCACCTCGGTCTCCCAAAG TGCTGGGATTACAGGCTTGAGCCACCGGGTGACCGGCTTACAGGGATATTTTT AATCCCGTTATGGACTCTGTCTCCAGGAGAGGGGTCTATCCACCCCTGCTCAT TGGTGGATGTTAAACCAATATTCCTTTCAACTGCTGCCTGCTAGGGAAAAACT ACTCCTCATTATCATCATTATTATTGCTCTCCACTGTATCCCCTCTACCTGGC ATGTGCTTGTCAAGTTCTAGTTGTTCAATAAATTTGTTAATAATGCTGA (SEQ ID NO: 93) |
| | >NP_008979.3 butyrophilin subfamily 3 member A1 isoform a precursor [*Homo sapiens*] MKMASFLAFLLLNFRVCLLLLQLLMPHSAQFSVLGPSGPILAMVGEDADLPCH LFPTMSAETMELKWVSSSLRQVVNVYADGKEVEDRQSAPYRGRTSILRDGITA GKAALRIHNVTASDSGKYLCYFQDGDFYEKALVELKVAALGSDLHVDVKGYKD GGIHLECRSTGWYPQPQIQWSNNKGENIPTVEAPVVADGVGLYAVAASVIMRG SSGEGVSCTIRSSLLGLEKTASISIADPFFRSAQRWIAALAGTLPVLLLLLGG AGYFLWQQQEEKKTQFRKKKREQELREMAWSTMKQEQSTRVKLLEELRWRSIQ YASRGERHSAYNEWKKALFKPADVILDPKTANPILLVSEDQRSVQRAKEPQDL PDNPERFNWHYCVLGCESFISGRHYWEVEVGDRKEWHIGVCSKNVQRKGWVKM TPENGFWTMGLTDGNKYRTLTEPRTNLKLPKPPKKVGVFLDYETGDISFYNAV DGSHIHTFLDVSFSEALYPVFRILTLEPTALTICPA (SEQ ID NO: 94) |
| Human BTN3A2 | >NM_007047.5 *Homo sapiens* butyrophilin subfamily 3 member A2 (BTN3A2), transcript variant 1, mRNA GACTCTTACTGTTTCTCATGGTGAGAAGACAATATTTGCTTTCTCTTTTTCCT TTCTTCCGGATGAGAGGCTAAGCCATAATAGAAAGAATGGAGAATTATTGATT GACCGTCTTTATTCTGTGGGCTCTGATTCTCCAATGGGAATACCAAGGGATGG TTTTCCATACTGGAACCCAAAGGTAAAGACACTCAAGGACAGACATTTTTGGC AGAGCATAGATGAAAATGGCAAGTTCCCTGGCTTTCCTTCTGCTCAACTTTCA TGTCTCCCTCCTCTTGGTCCAGCTGCTCACTCCTTGCTCAGCTCAGTTTTCTG TGCTTGGACCCTCTGGGCCCATCCTGGCCATGGTGGGTGAAGACGCTGATCTG CCCTGTCACCTGTTCCCGACCATGAGTGCAGAGACCATGGAGCTGAAGTGGGT AAGTTCCAGCCTAAGGCAGGTGGTGAACGTGTATGCAGATGGAAAGGAAGTGG AAGACAGGCAGAGTGCACCGTATCGAGGGAGAACTTCGATTCTGCGGGATGGC ATCACTGCAGGGAAGGCTGCTCTCCGAATACACAACGTCACAGCCTCTGACAG TGGAAAGTACTTGTGTTATTTCCAAGATGGTGACTTCTATGAAAAAGCCCTGG TGGAGCTGAAGGTTGCAGCACTGGGTTCTAATCTTCACGTCGAAGTGAAGGGT TATGAGGATGGAGGGATCCATCTGGAGTGCAGGTCCACCGGCTGGTACCCCCA ACCCCAAATACAGTGGAGCAACGCCAAGGGAGAGAACATCCCAGCTGTGGAAG CACCTGTGGTTGCAGATGGAGTGGGCCTATATGAAGTAGCAGCATCTGTGATC ATGAGAGGCGGCTCCGGGGAGGGTGTATCCTGCATCATCAGAAATTCCCTCCT CGGCCTGGAAAAGACAGCCAGCATTTCCATCGCAGACCCCTTCTTCAGGAGCG CCCAGCCCTGGATCGCAGCCCTGGCAGGGACCCTGCCTATCTTGCTGCTGCTT CTCGCCGGAGCCAGTTACTTCTTGTGGAGACAACAGAAGGAAATAACTGCTCT GTCCAGTGAGATAGAAAGTGAGCAAGAGATGAAAGAAATGGGATATGCTGCAA CAGAGCGGGAAATAAGCCTAAGAGAGAGCCTCCAGGAGGAACTCAAGAGGAAA AAAATCCAGTACTTGACTCGTGGAGAGGAGTCTTCGTCCGATACCAATAAGTC AGCCTGATGCTCTAATGGAAAAATGGCCCTCTTCAAGCCTGGTGAGGAAATGC |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| | TTCAGATGAGGCTCCACCTTGTTAAATAAATTGGATGTATGGAAAAATAGACT<br>GCAGAAAAGGGGAACTCATTTAGCTCACGAGTGGTCGAGTGAAGATTGAAAAT<br>TAACCTCTGAGGGCCAGCACAGCAGCTCATGCCTGTAATCCTAGCACTTTGGA<br>AGGCTGAGGAGGGCGGATCACAAGGTCAGGAGATCAAGACCATCCTGGCTAAC<br>ACGGTGAAACCCCGTCTCTACTAAAAATACAAAAAATAAAAAATTAGCCGGGC<br>ATGGTGACGGGCACCTGTAGTCCCAGCTACTCGGGAGGCTGAGGCAGGAGAAT<br>GGCATGAACCCGGAAGGCAGAGCTTGCAGTGAGCCGAGATCACGCCACTGCAC<br>TCCAGCCTGGGAGACAGAGCGAGACTCTGTCTCAAGAAAAAAAAAAAAAAAAA<br>AAAAGAAAAGAAAATTAACCTCTGAGTATAAAGCATCAGTGGGCAGAATCAAT<br>GTGGGGAGGGAAACAACAAAAATGTAGAAAGAGGATCCTTGTTGCTTCTTGGG<br>GCCGCATCAGGGTATTGGGTTAGGCAGATACTGACCTTACTTTCATTTCCCCT<br>CTGGTCACTAGACCCCTGGGGCTTTCACCAATGACATTGATGAGAGAATCACA<br>TTCAGGGCAGGCTAGGGACACGGGGTTCTGGAAGGACCTCCTCAGCATGGCCC<br>AAGCCTTGCATGCTGTGGCTCTTAAATCCAGGAAAAATGGCTGACCCCATGGA<br>CACCTCCTCAAACTCTCTGCAGCAGATGTAATTCTGTATCCAGACATGGCAAA<br>TGCCATCCTCCTTGTTTCTGAGGACCAGAGGAGTGTACAGCGTGCTGAGGAGC<br>CCCATGACCTACCAGACAACCCTGAGAGATTTGAATGGCGTTACTGTGTGCTT<br>GGCTGTGAAAGCTTCATGTCAGAGAGACACTACTGGGAGGTGGAAGTGGGGGA<br>CAGAAAAGAGTGGCATATTGGGGTATGTAGTAAGAACGTGGAGAGGAAAAAAG<br>TTTGGGTCAAAATGACACCGGAGAACGGATACTGGACTATGGGCCTGACTGAT<br>GGGAATAAGTATCGGGCTCTCACTGAGCCCAGAACCAACCTGAAACTTCCTGA<br>GCCTCCTAGGAAAGTGGGGGTCATCCTGGACTATGAGACTGGACATATCTCGT<br>TCTACAATGCCACGGATGGATCTCATATCTACACATTTCTGCACGCCTCTTCC<br>TCTGAGCCTCTGTATCCTGTATTCAGAATTTTGACCTTGGAGCCCACTGCCCT<br>GACCGTTTGCCCAATACCAAAAGTAGAGAGTTCCCCCGATCCCGACCTAGTGC<br>CTGATCATTCCCTGGAGATACCACTGACCCCAGGCTTAGCTAATGAAAGTGGG<br>GAGCCTCAGGCTGAAGTAACATCTCTGCTTCTCCCTGCCCAGCCTGGAGCTAA<br>GGGTCTCACCCTCCACAACAGCCAGTCAGAACCATAAAGCTACAGGCACACAC<br>TGAAGCACTTTACTGATATTCATTCAATTATTCCATAGGACAGTTGTTTGAGT<br>TTGGTGCCACCTTATTGGCCCCTTTATACAGATAAGGAAACTGGGGTGTAGAA<br>AAGTGTATTGACTTTACAAAGCAGACAGGAATAGTGAACAACAGAGCTGGGAT<br>CTGAACAACAATGACTAACATTAATGGAGAATTTAAAACGTTCTGAGTGCTGT<br>GTTATGAGCTTTGGTGGGTGTCACTCCTTTAATCCTCACAACACCCTGTCAGG<br>TAGTCTCATTTGGCAAGTATGGAAGCAGAGGCAGGGCAACATTAAGTAGCTTA<br>CATAACTCACACGGTAATTTGTGCAGTTGGGAGATGTTCAGCTTCAGTCCCTG<br>GCCAATTGCCCGTTCTTTTCCAGCCTGATTTTTCCTGCATGGGAAGAGCCCAC<br>ATGTAGCCCTGAGGTTCCCTTCCCAGGACAGCTCCAGGATCGAGATCACTGTG<br>AGTGGTTGTGGAGTTAAGACCCCTATGGACTCCTTCCCAGCTGATTATCAGAG<br>CCTTAGACCCAGCACTCCTTGGATTGGCTCTGCAGAGTGTCTTGGTTGAGAGA<br>ATAACGTTGCAGTTCCCACAGGGCATGTGACTTTGAAAGAGACTAGAGGCCAC<br>ACTCAGTTAATAATGGGGCACAGATGTGTTCCCACCCAACAAATGTGATAAGT<br>GATCGTGCAGCCAGAGCCAGCCTTCCTTCAGTCAAGGTTTCCAGGCAGAGCAA<br>ATACCCTAGAGATTCTCTGTAATATTGGTAATTTGGATGAAGGAAGCTAGAAG<br>AATTACAGGGATGTTTTTAATCCCACTATGGACTCAGTCTCCTGGAAAAGGAT<br>CTGTCCACTCCTGGTCATTGGTGGATGTTAAACCCATATTCCTTTCAACTGCT<br>GCCTGCTAGGGAAAACTGCTCCTCATTATCATCACTATTATTGCTCACCACTG<br>TATCCCCTCTACTGGGCAAGTGCTTGTCAAGTTCTAGTTGTTCAATAAATTTG<br>TTAATAATGCTGA (SEQ ID NO: 95)<br><br>>NP_008978.2 butyrophilin subfamily 3 member A2 isoform a precursor [*Homo sapiens*]<br>MKMASSLAFLLLNFHVSLLLVQLLTPCSAQFSVLGPSGPILAMVGEDADLPCH<br>LFPTMSAETMELKWVSSSLRQVVNVYADGKEVEDRQSAPYRGRTSILRDGITA<br>GKAALRIHNVTASDSGKYLCYFQDGDFYEKALVELKVAALGSNLHVEVKGYED<br>GGIHLECRSTGWYPQPQIQWSNAKGENIPAVEAPVVADGVGLYEVAASVIMRG<br>GSGEGVSCIIRNSLLGLEKTASISIADPFFRSAQPWIAALAGTLPILLLLLAG<br>ASYFLWRQQKEITALSSEIESEQEMKEMGYAATEREISLRESLQEELKRKKIQ<br>YLTRGEESSSDTNKSA (SEQ ID NO: 96) |
| Human BTN2A1 | >NM_007049.5 *Homo sapiens* butyrophilin subfamily 2 member A1 (BTN2A1), transcript variant 1, mRNA<br>AGATTTCGTTTCCTGCATCTCCAAACATGGCGACCTAGGAGAAGGGGAAGAAC<br>AATTTTTTCTCCTCTTTTGGGAAGGTTTGTGTCTAGTAGTGCCTGTGCCCCTG<br>GGCAGATTGGAGAGAAGAGGGACGACTGGAGAATCGTCGAGAACCAGCGGAGA<br>AAAGAAAAAGCAACGTTTAATTCTAGAAGGCCTCCTGTCCCTGCCTGCTCTGG<br>GTGCTCATGGAATCAGCTGCTGCCCTGCACTTCTCCCGGCCAGCCTCCCTCCT<br>CCTCCTCCTCCTCAGCCTGTGTGCACTGGTCTCAGCCCAGTTTATTGTCGTGG<br>GGCCCACTGATCCCATCTTGGCCACGGTTGGAGAAAACACTACGTTACGCTGC<br>CATCTGTCACCCGAGAAAAATGCTGAGGACATGGAGGTGCGGTGGTTCCGGTC<br>TCAGTTCTCCCCCGCAGTGTTTGTGTATAAAGGTGGCAGAGAGAGAACAGAGG<br>AGCAGATGGAGGAGTACCGAGGAAGAACCACCTTTGTGAGCAAAGACATCAGC<br>AGGGGCAGCGTGGCCCTGGTCATACACAACATCACAGCCCAGGAAAACGGCAC<br>CTACCGCTGTTACTTCCAAGAAGGCAGGTCCTACGATGAGGCCATCCTGCACC<br>TCGTAGTGGCAGGACTAGGCTCTAAGCCCCTCATTTCAATGAGGGGCCATGAA<br>GACGGGGGCATCCGGCTGGAGTGCATATCTAGAGGGTGGTACCCAAAGCCCCT |

TABLE 1-continued

Type I Proteins of Interest Amino Acid Sequence

| Protein of Interest | Transcript Sequence (SEQ ID NO:)<br>Amino Acid Sequence (SEQ ID NO:) |
|---|---|
| | CACAGTGTGGAGGGACCCCTACGGTGGGGTTGCGCCTGCCCTGAAAGAGGTCT<br>CCATGCCTGATGCAGACGGCCTCTTCATGGTCACCACGGCTGTGATCATCAGA<br>GACAAGTCTGTGAGGAACATGTCCTGCTCTATCAACAACACCCTGCTCGGCCA<br>GAAGAAAGAAAGTGTCATTTTTATTCCAGAATCCTTTATGCCCAGTGTGTCTC<br>CCTGTGCAGTGGCCCTGCCTATCATTGTGGTTATTCTGATGATACCCATTGCC<br>GTATGCATCTATTGGATCAACAAACTCCAAAAGGAAAAAAAGATTCTGTCAGG<br>GGAAAAGGAGTTTGAACGGGAAACAAGAGAAATTGCTCTAAAGGAACTGGAGA<br>AAGAACGTGTGCAAAAAGAGGAAGAACTTCAAGTAAAAGAGAAACTTCAAGAA<br>GAATTGCGATGGAGAAGAACATTCTTACATGCTGTTGATGTGGTCCTGGATCC<br>AGACACCGCTCATCCCGATCTCTTCCTGTCAGAGGACCGGAGAAGTGTGAGAA<br>GGTGCCCCTTCAGGCACCTAGGGGAGAGCGTGCCTGACAACCCAGAGAGATTC<br>GACAGTCAGCCTTGTGTCCTAGGCCGGGAGAGCTTCGCTTCAGGGAAACATTA<br>CTGGGAGGTGGAGGTGGAAAACGTGATTGAGTGGACTGTGGGGGTCTGTAGAG<br>ACAGTGTTGAGAGGAAAGGGGAGGTCCTGCTGATTCCTCAGAATGGCTTCTGG<br>ACCTTGGAGATGCATAAAGGGCAATACCGGGCCGTGTCCTCCCCTGATAGGAT<br>TCTCCCTTTGAAGGAGTCCCTTTGCCGGGTGGGCGTCTTCCTGGACTATGAAG<br>CTGGAGATGTCTCCTTCTACAACATGAGGGACAGATCGCACATCTACACATGT<br>CCCCGTTCAGCCTTTTCCGTGCCTGTGAGGCCCTTCTTCAGGTTGGGGTGTGA<br>GGACAGCCCCATCTTCATCTGCCCTGCACTCACAGGAGCCAATGGGGTCACGG<br>TGCCTGAAGAGGGCCTGACACTTCACAGAGTGGGGACCCACCAGAGCCTATAG<br>AATCAATTCCTTGGTCTCACAGCCATGTAGACAAGCCCTGGTCATCTCAGCAG<br>CCACCGCACAACACCCCTGGTGGAAGACACGCCCTCCTCCCCTCTGGTCACAC<br>AAGAGAACATCTTCCAGCTGCCTCTTTCACACCCACTACAGACCTCAGCCCCA<br>GTTTTCTCCTCCTCACTAGGCTGTGTTTTTAGTAGTTCCTTTGCTTGTAACTA<br>TGGGATGGGATCCAGGCATAGGGAACTAGTTGTTACACAGCTCCCAGCCAAGA<br>AGAAAGTGTGAGAAGTTGATGGGCAGCAAACCTGCTGTTTAACATCAGGGTGA<br>CCACATTAAGCCCAGTATTCCAGTTGGCACCAGAAGATATGGACTTGGAATGA<br>GGCCTACAGGGTTCACCAGGATGTAAGAGGAGAGAGGAATCCACAGGACCACC<br>AGAGAGGAGAGGGAACCAGATATGCAGATCAGAGATAGAGGAAGTGGAACCAG<br>AGAGCTGGGAGGGACCAAGGTTGTAAGGGTGGCTAAGTCCCACCATAACAGCT<br>AAGGGGACCTGGGAGATGATGGCTCATTTCCACCCAGCCCCAGGATTTCCAGA<br>GCGCACATCCACAGGCCTGGACCTGGGATGAAGATGAATGAAGAACATGGATG<br>CACGTGGATGTAGTTTGGCTCAGGTGTCCCTGCAGTTGGCAAGGAGTCAGTAC<br>TCAGTCCCTGAGTGTGGCTGAAATTTGAGGTCCTGGCTGAGCCAAGGAGTAAT<br>GGACCAGATCTACCTCAGTATTCAAGTTCAGTGGGGACACCAGTGGCTTCAAA<br>CTTCCTGGTTTCATGATATCTTGAGACGCCTTACAAATGATGGAGGATTCCAA<br>AGAGTTTTTGTTTATTTGGGTTAATATTTGTTGGTATTTATGGCATTTGAGAT<br>TGAAACTAAGAAATGTTTTAATTTATTACCTTTACAACATTTATTTACATTAC<br>ATACATACATTTACAACATTTATTAATTTATATTAAAATAGCATGAATAAGCC<br>AATTATAGGTTAATATAAGTAGAATGTTTGTGAAAAATAAGTATGGTATCCAA<br>AGCAAAATAAATTTTATTGTGAAGTGTG (SEQ ID NO: 97)<br><br>>NP_008980.1 butyrophilin subfamily 2 member A1<br>isoform 1 precursor [*Homo sapiens*]<br>MESAAALHFSRPASLLLLLLSLCALVSAQFIVVGPTDPILATVGENTTLRCHL<br>SPEKNAEDMEVRWFRSQFSPAVFVYKGGRERTEEQMEEYRGRTTFVSKDISRG<br>SVALVIHNITAQENGTYRCYFQEGRSYDEAILHLVVAGLGSKPLISMRGHEDG<br>GIRLECISRGWYPKPLTVWRDPYGGVAPALKEVSMPDADGLFMVTTAVIIRDK<br>SVRNMSCSINNTLLGQKKESVIFIPESFMPSVSPCAVALPIIVVILMIPIAVC<br>IYWINKLQKEKKILSGEKEFERETREIALKELEKERVQKEEELQVKEKLQEEL<br>RWRRTFLHAVDVVLDPDTAHPDLFLSEDRRSVRRCPFRHLGESVPDNPERFDS<br>QPCVLGRESFASGKHYWEVEVENVIEWTVGVCRDSVERKGEVLLIPQNGFWTL<br>EMHKGQYRAVSSPDRILPLKESLCRVGVFLDYEAGDVSFYNMRDRSHIYTCPR<br>SAFSVPVRPFFRLGCEDSPIFICPALTGANGVTVPEEGLTLHRVGTHQSL<br>(SEQ ID NO: 98) |
| Human BTNL8 | >NM_001040462.3 *Homo sapiens* butyrophilin like 8<br>(BTNL8), transcript variant 2, mRNA<br>AGAACAGCGCAGTTTGCCCTCCGCTCACGCAGAGCCTCTCCGTGGCTTCCGCA<br>CCTTGAGCATTAGGCCAGTTCTCCTCTTCTCTCTAATCCATCCGTCACCTCTC<br>CTGTCATCCGTTTCCATGCCGTGAGGTCCATTCACAGAACACATCCATGGCTC<br>TCATGCTCAGTTTGGTTCTGAGTCTCCTCAAGCTGGGATCAGGGCAGTGGCAG<br>GTGTTTGGGCCAGACAAGCCTGTCCAGGCCTTGGTGGGGGAGGACGCAGCATT<br>CTCCTGTTTCCTGTCTCCTAAGACCAATGCAGAGGCCATGGAAGTGCGGTTCT<br>TCAGGGGCCAGTTCTCTAGCGTGGTCCACCTCTACAGGGACGGGAAGGACCAG<br>CCATTTATGCAGATGCCACAGTATCAAGGCAGGACAAAACTGGTGAAGGATTC<br>TATTGCGGAGGGGCGCATCTCTCTGAGGCTGGAAAACATTACTGTGTTGGATG<br>CTGGCCTCTATGGGTGCAGGATTAGTTCCCAGTCTTACTACCAGAAGGCCATC<br>TGGGAGCTACAGGTGTCAGCACTGGGCTCAGTTCCTCTCATTTCCATCACGGG<br>ATATGTTGATAGAGACATCCAGCTACTCTGTCAGTCCTCGGGCTGGTTCCCCC<br>GGCCCACAGCGAAGTGGAAAGGTCCACAAGGACAGGATTTGTCCACAGACTCC<br>AGGACAAACAGAGACATGCATGGCCTGTTTGATGTGGAGATCTCTCTGACCGT<br>CCAAGAGAACGCCGGGAGCATATCCTGTTCCATGCGGCATGCTCATCTGAGCC<br>GAGAGGTGGAATCCAGGGTACAGATAGGAGATACCTTTTCGAGCCTATATCG<br>TGGCACCTGGCTACCAAAGTACTGGGAATACTCTGCTGTGGCCTATTTTTGG |

TABLE 1-continued

Type I Proteins of Interest Amino Acid Sequence

| Protein of Interest | Transcript Sequence (SEQ ID NO:) Amino Acid Sequence (SEQ ID NO:) |
|---|---|
| | CATTGTTGGACTGAAGATTTTCTTCTCCAAATTCCAGTGGAAAATCCAGGCGG AACTGGACTGGAGAAGAAAGCACGGACAGGCAGAATTGAGAGACGCCCGGAAA CACGCAGTGGAGGTGACTCTGGATCCAGAGACGGCTCACCCGAAGCTCTGCGT TTCTGATCTGAAAACTGTAACCCATAGAAAAGCTCCCCAGGAGGTGCCTCACT CTGAGAAGAGATTTACAAGGAAGAGTGTGGTGGCTTCTCAGAGTTTCCAAGCA GGGAAACATTACTGGGAGGTGGACGGAGGACACAATAAAAGGTGGCGCGTGGG AGTGTGCCGGGATGATGTGGACAGGAGGAAGGAGTACGTGACTTTGTCTCCCG ATCATGGGTACTGGGTCCTCAGACTGAATGGAGAACATTTGTATTTCACATTA AATCCCCGTTTTATCAGCGTCTTCCCCAGGACCCCACCTACAAAAATAGGGGT CTTCCTGGACTATGAGTGTGGGACCATCTCCTTCTTCAACATAAATGACCAGT CCCTTATTTATACCCTGACATGTCGGTTTGAAGGCTTATTGAGGCCCTACATT GAGTATCCGTCCTATAATGAGCAAAATGGAACTCCCATAGTCATCTGCCCAGT CACCCAGGAATCAGAGAAAGAGGCCTCTTGGCAAAGGGCCTCTGCAATCCCAG AGACAAGCAACAGTGAGTCCTCCTCACAGGCAACCACGCCCTTCCTCCCCAGG GGTGAAATGTAGGATGAATCACATCCCACATTCTTCTTTAGGGATATTAAGGT CTCTCTCCCAGATCCAAAGTCCCGCAGCAGCCGGCCAAGGTGGCTTCCAGATG AAGGGGGACTGGCCTGTCCACATGGGAGTCAGGTGTCATGGCTGCCCTGAGCT GGGAGGGAAGAAGGCTGACATTACATTTAGTTTGCTCTCACTCCATCTGGCTA AGTGATCTTGAAATACCACCTCTCAGGTGAAGAACCGTCAGGAATTCCCATCT CACAGGCTGTGGTGTAGATTAAGTAGACAAGGAATGTGAATAATGCTTAGATC TTATTGATGACAGAGTGTATCCTAATGGTTTGTTCATTATATTACACTTTCAG TAA (SEQ ID NO: 99) |
| | >NP_001035552.1 butyrophilin-like protein 8 isoform 2 precursor [*Homo sapiens*] MALMLSLVLSLLKLGSGQWQVFGPDKPVQALVGEDAAFSCFLSPKTNAEAMEV RFFRGQFSSVVHLYRDGKDQPFMQMPQYQGRTKLVKDSIAEGRISLRLENITV LDAGLYGCRISSQSYYQKAIWELQVSALGSVPLISITGYVDRDIQLLCQSSGW FPRPTAKWKGPQGQDLSTDSRTNRDMHGLFDVEISLTVQENAGSISCSMRHAH LSREVESRVQIGDTFFEPISWHLATKVLGILCCGLFFGIVGLKIFFSKFQWKI QAELDWRRKHGQAELRDARKHAVEVTLDPETAHPKLCVSDLKTVTHRKAPQEV PHSEKRFTRKSVVASQSFQAGKHYWEVDGGHNKRWRVGVCRDDVDRRKEYVTL SPDHGYWVLRLNGEHLYFTLNPRFISVFPRTPPTKIGVFLDYECGTISFFNIN DQSLIYTLTCRFEGLLRPYIEYPSYNEQNGTPIVICPVTQESEKEASWQRASA IPETSNSESSSQATTPFLPRGEM (SEQ ID NO: 100) |
| Human BTN2A2 | >NM_006995.5 *Homo sapiens* butyrophilin subfamily 2 member A2 (BTN2A2), transcript variant 1, mRNA GGGACTTTTTGGACACCCAGAGAACAGGTCCCAGATACCGAGTCCGCAACTCC AAACATCGCGATTAATAGGAGGCCTCTGGTCTCTGCCTGCCCTGGGTGCTCAT GGAACCAGCTGCTGCTCTGCACTTCTCCCTGCCAGCCTCCCTCCTCCTCCTCC TGCTCCTCCTCCTTCTCAGCCTGTGTGCACTGGTCTCAGCCCAGTTTACTGTC GTGGGGCCAGCTAATCCCATCCTGGCCATGGTGGGAGAAAACACTACATTACG CTGCCATCTGTCACCCGAGAAAAATGCTGAGGACATGGAGGTGCGGTGGTTCC GGTCTCAGTTCTCCCCCGCAGTGTTTGTGTATAAGGGTGGGAGAGAGAGAACA GAGGAGCAGATGGAGGAGTACCGGGGAAGAATCACCTTTGTGAGCAAAGACAT CAACAGGGGCAGCGTGGCCCTGGTCATACATAACGTCACAGCCCAGGAGAATG GGATCTACCGCTGTTACTTCCAAGAAGGCAGGTCCTACGATGAGGCCATCCTA CGCCTCGTGGTGGCAGGCCTTGGGTCTAAGCCCCTCATTGAAATCAAGGCCCA AGAGGATGGGAGCATCTGGCTGGAGTGCATATCTGGAGGGTGGTACCCAGAGC CCCTCACAGTGTGGAGGGACCCCTACGGTGAGGTTGTGCCCGCCCTGAAGGAG GTTTCCATCGCTGATGCTGACGGCCTCTTCATGGTCACCACAGCTGTGATCAT CAGAGACAAGTATGTGAGGAATGTGTCCTGCTCTGTCAACAACACCCTGCTCG GCCAGGAGAAGGAAACTGTCATTTTTATTCCAGAATCCTTTATGCCCAGCGCA TCTCCCTGGATGGTGGCCCTAGCTGTCATCCTGACCGCATCTCCCTGGATGGT GTCCATGACTGTCATCCTGGCTGTTTTCATCATCTTCATGGCTGTCAGCATCT GTTGCATCAAGAAACTTCAAAGGGAAAAAAAGATTCTGTCAGGGGAAAAGAAA GTTGAACAAGAGGAAAAAGAAATTGCACAGCAACTTCAAGAAGAATTGCGATG GAGAAGAACATTCTTACATGCTGCTGATGTGGTCCTGGATCCAGACACCGCTC ATCCCGAGCTCTTCCTGTCAGAGGACCGGAGAAGTGTGAGGCGGGGCCCCTAC AGGCAGAGAGTGCCTGACAACCCAGAGAGATTCGACAGTCAGCCTTGTGTCCT GGGATGGGAGAGCTTCGCCTCAGGGAAACATTACTGGGAGGTGGAGGTGGAAA ACGTGATGGTGTGGACTGTGGGGGTCTGCAGACACAGTGTTGAGAGGAAAGGG GAGGTCCTGCTGATTCCTCAGAATGGCTTCTGGACCCTGGAGATGTTTGGAAA CCAATACCGGGCCCTGTCCTCCCCTGAGAGGATTCTCCCTTTGAAGGAGTCCC TTTGCCGGGTGGGCGTCTTCCTGGACTATGAAGCTGGAGATGTCTCCTTCTAC AACATGAGGGACAGATCGCACATCTACACATGTCCCCGTTCAGCCTTTACTGT GCCTGTGAGGCCCTTCTTCAGGTTAGGGTCTGATGACAGCCCCATCTTCATCT GCCCTGCACTCACAGGAGCCAGTGGGGTCATGGTGCCTGAAGAGGGCCTGAAA CTTCACAGAGTGGGGACCCACCAGAGCCTATAGAATCAATTCCTTGGACTCAC AGCCATGCAGATAAGCCCTGGCCATCTCAGCAGCCACCGCACAACCCCCCTAA TGAAAGACACGCCCTCCTCCCCTCTGGTCACGTAAGAGAACATCTTCCAGCTG CCTTTTTCACACCCACTCCAGCCCTCTGCCCCAGTTTTCTCCTCCTCACTAGT CTGTGGCTTTAGTAGTTCCTTTGCTTGTAATTATGGGATGGGATCCAGGCATA GGGAACTAGTTGTTTCATAGCTCCCAGTCAAAAAGAAAGTGAGAGAAGCTGTT |

TABLE 1-continued

Type I Proteins of Interest Amino Acid Sequence

| Protein of Interest | Transcript Sequence (SEQ ID NO:)<br>Amino Acid Sequence (SEQ ID NO:) |
|---|---|
| | GGGCAGCGAACCTACTGTTTAAAATCAGGATAACCACATTAAGCCCAATATGC<br>CAGTTGGCACCAGATGCTGTGGACTTGGAATGAGGCCAACAGGGTTCACCAGG<br>ATGAGAGAGGAGAGAGGAATCCACAGGACCACCAGAAGGGAGAGGGAACCAGA<br>TATGCAGATCAGAGATAGAGGAAGTGGAACCAGAGAGCTGGGAGGGACCAAGG<br>TTGTAAGGATGGCTAAGTCCCACCATAAGAGCTAAAGGGTCCTGGGAGATGAT<br>GGCTCATTTCCACCCAACCCCAGGATTTCCACAGCACACACCCACAGGCCTGG<br>ACCTGGGATGAAGATGAATGAAGAACATGGACTCATGTGGATGTGGTTTGGCT<br>CAGATGTCCCTGCAATAAACAAGGGGTCAGTACTTAGTCCCTGAGTGTGGTTG<br>AGGTTTGAGGTCCTGGTCGAGCAGGGCAGTACTGGACCAGGTCTACGTCAGCA<br>TTCAGGTTCAATGGGGACACCAGTGGCTTCAAACTTCCTGATCTAATTATGTT<br>TTTAGACACTTAGAAGTTATTGAGGACTTTAAAGAGCTTTTGTTTATTTGGGT<br>TAATATTTATGACATTTGACATTGAAACAAAAATTTAAAATGTTATCTTTTAA<br>TTTATGTTAAAATAGCATTAATAAATCAGTTATAGGTTAATGTAGATAGGATG<br>TTTTGTGAAAAAGCAATCTATTGTGTCCAAATAAAAAAACAAAAAGTGTGACA<br>CTGGTTAACTTTTTCCAGATCTCATGTCTGGCTTAATAAGAGATATTTGTATT<br>ATCATATCTGCCTTTGTATTAAACCTATTGGTATATCATAGGTCATGTTAGCT<br>CAAAAAAACTTTACTGCACACTACTGAGAGAATGAGATGAAAAACGATTAATG<br>TTTCATTATTATTATTGTGAAAATATTATTAACACTGGGGACTCCTTAAGAGT<br>ACATCAGAGTTCTCTCTAGGAATCCCAAAACCACATTTTGAAACTAGAATAGT<br>GGATCCTGGAAGTTAATCCATGTGCTGGTTAATTTTAGATGTCAACCTGACTG<br>GATTAAGGAATACCTAGACAGCTGGTACAACATTATTTCTGGGTGTGTCTGTG<br>AGTGTGTTTCCAGAAGAGATTGGCAAGTGAGTCAGTGGGAAATTCTCTCCTTC<br>TGTTGGCTGGGTGCCCAATACAACAAAAAGGCAGAGGAAAGGCAAATTCTTCT<br>CTCCTCTGGAGCTGAGACACTCTTCTTCTTCTGCCCTTGGACATCAGAACTCC<br>TGGCTCTCCGGCCTTTGAACTTCAGGACTTGTACCAGGAGGCCCTGGGTTCTC<br>AGGCCTTTGGCTTTGGACTGAGAGTTACACAATCAGCTTCCCTGGTTCTGAGG<br>CTTTCAGACTTAAACTGAGCCATGCTACCAGCATCCCAGGGTCTCCAGCCTAC<br>AGATGAGCTGTTGTGCGATTTCTTAGCCTCCATAATCACATGAGCCAATCTCC<br>TTAATAAATGCCTGCTCATAGATCTGTATCTACATCTATATCTGTATGTGCAT<br>CTATATCTATGCCTATATCTATATCTATATCATATTGATTTTGTCTCTCTGGA<br>GAACCCTGACTAATAAAATGAGGCATCTAAAA (SEQ ID NO: 101)<br><br>>NP_008926.2 butyrophilin subfamily 2 member A2 isoform a precursor [*Homo sapiens*]<br>MEPAAALHFSLPASLLLLLLLLLLSLCALVSAQFTVVGPANPILAMVGENTTL<br>RCHLSPEKNAEDMEVRWFRSQFSPAVFVYKGGRERTEEQMEEYRGRITFVSKD<br>INRGSVALVIHNVTAQENGIYRCYFQEGRSYDEAILRLVVAGLGSKPLIEIKA<br>QEDGSIWLECISGGWYPEPLTVWRDPYGEVVPALKEVSIADADGLFMVTTAVI<br>IRDKYVRNVSCSVNNTLLGQEKETVIFIPESFMPSASPWMVALAVILTASPWM<br>VSMTVILAVFIIFMAVSICCIKKLQREKKILSGEKKVEQEEKEIAQQLQEELR<br>WRRTFLHAADVVLDPDTAHPELFLSEDRRSVRRGPYRQRVPDNPERFDSQPCV<br>LGWESFASGKHYWEVEVENVMVWTVGVCRHSVERKGEVLLIPQNGFWTLEMFG<br>NQYRALSSPERILPLKESLCRVGVFLDYEAGDVSFYNMRDRSHIYTCPRSAFT<br>VPVRPFFRLGSDDSPIFICPALTGASGVMVPEEGLKLHRVGTHQSL (SEQ ID NO: 102) |
| Mouse BTN2A2 | >NM_175938.3 *Mus musculus* butyrophilin, subfamily 2, member A2 (Btn2a2), transcript variant 1, mRNA<br>GAAATTGTGAGACTTGCACGCGGAATGGGTCCTCCGAGGTCTGCTGTCGCGAG<br>TCCCAGCACTTTGCAAGTAATGGAGAACAGAAAATTCTTTCCTCTCTACTGTA<br>GCAGTTTGTTCTCTGGTGGCGACTGTGCTCAGCGACAAGTTGGAGAGTAGAGA<br>AAAGGCAAGATAATCAGCATTTGAGGGTCAGAGAAGAAAAGAAAACGCAGTTA<br>ATTCTAGAAGGTTTTCTGTCCACACGTGACCTAGGTGACTCTGTCCTGAAGAC<br>CTATGGAGCCTACAACTTCCCTGCGTTCTTGCCCGATAGCCTCCCTTCTCTTC<br>TTCTTGGTCCTCAGCCTGTTTGTGCTGGTCTCAGCCCAGTTTACTGTCATAGG<br>ACCAGCTGAGCCCATCCTGGCCATGGTAGGAGAGAATACCACACTACACTGCC<br>ACCTGTCACCAGAGAGAAATGCCGAAGAGATGGAGGTGCGGTGGTTCCGGTGG<br>CGTTTCTTCCCTGCAGTGCTGGTGTACAGAGGCCATCAAGAGAGACCAGAGGA<br>GCAGATGGTGGCATACCGAGGAAGAACCACCTTCATGCGCACAGACATCAGCA<br>AGGGAAGAGTTGCGCTCATTATCCACAATGTCACAGCCTATGACAATGGCATC<br>TACTGCTGTTACTTCCAGGAAGGCAGGTCCTATGACCAGGCAACCATGAAGCT<br>TATGGTGGCAAGCCTTGGCTCTGAGCCACTTATTAAAATGAAGACACTTGAGG<br>ATGGGAGCATCTTGCTAGAGTGCACATCTGAAGGGTGGTACCCAGAGCCCCGA<br>GCTGTGTGGAGAGACCCCTATGATGAAGTTGTACCTGCCCTGGAGGAGGAGTA<br>TACAGCTGACAGAGAAGGCCTCTTCACAGTCACCATGACTATAATCATCAGGG<br>ACTGCTCTGTGAGGAACATGACCTGCTCTGTCAATAACACTCTGCTCAGCCAG<br>GAGGTGGAAAGTGTGATTCTCATTCCAGAATCCTTCGTGCCCAGCCTTCCTCT<br>GTGGATGGTGGCTGTGGCTGTCACTCTGCCTGTAGTAATGCTGATTCTCCTCA<br>CATCTGGAAGCATCTGCCTTGTCAAGAAACACCGCAGGAAGAAATCTATTCTG<br>TCAGCTGAAAAAGAAGCCGAATATGAAGAGAAGGAAGCTGCACGGCAACTTCA<br>AGAGGAACTGCGATGGAGACGAACCCTCTTACATGCTGCTGACGTGGTCCTGG<br>ACCCAGATACAGCTCATCCTGAGCTCTTCCTGTCAGATGACCAGAGAAGTGTA<br>ATACGAGGCTCTTCGAGGCAGAGTGTGCCTGACAACCCTGAGAGATTTGACTG<br>CCGTCCATGTGTCCTGGGCAGGGAAAGCTTCTCCTCAGGGAAGCATTACTGGG<br>AGGTGGAGGTGGAAAATGTAATGGTGTGGGCCATTGGTGTTTGTAGAGACAGC |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| | GTGGAAAGGAAAGGGGAGGCCCTGTTGGTTCCTCAGAATGGCTTCTGGACCCT<br>GGAGATGTTTGGAAGCCAGTATCGAGCCCTGTCCTCCCCAGAAAAGATCATAC<br>CTCTGAAAGAGCGTCTTCACCGTATAGCTGTCTTCCTGGACTGTGAGGGTGGA<br>GATATTTCTTTCTACAACATGAGAGACAGATCACACATTTACACATGTCCTCC<br>TGTGACTTTCACTGGGCCCCTGAGACCCTTCTTTAGGCTTGGTTCTGATGACA<br>GTCCCCTGTTCATCTGTCCAGCATTCACAGGGGCACAGGGAGTTACAATACCT<br>GAGGGTGGCTTATTCCTATATAAGACAAGACCAATTTCTCAGAGCCTTGTAAG<br>GAAGCCATAGCTCTCTACACAGTACCATCTGTTGGAGACTAGACCCCATGTCC<br>TTCAGATCACATGGAGCATCTTCCAGCTGCCACCTTCACACATACTTCAGGCC<br>CAGTCCTCAGATTACTACATCATTTCTTCTAACTATGGGCCTAGGTAGAGCCA<br>GTCTTAGGGGACTATTGCTGTAATACAGCTCTCTCCTGAGAAGAAAGTGTGAG<br>AAGGGCAGAAAACTTGGAGTTTCAACATGCTGCTCTGGTCACAGTGGATATCA<br>GGCAAGAGCAACAGGGTGGATCAGGATGTAAGAAGTGAGAACTACAGAGGAAG<br>GAGACAGATAAAGATGAATTGAGGCCGAAGATGGAGGAAATGGACTGAAGAGC<br>TCTGGGGTAAGCCCTATGTGACAGCTGTGGATAGGTAGGAGCTAATGGTCCAT<br>TGATATCCAAAGCCAAAGATTTAAATATCACATAGTGTGTCTGGAGTGTATAT<br>CTGTAGACCTACACATGAGAGGAAACAATCATAGTGATGAACTGGATGTAAGC<br>TGGCTCAGACGTCCCTACAATAAACACTTCTGAGTTCCATGTCTGTGCTCAGT<br>AAGAATGGCTTGAGGCTTGCGGTCCATGCTGAGCAGCCAGGTCCACATGAATC<br>GGATTTACTAGAGTAGGTAGCAGTTCAAGTTCCTTAGGCTCAGGATGTCTTCC<br>TTTCCCCCAAGCCCTTCCCCCTTCAAGATAGGTCTCACTATGTAGACCAGGCC<br>AGCCTCCACCTCCAGAGTTCTGGGATTAAAGACAAGCACAACCATGTCCAGTT<br>TATGAGCTTGTGATATATACAGAAGATTAAGTTCTGTGTTCTTGGGTTAGTAA<br>CTGTTGAGATTTGTTTTGAGTCATGCTCTCACTGGCTAGCACTGCTCTTGACT<br>TTCTCTCCCCATCTTTTTGTTATTGCTTTTCAAGACATGGTTTCACTGTGTAT<br>TTCTGGCTGATAAGCTGATTTTGAATTCACAGAGATCTGCCTCTGCCTCCTGA<br>GTGCTGGGATTAAAGGTGTGTTACACTACGCCTGGCTTCACTCTATCTCTTCA<br>GTGTGGGGATTATAGGTTTATACTATCATGCCTAACTAATGTCTGTTGCTGCA<br>TATGACATTTGAACTTTAGAACAGAAAAACAACTATACATATTAATATATATT<br>AAACTAATAATAAGC (SEQ ID NO: 103) |
| | >NP_787952.2 butyrophilin subfamily 2 member A2<br>isoform 1 precursor [*Mus musculus*]<br>MEPTTSLRSCPIASLLFFLVLSLFVLVSAQFTVIGPAEPILAMVGENTTLHCH<br>LSPERNAEEMEVRWFRWRFFPAVLVYRGHQERPEEQMVAYRGRTTFMRTDISK<br>GRVALIIHNVTAYDNGIYCCYFQEGRSYDQATMKLMVASLGSEPLIKMKTLED<br>GSILLECTSEGWYPEPRAVWRDPYDEVVPALEEEYTADREGLFTVTMTIIIRD<br>CSVRNMTCSVNNTLLSQEVESVILIPESFVPSLPLWMVAVAVTLPVVMLILLT<br>SGSICLVKKHRRKKSILSAEKEAEYEEKEAARQLQEELRWRRTLLHAADVVLD<br>PDTAHPELFLSDDQRSVIRGSSRQSVPDNPERFDCRPCVLGRESFSSGKHYWE<br>VEVENVMVWAIGVCRDSVERKGEALLVPQNGFWTLEMFGSQYRALSSPEKIIP<br>LKERLHRIAVFLDCEGGDISFYNMRDRSHIYTCPPVTFTGPLRPFFRLGSDDS<br>PLFICPAFTGAQGVTIPEGGLFLYKTRPISQSLVRKP(SEQ ID NO: 104) |
| Human<br>BTN1A1 | >NM_001732.3 *Homo sapiens* butyrophilin subfamily 1<br>member A1 (BTN1A1), mRNA<br>AGCTTTCTCACTTGGTAGCAGTGGCCTCTTGTGCCTTTTTCTCCAAGATCACC<br>CAGGCTGAAGCTCCTGAGGGGACTCACATCAGTTATCTTGCTGCTCCAGAAGG<br>GTGGGAGATGGCAGTTTTCCCAAGCTCCGGTCTCCCCAGATGTCTGCTCACCC<br>TCATTCTCCTCCAGCTGCCCAAACTGGATTCAGCTCCCTTTGACGTGATTGGA<br>CCCCCGGAGCCCATCCTGGCCGTTGTGGGTGAGGACGCCGAGCTGCCCTGTCG<br>CCTGTCTCCGAACGCGAGCGCCGAGCACTTGGAGCTACGCTGGTTCCGAAAGA<br>AGGTTTCGCCGGCCGTGCTGGTGCATAGGGACGGGCGCGAGCAGGAAGCCGAG<br>CAGATGCCCGAGTACCGCGGGCGGGCGACGCTGGTCCAGGACGGCATCGCCAA<br>GGGGCGCGTGGCCTTGAGGATCCGTGGCGTCAGAGTCTCTGACGACGGGGAGT<br>ACACGTGCTTTTTCAGGGAGGATGGAAGCTACGAAGAAGCCCTGGTGCATCTG<br>AAGGTGGCTGCTCTGGGCTCTGACCCTCACATCAGTATGCAAGTTCAAGAGAA<br>TGGAGAAATCTGTCTGGAGTGCACCTCAGTGGGATGGTACCCAGAGCCCCAGG<br>TGCAGTGGAGAACTTCCAAGGGAGAGAAGTTTCCATCTACATCAGAGTCCAGG<br>AATCCTGATGAAGAAGGTTTGTTCACTGTGGCTGCTTCAGTGATCATCAGAGA<br>CACTTCTGCGAAAAATGTGTCCTGCTACATCCAGAATCTCCTTCTTGGCCAGG<br>AGAAGAAAGTAGAAATATCCATACCAGCTTCCTCCCTCCCAAGGCTGACTCCC<br>TGGATAGTGGCTGTGGCTGTCATCCTGATGGTTCTAGGACTTCTCACCATTGG<br>GTCCATATTTTTCACTTGGAGACTATACAACGAAAGACCCAGAGAGAGGAGGA<br>ATGAATTCAGCTCTAAAGAGAGACTCCTGGAAGAACTCAAATGGAAAAAGGCT<br>ACCTTGCATGCAGTTGATGTGACTCTGGACCCAGACACAGCTCATCCCCACCT<br>CTTTCTTTATGAGGATTCAAAATCTGTTCGACTGGAAGATTCACGTCAGAAAC<br>TGCCTGAGAAAACAGAGAGATTTGACTCCTGGCCCTGTGTGTTGGGCCGTGAG<br>ACCTTCACCTCAGGAAGGCATTACTGGGAGGTGGAGGTGGGAGACAGGACTGA<br>CTGGGCAATCGGCGTGTGTAGGGAGAATGTGATGAAGAAAGGATTTGACCCCA<br>TGACTCCTGAGAATGGGTTCTGGGCTGTAGAGTTGTATGGAAATGGGTACTGG<br>GCCCTCACTCCTCTCCGGACCCCTCTCCCATTGGCAGGGCCCCCACGCCGGGT<br>TGGGATTTTCCTAGACTATGAATCAGGAGACATCTCCTTCTACAACATGAATG<br>ATGGATCTGATATCTATACTTTCTCCAATGTCACTTTCTCTGGCCCCCTCCGG<br>CCCTTCTTTTGCCTATGGTCTAGCGGTAAAAAGCCCCTGACCATCTGCCCAAT |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| | TGCTGATGGGCCTGAGAGGGTCACAGTCATTGCTAATGCCCAGGACCTTTCTA<br>AGGAGATCCCATTGTCCCCCATGGGGGAGGACTCTGCCCCTAGGGATGCAGAC<br>ACTCTCCATTCTAAGCTAATCCCTACCCAACCCAGCCAAGGGGCACCTTAAGG<br>AATATCTCAGCTCATCTGTTTTCCTTTCCTCTAACCCCTCTCCTCCATAGCCT<br>TCTGAGGCTTCACCTGCTAGCTTTACCCAGTCTGTTTCTTCCTGTTGGGTGGC<br>AATTAATTAATCCTGTGAAGGTTACATTGCTGCTGCTAGAGAGGGTGGGGATT<br>GCACCTTCCAAATCTGTTTCTGTACCAATATTTGGGGGATGGAGGGGTGACTC<br>AAACTGCTTCTAGTGTTCTCCTAATCCCTTAAGACTAGAACCTATAGGAAACT<br>ACTTGGAGCAAACTCAAAGGACAGATTAGGGATCGAGATTGGGTCAGGTTAGC<br>ATGGGGTTGTGGTTGAAATATCTTGGTATCCAGGATAAGGGTATGTGGAAAAA<br>CAGGCTTTAGGCAAGTGGAAAATTCAAAATGTGCTGTGAAAGGACAATCTCAG<br>GCTGAAATCCCATAAAGGAACTTGGAGGGAATATTATGATGGAGGGAAGTGAG<br>GTGAATCCAGGCACATGATGAACACCTGGCTCATCCATAGAGTTTTCACAGCC<br>TATATCGCAAATTTTCTAAGCCACGTCCTATAGGACAGAGGAGACTGGCCCCA<br>CTTCTATGGGTCTGAGCTGTGGAAAAGGGAGAGCAGAGAGGAACTGAGATGAG<br>CAGGGATGAAGGGTCAGGCAGAAAGCGTGATAGAGGAGAGAATTTTTGACAAA<br>ACTCAAAAGTTGTTTGCACAGCTGTTCTTTGTACCCTGTTCCTTTCTCTGCGC<br>CCTCCTGTTTCTCCCTTGCCTGGAAGTCATTCCACCCTCAATTTGTTGATCCA<br>CAAGTTTCCAGTTGTCCTCTTCTTTTTGTTATAGCATCTCTCTATTTCAAAGA<br>CATTCCTAGAAGTCATCCTTCAGTGATATCACCACTTGCTCAGTCACCATCTC<br>AACCTTATGTCACCTCAGCCCTCATCTCAATGCCCAAACCCCTTACACACACC<br>TTCAGTTAGCTTCAACTGCCTCCGTTTCCACACTGTGCACCTTTCACTTTCCC<br>TACCCAGCTTTCCTACATGCTGCCTCTCCTCAGGGTCCCCTGAATGCTGCATC<br>ATTGTGTTCAGTGCAGCTGGACTGATTGCACCTGTGTATTTGCCCCTGAGCAC<br>TTTCCTTTACACATGTGGCTTGTCTTGCCAATAGACTCCAGGCTTATACCTTC<br>CATTTCCATCGTATTCTCCAGTTTCCAGGATAGACGTTGCTCATCGTCTTTAC<br>CTAATAAATAAGTTTGTCTGATTGCTGAAA (SEQ ID NO: 105)<br><br>>NP_001723.2 butyrophilin subfamily 1 member A1 precursor [*Homo sapiens*]<br>MAVFPSSGLPRCLLTLILLQLPKLDSAPFDVIGPPEPILAVVGEDAELPCRLS<br>PNASAEHLELRWFRKKVSPAVLVHRDGREQEAEQMPEYRGRATLVQDGIAKGR<br>VALRIRGVRVSDDGEYTCFFREDGSYEEALVHLKVAALGSDPHISMQVQENGE<br>ICLECTSVGWYPEPQVQWRTSKGEKFPSTSESRNPDEEGLFTVAASVIIRDTS<br>AKNVSCYIQNLLLGQEKKVEISIPASSLPRLTPWIVAVAVILMVLGLLTIGSI<br>FFTWRLYNERPRERRNEFSSKERLLEELKWKKATLHAVDVTLDPDTAHPHLFL<br>YEDSKSVRLEDSRQKLPEKTERFDSWPCVLGRETFTSGRHYWEVEVGDRTDWA<br>IGVCRENVMKKGFDPMTPENGFWAVELYGNGYWALTPLRTPLPLAGPPRRVGI<br>FLDYESGDISFYNMNDGSDIYTFSNVTFSGPLRPFFCLWSSGKKPLTICPIAD<br>GPERVTVIANAQDLSKEIPLSPMGEDSAPRDADTLHSKLIPTQPSQGAP<br>(SEQ ID NO: 106) |
| Mouse BTN1A1 | >NM_013483.3 *Mus musculus* butyrophilin, subfamily 1, member A1 (Btn1a1), mRNA<br>AACAGCACACAGCCTTCTTCCTTCTGAAGAGCTCTCTCTTTGGCCCCGGGGTG<br>ACAAGCAGCCCTTTTCACTTGATCACTGTGGCTCTGGCTCCCTTTTCCTCTGG<br>GTCTGTCGAAATCGCCTGAAGCTCTTGGCGGGCTTCATTGCCCCAGTTAGCTC<br>AGAGATGGCAGTTCCCACCAACTCCTGCCTCCTGGTCTGTCTGCTCACCCTCA<br>CTGTCCTACAGCTGCCCACGCTGGATTCGGCAGCTCCCTTCGATGTGACCGCA<br>CCTCAGGAGCCAGTGTTGGCCCTAGTGGGCTCAGATGCCGAGCTGACCTGTGG<br>CTTTTCCCCAAACGCGAGCTCAGAATACATGGAGCTGCTGTGGTTTCGACAGA<br>CGAGGTCGACAGCGGTACTTCTATACCGGGATGGCCAGGAGCAGGAGGGCCAG<br>CAGATGACGGAGTACCGCGGGAGGGCGACGCTGGCGACAGCCGGGCTTCTAGA<br>CGGCCGCGCTACTCTGCTGATCCGAGATGTCAGGGTCTCAGACCAGGGGGAGT<br>ACCGGTGCCTTTTCAAAGACAACGACGACTTCGAGGAGGCCGCCGTATACCTC<br>AAAGTGGCTGCTGTGGGTTCAGATCCTCAAATCAGTATGACGGTTCAAGAGAA<br>TGGAGAAATGGAGCTGGAGTGCACCTCCTCTGGATGGTACCCAGAGCCTCAGG<br>TGCAGTGGAGAACAGGCAACAGAGAGATGCTACCATCCACGTCAGAGTCCAAG<br>AAGCATAATGAGGAAGGCCTGTTCACTGTGGCAGTTTCAATGATGATCAGAGA<br>CAGCTCCATAAAGAACATGTCCTGCTGCATCCAGAATATCCTCCTTGGCCAGG<br>GGAAGGAAGTAGAGATCTCCTTACCAGCTCCCTTCGTGCCAAGGCTGACTCCC<br>TGGATAGTAGCTGTGGCTATCATCTTACTGGCCTTAGGATTTCTCACCATTGG<br>GTCCATATTTTTCACTTGGAAACTATACAAGGAAAGATCCAGTCTGCGGAAGA<br>AGGAATTTGGCTCTAAAGAGAGACTTCTGGAAGAACTCAGATGCAAAAAGACT<br>GTACTGCATGAAGTTGACGTGACTCTGGATCCAGACACAGCCCACCCCCACCT<br>CTTCCTGTATGAAGATTCAAAGTCAGTTCGATTGGAAGATTCACGTCAGATCC<br>TGCCTGATAGACCAGAGAGATTTGACTCCTGGCCCTGTGTGTTGGGCCGTGAG<br>ACCTTTACTTCAGGGAGACATTACTGGGAGGTGGAGGTGGGAGATAGAACTGA<br>CTGGGCCATTGGTGTGTGTAGGGAGAATGTGGTGAAGAAAGGGTTTGACCCCA<br>TGACTCCTGATAATGGGTTCTGGGCTGTGGAGTTGTATGGAAATGGGTACTGG<br>GCCCTCACCCCACTCAGGACCTCTCTCCGATTAGCAGGGCCCCCTCGCAGAGT<br>TGGGGTTTTTCTGGACTATGACGCAGGAGACATTTCCTTCTACAACATGAGTA<br>ACGGATCTCTTATCTATACTTTCCCTAGCATCTCTTTCTCTGGCCCCCTCCGT<br>CCCTTCTTTTGTCTGTGGTCCTGTGGTAAAAAGCCCCTGACCATCTGTTCAAC<br>TGCCAATGGGCCTGAGAAAGTCACAGTCATTGCTAATGTCCAGGACGACATTC |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| | CCTTGTCCCCGCTGGGGGAAGGCTGTACTTCTGGAGACAAAGACACTCTCCAT TCTAAACTGATCCCGTTCTCACCTAGCCAAGCGGCACCATAACAAATATTCCA GCTTCACGACTTTGCCTTCCTTTGACTAATCCCTCATGCCCCGAAGCTTCAGC TGTTGGCTTCTTGCAGCCCTGCTTCTTCCTGGTGGATGGAGATTAATTCACAT TGGGAAGGTTAGGTATGTTGCTGCCAGACAAGGCAGGAAGAAAGGCCATCCTA GTTTGTTTCTGTACTAACAGTGGGGAGGAAGAGAGCTGAATCCTAAACTATTT CCAGTGCTCATATTCCTTCAGGCCAGAGCCTATAGAGAAGGATTTGGTACAAT CACTCGAGGGATCAAGAGGCAATTAGGTTGGCATGGAATTATGGCAGAAACAT CTGGAATAGGGGTATGTGGAATGACAGGTTTTAGGTAAGGGAGAACAAAACCA AACCATAGGATGCTGAGAAAGAAAGATCTTGGACTAAACTCCTAAAAAAGCAC TTAGAGAAGATATGACAGGCAAATGAAGTGAATTTGGTCTAATTTGATACACT TGCCCTGTCCCTAGGGTTTTTCAGTTATATCTCAATTTTTTTGTTGTTAATTA CATTTTTGACAGCTTCATACATGTATATAATGCATTCTAATTACTCTCACTCT CCTCTATTCTGTCTTATTTCCCTCCCCTCCCCTCATACCTTCCTTCTTGCTTC AAACCTGGCACACTGAGTTTAATGGGCTATCATGGGAACATGGATTTAGAGCT TTCCTCTGAGCTCAAGAGAGCAGGTGTGACTGAATACAGTGATTTCCCCTCTC CTACAATCAATCAGCAGTCAATAGCTCAGCTGGGAGGGGTAGGGCCTCATGAG ACTTCCCCTATCAAGGCTAAATGTTGAAAGGGCCAGTTTTTAGCACCTGTGAG ATCATGATTGCAAGAGCCCAGAAGACAGCATTGCTCGGTCATTCTCCCTACCC TTTGGCTTTTCTGGTOTTTTGTCCTCTCTTTCAGGATGTGTCTGAACTCTGTA TCTTAAGTTTTCTATGTCATGTTCTATAAGATAGAGGAGACTGGCCCTGCTTG TTTGAGAGCAATGTGAGCAAGCTAGCAAGAGACAGAAAGGAGCGGAGATGAAT AGGGGTAGAGAAAATTTTTAAACAAACCCTCCAGGTGTGTGTGTGTGTGTGTG TGTCTTCCTCTTTTTTGACCTCCCTAAAGGTCAATCCAACCTCACATTATTGA CTCCACTAGGTGGGGGTTCTGTGTGTGTGTGTGTGTGTGTGTGTGTGTGTGTG TGTGTTTTAAGATAGAGGTTTACTATGTAGCTTAGGCTGGCTTTGAATTCCTG ATCCTCCTGCCTCTACCTTCCAAGTGCTGGAAACATAGCCACATCCACCACCC CTATCCAGTCCACCTGGTTTGATTCAGCAACGCTCAGGTAGCATCGCTGTTTG ATCTGGAGCTGCCAGCTCCCTCGGCCCCCACTGCAATGCTTAACCCCCTCACA GGCACCTTCCCTTGCCTAACACTGCCATCCTTTTCCACACTGAGCCATTTGCT CAATGTAGCCTACCCAGGTATCCTGCTTTCTGGTCCCCAAAGTTACACCATGA TGCTCAGCACAGCTGGACAGTTTGTCCCAATTTGTGTGTGTCCTCCTGTTTGT ATGGGACTTCTTTTTGTCAATGGCCTGTGTGTGTATCCAAGCTCTTCCACTTC TATTGTATTTTTCCGGCTTCTAAAACAGATGTTACCAAATAAAGAAAGAGAAA GAAAAAAAA (SEQ ID NO: 107) |
| | >NP_038511.1 butyrophilin subfamily 1 member A1 precursor [*Mus musculus*]<br>MAVPTNSCLLVCLLTLTVLQLPTLDSAAPFDVTAPQEPVLALVGSDAELTCGF SPNASSEYMELLWFRQTRSTAVLLYRDGQEQEGQQMTEYRGRATLATAGLLDG RATLLIRDVRVSDQGEYRCLFKDNDDFEEAAVYLKVAAVGSDPQISMTVQENG EMELECTSSGWYPEPQVQWRTGNREMLPSTSESKKHNEEGLFTVAVSMMIRDS SIKNMSCCIQNILLGQGKEVEISLPAPFVPRLTPWIVAVAIILLALGFLTIGS IFFTWKLYKERSSLRKKEFGSKERLLEELRCKKTVLHEVDVTLDPDTAHPHLF LYEDSKSVRLEDSRQILPDRPERFDSWPCVLGRETFTSGRHYWEVEVGDRTDW AIGVCRENVVKKGFDPMTPDNGFWAVELYGNGYWALTPLRTSLRLAGPPRRVG VFLDYDAGDISFYNMSNGSLIYTFPSISFSGPLRPFFCLWSCGKKPLTICSTA NGPEKVTVIANVQDDIPLSPLGEGCTSGDKDTLHSKLIPFSPSQAAP (SEQ ID NO: 108) |
| Human TIGIT | >NM_173799.4 *Homo sapiens* T cell immunoreceptor with Ig and ITIM domains (TIGIT), mRNA<br>ACATCTGCTTCCTGTAGGCCCTCTGGGCAGAAGCATGCGCTGGTGTCTCCTCC TGATCTGGGCCCAGGGGCTGAGGCAGGCTCCCCTCGCCTCAGGAATGATGACA GGCACAATAGAAACAACGGGGAACATTTCTGCAGAGAAAGGTGGCTCTATCAT CTTACAATGTCACCTCTCCTCCACCACGGCACAAGTGACCCAGGTCAACTGGG AGCAGCAGGACCAGCTTCTGGCCATTTGTAATGCTGACTTGGGGTGGCACATC TCCCCATCCTTCAAGGATCGAGTGGCCCCAGGTCCCGGCCTGGGCCTCACCCT CCAGTCGCTGACCGTGAACGATACAGGGGAGTACTTCTGCATCTATCACACCT ACCCTGATGGGACGTACACTGGGAGAATCTTCCTGGAGGTCCTAGAAAGCTCA GTGGCTGAGCACGGTGCCAGGTTCCAGATTCCATTGCTTGGAGCCATGGCCGC GACGCTGGTGGTCATCTGCACAGCAGTCATCGTGGTGGTCGCGTTGACTAGAA AGAAGAAAGCCCTCAGAATCCATTCTGTGGAAGGTGACCTCAGGAGAAAATCA GCTGGACAGGAGGAATGGAGCCCCAGTGCTCCCTCACCCCCAGGAAGCTGTGT CCAGGCAGAAGCTGCACCTGCTGGGCTCTGTGGAGAGCAGCGGGGAGAGGACT GTGCCGAGCTGCATGACTACTTCAATGTCCTGAGTTACAGAAGCCTGGGTAAC TGCAGCTTCTTCACAGAGACTGGTTAGCAACCAGAGGCATCTTCTGGAAGATA CACTTTTGTCTTTGCTATTATAGATGAATATATAAGCAGCTGTACTCTCCATC AGTGCTGCGTGTGTGTGTGTGTGTGTATGTGTGTGTGTGTTCAGTTGAGTGAA TAAATGTCATCCTCTTCTCCATCTTCATTTCCTTGGCCTTTTCGTTCTATTCC ATTTTGCATTATGGCAGGCCTAGGGTGAGTAACGTGGATCTTGATCATAAATG CAAAATTAAAAAATATCTTGACCTGGTTTTAAATCTGGCAGTTTGAGCAGATC CTATGTCTCTGAGAGACACATTCCTCATAATGGCCAGCATTTTGGGCTACAAG GTTTTGTGGTTGATGATGAGGATGGCATGACTGCAGAGCCATCCTCATCTCAT TTTTTCACGTCATTTTCAGTAACTTTCACTCATTCAAAGGCAGGTTATAAGTA |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| | AGTCCTGGTAGCAGCCTCTATGGGGAGATTTGAGAGTGACTAAATCTTGGTAT<br>CTGCCCTCAAGAACTTACAGTTAAATGGGGAGACAATGTTGTCATGAAAAGGT<br>ATTATAGTAAGGAGAGAAGGAGACATACACAGGCCTTCAGGAAGAGACGACAG<br>TTTGGGGTGAGGTAGTTGGCATAGGCTTATCTGTGATGAAGTGGCCTGGGAGC<br>ACCAAGGGGATGTTGAGGCTAGTCTGGGAGGAGCAGGAGTTTTGTCTAGGGAA<br>CTTGTAGGAAATTCTTGGAGCTGAAAGTCCCACAAAGAAGGCCCTGGCACCAA<br>GGGAGTCAGCAAACTTCAGATTTTATTCTCTGGGCAGGCATTTCAAGTTTCCT<br>TTTGCTGTGACATACTCATCCATTAGACAGCCTGATACAGGCCTGTAGCCTCT<br>TCCGGCCGTGTGTGCTGGGGAAGCCCCAGGAAACGCACATGCCCACACAGGGA<br>GCCAAGTCGTAGCATTTGGGCCTTGATCTACCTTTTCTGCATCAATACACTCT<br>TGAGCCTTTGAAAAAAGAACGTTTCCCACTAAAAAGAAAATGTGGATTTTTAA<br>AATAGGGACTCTTCCTAGGGGAAAAAGGGGGGCTGGGAGTGATAGAGGGTTTA<br>AAAAATAAACACCTTCAAACTAACTTCTTCGAACCCTTTTATTCACTCCCTGA<br>CGACTTTGTGCTGGGGTTGGGGTAACTGAACCGCTTATTTCTGTTTAATTGCA<br>TTCAGGCTGGATCTTAGAAGACTTTTATCCTTCCACCATCTCTCTCAGAGGAA<br>TGAGCGGGGAGGTTGGATTTACTGGTGACTGATTTTCTTTCATGGGCCAAGGA<br>ACTGAAAGAGAATGTGAAGCAAGGTTGTGTCTTGCGCATGGTTAAAAATAAAG<br>CATTGTCCTGCTTCCTAAGACTTAGACTGGGGTTGACAATTGTTTTAGCAACA<br>AGACAATTCAACTATTTCTCCTAGGATTTTTATTATTATTATTTTTTCACTTT<br>TCTACCAAATGGGTTACATAGGAAGAATGAACTGAAATCTGTCCAGAGCTCCA<br>AGTCCTTTGGAAGAAAGATTAGATGAACGTAAAAATGTTGTTGTTTGCTGTGG<br>CAGTTTACAGCATTTTTCTTGCAAAATTAGTGCAAATCTGTTGGAAATAGAAC<br>ACAATTCACAAATTGGAAGTGAACTAAAATGTAATGACGAAAAGGGAGTAGTG<br>TTTTGATTTGGAGGAGGTGTATATTCGGCAGAGGTTGGACTGAGAGTTGGGTG<br>TTATTTAACATAATTATGGTAATTGGGAAACATTTATAAACACTATTGGGATG<br>GTGATAAAATACAAAAGGGCCTATAGATGTTAGAAATGGGTCAGGTTACTGAA<br>ATGGGATTCAATTTGAAAAAAATTTTTTTAAATAGAACTCACTGAACTAGATT<br>CTCCTCTGAGAACCAGAGAAGACCATTTCATAGTTGGATTCCTGGAGACATGC<br>GCTATCCACCACGTAGCCACTTTCCACATGTGGCCATCAACCACTTAAGATGG<br>GGTTAGTTTAAATCAAGATGTGCTGTTATAATTGGTATAAGCATAAAATCACA<br>CTAGATTCTGGAGATTTAATATGAATAATAAGAATACTATTTCAGTAGTTTTG<br>GTATATTGTGTGTCAAAAATGATAATATTTGGATGTATTGGGTGAAATAAAA<br>TATTAACATTA (SEQ ID NO: 109)<br><br>>NP_776160.2 T-cell immunoreceptor with Ig and ITIM domains precursor [*Homo sapiens*]<br>MRWCLLLIWAQGLRQAPLASGMMTGTIETTGNISAEKGGSIILQCHLSSTTAQ<br>VTQVNWEQQDQLLAICNADLGWHISPSFKDRVAPGPGLGLTLQSLTVNDTGEY<br>FCIYHTYPDGTYTGRIFLEVLESSVAEHGARFQIPLLGAMAATLVVICTAVIV<br>VVALTRKKKALRIHSVEGDLRRKSAGQEEWSPSAPSPPGSCVQAEAAPAGLCG<br>EQRGEDCAELHDYFNVLSYRSLGNCSFFTETG (SEQ ID NO: 110) |
| Mouse TIGIT | >NM_001146325.1:98-823 *Mus musculus* T cell immunoreceptor with Ig and ITIM domains (Tigit), mRNA<br>ATGCATGGCTGGCTGCTCCTGGTCTGGGTCCAGGGGCTGATACAGGCTGCCTT<br>CCTCGCTACAGGAGCCACAGCAGGCACGATAGATACAAAGAGGAACATCTCTG<br>CAGAGGAAGGTGGCTCTGTCATCTTACAGTGTCACTTCTCCTCTGACACAGCT<br>GAAGTGACCCAAGTCGACTGGAAGCAGCAGGACCAGCTTCTGGCCATTTATAG<br>TGTTGACCTGGGGTGGCATGTCGCTTCAGTCTTCAGTGATCGGGTGGTCCCAG<br>GCCCCAGCCTAGGCCTCACCTTCCAGTCTCTGACAATGAATGACACGGGAGAG<br>TACTTCTGTACCTATCATACGTATCCTGGTGGGATTTACAAGGGGAGAATATT<br>CCTGAAGGTCCAAGAAAGCTCAGTGGCTCAGTTCCAGACTGCCCCGCTTGGAG<br>GAACCATGGCTGCTGTGCTGGGACTCATTTGCTTAATGGTCACAGGAGTGACT<br>GTACTGGCTAGAAAGAAGTCTATTAGAATGCATTCTATAGAAAGTGGCCTTGG<br>GAGAACAGAAGCGGAGCCACAGGAATGGAACCTGAGGAGTCTCTCATCCCCTG<br>GAAGCCCTGTCCAGACACAAACTGCCCCTGCTGGTCCCTGTGGAGAGCAGGCA<br>GAAGATGACTATGCTGACCCACAGGAATACTTTAATGTCCTGAGCTACAGAAG<br>CCTAGAGAGCTTCATTGCTGTATCGAAGACTGGCTAA (SEQ ID NO: 111)<br><br>>NP_001139797.1 T-cell immunoreceptor with Ig and ITIM domains precursor [*Mus musculus*]<br>MHGWLLLVWVQGLIQAAFLATGATAGTIDTKRNISAEEGGSVILQCHFSSDTA<br>EVTQVDWKQQDQLLAIYSVDLGWHVASVFSDRVVPGPSLGLTFQSLTMNDTGE<br>YFCTYHTYPGGIYKGRIFLKVQESSVAQFQTAPLGGTMAAVLGLICLMVTGVT<br>VLARKKSIRMHSIESGLGRTEAEPQEWNLRSLSSPGSPVQTQTAPAGPCGEQA<br>EDDYADPQEYFNVLSYRSLESFIAVSKTG (SEQ ID NO: 112) |
| Human CD27L (CD70) | >NM_001252.5 *Homo sapiens* CD70 molecule (CD70), transcript variant 1, mRNA<br>AGAGAGGGGCAGGCTGGTCCCCTGACAGGTTGAAGCAAGTAGACGCCCAGGAG<br>CCCCGGGAGGGGGCTGCAGTTTCCTTCCTTCCTTCTCGGCAGCGCTCCGCGCC<br>CCCATCGCCCCTCCTGCGCTAGCGGAGGTGATCGCCGCGGCGATGCCGGAGGA<br>GGGTTCGGGCTGCTCGGTGCGGCGCAGGCCCTATGGGTGCGTCCTGCGGGCTG<br>CTTTGGTCCCATTGGTCGCGGGCTTGGTGATCTGCCTCGTGGTGTGCATCCAG<br>CGCTTCGCACAGGCTCAGCAGCAGCTGCCGCTCGAGTCACTTGGGTGGGACGT |

TABLE 1-continued

Type I Proteins of Interest Amino Acid Sequence

| Protein of Interest | Transcript Sequence (SEQ ID NO:)<br>Amino Acid Sequence (SEQ ID NO:) |
|---|---|
| | AGCTGAGCTGCAGCTGAATCACACAGGACCTCAGCAGGACCCCAGGCTATACT GGCAGGGGGGCCCAGCACTGGGCCGCTCCTTCCTGCATGGACCAGAGCTGGAC AAGGGGCAGCTACGTATCCATCGTGATGGCATCTACATGGTACACATCCAGGT GACGCTGGCCATCTGCTCCTCCACGACGGCCTCCAGGCACCACCCCACCACCC TGGCCGTGGGAATCTGCTCTCCCGCCTCCCGTAGCATCAGCCTGCTGCGTCTC AGCTTCCACCAAGGTTGTACCATTGCCTCCCAGCGCCTGACGCCCCTGGCCCG AGGGGACACACTCTGCACCAACCTCACTGGGACACTTTTGCCTTCCCGAAACA CTGATGAGACCTTCTTTGGAGTGCAGTGGGTGCGCCCCTGACCACTGCTGCTG ATTAGGGTTTTTTAAATTTTATTTTATTTTATTTAAGTTCAAGAGAAAAAGTG TACACACAGGGGCCACCCGGGGTTGGGGTGGAGTGTGGTGGGGGGTAGTGGT GGCAGGACAAGAGAAGGCATTGAGCTTTTTCTTTCATTTTCCTATTAAAAAAT ACAAAAATCA (SEQ ID NO: 113)<br><br>>NP_001243.1 CD70 antigen isoform 1 [*Homo sapiens*]<br>MPEEGSGCSVRRRPYGCVLRAALVPLVAGLVICLVVCIQRFAQAQQQLPLESL GWDVAELQLNHTGPQQDPRLYWQGGPALGRSFLHGPELDKGQLRIHRDGIYMV HIQVTLAICSSTTASRHHPTTLAVGICSPASRSISLLRLSFHQGCTIASQRLT PLARGDTLCTNLTGTLLPSRNTDETFFGVQWVRP (SEQ ID NO: 114) |
| Mouse CD27L (CD70) | >NM_011617.2 *Mus musculus* CD70 antigen (Cd70), mRNA<br>GAAGGTGCCAAAAGCTCCAGGGGATTTCCCTGCCCTCCGAGAAGAGGCCCAGT TCTTCCCCTGCATCGGACATCCCCGAGGTTCTAAGGGCAGGTCAAGGCAGGCA GAAGCTTCAAAAGCTCGGCTGAGGAGGCTACAGCTTCCCGCTGCCTTCAGGCC GCTGCTTCCGTGCAGGGATGCCGGAGGAAGGTCGCCCTTGCCCCTGGGTTCGC TGGAGCGGGACCGCGTTCCAGCGCCAATGGCCATGGCTGCTGCTGGTGGTGTT TATTACTGTGTTTTGCTGTTGGTTTCATTGTAGCGGACTACTCAGTAAGCAGC AACAGAGGCTGCTGGAGCACCCTGAGCCGCACACAGCTGAGTTACAGCTGAAT CTCACAGTTCCTCGGAAGGACCCCACACTGCGCTGGGGAGCAGGCCCAGCCTT GGGAAGGTCCTTCACACACGGACCAGAGCTGGAGGAGGGCCATCTGCGTATCC ATCAAGATGGCCTCTACAGGCTGCATATCCAGGTGACACTGGCCAACTGCTCT TCCCCAGGCAGCACCCTGCAGCACAGGGCCACCCTGGCTGTGGGCATCTGCTC CCCCGCTGCGCACGGCATCAGCTTGCTGCGTGGGCGCTTTGGACAGGACTGTA CAGTGGCATTACAGCGCCTGACATACCTGGTCCACGGAGATGTCCTCTGTACC AACCTCACCCTGCCTCTGCTGCCGTCCCGCAACGCTGATGAGACCTTCTTTGG AGTTCAGTGGATATGCCCTTGACCACAACTCCAGGATGACTTGTGAATATTTT TTTTCTTTTCAAGTTCTACGTATTTATAAATGTATATAGTACACATA (SEQ ID NO: 115)<br><br>>NP_035747.1 0D70 antigen [*Mus musculus*]<br>MPEEGRPCPWVRWSGTAFQRQWPWLLLVVFITVFCCWFHCSGLLSKQQQRLLE HPEPHTAELQLNLTVPRKDPTLRWGAGPALGRSFTHGPELEEGHLRIHQDGLY RLHIQVTLANCSSPGSTLQHRATLAVGICSPAAHGISLLRGRFGQDCTVALQR LTYLVHGDVLCTNLTLPLLPSRNADETFFGVQWICP (SEQ ID NO: 116) |
| Human CD30L (CD153) | >NM_001244.4 *Homo sapiens* TNF superfamily member 8 (TNFSF8), transcript variant 1, mRNA<br>GTCATTTTCCTACGCGCCCTCTGACATCAGCCACCTTCTCTGTAGCTAGTTTC TCTGCACACAACTTAATCCCTGGCAATGAAAAATGAACCTCTCCCCCACCCTT GCTGCCGCCTCTCGCCTCACGCCCCCAGAGAAGAGTTTCTCCACCAGGCAGCA GGTGAAGGTTTTTTTCCAAGTCACATGATTCAGGATTCAGGGGGAGAATCCTT CTTGGAACAGAGATGGGCCCAGAACTGATCAGATGAAGAGAGATAAGGTGTG ATGTGGGGAAGACTATATAAAGAATGGACCCAGGGCTGCAGCAAGCACTCAAC GGAATGGCCCCTCCTGGAGACACAGCCATGCATGTGCCGGCGGGCTCCGTGGC CAGCCACCTGGGGACCACGAGCCGCAGCTATTTCTATTTGACCACAGCCACTC TGGCTCTGTGCCTTGTCTTCACGGTGGCCACTATTATGGTGTTGGTCGTTCAG AGGACGGACTCCATTCCCAACTCACCTGACAACGTCCCCCTCAAAGGAGGAAA TTGCTCAGAAGACCTCTTATGTATCCTGAAAAGGGCTCCATTCAAGAAGTCAT GGGCCTACCTCCAAGTGGCAAAGCATCTAAACAAAACCAAGTTGTCTTGGAAC AAAGATGGCATTCTCCATGGAGTCAGATATCAGGATGGGAATCTGGTGATCCA ATTCCCTGGTTTGTACTTCATCATTTGCCAACTGCAGTTTCTTGTACAATGCC CAAATAATTCTGTCGATCTGAAGTTGGAGCTTCTCATCAACAAGCATATCAAA AAACAGGCCCTGGTGACAGTGTGTGAGTCTGGAATGCAAACGAAACACGTATA CCAGAATCTCTCTCAATTCTTGCTGGATTACCTGCAGGTCAACACCACCATAT CAGTCAATGTGGATACATTCCAGTACATAGATACAAGCACCTTTCCTCTTGAG AATGTGTTGTCCATCTTCTTATACAGTAATTCAGACTGAACAGTTTCTCTTGG CCTTCAGGAAGAAAGCGCCTCTCTACCATACAGTATTTCATCCCTCCAAACAC TTGGGCAAAAAGAAAACTTTAGACCAAGACAAACTACACAGGGTATTAAATAG TATACTTCTCCTTCTGTCTCTTGGAAAGATACAGCTCCAGGGTTAAAAAGAGA GTTTTTAGTGAAGTATCTTTCAGATAGCAGGCAGGGAAGCAATGTAGTGTGGT GGGCAGAGCCCCACACAGAATCAGAAGGGATGAATGGATGTCCCAGCCCAACC TCTAATTCACTGTATGGTCTTGATCTATTTCTTCTGTTTTGAGAGCCTCCAGT TAAAATGGGGCTCCAGTACCAGAGCAGCTAGCAACTCTGCCCTAATGGGAAAT GAAGGGGAGCTGGGTGTGAGTGTTTACACTGTGCCCTTCACGGGATACTTCTT TTATCTGCAGATGGCCTAATACTTAGTTGTCCAAGTCGCGATCAAGGACTCTC TCACACAGGAAACTTCCCTATACTGGCAGATACACTTGTGACTGAACCATGCC |

TABLE 1-continued

Type I Proteins of Interest Amino Acid Sequence

| Protein of Interest | Transcript Sequence (SEQ ID NO:) Amino Acid Sequence (SEQ ID NO:) |
|---|---|
| | CAGTTTATGCCTGTCTGACTGTCACTCTGGCACTAGGAGGCTGATCTTGTACT CCATATGACCCCACCCCTAGGAACCCCCAGGGAAAACCAGGCTGGGACAGCCC CCTGTTCCTGAGATGGAAAGCACAAATTTAATACACCACCACAATGGAAAACA AGTTCAAAGACTTTTACTTACAGATCCTGGACAGAAAGGGCATAATGAGTCTG AAGGGCAGTCCTCCTTCTCTAGGTTACATGAGGCAGGAATAAGAAGTCAGACA GAGACAGCAAGACAGTTAACAATGTAGGTAAAGAAATAGGGTGTGGTCACTCT CAATTCACTGGCAAATGCCTGAATGGTCTGTCTGAAGGAAGCAACAGAGAAGT GGGGAATCCAGTCTGCTAGGCAGGAAAGATGCCTCTAAGTTCTTGTCTCTGGC CAGAGGTGTGGTATAGAACCAGAAACCCATATCAAGGGTGACTAAGCCCGGCT TCTGGTATGAGAAATTAAACTTGTATACAAAATGGTTGCCAAGGCAACATAAA ATTATAAGAATTCACTATACCTTCCCCTCCCTGGAACTCAGGATCCAAGTCTA GAAAATGAAAGGACTGGGTTTGAATTGCTTCAAAACCTCTTCCATCTCAGAAG ACCAGACCCTGGGAACTGAGATTCCAGACACAATTTTGGAAGCTCTCCAACCA AAATAAGGCCCCCCTACCCCAGTATATAATTGAAGACACTAGTAACACCTGAC TGCATCTCATCTCAGCAGAGCCAGAATATGGGGACAAGGTTCAGGGTGCCCTG CTGAATGGTGTGAACAGCAGGATCTCAAGGATGTAATGGAAAGAACTACCACA CTGACCATCCAGAATCTAAGAGACCATCTGGGTGTTTGGGAAACCATCTGACG AGGCCTGACTCTATTCCAGTTAGATTGACAATAATTGAGCAGCAGGCATTTTT CATTTCTGGTCAGGAAAGCATTGTGCCTTTAGCAAACAATCAGTGTGCAACAG TGATGTGGTCATCTAGCCAGGGAATGGCTGCTCCATCCCCTGCATAATATATT CCTGCTTCAAACACCTCTCAGAAAACCAGTTCCGCGAGGGTTTTTATATCCCC ACAAAGTTGTTGAGAGACAATGATGACCCTGGAAGTGGGGAGGAGGACTTCTG AGAAACAGCAACCTCTCTCCTGATTGGGGTAGCCATGAGATTTCTCTAGCTAT ATCCAACTTGGCATCTGTACATCATCTTTGGAGGAACATCTTATTTGTGGAAG GACCTTGACAAGCCGTTTGAGATGGAATGTAGGCCCTGATGTTATGCTTCAGT AAAAAAAGATGGAAGCTTCCCTGCTATACCAAAACATGGAGCAAAATTTGCAT TTTTCTCAAGAAGGAGAGAAAAGGAGTAGGACTCCAGCAAAGTTTGTCAGAAG GAAAGCTAGAAAAGATTTAAAAGAAAAAAAGAAAGAACAAATCAGCAGTGGTG GTATGGATGAAAGGGACTTGAGAGAACAAAAATGGCTAAGGGAAAATTTTAAG TCATCTGCTGAGCAGTGTGCTGTGTCAACCTCCTCCTAGGTCTCCTCTATGAA ATATTTAGTAAAGTCTACATTTCTCTTTAACTCTTTCTGTGAGTAGATTCTTT GGGAGAAGCAGGCATTGGAAGAGGTGTTGAATTCAGCAAGCCAAATGGTCTGT GGTAAAAAACAAAACAGACTTTGAGACTCAAGGCTAAAAAAACAGGGAAATGG CTGGCATTTGAGTCACACACTAACTGCATAGGACAAATGAATCTTGCTTAAAC CAACTCATGCATTCTTGAAAAGGTATATGCAACCCAACTGTGTGTTAACTAAG CAATTTTTTTGCCATCTCACATTCTAACTCGAGAAAGATTCCATTTTCATTTT TCACCAACTGTTCTCTGAGCAGAGGTACCTGACTTTTGCACTGTGAGTGGTTT CTAATCTCAGTCTCTGTCAAGCAATGCTAAGAAAGCCAACACCTAAAGACACA AGGGGTACATCATTTAAATGAATAATGTAACCAAACAAACAAAAAAAGAGAAT AATCATTAATAACTCAACTGATAGATATGTAGGGAGTAGGCAACCCAGGAAGT TTAAAACTAAATTCTGTTACTCTTGAGGGTTAACCAGCCCCTGGGAATGTTAT GAGCAAATGATACTCCATGAGTAAAATGATATCTATGCAAGTAAAATAAATAA TTTATCTAACTGGGAA (SEQ ID NO: 117) |
| | >NP_001235.1 tumor necrosis factor ligand superfamily member 8 isoform 1 [*Homo sapiens*] MDPGLQQALNGMAPPGDTAMHVPAGSVASHLGTTSRSYFYLTTATLALCLVFT VATIMVLVVQRTDSIPNSPDNVPLKGGNCSEDLLCILKRAPFKKSWAYLQVAK HLNKTKLSWNKDGILHGVRYQDGNLVIQFPGLYFIICQLQFLVQCPNNSVDLK LELLINKHIKKQALVTVCESGMQTKHVYQNLSQFLLDYLQVNTTISVNVDTFQ YIDTSTFPLENVLSIFLYSNSD (SEQ ID NO: 118) |
| Mouse CD30L (CD153) | >NM_009403.3 *Mus musculus* tumor necrosis factor (ligand) superfamily, member 8 (Tnfsf8), mRNA AGATTAATCCCAGGCGATGAAAAATGAACCTCTCCCCCACCCTTGCAGCCACC CTTCGCCTCACGCCCCCAGAGAAGAGTTTCTCCATCCGGCAACTGGTGAAGGC TTTTTTCCAAGTCACATGATCCAGGATGCAGGGGAAAATCCTTCTTGGAACAG AGCTGGGTACAGAACCGAATCAGATGAGGAGAGATAAGGTGTGATGTGGGACA GACTATATAAAGCATGGAGCCAGGGCTGCAACAAGCAGGCAGCTGTGGGGCTC CTTCCCCTGACCCAGCCATGCAGGTGCAGCCCGGCTCGGTAGCCAGCCCCTGG AGAAGCACGAGGCCCTGGAGAAGCACAAGTCGCAGCTACTTCTACCTCAGCAC CACCGCACTGGTGTGCCTTGTTGTGGCAGTGGCGATCATTCTGGTACTGGTAG TCCAGAAAAAGGACTCCACTCCAAATACAACTGAGAAGGCCCCCCTTAAAGGA GGAAATTGCTCAGAGGATCTCTTCTGTACCCTGAAAAGTACTCCATCCAAGAA GTCATGGGCCTACCTCCAAGTGTCAAAGCATCTCAACAATACCAAACTGTCAT GGAACGAAGATGGCACCATCCACGGACTCATATACCAGGACGGGAACCTGATA GTCCAATTCCCTGGCTTGTACTTCATCGTTTGCCAACTGCAGTTCCTCGTGCA GTGCTCAAATCATTCTGTGGACCTGACATTGCAGCTCCTCATCAATTCCAAGA TCAAAAAGCAGACGTTGGTAACAGTGTGTGAGTCTGGAGTTCAGAGTAAGAAC ATCTACCAGAATCTCTCTCAGTTTTTGCTGCATTACTTACAGGTCAACTCTAC CATATCAGTCAGGGTGGATAATTTCCAGTATGTGGATACAAACACTTTCCCTC TTGATAATGTGCTATCCGTCTTCTTATATAGTAGCTCAGACTGAATAGTTGTT CTTAACCTTTATGAAAATGCTGTCTACCATACAGTACTTCATCTGTCCAAACA TGGGCCAAAGAAAATATTAGGACAACTCAAACTAAGCATGTGAGTTAGTGCAC TTCTCTTTCTGTCCTTTGGAAAAATACAAACCCAGGATTTAGAAAGTGGAGTC |

TABLE 1-continued

Type I Proteins of Interest Amino Acid Sequence

| Protein of Interest | Transcript Sequence (SEQ ID NO:)<br>Amino Acid Sequence (SEQ ID NO:) |
|---|---|
| | TCCTTCAGATGCACAAACAGGAAAGAATGTGATATGTGCACAGAGACCTACTT<br>GGGCACTAGAAGGGGTTGAGTTGTCCCAGTATAACCACTAATTCACTGACCTT<br>GAGCCATTTTTCCTTCCCCTGGAACTTGGGGTCTGAATCTGGAAAAGTAGGAG<br>ATGAGATTTACATTTCCCCAATATTTTCTTCAACTCAGAAGACGAGACTGTGG<br>AGCTGAGCTCCCTACACAGATGAAGGCCTCCCATGGCATGAGGAAAATGATGG<br>TACCAGTAATGTCTGTCTGACTGTCATCTCAGCAAGTCCTAAGGACTTCCATG<br>CTGCCTTGTTGAAAGATACTCTAACCTCTTGTAATGGGCAAAGTGATCCTGTC<br>TCTCACTGAGGGGAGTAGCTGCTGCCATCTCCTGAGACATACATGGAGACATT<br>TTCTGCCCAAATTCCATTCTGTGTGCAGTTTTTAAGTATTCCCCCAAAAGTTC<br>TTGACAATGAGAACTTTGAATGTGGGAAGAGCTTCTGGACAGCAAACATTAAC<br>AGCTTCTCCTGACCAGAGAGACCATGCAAGCTTGGTCTTAGACCCATCAAGCT<br>TGAGGTTTCTACATTGTGGGAGACAGACTTTTGACAAACCATTTGAGTTGATG<br>TCTGGGCCCCTGGGAGTTCTCCTTCAGTAAGGAGAGCAAGCCGTTCTAGTGCT<br>GTGTCAGAGGATGGAGTAAAATAGACACTTTTCTGAAGGAAAGGAGAACAAAG<br>TTCCAGAAAAAGGCTAGAAAATGTTTAAAAGGAAAAGAAAAAACTCAGCTTTT<br>CTCATATGAGAGGAACCCAGAAAAACAACACTGAAAAAGAAGAGTGGCTCTGT<br>CAACCTCCTCTTAGGTCTCCTCCTCTCTAGTTATTGGGAAAGGAGTTGCATGG<br>TACAGGACAAGTTCTGGTGTGTGGTCAAATAGAATCAGATGTGGAGAACACCA<br>TGCAGAGAATAAGGAGACCTGTCATATTTGTGTTGTACTCAAATGAGGGGCAA<br>ATGAATCTTAGGCTAAATCAAATAACAGTCTCTGTCAAGCTGTGCTCAGAAAG<br>TCAACCACTGAAGATGGAGGGTGAGGCACGTCATTTAAAAAAAGTGAAATGTA<br>GC (SEQ ID NO: 119)<br><br>>NP_033429.1 tumor necrosis factor ligand superfamily member 8 [*Mus musculus*]<br>MEPGLQQAGSCGAPSPDPAMQVQPGSVASPWRSTRPWRSTSRSYFYLSTTALV<br>CLVVAVAIILVLVVQKKDSTPNTTEKAPLKGGNCSEDLFCTLKSTPSKKSWAY<br>LQVSKHLNNTKLSWNEDGTIHGLIYQDGNLIVQFPGLYFIVCQLQFLVQCSNH<br>SVDLTLQLLINSKIKKQTLVTVCESGVQSKNIYQNLSQFLLHYLQVNSTISVR<br>VDNFQYVDTNTFPLDNVLSVFLYSSSD (SEQ ID NO: 120) |
| Human GITRL | >NM_005092.4 *Homo sapiens* TNF superfamily member 18 (TNFSF18), mRNA<br>ATCACTTGTGAATTTTTGTTTTCCACAGCTCTCATTTCTCCAAAAATGTGTTT<br>GAGCCACTTGGAAAATATGCCTTTAAGCCATTCAAGAACTCAAGGAGCTCAGA<br>GATCATCCTGGAAGCTGTGGCTCTTTTGCTCAATAGTTATGTTGCTATTTCTT<br>TGCTCCTTCAGTTGGCTAATCTTTATTTTTCTCCAATTAGAGACTGCTAAGGA<br>GCCCTGTATGGCTAAGTTTGGACCATTACCCTCAAAATGGCAAATGGCATCTT<br>CTGAACCTCCTTGCGTGAATAAGGTGTCTGACTGGAAGCTGGAGATACTTCAG<br>AATGGCTTATATTTAATTTATGGCCAAGTGGCTCCCAATGCAAACTACAATGA<br>TGTAGCTCCTTTTGAGGTGCGGCTGTATAAAAACAAAGACATGATACAAACTC<br>TAACAAACAAATCTAAAATCCAAAATGTAGGAGGGACTTATGAATTGCATGTT<br>GGGGACACCATAGACTTGATATTCAACTCTGAGCATCAGGTTCTAAAAAATAA<br>TACATACTGGGGTATCATTTTACTAGCAAATCCCCAATTCATCTCCTAGAGAC<br>TTGATTTGATCTCCTCATTCCCTTCAGCACATGTAGAGGTGCCAGTGGGTGGA<br>TTGGAGGGAGAAGATATTCAATTTCTAGAGTTTGTCTGTCTACAAAAATCAAC<br>ACAAACAGAACTCCTCTGCACGTGAATTTTCATCTATCATGCCTATCTGAAAG<br>AGACTCAGGGGAAGAGCCAAAGACTTTTGGTTGGATCTGCAGAGATACTTCAT<br>TAATCCATGATAAAACAAATATGGATGACAGAGGACATGTGCTTTTCAAAGAA<br>TCTTTATCTAATTCTTGAATTCATGAGTGGAAAAATGGAGTTCTATTCCCATG<br>GAAGATTTACCTGGTATGCAAAAAGGATCTGGGGCAGTAGCCTGGCTTTGTTC<br>TCATATTCTTGGGCTGCTGTAATTCATTCTTCTCATACTCCCATCTTCTGAGA<br>CCCTCCCAATAAAAAGTAGACTGATAGGATGGCCACAGATATGCCTACCATAC<br>CCTACTTTAGATATGGTGGTGTTAGAAGATAAAGAACAATCTGAGAACTATTG<br>GAATAGAGGTACAAGTGGCATAAAATGGAATGTACGCTATCTGGAAATTTCTC<br>TTGGTTTTATCTTCCTCAGGATGCAGGGTGCTTTAAAAAGCCTTATCAAAGGA<br>GTCATTCCGAACCCTCACGTAGAGCTTTGTGAGACCTTACTGTTGGTGTGTGT<br>GTCTAAACATTGCTAATTGTAAAGAAAGAGTAACCATTAGTAATCATTAGGTT<br>TAACCCCAGAATGGTATTATCATTACTGGATTATGTCATGTAATGATTTAGTA<br>TTTTTAGCTAGCTTTCCACAGTTTGCAAAGTGCTTTCGTAAAACAGTTAGCAA<br>TTCTATGAAGTTAATTGGGCAGGCATTTGGGGGAAAATTTTAGTGATGAGAAT<br>GTGATAGCATAGCATAGCCAACTTTCCTCAACTCATAGGACAAGTGACTACAA<br>GAGGCAATGGGTAGTCCCCTGCATTGCACTGTCTCAGCTTTAGAATTGTTATT<br>TCTGCTATCGTGTTATAAGACTCTAAAACTTAGCGAATTCACTTTTCAGGAAG<br>CATATTCCCCTTTAGCCCAAGGTGAGCAGAGTGAAGCTACAACAGATCTTTCC<br>TTTACCAGCACACTTTTTTTTTTTTTCCTGCCTGAATCAGGGAGATCCAGGAT<br>GCTGTTCAGGCCTTATCCCAACCAAATTCCCCTCTTCACTTTGCAGGGCCCAT<br>CTTAGTCAAATGTGCTAACTTCTAAAATAATAAATAGCACTAATTCAAAATTT<br>TTGGACTCTTAAATTAGCTACTTGCAGGTTCTTGTTGAAAGGTATATAATATT<br>ACATTGTAAACAAATTTAAAATATTTATGGATATTTGTGAAAAGCTGCATTAT<br>GTTAAATAATATTACATGTAAAGCTATTTAAAAGAGGTTTTTTTTGTATTTTG<br>TTTAACAAAAATTGCTCAGGAGCATGCTAAGCCTGAGGCCAAGTTGTTTCTTA<br>GTATGACTTTTTAAAAAAACATCTGCTGAGTAGCTACAGGGCCAAAGACTTGG<br>AGAGCTTGTTTCTGTTGCATTTGCATATCTTCTCAGGAAATTAAAGTGTGTCA<br>TACATATGTGTGTGTGTGTGTGTGTGTGTGTGTATATGTGTGTGTGTATATAT |

TABLE 1-continued

Type I Proteins of Interest Amino Acid Sequence

| Protein of Interest | Transcript Sequence (SEQ ID NO:)<br>Amino Acid Sequence (SEQ ID NO:) |
|---|---|
| | ATGTATACTTATAAAATCTTGGTGTTCTTGATCTTTGTTGTGTTATAAGCAAT<br>GTGTGCTGGAGTGGGCTGGTGCTAGCTTATAAGCACATATTATTAAATTTTCA<br>GGAATGTTGCACTTTAGTTATTAACTATAGGCATTCTTGAAATTGGCTATGGT<br>GGGAGTATTTATACCATGTAAATTGGCAAACACTACACATTTTCCTTTTGGAC<br>AGCTAGTTCACCAGCACACCACTGTGAAACTCTCCTTAATGACTCCTCTCTGC<br>CCCCGCTTCATTCCTGGGATAATCATAGCAGACTAAGGGAGAAAATGAAATTG<br>TAAAAATTTGGCATACTGGTGATTTCTCAGGGCAAGCAGAGGTTACTACAGCT<br>GCAGCTAGAGGGATGACTACCAACAGGTGACCTTTACATTTTCCTGATGTTAT<br>AATTTTAGCTTTTGTTTTCAATGTATACTGTTTTCCTGTTTCTCCACATAGTA<br>GTCTGCATTTTAAATCTATAATAAAACATGCTGATAACTGG (SEQ ID NO: 121)<br><br>>NP_005083.3 tumor necrosis factor ligand superfamily member 18 [*Homo sapiens*]<br>MCLSHLENMPLSHSRTQGAQRSSWKLWLFCSIVMLLFLCSFSWLIFIFLQLET<br>AKEPCMAKFGPLPSKWQMASSEPPCVNKVSDWKLEILQNGLYLIYGQVAPNAN<br>YNDVAPFEVRLYKNKDMIQTLTNKSKIQNVGGTYELHVGDTIDLIFNSEHQVL<br>KNNTYWGIILLANPQFIS (SEQ ID NO: 122) |
| Mouse GITRL | >NM_183391.3 *Mus musculus* tumor necrosis factor (ligand) superfamily, member 18 (Tnfsf18), mRNA<br>TTGTGGGTATCTGCTTTCCCCAGTTCTCATTCCATCAGAGAACGAGTTCTAGC<br>CTCATGGAGGAAATGCCTTTGAGAGAATCAAGTCCTCAAAGGGCAGAGAGGTG<br>CAAGAAGTCATGGCTCTTGTGCATAGTGGCTCTGTTACTGATGTTGCTCTGTT<br>CTTTGGGTACACTGATCTATACTTCACTCAAGCCAACTGCCATCGAGTCCTGC<br>ATGGTTAAGTTTGAACTATCATCCTCAAAATGGCACATGACATCTCCCAAACC<br>TCACTGTGTGAATACGACATCTGATGGGAAGCTGAAGATACTGCAGAGTGGCA<br>CATATTTAATCTACGGCCAAGTGATTCCTGTGGATAAGAAATACATAAAAGAC<br>AATGCCCCCTTCGTAGTACAGATATATAAAAAGAATGATGTCCTACAAACTCT<br>AATGAATGATTTTCAAATCTTGCCTATAGGAGGGGTTTATGAACTGCATGCTG<br>GAGATAACATATATCTGAAGTTCAACTCTAAAGACCATATTCAGAAAACTAAC<br>ACATACTGGGGGATCATCTTAATGCCTGATCTACCATTCATCTCTTAGAGATT<br>GGGTTTGGTCTCCTCATCTTCTTCTTTGTATCCCGAGATGCTGGTGGGTGGGT<br>TGGAGGGGGATGATTGATGGCAATGCACACAGTTTGTGAGGGCTTACAAATTG<br>ACACAATCAGAGCCTCTTGGCATATAAAATTTTAGCCCTCATATCTGTCTGAA<br>GAGGACTCAGCAAATGGGCCAATCCCTAATGTTGGGTCTGCAAATGGACTTGT<br>ACAATCCATGATAAAAAGGAGTATGGGCCACAGAAGACAGAAACTCTTCCAAA<br>GAATGTCTTTCTAACCTTGATCCCTGGGTAGAATGAGATCCTGTTTCCATGGG<br>AGTCTTACTTGGCTTGCAAAAAAGGGTGTAGGGCAGTAGCTTGGCCTTTTTTC<br>CATCATAATTTCCTTGAGCTGTTTTACCTTAATCCCTCCAAACTCTCACCTTC<br>TGAGAGCCTCCTAATGAAACATTGTTAGACTGGTGGGGTGGCCAAGACATGCC<br>AACAACACCCTTCTTTAGAGGTGGTGTTTTTAGAGGACAGAGAACATTATGAA<br>GCCTAGAGCAGCAGAGGTCAAGATGCCACGAAATGGAATTGATCTGGGAATTT<br>TTTTTTTTTTTCATTCTCAGGATGCAGGTTCATTCTGAACTTTCCCCTAGGCC<br>TTCATTGCTTTTGTGTGTATGTGTGCATAAATTCTGCAAATAGAAAAATGAGA<br>GTTTGCACCAGTACTCACTAGATTTAACACCAGAAAGTGGTACTTTTCTGGCT<br>GTATTATGCCATGATAGCACATTTTCTGTTGGTGTTCCCTAACTGACAAGTAT<br>AACAGTTTTCCTAAACCACACAACAATGCTATGATGATGTTAATGGGGTAGATATT<br>TTTGGAAAAAAATTGCACAGTGAGAACATGGGTAGATGAACCCTAAGACTCTT<br>ACCTCAATTCAGAACTCGCAAGGAGTTAAGTGAGTGGGGTCTTCATTAGACCA<br>TTCACATGGTCTCTGCTTTGAAACTGGCGTTGCTACTGTCTCATTATACATCA<br>CTAAAATGGAATTAACTCAACTTTGAAATGGATGCATCGACTTTACCCCAAGG<br>TGTCCAGAATGAAGCTACAAGACTTTTACCAGCAGTCATTTTCCTTTTGCCTG<br>GAGCAAGAAGATCCAGGATACTGTTGGAAGAGTTCATCTCACTCAACCATGCT<br>GACTTTCCAAAGTAATAATGAACATTTGTGTTCAAATTTTGGATTCTGTTAAA<br>TTTAGCCAGCTTGTGAGTTCTTGTCGAAAAGTATTTTAAACCAATTTACACTA<br>TTTATGGGTATTTGTGAAAAGCTATATAGTGATATTTTATATATAACTAATTT<br>AAAATATTTTTATTTTATGTAACAAAAATACTATAGGCTAAGCTATTTCTTCT<br>TATTTTTTTATGAATACTTGCTGAATTGCCATAGGGCACAAAGACTCTTCTGT<br>TTGCATATCTTCTCAGGAAATTAAAATTGTATCACATGTATTTATAAGAA<br>(SEQ ID NO: 123)<br><br>>NP_899247.3 tumor necrosis factor ligand superfamily member 18 [*Mus musculus*]<br>MEEMPLRESSPQRAERCKKSWLLCIVALLLMLLCSLGTLIYTSLKPTAIESCM<br>VKFELSSSKWHMTSPKPHCVNTTSDGKLKILQSGTYLIYGQVIPVDKKYIKDN<br>APFVVQIYKKNDVLQTLMNDFQILPIGGVYELHAGDNIYLKFNSKDHIQKTNT<br>YWGIILMPDLPFIS (SEQ ID NO: 124) |
| Human CD40L (CD154) | >NM_000074.3 *Homo sapiens* CD40 ligand (CD40LG), mRNA<br>AATCCTGAGTAAGGTGGCCACTTTGACAGTCTTCTCATGCTGCCTCTGCCACC<br>TTCTCTGCCAGAAGATACCATTTCAACTTTAACACAGCATGATCGAAACATAC<br>AACCAAACTTCTCCCCGATCTGCGGCCACTGGACTGCCCATCAGCATGAAAAT<br>TTTTATGTATTTACTTACTGTTTTTCTTATCACCCAGATGATTGGGTCAGCAC<br>TTTTTGCTGTGTATCTTCATAGAAGGTTGGACAAGATAGAAGATGAAAGGAAT |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| | CTTCATGAAGATTTTGTATTCATGAAAACGATACAGAGATGCAACACAGGAGA AAGATCCTTATCCTTACTGAACTGTGAGGAGATTAAAAGCCAGTTTGAAGGCT TTGTGAAGGATATAATGTTAAACAAAGAGGAGACGAAGAAAGAAAACAGCTTT GAAATGCAAAAAGGTGATCAGAATCCTCAAATTGCGGCACATGTCATAAGTGA GGCCAGCAGTAAAACAACATCTGTGTTACAGTGGGCTGAAAAAGGATACTACA CCATGAGCAACAACTTGGTAACCCTGGAAAATGGGAAACAGCTGACCGTTAAA AGACAAGGACTCTATTATATCTATGCCCAAGTCACCTTCTGTTCCAATCGGGA AGCTTCGAGTCAAGCTCCATTTATAGCCAGCCTCTGCCTAAAGTCCCCGGTA GATTCGAGAGAATCTTACTCAGAGCTGCAAATACCCACAGTTCCGCCAAACCT TGCGGGCAACAATCCATTCACTTGGGAGGAGTATTTGAATTGCAACCAGGTGC TTCGGTGTTTGTCAATGTGACTGATCCAAGCCAAGTGAGCCATGGCACTGGCT TCACGTCCTTTGGCTTACTCAAACTCTGAACAGTGTCACCTTGCAGGCTGTGG TGGAGCTGACGCTGGGAGTCTTCATAATACAGCACAGCGGTTAAGCCCACCCC CTGTTAACTGCCTATTTATAACCCTAGGATCCTCCTTATGGAGAACTATTTAT TATACACTCCAAGGCATGTAGAACTGTAATAAGTGAATTACAGGTCACATGAA ACCAAAACGGGCCCTGCTCCATAAGAGCTTATATATCTGAAGCAGCAACCCCA CTGATGCAGACATCCAGAGAGTCCTATGAAAAGACAAGGCCATTATGCACAGG TTGAATTCTGAGTAAACAGCAGATAACTTGCCAAGTTCAGTTTTGTTTCTTTG CGTGCAGTGTCTTTCCATGGATAATGCATTTGATTTATCAGTGAAGATGCAGA AGGGAAATGGGGAGCCTCAGCTCACATTCAGTTATGGTTGACTCTGGGTTCCT ATGGCCTTGTTGGAGGGGGCCAGGCTCTAGAACGTCTAACACAGTGGAGAACC GAAACCCCCCCCCCCCCCCCGCCACCCTCTCGGACAGTTATTCATTCTCTTTC AATCTCTCTCTCTCCATCTCTCTCTTTCAGTCTCTCTCTCTCAACCTCTTTCT TCCAATCTCTCTTTCTCAATCTCTCTGTTTCCCTTTGTCAGTCTCTTCCCTCC CCCAGTCTCTCTTCTCAATCCCCCTTTCTAACACACACACACACACACACACA CACACACACACACACACACACACACACAGAGTCAGGCCGTTGCTAGTCAGT TCTCTTCTTTCCACCCTGTCCCTATCTCTACCACTATAGATGAGGGTGAGGAG TAGGGAGTGCAGCCCTGAGCCTGCCCACTCCTCATTACGAAATGACTGTATTT AAAGGAAATCTATTGTATCTACCTGCAGTCTCCATTGTTTCCAGAGTGAACTT GTAATTATCTTGTTATTTATTTTTTGAATAATAAAGACCTCTTAACATTA (SEQ ID NO: 125) |
| | >NP_000065.1 CD40 ligand [*Homo sapiens*]<br>MIETYNQTSPRSAATGLPISMKIFMYLLTVFLITQMIGSALFAVYLHRRLDKI EDERNLHEDFVFMKTIQRCNTGERSLSLLNCEEIKSQFEGFVKDIMLNKEETK KENSFEMQKGDQNPQIAAHVISEASSKTTSVLQWAEKGYYTMSNNLVTLENGK QLTVKRQGLYYIYAQVTFCSNREASSQAPFIASLCLKSPGRFERILLRAANTH SSAKPCGQQSIHLGGVFELQPGASVFVNVTDPSQVSHGTGFTSFGLLKL (SEQ ID NO: 126) |
| Mouse CD40L | >NM_011616.2 *Mus musculus* CD40 ligand (Cd40lg), mRNA<br>CTTTCAGTCAGCATGATAGAAACATACAGCCAACCTTCCCCCAGATCCGTGGC AACTGGACTTCCAGCGAGCATGAAGATTTTTATGTATTTACTTACTGTTTTCC TTATCACCCAAATGATTGGATCTGTGCTTTTTGCTGTGTATCTTCATAGAAGA TTGGATAAGGTCGAAGAGGAAGTAAACCTTCATGAAGATTTTGTATTCATAAA AAAGCTAAAGAGATGCAACAAAGGAGAAGGATCTTTATCCTTGCTGAACTGTG AGGAGATGAGAAGGCAATTTGAAGACCTTGTCAAGGATATAACGTTAAACAAA GAAGAGAAAAAAGAAAACAGCTTTGAAATGCAAAGAGGTGATGAGGATCCTCA AATTGCAGCACACGTTGTAAGCGAAGCCAACAGTAATGCAGCATCCGTTCTAC AGTGGGCCAAGAAAGGATATTATACCATGAAAAGCAACTTGGTAATGCTTGAA AATGGGAAACAGCTGACGGTTAAAAGAGAAGGACTCTATTATGTCTACACTCA AGTCACCTTCTGCTCTAATCGGGAGCCTTCGAGTCAACGCCCATTCATCGTCG GCCTCTGGCTGAAGCCCAGCAGTGGATCTGAGAGAATCTTACTCAAGGCGGCA AATACCCACAGTTCCTCCCAGCTTTGCGAGCAGCAGTCTGTTCACTTGGGCGG AGTGTTTGAATTACAAGCTGGTGCTTCTGTGTTTGTCAACGTGACTGAAGCAA GCCAAGTGATCCACAGAGTTGGCTTCTCATCTTTTGGCTTACTCAAACTCTGA ACAGTGCGCTGTCCTAGGCTGCAGCAGGGCTGATGCTGGCAGTCTTCCCTATA CAGCAAGTCAGTTAGGACCTGCCCTGTGTTGAACTGCCTATTTATAACCCTAG GATCCTCCTCATGGAGAACTATTTATTATGTACCCCCAAGGCACATAGAGCTG GAATAAGAGAATTACAGGGCAGGCAAAAATCCCAAGGGACCCTGCTCCCTAAG AACTTACAATCTGAAACAGCAACCCCACTGATTCAGACAACCAGAAAAGACAA AGCCATAATACACAGATGACAGAGCTCTGATGAAACAACAGATAACTAATGAG CACAGTTTTGTTGTTTTATGGGTGTGTCGTTCAATGGACAGTGTACTTGACTT ACCAGGGAAGATGCAGAAGGGCAACTGTGAGCCTCAGCTCACAATCTGTTATG GTTGACCTGGGCTCCCTGCGGCCCTAGTAGG (SEQ ID NO: 127) |
| | >NP_035746.2 CD40 ligand [*Mus musculus*]<br>MIETYSQPSPRSVATGLPASMKIFMYLLTVFLITQMIGSVLFAVYLHRRLDKV EEEVNLHEDFVFIKKLKRCNKGEGSLSLLNCEEMRRQFEDLVKDITLNKEEKK ENSFEMQRGDEDPQIAAHVVSEANSNAASVLQWAKKGYYTMKSNLVMLENGKQ LTVKREGLYYVYTQVTFCSNREPSSQRPFIVGLWLKPSSGSERILLKAANTHS SSQLCEQQSVHLGGVFELQAGASVFVNVTEASQVIHRVGFSSFGLLKL (SEQ ID NO: 128) |

TABLE 1-continued

Type I Proteins of Interest Amino Acid Sequence

| Protein of Interest | Transcript Sequence (SEQ ID NO:)<br>Amino Acid Sequence (SEQ ID NO:) |
|---|---|
| Human<br>LIGHT<br>(CD258) | >NM_003807.5 *Homo sapiens* TNF superfamily member 14 (TNFSF14), transcript variant 1, mRNA<br>CGAGACTCCATCTCAAAAACAAAACAAATAAACGAACAAAAAAACCCACAACG<br>TATTATTTTCTTGTTTACGAGGTTTCTTGTCTCTCTGGCTCCACCAGAAGAGG<br>AGCAGGGACCCTTCTTGCTGTTGTTCATTGCTGCATCCCCCACACCGAGAGCA<br>GAGCCTGGCATGGGCAGAAAGTCCTCAGTCGATATTTGGTGGCCCCAAGCGAA<br>TGAAGCATCCAAGAAGGGAAAGCTGGGGGCTCCCCACTGCACTTGCCACCTGA<br>GTCACATTTTCAGAAGCCTCTGGAAAGTCGTGCACAGCCCAGGAGTGTTGAGC<br>AATTTCGGTTTCCTCTGAGGTTGAAGGACCCAGGCGTGTCAGCCCTGCTCCAG<br>ACACCTTGGGCATGGAGGAGAGTGTCGTACGGCCCTCAGTGTTTGTGGTGGAT<br>GGACAGACCGACATCCCATTCACGAGGCTGGGACGAAGCCACCGGAGACAGTC<br>GTGCAGTGTGGCCCGGGTGGGTCTGGGTCTCTTGCTGTTGCTGATGGGGGCCG<br>GGCTGGCCGTCCAAGGCTGGTTCCTCCTGCAGCTGCACTGGCGTCTAGGAGAG<br>ATGGTCACCCGCCTGCCTGACGGACCTGCAGGCTCCTGGGAGCAGCTGATACA<br>AGAGCGAAGGTCTCACGAGGTCAACCCAGCAGCGCATCTCACAGGGGCCAACT<br>CCAGCTTGACCGGCAGCGGGGGGCCGCTGTTATGGGAGACTCAGCTGGGCCTG<br>GCCTTCCTGAGGGGCCTCAGCTACCACGATGGGGCCCTTGTGGTCACCAAAGC<br>TGGCTACTACTACATCTACTCCAAGGTGCAGCTGGGCGGTGTGGGCTGCCCGC<br>TGGGCCTGGCCAGCACCATCACCCACGGCCTCTACAAGCGCACACCCCGCTAC<br>CCCGAGGAGCTGGAGCTGTTGGTCAGCCAGCAGTCACCCTGCGGACGGGCCAC<br>CAGCAGCTCCCGGGTCTGGTGGGACAGCAGCTTCCTGGGTGGTGTGGTACACC<br>TGGAGGCTGGGGAGAAGGTGGTCGTCCGTGTGCTGGATGAACGCCTGGTTCGA<br>CTGCGTGATGGTACCCGGTCTTACTTCGGGGCTTTCATGGTGTGAAGGAAGGA<br>GCGTGGTGCATTGGACATGGGTCTGACACGTGGAGAACTCAGAGGGTGCCTCA<br>GGGGAAAGAAAACTCACGAAGCAGAGGCTGGGCGTGGTGGCTCTCGCCTGTAA<br>TCCCAGCACTTTGGGAGGCCAAGGCAGGCGGATCACCTGAGGTCAGGAGTTCG<br>AGACCAGCCTGGCTAACATGGCAAAACCCCATCTCTACTAAAAATACAAAAAT<br>TAGCCGGACGTGGTGGTGCCTGCCTGTAATCCAGCTACTCAGGAGGCTGAGGC<br>AGGATAATTTTGCTTAAACCCGGGAGGCGGAGGTTGCAGTGAGCCGAGATCAC<br>ACCACTGCACTCCAACCTGGGAAACGCAGTGAGACTGTGCCTCAAAAAAAAGA<br>AAGGAAGAAAAAAGAAAACTCAGGAAACAGATCTTGGGGGACACTCCAGGGAA<br>CCCAAAACTCAAAGGCGGAGAGCTCAGTGGGCACCACCAAGGCGAGATGAAGC<br>CCCAGCAGGCACCTTCAGAAGACCCACGTAGACTGCAGACCCTGCCACGGACA<br>ATACTAAGGACAAAAACCCAGAGACTTGGGGTCTGTGGCCCCCAAACATGGG<br>GTAAAGTTGATTTGCCTGATATTCAGGAAGAAGGGGTGAGGGGTGGGTATTTA<br>TGCTTTTGATTCAGAAGAAAGTGGGGCTTGGGATTCCAGGGACTTGGCTGGGG<br>GTGGGAAACTTCATCCACTTCCCTACTCTCATCATGAGTACGGACAGGGTGGG<br>CGGGAGACTGATCATCGGGACTCATCATGAAGAGCCCAGCCCCACCCCACATA<br>CTCAGATCCCACCCACAGACTGGTGGCCACACCTCAGCCTGGTCACAAAGAGT<br>TACACTCAGATACATGAGCACGGCAGCGTGCTCATAACTGTTTAACAACCAGC<br>TGTCCTGGGAGGGGGACAGCTTTGTAATGTTTGCCAATTTCCATGGTGTAAAT<br>GCTACCACCATGGCTGATTTCATCACTGCCAAGCATAGACATCCCTAATAGGA<br>CACCACGGATCTGTCCCCGGCATCCGGCCCAGGGCCTGGCACAAAGCATGCTC<br>TAGGGAAATGCTTGCTGATTGAAAGGAAGGAAGAATGACTCTACAGTCACACC<br>TATGGCATCCCACAAAATCTGTCACATGGCTGCATAATCTCAGCCACTCTTTC<br>ACAACTATAGACTCATACACGCGAAGTGCCAGATTCATGCACAACCACACAAT<br>CACATGGAAGTCACAGACGGCATCACAGACAGTCACAGCACTGTGTGTATGTT<br>ATAACACAAGCACACAAAACTCAGACAGCATCCCAGCTACACAGCCACTCCCA<br>GAGGTGTCACCGTCACACTTGGTAATTAATACTCATTACATTAGACACAGACA<br>GACCAAGTTATAGTCAGACCTGGTTACACACATACACACACACAATATCACCA<br>TGACAAATACACATTACACACACACAACATCACAATGACAAACACACATTACA<br>CACACAACATCACGATGACAAACACACATTACACACACAACATCACGATGACA<br>AACACACATTACACACACATCACAATGACAAACACAACATTACACACACACAA<br>CATCACAATGACACACACATCACACACACATCACAATGACAAACACACAACAT<br>TACACACATATACACACAGCCTGAGGGCCCTCCCCAGCCCAGACTAACACATC<br>TCGGGGTGAGGACCAGACCTTGTTCATAACCCTGGGCCTCTTAACCACTGATC<br>TTTGAAATAAATGGCAAATAGTTGTACCTGGATCTGTCTAGTTCTTAGGGGAA<br>CAAACTGAAGAAGGGTGGAGAGGAATTGTCAGGCCTAAAGAGCCCCACAGGGA<br>AAGGGAGGAGTCGGATGGGGGGCAACCATCAGCAACAAGTGGTGGCTCCTAGA<br>GGCAGAGGGATGGAGGTAATGACCCATGGAGGTCATTCTACAGATGAGGAACC<br>TGGACCCAGTTGGCTCAAGTCCATGCAGGAAATGTGGGGGAAACCAGAGACCT<br>CACGTCTGGATCTGGCTTCCTCTCCAATCCACAATTCCTGAGGAAGTAGAGGC<br>TACATCCCGCAAGACGCCCTTATTAGACACATCCAGGACAGAATGACAATCCG<br>CCAAGCCAGCTGGAAGCATAAAACACAGGGAGCTGGTGGGTTGGGTGGGGGCA<br>GATAATGATATGCATACAAATTAGAGGGTCTATGCAAATGAGCATTGCTGCAG<br>TGTGGCTGGAGGGAATCCTTAGTTCCTAGGATTCTAGGATATGGGTTTCGACC<br>CCAGAGGTGAATGTATTGTTATTATTGTTTTGTTGTTGTTGTGAATGACAAGT<br>CAAAATTTGTGGGTTATTGTTGTTATCGCCAATAGTATTCTTGTCATTGTTGC<br>ACAGTACAGAGATGAAGGAAACAGATTTTGCAATCAGATGATCCTGGGTTCTG<br>AGTCCACTCTGCCACTCACCAGCTATATGACCTCCAGCAATTTCCATCACCTC<br>TCAATGCTTCAGTTTCCCCATCGGCAAGATGGTTGTGGGGGGAGAGGAACAAC<br>AGTACAGATTCACCATCCCAAATTCAAAATGCTCCAAAATCTAGGCCGGGCGT<br>GGTGGCTCATACCTGTAATCCCAGCACTTTGGGAGGTCAAAGTGGACGGATAA<br>CCTGAGGTCAGGAGCTCCAGACCAGCCTGGCCAACATGGCGAAACCCCATCTC |

TABLE 1-continued

Type I Proteins of Interest Amino Acid Sequence

| Protein of Interest | Transcript Sequence (SEQ ID NO:)<br>Amino Acid Sequence (SEQ ID NO:) |
|---|---|
| | TACTAAAAATACAAAAAATTACCTGGGTGTGGTGGGGGGCACCTGTAACCCCA<br>GCTACTCGGGAGGCTGAGGCAGGAACCCTGGAGGTTGAGGTTGCAGTGAGCTG<br>AGATCACACCACTGCACTCCAGCCTGGGTGACAGAGCAAGGCTCCCATCTCAA<br>AAAACAAAAAAACATGCTCCAAAATCTGAAACTCTTTGAGCCCCAGTGTGATG<br>CCACAAGTGGGAAATTCCACAACTCATCACATGTGATAGATTGCAGTGGAAAT<br>GCAGGCACACACCACGAAGTTTACTCAGCATCCTCAAAGGAAATCCCCGTCAG<br>TAGCTATATATCATTTTCTCACATGCCAGATAGGTATCTCTCATCTTTTACTG<br>TTAGGTACTTCTGTGTTGAATAGGTGGAGGAAAATGATTGCTGGTTAGTAGTA<br>TATAAATTCAGAGTCAGGAAGGATGGTGATGTCGGCTGGGTGCAGTGGCTCAT<br>GCCTGTAATTCCAATGTGATACCCTACCTTGTGTTTAACGTGATTGACTCTCC<br>CTTAGCTGAGAGGGCCAGGCAGACTCTATTTTGGCTTCTTCGCTTGCAGTCTC<br>TCACCCACCCCCCTTCCTCAAGGACTTAAGCTGACTCCCAGCACATCCAAGAA<br>TGCGATTACTGATAAGATACTGTGACAAGCTATATCCACAATTCCCAGGAATT<br>CGTCCGGTTGATAGCACCCAAAGCCCCCGCGTCTATCACCTTGTGATAGATTT<br>AAAGCCCCTGCACCTGGAACTGTTTGTTTTTCTGTTACCATTTATCTTTTTCA<br>CTTTCTTGCCTGTTTTGCTTCTGTAAAATTGCTTCAGCTCGGCTCCCTCTTCC<br>CCTTCTAAACCAAGGTATAAAAAGAAACCTAGCCCCTTCTTTGGGGTGGAGAG<br>AATTTTGAGCGCTAGCCGTCTCTCAGTCGCCGGCTAATAAAGGACTCCTGAAT<br>TAGTCTAA (SEQ ID NO: 129)<br><br>>NP_003798.2 tumor necrosis factor ligand superfamily member 14 isoform 1 [*Homo sapiens*]<br>MEESVVRPSVFVVDGQTDIPFTRLGRSHRRQSCSVARVGLGLLLLLMGAGLAV<br>QGWFLLQLHWRLGEMVTRLPDGPAGSWEQLIQERRSHEVNPAAHLTGANSSLT<br>GSGGPLLWETQLGLAFLRGLSYHDGALVVTKAGYYYIYSKVQLGGVGCPLGLA<br>STITHGLYKRTPRYPEELELLVSQQSPCGRATSSSRVWWDSSFLGGVVHLEAG<br>EKVVVRVLDERLVRLRDGTRSYFGAFMV (SEQ ID NO: 130) |
| Mouse LIGHT | >NM_019418.3 *Mus musculus* tumor necrosis factor (ligand) superfamily, member 14 (Tnfsf14), mRNA<br>TTTTGCAGTTTGCACAGCCCGAGCGTGTTGGGCAATTGTGGTTTCCTCCGGAG<br>AGGAGGAACTCAGGCTTGCCAACCCTTTCCCTGGGCTTCGGAGCCTCAGCTGC<br>TCTGGCATGGAGAGTGTGGTACAGCCTTCAGTGTTTGTGGTGGATGGACAGAC<br>GGACATCCCATTCAGGCGGCTGGAACAGAACCACCGGAGACGGCGCTGTGGCA<br>CTGTCCAGGTCAGCCTGGCCCTGGTGCTGCTGCTAGGTGCTGGGCTGGCCACT<br>CAGGGCTGGTTTCTCCTGAGACTGCATCAACGTCTTGGAGACATAGTAGCTCA<br>TCTGCCAGATGGAGGCAAAGGCTCCTGGGAGAAGCTGATACAAGATCAACGAT<br>CTCACCAGGCCAACCCAGCAGCACATCTTACAGGAGCCAACGCCAGCTTGATA<br>GGTATTGGTGGACCTCTGTTATGGGAGACACGACTTGGCCTGGCCTTCTTGAG<br>GGGCTTGACGTATCATGATGGGGCCCTGGTGACCATGGAGCCCGGTTACTACT<br>ATGTGTACTCCAAAGTGCAGCTGAGCGGCGTGGGCTGCCCCCAGGGGCTGGCC<br>AATGGCCTCCCCATCACCCATGGACTATACAAGCGCACATCCCGCTACCCGAA<br>GGAGTTAGAACTGCTGGTCAGTCGGCGGTCACCCTGTGGCCGGGCCAACAGCT<br>CCCGAGTCTGGTGGGACAGCAGCTTCCTGGGCGGCGTGGTACATCTGGAGGCT<br>GGGGAAGAGGTGGTGGTCCGCGTGCCTGGAAACCGCCTGGTCAGACCACGTGA<br>CGGCACCAGGTCCTATTTCGGAGCTTTCATGGTCTGAAGGCTGCGGTGACAAT<br>GTATTTTGTGGAGGGACCTCTCCAGGACTCACCTCAAACCCAGCAATAGGGTT<br>TGAAGTCCTCCCTTTAAGGAGCCCTGAACTCTGCAGTGCTCGGGGCGGTGTAG<br>ACTGOTGACCTGCTTTGGGCAATCTTCAAATCAGAGACCTGGAGACTTGGGGC<br>GTGGAGCCCAGGAGCGAGGGGTCAGCTCATTTGCCTGATATTCAGGAAGAAAG<br>AATCAAGCTGGGGTATTTATGCTTCTGATGCAAACACTGAGATTTCGGCTTTC<br>TGGGTTTTGAGCTGGAGGCAAGAAACCTTCCCAGAGTGTCATCAGGACCATGT<br>TGGCAGGACTTGGGGCTCCAGACTTGCCACCACACTCTGGCCTCTCCCATCCA<br>TCCGCTGCATTGGTTTCCAGCCACCAAAACAGCACTGGCCCCCTGGCTGCAAC<br>TGGCCAGGTACGAGCTTCTGAGCACCTACATTCCTCAGGGACATCTTGATGAG<br>ATCTCAGTACTCAGTCCAATGCGCAGCAGCGACAGACATGCCAGGAATGGTTG<br>GTCAGAAGGGAAGGGAGGAAAGGGAGGAAAGAAGGGAATGCAGAAGAGAAGGG<br>GGGAAAACAAGACCAAAACAAAACAGCAACAACAAAGCGGCAGGGAGGAGGTG<br>ACACCCTTGGGGATACTTTAGTCAACACACTTAGAACAGATTGTGCCAGGCCT<br>GTTGGATTCCTGGAGTTGATGGGATCGTGGGAAGGCACAATGGGGAGCAAGTG<br>GGCTTGGGTTATGGCTCAGTGGGTAAAGTGCAATTATGGGGATCTGAGTTTGA<br>ATCCCTGGTACCCATATAAAGACACAGATGCGGTGATGGGCACTTGTGACAAT<br>GAGATCATCAATAGGGAATGGAGACAGGAGGGACCTCTGGGGTTCACTGGCCA<br>GGCAGTCTAGCTGAATCAAAGAGCTCCAAGTTCAGTCGATAGCTCCTGAAGAT<br>GACAACTGAGGCTATTCTCCAAACCCCACACGCAGGACACATGCGTAATAAAT<br>AAAATTTTAAAAAT (SEQ ID NO: 131)<br><br>>NP_062291.1 tumor necrosis factor ligand superfamily member 14 [*Mus musculus*]<br>MESVVQPSVFVVDGQTDIPFRRLEQNHRRRRCGTVQVSLALVLLLGAGLATQG<br>WFLLRLHQRLGDIVAHLPDGGKGSWEKLIQDQRSHQANPAAHLTGANASLIGI<br>GGPLLWETRLGLAFLRGLTYHDGALVTMEPGYYYVYSKVQLSGVGCPQGLANG<br>LPITHGLYKRTSRYPKELELLVSRRSPCGRANSSRVWWDSSFLGGVVHLEAGE<br>EVVVRVPGNRLVRPRDGTRSYFGAFMV (SEQ ID NO: 132) |

TABLE 1-continued

Type I Proteins of Interest Amino Acid Sequence

| Protein of Interest | Transcript Sequence (SEQ ID NO:)<br>Amino Acid Sequence (SEQ ID NO:) |
|---|---|
| Human TL1 | >NM_005118.4 *Homo sapiens* TNF superfamily member 15 (TNFSF15), transcript variant 1, mRNA<br>AGAGGTGCCTCCAGGAGCAGCAGGAGCATGGCCGAGGATCTGGGACTGAGCTT<br>TGGGGAAACAGCCAGTGTGGAAATGCTGCCAGAGCACGGCAGCTGCAGGCCCA<br>AGGCCAGGAGCAGCAGCGCACGCTGGGCTCTCACCTGCTGCCTGGTGTTGCTC<br>CCCTTCCTTGCAGGACTCACCACATACCTGCTTGTCAGCCAGCTCCGGGCCCA<br>GGGAGAGGCCTGTGTGCAGTTCCAGGCTCTAAAAGGACAGGAGTTTGCACCTT<br>CACATCAGCAAGTTTATGCACCTCTTAGAGCAGACGGAGATAAGCCAAGGGCA<br>CACCTGACAGTTGTGAGACAAACTCCCACACAGCACTTTAAAAATCAGTTCCC<br>AGCTCTGCACTGGGAACATGAACTAGGCCTGGCCTTCACCAAGAACCGAATGA<br>ACTATACCAACAAATTCCTGCTGATCCCAGAGTCGGGAGACTACTTCATTTAC<br>TCCCAGGTCACATTCCGTGGGATGACCTCTGAGTGCAGTGAAATCAGACAAGC<br>AGGCCGACCAAACAAGCCAGACTCCATCACTGTGGTCATCACCAAGGTAACAG<br>ACAGCTACCCTGAGCCAACCCAGCTCCTCATGGGGACCAAGTCTGTATGCGAA<br>GTAGGTAGCAACTGGTTCCAGCCCATCTACCTCGGAGCCATGTTCTCCTTGCA<br>AGAAGGGGACAAGCTAATGGTGAACGTCAGTGACATCTCTTTGGTGGATTACA<br>CAAAAGAAGATAAAACCTTCTTTGGAGCCTTCTTACTATAGGAGGAGAGCAAA<br>TATCATTATATGAAAGTCCTCTGCCACCGAGTTCCTAATTTTCTTTGTTCAAA<br>TGTAATTATAACCAGGGGTTTTCTTGGGGCCGGGAGTAGGGGGCATTCCACAG<br>GGACAACGGTTTAGCTATGAAATTTGGGGCCCAAAATTTCACACTTCATGTGC<br>CTTACTGATGAGAGTACTAACTGGAAAAAGGCTGAAGAGAGCAAATATATTAT<br>TAAGATGGGTTGGAGGATTGGCGAGTTTCTAAATATTAAGACACTGATCACTA<br>AATGAATGGATGATCTACTCGGGTCAGGATTGAAAGAGAAATATTTCAACACC<br>TTCCTGCTATACAATGGTCACCAGTGGTCCAGTTATTGTTCAATTTGATCATA<br>AATTTGCTTCAATTCAGGAGCTTTGAAGGAAGTCCAAGGAAAGCTCTAGAAAA<br>CAGTATAAACTTTCAGAGGCAAAATCCTTCACCAATTTTTCCACATACTTTCA<br>TGCCTTGCCTAAAAAAAATGAAAAGAGAGTTGGTATGTCTCATGAATGTTCAC<br>ACAGAAGGAGTTGGTTTTCATGTCATCTACAGCATATGAGAAAAGCTACCTTT<br>CTTTTGATTATGTACACAGATATCTAAATAAGGAAGTATGAGTTTCACATGTA<br>TATCAAAAATACAACAGTTGCTTGTATTCAGTAGAGTTTTCTTGCCCACCTAT<br>TTTGTGCTGGGTTCTACCTTAACCCAGAAGACACTATGAAAAACAAGACAGAC<br>TCCACTCAAAATTTATATGAACACCACTAGATACTTCCTGATCAAACATCAGT<br>CAACATACTCTAAAGAATAACTCCAAGTCTTGGCCAGGCGCAGTGGCTCACAC<br>CTGTAATCCCAACACTTTGGGAGGCCAAGGTGGGTGGATCATCTAAGGCCGGG<br>AGTTCAAGACCAGCCTGACCAACGTGGAGAAACCCCATCTCTACTAAAAATAC<br>AAAATTAGCCGGGCGTGGTAGCGCATGGCTGTAATCCTGGCTACTCAGGAGGC<br>CGAGGCAGAAGAATTGCTTGAACTGGGGAGGCAGAGGTTGCGGTGAGCCCAGA<br>TCGCGCCATTGCACTCCAGCCTGGGTAACAAGAGCAAAACTCTGTCCAAAAAA<br>AAAAAAATAAAATAATAACTCCAAGCCTTTAAAAAATATCATCTGAAACTGTT<br>ACATCAGATTTCTGGCACTCTACTGACTGTGGAAGATAGCCAGCTGACTGGAA<br>GATAGCCAGCTGATTAGTTCCCTGAAGAAACCTGAAGACAGATACCTGGTTAA<br>CTAGATCAACTACACTGCCAACTTGTTTGATGCTGAGAGACAATGGACTTATT<br>CCATGGGGGAAGGGAAAAAAGAAGTCAATCACCAAATCTGAAGAAGTTAACCT<br>AGATCTTTGAGGTTTGATTTGCAACTTTATATGCAGAGTATTATGTGGGTATT<br>TTCCCTTAAAATATTCAAAGGGATTTACATATGGGATTAGCTAATGAGCCTAG<br>CCAAGACCTTCCCTGGAGGACAGGCTGGTCATTGCGGAGGTCCCTTCTGTGCT<br>TCAGTGGGTTCATATCCTCTAGTCCGTATGATTTTCCTACGCTAATATGTCAA<br>GGGCAGGAGAGGCAGCTCTGTTCTCCTAGCCTTTGTTGACTTGTCTGCAAAGC<br>AGGAATCTGCCCATTTGTTTCCAAGGAGCAAATGAGCTCATGAGAATGAAAGA<br>TGTTAACTTCATGCATTCTGTGCCATCTGAGCATTTCGGTATTATATGACTGG<br>TGACCCTTGGCCCGTATTATAAATGCTTCCTATCCTGGGAGACCTCATGGATG<br>AGTCTGAGAGGAAATTTGGCACCAAAATCACTCTCACTCTGGTTTCCAGTAGA<br>CTATAGAGGCAGAGAGGCATTTGAGAGGCTCCTGAGCAAAGTGTCCAGTGTAG<br>CAGGAGCACTTCATTAATATTTATTGAGTTATAATTAAATAAAAATTAATTTC<br>TGATTTCTCAGTTTGGAGGTTAAGGCTCTAAATATATTTTCTAACCTCTGCTA<br>GGCTAACTTAAGCCAGGCCTTTTTCTTGCCTTCCCTTTCTCAAAACAGTCAGC<br>ACAGACTCAGTGGGAGCACAGAGGAGTGTGGTCACCTCCACCTGGCTCACCAG<br>AGTCTTCATAGAGGAAGTGAAGCCTGGAAGAAACTGGGCGGGCCCCAGATGAC<br>CACAGGGAAAGGGCATCTCAGATGGAGGAATTACCCTTGACTTAAAGCAGAAA<br>AGAAAGATTTCTCAGTAACTCCAAAACTTGCTTGATAGGAGAATATTCCCTCA<br>ACCAATTCCTAGGACAATATTTATTGGTAGATCAAGAATGTTTCCTCAATAAC<br>TCTAGTCTAGCTCCATGATCAGAACTAACACCCATTAAAAACATAAAATGTTC<br>TTTCTGAACCGGTCTTCATGGTGCGTGAGAGCACCAAGCAGCTTTGGTATGCA<br>GGAGGAGTTTTGCACAGAAGAGTGGCCTGCTCAAACCTGCCCACTGTTCTGTA<br>GGTGATCTGGTGGATCTGGAAATTTATCCCAAGACAGGAATTTCCTAATATTC<br>GAAGACATTTGAGGCTTTGGGAAATTCTCTGCTGTGCATTTATTTGGCTCCTG<br>TCATAAGCTTGTTTTTTAAAGAATGTATCATAGCTCAAGTTTTTACTGCTGAT<br>TTTGTTAAATTCTGTATAGTATATTTTTTACGGAAAGGCACAGTCAGACATTC<br>CTAATAGGGCTCATGTCAGAACTTCTGTTCCCAAGGCATTATCTCCATAGCAA<br>AAATTAGTGCACTGTTTTCAAAAGTGAGGTGGGAAAATGCTTTTAAGATCATG<br>TGATGTTCCCCTAAAAGGGGTTAATGGGGTGTATTCAGGGTTTGGGAGGGAGG<br>AAGAAGCATGCTTTAGAAAACAGTAAATTTAGGGAGAAAATGCTTTGTTGGTT<br>AAATGTCACTCAAAAGGCTGAATTCAAATCAATTCCACAAACATTTACTGAGT<br>ACCTACTGCCCCTGGGGACACAGAGATAAATTATTTAGTCTCAGACACACTCA<br>TTCTAACTTCCCAGCACCTCTACTGTCTGCAGATTCTTTAATTTATTTTGGTT |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| | GTATTAGCTAATTAATTCGTAAACTTTAGGCACATGGATCTATTCTCATTATG<br>AAAATGGATGCCATTTGATTAAGGCTGATGACTAACAAAATGATTTGTGTTTA<br>CTCGAAGTGTTTTTTTAAAAATAGCTACTCAAGGATAGTTTTCCATAAATCAA<br>GAAGGTAAAAAAGTTCCCATTTTTTATTGTAGAATCCATTATTTAAACTACAT<br>GTAGAGACAGGTTATTATTTGCTATATTCAAGTTTGGTCATCAATACCCTTAA<br>AAATATTAGAATTTTATGGATGACCCAGAAATGCTTTGAAAATCTGTGTTCCT<br>CAGCAAATACAGAGACCATGATCAAAATGCACAGAATCACTAACATTTTGATG<br>CTAGCATGGTTTCAGTCTATTTGGCAGAACAGAATTGATTATGCTACTAAAAT<br>TTCTTTTTCTTTTTTTTTTTTTTTTTTTTTGAGACAGAGTCTTGCTTTGTCAC<br>CCAGGCTGAAGTGCAGTGGCAGGATCTCAGTTCACTGCAACCTCTGCCTCCCA<br>GGTTCACGCCATTCTCCTGCTTCAGCCTCCCGAGTAGCTGGGACTACAGGCTC<br>CCACCACCATGCCCGGCTAATTTTTTGCATTTTTAGTAGAGACGGGGTTTCAC<br>CGTGTTAGCCAGGATGGTCTCGATCTCCTGACCTCGTGATCCGCCCGCCTCAG<br>CCTTCCAAAGTGCTGGGATTACAGGCGTGAGCCACTGTGCCCGGACTCTGATT<br>TTTTTTTTACTAAGGTACAGTAAGAAAAGGGAAAAGTGTACGTTTTCACTTCC<br>TGAAATATGTCAGGTTGAATCAATAATAGAGCACACCAGAACTCTTGGCTCCA<br>TTTCAACCTAAACTATTCAGTTCTCATCACCCCAGAGGAAATTCCGCCTCTGT<br>GCTGGTCAGTAATCCCCCTGGATTATAAAAGTTTAACTAACTCACTGTGCACA<br>AGGCACGGCCATTGCCAACATTCTCTTGCAAGGTATTTTCCCAAGCCCTTACC<br>CAATTCTGTTTCCATGATTGTGACATTGGGGATTAATTCTGCAAGACAGAACT<br>GTTTATATTCTGTACCTTAAAAACACATGCAAACATCTCTTGCCTTAAGATTT<br>CTGGCTTTCCTATGGCCCAGAGTCCTAGAAGTGTTTTGATATTTGTAGCAGAA<br>TTTTCAAGTGTACATCCTTATCCTGGATATTAACATTTTTGCATCATATTGGC<br>AGCTGGACCTACAGAGAATTTAGTAGACTGTTAACCTAATAAGCCTTGAATCC<br>TTTTGCACCAGTGGTGAGAGAATGTGGATCAGAGCCATCACCTCCATGCCCCG<br>TCACCCTCTAACAACCACATTTACAACTTCCCCAGCTCTGAGACACACTTGCC<br>TCCACCCCTTCCATCACCCCATTTTAAGATGAAAATACCACACCAGCCTGGAA<br>GGAAGAAGTTACTTGCCCAGGGCCACATAGTGAGTTAAGGGCTGATCTAGAGC<br>TAGGAAGCTGTCTTCCTGAACCATAATCCTGGACTCTTCTAACCTCTCTACTC<br>ATCGCAAATAGAGTTCATTTTAGTGATTTGAAGGAAGATGGGACAAGTATTTT<br>CAAACACCTGTAGGACAACATGGAAGTGGGAGGAGACTTCTACTGTAGCTCCC<br>CAGAGAAGAGAGCTAGGGCTACAGAGTTGCAGTTACAAGGTTGCCCTCTCTGG<br>CTTGATCCCCAAAGGAATTTTCTACTCCAAAATAGAATTTTTCTAGGATGCTA<br>TTTCTCAGTCCCTGGAGATACTCAAACAAAGGGCTTGTCACAAGGGTTTTTGT<br>AGAAGCTATTCTTCACAGAGGTTGGGGGAGAGATTAAGCCAAAGGATCTCTGA<br>GGTCTTTTTCAAATCTATAATTATGTGGCCTTTTGTTCATTGACTTCCATGTG<br>TTCTAGTTGATCATTACAAACCTGGCAGGCCTTCTCAAGGGTTCAGTAATTAG<br>CTGTCATTTCCCATTTGTCCAGAGAGTGTCCAACACAAAATACCCCTAAGATC<br>TTGGCCAATAGAGAAATGTCATGGAATTTTAGAAATGACAGTATCTGCGGAGT<br>TTATTCCAAGTTATATCATTTCAAAGATGAAGAAACCCAGGCTCAGAGGGAGC<br>CATCACATCCACACCCTGTCACCCTTCGTGGCCAGTGCCAGACAGTAGCTAGT<br>TGGATGCTAAAAGTAGAATTTAGATATCTTAACAATAAGCCCAGCAGTCTTTC<br>AACTTCATTCGTAAATCATTTTTGTTTTGAGCATCTGTCACGTGGCAGCACTT<br>GCCTGGATACTGGAGAGCTGAGAAGGAATGCGACAGGCAAGTCCTACTCTCAC<br>AGTGTATACATTCAGGAGGAACAAGACACACAGTGCCAAGTAAATAAAGTAGC<br>TGAACTTCATCAAATGATTTTATTCTTAAAGTCATTAAAGCATGTAATGTTCC<br>CCTTTTTTTGTTTCAGGGGTGTACAGATTGAAGAAGTGTAGGTGTTTATGTGG<br>TTTTAGTGACAAACCCCATGTGCTTTCATTGATTTTATGTTTTATGTTAAAAC<br>ATCAACCGCAAGGTAAAATGCATATTGTATGTTGTTGGATACGTACTTAACTG<br>GTATGCATCCCATGTCTTTGGGTACTAGTGTATGAATTCTAATCTCTGTAAAT<br>GAAATGTTGTATGTGTTAATATATTTAATAGATGTAACTTAATAAACTGGCAT<br>TGAAGACTGAA (SEQ ID NO: 133)<br><br>>NP_005109.2 tumor necrosis factor ligand superfamily member 15 isoform VEGI-251 precursor [*Homo sapiens*]<br>MAEDLGLSFGETASVEMLPEHGSCRPKARSSSARWALTCCLVLLPFLAGLTTY<br>LLVSQLRAQGEACVQFQALKGQEFAPSHQQVYAPLRADGDKPRAHLTVVRQTP<br>TQHFKNQFPALHWEHELGLAFTKNRMNYTNKFLLIPESGDYFIYSQVTFRGMT<br>SECSEIRQAGRPNKPDSITVVITKVTDSYPEPTQLLMGTKSVCEVGSNWFQPI<br>YLGAMFSLQEGDKLMVNVSDISLVDYTKEDKTFFGAFLL (SEQ ID NO: 134) |
| Mouse TL1 | >NM_177371.4 *Mus musculus* tumor necrosis factor (ligand) superfamily, member 15 (Tnfsf15), mRNA<br>ATCAGAAGTCTCTCCAAGACAGCAGAAGGATGGCAGAGGAGCTGGGGTTGGGC<br>TTCGGAGAAGGAGTCCCAGTGGAAGTGCTGCCGGAAGGCTGTAGACACAGGCC<br>AGAGGCCAGGGCCGGGCTAGCTGCCAGGAGCAAAGCCTGCCTGGCTCTCACCT<br>GCTGCCTGTTGTCATTTCCCATCCTCGCAGGACTTAGCACCCTCCTAATGGCT<br>GGCCAGCTCCGGGTCCCCGGAAAAGACTGTATGCTTCGGGCCATAACAGAAGA<br>GAGATCTGAGCCTTCACCACAGCAAGTTTACTCACCTCCCAGAGGCAAGCCGA<br>GAGCACACCTGACAATTAAGAAACAAACCCCAGCACCACATCTGAAAAATCAG<br>CTCTCTGCTCTACACTGGGAACATGACCTAGGGATGGCCTTCACCAAGAACGG<br>GATGAAGTACATCAACAAATCCCTGGTGATCCCAGAGTCAGGAGACTATTTCA<br>TCTACTCCCAGATCACATTCCGAGGGACCACATCTGTGTGTGGTGACATCAGT<br>CGGGGGAGACGACCAAACAAGCCAGACTCCATCACCATGGTTATCACCAAGGT |

TABLE 1-continued

Type I Proteins of Interest Amino Acid Sequence

| Protein of Interest | Transcript Sequence (SEQ ID NO:) Amino Acid Sequence (SEQ ID NO:) |
|---|---|
| | AGCAGACAGCTACCCTGAGCCTGCCCGCCTACTAACAGGGTCCAAGTCTGTGT GTGAAATAAGCAACAACTGGTTCCAGTCCCTCTACCTTGGGGCCACGTTCTCC TTGGAAGAAGGAGACAGACTAATGGTAAACGTCAGTGACATCTCCTTGGTGGA TTACACAAAAGAAGATAAAACTTTCTTTGGAGCTTTCTTGCTATAAGGAGGAG AAAACCATCATTCCAAGGGGCTCCCCTGCCTCCTACTTTCCAATTTCCTTTTC TCATATGGATCTATAAACAGGGGCTTTAGAGGGATCAGGGAAGGGGACAGTGG TTTAGCTATATAATTTAGGAACCCAATATTGATCCGTATATGCCTTATGGACT AAAATAGTAAATGGAAAACCCAGTACAGCTCATGTTTGATAGAGACCTGCTGG GTTTTAAAAATTGAAACACGCCTCATCCAATGGCACAATCTACTGATTTCAGG ACAGAACCTTTCCACAGTGCCCTCTGTCCAAGTCCTTTCTGAATTCAGCAGTT CAGTTAGAGCTGAATTCGACAATGAACTTACTCCAGATCAAGAGCTAAAGACA GAATCCAAAGAAAGACTGAGAAAATGATGTTATTTCTCCAAGAGGCAATGCAT TTCCACATTCTTTTGTGCCTAACCTAAAAAATAAGAAAGAAGAAAGGAAGGAA GGAAGGAAGGAAGGAAGGAAGGAAGGAAGGAAGGAAGGAAGGAAGGAAGGAAG GAAGGAAGGGACAAGAAAAGACAAGACAAGACAAGACAAGAAAAAAGAAAAAATGGTA TTTCTCGTGAATATTCCCTAAAAGGAATTGGTTTTCTGCTGTGAAGGAGAAAC CTCACCTTTCTTCTGATTGCATCCTTTAGTATCCAAACATACAAGTGGGAATT CCAAATGCACATGGAACATAGAACACTTTTATTATTGTGAGAACATGTTTATT GAGTACCTACTATGCTCTGGGCACTCAGCCCACAGGACCATGAAGAGAAAGTC AAATTTTCTTAAAAACTAAATGAATCCTCAATACATACTTCCTGATCAACTAC CACTCAAAATGTATAACTTCCAAAGTATAACTTCAAGTCAGCCATCTAGGTGG TTTCTTGGGTAAAGGTGCTTGTCATTAAGCCTGACACCTGGGTTTGACCTCCC AGAACCCAAAAGCTGGAAGGAGAGAATTGGTTCCCACAAATTATCCTCAAACC CCCATACAAATGATGTGGCATGCACACATGTAACTAAATAAATAAGTGTAAAA CAAAAACAAAAACAAAATTTTAAAGAAAAATTTCAAGTCCTGAAAGACAGCAT TCCTGAGAATGTTGTCTCCATCGTTGTCCAGTATAGGCTAACCAGCTGATAGA GACACTGAAGGAATTTAAAGACAGACATCAAGTGAAATGGAGCACTGTAGAAA CACTTGATTCATGCCAGGAGTCAATGTACTATGAAGACCAACAACAAAGTGTC AGTCATCAAATCCAGAGGTGTTTATCTAGATCTGCTTTCAAGTTTGGTTTGCA GCCTTTATATAGTCTCTATTACAAATGCTCGTGTCATGGTAGATGCCACAAGG AGTCAGAGGGTAAACTTAGCCCCAAACCACTGCTGAGCCATCTTCTAGGAAAC CTTCGAAGCAGAGCTGGGCAGCGTGACTCCCACACAATGACTGGGAAAGTAGT AGCTGATCAAAATTTGTTGAGTAATAATTTGTTAGAAAATTCATCTCCACTGC CTACTAAACCTAAGTTGTATACTATCTAGCTTCTGCTAAGCCAACTTACATTG GCCACTTTTTCTGTCTTCAACTTCTTGAAGTATCACAGGTCTCAGTGAGAACA CAGGGAAAGGTGAGGTCGCCTTCCCCTGGTTCTTCATAGGGGAAACCACACCT GAAAGAAGATGAGCAGCCTGAGGTGACCTGGAGGAAGGGCTGTCTCAGAAGAA GGACTTATTTTTTGGCTTAGGTCTAAAACCTTGAGAGTAATGCTCACTGGTCA ATTGAGGATGCTTTATCAATGACTCCAGTCTGACTCCAAGGTCAGAAAGGAGA GTGAGATGCTCTCTCTGCCTGCATATATCTTCATGGAACATGAGAATATTGAG CAACATAGACTTATAGGAAAACACTTGCCCAAAAGTAGCCAGAGTGACCTGGT CATCCCCTCTACTAAACCCAAGCTTTGTGTCAAGGGCCTTCAAAGCTGCCCAG AAGTGATCTGGATGGCTTGGGAATTTATCCAAGACAGGAATTTCCTGACAGCC AAAGATGCTTGAGTCCTTGTGCCTGACATGCATTTATTTTGCCCCTGTTTATT GAAGACTGTAACTGTTGATTTGTGGGTATACATACATACATACATACATACAT ACATACATACATACATATGCTGTCATGAAGGCAGCATCAAACATTACTAATTG GACTCAAACCAGCATTTCTGTTTCCAAGATACTAAGTATTCCCATGCAAACAG GAGCATGCTATTTTTCTAAAGCAAAATGAAAAAAATAGTTTTGAAAGTATATA TATGATGGAGTCAAGTGTAATGGCATACATCTGTAAACCCAGCACATGGGATG CTGAGCCAGGAGGATTGCCGTGAGTTTGAGGAGAACAGGGGCTAAATAGTAAT TTTCAGGAAAGCCTTGCCTATATAACAAGACCTTGTCTCAAATGAAAAAAAAA AAAAAAATAGACCCCAGGCTGGTCCTTGGAGATAAGGTAATATATTCATTGGG TGAGGGGGTGTGTGTTTTGGAAAATAGTTAATTTAGTGAGAAATGCTTTTCGG TCAAATGCATCTCAAAGGCTGCTGAATTCAAATCGGGTCTGTAAATGCTTACC TAGTGCTTGCTTGCCCTGGGGACAGAGACATAAATTACTTTAGTCTCAGATCC ACTCGTTCTAACAGATTGGCATCTCCATCGTCTGTGGAGCTTTTAATCACTCT GTTTGTATTAGCTAATTAATTAGCTAACTTGAGACACACTGATATTTTCTTAT TATAAACATGGGTGCCATTTGATAAAAGACAATCATTAACAAAATGGTTCGAA TTTCCGCTTAAGTGATCTTCTTTTTTCCTTTTCATTTTTTTTAACTAGCTAAT CAAAGGTAGTTTCCCAAAAATAAATGCAAAGGGAGTATAAAGAAAAAATTCCC TGTGGTGGGAGCTAGTATTGAAACAACAGTATCAAAGAGGCTGTTACCTACTG GCCTCAAATTTTGGCAGGAACGCCTTTGAAAATGTTAGAACTTTACGGACAGC CTAGAGGTGCTTTGAAAAGTCTCTGTTGCCAACAAAAGCCATTAATCAGCATG CGGCACAGGTTACTCAAATTTTGACCTTGACTGTTTTTTAGATCTGTTACACA GAACACAACTTCTGGGCTGTAATCTCTGATGTGGATTTGGTGATTTACTAAGG TACCGTGGGAAACAAGGAAAGTGTACTTGTACCACATCGTTTCTCAGTGCATG TCAGAGTCTACTCAACAGCAGGGCATGCCAGAGCCTTGGATACATTCCGGGAC AAACTATGTCACTCCTAAGGAAATTCCAAGTGTGTGCCTGTCAAGCACTCTGG ATCATAGAAGCCCACGAGTTCACTGTGCACAAGGCACAGCCATGGCCAGCACT CTCTTGCATGGTATTTCTCTTAAGCTCTTACTCAATCACGGTCCCATGATTGT GACATTGGGGATTAATTGCTTGAGCAGGTTTATTTACAGTCTGTTCCTTGCAA AATACATGCAGATATGTCTGGCCTCAAAATCCCCTGATTGTTTTAGGGCTTAG AGAATACTGGGGATGTTTTTGCTGTTTTCAGATGTACTTTATTTAAGCTTGCA GAATTACCCTGAATATTAACAGTGTTCTAAGATATTGCCTGCTAGCTTCTGGC TAATTTACTAGTGGTGACAGTATCAGATCAGAGTATCTATATTTATGTCTTGC |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| | TATTATAGTTAAAACTTCCTGATCTCTGTAACACACTCACCCCTACCTCATCT<br>ATCTACCCATCTTGTGGATGTAGCTGTGAGAAGACTCACAAGCCCGAGTTGCA<br>GTTACTTTTCTGAAGCAACATAGTATGTTAATGGAATGGCCAGAACTCTACTC<br>TTGGCACATGGCACTGAATTTGATGCCACTAAAAGAAAAATTGAAGGCAGAAA<br>TATTTTTTACTATGCATGGGACAACGTAGAAGAGCAAGGAGACTGCTTACACA<br>TGGTGGTCACATCTCTGGCTTCATCCCTAAACCAATTTTCTGACCCCAAGTCG<br>ATTTTTTTTCATGTAGTTATTGTTCATTTTCTGGAAAGAGTCAAGCAAAAAGA<br>GAGTTTTATAGAAACCATTGCATCATGGAGGTCAGGGGAGGGATTAAGCCAAA<br>GAATTCCTTCTCCAAATCTATAGCCATATGGCCACCCTTTGGTGTACTTCTAT<br>TTGATCATGACAAACCTGAGAGCCCTGCCCAGAGTTCAGTGGATCCTAATGAA<br>CTCCAAGAGTAATTCATTCCCTCACCAACTCTAGGGGCTTGGCCAGTGCAGAA<br>AATGTCATGGGATTTTAAAGTTAACATGAGCTGCTATCCAAACTTATGTCTCT<br>TTAAGAATGGAGAGACACAGGCCAGGAGAGGTAACATATGAAGCCTGGTATTG<br>GGCAGTAGCTTGATGGAGTATTGAGGCTAAAAGTAGACTTCCTGCCCCTGACC<br>ATACACAACACCCTTTCAGTTTGATCCATGGTGGTCTTATTCTACTTTATTTT<br>GAGCACCTGTCACACCTAGTTACTGTCATGCCAAGAAGGTCCATAACAGGCAA<br>ATCCTACTCTGCTGTGTGCACACAAGAGGAAGGAGGCTCACAGTAGCAAGTAA<br>ACAGATAAGCAAACGTACACGATTTTCGTCTTAAAGTCATTAAGACACACGCG<br>TACCCCTCTTTTGTTTCAGAGGGTATACAGGCTGAACAGATGTCAGTGTTCAC<br>CTATTCTTATTGATAAGCCCCATGTGCTTTCATTGGTTGAATGTTTTATGTTA<br>AAACGTCATATTGCCATCGTAAAATGCATATTGTATGTTGTTGGGTATATAAT<br>TAACTAATATGCATCGCATGTATGAATTCTAATCTCTGTAAATGAAAACTTAT<br>ATATGTTAACATATGTAATAGTTATAATTTAATAAACTGACACTGGAGACTAC<br>(SEQ ID NO: 135)<br><br>>NP_796345.4 tumor necrosis factor ligand superfamily member 15 [*Mus musculus*]<br>MAEELGLGFGEGVPVEVLPEGCRHRPEARAGLAARSKACLALTCCLLSFPILA<br>GLSTLLMAGQLRVPGKDCMLRAITEERSEPSPQQVYSPPRGKPRAHLTIKKQT<br>PAPHLKNQLSALHWEHDLGMAFTKNGMKYINKSLVIPESGDYFIYSQITFRGT<br>TSVCGDISRGRRPNKPDSITMVITKVADSYPEPARLLTGSKSVCEISNNWFQS<br>LYLGATFSLEEGDRLMVNVSDISLVDYTKEDKTFFGAFLL (SEQ ID NO: 136) |
| Human CD80 | >NM_005191.4 *Homo sapiens* CD80 molecule (CD80), mRNA<br>AAACCCTCTGTAAAGTAACAGAAGTTAGAAGGGGAAATGTCGCCTCTCTGAAG<br>ATTACCCAAAGAAAAAGTGATTTGTCATTGCTTTATAGACTGTAAGAAGAGAA<br>CATCTCAGAAGTGGAGTCTTACCCTGAAATCAAAGGATTTAAAGAAAAAGTGG<br>AATTTTTCTTCAGCAAGCTGTGAAACTAAATCCACAACCTTTGGAGACCCAGG<br>AACACCCTCCAATCTCTGTGTGTTTTGTAAACATCACTGGAGGGTCTTCTACG<br>TGAGCAATTGGATTGTCATCAGCCCTGCCTGTTTTGCACCTGGGAAGTGCCCT<br>GGTCTTACTTGGGTCCAAATTGTTGGCTTTCACTTTTGACCCTAAGCATCTGA<br>AGCCATGGGCCACACACGGAGGCAGGGAACATCACCATCCAAGTGTCCATACC<br>TCAATTTCTTTCAGCTCTTGGTGCTGGCTGGTCTTTCTCACTTCTGTTCAGGT<br>GTTATCCACGTGACCAAGGAAGTGAAAGAAGTGGCAACGCTGTCCTGTGGTCA<br>CAATGTTTCTGTTGAAGAGCTGGCACAAACTCGCATCTACTGGCAAAAGGAGA<br>AGAAAATGGTGCTGACTATGATGTCTGGGGACATGAATATATGGCCCGAGTAC<br>AAGAACCGGACCATCTTTGATATCACTAATAACCTCTCCATTGTGATCCTGGC<br>TCTGCGCCCATCTGACGAGGGCACATACGAGTGTGTTGTTCTGAAGTATGAAA<br>AAGACGCTTTCAAGCGGGAACACCTGGCTGAAGTGACGTTATCAGTCAAAGCT<br>GACTTCCCTACACCTAGTATATCTGACTTTGAAATTCCAACTTCTAATATTAG<br>AAGGATAATTTGCTCAACCTCTGGAGGTTTTCCAGAGCCTCACCTCTCCTGGT<br>TGGAAAATGGAGAAGAATTAAATGCCATCAACACAACAGTTTCCCAAGATCCT<br>GAAACTGAGCTCTATGCTGTTAGCAGCAAACTGGATTTCAATATGACAACCAA<br>CCACAGCTTCATGTGTCTCATCAAGTATGGACATTTAAGAGTGAATCAGACCT<br>TCAACTGGAATACAACCAAGCAAGAGCATTTTCCTGATAACCTGCTCCCATCC<br>TGGGCCATTACCTTAATCTCAGTAAATGGAATTTTTGTGATATGCTGCCTGAC<br>CTACTGCTTTGCCCCAAGATGCAGAGAGAGAAGGAGGAATGAGAGATTGAGAA<br>GGGAAAGTGTACGCCCTGTATAACAGTGTCCGCAGAAGCAAGGGGCTGAAAAG<br>ATCTGAAGGTCCCACCTCCATTTGCAATTGACCTCTTCTGGGAACTTCCTCAG<br>ATGGACAAGATTACCCCACCTTGCCCTTTACGTATCTGCTCTTAGGTGCTTCT<br>TCACTTCAGTTGCTTTGCAGGAAGTGTCTAGAGGAATATGGTGGGCACAGAAG<br>TAGCTCTGGTGACCTTGATCAAGGTGTTTTGAAATGCAGAATTCTTGAGTTCT<br>GGAAGGGACTTTAGAGAATACCAGTGTTATTAATGACAAAGGCACTGAGGCCC<br>AGGGAGGTGACCCGAATTATAAAGGCCAGCGCCAGAACCCAGATTTCCTAACT<br>CTGGTGCTCTTTCCCTTTATCAGTTTGACTGTGGCCTGTTAACTGGTATATAC<br>ATATATATGTCAGGCAAAGTGCTGCTGGAAGTAGAATTTGTCCAATAACAGGT<br>CAACTTCAGAGACTATCTGATTTCCTAATGTCAGAGTAGAAGATTTTATGCTG<br>CTGTTTACAAAAGCCCAATGTAATGCATAGGAAGTATGGCATGAACATCTTTA<br>GGAGACTAATGGAAATATTATTGGTGTTTACCCAGTATTCCATTTTTTTCATT<br>GTGTTCTCTATTGCTGCTCTCTCACTCCCCCATGAGGTACAGCAGAAAGGAGA<br>ACTATCCAAAACTAATTTCCTCTGACATGTAAGACGAATGATTTAGGTACGTC<br>AAAGCAGTAGTCAAGGAGGAAAGGGATAGTCCAAAGACTTAACTGGTTCATAT<br>TGGACTGATAATCTCTTTAAATGGCTTTATGCTAGTTTGACCTCATTTGTAAA<br>ATATTTATGAGAAAGTTCTCATTTAAAATGAGATCGTTGTTTACAGTGTATGT |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| | ACTAAGCAGTAAGCTATCTTCAAATGTCTAAGGTAGTAACTTTCCATAGGGCC<br>TCCTTAGATCCCTAAGATGGCTTTTTCTCCTTGGTATTTCTGGGTCTTTCTGA<br>CATCAGCAGAGAACTGGAAAGACATAGCCAACTGCTGTTCATGTTACTCATGA<br>CTCCTTTCTCTAAAACTGCCTTCCACAATTCACTAGACCAGAAGTGGACGCAA<br>CTTAAGCTGGGATAATCACATTATCATCTGAAAATCTGGAGTTGAACAGCAAA<br>AGAAGACAACATTTCTCAAATGCACATCTCATGGCAGCTAAGCCACATGGCTG<br>GGATTTAAAGCCTTTAGAGCCAGCCCATGGCTTTAGCTACCTCACTATGCTGC<br>TTCACAAACCTTGCTCCTGTGTAAAACTATATTCTCAGTGTAGGGCAGAGAGG<br>TCTAACACCAACATAAGGTACTAGCAGTGTTTCCCGTATTGACAGGAATACTT<br>AACTCAATAATTCTTTTCTTTTCCATTTAGTAACAGTTGTGATGACTATGTTT<br>CTATTCTAAGTAATTCCTGTATTCTACAGCAGATACTTTGTCAGCAATACTAA<br>GGGAAGAAACAAAGTTGAACCGTTTCTTTAATAA (SEQ ID NO: 137)<br><br>>NP__005182.1 T-lymphocyte activation antigen CD80<br>precursor [*Homo sapiens*]<br>MGHTRRQGTSPSKCPYLNFFQLLVLAGLSHFCSGVIHVTKEVKEVATLSCGHN<br>VSVEELAQTRIYWQKEKKMVLTMMSGDMNIWPEYKNRTIFDITNNLSIVILAL<br>RPSDEGTYECVVLKYEKDAFKREHLAEVTLSVKADFPTPSISDFEIPTSNIRR<br>IICSTSGGFPEPHLSWLENGEELNAINTTVSQDPETELYAVSSKLDFNMTTNH<br>SFMCLIKYGHLRVNQTFNWNTTKQEHFPDNLLPSWAITLISVNGIFVICCLTY<br>CFAPRCRERRRNERLRRESVRPV (SEQ ID NO: 138) |
| Mouse CD80 | >NM_009855.2 *Mus musculus* CD80 antigen (Cd80),<br>transcript variant 2, mRNA<br>GAGTTTTATACCTCAATAGACTCTTACTAGTTTCTCTTTTTCAGGTTGTGAAA<br>CTCAACCTTCAAAGACACTCTGTTCCATTTCTGTGGACTAATAGGATCATCTT<br>TAGCATCTGCCGGGTGGATGCCATCCAGGCTTCTTTTTCTACATCTCTGTTTC<br>TCGATTTTTGTGAGCCTAGGAGGTGCCTAAGCTCCATTGGCTCTAGATTCCTG<br>GCTTTCCCCATCATGTTCTCCAAAGCATCTGAAGCTATGGCTTGCAATTGTCA<br>GTTGATGCAGGATACACCACTCCTCAAGTTTCCATGTCCAAGGCTCATTCTTC<br>TCTTTGTGCTGCTGATTCGTCTTTCACAAGTGTCTTCAGATGTTGATGAACAA<br>CTGTCCAAGTCAGTGAAAGATAAGGTATTGCTGCCTTGCCGTTACAACTCTCC<br>TCATGAAGATGAGTCTGAAGACCGAATCTACTGGCAAAAACATGACAAAGTGG<br>TGCTGTCTGTCATTGCTGGGAAACTAAAAGTGTGGCCCGAGTATAAGAACCGG<br>ACTTTATATGACAACACTACCTACTCTCTTATCATCCTGGGCCTGGTCCTTTC<br>AGACCGGGGCACATACAGCTGTGTCGTTCAAAAGAAGGAAAGAGGAACGTATG<br>AAGTTAAACACTTGGCTTTAGTAAAGTTGTCCATCAAAGCTGACTTCTCTACC<br>CCCAACATAACTGAGTCTGGAAACCCATCTGCAGACACTAAAAGGATTACCTG<br>CTTTGCTTCCGGGGGTTTCCCAAAGCCTCGCTTCTCTTGGTTGGAAAATGGAA<br>GAGAATTACCTGGCATCAATACGACAATTTCCCAGGATCCTGAATCTGAATTG<br>TACACCATTAGTAGCCAACTAGATTTCAATACGACTCGCAACCACACCATTAA<br>GTGTCTCATTAAATATGGAGATGCTCACGTGTCAGAGGACTTCACCTGGGAAA<br>AACCCCCAGAAGACCCTCCTGATAGCAAGAACACACTTGTGCTCTTTGGGGCA<br>GGATTCGGCGCAGTAATAACAGTCGTCGTCATCGTTGTCATCATCAAATGCTT<br>CTGTAAGCACAGAAGCTGTTTCAGAAGAAATGAGGCAAGCAGAGAAACAAACA<br>ACAGCCTTACCTTCGGGCCTGAAGAAGCATTAGCTGAACAGACCGTCTTCCTT<br>TAGTTCTTCTCTGTCCATGTGGGATACATGGTATTATGTGGCTCATGAGGTAC<br>AATCTTTCTTTCAGCACCGTGCTAGCTGATCTTTCGGACAACTTGACACAAGA<br>TAGAGTTAACTGGGAAGAGAAAGCCTTGAATGAGGATTTCTTTCCATCAGGAA<br>GCCTACGGGCAAGTTTGCTGGGCCTTTGATTGCTTGATGACTGAAGTGGAAAG<br>GCTGAGCCCACTGTGGGTGGTGCTAGCCCTGGGCAGGGGCAGGTGACCCTGGG<br>TGGTATAAGAAAAAGAGCTGTCACTAAAAGGAGAGGTGCCTAGTCTTACTGCA<br>ACTTGATATGTCATGTTTGGTTGGTGTCTGTGGGAGGCCTGCCCTTTTCTGAA<br>GAGAAGTGGTGGGAGAGTGGATGGGGTGGGGGCAGAGGAAAAGTGGGGGAGAG<br>GGCCTGGGAGGAGAGGAGGGAGGGGGACGGGGTGGGGGTGGGGAAAACTATGG<br>TTGGGATGTAAAAACGATAATAATATAAATATTAAATAAAAAGAGAGTATTGA<br>GCAAA (SEQ ID NO: 139)<br><br>>NP_033985.3 T-lymphocyte activation antigen CD80<br>precursor [*Mus musculus*]<br>MACNCQLMQDTPLLKFPCPRLILLFVLLIRLSQVSSDVDEQLSKSVKDKVLLP<br>CRYNSPHEDESEDRIYWQKHDKVVLSVIAGKLKVWPEYKNRTLYDNTTYSLII<br>LGLVLSDRGTYSCVVQKKERGTYEVKHLALVKLSIKADFSTPNITESGNPSAD<br>TKRITCFASGGFPKPRFSWLENGRELPGINTTISQDPESELYTISSQLDFNTT<br>RNHTIKCLIKYGDAHVSEDFTWEKPPEDPPDSKNTLVLFGAGFGAVITVVVIV<br>VIIKCFCKHRSCFRRNEASRETNNSLTFGPEEALAEQTVFL (SEQ ID NO:<br>140) |
| Human CD86 | >NM_175862.5 *Homo sapiens* CD86 molecule (CD86),<br>transcript variant 1, mRNA<br>AGTCATTGCCGAGGAAGGCTTGCACAGGGTGAAAGCTTTGCTTCTCTGCTGCT<br>GTAACAGGGACTAGCACAGACACACGGATGAGTGGGGTCATTTCCAGATATTA<br>GGTCACAGCAGAAGCAGCCAAAATGGATCCCCAGTGCACTATGGGACTGAGTA<br>ACATTCTCTTTGTGATGGCCTTOCTGOTCTCTGGTGCTGCTCCTCTGAAGATT<br>CAAGCTTATTTCAATGAGACTGCAGACCTGCCATGCCAATTTGCAAACTCTCA |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| | AAACCAAAGCCTGAGTGAGCTAGTAGTATTTTGGCAGGACCAGGAAAACTTGG<br>TTCTGAATGAGGTATACTTAGGCAAAGAGAAATTTGACAGTGTTCATTCCAAG<br>TATATGGGCCGCACAAGTTTTGATTCGGACAGTTGGACCCTGAGACTTCACAA<br>TCTTCAGATCAAGGACAAGGGCTTGTATCAATGTATCATCCATCACAAAAAGC<br>CCACAGGAATGATTCGCATCCACCAGATGAATTCTGAACTGTCAGTGCTTGCT<br>AACTTCAGTCAACCTGAAATAGTACCAATTTCTAATATAACAGAAAATGTGTA<br>CATAAATTTGACCTGCTCATCTATACACGGTTACCCAGAACCTAAGAAGATGA<br>GTGTTTTGCTAAGAACCAAGAATTCAACTATCGAGTATGATGGTGTTATGCAG<br>AAATCTCAAGATAATGTCACAGAACTGTACGACGTTTCCATCAGCTTGTCTGT<br>TTCATTCCCTGATGTTACGAGCAATATGACCATCTTCTGTATTCTGGAAACTG<br>ACAAGACGCGGCTTTTATCTTCACCTTTCTCTATAGAGCTTGAGGACCCTCAG<br>CCTCCCCCAGACCACATTCCTTGGATTACAGCTGTACTTCCAACAGTTATTAT<br>ATGTGTGATGGTTTTCTGTCTAATTCTATGGAAATGGAAGAAGAAGAAGCGGC<br>CTCGCAACTCTTATAAATGTGGAACCAACACAATGGAGAGGGAAGAGAGTGAA<br>CAGACCAAGAAAAGAGAAAAAATCCATATACCTGAAAGATCTGATGAAGCCCA<br>GCGTGTTTTTAAAAGTTCGAAGACATCTTCATGCGACAAAAGTGATACATGTT<br>TTTAATTAAAGAGTAAAGCCCATACAAGTATTCATTTTTTCTACCCTTTCCTT<br>TGTAAGTTCCTGGGCAACCTTTTTGATTTCTTCCAGAAGGCAAAAAGACATTA<br>CCATGAGTAATAAGGGGGCTCCAGGACTCCCTCTAAGTGGAATAGCCTCCCTG<br>TAACTCCAGCTCTGCTCCGTATGCCAAGAGGAGACTTTAATTCTCTTACTGCT<br>TCTTTTCACTTCAGAGCACACTTATGGGCCAAGCCCAGCTTAATGGCTCATGA<br>CCTGGAAATAAAATTTAGGACCAATACCTCCTCCAGATCAGATTCTTCTCTTA<br>ATTTCATAGATTGTGTTTTTTTTTTAAATAGACCTCTCAATTTCTGGAAAACT<br>GCCTTTTATCTGCCCAGAATTCTAAGCTGGTGCCCCCACTGAATTTTGTGTGTA<br>CCTGTGACTAAACAACTACCTCCTCAGTCTGGGTGGGACTTATGTATTTATGA<br>CCTTATAGTGTTAATATCTTGAAACATAGAGATCTATGTACTGTAATAGTGTG<br>ATTACTATGCTCTAGAGAAAAGTCTACCCCTGCTAAGGAGTTCTCATCCCTCT<br>GTCAGGGTCAGTAAGGAAAACGGTGGCCTAGGGTACAGGCAACAATGAGCAGA<br>CCAACCTAAATTTGGGGAAATTAGGAGAGGCAGAGATAGAACCTGGAGCCACT<br>TCTATCTGGGCTGTTGCTAATATTGAGGAGGCTTGCCCCACCCAACAAGCCAT<br>AGTGGAGAGAACTGAATAAACAGGAAAATGCCAGAGCTTGTGAACCCTGTTTC<br>TCTTGAAGAACTGACTAGTGAGATGGCCTGGGGAAGCTGTGAAAGAACCAAAA<br>GAGATCACAATACTCAAAAGAGAGAGAGAGAGAGAAAAAAGAGAGATCTTGATCC<br>ACAGAAATACATGAAATGTCTGGTCTGTCCACCCCATCAACAAGTCTTGAAAC<br>AAGCAACAGATGGATAGTCTGTCCAAATGGACATAAGACAGACAGCAGTTTCC<br>CTGGTGGTCAGGGAGGGGTTTGGTGATACCCAAGTTATTGGGATGTCATCTT<br>CCTGGAAGCAGAGCTGGGGAGGGAGAGCCATCACCTTGATAATGGGATGAATG<br>GAAGGAGGCTTAGGACTTTCCACTCCTGGCTGAGAGAGGAAGAGCTGCAACGG<br>AATTAGGAAGACCAAGACACAGATCACCCGGGGCTTACTTAGCCTACAGATGT<br>CCTACGGGAACGTGGGCTGGCCCAGCATAGGGCTAGCAAATTTGAGTTGGATG<br>ATTGTTTTGCTCAAGGCAACCAGAGGAAACTTGCATACAGAGACAGATATAC<br>TGGGAGAAATGACTTTGAAAACCTGGCTCTAAGGTGGGATCACTAAGGGATGG<br>GGCAGTCTCTGCCCAAACATAAAGAGAACTCTGGGGAGCCTGAGCCACAAAAA<br>TGTTCCTTTATTTTATGTAAACCCTCAAGGGTTATAGACTGCCATGCTAGACA<br>AGCTTGTCCATGTAATATTCCCATGTTTTTACCCTGCCCCTGCCTTGATTAGA<br>CTCCTAGCACCTGGCTAGTTTCTAACATGTTTTGTGCAGCACAGTTTTTAATA<br>AATGCTTGTTACATTCA (SEQ ID NO: 141)<br><br>>NP_787058.5 T-lymphocyte activation antigen CD86<br>isoform 1 precursor [*Homo sapiens*]<br>MDPQCTMGLSNILFVMAFLLSGAAPLKIQAYFNETADLPCQFANSQNQSLSEL<br>VVFWQDQENLVLNEVYLGKEKFDSVHSKYMGRTSFDSDSWTLRLHNLQIKDKG<br>LYQCIIHHKKPTGMIRIHQMNSELSVLANFSQPEIVPISNITENVYINLTCSS<br>IHGYPEPKKMSVLLRTKNSTIEYDGVMQKSQDNVTELYDVSISLSVSFPDVTS<br>NMTIFCILETDKTRLLSSPFSIELEDPQPPPDHIPWITAVLPTVIICVMVFCL<br>ILWKWKKKKRPRNSYKCGTNTMEREESEQTKKREKIHIPERSDEAQRVFKSSK<br>TSSCDKSDTCF (SEQ ID NO: 142) |
| Mouse CD86 | >NM_019388.3 *Mus musculus* CD86 antigen (Cd86), mRNA<br>ATTGCTGAGGAAGAAAGAGGAGCAAGCAGACGCGTAAGAGTGGCTCCTGTAGG<br>CAGCACGGACTTGAACAACCAGACTCCTGTAGACGTGTTCCAGAACTTACGGA<br>AGCACCCACGATGGACCCCAGATGCACCATGGGCTTGGCAATCCTTATCTTTG<br>TGACAGTCTTGCTGATCTCAGATGCTGTTTCCGTGGAGACGCAAGCTTATTTC<br>AATGGGACTGCATATCTGCCGTGCCCATTTACAAAGGCTCAAAACATAAGCCT<br>GAGTGAGCTGGTAGTATTTTGGCAGGACCAGCAAAAGTTGGTTCTGTACGAGC<br>ACTATTTGGGCACAGAGAAACTTGATAGTGTGAATGCCAAGTACCTGGGCCGC<br>ACGAGCTTTGACAGGAACAACTGGACTCTACGACTTCACAATGTTCAGATCAA<br>GGACATGGGCTCGTATGATTGTTTTATACAAAAAAAGCCACCCACAGGATCAA<br>TTATCCTCCAACAGACATTAACAGAACTGTCAGTGATCGCCAACTTCAGTGAA<br>CCTGAAATAAAACTGGCTCAGAATGTAACAGGAAATTCTGGCATAAATTTGAC<br>CTGCACGTCTAAGCAAGGTCACCCGAAACCTAAGAAGATGTATTTTCTGATAA<br>CTAATTCAACTAATGAGTATGGTGATAACATGCAGATATCACAAGATAATGTC<br>ACAGAACTGTTCAGTATCTCCAACAGCCTCTCTCTTTCATTCCCGGATGGTGT<br>GTGGCATATGACCGTTGTGTGTGTTCTGGAAACGGAGTCAATGAAGATTTCCT<br>CCAAACCTCTCAATTTCACTCAAGAGTTTCCATCTCCTCAAACGTATTGGAAG |

TABLE 1-continued

| Protein of Interest | Type I Proteins of Interest Amino Acid Sequence<br>Transcript Sequence (SEQ ID NO:)<br>Amino Acid Sequence (SEQ ID NO:) |
|---|---|
| | GAGATTACAGCTTCAGTTACTGTGGCCCTCCTCCTTGTGATGCTGCTCATCAT<br>TGTATGTCACAAGAAGCCGAATCAGCCTAGCAGGCCCAGCAACACAGCCTCTA<br>AGTTAGAGCGGGATAGTAACGCTGACAGAGAGACTATCAACCTGAAGGAACTT<br>GAACCCCAAATTGCTTCAGCAAAACCAAATGCAGAGTGAAGGCAGTGAGAGCC<br>TGAGGAAAGAGTTAAAAATTGCTTTGCCTGAAATAAGAAGTGCAGAGTTTCTC<br>AGAATTCAAAAATGTTCTCAGCTGATTGGAATTCTACAGTTGAATAATTAAAG<br>AACAAAATACACAACAGTGTCCATATTTTATCCTGTTTCCTTTCCAAGTTTTT<br>GGGCAATGTCAATTGTGTCCCCTATGCCAGGAGCAGACATCTATTTTGTCTTG<br>CTTTGTTTAACTCAGTGCACACTCATAGGCCAAGAGCACTGAAATGGCTTCTT<br>TCCCAGGAATAACATTTTGGATCAATCTCTCCTACTTGAGATCAGATTCTTCT<br>TCTAATTTTGCATAGTGTGTTTTTATATGGAACTCCTTGTTGTAGGAATACTG<br>GCTTTTATCTGTCTTGCACACTTGCATACTTATATACTTATACCTGGACAGCT<br>ACCTCTTCAGTCAGGATGGGAGTGGTATATTTGGTGATGTTATTTGATGTGTT<br>CGTGTTGCTATCTTAAAACAGCAAAGAGCATATACTATAGTAGCTCAACTACA<br>ATGATCTAGAGAAAGACCCAGCACTTATAAGAAACACTGTCCCTCCATCAGGG<br>TCAATAATGAATACAATGACCTAAGTAATATACAGGTGACAGCAACAGCACAG<br>AGTTCTCAGTGCTGGCAAATCAAGAAACACAAATATGGAACCATCTCTAGATC<br>CAAGAGCCACTCCTACCTGGGCTGCCACAGATACTGGAAGAATCCACCTGCCT<br>GGCCAGCAAGTCACAACTTAGCAGGCAGCACTGAAGAAAGCAAGATGTACTGT<br>ATGCCCTTTTAAGAAAATGCCTGGAAAGGTCTGGAGAATGCTGTGCAAGGATA<br>AGACAGCCAAGCACTCAAAACCAGGAGACATCACTAGAATCCAACCAACAAAT<br>GTTTATGGAAGGACTGATCTGCCCAGTCCATTGAAAAGTCAAGAGGTCAGAGA<br>TAGACCAGTGTGTGTCTCAATGGATGTAGATATCAGCCACCTCGGTGCTCAAC<br>AGGTATTTTATGATCTCCTTGTTTCAAATTCATCTAGATGTAGAACTAGGGAG<br>AGAGCAGTCACATTGATGAAAGGCTAGGACTCTTTCAGCTCATGGCTTGTGTG<br>GAAGGAGGGAAAGCAGAAATCACAACACTCTGAGACTACTGTAGTCTGCAGAT<br>ACCTGAGTGGGTGTGGCTTGGCCTTTCAAAGGACAAAGAGCAACTAATGCTGA<br>AAGCACATAGTGTATCTATACGGCATGGAATAGTCATCACCCAGACTTAAAGA<br>GAACTTTGGCAGGTCTGAGCAGCAAAATATTGTTGTTTCCATTTTACATAAAG<br>GGCCCTGGAGGGCTATAGACTATTCCGCTGGCAGGGCTCATGCTTGTAATGTG<br>TCCATCTTGATTCACCCTGTGCAGACTCTTAAGATCTGGCCAGTTACCAACAT<br>GTTCTGTACAGAGTGGATTTCAATAAAGTTTTCTTGAATTTTTTCAAG<br>(SEQ ID NO: 143)<br><br>>NP_062261.3 T-lymphocyte activation antigen 0D86<br>precursor [*Mus musculus*]<br>MDPRCTMGLAILIFVTVLLISDAVSVETQAYFNGTAYLPCPFTKAQNISLSEL<br>VVFWQDQQKLVLYEHYLGTEKLDSVNAKYLGRTSFDRNNWTLRLHNVQIKDMG<br>SYDCFIQKKPPTGSIILQQTLTELSVIANFSEPEIKLAQNVTGNSGINLTCTS<br>KQGHPKPKKMYFLITNSTNEYGDNMQISQDNVTELFSISNSLSLSFPDGVWHM<br>TVVCVLETESMKISSKPLNFTQEFPSPQTYWKEITASVTVALLLVMLLIIVCH<br>KKPNQPSRPSNTASKLERDSNADRETINLKELEPQIASAKPNAE (SEQ ID<br>NO: 144) |
| Human LFA-3 (CD58) | >NM_001779.3 *Homo sapiens* CD58 molecule (CD58),<br>transcript variant 1, mRNA<br>GAACTTAGGGCTGCTTGTGGCTGGGCACTCGCGCAGAGGCCGGCCCGACGAGC<br>CATGGTTGCTGGGAGCGACGCGGGGCGGGCCCTGGGGGTCCTCAGCGTGGTCT<br>GCCTGCTGCACTGCTTTGGTTTCATCAGCTGTTTTTCCCAACAAATATATGGT<br>GTTGTGTATGGGAATGTAACTTTCCATGTACCAAGCAATGTGCCTTTAAAAGA<br>GGTCCTATGGAAAAAACAAAAGGATAAAGTTGCAGAACTGGAAAATTCTGAAT<br>TCAGAGCTTTCTCATCTTTTAAAAATAGGGTTTATTTAGACACTGTGTCAGGT<br>AGCCTCACTATCTACAACTTAACATCATCAGATGAAGATGAGTATGAAATGGA<br>ATCGCCAAATATTACTGATACCATGAAGTTCTTTCTTTATGTGCTTGAGTCTC<br>TTCCATCTCCCACACTAACTTGTGCATTGACTAATGGAAGCATTGAAGTCCAA<br>TGCATGATACCAGAGCATTACAACAGCCATCGAGGACTTATAATGTACTCATG<br>GGATTGTCCTATGGAGCAATGTAAACGTAACTCAACCAGTATATATTTTAAGA<br>TGGAAAATGATCTTCCACAAAAAATACAGTGTACTCTTAGCAATCCATTATTT<br>AATACAACATCATCAATCATTTTGACAACCTGTATCCCAAGCAGCGGTCATTC<br>AAGACACAGATATGCACTTATACCCATACCATTAGCAGTAATTACAACATGTA<br>TTGTGCTGTATATGAATGGTATTCTGAAATGTGACAGAAAACCAGACAGAACC<br>AACTCCAATTGATTGGTAACAGAAGATGAAGACAACAGCATAACTAAATTATT<br>TTAAAAACTAAAAAGCCATCTGATTTCTCATTTGAGTATTACAATTTTTGAAC<br>AACTGTTGGAAATGTAACTTGAAGCAGCTGCTTTAAGAAGAAATACCCACTAA<br>CAAAGAACAAGCATTAGTTTTGGCTGTCATCAACTTATTATATGACTAGGTGC<br>TTGCTTTTTTTGTCAGTAAATTGTTTTTACTGATGATGTAGATACTTTTGTAA<br>ATAAATGTAAATATGTACACAAGTGA (SEQ ID NO: 145) |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| | >NP_001770.1 lymphocyte function-associated antigen 3 isoform 1 [*Homo sapiens*]<br>MVAGSDAGRALGVLSVVCLLHCFGFISCFSQQIYGVVYGNVTFHVPSNVPLKE<br>VLWKKQKDKVAELENSEFRAFSSFKNRVYLDTVSGSLTIYNLTSSDEDEYEME<br>SPNITDTMKFFLYVLESLPSPTLTCALTNGSIEVQCMIPEHYNSHRGLIMYSW<br>DCPMEQCKRNSTSIYFKMENDLPQKIQCTLSNPLFNTTSSIILTTCIPSSGHS<br>RHRYALIPIPLAVITTCIVLYMNGILKCDRKPDRTNSN (SEQ ID NO: 146) |
| Human SLAM (CD150) | >NM_003037.5 *Homo sapiens* signaling lymphocytic activation molecule family member 1 (SLAMF1), transcript variant 1, mRNA<br>AGACAGCCTCTGCTGCATGACACGAAGCTTGCTTCTGCCTGGCATCTGTGAGC<br>AGCTGCCAGGCTCCGGCCAGGATCCCTTCCTTCTCCTCATTGGCTGATGGATC<br>CCAAGGGGCTCCTCTCCTTGACCTTCGTGCTGTTTCTCTCCCTGGCTTTTGGG<br>GCAAGCTACGGAACAGGTGGGCGCATGATGAACTGCCCAAAGATTCTCCGGCA<br>GTTGGGAAGCAAAGTGCTGCTGCCCCTGACATATGAAAGGATAAATAAGAGCA<br>TGAACAAAAGCATCCACATTGTCGTCACAATGGCAAAATCACTGGAGAACAGT<br>GTCGAGAACAAAATAGTGTCTCTTGATCCATCCGAAGCAGGCCCTCCACGTTA<br>TCTAGGAGATCGCTACAAGTTTTATCTGGAGAATCTCACCCTGGGGATACGGG<br>AAAGCAGGAAGGAGGATGAGGGATGGTACCTTATGACCCTGGAGAAAAATGTT<br>TCAGTTCAGCGCTTTTGCCTGCAGTTGAGGCTTTATGAGCAGGTCTCCACTCC<br>AGAAATTAAAGTTTTAAACAAGACCCAGGAGAACGGGACCTGCACCTTGATAC<br>TGGGCTGCACAGTGGAGAAGGGGGACCATGTGGCTTACAGCTGGAGTGAAAAG<br>GCGGGCACCCACCCACTGAACCCAGCCAACAGCTCCCACCTCCTGTCCCTCAC<br>CCTCGGCCCCCAGCATGCTGACAATATCTACATCTGCACCGTGAGCAACCCTA<br>TCAGCAACAATTCCCAGACCTTCAGCCCGTGGCCCGGATGCAGGACAGACCCC<br>TCAGAAACAAAACCATGGGCAGTGTATGCTGGGCTGTTAGGGGGTGTCATCAT<br>GATTCTCATCATGGTGGTAATACTACAGTTGAGAAGAAGAGGTAAAACGAACC<br>ATTACCAGACAACAGTGGAAAAAAAAAGCCTTACGATCTATGCCCAAGTCCAG<br>AAACCAGGTCCTCTTCAGAAGAAACTTGACTCCTTCCCAGCTCAGGACCCTTG<br>CACCACCATATATGTTGCTGCCACAGAGCCTGTCCCAGAGTCTGTCCAGGAAA<br>CAAATTCCATCACAGTCTATGCTAGTGTGACACTTCCAGAGAGCTGACACCAG<br>AGACCAACAAAGGGACTTTCTGAAGGAAAATGGAAAAACCAAAATGAACACTG<br>AACTTGGCCACAGGCCCCAAGTTTCCTCTGGCAGACATGCTGCACGTCTGTAC<br>CCTTCTCAGATCAACTCCCTGGTGATGTTTCTTCCACATACATCTGTGAAATG<br>AACAAGGAAGTGAGGCTTCCCAAGAATTTAGCTTGCTGTGCAGTGGCTGCAGG<br>CGCAGAACAGAGCGTTACTTGATAACAGCGTTCCATCTTTGTGTTGTAGCAGA<br>TGAAATGGACAGTAATGTGAGTTCAGACTTTGGGCATCTTGCTCTTGGCTGGA<br>ACTGGATAATAAAAATCAGACTGAAAGCCAGGACATCTGAGTACCTATCTCAC<br>ACACTGGACCACCAGTCACAAAGTCTGGAAAAGTTTACATTTTGGCTATCTTT<br>ACTTTGTTCTGGGAGCTGATCATGATAACCTGCAGACCTGATCAAGCCTCTGT<br>GCCTCAGTTTCTCTCTCAGGATAAAGAGTGAATAGAGGCTGAAGGGTGAATTT<br>CTTATTATACATAAAACACTCTGATATTATTGTATAAAGGAAGCTAAGAATAT<br>TATTTTATTTGCAAAACCCAGAAGCTAAAAAGTCAATAAACAGAAAGAATGAT<br>TTTGAGATCTCTGAGTTTTGAACAGTGGACTGGAAACCATGTAAGAGCCTTAA<br>AAGTACAGTTCTGTGCAAATGGCATTCAGTTTTAAAGAAAAACGTAGCAAATG<br>TTTGATGGTGCTGTTACAAAGGAGCTTGGAATACTCAGAGGAACTTGTCCCAT<br>GGTGATTTTTCACTTCTCAAAATGATGTTTAAATCCCAGTTCTCTGTTGATTC<br>CCTTGAACAACAAACCTGGAACCTCAGCTAAGACTCTCTGTGACCAGATTCTG<br>AACCTCTTATATCCAGGGCTTCAAGGGGTATTGCAGGTCAAGGTOTTTCCTAG<br>GCACTTTCTACTCCCTGCATACCTCTCCTCACACTAAATTTATCCTCTAGTAG<br>AAAATTAAGTTATTTTGGTCTAACAGCTTCAAATCTTTGAATGCTCAATAACT<br>TATTTTGCAAGCTGCAGGCAGAAAGAGACTTTTTAAGTAAAGTCCTTTGTTTT<br>TTCCTATTCTCTGCTTTTAGACAGGCTGTCCTCAATTTAAGCCCTGCTTTTTC<br>TTATTGTTTCTTATATAAACTTGGTAAGTACTGTAAGAAACAGCCACTATCAT<br>ACCATTGCATAATAAGGAGCACCAACTTCCCAGCTCAAAACTCAGGTCCTTAT<br>TGCCTTGTATCTTACCTCCTCTATGAGGTCAATTCACATTGTAAGCCTGTTGC<br>TTAGTGCATCTCGTTTCCTGGTACCAGCTTCTTTAATAGAGTTCTTAGTTGCA<br>ATCAACAGAAGCTGGCTTTGGCTTTTTTATGTAGAAAAGGAACCTATTGAAAA<br>GATACTGATTGGTTCCAATAACTGCTAGAAGTTTCTGCAAAACCATGCTTTGA<br>AAGTGAGCAGGAAAAGAAGAGACTAGGCTGTGGCTGGGAGCACAGCCAAAATT<br>ACAAAACCAGCCCAGGGATGATGATCCTGTTCATGCACAGCCACTGTCCCCAG<br>CACTAGGCACAGACTCTACCACTGCCTCACTGTCTCTGOTGGACTTGGAAACT<br>TGATATTACTGTTACTGCTGCACTGTCTGCCATGAAAATGAATTCTCCAGGGT<br>CCCTTCTTCATCCTTTCATCTCTAGCTTATAATTCAAAGTCTGGGATTGAGTG<br>GCCAATCCTAGGTCACATGTCCATGTCCTATCTCCAAGGGGGGCTGGGAATTG<br>AATATCTGGCATTTTCCACTTTCACTTCTTATGAATTAAGGAATTCTACAAAT<br>AATAGAAGTGGGATTCAGGTGGTAGGCAGACAAAAAAGCCTCACAATTATCCA<br>CTACGCCACCCTTGTATAACCTTACCCTCATTCACTGTCTACTCTCAAAACTG<br>TGGAGCTACTAATGAAGATTTGTAAACCCGGGCTTATGAGCACCCATTCCTTT<br>ACTACAACTCAGATTGCTCTAGAAGCTCAGTTCCCAGCACTTGGATTTTTCCA<br>GTAGCTGAATTCTACCTGAAGGAAGGGCAGAAACAAAGGGTGAAGAAGAGGCT<br>ATCACTTCCAAGTATCCTGCACCCCTGGGCTCAAGACCTCACTGGGGAGGGAG |

TABLE 1-continued

Type I Proteins of Interest Amino Acid Sequence

| Protein of Interest | Transcript Sequence (SEQ ID NO:)<br>Amino Acid Sequence (SEQ ID NO:) |
|---|---|
| | TCTTTTGGGCCACCCACCAAACAGCACTGGCATTATGCCTCTCACCCTAGACC ATGGTTACACGTGGTAAAACAACCCCTTCTGGTGATACATTCACAACTCTCTA GTTTCCCCCAAATGGCACTATGGGGAGCGGGAGCTTGCCTTTTCCTCAGACTT AAAACAATAAGTTTTCCCCGTGTTTCCCCTCTAATGCTGTTTTCTTTTGACCA AGCATGTCTGAATTCTAGAGAAGTCAGGAGGAACACACCCATTCTCGGTTTGA AGGGACTGATGTTCTGAAGTACAACTGGGCACAGTCCCAGGCTCTTCAGGACG CTTCCTCCATTCACACAGCGGGGATGTGATTGTTACAGCGGGTGGTGTGTGCT GGCTGAGAAGCCACTGTGAATTGATTCTTCTTCTGAAGTTTATGTTTCTACTT TTTGGAAATGAATAAATTACAGCCAGTCCATCAAGGAAA (SEQ ID NO: 147) |
| | >NP_003028.1 signaling lymphocytic activation molecule isoform b precursor [*Homo sapiens*] MDPKGLLSLTFVLFLSLAFGASYGTGGRMMNCPKILRQLGSKVLLPLTYERIN KSMNKSIHIVVTMAKSLENSVENKIVSLDPSEAGPPRYLGDRYKFYLENLTLG IRESRKEDEGWYLMTLEKNVSVQRFCLQLRLYEQVSTPEIKVLNKTQENGTCT LILGCTVEKGDHVAYSWSEKAGTHPLNPANSSHLLSLTLGPQHADNIYICTVS NPISNNSQTFSPWPGCRTDPSETKPWAVYAGLLGGVIMILIMVVILQLRRRGK TNHYQTTVEKKSLTIYAQVQKPGPLQKKLDSFPAQDPCTTIYVAATEPVPESV QETNSITVYASVTLPES (SEQ ID NO: 148) |
| Mouse SLAM (CD150) | >NM_013730.4 *Mus musculus* signaling lymphocytic activation molecule family member 1 (Slamf1), transcript variant 1, mRNA GAGCTTCTTCCTTGGGGGTAACAGTAAGCAGCTGTCCTGCCGAGCTGAGCTGA GCTGAGCTCACAGCTGGGGACCCTGTCTGCGATTGCTGGCTAATGGATCCCAA AGGATCCCTTTCCTGGAGAATACTTCTGTTTCTCTCCCTGGCTTTTGAGTTGA GCTACGGAACAGGTGGAGGTGTGATGGATTGCCCAGTGATTCTCCAGAAGCTG GGACAGGACACGTGGCTGCCCCTGACGAATGAACATCAGATAAATAAGAGCGT GAACAAAAGTGTCCGCATCCTCGTCACCATGGCGACGTCCCCAGGAAGCAAAT CCAACAAGAAAATTGTGTCTTTTGATCTCTCTAAAGGGAGCTATCCAGATCAC CTGGAGGATGGCTACCACTTTCAATCAAAAAACCTGAGCCTGAAGATCCTCGG GAACAGGCGGGAGAGTGAAGGATGGTACTTGGTGAGCGTGGAGGAGAACGTTT CTGTTCAGCAATTCTGCAAGCAGCTGAAGCTTTATGAACAGGTCTCCCCTCCA GAGATTAAAGTGCTAAACAAAACCCAGGAGAACGAGAATGGGACCTGCAGCTT GCTGTTGGCCTGCACAGTGAAGAAAGGGGACCATGTGACTTACAGCTGGAGTG ATGAGGCAGGCACCCACCTGCTGAGCCGAGCCAACCGCTCCCACCTCCTGCAC ATCACTCTTAGCAACCAGCATCAAGACAGCATCTACAACTGCACCGCAAGCAA CCCTGTCAGCAGTATCTCTAGGACCTTCAACCTATCATCGCAAGCATGCAAGC AGGAATCCTCCTCAGAATCGAGTCCATGGATGCAATATACTCTTGTACCACTG GGGGTCGTTATAATCTTCATCCTGGTTTTCACGGCAATAATAATGATGAAAAG ACAAGGTAAATCAAATCACTGCCAGCCACCAGTGGAAGAAAAAAGCCTTACTA TTTATGCCCAAGTACAGAAATCAGGGCCTCAAGAGAAGAAACTTCATGATGCC CTAACAGATCAGGACCCCTGCACAACCATTTATGTGGCTGCCACAGAGCCTGC CCCAGAGTCTGTCCAGGAACCAAACCCCACCACAGTTTATGCCAGTGTGACAC TGCCAGAGAGCTGACCCATATACCCAGTGAAAGGACTTTTTGAAGGAGGATAG AAGAACCAAAATCCACACTGAACTGGACCCCGGGTCCCAAGTTCTCTGTGACA GAAACTGCACATCTGTAACCTTCTCCAATCAGTTCCCTGGTGACGGATCTGCA CAGGCGTGCTTATGAAGTAGATGAGAAGTGAGGCTTCCTGGGCATGCAACCTG CTCTGCTGCTGACACAGATATGAAGCAGAGATCCCGTGGTACAGTGTACCATC TTTGCTGTAGCAGATAATGTGGGTTTAGGCATCTCACTCTTTGCTGGACTGGA TAACAGAACTCAAAAAAAAACCAACAAGCCAAAGACATAGACTCCATCTCAGA TGGCTGAGCACAAAGTATAAAAGCCATTTTGGCTCTCTGGACTTTATTCTGGA AGCTGATCCTGATCACCTCAAGGCCAAGGGCTCCATGCCTCAGTTTCTCTCTC ACCCTCTAGATGAAGAGGGAACAAAGCATAAAGAGTGAAATCCTTGTTGTCTG AGATCATTCTATAAACGAACTGACATTTTATTTGCAAAACTCAAGCTAGTAAT TCAGTAGACTTGAAGATGATTTTAGAGCCTCTTATGCTTCAAACAACAGAATG AAATCCATCCAATGTTCTTCAAAGTGTGGTTCTCTGATTAAGTCAAAGCAACA CTGTTTGGCAATGCTGCTGTAAAGTTGCCTGGAATACTCAGAGGAACTTGTCC CAGGGAGGTTTTTTTCACTTCTTCAAAGAACTTTTGAATTTAAGTTCTCTGTT TATTCCCTTGAGCAAAACTCTGGAACCTCAAGAGTCTCTCTCCGTTGGTTCTG AGGCCATTTTATAGCCTAGGCCTCCTGTGGATCTACATGTGTATCACCCACTT CCTATCTCACTGCATACCTCTGTGTAGTAGTAAATTTAACCTCAAGTAGAAAA TTAAATTATTTGGATGATCAGTTCCAAATGATTAGATGTTTAGTCTCTTATA ATAGGATGTAGGTAGAGTCTATATAAAGTCCTATATTCTTCACGTTGTCTGTC CTCAGAGAGACCATCTTTCAACCTATCTTCCTTCTTGCACAACTTTGGCAAAT ACTTTAAAAATAACCATTGTGGAGATGGGGAGAGGTCTAAATGGATAATAGTA CTTGCTTTGCAAACATGAAGATCTGGGTTCAAACTCCCAGTGTCCATGTAAAA AGATAAGTGTGGTTGAGTGTGCCAGTAACATAGACACAGATAGGTCCTGAGAC TTTGCTCCCTAGCCTTCCCAGCCAGGCATAAATGTCAAGTCCCCTGAGAGTGA CAGAGGAAGATACTCCCCCCACACACACACACATACACGCACAGTGATACACA |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| | TATACATGCATACAAAAAAAAAACTTATTGTAACAAAGAACACCAACTGCCTG GCTCAAAACTCTCATGTCCCATTACTCTGTACCTTTCTGTATTTAGATAATTT ACAGTGTGAGTTCTGOTGTTCCATGTATCCTATTTGTGTTACTAACTTATGTC AAAGTATTTCTAATTATAATCAACAAAAGCTAACTTTG (SEQ ID NO: 149) |
| | >NP_038758.2 signaling lymphocytic activation molecule isoform 1 precursor [*Mus musculus*]<br>MDPKGSLSWRILLFLSLAFELSYGTGGGVMDCPVILQKLGQDTWLPLTNEHQI NKSVNKSVRILVTMATSPGSKSNKKIVSFDLSKGSYPDHLEDGYHFQSKNLSL KILGNRRESEGWYLVSVEENVSVQQFCKQLKLYEQVSPPEIKVLNKTQENENG TCSLLLACTVKKGDHVTYSWSDEAGTHLLSRANRSHLLHITLSNQHQDSIYNC TASNPVSSISRTFNLSSQACKQESSSESSPWMQYTLVPLGVVIIFILVFTAII MMKRQGKSNHCQPPVEEKSLTIYAQVQKSGPQEKKLHDALTDQDPCTTIYVAA TEPAPESVQEPNPTTVYASVTLPES (SEQ ID NO: 150) |
| Human CD40 | >NM_001250.6 *Homo sapiens* CD40 molecule (CD40), transcript variant 1, mRNA<br>AGTGGTCCTGCCGCCTGGTCTCACCTCGCTATGGTTCGTCTGCCTCTGCAGTG CGTCCTCTGGGGCTGCTTGCTGACCGCTGTCCATCCAGAACCACCCACTGCAT GCAGAGAAAAACAGTACCTAATAAACAGTCAGTGOTGTTCTTTGTGCCAGCCA GGACAGAAACTGGTGAGTGACTGCACAGAGTTCACTGAAACGGAATGCCTTCC TTGCGGTGAAAGCGAATTCCTAGACACCTGGAACAGAGAGACACACTGCCACC AGCACAAATACTGCGACCCCAACCTAGGGCTTCGGGTCCAGCAGAAGGGCACC TCAGAAACAGACACCATCTGCACCTGTGAAGAAGGCTGGCACTGTACGAGTGA GGCCTGTGAGAGCTGTGTCCTGCACCGCTCATGCTCGCCCGGCTTTGGGGTCA AGCAGATTGCTACAGGGGTTTCTGATACCATCTGCGAGCCCTGCCCAGTCGGC TTCTTCTCCAATGTGTCATCTGCTTTCGAAAAATGTCACCCTTGGACAAGCTG TGAGACCAAAGACCTGGTTGTGCAACAGGCAGGCACAAACAAGACTGATGTTG TCTGTGGTCCCCAGGATCGGCTGAGAGCCCTGGTGGTGATCCCCATCATCTTC GGGATCCTGTTTGCCATCCTCTTGGTGCTGGTCTTTATCAAAAAGGTGGCCAA GAAGCCAACCAATAAGGCCCCCCACCCCAAGCAGGAACCCCAGGAGATCAATT TTCCCGACGATCTTCCTGGCTCCAACACTGCTGCTCCAGTGCAGGAGACTTTA CATGGATGCCAACCGGTCACCCAGGAGGATGGCAAAGAGAGTCGCATCTCAGT GCAGGAGAGACAGTGAGGCTGCACCCACCCAGGAGTGTGGCCACGTGGGCAAA CAGGCAGTTGGCCAGAGAGCCTGGTGCTGCTGCTGCTGTGGCGTGAGGGTGAG GGGCTGGCACTGACTGGGCATAGCTCCCCGCTTCTGCCTGCACCCCTGCAGTT TGAGACAGGAGACCTGGCACTGGATGCAGAAACAGTTCACCTTGAAGAACCTC TCACTTCACCCTGGAGCCCATCCAGTCTCCCAACTTGTATTAAAGACAGAGGC AGAAGTTTGGTGGTGGTGGTGTTGGGGTATGGTTTAGTAATATCCACCAGACC TTCCGATCCAGCAGTTTGGTGCCCAGAGAGGCATCATGGTGGCTTCCCTGCGC CCAGGAAGCCATATACACAGATGCCCATTGCAGCATTGTTTGTGATAGTGAAC AACTGGAAGCTGCTTAACTGTCCATCAGCAGGAGACTGGCTAAATAAAATTAG AATATATTTATACAACAGAATCTCAAAAACACTGTTGAGTAAGGAAAAAAAGG CATGCTGCTGAATGATGGGTATGGAACTTTTTAAAAAAGTACATGCTTTTATG TATGTATATTGCCTATGGATATATGTATAAATACAATATGCATCATATATTGA TATAACAAGGGTTCTGGAAGGGTACACAGAAAACCCACAGCTCGAAGAGTGGT GACGTCTGGGGTGGGGAAGAAGGGTCTGGGGGAGGGTTGGTTAAAGGGAGATT TGGCTTTCCCATAATGCTTCATCATTTTTCCCAAAAGGAGAGTGAATTCACAT AATGCTTATGTAATTAAAAAATCATCAAACATGTAAAAA (SEQ ID NO: 151) |
| | >NP_001241.1 tumor necrosis factor receptor superfamily member 5 isoform 1 precursor [*Homo sapiens*]<br>MVRLPLQCVLWGCLLTAVHPEPPTACREKQYLINSQCCSLCQPGQKLVSDCTE FTETECLPCGESEFLDTWNRETHCHQHKYCDPNLGLRVQQKGTSETDTICTCE EGWHCTSEACESCVLHRSCSPGFGVKQIATGVSDTICEPCPVGFFSNVSSAFE KCHPWTSCETKDLVVQQAGTNKTDVVCGPQDRLRALVVIPIIFGILFAILLVL VFIKKVAKKPTNKAPHPKQEPQEINFPDDLPGSNTAAPVQETLHGCQPVTQED GKESRISVQERQ (SEQ ID NO: 152) |
| Mouse CD40 | >NM_170703.2 *Mus musculus* CD40 antigen (Cd40), transcript variant 2, mRNA<br>AGCAGGGACTTTGGAGTGACTTGTGGCTTCAGCAGGAGCCCTGTGATTTGGCT CTTCTGATCTCGCCCTGCGATGGTGTCTTTGCCTCGGCTGTGCGCGCTATGGG GCTGCTTGTTGACAGCGGTCCATCTAGGGCAGTGTGTTACGTGCAGTGACAAA CAGTACCTCCACGATGGCCAGTGCTGTGATTTGTGCCAGCCAGGAAGCCGACT GACAAGCCACTGCACAGCTCTTGAGAAGACCCAATGCCACCCATGTGACTCAG GCGAATTCTCAGCCCAGTGGAACAGGGAGATTCGCTGTCACCAGCACAGACAC TGTGAACCCAATCAAGGGCTTCGGGTTAAGAAGGAGGGCACCGCAGAATCAGA CACTGTCTGTACCTGTAAGGAAGGACAACACTGCACCAGCAAGGATTGCGAGG CATGTGCTCAGCACACGCCCTGTATCCCTGGCTTTGGAGTTATGGAGATGGCC ACTGAGACCACTGATACCGTCTGTCATCCCTGCCCAGTCGGCTTCTTCTCCAA TCAGTCATCACTTTTCGAAAAGTGTTATCCCTGGACAAGGTTTAAAGTCCCGG |

TABLE 1-continued

| Protein of Interest | Transcript Sequence (SEQ ID NO:) Amino Acid Sequence (SEQ ID NO:) |
|---|---|
| | ATGCGAGCCCTGCTGGTCATTCCTGTCGTGATGGGCATCCTCATCACCATTTTCGGGGTGTTTCTCTATATCAAAAAGGTGGTCAAGAAACCAAAGGATAATGAGATCTTACCCCCTGCGGCTCGACGGCAAGATCCCCAGGAGATGGAAGATTATCCCGGTCATAACACCGCTGCTCCAGTGCAGGAGACGCTGCACGGGTGTCAGCCTGTCACACAGGAGGATGGTAAAGAGAGTCGCATCTCAGTGCAGGAGCGGCAGGTGACAGACAGCATAGCCTTGAGGCCCCTGGTCTGAACCCTGGAACTGCTTTGGAGGCGATGGCTCGGCTCGGGAGCAGGGGCCTGGCTCTGAGGACTGCTTGCTGACCTTTGAAGTTTGAGATGAGCCAAGACAGAGCCCAGTGCAGCTAACTCTCATGCCTGCCCCCTATCATTTCTCAACTTGCTTTTTAAGGATGGAGGGAGAGCTCGGGCATCGGGGGTCCACAGTGATACCTACCAAGTGCAGCAGTGCAGGACCCAGAGTCGTCTTGCTGCGGCGTTCACTGTAAGGAGTCATGGACACAGGAGTCCGTGGCCCACAGCTTGTGCTGCTAGAGGGCACCTGGTTGCCCATCAGCAGGGTACTGGCTAAATAAATCTGTAATTATTTATACAATGACATCTCAGAAACTCTAGCAGGTGGGGCAGAAAACAGGTAGTAGAATGATGGGTAGAGAAATAGCTTTTAAAACACATTCCAAGGCAGGTAAGATGGCTTTTGTGAGTAAAGGAGCTTGCTGCCCAAACCCGGTTACCTGATTTTGATCCCTGGGACTTCATGGTAAAAGGGAGAGAACCAAATCCAGAGGGTTGTCATTTGACCTCCATGTGTGCTCTGTGGTAATGTACCCCGTGTGTGCACATGTGCACATATCCTAAAATGGATGTGGTGGTGTATTGTAGAAATTATTTAATCCCGCCCTGGGGTTTCTACCTGTGTGTTACCATTTAGTTCTTGAATAAAAGACACACTCAACCTTTATATTTACAATAA (SEQ ID NO: 153)<br><br>>NP_733804.1 tumor necrosis factor receptor superfamily member 5 isoform 2 precursor [*Mus musculus*]<br>MVSLPRLCALWGCLLTAVHLGQCVTCSDKQYLHDGQCCDLCQPGSRLTSHCTALEKTQCHPCDSGEFSAQWNREIRCHQHRHCEPNQGLRVKKEGTAESDTVCTCKEGQHCTSKDCEACAQHTPCIPGFGVMEMATETTDTVCHPCPVGFFSNQSSLFEKCYPWTRFKVPDASPAGHSCRDGHPHHHFRGVSLYQKGGQETKG (SEQ ID NO: 154) |
| Human CD28 | >NM_006139.4 *Homo sapiens* CD28 molecule (CD28), transcript variant 1, mRNA<br>ACACTTCGGGTTCCTCGGGGAGGAGGGGCTGGAACCCTAGCCCATCGTCAGGACAAAGATGCTCAGGCTGCTCTTGGCTCTCAACTTATTCCCTTCAATTCAAGTAACAGGAAACAAGATTTTGGTGAAGCAGTCGCCCATGCTTGTAGCGTACGACAATGCGGTCAACCTTAGCTGCAAGTATTCCTACAATCTCTTCTCAAGGGAGTTCCGGGCATCCCTTCACAAAGGACTGGATAGTGCTGTGGAAGTCTGTGTTGTATATGGGAATTACTCCCAGCAGCTTCAGGTTTACTCAAAAACGGGGTTCAACTGTGATGGGAAATTGGGCAATGAATCAGTGACATTCTACCTCCAGAATTTGTATGTTAACCAAACAGATATTTACTTCTGCAAAATTGAAGTTATGTATCCTCCTCCTTACCTAGACAATGAGAAGAGCAATGGAACCATTATCCATGTGAAAGGGAAACACCTTTGTCCAAGTCCCCTATTTCCCGGACCTTCTAAGCCCTTTTGGGTGCTGGTGGTGGTTGGTGGAGTCCTGGCTTGCTATAGCTTGCTAGTAACAGTGGCCTTTATTATTTTCTGGGTGAGGAGTAAGAGGAGCAGGCTCCTGCACAGTGACTACATGAACATGACTCCCCGCCGCCCCGGGCCCACCCGCAAGCATTACCAGCCCTATGCCCCACCACGCGACTTCGCAGCCTATCGCTCCTGACACGGACGCCTATCCAGAAGCCAGCCGGCTGGCAGCCCCCATCTGCTCAATATCACTGCTCTGGATAGGAAATGACCGCCATCTCCAGCCGGCCACCTCAGGCCCCTGTTGGGCCACCAATGCCAATTTTTCTCGAGTGACTAGACCAAATATCAAGATCATTTTGAGACTCTGAAATGAAGTAAAAGAGATTTCCTGTGACAGGCCAAGTCTTACAGTGCCATGGCCCACATTCCAACTTACCATGTACTTAGTGACTTGACTGAGAAGTTAGGGTAGAAAACAAAAAGGGAGTGGATTCTGGGAGCCTCTTCCCTTTCTCACTCACCTGCACATCTCAGTCAAGCAAAGTGTGGTATCCACAGACATTTTAGTTGCAGAAGAAAGGCTAGGAAATCATTCCTTTTGGTTAAATGGGTGTTTAATCTTTTGGTTAGTGGGTTAAACGGGGTAAGTTAGAGTAGGGGGAGGGATAGGAAGACATATTTAAAAACCATTAAAACACTGTCTCCCACTCATGAAATGAGCCACGTAGTTCCTATTTAATGCTGTTTTCCTTTAGTTTAGAAATACATAGACATTGTCTTTTATGAATTCTGATCATATTTAGTCATTTTGACCAAATGAGGGATTTGGTCAAATGAGGGATTCCCTCAAAGCAATATCAGGTAAACCAAGTTGCTTTCCTCACTCCCTGTCATGAGACTTCAGTGTTAATGTTCACAATATACTTTCGAAAGAATAAAATAGTTCTCCTACATGAAGAAAGAATATGTCAGGAAATAAGGTCACTTTATGTCAAAATTATTTGAGTACTATGGGACCTGGCGCAGTGGCTCATGCTTGTAATCCCAGCACTTTGGGAGGCCGAGGTGGGCAGATCACTTGAGATCAGGACCAGCCTGGTCAAGATGGTGAAACTCCGTCTGTACTAAAAATACAAAATTTAGCTTGGCCTGGTGGCAGGCACCTGTAATCCCAGCTGCCCAAGAGGCTGAGGCATGAGAATCGCTTGAACCTGGCAGGCGGAGGTTGCAGTGAGCCGAGATAGTGCCACAGCTCTCCAGCCTGGGCGACAGAGTGAGACTCCATCTCAAACAACAACAACAACAACAACAACAACAACAAACCACAAAATTATTTGAGTACTGTGAAGGATTATTTGTCTAACAGTTCATTCCAATCAGACCAGGTAGGAGCTTTCCTGTTTCATATGTTTCAGGGTTGCACAGTTGGTCTCTTTAATGTCGGTGTGGAGATCCAAAGTGGGTTGTGGAAAGAGCGTCCATAGGAGAAGTGAGAATACTGTGAAAAAGGGATGTTAGCATTCATTAGAGTATGAGGATGAGTCCCAAGAAGGTTCTTTGGAAGGAGGACGAATAGAATGGAGTAATGAAATTCTTGCCATGTGCTGAGGAGATAGCCAGCATTAGGTGACAATCTTCCAGAAGTGGTCAGGCAGAAGGTGCCCTGGTGAGAGCTCCTTTACAGGGACTTTATGTGGTTTAGGGCTCAGAGCTCCAAAACTCTGGGCTCAGCTGCTCCTGTACCTTGGAGG |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| | TCCATTCACATGGGAAAGTATTTTGGAATGTGTCTTTTGAAGAGAGCATCAGA<br>GTTCTTAAGGGACTGGGTAAGGCCTGACCCTGAAATGACCATGGATATTTTTC<br>TACCTACAGTTTGAGTCAACTAGAATATGCCTGGGGACCTTGAAGAATGGCCC<br>TTCAGTGGCCCTCACCATTTGTTCATGCTTCAGTTAATTCAGGTGTTGAAGGA<br>GCTTAGGTTTTAGAGGCACGTAGACTTGGTTCAAGTCTCGTTAGTAGTTGAAT<br>AGCCTCAGGCAAGTCACTGCCCACCTAAGATGATGGTTCTTCAACTATAAAAT<br>GGAGATAATGGTTACAAATGTCTCTTCCTATAGTATAATCTCCATAAGGGCAT<br>GGCCCAAGTCTGTCTTTGACTCTGCCTATCCCTGACATTTAGTAGCATGCCCG<br>ACATACAATGTTAGCTATTGGTATTATTGCCATATAGATAAATTATGTATAAA<br>AATTAAACTGGGCAATAGCCTAAGAAGGGGGGAATATTGTAACACAAATTTAA<br>ACCCACTACGCAGGGATGAGGTGCTATAATATGAGGACCTTTTAACTTCCATC<br>ATTTTCCTGTTTCTTGAAATAGTTTATCTTGTAATGAAATATAAGGCACCTCC<br>CACTTTTATGTATAGAAAGAGGTCTTTTAATTTTTTTTAATGTGAGAAGGAA<br>GGGAGGAGTAGGAATCTTGAGATTCCAGATCGAAAATACTGTACTTTGGTTGA<br>TTTTTAAGTGGGCTTCCATTCCATGGATTTAATCAGTCCCAAGAAGATCAAAC<br>TCAGCAGTACTTGGGTGCTGAAGAACTGTTGGATTTACCCTGGCACGTGTGCC<br>ACTTGCCAGCTTCTTGGGCACACAGAGTTCTTCAATCCAAGTTATCAGATTGT<br>ATTTGAAAATGACAGAGCTGGAGAGTTTTTTGAAATGGCAGTGGCAAATAAAT<br>AAATACTTTTTTTTAAATGGAAAGACTTGATCTATGGTAATAAATGATTTTGT<br>TTTCTGACTGGAAAAATAGGCCTACTAAAGATGAATCACACTTGAGATGTTTC<br>TTACTCACTCTGCACAGAAACAAAGAAGAAATGTTATACAGGGAAGTCCGTTT<br>TCACTATTAGTATGAACCAAGAAATGGTTCAAAAACAGTGGTAGGAGCAATGC<br>TTTCATAGTTTCAGATATGGTAGTTATGAAGAAAACAATGTCATTTGCTGCTA<br>TTATTGTAAGAGTCTTATAATTAATGGTACTCCTATAATTTTTGATTGTGAGC<br>TCACCTATTTGGGTTAAGCATGCCAATTTAAAGAGACCAAGTGTATGTACATT<br>ATGTTCTACATATTCAGTGATAAAATTACTAAACTACTATATGTCTGCTTTAA<br>ATTTGTACTTTAATATTGTCTTTTGGTATTAAGAAAGATATGCTTTCAGAATA<br>GATATGCTTCGCTTTGGCAAGGAATTTGGATAGAACTTGCTATTTAAAAGAGG<br>TGTGGGGTAAATCCTTGTATAAATCTCCAGTTTAGCCTTTTTTGAAAAAGCTA<br>GACTTTCAAATACTAATTTCACTTCAAGCAGGGTACGTTTCTGGTTTGTTTGC<br>TTGACTTCAGTCACAATTTCTTATCAGACCAATGGCTGACCTCTTTGAGATGT<br>CAGGCTAGGCTTACCTATGTGTTCTGTGTCATGTGAATGCTGAGAAGTTTGAC<br>AGAGATCCAACTTCAGCCTTGACCCCATCAGTCCCTCGGGTTAACTAACTGAG<br>CCACCGGTCCTCATGGCTATTTTAATGAGGGTATTGATGGTTAAATGCATGTC<br>TGATCCCTTATCCCAGCCATTTGCACTGCCAGCTGGGAACTATACCAGACCTG<br>GATACTGATCCCAAAGTGTTAAATTCAACTACATGCTGGAGATTAGAGATGGT<br>GCCAATAAAGGACCCAGAACCAGGATCTTGATTGCTATAGACTTATTAATAAT<br>CCAGGTCAAAGAGAGTGACACACACTCTCTCAAGACCTGGGGTGAGGGAGTCT<br>GTGTTATCTGCAAGGCCATTTGAGGCTCAGAAAGTCTCTCTTTCCTATAGATA<br>TATGCATACTTTCTGACATATAGGAATGTATCAGGAATACTCAACCATCACAG<br>GCATGTTCCTACCTCAGGGCCTTTACATGTCCTGTTTACTCTGTCTAGAATGT<br>CCTTCTGTAGATGACCTGGCTTGCCTCGTCACCCTTCAGGTCCTTGCTCAAGT<br>GTCATCTTCTCCCCTAGTTAAACTACCCCACACCCTGTCTGCTTTCCTTGCTT<br>ATTTTTCTCCATAGCATTTTACCATCTCTTACATTAGACATTTTTCTTATTTA<br>TTTGTAGTTTATAAGCTTCATGAGGCAAGTAACTTTGCTTTGTTTCTTGCTGT<br>ATCTCCAGTGCCCAGAGCAGTGCCTGGTATATAATAAATATTTATTGACTGAG<br>TGAA (SEQ ID NO: 155)<br><br>>NP_006130.1 T-cell-specific surface glycoprotein<br>CD28 isoform 1 precursor [*Homo sapiens*]<br>MLRLLLALNLFPSIQVTGNKILVKQSPMLVAYDNAVNLSCKYSYNLFSREFRA<br>SLHKGLDSAVEVCVVYGNYSQQLQVYSKTGFNCDGKLGNESVTFYLQNLYVNQ<br>TDIYFCKIEVMYPPPYLDNEKSNGTIIHVKGKHLCPSPLFPGPSKPFWVLVVV<br>GGVLACYSLLVTVAFIIFWVRSKRSRLLHSDYMNMTPRRPGPTRKHYQPYAPP<br>RDFAAYRS (SEQ ID NO: 156) |
| Mouse CD28 | >NM_007642.4 *Mus musculus* CD28 antigen (Cd28), mRNA<br>AGACCTTGGCAGATGTGACTTCAGTTCACACCACACTCTGCCTTGCTCACAGA<br>GGAGGGGCTGCAGCCCTGGCCCTCATCAGAACAATGACACTCAGGCTGCTGTT<br>CTTGGCTCTCAACTTCTTCTCAGTTCAAGTAACAGAAAACAAGATTTTGGTAA<br>AGCAGTCGCCCCTGCTTGTGGTAGATAGCAACGAGGTCAGCCTCAGCTGCAGG<br>TATTCCTACAACCTTCTCGCAAAGGAATTCCGGGCATCCCTGTACAAGGGCGT<br>GAACAGCGACGTGGAAGTCTGTGTCGGGAATGGGAATTTTACCTATCAGCCCC<br>AGTTTCGCTCGAATGCCGAGTTCAACTGCGACGGGGATTTCGACAACGAAACA<br>GTGACGTTCCGTCTCTGGAATCTGCACGTCAATCACACAGATATTTACTTCTG<br>CAAAATTGAGTTCATGTACCCTCCGCCTTACCTAGACAACGAGAGGAGCAATG<br>GAACTATTATTCACATAAAAGAGAAACATCTTTGTCATACTCAGTCATCTCCT<br>AAGCTGTTTTGGGCACTGGTCGTGGTTGCTGGAGTCCTGTTTTGTTATGGCTT<br>GCTAGTGACAGTGGCTCTTTGTGTTATCTGGACAAATAGTAGAAGGAACAGAC<br>TCCTTCAAAGTGACTACATGAACATGACTCCCCGGAGGCCTGGGCTCACTCGA<br>AAGCCTTACCAGCCCTACGCCCCTGCCAGAGACTTTGCAGCGTACCGCCCCTG<br>ACAGGGACCCCTATCCAGAAGCCCGCCGGCTGGTACCCGTCTACCTGCTCATC<br>ATCACTGCTCTGGATAGGAAAGGACAGCCTCATCTTCAGCCGGCCACTTTGGA<br>CCTCTACTGGGCCACCAATGCCAACTATTTAGAGTGTCTAGATCTAACATCA<br>TGATCATCTTGAGACTCTGGAATGAATGACAGAAGCTTCTATGGCAGGATAAA |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| | GTCTGTGTGGCTTGACCCAAACTCAAGCTTAATACATTTATTGACTTGATTGG<br>GGAAGTTAGAGTAGAGCAATCAAAAAGATCATTCATTCAGCCTTGGGAAGTCA<br>ATTTGCAGGCTCCTGGATGAGCCCTGCCCCGTTTTCACTTGCCAGCACATTTC<br>AGTCATGTGGTGTGATAGCCAAAGATGTTTTGGACAGAGAAGAAAGGATAGAA<br>AAACCTTCTCTTTGGCTAAGTTGGTGTTTGGGGTGGGGATAGGTTAGAGTATA<br>GTACTTAACTATTTGAAAAATAATGAAAACACTTTTTTCACTCATGAAATGAG<br>CCACTTAGCTCCTAAATAGTGTTTTCCTGTTAGTTTAGAAAGTTGTGGACATA<br>TTTTTTTAATGATTTCTGACCATTTTTAATCACATTGACTCATGGAATGGCCT<br>CAAAGCACCCCCCAGTGCTTCTTTCCTCATTCCCGGTCATGGGAACTCAGTAT<br>TATTAATAGTCACAACATGATTTCAGAACTAGATAGCCCTCCCACACCAAGAA<br>GAATGTGAGAGGAAGTAAGGTCACTTTATGTAAAAAAAAAAAAAAACAAACGC<br>GTACACATATGTATGTATACATACATACCTATGTGCACACACACACACATATA<br>CATACACACAAAATGCTATGAAGAGTTATCTGTTTAGTAGCCTGTTATAGTCA<br>AATCATTTTAAGTTTCAACTTCTTACAGTTGGGCCACTTGTTGTCCTTTGTGG<br>ATGGATATCTGAAATTGTGTCTATATATTGCTAGTCATGATACTGTGAACAAA<br>AAGGGTAGTGTTAGTATTTGTCAGGGTGGTAAGGATGCATTCCAGGAAGCTTC<br>CTCTGAGGAAGGGAATGAGGTCATTCTTGCCATGTATGAAAGACATAGATGTT<br>TTCCAGAAGGCACCATTGGGAGCCCCAGTATAAGTTCCTTTAGACTCTACAGT<br>TTAGAGGGATTTTATATGTCCTAGGACTCAGGACTCCAGAACTTTGTGGGCTC<br>AGCTGCTTCATACCATGGGGATACATTGACATGAACAATTATTTTGGAATGTG<br>TCTTTAGGGACGACATCAAAGTTCTCAAGTACCTACAAGACCTGATACTGGAA<br>TGAAGGTGGACTTTCTTTTTTGCTTCCAGTTCGGATCAACTGGAATGTATCTG<br>GGGACCTTGAAGAACGGCTGTCCAGCTGTCTTCACCATTTGTATAGTGCTTTG<br>AATTATTCAGAGGTTTTAAAGTCAGGAAGACCTGGTTTAAAAAACATTTCATT<br>ATGAGTTAAATGGCCTCAGGCAAGTCACTGTTCATCCAAGTCTATGACTCCTC<br>AACTGTAAGATGGCCACACTGAAACTTGCTAAGATCCTCTGGCCTCTGCCTCC<br>CAAGAGTTGGGATTTCAGGAGTGCACAATCATGACCCAAACTCGTGATAATCT<br>CTCAGCTTCAATAACTTTCCAGCTAATTGGAATATCCTGTAATCAAACATGAG<br>GCATTTCCCCTCCCCCCACTGTTTTTGTGTATAAAGAGATCTTTAAACTTTTT<br>TTTTAATATGAGGGGTAAGAAAAGATAGGAATCTTTTAATTCTAGACAGAAGA<br>TATTGTGCTTTGGTTTTTTTTTTTTTTAATGGCTTCTATTCTGTGCTTTTAAT<br>TAAACCAGAGAAGGCCAAGATTAGCCCTACTTGTGTGATAAAAGAATGCTGGC<br>CCTTGTGATTGCAGTCAGCCTCTTGACACATAGAGTTCTTGAATCTAAGTTAT<br>AAAATTATATTTGAAAATGACAGAGCTGGAGAATTTATAGAAAGGGTCATAGC<br>AAATAACAAACCATTTTTTTTTAAACGGAAAGATTTGGTCTTTGGCAATCAAT<br>AACTTTGTTTTCTAACTGGAAAAGGAGGTTTACTGGAGATGAATCACACCTGA<br>AAGTTTTCATACCTCCTCTGAACACAACCGAAACATAGGTGTCCAAAGCCTTT<br>CGCTCTCGGTATGAACCAACAGGCGGGTTAAAAACACTGGGTCAGAGTAAAGC<br>TTTTGCAGTTTCAGATGTAGTGTGTATGAAGAAAACTATGTCACTTGCTGCTA<br>TTATTGTAAGAGTCTAAGAACTAAAGGTGTGCCTGTAATTTCTAATTATGAGC<br>TCACCTATTTGGTACCGAGCATGCCAATTTTAAAGAGACCCGGTGTACCTTAT<br>AGCTACATCCAATGATAAAATTACCACACTAGCACATGCCTGTGTTTAAACTC<br>GTGCTTTAATGTTTTTCTTAGGGCAGGTATGCACCCCCCTTTGCAGTGAGTTGG<br>GAGAGATTTTGAAAAAGTGTATGACAAACATTTTTAACACCTTTGGTTTCCTC<br>TCTCTGTGTCTCTTTGTCTCTGTCTCTCTCTTTCTCTCCTGTGCATATGTCTC<br>CCCTCCCTCACTTCTCTGTCTCTTCCTCTCTCCCTCTCTCTGTCTTTCTCTGT<br>GTGTCTCTCTGTCTCTGTGTATCTCTCTGTCTGTCTCTTTCTCTGCAGATTTT<br>CAAAACGTTGTTTTTCTATGGAAGAAATACAAGCTGTGGTTGGTTTGCTACGA<br>GTCAGTAGCAGTTTATCAGTAGGCCAATGTTTTATCTCTTGGAGATTTCAGTC<br>TGGGTTTACCCAATGTATTCTCTGTAATGTGACTGCTGGGGACAGATATAACT<br>TGATTGAGCCTTCAAATCATTTAGGTCTTCAATCATTTAGTCAACGGAGTGAG<br>CCACTAATCTGCAATGGCTATTTTAATATGCATACTGATGGTCAAATGGATGT<br>CTGATCTCTCATCCCAGCTTTCTGTACTACCATATGGGAACTATATGTAACTT<br>GTATACTTACCTGAATATGTTAAATTCAACTACATGGTAAGATGGACCAGAAA<br>TTGCAATGTTCATGTCCATATAGCCACCATTAACCCAAGTTAAGCACAGTAGT<br>GTGGGTTCTCTCAGGACTTGTGAATGAGTTTATGCTCTCTACAAAGACAGGTG<br>AAGCTTAAATCTCTCTTGCACTGCTATGTTTATGCAAATATCAAGATTGTTTC<br>TGTACCAGGGACTTAACACATTCTATTCATACTATTTTCCCTGTCTACAATGT<br>TATTTCATAGATATCTACTTGGTTTGCTCTTACTTCCTTGACATATTTGCCCA<br>AATGCCACCTTCAACTGTAGTTAATTACCTGTACAACCTGTCTCCATGCCTTG<br>TTTTATTTTCTCTATAACTCTACTAATAGGTATTTTTCTTATTTATTGGTTTA<br>TTGCCTGTTTTTTTTCCTAAATCTACACCGGATCTCCAAAGGGAAAGAACTCC<br>ATTTGCTTTGATTTTATTGCTGTATCCCCAGTGCCTAGAATAATGCTTAGCCT<br>GCAATAAATATTTATTCATTGACT (SEQ ID NO: 157) |
| | >NP_031668.3 T-cell-specific surface glycoprotein CD28 precursor [*Mus musculus*]<br>MTLRLLFLALNFFSVQVTENKILVKQSPLLVVDSNEVSLSCRYSYNLLAKEFR<br>ASLYKGVNSDVEVCVGNGNFTYQPQFRSNAEFNCDGDFDNETVTFRLWNLHVN<br>HTDIYFCKIEFMYPPPYLDNERSNGTIIHIKEKHLCHTQSSPKLFWALVVVAG<br>VLFCYGLLVTVALCVIWTNSRRNRLLQSDYMNMTPRRPGLTRKPYQPYAPARD<br>FAAYRP (SEQ ID NO: 158) |

TABLE 1-continued

Type I Proteins of Interest Amino Acid Sequence

| Protein of Interest | Transcript Sequence (SEQ ID NO:)<br>Amino Acid Sequence (SEQ ID NO:) |
|---|---|
| Human CD28H | >NM_144615.2 *Homo sapiens* transmembrane and immunoglobulin domain containing 2 (TMIGD2), transcript variant 1, mRNA<br>GGAAGTCTGTCAACTGGGAGGGGGAGAGGGGGGTGATGGGCCAGGAATGGGGT<br>CCCCGGGCATGGTGCTGGGCCTCCTGGTGCAGATCTGGGCCCTGCAAGAAGCC<br>TCAAGCCTGAGCGTGCAGCAGGGGCCCAACTTGCTGCAGGTGAGGCAGGGCAG<br>TCAGGCGACCCTGGTCTGCCAGGTGGACCAGGCCACAGCCTGGGAACGGCTCC<br>GTGTTAAGTGGACAAAGGATGGGGCCATCCTGTGTCAACCGTACATCACCAAC<br>GGCAGCCTCAGCCTGGGGGTCTGCGGGCCCCAGGGACGGCTCTCCTGGCAGGC<br>ACCCAGCCATCTCACCCTGCAGCTGGACCCTGTGAGCCTCAACCACAGCGGGG<br>CGTACGTGTGCTGGGCGGCCGTAGAGATTCCTGAGTTGGAGGAGGCTGAGGGC<br>AACATAACAAGGCTCTTTGTGGACCCAGATGACCCCACACAGAACAGAAACCG<br>GATCGCAAGCTTCCCAGGATTCCTCTTCGTGCTGCTGGGGGTGGGAAGCATGG<br>GTGTGGCTGCGATCGTGTGGGGTGCCTGGTTCTGGGGCCGCCGCAGCTGCCAG<br>CAAAGGGACTCAGGTAACAGCCCAGGAAATGCATTCTACAGCAACGTCCTATA<br>CCGGCCCCGGGGGGCCCCAAAGAAGAGTGAGGACTGCTCTGGAGAGGGGAAGG<br>ACCAGAGGGGCCAGAGCATTTATTCAACCTCCTTCCCGCAACCGGCCCCCCGC<br>CAGCCGCACCTGGCGTCAAGACCCTGCCCCAGCCCGAGACCCTGCCCCAGCCC<br>CAGGCCCGGCCACCCCGTCTCTATGGTCAGGGTCTCTCCTAGACCAAGCCCCA<br>CCCAGCAGCCGAGGCCAAAAGGGTTCCCCAAAGTGGGAGAGGAGTGAGAGATC<br>CCAGGAGACCTCAACAGGACCCCACCCATAGGTACACACAAAAAAGGGGGGAT<br>CGAGGCCAGACACGGTGGCTCACGCCTGTAATCCCAGCAGTTTGGGAAGCCGA<br>GGCGGGTGGAACACTTGAGGTCAGGGGTTTGAGACCAGCCTGGCTTGAACCTG<br>GGAGGCGGAGGTTGCAGTGAGCCGAGATTGCGCCACTGCACTCCAGCCTGGGC<br>GACAGAGTGAGACTCCGTCTCAAAAAAAACAAAAAGCAGGAGGATTGGGAGCC<br>TGTCAGCCCCATCCTGAGACCCCGTCCTCATTTCTGTAATGATGGATCTCGCT<br>CCCACTTTCCCCCAAGAACCTAATAAAGGCTTGTGAAGAAAAAGCAAAAAAAA<br>AAAAAAAAAA (SEQ ID NO: 159)<br><br>>NP_653216.2 transmembrane and immunoglobulin domain-containing protein 2 isoform 1 precursor [*Homo sapiens*]<br>MGSPGMVLGLLVQIWALQEASSLSVQQGPNLLQVRQGSQATLVCQVDQATAWE<br>RLRVKWTKDGAILCQPYITNGSLSLGVCGPQGRLSWQAPSHLTLQLDPVSLNH<br>SGAYVCWAAVEIPELEEAEGNITRLFVDPDDPTQNRNRIASFPGFLFVLLGVG<br>SMGVAAIVWGAWFWGRRSCQQRDSGNSPGNAFYSNVLYRPRGAPKKSEDCSGE<br>GKDQRGQSIYSTSFPQPAPRQPHLASRPCPSPRPCPSPRPGHPVSMVRVSPRP<br>SPTQQPRPKGFPKVGEE (SEQ ID NO: 160) |
| Human CD2 | >NM_001328609.2 *Homo sapiens* CD2 molecule (CD2), transcript variant 1, mRNA<br>AGTCTCACTTCAGTTCCTTTTGCATGAAGAGCTCAGAATCAAAAGAGGAAACC<br>AACCCCTAAGATGAGCTTTCCATGTAAATTTGTAGCCAGCTTCCTTCTGATTT<br>TCAATGTTTCTTCCAAAGGTGCAGTCTCCAAAGAGATTACGAATGCCTTGGAA<br>ACCTGGGGTGCCTTGGGTCAGGACATCAACTTGGACATTCCTAGTTTTCAAAT<br>GAGTGATGATATTGACGATATAAAATGGGAAAAAACTTCAGACAAGAAAAAGA<br>TTGCACAATTCAGAAAAGAGAAAGAGACTTTCAAGGAAAAAGATACATATAAG<br>CTATTTAAAAATGGAACTCTGAAAATTAAGCATCTGAAGACCGATGATCAGGA<br>TATCTACAAGGTATCAATATATGATACAAAAGGAAAAAATGTGTTGGAAAAAA<br>TATTTGATTTGAAGATTCAAGAGAGGGTCTCAAAACCAAAGATCTCCTGGACT<br>TGTATCAACACAACCCTGACCTGTGAGGTAATGAATGGAACTGACCCCGAATT<br>AAACCTGTATCAAGATGGGAAACATCTAAAACTTTCTCAGAGGGTCATCACAC<br>ACAAGTGGACCACCAGCCTGAGTGCAAAATTCAAGTGCACAGCAGGGAACAAA<br>GTCAGCAAGGAATCCAGTGTCGAGCCTGTCAGCTGTCCAGGAGGCAGCATCCT<br>TGGCCAGAGTAATGGGCTCTCTGCCTGGACCCCTCCCAGCCATCCCACTTCTC<br>TTCCTTTTGCAGAGAAAGGTCTGGACATCTATCTCATCATTGGCATATGTGGA<br>GGAGGCAGCCTCTTGATGGTCTTTGTGGCACTGCTCGTTTTCTATATCACCAA<br>AAGGAAAAAACAGAGGAGTCGGAGAAATGATGAGGAGCTGGAGACAAGAGCCC<br>ACAGAGTAGCTACTGAAGAAAGGGGCCGGAAGCCCCACCAAATTCCAGCTTCA<br>ACCCCTCAGAATCCAGCAACTTCCCAACATCCTCCTCCACCACCTGGTCATCG<br>TTCCCAGGCACCTAGTCATCGTCCCCCGCCTCCTGGACACCGTGTTCAGCACC<br>AGCCTCAGAAGAGGCCTCCTGCTCCGTCGGGCACACAAGTTCACCAGCAGAAA<br>GGCCCGCCCCTCCCCAGACCTCGAGTTCAGCCAAAACCTCCCCATGGGGCAGC<br>AGAAAACTCATTGTCCCCTTCCTCTAATTAAAAAGATAGAAACTGTCTTTTT<br>CAATAAAAAGCACTGTGGATTTCTGCCCTCCTGATGTGCATATCCGTACTTCC<br>ATGAGGTGTTTTCTGTGTGCAGAACATTGTCACCTCCTGAGGCTGTGGGCCAC<br>AGCCACCTCTGCATCTTCGAACTCAGCCATGTGGTCAACATCTGGAGTTTTTG<br>GTCTCCTCAGAGAGCTCCATCACACCAGTAAGGAGAAGCAATATAAGTGTGAT<br>TGCAAGAATGGTAGAGGACCGAGCACAGAAATCTTAGAGATTTCTTGTCCCCT<br>CTCAGGTCATGTGTAGATGCGATAAATCAAGTGATTGGTGTGCCTGGGTCTCA<br>CTACAAGCAGCCTATCTGCTTAAGAGACTCTGGAGTTTCTTATGTGCCCTGGT<br>GGACACTTGCCCACCATCCTGTGAGTAAAAGTGAAATAAAAGCTTTGACTAGA<br>(SEQ ID NO: 161) |

TABLE 1-continued

Type I Proteins of Interest Amino Acid Sequence

| Protein of Interest | Transcript Sequence (SEQ ID NO:)<br>Amino Acid Sequence (SEQ ID NO:) |
|---|---|
| | >NP_001315538.1 T-cell surface antigen CD2 isoform 1 precursor [*Homo sapiens*]<br>MSFPCKFVASFLLIFNVSSKGAVSKEITNALETWGALGQDINLDIPSFQMSDD<br>IDDIKWEKTSDKKKIAQFRKEKETFKEKDTYKLFKNGTLKIKHLKTDDQDIYK<br>VSIYDTKGKNVLEKIFDLKIQERVSKPKISWTCINTTLTCEVMNGTDPELNLY<br>QDGKHLKLSQRVITHKWTTSLSAKFKCTAGNKVSKESSVEPVSCPGGSILGQS<br>NGLSAWTPPSHPTSLPFAEKGLDIYLIIGICGGGSLLMVFVALLVFYITKRKK<br>QRSRRNDEELETRAHRVATEERGRKPHQIPASTPQNPATSQHPPPPPGHRSQA<br>PSHRPPPPGHRVQHQPQKRPPAPSGTQVHQQKGPPLPRPRVQPKPPHGAAENS<br>LSPSSN (SEQ ID NO: 162) |
| Mouse CD2 | >NM_013486.2 *Mus musculus* CD2 antigen (Cd2), mRNA<br>GCCTCACCACAGTCCTGACAGAAAGAACTCAGAGTCACCCCTGGGAAAAGAAC<br>TCTAAAGATGAAATGTAAATTCCTGGGTAGCTTCTTTCTGCTCTTCAGCCTTT<br>CCGGCAAAGGGGCGGACTGCAGAGACAATGAGACCATCTGGGGTGTCTTGGGT<br>CATGGCATCACCCTGAACATCCCCAACTTTCAAATGACTGATGATATTGATGA<br>GGTGCGATGGGTAAGGAGGGGCACCCTGGTCGCAGAGTTTAAAAGGAAGAAGC<br>CACCTTTTTTGATATCAGAAACGTATGAGGTCTTAGCAAACGGATCCCTGAAG<br>ATAAAGAAGCCGATGATGAGAAACGACAGTGGCACCTATAATGTAATGGTGTA<br>TGGCACAAATGGGATGACTAGGCTGGAGAAGGACCTGGACGTGAGGATTCTGG<br>AGAGGGTCTCAAAGCCCATGATCCACTGGGAATGCCCCAACACAACCCTGACC<br>TGTGCGGTCTTGCAAGGGACAGATTTTGAACTGAAGCTGTATCAAGGGGAAAC<br>ACTACTCAATAGTCTCCCCCAGAAGAACATGAGTTACCAGTGGACCAACCTGA<br>ACGCACCATTCAAGTGTGAGGCGATAAACCCGGTCAGCAAGGAGTCTAAGATG<br>GAAGTTGTTAACTGTCCAGAGAAAGGTCTGTCCTTCTATGTCACAGTGGGGGT<br>CGGTGCAGGAGGACTCCTCTTGGTGCTCTTGGTGGCGCTTTTTATTTTCTGTA<br>TCTGCAAGAGGAGAAAACGGAACAGGAGGAGAAAAGATGAAGAGCTGGAAATA<br>AAAGCTTCCAGAACAAGCACTGTGGAAAGGGGCCCCAAGCCGCACTCAACCCC<br>AGCCGCAGCAGCGCAGAATTCAGTGGCGCTCCAAGCTCCTCCTCCACCTGGCC<br>ATCACCTCCAGACACCTGGCCATCGTCCCTTGCCTCCAGGCCACCGTACCCGT<br>GAGCACCAGCAGAAGAAGAGACCTCCTCCATCAGGCACACAGATTCACCAGCA<br>GAAAGGCCCTCCTTTACCCAGACCCCGAGTTCAGCCAAAACCTCCCTGTGGGA<br>GTGGAGATGGTGTTTCACTGCCGCCCCCTAATTAAGAAGGCAGAGTTCGTCAT<br>TTCCAATAAAAAGCTGTGTGGATTTATCTTC (SEQ ID NO: 163)<br><br>>NP_038514.1 T-cell surface antigen CD2 precursor [*Mus musculus*]<br>MKCKFLGSFFLLFSLSGKGADCRDNETIWGVLGHGITLNIPNFQMTDDIDEVR<br>WVRRGTLVAEFKRKKPPFLISETYEVLANGSLKIKKPMMRNDSGTYNVMVYGT<br>NGMTRLEKDLDVRILERVSKPMIHWECPNTTLTCAVLQGTDFELKLYQGETLL<br>NSLPQKNMSYQWTNLNAPFKCEAINPVSKESKMEVVNCPEKGLSFYVTVGVGA<br>GGLLLVLLVALFIFCICKRRKRNRRRKDEELEIKASRTSTVERGPKPHSTPAA<br>AAQNSVALQAPPPPGHHLQTPGHRPLPPGHRTREHQQKKRPPPSGTQIHQQKG<br>PPLPRPRVQPKPPCGSGDGVSLPPPN (SEQ ID NO: 164) |
| Human LFA-3 (CD58) | >NM_001779.3 *Homo sapiens* CD58 molecule (CD58), transcript variant 1, mRNA<br>GAACTTAGGGCTGCTTGTGGCTGGGCACTCGCGCAGAGGCCGGCCCGACGAGC<br>CATGGTTGCTGGGAGCGACGCGGGGCGGGCCCTGGGGGTCCTCAGCGTGGTCT<br>GCCTGCTGCACTGCTTTGGTTTCATCAGCTGTTTTTCCCAACAAATATATGGT<br>GTTGTGTATGGGAATGTAACTTTCCATGTACCAAGCAATGTGCCTTTAAAAGA<br>GGTCCTATGGAAAAAACAAAAGGATAAAGTTGCAGAACTGGAAAATTCTGAAT<br>TCAGAGCTTTCTCATCTTTTAAAAATAGGGTTTATTTAGACACTGTGTCAGGT<br>AGCCTCACTATCTACAACTTAACATCATCAGATGAAGATGAGTATGAAATGGA<br>ATCGCCAAATATTACTGATACCATGAAGTTCTTTCTTTATGTGCTTGAGTCTC<br>TTCCATCTCCCACACTAACTTGTGCATTGACTAATGGAAGCATTGAAGTCCAA<br>TGCATGATACCAGAGCATTACAACAGCCATCGAGGACTTATAATGTACTCATG<br>GGATTGTCCTATGGAGCAATGTAAACGTAACTCAACCAGTATATATTTTAAGA<br>TGGAAAATGATCTTCCACAAAAAATACAGTGTACTCTTAGCAATCCATTATTT<br>AATACAACATCATCAATCATTTTGACAACCTGTATCCCAAGCAGCGGTCATTC<br>AAGACACAGATATGCACTTATACCCATACCATTAGCAGTAATTACAACATGTA<br>TTGTGCTGTATATGAATGGTATTCTGAAATGTGACAGAAAACCAGACAGAACC<br>AACTCCAATTGATTGGTAACAGAAGATGAAGACAACAGCATAACTAAATTATT<br>TTAAAACTAAAAAGCCATCTGATTTCTCATTTGAGTATTACAATTTTTGAAC<br>AACTGTTGGAAATGTAACTTGAAGCAGCTGCTTTAAGAAGAAATACCCACTAA<br>CAAAGAACAAGCATTAGTTTTGGCTGTCATCAACTTATTATATGACTAGGTGC<br>TTGCTTTTTTTGTCAGTAAATTGTTTTTACTGATGATGTAGATACTTTTGTAA<br>ATAAATGTAAATATGTACACAAGTGA (SEQ ID NO: 165)<br><br>>NP_001770.1 lymphocyte function-associated antigen 3 isoform 1 [*Homo sapiens*]<br>MVAGSDAGRALGVLSVVCLLHCFGFISCFSQQIYGVVYGNVTFHVPSNVPLKE<br>VLWKKQKDKVAELENSEFRAFSSFKNRVYLDTVSGSLTIYNLTSSDEDEYEME |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| | SPNITDTMKFFLYVLESLPSPTLTCALTNGSIEVQCMIPEHYNSHRGLIMYSW<br>DCPMEQCKRNSTSIYFKMENDLPQKIQCTLSNPLFNTTSSIILTTCIPSSGHS<br>RHRYALIPIPLAVITTCIVLYMNGILKCDRKPDRTNSN (SEQ ID NO:<br>166) |
| Human CD48 | >NM_001778.4 *Homo sapiens* CD48 molecule (CD48),<br>transcript variant 1, mRNA<br>CTTTTTCTAGCCAGGCTCTCAACTGTCTCCTGCGTTGCTGGGAAGTTCTGGAA<br>GGAAGCATGTGCTCCAGAGGTTGGGATTCGTGTCTGGCTCTGGAATTGCTACT<br>GCTGCCTCTGTCACTCCTGGTGACCAGCATTCAAGGTCACTTGGTACATATGA<br>CCGTGGTCTCCGGCAGCAACGTGACTCTGAACATCTCTGAGAGCCTGCCTGAG<br>AACTACAAACAACTAACCTGGTTTTATACTTTCGACCAGAAGATTGTAGAATG<br>GGATTCCAGAAAATCTAAGTACTTTGAATCCAAATTTAAAGGCAGGGTCAGAC<br>TTGATCCTCAGAGTGGCGCACTGTACATCTCTAAGGTCCAGAAAGAGGACAAC<br>AGCACCTACATCATGAGGGTGTTGAAAAAGACTGGGAATGAGCAAGAATGGAA<br>GATCAAGCTGCAAGTGCTTGACCCTGTACCCAAGCCTGTCATCAAAATTGAGA<br>AGATAGAAGACATGGATGACAACTGTTATCTGAAACTGTCATGTGTGATACCT<br>GGCGAGTCTGTAAACTACACCTGGTATGGGGACAAAAGGCCCTTCCCAAAGGA<br>GCTCCAGAACAGTGTGCTTGAAACCACCCTTATGCCACATAATTACTCCAGGT<br>GTTATACTTGCCAAGTCAGCAATTCTGTGAGCAGCAAGAATGGCACGGTCTGC<br>CTCAGTCCACCCTGTACCCTGGCCCGGTCCTTTGGAGTAGAATGGATTGCAAG<br>TTGGCTAGTGGTCACGGTGCCCACCATTCTTGGCCTGTTACTTACCTGAGATG<br>AGCTCTTTTAACTCAAGCGAAACTTCAAGGCCAGAAGATCTTGCCTGTTGGTG<br>ATCATGCTCCTCACCAGGACAGAGACTGTATAGGCTGACCAGAAGCATGCTGC<br>TGAATTATCAACGAGGATTTTCAAGTTAACTTTTAAATACTGGTTATTATTTA<br>ATTTTATATCCCTTTGTTGTTTTCTAGTACACAGAGATATAGAGATACACATG<br>CTTTTTCCCACCCAAAATTGTGACAACATTATGTGAATGTTTTATTATTTTT<br>TAAAATAAACATTTGATATAATTGTCAATTAACTGAA (SEQ ID NO: 167)<br><br>>NP_001769.2 CD48 antigen isoform 1 precursor [*Homo<br>sapiens*]<br>MCSRGWDSCLALELLLLPLSLLVTSIQGHLVHMTVVSGSNVTLNISESLPENY<br>KQLTWFYTFDQKIVEWDSRKSKYFESKFKGRVRLDPQSGALYISKVQKEDNST<br>YIMRVLKKTGNEQEWKIKLQVLDPVPKPVIKIEKIEDMDDNCYLKLSCVIPGE<br>SVNYTWYGDKRPFPKELQNSVLETTLMPHNYSRCYTCQVSNSVSSKNGTVCLS<br>PPCTLARSFGVEWIASWLVVTVPTILGLLLT (SEQ ID NO: 168) |
| Mouse CD48 | >NM_007649.5 *Mus musculus* CD48 antigen (Cd48),<br>transcript variant 1, mRNA<br>ATACGACTTCCGGTTTTGGGTTTTGCTTCCTGATTGAAGGGCAGGCGCCCTGA<br>CTTCTCTTACAGTTGTCTCCAGTGTTCTGGGGAAGCTTCTCTAAGTATTATGT<br>GCTTCATAAAACAGGGATGGTGTCTGGTCCTGGAACTGCTACTGCTGCCCTTG<br>GGAACTGGATTTCAAGGTCATTCAATACCAGATATAAATGCCACCACCGGCAG<br>CAATGTAACCCTGAAAATCCATAAGGACCCACTTGGACCATATAAACGTATCA<br>CCTGGCTTCATACTAAAAATCAGAAGATTTTAGAGTACAACTATAATAGTACA<br>AAGACAATCTTCGAGTCTGAATTTAAAGGCAGGGTTTATCTTGAAGAAAACAA<br>TGGTGCACTTCATATCTCTAATGTCCGGAAAGAGGACAAAGGTACCTACTACA<br>TGAGAGTGCTGCGTGAAACTGAGAACGAGTTGAAGATAACCCTGGAAGTATTT<br>GATCCTGTGCCCAAGCCTTCCATAGAAATCAATAAGACTGAAGCGTCGACTGA<br>TTCCTGTCACCTGAGGCTATCGTGTGAGGTAAAGGACCAGCATGTTGACTATA<br>CTTGGTATGAGAGCTCGGGACCTTTCCCCAAAAAGAGTCCAGGATATGTGCTC<br>GATCTCATCGTCACACCACAGAACAAGTCTACATTTTACACCTGCCAAGTCAG<br>CAATCCTGTAAGCAGCAAGAACGACACAGTGTACTTCACTCTACCTTGTGATC<br>TAGCCAGATCTTCTGGAGTATGTTGGACTGCAACTTGGCTAGTGGTCACAACA<br>CTCATCATTCACAGGATCCTGTTAACCTGACAAGAACTCTTCTCACCCAAGAA<br>GGCAACTTGGAAGCACAGAGTCTTGCCTTCATCCCTAGCAGTGTTCCTAGCCA<br>GCGAAGCAACTCTGGCTCTATTGGACAAAGGAAAATGTGTTACTGAACGTCTG<br>CGAGAGTTTGCATGCATGCTCTATGAAACAAGCACAGGACCTTGTACAGTGCT<br>CCACCACTGACCTGTGTGCCCAGTCCTTTACAAAGATTTCAAATCAACCTTTT<br>AAAAACTGTGCATAATATCTAATTTTATATACCCTAGTTGTTTCCCAACATAT<br>ATTAAAGATAAATGCATTCTTTTTACCAAAATGTGACTATATTATTTTCATGT<br>TTTCATATCTCTTTTTAAAATAAATTCTTTTAAAAAACT (SEQ ID NO:<br>169)<br><br>>NP_031675.1 0048 antigen isoform 1 precursor [*Mus<br>musculus*]<br>MCFIKQGWCLVLELLLLPLGTGFQGHSIPDINATTGSNVTLKIHKDPLGPYKR<br>ITWLHTKNQKILEYNYNSTKTIFESEFKGRVYLEENNGALHISNVRKEDKGTY<br>YMRVLRETENELKITLEVFDPVPKPSIEINKTEASTDSCHLRLSCEVKDQHVD<br>YTWYESSGPFPKKSPGYVLDLIVTPQNKSTFYTCQVSNPVSSKNDTVYFTLPC<br>DLARSSGVCWTATWLVVTTLIIHRILLT (SEQ ID NO: 170) |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| Human CD226 | >NM_006566.4 *Homo sapiens* CD226 molecule (CD226), transcript variant 1, mRNA<br>GCAGATGGGAAGAAGCGTTAGAGCGAGCAGCACTCACATCTCAAGAACCAGCC<br>TTTCAAACAGTTTCCAGAGATGGATTATCCTACTTTACTTTTGGCTCTTCTTC<br>ATGTATACAGAGCTCTATGTGAAGAGGTGCTTTGGCATACATCAGTTCCCTTT<br>GCCGAGAACATGTCTCTAGAATGTGTGTATCCATCAATGGGCATCTTAACACA<br>GGTGGAGTGGTTCAAGATCGGGACCCAGCAGGATTCCATAGCCATTTTCAGCC<br>CTACTCATGGCATGGTCATAAGGAAGCCCTATGCTGAGAGGGTTTACTTTTTG<br>AATTCAACGATGGCTTCCAATAACATGACTCTTTTCTTTCGGAATGCCTCTGA<br>AGATGATGTTGGCTACTATTCCTGCTCTCTTTACACTTACCCACAGGGAACTT<br>GGCAGAAGGTGATACAGGTGGTTCAGTCAGATAGTTTTGAGGCAGCTGTGCCA<br>TCAAATAGCCACATTGTTTCGGAACCTGGAAAGAATGTCACACTCACTTGTCA<br>GCCTCAGATGACGTGGCCTGTGCAGGCAGTGAGGTGGGAAAAGATCCAGCCCC<br>GTCAGATCGACCTCTTAACTTACTGCAACTTGGTCCATGGCAGAAATTTCACC<br>TCCAAGTTCCCAAGACAAATAGTGAGCAACTGCAGCCACGGAAGGTGGAGCGT<br>CATCGTCATCCCCGATGTCACAGTCTCAGACTCGGGGCTTTACCGCTGCTACT<br>TGCAGGCCAGCGCAGGAGAAAACGAAACCTTCGTGATGAGATTGACTGTAGCC<br>GAGGGTAAAACCGATAACCAATATACCCTCTTTGTGGCTGGAGGGACAGTTTT<br>ATTGTTGTTGTTTGTTATCTCAATTACCACCATCATTGTCATTTTCCTTAACA<br>GAAGGAGAAGGAGAGAGAGAAGAGATCTATTTACAGAGTCCTGGGATACACAG<br>AAGGCACCCAATAACTATAGAAGTCCCATCTCTACCAGTCAACCTACCAATCA<br>ATCCATGGATGATACAAGAGAGGATATTTATGTCAACTATCCAACCTTCTCTC<br>GCAGACCAAAGACTAGAGTTTAAGCTTATTCTTGACATGAGTGCATTAGTAAT<br>GACTCTTATGTACTCATGCATGGATCTTTATGCAATTTTTTTCCACTACCCAA<br>GGTCTACCTTAGATACTAGTTGTCTGAATTGAGTTACTTTGATAGGAAAAATA<br>CTTCATTACCTAAAATCATTTTTCATAGAACTGTTTCAGAAAACCTGACTCTA<br>ACTGGTTTATATACAAAAGAAAACTTACTGTATCATATAACAGAATGATCCAG<br>GGGAGATTAAGCTTTGGGCAAGGGCTATTTACCAGGGCTTAAATGTTGTGTCT<br>AGAATTAAGTATGGGCATAAACTGGCTTCTGAATCCCTTTCCAGAGTGTTGGA<br>TCCATTTCCCTGGTCTTGGCCTCACTCTCATGCAGGCTTTCCTCTTGTGTTGG<br>CAAGATGGCTGCCAACTCTTGGCAATTCATACATCCTTGTTTCTGTCTGGTAG<br>AGAGTTTGCTTCTCAAATGGAGCAAACAAATTTGATTATTTTTTCATTGTTAA<br>ATAGGCAACATGACCAGAAAGGATGGAATGGCTTAAGTAAACTAAGGGTTCAC<br>TTCTAGAGCTGAGAAGCAGGGTCAAAGCACAATACTGGGCAATTCAGAGCATG<br>GTTAGAAGAGGAAAGGGGAGTCTCAAAGCTGGAGAGTTTACCAACAAATATTG<br>ACTGCAGTGATTAACCAAGACATTTTTGTTAACTAAAAAGTGAAATATGGGAT<br>GGATTCTAGAAATGGGGTATCTCTGTCCATACTTCTAGAATCCACTCTATCAG<br>CATAGTCCAGAAGAATACCTGGCAGTAGAAGAAATGAATATTCAAGAGGAAGA<br>TAAATGCGAGAGGGCAATCCTTTACTATTCTCATATTTATTTATCTCTCATTC<br>TGTATAGAATTCTTGCCGCCATCCCAGGTCTAGCCTTAGGAGCAAATGTAGTA<br>GATAGTCGAATAATAAATAACTTAATGTTTTGGACATATTTTGTCTACTTTTG<br>AGAATTATTTTTAATATGTAAATTCTCTCAAAAGGGTCAGGCACCTAGTTATT<br>ATTTTTTAATGATTATGTGAAAGTTGAATATAATATACCACTAAAAGTGACAG<br>TTGAAAGTGGTGGCATAGGACGGTAGGGTAGAAATTTGGGAGGGAAAAAAGAA<br>ATTGGGAGGGTACAGGCAACAGGAGAAAGGAATCAAACCACAGAAAAATACAA<br>AGGGAAACTTCTGCTTCACTATTCAGACAAAGACAGCCCTAATGACATCACCA<br>ACAGTCAAAGCAATTAGAGACCATACCTAATATTGTTTAAATTCTAGATGTAG<br>GCTAACAATGAAAAGTATTTGCCAAACTGAATAAAACTGTCATGGTTACCTTG<br>AAAGGACAATGGTTATTGTTAAATATAGTGATCATTCATGTCTAAAAGATTCA<br>TTATTTATCTCTAAAGATTTCTAAAGACCACCATCTAGAAAAGATTCATTATG<br>AAGGCTGTATTTAAATATCAAAGTTGTGGACTTCATGATAATCTTAAATAAAG<br>CAAATCCAAATTCTCCTGTTGCCTAGACAGATTCTAAGATGTAATTTACACTT<br>TTAAGCTAATTAGTGAGTATTTTATGATTTTAGCCTTAAACACCATGTATGCC<br>AAATAATGCACTTGTTTTGTGAATTACAGAAATGGTAAGTGCCCACATTTCTG<br>TGAATTATAAAATTTGTGAGTTTCTTTTAACCCTTTTCAGGAGTGAAAAAATA<br>AAAACGACCATTTCCTGGTTGTGCTTAAGTATATGCAAGAAGGGTAAACTCTC<br>ATTTTTATTATGTTTGCTTAAAGATCTTTTTATACCTGGATTCATGAAATGTT<br>TCCACAAATATATTAGTGTAACAAACTTGAAAGGCAGTTTACAAGAAAGCACT<br>CTACTATCAGATCAATCAAAGATTCTGTGAGTGAATTTATTGGTTTGCATGGT<br>GAAGCAAGCTTAGCATCAATTAAAAGGTAAATAATTTCTTTTCTGAATGGTAA<br>AGACAATCAAAATATTACTTTCTGGAAAACTCCAATAACCAAATTCTCAATGA<br>TTAGTGTATGTGAGCAGGAAAACATTTTTACAGTTGTAGTATGGGGAAATATA<br>AATCCAATTTTAAGAGAGAAAATTATGACTGGGTGTGGAAGGGACAGTATAGT<br>CAGATACCATTGTCATGGTGGTTTTTACTGGGAACTTCATGAAAGACTTTTGT<br>AGCAAACCACTGCAGTATTGCAAAGCCTCCAGAACATTTGGAACTTGTCTCTT<br>TTTCCTTGTGTGTGTTTGTGTTTTTGGTCTCTCATTCAAAATATTGATGAGAA<br>CTATTTACTCTGTCCTTTCTTCTCTATATATTCTTCCTCTACAGAGTGTAGGG<br>TTTTTTCAGGAATTTGGAGCCATCTGAAGTCCTCCCAAAAATTCTCTGACGTC<br>TTCTGATGCTCCTGTTATACCCTCAGGGGTAATGCTTGTGAAATTCCATTCAT<br>TCATTTTCTTTCTCTGGACATCTTTACTTACCAAAGCACTTTCATTGTCATCT<br>TTTTAACATCATTCTTAATTCGTGATAGTTTTGGGACTCTCCCTAGTGTATGT<br>TTCTCCCCCTCTACTCTTTTGCACCTATGATTCTGATTGTTACTAAGAAAGCA<br>GATGAAAAACAGATCCACAGAATAAACGATCAGAATTCCAGTAAATTCTATTT<br>TAAATACAGATACTTTTTACAAGTTGCTGCTTTGGAAGCAAAATGCTTCTTAA |

TABLE 1-continued

| Protein of Interest | Type I Proteins of Interest Amino Acid Sequence<br>Transcript Sequence (SEQ ID NO:)<br>Amino Acid Sequence (SEQ ID NO:) |
|---|---|
| | GTTTTACATATATATATATATATATACATATATATATACACATATAATTTATA<br>TCGATGGATAATACATTAAGAATCTATGCTTCCTTTGAATGCCATTAATATTT<br>ATGTTAAAGTAACCAATGAAAGGAAATTACTTTGTTATAATAAGATAGGAAGA<br>CTTGTTAATGGAGTACACAGTTTTGTCAGGGAAAGAACACATCTTATTGAACT<br>ATGATGACTATGCATTGACTATATTATTATAAGAGATACCTTCAAACTTTATT<br>TAAAGAACTTTAGGTATAATATGTTGAGAAAATAAAATAGAAATTTCATTTAC<br>TTGTAATCATGCTTAAAATGGGAGGCAGGTAGGTGAAGATATAATTTTTAGTA<br>AAAACTCCAATTTATGTTTTAAGTAATTCAGTGTATTACTAAAATACTATATA<br>TATAAACTTAAAATACATGGGTTATCAATTTAAAAGACAAAGTAAGTAAAAAT<br>ACTTTTAGTAGGCATTCGTGGATTGTGAACATCCAAGTTATATTGGTTTGTAT<br>AGAATGGCATTAAGTAAAAATTACAGCTGTATAACAGTAGTTTTCTAAATTGA<br>GAGAGTCCACATTGTAATTAGAGATCACTGTGACCAAAATGCTTCTCCTTGAT<br>TTATAATGATGTACTGTATTTTGTACTGCTTATATGAAATTTCAGCAAGATTG<br>ACGATATTATAAAGATGCTTATAAAGTGTAAGTGGAGACGCTAAATTGTGAGT<br>ACAAAGTTTCTTTTTCACAACAGTGATAAGAAAATATCTTTAAAAAAATATAAG<br>ACAATATAAACATGTCATCATTAGTTTAGCTACTATTAAAATGTAACATCTAG<br>AAAGTACTGATCTCCACCTTCAGACTTCTGTATAAGTATATTTTTTCACTGAT<br>CTGTTCATTAGAGTTCTTCCAGCCAAGACTCTGGGCTCTTAAAACATGTATCT<br>GAAAACTAAAAACAAGTTAATTTTTTTAAAAGCTTCTCTATTTCTAGTGATTC<br>AATAGGTAGAAAAATAGCTTCTAGAATTAACTGCAATGCTTTCTAAGGAAATT<br>TTATAAATCCTCAAGGTCGGTTTACACATATTTTTCCAGATTCAGAGCACTAA<br>CTATCTTGTAAGATGTAAGAAAAGGTCCATTTGGAAGTATGAGTAATAAATGT<br>CTGGGATAATTCTGGTTTATTTCGTATTATCCTTGTTAGAATAAGTTATATGG<br>TCAACCTGTTCAGAACACTTTTTCTAGTGTTAGTGTGTACTTTTGGATTTTTG<br>GTTCTTGTAGGGTATAGAAATATTTTCCTTTGTCTTGTATTCTGTTGTTTTGA<br>ATGAATAAAACACAATGTTTCACGATCACTACTTTCATTTGCCATGGAGAAAT<br>AGCAGGGAAAAATTTCTACAGAATAAAATTAACTGATGAATTACATGCAGAAA<br>AAATTCAAATCAATGATACATTGTAATTTTTATCTCAATGCAATGTTCTTTGT<br>ATTTTATTTTATTATTATTATTTTTTTGAGACGGAGTTTCACTTTTGTTGCCCGGG<br>CTGGAGTGCAATGGCACAATCTCGGCTCACCACAACCTCTGCCTCCCGGATTC<br>AAGTGATTCTCCTGCCTCAGCCTCCTGAATAGCTGGGATTACAGGCATATGCC<br>AACATGCCTGGCTAATTTTGTATTTTTAGTGGAGACGGGGTTTCTCCACGTTG<br>GTCAGACTTGTCTTGAACTCTGGACCTCAGGTGATCCACCTGCCTCAGCCTCC<br>TAAATTGCTGGGATTACAGGCATGAGCGACCACTCCTGGCCTTGTTCTTTGTA<br>TTTTATAAGTGCATGTAGTGCAAAGGGTCAAAGGGCTTTACAGGTTTTTTGTT<br>TGTTTGTTTTTGTTTTTCCCGAAACATAGTAGTCCCTTGCCCTTCCTCATTTT<br>TGTTACCTTGAGACAACAAATTTTACTACTTCTAACTCATTATTTTATTTATG<br>TTCACTTTTCTGAATAGCATGCTTATGACACTAATACTTTTTTTTTCAATTTT<br>AGACATTCATTATTCATTTAGATGTCTTTCTCTCCCCAAACTCACCACATAAA<br>ATACTCTTCTCATGTCTCTTTCAGAAATATTTGTATTAAAATATGATTATATC<br>AATATTTGGCATTTATTTCTTATGACCTTGCCAGTACTCTTAGTTAAACTACA<br>TGGTAAAAATGATTTTGCTTTCCCTCCTACATAACTTTTTTTCCACCTAGAGC<br>TAATAATTGTCATTCTGGGGACTGACTTTTTCTGTATTTACCATAAATTGACC<br>TGAAACTCCCCTGTGATGCAGCAGGAATTCTACCAACGTCAACTTCCTTAGAA<br>AGACTCCATTAGAAGCTTGACTTGGGGCTAGAAGGAGAGGCACACAACTGCCA<br>TCCTGGTGTCTCCCTTCATCCAGAAAAAGGGGGAGGAATACATGAAACCTAGA<br>ATCCACTCTAAAACATTTTCCAGAACAAAAGGACATGTGTTTCCGTGTTGTAA<br>ATGTTTAACGAGTGCCCATAACAAGGAATAATAAGTCTATTATGTTTGCTTTT<br>GTGTCTGTAAAAGTTGGGGGTATTGGTTGTAAGCACGAAAACAGATACTGACT<br>GTTGAAGAAAAAAAAAAAATACGAGGTCAGGAGTTTGAGACCAACTTGGCCAAT<br>ATGGTGAAACCCTGTCTTAGTAAAAATAGAAAAATTAGCCAGGCCTGGTGGCA<br>CGCACCTGTAGTCCCAGCTACTTGGGAGGCTGAGGCAGAAGAATCGCTTGAAC<br>CCGGGAGGCAGAGGTTGCAGTGAGCCAAGATCGCACCACTGCACTCCACCCTG<br>GGCAACAGAGCGAGACTCCGTCTCAAAAAAAAAAAAAAAAAAAAAAAAAAAAA<br>GTTAAGTATTTGAACATAGGGGTGGCTCATAGAATTCCCAGGACACCCGATGG<br>AGTAGGCTTGCAAAACACAACATGTGGCAACTCCAGTGGGAAACGAGGCAGGA<br>AACACTCGTTTCCTGCAGAAAGCAACAATTTGGGCTTCGATACCCTCCCTAGA<br>ACACAGGGCAGTGAATCTGAGCAGCATCAGTACCCCACGTTCGGATGAGTCCT<br>GAGCCCCTATTTTTATTCACTGACTTATTCCAAAATCAGTGTCTCTTAAATAT<br>ATCTGGAAGGCAGCAGCTTGTATCTCCCCCTTCAGCTTCCATAGTGGCAGTCA<br>GGGTACAACTTACTTTCCAAACAGAACACACTGCGACATTCCCTCCAGGCTCG<br>TTGAAGAACTTCAACTGACAAATGTCCCTCCTCGACCAGATGATAGTTTTCTT<br>AAAGGCAGGGTTTAATATACCCTTTTATAAATGTTTCAAGGCCCTGTGTAATA<br>CCTGAGTTTATTCCAGATGTAACTAAATATATCCAAGATTGTTTTAAAATAAA<br>TTGCTGAAAAAACAAATAAATACAGTTAGTATCTATATCAATATTCTCAGTTG<br>GCAGTTTTGCAATAATGGCCGATAGTTCATTTTTAGTAACACTATTGACATTG<br>CATTTGGATATTAGGGTTTACTAATCATCCGCATGTATACATTGCATATTTTT<br>CTAGACTTTAACTTTATTCAAATCTATTGATTTTTAAACCTGCAACTTATGTC<br>TAGACACAGGTATACCTTTACAAGAACTACCATTTTTTTTGGTAACATACTAC<br>CTCCAAAATTTCAAGTAAGAAGTTGATTTTTGTCCATTTTTAAATGGAAAACT<br>TGTAATCAAAATGCCACAAAATTATACTGTGTATCATTTGACCTATAGAAACC<br>AATATTATTACAGGAAGAAAGCAGAGCCAATCTTCTACCTGTGGTCAAATAAG<br>TGGAGGCCCTTTCTAGACTAAGTTCTCATGAGTTTAAAATACCAAGCATAAGT<br>TCTCCAAATTCCTGAAAAGGAAGCCTTGTGTTGTATTGCCCAGCCATATTTGT<br>AAGACATAAAAATAAAACTTGAGAAGAAGCTATGATAACTTACTTTCTTCATT |

TABLE 1-continued

Type I Proteins of Interest Amino Acid Sequence

| Protein of Interest | Transcript Sequence (SEQ ID NO:)<br>Amino Acid Sequence (SEQ ID NO:) |
|---|---|
| | CTTCAAAATTTACATAATCTCAACTGATTTTATGTTTTTATGAAAATGCATTC |
| | TTAAGATATATCCTTATTCAATCATGTATTCATTACATCCTTTATGCCAGGTA |
| | TCCAAAAGTACTTACAGTGACTAAGACCATTATTCTTTGATCAGCTGCCTGAG |
| | TAAGACTTTGAGCTCTCCAATATACTCTCAGTGATACTAAGTTTTCTGAGTAA |
| | CAGCTTTGGATGTGGCTTCAGTTGAGCTGATTTATCCCACACTTTATTTTTAT |
| | CGTATAATGGTCCTCAGAAGCAAATTTTGATTTTAGCTCACATAAAAAATGTA |
| | CAAAGAAATGTAATGGCTCAGTAGCTTCTAGAGATAGAGATTACTCTTCTAAC |
| | CTTTCTGTAATTTTGTATGTCTATTTTATAATTCTTTCAATGTCTAATGAATA |
| | GCTATCTTTTTTTGAGACGGAGTCTCGCTCTGTCGCCCAGGCTGGAGTGCAGT |
| | GGTGCGACCTCGGCTCACCGCAAGCTGCGTCTTCCAGGTTCACGCCATTCTCC |
| | TGCCTCAGCCTCCCGAGTAGCTGGGACTTCAGGCGCCCACCACCATGCCCAGC |
| | TAATTTTTTTGTATTTTTAGTAGAGACGGGGTTTCACCGTGTTAGCCAGGGTG |
| | GTCTCGATCTCCTGACCTCGTGATCCGCCCGCCTCGGCCTCCCAACGTGCTGG |
| | GATTACAGGAGTGAGCCACCGCGCCCGGCCTCCTTAGTTTCTTAAGGTGGAAG |
| | CCTAGATTATTGATTTTATATGTTGTTTTCTTTTCCAATAGTGGCACTTAATG |
| | CTATAAATTTCACTTTGTTCCACAAGTTTTGGTAAGCTCTATTTTTATTTTCA |
| | TTTAGTCCAAAATATTTTAAAATTTCTTTTGATATTTCTTCTTTGAGCCATGA |
| | ATTATTTACAATGTGTTGTTTAATCTCTATATATTTTGGGATTTTTCTACTTT |
| | ATATCTCTTACAGATTTCTAACTTAATTTCATCATGTTTTAAAAACATTCTTT |
| | GTATAATTTCTATTCTTTTAAATTTTTCAGGTGTATTTTATGGCCCAGAATAT |
| | GGTCTATCTTGTAGAATGTTTCATGTGATCTTAAGAAGAATGTTCATTCTGCT |
| | GTTGAGTGTAATATTCTACAAATGTCCATTAGATTAAACTGATTGATACCACC |
| | GTTCAGATTATCTATATCCTTTCTGATTTTCCCTCTTCTTGATCTATCACATA |
| | CTGACAGATCAAGTGATCAAGTCTCGTTAAAGACTGCAAGTAAAATAGTGGAT |
| | TTTTCTATTTCTCCTTGCAGTTTTGTTAGTTTTTGTCTCATGTATCTTGATAC |
| | TCTTGTTAGTACATATACTTTCAGAATCGTTAGGTTTTCTTGGAGAATTGACC |
| | CCTTTACCACATGTAATGTCCCTTTTATTCTTGATAATCTTTCTTGTTCTGTC |
| | TGCTTTTTCTGATATTAACATAACTTTCAGTTTTTTAAAAAATTAACATTAGC |
| | ATCTCACATCTTTATCCTTTTAATTTTAAATTATCTAAATATTTATATTTAAT |
| | GTGCCTTTCTTATAGACAATGTATAGTTGCGTCTATTTGTAATTTCCCCACTT |
| | TTCTTACTTAAAAATGTTGTAGATATATAGGAGTTGTATATATTTGGGGGGTA |
| | CATGTGATGTTTTGATACCTGTATACAATATGTAATGATCATATTGGGTAATC |
| | GTGATATCTGTCACCTCTAACATTCATCTTTTTTGTGTGTTTAAACCCACCAC |
| | TTCTAATTGGTACATTTAGATTATTCAAATTTAAGTGATTATTGATATAGTTG |
| | GATTAATATCTACTATGTTTGTAACTTTTCTATCCTTGCACTCGTTCTTTCTT |
| | TTTTATCCTCCTTTTTCTGTGTTCTCTGATTTTAACTGGGGTTTTTACATGAT |
| | TTAATTTTCTCTCGTGGCATATCTTTCATTGATCAACCTAGGTTTTTCTCCTT |
| | TTCCCCTCTTTTTTTTGGTATTTATTCTATTTAGTGTTATCTGAGCTACCTGA |
| | GTTGGTGTCTATCACTAATTTTGGCAAGTTCCCAGACGTTATTACTTCTAACA |
| | TTCTTTTGCTCCATTCTTTCTTCTTCTTCAATTATTCCATAGTCTTGAATATT |
| | CTGGGTTTTTCCCACTCTTTGAATTTTAGTTTGAAAAGTTTCTATTGGCCTAG |
| | CTTCAAAGTCATTCATTCTTCCTTCGGGGTTCCAAGTCAACTGATAATTGCAT |
| | CAAAGATATCCTTCCTTTCTATTACTATGTTTTTTATTGCTACCATTTCTTTT |
| | TTATTCCTTCTTAGTGTTTCCATCTTTCTTCTTACATTATCCATCTGTTGTCT |
| | ATTTTTTTCATGAGAGCTCTTAACATATTAATGATAAGTTCCATGTCTGATAA |
| | TTCTGACACGTGTCATGTCTCTATCTGGTTCCAATGATTGCTTTATCTCTTCA |
| | GACCATGACTTTTCTTGCCTTTTGACGTTCTTTGACATTTTTTTTGAATTTTT |
| | TGTTGCAAGCCAGATCTGGTGTGTTATGTAATAGGAACAGGTAAATAAGTCTT |
| | TAGCTTGCAGACTTATCTTAATCTGACTAACTATTAGACTGTGTTTAAAGTCT |
| | GTTATAACCATAGGTGCTAAATTTCTTCAAATTCCTCTAGTGTCTTTGTTTTG |
| | TTTGTTCATGTGTTTTTCCCCTTCTTGAGTTCAGGCTTCCCTAAGTGCTCCTC |
| | TTCAGAGAGACTTTCTGTCTTTCAGCTCTTTCCTCTGCAATTCACTGTTACTA |
| | TACTGGAGCCCTGTTGGTGTAGTACTAAGCTGTGGAAAGGAGAGTGCTCTGT |
| | AATCTTACAGTGAAATCTCAGTOTTTAGTGGGTCTGTGTCTGGGACATTCAC |
| | AGAGCTTCTCCAGTGGTATTGCTTCCTCATCCTCAACTCTCTTTCCTGGCTGC |
| | AGCATTCCCAATGTATTTCTTTGAAGGCCTGCCCCCTGTTGACTGTTATTTTC |
| | CCTCTTTCCTTAAGTGGGACAGGGAGACTTCAGGGGCTGGGATGAGGTTTGGG |
| | AATTGTGCTTGGCAGAGTCCTTTCCATCTTTGTTACCAAGAAGGTTCATGGCT |
| | TATTTCTCAATGGATGTCCCTCTCTATCTGTTGCCAGAGCCACGAGGAAATTT |
| | TTCTTGGATCCTCATAATGAGAACCTTGGAGTTTCCTACTGGAAAAGCCCTTG |
| | AATGTGTGGAGTGCCTCAAGAGCACAGCCCCCATGGGTTTCTTGCTCACACCA |
| | GTCCACAAACAGATGCCAGCAATTCACCCAACTTACCATATAAAGGCTCATAC |
| | TAGTTTATGGCTCCAGTGCTTTGACTCCAGATAAATGGCTATTGGTTGCGTAT |
| | CTCTCTGGATGTATCTGTATCTCCAGATTTTGGGGTGGCAGTTTGCTCAGGAC |
| | CTTGGTTCTCTAATAGGTCTAATAAGAAAAGTCATTGATTTTCAGCTTTCCAA |
| | CTTTCCAGCTTTGTCTTGTTATAAGCATGGCAGCAACATCTTCCATGCCTTAA |
| | CATGATGACACTAAAGGCAGAAGTCGATCTCCATGTATAAACATTTTAACACA |
| | TATGTTTTTTGTTATCGTGGTTTCTGACCTGTCTCTTTGCCCTGACTTTCTGA |
| | TACTGCACTAGGGTTCCTGTTGCTGGACTCCATTCCATATGACTTGCTCTCGT |
| | CTAGGCTGCTCTTTGGCTCATCTTTATAAATCATGATCCAAAATGAAGCACAT |
| | ATTTATTTTTTAAATAAATATGAAATGAAGTATAGACATCAAACTGAAGATGA |
| | GTAGATCATACTGAGTTTCACTGTCTGTGCTTGGATCAACATCAGGCCTTATA |
| | CAAATATTCAAGTCCAGAGGCAAAAGGTAATAAGGAAAATTTGTAGCACAAGC |
| | CACAAGGAGATAACATGTCAAGTCTATGCGATTGGAAATAAACTAAAGATGAA |
| | CTGCTGGGGATGCTCACTCATCACAGAGCTCAGTCTAAAGCACCAGATTTCAC |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| | AAGCATTTTTTGGGGGAAATTCTGTTAAAATGAAATATGAGTCACATGGTGGT<br>GTTTCACTCATCATATGTGTTCAATATTAATTCATTTTAAGGTTTAGTTGCAC<br>AAAAGGTAAATGAGAATTAGAAGACTCCATGGGTAAGAGGAGCCACAGAAGTA<br>AAGCATTGTCAAGGGTTCTATGTCTATATATTTAGATATTAGGCTTCTGAGAA<br>AAAAACACAATAGGAAGGAAGATGAACACAACAGAGGGCAGAAGGTCTATACG<br>TCCTGAGGCCTTTTATGCAACGTTTGTTTGTGGAATGTTTTTTAAGAATGTGT<br>GAGAGTCATTTTAATGTGAAATAAAGACCTACGTCTACA (SEQ ID NO: 171) |
| | >NP_006557.2 CO226 antigen isoform a precursor [*Homo sapiens*]<br>MDYPTLLLALLHVYRALCEEVLWHTSVPFAENMSLECVYPSMGILTQVEWFKI<br>GTQQDSIAIFSPTHGMVIRKPYAERVYFLNSTMASNNMTLFFRNASEDDVGYY<br>SCSLYTYPQGTWQKVIQVVQSDSFEAAVPSNSHIVSEPGKNVTLTCQPQMTWP<br>VQAVRWEKIQPRQIDLLTYCNLVHGRNFTSKFPRQIVSNCSHGRWSVIVIPDV<br>TVSDSGLYRCYLQASAGENETFVMRLTVAEGKTDNQYTLFVAGGTVLLLLFVI<br>SITTIIVIFLNRRRRRERRDLFTESWDTQKAPNNYRSPISTSQPTNQSMDDTR<br>EDIYVNYPTFSRRPKTRV (SEQ ID NO: 172) |
| Mouse CD226 | >NM_178687.2 *Mus musculus* CD226 antigen (Cd226), transcript variant 1, mRNA<br>ACACAGAAGACTTCTTGACTTCAGGAGACACTGCTGTATGAAACAGTGCTTGC<br>TATCAGTGGCTGCTGGAAGAGGCTGTGGTGGAAAGAAAACCTCAACTGCAGGC<br>CAGAGTTGGTTCCCCAAAAGAGGCAAACTCCCAGTGCTAGCCAGAGGCTAGGA<br>AGCTCTAAGCAACCCACTTATCTGCAAGGAGAGTTACGCCCAAAGAGCATCAA<br>GTCCAACCTCCTGAACTGTTTCCAGAGATGGCTTATGTTACTTGGCTTTTGGC<br>TATTCTTCATGTGCACAAAGCACTGTGTGAAGAGACATTGTGGGACACAACAG<br>TTCGGCTTTCTGAGACTATGACTCTGGAATGTGTATATCCATTGACGCATAAC<br>TTAACCCAGGTGGAGTGGACCAAGAACACTGGCACAAAGACAGTGAGCATAGC<br>AGTTTACAACCCTAACCATAATATGCATATAGAATCTAACTACCTCCATAGAG<br>TACACTTCCTAAACTCAACAGTGGGGTTCCGCAACATGAGCCTTTCCTTTTAC<br>AATGCCTCAGAAGCAGACATTGGCATCTACTCCTGCTTGTTTCATGCTTTCCC<br>AAATGGACCTTGGGAAAAGAAGATAAAAGTAGTCTGGTCAGATAGTTTTGAGA<br>TAGCAGCACCCTCGGATAGCTACCTGTCTGCAGAACCTGGACAAGATGTCACA<br>CTCACTTGCCAGCTTCCAAGGACTTGGCCAGTGCAACAAGTCATATGGGAAAA<br>AGTCCAGCCCCATCAGGTAGACATCTTAGCTTCCTGTAACCTATCTCAAGAGA<br>CAAGATACACTTCAAAGTACCTAAGACAAACAAGGAGCAACTGTAGCCAGGGG<br>AGCATGAAGAGCATCCTCATCATTCCAAATGCCATGGCCGCTGACTCAGGACT<br>TTACAGATGTCGCTCAGAGGCCATTACAGGAAAAAACAAGTCCTTTGTCATAA<br>GGCTGATCATAACTGATGGTGGAACCAATAAACATTTTATCCTTCCCATCGTT<br>GGAGGGTTAGTTTCACTGTTACTTGTCATCCTAATTATCATCATTTTCATTTT<br>ATATAACAGGAAGAGACGGAGACAGGTGAGAATTCCACTTAAAGAGCCCAGGG<br>ATAAACAGAGTAAGGTAGCCACCAACTGCAGAAGTCCTACTTCTCCCATCCAG<br>TCTACAGATGATGAAAAAGAGGACATTTATGTAAACTATCCAACTTTCTCTCG<br>AAGACCAAAACCAAGACTCTAAGCTGCTCTTTTGGCCTGAACACATTAGTGAT<br>GACTTCTATGGCATGGAATTTTACCCATGATTTCCTTACCACTAGGATCTACA<br>TTGATAAAAAAAATTGATTAAATTTATTTCATCTCATATATAGAAGTACTTTA<br>TTACCTGGAAACATTCTTAATAGAGATTCATTAGAAAACCCAAATCTAATGTT<br>CATGTGTTCAAGGAACCTTCTTCCATTATGTAACAGAACAGTCTAGAGAAGAT<br>TAAGGACCACATGGCTTTCTTGCTCTACTTGAAATTAATTGTGAGCATAAGCT<br>TGTTTCTGGAGTCTTCTTACATTGTTGGTTCTACTTACATACTACTGGTCCAA<br>CTCTCATGCTGTTTCTCTCAGATGTTCCCATGATGGTTGCCAAGGACACTTGA<br>TAGAAAGACTACTGGTTAAACACAATAAACAAAGTTCATTATTCACTTATTAG<br>CAAGAAGGTAGCATTATCATAAAGGATTAGATGACTTAAGTTAGCTATAGGTT<br>CAAGACCTGGACTAAAGTATTACTTGGAAATTCTGAGTATTGCTAAAAAGGAG<br>GATGAAAGGGACCTAGAAGTTGAGTTATTACTAAAAACTTTGAGTGCGAAGAT<br>ATTACTCATTAACCAGATAACAAGTGAATATGCTGTAGCATCAACATAATTCA<br>AAAGAGTAAAGAAATGGCTAGGAATGAGGTAGTTGTGTAATTATTTCTTCTCT<br>TACTAGTTTCAAATAAATTCATCTCTAATTCTATAGAGAATTCTTGCCTCCCA<br>TTCAGGACTGGCCTTCTATACAGTGAGATGGTCCAGTAAGAAATAATTTTTAT<br>TAGTGTTTTTTCTATTTTGAGAATTATTTTAATATATATTTTAATATATAAAC<br>TTGTGAGTTAAATTTTTTTTTTGCAAAATTAGCACATGAAAAGAGATTGATGG<br>TTTTAAGTAGTAGAACACAGTAGTGTAGGAATCTGAGAGCAGAGAGTTTGGGA<br>GGGGGTGAAGAGAAAACAACATCACCAAATAGTGATATATAAGAGAAAATCTG<br>TGCTTCAGAGTTTGATCAGGGCCATCTCTCCCAACTCTGCTGGAACTGAGAGA<br>ATGCACCTGATGTTGTCTCCATTTTAGATAGAGAAAAAAAAAAACCCGAATATT<br>TATAAAACTAAATAAAACTATAGTTACCTCAAAACTATGGGGATCACTATAAC<br>ATAGAATAGAATAGAATAGAATAGAATAGAATAGAATAGAATAGAATAGAATAG<br>(SEQ ID NO: 173) |
| | >NP_848802.2 CD226 antigen isoform a precursor [*Mus musculus*]<br>MAYVTWLLAILHVHKALCEETLWDTTVRLSETMTLECVYPLTHNLTQVEWTKN<br>TGTKTVSIAVYNPNHNMHIESNYLHRVHFLNSTVGFRNMSLSFYNASEADIGI<br>YSCLFHAFPNGPWEKKIKVVWSDSFEIAAPSDSYLSAEPGQDVTLTCQLPRTW |

TABLE 1-continued

Type I Proteins of Interest Amino Acid Sequence

| Protein of Interest | Transcript Sequence (SEQ ID NO:)<br>Amino Acid Sequence (SEQ ID NO:) |
|---|---|
| | PVQQVIWEKVQPHQVDILASCNLSQETRYTSKYLRQTRSNCSQGSMKSILIIP<br>NAMAADSGLYRCRSEAITGKNKSFVIRLIITDGGTNKHFILPIVGGLVSLLLV<br>ILIIIIFILYNRKRRRQVRIPLKEPRDKQSKVATNCRSPTSPIQSTDDEKEDI<br>YVNYPTFSRRPKPRL (SEQ ID NO: 174) |
| Human DR3 | >NM_003790.3 *Homo sapiens* TNF receptor superfamily member 25 (TNFRSF25), transcript variant 2, mRNA<br>GAAGGCGGAACCACGACGGGCAGAGAGCACGGAGCCGGGAAGCCCCTGGGCGC<br>CCGTCGGAGGGCTATGGAGCAGCGGCCGCGGGGCTGCGCGGCGGTGGCGGCGG<br>CGCTCCTCCTGGTGCTGCTGGGGGCCCGGGCCCAGGGCGGCACTCGTAGCCCC<br>AGGTGTGACTGTGCCGGTGACTTCCACAAGAAGATTGGTCTGTTTTGTTGCAG<br>AGGCTGCCCAGCGGGGCACTACCTGAAGGCCCCTTGCACGGAGCCCTGCGGCA<br>ACTCCACCTGCCTTGTGTGTCCCCAAGACACCTTCTTGGCCTGGGAGAACCAC<br>CATAATTCTGAATGTGCCCGCTGCCAGGCCTGTGATGAGCAGGCCTCCCAGGT<br>GGCGCTGGAGAACTGTTCAGCAGTGGCCGACACCCGCTGTGGCTGTAAGCCAG<br>GCTGGTTTGTGGAGTGCCAGGTCAGCCAATGTGTCAGCAGTTCACCCTTCTAC<br>TGCCAACCATGCCTAGACTGCGGGGCCCTGCACCGCCACACACGGCTACTCTG<br>TTCCCGCAGAGATACTGACTGTGGGACCTGCCTGCCTGGCTTCTATGAACATG<br>GCGATGGCTGCGTGTCCTGCCCCACGAGCACCCTGGGGAGCTGTCCAGAGCGC<br>TGTGCCGCTGTCTGTGGCTGGAGGCAGATGTTCTGGGTCCAGGTGCTCCTGGC<br>TGGCCTTGTGGTCCCCCTCCTGCTTGGGGCCACCCTGACCTACACATACCGCC<br>ACTGCTGGCCTCACAAGCCCCTGGTTACTGCAGATGAAGCTGGGATGGAGGCT<br>CTGACCCCACCACCGGCCACCCATCTGTCACCCTTGGACAGCGCCCACACCCT<br>TCTAGCACCTCCTGACAGCAGTGAGAAGATCTGCACCGTCCAGTTGGTGGGTA<br>ACAGCTGGACCCCTGGCTACCCCGAGACCCAGGAGGCGCTCTGCCCGCAGGTG<br>ACATGGTCCTGGGACCAGTTGCCCAGCAGAGCTCTTGGCCCCGCTGCTGCGCC<br>CACACTCTCGCCAGAGTCCCCAGCCGGCTCGCCAGCCATGATGCTGCAGCCGG<br>GCCCGCAGCTCTACGACGTGATGGACGCGGTCCCAGCGCGGCGCTGGAAGGAG<br>TTCGTGCGCACGCTGGGGCTGCGCGAGGCAGAGATCGAAGCCGTGGAGGTGGA<br>GATCGGCCGCTTCCGAGACCAGCAGTACGAGATGCTCAAGCGCTGGCGCCAGC<br>AGCAGCCCGCGGGCCTCGGAGCCGTTTACGCGGCCCTGGAGCGCATGGGGCTG<br>GACGGCTGCGTGGAAGACTTGCGCAGCCGCCTGCAGCGCGGCCCGTGACACGG<br>CGCCCACTTGCCACCTAGGCGCTCTGGTGGCCCTTGCAGAAGCCCTAAGTACG<br>GTTACTTATGCGTGTAGACATTTTATGTCACTTATTAAGCCGCTGGCACGGCC<br>CTGCGTAGCAGCACCAGCCGGCCCCACCCCTGCTCGCCCCTATCGCTCCAGCC<br>AAGGCGAAGAAGCACGAACGAATGTCGAGAGGGGGTGAAGACATTTCTCAACT<br>TCTCGGCCGGAGTTTGGCTGAGATCGCGGTATTAAATCTGTGAAAGAAAACAA<br>AACAAAACAAAAACGGCTTCTTGGCGTTTCTGCGGGGCTGGGGTGTTAAGTGG<br>ACTGGACTTTTCTCGAGGGATTCGAAGGGGACGGGAATCTTGTCACCCCGGGA<br>TCTGGCACCCATGGTGGAGTCCAGTGTGGCCTTAGCTCCCAAGCCTGCCCCTC<br>CCGAGTCCACTCTGGCTCAATTACCCCGAGAAGGAGAGAGCAAGTCGCGGCCA<br>CAGCGAGTGAGTGAACCGGAGCCCAGATGAGAGCGCTTTAATGGGGCTGCGAG<br>GTGGCGGAGACAGGGTCGGGATGGGGTGCAGCAGTTGGAGACACAGGGTCAGG<br>GCCCCTCATCCTCTATTCACTCCACCGGGGCAGTGAAAGGGTCCCGGCAGCGA<br>GTGGGTC (SEQ ID NO: 175)<br><br>>NP_003781.1 tumor necrosis factor receptor superfamily member 25 isoform 2 precursor [*Homo sapiens*]<br>MEQRPRGCAAVAAALLLVLLGARAQGGTRSPRCDCAGDFHKKIGLFCCRGCPA<br>GHYLKAPCTEPCGNSTCLVCPQDTFLAWENHHNSECARCQACDEQASQVALEN<br>CSAVADTRCGCKPGWFVECQVSQCVSSSPFYCQPCLDCGALHRHTRLLCSRRD<br>TDCGTCLPGFYEHGDGCVSCPTSTLGSCPERCAAVCGWRQMFWVQVLLAGLVV<br>PLLLGATLTYTYRHCWPHKPLVTADEAGMEALTPPPATHLSPLDSAHTLLAPP<br>DSSEKICTVQLVGNSWTPGYPETQEALCPQVTWSWDQLPSRALGPAAAPTLSP<br>ESPAGSPAMMLQPGPQLYDVMDAVPARRWKEFVRTLGLREAEIEAVEVEIGRF<br>RDQQYEMLKRWRQQQPAGLGAVYAALERMGLDGCVEDLRSRLQRGP (SEQ ID NO: 176) |
| Mouse DR3 | >NM_033042.4 *Mus musculus* tumor necrosis factor receptor superfamily, member 25 (Tnfrsf25), transcript variant 2, mRNA<br>CTGCGTGGAGGGGAAATGGGCCAGAGGCTGCTGGCAGGGGGCCTCCTCTGCTG<br>TACACAAGCTGGTTTTGTAGACAGTGAGAGGGAAGCTGATCCCAGTCCCCTAA<br>CCCTGTTCTGCCCAGGAGCCTGAGAACTGAGCTTACTCGGGCAAATGCTAGGG<br>CTTCAGAAATGGAGGAGCTGCCTAGGAGGGAGAGGTCACCTCCTGGGGCAGCC<br>ACACCAGGGTCAACTGCACGTGTTCTCCAGCCTCTGTTCCTACCACTGCTGCT<br>GCTGCTGCTGCTGCTTGGTGGCCAGGGCCAGGGCGGCATGTCTGGCAGGT<br>GTGACTGTGCCAGTGAGTCCCAGAAGAGGTATGGCCCGTTTTGTTGCAGGGGC<br>TGCCCAAAGGGACACTACATGAAGGCCCCCTGCGCAGAACCCTGTGGCAACTC<br>CACCTGCCTTCCCTGTCCCTCGGACACCTTCTTGACCAGAGACAACCACTTTA<br>AGACTGACTGTACCCGCTGCCAAGTCTGTGATGAAGAGGCCCTTCAAGTGACC<br>CTTGAGAACTGCTCGGCAAAGTCGGACACCCACTGTGGCTGCCAGTCAGGCTG<br>GTGTGTTGACTGCTCCACCGAGCCATGTGGAAAAGCTCACCTTTCTCTTGTG<br>TCCCATGCGGGGCTACAACACCAGTCCATGAGGCTCCAACCCCCCTGTTTTGG |

TABLE 1-continued

Type I Proteins of Interest Amino Acid Sequence

| Protein of Interest | Transcript Sequence (SEQ ID NO:)<br>Amino Acid Sequence (SEQ ID NO:) |
|---|---|
| | GTCCAGGTGCTTCTAGGAGTCGCGTTCCTTTTTGGGGCTATCCTGATCTGTGC<br>ATATTGTCGATGGCAGCCTTGTAAGGCCGTGGTCACTGCAGACACAGCTGGGA<br>CGGAGACCCTGGCCTCACCACAGACTGCCCATCTCTCAGCCTCAGACAGCGCC<br>CACACCCTCCTGGCACCTCCAAGCAGTACTGGGAAAATCTGTACCACTGTOCA<br>GTTGGTAGGCAACAACTGGACCCCTGGCTTATCCCAGACTCAGGAGGTGGTCT<br>GCGGACAGGCCTCACAACCCTGGGATCAGCTGCCAAACAGAACTCTTGGAACT<br>CCTCTGGCATCTCCGCTCTCGCCAGCGCCCCCTGCGGGCTCTCCGGCTGCTGT<br>GCTCCAGCCTGGCCCGCAGCTCTACGATGTGATGGATGCGGTCCCAGCACGAA<br>GGTGGAAGGAGTTCGTGCGCACGCTGGGGCTGCGGGAAGCGGAAATTGAAGCC<br>GTGGAGGTGGAAATCTGCCGCTTCCGAGACCAGCAGTATGAGATGCTCAAGCG<br>CTGGCGTCAGCAGCAGCCTGCAGGCCTCGGTGCCATCTATGCGGCTCTGGAGC<br>GCATGGGTCTGGAAGGCTGTGCCGAGGACCTGCGCAGCCGCCTGCAGCGTGGC<br>CCGTGATGGAAGGTCCATCAGCCACTTTGACACCCTAGTGACCCTTGAAGGAG<br>CCTTAAGTATTGTTACTTATGCGTGTAGACATTTTATGTCAATTACTAACCCC<br>CTGCCGTGGTCCTGCGTAGCAGGGCTGGCTGCCTCACTTTTGCTTATCTGCAG<br>CACGGAGCTCCTGCTAAGGGAAGCGTCATGGAGAAATACCAGAAGGGGCCAAG<br>TGATTGGTTGCTCAGCTGTTAATTAGCCCGAGTTTGGACTTGGTATTAAATTT<br>CGTAAGAAAAGCAGCTGCTTG (SEQ ID NO: 177)<br><br>>NP_149031.2 tumor necrosis factor receptor superfamily member 25 isoform 2 precursor [*Mus musculus*]<br>MEELPRRERSPPGAATPGSTARVLQPLFLPLLLLLLLLLGGQGQGGMSGRCDC<br>ASESQKRYGPFCCRGCPKGHYMKAPCAEPCGNSTCLPCPSDTFLTRDNHFKTD<br>CTRCQVCDEEALQVTLENCSAKSDTHCGCQSGWCVDCSTEPCGKSSPFSCVPC<br>GATTPVHEAPTPLFWVQVLLGVAFLFGAILICAYCRWQPCKAVVTADTAGTET<br>LASPQTAHLSASDSAHTLLAPPSSTGKICTTVQLVGNNWTPGLSQTQEVVCGQ<br>ASQPWDQLPNRTLGTPLASPLSPAPPAGSPAAVLQPGPQLYDVMDAVPARRWK<br>EFVRTLGLREAEIEAVEVEICRFRDQQYEMLKRWRQQQPAGLGAIYAALERMG<br>LEGCAEDLRSRLQRGP (SEQ ID NO: 178) |
| Human DcR3 | >NM_003823.4 *Homo sapiens* TNF receptor superfamily member 6b (TNFRSF6B), mRNA<br>GGACTTGGGCGGCCCCTCCGCAGGCGGACCGGGGGCAAAGGAGGTGGCATGTC<br>GGTCAGGCACAGCAGGGTCCTGTGTCCGCGCTGAGCCGCGCTCTCCCTGCTCC<br>AGCAAGGACCATGAGGGCGCTGGAGGGGCCAGGCCTGTCGCTGCTGTGCCTGG<br>TGTTGGCGCTGCCTGCCCTGCTGCCGGTGCCGGCTGTACGCGGAGTGGCAGAA<br>ACACCCACCTACCCCTGGCGGGACGCAGAGACAGGGGAGCGGCTGGTGTGCGC<br>CCAGTGCCCCCCAGGCACCTTTGTGCAGCGGCCGTGCCGCCGAGACAGCCCCA<br>CGACGTGTGGCCCGTGTCCACCGCGCCACTACACGCAGTTCTGGAACTACCTA<br>GAGCGCTGCCGCTACTGCAACGTCCTCTGCGGGGAGCGTGAGGAGGAGGCACG<br>GGCTTGCCACGCCACCCACAACCGTGCCTGCCGCTGCCGCACCGGCTTCTTCG<br>CGCACGCTGGTTTCTGCTTGGAGCACGCATCGTGTCCACCTGGTGCCGGCGTG<br>ATTGCCCCGGGCACCCCCAGCCAGAACACGCAGTGCCAGCCGTGCCCCCCAGG<br>CACCTTCTCAGCCAGCAGCTCCAGCTCAGAGCAGTGCCAGCCCCACCGCAACT<br>GCACGGCCCTGGGCCTGGCCCTCAATGTGCCAGGCTCTTCCTCCCATGACACC<br>CTGTGCACCAGCTGCACTGGCTTCCCCCTCAGCACCAGGGTACCAGGAGCTGA<br>GGAGTGTGAGCGTGCCGTCATCGACTTTGTGGCTTTCCAGGACATCTCCATCA<br>AGAGGCTGCAGCGGCTGCTGCAGGCCCTCGAGGCCCCGGAGGGCTGGGGTCCG<br>ACACCAAGGGCGGGCCGCGCGGCCTTGCAGCTGAAGCTGCGTCGGCGGCTCAC<br>GGAGCTCCTGGGGGCGCAGGACGGGGCGCTGCTGGTGCGGCTGCTGCAGGCGC<br>TGCGCGTGGCCAGGATGCCCGGGCTGGAGCGGAGCGTCCGTGAGCGCTTCCTC<br>CCTGTGCACTGATCCTGGCCCCCTCTTATTTATTCTACATCCTTGGCACCCCA<br>CTTGCACTGAAAGAGGCTTTTTTTTAAATAGAAGAAATGAGGTTTCTTAAAGC<br>TTATTTTTATAAAGCTTTTTCATAAAA (SEQ ID NO: 179)<br><br>>NP_003814.1 tumor necrosis factor receptor superfamily member 6B precursor [*Homo sapiens*]<br>MRALEGPGLSLLCLVLALPALLPVPAVRGVAETPTYPWRDAETGERLVCAQCP<br>PGTFVQRPCRRDSPTTCGPCPPRHYTQFWNYLERCRYCNVLCGEREEEARACH<br>ATHNRACRCRTGFFAHAGFCLEHASCPPGAGVIAPGTPSQNTQCQPCPPGTFS<br>ASSSSSEQCQPHRNCTALGLALNVPGSSSHDTLCTSCTGFPLSTRVPGAEECE<br>RAVIDFVAFQDISIKRLQRLLQALEAPEGWGPTPRAGRAALQLKLRRRLTELL<br>GAQDGALLVRLLQALRVARMPGLERSVRERFLPVH (SEQ ID NO: 180) |
| Human FasL | >NM_000639.3 *Homo sapiens* Fas ligand (FASLG), transcript variant 1, mRNA<br>AGCAGTCAGCAACAGGGTCCCGTCCTTGACACCTCAGCCTCTACAGGACTGAG<br>AAGAAGTAAAACCGTTTGCTGGGGCTGGCCTGACTCACCAGCTGCCATGCAGC<br>AGCCCTTCAATTACCCATATCCCCAGATCTACTGGGTGGACAGCAGTGCCAGC<br>TCTCCCTGGGCCCCTCCAGGCACAGTTCTTCCCTGTCCAACCTCTGTGCCCAG<br>AAGGCCTGGTCAAAGGAGGCCACCACCACCACCGCCACCGCCACCACTACCAC<br>CTCCGCCGCCGCCGCCACCACTGCCTCCACTACCGCTGCCACCCCTGAAGAAG<br>AGAGGGAACCACAGCACAGGCCTGTGTCTCCTTGTGATGTTTTTCATGGTTCT<br>GGTTGCCTTGGTAGGATTGGGCCTGGGGATGTTTCAGCTCTTCCACCTACAGA |

TABLE 1-continued

Type I Proteins of Interest Amino Acid Sequence

| Protein of Interest | Transcript Sequence (SEQ ID NO:)<br>Amino Acid Sequence (SEQ ID NO:) |
|---|---|
| | AGGAGCTGGCAGAACTCCGAGAGTCTACCAGCCAGATGCACACAGCATCATCT<br>TTGGAGAAGCAAATAGGCCACCCCAGTCCACCCCCTGAAAAAAAGGAGCTGAG<br>GAAAGTGGCCCATTTAACAGGCAAGTCCAACTCAAGGTCCATGCCTCTGGAAT<br>GGGAAGACACCTATGGAATTGTCCTGCTTTCTGGAGTGAAGTATAAGAAGGGT<br>GGCCTTGTGATCAATGAAACTGGGCTGTACTTTGTATATTCCAAAGTATACTT<br>CCGGGGTCAATCTTGCAACAACCTGCCCCTGAGCCACAAGGTCTACATGAGGA<br>ACTCTAAGTATCCCCAGGATCTGGTGATGATGGAGGGGAAGATGATGAGCTAC<br>TGCACTACTGGGCAGATGTGGGCCCGCAGCAGCTACCTGGGGGCAGTGTTCAA<br>TCTTACCAGTGCTGATCATTTATATGTCAACGTATCTGAGCTCTCTCTGGTCA<br>ATTTTGAGGAATCTCAGACGTTTTTCGGCTTATATAAGCTCTAAGAGAAGCAC<br>TTTGGGATTCTTTCCATTATGATTCTTTGTTACAGGCACCGAGAATGTTGTAT<br>TCAGTGAGGGTCTTCTTACATGCATTTGAGGTCAAGTAAGAAGACATGAACCA<br>AGTGGACCTTGAGACCACAGGGTTCAAAATGTCTGTAGCTCCTCAACTCACCT<br>AATGTTTATGAGCCAGACAAATGGAGGAATATGACGGAAGAACATAGAACTCT<br>GGGCTGCCATGTGAAGAGGGAGAAGCATGAAAAAGCAGCTACCAGGTGTTCTA<br>CACTCATCTTAGTGCCTGAGAGTATTTAGGCAGATTGAAAAGGACACCTTTTA<br>ACTCACCTCTCAAGGTGGGCCTTGCTACCTCAAGGGGGACTGTCTTTCAGATA<br>CATGGTTGTGACCTGAGGATTTAAGGGATGGAAAAGGAAGACTAGAGGCTTGC<br>ATAATAAGCTAAAGAGGCTGAAAGAGGCCAATGCCCCACTGGCAGCATCTTCA<br>CTTCTAAATGCATATCCTGAGCCATCGGTGAAACTAACAGATAAGCAAGAGAG<br>ATGTTTTGGGGACTCATTTCATTCCTAACACAGCATGTGTATTTCCAGTGCAA<br>TTGTAGGGGTGTGTGTGTGTGTGTGTGTGTGTGTGTGTGTATGACTAAAGAGA<br>GAATGTAGATATTGTGAAGTACATATTAGGAAAATATGGGTTGCATTTGGTCA<br>AGATTTTGAATGCTTCCTGACAATCAACTCTAATAGTGCTTAAAAATCATTGA<br>TTGTCAGCTACTAATGATGTTTTCCTATAATATAATAAATATTTATGTAGATG<br>TGCATTTTTGTGAAATGAAAACATGTAATAAAAAGTATATGTTAGGATACAAA<br>TAA (SEQ ID NO: 181)<br><br>>NP_000630.1 tumor necrosis factor ligand superfamily member 6 isoform 1 [*Homo sapiens*]<br>MQQPFNYPYPQIYWVDSSASSPWAPPGTVLPCPTSVPRRPGQRRPPPPPPPP<br>LPPPPPPPLPPLPLPPLKKRGNHSTGLCLLVMFFMVLVALVGLGLGMFQLFH<br>LQKELAELRESTSQMHTASSLEKQIGHPSPPPEKKELRKVAHLTGKSNSRSMP<br>LEWEDTYGIVLLSGVKYKKGGLVINETGLYFVYSKVYFRGQSCNNLPLSHKVY<br>MRNSKYPQDLVMMEGKMMSYCTTGQMWARSSYLGAVFNLTSADHLYVNVSELS<br>LVNFEESQTFFGLYKL (SEQ ID NO: 182) |
| Mouse FasL | >NM_010177.4 *Mus musculus* Fas ligand (TNF superfamily, member 6) (Fasl), transcript variant 1, mRNA<br>TGAGGCTTCTCAGCTTCAGATGCAAGTGAGTGGGTGTCTCACAGAGAAGCAAA<br>GAGAAGAGAACAGGAGAAAGGTGTTTCCCTTGACTGCGGAAACTTTATAAAGA<br>AAACTTAGCTTCTCTGGAGCAGTCAGCGTCAGAGTTCTGTCCTTGACACCTGA<br>GTCTCCTCCACAAGGCTGTGAGAAGGAAACCCTTTCCTGGGGCTGGGTGCCAT<br>GCAGCAGCCCATGAATTACCCATGTCCCCAGATCTTCTGGGTAGACAGCAGTG<br>CCACTTCATCTTGGGCTCCTCCAGGGTCAGTTTTTCCCTGTCCATCTTGTGGG<br>CCTAGAGGGCCGGACCAAAGGAGACCGCCACCTCCACCACCACCTGTGTCACC<br>ACTACCACCGCCATCACAACCACTCCCACTGCCGCCACTGACCCCTCTAAAGA<br>AGAAGGACCACAACACAAATCTGTGGCTACCGGTGGTATTTTTCATGGTTCTG<br>GTGGCTCTGGTTGGAATGGGATTAGGAATGTATCAGCTCTTCCACCTGCAGAA<br>GGAACTGGCAGAACTCCGTGAGTTCACCAACCAAAGCCTTAAAGTATCATCTT<br>TTGAAAAGCAAATAGCCAACCCCAGTACACCCTCTGAAAAAAAAGAGCCGAGG<br>AGTGTGGCCCATTTAACAGGGAACCCCCACTCAAGGTCCATCCCTCTGGAATG<br>GGAAGACACATATGGAACCGCTCTGATCTCTGGAGTGAAGTATAAGAAAGGTG<br>GCCTTGTGATCAACGAAACTGGGTTGTACTTCGTGTATTCCAAAGTATACTTC<br>CGGGGTCAGTCTTGCAACAACCAGCCCCTAAACCACAAGGTCTATATGAGGAA<br>CTCTAAGTATCCTGAGGATCTGGTGCTAATGGAGGAGAAGAGGTTGAACTACT<br>GCACTACTGGACAGATATGGGCCCACAGCAGCTACCTGGGGGCAGTATTCAAT<br>CTTACCAGTGCTGACCATTTATATGTCAACATATCTCAACTCTCTCTGATCAA<br>TTTTGAGGAATCTAAGACCTTTTTCGGCTTGTATAAGCTTTAAAAGAAAAAGC<br>ATTTTAAAATGATCTACTATTCTTTATCATGGGCACCAGGAATATTGTCTTGA<br>ATGAGAGTCTTCTTAAGACCTATTGAGATTAATTAAGACTACATGAGCCACAA<br>AGACCTCATGACCGCAAGGTCCAACAGGTCAGCTATCCTTCATTTTCTCGAGG<br>TCCATGGAGTGGTCCTTAATGCCTGCATCATGAGCCAGATGGAAGGAGGTCTG<br>TGACTGAGGGACATAAAGCTTTGGGCTGCTGTGTGACAATGCAGAGGCACAGA<br>GAAAGAACTGTCTGATGTTAAATGGCCAAGAGAATTTTAACCATTGAAGAAGA<br>CACCTTTACACTCACTTCCAGGGTGGGTCTACTTACTACCTCACAGAGGCCGT<br>TTTTGAGACATAGTTGTGGTATGAATATACAAGGGTGAGAAAGGAGGCTCATT<br>TGACTGATAAGCTAGAGACTGAAAAAAAGACAGTGTCTCATTGGCACCATCTT<br>TACTGTTACCTAATGTTTTCTGAGCCGACCTTTGATCCTAACGGAGAAGTAAG<br>AGGGATGTTTGAGGCACAAATCATTCTCTACATAGCATGCATACCTCCAGTGC<br>AATGATGTCTGTGTGTTTGTATGTATGAGAGCAAACAGATTCTAAGGAGTCAT<br>ATAAATAAAATATGTACATTATGGAGTACATATTAGAAACCTGTTACATTTGA<br>TGCTAGATATCTGAATGTTTCTTGGCAATAAACTCTAATAGTCTTCAAAATCT<br>TTTATTATCAGCTACTGATGCTGTTTTTCTTTAATACAACTAGTATTTATGCT |

TABLE 1-continued

Type I Proteins of Interest Amino Acid Sequence

| Protein of Interest | Transcript Sequence (SEQ ID NO:)<br>Amino Acid Sequence (SEQ ID NO:) |
|---|---|
| | CTGAACATCCTAATGAGGAAAAGACAAATAAAATTATGTTATAGAATACAGAA<br>ATGCCTTAAGGACATAGACTTTGGAAA (SEQ ID NO: 183) |
| | >NP_034307.1 tumor necrosis factor ligand superfamily member 6 isoform 1 [*Mus musculus*]<br>MQQPMNYPCPQIFWVDSSATSSWAPPGSVFPCPSCGPRGPDQRRPPPPPPPVS<br>PLPPPSQPLPLPPLTPLKKKDHNTNLWLPVVFFMVLVALVGMGLGMYQLFHLQ<br>KELAELREFTNQSLKVSSFEKQIANPSTPSEKKEPRSVAHLTGNPHSRSIPLE<br>WEDTYGTALISGVKYKKGGLVINETGLYFVYSKVYFRGQSCNNQPLNHKVYMR<br>NSKYPEDLVLMEEKRLNYCTTGQIWAHSSYLGAVFNLTSADHLYVNISQLSLI<br>NFEESKTFFGLYKL (SEQ ID NO: 184) |
| Human TIM-1 (CD365) | >NM_012206.3 *Homo sapiens* hepatitis A virus cellular receptor 1 (HAVCR1), transcript variant 1, mRNA<br>GACCAGGAGTCAGTTTGGCGGTTATGTGTGGGGAAGAAGCTGGGAAGTCAGGG<br>GCTGTTTCTGTGGACAGCTTTCCCTGTCCTTTGGAAGGCACAGAGCTCTCAGC<br>TGCAGGGAACTAACAGAGCTCTGAAGCCGTTATATGTGGTCTTCTCTCATTTC<br>CAGCAGAGCAGGCTCATATGAATCAACCAACTGGGTGAAAAGATAAGTTGCAA<br>TCTGAGATTTAAGACTTGATCAGATACCATCTGGTGGAGGGTACCAACCAGCC<br>TGTCTGCTCATTTTCCTTCAGGCTGATCCCATAATGCATCCTCAAGTGGTCAT<br>CTTAAGCCTCATCCTACATCTGGCAGATTCTGTAGCTGGTTCTGTAAAGGTTG<br>GTGGAGAGGCAGGTCCATCTGTCACACTACCCTGCCACTACAGTGGAGCTGTC<br>ACATCCATGTGCTGGAATAGAGGCTCATGTTCTCTATTCACATGCCAAAATGG<br>CATTGTCTGGACCAATGGAACCCACGTCACCTATCGGAAGGACACACGCTATA<br>AGCTATTGGGGGACCTTTCAAGAAGGGATGTCTCTTTGACCATAGAAAATACA<br>GCTGTGTCTGACAGTGGCGTATATTGTTGCCGTGTTGAGCACCGTGGGTGGTT<br>CAATGACATGAAAATCACCGTATCATTGGAGATTGTGCCACCCAAGGTCACGA<br>CTACTCCAATTGTCACAACTGTTCCAACCGTCACGACTGTTCGAACGAGCACC<br>ACTGTTCCAACGACAACGACTGTTCCAATGACGACTGTTCCAACGACAACTGT<br>TCCAACAACAATGAGCATTCCAACGACAACGACTGTTCTGACGACAATGACTG<br>TTTCAACGACAACGAGCGTTCCAACGACAACGAGCATTCCAACAACAACAAGT<br>GTTCCAGTGACAACAACTGTCTCTACCTTTGTTCCTCCAATGCCTTTGCCCAG<br>GCAGAACCATGAACCAGTAGCCACTTCACCATCTTCACCTCAGCCAGCAGAAA<br>CCCACCCTACGACACTGCAGGGAGCAATAAGGAGAGAACCCACCAGCTCACCA<br>TTGTACTCTTACACAACAGATGGGAATGACACCGTGACAGAGTCTTCAGATGG<br>CCTTTGGAATAACAATCAAACTCAACTGTTCCTAGAACATAGTCTACTGACGG<br>CCAATACCACTAAAGGAATCTATGCTGGAGTCTGTATTTCTGTCTTGGTGCTT<br>CTTGCTCTTTTGGGTGTCATCATTGCCAAAAAGTATTTCTTCAAAAAGGAGGT<br>TCAACAACTAAGTGTTTCATTTAGCAGCCTTCAAATTAAAGCTTTGCAAAATG<br>CAGTTGAAAAGGAAGTCCAAGCAGAAGACAATATCTACATTGAGAATAGTCTT<br>TATGCCACGGACTAAGACCCAGTGGTGCTCTTTGAGAGTTTACGCCCATGAGT<br>GCAGAAGACTGAACAGACATCAGCACATCAGACGTCTTTTAGACCCCAAGACA<br>ATTTTTCTGTTTCAGTTTCATCTGGCATTCCAACATGTCAGTGATACTGGGTA<br>GAGTAACTCTCTCACTCCAAACTGTGTATAGTCAACCTCATCATTAATGTAGT<br>CCTAATTTTTTATGCTAAAACTGGCTCAATCCTTCTGATCATTGCAGTTTTCT<br>CTCAAATATGAACACTTTATAATTGTATGTTCTTTTTAGACCCCATAAATCCT<br>GTATACATCAAAGAGAA (SEQ ID NO: 185) |
| | >NP_036338.2 hepatitis A virus cellular receptor 1 isoform a precursor [*Homo sapiens*]<br>MHPQVVILSLILHLADSVAGSVKVGGEAGPSVTLPCHYSGAVTSMCWNRGSCS<br>LFTCQNGIVWTNGTHVTYRKDTRYKLLGDLSRRDVSLTIENTAVSDSGVYCCR<br>VEHRGWFNDMKITVSLEIVPPKVTTTPIVTTVPTVTTVRTSTTVPTTTTVPMT<br>TVPTTTVPTTMSIPTTTTVLTTMTVSTTTSVPTTTSIPTTTSVPVTTTVSTFV<br>PPMPLPRQNHEPVATSPSSPQPAETHPTTLQGAIRREPTSSPLYSYTTDGNDT<br>VTESSDGLWNNNQTQLFLEHSLLTANTTKGIYAGVCISVLVLLALLGVIIAKK<br>YFFKKEVQQLSVSFSSLQIKALQNAVEKEVQAEDNIYIENSLYATD (SEQ ID NO: 186) |
| Mouse TIM-1 | >NM_134248.2 *Mus musculus* hepatitis A virus cellular receptor 1 (Havcr1), transcript variant 1, mRNA<br>GTCAGTACCATGAATCAGATTCAAGTCTTCATTTCAGGCCTCATACTGCTTCT<br>CCCAGGCGCTGTGGATTCTTATGTGGAAGTAAAGGGGGTGGTGGGTCACCCTG<br>TCACACTTCCATGTACTTACTCAACATATCGTGGAATCACAACGACATGTTGG<br>GGCCGAGGGCAATGCCCATCTTCTGCTTGTCAAAATACACTTATTTGGACCAA<br>TGGACATCGTGTCACCTATCAGAAGAGCAGTCGGTACAACTTAAAGGGGCATA<br>TTTCAGAAGGAGATGTGTCCTTGACGATAGAGAACTCTGTTGAGAGTGACAGT<br>GOTCTGTATTGTTGTCGAGTGGAGATTOCTGOATGGTTTAATGATCAGAAAGT<br>GACCTTTTCATTGCAAGTTAAACCAGAGATTCCCACACGTCCTCCAAGAAGAC<br>CCACAACTACAAGGCCCACAGCTACAGGAAGACCCACGACTATTTCAACAAGA<br>TCCACACATGTACCAACATCAACCAGAGTCTCTACCTCCACTCCTCCAACATC<br>TACACACACATGGACTCACAAACCAGAACCCACTACATTTTGTCCCCATGAGA<br>CAACAGCTGAGGTGACAGGAATCCCATCCCATACTCCTACAGACTGGAATGGC<br>ACTGTGACATCCTCAGGAGATACCTGGAGTAATCACACTGAAGCAATCCCTCC<br>AGGGAAGCCGCAGAAAAACCCTACTAAGGGCTTCTATGTTGGCATCTGCATCG |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| | CAGCCCTGCTGCTACTGCTCCTTGTGAGCACCGTGGCTATCACCAGGTACATA<br>CTTATGAAAAGGAAGTCAGCATCTCTAAGCGTGGTTGCCTTCCGTGTCTCTAA<br>GATTGAAGCTTTGCAGAACGCAGCGGTTGTGCATTCCCGAGCTGAAGACAACA<br>TCTACATTGTTGAAGATAGACCTTGAGGGGCAGAATGAGTACCAGTGGCCCTC<br>TGAGGGACCTTCTGCCTGAGATTTATAGAGACTGTCACTGATGTCATAGAGTC<br>ACACCCATTACAGCGCCAAGGCGATTTTCTGTGTTGGTTCTTCCAGCTGCAGC<br>AGAGAGGGTAACCCTCTACTGTGTATACTCAAAACTCAGATTAACATCATCCT<br>AATTTTGGTATCTGCACCACCTCCGTGTCTCTGCTCACTACAGAGATTCTCTC<br>AAACATGAACGTTTTAGAAGTTTGTGTTTCCCTTAGTCAATGTAATCATTGGT<br>AATACTATTCTATTCTTGGTTACTAAAACCATTACTAAGAGAGGGATAGGAAT<br>TAAAAGTTGGTGTGAGGGGCCTCCTGAATTTAGAAGCACTTGATTCTGTTTTA<br>TCTACTTTCTTGAAATGTTACTTCTACCCTTCCCAATGGGTAAAATCATGGGA<br>GCATGGTGCCCTCATAGATAAATAGAAGAGAGTCTATTGCTGCCAATATAGAT<br>GGTTATGCTTTCTCATAGCTCTGAAAATATGACACATTTATTATGAGGTTGAT<br>CTTAGGATAAGGATAGGTGTTTTATGTCAGGAGAGGTTATCATGGTGAATATG<br>GACCAGCAGACAGCAGTGGAGGAAAATAATGAACCAAGGGATTGAGTTCATTA<br>GTGCTAATTCTACTCCACTCCTGTCTTTATGCTCCTAAACTTACTGACTGAGC<br>TCTGAATTAGGTGCTAGGAGGAGACAATGCAGACATGAAAGGGGAAGGAGCGC<br>CTTCAGGACACAGGCTCTCTGCTGAGAGAAGTCCTATTTGCAGGTGTGATAGA<br>GGTTGGGACAATCTCTGAGTTGTAAATTTCTAATTGTCTTCAGGCCATATTTA<br>TAGTTAAATTCATTTCCGAAAGACATAGCATCTTCCCCAATGGGTCAGTTTGT<br>CAAAATCAATAAAATATTTTGTTTTGCTAAGAATTAAAAAAAAAAAAAAAAAA<br>A (SEQ ID NO: 187) |
| | >NP_599009.2 hepatitis A virus cellular receptor 1 homolog isoform a precursor [*Mus musculus*]<br>MNQIQVFISGLILLLPGAVDSYVEVKGVVGHPVTLPCTYSTYRGITTTCWGRG<br>QCPSSACQNTLIWTNGHRVTYQKSSRYNLKGHISEGDVSLTIENSVESDSGLY<br>CCRVEIPGWFNDQKVTFSLQVKPEIPTRPPRRPTTTRPTATGRPTTISTRSTH<br>VPTSTRVSTSTPPTSTHTWTHKPEPTTFCPHETTAEVTGIPSHTPTDWNGTVT<br>SSGDTWSNHTEAIPPGKPQKNPTKGFYVGICIAALLLLLLVSTVAITRYILMK<br>RKSASLSVVAFRVSKIEALQNAAVVHSRAEDNIYIVEDRP (SEQ ID NO: 188) |
| Human PD-1 | >NM_005018.3 *Homo sapiens* programmed cell death 1 (PDCD1), mRNA<br>GCTCACCTCCGCCTGAGCAGTGGAGAAGGCGGCACTCTGGTGGGGCTGCTCCA<br>GGCATGCAGATCCCACAGGCGCCCTGGCCAGTCGTCTGGGCGGTGCTACAACT<br>GGGCTGGCGGCCAGGATGGTTCTTAGACTCCCCAGACAGGCCCTGGAACCCCC<br>CCACCTTCTCCCCAGCCCTGCTCGTGGTGACCGAAGGGGACAACGCCACCTTC<br>ACCTGCAGCTTCTCCAACACATCGGAGAGCTTCGTGCTAAACTGGTACCGCAT<br>GAGCCCCAGCAACCAGACGGACAAGCTGGCCGCCTTCCCCGAGGACCGCAGCC<br>AGCCCGGCCAGGACTGCCGCTTCCGTGTCACACAACTGCCCAACGGGCGTGAC<br>TTCCACATGAGCGTGGTCAGGGCCCGGCGCAATGACAGCGGCACCTACCTCTG<br>TGGGGCCATCTCCCTGGCCCCCAAGGCGCAGATCAAAGAGAGCCTGCGGGCAG<br>AGCTCAGGGTGACAGAGAGAAGGGCAGAAGTGCCCACAGCCCACCCCAGCCCC<br>TCACCCAGGCCAGCCGGCCAGTTCCAAACCCTGGTGGTTGGTGTCGTGGGCGG<br>CCTGCTGGGCAGCCTGGTGCTGCTAGTCTGGGTCCTGGCCGTCATCTGCTCCC<br>GGGCCGCACGAGGGACAATAGGAGCCAGGCGCACCGGCCAGCCCCTGAAGGAG<br>GACCCCTCAGCCGTGCCTGTGTTCTCTGTGGACTATGGGGAGCTGGATTTCCA<br>GTGGCGAGAGAAGACCCCGGAGCCCCCCGTGCCCTGTGTCCCTGAGCAGACGG<br>AGTATGCCACCATTGTCTTTCCTAGCGGAATGGGCACCTCATCCCCCGCCCGC<br>AGGGGCTCAGCTGACGGCCCTCGGAGTGCCCAGCCACTGAGGCCTGAGGATGG<br>ACACTGCTCTTGGCCCCTCTGACCGGCTTCCTTGGCCACCAGTGTTCTGCAGA<br>CCCTCCACCATGAGCCCGGGTCAGCGCATTTCCTCAGGAGAAGCAGGCAGGGT<br>GCAGGCCATTGCAGGCCGTCCAGGGGCTGAGCTGCCTGGGGGCGACCGGGGCT<br>CCAGCCTGCACCTGCACCAGGCACAGCCCCACCACAGGACTCATGTCTCAATG<br>CCCACAGTGAGCCCAGGCAGCAGGTGTCACCGTCCCCTACAGGGAGGGCCAGA<br>TGCAGTCACTGCTTCAGGTCCTGCCAGCACAGAGCTGCCTGCGTCCAGCTCCC<br>TGAATCTCTGCTGCTGCTGCTGCTGCTGCTGCTGCTGCCTGCGGCCCGGGGCT<br>GAAGGCGCCGTGGCCCTGCCTGACGCCCCGGAGCCTCCTGCCTGAACTTGGGG<br>GCTGGTTGGAGATGGCCTTGGAGCAGCCAAGGTGCCCCTGGCAGTGGCATCCC<br>GAAACGCCCTGGACGCAGGGCCCAAGACTGGGCACAGGAGTGGGAGGTACATG<br>GGGCTGGGGACTCCCCAGGAGTTATCTGCTCCCTGCAGGCCTAGAGAAGTTTC<br>AGGGAAGGTCAGAAGAGCTCCTGGCTGTGGTGGGCAGGGCAGGAAACCCCTCC<br>ACCTTTACACATGCCCAGGCAGCACCTCAGGCCCTTTGTGGGGCAGGGAAGCT<br>GAGGCAGTAAGCGGGCAGGCAGAGCTGGAGGCCTTTCAGGCCCAGCCAGCACT<br>CTGGCCTCCTGCCGCCGCATTCCACCCCAGCCCCTCACACCACTCGGGAGAGG<br>GACATCCTACGGTCCCAAGGTCAGGAGGGCAGGGCTGGGGTTGACTCAGGCCC<br>CTCCCAGCTGTGGCCACCTGGGTGTTGGGAGGGCAGAAGTGCAGGCACCTAGG<br>GCCCCCCATGTGCCCACCCTGGGAGCTCTCCTTGGAACCCATTCCTGAAATTA<br>TTTAAAGGGGTTGGCCGGGCTCCCACCAGGGCCTGGGTGGGAAGGTACAGGCG |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| | TTCCCCCGGGGCCTAGTACCCCCGCCGTGGCCTATCCACTCCTCACATCCACA<br>CACTGCACCCCCACTCCTGGGGCAGGGCCACCAGCATCCAGGCGGCCAGCAGG<br>CACCTGAGTGGCTGGGACAAGGGATCCCCCTTCCCTGTGGTTCTATTATATTA<br>TAATTATAATTAAATATGAGAGCATGCTAA (SEQ ID NO: 189)<br><br>>NP_005009.2 programmed cell death protein 1<br>precursor [*Homo sapiens*]<br>MQIPQAPWPVVWAVLQLGWRPGWFLDSPDRPWNPPTFSPALLVVTEGDNATFT<br>CSFSNTSESFVLNWYRMSPSNQTDKLAAFPEDRSQPGQDCRFRVTQLPNGRDF<br>HMSVVRARRNDSGTYLCGAISLAPKAQIKESLRAELRVTERRAEVPTAHPSPS<br>PRPAGQFQTLVVGVVGGLLGSLVLLVWVLAVICSRAARGTIGARRTGQPLKED<br>PSAVPVFSVDYGELDFQWREKTPEPPVPCVPEQTEYATIVFPSGMGTSSPARR<br>GSADGPRSAQPLRPEDGHCSWPL (SEQ ID NO: 190) |
| Mouse PD-1 | >NM_008798.3 *Mus musculus* programmed cell death 1<br>(Pdcd1), mRNA<br>TGAGCAGCGGGGAGGAGGAAGAGGAGACTGCTACTGAAGGCGACACTGCCAGG<br>GGCTCTGGGCATGTGGGTCCGGCAGGTACCCTGGTCATTCACTTGGGCTGTGC<br>TGCAGTTGAGCTGGCAATCAGGGTGGCTTCTAGAGGTCCCCAATGGGCCCTGG<br>AGGTCCCTCACCTTCTACCCAGCCTGGCTCACAGTGTCAGAGGGAGCAAATGC<br>CACCTTCACCTGCAGCTTGTCCAACTGGTCGGAGGATCTTATGCTGAACTGGA<br>ACCGCCTGAGTCCCAGCAACCAGACTGAAAAACAGGCCGCCTTCTGTAATGGT<br>TTGAGCCAACCCGTCCAGGATGCCCGCTTCCAGATCATACAGCTGCCCAACAG<br>GCATGACTTCCACATGAACATCCTTGACACACGGCGCAATGACAGTGGCATCT<br>ACCTCTGTGGGGCCATCTCCCTGCACCCCAAGGCAAAAATCGAGGAGAGCCCT<br>GGAGCAGAGCTCGTGGTAACAGAGAGAATCCTGGAGACCTCAACAAGATATCC<br>CAGCCCCTCGCCCAAACCAGAAGGCCGGTTTCAAGGCATGGTCATTGGTATCA<br>TGAGTGCCCTAGTGGGTATCCCTGTATTGCTGCTGCTGGCCTGGGCCCTAGCT<br>GTCTTCTGCTCAACAAGTATGTCAGAGGCCAGAGGAGCTGGAAGCAAGGACGA<br>CACTCTGAAGGAGGAGCCTTCAGCAGCACCTGTCCCTAGTGTGGCCTATGAGG<br>AGCTGGACTTCCAGGGACGAGAGAAGACACCAGAGCTCCCTACCGCCTGTGTG<br>CACACAGAATATGCCACCATTGTCTTCACTGAAGGGCTGGGTGCCTCGGCCAT<br>GGGACGTAGGGGCTCAGCTGATGGCCTGCAGGGTCCTCGGCCTCCAAGACATG<br>AGGATGGACATTGTTCTTGGCCTCTTTGACCAGATTCTTCAGCCATTAGCATG<br>CTGCAGACCCTCCACAGAGAGCACCGGTCCGTCCCTCAGTCAAGAGGAGCATG<br>CAGGCTACAGTTCAGCCAAGGCTCCCAGGGTCTGAGCTAGCTGGAGTGACAGC<br>CCAGCGCCTGCACCAATTCCAGCACATGCACTGTTGAGTGAGAGCTCACTTCA<br>GGTTTACCACAAGCTGGGAGCAGCAGGCTTCCCGGTTTCCTATTGTCACAAGG<br>TGCAGAGCTGGGGCCTAAGCCTATGTCTCCTGAATCCTACTGTTGGGCACTTC<br>TAGGGACTTGAGACACTATAGCCAATGGCCTCTGTGGGTTCTGTGCCTGGAAA<br>TGGAGAGATCTGAGTACAGCCTGCTTTGAATGGCCCTGTGAGGCAACCCCAAA<br>GCAAGGGGGTCCAGGTATACTATGGGCCCAGCACCTAAAGCCACCCTTGGGAG<br>ATGATACTCAGGTGGGAAATTCGTAGACTGGGGGACTGAACCAATCCCAAGAT<br>CTGGAAAAGTTTTGATGAAGACTTGAAAAGCTCCTAGCTTCGGGGGTCTGGGA<br>AGCATGAGCACTTACCAGGCAAAAGCTCCGTGAGCGTATCTGCTGTCCTTCTG<br>CATGCCCAGGTACCTCAGTTTTTTTCAACAGCAAGGAAACTAGGGCAATAAAG<br>GGAACCAGCAGAGCTAGAGCCACCCACACATCCAGGGGGGCACTTGACTCTCC<br>CTACTCCTCCTAGGAACCAAAAGGACAAAGTCCATGTTGACAGCAGGGAAGGA<br>AAGGGGGATATAACCTTGACGCAAACCAACACTGGGGTGTTAGAATCTCCTCA<br>TTCACTCTGTCCTGGAGTTGGGTTCTGGCTCTCCTTCACACCTAGGACTCTGA<br>AATGAGCAAGCACTTCAGACAGTCAGGGTAGCAAGAGTCTAGCTGTCTGGTGG<br>GCACCCAAAATGACCAGGGCTTAAGTCCCTTTCCTTTGGTTTAAGCCCGTTAT<br>AATTAAATGGTACCAAAAGCTTTAA (SEQ ID NO: 191)<br><br>>NP_032824.1 programmed cell death protein 1<br>precursor [*Mus musculus*]<br>MWVRQVPWSFTWAVLQLSWQSGWLLEVPNGPWRSLTFYPAWLTVSEGANATFT<br>CSLSNWSEDLMLNWNRLSPSNQTEKQAAFCNGLSQPVQDARFQIIQLPNRHDF<br>HMNILDTRRNDSGIYLCGAISLHPKAKIEESPGAELVVTERILETSTRYPSPS<br>PKPEGRFQGMVIGIMSALVGIPVLLLLAWALAVFCSTSMSEARGAGSKDDTLK<br>EEPSAAPVPSVAYEELDFQGREKTPELPTACVHTEYATIVFTEGLGASAMGRR<br>GSADGLQGPRPPRHEDGHCSWPL (SEQ ID NO: 317) |
| mScarlet | >KY021423.1 Synthetic construct mScarlet gene,<br>partial cds, mRNA<br>ATGGTGAGCAAGGGCGAGGCAGTGATCAAGGAGTTCATGCGGTTCAAGGTGCA<br>CATGGAGGGCTCCATGAACGGCCACGAGTTCGAGATCGAGGGCGAGGGCGAGG<br>GCCGCCCCTACGAGGGCACCCAGACCGCCAAGCTGAAGGTGACCAAGGGTGGC<br>CCCCTGCCCTTCTCCTGGGACATCCTGTCCCCTCAGTTCATGTACGGCTCCAG<br>GGCCTTCACCAAGCACCCCGCCGACATCCCCGACTACTATAAGCAGTCCTTCC<br>CCGAGGGCTTCAAGTGGGAGCGCGTGATGAACTTCGAGGACGGCGGCGCCGTG<br>ACCGTGACCCAGGACACCTCCCTGGAGGACGGCACCCTGATCTACAAGGTGAA<br>GCTCCGCGGCACCAACTTCCCTCCTGACGGCCCCGTAATGCAGAAGAAGACAA<br>TGGGCTGGGAAGCGTCCACCGAGCGGTTGTACCCCGAGGACGGCGTGCTGAAG<br>GGCGACATTAAGATGGCCCTGCGCCTGAAGGACGGCGGCCGCTACCTGGCGGA |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| | CTTCAAGACCACCTACAAGGCCAAGAAGCCCGTGCAGATGCCCGGCGCCTACA<br>ACGTCGACCGCAAGTTGGACATCACCTCCCACAACGAGGACTACACCGTGGTG<br>GAACAGTACGAACGCTCCGAGGGCCGCCACTCCACCGGCGGCATGGACGAGCT<br>GTACAAG (SEQ ID NO: 192) |
| | >APD76535.1 mScarlet, partial [synthetic construct]<br>MVSKGEAVIKEFMRFKVHMEGSMNGHEFEIEGEGEGRPYEGTQTAKLKVTKGG<br>PLPFSWDILSPQFMYGSRAFTKHPADIPDYYKQSFPEGFKWERVMNFEDGGAV<br>TVTQDTSLEDGTLIYKVKLRGTNFPPDGPVMQKKTMGWEASTERLYPEDGVLK<br>GDIKMALRLKDGGRYLADFKTTYKAKKPVQMPGAYNVDRKLDITSHNEDYTVV<br>EQYERSEGRHSTGGMDELYK (SEQ ID NO: 193) |
| Nanoluciferase | >JQ513379. 1 NanoLuc reporter vector<br>pNL1.1.CMV[Nluc/CMV], complete sequence, mRNA<br>GGCCTAACTGGCCTCAATATTGGCCATTAGCCATATTATTCATTGGTTATATA<br>GCATAAATCAATATTGGCTATTGGCCATTGCATACGTTGTATCTATATCATAA<br>TATGTACATTTATATTGGCTCATGTCCAATATGACCGCCATGTTGGCATTGAT<br>TATTGACTAGTTATTAATAGTAATCAATTACGGGGTCATTAGTTCATAGCCCA<br>TATATGGAGTTCCGCGTTACATAACTTACGGTAAATGGCCCGCCTGGCTGACC<br>GCCCAACGACCCCCGCCCATTGACGTCAATAATGACGTATGTTCCCATAGTAA<br>CGCCAATAGGGACTTTCCATTGACGTCAATGGGTGGAGTATTTACGGTAAACT<br>GCCCACTTGGCAGTACATCAAGTGTATCATATGCCAAGTCCGCCCCCTATTGA<br>CGTCAATGACGGTAAATGGCCCGCCTGGCATTATGCCCAGTACATGACCTTAC<br>GGGACTTTCCTACTTGGCAGTACATCTACGTATTAGTCATCGCTATTACCATG<br>GTGATGCGGTTTTGGCAGTACACCAATGGGCGTGGATAGCGGTTTGACTCACG<br>GGGATTTCCAAGTCTCCACCCCATTGACGTCAATGGGAGTTTGTTTTGGCACC<br>AAAATCAACGGGACTTTCCAAAATGTCGTAATAACCCCGCCCCGTTGACGCAA<br>ATGGGCGGTAGGCGTGTACGGTGGGAGGTCTATATAAGCAGAGCTCGTTTAGT<br>GAACCGTCAGATCACTAGAAGCTTTATTGCGGTAGTTTATCACAGTTAAATTG<br>CTAACGCAGTCAGTGGGCCTCGGCGGCCAAGCTTGGCAATCCGGTACTGTTGG<br>TAAAGCCACC**ATGGTCTTCACACTCGAAGATTTCGTTGGGGACTGGCGACAGA**<br>**CAGCCGGCTACAACCTGGACCAAGTCCTTGAACAGGGAGGTGTGTCCAGTTTG**<br>**TTTCAGAATCTCGGGGTGTCCGTAACTCCGATCCAAAGGATTGTCCTGAGCGG**<br>**TGAAAATGGGCTGAAGATCGACATCCATGTCATCATCCCGTATGAAGGTCTGA**<br>**GCGGCGACCAAATGGGCCAGATCGAAAAAATTTTTAAGGTGGTGTACCCTGTG**<br>**GATGATCATCACTTTAAGGTGATCCTGCACTATGGCACACTGGTAATCGACGG**<br>**GGTTACGCCGAACATGATCGACTATTTCGGACGGCCGTATGAAGGCATCGCCG**<br>**TGTTCGACGGCAAAAAGATCACTGTAACAGGGACCCTGTGGAACGGCAACAAA**<br>**ATTATCGACGAGCGCCTGATCAACCCCGACGGCTCCCTGCTGTTCCGAGTAAC**<br>**CATCAACGGAGTGACCGGCTGGCGGCTGTGCGAACGCATTCTGGCGTAA**TTCT<br>AGAGTCGGGGCGGCCGGCCGCTTCGAGCAGACATGATAAGATACATTGATGAG<br>TTTGGACAAACCACAACTAGAATGCAGTGAAAAAAATGCTTTATTTGTGAAAT<br>TTGTGATGCTATTGCTTTATTTGTAACCATTATAAGCTGCAATAAACAAGTTA<br>ACAACAACAATTGCATTCATTTTATGTTTCAGGTTCAGGGGGAGGTGTGGGAG<br>GTTTTTTAAAGCAAGTAAAACCTCTACAAATGTGGTAAAATCGATAAGGATCC<br>GTCGACCGATGCCCTTGAGAGCCTTCAACCCAGTCAGCTCCTTCCGGTGGGCG<br>CGGGGCATGACTATCGTCGCCGCACTTATGACTGTCTTCTTTATCATGCAACT<br>CGTAGGACAGGTGCCGGCAGCGCTCTTCCGCTTCCTCGCTCACTGACTCGCTG<br>CGCTCGGTCGTTCGGCTGCGGCGAGCGGTATCAGCTCACTCAAAGGCGGTAAT<br>ACGGTTATCCACAGAATCAGGGGATAACGCAGGAAAGAACATGTGAGCAAAAG<br>GCCAGCAAAAGGCCAGGAACCGTAAAAAGGCCGCGTTGCTGGCGTTTTTCCAT<br>AGGCTCCGCCCCCCTGACGAGCATCACAAAAATCGACGCTCAAGTCAGAGGTG<br>GCGAAACCCGACAGGACTATAAAGATACCAGGCGTTTCCCCCTGGAAGCTCCC<br>TCGTGCGCTCTCCTGTTCCGACCCTGCCGCTTACCGGATACCTGTCCGCCTTT<br>CTCCCTTCGGGAAGCGTGGCGCTTTCTCATAGCTCACGCTGTAGGTATCTCAG<br>TTCGGTGTAGGTCGTTCGCTCCAAGCTGGGCTGTGTGCACGAACCCCCCGTTC<br>AGCCCGACCGCTGCGCCTTATCCGGTAACTATCGTCTTGAGTCCAACCCGGTA<br>AGACACGACTTATCGCCACTGGCAGCAGCCACTGGTAACAGGATTAGCAGAGC<br>GAGGTATGTAGGCGGTGCTACAGAGTTCTTGAAGTGGTGGCCTAACTACGGCT<br>ACACTAGAAGAACAGTATTTGGTATCTGCGCTCTGCTGAAGCCAGTTACCTTC<br>GGAAAAAGAGTTGGTAGCTCTTGATCCGGCAAACAAACCACCGCTGGTAGCGG<br>TGGTTTTTTTGTTTGCAAGCAGCAGATTACGCGCAGAAAAAAAGGATCTCAAG<br>AAGATCCTTTGATCTTTTCTACGGGGTCTGACGCTCAGTGGAACGAAAACTCA<br>CGTTAAGGGATTTTGGTCATGAGATTATCAAAAAGGATCTTCACCTAGATCCT<br>TTTAAATTAAAAATGAAGTTTTAAATCAATCTAAAGTATATATGAGTAAACTT<br>GGTCTGACAGCGGCCGCAAATGCTAAACCACTGCAGTGGTTACCAGTGCTTGA<br>TCAGTGAGGCACCGATCTCAGCGATCTGCCTATTTCGTTCGTCCATAGTGGCC<br>TGACTCCCCGTCGTGTAGATCACTACGATTCGTGAGGGCTTACCATCAGGCCC<br>CAGCGCAGCAATGATGCCGCGAGAGCCGCGTTCACCGGCCCCCGATTTGTCAG<br>CAATGAACCAGCCAGCAGGGAGGGCCGAGCGAAGAAGTGGTCCTGCTACTTTG<br>TCCGCCTCCATCCAGTCTATGAGCTGCTGTCGTGATGCTAGAGTAAGAAGTTC<br>GCCAGTGAGTAGTTTCCGAAGAGTTGTGGCCATTGCTACTGGCATCGTGGTAT<br>CACGCTCGTCGTTCGGTATGGCTTCGTTCAACTCTGGTTCCCAGCGGTCAAGC<br>CGGGTCACATGATCACCCATATTATGAAGAAATGCAGTCAGCTCCTTAGGGCC<br>TCCGATCGTTGTCAGAAGTAAGTTGGCCGCGGTGTTGTCGCTCATGGTAATGG |

TABLE 1-continued

| Type I Proteins of Interest Amino Acid Sequence | |
|---|---|
| Protein of Interest | Transcript Sequence (SEQ ID NO:)<br>Amino Acid Sequence (SEQ ID NO:) |
| | CAGCACTACACAATTCTCTTACCGTCATGCCATCCGTAAGATGCTTTTCCGTG ACCGGCGAGTACTCAACCAAGTCGTTTTGTGAGTAGTGTATACGGCGACCAAG CTGCTCTTGCCCGGCGTCTATACGGGACAACACCGCGCCACATAGCAGTACTT TGAAAGTGCTCATCATCGGGAATCGTTCTTCGGGGCGGAAAGACTCAAGGATC TTGCCGCTATTGAGATCCAGTTCGATATAGCCCACTCTTGCACCCAGTTGATC TTCAGCATCTTTTACTTTCACCAGCGTTTCGGGGTGTGCAAAAACAGGCAAGC AAAATGCCGCAAAGAAGGGAATGAGTGCGACACGAAAATGTTGGATGCTCATA CTCGTCCTTTTTCAATATTATTGAAGCATTTATCAGGGTTACTAGTACGTCTC TCAAGGATAAGTAAGTAATATTAAGGTACGGGAGGTATTGGACAGGCCGCAAT AAAATATCTTTATTTTCATTACATCTGTGTGTTGGTTTTTTGTGTGAATCGAT AGTACTAACATACGCTCTCCATCAAAACAAAACGAAACAAAACAAACTAGCAA AATAGGCTGTCCCCAGTGCAAGTGCAGGTGCCAGAACATTTCTCT (SEQ ID NO: 194) |
| | >AFJ15599.1 NanoLuc luciferase [NanoLuc reporter vector pNL1.1.CMV[Nluc/CMV]] MVFTLEDFVGDWRQTAGYNLDQVLEQGGVSSLFQNLGVSVTPIQRIVLSGENG LKIDIHVIIPYEGLSGDQMGQIEKIFKVVYPVDDHHFKVILHYGTLVIDGVTP NMIDYFGRPYEGIAVFDGKKITVTGTLWNGNKIIDERLINPDGSLLFRVTING VTGWRLCERILA (SEQ ID NO: 195) |

The polypeptides provided in Table 1 above are involved in a range of biological processes, including but not limited to, suppressing the adaptive arm of the immune system (e.g., PD-L1); cellular adhesion (e.g., nectin), immune activation (e.g., HVEM), and the like. The POI domains can also be used to track, purify, or identify the engineered EVs from native EVs (e.g., mScarlet and nanoluciferase). The genes, transcripts, polypeptides, variants, and fragments thereof can be used in any combination from Table 1 to be expressed by an engineered EV provided herein. In some embodiments, the POI domain is the human polypeptide. In some embodiments, the POI domain is a homologue of the human polypeptide (e.g., mouse).

In some embodiments of any of the aspects, the engineered cell or EV provided herein comprises an exogenous nucleic acid encoding one or more exogenous polypeptide(s) selected from the group consisting of: the polypeptides listed in Table 1.

In some embodiments of any of the aspects, the POI domain is PD-L1 or a fragment thereof. In some embodiments of any of the aspects, the POI domain is PD-L2 or a fragment thereof. In some embodiments of any of the aspects, the POI domain is FGL1 or a fragment thereof. In some embodiments of any of the aspects, the POI domain is 4-1BBL or a fragment thereof. In some embodiments of any of the aspects, the POI domain is CTLA or a fragment thereof.

In some embodiments of any of the aspects, the POI domain substantially binds to one or more of a target polypeptide. In some embodiments of any of the aspects, the target polypeptide is a cellular receptor. In some embodiments of any of the aspects, the target polypeptide is an immunosuppressive polypeptide. In some embodiments of any of the aspects, the target polypeptide is an immunostimulatory polypeptide. The engineered exosomes provided herein can be designed to activate, block, or modulate a given target polypeptide with the appropriate POI domain that binds to or modulates the function or expression of the target polypeptide. Non-limiting examples of target polypeptides include those listed in Table 2 (below).

TABLE 2

| Exemplary Target Polypeptides | | | |
|---|---|---|---|
| PD-1 | VISTA | LAG-3 | CD44 |
| CD80 | BTLA | CD112 | IL10RA |
| CD86 | CD160 | CD200R | IL10RB |
| CD28 | HVEM | CD200 | Tim-3 |
| ICOS | CD2 | Galectin 9 | TNFRSF25 |
| CD28H | SLAM CD150 | TIM-3 | TNFRSF6B |
| PD-Ll | CD58 | CD226 | CD113 |
| CTLA-4 | TIM-1 | CD155 | CD27 |
| 4-1BB (CD137) | TIM-4 | CD112 | CD30 |
| GITR | CD40 | DR3 | LFA-3 (CD58) |
| CD27L | CD30L | GITRL | CD40L |
| CD48 | CD244 | DcR3 | CD28H |
| LFA-3 (CD58) | CD98 | TNF Receptor Superfamily members | TNF receptor associated factor (TRAF) family members |
| Butyrophilin family members | PD-L2 | Nectin | TIM family members |
| B7/CD28 family members | SLAM family members | Nectin-like binding receptors | Collagen family proteins |
| LAIR-1 (CD305) | | | |

The EVs provided herein further comprise at least one fusion protein comprising a vesicle targeting domain. In various embodiments, the vesicle targeting domain provided herein is capable of binding or anchoring the fusion polypeptide provided herein to an extracellular vesicle, e.g., via targeting of the phospholipid bilayer membrane. In various embodiments, the vesicle targeting domain is a GPI domain (i.e., GPI linker, GPI anchor), fatty acylation site, or prenylation site. One of skill in the art can appreciate that the aforementioned refer to peptide or protein sites, wherein covalent lipid attachment supports embedding of the lipid in a cell membrane (i.e., phospholipid bilayer).

Biochemical forces that anchor EV targeting domains to the EV phospholipid bilayer may include, but are not limited to, electrostatic forces, affinity for EVs through protein-protein interactions with natively resident proteins (e.g., CD81, CD63, CD9, ALIX, TSG101. CD98, CD298, MARCKS, PTGFRN, Lactadherin (MFGe8)), association or affinity for negatively or positively curved phospholipids, association or affinity for negatively or positively charged domains of resident membrane associated proteins, etc., or the like.

Additional non-limiting examples of membrane targeting domains that can be used and their properties are further described in detail, e.g., Alberts B, Johnson A, Lewis J, et al., Molecular Biology of the Cell, 4th edition, New York: Garland Science, 2002. Membrane Proteins; Marilyn D.Resh, Fatty acylation of proteins: new insights into membrane targeting of myristoylated and palmitoylated proteins. Biochimica et Biophysica Acta (BBA)-Molecular Cell Research. Volume 1451, Issue 1, 12 Aug. 1999, Pages 1-16, doi: 10.1016/S0167-4889 (99) 00075-0; Ann Apolloni, et al., H-ras but Not K-ras Traffics to the Plasma Membrane through the Exocytic Pathway, Molecular and Cellular Biology April 2000, 20 (7) 2475-2487, doi: 10.1128/MCB.20.7.2475-2487.2000; Rosie Dawaliby et. al., Phosphatidylethanolamine Is a Key Regulator of Membrane Fluidity in Eukaryotic Cells, Membrane Biology, VOLUME 291, ISSUE 7, doi: 10.1074/jbc.M115.706523; R. J. Deschenes, Protein Palmitoylation, Encyclopedia of Biological Chemistry (Second Edition), Academic Press, 2013, Pages 645-647, ISBN 9780123786319, doi: 10.1016/B978-O-12-378630-2.00022-0; Charuta C. Palsuledesai and Mark D. Distefano, Protein Prenylation: Enzymes, Therapeutics, and Biotechnology Applications, ACS Chemical Biology 2015 10 (1), 51-62, doi: 10.1021/cb500791f; Hung M E, Leonard J N. Stabilization of exosome-targeting peptides via engineered glycosylation, J Biol Chem, 2015 Mar. 27; 290 (13): 8166-72, doi: 10.1074/jbc.M114.621383; Udenwobele Daniel Ikenna, et. al., Myristoylation: An Important Protein Modification in the Immune Response, Frontiers in Immunology, Vol: 8, 2017, doi: 10.3389/fimmu.2017.00751; Kinoshita Taroh 2020Biosynthesis and biology of mammalian GPI-anchored proteins Open Biol. 10190290, doi: 10.1098/rsob.190290, the contents of which are incorporated herein by reference in their entireties.

In some embodiments, the fusion polypeptide comprises one or more, two or more, three or more, four or more, five or more, or six or more vesicle targeting domains on the same polypeptide or nucleic acid construct encoding said polypeptide. For example, the fusion polypeptides provided herein can comprise PD-L1 and Glycosylphosphatidylinositol (GPI).

In some embodiments, the vesicle targeting domain is a prenylated protein. Prenylated proteins are proteins that have at least one prenylation site. Prenylation occurs when a 15-carbon or 20-carbon, farnesyl or geranylgeranyl isoprenoid, respectively, is covalently bound via a thioether bond to a cysteine at or near the carboxy terminus of a protein. In general, a prenylation site comprises an amino acid sequence CAAX, wherein C represents cysteine, A represents an aliphatic amino acid (glycine, alanine, valine, leucine, or isoleucine), and X represents alanine, methionine, serine, leucine, or glutamine.

In some embodiments, the vesicle targeting domain is a fatty acylated protein. Fatty acylated proteins are proteins that have been modified post-translationally by covalent attachment of one or more fatty acids, generally with a saturated fatty acid that comprises 14-carbon (e.g., myristic acid) via myristoylation or 16-carbons (e.g., palmitic acid) via palmitoylation. For example, proteins destined to become myristoylated begin with the amino acids Met-Gly-X-X-X followed by a serine or threonine at position 6 and lysine or arginine at position 7 and/or 8 wherein X can be any amino acid. The methionine is removed and a myristate is linked to the glycine via an amide bond. Palmitoylation herein means a posttranslational covalent attachment of fatty acids (e.g., palmitic acid) to cysteine (S-palmitoylation), serine and/or threonine (O-palmitoylation), and to the amino group of lysine (N-palmitoylation) of proteins.

Palmitoylated proteins may be acylated by attachment of a thioester linkage to a sulfhydryl group of cysteine, or via a palmitate linked to the amino group of an N-terminal cysteine. Palmitoylation sites may be present near the N- or C-terminus of a protein.

In some embodiments, the vesicle targeting domain is a glycosylphosphatidylinositol (GPI) anchor. A glycosylphosphatidylinositol (GPI) anchor ("GPI anchor") or "GPI sticky binder" are used interchangeably and refer to a means of stably anchoring a protein to an outer leaflet (e.g., exterior layer of a phospholipid bilayer) of a cell membrane. A GPI anchor comprises a glycan, a phosphoethanolamine linker, a phospholipid tail, and may be modified by various glycan sidechains. The glycan core comprises phosphoinositol, glucosamine, and mannose residues wherein said mannose residues may be modified for example with phosphoethanolamine or carbohydrates. The phosphoethanolamine is amide-bonded to the carboxyl terminus of a protein during the process of GPI attachment. In some embodiments, the vesicle targeting domain may have affinity to EV resident proteins, e.g., CD81, CD63, CD9, ALIX, TSG101, CD98, CD298, MARCKS, PTGFRN, Lactadherin (MFGe8).

Sticky binders can include a sequence for one or more myristoylation and/or palmitoylation (Myr/Palm) sites fused to a transmembrane domain from 4F2 (CD98). For example, the myristoylation sequence from the MARCKS protein may be modified to encode for one or more myristoylation and palmitoylation sites, wherein the modified MARCKS protein sequence is fused to a protein sequence of the transmembrane domain from 4F2 via a covalent peptide bond. A Myr/Palm followed by the 4F2 transmembrane domain can improve loading of the fusion proteins provided herein when compared with 4F2 transmembrane domain alone or Myr/Palm alone.

Non-limiting examples of vesicle targeting domains that enhance fusion polypeptide structure and function on the extracellular vesicles are provided in Table 3 (below).

TABLE 3

| Exosome Targeting Domain | |
|---|---|
| Exosome Targeting Domain/Sticky Binder | Nucleic Acid Sequence (SEQ ID NO:)<br>Amino Acid Sequence (SEQ ID NO:) |
| Human CD55 (DAF) Glycosylphosphatidylinositol (GPI) | >NM_000574.5 *Homo sapiens* CD55 molecule (Cromer blood group) (CD55), transcript variant 1, mRNA<br>CTGCTTACTGCAACTCGCTCCGGCCGCTGGGCGTAGCTGCGACTCGGCGGAGTCCCG<br>GCGGCGCGTCCTTGTTCTAACCCGGCGCGCCATGACCGTCGCGCGGCCGAGCGTGCC<br>CGCGGCGCTGCCCCTCCTCGGGGAGCTGCCCCGGCTGCTGCTGCTGGTGCTGTTGTG<br>CCTGCCGGCCGTGTGGGGTGACTGTGGCCTTCCCCCAGATGTACCTAATGCCCAGCC<br>AGCTTTGGAAGGCCGTACAAGTTTTCCCGAGGATACTGTAATAACGTACAAATGTGA |

TABLE 3-continued

Exosome Targeting Domain

| Exosome Targeting Domain/Sticky Binder | Nucleic Acid Sequence (SEQ ID NO:)<br>Amino Acid Sequence (SEQ ID NO:) |
| --- | --- |
| | AGAAAGCTTTGTGAAAATTCCTGGCGAGAAGGACTCAGTGATCTGCCTTAAGGGCAG<br>TCAATGGTCAGATATTGAAGAGTTCTGCAATCGTAGCTGCGAGGTGCCAACAAGGCT<br>AAATTCTGCATCCCTCAAACAGCCTTATATCACTCAGAATTATTTTCCAGTCGGTAC<br>TGTTGTGGAATATGAGTGCCGTCCAGGTTACAGAAGAGAACCTTCTCTATCACCAAA<br>ACTAACTTGCCTTCAGAATTTAAAATGGTCCACAGCAGTCGAATTTTGTAAAAAGAA<br>ATCATGCCCTAATCCGGGAGAAATACGAAATGGTCAGATTGATGTACCAGGTGGCAT<br>ATTATTTGGTGCAACCATCTCCTTCTCATGTAACACAGGGTACAAATTATTTGGCTC<br>GACTTCTAGTTTTTGTCTTATTTCAGGCAGCTCTGTCCAGTGGAGTGACCCGTTGCC<br>AGAGTGCAGAGAAATTTATTGTCCAGCACCACCACAAATTGACAATGGAATAATTCA<br>AGGGGAACGTGACCATTATGGATATAGACAGTCTGTAACGTATGCATGTAATAAAGG<br>ATTCACCATGATTGGAGAGCACTCTATTTATTGTACTGTGAATAATGATGAAGGAGA<br>GTGGAGTGGCCCACCACCTGAATGCAGAGGAAAATCTCTAACTTCCAAGGTCCCACC<br>AACAGTTCAGAAACCTACCACAGTAAATGTTCCAACTACAGAAGTCTCACCAACTTC<br>TCAGAAAACCACCACAAAAACCACCACACCAAATGCTCAAGCAACACGGAGTACACC<br>TGTTTCCAGGACAACCAAGCATTTTCATGAAACAACC**CCAAATAAAGGAAGTGGAAC**<br>**CACTTCAGGTACTACCCGTCTTCTATCTGGGCAGACGTGTTTCACGTTGACAGGTTT**<br>**GCTTGGGACGCTAGTAACCATGGGCTTGCTGACTTAG**CCAAAGAAGAGTTAAGAAGA<br>AAATACACACAAGTATACAGACTGTTCCTAGTTTCTTAGACTTATCTGCATATTGGA<br>TAAAATAAATGCAATTGTGCTCTTCATTTAGGATGCTTTCATTGTCTTTAAGATGTG<br>TTAGGAATGTCAACAGAGCAAGGAGAAAAAAGGCAGTCCTGGAATCACATTCTTAGC<br>ACACCTACACCTCTTGAAAATAGAACAACTTGCAGAATTGAGAGTGATTCCTTTCCT<br>AAAAGTGTAAGAAAGCATAGAGATTTGTTCGTATTTAGAATGGGATCACGAGGAAAA<br>GAGAAGGAAAGTGATTTTTTTCCACAAGATCTGTAATGTTATTTCCACTTATAAAGG<br>AAATAAAAAATGAAAAACATTATTTGGATATCAAAAGCAAATAAAAACCCAATTCAG<br>TCTCTTCTAAGCAAAATTGCTAAAGAGAGATGAACCACATTATAAAGTAATCTTTGG<br>CTGTAAGGCATTTTCATCTTTCCTTCGGGTTGGCAAAATATTTTAAAGGTAAAACAT<br>GCTGGTGAACCAGGGGTGTTGATGGTGATAAGGGAGGAATATAGAATGAAAGACTGA<br>ATCTTCCTTTGTTGCACAAATAGAGTTTGGAAAAAGCCTGTGAAAGGTGTCTTCTTT<br>GACTTAATGTCTTTAAAAGTATCCAGAGATACTACAATATTAACATAAGAAAAGATT<br>ATATATTATTTCTGAATCGAGATGTCCATAGTCAAATTTGTAAATCTTATTCTTTTG<br>TAATATTTATTTATATTTATTTATGACAGTGAACATTCTGATTTTACATGTAAAACA<br>AGAAAAGTTGAAGAAGATATGTGAAGAAAAATGTATTTTTCCTAAATAGAAATAAAT<br>GATCCCATTTTTTGGTATCATGTAGTATGTGAAATTTATTCTTAAACGTGACTACTT<br>TATTTCTAAATAAGAAATTCCCTACCTGCTTCCTACAAGCAGTTCAGAATGCCATGC<br>CTTGGTTGTCCTAGTGTGAATAATTTTCAGCTACTTTAAAATTATATTGTACTTTCT<br>CAAGCATGTCATATCCTTTCCTATTAGAGTATCTATATTACTTGTTACTGATTTACC<br>TGAAGGCAATCTGATTAATTTCTAGGTTTTTACCATATTCTTGTCATCTTGCCAATT<br>ACATTTTAAGTGTTAGACTAGACTAAGATGTACTAGTTGTATAGAATATAACTAGA<br>TTTATTATGGCAATGTTTATTTTGTCATTTTGCTTCATCTGTTTTGTTGTTGAAGTA<br>CTTTAAATTTCATACGTTCATGGCATTTCACTGTAAAGACTTTAATGTGTATTTCTT<br>AAAATAAAACTTTTTTTCCTCCTTAA (SEQ ID NO: 196)<br>>NP_000565.1 complement decay-accelerating factor isoform 1 preproprotein [*Homo sapiens*]<br>MTVARPSVPAALPLLGELPRLLLLVLLCLPAVWGDCGLPPDVPNAQPALEGRTSFPE<br>DTVITYKCEESFVKIPGEKDSVICLKGSQWSDIEEFCNRSCEVPTRLNSASLKQPYI<br>TQNYFPVGTVVEYECRPGYRREPSLSPKLTCLQNLKWSTAVEFCKKKSCPNPGEIRN<br>GQIDVPGGILFGATISFSCNTGYKLFGSTSSFCLISGSSVQWSDPLPECREIYCPAP<br>PQIDNGIIQGERDHYGYRQSVTYACNKGFTMIGEHSIYCTVNNDEGEWSGPPPECRG<br>KSLTSKVPPTVQKPTTVNVPTTEVSPTSQKTTTKTTTPNAQATRSTPVSRTTKHFHE<br>TT**PNKGSGTTSGTTRLLSGHTCFTLTGLLGTLVTMGLLT** (SEQ ID NO: 197) |
| Human CD59 Glycosylphosphatidylinositol (GPI) | >NM_203330.2 *Homo sapiens* CD59 molecule (CD59 blood group) (CD59), transcript variant 1, mRNA<br>GGGGCCGGGGGGCGGAGCCTTGCGGGCTGGAGCGAAAGAATGCGGGGGCTGA<br>GCGCAGAAGCGGCTCGAGGCTGGAAGAGGATCTTGGGCGCCGCCAGTCTCTC<br>TCTGTTGCCCAAGCTGGAGTGCAGTGGCACAGTCTTGGCTCACTGCAACCTC<br>CACCTCCTGGGTGCAAGCGATTCTCGTGTCTCAGCCTCTCAAGTAGCTGGGA<br>TTACAGTCTTTAGCACCAGTTGGTGTAGGAGTTGAGACCTACTTCACAGTAG<br>TTCTGTGGACAATCACAATGGGAATCCAAGGAGGGTCTGTCCTGTTCGGGCT<br>GCTGCTCGTCCTGGCTGTCTTCTGCCATTCAGGTCATAGCCTGCAGTGCTAC<br>AACTGTCCTAACCCAACTGCTGACTGCAAAACAGCCGTCAATTGTTCATCTG<br>ATTTTGATGCGTGTCTCATTACCAAAGCTGGGTTACAAGTGTATAACAAGTG<br>TTGGAAGTTTGAGCATTGCAATTTCAACGACGTCACAACCCGCTTGAGGGAA<br>AATGAGCTAACGTACTACTGCTGCAAGAAG**GACCTGTGTAACTTTAACGAAC**<br>**AGCTTGAAAATGGTGGGACATCCTTATCAGAGAAAACAGTTCTTCTGCTGGT**<br>**GACTCCATTTCTGGCAGCAGCCTGGAGCCTTCATCCCTAA**GTCAACACCAGG<br>AGAGCTTCTCCCAAACTCCCCGTTCCTGCGTAGTCCGCTTTCTCTTGCTGCC<br>ACATTCTAAAGGCTTGATATTTTCCAAATGGATCCTGTTGGGAAAGAATAAA<br>ATTAGCTTGAGCAACCTGGCTAAGATAGAGGGGCTCTGGGAGACTTTGAAGA<br>CCAGTCCTGTTTGCAGGGAAGCCCCACTTGAAGGAAGAAGTCTAAGAGTGAA<br>GTAGGTGTGACTTGAACTAGATTGCATGCTTCCTCCTTTGCTCTTGGGAAGA<br>CCAGCTTTGCAGTGACAGCTTGAGTGGGTTCTCTGCAGCCCTCAGATTATTT<br>TTCCTCTGGCTCCTTGGATGTAGTCAGTTAGCATCATTAGTACATCTTTGGA<br>GGGTGGGGCAGGAGTATATGAGCATCCTCTCTCACATGGAACGCTTTCATAA |

TABLE 3-continued

| Exosome Targeting Domain | |
|---|---|
| Exosome Targeting Domain/Sticky Binder | Nucleic Acid Sequence (SEQ ID NO:)<br>Amino Acid Sequence (SEQ ID NO:) |
| | ACTTCAGGGATCCCGTGTTGCCATGGAGGCATGCCAAATGTTCCATATGTGG<br>GTGTCAGTCAGGGACAACAAGATCCTTAATGCAGAGCTAGAGGACTTCTGGC<br>AGGGAAGTGGGGAAGTGTTCCAGATAGCAGGGCATGAAAACTTAGAGAGGTA<br>CAAGTGGCTGAAAATCGAGTTTTTCCTCTGTCTTTAAATTTTATATGGGCTT<br>TGTTATCTTCCACTGGAAAAGTGTAATAGCATACATCAATGGTGTGTTAAAG<br>CTATTTCCTTGCCTTTTTTTTATTGGAATGGTAGGATATCTTGGCTTTGCCA<br>CACACAGTTACAGAGTGAACACTCTACTACATGTGACTGGCAGTATTAAGTG<br>TGCTTATTTTAAATGTTACTGGTAGAAAGGCAGTTCAGGTATGTGTGTATAT<br>AGTATGAATGCAGTGGGGACACCCTTTGTGGTTACAGTTTGAGACTTCCAAA<br>GGTCATCCTTAATAACAACAGATCTGCAGGGGTATGTTTTACCATCTGCATC<br>CAGCCTCCTGCTAACTCCTAGCTGACTCAGCATAGATTGTATAAAATACCTT<br>TGTAACGGCTCTTAGCACACTCACAGATGTTTGAGGCTTTCAGAAGCTCTTC<br>TAAAAAATGATACACACCTTTCACAAGGGCAAACTTTTTCCTTTTCCCTGTG<br>TATTCTAGTGAATGAATCTCAAGATTCAGTAGACCTAATGACATTTGTATTT<br>TATGATCTTGGCTGTATTTAATGGCATAGGCTGACTTTTGCAGATGGAGGAA<br>TTTCTTGATTAATGTTGAAAAAAAACCCTTGATTATACTCTGTTGGACAAAC<br>CGAGTGCAATGAATGATGCTTTTCTGAAAATGAAATATAACAAGTGGGTGAA<br>TGTGGTTATGGCCGAAAAGGATATGCAGTATGCTTAATGGTAGCAACTGAAA<br>GAAGACATCCTGAGCAGTGCCAGCTTTCTTCTGTTGATGCCGTTCCCTGAAC<br>ATAGGAAAATAGAAACTTGCTTATCAAAACTTAGCATTACCTTGGTGCTCTG<br>TGTTCTCTGTTAGCTCAGTGTCTTTCCTTACATCAATAGGTTTTTTTTTTTT<br>TTTTTGGCCTGAGGAAGTACTGACCATGCCCACAGCCACCGGCTGAGCAAAG<br>AAGCTCATTTCATGTGAGTTCTAAGGAATGAGAAACAATTTTGATGAATTTA<br>AGCAGAAAATGAATTTCTGGGAACTTTTTTGGGGGCGGGGGGGTGGGGAATT<br>CAGCCACACTCCAGAAAGCCAGGAGTCGACAGTTTTGGAAGCCTCTCTCAGG<br>ATTGAGATTCTAGGATGAGATTGGCTTACTGCTATCTTGTGTCATGTACCCA<br>CTTTTTGGCCAGACTACACTGGGAAGAAGGTAGTCCTCTAAAGCAAAATCTG<br>AGTGCCACTAAATGGGGAGATGGGGCTGTTAAGCTGTCCAAATCAACAAGGG<br>TCATATAAATGGCCTTAAACTTTGGGGTTGCTTTCTGCAAAAAGTTGCTGTG<br>ACTCATGCCATAGACAAGGTTGAGTGCCTGGACCCAAAGGCAATACTGTAAT<br>GTAAAGACATTTATAGTACTAGGCAAACAGCACCCCAGGTACTCCAGGCCCT<br>CCTGGCTGGAGAGGGCTGTGGCAATAGAAAATTAGTGCCAACTGCAGTGAGT<br>CAGCCTAGGTTAAATAGAGAGTGTAAGAGTGCTGGACAGGAACCTCCACCCT<br>CATGTCACATTTCTTCAATGTGACCCTTCTGGCCCCTCTCCTCCTGACAGCG<br>GAACAATGACTGCCCCGATAGGTGAGGCTGGAGGAAGAATCAGTCCTGTCCT<br>TGGCAAGCTCTTCACTATGACAGTAAAGGCTCTCTGCCTGCTGCCAAGGCCT<br>GTGACTTTCTAACCTGGCCTCACGCTGGGTAAGCTTAAGGTAGAGGTGCAGG<br>ATTAGCAAGCCCACCTGGCTACCAGGCCGACAGCTACATCCTCCAACTGACC<br>CTGATCAACGAAGAGGGATTCATGTGTCTGTCTCAGTTGGTTCCAAATGAAA<br>CCAGGGAGCAGGGGAGTTAGGAATCGAACACCAGTCATGCCTACTGGCTCTC<br>TGCTCGAGAGCCAATACCCTGTGCCCTCCACTCATCTGGATTTACAGGAACT<br>GTCATAGTGTTCAGTATTGGGTGGTGATAAGCCCATTGGATTGTCCCCTTGG<br>GGGGATGAGCTAGGGGTGCAAGGAACACCTGATGAGTAGATAAGTGGAGCTC<br>ATGGTATTTCCTGAAAGATGCTAATCTATTTGCCAAACTTGGTCTTGAATGT<br>ACTGGGGGCTTCAAGGTATGGGTATATTTTTCTTGTGTCCTTGCAGTTAGCC<br>CCCATGTCTTATGTGTGTCCTGAAAAAATAAGAGCCTGCCCAAGACTTTGGG<br>CCTCTTGACAGAATTAACCACTTTTATACATCTGAGTTCTCTTGGTAAGTTC<br>TTTAGCAGTGTTCAAAGTCTACTAGCTCGCATTAGTTTCTGTTGCTGCCAAC<br>AGATCTGAACTAATGCTAACAGATCCCCCTGAGGGATTCTTGATGGGCTGAG<br>CAGCTGGCTGGAGCTAGTACTGACTGACATTCATTGTGATGAGGGCAGCTTT<br>CTGGTACAGGATTCTAAGCTCTATGTTTTATATACATTTTCATCTGTACTTG<br>CACCTCACTTTACACAAGAGGAAACTATGCAAAGTTAGCTGGATCGCTCAAG<br>GTCACTTAGGTAAGTTGGCAAGTCCATGCTTCCCACTCAGCTCCTCAGGTCA<br>GCAAGTCTACTTCTCTGCCTATTTTGTATACTCTCTTTAATATGTGCCTAGC<br>TTTGGAAAGTCTAGAATGGGTCCCTGGTGCCTTTTTACTTTGAAGAAATCAG<br>TTTCTGCCTCTTTTTGGAAAAGAAAACAAAGTGCAATTGTTTTTTACTGGAA<br>AGTTACCCAATAGCATGAGGTGAACAGGACGTAGTTAGGCCTTCCTGTAAAC<br>AGAAAATCATATCAAAACACTATCTTCCCATCTGTTTCTCAATGCCTGCTAC<br>TTCTTGTAGATATTTCATTTCAGGAGAGCAGCAGTTAAACCCGTGGATTTTG<br>TAGTTAGGAACCTGGGTTCAAACCCTCTTCCACTAATTGGCTATGTCTCTGG<br>ACAAGTTTTTTTTTTTTTTTTTTTTTAAACCCTTTCTGAACTTTCACTTTCT<br>ATGTCTACCTCAAAGAATTGTTGTGAGGCTTGAGATAATGCATTTGTAAAGG<br>GTCTGCCAGATAGGAAGATGCTAGTTATGGATTTACAAGGTTGTTAAGGCTG<br>TAAGAGTCTAAAACCTACAGTGAATCACAATGCATTTACCCCCACTGACTTG<br>GACATAAGTGAAAACTAGCCAGAAGTCTCTTTTTCAAATTACTTACAGGTTA<br>TTCAATATAAAATTTTTGTAATGGATAATCTTATTTATCTAAACTAAAGCTT<br>CCTGTTTATACACACTCCTGTTATTCTGGGATAAGATAAATGACCACAGTAC<br>CTTAATTTCTAGGTGGGTGCCTGTGATGGTTCATTGTAGGTAAGGACATTTT<br>CTCTTTTTCAGCAGCTGTGTAGGTCCAGAGCCTCTGGGAGAGGAGGGGGGTA<br>GCATGCACCCAGCAGGGGACTGAACTGGGAAACTCAAGGTTCTTTTTACTGT<br>GGGGTAGTGAGCTGCCTTTCTGTGATCGGTTTCCCTAGGGATGTTGCTGTTC<br>CCCTCCTTGCTATTCGCAGCTACATACAACGTGGCCAACCCCAGTAGGCTGA<br>TCCTATATATGATCAGTGCTGGTGCTGACTCTCAATAGCCCCACCCAAGCTG<br>GCTATAGGTTTACAGATACATTAATTAGGCAACCTAAAATATTGATGCTGGT |

TABLE 3-continued

| Exosome Targeting Domain | |
|---|---|
| Exosome Targeting Domain/Sticky Binder | Nucleic Acid Sequence (SEQ ID NO:)<br>Amino Acid Sequence (SEQ ID NO:) |
| | GTTGGTGTGACATAATGCTATGGCCAGAACTGAAACTTAGAGTTATAATTCA<br>TGTATTAGGGTTCTCCAGAGGGACAGAATTAGTAGGATATATGTATATATGA<br>AAGGGAGGTTATTAGGGAGAACTGGCTCCCACAGTTAGAAGGCGAAGTCGCA<br>CAATAGGCCGTCTGCAAGCTGGGTTAGAGAGAAGCCAGTAGTGGCTCAGCCT<br>GAGTTCAAAAACCTCAAAACTGGGGAAGCTGACAGTGCAGCCAGCCTTCAGT<br>CTGTGGCCAAAGGCCCAAGAGCCCCTGGCAACCAACCCACTGGTGCAAGTCC<br>TAGATTCCAAAGGCTGAAGAACCTGGAGTCTGATGTCCAAGAGCAGGAAGAG<br>TGGAAGAAAGCCAGAAGACTCAGCAAACAAGGTAGACAGTGTCTACCACCAT<br>AGTGGCCATACCAAAGAGGCTACCGATTCCTTCCTGCTACCTGGATCCCTGA<br>AGTTGCCCTGGTCTCTGCACCTTCTAAACCTAGTTCTTAAGAGCTTTCCATT<br>ACATGAGCTGTCTCAAAGCCCTCCAATAAATTCTCAGTGTAAGCTTCTGTTG<br>CTTGTGGACAGAAAATTCTGACAGACCTACCCTATAAGTGTTACTGTCAGGA<br>TAACATGAGAACGCACAACAGTAAGTGGTCACTAAGTGTTAGCTACGGTTAT<br>TTTGCCCAAGGTAGCATGGCTAGTTGATGCCGGTTGATGGGGCTTAAACCCA<br>GCTCCCTCATCTTCCAGGCCTCTGTACTCCCTATTCCACTAAACTACCTCTC<br>AGGTTTATTTTTTTAAATTCTTACTCTGCAAGTACATAGGACCACATTTACC<br>TGGGAAAACAAGAATAAAGGCTGCTCTGCATTTTTTAGAAACTTTTTTGAAA<br>GGGAGATGGGAATGCCTGCACCCCCAAGTCCAGACCAACACAATGGTTAATT<br>GAGATGAATAATAAAGGAAAGACTGTTCTGGGCTTCCCAGAATAGCTTGGTC<br>CTTAAATTGTGGCACAAACAACCTCCTGTCAGAGCCAGCCTCCTGCCAGGAA<br>GAGGGGTAGGAGACTAGAGGCCGTGTGTGCAGCCTTGCCCTGAAGGCTAGGG<br>TGACAATTTGGAGGCTGTCCAAACACCCTGGCCTCTAGAGCTGGCCTGTCTA<br>TTTGAAATGCCGGCTCTGATGCTAATCGGCGACCCTCAGGCAAGTTACTTAA<br>CCTTACATGCCTCAGTTTTCTCATCTGGAAAATGAGAACCCTAGGTTTAGGG<br>TTGTTAGAAAAGTTAAATGAGTTAAGACAAGTGCCTGGGACACAGTAGCCTC<br>TTGTGTGTGTTTATCATTATGTCCTCAGCAGGTCGTAGAAGCAGCTTCTCAG<br>GTGTGAGGCTGGCGCGATTATCTGGAGTGGGTTGGGTTTTCTAGGATGGACC<br>CCCTGCTGCATTTTCCTCATTCATCCACCAGGGCTTAATGGGGAATCAAGGA<br>ATCCATGTGTAACTGTATAATAACTGTAGCCACACTCCAATGACCACCTACT<br>AGTTGTCCCTGGCACTGCTTATACATATGTCCATCAAATCAATCCTATGAAG<br>TAGATACTGTCTTCATTTTATAGATCAGAGACAATTGGGGTTCAGAGAGCTG<br>ATGTGATTTTCCCAGGGTCACAGAGAGTCCCAGATTCAGGCACAACTCTTGT<br>ATTCCAAGACACAACCACTACATGTCCAAAGGCTGCCCAGAGCCACCGGGCA<br>CGGCAAATTGTGACATATCCCTAAAGAGGCTGAGCACCTGGTCAGGATCTGA<br>TGGCTGACAGTGTGTCCAGATGCAGAGCTGGAGTGGGGGAGGGGAAGGGGGG<br>CTCCTTGGGACAGAGAAGGCTTTCTGTGCTTTCTCTGAAGGGAGCAGTCTGA<br>GGACCAAGGGAACCCGGCAAACAGCACCTCAGGTACTCCAGGCCCTCCTGGC<br>TGGAGAGGGCTGTGGCAATGGAAAATTAGTGCCAACTGCAATGAGTCAGCCT<br>CGGTTAAATAGAGAGTGAAGAATGCTGGACAGGAACCTCCACCCTCATGTCA<br>CATTTCTTCAGTGTGACCCTTCTGGCCCCTCTCCTCCTGACAGCGGAACAAT<br>GACTGCCCCGATAGGTGAGGCTGGAGGAAGAATCAGTCCTGTCCTTGGCAAG<br>CTCTTCACTATGACAGTAAAGGCTCTCTGCCTGCTGCCAAGGCCTGTGACTT<br>TCTAACCTGGCCTCACGCTGGGTAAGCTTAAGGTAGAGGTGCAGGATTAGCA<br>AGCCCACCTGGCTACCAGGCCGACAGCTACATCTTTCAACTGACCCTGATCA<br>ACGAAGAGGGACTTGTGTCTCTCAGTTGGTTCCAAATGAAACCAGGGAGCAG<br>GGGCGTTAGGAAGCTCCAACAGGATGGTACTTAATGGGGCATTTGAGTGGAG<br>AGGTAGGTGACATAGTGCTTTGGAGCCCAGGGAGGGAAAGGTTCTGCTGAAG<br>TTGAATTCAAGACTGTTCTTTCATCACAAACTTGAGTTTCCTGGACATTTGT<br>TTGCAGAAACAACCGTAGGGTTTTGCCTTAACCTCGTGGGTTTATTATTACC<br>TCATAGGGACTTTGCCTCCTGACAGCAGTTTATGGGTGTTCATTGTGGCACT<br>TGAGTTTTCTTGCATACTTGTTAGAGAAACCAAGTTTGTCATCAACTTCTTA<br>TTTAACCCCCTGGCTATAACTTCATGGATTATGTTATAATTAAGCCATCCAG<br>AGTAAAATCTGTTTAGATTATCTTGGAGTAAGGGGGAAAAAATCTGTAATTT<br>TTTCTCCTCAACTAGATATATACATAAAAAATGATTGTATTGCTTCATTTAA<br>AAAATATAACGCAAAATCTCTTTTCCTTCTAAAAAAAAAAAAAAAAAA<br>(SEQ ID NO: 321)<br>>NP_976075.1 CD59 glycoprotein preproprotein [*Homo sapiens*]<br>MGIQGGSVLFGLLLVLAVFCHSGHSLQCYNCPNPTADCKTAVNCSSDFDACL<br>ITKAGLQVYNKCWKFEHCNFNDVTTRLRENELTYYCCKK**DLCNFNEQLENGG**<br>**TSLSEKTVLLLVTPFLAAAWSLHP** (SEQ ID NO: 198) |
| Human C1C2 from MFGE8 | NM_005928.4 *Homo sapiens* milk fat globule-EGF factor 8 protein (MFGE8), transcript variant 1, mRNA<br>AGAACCCCGCGGGGTCTGAGCAGCCCAGCGTGCCCATTCCAGCGCCCGCGTCCCCGC<br>AGCATGCCGCGCCCCCGCCTGCTGGCCGCGCTGTGCGGCGCGCTGCTCTGCGCCCCC<br>AGCCTCCTCGTCGCCCTGGATATCTGTTCCAAAAACCCCTGCCACAACGGTGGTTTA<br>TGCGAGGAGATTTCCCAAGAAGTGCGAGGAGATGTCTTCCCCTCGTACACCTGCACG<br>TGCCTTAAGGGCTACGCGGGCAACCACTGTGAGACGAAATGT**GTCGAGCCACTGGGC**<br>**CTGGAGAATGGGAACATTGCCAACTCACAGATCGCCGCCTCGTCTGTGCGTGTGACC**<br>**TTCTTGGGTTTGCAGCATTGGGTCCCGGAGCTGGCCCGCCTGAACCGCGCAGGCATG**<br>**GTCAATGCCTGGACACCCAGCAGCAATGACGATAACCCCTGGATCCAGGTGAACCTG**<br>**CTGCGGAGGATGTGGGTAACAGGTGTGGTGACGCAGGGTGCCAGCCGCTTGGCCAGT**<br>**CATGAGTACCTGAAGGCCTTCAAGGTGGCCTACAGCCTTAATGGACACGAATTCGAT** |

TABLE 3-continued

Exosome Targeting Domain

| Exosome Targeting Domain/Sticky Binder | Nucleic Acid Sequence (SEQ ID NO:)<br>Amino Acid Sequence (SEQ ID NO:) |
|---|---|
| | **TTCATCCATGATGTTAATAAAAAACACAAGGAGTTTGTGGGTAACTGGAACAAAAAC<br>GCGGTGCATGTCAACCTGTTTGAGACCCCTGTGGAGGCTCAGTACGTGAGATTGTAC<br>CCCACGAGCTGCCACACGGCCTGCACTCTGCGCTTTGAGCTACTGGGCTGTGAGCTG<br>AACGGATGCGCCAATCCCCTGGGCCTGAAGAATAACAGCATCCCTGACAAGCAGATC<br>ACGGCCTCCAGCAGCTACAAGACCTGGGGCTTGCATCTCTTCAGCTGGAACCCCTCC<br>TATGCACGGCTGGACAAGCAGGGCAACTTCAACGCCTGGGTTGCGGGGAGCTACGGT<br>AACGATCAGTGGCTGCAGGTGGACCTGGGCTCCTCGAAGGAGGTGACAGGCATCATC<br>ACCCAGGGGGCCCGTAACTTTGGCTCTGTCCAGTTTGTGGCATCCTACAAGGTTGCC<br>TACAGTAATGACAGTGCGAACTGGACTGAGTACCAGGACCCCAGGACTGGCAGCAGT<br>AAGATCTTCCCTGGCAACTGGGACAACCACTCCCACAAGAAGAACTTGTTTGAGACG<br>CCCATCCTGGCTCGCTATGTGCGCATCCTGCCTGTAGCCTGGCACAACCGCATCGCC<br>CTGCGCCTGGAGCTGCTGGGCTGTTAG**TGGCCACCTGCCACCCCCAGGTCTTCCTGC<br>TTTCCATGGGCCCGCTGCCTCTTGGCTTCTCAGCCCCTTTAAATCACCATAGGGCTG<br>GGGACTGGGGAAGGGGAGGGTGTTCAGAGGCAGCACCACCACACAGTCACCCCTCCC<br>TCCCTCTTTCCCACCCTCCACCTCTCACGGGCCCTGCCCCAGCCCCTAAGCCCCGTC<br>CCCTAACCCCCAGTCCTCACTGTCCTGTTTTCTTAGGCACTGAGGGATCTGAGTAGG<br>TCTGGGATGGACAGGAAAGGGCAAAGTAGGGCGTGTGGTTTCCCTGCCCCTGTCCGG<br>ACCGCCGATCCCAGGTGCGTGTGTCTCTGTCTCTCCTAGCCCCTCTCTCACACATCA<br>CATTCCCATGGTGGCCTCAAGAAAGGCCCGGAAGCGCCAGGCTGGAGATAACAGCCT<br>CTTGCCCGTCGGCCCTGCGTCGGCCCTGGGGTACCATGTGGCCACAACTGCTGTGGC<br>CCCCTGTCCCCAAGACACTTCCCCTTGTCTCCCTGGTTGCCTCTCTTGCCCCTTGTC<br>CTGAAGCCCAGCGACACAGAAGGGGGTGGGGCGGGTCTATGGGGAGAAAGGGAGCGA<br>GGTCAGAGGAGGGCATGGGTTGGCAGGGTGGGCGTTTGGGGCCCTCTATGCTGGCTT<br>TTCACCCCAGAGGACACAGGCAGCTTCCAAAATATATTTATCTTCTTCACGGGAA<br>(SEQ ID NO: 199)<br>>NP_005919.2 lactadherin isoform a preproprotein [*Homo sapiens*]<br>MPRPRLLAALCGALLCAPSLLVALDICSKNPCHNGGLCEEISQEVRGDVFPSYTCTC<br>LKGYAGNHCETKC**VEPLGLENGNIANSQIAASSVRVTFLGLQHWVPELARLNRAGMV<br>NAWTPSSNDDNPWIQVNLLRRMWVTGVVTQGASRLASHEYLKAFKVAYSLNGHEFDF<br>IHDVNKKHKEFVGNWNKNAVHVNLFETPVEAQYVRLYPTSCHTACTLRFELLGCELN<br>GCANPLGLKNNSIPDKQITASSSYKTWGLHLFSWNPSYARLDKQGNFNAWVAGSYGN<br>DQWLQVDLGSSKEVTGIITQGARNFGSVQFVASYKVAYSNDSANWTEYQDPRTGSSK<br>IFPGNWDNHSHKKNLFETPILARYVRILPVAWHNRIALRLELLGC** (SEQ ID NO: 200) |
| Human 4F2 (CD98) | >NM_002394.6 *Homo sapiens* solute carrier family 3 member 2 (SLC3A2), transcript variant 3, mRNA<br>GCATTGCGGCTTGGTTTTCTCACCCAGTGCATGTGGCAGGAGCGGTGAGATC<br>ACTGCCTCACGGCGATCCTGGACTGACGGTCACGACTGCCTACCCTCTAACC<br>CTGTTCTGAGCTGCCCCTTGCCCACACACCCCAAACCTGTGTGCAGGATCCG<br>CCTCCATGGAGCTACAGCCTCCTGAAGCCTCGATCGCCGTCGTGTCGATTCC<br>GCGCCAGTTGCCTGGCTCACATTCGGAGGCTGGTGTCCAGGGTCTCAGCGCG<br>GGGGACGACTCAGAGTTGGGGTCTCACTGTGTTGCCCAGACTGGTCTCGAAC<br>TCTTGGCCTCAGGTGATCCTCTTCCCTCAGCTTCCCAGAATGCCGAGATGAT<br>AGAGACGGGGTCTGACTGTGTTACCCAGGCTGGTCTTCAACTCTTGGCCTCA<br>AGTGATCCTCCTGCCTTAGCTTCCAAGAATGCTGAGGTTACAGGCACC**ATGA<br>GCCAGGACACCGAGGTGGATATGAAGGAGGTGGAGCTGAATGAGTTAGAGCC<br>CGAGAAGCAGCCGATGAACGCGGCGTCTGGGGCGGCCATGTCCCTGGCGGGA<br>GCCGAGAAGAATGGTCTGGTGAAGATCAAGGTGGCGGAAGACGAGGCGGAGG<br>CGGCAGCCGCGGCTAAGTTCACGGGCCTGTCCAAGGAGGAGCTGCTGAAGGT<br>GGCAGGCAGCCCCGGCTGGGTACGCACCCGCTGGGCACTGCTG**CTGCTCTTC<br>TGGCTCGGCTGGCTCGGCATGCTTGCTGGTGCCGTGGTCATAATCGTGCGAG<br>CGCCGCGTTGTCGCGAGCTACCGGCGCAGAAGTGGTGGCACACGGGCGCCCT<br>CTACCGCATCGGCGACCTTCAGGCCTTCCAGGGCCACGGCGCGGGCAACCTG<br>GCGGGTCTGAAGGGGCGTCTCGATTACCTGAGCTCTCTGAAGGTGAAGGGCC<br>TTGTGCTGGGTCCAATTCACAAGAACCAGAAGGATGATGTCGCTCAGACTGA<br>CTTGCTGCAGATCGACCCCAATTTTGGCTCCAAGGAAGATTTTGACAGTCTC<br>TTGCAATCGGCTAAAAAAAAGAGCATCCGTGTCATTCTGGACCTTACTCCCA<br>ACTACCGGGGTGAGAACTCGTGGTTCTCCACTCAGGTTGACACTGTGGCCAC<br>CAAGGTGAAGGATGCTCTGGAGTTTTGGCTGCAAGCTGGCGTGGATGGGTTC<br>CAGGTTCGGGACATAGAGAATCTGAAGGATGCATCCTCATTCTTGGCTGAGT<br>GGCAAAATATCACCAAGGGCTTCAGTGAAGACAGGCTCTTGATTGCGGGGAC<br>TAACTCCTCCGACCTTCAGCAGATCCTGAGCCTACTCGAATCCAACAAAGAC<br>TTGCTGTTGACTAGCTCATACCTGTCTGATTCTGGTTCTACTGGGGAGCATA<br>CAAAATCCCTAGTCACACAGTATTTGAATGCCACTGGCAATCGCTGGTGCAG<br>CTGGAGTTTGTCTCAGGCAAGGCTCCTGACTTCCTTCTTGCCGGCTCAACTT<br>CTCCGACTCTACCAGCTGATGCTCTTCACCCTGCCAGGGACCCCTGTTTTCA<br>GCTACGGGGATGAGATTGGCCTGGATGCAGCTGCCCTTCCTGGACAGCCTAT<br>GGAGGCTCCAGTCATGCTGTGGGATGAGTCCAGCTTCCCTGACATCCCAGGG<br>GCTGTAAGTGCCAACATGACTGTGAAGGGCCAGAGTGAAGACCCTGGCTCCC<br>TCCTTTCCTTGTTCCGGCGGCTGAGTGACCAGCGGAGTAAGGAGCGCTCCCT<br>ACTGCATGGGGACTTCCACGCGTTCTCCGCTGGGCCTGGACTCTTCTCCTAT<br>ATCCGCCACTGGGACCAGAATGAGCGTTTTCTGGTAGTGCTTAACTTTGGGG |

TABLE 3-continued

| Exosome Targeting Domain | |
|---|---|
| Exosome Targeting Domain/Sticky Binder | Nucleic Acid Sequence (SEQ ID NO:)<br>Amino Acid Sequence (SEQ ID NO:) |
| | ATGTGGGCCTCTCGGCTGGACTGCAGGCCTCCGACCTGCCTGCCAGCGCCAG<br>CCTGCCAGCCAAGGCTGACCTCCTGCTCAGCACCCAGCCAGGCCGTGAGGAG<br>GGCTCCCCTCTTGAGCTGGAACGCCTGAAACTGGAGCCTCACGAAGGGCTGC<br>TGCTCCGCTTCCCCTACGCGGCCTGACTTCAGCCTGACATGGACCCACTACC<br>CTTCTCCTTTCCTTCCCAGGCCCTTTGGCTTCTGATTTTTCTCTTTTTTAAA<br>AACAAACAAACAAACTGTTGCAGATTATGAGTGAACCCCCAAATAGGGTGTT<br>TTCTGCCTTCAAATAAAAGTCACCCCTGCATGGTGAA (SEQ ID NO: 201)<br>>NP_002385.3 4F2 cell-surface antigen heavy chain isoform c [*Homo sapiens*]<br>**MELQPPEASIAVVSIPRQLPGSHSEAGVQGLSAGDDSELGSHCVAQTGLELL**<br>**ASGDPLPSASQNAEMIETGSDCVTQAGLQLLASSDPPALASKNAEVTGTMSQ**<br>**DTEVDMKEVELNELEPEKQPMNAASGAAMSLAGAEKNGLVKIKVAEDEAEAA**<br>**AAAKFTGLSKEELLKVAGSPGWVRTRWALLLLFWLGWLGMLAGAVVIIV**RAP<br>RCRELPAQKWWHTGALYRIGDLQAFQGHGAGNLAGLKGRLDYLSSLKVKGLV<br>LGPIHKNQKDDVAQTDLLQIDPNFGSKEDFDSLLQSAKKKSIRVILDLTPNY<br>RGENSWFSTQVDTVATKVKDALEFWLQAGVDGFQVRDIENLKDASSFLAEWQ<br>NITKGFSEDRLLIAGTNSSDLQQILSLLESNKDLLLTSSYLSDSGSTGEHTK<br>SLVTQYLNATGNRWCSWSLSQARLLTSFLPAQLLRLYQLMLFTLPGTPVFSY<br>GDEIGLDAAALPGQPMEAPVMLWDESSFPDIPGAVSANMTVKGQSEDPGSLL<br>SLFRRLSDQRSKERSLLHGDFHAFSAGPGLFSYIRHWDQNERFLVVLNFGDV<br>GLSAGLQASDLPASASLPAKADLLLSTQPGREEGSPLELERLKLEPHEGLLL<br>RFPYAA (SEQ ID NO: 202) |
| Human TFR2 | >NM_003227.4 *Homo sapiens* transferrin receptor 2 (TFR2), transcript variant 1, mRNA<br>ATCGCTGGGGGACAGCCTGCAGGCTTCAGGAGGGGACACAAGC**ATGGAGCGG**<br>**CTTTGGGGTCTATTCCAGAGAGCGCAACAACTGTCCCCAAGATCCTCTCAGA**<br>**CCGTCTACCAGCGTGTGGAAGGCCCCCGGAAAGGGCACCTGGAGGAGGAAGA**<br>**GGAAGACGGGGAGGAGGGGGCGGAGACATTGGCCCACTTCTGCCCCATGGAG**<br>**CTGAGGGGCCCTGAGCCCCTGGGCTCTAGACCCAGGCAGCCAAACCTCATTC**<br>**CCTGGGCGGCAGCAGGACGGAGGGCTGCCCCCTACCTG**GTCCTGACGGCCCT<br>GCTGATCTTCACTGGGGCCTTCCTACTGGGCTACGTCGCCTTCCGAGGGTCC<br>TGCCAGGCGTGCGGAGACTCTGTGTTGGTGGTCAGTGAGGATGTCAACTATG<br>AGCCTGACCTGGATTTCCACCAGGGCAGACTCTACTGGAGCGACCTCCAGGC<br>CATGTTCCTGCAGTTCCTGGGGGAGGGGCGCCTGGAGGACACCATCAGGCAA<br>ACCAGCCTTCGGGAACGGGTGGCAGGCTCGGCCGGGATGGCCGCTCTGACTC<br>AGGACATTCGCGCGGCGCTCTCCCGCCAGAAGCTGGACCACGTGTGGACCGA<br>CACGCACTACGTGGGGCTGCAATTCCCGGATCCGGCTCACCCCAACACCCTG<br>CACTGGGTCGATGAGGCCGGGAAGGTCGGAGAGCAGCTGCCGCTGGAGGACC<br>CTGACGTCTACTGCCCCTACAGCGCCATCGGCAACGTCACGGGAGAGCTGGT<br>GTACGCCCACTACGGGCGGCCCGAAGACCTGCAGGACCTGCGGGCCAGGGGC<br>GTGGATCCAGTGGGCCGCCTGCTGCTGGTGCGCGTGGGGGTGATCAGCTTCG<br>CCCAGAAGGTGACCAATGCTCAGGACTTCGGGGCTCAAGGAGTGCTCATATA<br>CCCAGAGCCAGCGGACTTCTCCCAGGACCCACCCAAGCCAAGCCTGTCCAGC<br>CAGCAGGCAGTGTATGGACATGTGCACCTGGGAACTGGAGACCCCTACACAC<br>CTGGCTTCCCTTCCTTCAATCAAACCCAGTTCCCTCCAGTTGCATCATCAGG<br>CCTTCCCAGCATCCCAGCCCAGCCCATCAGTGCAGACATTGCCTCCCGCCTG<br>CTGAGGAAGCTCAAAGGCCCTGTGGCCCCCCAAGAATGGCAGGGGAGCCTCC<br>TAGGCTCCCCTTATCACCTGGGCCCCGGGCCACGACTGCGGCTAGTGGTCAA<br>CAATCACAGGACCTCCACCCCCATCAACAACATCTTCGGCTGCATCGAAGGC<br>CGCTCAGAGCCAGATCACTACGTTGTCATCGGGGCCCAGAGGGATGCATGGG<br>GCCCAGGAGCAGCTAAATCCGCTGTGGGGACGGCTATACTCCTGGAGCTGGT<br>GCGGACCTTTTCCTCCATGGTGAGCAACGGCTTCCGGCCCCGCAGAAGTCTC<br>CTCTTCATCAGCTGGGACGGTGGTGACTTTGGAAGCGTGGGCTCCACGGAGT<br>GGCTAGAGGGCTACCTCAGCGTGCTGCACCTCAAAGCCGTAGTGTACGTGAG<br>CCTGGACAACGCAGTGCTGGGGGATGACAAGTTTCATGCCAAGACCAGCCCC<br>CTTCTGACAAGTCTCATTGAGAGTGTCCTGAAGCAGGTGGATTCTCCCAACC<br>ACAGTGGGCAGACTCTCTATGAACAGGTGGTGTTCACCAATCCCAGCTGGGA<br>TGCTGAGGTGATCCGGCCCCTACCCATGGACAGCAGTGCCTATTCCTTCACG<br>GCCTTTGTGGGAGTCCCTGCCGTCGAGTTCTCCTTTATGGAGGACGACCAGG<br>CCTACCCATTCCTGCACACAAAGGAGGACACTTATGAGAACCTGCATAAGGT<br>GCTGCAAGGCCGCCTGCCCGCCGTGGCCCAGGCCGTGGCCCAGCTCGCAGGG<br>CAGCTCCTCATCCGGCTCAGCCACGATCGCCTGCTGCCCCTCGACTTCGGCC<br>GCTACGGGGACGTCGTCCTCAGGCACATCGGGAACCTCAACGAGTTCTCTGG<br>GGACCTCAAGGCCCGCGGGCTGACCCTGCAGTGGGTGTACTCGGCGCGGGGG<br>GACTACATCCGGGCGGCGGAAAAGCTGCGGCAGGAGATCTACAGCTCGGAGG<br>AGAGAGACGAGCGACTGACACGCATGTACAACGTGCGCATAATGCGGGTGGA<br>GTTCTACTTCCTTTCCCAGTACGTGTCGCCAGCCGACTCCCCGTTCCGCCAC<br>ATCTTCATGGGCCGTGGAGACCACACGCTGGGCGCCCTGCTGGACCACCTGC<br>GGCTGCTGCGCTCCAACAGCTCCGGGACCCCCGGGGCCACCTCCTCCACTGG<br>CTTCCAGGAGAGCCGTTTCCGGCGTCAGCTAGCCCTGCTCACCTGGACGCTG<br>CAAGGGGCAGCCAATGCGCTTAGCGGGGATGTCTGGAACATTGATAACAACT<br>TCTGAGGCCCTGGGGATCCTCACATCCCCGTCCCCCAGTCAAGAGCTCCTCT<br>GCTCCTCGCTTGAATGATTCAGGGTCAGGGAGGTGGCTCAGAGTCCACCTCT |

TABLE 3-continued

| Exosome Targeting Domain | |
|---|---|
| Exosome Targeting Domain/Sticky Binder | Nucleic Acid Sequence (SEQ ID NO:)<br>Amino Acid Sequence (SEQ ID NO:) |
| | CATTGCTGATCAATTTCTCATTACCCCTACACATCTCTCCACGGAGCCCAGA<br>CCCCAGCACAGATATCCACACACCCCAGCCCTGCAGTGTAGCTGACCCTAAT<br>GTGACGGTCATACTGTCGGTTAATCAGAGAGTAGCATCCCTTCAATCACAGC<br>CCCTTCCCCTTTCTGGGGTCCTCCATACCTAGAGACCACTCTGGGAGGTTTG<br>CTAGGCCCTGGGACCTGGCCAGCTCTGTTAGTGGGAGAGATCGCTGGCACCA<br>TAGCCTTATGGCCAACAGGTGGTCTGTGGTGAAAGGGGCGTGGAGTTTCAAT<br>ATCAATAAACCACCTGATATCAATAA (SEQ ID NO: 203)<br>>NP_003218.2 transferrin receptor protein 2 isoform 1 [*Homo sapiens*]<br>**MERLWGLFQRAQQLSPRSSQTVYQRVEGPRKGHLEEEEEDGEEGAETLAHFC**<br>**PMELRGPEPLGSRPRQPNLIPWAAAGRRAAPYLVLTALLIFTGAFLLGYVAF**<br>**RGS**CQACGDSVLVVSEDVNYEPDLDFHQGRLYWSDLQAMFLQFLGEGRLEDT<br>IRQTSLRERVAGSAGMAALTQDIRAALSRQKLDHVWTDTHYVGLQFPDPAHP<br>NTLHWVDEAGKVGEQLPLEDPDVYCPYSAIGNVTGELVYAHYGRPEDLQDLR<br>ARGVDPVGRLLLVRVGVISFAQKVTNAQDFGAQGVLIYPEPADFSQDPPKPS<br>LSSQQAVYGHVHLGTGDPYTPGFPSFNQTQFPPVASSGLPSIPAQPISADIA<br>SRLLRKLKGPVAPQEWQGSLLGSPYHLGPGPRLRLVVNNHRTSTPINNIFGC<br>IEGRSEPDHYVVIGAQRDAWGPGAAKSAVGTAILLELVRTFSSMVSNGFRPR<br>RSLLFISWDGGDFGSVGSTEWLEGYLSVLHLKAVVYVSLDNAVLGDDKFHAK<br>TSPLLTSLIESVLKQVDSPNHSGQTLYEQVVFTNPSWDAEVIRPLPMDSSAY<br>SFTAFVGVPAVEFSFMEDDQAYPFLHTKEDTYENLHKVLQGRLPAVAQAVAQ<br>LAGQLLIRLSHDRLLPLDFGRYGDVVLRHIGNLNEFSGDLKARGLTLQWVYS<br>ARGDYIRAAEKLRQEIYSSEERDERLTRMYNVRIMRVEFYFLSQYVSPADSP<br>FRHIFMGRGDHTLGALLDHLRLLRSNSSGTPGATSSTGFQESRFRRQLALLT<br>WTLQGAANALSGDVWNIDNNF<br>(SEQ ID NO: 204) |
| Human ADAM10 | >NM_001110.4 *Homo sapiens* ADAM metallopeptidase domain 10 (ADAM10), transcript variant 1, mRNA<br>GTTGCCGGCCCCTGAAGTGGAGCGAGAGGGAGGTGCTTCGCCGTTTCTCCTG<br>CCAGGGGAGGTCCCGGCTTCCCGTGGAGGCTCCGGACCAAGCCCCTTCAGCT<br>TCTCCCTCCGGATCGATGTGCTGCTGTTAACCCGTGAGGAGGCGGCGGCGGC<br>GGCAGCGGCAGCGGAAGATGGTGTTGCTGAGAGTGTTAATTCTGCTCCTCTC<br>CTGGGCGGCGGGGATGGGAGGTCAGTATGGGAATCCTTTAAATAAATATATC<br>AGACATTATGAAGGATTATCTTACAATGTGGATTCATTACACCAAAAACACC<br>AGCGTGCCAAAAGAGCAGTCTCACATGAAGACCAATTTTTACGTCTAGATTT<br>CCATGCCCATGGAAGACATTTCAACCTACGAATGAAGAGGGACACTTCCCTT<br>TTCAGTGATGAATTTAAAGTAGAAACATCAAATAAAGTACTTGATTATGATA<br>CCTCTCATATTTACACTGGACATATTTATGGTGAAGAAGGAAGTTTTAGCCA<br>TGGGTCTGTTATTGATGGAAGATTTGAAGGATTCATCCAGACTCGTGGTGGC<br>ACATTTTATGTTGAGCCAGCAGAGAGATATATTAAAGACCGAACTCTGCCAT<br>TTCACTCTGTCATTTATCATGAAGATGATATTAACTATCCCCATAAATACGG<br>TCCTCAGGGGGGCTGTGCAGATCATTCAGTATTTGAAAGAATGAGGAAATAC<br>CAGATGACTGGTGTAGAGGAAGTAACACAGATACCTCAAGAAGAACATGCTG<br>CTAATGGTCCAGAACTTCTGAGGAAAAAACGTACAACTTCAGCTGAAAAAAA<br>TACTTGTCAGCTTTATATTCAGACTGATCATTTGTTCTTTAAATATTACGGA<br>ACACGAGAAGCTGTGATTGCCCAGATATCCAGTCATGTTAAAGCGATTGATA<br>CAATTTACCAGACCACAGACTTCTCCGGAATCCGTAACATCAGTTTCATGGT<br>GAAACGCATAAGAATCAATACAACTGCTGATGAGAAGGACCCTACAAATCCT<br>TTCCGTTTCCCAAATATTGGTGTGGAGAAGTTTCTGGAATTGAATTCTGAGC<br>AGAATCATGATGACTACTGTTTGGCCTATGTCTTCACAGACCGAGATTTTGA<br>TGATGGCGTACTTGGTCTGGCTTGGGTTGGAGCACCTTCAGGAAGCTCTGGA<br>GGAATATGTGAAAAAAGTAAACTCTATTCAGATGGTAAGAAGAAGTCCTTAA<br>ACACTGGAATTATTACTGTTCAGAACTATGGGTCTCATGTACCTCCCAAAGT<br>CTCTCACATTACTTTTGCTCACGAAGTTGGACATAACTTTGGATCCCCACAT<br>GATTCTGGAACAGAGTGCACACCAGGAGAATCTAAGAATTTGGGTCAAAAAG<br>AAAATGGCAATTACATCATGTATGCAAGAGCAACATCTGGGGACAAACTTAA<br>CAACAATAAATTCTCACTCTGTAGTATTAGAAATATAAGCCAAGTTCTTGAG<br>AAGAAGAGAAACAACTGTTTTGTTGAATCTGGCCAACCTATT**TGTGGAAATG**<br>**GAATGGTAGAACAAGGTGAAGAATGTGATTGTGGCTATAGTGACCAGTGTAA**<br>**AGATGAATGCTGCTTCGATGCAAATCAACCAGAGGGAAGAAAATGCAAACTG**<br>**AAACCTGGGAAACAGTGCAGTCCAAGTCAAGGTCCTTGTTGTACAGCACAGT**<br>**GTGCATTCAAGTCAAAGTCTGAGAAGTGTCGGGATGATTCAGACTGTGCAAG**<br>**GGAAGGAATATGTAATGGCTTCACAGCTCTCTGCCCAGCATCTGACCCTAAA**<br>**CCAAACTTCACAGACTGTAATAGGCATACACAAGTGTGCATTAATGGGCAAT**<br>**GTGCAGGTTCTATCTGTGAGAAATATGGCTTAGAGGAGTGTACGTGTGCCAG**<br>**TTCTGATGGCAAAGATGATAAAGAATTATGCCATGTATGCTGTATGAAGAAA**<br>**ATGGACCCATCAACTTGTGCCAGTACAGGGTCTGTGCAGTGGAGTAGGCACT**<br>**TCAGTGGTCGAACCATCACCCTGCAACCTGGATCCCCTTGCAACGATTTTAG**<br>**AGGTTACTGTGATGTTTTCATGCGGTGCAGATTAGTAGATGCTGATGGTCCT**<br>**CTAGCTAGGCTTAAAAAAGCAATTTTTAGTCCAGAGCTCTATGAAAACATTG**<br>**CTGAATGGATTGTGGCTCATTGGTGGGCAGTATTACTTATGGGAATTGCTCT**<br>**GATCATGCTAATGGCTGGATTTATTAAGATATGCAGTGTTCATACTCCAAGT**<br>**AGTAATCCAAAGTTGCCTCCTCCTAAACCACTTCCAGGCACTTTAAAGAGGA** |

TABLE 3-continued

| Exosome Targeting Domain | |
|---|---|
| Exosome Targeting Domain/Sticky Binder | Nucleic Acid Sequence (SEQ ID NO:)<br>Amino Acid Sequence (SEQ ID NO:) |
| | **GGAGACCTCCACAGCCCATTCAGCAACCCCAGCGTCAGCGGCCCCGAGAGAG**<br>**TTATCAAATGGGACACATGAGACGC**TAACTGCAGCTTTTGCCTTGGTTCTTC<br>CTAGTGCCTACAATGGGAAAACTTCACTCCAAAGAGAAACCTATTAAGTCAT<br>CATCTCCAAACTAAACCCTCACAAGTAACAGTTGAAGAAAAAATGGCAAGAG<br>ATCATATCCTCAGACCAGGTGGAATTACTTAAATTTTAAAGCCTGAAAATTC<br>CAATTTGGGGGTGGGAGGTGGAAAAGGAACCCAATTTTCTTATGAACAGATA<br>TTTTTAACTTAATGGCACAAAGTCTTAGAATATTATTATGTGCCCCGTGTTC<br>CCTGTTCTTCGTTGCTGCATTTTCTTCACTTGCAGGCAAACTTGGCTCTCAA<br>TAAACTTTTACCACAAATTGAAATAAATATATTTTTTTCAACTGCCAATCAA<br>GGCTAGGAGGCTCGACCACCTCAACATTGGAGACATCACTTGCCAATGTACA<br>TACCTTGTTATATGCAGACATGTATTTCTTACGTACACTGTACTTCTGTGTG<br>CAATTGTAAACAGAAATTGCAATATGGATGTTTCTTTGTATTATAAAATTTT<br>TCCGCTCTTAATTAAAAATTACTGTTTAATTGACATACTCAGGATAACAGAG<br>AATGGTGGTATTCAGTGGTCCAGGATTCTGTAATGCTTTACACAGGCAGTTT<br>TGAAATGAAAATCAATTTACCTTTCTGTTACGATGGAGTTGGTTTTGATACT<br>CATTTTTTCTTTATCACATGGCTGCTACGGGCACAAGTGACTATACTGAAGA<br>ACACAGTTAAGTGTTGTGCAAACTGGACATAGCAGCACATACTACTTCAGAG<br>TTCATGATGTAGATGTCTGGTTTCTGCTTACGTCTTTTAAACTTTCTAATTC<br>AATTCCATTTTTCAATTAATAGGTGAAATTTTATTCATGCTTTGATAGAAAT<br>TATGTCAATGAAATGATTCTTTTTATTTGTAGCCTACTTATTTGTGTTTTTC<br>ATATATCTGAAATATGCTAATTATGTTTTCTGTCTGATATGGAAAAGAAAAG<br>CTGTGTCTTTATCAAAATATTTAAACGGTTTTTTCAGCATATCATCACTGAT<br>CATTGGTAACCACTAAAGATGAGTAATTTGCTTAAGTAGTAGTTAAAATTGT<br>AGATAGGCCTTCTGACATTTTTTTTCCTAAAATTTTTAACAGCATTGAAGGT<br>GAAACAGCACAATGTCCCATTCCAAATTTATTTTTGAAACAGATGTAAATAA<br>TTGGCATTTTAAAGAGAAAGCAAAAACATTTAATGTATTAACAGGCTTATTG<br>CTATGCAGGAAATAGAAGGGGCATTACAAAAATTGAAGCTTGTGACATATTT<br>ATTGCTTCTGTTTTCCAACTACATCACTTCAACTAGAAGTAAAGCTATGATT<br>TTCCTGACTTCACATAGGAGGCAAATTTAGAGAAAGTTGTAAAGATTTCTAT<br>GTTTTGGGTTTTTTTTTTTCCTTTTTTTTTTTAAGAGTATAAGGTTTACACA<br>ATCATTCTCATAATGTGACGCAAGCCAGCAAGGCCAAAAATGCTAGAGAAAA<br>TAACGGGATCTCTTCCTTGTAAACTTGTACAGTATGTGGTGACTTTTTCAAA<br>ATACAGCTTTTTGTACATGATTTAGAGACAAATTTTGTACATGAAACCCCAG<br>ATAGACTATAAATAATTCTAAACAAACAAGTAGGTAGATATGTATGTAATTG<br>CTTTTAAATCATTTAAATGCCTTTGTTTTTGGACTGTGCAAAGGTTGGAAGT<br>GGGTTTGCATTTCTAAAATGGTGACTTTTATTCTGCAAGAGTTCTTAGTAAC<br>TTCTTGAGTGTGGTAGACTTTGGAACATGTAAATTTTTTGCTTGTAATGTTA<br>TCCTGTGGTAGGATTTTGGCAGGTACACACACTGCCCTATTTTATTTTGAGT<br>CTAAGTTAAATGTTTTCTGAAAAGAGATACATGCACTGAACTCTTTCCACTG<br>CGAATCAAGATGTGGTAATATAAAAGGATCAAGACAAATGAGATCTAATACT<br>ACTGTCAGTTTTAATGTCCACTGTGTTTTATACAGTATCTTTTTTTGTTCAC<br>TTTGGAAATTTTTACTAAAAATTGCAAAAAATAAAGTATTGTGCAAAGATGT<br>AAGGTTTTTTGAAACTTGAAATGCATTAATAAATAGACGATTAAATCAACTT<br>GAAGGTTCTATACTCTTTGAACTCTGAGAACTATCACAAGAAGCTTCCCACA<br>AGGCAGTGTTTTCTTACAGTTGTCTCTTCCTACAAAAGTATAGATTATCTTT<br>ATTCTTAATACTTTGGAATCCATGTAGAAAATTTCCAGTTAGATACTCTGCG<br>TACACACAATAAACCTTTTTAAAACACCCAACTAATCTCAACTGCATTACAT<br>TGTTTCTAATCAATATTCAGTGCTTGTCTTGGTGGAAGAGGTGAGTCATTTT<br>GAAAACTTATGGTCTTGTTTTTATGTGTTTTTCAAAGTTTTGAATGCTAAGT<br>ACCTCATTTATTTTAAAAAGCCTAGTTTAATGATAAGTTTGTTTAAAATTTT<br>GAGCCATCATTTTTCTCTTCATAGCAAATAAGGAGAGAATTGACATTTCAGT<br>GTTACCTAGAAAAGGAATTGTAAGCCCAGAATAATTCCCTGCATGAGGTAAT<br>CTGCTTCAAATTCTTTTTTTAGTCAAGGTTAGCTATAAGTAATACTTGTTAA<br>ATGAGTAAATATGTAATACTTTGTGAATTACTTTGTTAATTTAGGAGCATCA<br>AATGTATATTATGTTTAGTTATTTATGAAACTCTCAATATTGATTGATTTGG<br>GTAATTATAAATTAGTTATTTTTACTTGTAATTGAATGCTTAAATTCTGTTT<br>ACAGTCCGTCCTCTCTCCCTCCATCCCTCCCTCCCCAGTTTTATAAATTCAG<br>GTACCAATTCACAAACAAAATCAGAAATAAAATAAATTTATTGACTGCTTCT<br>GGATTTAGCATTCCCTGTAGTGTCAAGCAATGTCATGCAGTTTGGGGAAGCA<br>TTTATTTAAGGAAATGACAACTTTCTCTGATCAGTCTTGTTTTGTGAGGTGT<br>CTTCAACACTTTATGCTTTGGGTACTTCGTGTTTGTCACAGTCTTAGGATAG<br>TGAAATCTGATTTGTCCAAGCGGAGCAAACTACTCGACCCTCAGTCCTTGTA<br>TTTGTCCCTGTAGTAAGACCTAATTATTATTATTTCTTAAAGATGGGATTGG<br>TGTCCTTGGCAACTATGAAATTTCGGGGCTTGTGCATGAGAAGGCATTTCTT<br>ATTAAGTATTTCTAATTGAAGGTATCAGAGTGTCAAGCATTACAAACCTGGA<br>CAGTTCACCTGGAGGAGTACAAGAAGAGATATTCATTATCCATATTTAAAGG<br>GTCAAGGTTTCCCAAAACCAGGGTGCAAGCCAGATGTAGTTTTAAAGCAGCT<br>GCCAGGGACAGTTCATCTTTAGAGAAGTCACTAAAGTTGTAAGAAATTTTAG<br>TTTCCCCAAAACCACTTTCAACTTCTTAGAAACTAGAAAGACAATTGGTTTG<br>CCCCACAGAGGACAACTTCAGTTTCAGCATCTCTCATGTTGTGTTCTTGATT<br>AAAAACAACTTCCATTTGATATACTTTTCCGTTTATTACCAGTTTAGTTTTT<br>TCACTATTGTTTCTGTATTCAACTCTTTATATGATTAGGATAGAAATTTAGC<br>CCTTCTGTTTTATATTACTATATTGTTTGTGTGTCTTAGATATATACATGTA<br>TGTACTATTTTCAGTAGAAATTCATGTATTTTATAATTGGTAAGTTCTTCAG |

TABLE 3-continued

Exosome Targeting Domain

| Exosome Targeting Domain/Sticky Binder | Nucleic Acid Sequence (SEQ ID NO:)<br>Amino Acid Sequence (SEQ ID NO:) |
|---|---|
| | AGCATCTCTTCTATAAAAAGCAACAGGATGCTAGGTAAAACGGAGCATTGAG<br>CAAAATACTGATTAGTTTTTGCTTTTTCCTGAAATCTACACTAAAGTGATAG<br>GGTGTGGGGTAATCCAACAAGGACAAGGTGAATTGAACAAGAACGAAATCTG<br>GAAGCAGATGAAGGAGTACTATTGATTGGGCAGACCCAGGGAAGTCAAATCC<br>TAAACCAGCAGTGGGAACACAACAGAATGGTGTAGTTTGCACTGGTAAGATT<br>TGGGTACCTGGCAGGGCTGGGTGCGGTGGCTCACACCTGTAATCCCAGCACT<br>TTGGGAGGCCAAGGCGGGTGGATCACTTGAGGTCAGGAGTTCGAGACCACCC<br>TGGCCAACATGGTGAAACCCCGTCTCTACTAAAAATACAGCTGGGCGTGGTG<br>GCACATGCTTGTAATCCCAGCTACTCGGGAGGCAGAGGCAGGAGATTTGCTT<br>GAACCCGGGAGGCAGAGGCAGGAGATTTGCTTGAACCCAGGAGGCAGAGGCT<br>GCAGTGAGCCGCGATTGCGCCATTGCACTCCAGCCTGGGTGACAGAGCGAGA<br>CTCTGTCTCAAAAAAAAAAAAAAAAAAAAAAAAAAAAAAAAAAAAAAAAAAA<br>AAAAATTTGAGTACCTGGCCTTTGTTACTTTTTTTCTATGTGTGTGACAAAA<br>ACATAATATGCACACTTTTGTAACCCACCTTTCTCATTTAATGGTACATTGA<br>TAATGTATATCACATTAACTACTCTAAATATTTCTGTGGATGTATGTTTTTT<br>TTTTTCTTAACCAATTTCCCATTGTTTGGACATGTAGGTTCCACATTGTTTA<br>TTATTTTAAACAATTCTAAAGAATTTTAAACAATTCTTAGGAAAATCCTCAG<br>CCTAATAATGAAATTAATTCCTAAAAGTGGAATTGTTGGGGTAAAGGTTTTT<br>TGAGGGACATTGATAAAAATTATGGTACTGTCTCCCAGATAGATGTACCAAG<br>TTATACTACCACGATTTAATATATATATATATATATATTAAATCAGAGTCCC<br>ATCCTTAGAAATCCACATATATGCAGCCACATGAATGTATTAGAAACAATAA<br>TAGAAGACTCATGCTTAATTCAGTTGATTAGCTTTAGACATAATTCAAATGC<br>AAGTCAAATTGAGTGCCCTAATTGTGGTCTCTTAAGTACCATTTTTCTTCAA<br>GGGAACCAGACTCCTTTGGATAAATCACTAATTCCACCTGTAAGAAAGAAAT<br>GTACAAGAAGAACCTAGGAAACATTGTTTTGTACCAGATCAGAAAGATTCAG<br>GAGGCACCTTAGAAGTTACCACTGGCCAAGGCTGAGATAACTTTAGCATCAG<br>CAAGGATAATATCTGCAAGAGATTGAAACTCATAGTATTGTATTTAACTCTG<br>TGAGTTAATGATGGTAGTGGACAGAATTATAGTTACCTTTGGGATACGCTTT<br>TAAAGAAATTCCAGGTAATAAGAGAAATGATAGAATTAGGATATCACCATTT<br>TACCCCCCCAACAATTTATGGATCTAGACAATAATCGCCAGTGACTGCTAAC<br>CTCACAAAGTGAGAGCAATCAGATTTTGTGCCTCCTAATGGAAGTACATATA<br>CCACCTATGAAGCAGTTCTGCCAAAAGTCACATCTCATCATGATGAAGCCTC<br>CTGATCTAACTACCCCTTCATTAGAAATACAGGGGACAGAGGGACAAATAAT<br>ATACAAGGGACTCAATCAGCAAAATCCAGACTCTGGAAAACTACAAGACATA<br>TGGTCCTGCTTCAACAACAGAAATGCAAAGAGAAAAGACAACGATGGGTTAA<br>AGGAGACTTAAGAGCTACATCTATCAAGACAATTTATGGACTTATTTGGATA<br>CTGATTTGAACAAACTGTTGAGACCATTGGAAAAATGTGAAAAGTGGATATT<br>TGATATTAAGGTTTTTAATTATTTTTAGGTGTGATAATGGTATTGTTACATT<br>TTTTAAAGGACCCCTTTTAGAGATGCAAATTGAAACACTTAAAAAATGAAAT<br>GATACGATGTATAAGTTTTTGCTTAAAAATAAGGATTGAAGTTGGCTGGTGT<br>GTGTGGATATAGTTGAAACAAGATTGGCTGTGAGTTGATAATTATTGAAGCT<br>GGGTGATGGGCACTTGGGGATTTATTATACTATTTTCTCTACCTGTGTTTAT<br>ATTTGAAATTTTTCATAGAAGTTTTAAAATGTGGCCAGTTGTGATGGCTCAT<br>ACCTGTAATCCCAACACTTTGGGAGGCCAAGGTGGGAGGATCACTTGAGCTC<br>AGGAGTTAGAGACCAGCCTGGGCAAAATAGTGAGACTCCATCTCAAAGAAAA<br>AAAAAAAGTGTTTTAAATGTGAATCAAATTCCTATAGAAGCTGATTCATTAC<br>TGTTTTTATTTTAGCAGTAATTCATGATAATGACCTGTATTCATAATGATTT<br>TCATAATGATTGTTTTAGTGGAATTAAACTTGAACCAGTCAAGCTAACATAA<br>TTATATTCTGCTCCAGTTACAATGAATAATTAATTGATTTCAACTGCTAGGG<br>TGAACTCTTGAAGCTATCAGTCATCCAGCAATCTTAGCAAGCAGGCCATTGG<br>GTCCCTGTTTGCTCTGTCTCTCTCTCTCTCTCACTGTTGAAGGGCTTAGC<br>TAACTACTTAAGTAAAATATTTGTTCTCTGTTAAACATGTCAAGGAGTATGG<br>TCAGCTTATCCACATTAAGCCTGTGTGTCCCACGTTGGAGTAAATGTTAAGT<br>AGCTCACTACAATAAACTAGATTCTTCTGCCCTCTCTTGTTTAAATGATCAT<br>GTTCCCTGGAGGTGGAAATAGATCTTTAAAAAGATATTCTGTAGTTGTTTGT<br>TCTCAGTGTAAAAAAATGAGAATAATTTGATAAGAGTGTAGGTTGTCTTATA<br>TAAAAAGTGGTTCCATTTGCATGAATTTTAGAAAAATCATTTTGGAAAAATG<br>AAGGCTATGTGGTTATACTGAACACATTAAGCAATTTTATTCTTTATTTTAA<br>ATGAATATTTTATTATCGTTTTCTTCCCTTGCCCTTTGGGTATGGGAGTTAG<br>CCTTTGTGTTTCTAAATACAACAGGCCGGTTTTTATAAATTAAGGTGTCAAT<br>ATATTCTTCATTATTTAGTTTTGTGATTGTGGTTAGTTTTCATTTTTCTTAA<br>GTATCTGCTAGTAGCATCTGTAATTAAGTGAAGTGACCTGTTAACCATTTTC<br>CTCTTTCTCCTCCTTTCCTCCTCCTTGAAACATATCAGAGCATGTTTGAAAT<br>TCTTTGGCTTTTATGGTATGCATTTGCTGATATGCATTGACCAGTTACCTTA<br>CTCACAGATACTTCTTAGGCACTTGATTGTGCCAGGGCCTTGGCTAGATGAT<br>AAGAATACAGTAGTGAACTTAACAGTTTCCCTGCCCTGGTGAAGCGTATGGT<br>CTTGTAGGTGAGATAGATATCAGATAATCATGTGAATAAATGTACAATTCCA<br>GCTGTGATACATGCTGAGGAGGAGGTTTTTGGTGATCCAAGAGCTGATCATG<br>CAGAGATAGGACTGAGAAAGGAGGGTGGGACGTTGTCACAGCTGATAATGCA<br>GAGATAGGACTGAGAAAGGAGGGTGGGACATCAGGAAGGTCAGAGAATTCCT<br>TATGAAAGTGATGCTTGAGTCAAAATATGATGGATGAAGAGAGTTTAAATAG<br>ATTACATAGAATTTTTAATAATGTCGATTGGTTATATACTGGGCACTGATAG<br>CTGATTTTTCTTTGGGGAAAGGTATGTCAGCCTAGTCATTCAGATTCCTTTA<br>TTTTTTTAAATGTTTTTTCATTTTTTGCTTTGCATTGCATTCATTTGCTGAA |

TABLE 3-continued

| Exosome Targeting Domain | |
|---|---|
| Exosome Targeting Domain/Sticky Binder | Nucleic Acid Sequence (SEQ ID NO:)<br>Amino Acid Sequence (SEQ ID NO:) |
| | GAGCTGGCTTGTACTTTGGCAGGTGTCATACTTGGTTATTCTCCTTAGGATA<br>TTGGCCCAACAATCTGGGAGTTGTGAAAGGCGCTTCGCTTTTCAGACCTGGG<br>CGTCTGTATCATGACTATCATAAATTTAGGATTAAGACACCTAGCCTCCTAC<br>CAGGATGAATGAGGTGTCCATGTGACCTGCTGTGCCCTGGAATTTTATACAT<br>CTTTCTCTCATAGCACACACCATATTACAATATAATCCTGCCTCATCTAAGC<br>CAAACTTTCGAGAGAATCATTTACACTCAGTGGCTACTTCAGCTCCCATTCA<br>CTTATCAACCTGCTGCAATTTTTCACAGCCCCCAAAGGACTGCAGTCTGTGC<br>CTTCAGGGAGCTGAGGGTCTAGCGGAAGGAAAGAAACCAGCAGTTACAGTAC<br>AGAGGGGTTTGTGTTGGAAACTCTACAAACACAGGATGCCCTGGTAGCTCAG<br>AGGAAGTGCATATCGAGCATGGTAGGTAGGTAGTGGGAAGAGCCAAGATGAC<br>TTCCCAGAGGAGAAAAGCTGGACCTGAGTTTTGGAGTTTCGGTAAAAGTTTG<br>CTCTAACTAGTCCAAGCTGCTGTCACAAGCTTTTAGAAATGATGTAACCATG<br>GGGCAGTTGACTGTCGTCATGTTCTTTGCTATTTTCATGACTCTGGATGTGC<br>TTTTCCTATTCCCTGGATTGCCCTTTCCCTCGATTCCTCTGCAGGACTGGGC<br>TTTATTAATCTCCATTTCCTTGAGCTTGGCTATAGTAGGTGTTCAATAAACA<br>TTTGTTTTGTTGTGTGCTTTGTAAATAGGCAATGAAGCTGATTTCACAAGAT<br>AGGCACAAAAGTTAGTTTCATTACAACACATTACCAACAGCTGTATTTTTAA<br>CTTTTAACATATCTCATTCTAAATCCTGTGGCAGCACAACCTCCTTCCGTCA<br>TACCTGGAGATAAATTTTCTTTCAAAATCTAATATGCACTGTATTTATAGAA<br>TATGAAACATACCGACCATGTTTTGCAAAAATGGGAAAGGCATAACTTAGCT<br>TTGGGGCATGTAAGTAACAACTCCTGATAGGAGAAGAAATGTATTCAGAAAG<br>CTCAAATTAGAAATAAAATGGGAGACTCTA (SEQ ID NO: 205)<br>>NP_001101.1 disintegrin and metalloproteinase domain-containing protein 10 isoform 1 preproprotein [*Homo sapiens*]<br>MVLLRVLILLLSWAAGMGGQYGNPLNKYIRHYEGLSYNVDSLHQKHQRAKRA<br>VSHEDQFLRLDFHAHGRHFNLRMKRDTSLFSDEFKVETSNKVLDYDTSHIYT<br>GHIYGEEGSFSHGSVIDGRFEGFIQTRGGTFYVEPAERYIKDRTLPFHSVIY<br>HEDDINYPHKYGPQGGCADHSVFERMRKYQMTGVEEVTQIPQEEHAANGPEL<br>LRKKRTTSAEKNTCQLYIQTDHLFFKYYGTREAVIAQISSHVKAIDTIYQTT<br>DFSGIRNISFMVKRIRINTTADEKDPTNPFRFPNIGVEKFLELNSEQNHDDY<br>CLAYVFTDRDFDDGVLGLAWVGAPSGSSGGICEKSKLYSDGKKKSLNTGIIT<br>VQNYGSHVPPKVSHITFAHEVGHNFGSPHDSGTECTPGESKNLGQKENGNYI<br>MYARATSGDKLNNNKFSLCSIRNISQVLEKKRNNCFVESGQPI**CGNGMVEQG**<br>**EECDCGYSDQCKDECCFDANQPEGRKCKLKPGKQCSPSQGPCCTAQCAFKSK**<br>**SEKCRDDSDCAREGICNGFTALCPASDPKPNFTDCNRHTQVCINGQCAGSIC**<br>**EKYGLEECTCASSDGKDDKELCHVCCMKKMDPSTCASTGSVQWSRHFSGRTI**<br>**TLQPGSPCNDFRGYCDVFMRCRLVDADGPLARLKKAIFSPELYENIAEWIVA**<br>**HWWAVLLMGIALIMLMAGFIKICSVHTPSSNPKLPPPKPLPGTLKRRRPPQP**<br>**IQQPQRQRPRESYQMGHMRR** (SEQ ID NO: 206) |
| Transmembrane domain 2 or transmembrane domain 3 from Human CD9 | >NM_001769.4 *Homo sapiens* CD9 molecule (CD9), transcript variant 1, mRNA<br>AGCCGCCTGCATCTGTATCCAGCGCCAGGTCCCGCCAGTCCCAGCTGCGCGC<br>GCCCCCCAGTCCCGCACCCGTTCGGCCCAGGCTAAGTTAGCCCTCACCATGC<br>CGGTCAAAGGAGGCACCAAGTGCATCAAATACCTGCTGTTCGGATTTAACTT<br>CATCTTCTGGCTTGCCGGGATTGCTGTCCTTGCCATTGGACTATGGCTCCGA<br>TTCGACTCTCAGACCAAGAGCATCTTCGAGCAAGAAACTAATAATAATAATT<br>CCAGC**TTCTACACAGGAGTCTATATTCTGATCGGAGCCGGCGCCCTCATGAT**<br>**GCTGGTGGGCTTCCTGGGCTGCTGCGGGGCTGTGCAGGAGTCCCAGTGC**ATG<br>CTGGGACTGTTCTTCGGCTTCCTCTTGGTGATATTCGCCATTGAAATAGCTG<br>CGGCCATCTGGGGATATTCCCACAAGGATGAGGTGATTAAGGAAGTCCAGGA<br>GTTTTACAAGGACACCTACAACAAGCTGAAAACCAAGGATGAGCCCCAGCGG<br>GAAACGCTGAAAGCCATCCACTATGCGTTGAACTGCTGTGGTTTGGCTGGGG<br>GCGTGGAACAGTTTATCTCAGACATCTGCCCCAAGAAGGACGTACTCGAAAC<br>CTTCACCGTGAAGTCCTGTCCTGATGCCATCAAAGAGGTCTTCGACAATAAA<br>TTCCACATCATCGGCGCAGTGGGCATCGGCATTGCCGTGGTCATGATATTTG<br>GCATGATCTTCAGTATGATCTTGTGCTGTGCTATCCGCAGGAACCGCGAGAT<br>GGTCTAGAGTCAGCTTACATCCCTGAGCAGGAAAGTTTACCCATGAAGATTG<br>GTGGGATTTTTTGTTTGTTTGTTTTGTTTTGTTTGTTGTTTGTTGTTTGTTT<br>TTTTGCCACTAATTTTAGTATTCATTCTGCATTGCTAGATAAAAGCTGAAGT<br>TACTTTATGTTTGTCTTTTAATGCTTCATTCAATATTGACATTTGTAGTTGA<br>GCGGGGGGTTTGGTTTGCTTTGGTTTATATTTTTCAGTTGTTTGTTTTTGC<br>TTGTTATATTAAGCAGAAATCCTGCAATGAAAGGTACTATATTTGCTAGACT<br>CTAGACAAGATATTGTACATAAAAGAATTTTTTTGTCTTTAAATAGATACAA<br>ATGTCTATCAACTTTAATCAAGTTGTAACTTATATTGAAGACAATTTGATAC<br>ATAATAAAAAATTATGACAATGTCCTGGA (SEQ ID NO: 207)<br>>NP_001760.1 CD9 antigen isoform 1 [*Homo sapiens*]<br>MPVKGGTKCIKYLLFGFNFIFWLAGIAVLAIGLWLRFDSQTKSIFEQETNNN<br>NSS**FYTGVYILIGAGALMMLVGFLGCCGAVQESQC**MLGLFFGFLLVIFAIEI<br>AAAIWGYSHKDEVIKEVQEFYKDTYNKLKTKDEPQRETLKAIHYALNCCGLA<br>GGVEQFISDICPKKDVLETFTVKSCPDAIKEVFDNKFHIIGAVGIGIAVVMI<br>FGMIFSMILCCAIRRNREMV (SEQ ID NO: 208) |

TABLE 3-continued

| Exosome Targeting Domain | |
|---|---|
| Exosome Targeting Domain/Sticky Binder | Nucleic Acid Sequence (SEQ ID NO:)<br>Amino Acid Sequence (SEQ ID NO:) |
| Human CD298 | >NM_001679.4 *Homo sapiens* ATPase Na+/K+ transporting subunit beta 3 (ATP1B3), mRNA<br>AGTCGGCTCGAGTACTCCCCGTAACGAGGAGGTGTTCTCGGCCGTCCCACCC<br>TTCACTGCCGTCTCCGGGCTGCGCCGCCGGAGCCGGGACGCGCCTCCGCAGC<br>CCTCGCCGCCTCCATCCCCGCGGCCGCAGCTCCTCTCGCCGTCCGCGCGCAC<br>ACCATGACGAAGAACGAGAAGAAGTCCCTCAACCAGAGCCTGGCCGAGTGGA<br>AGCTCTTCATCTACAACCCGACCACCGGAGAATTCCTGGGGCGCACCGCCAA<br>GAGCTGGGGTTTGATCTTGCTCTTCTACCTAGTTTTTTATGGGTTCCTGGCT<br>GCACTCTTCTCATTCACGATGTGGGTTATGCTTCAGACTCTCAACGATGAGG<br>TTCCAAAATACCGTGACCAGATTCCTAGCCCAGGACTCATGGTTTTTCCAAA<br>ACCAGTGACCGCATTGGAATATACATTCAGTAGGTCTGATCCAACTTCGTAT<br>GCAGGGTACATTGAAGACCTTAAGAAGTTTCTAAAACCATATACTTTAGAAG<br>AACAGAAGAACCTCACAGTCTGTCCTGATGGAGCACTTTTTGAACAGAAGGG<br>TCCAGTTTATGTTGCATGTCAGTTTCCTATTTCATTACTTCAAGCATGCAGT<br>GGTATGAATGATCCTGATTTTGGCTATTCTCAAGGAAACCCTTGTATTCTTG<br>TGAAAATGAACAGAATAATTGGATTAAAGCCTGAAGGAGTGCCAAGGATAGA<br>TTGTGTTTCAAAGAATGAAGATATACCAAATGTAGCAGTTTATCCTCATAAT<br>GGAATGATAGACTTAAAATATTTCCCATATTATGGGAAAAAACTGCATGTTG<br>GGTATCTACAGCCATTGGTTGCTGTTCAGGTCAGCTTTGCTCCTAACAACAC<br>TGGGAAAGAAGTAACAGTTGAGTGCAAGATTGATGGATCAGCCAACCTAAAA<br>AGTCAGGATGATCGTGACAAGTTTTTGGGACGAGTTATGTTCAAAATCACAG<br>CACGTGCATAGTATGAGTAGGATATCTCCACAGAGTAAATGTTGTGTTGTCT<br>GTCTTCATTTTGTAACAGCTGGACCTTCCATTCTAGAATTATGAGACCACCT<br>TGGAGAAAGGTGTGTGGTACATGACATTGGGTTACATCATAACGTGCTTCCA<br>GATCATAGTGTTCAGTGTCCTCTGAAGTAACTGCCTGTTGCCTCTGCTGCCC<br>TTTGAACCAGTGTACAGTCGCCAGATAGGGACCGGTGAACACCTGATTCCAA<br>ACATGTAGGATGGGGGTCTTGTCCTCTTTTTATGTGGTTTAATTGCCAAGTG<br>TCTAAAGCTTAATATGCCGTGCTATGTAAATATTTTATGGATATAACAACTG<br>TCATATTTTGATGTCAACAGAGTTTTAGGGATAAAATGGTACCCGGCCAACA<br>TCAAGTGACTTTATAGCTGCAAGAAATGTGGTATGTGGAGAAGTTCTGTATG<br>TGAGGAAGGAAAAAAAGAAAATAAAAGTGTGTTTGAAAAATATTATCTTGGG<br>TTCTTTGTAAAATTTATTTTTTACATGCTGAATTAGCCTCGATCTTTTTGAT<br>TAAGAGCACAAACTTTTTTTTGTAAAACATGTAAAAAAAAAAACTGGGATTA<br>ATTTTTAGTGTTGGAACTGCCTCTTATTTTAGGCTGTAGATAAAATAGCATT<br>TTTAGGTTAGCCAGTGTGACTATGCACCTAATTTTTTATGAGATTAAATTCA<br>TAAGACTTAATTTGTACAATAGTTTGTGAAATATCTTGTTACTGCTTTTATT<br>TAGCAGACTGTGGACTGTAATAAAGTATATAAATTGTGAAATATAAAAACTT<br>GGAACTTATTCAAAGCTTCAAAGCAAA (SEQ ID NO: 209)<br>>NP_001670.1 sodium/potassium-transporting ATPase subunit beta-3 [*Homo sapiens*]<br>MTKNEKKSLNQSLAEWKLFIYNPTTGEFLGRTAKSWGLILLFYLVFYGFLAA<br>LFSFTMWVMLQTLNDEVPKYRDQIPSPGLMVFPKPVTALEYTFSRSDPTSYA<br>GYIEDLKKFLKPYTLEEQKNLTVCPDGALFEQKGPVYVACQFPISLLQACSG<br>MNDPDFGYSQGNPCILVKMNRIIGLKPEGVPRIDCVSKNEDIPNVAVYPHNG<br>MIDLKYFPYYGKKLHVGYLQPLVAVQVSFAPNNTGKEVTVECKIDGSANLKS<br>QDDRDKFLGRVMFKITARA (SEQ ID NO: 210) |
| Lipid affinity tag modified from Human KRAS | >NM_004985.5 *Homo sapiens* KRAS proto-oncogene, GTPase (KRAS), transcript variant b, mRNA<br>CTAGGCGGCGGCCGCGGCGGCGGAGGCAGCAGCGGCGGCGGCAGTGGCGGCG<br>GCGAAGGTGGCGGCGGCTCGGCCAGTACTCCCGGCCCCCGCCATTTCGGACT<br>GGGAGCGAGCGCGGCGCAGGCACTGAAGGCGGCGGCGGGGCCAGAGGCTCAG<br>CGGCTCCCAGGTGCGGGAGAGAGGCCTGCTGAAAATGACTGAATATAAACTT<br>GTGGTAGTTGGAGCTGGTGGCGTAGGCAAGAGTGCCTTGACGATACAGCTAA<br>TTCAGAATCATTTTGTGGACGAATATGATCCAACAATAGAGGATTCCTACAG<br>GAAGCAAGTAGTAATTGATGGAGAAACCTGTCTCTTGGATATTCTCGACACA<br>GCAGGTCAAGAGGAGTACAGTGCAATGAGGGACCAGTACATGAGGACTGGGG<br>AGGGCTTTCTTTGTGTATTTGCCATAAATAATACTAAATCATTTGAAGATAT<br>TCACCATTATAGAGAACAAATTAAAAGAGTTAAGGACTCTGAAGATGTACCT<br>ATGGTCCTAGTAGGAAATAAATGTGATTTGCCTTCTAGAACAGTAGACACAA<br>AACAGGCTCAGGACTTAGCAAGAAGTTATGGAATTCCTTTTATTGAAACATC<br>AGCAAAGACAAGACAGGGTGTTGATGATGCCTTCTATACATTAGTTCGAGAA<br>ATTCGAAAACATAAAGAAAAGATGAGCAAAGATGGT**AAAAAGAAGAAAAAGA**<br>**AGTCAAAGACAAAGTGTGTAATTATG**TAAATACAATTTGTACTTTTTTCTTA<br>AGGCATACTAGTACAAGTGGTAATTTTTGTACATTACACTAAATTATTAGCA<br>TTTGTTTTAGCATTACCTAATTTTTTTCCTGCTCCATGCAGACTGTTAGCTT<br>TTACCTTAAATGCTTATTTTAAAATGACAGTGGAAGTTTTTTTTTCCTCTAA<br>GTGCCAGTATTCCCAGAGTTTTGGTTTTTGAACTAGCAATGCCTGTGAAAAA<br>GAAACTGAATACCTAAGATTTCTGTCTTGGGGCTTTTGGTGCATGCAGTTGA<br>TTACTTCTTATTTTTCTTACCAATTGTGAATGTTGGTGTGAAACAAATTAAT<br>GAAGCTTTTGAATCATCCCTATTCTGTGTTTTATCTAGTCACATAAATGGAT<br>TAATTACTAATTTCAGTTGAGACCTTCTAATTGGTTTTTACTGAAACATTGA<br>GGGAACACAAATTTATGGGCTTCCTGATGATGATTCTTCTAGGCATCATGTC<br>CTATAGTTTGTCATCCCTGATGAATGTAAAGTTACACTGTTCACAAGGTTT |

TABLE 3-continued

Exosome Targeting Domain

| Exosome Targeting Domain/Sticky Binder | Nucleic Acid Sequence (SEQ ID NO:) Amino Acid Sequence (SEQ ID NO:) |
|---|---|
| | TGTCTCCTTTCCACTGCTATTAGTCATGGTCACTCTCCCCAAAATATTATAT |
| | TTTTTCTATAAAAAGAAAAAAATGGAAAAAAATTACAAGGCAATGGAAACTA |
| | TTATAAGGCCATTTCCTTTTCACATTAGATAAATTACTATAAAGACTCCTAA |
| | TAGCTTTTCCTGTTAAGGCAGACCCAGTATGAAATGGGGATTATTATAGCAA |
| | CCATTTTGGGGCTATATTTACATGCTACTAAATTTTTATAATAATTGAAAAG |
| | ATTTTAACAAGTATAAAAAATTCTCATAGGAATTAAATGTAGTCTCCCTGTG |
| | TCAGACTGCTCTTTCATAGTATAACTTTAAATCTTTTCTTCAACTTGAGTCT |
| | TTGAAGATAGTTTTAATTCTGCTTGTGACATTAAAAGATTATTTGGGCCAGT |
| | TATAGCTTATTAGGTGTTGAAGAGACCAAGGTTGCAAGGCCAGGCCCTGTGT |
| | GAACCTTTGAGCTTTCATAGAGAGTTTCACAGCATGGACTGTGTCCCCACGG |
| | TCATCCAGTGTTGTCATGCATTGGTTAGTCAAAATGGGGAGGGACTAGGGCA |
| | GTTTGGATAGCTCAACAAGATACAATCTCACTCTGTGGTGGTCCTGCTGACA |
| | AATCAAGAGCATTGCTTTTGTTTCTTAAGAAAACAAACTCTTTTTTAAAAAT |
| | TACTTTTAAATATTAACTCAAAAGTTGAGATTTTGGGGTGGTGGTGTGCCAA |
| | GACATTAATTTTTTTTTTAAACAATGAAGTGAAAAAGTTTTACAATCTCTAG |
| | GTTTGGCTAGTTCTCTTAACACTGGTTAAATTAACATTGCATAAACACTTTT |
| | CAAGTCTGATCCATATTTAATAATGCTTTAAAATAAAAATAAAAACAATCCT |
| | TTTGATAAATTTAAAATGTTACTTATTTTAAAATAAATGAAGTGAGATGGCA |
| | TGGTGAGGTGAAAGTATCACTGGACTAGGAAGAAGGTGACTTAGGTTCTAGA |
| | TAGGTGTCTTTTAGGACTCTGATTTTGAGGACATCACTTACTATCCATTTCT |
| | TCATGTTAAAAGAAGTCATCTCAAACTCTTAGTTTTTTTTTTTTACAACTAT |
| | GTAATTTATATTCCATTTACATAAGGATACACTTATTTGTCAAGCTCAGCAC |
| | AATCTGTAAATTTTTAACCTATGTTACACCATCTTCAGTGCCAGTCTTGGGC |
| | AAAATTGTGCAAGAGGTGAAGTTTATATTTGAATATCCATTCTCGTTTTAGG |
| | ACTCTTCTTCCATATTAGTGTCATCTTGCCTCCCTACCTTCCACATGCCCCA |
| | TGACTTGATGCAGTTTTAATACTTGTAATTCCCCTAACCATAAGATTTACTG |
| | CTGCTGTGGATATCTCCATGAAGTTTTCCCACTGAGTCACATCAGAAATGCC |
| | CTACATCTTATTTCCTCAGGGCTCAAGAGAATCTGACAGATACCATAAAGGG |
| | ATTTGACCTAATCACTAATTTTCAGGTGGTGGCTGATGCTTTGAACATCTCT |
| | TTGCTGCCCAATCCATTAGCGACAGTAGGATTTTTCAAACCTGGTATGAATA |
| | GACAGAACCCTATCCAGTGGAAGGAGAATTTAATAAAGATAGTGCTGAAAGA |
| | ATTCCTTAGGTAATCTATAACTAGGACTACTCCTGGTAACAGTAATACATTC |
| | CATTGTTTTAGTAACCAGAAATCTTCATGCAATGAAAAATACTTTAATTCAT |
| | GAAGCTTACTTTTTTTTTTTGGTGTCAGAGTCTCGCTCTTGTCACCCAGGCT |
| | GGAATGCAGTGGCGCCATCTCAGCTCACTGCAACCTCCATCTCCCAGGTTCA |
| | AGCGATTCTCGTGCCTCGGCCTCCTGAGTAGCTGGGATTACAGGCGTGTGCC |
| | ACTACACTCAACTAATTTTTGTATTTTTAGGAGAGACGGGGTTTCACCCTGT |
| | TGGCCAGGCTGGTCTCGAACTCCTGACCTCAAGTGATTCACCCACCTTGGCC |
| | TCATAAACCTGTTTTGCAGAACTCATTTATTCAGCAAATATTTATTGAGTGC |
| | CTACCAGATGCCAGTCACCACACAAGGCACTGGGTATATGGTATCCCCAAAC |
| | AAGAGACATAATCCCGGTCCTTAGGTAGTGCTAGTGTGGTCTGTAATATCTT |
| | ACTAAGGCCTTTGGTATACGACCCAGAGATAACACGATGCGTATTTTAGTTT |
| | TGCAAAGAAGGGGTTTGGTCTCTGTGCCAGCTCTATAATTGTTTTGCTACGA |
| | TTCCACTGAAACTCTTCGATCAAGCTACTTTATGTAAATCACTTCATTGTTT |
| | TAAAGGAATAAACTTGATTATATTGTTTTTTTATTTGGCATAACTGTGATTC |
| | TTTTAGGACAATTACTGTACACATTAAGGTGTATGTCAGATATTCATATTGA |
| | CCCAAATGTGTAATATTCCAGTTTTCTCTGCATAAGTAATTAAAATATACTT |
| | AAAAATTAATAGTTTTATCTGGGTACAAATAAACAGGTGCCTGAACTAGTTC |
| | ACAGACAAGGAAACTTCTATGTAAAAATCACTATGATTTCTGAATTGCTATG |
| | TGAAACTACAGATCTTTGGAACACTGTTTAGGTAGGGTGTTAAGACTTACAC |
| | AGTACCTCGTTTCTACACAGAGAAAGAAATGGCCATACTTCAGGAACTGCAG |
| | TGCTTATGAGGGGATATTTAGGCCTCTTGAATTTTTGATGTAGATGGGCATT |
| | TTTTTAAGGTAGTGGTTAATTACCTTTATGTGAACTTTGAATGGTTTAACAA |
| | AAGATTTGTTTTTGTAGAGATTTTAAAGGGGGAGAATTCTAGAAATAAATGT |
| | TACCTAATTATTACAGCCTTAAAGACAAAAATCCTTGTTGAAGTTTTTTTAA |
| | AAAAAGCTAAATTACATAGACTTAGGCATTAACATGTTTGTGGAAGAATATA |
| | GCAGACGTATATTGTATCATTTGAGTGAATGTTCCCAAGTAGGCATTCTAGG |
| | CTCTATTTAACTGAGTCACACTGCATAGGAATTTAGAACCTAACTTTTATAG |
| | GTTATCAAAACTGTTGTCACCATTGCACAATTTTGTCCTAATATATATACATAG |
| | AAACTTTGTGGGGCATGTTAAGTTACAGTTTGCACAAGTTCATCTCATTTGT |
| | ATTCCATTGATTTTTTTTTTCTTCTAAACATTTTTTCTTCAAACAGTATATA |
| | ACTTTTTTTAGGGGATTTTTTTTTAGACAGCAAAAACTATCTGAAGATTTCC |
| | ATTTGTCAAAAAGTAATGATTTCTTGATAATTGTGTAGTAATGTTTTTTAGA |
| | ACCCAGCAGTTACCTTAAAGCTGAATTTATATTTAGTAACTTCTGTGTTAAT |
| | ACTGGATAGCATGAATTCTGCATTGAGAAACTGAATAGCTGTCATAAAATGA |
| | AACTTTCTTTCTAAAGAAAGATACTCACATGAGTTCTTGAAGAATAGTCATA |
| | ACTAGATTAAGATCTGTGTTTTAGTTTAATAGTTTGAAGTGCCTGTTTGGGA |
| | TAATGATAGGTAATTTAGATGAATTTAGGGGAAAAAAAAGTTATCTGCAGAT |
| | ATGTTGAGGGCCCATCTCTCCCCCCACACCCCCACAGAGCTAACTGGGTTAC |
| | AGTGTTTTATCCGAAAGTTTCCAATTCCACTGTCTTGTGTTTTCATGTTGAA |
| | AATACTTTTGCATTTTTCCTTTGAGTGCCAATTTCTTACTAGTACTATTTCT |
| | TAATGTAACATGTTTACCTGGAATGTATTTTAACTATTTTTGTATAGTGTAA |
| | ACTGAAACATGCACATTTTGTACATTGTGCTTTCTTTTGTGGGACATATGCA |
| | GTGTGATCCAGTTGTTTTCCATCATTTGGTTGCGCTGACCTAGGAATGTTGG |

TABLE 3-continued

| Exosome Targeting Domain | |
|---|---|
| Exosome Targeting Domain/Sticky Binder | Nucleic Acid Sequence (SEQ ID NO:)<br>Amino Acid Sequence (SEQ ID NO:) |
| | TCATATCAAACATTAAAAATGACCACTCTTTTAATTGAAATTAACTTTTAAA<br>TGTTTATAGGAGTATGTGCTGTGAAGTGATCTAAAATTTGTAATATTTTTGT<br>CATGAACTGTACTACTCCTAATTATTGTAATGTAATAAAAATAGTTACAGTG<br>AC (SEQ ID NO: 211)<br>>NP_004976.2 GTPase KRas isoform b [*Homo sapiens*]<br>MTEYKLVVVGAGGVGKSALTIQLIQNHFVDEYDPTIEDSYRKQVVIDGETCL<br>LDILDTAGQEEYSAMRDQYMRTGEGFLCVFAINNTKSFEDIHHYREQIKRVK<br>DSEDVPMVLVGNKCDLPSRTVDTKQAQDLARSYGIPFIETSAKTRQGVDDAF<br>YTLVREIRKHKEKMSKDG**KKKKKKSKTKCVIM** (SEQ ID NO: 212)<br>>Lipid affinity tag nucleotide sequence<br>AAAAAGAAGAAAAAGAAGAAGAAGACAAAGTGTGTAATTATG<br>(SEQ ID NO: 213)<br>>Lipid affinity tag peptide sequence<br>KKKKKKKKTKCVIM (SEQ ID NO: 214) |
| Myr/Palm tag modified from Human MARCKS | >NM_002356.7 *Homo sapiens* myristoylated alanine rich<br>protein kinase C substrate (MARCKS), mRNA<br>GCACTTGGGCGTTGGACCCCGCATCTTATTAGCAACCAGGGAGATTTCTCCA<br>TTTTCCTCTTGTCTACAGTGCGGCTACAAATCTGGGATTTTTTTATTACTTC<br>TTTTTTTTTCGAACTACACTTGGGCTCCTTTTTTTGTGCTCGACTTTTCCAC<br>CCTTTTTCCCTCCCTCCTGTGCTGCTGCTTTTTGATCTCTTCGACTAAAATT<br>TTTTTATCCGGAGTGTATTTAATCGGTTCTGTTCTGTCCTCTCCACCACCCC<br>CACCCCCCTCCCTCCGGTGTGTGTGCCGCTGCCGCTGTTGCCGCCGCCGCTG<br>CTGCTGCTGCTCGCCCCGTCGTTACACCAACCCGAGGCTCTTTGTTTCCCCT<br>CTTGGATCTGTTGAGTTTCTTTGTTGAAGAAGCCAGC**ATGGGTGCCCAGTTC**<br>**TCCAAGACC**GCAGCGAAGGGAGAAGCCGCCGCGGAGAGGCCTGGGGAGGCGG<br>CTGTGGCCTCGTCGCCTTCCAAAGCGAACGGACAGGAGAATGGCCACGTGAA<br>GGTAAACGGCGACGCTTCGCCCGCGGCCGCCGAGTCGGGCGCCAAGGAGGAG<br>CTGCAGGCCAACGGCAGCGCCCCGGCCGCCGACAAGGAGGAGCCCGCGGCCG<br>CCGGGAGCGGGGCGGCGTCGCCCTCCGCGGCCGAGAAAGGTGAGCCGGCCGC<br>CGCCGCTGCCCCCGAGGCCGGGGCCAGCCCGGTAGAGAAGGAGGCCCCCGCG<br>GAAGGCGAGGCTGCCGAGCCCGGCTCGCCCACGGCCGCGGAGGGAGAGGCCG<br>CGTCGGCCGCCTCCTCGACTTCTTCGCCCAAGGCCGAGGACGGGGCCACGCC<br>CTCGCCCAGCAACGAGACCCCGAAAAAAAAAAAGAAGCGCTTTTCCTTCAAG<br>AAGTCTTTCAAGCTGAGCGGCTTCTCCTTCAAGAAGAACAAGAAGGAGGCTG<br>GAGAAGGCGGTGAGGCTGAGGCGCCCGCTGCCGAAGGCGGCAAGGACGAGGC<br>CGCCGGGGGCGCAGCTGCGGCCGCCGCCGAGGCGGGCGCGGCCTCCGGGGAG<br>CAGGCAGCGGCGCCGGGCGAGGAGGCGGCAGCGGGCGAGGAGGGGGCGGCGG<br>GTGGCGACCCGCAGGAGGCCAAGCCCCAGGAGGCCGCTGTCGCGCCAGAGAA<br>GCCGCCCGCCAGCGACGAGACCAAGGCCGCCGAGGAGCCCAGCAAGGTGGAG<br>GAGAAAAAGGCCGAGGAGGCCGGGGCCAGCGCCGCCGCCTGCGAGGCCCCCT<br>CCGCCGCCGGGCCCGGCGCGCCCCCGGAGCAGGAGGCAGCCCCCGCGGAGGA<br>GCCCGCGGCCGCCGCAGCCTCGTCAGCCTGCGCAGCCCCCTCACAGGAGGCC<br>CAGCCCGAGTGCAGTCCAGAAGCCCCCCCAGCGGAGGCGGCAGAGTAAAAGA<br>GCAAGCTTTTGTGAGATAATCGAAGAACTTTTCTCCCCCGTTTGTTTGTTGG<br>AGTGGTGCCAGGTACTGGTTTTGGAGAACTTGTCTACAACCAGGGATTGATT<br>TTAAAGATGTCTTTTTTTATTTTACTTTTTTTTAAGCACCAAATTTTGTTGT<br>TTTTTTTTTTTCTCCCCTCCCCACAGATCCCATCTCAAATCATTCTGTTAAC<br>CACCATTCCAACAGGTCGAGGAGAGCTTAAACACCTTCTTCCTCTGCCTTGT<br>TTCTCTTTTATTTTTTATTTTTTCGCATCAGTATTAATGTTTTTGCATACTT<br>TGCATCTTTATTCAAAAGTGTAAACTTTCTTTGTCAATCTATGGACATGCCC<br>ATATATGAAGGAGATGGGTGGGTCAAAAAGGGATATCAAATGAAGTGATGGG<br>GTCACAATGGGGAAATTGAAGTGGTGCATAACATTGCCAAAATAGTGTGCCA<br>CTAGAAATGGTGTAAAGGCTGTCTTTTTTTTTTTTTTAAAAGAAAAGTTATT<br>ACCATGTATTTGTGAGGCAGGTTTACAACACTACAAGTCTTGAGTTAAGAA<br>GGAAAGAGGAAAAAAGAAAAAACACCAATACCCAGATTTAAAAAAAAAAAAA<br>CGATCATAGTCTTAGGAGTTCATTTAAACCATAGGAACTTTTCACTTATCTC<br>ATGTTAGCTGTACCAGTCAGTGATTAAGTAGAACTACAAGTTGTATAGGCTT<br>TATTGTTTATTGCTGGTTTATGACCTTAATAAAGTGTAATTATGTATTACCA<br>GCAGGGTGTTTTTAACTGTGACTATTGTATAAAAACAAATCTTGATATCCAG<br>AAGCACATGAAGTTTGCAACTTTCCACCCTGCCCATTTTTGTAAAACTGCAG<br>TCATCTTGGACCTTTTAAAACACAAATTTTAAACTCAACCAAGCTGTGATAA<br>GTGGAATGGTTACTGTTTATACTGTGGTATGTTTTTGATTACAGCAGATAAT<br>GCTTTCTTTTCCAGTCGTCTTTGAGAATAAAGGAAAAAAAATCTTCAGATGC<br>AATGGTTTTGTGTAGCATCTTGTCTATCATGTTTTGTAAATACTGGAGAAGC<br>TTTGACCAATTTGACTTAGAGATGGAATGTAACTTTGCTTACAAAAATTGCT<br>ATTAAACTCCTGCTTAAGGTGTTCTAATTTTCTGTGAGCACACTAAAAGCGA<br>AAAATAAATGTGAATAAAATGTACAAATTTGTTGTGTTTTTTTATGTTCTAA<br>TAATACTGAGACTTCTAGGTCTTAGGTTAATTTTTAGGAAGATCTTGCATGC<br>CATCAGGAGTAAATTTTATTGTGGTTCTTAATCTGAAGTTTTCAAGCTCTGA<br>AATTCATAATCCGCAGTGTCAGATTACGTAGAGGAAGATCTTACAACATTTC<br>CATGTCAAATCTGTTACCATTTATTGGCATTTAGTTTTCATTTAAGAATTGA<br>ACATAATTATTTTTATTGTAGCTATATAGCATGTCAGATTAAATCATTTACA<br>ACAAAAGGGGTGTGAACCTAAGACTATTTAAATGTCTTATGAGAAAATTTCA |

TABLE 3-continued

| Exosome Targeting Domain | |
|---|---|
| Exosome Targeting Domain/Sticky Binder | Nucleic Acid Sequence (SEQ ID NO:)<br>Amino Acid Sequence (SEQ ID NO:) |
| | TAAAGCCATTCTCTTGTCATTCAGGTCCAGAAACAAATTTTAAACTGAGTGA<br>GAGTCTATAGAATCCATACTGCAGATGGGTCATGAAATGTGACCAAATGTGT<br>TTCAAAAATTGATGGTGTATTACCTGCTATTGTAATTGCTTAGTGCTTGGCT<br>AATTTCCAAATTATTGCATAATATGTTCTACCTTAAGAAAACAGGTTTATGT<br>AACAAAGTAATGGTGTTGAATGGATGATGTCAGTTCATGGGCCTTTAGCATA<br>GTTTTAAGCATCCTTTTTTTTTTTTTTTTTTGAAAGTGTGTTAGCATCTTGT<br>TACTCAAAGGATAAGACAGACAATAATACTTCACTGAATCTTAATAATCTTT<br>ACTAGTTTACCTCCTCTGCTCTTTGCCACCCGATAACTGGATATCTTTTCCT<br>TCAAAGGACCCTAAACTGATTGAAATTTAAGATATGTATCAAAAACATTATT<br>TCATTTAATGCACATCTGTTTTGCTGTTTTTGAGCAGTGTGCAGTTTAGGGT<br>TCATGATAAATCATTGAACCACATGTGTAACAACTGAATGCCAAATCTTAAA<br>CTCATTAGAAAAATAACAAATTAGGTTTTGACACGCATTCTTAATTGGAATA<br>ATGGATCAAAAATAGTGGTTCATGACCTTACCAAACACCCTTGCTACTAATA<br>AAATCAAATAACACTTAGAAGGGTATGTATTTTTAGTTAGGGTTTCTTGATC<br>TTGGAGGATGTTTGAAAGTTAAAAATTGAATTTGGTAACCAAAGGACTGATT<br>TATGGGTCTTTCCTATCTTAACCAACGTTTTCTTAGTTACCTAGATGGCCAA<br>GTACAGTGCCTGGTATGTAGTAAGACTCAGTAAAAAAGTGGATTTTTAAAAA<br>TAACTCCCAAAGTGAATAGTCAAAAATCCTGTTAGCAAACTGTTATATATTG<br>CTAAGTTTGTTCTTTTAACAGCTGGAATTTATTAAGATGCATTATTTTGATT<br>TTATTCACTGCCTAAAACACTTTGGGTGGTATTGATGGAGTTGGTGGATTTT<br>CCTCCAAGTGATTAAATGAAATTTGACGTATCTTTTCATCCAAAGTTTTGTA<br>CATCATGTTTTCTAACGGAAAAAAATGTTAATATGGCTTTTTTGTATTACTA<br>AAAATAGCTTTGAGATTAAGGAAAAATAAATAACTCTTGTACAGTTCAGTAT<br>TGTCTATTAAATCTGTATTGGCAGTATGTATAATGGCATTTGCTGTGGTTAC<br>AAAATACTTCCTCTGGGTTATAATAATCATTTGATCCAATTCCTATTGCTTG<br>TAAAATAAAGTTTTACCAGTTGATATAATCAA (SEQ ID NO: 215)<br>>NP_002347.5 myristoylated alanine-rich C-kinase substrate [*Homo sapiens*]<br>**MGAQFSKT**AAKGEAAAERPGEAAVASSPSKANGQENGHVKVNGDASPAAAES<br>GAKEELQANGSAPAADKEEPAAAGSGAASPSAAEKGEPAAAAAPEAGASPVE<br>KEAPAEGEAAEPGSPTAAEGEAASAASSTSSPKAEDGATPSPSNETPKKKKK<br>RFSFKKSFKLSGFSFKKNKKEAGEGGEAEAPAAEGGKDEAAGGAAAAAAEAG<br>AASGEQAAAPGEEAAAGEEGAAGGDPQEAKPQEAAVAPEKPPASDETKAAEE<br>PSKVEEKKAEEAGASAAACEAPSAAGPGAPPEQEAAPAEEPAAAAASSACAA<br>PSQEAQPECSPEAPPAEAAE (SEQ ID NO: 216)<br>>Myr/Palm tag modified from Human MARCKS, nucleotide sequence<br>ATGGGTTGCTGTTTCTCCAAGACC (SEQ ID NO: 217)<br>>Myr/Palm tag modified from Human MARCKS, peptide sequence<br>MGCCFSKT (SEQ ID NO: 218) |

In some embodiments of any of the aspects provided herein, the fusion polypeptide further comprises a peptide linker. The linker may be flexible, rigid, or cleavable. Further, the linker can be linked directly or via another linker (e.g., a peptide of one, two, three, four, five, six, seven, eight, nine, ten or more amino acids) to the fusion polypeptides described herein. Linkers can be configured according to a specific need, e.g., based on at least one of the following characteristics. In some embodiments of any of the aspects, linkers can be configured to have a sufficient length and flexibility such that it can allow for a cleavage at a target site. In some embodiments of any of the aspects, linkers can be configured to allow multimerization of the fusion polypeptides provided herein. In some embodiments of any of the aspects, linkers can be configured to facilitate expression and purification of the fusion proteins or engineered extracellular vesicles provided herein.

In some embodiments of any of the aspects, a linker can be configured to have any length in a form of a peptide, peptidomimetic, an aptamer, a protein, a nucleic acid (e.g., DNA or RNA), or any combinations thereof. For example, in one embodiment, the linker may be a polypeptide linker such as Gly-Ser-Ser-Gly (SEQ ID NO: 319) or a variation thereof as known by one of ordinary skill in the art. In another embodiment the linker may be a protein sequence for a self-cleavable peptide. For example, 2A sequences such as P2A, E2A, F2A, and T2A code for self-cleavable peptides by inducing ribosomal slippage on the mRNA at the 2A site which prevents peptide bond formation. The slippage will result in two separate peptides after translation. This allows the expression of two separate proteins from one promoter region. Any combination of the proteins described herein may be expressed with a self-cleavable peptide as known by one of ordinary skill in the art.

In some embodiments of any of the aspects, the polypeptide linker is a non-cleavable linker. In some embodiments of any of the aspects, a linker can be a chemical linker of any length.

In some embodiments of any of the aspects, the linker is an Fc linker. An exemplary nucleic acid sequence encoding an Fc polypeptide is:

>KY053479.1 Synthetic construct Fc-adiponectin gene, complete cds (SEQ ID NO: 219)

ATGTACAGGATGCAACTCCTGTCTTGCATTGCACTAAGTCTTGCACTTGTC

ACGAACTCGATATCGGCCATGGTTAGATCTGACAAAACTCACACATGCCCA

-continued

CCGTGCCCAGCACCTGAACTCCTGGGGGGACCGTCAGTCTTCCTCTTCCCC

CCAAAACCCAAGGACACCCTCATGATCTCCCGGACCCCTGAGGTCACATGC

GTGGTGGTGGACGTGAGCCACGAAGACCCTGAGGTCAAGTTCAACTGGTAC

GTGGACGGCGTGGAGGTGCATAATGCCAAGACAAAGCCGCGGGAGGAGCAG

TACAACAGCACGTACCGTGTGGTCAGCGTCCTCACCGTCCTGCACCAGGAC

TGGCTGAATGGCAAGGAGTACAAGTGCAAGGTCTCCAACAAAGCCCTCCCA

GCCCCCATCGAGAAAACCATCTCCAAAGCCAAAGGGCAGCCCCGAGAACCA

CAGGTGTACACCCTGCCCCCATCCCGGGAGGAGATGACCAAGAACCAGGTC

AGCCTGACCTGCCTGGTCAAAGGCTTCTATCCCAGCGACATCGCCGTGGAG

TGGGAGAGCAATGGGCAGCCGGAGAACAACTACAAGACCACGCCTCCCGTG

CTGGACTCCGACGGCTCCTTCTTCCTCTACAGCAAGCTCACCGTGGACAAG

AGCAGGTGGCAGCAGGGGAACGTCTTCTCATGCTCCGTGATGCACGAGGCT

CTGCACAACCACTACACGCAGAAGAGCCTCTCCCTGTCTCCGGGTAAAGCC

AGCGGAAGTGGCGGAGGAGGCGGTCCTGGAGAAGGTGCCTATGTATACCGC

TCAGCATTCAGTGTGGGATTGGAGACTTACGTTACTATCCCCAACATGCCC

ATTCGCTTTACCAAGATCTTCTACAATCAGCAAAACCACTATGATGGCTCC

ACTGGTAAATTCCACTGCAACATTCCTGGGCTGTACTACTTTGCCTACCAC

ATCACAGTCTATATGAAGGATGTGAAGGTCAGCCTCTTCAAGAAGGACAAG

GCTATGCTCTTCACCTATGATCAGTACCAGGAAAATAATGTGGACCAGGCC

TCCGGCTCTGTGCTCCTGCATCTGGAGGTGGGCGACCAAGTCTGGCTCCAG

GTGTATGGGGAAGGAGAGCGTAATGGACTCTATGCTGATAATGACAATGAC

TCCACCTTCACAGGCTTTCTTCTCTACCATGACACCAACTCTAGAAAGCTT

CCTGGAGAAGGTGCCTATGTATACCGCTCAGCATTCAGTGTGGGATTGGAG

ACTTACGTTACTATCCCCAACATGCCCATTCGCTTTACCAAGATCTTCTAC

AATCAGCAAAACCACTATGATGGCTCCACTGGTAAATTCCACTGCAACATT

CCTGGGCTGTACTACTTTGCCTACCACATCACAGTCTATATGAAGGATGTG

AAGGTCAGCCTCTTCAAGAAGGACAAGGCTATGCTCTTCACCTATGATCAG

TACCAGGAAAATAATGTGGACCAGGCCTCCGGCTCTGTGCTCCTGCATCTG

GAGGTGGGCGACCAAGTCTGGCTCCAGGTGTATGGGGAAGGAGAGCGTAAT

GGACTCTATGCTGATAATGACAATGACTCCACCTTCACAGGCTTTCTTCTC

TACCATGACACCAACACTAGTCCTGGAGAAGGTGCCTATGTATACCGCTCA

GCATTCAGTGTGGGATTGGAGACTTACGTTACTATCCCCAACATGCCCATT

CGCTTTACCAAGATCTTCTACAATCAGCAAAACCACTATGATGGCTCCACT

GGTAAATTCCACTGCAACATTCCTGGGCTGTACTACTTTGCCTACCACATC

ACAGTCTATATGAAGGATGTGAAGGTCAGCCTCTTCAAGAAGGACAAGGCT

ATGCTCTTCACCTATGATCAGTACCAGGAAAATAATGTGGACCAGGCCTCC

GGCTCTGTGCTCCTGCATCTGGAGGTGGGCGACCAAGTCTGGCTCCAGGTG

TATGGGGAAGGAGAGCGTAATGGACTCTATGCTGATAATGACAATGACTCC

ACCTTCACAGGCTTTCTTCTCTACCATGACACCAACTAA.

The amino acid sequence of the Fc linker is:

```
>Fc Translation
                                          (SEQ ID NO: 220)
DKTHTCPPCPAPELLGGPSVFLFPPKPKDTLMISRTPEVTCVVVDVSHEDP

EVKFNWYVDGVEVHNAKTKPREEQYNSTYRVVSVLTVLHQDWLNGKEYKCK

VSNKALPAPIEKTISKAKGQPREPQVYTLPPSREEMTKNQVSLTCLVKGFY

PSDIAVEWESNGQPENNYKTTPPVLDSDGSFFLYSKLTVDKSRWQQGNVFS

CSVMHEALHNHYTQKSLSLSPGK.
```

In some embodiments of any of the aspects, the linker is a P2A peptide linker. P2A is a self-cleaving peptide sequence allowing for expression of two proteins from one promoter. In some embodiments, the P2A linker is encoded by the nucleic acid sequence: GCTACTAACTTCAGCCTGCTGAAGCAG (SEQ ID NO: 221). The amino acid sequence of P2A is ATNFSLKQAGD-VENPGP (SEQ ID NO: 222).

In some embodiments of any of the aspects, the linker provides a multimerization (e.g., dimerization) domain wherein one fusion polypeptide may connect with another fusion polypeptide at each fusion polypeptide's respective multimerization domain. Multimerization of multiple fusion polypeptides will provide multiple fusion polypeptides within close proximity to one another to one or more a target receptor on the target cell, wherein the multiple fusion peptides will enhance receptor clustering on the target cell. Clustering receptors on a target cell will result in enhanced signal transduction. Without receptor clustering a signal may be weaker or not occur all together. For example, Fc domain sequences presented herein dimerize resulting in two fusion polypeptides connected by a covalent bond via the two Fc domains on their respective fusion polypeptide. One preferred embodiment of an Fc domain is from IgG4, herein labeled 4Fc. In other embodiments Fc may be from IgG1, herein labeled Fc. In certain embodiments Fc from other immunoglobulin, (e.g., IgG2, IgG3, etc.) may be used.

Additional non-limiting examples of linkers that can be used and their properties are further described in detail, e.g., in Chen X, Zaro J L, Shen W C. Fusion protein linkers: property, design and functionality. *Adv Drug Deliv Rev.* 2013; 65 (10): 1357-1369. doi: 10.1016/j.addr.2012.09.039; O'Shea E K, Lumb K J, Kim P S. Peptide 'Velcro': design of a heterodimeric coiled coil. Curr Biol. 1993 Oct. 1; 3 (10): 658-67. doi: 10.1016/0960-9822 (93) 90063-t. PMID: 15335856; and Müller K M, Arndt K M, Alber T. Protein fusions to coiled-coil domains. Methods Enzymol. 2000; 328:261-82. doi: 10.1016/s0076-6879 (00) 28402-4. PMID: 11075350, the contents of which are incorporated herein by reference in their entireties.

The engineered extracellular vesicle compositions provided herein can comprise variations in the configuration of the POI domain, linkers, and/or vesicle targeting domain. The specific combination and localization of these domains can enhance fusion polypeptide anchoring, function, or therapeutic effect, e.g., modulating inflammation.

Thus, in one aspect, provided herein is an engineered extracellular vesicle comprising: at least one fusion polypeptide comprising: (i) at least one protein of interest (POI) domain or a fragment thereof; and (ii) at least one vesicle targeting domain, wherein the POI domain is in an extracellular position relative to a lipid membrane of the extracellular vesicle.

In some embodiments, the POI domain or a fragment thereof is a N-terminal domain of the fusion polypeptide. In some embodiments, the vesicle targeting domain or a fragment thereof is a C-terminal domain of the fusion polypeptide.

In another aspect, provided herein is an engineered extracellular vesicle comprising: at least one fusion polypeptide comprising: (i) at least one protein of interest (POI) domain or a fragment thereof; and (ii) at least one vesicle targeting domain, wherein the POI domain is in an extracellular position relative to a lipid membrane of the extracellular vesicle, and wherein the vesicle targeting domain is a transmembrane domain relative to a lipid membrane of the extracellular vesicle.

In some embodiments, the POI domain or a fragment thereof is a C-terminal domain of the fusion polypeptide. In some embodiments, the vesicle targeting domain or a fragment thereof is a N-terminal domain of the fusion polypeptide. In some embodiments, the vesicle targeting domain is in a luminal position relative to the lipid membrane of the extracellular vesicle.

In some embodiments, the linker is in an exterior position relative to the lipid membrane of the extracellular vesicle. In some embodiments, the linker is a transmembrane linker. In some embodiments, the linker is in a luminal position relative to the lipid membrane of the extracellular vesicle.

The engineered extracellular vesicle compositions provided herein can comprise one or more of the following fusion polypeptide sequences in Table 4.

TABLE 4

Full Length Constructs

| Fusion Polypeptide | Nucleic Acid Sequence (SEQ ID NO:)<br>Amino Acid Sequence (SEQ ID NO:) |
|---|---|
| hCTLA4-Fc-GPI | >Artificial sequence; **hCTLA4**-Fc-*GPI*, DNA<br>**ATGGCTTGCCTTGGATTTCAGCGGCACAAGGCTCAGCTGAACCTGGCTACCAGGACC**<br>**TGGCCCTGCACTCTCCTGTTTTTCTTCTCTTCATCCCTGTCTTCTGCAAAGCAATG**<br>**CACGTGGCCCAGCCTGCTGTGGTACTGGCCAGCAGCCGAGGCATCGCCAGCTTTGTG**<br>**TGTGAGTATGCATCTCCAGGCAAAGCCACTGAGGTCCGGGTGACAGTGCTTCGGCAG**<br>**GCTGACAGCCAGGTGACTGAAGTCTGTGCGGCAACCTACATGATGGGGAATGAGTTG**<br>**ACCTTCCTAGATGATTCCATCTGCACGGGCACCTCCAGTGGAAATCAAGTGAACCTC**<br>**ACTATCCAAGGACTGAGGGCCATGGACACGGGACTCTACATCTGCAAGGTGGAGCTC**<br>**ATGTACCCACCGCCATACTACCTGGGCATAGGCAACGGAACCCAGATTTATGTAATT**<br>**GATCCAGAACCGTGCCCAGATTCTGAC**ATCGATGACAAAACTCACACATGCCCACCG<br>TGCCCAGCACCTGAACTCCTGGGGGGACCGTCAGTCTTCCTCTTCCCCCCAAAACCC<br>AAGGACACCCTCATGATCTCCCGGACCCCTGAGGTCACATGCGTGGTGGTGGACGTG<br>AGCCACGAAGACCCTGAGGTCAAGTTCAACTGGTACGTGGACGGCGTGGAGGTGCAT<br>AATGCCAAGACAAAGCCGCGGGAGGAGCAGTACAACAGCACGTACCGTGTGGTCAGC<br>GTCCTCACCGTCCTGCACCAGGACTGGCTGAATGGCAAGGAGTACAAGTGCAAGGTC<br>TCCAACAAAGCCCTCCCAGCCCCCATCGAGAAAACCATCTCCAAAGCCAAAGGGCAG<br>CCCCGAGAACCACAGGTGTACACCCTGCCCCCATCCCGGGAGGAGATGACCAAGAAC<br>CAGGTCAGCCTGACCTGCCTGGTCAAAGGCTTCTATCCCAGCGACATCGCCGTGGAG<br>TGGGAGAGCAATGGGCAGCCGGAGAACAACTACAAGACCACGCCTCCCGTGCTGGAC<br>TCCGACGGCTCCTTCTTCCTCTACAGCAAGCTCACCGTGGACAAGAGCAGGTGGCAG<br>CAGGGGAACGTCTTCTCATGCTCCGTGATGCACGAGGCTCTGCACAACCACTACACG<br>CAGAAGAGCCTCTCCCTGTCTCCGGGTAAAATCGAT*CCAAATAAAGGAAGTGGAACC*<br>*ACTTCAGGTACTACCCGTCTTCTATCTGGGCACACGTGTTTCACGTTGACAGGTTTG*<br>*CTTGGGACGCTAGTAACCATGGGCTTGCTGACTTAG*<br>(SEQ ID NO: 223)<br>> Artificial sequence; **hCTLA4**-Fc-*GPI*, Amino Acid<br>**MACLGFQRHKAQLNLATRTWPCTLLFFLLFIPVFCKAMHVAQPAVVLASSRGIASFV**<br>**CEYASPGKATEVRVTVLRQADSQVTEVCAATYMMGNELTFLDDSICTGTSSGNQVNL**<br>**TIQGLRAMDTGLYICKVELMYPPPYYLGIGNGTQIYVIDPEPCPDSD**IDDKTHTCPP<br>CPAPELLGGPSVFLFPPKPKDTLMISRTPEVTCVVVDVSHEDPEVKFNWYVDGVEVH<br>NAKTKPREEQYNSTYRVVSVLTVLHQDWLNGKEYKCKVSNKALPAPIEKTISKAKGQ<br>PREPQVYTLPPSREEMTKNQVSLTCLVKGFYPSDIAVEWESNGQPENNYKTTPPVLD<br>SDGSFFLYSKLTVDKSRWQQGNVFSCSVMHEALHNHYTQKSLSLSPGKID*PNKGSGT*<br>*TSGTTRLLSGHTCFTLTGLLGTLVTMGLLT*<br>(SEQ ID NO: 224) |
| hPDL1-GPI | > Artificial sequence; **hPDL1**-*GPI*, DNA<br>**ATGAGGATATTTGCTGTCTTTATATTCATGACCTACTGGCATTTGCTGAACGCATTT**<br>**ACTGTCACGGTTCCCAAGGACCTATATGTGGTAGAGTATGGTAGCAATATGACAATT**<br>**GAATGCAAATTCCCAGTAGAAAAACAATTAGACCTGGCTGCACTAATTGTCTATTGG**<br>**GAAATGGAGGATAAGAACATTATTCAATTTGTGCATGGAGAGGAAGACCTGAAGGTT**<br>**CAGCATAGTAGCTACAGACAGAGGGCCCGGCTGTTGAAGGACCAGCTCTCCCTGGGA**<br>**AATGCTGCACTTCAGATCACAGATGTGAAATTGCAGGATGCAGGGGTGTACCGCTGC**<br>**ATGATCAGCTATGGTGGTGCCGACTACAAGCGAATTACTGTGAAAGTCAATGCCCCA**<br>**TACAACAAAATCAACCAAAGAATTTTGGTTGTGGATCCAGTCACCTCTGAACATGAA**<br>**CTGACATGTCAGGCTGAGGGCTACCCCAAGGCCGAAGTCATCTGGACAAGCAGTGAC**<br>**CATCAAGTCCTGAGTGGTAAGACCACCACCACCAATTCCAAGAGAGAGGAGAAGCTT**<br>**TTCAATGTGACCAGCACACTGAGAATCAACACAACAACTAATGAGATTTTCTACTGC**<br>**ACTTTTAGGAGATTAGATCCTGAGGAAAACCATACAGCTGAATTGGTCATCCCAGAA**<br>**CTACCTCTGGCACATCCTCCAAATGAAAGG***CCAAATAAAGGAAGTGGAACCACTTCA*<br>*GGTACTACCCGTCTTCTATCTGGGCACACGTGTTTCACGTTGACAGGTTTGCTTGGG*<br>*ACGCTAGTAACCATGGGCTTGCTGACTTAG*<br>(SEQ ID NO: 225)<br>>Amino Acid Sequence; **hPDL1**-GPI, Amino Acid<br>**MRIFAVFIFMTYWHLLNAFTVTVPKDLYVVEYGSNMTIECKFPVEKQLDLAALIVYW**<br>**EMEDKNIIQFVHGEEDLKVQHSSYRQRARLLKDQLSLGNAALQITDVKLQDAGVYRC** |

TABLE 4-continued

| Full Length Constructs | |
|---|---|
| Fusion Polypeptide | Nucleic Acid Sequence (SEQ ID NO:)<br>Amino Acid Sequence (SEQ ID NO:) |
| | **MISYGGADYKRITVKVNAPYNKINQRILVVDPVTSEHELTCQAEGYPKAEVIWTSSD**<br>**HQVLSGKTTTTNSKREEKLFNVTSTLRINTTTNEIFYCTFRRLDPEENHTAELVIPE**<br>**LPLAHPPNER***PNKGSGTTSGTTRLLSGHTCFTLTGLLGTLVTMGLLT*<br>(SEQ ID NO: 226) |
| hPDL1-C1C2 | >Artificial Sequence; **hPDL1**-*C1C2*, DNA<br>**ATGAGGATATTTGCTGTCTTTATATTCATGACCTACTGGCATTTGCTGAACGCATTT**<br>**ACTGTCACGGTTCCCAAGGACCTATATGTGGTAGAGTATGGTAGCAATATGACAATT**<br>**GAATGCAAATTCCCAGTAGAAAAACAATTAGACCTGGCTGCACTAATTGTCTATTGG**<br>**GAAATGGAGGATAAGAACATTATTCAATTTGTGCATGGAGAGGAAGACCTGAAGGTT**<br>**CAGCATAGTAGCTACAGACAGAGGGCCCGGCTGTTGAAGGACCAGCTCTCCCTGGGA**<br>**AATGCTGCACTTCAGATCACAGATGTGAAATTGCAGGATGCAGGGGTGTACCGCTGC**<br>**ATGATCAGCTATGGTGGTGCCGACTACAAGCGAATTACTGTGAAAGTCAATGCCCCA**<br>**TACAACAAAATCAACCAAAGAATTTTGGTTGTGGATCCAGTCACCTCTGAACATGAA**<br>**CTGACATGTCAGGCTGAGGGCTACCCCAAGGCCGAAGTCATCTGGACAAGCAGTGAC**<br>**CATCAAGTCCTGAGTGGTAAGACCACCACCACCAATTCCAAGAGAGAGGAGAAGCTT**<br>**TTCAATGTGACCAGCACACTGAGAATCAACACAACAACTAATGAGATTTTCTACTGC**<br>**ACTTTTAGGAGATTAGATCCTGAGGAAAACCATACAGCTGAATTGGTCATCCCAGAA**<br>**CTACCTCTGGCACATCCTCCAAATGAAAGG**ATCGAT*GTCGAGCCACTGGGCATGGAG*<br>*AATGGGAACATTGCCAACTCACAGATCGCCGCCTCATCTGTGCGTGTGACCTTCTTG*<br>*GGTTTGCAGCATTGGGTCCCGGAGCTGGCCCGCCTGAACCGCGCAGGCATGGTCAAT*<br>*GCCTGGACACCCAGCAGCAATGACGATAACCCCTGGATCCAGGTGAACCTGCTGCGG*<br>*AGGATGTGGGTAACAGGTGTGGTGACGCAGGGTGCCAGCCGCTTGGCCAGTCATGAG*<br>*TACCTGAAGGCCTTCAAGGTGGCCTACAGCCTTAATGGACACGAATTCGATTTCATC*<br>*CATGATGTTAATAAAAAACACAAGGAGTTTGTGGGTAACTGGAACAAAAACGCGGTG*<br>*CATGTCAACCTGTTTGAGACCCCTGTGGAGGCTCAGTACGTGAGATTGTACCCCACG*<br>*AGCTGCCACACGGCCTGCACTCTGCGCTTTGAGCTACTGGGCTGTGAGCTGAACGGA*<br>*TGCGCCAATCCCCTGGGCCTGAAGAATAACAGCATCCCTGACAAGCAGATCACGGCC*<br>*TCCAGCAGCTACAAGACCTGGGGCTTGCATCTCTTCAGCTGGAACCCCTCCTATGCA*<br>*CGGCTGGACAAGCAGGGCAACTTCAACGCCTGGGTTGCGGGGAGCTACGGTAACGAT*<br>*CAGTGGCTGCAGATCTTCCCTGGCAACTGGGACAACCACTCCCACAAGAAGAACTTG*<br>*TTTGAGACGCCCATCCTGGCTCGCTATGTGCGCATCCTGCCTGTAGCCTGGCACAAC*<br>*CGCATCGCCCTGCGCCTGGAGCTGCTGGGCTGTTAG*<br>(SEQ ID NO: 227)<br>>Artificial Sequence, **hPDL1**-*C1C2*, Amino Acid<br>**MRIFAVFIFMTYWHLLNAFTVTVPKDLYVVEYGSNMTIECKFPVEKQLDLAALIVYW**<br>**EMEDKNIIQFVHGEEDLKVQHSSYRQRARLLKDQLSLGNAALQITDVKLQDAGVYRC**<br>**MISYGGADYKRITVKVNAPYNKINQRILVVDPVTSEHELTCQAEGYPKAEVIWTSSD**<br>**HQVLSGKTTTTNSKREEKLFNVTSTLRINTTTNEIFYCTFRRLDPEENHTAELVIPE**<br>**LPLAHPPNER**ID*VEPLGMENGNIANSQIAASSVRVTFLGLQHWVPELARLNRAGMVN*<br>*AWTPSSNDDNPWIQVNLLRRMWVTGVVTQGASRLASHEYLKAFKVAYSLNGHEFDFI*<br>*HDVNKKHKEFVGNWNKNAVHVNLFETPVEAQYVRLYPTSCHTACTLRFELLGCELNG*<br>*CANPLGLKNNSIPDKQITASSSYKTWGLHLFSWNPSYARLDKQGNFNAWVAGSYGND*<br>*QWLQIFPGNWDNHSHKKNLFETPILARYVRILPVAWHNRIALRLELLGC*<br>(SEQ ID NO: 228) |
| hPDL1-Fc-GPI | >Artificial Sequence; **hPDL1**-Fc-GPI, DNA<br>**ATGAGGATATTTGCTGTCTTTATATTCATGACCTACTGGCATTTGCTGAACGCATTT**<br>**ACTGTCACGGTTCCCAAGGACCTATATGTGGTAGAGTATGGTAGCAATATGACAATT**<br>**GAATGCAAATTCCCAGTAGAAAAACAATTAGACCTGGCTGCACTAATTGTCTATTGG**<br>**GAAATGGAGGATAAGAACATTATTCAATTTGTGCATGGAGAGGAAGACCTGAAGGTT**<br>**CAGCATAGTAGCTACAGACAGAGGGCCCGGCTGTTGAAGGACCAGCTCTCCCTGGGA**<br>**AATGCTGCACTTCAGATCACAGATGTGAAATTGCAGGATGCAGGGGTGTACCGCTGC**<br>**ATGATCAGCTATGGTGGTGCCGACTACAAGCGAATTACTGTGAAAGTCAATGCCCCA**<br>**TACAACAAAATCAACCAAAGAATTTTGGTTGTGGATCCAGTCACCTCTGAACATGAA**<br>**CTGACATGTCAGGCTGAGGGCTACCCCAAGGCCGAAGTCATCTGGACAAGCAGTGAC**<br>**CATCAAGTCCTGAGTGGTAAGACCACCACCACCAATTCCAAGAGAGAGGAGAAGCTT**<br>**TTCAATGTGACCAGCACACTGAGAATCAACACAACAACTAATGAGATTTTCTACTGC**<br>**ACTTTTAGGAGATTAGATCCTGAGGAAAACCATACAGCTGAATTGGTCATCCCAGAA**<br>**CTACCTCTGGCACATCCTCCAAATGAAAGG**ATCGATGACAAAACTCACACATGCCCA<br>CCGTGCCCAGCACCTGAACTCCTGGGGGGACCGTCAGTCTTCCTCTTCCCCCCAAAA<br>CCCAAGGACACCCTCATGATCTCCCGGACCCCTGAGGTCACATGCGTGGTGGTGGAC<br>GTGAGCCACGAAGACCCTGAGGTCAAGTTCAACTGGTACGTGGACGGCGTGGAGGTG<br>CATAATGCCAAGACAAAGCCGCGGGAGGAGCAGTACAACAGCACGTACCGTGTGGTC<br>AGCGTCCTCACCGTCCTGCACCAGGACTGGCTGAATGGCAAGGAGTACAAGTGCAAG<br>GTCTCCAACAAAGCCCTCCCAGCCCCCATCGAGAAAACCATCTCCAAAGCCAAAGGG<br>CAGCCCCGAGAACCACAGGTGTACACCCTGCCCCCATCCCGGGAGGAGATGACCAAG<br>AACCAGGTCAGCCTGACCTGCCTGGTCAAAGGCTTCTATCCCAGCGACATCGCCGTG<br>GAGTGGGAGAGCAATGGGCAGCCGGAGAACAACTACAAGACCACGCCTCCCGTGCTG<br>GACTCCGACGGCTCCTTCTTCCTCTACAGCAAGCTCACCGTGGACAAGAGCAGGTGG<br>CAGCAGGGGAACGTCTTCTCATGCTCCGTGATGCACGAGGCTCTGCACAACCACTAC<br>ACGCAGAAGAGCCTCTCCCTGTCTCCGGGTAAAATCGAT*CCAAATAAAGGAAGTGGA*<br>*ACCACTTCAGGTACTACCCGTCTTCTATCTGGGCACACGTGTTTCACGTTGACAGGT*<br>*TTGCTTGGGACGCTAGTAACCATGGGCTTGCTGACTTAG*<br>(SEQ ID NO: 229) |

TABLE 4-continued

| Full Length Constructs | |
|---|---|
| Fusion Polypeptide | Nucleic Acid Sequence (SEQ ID NO:)<br>Amino Acid Sequence (SEQ ID NO:) |
| | > Artificial Sequence; **hPDL1**-Fc-*GPI*, Amino Acid<br>**MRIFAVFIFMTYWHLLNAFTVTVPKDLYVVEYGSNMTIECKFPVEKQLDLAALIVYW**<br>**EMEDKNIIQFVHGEEDLKVQHSSYRQRARLLKDQLSLGNAALQITDVKLQDAGVYRC**<br>**MISYGGADYKRITVKVNAPYNKINQRILVVDPVTSEHELTCQAEGYPKAEVIWTSSD**<br>**HQVLSGKTTTTNSKREEKLFNVTSTLRINTTTNEIFYCTFRRLDPEENHTAELVIPE**<br>**LPLAHPPNER**IDDKTHTCPPCPAPELLGGPSVFLFPPKPKDTLMISRTPEVTCVVVD<br>VSHEDPEVKFNWYVDGVEVHNAKTKPREEQYNSTYRVVSVLTVLHQDWLNGKEYKCK<br>VSNKALPAPIEKTISKAKGQPREPQVYTLPPSREEMTKNQVSLTCLVKGFYPSDIAV<br>EWESNGQPENNYKTTPPVLDSDGSFFLYSKLTVDKSRWQQGNVFSCSVMHEALHNHY<br>TQKSLSLSPGKID*PNKGSGTTSGTTRLLSGHTCFTLTGLLGTLVTMGLLT*<br>(SEQ ID NO: 230) |
| hPDL2-C1C2 | >Artificial Sequence; **hPDL2**-*C1C2*, DNA<br>**ATGATCTTCCTCCTGCTAATGTTGAGCCTGGAATTGCAGCTTCACCAGATAGCAGCT**<br>**TTATTCACAGTGACAGTCCCTAAGGAACTGTACATAATAGAGCATGGCAGCAATGTG**<br>**ACCCTGGAATGCAACTTTGACACTGGAAGTCATGTGAACCTTGGAGCAATAACAGCC**<br>**AGTTTGCAAAAGGTGGAAAATGATACATCCCCACACCGTGAAAGAGCCACTTTGCTG**<br>**GAGGAGCAGCTGCCCCTAGGGAAGGCCTCGTTCCACATACCTCAAGTCCAAGTGAGG**<br>**GACGAAGGACAGTACCAATGCATAATCATCTATGGGGTCGCCTGGGACTACAAGTAC**<br>**CTGACTCTGAAAGTCAAAGCTTCCTACAGGAAAATAAACACTCACATCCTAAAGGTT**<br>**CCAGAAACAGATGAGGTAGAGCTCACCTGCCAGGCTACAGGTTATCCTCTGGCAGAA**<br>**GTATCCTGGCCAAACGTCAGCGTTCCTGCCAACACCAGCCACTCCAGGACCCCTGAA**<br>**GGCCTCTACCAGGTCACCAGTGTTCTGCGCCTAAAGCCACCCCCTGGCAGAAACTTC**<br>**AGCTGTGTGTTCTGGAATACTCACGTGAGGGAACTTACTTTGGCCAGCATTGACCTT**<br>**CAAAGTCAGATGGAACCCAGGACCCATCCAACT**ATCGAT*GTCGAGCCACTGGGCATG*<br>*GAGAATGGGAACATTGCCAACTCACAGATCGCCGCCTCATCTGTGCGTGTGACCTTC*<br>*TTGGGTTTGCAGCATTGGGTCCCGGAGCTGGCCCGCCTGAACCGCGCAGGCATGGTC*<br>*AATGCCTGGACACCCAGCAGCAATGACGATAACCCCTGGATCCAGGTGAACCTGCTG*<br>*CGGAGGATGTGGGTAACAGGTGTGGTGACGCAGGGTGCCAGCCGCTTGGCCAGTCAT*<br>*GAGTACCTGAAGGCCTTCAAGGTGGCCTACAGCCTTAATGGACACGAATTCGATTTC*<br>*ATCCATGATGTTAATAAAAAACACAAGGAGTTTGTGGGTAACTGGAACAAAAACGCG*<br>*GTGCATGTCAACCTGTTTGAGACCCCTGTGGAGGCTCAGTACGTGAGATTGTACCCC*<br>*ACGAGCTGCCACACGGCCTGCACTCTGCGCTTTGAGCTACTGGGCTGTGAGCTGAAC*<br>*GGATGCGCCAATCCCCTGGGCCTGAAGAATAACAGCATCCCTGACAAGCAGATCACG*<br>*GCCTCCAGCAGCTACAAGACCTGGGGCTTGCATCTCTTCAGCTGGAACCCCTCCTAT*<br>*GCACGGCTGGACAAGCAGGGCAACTTCAACGCCTGGGTTGCGGGGAGCTACGGTAAC*<br>*GATCAGTGGCTGCAGATCTTCCCTGGCAACTGGGACAACCACTCCCACAAGAAGAAC*<br>*TTGTTTGAGACGCCCATCCTGGCTCGCTATGTGCGCATCCTGCCTGTAGCCTGGCAC*<br>*AACCGCATCGCCCTGCGCCTGGAGCTGCTGGGCTGTTAG*<br>(SEQ ID NO: 231)<br>>Artificial Sequence; **hPDL2**-*C1C2*, Amino Acid<br>**MIFLLLMLSLELQLHQIAALFTVTVPKELYIIEHGSNVTLECNFDTGSHVNLGAITA**<br>**SLQKVENDTSPHRERATLLEEQLPLGKASFHIPQVQVRDEGQYQCIIIYGVAWDYKY**<br>**LTLKVKASYRKINTHILKVPETDEVELTCQATGYPLAEVSWPNVSVPANTSHSRTPE**<br>**GLYQVTSVLRLKPPPGRNFSCVFWNTHVRELTLASIDLQSQMEPRTHPT**ID*VEPLGM*<br>*ENGNIANSQIAASSVRVTFLGLQHWVPELARLNRAGMVNAWTPSSNDDNPWIQVNLL*<br>*RRMWVTGVVTQGASRLASHEYLKAFKVAYSLNGHEFDFIHDVNKKHKEFVGNWNKNA*<br>*VHVNLFETPVEAQYVRLYPTSCHTACTLRFELLGCELNGCANPLGLKNNSIPDKQIT*<br>*ASSSYKTWGLHLFSWNPSYARLDKQGNFNAWVAGSYGNDQWLQIFPGNWDNHSHKKN*<br>*LFETPILARYVRILPVAWHNRIALRLELLGC*<br>(SEQ ID NO: 232) |
| hPDL2-Fc-GPI | >Artificial Sequence; **hPDL2**-Fc-*GPI*, DNA<br>**ATGATCTTCCTCCTGCTAATGTTGAGCCTGGAATTGCAGCTTCACCAGATAGCAGCT**<br>**TTATTCACAGTGACAGTCCCTAAGGAACTGTACATAATAGAGCATGGCAGCAATGTG**<br>**ACCCTGGAATGCAACTTTGACACTGGAAGTCATGTGAACCTTGGAGCAATAACAGCC**<br>**AGTTTGCAAAAGGTGGAAAATGATACATCCCCACACCGTGAAAGAGCCACTTTGCTG**<br>**GAGGAGCAGCTGCCCCTAGGGAAGGCCTCGTTCCACATACCTCAAGTCCAAGTGAGG**<br>**GACGAAGGACAGTACCAATGCATAATCATCTATGGGGTCGCCTGGGACTACAAGTAC**<br>**CTGACTCTGAAAGTCAAAGCTTCCTACAGGAAAATAAACACTCACATCCTAAAGGTT**<br>**CCAGAAACAGATGAGGTAGAGCTCACCTGCCAGGCTACAGGTTATCCTCTGGCAGAA**<br>**GTATCCTGGCCAAACGTCAGCGTTCCTGCCAACACCAGCCACTCCAGGACCCCTGAA**<br>**GGCCTCTACCAGGTCACCAGTGTTCTGCGCCTAAAGCCACCCCCTGGCAGAAACTTC**<br>**AGCTGTGTGTTCTGGAATACTCACGTGAGGGAACTTACTTTGGCCAGCATTGACCTT**<br>**CAAAGTCAGATGGAACCCAGGACCCATCCAACT**ATCGATGACAAAACTCACACATGC<br>CCACCGTGCCCAGCACCTGAACTCCTGGGGGGACCGTCAGTCTTCCTCTTCCCCCCA<br>AAACCCAAGGACACCCTCATGATCTCCCGGACCCCTGAGGTCACATGCGTGGTGGTG<br>GACGTGAGCCACGAAGACCCTGAGGTCAAGTTCAACTGGTACGTGGACGGCGTGGAG<br>GTGCATAATGCCAAGACAAAGCCGCGGGAGGAGCAGTACAACAGCACGTACCGTGTG<br>GTCAGCGTCCTCACCGTCCTGCACCAGGACTGGCTGAATGGCAAGGAGTACAAGTGC<br>AAGGTCTCCAACAAAGCCCTCCCAGCCCCCATCGAGAAAACCATCTCCAAAGCCAAA<br>GGGCAGCCCCGAGAACCACAGGTGTACACCCTGCCCCCATCCCGGGAGGAGATGACC<br>AAGAACCAGGTCAGCCTGACCTGCCTGGTCAAAGGCTTCTATCCCAGCGACATCGCC<br>GTGGAGTGGGAGAGCAATGGGCAGCCGGAGAACAACTACAAGACCACGCCTCCCGTG<br>CTGGACTCCGACGGCTCCTTCTTCCTCTACAGCAAGCTCACCGTGGACAAGAGCAGG |

TABLE 4-continued

| Full Length Constructs | |
|---|---|
| Fusion Polypeptide | Nucleic Acid Sequence (SEQ ID NO:)<br>Amino Acid Sequence (SEQ ID NO:) |
| | TGGCAGCAGGGGAACGTCTTCTCATGCTCCGTGATGCACGAGGCTCTGCACAACCAC<br>TACACGCAGAAGAGCCTCTCCCTGTCTCCGGGTAAAATCGAT*CCAAATAAAGGAAGT*<br>*GGAACCACTTCAGGTACTACCCGTCTTCTATCTGGGCACACGTGTTTCACGTTGACA*<br>*GGTTTGCTTGGGACGCTAGTAACCATGGGCTTGCTGACTTAG*<br>(SEQ ID NO: 233)<br>>Artificial Sequence; **hPDL2**-Fc-*GPI*, Amino Acid<br>**MIFLLLMLSLELQLHQIAALFTVTVPKELYIIEHGSNVTLECNFDTGSHVNLGAITA**<br>**SLQKVENDTSPHRERATLLEEQLPLGKASFHIPQVQVRDEGQYQCIIIYGVAWDYKY**<br>**LTLKVKASYRKINTHILKVPETDEVELTCQATGYPLAEVSWPNVSVPANTSHSRTPE**<br>**GLYQVTSVLRLKPPPGRNFSCVFWNTHVRELTLASIDLQSQMEPRTHPT**IDDKTHTC<br>PPCPAPELLGGPSVFLFPPKPKDTLMISRTPEVTCVVVDVSHEDPEVKFNWYVDGVE<br>VHNAKTKPREEQYNSTYRVVSVLTVLHQDWLNGKEYKCKVSNKALPAPIEKTISKAK<br>GQPREPQVYTLPPSREEMTKNQVSLTCLVKGFYPSDIAVEWESNGQPENNYKTTPPV<br>LDSDGSFFLYSKLTVDKSRWQQGNVFSCSVMHEALHNHYTQKSLSLSPGKID*PNKGS*<br>*GTTSGTTRLLSGHTCFTLTGLLGTLVTMGLLT*<br>(SEQ ID NO: 234) |
| 4F2-h41BBL | >Artificial Sequence; *4F2*-**41BBL**, DNA<br>*ATGAGCCAGGACACCGAGGTGGATATGAAGGAGGTGGAGCTGAATGAGTTAGAGCCC*<br>*GAGAAGCAGCCGATGAACGCGGCGTCTGGGGCGGCCATGTCCCTGGCGGGAGCCGAG*<br>*AAGAATGGTCTGGTGAAGATCAAGGTGGCGGAAGACGAGGCGGAGGCGGCAGCCGCG*<br>*GCTAAGTTCACGGGCCTGTCCAAGGAGGAGCTGCTGAAGGTGGCAGGCAGCCCCGGC*<br>*TGGGTACGCACCCGCTGGGCACTGCTGCTGCTCTTCTGGCTCGGCTGGCTCGGCATG*<br>*CTTGCTGGTGCCGTGGTCATAATCGTG***GCCTGCCCCTGGGCCGTGTCCGGGGCTCGC**<br>**GCCTCGCCCGGCTCCGCGGCCAGCCCGAGACTCCGCGAGGGTCCCGAGCTTTCGCCC**<br>**GACGATCCCGCCGGCCTCTTGGACCTGCGGCAGGGCATGTTTGCGCAGCTGGTGGCC**<br>**CAAAATGTTCTGCTGATCGATGGGCCCCTGAGCTGGTACAGTGACCCAGGCCTGGCA**<br>**GGCGTGTCCCTGACGGGGGGCCTGAGCTACAAAGAGGACACGAAGGAGCTGGTGGTG**<br>**GCCAAGGCTGGAGTCTACTATGTCTTCTTTCAACTAGAGCTGCGGCGCGTGGTGGCC**<br>**GGCGAGGGCTCAGGCTCCGTTTCACTTGCGCTGCACCTGCAGCCACTGCGCTCTGCT**<br>**GCTGGGGCCGCCGCCCTGGCTTTGACCGTGGACCTGCCACCCGCCTCCTCCGAGGCT**<br>**CGGAACTCGGCCTTCGGTTTCCAGGGCCGCTTGCTGCACCTGAGTGCCGGCCAGCGC**<br>**CTGGGCGTCCATCTTCACACTGAGGCCAGGGCACGCCATGCCTGGCAGCTTACCCAG**<br>**GGCGCCACAGTCTTGGGACTCTTCCGGGTGACCCCCGAAATCCCAGCCGGACTCCCT**<br>**TCACCGAGGTCGGAATAA**<br>(SEQ ID NO: 235)<br>>Artificial Sequence; *4F2*-**h41BBL**, Amino Acid<br>*MSQDTEVDMKEVELNELEPEKQPMNAASGAAMSLAGAEKNGLVKIKVAEDEAEAAAA*<br>*AKFTGLSKEELLKVAGSPGWVRTRWALLLLFWLGWLGMLAGAVVIIV***ACPWAVSGAR**<br>**ASPGSAASPRLREGPELSPDDPAGLLDLRQGMFAQLVAQNVLLIDGPLSWYSDPGLA**<br>**GVSLTGGLSYKEDTKELVVAKAGVYYVFFQLELRRVVAGEGSGSVSLALHLQPLRSA**<br>**AGAAALALTVDLPPASSEARNSAFGFQGRLLHLSAGQRLGVHLHTEARARHAWQLTQ**<br>**GATVLGLFRVTPEIPAGLPSPRSE**<br>(SEQ ID NO: 236) |
| hPDL1-4Fc-GPI | >Artificial Sequence; **hPDL1**-4Fc-*GPI*, DNA<br>**ATGAGGATATTTGCTGTCTTTATATTCATGACCTACTGGCATTTGCTGAACGCATTT**<br>**ACTGTCACGGTTCCCAAGGACCTATATGTGGTAGAGTATGGTAGCAATATGACAATT**<br>**GAATGCAAATTCCCAGTAGAAAAACAATTAGACCTGGCTGCACTAATTGTCTATTGG**<br>**GAAATGGAGGATAAGAACATTATTCAATTTGTGCATGGAGAGGAAGACCTGAAGGTT**<br>**CAGCATAGTAGCTACAGACAGAGGGCCCGGCTGTTGAAGGACCAGCTCTCCCTGGGA**<br>**AATGCTGCACTTCAGATCACAGATGTGAAATTGCAGGATGCAGGGGTGTACCGCTGC**<br>**ATGATCAGCTATGGTGGTGCCGACTACAAGCGAATTACTGTGAAAGTCAATGCCCCA**<br>**TACAACAAAATCAACCAAAGAATTTTGGTTGTGGATCCAGTCACCTCTGAACATGAA**<br>**CTGACATGTCAGGCTGAGGGCTACCCCAAGGCCGAAGTCATCTGGACAAGCAGTGAC**<br>**CATCAAGTCCTGAGTGGTAAGACCACCACCACCAATTCCAAGAGAGAGGAGAAGCTT**<br>**TTCAATGTGACCAGCACACTGAGAATCAACACAACAACTAATGAGATTTTCTACTGC**<br>**ACTTTTAGGAGATTAGATCCTGAGGAAAACCATACAGCTGAATTGGTCATCCCAGAA**<br>**CTACCTCTGGCACATCCTCCAAATGAAAGG**GAGTCCAAATATGGTCCCCCATGCCCA<br>TCATGCCCAGCACCTGAGTTCCTGGGGGGACCATCAGTCTTCCTGTTCCCCCCAAAA<br>CCCAAGGACACTCTCATGATCTCCCGGACCCCTGAGGTCACGTGCGTGGTGGTGGAC<br>GTGAGCCAGGAAGACCCCGAGGTCCAGTTCAACTGGTACGTGGATGGCGTGGAGGTG<br>CATAATGCCAAGACAAAGCCGCGGGAGGAGCAGTTCAACAGCACGTACCGTGTGGTC<br>AGGGTCCTCACCGTCCTGCACCAGGACTGGCTGAACGGTAAGGAGTACAAGTGCAAG<br>GTCTCCAACAAAGGCCTCCCGTCCTCCATCGAGAAAACCATCTCCAAAGCCAAAGGG<br>CAGCCCCGAGAGCCACAGGTGTACACCCTGCCCCCATCCCAGGAGGAGATGACCAAG<br>AACCAGGTCAGCCTGACCTGCCTGGTCAAAGGCTTCTACCCCAGCGACATCGCCGTG<br>GAGTGGGAGAGCAATGGGCAGCCGGAGGACAACTACAAGACCACGCCTCCCGTGCTG |

TABLE 4-continued

Full Length Constructs

| Fusion Polypeptide | Nucleic Acid Sequence (SEQ ID NO:)<br>Amino Acid Sequence (SEQ ID NO:) |
|---|---|
| | GACTCCGACGGCTCCTTCTTCCTCTACAGCAGGCTAACCGTGGACAAGAGCAGGTGG<br>CAGGAGGGGAATGTCTTCTCATGCTCCGTGATGCATGAGGCTCTGCACAACCACTAC<br>ACACAGAAGAGCCTCTCCCTGTCTCCGGGTAAACCAAATAAAGGAAGTGGAACCACT<br>TCAGGTACTACCCGTCTTCTATCTGGGCACACGTGTTTCACGTTGACAGGTTTGCTT<br>GGGACGCTAGTAACCATGGGCTTGCTGACTTAG<br>(SEQ ID NO: 237)<br>>Artificial Sequence; **hPDL1-4Fc**-GPI, Amino Acid<br>MRIFAVFIFMTYWHLLNAFTVTVPKDLYVVEYGSNMTIECKFPVEKQLDLAALIVYW<br>EMEDKNIIQFVHGEEDLKVQHSSYRQRARLLKDQLSLGNAALQITDVKLQDAGVYRC<br>MISYGGADYKRITVKVNAPYNKINQRILVVDPVTSEHELTCQAEGYPKAEVIWTSSD<br>HQVLSGKTTTTNSKREEKLFNVTSTLRINTTTNEIFYCTFRRLDPEENHTAELVIPE<br>LPLAHPPNERESKYGPPCPSCPAPEFLGGPSVFLFPPKPKDTLMISRTPEVTCVVVD<br>VSQEDPEVQFNWYVDGVEVHNAKTKPREEQFNSTYRVVRVLTVLHQDWLNGKEYKCK<br>VSNKGLPSSIEKTISKAKGQPREPQVYTLPPSQEEMTKNQVSLTCLVKGFYPSDIAV<br>EWESNGQPEDNYKTTPPVLDSDGSFFLYSRLTVDKSRWQEGNVFSCSVMHEALHNHY<br>TQKSLSLSPGK*PNKGSGTTSGTTRLLSGHTCFTLTGLLGTLVTMGLLT*<br>(SEQ ID NO: 238) |
| hPDL1-GPI-P2A-<br>hFGL1-GPI | >Artificial Sequence; **hPDL1**-GPI-P2A-**hFGL1**-GPI, DNA<br>ATGAGGATATTTGCTGTCTTTATATTCATGACCTACTGGCATTTGCTGAACGCATTT<br>ACTGTCACGGTTCCCAAGGACCTATATGTGGTAGAGTATGGTAGCAATATGACAATT<br>GAATGCAAATTCCCAGTAGAAAAACAATTAGACCTGGCTGCACTAATTGTCTATTGG<br>GAAATGGAGGATAAGAACATTATTCAATTTGTGCATGGAGAGGAAGACCTGAAGGTT<br>CAGCATAGTAGCTACAGACAGAGGGCCCGGCTGTTGAAGGACCAGCTCTCCCTGGGA<br>AATGCTGCACTTCAGATCACAGATGTGAAATTGCAGGATGCAGGGGTGTACCGCTGC<br>ATGATCAGCTATGGTGGTGCCGACTACAAGCGAATTACTGTGAAAGTCAATGCCCCA<br>TACAACAAAATCAACCAAAGAATTTTGGTTGTGGATCCAGTCACCTCTGAACATGAA<br>CTGACATGTCAGGCTGAGGGCTACCCCAAGGCCGAAGTCATCTGGACAAGCAGTGAC<br>CATCAAGTCCTGAGTGGTAAGACCACCACCACCAATTCCAAGAGAGAGGAGAAGCTT<br>TTCAATGTGACCAGCACACTGAGAATCAACACAACAACTAATGAGATTTTCTACTGC<br>ACTTTTAGGAGATTAGATCCTGAGGAAAACCATACAGCTGAATTGGTCATCCCAGAA<br>CTACCTCTGGCACATCCTCCAAATGAAAGG*CCAAATAAAGGAAGTGGAACCACTTCA<br>GGTACTACCCGTCTTCTATCTGGGCACACGTGTTTCACGTTGACAGGTTTGCTTGGG<br>ACGCTAGTAACCATGGGCTTGCTGACT*GGAAGCGGAGCTACTAACTTCAGCCTGCTG<br>AAGCAGGCTGGCGACGTGGAGGAGAACCCTGGACCTATGGCAAAGGTGTTCAGTTTC<br>ATCCTTGTTACCACCGCTCTGACAATGGGCAGGGAAATTTCGGCGCTCGAGGACTGT<br>GCCCAGGAGCAGATGCGGCTCAGAGCCCAGGTGCGCCTGCTTGAGACCCGGGTCAAA<br>CAGCAACAGGTCAAGATCAAGCAGCTTTTGCAGGAGAATGAAGTCCAGTTCCTTGAT<br>AAAGGAGATGAGAATACTGTCATTGATCTTGGAAGCAAGAGGCAGTATGCAGATTGT<br>TCAGAGATTTTCAATGATGGGTATAAGCTCAGTGGATTTTACAAAATCAAACCTCTC<br>CAGAGCCCAGCAGAATTTTCTGTTTATTGTGACATGTCCGATGGAGGAGGATGGACT<br>GTAATTCAGAGACGATCTGATGGCAGTGAAAACTTTAACAGAGGATGGAAAGACTAT<br>GAAAATGGCTTTGGAAATTTTGTCCAAAAACATGGTGAATATTGGCTGGGCAATAAA<br>AATCTTCACTTCTTGACCACTCAAGAAGACTACACTTTAAAAATCGACCTTGCAGAT<br>TTTGAAAAAAATAGCCGTTATGCACAATATAAGAATTTCAAAGTTGGAGATGAAAAG<br>AATTTCTACGAGTTGAATATTGGGGAATATTCTGGAACAGCTGGAGATTCCCTTGCG<br>GGGAATTTTCATCCTGAGGTGCAGTGGTGGGCTAGTCACCAAAGAATGAAATTCAGC<br>ACGTGGGACAGAGATCATGACAACTATGAAGGGAACTGCGCAGAAGAAGATCAGTCT<br>GGCTGGTGGTTTAACAGGTGTCACTCTGCAAACCTGAATGGTGTATACTACAGCGGC<br>CCCTACACGGCTAAAACAGACAATGGGATTGTCTGGTACACCTGGCATGGGTGGTGG<br>TATTCTCTGAAATCTGTGGTTATGAAAATTAGGCCAAATGATTTTATTCCAAATGTA<br>ATT*CCAAATAAAGGAAGTGGAACCACTTCAGGTACTACCCGTCTTCTATCTGGGCAC<br>ACGTGTTTCACGTTGACAGGTTTGCTTGGGACGCTAGTAACCATGGGCTTGCTGACT<br>TAG*<br>(SEQ ID NO: 239)<br>>Artificial Sequence; **hPDL1**-GPI-P2A-**hFGL1**-GPI, Amino Acid<br>MRIFAVFIFMTYWHLLNAFTVTVPKDLYVVEYGSNMTIECKFPVEKQLDLAALIVYW<br>EMEDKNIIQFVHGEEDLKVQHSSYRQRARLLKDQLSLGNAALQITDVKLQDAGVYRC<br>MISYGGADYKRITVKVNAPYNKINQRILVVDPVTSEHELTCQAEGYPKAEVIWTSSD<br>HQVLSGKTTTTNSKREEKLFNVTSTLRINTTTNEIFYCTFRRLDPEENHTAELVIPE<br>LPLAHPPNER*PNKGSGTTSGTTRLLSGHTCFTLTGLLGTLVTMGLLT*GSGATNFSLL<br>KQAGDVEENPGPMAKVFSFILVTTALTMGREISALEDCAQEQMRLRAQVRLLETRVK<br>QQQVKIKQLLQENEVQFLDKGDENTVIDLGSKRQYADCSEIFNDGYKLSGFYKIKPL<br>QSPAEFSVYCDMSDGGGWTVIQRRSDGSENFNRGWKDYENGFGNFVQKHGEYWLGNK<br>NLHFLTTQEDYTLKIDLADFEKNSRYAQYKNFKVGDEKNFYELNIGEYSGTAGDSLA<br>GNFHPEVQWWASHQRMKFSTWDRDHDNYEGNCAEEDQSGWWFNRCHSANLNGVYYSG<br>PYTAKTDNGIVWYTWHGWWYSLKSVVMKIRPNDFIPNVI*PNKGSGTTSGTTRLLSGH<br>TCFTLTGLLGTLVTMGLLT*<br>(SEQ ID NO: 240) |
| Myr-mScarlet | >Artificial Sequence; **Myr**-**mScarlet**, DNA<br>*ATGGGTTGCTGTTTCTCCAAGAC*CGGCTCGAGCGGCGTGAGCAAGGGCGAGGCAGTG<br>ATCAAGGAGTTCATGCGGTTCAAGGTGCACATGGAGGGCTCCATGAACGGCCACGAG<br>TTCGAGATCGAGGGCGAGGGCGAGGGCCGCCCCTACGAGGGCACCCAGACCGCCAAG<br>CTGAAGGTGACCAAGGGTGGCCCCCTGCCCTTCTCCTGGGACATCCTGTCCCCTCAG |

TABLE 4-continued

| Full Length Constructs | |
|---|---|
| Fusion Polypeptide | Nucleic Acid Sequence (SEQ ID NO:)<br>Amino Acid Sequence (SEQ ID NO:) |
| | TTCATGTACGGCTCCAGGGCCTTCACCAAGCACCCCGCCGACATCCCCGACTACTAT<br>AAGCAGTCCTTCCCCGAGGGCTTCAAGTGGGAGCGCGTGATGAACTTCGAGGACGGC<br>GGCGCCGTGACCGTGACCCAGGACACCTCCCTGGAGGACGGCACCCTGATCTACAAG<br>GTGAAGCTCCGCGGCACCAACTTCCCTCCTGACGGCCCCGTAATGCAGAAGAAGACA<br>ATGGGCTGGGAAGCGTCCACCGAGCGGTTGTACCCCGAGGACGGCGTGCTGAAGGGC<br>GACATTAAGATGGCCCTGCGCCTGAAGGACGGCGGCCGCTACCTGGCGGACTTCAAG<br>ACCACCTACAAGGCCAAGAAGCCCGTGCAGATGCCCGGCGCCTACAACGTCGACCGC<br>AAGTTGGACATCACCTCCCACAACGAGGACTACACCGTGGTGGAACAGTACGAACGC<br>TCCGAGGGCCGCCACTCCACCGGCGGCATGGACGAGCTGTACAAG<br>(SEQ ID NO: 241)<br>>Artificial Sequence; *Myr*-**mScarlet**, Amino Acid<br>*MGCCFSKT*GSSG**VSKGEAVIKEFMRFKVHMEGSMNGHEFEIEGEGEGRPYEGTQTAK**<br>**LKVTKGGPLPFSWDILSPQFMYGSRAFTKHPADIPDYYKQSFPEGFKWERVMNFEDG**<br>**GAVTVTQDTSLEDGTLIYKVKLRGTNFPPDGPVMQKKTMGWEASTERLYPEDGVLKG**<br>**DIKMALRLKDGGRYLADFKTTYKAKKPVQMPGAYNVDRKLDITSHNEDYTVVEQYER**<br>**SEGRHSTGGMDELYK**<br>(SEQ ID NO: 242) |
| Myr-NanoLuc Luciferase | > Artificial Sequence; *Myr*-**NanoLuc**, DNA<br>*ATGGGTTGCTGTTTCTCCAAGACC*GGCTCGAGCGGC**GTCTTCACACTCGAAGATTTC**<br>**GTTGGGGACTGGCGACAGACAGCCGGCTACAACCTGGACCAAGTCCTTGAACAGGGA**<br>**GGTGTGTCCAGTTTGTTTCAGAATCTCGGGGTGTCCGTAACTCCGATCCAAAGGATT**<br>**GTCCTGAGCGGTGAAAATGGGCTGAAGATCGACATCCATGTCATCATCCCGTATGAA**<br>**GGTCTGAGCGGCGACCAAATGGGCCAGATCGAAAAAATTTTTAAGGTGGTGTACCCT**<br>**GTGGATGATCATCACTTTAAGGTGATCCTGCACTATGGCACACTGGTAATCGACGGG**<br>**GTTACGCCGAACATGATCGACTATTTCGGACGGCCGTATGAAGGCATCGCCGTGTTC**<br>**GACGGCAAAAAGATCACTGTAACAGGGACCCTGTGGAACGGCAACAAAATTATCGAC**<br>**GAGCGCCTGATCAACCCCGACGGCTCCCTGCTGTTCCGAGTAACCATCAACGGAGTG**<br>**ACCGGCTGGCGGCTGTGCGAACGCATTCTGGCGTAA**<br>(SEQ ID NO: 243)<br>>Artificial Sequence; *Myr*-**NanoLuc**, Amino Acid<br>*MGCCFSKT*GSSGVFTLEDFVGDWRQTAGYNLDQVLEQGGVSSLFQNLGVSVTPIQRI<br>VLSGENGLKIDIHVIIPYEGLSGDQMGQIEKIFKVVYPVDDHHFKVILHYGTLVIDG<br>VTPNMIDYFGRPYEGIAVFDGKKITVTGTLWNGNKIIDERLINPDGSLLFRVTINGV<br>TGWRLCERILA<br>(SEQ ID NO: 244) |
| hSecPDL1-GPI | >Artificial Sequence; **hSecPDL1**-*GPI*, DNA<br>**ATGAGGATATTTGCTGTCTTTATATTCATGACCTACTGGCATTTGCTGAACGCATTT**<br>**ACTGTCACGGTTCCCAAGGACCTATATGTGGTAGAGTATGGTAGCAATATGACAATT**<br>**GAATGCAAATTCCCAGTAGAAAAACAATTAGACCTGGCTGCACTAATTGTCTATTGG**<br>**GAAATGGAGGATAAGAACATTATTCAATTTGTGCATGGAGAGGAAGACCTGAAGGTT**<br>**CAGCATAGTAGCTACAGACAGAGGGCCCGGCTGTTGAAGGACCAGCTCTCCCTGGGA**<br>**AATGCTGCACTTCAGATCACAGATGTGAAATTGCAGGATGCAGGGGTGTACCGCTGC**<br>**ATGATCAGCTATGGTGGTGCCGACTACAAGCGAATTACTGTGAAAGTCAATGCCCCA**<br>**TACAACAAAATCAACCAAAGAATTTTGGTTGTGGATCCAGTCACCTCTGAACATGAA**<br>**CTGACATGTCAGGCTGAGGGCTACCCCAAGGCCGAAGTCATCTGGACAAGCAGTGAC**<br>**CATCAAGTCCTGAGTGGTAAGACCACCACCACCAATTCCAAGAGAGAGGAGAAGCTT**<br>**TTCAATGTGACCAGCACACTGAGAATCAACACAACAACTAATGAGATTTTCTACTGC**<br>**ACTTTTAGGAGATTAGATCCTGAGGAAAACCATACAGCTGAATTGGTCATCCCAGGT**<br>**AATATTCTGAATGTGTCCATTAAAATATGTCTAACACTGTCCCCTAGCACC***CCAAAT*<br>*AAAGGAAGTGGAACCACTTCAGGTACTACCCGTCTTCTATCTGGGCACACGTGTTTC*<br>*ACGTTGACAGGTTTGCTTGGGACGCTAGTAACCATGGGCTTGCTGACTTAG*<br>(SEQ ID NO: 245)<br>>Artificial Sequence; **hSecPDL1**-*GPI*, Amino Acid<br>**MRIFAVFIFMTYWHLLNAFTVTVPKDLYVVEYGSNMTIECKFPVEKQLDLAALIVYW**<br>**EMEDKNIIQFVHGEEDLKVQHSSYRQRARLLKDQLSLGNAALQITDVKLQDAGVYRC**<br>**MISYGGADYKRITVKVNAPYNKINQRILVVDPVTSEHELTCQAEGYPKAEVIWTSSD**<br>**HQVLSGKTTTTNSKREEKLFNVTSTLRINTTTNEIFYCTFRRLDPEENHTAELVIPG**<br>**NILNVSIKICLTLSPST***PNKGSGTTSGTTRLLSGHTCFTLTGLLGTLVTMGLLT*<br>(SEQ ID NO: 246) |
| Tfr2-h41BBL | >Artificial Sequence; *Tfr2*-**h41BBL**, DNA<br>*ATGGAGCGGCTTTGGGGTCTATTCCAGAGAGCGCAACAACTGTCCCCAAGATCCTCT*<br>*CAGACCGTCTACCAGCGTGTGGAAGGCCCCCGGAAAGGGCACCTGGAGGAGGAAGAG*<br>*GAAGACGGGGAGGAGGGGGCGGAGACATTGGCCCACTTCTGCCCCATGGAGCTGAGG*<br>*GGCCCTGAGCCCCTGGGCTCTAGACCCAGGCAGCCAAACCTCATTCCCTGGGCGGCA*<br>*GCAGGACGGAGGGCTGCCCCCTACCTGGTCCTGACGGCCCTGCTGATCTTCACTGGG*<br>*GCCTTCCTACTGGGCTACGTCGCCTTCCGAGGGTCC***GCCTGCCCCTGGGCCGTGTCC**<br>***GGGGCTCGCGCCTCGCCCGGCTCCGCGGCCAGCCCGAGACTCCGCGAGGGTCCCGAG***<br>***CTTTCGCCCGACGATCCCGCCGGCCTCTTGGACCTGCGGCAGGGCATGTTTGCGCAG***<br>***CTGGTGGCCCAAAATGTTCTGCTGATCGATGGGCCCCTGAGCTGGTACAGTGACCCA***<br>***GGCCTGGCAGGCGTGTCCCTGACGGGGGGCCTGAGCTACAAAGAGGACACGAAGGAG***<br>***CTGGTGGTGGCCAAGGCTGGAGTCTACTATGTCTTCTTTCAACTAGAGCTGCGGCGC***<br>***GTGGTGGCCGGCGAGGGCTCAGGCTCCGTTTCACTTGCGCTGCACCTGCAGCCACTG*** |

TABLE 4-continued

| Full Length Constructs | |
|---|---|
| Fusion Polypeptide | Nucleic Acid Sequence (SEQ ID NO:)<br>Amino Acid Sequence (SEQ ID NO:) |
| | ***CGCTCTGCTGCTGGGGCCGCCGCCCTGGCTTTGACCGTGGACCTGCCACCCGCCTCC***<br>***TCCGAGGCTCGGAACTCGGCCTCGGTTTCCAGGGCCGCTTGCTGCACCTGAGTGCCG***<br>***GCCAGCGCCTGGGCGTCCATCTTCACACTGAGGCCAGGGCACGCCATGCCTGGCAGC***<br>***TTACCCAGGGCGCCACAGTCTTGGGACTCTTCCGGGTGACCCCCGAAATCCCAGCCG***<br>***GACTCCCTTCACCGAGGTCGGAATAA***<br>(SEQ ID NO: 247)<br>>Artificial Sequence; *Tfr2*-**h41BBL**, Amino Acid<br>*MERLWGLFQRAQQLSPRSSQTVYQRVEGPRKGHLEEEEEDGEEGAETLAHFCPMELR*<br>*GPEPLGSRPRQPNLIPWAAAGRRAAPYLVLTALLIFTGAFLLGYVAFRGS***ACPWAVS**<br>**GARASPGSAASPRLRGPELSPDDPAGLLDLRQGMFAQLVAQNVLLIDGPLSWYSDPG**<br>**LAGVSLTGGLSYKEDTKELVVAKAGVYYVFFQLELRRVVAGEGSGSVSLALHLQPLR**<br>**SAAGAAALALTVDLPPASSEARNSAFGFQGRLLHLSAGQRLGVHLHTEARARHAWQL**<br>**TQGATVLGLFRVTPEIPAGLPSPRSE**<br>(SEQ ID NO: 248) |
| CD9tm3-h41BBL | >Artificial Sequence; *CD9tm3*-**h41BBL**, DNA<br>*ATGGGCTGCTGCGGGGCTGTGCAGGAGTCCCAGTGCATGCTGGGACTGTTCTTCGGC*<br>*TTCCTCTTGGTGATATTCGCCATTGAAATAGCTGCGGCCATCTGGGGATATTCCCAC*<br>*AAGGATGAG***GCCTGCCCCTGGGCCGTGTCCGGGGCTCGCGCCTCGCCCGGCTCCGCG**<br>**GCCAGCCCGAGACTCCGCGAGGGTCCCGAGCTTTCGCCCGACGATCCCGCCGGCCTC**<br>**TTGGACCTGCGGCAGGGCATGTTTGCGCAGCTGGTGGCCCAAAATGTTCTGCTGATC**<br>**GATGGGCCCCTGAGCTGGTACAGTGACCCAGGCCTGGCAGGCGTGTCCCTGACGGGG**<br>**GGCCTGAGCTACAAAGAGGACACGAAGGAGCTGGTGGTGGCCAAGGCTGGAGTCTAC**<br>**TATGTCTTCTTTCAACTAGAGCTGCGGCGCGTGGTGGCCGGCGAGGGCTCAGGCTCC**<br>**GTTTCACTTGCGCTGCACCTGCAGCCACTGCGCTCTGCTGCTGGGGCCGCCGCCCTG**<br>**GCTTTGACCGTGGACCTGCCACCCGCCTCCTCCGAGGCTCGGAACTCGGCCTTCGGT**<br>**TTCCAGGGCCGCTTGCTGCACCTGAGTGCCGGCCAGCGCCTGGGCGTCCATCTTCAC**<br>**ACTGAGGCCAGGGCACGCCATGCCTGGCAGCTTACCCAGGGCGCCACAGTCTTGGGA**<br>**CTCTTCCGGGTGACCCCCGAAATCCCAGCCGGACTCCCTTCACCGAGGTCGGAATAA**<br>(SEQ ID NO: 249)<br>>Artificial Sequence; *CD9tm3*-**h41BBL**, Amino Acid<br>*MGCCGAVQESQCMLGLFFGFLLVIFAIEIAAAIWGYSHKDE***ACPWAVSGARASPGSA**<br>**ASPRLREGPELSPDDPAGLLDLRQGMFAQLVAQNVLLIDGPLSWYSDPGLAGVSLTG**<br>**GLSYKEDTKELVVAKAGVYYVFFQLELRRVVAGEGSGSVSLALHLQPLRSAAGAAAL**<br>**ALTVDLPPASSEARNSAFGFQGRLLHLSAGQRLGVHLHTEARARHAWQLTQGATVLG**<br>**LFRVTPEIPAGLPSPRSE**<br>(SEQ ID NO: 250) |
| Myr/Palm-4F2-h41BBL | >Artificial Sequence; *Myr/Palm-4F2*-**h41BBL**, DNA<br>*ATGGGTTGCTGTTTCTCCAAGACC*GGCTCGAGOGGC*AGCCAGGACACCGAGGTGGAT*<br>*ATGAAGGAGGTGGAGCTGAATGAGTTAGAGCCCGAGAAGCAGCCGATGAACGCGGCG*<br>*TCTGGGGCGGCCATGTCCCTGGCGGGAGCCGAGAAGAATGGTCTGGTGAAGATCAAG*<br>*GTGGCGGAAGACGAGGCGGAGGCGGCAGCCGCGGCTAAGTTCACGGGCCTGTCCAAG*<br>*GAGGAGCTGCTGAAGGTGGCAGGCAGCCCCGGCTGGGTACGCACCCGCTGGGCACTG*<br>*CTGCTGCTCTTCTGGCTCGGCTGGCTCGGCATGCTTGCTGGTGCCGTGGTCATAATC*<br>*GTG***GCCTGCCCCTGGGCCGTGTCCGGGGCTCGCGCCTCGCCCGGCTCCGCGGCCAGC**<br>**CCGAGACTCCGCGAGGGTCCCGAGCTTTCGCCCGACGATCCCGCCGGCCTCTTGGAC**<br>**CTGCGGCAGGGCATGTTTGCGCAGCTGGTGGCCCAAAATGTTCTGCTGATCGATGGG**<br>**CCCCTGAGCTGGTACAGTGACCCAGGCCTGGCAGGCGTGTCCCTGACGGGGGGCCTG**<br>**AGCTACAAAGAGGACACGAAGGAGCTGGTGGTGGCCAAGGCTGGAGTCTACTATGTC**<br>**TTCTTTCAACTAGAGCTGCGGCGCGTGGTGGCCGGCGAGGGCTCAGGCTCCGTTTCA**<br>**CTTGCGCTGCACCTGCAGCCACTGCGCTCTGCTGCTGGGGCCGCCGCCCTGGCTTTG**<br>**ACCGTGGACCTGCCACCCGCCTCCTCCGAGGCTCGGAACTCGGCCTTCGGTTTCCAG**<br>**GGCCGCTTGCTGCACCTGAGTGCCGGCCAGCGCCTGGGCGTCCATCTTCACACTGAG**<br>**GCCAGGGCACGCCATGCCTGGCAGCTTACCCAGGGCGCCACAGTCTTGGGACTCTTC**<br>**CGGGTGACCCCCGAAATCCCAGCCGGACTCCCTTCACCGAGGTCGGAATAA**<br>(SEQ ID NO: 251)<br>>Artificial Sequence; *Myr/Palm-4F2*-**h41BBL**, Amino Acid<br>*MGCCFSKT*GSSG*SQDTEVDMKEVELNELEPEKQPMNAASGAAMSLAGAEKNGLVKIK*<br>*VAEDEAEAAAAAKFTGLSKEELLKVAGSPGWVRTRWALLLLFWLGWLGMLAGAVVII*<br>*V***ACPWAVSGARASPGSAASPRLREGPELSPDDPAGLLDLRQGMFAQLVAQNVLLIDG**<br>**PLSWYSDPGLAGVSLTGGLSYKEDTKELVVAKAGVYYVFFQLELRRVVAGEGSGSVS**<br>**LALHLQPLRSAAGAAALALTVDLPPASSEARNSAFGFQGRLLHLSAGQRLGVHLHTE**<br>**ARARHAWQLTQGATVLGLFRVTPEIPAGLPSPRSE**<br>(SEQ ID NO: 252) |
| Myr/Palm-Link-41BBL (41BBL transmembrane domain included) | >Artificial Sequence; Myr/Palm-Link-**41BBL**, DNA<br>*ATGGGTTGCTGTTTCTCCAAGACC*GGCTCGAGCGGC**TGGGCCCTGGTCGCGGGGCTG**<br>**CTGCTGCTGCTGCTGCTCGCTGCCGCCTGCGCCGTCTTCCTCGCCTGCCCCTGGGCC**<br>**GTGTCCGGGGCTCGCGCCTCGCCCGGCTCCGCGGCCAGCCCGAGACTCCGCGAGGGT**<br>**CCCGAGCTTTCGCCCGACGATCCCGCCGGCCTCTTGGACCTGCGGCAGGGCATGTTT**<br>**GCGCAGCTGGTGGCCCAAAATGTTCTGCTGATCGATGGGCCCCTGAGCTGGTACAGT**<br>**GACCCAGGCCTGGCAGGCGTGTCCCTGACGGGGGGCCTGAGCTACAAAGAGGACACG**<br>**AAGGAGCTGGTGGTGGCCAAGGCTGGAGTCTACTATGTCTTCTTTCAACTAGAGCTG**<br>**CGGCGCGTGGTGGCCGGCGAGGGCTCAGGCTCCGTTTCACTTGCGCTGCACCTGCAG** |

TABLE 4-continued

Full Length Constructs

| Fusion Polypeptide | Nucleic Acid Sequence (SEQ ID NO:)<br>Amino Acid Sequence (SEQ ID NO:) |
|---|---|
| | CCACTGCGCTCTGCTGCTGGGGCCGCCGCCCTGGCTTTGACCGTGGACCTGCCACCC<br>GCCTCCTCCGAGGCTCGGAACTCGGCCTTCGGTTTCCAGGGCCGCTTGCTGCACCTG<br>AGTGCCGGCCAGCGCCTGGGCGTCCATCTTCACACTGAGGCCAGGGCACGCCATGCC<br>TGGCAGCTTACCCAGGGCGCCACAGTCTTGGGACTCTTCCGGGTGACCCCCGAAATC<br>CCAGCCGGACTCCCTTCACCGAGGTCGGAATAA<br>(SEQ ID NO: 253)<br>>Artificial Sequence; *Myr/Palm*-Link-**41BBL**, Amino Acid<br>*MGCCFSKT*GSSG**WALVAGLLLLLLLAAACAVFLACPWAVSGARASPGSAASPRLREG**<br>**PELSPDDPAGLLDLRQGMFAQLVAQNVLLIDGPLSWYSDPGLAGVSLTGGLSYKEDT**<br>**KELVVAKAGVYYVFFQLELRRVVAGEGSGSVSLALHLQPLRSAAGAAALALTVDLPP**<br>**ASSEARNSAFGFQGRLLHLSAGQRLGVHLHTEARARHAWQLTQGATVLGLFRVTPEI**<br>**PAGLPSPRSE**<br>(SEQ ID NO: 254) |
| hPDL1-Link-GPI | >Artificial Sequence; **hPDL1**-Link-*GPI*, DNA<br>**ATGAGGATATTTGCTGTCTTTATATTCATGACCTACTGGCATTTGCTGAACGCATTT**<br>**ACTGTCACGGTTCCCAAGGACCTATATGTGGTAGAGTATGGTAGCAATATGACAATT**<br>**GAATGCAAATTCCCAGTAGAAAAACAATTAGACCTGGCTGCACTAATTGTCTATTGG**<br>**GAAATGGAGGATAAGAACATTATTCAATTTGTGCATGGAGAGGAAGACCTGAAGGTT**<br>**CAGCATAGTAGCTACAGACAGAGGGCCCGGCTGTTGAAGGACCAGCTCTCCCTGGGA**<br>**AATGCTGCACTTCAGATCACAGATGTGAAATTGCAGGATGCAGGGGTGTACCGCTGC**<br>**ATGATCAGCTATGGTGGTGCCGACTACAAGCGAATTACTGTGAAAGTCAATGCCCCA**<br>**TACAACAAAATCAACCAAAGAATTTTGGTTGTGGATCCAGTCACCTCTGAACATGAA**<br>**CTGACATGTCAGGCTGAGGGCTACCCCAAGGCCGAAGTCATCTGGACAAGCAGTGAC**<br>**CATCAAGTCCTGAGTGGTAAGACCACCACCACCAATTCCAAGAGAGAGGAGAAGCTT**<br>**TTCAANGTGACCAGCACACTGAGAATCAACACAACAACTAATGAGATTTTCTACTGC**<br>**ACTTTTAGGAGATTAGATCCTGAGGAAAACCATACAGCTGAATTG**GGCTCGAGCGGC<br>*CCAAATAAAGGAAGTGGAACCACTTCAGGTACTACCCGTCTTCTATCTGGGCACACG*<br>*TGTTTCACGTTGACAGGTTTGCTTGGGACGCTAGTAACCATGGGCTTGCTGACTTAG*<br>(SEQ ID NO: 255)<br>>Artificial Sequence; **hPDL1**-Link-*GPI*, Amino Acid<br>**MRIFAVFIFMTYWHLLNAFTVTVPKDLYVVEYGSNMTIECKFPVEKQLDLAALIVYW**<br>**EMEDKNIIQFVHGEEDLKVQHSSYRQRARLLKDQLSLGNAALQITDVKLQDAGVYRC**<br>**MISYGGADYKRITVKVNAPYNKINQRILVVDPVTSEHELTCQAEGYPKAEVIWTSSD**<br>**HQVLSGKTTTTNSKREEKLFNVTSTLRINTTTNEIFYCTFRRLDPEENHTAEL**GSSG<br>*PNKGSGTTSGTTRLLSGHTCFTLTGLLGTLVTMGLLT*<br>(SEQ ID NO: 256) |
| hSecPDL1-<br>CD9tm2 | >Artificial Sequence; **hSecPDL1**-*CD9tm2*, DNA<br>**ATGAGGATATTTGCTGTCTTTATATTCATGACCTACTGGCATTTGCTGAACGCATTT**<br>**ACTGTCACGGTTCCCAAGGACCTATATGTGGTAGAGTATGGTAGCAATATGACAATT**<br>**GAATGCAAATTCCCAGTAGAAAAACAATTAGACCTGGCTGCACTAATTGTCTATTGG**<br>**GAAATGGAGGATAAGAACATTATTCAATTTGTGCATGGAGAGGAAGACCTGAAGGTT**<br>**CAGCATAGTAGCTACAGACAGAGGGCCCGGCTGTTGAAGGACCAGCTCTCCCTGGGA**<br>**AATGCTGCACTTCAGATCACAGATGTGAAATTGCAGGATGCAGGGGTGTACCGCTGC**<br>**ATGATCAGCTATGGTGGTGCCGACTACAAGCGAATTACTGTGAAAGTCAATGCCCCA**<br>**TACAACAAAATCAACCAAAGAATTTTGGTTGTGGATCCAGTCACCTCTGAACATGAA**<br>**CTGACATGTCAGGCTGAGGGCTACCCCAAGGCCGAAGTCATCTGGACAAGCAGTGAC**<br>**CATCAAGTCCTGAGTGGTAAGACCACCACCACCAATTCCAAGAGAGAGGAGAAGCTT**<br>**TTCAATGTGACCAGCACACTGAGAATCAACACAACAACTAATGAGATTTTCTACTGC**<br>**ACTTTTAGGAGATTAGATCCTGAGGAAAACCATACAGCTGAATTGGTCATCCCAGGT**<br>**AATATTCTGAATGTGTCCATTAAAATATGTCTAACACTGTCCCCTAGCACC***TTCTAC*<br>*ACAGGAGTCTATATTCTGATCGGAGCCGGCGCCCTCATGATGCTGGTGGGCTTCCTG*<br>*GGCTGCTGCGGGGCTGTGCAGGAGTCCCAGTGCTAG*<br>(SEQ ID NO: 257)<br>>Artificial Sequence; **hSecPDL1**-*CD9tm2*, Amino Acid<br>**MRIFAVFIFMTYWHLLNAFTVTVPKDLYVVEYGSNMTIECKFPVEKQLDLAALIVYW**<br>**EMEDKNIIQFVHGEEDLKVQHSSYRQRARLLKDQLSLGNAALQITDVKLQDAGVYRC**<br>**MISYGGADYKRITVKVNAPYNKINQRILVVDPVTSEHELTCQAEGYPKAEVIWTSSD**<br>**HQVLSGKTTTTNSKREEKLFNVTSTLRINTTTNEIFYCTFRRLDPEENHTAELVIPG**<br>**NILNVSIKICLTLSPST***FYTGVYILIGAGALMMLVGFLGCCGAVQESQC*<br>(SEQ ID NO: 258) |
| hSecPDL1-<br>CD9tm2-<br>modified KRAS | >Artificial Sequence; hSecPDL1-*CD9tm2*-*KRAS*, DNA<br>**ATGAGGATATTTGCTGTCTTTATATTCATGACCTACTGGCATTTGCTGAACGCATTT**<br>**ACTGTCACGGTTCCCAAGGACCTATATGTGGTAGAGTATGGTAGCAATATGACAATT**<br>**GAATGCAAATTCCCAGTAGAAAAACAATTAGACCTGGCTGCACTAATTGTCTATTGG**<br>**GAAATGGAGGATAAGAACATTATTCAATTTGTGCATGGAGAGGAAGACCTGAAGGTT**<br>**CAGCATAGTAGCTACAGACAGAGGGCCCGGCTGTTGAAGGACCAGCTCTCCCTGGGA**<br>**AATGCTGCACTTCAGATCACAGATGTGAAATTGCAGGATGCAGGGGTGTACCGCTGC**<br>**ATGATCAGCTATGGTGGTGCCGACTACAAGCGAATTACTGTGAAAGTCAATGCCCCA**<br>**TACAACAAAATCAACCAAAGAATTTTGGTTGTGGATCCAGTCACCTCTGAACATGAA**<br>**CTGACATGTCAGGCTGAGGGCTACCCCAAGGCCGAAGTCATCTGGACAAGCAGTGAC**<br>**CATCAAGTCCTGAGTGGTAAGACCACCACCACCAATTCCAAGAGAGAGGAGAAGCTT**<br>**TTCAATGTGACCAGCACACTGAGAATCAACACAACAACTAATGAGATTTTCTACTGC** |

TABLE 4-continued

| Full Length Constructs | |
|---|---|
| Fusion Polypeptide | Nucleic Acid Sequence (SEQ ID NO:)<br>Amino Acid Sequence (SEQ ID NO:) |
| | **ACTTTTAGGAGATTAGATCCTGAGGAAAACCATACAGCTGAATTGGTCATCCCAGGT**<br>**AATATTCTGAATGTGTCCATTAAAATATGTCTAACACTGTCCCCTAGCACC***TTCTAC*<br>*ACAGGAGTCTATATTCTGATCGGAGCCGGCGCCCTCATGATGCTGGTGGGCTTCCTG*<br>*GGCTGCTGCGGGGCTGTGCAGGAGTCCCAGTGCAAAAAGAAGAAAAAGAAGTCAAAG*<br>*ACAAAGTGTGTAATTATGTAA*<br>(SEQ ID NO: 259)<br>>Artificial Sequence; **hSecPDL1**-*CD9tm2-KRAS*, Amino Acid<br>**MRIFAVFIFMTYWHLLNAFTVTVPKDLYVVEYGSNMTIECKFPVEKQLDLAALIVYW**<br>**EMEDKNIIQFVHGEEDLKVQHSSYRQRARLLKDQLSLGNAALQITDVKLQDAGVYRC**<br>**MISYGGADYKRITVKVNAPYNKINQRILVVDPVTSEHELTCQAEGYPKAEVIWTSSD**<br>**HQVLSGKTTTTNSKREEKLFNVTSTLRINTTTNEIFYCTFRRLDPEENHTAELVIPG**<br>**NILNVSIKICLTLSPST***FYTGVYILIGAGALMMLVGFLGCCGAVQESQCKKKKKKSK*<br>*TKCVIM*<br>(SEQ ID NO: 260) |
| hSecPDL1-CD9tm4 | >Artificial Sequence; **hSecPDL1**-*CD9tm4*, DNA<br>**ATGAGGATATTTGCTGTCTTTATATTCATGACCTACTGGCATTTGCTGAACGCATTT**<br>**ACTGTCACGGTTCCCAAGGACCTATATGTGGTAGAGTATGGTAGCAATATGACAATT**<br>**GAATGCAAATTCCCAGTAGAAAAACAATTAGACCTGGCTGCACTAATTGTCTATTGG**<br>**GAAATGGAGGATAAGAACATTATTCAATTTGTGCATGGAGAGGAAGACCTGAAGGTT**<br>**CAGCATAGTAGCTACAGACAGAGGGCCCGGCTGTTGAAGGACCAGCTCTCCCTGGGA**<br>**AATGCTGCACTTCAGATCACAGATGTGAAATTGCAGGATGCAGGGGTGTACCGCTGC**<br>**ATGATCAGCTATGGTGGTGCCGACTACAAGCGAATTACTGTGAAAGTCAATGCCCCA**<br>**TACAACAAAATCAACCAAAGAATTTTGGTTGTGGATCCAGTCACCTCTGAACATGAA**<br>**CTGACATGTCAGGCTGAGGGCTACCCCAAGGCCGAAGTCATCTGGACAAGCAGTGAC**<br>**CATCAAGTCCTGAGTGGTAAGACCACCACCACCAATTCCAAGAGAGAGGAGAAGCTT**<br>**TTCAATGTGACCAGCACACTGAGAATCAACACAACAACTAATGAGATTTTCTACTGC**<br>**ACTTTTAGGAGATTAGATCCTGAGGAAAACCATACAGCTGAATTGGTCATCCCAGGT**<br>**AATATTCTGAATGTGTCCATTAAAATATGTCTAACACTGTCCCCTAGCACC***ATCGGC*<br>*GCAGTGGGCATCGGCATTGCCGTGGTCATGATATTTGGCATGATCTTCAGTATGATC*<br>*TTGTGCTGTGCTATCCGCAGGAACCGCGAGATGGTCTAG*<br>(SEQ ID NO: 261)<br>>Artificial Sequence; **hSecPDL1**-*CD9tm4*, Amino Acid<br>**MRIFAVFIFMTYWHLLNAFTVTVPKDLYVVEYGSNMTIECKFPVEKQLDLAALIVYW**<br>**EMEDKNIIQFVHGEEDLKVQHSSYRQRARLLKDQLSLGNAALQITDVKLQDAGVYRC**<br>**MISYGGADYKRITVKVNAPYNKINQRILVVDPVTSEHELTCQAEGYPKAEVIWTSSD**<br>**HQVLSGKTTTTNSKREEKLFNVTSTIAINTTTNEIFYCTFRRLDPEENHTAELVIPG**<br>**NILNVSIKICLTLSPST***IGAVGIGIAVVMIFGMIFSMILCCAIRRNREMV*<br>(SEQ ID NO: 262) |
| hSecPDL1-CD81 | >Artificial Sequence; **hSecPDL1**-*CD81*, DNA<br>**ATGAGGATATTTGCTGTCTTTATATTCATGACCTACTGGCATTTGCTGAACGCATTT**<br>**ACTGTCACGGTTCCCAAGGACCTATATGTGGTAGAGTATGGTAGCAATATGACAATT**<br>**GAATGCAAATTCCCAGTAGAAAAACAATTAGACCTGGCTGCACTAATTGTCTATTGG**<br>**GAAATGGAGGATAAGAACATTATTCAATTTGTGCATGGAGAGGAAGACCTGAAGGTT**<br>**CAGCATAGTAGCTACAGACAGAGGGCCCGGCTGTTGAAGGACCAGCTCTCCCTGGGA**<br>**AATGCTGCACTTCAGATCACAGATGTGAAATTGCAGGATGCAGGGGTGTACCGCTGC**<br>**ATGATCAGCTATGGTGGTGCCGACTACAAGCGAATTACTGTGAAAGTCAATGCCCCA**<br>**TACAACAAAATCAACCAAAGAATTTTGGTTGTGGATCCAGTCACCTCTGAACATGAA**<br>**CTGACATGTCAGGCTGAGGGCTACCCCAAGGCCGAAGTCATCTGGACAAGCAGTGAC**<br>**CATCAAGTCCTGAGTGGTAAGACCACCACCACCAATTCCAAGAGAGAGGAGAAGCTT**<br>**TTCAATGTGACCAGCACACTGAGAATCAACACAACAACTAATGAGATTTTCTACTGC**<br>**ACTTTTAGGAGATTAGATCCTGAGGAAAACCATACAGCTGAATTGGTCATCCCAGGT**<br>**AATATTCTGAATGTGTCCATTAAAATATGTCTAACACTGTCCCCTAGCACC***CTGTAC*<br>*CTCATCGGCATTGCTGCCATCGTGGTCGCTGTGATCATGATCTTCGAGATGATCCTG*<br>*AGCATGGTGCTGTGCTGTGGCATCCGGAACAGCTCCGTGTACTGA*<br>(SEQ ID NO: 263)<br>>Artificial Sequence; **hSecPDL1**-*CD81*, Amino Acid<br>**MRIFAVFIFMTYWHLLNAFTVTVPKDLYVVEYGSNMTIECKFPVEKQLDLAALIVYW**<br>**EMEDKNIIQFVHGEEDLKVQHSSYRQRARLLKDQLSLGNAALQITDVKLQDAGVYRC**<br>**MISYGGADYKRITVKVNAPYNKINQRILVVDPVTSEHELTCQAEGYPKAEVIWTSSD**<br>**HQVLSGKTTTTNSKREEKLFNVTSTLRINTTTNEIFYCTFRRLDPEENHTAELVIPG**<br>**NILNVSIKICLTLSPST***LYLIGIAAIVVAVIMIFEMILSMVLCCGIRNSSVY*<br>(SEQ ID NO: 264) |
| hCD200-Fc-GPI | >Artificial Sequence; **hCD200**-Fc-*GPI*, DNA<br>**ATGGAGAGGCTGGTGATCAGGATGCCCTTCTCTCATCTGTCTACCTACAGCCTGGTT**<br>**TGGGTCATGGCAGCAGTGGTGCTGTGCACAGCACAAGTGCAAGTGGTGACCCAGGAT**<br>**GAAAGAGAGCAGCTGTACACACCTGCTTCCTTAAAATGCTCTCTGCAAAATGCCCAG**<br>**GAAGCCCTCATTGTGACATGGCAGAAAAAGAAAGCTGTAAGCCCAGAAAACATGGTC**<br>**ACCTTCAGCGAGAACCATGGGGTGGTGATCCAGCCTGCCTATAAGGACAAGATAAAC**<br>**ATTACCCAGCTGGGACTCCAAAACTCAACCATCACCTTCTGGAATATCACCCTGGAG**<br>**GATGAAGGGTGTTACATGTGTCTCTTCAATACCTTTGGTTTTGGGAAGATCTCAGGA**<br>**ACGGCCTGCCTCACCGTCTATGTACAGCCCATAGTATCCCTTCACTACAAATTCTCT**<br>**GAAGACCACCTAAATATCACTTGCTCTGCCACTGCCCGCCCAGCCCCCATGGTCTTC** |

TABLE 4-continued

| Full Length Constructs | |
|---|---|
| Fusion Polypeptide | Nucleic Acid Sequence (SEQ ID NO:)<br>Amino Acid Sequence (SEQ ID NO:) |
| | **TGGAAGGTCCCTCGGTCAGGGATTGAAAATAGTACAGTGACTCTGTCTCACCCAAAT**<br>**GGGACCACGTCTGTTACCAGCATCCTCCATATCAAAGACCCTAAGAATCAGGTGGGG**<br>**AAGGAGGTGATCTGCCAGGTGCTGCACCTGGGGACTGTGACCGACTTTAAGCAAACC**<br>**GTCAACAAAGGC**ATCGATGACAAAACTCACACATGCCCACCGTGCCCAGCACCTGAA<br>CTCCTGGGGGGACCGTCAGTCTTCCTCTTCCCCCCAAAACCCAAGGACACCCTCATG<br>ATCTCCCGGACCCCTGAGGTCACATGCGTGGTGGTGGACGTGAGCCACGAAGACCCT<br>GAGGTCAAGTTCAACTGGTACGTGGACGGCGTGGAGGTGCATAATGCCAAGACAAAG<br>CCGCGGGAGGAGCAGTACAACAGCACGTACCGTGTGGTCAGCGTCCTCACCGTCCTG<br>CACCAGGACTGGCTGAATGGCAAGGAGTACAAGTGCAAGGTCTCCAACAAAGCCCTC<br>CCAGCCCCCATCGAGAAAACCATCTCCAAAGCCAAAGGGCAGCCCCGAGAACCACAG<br>GTGTACACCCTGCCCCCATCCCGGGAGGAGATGACCAAGAACCAGGTCAGCCTGACC<br>TGCCTGGTCAAAGGCTTCTATCCCAGCGACATCGCCGTGGAGTGGGAGAGCAATGGG<br>CAGCCGGAGAACAACTACAAGACCACGCCTCCCGTGCTGGACTCCGACGGCTCCTTC<br>TTCCTCTACAGCAAGCTCACCGTGGACAAGAGCAGGTGGCAGCAGGGGAACGTCTTC<br>TCATGCTCCGTGATGCACGAGGCTCTGCACAACCACTACACGCAGAAGAGCCTCTCC<br>CTGTCTCCGGGTAAAATCGAT*CCAAATAAAGGAAGTGGAACCACTTCAGGTACTACC*<br>*CGTCTTCTATCTGGGCACACGTGTTTCACGTTGACAGGTTTGCTTGGGACGCTAGTA*<br>*ACCATGGGCTTGCTGACTTAG*<br>(SEQ ID NO: 265)<br>>Artificial Sequence; **hCD200**-Fc-*GPI*, Amino Acid<br>**MERLVIRMPFSHLSTYSLVWVMAAVVLCTAQVQVVTQDEREQLYTPASLKCSLQNAQ**<br>**EALIVTWQKKKAVSPENMVTFSENHGVVIQPAYKDKINITQLGLQNSTITFWNITLE**<br>**DEGCYMCLFNTFGFGKISGTACLTVYVQPIVSLHYKFSEDHLNITCSATARPAPMVF**<br>**WKVPRSGIENSTVTLSHPNGTTSVTSILHIKDPKNQVGKEVICQVLHLGTVTDFKQT**<br>**VNKG**IDDKTHTCPPCPAPELLGGPSVFLFPPKPKDTLMISRTPEVTCVVVDVSHEDP<br>EVKFNWYVDGVEVHNAKTKPREEQYNSTYRVVSVLTVLHQDWLNGKEYKCKVSNKAL<br>PAPIEKTISKAKGQPREPQVYTLPPSREEMTKNQVSLTCLVKGFYPSDIAVEWESNG<br>QPENNYKTTPPVLDSDGSFFLYSKLTVDKSRWQQGNVFSCSVMHEALHNHYTQKSLS<br>LSPGKID*PNKGSGTTSGTTRLLSGHTCFTLTGLLGTLVTMGLLT*<br>(SEQ ID NO: 266) |
| hFGL1-GPI | >Artificial Sequence; **hFGL1**-*GPI*, DNA<br>**ATGGCAAAGGTGTTCAGTTTCATCCTTGTTACCACCGCTCTGACAATGGGCAGGGAA**<br>**ATTTCGGCGCTCGAGGACTGTGCCCAGGAGCAGATGCGGCTCAGAGCCCAGGTGCGC**<br>**CTGCTTGAGACCCGGGTCAAACAGCAACAGGTCAAGATCAAGCAGCTTTTGCAGGAG**<br>**AATGAAGTCCAGTTCCTTGATAAAGGAGATGAGAATACTGTCATTGATCTTGGAAGC**<br>**AAGAGGCAGTATGCAGATTGTTCAGAGATTTTCAATGATGGGTATAAGCTCAGTGGA**<br>**TTTTACAAAATCAAACCTCTCCAGAGCCCAGCAGAATTTTCTGTTTATTGTGACATG**<br>**TCCGATGGAGGAGGATGGACTGTAATTCAGAGACGATCTGATGGCAGTGAAAACTTT**<br>**AACAGAGGATGGAAAGACTATGAAAATGGCTTTGGAAATTTTGTCCAAAAACATGGT**<br>**GAATATTGGCTGGGCAATAAAAATCTTCACTTCTTGACCACTCAAGAAGACTACACT**<br>**TTAAAAATCGACCTTGCAGATTTTGAAAAAAATAGCCGTTATGCACAATATAAGAAT**<br>**TTCAAAGTTGGAGATGAAAAGAATTTCTACGAGTTGAATATTGGGGAATATTCTGGA**<br>**ACAGCTGGAGATTCCCTTGCGGGGAATTTTCATCCTGAGGTGCAGTGGTGGGCTAGT**<br>**CACCAAAGAATGAAATTCAGCACGTGGGACAGAGATCATGACAACTATGAAGGGAAC**<br>**TGCGCAGAAGAAGATCAGTCTGGCTGGTGGTTTAACAGGTGTCACTCTGCAAACCTG**<br>**AATGGTGTATACTACAGCGGCCCCTACACGGCTAAAACAGACAATGGGATTGTCTGG**<br>**TACACCTGGCATGGGTGGTGGTATTCTCTGAAATCTGTGGTTATGAAAATTAGGCCA**<br>**AATGATTTTATTCCAAATGTAATT***CCAAATAAAGGAAGTGGAACCACTTCAGGTACT*<br>*ACCCGTCTTCTATCTGGGCACACGTGTTTCACGTTGACAGGTTTGCTTGGGACGCTA*<br>*GTAACCATGGGCTTGCTGACTTAG*<br>(SEQ ID NO: 267)<br>>Artificial Sequence; **hFGL1**-*GPI*, Amino Acid<br>**MAKVFSFILVTTALTMGREISALEDCAQEQMRLRAQVRLLETRVKQQQVKIKQLLQE**<br>**NEVQFLDKGDENTVIDLGSKRQYADCSEIFNDGYKLSGFYKIKPLQSPAEFSVYCDM**<br>**SDGGGWTVIQRRSDGSENFNRGWKDYENGFGNFVQKHGEYWLGNKNLHFLTTQEDYT**<br>**LKIDLADFEKNSRYAQYKNFKVGDEKNFYELNIGEYSGTAGDSLAGNFHPEVQWWAS**<br>**HQRMKFSTWDRDHDNYEGNCAEEDQSGWWFNRCHSANLNGVYYSGPYTAKTDNGIVW**<br>**YTWHGWWYSLKSVVMKIRPNDFIPNVI***PNKGSGTTSGTTRLLSGHTCFTLTGLLGTL*<br>*VTMGLLT*<br>(SEQ ID NO: 268) |
| hGal9-Fc-GPI | >Artificial Sequence; **hGal9**-Fc-*GPI*, DNA<br>**ATGGCCTTCAGCGGTTCCCAGGCTCCCTACCTGAGTCCAGCTGTCCCCTTTTCTGGG**<br>**ACTATTCAAGGAGGTCTCCAGGACGGACTTCAGATCACTGTCAATGGGACCGTTCTC**<br>**AGCTCCAGTGGAACCAGGTTTGCTGTGAACTTTCAGACTGGCTTCAGTGGAAATGAC**<br>**ATTGCCTTCCACTTCAACCCTCGGTTTGAAGATGGAGGGTACGTGGTGTGCAACACG**<br>**AGGCAGAACGGAAGCTGGGGGCCCGAGGAGAGGAAGACACACATGCCTTTCCAGAAG**<br>**GGGATGCCCTTTGACCTCTGCTTCCTGGTGCAGAGCTCAGATTTCAAGGTGATGGTG**<br>**AACGGGATCCTCTTCGTGCAGTACTTCCACCGCGTGCCCTTCCACCGTGTGGACACC**<br>**ATCTCCGTCAATGGCTCTGTGCAGCTGTCCTACATCAGCTTCCAGAACCCCCGCACA**<br>**GTCCCTGTTCAGCCTGCCTTCTCCACGGTGCCGTTCTCCCAGCCTGTCTGTTTCCCA**<br>**CCCAGGCCCAGGGGGCGCAGACAAAAACCTCCCGGCGTGTGGCCTGCCAACCCGGCT**<br>**CCCATTACCCAGACAGTCATCCACACAGTGCAGAGCGCCCCTGGACAGATGTTCTCT**<br>**ACTCCCGCCATCCCACCTATGATGTACCCCCACCCCGCCTATCCGATGCCTTTCATC** |

TABLE 4-continued

| Full Length Constructs | |
|---|---|
| Fusion Polypeptide | Nucleic Acid Sequence (SEQ ID NO:)<br>Amino Acid Sequence (SEQ ID NO:) |
| | **ACCACCATTCTGGGAGGGCTGTACCCATCCAAGTCCATCCTCCTGTCAGGCACTGTC**<br>**CTGCCCAGTGCTCAGAGGTTCCACATCAACCTGTGCTCTGGGAACCACATCGCCTTC**<br>**CACCTGAACCCCCGTTTTGATGAGAATGCTGTGGTCCGCAACACCCAGATCGACAAC**<br>**TCCTGGGGGTCTGAGGAGCGAAGTCTGCCCCGAAAAATGCCCTTCGTCCGTGGCCAG**<br>**AGCTTCTCAGTGTGGATCTTGTGTGAAGCTCACTGCCTCAAGGTGGCCGTGGATGGT**<br>**CAGCACCTGTTTGAATACTACCATCGCCTGAGGAACCTGCCCACCATCAACAGACTG**<br>**GAAGTGGGGGGCGACATCCAGCTGACCCATGTGCAGACA**ATCGATGACAAAACTCAC<br>ACATGCCCACCGTGCCCAGCACCTGAACTCCTGGGGGGACCGTCAGTCTTCCTCTTC<br>CCCCCAAAACCCAAGGACACCCTCATGATCTCCCGGACCCCTGAGGTCACATGCGTG<br>GTGGTGGACGTGAGCCACGAAGACCCTGAGGTCAAGTTCAACTGGTACGTGGACGGC<br>GTGGAGGTGCATAATGCCAAGACAAAGCCGCGGGAGGAGCAGTACAACAGCACGTAC<br>CGTGTGGTCAGCGTCCTCACCGTCCTGCACCAGGACTGGCTGAATGGCAAGGAGTAC<br>AAGTGCAAGGTCTCCAACAAAGCCCTCCCAGCCCCCATCGAGAAAACCATCTCCAAA<br>GCCAAAGGGCAGCCCCGAGAACCACAGGTGTACACCCTGCCCCCATCCCGGGAGGAG<br>ATGACCAAGAACCAGGTCAGCCTGACCTGCCTGGTCAAAGGCTTCTATCCCAGCGAC<br>ATCGCCGTGGAGTGGGAGAGCAATGGGCAGCCGGAGAACAACTACAAGACCACGCCT<br>CCCGTGCTGGACTCCGACGGCTCCTTCTTCCTCTACAGCAAGCTCACCGTGGACAAG<br>AGCAGGTGGCAGCAGGGGAACGTCTTCTCATGCTCCGTGATGCACGAGGCTCTGCAC<br>AACCACTACACGCAGAAGAGCCTCTCCCTGTCTCCGGGTAAAATCGAT*CCAAATAAA*<br>*GGAAGTGGAACCACTTCAGGTACTACCCGTCTTCTATCTGGGCACACGTGTTTCACG*<br>*TTGACAGGTTTGCTTGGGACGCTAGTAACCATGGGCTTGCTGACTTAG*<br>(SEQ ID NO: 269)<br>>Artificial Sequence; **hGal9**-Fc-*GPI*, Amino Acid<br>**MAFSGSQAPYLSPAVPFSGTIQGGLQDGLQITVNGTVLSSSGTRFAVNFQTGFSGND**<br>**IAFHFNPRFEDGGYVVCNTRQNGSWGPEERKTHMPFQKGMPFDLCFLVQSSDFKVMV**<br>**NGILFVQYFHRVPFHRVDTISVNGSVQLSYISFQNPRTVPVQPAFSTVPFSQPVCFP**<br>**PRPRGRRQKPPGVWPANPAPITQTVIHTVQSAPGQMFSTPAIPPMMYPHPAYPMPFI**<br>**TTILGGLYPSKSILLSGTVLPSAQRFHINLCSGNHIAFHLNPRFDENAVVRNTQIDN**<br>**SWGSEERSLPRKMPFVRGQSFSVWILCEAHCLKVAVDGQHLFEYYHRLRNLPTINRL**<br>**EVGGDIQLTHVQT**IDDKTHTCPPCPAPELLGGPSVFLFPPKPKDTLMISRTPEVTCV<br>VVDVSHEDPEVKFNWYVDGVEVHNAKTKPREEQYNSTYRVVSVLTVLHQDWLNGKEY<br>KCKVSNKALPAPIEKTISKAKGQPREPQVYTLPPSREEMTKNQVSLTCLVKGFYPSD<br>IAVEWESNGQPENNYKTTPPVLDSDGSFFLYSKLTVDKSRWQQGNVFSCSVMHEALH<br>NHYTQKSLSLSPGKID*PNKGSGTTSGTTRLLSGHTCFTLTGLLGTLVTMGLLT*<br>(SEQ ID NO: 270) |
| hCD200-GPI | >Artificial Sequence; **hCD200**-*GPI*, DNA<br>**ATGGAGAGGCTGGTGATCAGGATGCCCTTCTCTCATCTGTCTACCTACAGCCTGGTT**<br>**TGGGTCATGGCAGCAGTGGTGCTGTGCACAGCACAAGTGCAAGTGGTGACCCAGGAT**<br>**GAAAGAGAGCAGCTGTACACACCTGCTTCCTTAAAATGCTCTCTGCAAAATGCCCAG**<br>**GAAGCCCTCATTGTGACATGGCAGAAAAAGAAAGCTGTAAGCCCAGAAAACATGGTC**<br>**ACCTTCAGCGAGAACCATGGGGTGGTGATCCAGCCTGCCTATAAGGACAAGATAAAC**<br>**ATTACCCAGCTGGGACTCCAAAACTCAACCATCACCTTCTGGAATATCACCCTGGAG**<br>**GATGAAGGGTGTTACATGTGTCTCTTCAATACCTTTGGTTTTGGGAAGATCTCAGGA**<br>**ACGGCCTGCCTCACCGTCTATGTACAGCCCATAGTATCCCTTCACTACAAATTCTCT**<br>**GAAGACCACCTAAATATCACTTGCTCTGCCACTGCCCGCCCAGCCCCCATGGTCTTC**<br>**TGGAAGGTCCCTCGGTCAGGGATTGAAAATAGTACAGTGACTCTGTCTCACCCAAAT**<br>**GGGACCACGTCTGTTACCAGCATCCTCCATATCAAAGACCCTAAGAATCAGGTGGGG**<br>**AAGGAGGTGATCTGCCAGGTGCTGCACCTGGGGACTGTGACCGACTTTAAGCAAACC**<br>**GTCAACAAAGGC***CCAAATAAAGGAAGTGGAACCACTTCAGGTACTACCCGTCTTCTA*<br>*TCTGGGCACACGTGTTTCACGTTGACAGGTTTGCTTGGGACGCTAGTAACCATGGGC*<br>*TTGCTGACTTAG*<br>(SEQ ID NO: 271)<br>>Artificial Sequence; **hCD200**-*GPI*, Amino Acid<br>**MERLVIRMPFSHLSTYSLVWVMAAVVLCTAQVQVVTQDEREQLYTPASLKCSLQNAQ**<br>**EALIVTWQKKKAVSPENMVTFSENHGVVIQPAYKDKINITQLGLQNSTITFWNITLE**<br>**DEGCYMCLFNTFGFGKISGTACLTVYVQPIVSLHYKFSEDHLNITCSATARPAPMVF**<br>**WKVPRSGIENSTVTLSHPNGTTSVTSILHIKDPKNQVGKEVICQVLHLGTVTDFKQT**<br>**VNKG***PNKGSGTTSGTTRLLSGHTCFTLTGLLGTLVTMGLLT*<br>(SEQ ID NO: 272) |
| hGal9-GPI | >Artificial Sequence; **hGal9**-*GPI*, DNA<br>**ATGGCCTTCAGCGGTTCCCAGGCTCCCTACCTGAGTCCAGCTGTCCCCTTTTCTGGG**<br>**ACTATTCAAGGAGGTCTCCAGGACGGACTTCAGATCACTGTCAATGGGACCGTTCTC**<br>**AGCTCCAGTGGAACCAGGTTTGCTGTGAACTTTCAGACTGGCTTCAGTGGAAATGAC**<br>**ATTGCCTTCCACTTCAACCCTCGGTTTGAAGATGGAGGGTACGTGGTGTGCAACACG**<br>**AGGCAGAACGGAAGCTGGGGGCCCGAGGAGAGGAAGACACACATGCCTTTCCAGAAG**<br>**GGGATGCCCTTTGACCTCTGCTTCCTGGTGCAGAGCTCAGATTTCAAGGTGATGGTG**<br>**AACGGGATCCTCTTCGTGCAGTACTTCCACCGCGTGCCCTTCCACCGTGTGGACACC**<br>**ATCTCCGTCAATGGCTCTGTGCAGCTGTCCTACATCAGCTTCCAGAACCCCCGCACA**<br>**GTCCCTGTTCAGCCTGCCTTCTCCACGGTGCCGTTCTCCCAGCCTGTCTGTTTCCCA**<br>**CCCAGGCCCAGGGGGCGCAGACAAAAACCTCCCGGCGTGTGGCCTGCCAACCCGGCT**<br>**CCCATTACCCAGACAGTCATCCACACAGTGCAGAGCGCCCCTGGACAGATGTTCTCT**<br>**ACTCCCGCCATCCCACCTATGATGTACCCCCACCCCGCCTATCCGATGCCTTTCATC**<br>**ACCACCATTCTGGGAGGGCTGTACCCATCCAAGTCCATCCTCCTGTCAGGCACTGTC** |

TABLE 4-continued

| Full Length Constructs | |
|---|---|
| Fusion Polypeptide | Nucleic Acid Sequence (SEQ ID NO:)<br>Amino Acid Sequence (SEQ ID NO:) |
| | **CTGCCCAGTGCTCAGAGGTTCCACATCAACCTGTGCTCTGGGAACCACATCGCCTTC**<br>**CACCTGAACCCCCGTTTTGATGAGAATGCTGTGGTCCGCAACACCCAGATCGACAAC**<br>**TCCTGGGGGTCTGAGGAGCGAAGTCTGCCCCGAAAAATGCCCTTCGTCCGTGGCCAG**<br>**AGCTTCTCAGTGTGGATCTTGTGTGAAGCTCACTGCCTCAAGGTGGCCGTGGATGGT**<br>**CAGCACCTGTTTGAATACTACCATCGCCTGAGGAACCTGCCCACCATCAACAGACTG**<br>**GAAGTGGGGGGCGACATCCAGCTGACCCATGTGCAGACA***CCAAATAAAGGAAGTGGA*<br>*ACCACTTCAGGTACTACCCGTCTTCTATCTGGGCACACGTGTTTCACGTTGACAGGT*<br>*TTGCTTGGGACGCTAGTAACCATGGGCTTGCTGACTTAG*<br>(SEQ ID NO: 273)<br>>Artificial Sequence; **hGal9**-*GPI*, Amino Acid<br>**MAFSGSQAPYLSPAVPFSGTIQGGLQDGLQITVNGTVLSSSGTRFAVNFQTGFSGND**<br>**IAFHFNPRFEDGGYVVCNTRQNGSWGPEERKTHMPFQKGMPFDLCFLVQSSDFKVMV**<br>**NGILFVQYFHRVPFHRVDTISVNGSVQLSYISFQNPRTVPVQPAFSTVPFSQPVCFP**<br>**PRPRGRRQKPPGVWPANPAPITQTVIHTVQSAPGQMPSTPAIPPMMYPHPAYPMPFI**<br>**TTILGGLYPSKSILLSGTVLPSAQRFHINLCSGNHIAFHLNPRFDENAVVRNTQIDN**<br>**SWGSEERSLPRKMPFVRGQSFSVWILCEAHCLKVAVDGQHLFEYYHRLRNLPTINRL**<br>**EVGGDIQLTHVQT***PNKGSGTTSGTTRLLSGHTCFTLTGLLGTLVTMGLLT*<br>(SEQ ID NO: 274) |
| hHVEM-GPI | >Artificial Sequence; **hHVEM**-*GPI*, DNA<br>***ATGGAGCCTCCTGGAGACTGGGGGCCTCCTCCCTGGAGATCCACCCCCAAAACCGAC***<br>***GTCTTGAGGCTGGTGCTGTATCTCACCTTCCTGGGAGCCCCCTGCTACGCCCCAGCT***<br>***CTGCCGTCCTGCAAGGAGGACGAGTACCCAGTGGGCTCCGAGTGCTGCCCCAAGTGC***<br>***AGTCCAGGTTATCGTGTGAAGGAGGCCTGCGGGGAGCTGACGGGCACAGTGTGTGAA***<br>***CCCTGCCCTCCAGGCACCTACATTGCCCACCTCAATGGCCTAAGCAAGTGTCTGCAG***<br>***TGCCAAATGTGTGACCCAGCCATGGGCCTGCGCGCGAGCCGGAACTGCTCCAGGACA***<br>***GAGAACGCCGTGTGTGGCTGCAGCCCAGGCCACTTCTGCATCGTCCAGGACGGGGAC***<br>***CACTGCGCCGCGTGCCGCGCTTACGCCACCTCCAGCCCGGGCCAGAGGGTGCAGAAG***<br>***GGAGGCACCGAGAGTCAGGACACCCTGTGTCAGAACTGCCCCCCGGGGACCTTCTCT***<br>***CCCAATGGGACCCTGGAGGAATGTCAGCACCAGACCAAGTGCAGCTGGCTGGTGACG***<br>***AAGGCCGGAGCTGGGACCAGCAGCTCCCACTGGGTA***<br>*CCAAATAAAGGAAGTGGAACC*<br>*ACTTCAGGTACTACCCGTCTTCTATCTGGGCACACGTGTTTCACGTTGACAGGTTTG*<br>*CTTGGGACGCTAGTAACCATGGGCTTGCTGACTTAG*<br>(SEQ ID NO: 275)<br>>Artificial Sequence; **hHVEM**-*GPI*, Amino Acid<br>**MEPPGDWGPPPWRSTPKTDVLRLVLYLTFLGAPCYAPALPSCKEDEYPVGSECCPKC**<br>**SPGYRVKEACGELTGTVCEPCPPGTYIAHLNGLSKCLQCQMCDPAMGLRASRNCSRT**<br>**ENAVCGCSPGHFCIVQDGDHCAACRAYATSSPGQRVQKGGTESQDTLCQNCPPGTFS**<br>**PNGTLEECQHQTKCSWLVTKAGAGTSSSHWV***PNKGSGTTSGTTRLLSGHTCFTLTGL*<br>*LGTLVTMGLLT*<br>(SEQ ID NO: 276) |
| hPDL2-GPI | >Artificial Sequence; **hPDL2**-*GPI*, DNA<br>**ATGATCTTCCTCCTGCTAATGTTGAGCCTGGAATTGCAGCTTCACCAGATAGCAGCT**<br>**TTATTCACAGTGACAGTCCCTAAGGAACTGTACATAATAGAGCATGGCAGCAATGTG**<br>**ACCCTGGAATGCAACTTTGACACTGGAAGTCATGTGAACCTTGGAGCAATAACAGCC**<br>**AGTTTGCAAAAGGTGGAAAATGATACATCCCCACACCGTGAAAGAGCCACTTTGCTG**<br>**GAGGAGCAGCTGCCCCTAGGGAAGGCCTCGTTCCACATACCTCAAGTCCAAGTGAGG**<br>**GACGAAGGACAGTACCAATGCATAATCATCTATGGGGTCGCCTGGGACTACAAGTAC**<br>**CTGACTCTGAAAGTCAAAGCTTCCTACAGGAAAATAAACACTCACATCCTAAAGGTT**<br>**CCAGAAACAGATGAGGTAGAGCTCACCTGCCAGGCTACAGGTTATCCTCTGGCAGAA**<br>**GTATCCTGGCCAAACGTCAGCGTTCCTGCCAACACCAGCCACTCCAGGACCCCTGAA**<br>**GGCCTCTACCAGGTCACCAGTGTTCTGCGCCTAAAGCCACCCCCTGGCAGAAACTTC**<br>**AGCTGTGTGTTCTGGAATACTCACGTGAGGGAACTTACTTTGGCCAGCATTGACCTT**<br>**CAAAGTCAGATGGAACCCAGGACCCATCCAACT***CCAAATAAAGGAAGTGGAACCACT*<br>*TCAGGTACTACCCGTCTTCTATCTGGGCACACGTGTTTCACGTTGACAGGTTTGCTT*<br>*GGGACGCTAGTAACCATGGGCTTGCTGACTTAG*<br>(SEQ ID NO: 277)<br>>Artificial Sequence; **hPDL2**-*GPI*, Amino Acid<br>**MIFLLLMLSLELQLHQIAALFTVTVPKELYIIEHGSNVTLECNFDTGSHVNLGAITA**<br>**SLQKVENDTSPHRERATLLEEQLPLGKASFHIPQVQVRDEGQYQCIIIYGVAWDYKY**<br>**LTLKVKASYRKINTHILKVPETDEVELTCQATGYPLAEVSWPNVSVPANTSHSRTPE**<br>**GLYQVTSVLRLKPPPGRNFSCVFWNTHVRELTLASIDLQSQMEPRTHPT***PNKGSGTT*<br>*SGTTRLLSGHTCFTLTGLLGTLVTMGLLT*<br>(SEQ ID NO: 278) |
| hTSG6-GPI | >Artificial Sequence; **hTSG6**-*GPI*, DNA<br>**ATGATCATCTTAATTTACTTATTTCTCTTGCTATGGGAAGACACTCAAGGATGGGGA**<br>**TTCAAGGATGGAATTTTTCATAACTCCATATGGCTTGAACGAGCAGCCGGTGTGTAC**<br>**CACAGAGAAGCACGGTCTGGCAAATACAAGCTCACCTACGCAGAAGCTAAGGCGGTG**<br>**TGTGAATTTGAAGGCGGCCATCTCGCAACTTACAAGCAGCTAGAGGCAGCCAGAAAA**<br>**ATTGGATTTCATGTCTGTGCTGCTGGATGGATGGCTAAGGGCAGAGTTGGATACCCC**<br>**ATTGTGAAGCCAGGGCCCAACTGTGGATTTGGAAAAACTGGCATTATTGATTATGGA**<br>**ATCCGTCTCAATAGGAGTGAAAGATGGGATGCCTATTGCTACAACCCACACGCAAAG**<br>**GAGTGTGGTGGCGTCTTTACAGATCCAAAGCAAATTTTTAAATCTCCAGGCTTCCCA** |

TABLE 4-continued

Full Length Constructs

| Fusion Polypeptide | Nucleic Acid Sequence (SEQ ID NO:)<br>Amino Acid Sequence (SEQ ID NO:) |
|---|---|
| | AATGAGTACGAAGATAACCAAATCTGCTACTGGCACATTAGACTCAAGTATGGTCAG<br>CGTATTCACCTGAGTTTTTTAGATTTTGACCTTGAAGATGACCCAGGTTGCTTGGCT<br>GATTATGTTGAAATATATGACAGTTACGATGATGTCCATGGCTTTGTGGGAAGATAC<br>TGTGGAGATGAGCTTCCAGATGACATCATCAGTACAGGAAATGTCATGACCTTGAAG<br>TTTCTAAGTGATGCTTCAGTGACAGCTGGAGGTTTCCAAATCAAATATGTTGCAATG<br>GATCCTGTATCCAAATCCAGTCAAGGAAAAAATACAAGTACTACTTCTACTGGAAAT<br>AAAAACTTTTTAGCTGGAAGATTTAGCCACTTAATCGATCCAAATAAAGGAAGTGGA<br>ACCACTTCAGGTACTACCCGTCTTCTATCTGGGCACACGTGTTTCACGTTGACAGGT<br>TTGCTTGGGACGCTAGTAACCATGGGCTTGCTGACTTAG<br>(SEQ ID NO: 279)<br>>Artificial Sequence; **hTSG6**-*GPI*, Amino Acid<br>MIILIYLFLLLWEDTQGWGFKDGIFHNSIWLERAAGVYHREARSGKYKLTYAEAKAV<br>CEFEGGHLATYKQLEAARKIGFHVCAAGWMAKGRVGYPIVKPGPNCGFGKTGIIDYG<br>IRLNRSERWDAYCYNPHAKECGGVFTDPKQIFKSPGFPNEYEDNQICYWHIRLKYGQ<br>RIHLSFLDFDLEDDPGCLADYVEIYDSYDDVHGFVGRYCGDELPDDIISTGNVMTLK<br>FLSDASVTAGGFQIKYVAMDPVSKSSQGKNTSTTSTGNKNFLAGRFSHLIDPNKGSG<br>TTSGTTRLLSGHTCFTLTGLLGTLVTMGLLT<br>(SEQ ID NO: 280) |
| hHVEM-Fc-GPI | >Artificial Sequence; **hHVEM**-Fc-*GPI*, DNA<br>ATGGAGCCTCCTGGAGACTGGGGGCCTCCTCCCTGGAGATCCACCCCCAAAACCGAC<br>GTCTTGAGGCTGGTGCTGTATCTCACCTTCCTGGGAGCCCCCTGCTACGCCCCAGCT<br>CTGCCGTCCTGCAAGGAGGACGAGTACCCAGTGGGCTCCGAGTGCTGCCCCAAGTGC<br>AGTCCAGGTTATCGTGTGAAGGAGGCCTGCGGGGAGCTGACGGGCACAGTGTGTGAA<br>CCCTGCCCTCCAGGCACCTACATTGCCCACCTCAATGGCCTAAGCAAGTGTCTGCAG<br>TGCCAAATGTGTGACCCAGCCATGGGCCTGCGCGCGAGCCGGAACTGCTCCAGGACA<br>GAGAACGCCGTGTGTGGCTGCAGCCCAGGCCACTTCTGCATCGTCCAGGACGGGGAC<br>CACTGCGCCGCGTGCCGCGCTTACGCCACCTCCAGCCCGGGCCAGAGGGTGCAGAAG<br>GGAGGCACCGAGAGTCAGGACACCCTGTGTCAGAACTGCCCCCCGGGGACCTTCTCT<br>CCCAATGGGACCCTGGAGGAATGTCAGCACCAGACCAAGTGCAGCTGGCTGGTGACG<br>AAGGCCGGAGCTGGGACCAGCAGCTCCCACTGGGTAATCGATGACAAAACTCACACA<br>TGCCCACCGTGCCCAGCACCTGAACTCCTGGGGGGACCGTCAGTCTTCCTCTTCCCC<br>CCAAAACCCAAGGACACCCTCATGATCTCCCGGACCCCTGAGGTCACATGCGTGGTG<br>GTGGACGTGAGCCACGAAGACCCTGAGGTCAAGTTCAACTGGTACGTGGACGGCGTG<br>GAGGTGCATAATGCCAAGACAAAGCCGCGGGAGGAGCAGTACAACAGCACGTACCGT<br>GTGGTCAGCGTCCTCACCGTCCTGCACCAGGACTGGCTGAATGGCAAGGAGTACAAG<br>TGCAAGGTCTCCAACAAAGCCCTCCCAGCCCCCATCGAGAAAACCATCTCCAAAGCC<br>AAAGGGCAGCCCCGAGAACCACAGGTGTACACCCTGCCCCCATCCCGGGAGGAGATG<br>ACCAAGAACCAGGTCAGCCTGACCTGCCTGGTCAAAGGCTTCTATCCCAGCGACATC<br>GCCGTGGAGTGGGAGAGCAATGGGCAGCCGGAGAACAACTACAAGACCACGCCTCCC<br>GTGCTGGACTCCGACGGCTCCTTCTTCCTCTACAGCAAGCTCACCGTGGACAAGAGC<br>AGGTGGCAGCAGGGGAACGTCTTCTCATGCTCCGTGATGCACGAGGCTCTGCACAAC<br>CACTACACGCAGAAGAGCCTCTCCCTGTCTCCGGGTAAAATCGATCCAAATAAAGGA<br>AGTGGAACCACTTCAGGTACTACCCGTCTTCTATCTGGGCACACGTGTTTCACGTTG<br>ACAGGTTTGCTTGGGACGCTAGTAACCATGGGCTTGCTGACTTAG<br>(SEQ ID NO: 281)<br>>Artificial Sequence; **hHVEM**-Fc-*GPI*, Amino Acid<br>MEPPGDWGPPPWRSTPKTDVLRLVLYLTFLGAPCYAPALPSCKEDEYPVGSECCPKC<br>SPGYRVKEACGELTGTVCEPCPPGTYIAHLNGLSKCLQCQMCDPAMGLRASRNCSRT<br>ENAVCGCSPGHFCIVQDGDHCAACRAYATSSPGQRVQKGGTESQDTLCQNCPPGTFS<br>PNGTLEECQHQTKCSWLVTKAGAGTSSSHWVIDDKTHTCPPCPAPELLGGPSVFLFP<br>PKPKDTLMISRTPEVTCVVVDVSHEDPEVKFNWYVDGVEVHNAKTKPREEQYNSTYR<br>VVSVLTVLHQDWLNGKEYKCKVSNKALPAPIEKTISKAKGQPREPQVYTLPPSREEM<br>TKNQVSLTCLVKGFYPSDIAVEWESNGQPENNYKTTPPVLDSDGSFFLYSKLTVDKS<br>RWQQGNVFSCSVMHEALHNHYTQKSLSLSPGKIDPNKGSGTTSGTTRLLSGHTCFTL<br>TGLLGTLVTMGLLT<br>(SEQ ID NO: 282) |
| hPDL1-GPI-P2A-<br>hHVEM-GPI | >Artificial Sequence; **hPDL1**-*GPI*-P2A-**hHVEM**-*GPI*, DNA<br>ATGAGGATATTTGCTGTCTTTATATTCATGACCTACTGGCATTTGCTGAACGCATTT<br>ACTGTCACGGTTCCCAAGGACCTATATGTGGTAGAGTATGGTAGCAATATGACAATT<br>GAATGCAAATTCCCAGTAGAAAAACAATTAGACCTGGCTGCACTAATTGTCTATTGG<br>GAAATGGAGGATAAGAACATTATTCAATTTGTGCATGGAGAGGAAGACCTGAAGGTT<br>CAGCATAGTAGCTACAGACAGAGGGCCCGGCTGTTGAAGGACCAGCTCTCCCTGGGA<br>AATGCTGCACTTCAGATCACAGATGTGAAATTGCAGGATGCAGGGGTGTACCGCTGC<br>ATGATCAGCTATGGTGGTGCCGACTACAAGCGAATTACTGTGAAAGTCAATGCCCCA<br>TACAACAAAATCAACCAAAGAATTTTGGTTGTGGATCCAGTCACCTCTGAACATGAA<br>CTGACATGTCAGGCTGAGGGCTACCCCAAGGCCGAAGTCATCTGGACAAGCAGTGAC<br>CATCAAGTCCTGAGTGGTAAGACCACCACCACCAATTCCAAGAGAGAGGAGAAGCTT<br>TTCAATGTGACCAGCACACTGAGAATCAACACAACAACTAATGAGATTTTCTACTGC<br>ACTTTTAGGAGATTAGATCCTGAGGAAAACCATACAGCTGAATTGGTCATCCCAGAA<br>CTACCTCTGGCACATCCTCCAAATGAAAGGCCAAATAAAGGAAGTGGAACCACTTCA<br>GGTACTACCCGTCTTCTATCTGGGCACACGTGTTTCACGTTGACAGGTTTGCTTGGG<br>ACGCTAGTAACCATGGGCTTGCTGACTGGAAGCGGAGCTACTAACTTCAGCCTGCTG<br>AAGCAGGCTGGCGACGTGGAGGAGAACCCTGGACCTATGGAGCCTCCTGGAGACTGG |

TABLE 4-continued

| Full Length Constructs | |
|---|---|
| Fusion Polypeptide | Nucleic Acid Sequence (SEQ ID NO:)<br>Amino Acid Sequence (SEQ ID NO:) |
| | GGGCCTCCTCCCTGGAGATCCACCCCCAAAACCGACGTCTTGAGGCTGGTGCTGTAT<br>CTCACCTTCCTGGGAGCCCCCTGCTACGCCCCAGCTCTGCCGTCCTGCAAGGAGGAC<br>GAGTACCCAGTGGGCTCCGAGTGCTGCCCCAAGTGCAGTCCAGGTTATCGTGTGAAG<br>GAGGCCTGCGGGGAGCTGACGGGCACAGTGTGTGAACCCTGCCCTCCAGGCACCTAC<br>ATTGCCCACCTCAATGGCCTAAGCAAGTGTCTGCAGTGCCAAATGTGTGACCCAGCC<br>ATGGGCCTGCGCGCGAGCCGGAACTGCTCCAGGACAGAGAACGCCGTGTGTGGCTGC<br>AGCCCAGGCCACTTCTGCATCGTCCAGGACGGGGACCACTGCGCCGCGTGCCGCGCT<br>TACGCCACCTCCAGCCCGGGCCAGAGGGTGCAGAAGGGAGGCACCGAGAGTCAGGAC<br>ACCCTGTGTCAGAACTGCCCCCCGGGGACCTTCTCTCCCAATGGGACCCTGGAGGAA<br>TGTCAGCACCAGACCAAGTGCAGCTGGCTGGTGACGAAGGCCGGAGCTGGGACCAGC<br>AGCTCCCACTGGGTA*CCAAATAAAGGAAGTGGAACCACTTCAGGTACTACCCGTCTT*<br>*CTATCTGGGCACACGTGTTTCACGTTGACAGGTTTGCTTGGGACGCTAGTAACCATG*<br>*GGCTTGCTGACTTAG*<br>(SEQ ID NO: 283)<br>>Artificial Sequence; **hPDL1**-*GPI*-P2A-**hHVEM**-*GPI*, Amino Acid<br>MRIFAVFIFMTYWHLLNAFTVTVPKDLYVVEYGSNMTIECKFPVEKQLDLAALIVYW<br>EMEDKNIIQFVHGEEDLKVQHSSYRQRARLLKDQLSLGNAALQITDVKLQDAGVYRC<br>MISYGGADYKRITVKVNAPYNKINQRILVVDPVTSEHELTCQAEGYPKAEVIWTSSD<br>HQVLSGKTTTTNSKREEKLFNVTSTLRINTTTNEIFYCTFRRLDPEENHTAELVIPE<br>LPLAHPPNER*PNKGSGTTSGTTRLLSGHTCFTLTGLLGTLVTMGLLTGS*GATNFSLL<br>KQAGDVEENPGPMEPPGDWGPPPWRSTPKTDVLRLVLYLTFLGAPCYAPALPSCKED<br>EYPVGSECCPKCSPGYRVKEACGELTGTVCEPCPPGTYIAHLNGLSKCLQCQMCDPA<br>MGLRASRNCSRTENAVCGCSPGHFCIVQDGDHCAACRAYATSSPGQRVQKGGTESQD<br>TLCQNCPPGTFSPNGTLEECQHQTKCSWINTKAGAGTSSSHWV*PNKGSGTTSGTTRL*<br>*LSGHTCFTLTGLLGTLVTMGLLT*<br>(SEQ ID NO: 284) |
| mCTLA4-Fc-GPI | >Artificial Sequence; **mCTLA4**-Fc-*GPI*, DNA<br>ATGGCTTGTCTTGGACTCCGGAGGTACAAAGCTCAACTGCAGCTGCCTTCTAGGACT<br>TGGCCTTTTGTAGCCCTGCTCACTCTTCTTTTCATCCCAGTCTTCTCTGAAGCCATA<br>CAGGTGACCCAACCTTCAGTGGTGTTGGCTAGCAGCCATGGTGTCGCCAGCTTTCCA<br>TGTGAATATTCACCATCACACAACACTGATGAGGTCCGGGTGACTGTGCTGCGGCAG<br>ACAAATGACCAAATGACTGAGGTCTGTGCCACGACATTCACAGAGAAGAATACAGTG<br>GGCTTCCTAGATTACCCCTTCTGCAGTGGTACCTTTAATGAAAGCAGAGTGAACCTC<br>ACCATCCAAGGACTGAGAGCTGTTGACACGGGACTGTACCTCTGCAAGGTGGAACTC<br>ATGTACCCACCGCCATACTTTGTGGGCATGGGCAACGGGACGCAGATTTATGTCATT<br>GATCCAGAACCATGCCCGGATTCTGAATCGATGACAAAACTCACACATGCCCACCGT<br>GCCCAGCACCTGAACTCCTGGGGGGACCGTCAGTCTTCCTCTTCCCCCCAAAACCCA<br>AGGACACCCTCATGATCTCCCGGACCCCTGAGGTCACATGCGTGGTGGTGGACGTGA<br>GCCACGAAGACCCTGAGGTCAAGTTCAACTGGTACGTGGACGGCGTGGAGGTGCATA<br>ATGCCAAGACAAAGCCGCGGGAGGAGCAGTACAACAGCACGTACCGTGTGGTCAGCG<br>TCCTCACCGTCCTGCACCAGGACTGGCTGAATGGCAAGGAGTACAAGTGCAAGGTCT<br>CCAACAAAGCCCTCCCAGCCCCCATCGAGAAAACCATCTCCAAAGCCAAAGGGCAGC<br>CCCGAGAACCACAGGTGTACACCCTGCCCCCATCCCGGGAGGAGATGACCAAGAACC<br>AGGTCAGCCTGACCTGCCTGGTCAAAGGCTTCTATCCCAGCGACATCGCCGTGGAGT<br>GGGAGAGCAATGGGCAGCCGGAGAACAACTACAAGACCACGCCTCCCGTGCTGGACT<br>CCGACGGCTCCTTCTTCCTCTACAGCAAGCTCACCGTGGACAAGAGCAGGTGGCAGC<br>AGGGGAACGTCTTCTCATGCTCCGTGATGCACGAGGCTCTGCACAACCACTACACGC<br>AGAAGAGCCTCTCCCTGTCTCCGGGTAAAATCGAT*CCAAATAAAGGAAGTGGAACCA*<br>*CTTCAGGTACTACCCGTCTTCTATCTGGGCACACGTGTTTCACGTTGACAGGTTTGC*<br>*TTGGGACGCTAGTAACCATGGGCTTGCTGACTTAG*<br>(SEQ ID NO: 285)<br>>Artificial Sequence; **mCTLA4**-Fc-*GPI*, Amino Acid<br>MACLGLRRYKAQLQLPSRTWPFVALLTLLFIPVFSEAIQVTQPSVVLASSHGVASFP<br>CEYSPSHNTDEVRVTVLRQTNDQMTEVCATTFTEKNTVGFLDYPFCSGTFNESRVNL<br>TIQGLRAVDTGLYLCKVELMYPPPYFVGMGNGTQIYVIDPEPCPDSD<br>IDDKTHTCPPCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALPAPI<br>EKTISKAKGQPREPQVYTLPPSREEMTKNQVSLTCLVKGFYPSDIAVEWESNGQPEN<br>NYKTTPPVLDSDGSFFLYSKLTVDKSRWQQGNVFSCSVMHEALHNHYTQKSLSLSPG<br>KID*PNKGSGTTSGTTRLLSGHTCFTLTGLLGTLVTMGLLT*<br>(SEQ ID NO: 286) |
| mPDL1-C1C2 | >Artificial Sequence; **mPDL1**-*C1C2*, DNA<br>ATGAGGATATTTGCTGGCATTATATTCACAGCCTGCTGTCACTTGCTACGGGCGTTT<br>ACTATCACGGCTCCAAAGGACTTGTACGTGGTGGAGTATGGCAGCAACGTCACGATG<br>GAGTGCAGATTCCCTGTAGAACGGGAGCTGGACCTGCTTGCGTTAGTGGTGTACTGG<br>GAAAAGGAAGATGAGCAAGTGATTCAGTTTGTGGCAGGAGAGGAGGACCTTAAGCCT<br>CAGCACAGCAACTTCAGGGGGAGAGCCTCGCTGCCAAAGGACCAGCTTTTGAAGGGA<br>AATGCTGCCCTTCAGATCACAGACGTCAAGCTGCAGGACGCAGGCGTTTACTGCTGC<br>ATAATCAGCTACGGTGGTGCGGACTACAAGCGAATCACGCTGAAAGTCAATGCCCCA<br>TACCGCAAAATCAACCAGAGAATTTCCGTGGATCCAGCCACTTCTGAGCATGAACTA<br>ATATGTCAGGCCGAGGGTTATCCAGAAGCTGAGGTAATCTGGACAAACAGTGACCAC<br>CAACCCGTGAGTGGGAAGAGAAGTGTCACCACTTCCCGGACAGAGGGGATGCTTCTC<br>AATGTGACCAGCAGTCTGAGGGTCAACGCCACAGCGAATGATGTTTTCTACTGTACG |

TABLE 4-continued

| Full Length Constructs | |
|---|---|
| Fusion Polypeptide | Nucleic Acid Sequence (SEQ ID NO:)<br>Amino Acid Sequence (SEQ ID NO:) |
| | **TTTTGGAGATCACAGCCAGGGCAAAACCACACAGCGGAGCTGATCATCCCAGAACTG**<br>**CCTGCAACACATCCTCCACAGAACAGGACT**ATCGAT*GTCGAGCCACTGGGCATGGAG*<br>*AATGGGAACATTGCCAACTCACAGATCGCCGCCTCATCTGTGCGTGTGACCTTCTTG*<br>*GGTTTGCAGCATTGGGTCCCGGAGCTGGCCCGCCTGAACCGCGCAGGCATGGTCAAT*<br>*GCCTGGACACCCAGCAGCAATGACGATAACCCCTGGATCCAGGTGAACCTGCTGCGG*<br>*AGGATGTGGGTAACAGGTGTGGTGACGCAGGGTGCCAGCCGCTTGGCCAGTCATGAG*<br>*TACCTGAAGGCCTTCAAGGTGGCCTACAGCCTTAATGGACACGAATTCGATTTCATC*<br>*CATGATGTTAATAAAAAACACAAGGAGTTTGTGGGTAACTGGAACAAAAACGCGGTG*<br>*CATGTCAACCTGTTTGAGACCCCTGTGGAGGCTCAGTACGTGAGATTGTACCCCACG*<br>*AGCTGCCACACGGCCTGCACTCTGCGCTTTGAGCTACTGGGCTGTGAGCTGAACGGA*<br>*TGCGCCAATCCCCTGGGCCTGAAGAATAACAGCATCCCTGACAAGCAGATCACGGCC*<br>*TCCAGCAGCTACAAGACCTGGGGCTTGCATCTCTTCAGCTGGAACCCCTCCTATGCA*<br>*CGGCTGGACAAGCAGGGCAACTTCAACGCCTGGGTTGCGGGGAGCTACGGTAACGAT*<br>*CAGTGGCTGCAGATCTTCCCTGGCAACTGGGACAACCACTCCCACAAGAAGAACTTG*<br>*TTTGAGACGCCCATCCTGGCTCGCTATGTGCGCATCCTGCCTGTAGCCTGGCACAAC*<br>*CGCATCGCCCTGCGCCTGGAGCTGCTGGGCTGTTAG*<br>(SEQ ID NO: 287)<br>>Artificial Sequence; **mPDL1**-*C1C2*, Amino Acid<br>**MRIFAGIIFTACCHLLRAFTITAPKDLYVVEYGSNVTMECRFPVERELDLLALVVYW**<br>**EKEDEQVIQFVAGEEDLKPQHSNFSGRASLPKDQLLKGNAALQITDVKLQDAGVYCC**<br>**IISYGGADYKRITLKVNAPYRKINQRISVDPATSEHELICQAEGYPEAEVIWTNSDH**<br>**QPVSGKRSVTTSRTEGMLLNVTSSLRVNATANDVFYCTFWRSQPGQNHTAELIIPEL**<br>**PATHPPQNRT**ID*VEPLGMENGNIANSQIAASSVRVTFLGLQHWVPELARLNRAGMVN*<br>*AWTPSSNDDNPWIQVNLLRRMWVTGVVTQGASRLASHEYLKAFKVAYSLNGHEFDFI*<br>*HDVNKKHKEFVGNWNKNAVHVNLFETPVEAQYVRLYPTSCHTACTLRFELLGCELNG*<br>*CANPLGLKNNSIPDKQITASSSYKTWGLHLFSWNPSYARLDKQGNFNAWVAGSYGND*<br>*QWLQIFPGNWDNHSHKKNLFETPILARYVRILPVAWHNRIALRLELLGC*<br>(SEQ ID NO: 288) |
| mPDL1-Fc-GPI | >Artificial Sequence; **mPDL1**-Fc-*GPI*, DNA<br>**ATGAGGATATTTGCTGGCATTATATTCACAGCCTGCTGTCACTTGCTACGGGCGTTT**<br>**ACTATCACGGCTCCAAAGGACTTGTACGTGGTGGAGTATGGCAGCAACGTCACGATG**<br>**GAGTGCAGATTCCCTGTAGAACGGGAGCTGGACCTGCTTGCGTTAGTGGTGTACTGG**<br>**GAAAAGGAAGATGAGCAAGTGATTCAGTTTGTGGCAGGAGAGGAGGACCTTAAGCCT**<br>**CAGCACAGCAACTTCAGGGGGAGAGCCTCGCTGCCAAAGGACCAGCTTTTGAAGGGA**<br>**AATGCTGCCCTTCAGATCACAGACGTCAAGCTGCAGGACGCAGGCGTTTACTGCTGC**<br>**ATAATCAGCTACGGTGGTGCGGACTACAAGCGAATCACGCTGAAAGTCAATGCCCCA**<br>**TACCGCAAAATCAACCAGAGAATTTCCGTGGATCCAGCCACTTCTGAGCATGAACTA**<br>**ATATGTCAGGCCGAGGGTTATCCAGAAGCTGAGGTAATCTGGACAAACAGTGACCAC**<br>**CAACCCGTGAGTGGGAAGAGAAGTGTCACCACTTCCCGGACAGAGGGGATGCTTCTC**<br>**AATGTGACCAGCAGTCTGAGGGTCAACGCCACAGCGAATGATGTTTTCTACTGTACG**<br>**TTTTGGAGATCACAGCCAGGGCAAAACCACACAGCGGAGCTGATCATCCCAGAACTG**<br>**CCTGCAACACATCCTCCACAGAACAGGACT**ATCGATGACAAAACTCACACATGCCCA<br>CCGTGCCCAGCACCTGAACTCCTGGGGGGACCGTCAGTCTTCCTCTTCCCCCCAAAA<br>CCCAAGGACACCCTCATGATCTCCCGGACCCCTGAGGTCACATGCGTGGTGGTGGAC<br>GTGAGCCACGAAGACCCTGAGGTCAAGTTCAACTGGTACGTGGACGGCGTGGAGGTG<br>CATAATGCCAAGACAAAGCCGCGGGAGGAGCAGTACAACAGCACGTACCGTGTGGTC<br>AGCGTCCTCACCGTCCTGCACCAGGACTGGCTGAATGGCAAGGAGTACAAGTGCAAG<br>GTCTCCAACAAAGCCCTCCCAGCCCCCATCGAGAAAACCATCTCCAAAGCCAAAGGG<br>CAGCCCCGAGAACCACAGGTGTACACCCTGCCCCCATCCCGGGAGGAGATGACCAAG<br>AACCAGGTCAGCCTGACCTGCCTGGTCAAAGGCTTCTATCCCAGCGACATCGCCGTG<br>GAGTGGGAGAGCAATGGGCAGCCGGAGAACAACTACAAGACCACGCCTCCCGTGCTG<br>GACTCCGACGGCTCCTTCTTCCTCTACAGCAAGCTCACCGTGGACAAGAGCAGGTGG<br>CAGCAGGGGAACGTCTTCTCATGCTCCGTGATGCACGAGGCTCTGCACAACCACTAC<br>ACGCAGAAGAGCCTCTCCCTGTCTCCGGGTAAAATCGAT*CCAAATAAAGGAAGTGGA*<br>*ACCACTTCAGGTACTACCCGTCTTCTATCTGGGCACACGTGTTTCACGTTGACAGGT*<br>*TTGCTTGGGACGCTAGTAACCATGGGCTTGCTGACTTAG*<br>(SEQ ID NO: 289)<br>>Artificial Sequence; **mPDL1**-Fc-*GPI*, Amino Acid<br>**MRIFAGIIFTACCHLLRAFTITAPKDLYVVEYGSNVTMECRFPVERELDLLALVVYW**<br>**EKEDEQVIQFVAGEEDLKPQHSNFRGRASLPKDQLLKGNAALQITDVKLQDAGVYCC**<br>**IISYGGADYKRITLKVNAPYRKINQRISVDPATSEHELICQAEGYPEAEVIWTNSDH**<br>**QPVSGKRSVTTSRTEGMLLNVTSSLRVNATANDVPYCTFWRSQPGQNHTAELIIPEL**<br>**PATHPPQNRT**IDDKTHTCPPCPAPELLGGPSVFLFPPKPKDTLMISRTPEVTCVVVD<br>VSHEDPEVKFNWYVDGVEVHNAKTKPREEQYNSTYRVVSVLTVLHQDWLNGKEYKCK<br>VSNKALPAPIEKTISKAKGQPREPQVYTLPPSREEMTKNQVSLTCLVKGFYPSDIAV<br>EWESNGQPENNYKTTPPVLDSDGSFFLYSKLTVDKSRWQQGNVFSCSVMHEALHNHY<br>TQKSLSLSPGKID*PNKGSGTTSGTTRLLSGHTCFTLTGLLGTLVTMGLLT*<br>(SEQ ID NO: 290) |
| mPDL1-GPI | >Artificial Sequence; **mPDL1**-*GPI*, DNA<br>**ATGAGGATATTTGCTGGCATTATATTCACAGCCTGCTGTCACTTGCTACGGGCGTTT**<br>**ACTATCACGGCTCCAAAGGACTTGTACGTGGTGGAGTATGGCAGCAACGTCACGATG**<br>**GAGTGCAGATTCCCTGTAGAACGGGAGCTGGACCTGCTTGCGTTAGTGGTGTACTGG**<br>**GAAAAGGAAGATGAGCAAGTGATTCAGTTTGTGGCAGGAGAGGAGGACCTTAAGCCT** |

TABLE 4-continued

| Full Length Constructs | |
|---|---|
| Fusion Polypeptide | Nucleic Acid Sequence (SEQ ID NO:)<br>Amino Acid Sequence (SEQ ID NO:) |
| | **CAGCACAGCAACTTCAGGGGGAGAGCCTCGCTGCCAAAGGACCAGCTTTTGAAGGGA**<br>**AATGCTGCCCTTCAGATCACAGACGTCAAGCTGCAGGACGCAGGCGTTTACTGCTGC**<br>**ATAATCAGCTACGGTGGTGCGGACTACAAGCGAATCACGCTGAAAGTCAATGCCCCA**<br>**TACCGCAAAATCAACCAGAGAATTTCCGTGGATCCAGCCACTTCTGAGCATGAACTA**<br>**ATATGTCAGGCCGAGGGTTATCCAGAAGCTGAGGTAATCTGGACAAACAGTGACCAC**<br>**CAACCCGTGAGTGGGAAGAGAAGTGTCACCACTTCCCGGAZAGAGGGGATGCTTCTC**<br>**AATGTGACCAGCAGTCTGAGGGTCAACGCCACAGCGAATGATGTTTTCTACTGTACG**<br>**TTTTGGAGATCACAGCCAGGGCAAAACCACACAGCGGAGCTGATCATCCCAGAACTG**<br>**CCTGCAACACATCCTCCACAGAACAGGACT***CCAAATAAAGGAAGTGGAACCACTTCA*<br>*GGTACTACCCGTCTTCTATCTGGGCACACGTGTTTCACGTTGACAGGTTTGCTTGGG*<br>*ACGCTAGTAACCATGGGCTTGCTGACTTAG*<br>(SEQ ID NO: 291)<br>>Artificial Sequence; **mPDL1**-*GPI*, Amino Acid<br>**MRIFAGIIFTACCHLLRAFTITAPKDLYVVEYGSNVTMECRFPVERELDLLALVVYW**<br>**EKEDEQVIQFVAGEEDLKPQHSNFRGRASLPKDQLLKGNAALQITDVKLQDAGVYCC**<br>**IISYGGADYKRITLKVNAPYRKINQRISVDPATSEHELICQAEGYPEAEVIWTNSDH**<br>**QPVSGKRSVTTSRTEGMLLNVTSSLRVNATANDVFYCTFWRSQPGQNHTAELIIPEL**<br>**PATHPPQNRT***PNKGSGTTSGTTRLLSGHTCFTLTGLLGTLVTMGLLT*<br>(SEQ ID NO: 292) |
| mPDL2-C1C2 | >Artificial Sequence; **mPDL2**-*C1C2*, DNA<br>**ATGCTGCTCCTGCTGCCGATACTGAACCTGAGCTTACAACTTCATCCTGTAGCAGCT**<br>**TTATTCACCGTGACAGCCCCTAAAGAAGTGTACACCGTAGACGTCGGCAGCAGTGTG**<br>**AGCCTGGAGTGCGATTTTGACCGCAGAGAATGCACTGAACTGGAAGGGATAAGAGCC**<br>**AGTTTGCAGAAGGTAGAAAATGATACGTCTCTGCAAAGTGAAAGAGCCACCCTGCTG**<br>**GAGGAGCAGCTGCCCCTGGGAAAGGCTTTGTTCCACATCCCTAGTGTCCAAGTGAGA**<br>**GATTCCGGGCAGTACCGTTGCCTGGTCATCTGCGGGGCCGCCTGGGACTACAAGTAC**<br>**CTGACGGTGAAAGTCAAAGCTTCTTACATGAGGATAGACACTAGGATCCTGGAGGTT**<br>**CCAGGTACAGGGGAGGTGCAGCTTACCTGCCAGGCTAGAGGTTATCCCCTAGCAGAA**<br>**GTGTCCTGGCAAAATGTCAGTGTTCCTGCCAACACCAGCCACATCAGGACCCCCGAA**<br>**GGCCTCTACCAGGTCACCAGTGTTCTGCGCCTCAAGCCTCAGCCTAGCAGAAACTTC**<br>**AGCTGCATGTTCTGGAATGCTCACATGAAGGAGCTGACTTCAGCCATCATTGACCCT**<br>**CTGAGTCGGATGGAACCCAAAGTCCCCAGAACG**ATCGAT*GTCGAGCCACTGGGCATG*<br>*GAGAATGGGAACATTGCCAACTCACAGATCGCCGCCTCATCTGTGCGTGTGACCTTC*<br>*TTGGGTTTGCAGCATTGGGTCCCGGAGCTGGCCCGCCTGAACCGCGCAGGCATGGTC*<br>*AATGCCTGGACACCCAGCAGCAATGACGATAACCCCTGGATCCAGGTGAACCTGCTG*<br>*CGGAGGATGTGGGTAACAGGTGTGGTGACGCAGGGTGCCAGCCGCTTGGCCAGTCAT*<br>*GAGTACCTGAAGGCCTTCAAGGTGGCCTACAGCCTTAATGGACACGAATTCGATTTC*<br>*ATCCATGATGTTAATAAAAAACACAAGGAGTTTGTGGGTAACTGGAACAAAAACGCG*<br>*GTGCATGTCAACCTGTTTGAGACCCCTGTGGAGGCTCAGTACGTGAGATTGTACCCC*<br>*ACGAGCTGCCACACGGCCTGCACTCTGCGCTTTGAGCTACTGGGCTGTGAGCTGAAC*<br>*GGATGCGCCAATCCCCTGGGCCTGAAGAATAACAGCATCCCTGACAAGCAGATCACG*<br>*GCCTCCAGCAGCTACAAGACCTGGGGCTTGCATCTCTTCAGCTGGAACCCCTCCTAT*<br>*GCACGGCTGGACAAGCAGGGCAACTTCAACGCCTGGGTTGCGGGGAGCTACGGTAAC*<br>*GATCAGTGGCTGCAGATCTTCCCTGGCAACTGGGACAACCACTCCCACAAGAAGAAC*<br>*TTGTTTGAGACGCCCATCCTGGCTCGCTATGTGCGCATCCTGCCTGTAGCCTGGCAC*<br>*AACCGCATCGCCCTGCGCCTGGAGCTGCTGGGCTGTTAG*<br>(SEQ ID NO: 293)<br>>Artificial Sequence; **mPDL2**-*C1C2*, Amino Acid<br>**MLLLLPILNLSLQLHPVAALFTVTAPKEVYTVDVGSSVSLECDFDRRECTELEGIRA**<br>**SLQKVENDTSLQSERATLLEEQLPLGKALFHIPSVQVRDSGQYRCLVICGAAWDYKY**<br>**LTVKVKASYMRIDTRILEVPGTGEVQLTCQARGYPLAEVSWQNVSVPANTSHIRTPE**<br>**GLYQVTSVLRLKPQPSRNFSCMFWNAHMKELTSAIIDPLSRMEPKVPRT**ID*VEPLGM*<br>*ENGNIANSQIAASSVRVTFLGLQHWVPELARLNRAGMVNAWTPSSNDDNPWIQVNLL*<br>*RRMWVTGVVTQGASRLASHEYLKAFKVAYSLNGHEFDFIHDVNKKHKEFVGNWNKNA*<br>*VHVNLFETPVEAQYVRLYPTSCHTACTLRFELLGCELNGCANPLGLKNNSIPDKQIT*<br>*ASSSYKTWGLHLFSWNPSYARLDKQGNFNAWVAGSYGNDQWLQIFPGNWDNHSHKKN*<br>*LFETPILARYVRILPVAWHNRIALRLELLGC*<br>(SEQ ID NO: 294) |
| mPDL2-Fc-GPI | >Artificial Sequence; **mPDL2**-Fc-*GPI*, DNA<br>**ATGCTGCTCCTGCTGCCGATACTGAACCTGAGCTTACAACTTCATCCTGTAGCAGCT**<br>**TTATTCACCGTGACAGCCCCTAAAGAAGTGTACACCGTAGACGTCGGCAGCAGTGTG**<br>**AGCCTGGAGTGCGATTTTGACCGCAGAGAATGCACTGAACTGGAAGGGATAAGAGCC**<br>**AGTTTGCAGAAGGTAGAAAATGATACGTCTCTGCAAAGTGAAAGAGCCACCCTGCTG**<br>**GAGGAGCAGCTGCCCCTGGGAAAGGCTTTGTTCCACATCCCTAGTGTCCAAGTGAGA**<br>**GATTCCGGGCAGTACCGTTGCCTGGTCATCTGCGGGGCCGCCTGGGACTACAAGTAC**<br>**CTGACGGTGAAAGTCAAAGCTTCTTACATGAGGATAGACACTAGGATCCTGGAGGTT**<br>**CCAGGTACAGGGGAGGTGCAGCTTACCTGCCAGGCTAGAGGTTATCCCCTAGCAGAA**<br>**GTGTCCTGGCAAAATGTCAGTGTTCCTGCCAACACCAGCCACATCAGGACCCCCGAA**<br>**GGCCTCTACCAGGTCACCAGTGTTCTGCGCCTCAAGCCTCAGCCTAGCAGAAACTTC**<br>**AGCTGCATGTTCTGGAATGCTCACATGAAGGAGCTGACTTCAGCCATCATTGACCCT**<br>**CTGAGTCGGATGGAACCCAAAGTCCCCAGAACG**ATCGATGACAAAACTCACACATGC<br>CCACCGTGCCCAGCACCTGAACTCCTGGGGGGACCGTCAGTCTTCCTCTTCCCCCCA<br>AAACCCAAGGACACCCTCATGATCTCCCGGACCCCTGAGGTCACATGCGTGGTGGTG |

TABLE 4-continued

| Full Length Constructs | |
|---|---|
| Fusion Polypeptide | Nucleic Acid Sequence (SEQ ID NO:)<br>Amino Acid Sequence (SEQ ID NO:) |
| | GACGTGAGCCACGAAGACCCTGAGGTCAAGTTCAACTGGTACGTGGACGGCGTGGAG<br>GTGCATAATGCCAAGACAAAGCCGCGGGAGGAGCAGTACAACAGCACGTACCGTGTG<br>GTCAGCGTCCTCACCGTCCTGCACCAGGACTGGCTGAATGGCAAGGAGTACAAGTGC<br>AAGGTCTCCAACAAAGCCCTCCCAGCCCCCATCGAGAAAACCATCTCCAAAGCCAAA<br>GGGCAGCCCCGAGAACCACAGGTGTACACCCTGCCCCCATCCCGGGAGGAGATGACC<br>AAGAACCAGGTCAGCCTGACCTGCCTGGTCAAAGGCTTCTATCCCAGCGACATCGCC<br>GTGGAGTGGGAGAGCAATGGGCAGCCGGAGAACAACTACAAGACCACGCCTCCCGTG<br>CTGGACTCCGACGGCTCCTTCTTCCTCTACAGCAAGCTCACCGTGGACAAGAGCAGG<br>TGGCAGCAGGGGAACGTCTTCTCATGCTCCGTGATGCACGAGGCTCTGCACAACCAC<br>TACACGCAGAAGAGCCTCTCCCTGTCTCCGGGTAAAATCGAT*CCAAATAAAGGAAGT*<br>*GGAACCACTTCAGGTACTACCCGTCTTCTATCTGGGCACACGTGTTTCACGTTGACA*<br>*GGTTTGCTTGGGACGCTAGTAACCATGGGCTTGCTGACTTAG*<br>(SEQ ID NO: 295)<br>>Artificial Sequence; **mPDL2**-Fc-*GPI*, Amino Acid<br>**MLLLLPILNLSLQLHPVAALFTVTAPKEVYTVDVGSSVSLECDFDRRECTELEGIRA**<br>**SLQKVENDTSLQSERATLLEEQLPLGKALFHIPSVQVRDSGQYRCLVICGAAWDYKY**<br>**LTVKVKASYMRIDTRILEVPGTGEVQLTCQARGYPLAEVSWQNVSVPANTSHIRTPE**<br>**GLYQVTSVLRLKPQPSRNFSCMFWNAHNKELTSAIIDPLSRMEPKVPRT**IDDKTHTC<br>PPCPAPELLGGPSVFLFPPKPKDTLMISRTPEVTCVVVDVSHEDPEVKFNWYVDGVE<br>VHNAKTKPREEQYNSTYRVVSVLTVLHQDWLNGKEYKCKVSNKALPAPIEKTISKAK<br>GQPREPQVYTLPPSREEMTKNQVSLTCLVKGFYPSDIAVEWESNGQPENNYKTTPPV<br>LDSDGSFFLYSKLTVDKSRWQQGNVFSCSVMHEALHNHYTQKSLSLSPGKID*PNKGS*<br>*GTTSGTTRLLSGHTCFTLTGLLGTLVTMGLLT*<br>(SEQ ID NO: 296) |
| mPDL1-mFc-GPI | >Artificial Sequence; **mPDL1**-mFc-*GPI*, DNA<br>**ATGAGGATATTTGCTGGCATTATATTCACAGCCTGCTGTCACTTGCTACGGGCGTTT**<br>**ACTATCACGGCTCCAAAGGACTTGTACGTGGTGGAGTATGGCAGCAACGTCACGATG**<br>**GAGTGCAGATTCCCTGTAGAACGGGAGCTGGACCTGCTTGCGTTAGTGGTGTACTGG**<br>**GAAAAGGAAGATGAGCAAGTGATTCAGTTTGTGGCAGGAGAGGAGGACCTTAAGCCT**<br>**CAGCACAGCAACTTCAGGGGGAGAGCCTCGCTGCCAAAGGACCAGCTTTTGAAGGGA**<br>**AATGCTGCCCTTCAGATCACAGACGTCAAGCTGCAGGACGCAGGCGTTTACTGCTGC**<br>**ATAATCAGCTACGGTGGTGCGGACTACAAGCGAATCACGCTGAAAGTCAATGCCCCA**<br>**TACCGCAAAATCAACCAGAGAATTTCCGTGGATCCAGCCACTTCTGAGCATGAACTA**<br>**ATATGTCAGGCCGAGGGTTATCCAGAAGCTGAGGTAATCTGGACAAACAGTGACCAC**<br>**CAACCCGTGAGTGGGAAGAGAAGTGTCACCACTTCCCGGACAGAGGGGATGCTTCTC**<br>**AATGTGACCAGCAGTCTGAGGGTCAACGCCACAGCGAATGATGTTTTCTACTGTACG**<br>**TTTTGGAGATCACAGCCAGGGCAAAACCACACAGCGGAGCTGATCATCCCAGAACTG**<br>**CCTGCAACACATCCTCCACAGAACAGGACT**GGTTGTAAGCCTTGCATATGTACAGTC<br>CCAGAAGTATCATCTGTCTTCATCTTCCCCCCAAAGCCCAAGGATGTGCTCACCATT<br>ACTCTGACTCCTAAGGTCACGTGTGTTGTGGTAGACATCAGCAAGGATGATCCCGAG<br>GTCCAGTTCAGCTGGTTTGTAGATGATGTGGAGGTGCACACAGCTCAGACGCAACCC<br>CGGGAGGAGCAGTTCAACAGCACTTTCCGCTCAGTCAGTGAACTTCCCATCATGCAC<br>CAGGACTGGCTCAATGGCAAGGAGTTCAAATGCAGGGTCAACAGTGCAGCTTTCCCT<br>GCCCCCATCGAGAAAACCATCTCCAAAACCAAAGGCAGACCGAAGGCTCCACAGGTG<br>TACACCATTCCACCTCCCAAGGAGCAGATGGCCAAGGATAAAGTCAGTCTGACCTGC<br>ATGATAACAGACTTCTTCCCTGAAGACATTACTGTGGAGTGGCAGTGGAATGGGCAG<br>CCAGCGGAGAACTACAAGAACACTCAGCCCATCATGGACACAGATGGCTCTTACTTC<br>GTCTACAGCAAGCTCAATGTGCAGAAGAGCAACTGGGAGGCAGGAAATACTTTCACC<br>TGCTCTGTGTTACATGAGGGCCTGCACAACCACCATACTGAGAAGAGCCTCTCCCAC<br>TCTCCTGGTAAA*CCAAATAAAGGAAGTGGAACCACTTCAGGTACTACCCGTCTTCTA*<br>*TCTGGGCACACGTGTTTCACGTTGACAGGTTTGCTTGGGACGCTAGTAACCATGGGC*<br>*TTGCTGACTTAG*<br>(SEQ ID NO: 297)<br>>Artificial Sequence; **mPDL1**-mFc-*GPI*, Amino Acid<br>**MRIFAGIIFTACCHLLRAFTITAPKDLYVVEYGSNVTMECRFPVERELDLLALVVYW**<br>**EKEDEQVIQFVAGEEDLKPQHSNFRGRASLPKDQLLKGNAALQITDVKLQDAGVYCC**<br>**IISYGGADYKRITLKVNAPYRKINQRISVDPATSEHELICQAEGYPEAEVIWTNSDH**<br>**QPVSGKRSVTTSRTEGMLLNVTSSLRVNATANDVFYCTFWRSQPGQNHTAELIIPEL**<br>**PATHPPQNRT**GCKPCICTVPEVSSVFIFPPKPKDVLTITLTPKVTCVVVDISKDDPE<br>VQFSWFVDDVEVHTAQTQPREEQFNSTFRSVSELPIMHQDWLNGKEFKCRVNSAAFP<br>APIEKTISKTKGRPKAPQVYTIPPPKEQMAKDKVSLTCMITDFFPEDITVEWQWNGQ<br>PAENYKNTQPIMDTDGSYFVYSKLNVQKSNWEAGNTFTCSVLHEGLHNHHTEKSLSH<br>SPGK*PNKGSGTTSGTTRLLSGHTCFTLTGLLGTLVTMGLLT*<br>(SEQ ID NO: 298) |
| mPDL2-GPI | >Artificial Sequence; **mPDL2**-*GPI*, DNA<br>**ATGCTGCTCCTGCTGCCGATACTGAACCTGAGCTTACAACTTCATCCTGTAGCAGCT**<br>**TTATTCACCGTGACAGCCCCTAAAGAAGTGTACACCGTAGACGTCGGCAGCAGTGTG**<br>**AGCCTGGAGTGCGATTTTGACCGCAGAGAATGCACTGAACTGGAAGGGATAAGAGCC**<br>**AGTTTGCAGAAGGTAGAAAATGATACGTCTCTGCAAAGTGAAAGAGCCACCCTGCTG**<br>**GAGGAGCAGCTGCCCCTGGGAAAGGCTTTGTTCCACATCCCTAGTGTCCAAGTGAGA**<br>**GATTCCGGGCAGTACCGTTGCCTGGTCATCTGCGGGGCCGCCTGGGACTACAAGTAC**<br>**CTGACGGTGAAAGTCAAAGCTTCTTACATGAGGATAGACACTAGGATCCTGGAGGTT**<br>**CCAGGTACAGGGGAGGTGCAGCTTACCTGCCAGGCTAGAGGTTATCCCCTAGCAGAA** |

TABLE 4-continued

Full Length Constructs

| Fusion Polypeptide | Nucleic Acid Sequence (SEQ ID NO:)<br>Amino Acid Sequence (SEQ ID NO:) |
|---|---|
| | GTGTCCTGGCAAAATGTCAGTGTTCCTGCCAACACCAGCCACATCAGGACCCCCGAA<br>GGCCTCTACCAGGTCACCAGTGTTCTGCGCCTCAAGCCTCAGCCTAGCAGAAACTTC<br>AGCTGCATGTTCTGGAATGCTCACATGAAGGAGCTGACTTCAGCCATCATTGACCCT<br>CTGAGTCGGATGGAACCCAAAGTCCCCAGAACGCCAAATAAAGGAAGTGGAACCACT<br>TCAGGTACTACCCGTCTTCTATCTGGGCACACGTGTTTCACGTTGACAGGTTTGCTT<br>GGGACGCTAGTAACCATGGGCTTGCTGACTTAG<br>(SEQ ID NO: 299)<br>>Artificial Sequence; mPDL2-GPI, Amino Acid<br>MLLLLPILNLSLQLHPVAALFTVTAPKEVYTVDVGSSVSLECDFDRRECTELEGIRA<br>SLQKVENDTSLQSERATLLEEQLPLGKALFHIPSVQVRDSGQYRCLVICGAAWDYKY<br>LTVKVKASYMRIDTRILEVPGTGEVQLTCQARGYPLAEVSWQNVSVPANTSHIRTPE<br>GLYQVTSVLRLKPQPSRNFSCMFWNAHMKELTSAIIDPLSRMEPKVPRTPNKGSGTT<br>SGTTRLLSGHTCFTLTGLLGTLVTMGLLT<br>(SEQ ID NO: 300) |
| mPDL1-GPI-P2A-mHVEM-GPI | >Artificial Sequence; mPDL1-GPI-P2A-mHVEM-GPI, DNA<br>ATGAGGATATTTGCTGGCATTATATTCACAGCCTGCTGTCACTTGCTACGGGCGTTT<br>ACTATCACGGCTCCAAAGGACTTGTACGTGGTGGAGTATGGCAGCAACGTCACGATG<br>GAGTGCAGATTCCCTGTAGAACGGGAGCTGGACCTGCTTGCGTTAGTGGTGTACTGG<br>GAAAAGGAAGATGAGCAAGTGATTCAGTTTGTGGCAGGAGAGGAGGACCTTAAGCCT<br>CAGCACAGCAACTTCAGGGGGAGAGCCTCGCTGCCAAAGGACCAGCTTTTGAAGGGA<br>AATGCTGCCCTTCAGATCACAGACGTCAAGCTGCAGGACGCAGGCGTTTACTGCTGC<br>ATAATCAGCTACGGTGGTGCGGACTACAAGCGAATCACGCTGAAAGTCAATGCCCCA<br>TACCGCAAAATCAACCAGAGAATTTCCGTGGATCCAGCCACTTCTGAGCATGAACTA<br>ATATGTCAGGCCGAGGGTTATCCAGAAGCTGAGGTAATCTGGACAAACAGTGACCAC<br>CAACCCGTGAGTGGGAAGAGAAGTGTCACCACTTCCCGGACAGAGGGGATGCTTCTC<br>AATGTGACCAGCAGTCTGAGGGTCAACGCCACAGCGAATGATGTTTTCTACTGTACG<br>TTTTGGAGATCACAGCCAGGGCAAAACCACACAGCGGAGCTGATCATCCCAGAACTG<br>CCTGCAACACATCCTCCACAGAACAGGACTCCAAATAAAGGAAGTGGAACCACTTCA<br>GGTACTACCCGTCTTCTATCTGGGCACACGTGTTTCACGTTGACAGGTTTGCTTGGG<br>ACGCTAGTAACCATGGGCTTGCTGACTGGAAGCGGAGCTACTAACTTCAGCCTGCTG<br>AAGCAGGCTGGCGACGTGGAGGAGAACCCTGGACCTATGGAACCTCTCCCAGGATGG<br>GGGTCGGCACCCTGGAGCCAGGCCCCTACAGACAACACCTTCAGGCTGGTGCCTTGT<br>GTCTTCCTTTTGAACTTGCTGCAGCGCATCTCTGCCCAGCCCTCATGCAGACAGGAG<br>GAGTTCCTTGTGGGAGACGAGTGCTGCCCCATGTGCAACCCAGGTTACCATGTGAAG<br>CAGGTCTGCAGTGAGCATACAGGCACAGTGTGTGCCCCCTGTCCCCCACAGACATAT<br>ACCGCCCATGCAAATGGCCTGAGCAAGTGTCTGCCCTGCGGAGTCTGTGATCCAGAC<br>ATGGGCCTGCTGACCTGGCAGGAGTGCTCCAGCTGGAAGGACACTGTGTGCAGATGC<br>ATCCCAGGCTACTTCTGTGAGAACCAGGATGGGAGCCACTGTTCCACATGCTTGCAG<br>CACACCACCTGCCCTCCAGGGCAGAGGGTAGAGAAGAGAGGGACTCACGACCAGGAC<br>ACTGTATGTGCTGACTGCCTAACAGGGACCTTCTCACTTGGAGGGACTCAGGAGGAA<br>TGCCTGCCCTGGACCAACTGCAGTGCATTTCAACAGGAAGTAAGACGTGGGACCAAC<br>AGCACAGACACCACCTGCTCCTCCCAGCCAAATAAAGGAAGTGGAACCACTTCAGGT<br>ACTACCCGTCTTCTATCTGGGCACACGTGTTTCACGTTGACAGGTTTGCTTGGGACG<br>CTAGTAACCATGGGCTTGCTGACTTAG<br>(SEQ ID NO: 301)<br>>Artificial Sequence; mPDL1-GPI-P2A-mHVEM-GPI, Amino Acid<br>MRIFAGIIFTACCHLLRAFTITAPKDLYVVEYGSNVTMECRFPVERELDLLALVVYW<br>EKEDEQVIQFVAGEEDLKPQHSNFRGRASLPKDQLLKGNAALQITDVKLQDAGVYCC<br>IISYGGADYKRITLKVNAPYRKINQRISVDPATSEHELICQAEGYPEAEVIWTNSDH<br>QPVSGKRSVTTSRTEGMLLNVTSSLRVNATANDVFYCTFWRSQPGQNHTAELIIPEL<br>PATHPPQNRTPNKGSGTTSGTTRLLSGHTCFTLTGLLGTLVTMGLLTGSGATNFSLL<br>KQAGDVEENPGPMEPLPGWGSAPWSQAPTDNTFRLVPCVFLLNLLQRISAQPSCRQE<br>EFLVGDECCPMCNPGYHVKQVCSEHTGTVCAPCPPQTYTAHANGLSKCLPCGVCDPD<br>MGLLTWQECSSWKDTVCRCIPGYFCENQDGSHCSTCLQHTTCPPGQRVEKRGTHDQD<br>TVCADCLTGTFSLGGTQEECLPWTNCSAFQQEVRRGTNSTDTTCSSQPNKGSGTTSG<br>TTRLLSGHTCFTLTGLLGTLVTMGLLT<br>(SEQ ID NO: 302) |
| hPDL1-ADAM10 | >Artificial Sequence; hPDL1-ADAM10, DNA<br>ATGAGGATATTTGCTGTCTTTATATTCATGACCTACTGGCATTTGCTGAACGCATTT<br>ACTGTCACGGTTCCCAAGGACCTATATGTGGTAGAGTATGGTAGCAATATGACAATT<br>GAATGCAAATTCCCAGTAGAAAAACAATTAGACCTGGCTGCACTAATTGTCTATTGG<br>GAAATGGAGGATAAGAACATTATTCAATTTGTGCATGGAGAGGAAGACCTGAAGGTT<br>CAGCATAGTAGCTACAGACAGAGGGCCCGGCTGTTGAAGGACCAGCTCTCCCTGGGA<br>AATGCTGCACTTCAGATCACAGATGTGAAATTGCAGGATGCAGGGGTGTACCGCTGC<br>ATGATCAGCTATGGTGGTGCCGACTACAAGCGAATTACTGTGAAAGTCAATGCCCCA<br>TACAACAAAATCAACCAAAGAATTTTGGTTGTGGATCCAGTCACCTCTGAACATGAA<br>CTGACATGTCAGGCTGAGGGCTACCCCAAGGCCGAAGTCATCTGGACAAGCAGTGAC<br>CATCAAGTCCTGAGTGGTAAGACCACCACCACCAATTCCAAGAGAGAGGAGAAGCTT<br>TTCAATGTGACCAGCACACTGAGAATCAACACAACAACTAATGAGATTTTCTACTGC<br>ACTTTTAGGAGATTAGATCCTGAGGAAAACCATACAGCTGAATTGGTCATCCCAGAA<br>CTACCTCTGGCACATCCTCCAAATGAAAGGTGTGGAAATGGAATGGTAGAACAAGGT<br>GAAGAATGTGATTGTGGCTATAGTGACCAGTGTAAAGATGAATGCTGCTTCGATGCA<br>AATCAACCAGAGGGAAGAAAATGCAAACTGAAACCTGGGAAACAGTGCAGTCCAAGT |

TABLE 4-continued

Full Length Constructs

| Fusion Polypeptide | Nucleic Acid Sequence (SEQ ID NO:)<br>Amino Acid Sequence (SEQ ID NO:) |
|---|---|
| | *CAAGGTCCTTGTTGTACAGCACAGTGTGCATTCAAGTCAAAGTCTGAGAAGTGTCGG*<br>*GATGATTCAGACTGTGCAAGGGAAGGAATATGTAATGGCTTCACAGCTCTCTGCCCA*<br>*GCATCTGACCCTAAACCAAACTTCACAGACTGTAATAGGCATACACAAGTGTGCATT*<br>*AATGGGCAATGTGCAGGTTCTATCTGTGAGAAATATGGCTTAGAGGAGTGTACGTGT*<br>*GCCAGTTCTGATGGCAAAGATGATAAAGAATTATGCCATGTATGCTGTATGAAGAAA*<br>*ATGGACCCATCAACTTGTGCCAGTACAGGGTCTGTGCAGTGGAGTAGGCACTTCAGT*<br>*GGTCGAACCATCACCCTGCAACCTGGATCCCCTTGCAACGATTTTAGAGGTTACTGT*<br>*GATGTTTTCATGCGGTGCAGATTAGTAGATGCTGATGGTCCTCTAGCTAGGCTTAAA*<br>*AAAGCAATTTTTAGTCCAGAGCTCTATGAAAACATTGCTGAATGGATTGTGGCTCAT*<br>*TGGTGGGCAGTATTACTTATGGGAATTGCTCTGATCATGCTAATGGCTGGATTTATT*<br>*AAGATATGCAGTGTTaATACTCCAAGTAGTAATCCAAAGTTGCCTCCTCCTAAACCA*<br>*CTTCCAGGCACTTTAAAGAGGAGGAGACCTCCACAGCCCATTCAGCAACCCCAGCGT*<br>*CAGCGGCCCCGAGAGAGTTATCAAATGGGACACATGAGACGCTAA*<br>(SEQ ID NO: 303)<br>>Artificial Sequence; **hPDL1**-ADAM10, Amino Acid<br>**MRIFAVFIFMTYWHLLNAFTVTVPKDLYVVEYGSNMTIECKEPVEKQLDLAALIVYW**<br>**EMEDKNIIQFVHGEEDLKVQHSSYRQRARLLKDQLSLGNAALQITDVKLQDAGVYRC**<br>**MISYGGADYKRITVKVNAPYNKINQRILVVDPVTSEHELTCQAEGYPKAEVIWTSSD**<br>**HQVLSGKTTTTNSKREEKLFNVTSTLRINTTTNEIFYCTFRRLDPEENHTAELVIPE**<br>**LPLAHPPNER***CGNGMVEQGEECDCGYSDQCKDECCFDANQPEGRKCKLKPGKQCSPS*<br>*QGPCCTAQCAFKSKSEKCRDDSDCAREGICNGFTALCPASDPKPNFTDCNRHTQVCI*<br>*NGQCAGSICEKYGLEECTCASSDGKDDEELCHVCCMKKMDPSTCASTGSVQWSRHFS*<br>*GRTITLQPGSPCNDFRGYCDVFMRCRLVDADGPLARLKKAIFSPELYENIAEWIVAH*<br>*WWAVLLMGIALIMLMAGFIKICSVHTPSSNPKLPPPKPLPGTLKRRRPPQPIQQPQR*<br>*QRPRESYQMGHMRR*<br>(SEQ ID NO: 304) |
| hPDL1-4Fc-CD9tm2 | >Artificial Sequence; **hPDL1**-4Fc-*CD9tm2*, DNA<br>**ATGAGGATATTTGCTGTCTTTATATTCATGACCTACTGGCATTTGCTGAACGCATTT**<br>**ACTGTCACGGTTCCCAAGGACCTATATGTGGTAGAGTATGGTAGCAATATGACAATT**<br>**GAATGCAAATTCCCAGTAGAAAAACAATTAGACCTGGCTGCACTAATTGTCTATTGG**<br>**GAAATGGAGGATAAGAACATTATTCAATTTGTGCATGGAGAGGAAGACCTGAAGGTT**<br>**CAGCATAGTAGCTACAGACAGAGGGCCCGGCTGTTGAAGGACCAGCTCTCCCTGGGA**<br>**AATGCTGCACTTCAGATCACAGATGTGAAATTGCAGGATGCAGGGGTGTACCGCTGC**<br>**ATGATCAGCTATGGTGGTGCCGACTACAAGCGAATTACTGTGAAAGTCAATGCCCCA**<br>**TACAACAAAATCAACCAAAGAATTTTGGTTGTGGATCCAGTCACCTCTGAACATGAA**<br>**CTGACATGTCAGGCTGAGGGCTACCCCAAGGCCGAAGTCATCTGGACAAGCAGTGAC**<br>**CATCAAGTCCTGAGTGGTAAGACCACCACCACCAATTCCAAGAGAGAGGAGAAGCTT**<br>**TTCAATGTGACCAGCACACTGAGAATCAACACAACAACTAATGAGATTTTCTACTGC**<br>**ACTTTTAGGAGATTAGATCCTGAGGAAAACCATACAGCTGAATTGGTCATCCCAGAA**<br>**CTACCTCTGGCACATCCTCCAAATGAAAGG**GAGTCCAAATATGGTCCCCCATGCCCA<br>TCATGCCCAGCACCTGAGTTCCTGGGGGGACCATCAGTCTTCCTGTTCCCCCCAAAA<br>CCCAAGGACACTCTCATGATCTCCCGGACCCCTGAGGTCACGTGCGTGGTGGTGGAC<br>GTGAGCCAGGAAGACCCCGAGGTCCAGTTCAACTGGTACGTGGATGGCGTGGAGGTG<br>CATAATGCCAAGACAAAGCCGCGGGAGGAGCAGTTCAACAGCACGTACCGTGTGGTC<br>AGGGTCCTCACCGTCCTGCACCAGGACTGGCTGAACGGTAAGGAGTACAAGTGCAAG<br>GTCTCCAACAAAGGCCTCCCGTCCTCCATCGAGAAAACCATCTCCAAAGCCAAAGGG<br>CAGCCCCGAGAGCCACAGGTGTACACCCTGCCCCCATCCCAGGAGGAGATGACCAAG<br>AACCAGGTCAGCCTGACCTGCCTGGTCAAAGGCTTCTACCCCAGCGACATCGCCGTG<br>GAGTGGGAGAGCAATGGGCAGCCGGAGGACAACTACAAGACCACGCCTCCCGTGCTG<br>GACTCCGACGGCTCCTTCTTCCTCTACAGCAGGCTAACCGTGGACAAGAGCAGGTGG<br>CAGGAGGGGAATGTCTTCTCATGCTCCGTGATGCATGAGGCTCTGCACAACCACTAC<br>ACACAGAAGAGCCTCTCCCTGTCTCCGGGTAAA*TTCTACACAGGAGTCTATATTCTG*<br>*ATCGGAGCCGGCGCCCTCATGATGCTGGTGGGCTTCCTGGGCTGCTGCGGGGCTGTG*<br>*CAGGAGTCCCAGTGC*<br>(SEQ ID NO: 305)<br>>Artificial Sequence; **hPDL1**-4Fc-*CD9tm2*, Amino Acid<br>**MRIFAVFIFMTYWHLLNAFTVTVPKDLYVVEYGSNMTIECKFPVEKQLDLAALIVYW**<br>**EMEDKNIIQFVHGEEDLKVQHSSYRQRARLLKDQLSLGNAALQITDVKLQDAGVYRC**<br>**MISYGGADYKRITVKVNAPYNKINQRILVVDPVTSEHELTCQAEGYPKAEVIWTSSD**<br>**HQVLSGKTTTTNSKREEKLFNVTSTLRINTTTNEIFYCTFRRLDPEENHTAELVIPE**<br>**LPLAHPPNER**ESKYGPPCPSCPAPEFLGGPSVFLFPPKPKDTLMISRTPEVTCVVVD<br>VSQEDPEVQFNWYVDGVEVHNAKTKPREEQFNSTYRVVRVLTVLHQDWLNGKEYKCK<br>VSNKGLPSSIEKTISKAKGQPREPQVYTLPPSQEEMTKNQVSLTCLVKGFYPSDIAV<br>EWESNGQPEDNYKTTPPVLDSDGSFFLYSRLTVDKSRWQEGNVFSCSVMHEALHNHY<br>TQKSLSLSPGK*FYTGVYILIGAGALMMLVGFLGCCGAVQESQCVIM*<br>(SEQ ID NO: 306) |
| hPDL1-4Fc-CD9tm2-modified KRas | >Artificial Sequence; **hPDL1**-4Fc-*CD9tm2*-*KRAS*, DNA<br>**ATGAGGATATTTGCTGTCTTTATATTCATGACCTACTGGCATTTGCTGAACGCATTT**<br>**ACTGTCACGGTTCCCAAGGACCTATATGTGGTAGAGTATGGTAGCAATATGACAATT**<br>**GAATGCAAATTCCCAGTAGAAAAACAATTAGACCTGGCTGCACTAATTGTCTATTGG**<br>**GAAATGGAGGATAAGAACATTATTCAATTTGTGCATGGAGAGGAAGACCTGAAGGTT**<br>**CAGCATAGTAGCTACAGACAGAGGGCCCGGCTGTTGAAGGACCAGCTCTCCCTGGGA**<br>**AATGCTGCACTTCAGATCACAGATGTGAAATTGCAGGATGCAGGGGTGTACCGCTGC** |

TABLE 4-continued

| Full Length Constructs | |
|---|---|
| Fusion Polypeptide | Nucleic Acid Sequence (SEQ ID NO:)<br>Amino Acid Sequence (SEQ ID NO:) |
| | ATGATCAGCTATGGTGGTGCCGACTACAAGCGAATTACTGTGAAAGTCAATGCCCCA<br>TACAACAAAATCAACCAAAGAATTTTGGTTGTGGATCCAGTCACCTCTGAACATGAA<br>CTGACATGTCAGGCTGAGGGCTACCCCAAGGCCGAAGTCATCTGGACAAGCAGTGAC<br>CATCAAGTCCTGAGTGGTAAGACCACCACCACCAATTCCAAGAGAGAGGAGAAGCTT<br>TTCAATGTGACCAGCACACTGAGAATCAACACAACAACTAATGAGATTTTCTACTGC<br>ACTTTTAGGAGATTAGATCCTGAGGAAAACCATACAGCTGAATTGGTCATCCCAGAA<br>CTACCTCTGGCACATCCTCCAAATGAAAGGGAGTCCAAATATGGTCCCCCATGCCCA<br>TCATGCCCAGCACCTGAGTTCCTGGGGGGACCATCAGTCTTCCTGTTCCCCCCAAAA<br>CCCAAGGACACTCTCATGATCTCCCGGACCCCTGAGGTCACGTGCGTGGTGGTGGAC<br>GTGAGCCAGGAAGACCCCGAGGTCCAGTTCAACTGGTACGTGGATGGCGTGGAGGTG<br>CATAATGCCAAGACAAAGCCGCGGGAGGAGCAGTTCAACAGCACGTACCGTGTGGTC<br>AGGGTCCTCACCGTCCTGCACCAGGACTGGCTGAACGGTAAGGAGTACAAGTGCAAG<br>GTCTCCAACAAAGGCCTCCCGTCCTCCATCGAGAAAACCATCTCCAAAGCCAAAGGG<br>CAGCCCCGAGAGCCACAGGTGTACACCCTGCCCCCATCCCAGGAGGAGATGACCAAG<br>AACCAGGTCAGCCTGACCTGCCTGGTCAAAGGCTTCTACCCCAGCGACATCGCCGTG<br>GAGTGGGAGAGCAATGGGCAGCCGGAGGACAACTACAAGACCACGCCTCCCGTGCTG<br>GACTCCGACGGCTCCTTCTTCCTCTACAGCAGGCTAACCGTGGACAAGAGCAGGTGG<br>CAGGAGGGGAATGTCTTCTCATGCTCCGTGATGCATGAGGCTCTGCACAACCACTAC<br>ACACAGAAGAGCCTCTCCCTGTCTCCGGGTAAA*TTCTACACAGGAGTCTATATTCTG*<br>*ATCGGAGCCGGCGCCCTCATGATGCTGGTGGGCTTCCTGGGCTGCTGCGGGGCTGTG*<br>*CAGGAGTCCCAGTGCAAAAAGAAGAAAAAGAAGAAGAAGACAAAGTGTGTAATTATG*<br>*TAA*<br>(SEQ ID NO: 307)<br>>Artificial Sequence; **hPDL1**-4Fc-*CD9tm2*-*KRAS*, Amino Acid<br>**MRIFAVFIFMTYWHLLNAFTVTVPKDLYVVEYGSNMTIECKFPVEKQLDLAALIVYW**<br>**EMEDKNIIQFVHGEEDLKVQHSSYRQRARLLKDQLSLGNAALQITDVKLQDAGVYRC**<br>**MISYGGADYKRITVKVNAPYNKINQRILVVDPVTSEHELTCQAEGYPKAEVIWTSSD**<br>**HQVLSGKTTTTNSKREEKLFNVTSTLRINTTTNEIFYCTFRRLDPEENHTAELVIPE**<br>**LPLAHPPNER**ESKYGPPCPSCPAPEFLGGPSVFLFPPKPKDTLMISRTPEVTCVVVD<br>VSQEDPEVQFNWYVDGVEVHNAKTKPREEQFNSTYRVVRVLTVLHQDWLNGKEYKCK<br>VSNKGLPSSIEKTISKAKGQPREPQVYTLPPSQEEMTKNQVSLTCLVKGFYPSDIAV<br>EWESNGQPEDNYKTTPPVLDSDGSFFLYSRLTVDKSRWQEGNVFSCSVMHEALHNHY<br>TQKSLSLSPGK*FYTGVYILIGAGALMMLVGFLGCCGAVQESQCKKKKKKKTKCVIM*<br>(SEQ ID NO: 308) |
| hPDL1-Fc-CD9tm2 | >Artificial Sequence; **hPDL1**-Fc-*CD9tm2*, DNA<br>**ATGAGGATATTTGCTGTCTTTATATTCATGACCTACTGGCATTTGCTGAACGCATTT**<br>**ACTGTCACGGTTCCCAAGGACCTATATGTGGTAGAGTATGGTAGCAATATGACAATT**<br>**GAATGCAAATTCCCAGTAGAAAAACAATTAGACCTGGCTGCACTAATTGTCTATTGG**<br>**GAAATGGAGGATAAGAACATTATTCAATTTGTGCATGGAGAGGAAGACCTGAAGGTT**<br>**CAGCATAGTAGCTACAGACAGAGGGCCCGGCTGTTGAAGGACCAGCTCTCCCTGGGA**<br>**AATGCTGCACTTCAGATCACAGATGTGAAATTGCAGGATGCAGGGGTGTACCGCTGC**<br>**ATGATCAGCTATGGTGGTGCCGACTACAAGCGAATTACTGTGAAAGTCAATGCCCCA**<br>**TACAACAAAATCAACCAAAGAATTTTGGTTGTGGATCCAGTCACCTCTGAACATGAA**<br>**CTGACATGTCAGGCTGAGGGCTACCCCAAGGCCGAAGTCATCTGGACAAGCAGTGAC**<br>**CATCAAGTCCTGAGTGGTAAGACCACCACCACCAATTCCAAGAGAGAGGAGAAGCTT**<br>**TTCAATGTGACCAGCACACTGAGAATCAACACAACAACTAATGAGATTTTCTACTGC**<br>**ACTTTTAGGAGATTAGATCCTGAGGAAAACCATACAGCTGAATTGGTCATCCCAGAA**<br>**CTACCTCTGGCACATCCTCCAAATGAAAGG**ATCGATGACAAAACTCACACATGCCCA<br>CCGTGCCCAGCACCTGAACTCCTGGGGGGACCGTCAGTCTTCCTCTTCCCCCCAAAA<br>CCCAAGGACACCCTCATGATCTCCCGGACCCCTGAGGTCACATGCGTGGTGGTGGAC<br>GTGAGCCACGAAGACCCTGAGGTCAAGTTCAACTGGTACGTGGACGGCGTGGAGGTG<br>CATAATGCCAAGACAAAGCCGCGGGAGGAGCAGTACAACAGCACGTACCGTGTGGTC<br>AGCGTCCTCACCGTCCTGCACCAGGACTGGCTGAATGGCAAGGAGTACAAGTGCAAG<br>GTCTCCAACAAAGCCCTCCCAGCCCCCATCGAGAAAACCATCTCCAAAGCCAAAGGG<br>CAGCCCCGAGAACCACAGGTGTACACCCTGCCCCCATCCCGGGAGGAGATGACCAAG<br>AACCAGGTCAGCCTGACCTGCCTGGTCAAAGGCTTCTATCCCAGCGACATCGCCGTG<br>GAGTGGGAGAGCAATGGGCAGCCGGAGAACAACTACAAGACCACGCCTCCCGTGCTG<br>GACTCCGACGGCTCCTTCTTCCTCTACAGCAAGCTCACCGTGGACAAGAGCAGGTGG<br>CAGCAGGGGAACGTCTTCTCATGCTCCGTGATGCACGAGGCTCTGCACAACCACTAC<br>ACGCAGAAGAGCCTCTCCCTGTCTCCGGGTAAAATCGAT*TTCTACACAGGAGTCTAT*<br>*ATTCTGATCGGAGCCGGCGCCCTCATGATGCTGGTGGGCTTCCTGGGCTGCTGCGGG*<br>*GCTGTGCAGGAGTCCCAGTGCGTAATTATGTAA*<br>(SEQ ID NO: 309)<br>>Artificial Sequence; **hPDL1**-Fc-*CD9tm2*, Amino Acid<br>**MRIFAVFIFMTYWHLLNAFTVTVPKDLYVVEYGSNMTIECKFPVEKQLDLAALIVYW**<br>**EMEDKNIIQFVHGEEDLKVQHSSYRQRARLLKDQLSLGNAALQITDVKLQDAGVYRC**<br>**MISYGGADYKRITVKVNAPYNKINQRILVVDPVTSEHELTCQAEGYPKAEVIWTSSD**<br>**HQVLSGKTTTTNSKREEKLFNVTSTLRINTTTNEIFYCTFRRLDPEENHTAELVIPE**<br>**LPLAHPPNER**IDDKTHTCPPCPAPELLGGPSVFLFPPKPKDTLMISRTPEVTCVVVD<br>VSHEDPEVKFNWYVDGVEVHNAKTKPREEQYNSTYRVVSVLTVLHQDWLNGKEYKCK<br>VSNKALPAPIEKTISKAKGQPREPQVYTLPPSREEMTKNQVSLTCLVKGFYPSDIAV<br>EWESNGQPENNYKTTPPVLDSDGSFFLYSKLTVDKSRWQQGNVFSCSVMHEALHNHY<br>TQKSLSLSPGKID*FYTGVYILIGAGALMMLVGFLGCCGAVQESQCVIM*<br>(SEQ ID NO: 310) |

TABLE 4-continued

| Full Length Constructs | |
|---|---|
| Fusion Polypeptide | Nucleic Acid Sequence (SEQ ID NO:)<br>Amino Acid Sequence (SEQ ID NO:) |
| hPDL1-Fc-CD9tm2-modified KRAS | >Artificial Sequence; hPDL1-Fc-CD9tm2-KRAS, DNA<br>ATGAGGATATTTGCTGTCTTTATATTCATGACCTACTGGCATTTGCTGAACGCATTT<br>ACTGTCACGGTTCCCAAGGACCTATATGTGGTAGAGTATGGTAGCAATATGACAATT<br>GAATGCAAATTCCCAGTAGAAAAACAATTAGACCTGGCTGCACTAATTGTCTATTGG<br>GAAATGGAGGATAAGAACATTATTCAATTTGTGCATGGAGAGGAAGACCTGAAGGTT<br>CAGCATAGTAGCTACAGACAGAGGGCCCGGCTGTTGAAGGACCAGCTCTCCCTGGGA<br>AATGCTGCACTTCAGATCACAGATGTGAAATTGCAGGATGCAGGGGTGTACCGCTGC<br>ATGATCAGCTATGGTGGTGCCGACTACAAGCGAATTACTGTGAAAGTCAATGCCCCA<br>TACAACAAAATCAACCAAAGAATTTTGGTTGTGGATCCAGTCACCTCTGAACATGAA<br>CTGACATGTCAGGCTGAGGGCTACCCCAAGGCCGAAGTCATCTCTGGAAGCAGTGAC<br>CATCAAGTCCTGAGTGGTAAGACCACCACCACCAATTCCAAGAGAGAGGAGAAGCTT<br>TTCAATGTGACCAGCACACTGAGAATCAACACAACAACTAATGAGATTTTCTACTGC<br>ACTTTTAGGAGATTAGATCCTGAGGAAAACCATACAGCTGAATTGGTCATCCCAGAA<br>CTACCTCTGGCACATCCTCCAAATGAAAGGATCGATGACAAAACTCACACATGCCCA<br>CCGTGCCCAGCACCTGAACTCCTGGGGGGACCGTCAGTCTTCCTCTTCQCCCCAAAA<br>CCCAAGGACACCCTCATGATCTCCCGGACCCCTGAGGTCACATGCGTGGTGGTGGAC<br>GTGAGCCACGAAGACCCTGAGGTCAAGTTCAACTGGTACGTGGACGGCGTGGAGGTG<br>CATAATGCCAAGACAAAGCCGCGGGAGGAGCAGTACAACAGCACGTACCGTGTGGTC<br>AGCGTCCTCACCGTCCTGCACCAGGACTGGCTGAATGGCAAGGAGTACAAGTGCAAG<br>GTCTCCAACAAAGCCCTCCCAGCCCCCATCGAGAAAACCATCTCCAAAGCCAAAGGG<br>CAGCCCCGAGAACCACAGGTGTACACCCTGCCCCCATCCCGGGAGGAGATGACCAAG<br>AACCAGGTCAGCCTGACCTGCCTGGTCAAAGGCTTCTATCCCAGCGACATCGCCGTG<br>GAGTGGGAGAGCAATGGGCAGCCGGAGAACAACTACAAGACCACGCCTCCCGTGCTG<br>GACTCCGACGGCTCCTTCTTCCTCTACAGCAAGCTCACCGTGGACAAGAGCAGGTGG<br>CAGCAGGGGAACGTCTTCTCATGCTCCGTGATGCACGAGGCTCTGCACAACCACTAC<br>ACGCAGAAGAGCCTCTCCCTGTCTCCGGGTAAAATCGATTTCTACACAGGAGTCTAT<br>ATTCTGATCGGAGCCGGCGCCCTCATGATGCTGGTGGGCTTCCTGGGCTGCTGCGGG<br>GCTGTGCAGGAGTCCCAGTGCAAAAAGAAGAAAAAGAAGAAGAAGACAAAGTGTGTA<br>ATTATGTAA (SEQ ID NO: 311)<br>>Artificial Sequence; hPDL1-Fc-CD9tm2-KRAS, Amino Acid<br>MRIFAVFIFMTYWHLLNAFTVTVPKDLYVVEYGSNMTIECKFPVEKQLDLAALIVYW<br>EMEDKNIIQFVHGEEDLKVQHSSYRQRARLLKDQLSLGNAALQITDVKLQDAGVYRC<br>MISYGGADYKRITVKVNAPYNKINQRILVVDPVTSEHELTCQAEGYPKAEVIWTSSD<br>HQVLSGKTTTTNSKREEKLFNVTSTLRINTTTNEIFYCTFRRLDPEENHTAELVIPE<br>LPLAHPPNERIDDKTHTCPPCPAPELLGGPSVFLFPPKPKDTLMISRTPEVTCVVVD<br>VSHEDPEVKFNWYVDGVEVHNAKTKPREEQYNSTYRVVSVLTVLHQDWLNGKEYKCK<br>VSNKALPAPIEKTISKAKGQPREPQVYTLPPSREEMTKNQVSLTCLVKGFYPSDIAV<br>EWESNGQPENNYKTTPPVLDSDGSFFLYSKLTVDKSRWQQGNVFSCSVMHEALHNHY<br>TQKSLSLSPGKIDFYTGVYILIGAGALMMLVGFLGCCGAVQESQCKKKKKKKTKCV<br>IM<br>(SEQ ID NO: 312) |
| mPDL1-mFc-CD9tm2 | >Artificial Sequence; mPDL1-mFc-CD9tm2, DNA<br>ATGAGGATATTTGCTGGCATTATATTCACAGCCTGCTGTCACTTGCTACGGGCGTTT<br>ACTATCACGGCTCCAAAGGACTTGTACGTGGTGGAGTATGGCAGCAACGTCACGATG<br>GAGTGCAGATTCCCTGTAGAACGGGAGCTGGACCTGCTTGCGTTAGTGGTGTACTGG<br>GAAAAGGAAGATGAGCAAGTGATTCAGTTTGTGGCAGGAGAGGAGGACCTTAAGCCT<br>CAGCACAGCAACTTCAGGGGGAGAGCCTCGCTGCCAAAGGACCAGCTTTTGAAGGGA<br>AATGCTGCCCTTCAGATCACAGACGTCAAGCTGCAGGACGCAGGCGTTTACTGCTGC<br>ATAATCAGCTACGGTGGTGCGGACTACAAGCGAATCACGCTGAAAGTCAATGCCCCA<br>TACCGCAAAATCAACCAGAGAATTTCCGTGGATCCAGCCACTTCTGAGCATGAACTA<br>ATATGTCAGGCCGAGGGTTATCCAGAAGCTGAGGTAATCTGGACAAACAGTGACCAC<br>CAACCCGTGAGTGGGAAGAGAAGTGTCACCACTTCCCGGACAGAGGGGATGCTTCTC<br>AATGTGACCAGCAGTCTGAGGGTCAACGCCACAGCGAATGATGTTTTCTACTGTACG<br>TTTTGGAGATCACAGCCAGGGCAAAACCACACAGCGGAGCTGATCATCCCAGAACTG<br>CCTGCAACACATCCTCCACAGAACAGGACTGGTTGTAAGCCTTGCATATGTACAGTC<br>CCAGAAGTATCATCTGTCTTCATCTTCCCCCCAAAGCCCAAGGATGTGCTCACCATT<br>ACTCTGACTCCTAAGGTCACGTGTGTTGTGGTAGACATCAGCAAGGATGATCCCGAG<br>GTCCAGTTCAGCTGGTTTGTAGATGATGTGGAGGTGCACACAGCTCAGACGCAACCC<br>CGGGAGGAGCAGTTCAACAGCACTTTCCGCTCAGTCAGTGAACTTCCCATCATGCAC<br>CAGGACTGGCTCAATGGCAAGGAGTTCAAATGCAGGGTCAACAGTGCAGCTTTCCCT<br>GCCCCCATCGAGAAAACCATCTCCAAAACCAAAGGCAGACCGAAGGCTCCACAGGTG<br>TACACCATTCCACCTCCCAAGGAGCAGATGGCCAAGGATAAAGTCAGTCTGACCTGC<br>ATGATAACAGACTTCTTCCCTGAAGACATTACTGTGGAGTGGCAGTGGAATGGGCAG<br>CCAGCGGAGAACTACAAGAACACTCAGCCCATCATGGACACAGATGGCTCTTACTTC<br>GTCTACAGCAAGCTCAATGTGCAGAAGAGCAACTGGGAGGCAGGAAATACTTTCACC<br>TGCTCTGTGTTACATGAGGGCCTGCACAACCACCATACTGAGAAGAGCCTCTCCCAC<br>TCTCCTGGTAAATTCTACACAGGAGTCTATATTCTGATCGGAGCCGGCGCCCTCATG<br>ATGCTGGTGGGCTTCCTGGGCTGCTGCGGGGCTGTGCAGGAGTCCCAGTGCGTAATT<br>ATGTAA<br>(SEQ ID NO: 313)<br>>Artificial Sequence; mPDL1-mFc-CD9tm2, Amino Acid<br>MRIFAGIIFTACCHLLRAFTITAPKDLYVVEYGSNVTMECRFPVERELDLLALVVYW<br>EKEDEQVIQFVAGEEDLKPQHSNFRGRASLPKDQLLKGNAALQITDVKLQDAGVYCC |

TABLE 4-continued

Full Length Constructs

| Fusion Polypeptide | Nucleic Acid Sequence (SEQ ID NO:)<br>Amino Acid Sequence (SEQ ID NO:) |
|---|---|
| | IISYGGADYKRITLKVNAPYRKINQRISVDPATSEHELICQAEGYPEAEVIWTNSDH<br>QPVSGKRSVTTSRTEGMLLNVTSSLRVNATANDVFYCTFWRSQPGQNHTAELIIPEL<br>PATHPPQNRTGCKPCICTVPEVSSVFIFPPKPKDVLTITLTPKVTCVVVDISKDDPE<br>VQFSWFVDDVEVHTAQTQPREEQFNSTFRSVSELPIMHQDWLNGKEFKCRVNSAAFP<br>APIEKTISKTKGRPKAPQVYTIPPPKEQMAKDKVSLTCMITDFFPEDITVEWQWNGQ<br>PAENYKNTQPIMDTDGSYFVYSKLNVQKSNWEAGNTFTCSVLHEGLHNHHTEKSLSH<br>SPGKPFYTGVYILIGAGALMMLVGFLGCCGAVQESQCVIM<br>(SEQ ID NO: 314) |
| mPDL1-mFc-<br>CD9tm2-<br>modified KRAS | >Artificial Sequence; mPDL1-mFc-CD9tm2-KRAS, DNA<br>ATGAGGATATTTGCTGGCATTATATTCACAGCCTGCTGTCACTTGCTACGGGCGTTT<br>ACTATCACGGCTCCAAAGGACTTGTACGTGGTGGAGTATGGCAGCAACGTCACGATG<br>GAGTGCAGATTCCCTGTAGAACGGGAGCTGGACCTGCTTGCGTTAGTGGTGTACTGG<br>GAAAAGGAAGATGAGCAAGTGATTCAGTTTGTGGCAGGAGAGGAGGACCTTAAGCCT<br>CAGCACAGCAACTTCAGGGGGAGAGCCTCGCTGCCAAAGGACCAGCTTTTGAAGGGA<br>AATGCTGCCCTTCAGATCACAGACGTCAAGCTGCAGGACGCAGGCGTTTACTGCTGC<br>ATAATCAGCTACGGTGGTGCGGACTACAAGCGAATCACGCTGAAAGTCAATGCCCCA<br>TACCGCAAAATCAACCAGAGAATTTCCGTGGATCCAGCCACTTCTGAGCATGAACTA<br>ATATGTCAGGCCGAGGGTTATCCAGAAGCTGAGGTAATCTGGACAAACAGTGACCAC<br>CAACCCGTGAGTGGGAAGAGAAGTGTCACCACTTCCCGGACAGAGGGGATGCTTCTC<br>AATGTGACCAGCAGTCTGAGGGTCAACGCCACAGCGAATGATGTTTTCTACTGTACG<br>TTTTGGAGATCACAGCCAGGGCAAAACCACACAGCGGAGCTGATCATCCCAGAACTG<br>CCTGCAACACATCCTCCACAGAACAGGACTGGTTGTAAGCCTTGCATATGTACAGTC<br>CCAGAAGTATCATCTGTCTTCATCTTCCCCCCAAAGCCCAAGGATGTGCTCACCATT<br>ACTCTGACTCCTAAGGTCACGTGTGTTGTGGTAGACATCAGCAAGGATGATCCCGAG<br>GTCCAGTTCAGCTGGTTTGTAGATGATGTGGAGGTGCACACAGCTCAGACGCAACCC<br>CGGGAGGAGCAGTTCAACAGCACTTTCCGCTCAGTCAGTGAACTTCCCATCATGCAC<br>CAGGACTGGCTCAATGGCAAGGAGTTCAAATGCAGGGTCAACAGTGCAGCTTTCCCT<br>GCCCCCATCGAGAAAACCATCTCCAAAACCAAAGGCAGACCGAAGGCTCCACAGGTG<br>TACACCATTCCACCTCCCAAGGAGCAGATGGCCAAGGATAAAGTCAGTCTGACCTGC<br>ATGATAACAGACTTCTTCCCTGAAGACATTACTGTGGAGTGGCAGTGGAATGGGCAG<br>CCAGCGGAGAACTACAAGAACACTCAGCCCATCATGGACACAGATGGCTCTTACTTC<br>GTCTACAGCAAGCTCAATGTGCAGAAGAGCAACTGGGAGGCAGGAAATACTTTCACC<br>TGCTCTGTGTTACATGAGGGCCTGCACAACCACCATACTGAGAAGAGCCTCTCCCAC<br>TCTCCTGGTAAATTCTACACAGGAGTCTATATTCTGATCGGAGCCGGCGCCCTCATG<br>ATGCTGGTGGGCTTCCTGGGCTGCTGCGGGGCTGTGCAGGAGTCCCAGTGCAAAAAG<br>AAGAAAAAGAAGAAGAAGACAAAGTGTGTAATTATGTAA<br>(SEQ ID NO: 315)<br>>Artificial Sequence; mPDL1-mFc-CD9tm2-KRAS, Amino Acid<br>MRIFAGIIFTACCHLLRAFTITAPEDLYVVEYGSNVTMECRFPVERELDLLALVVYW<br>EKEDEQVIQFVAGEEDLKPQHSNFRGRASLPKDQLLKGNAALQITDVKLQDAGVYCC<br>IISYGGADYKRITLKVNAPYRKINQRISVDPATSEHELICQAEGYPEAEVIWTNSDH<br>QPVSGKRSVTTSRTEGMLLNVTSSLRVNATANDVFYCTFWRSQPGQNHTAELIIPEL<br>PATHPPQNRTGCKPCICTVPEVSSVFIFPPKPKDVLTITLTPKVTCVVVDISKDDPE<br>VQFSWFVDDVEVHTAQTQPREEQFNSTFRSVSELPIMHQDWLNGKEFKCRVNSAAFP<br>APIEKTISKTKGRPKAPQVYTIPPPKEQMAKDKVSLTCMITDFFPEDITVEWQWNGQ<br>PAENYKNTQPIMDTDGSYFVYSKLNVQKSNWEAGNTFTCSVLHEGLHNHHTEKSLSH<br>SPGKFYTGVYILIGAGALMMLVGFLGCCGAVQESQCKKKKKKKKTKCVIM<br>(SEQ ID NO: 316) |

In some embodiments of any of the aspects, the fusion polypeptides provided herein comprise two or more POI domains. The specific combinations of POI domains can be used to regulate inflammatory immune responses. Non-limiting examples of additive and synergistic combinations of POIs that can modulate inflammatory signaling pathways are provided in Table 5 (below).

TABLE 5

Exemplary POI combinations and combined targets for modulating inflammation.

| POIs (LIGANDS) | COMBINED TARGETS | PUTATIVE ADDITIVE or SYNERGISTIC MOA |
|---|---|---|
| PD-L1 or PD-L2<br>HVEM | PD-1<br>BTLA | Differential use of Shp phosphatases. BTLA inhibits both TCR and CD28 phosphorylation (via Shp1) while PD-1 inhibits CD28 phosphorylation (via Shp2). |
| PD-L1 or PD-L2<br>FGL1 | PD-1<br>LAG-3 | LAG-3 exerts differential inhibitory impacts on various types of lymphocytes and shows synergy with PD-1 to inhibit immune responses. |
| PD-L1 or PD-L2<br>CEACAM-1 or GAL9 | PD-1<br>TIM-3 | PD-1 and Tim-3 have non-redundant downstream signaling mechanisms. |
| PD-L1 or PD-L2<br>CD155 | PD-1<br>TIGIT | Differential use of Shp phosphatases. Non-redundantly regulate T cell responses. |

TABLE 5-continued

Exemplary POI combinations and combined targets for modulating inflammation.

| POIs (LIGANDS) | COMBINED TARGETS | PUTATIVE ADDITIVE or SYNERGISTIC MOA |
|---|---|---|
| PD-L1 or PD-L2<br>VSIG3 | PD-1<br>VISTA | PD-1 and VISTA non-redundantly regulate T cell responses. VISTA contains cytosolic SH3 binding domains for adapter proteins. |
| CEACAM-1 or GAL9<br>CD155 | TIM-3<br>TIGIT | TIGIT and TIM-3 have non-redundant downstream signaling mechanisms. |
| PD-L1 or PD-L2<br>FGL1<br>CEACAM-1 or GAL9 | PD-1<br>LAG-3<br>TIM-3 | PD-1, LAG-3 and TIM-3 have non-redundant downstream signaling mechanisms. |

Methods of Preparing Extracellular Vesicle Compositions

In another aspect, provided herein is a method of preparing an engineered extracellular vesicle provided herein. Generally, the method comprises providing a population of cells expressing a vector construct encoding one or more sticky binder (vesicle targeting domain) and one or more signaling domains (POI domain).

The EVs provided herein can be isolated and purified form any biological source, e.g., cells. The cells that produce the engineered EVs provided herein can be from any viable non-human source or organism. Usually the organism is an animal, vertebrate, or mammal. In some embodiments, the cell described herein is from a human. The cells described herein can be from any tissue isolated from an organism by methods known in the art. The scientific literature provides guidance for one of ordinary skill in the art to isolate, prepare, and culture cells as necessary for use in the compositions and methods described herein. One of skill in the art can appreciate that the cell source of the EVs may alter the cellular protein expression and the native or endogenous cargo within the EV. It is contemplated herein that this can be leveraged for therapeutic effect depending on the disease or disorder being treated.

In some embodiments, the population of cells has been altered by exposure to environmental conditions (e.g., hypoxia), small molecule addition, presence/absence of exogenous factors (e.g., growth factors, cytokines) at the time, or substantially contemporaneous with, isolating the plurality of artificial synapses in a manner altering the regulatory state of the cell. In various embodiments, the cells are HEK 293 cells, MSCs, PER.C, fibrosarcoma HT-1080 or HuH7 cell lines.

The method comprises providing a population of cells and culturing the cells in serum-free or un-concentrated conditioned medium. This includes, for example, artificial synapses secreted into media as conditioned by a population of cells in culture, further including cell lines capable of serial passaging. In certain embodiments, the cells in culture are grown to 10, 20, 30, 40, 50, 60, 70, 80, 90, or 90% or more confluency when artificial synapses (engineered EVs) are isolated.

The methods provided herein further comprise contacting the cells provided herein with a nucleic acid vector encoding the at least one fusion polypeptide provided herein. The vector can be added to the cell culture medium of the cells by methods known in the art and discussed further below.

A vector is a nucleic acid construct designed for delivery to a host cell or for transfer of genetic material between different host cells. As used herein, a vector can be viral or non-viral. The term "vector" encompasses any genetic element that is capable of replication when associated with the proper control elements and that can transfer genetic material to cells. A vector can include, but is not limited to, a cloning vector, an expression vector, a plasmid, phage, transposon, cosmid, artificial chromosome, virus, virion, etc. In some embodiments of any of the aspects, the vector is selected from the group consisting of: a plasmid, a cosmid and a viral vector.

"Expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene.

In some embodiments, a vector is capable of driving expression of one or more sequences in a mammalian cell; i.e., the vector is a mammalian expression vector. Examples of mammalian expression vectors include pCDM8 (Seed, 1987. Nature 329:840) and pMT2PC (Kaufman, et al., 1987. *EMBO J.* 6:187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant expression vector is capable of directing expression of the exogenous fusion polypeptide nucleic acid sequence preferentially in a particular cell type (e.g., via tissue-specific regulatory elements).

Tissue-specific and inducible regulatory elements are known in the art. Non-limiting examples of suitable tissue-specific promoters include the albumin promoter (liver-specific; Pinkert, et al., 1987. *Genes Dev.* 1:268-277), lymphoid-specific promoters (Calame and Eaton, 1988. *Adv. hnmunol.* 43:235-275), in particular promoters of T cell receptors (Winoto and Baltimore, 1989. *EMBO J.* 8:729-733) and immunoglobulins (Baneiji, et al., 1983. *Cell* 33:729-740; Queen and Baltimore, 1983. *Cell* 33:741-748), neuron-specific promoters (e.g., the neurofilament promoter; Byrne and Ruddle, 1989. *Proc. Natl. Acad. Sci. USA* 86:5473-5477), pancreas-specific promoters (Edlund, et al., 1985. *Science* 230:912-916), and mammary gland-specific promoters (e.g., milk whey promoter; U.S. Pat. No. 4,873,316 and European Application Publication No. 264, 166). Developmentally-regulated promoters are also encompassed, e.g., the murine hox promoters (Kessel and Gruss, 1990. *Science* 249:374-379) and the α-fetoprotein promoter (Campes and Tilghman, 1989. *Genes Dev.* 3:537-546).

In some embodiments, the at least one nucleic acid sequence described herein is delivered to the cell described herein via an integrating vector. Integrating vectors have their delivered genetic material (or a copy of it) permanently incorporated into a host cell chromosome. Non-integrating vectors remain episomal which means the nucleic acid contained therein is never integrated into a host cell chromosome. Examples of integrating vectors include retroviral vectors, lentiviral vectors, hybrid adenoviral vectors, and herpes simplex viral vectors.

In some embodiments, the at least one nucleic acid sequence described herein is delivered to the cell described herein via a non-integrative vector. Non-integrative vectors include non-integrative viral vectors. Non-integrative viral vectors eliminate one of the primary risks posed by integrative retroviruses, as they do not incorporate their genome into the host DNA. One example is the Epstein Barr oriP/Nuclear Antigen-1 ("EBNA1") vector, which is capable of limited self-replication and known to function in mammalian cells. Containing two elements from Epstein-Barr virus, oriP and EBNA1, binding of the EBNA1 protein to the virus replicon region oriP maintains a relatively long-term episomal presence of plasmids in mammalian cells. This particular feature of the oriP/EBNA1 vector makes it ideal for generation of integration-free host cells. Other non-integrative viral vectors include adenoviral vectors and the adeno-associated viral (AAV) vectors.

Another non-integrative viral vector is RNA Sendai viral vector, which can produce protein without entering the nucleus of an infected cell. The F-deficient Sendai virus vector remains in the cytoplasm of infected cells for a few passages, but is diluted out quickly and completely lost after several passages (e.g., 10 passages). This permits a self-limiting transient expression of a chosen heterologous gene or genes in a target cell. This aspect can be helpful, e.g., for the transient introduction of reprogramming factors, among other uses. As noted above, in some embodiments, the nucleic acid sequence described herein is expressed in the cells from a viral vector.

A "viral vector" includes a nucleic acid vector construct that includes at least one element of viral origin and has the capacity to be packaged into a viral vector particle. The viral vector can contain a nucleic acid encoding a polypeptide described herein in place of non-essential viral genes. The vector and/or particle can be utilized for the purpose of transferring nucleic acids into cells either in vitro or in vivo.

The nucleic acids described herein can be delivered using any transfection reagent or other physical means that facilitates entry of nucleic acids into a cell. Methods of non-viral delivery of nucleic acids include lipofection, nucleofection, microinjection, electroporation, biolistics, virosomes, liposomes, immunoliposomes, polycation or lipid: nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g., in vitro or ex vivo administration) or target tissues (e.g., in vivo administration).

The preparation of lipid: nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

An "agent that increases cellular uptake" is a molecule that facilitates transport of a molecule, e.g., nucleic acid, or peptide or polypeptide, or other molecule that does not otherwise efficiently transit the cell membrane across a lipid membrane. For example, a nucleic acid can be conjugated to a lipophilic compound (e.g., cholesterol, tocopherol, etc.), a cell penetrating peptide (CPP) (e.g., penetratin, TAT, Syn1B, etc.), or a polyamine (e.g., spermine). Further examples of agents that increase cellular uptake are disclosed, for example, in Winkler (2013). *Oligonucleotide conjugates for therapeutic applications. Ther. Deliv.* 4 (7); 791-809. The one or more nucleic acid sequences encoding the fusion polypeptides provided herein can be delivered to the cell by any method discussed above or known in the art.

In some embodiments of any of the aspects, the vectors provided herein comprise a nucleic acid modification by methods known in the art. In some embodiments, the cell can be genetically manipulated to express one or more vectors, each encoding one or more vesicle targeting domains and/or one or more signaling domains. In certain embodiments, the population of cells has been genetically manipulated. This includes, for example, knockout (KO) or transgenic (TG) cell lines, wherein an endogenous gene has been removed and/or an exogenous introduced in a stable, persistent manner. In certain embodiments, this further includes transient knockdown of one or more genes and associated coding and non-coding transcripts within the population of cells, via any number of methods known in the art, such as introduction of dsRNA, siRNA, microRNA, etc. This further includes transient expression of one or more genes and associated coding and non-coding transcripts within the population of cells, via any number of methods known in the art, such as introduction of a vector, plasmid, artificial plasmid, replicative and/or non-replicative virus, etc.

In certain embodiments the cell population has been manipulated to knockout the expression of one or more endogenous gene sequences that encode for metalloendopeptidases. In certain embodiments the cell population has been manipulated to knockout the expression of one or more endogenous gene sequences that code for metalloproteinases. In certain embodiments the cell population has been manipulated to knockout the expression of one or more endogenous gene sequences that encode for a disintegrin and metalloproteinase (ADAM). For example, the cell population can be manipulated to knock of the expression of one or more gene sequences that encode for ADAM1, ADAM2, ADAM7, ADAM8, ADAM9, ADAM10, ADAM11, ADAM12, ADAM15, ADAM17, ADAM18, ADAM19, ADAM20, ADAM21, ADAM22, ADAM23, ADAM28, ADAM29, ADAM30, ADAM33, etc.

In certain embodiments the cell population has been manipulated to knockout the expression of one or more endogenous genes that encode for enzymes that hydrolyze the inositol phosphate linkage in proteins anchored by phosphatidylinositol glycans, thereby preventing the release of proteins attached to the plasma membrane via GPI anchors. For example, the cell population can be manipulated to knock of the expression of phosphatidylinositol-glycan-specific phospholipase D (GPLD1).

In certain embodiments, the population of cells has been genetically manipulated. This includes, for example, knock-in of an exogenous genetic sequence, wherein the exogenous genetic sequence is expressed in a stable, persistent manner. In certain embodiments, the cell population has been manipulated to knock-in recombinase recognition sequences (e.g., FRT), transgenic reporters such as antibiotic resistance genes, fluorescent or enzymatic reporter genes, etc. or the like.

In some embodiments, the method comprises a step of isolating the engineered extracellular vesicles provided herein. Particulates within the medium are removed by a series of specific centrifugation steps and the media is filtered. The general method of isolating extracellular vesicles as provided herein is depicted in FIG. 21 of the working examples. Methods of isolating and purifying the extracellular vesicles and exosomes are known in the art and further described, e.g., in Whitford W, Guterstam P. Exosome manufacturing status. Future Med Chem. 2019 May; 11(10):1225-1236. doi: 10.4155/fmc-2018-0417. PMID: 31280675, Patel D B, Santoro M, Born L J, Fisher J P, Jay S M. Towards rationally designed biomanufacturing of therapeutic extracellular vesicles: impact of the bioproduction microenvironment. Biotechnol Adv. 2018 December; 36 (8):2051-2059 . . . doi: 10.1016/j.biotechadv.2018.09.001. Epub 2018 Sep. 12. PMID: 30218694; PMCID: PMC6250573, Ng K S, Smith J A, McAteer M P, Mead B E, Ware J, Jackson F O, Carter A, Ferreira L, Bure K, Rowley J A, Reeve B, Brindley D A, Karp J M. Bioprocess decision support tool for scalable manufacture of extracellular vesicles. Biotechnol Bioeng. 2019 February; 116 (2):307-319. doi: 10.1002/bit.26809. Epub 2018 Nov. 8. PMID: 30063243; PMCID: PMC6322973, Paganini C, Capasso Palmiero U, Pocsfalvi G, Touzet N, Bongiovanni A, Arosio P. Scalable Production and Isolation of Extracellular Vesicles: Available Sources and Lessons from Current Industrial Bioprocesses. Biotechnol J. 2019 October; 14 (10):e1800528. doi: 10.1002/biot.201800528. Epub 2019 Jul. 8. PMID: 31140717, which are incorporated herein by reference in their entireties.

In some embodiments, isolating the plurality of engineered EVs (artificial synapses) includes precipitation, centrifugation, filtration, immuno-separation, tangential flow, liquid chromatography, and/or flow fractionation. For example, differential ultracentrifugation has become a technique wherein secreted exosomes are isolated from the supernatants of cultured cells. This approach allows for separation of exosomes from non-membranous particles, by exploiting their relatively low buoyant density. Size exclusion allows for their separation from biochemically similar, but biophysically different microvesicles, which possess larger diameters of up to 1,000 nm. Differences in floatation velocity further allows for separation of differentially sized exosomes. In general, exosome sizes will possess a diameter ranging from 30-300 nm, including sizes of 30-150 nm. Further purification may rely on specific properties of the particular exosomes of interest. This includes, for example, use of immunoadsorption with a protein of interest to select specific vesicles with exoplasmic or outward orientations.

Among current methods (differential centrifugation, discontinuous density gradients, immunoaffinity, ultrafiltration and liquid chromatography (e.g., fast protein liquid chromatography (FPLC)), differential ultracentrifugation is the most commonly used for exosome isolation. This technique utilizes increasing centrifugal force from 2000×g to 10,000×g to separate the medium- and larger-sized particles and cell debris from the exosome pellet at 100,000×g. Centrifugation alone allows for significant separation/collection of exosomes from a conditioned medium, although it is insufficient to remove various protein aggregates, genetic materials, particulates from media and cell debris that are common contaminants. Enhanced specificity of exosome purification may deploy sequential centrifugation in combination with ultrafiltration, or equilibrium density gradient centrifugation in a sucrose density gradient, to provide for the greater purity of the exosome preparation (flotation density 1.1-1.2 g/ml) or application of a discrete sugar cushion in preparation.

Ultrafiltration can be used to purify exosomes without compromising their biological activity. Membranes with different pore sizes-such as 100 kDa molecular weight cut-off (MWCO) or 300 kDa MWCO and gel filtration to eliminate smaller particles—have been used to avoid the use of a nonneutral pH or non-physiological salt concentration. Currently available tangential flow filtration (TFF) systems are scalable (to >10,000 L), allowing one to not only purify, but concentrate the exosome fractions, and such approaches are less time consuming than differential centrifugation. Liquid Chromatography can also be used to purify exosomes to homogeneously sized particles and preserve their biological activity as the preparation is maintained at a physiological pH and salt concentration.

Other chemical methods have exploit differential solubility of exosomes for precipitation techniques, addition to volume-excluding polymers (e.g., polyethylene glycols (PEGs)), possibly combined additional rounds of centrifugation or filtration. For example, a precipitation reagent, ExoQuick®, can be added to conditioned cell media to quickly and rapidly precipitate a population of exosomes, although re-suspension of pellets prepared via this technique may be difficult. Flow field-flow fractionation (FlFFF) is an elution-based technique that is used to separate and characterize macromolecules (e.g., proteins) and nano- to micro-sized particles (e.g., organelles and cells) and which has been successfully applied to fractionate exosomes from culture media.

Beyond these techniques relying on general biochemical and biophysical features, focused techniques may be applied to isolated specific exosomes of interest. This includes relying on antibody immunoaffinity to recognizing certain exosome-associated antigens. Conjugation to magnetic beads, chromatography matrices, plates or microfluidic devices allows isolating of specific exosome populations of interest as may be related to their production from a parent cell of interest or associated cellular regulatory state. Other affinity-capture methods use lectins which bind to specific saccharide residues on the exosome surface.

In several embodiments, isolating a plurality of artificial synapses from the population of cells includes centrifugation of the cells and/or media conditioned by the cells. In several embodiments, ultracentrifugation is used. In several embodiments, isolating a plurality of artificial synapses from the population of cells is via size-exclusion filtration. In other embodiments, isolating a plurality of artificial synapses from the population of cells includes use of discontinuous density gradients, immunoaffinity, ultrafiltration, tangential flow and/or liquid chromatography.

In certain embodiments, differential ultracentrifugation includes using centrifugal force from 1000-2000×g, 2000-3000×g, 3000-4000×g, 4000-5000×g, 5000×g-6000×g, 6000-7000×g, 7000-8000×g, 8000-9000×g, 9000-10,000×g, to 10,000×g or more to separate larger-sized particles from a plurality of artificial synapses derived from the cells.

In other embodiments, isolating a plurality of artificial synapses from the population of cells includes use of filtration or ultrafiltration. In certain embodiments, a size exclusion membrane with different pore sizes is used. For example, a size exclusion membrane can include use of a filter with a pore size of 0.1-0.5 micron (μm), 0.5-1.0 μm, 1-2.5 μm, 2.5-5 μm, 5 or more μm. In certain embodiments, the pore size is about 0.2 μm. In certain embodiments, filtration or ultrafiltration includes size exclusion ranging from 100-500 daltons (Da), 500-1 kDa, 1-2 kDa, 2-5 kDa, 5-10 kDa, 10-25 kDa, 25-50 kDa, 50-100 kDa, 100-250 kDa, 250-500 kDa, 500 or more kDa. In certain embodiments, the size exclusion is for about 2-5 kDa. In certain embodiments, the size exclusion is for about 3 kDa. In other embodiments, filtration or ultrafiltration includes size exclusion includes use of hollow fiber membranes capable of isolating particles ranging from 100-500 daltons (Da), 500-1 kDa, 1-2 kDa, 2-5 kDa, 5-10 kDa, 10-25 kDa, 25-50 kDa, 50-100 kDa, 100-250 kDa, 250-500 kDa, 500 or more kDa. In certain embodiments, the size exclusion is for about 2-5 kDa. In certain embodiments, the size exclusion is for about 3 kDa. In other embodiments, a molecular weight cut-off (MWCO) gel filtration capable of isolating particles ranging from 100-500 daltons (Da), 500-1 kDa, 1-2 kDa, 2-5 kDa, 5-10 kDa, 10-25 kDa, 25-50 kDa, 50-100 kDa, 100-250 kDa, 250-500 kDa, 500 or more kDa. In certain embodiments, the size exclusion is for about 2-5 kDa. In certain embodiments, the size exclusion is for about 3 kDa. In various embodiments, such systems are used in combination with variable fluid flow systems. In certain embodiments, a size exclusion membrane with different pore sizes is used to purify extracellular vesicles from a solution comprising undesirable proteins or nucleic acids.

In other embodiments, isolating a plurality of artificial synapses from the population of cells includes use of tangential flow filtration (TFF) systems are used purify and/or concentrate the exosome fractions. In other embodiments, isolating a plurality of artificial synapses from the population of cells includes use of liquid chromatography can also be used to purify artificial synapses to homogeneously sized particles. In various embodiments, density gradients as used, such as centrifugation in a sucrose density gradient or application of a discrete sugar cushion in preparation.

In other embodiments, isolating a plurality of artificial synapses from the population of cells includes use of a precipitation reagent. For example, a precipitation reagent, ExoQuick®, can be added to conditioned cell media to quickly and rapidly precipitate a population of artificial synapses. In other embodiments, isolating a plurality of artificial synapses from the population of cells includes use of volume-excluding polymers (e.g., polyethylene glycols (PEGs)) are used. In another embodiment, isolating a plurality of artificial synapses from the population of cells includes use of flow field-flow fractionation (FlFFF), an elution-based technique.

In certain embodiments, isolating a plurality of artificial synapses from the population of cells includes use of one or more capture agents to isolate one or more artificial synapses possessing specific biomarkers or containing particular biological molecules. In one embodiment, one or more capture agents include at least one antibody. For example, antibody immunoaffinity recognizing exosome-associated antigens is used to capture specific artificial synapses. In other embodiments, the at least one antibody are conjugated to a fixed surface, such as magnetic beads, chromatography matrices, plates or microfluidic devices, thereby allowing isolation of the specific exosome populations of interest. In other embodiments, isolating a plurality of artificial synapses from the population of cells includes use of one or more capture agents that is not an antibody. This includes, for example, use of a "bait" molecule presenting an antigenic feature complementary to a corresponding molecule of interest on the exosome surface, such as a receptor or other coupling molecule. In one embodiment, the non-antibody capture agent is a lectin capable of binding to polysaccharide residues on the exosome surface.

In other embodiments, isolating a plurality of artificial synapses from the population of cells includes use of ion exchange chromatography. In other embodiments, isolating a plurality of artificial synapses from the population of cells includes use of anion exchange chromatography. In other embodiments, isolating a plurality of artificial synapses from the population of cells includes use of caion exchange chromatography. In certain embodiments, ion exchange chromatography comprises a chromatography resin with a functional group selected from the group consisting of diethylaminoethyl (DEAE), quaternary aminoethyl (QAE), quaternary ammonium (Q), carboxymethyl (CM), sulfopropyl (SP), or methyl sulfate(S). In certain embodiments, ion exchange chromatography comprises a chromatography resin which may have properties of a weak acid, strong acid, weak base, or strong basic. In certain embodiments, ion exchange chromatography comprises a chromatography selected from the group consisting of DEAE cellulose, DEAE Sephadex, Mono Q, Mini Q, HiTrap Capto, Capto Core 700, HiPrep Q, QAE Sephadex, Q Sepharose, CM Cellulose, SP Sepharose, SOURCE S, EAH-Sepharose, sulfoxyethyl cellulose, CM Sephadex, or CM Sepharose. Isolating a plurality of artificial synapses can be prepared by any of a variety of ion exchange chromatography techniques that are known in the art.

In other embodiments, isolating a plurality of artificial synapses from the population of cells includes use of a nuclease enzyme (e.g., a DNase or RNase). For example, a working concentration of Benzonase® nuclease may be added to an extracellular vesicle sample preparation in the presence of a divalent cation, for example 1-2 mM $Mg^{2+}$, 2-5 mM $Mg^{2+}$, 10-20 mM $Mg^{2+}$, 20-50 mM $Mg^{2+}$, 50-100 mM $Mg^{2+}$, or more than 100 mM $Mg^{2+}$.

Following isolation and purification of the engineered EVs provided herein, EVs can be further evaluated for the desired structural and functional properties by methods known in the art. For example, the engineered exosomes provided herein can be assayed for functional activity on a target cell using a cell-based bioassays (e.g., those commercially available, PROMEGA® DISCOVERX®), ligand-receptor binding assays, vesicle flow cytometric assays, enzyme-linked immunosorbent assays, tunable resistive pulse sensing (TRPS), nanoparticle tracking analysis (NTA), surface plasmon resonance (SSPR), nucleotide sequencing, lipidomics, proteomics, colorimetric assays, fluorescence assays, luminescence assays, immunoblotting, radioimmunoassays, electron microscopy, or EV automated analysis (e.g., EXOVIEW®). Additional methods of characterizing EVs are found, e.g., in Zhang Y, Bi J, Huang J, Tang Y, Du S, Li P. Exosome: A Review of Its Classification, Isolation Techniques, Storage, Diagnostic and Targeted Therapy Applications. Int J Nanomedicine. 2020 Sep. 22; 15:6917-6934. doi: 10.2147/IJN.S264498. PMID: 33061359; PMCID: PMC7519827, Kluszczyńska K, Czernek L, Cypryk W, Pęczek Ł, Düchler M. Methods for the Determination of the Purity of Exosomes. Curr Pharm Des. 2019; 25(42):4464-4485. doi: 10.2174/1381612825666191206162712. PMID: 31808383, Nolan J P, Duggan E. Analysis of Individual Extracellular Vesicles by Flow Cytometry. Methods Mol Biol. 2018; 1678:79-92. doi: 10.1007/978-1-4939-7346-O_5. PMID: 29071676; Doyle L M, Wang M Z. Overview of Extracellular Vesicles, Their Origin, Composition, Purpose, and Methods for Exosome Isolation and Analysis. Cells. 2019 Jul. 15; 8(7):727. doi: 10.3390/cells8070727. PMID: 31311206; PMCID: PMC6678302, Pugholm L H, Revenfeld A L, Søndergaard E K, Jørgensen M M. Antibody-Based Assays for Phenotyping of Extracellular Vesicles. Biomed Res Int. 2015; 2015: 524817. doi: 10.1155/2015/524817. Epub 2015 Dec. 3. PMID: 26770974; PMCID: PMC4681819, Shao H, Im H, Castro C M, Breakefield X, Weissleder R, Lee H. New Technologies for Analysis of Extracellular Vesicles. Chem Rev. 2018 Feb. 28; 118(4):1917-1950. doi: 10.1021/acs.chemrev.7b00534. Epub 2018 Jan. 31. PMID: 29384376; PMCID: PMC6029891, which are incorporated herein by reference in their entireties.

Pharmaceutical Compositions

Provided herein are compositions comprising the engineered extracellular vesicles (artificial synapses) provided herein.

In one aspect, provided herein is a composition comprising: a plurality of the engineered extracellular vesicles provided herein. In some embodiments of any of the aspects, the compositions and engineered EVs provided herein further comprise a pharmaceutically acceptable carrier.

For clinical use of the methods and compositions described herein, administration of the engineered EVs/artificial synapses provided herein can include formulation into pharmaceutical compositions or pharmaceutical formulations for parenteral administration, e.g., intravenous; mucosal, e.g., intranasal; ocular, or other mode of administration. In some embodiments, the engineered EVs described herein can be administered along with any pharmaceutically acceptable carrier compound, material, or composition which results in an effective treatment in the subject. Thus, a pharmaceutical formulation for use in the methods described herein can contain the engineered EVs described herein in combination with one or more pharmaceutically acceptable ingredients. The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or steric acid), or solvent encapsulating material, involved in maintaining the stability, solubility, or activity of, an engineered EV as described herein. Each carrier must be "acceptable" in the sense of being compatible with the other ingredients of the formulation and not injurious to the patient. The terms "excipient," "carrier," "pharmaceutically acceptable carrier" or the like are used interchangeably herein.

The engineered EVs provided herein can be formulated for administration of the compound to a subject in solid, liquid, or gel form, including those adapted for the following: (1) parenteral administration, for example, by subcutaneous, intramuscular, intravenous or epidural injection as, for example, a sterile solution or suspension, or sustained-release formulation; (2) transdermally; (3) transmucosally; (4) via bronchoalveolar lavage.

In some embodiments, the compositions described herein comprise a particle or polymer-based vehicle. Exemplary particle or polymer-based vehicles include, but are not limited to, nanoparticles, microparticles, polymer microspheres, or polymer-drug conjugates.

In one embodiment of any of the aspects, the compositions described herein further comprise a lipid vehicle. Exemplary lipid vehicles include, but are not limited to, liposomes, phospholipids, micelles, lipid emulsions, and lipid-drug complexes.

Formulations can be adapted for delivery to the airway, e.g., to address respiratory inflammation. Such formulations can be adapted for delivery as an aerosol, e.g., for inhalation. In some embodiments, the compositions described herein are formulated for aerosol administration, nebulizer administration, tracheal lavage administration, or for a pulmonary delivery device.

As used herein, the term "pulmonary delivery device" refers to a device used to deliver a therapeutic dose of a composition of the present invention to the respiratory system including, but not limited to, a nebulizer, metered-dose inhaler, or dry powder inhaler.

Examples of nebulizers include, but are not limited to, soft mist inhalers (for example Respimat® Boehringer Ingelheim) jet nebulizers (use compressed gas or air), ultrasonic nebulizers (produce aerosols using a piezoelectric crystal vibrating at high frequencies), and vibrating mesh nebulizers.

As used herein, the term "jet nebulizer" refers to a device that flows compressed air or gas through a composition of the present invention for aerosolization. The aerosolized composition of the present invention may be inhaled by a patient. Jet nebulizer may include, but is not limited to, jet nebulizers with a corrugated tube, jet nebulizers with a collection bag, breath enhanced jet nebulizers, breath actuated jet nebulizers, and metered-dose inhalers. Examples of jet nebulizers include, but are not limited to, Circulaire (Westmed INC, Tucson, AZ), Pari Inhalierboy (PARI, Midlothian, VA), Pari LC Plus (PARI, Midlothian, VA), NebuTech (Salter Labs, Arvin, CA), AeroEclipse (Monoghan/Trudell Medical International, London, Ontario, Canada), and Maxin MA-2 (MA-2; Clinova Medical AB, Malmö, Sweden). Examples of ultrasonic nebulizers include, but are not limited to, De Vilbiss-Pulmosonic (Somerset, PA), Omron-Microair (Omron, Kyoto, Japan), Omron NE-U17 (Omron, Kyoto, Japan), Rhone Poulenc-Rorer-Fisoneb (Sanofi, Paris, France), and Beurer Nebulizer IH30 (Beurer GmbH, Neu-Ulm, Germany).

As used herein, the term "mesh nebulizer" refers to forcing a liquid, gel, fluid, solution, tincture, or the like through apertures in a mesh or aperture plate to generate aerosol. Mesh nebulizer may include, but is not limited to, active mesh nebulizers and passive mesh nebulizers. Examples of active mesh nebulizers include, but is not limited to, Aeroneb® (Aerogen, Galway, Ireland) and eFlow® (PARI, Midlothian, VA). Examples of passive mesh nebulizers are, but not limited to, I-neb (Philips Respironics, Newark, USA), AKITA (Activaero, Gemunden/Wohra, Germany), and Microair NE-U22® (Omron, Kyoto, Japan).

For use as aerosols, the compositions described herein can be prepared in a solution or suspension and may be packaged in a pressurized aerosol container together with suitable propellants, for example, hydrocarbon propellants like propane, butane, or isobutane with conventional excipients.

The engineered EVs provided herein can also be administered in a non-pressurized form such as in a nebulizer or atomizer that reduces a liquid to a fine spray. Preferably, by such nebulization small liquid droplets of uniform size are produced from a larger body of liquid in a controlled manner. Nebulization can be achieved by any suitable means therefor, including by using many nebulizers known and marketed today. For example, an AEROMIST™ pneumatic nebulizer available from Inhalation Plastic, Inc. of Niles, Ill.

When the active ingredients are adapted to be administered, either together or individually, via nebulizer(s) they can be in the form of a nebulized aqueous suspension or solution, with or without a suitable pH or tonicity adjustment, either as a unit dose or multi-dose device.

Furthermore, any suitable gas can be used to apply pressure during the nebulization, with preferred gases to date being those which are chemically inert. Exemplary gases including, but are not limited to, nitrogen, argon, or helium can be used to advantage.

In some embodiments, the compositions described herein can also be administered directly to the airways in the form of a dry powder. Thus, the engineered EVs can be administered via an inhaler. Exemplary inhalers include metered dose inhalers and dry powdered inhalers.

A metered dose inhaler or "MDI" is a pressure resistant canister or container filled with a product such as a pharmaceutical composition dissolved in a liquefied propellant or micronized particles suspended in a liquefied propellant. The propellants which can be used include chlorofluorocarbons, hydrocarbons or hydrofluoroalkanes. Commonly used propellants are P134a (tetrafluoroethane) and P227 (heptafluoropropane) each of which may be used alone or in combination. They are optionally used in combination with one or more other propellants and/or one or more surfactants and/or one or more other excipients, for example ethanol, a lubricant, an anti-oxidant and/or a stabilizing agent.

As used herein, the term "dry powder inhaler" refers to a device that delivers a therapeutic dose of a composition of the present invention in a powdered form without propellants to the respiratory system. A dry powder inhaler (i.e., Turbuhaler™ (Astra AB)) is a system operable with a source of pressurized air to produce dry powder particles of a pharmaceutical composition that is compacted into a very small volume. Examples of dry powder inhalers include, but are not limited to, Spinhaler® (Fisons Pharmaceuticals, Rochester, NY), Rotahaler® (GlaxoSmithKline, NC), Turbuhaler® (AstraZeneca, UK), and Diskhaler® (GlaxoSmithKline, NC).

Dry powder aerosols for inhalation therapy are generally produced with mean diameters primarily in the range of <5 μm. As the diameter of particles exceeds 3 μm, there is increasingly less phagocytosis by macrophages. However, increasing the particle size also has been found to minimize the probability of particles (possessing standard mass density) entering the airways and acini due to excessive deposition in the oropharyngeal or nasal regions.

Suitable powder compositions include, by way of illustration, powdered preparations including the engineered EVs described herein. These can be intermixed with lactose, or other inert powders acceptable for intrabronchial administration. The powder compositions can be administered via an aerosol dispenser or encased in a breakable capsule which may be inserted by the patient or clinician into a device that punctures the capsule and blows the powder out in a steady stream suitable for inhalation. The compositions can include propellants, surfactants, and co-solvents and may be filled into conventional aerosol containers that are closed by a suitable metering valve.

Aerosols for the delivery to the respiratory tract are described, for example, by Adjei, A. and Garren, J. Pharm. Res., 1:565-569 (1990); Zanen, P. and Lamm, J.-W. J. Int. J. Pharm., 114:111-115 (1995); Gonda, I. "Aerosols for delivery of therapeutic and diagnostic agents to the respiratory tract," in Critical Reviews in Therapeutic Drug Carrier Systems, 6:273-313 (1990); Anderson et al., Am. Rev. Respir. Dis., 140:1317-1324 (1989)) and have potential for the systemic delivery of peptides and proteins as well (Patton and Platz, Advanced Drug Delivery Reviews, 8:179-196 (1992)); Timsina et al., Int. J. Pharm., 101:1-13 (1995); and Tansey, I. P., Spray Technol. Market, 4:26-29 (1994); French, D. L., Edwards, D. A. and Niven, R. W., Aerosol Sci., 27:769-783 (1996); Visser, J., Powder Technology 58:1-10 (1989)); Rudt, S. and R. H. Muller, J. Controlled Release, 22:263-272 (1992); Tabata, Y, and Y. Ikada, Biomed. Mater. Res., 22:837-858 (1988); Wall, D. A., Drug Delivery, 2:10 1-20 1995); Patton, J. and Platz, R., Adv. Drug Del. Rev., 8:179-196 (1992); Bryon, P., Adv. Drug. Del. Rev., 5:107-132 (1990); Patton, J. S., et al., Controlled Release, 28:15 79-85 (1994); Damms, B. and Bains, W., Nature Biotechnology (1996); Niven, R. W., et al., Pharm. Res., 12 (9); 1343-1349 (1995); and Kobayashi, S., et al., Pharm. Res., 13 (1): 80-83 (1996), the contents of each of which are incorporated herein by reference in their entirety.

Microemulsification technology can improve bioavailability of some lipophilic (water insoluble) pharmaceutical agents. Examples include Trimetrine (Dordunoo, S. K., et al., Drug Development and Industrial Pharmacy, 17 (12), 1685-1713, 1991 and REV 5901 (Sheen, P. C., et al., J Pharm Sci 80 (7), 712-714, 1991). Among other things, microemulsification provides enhanced bioavailability by preferentially directing absorption to the lymphatic system instead of the circulatory system, which thereby bypasses the liver, and prevents destruction of the cell-based compositions in the hepatobiliary circulation.

The engineered EVs described herein can be formulated with an amphiphilic carrier. Amphiphilic carriers are saturated and monounsaturated polyethyleneglycolyzed fatty acid glycerides, such as those obtained from fully or partially hydrogenated various vegetable oils. Such oils may advantageously consist of tri-, di-, and mono-fatty acid glycerides and di- and mono-polyethyleneglycol esters of the corresponding fatty acids, with a particularly preferred fatty acid composition including capric acid 4-10, capric acid 3-9, lauric acid 40-50, myristic acid 14-24, palmitic acid 4-14 and stearic acid 5-15%. Another useful class of amphiphilic carriers includes partially esterified sorbitan and/or sorbitol, with saturated or mono-unsaturated fatty acids (SPAN-series) or corresponding ethoxylated analogs (TWEEN-series).

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc. (produced and distributed by a number of companies in USA and worldwide).

The engineered EV compositions provided herein can be formulated with hydrophilic polymers. Hydrophilic polymers are water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Other hydrophilic polymers which may be suitable include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a pharmaceutical composition as described herein comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho) esters, poly (butic acid), poly(valeric acid), poly(lactide-co-caprolactone), polysaccharides, proteins, polyhyaluronic acids, polycyanoacrylates, and blends, mixtures, or copolymers thereof.

In certain embodiments, a pharmaceutical composition described herein is formulated as a liposome. Liposomes can be prepared by any of a variety of techniques that are known in the art. See, e.g., U.S. Pat. No. 4,235,871; Published PCT applications WO 96/14057; New RRC, Liposomes: A practical approach, IRL Press, Oxford (1990), pages 33-104; Lasic DD, Liposomes from physics to applications, Elsevier Science Publishers BV, Amsterdam, 1993.

Therapeutic formulations of the engineered EV compositions as described herein can be prepared for storage by with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Vaccine or other pharmaceutical compositions comprising an engineered EV composition as described herein can contain a pharmaceutically acceptable salt, typically, e.g., sodium chloride, and preferably at about physiological concentrations. The formulations of the vaccine or other pharmaceutical compositions described herein can contain a pharmaceutically acceptable preservative. In some embodiments, the preservative concentration ranges from 0.1 to 2.0%, typically v/v. Suitable preservatives include those known in the pharmaceutical arts. Benzyl alcohol, phenol, m-cresol, methylparaben, and propylparaben are examples of preservatives. The formulations of the vaccine or other pharmaceutical compositions described herein can include a pharmaceutically acceptable surfactant at a concentration of 0.005 to 0.02%.

Therapeutic pharmaceutical compositions described herein can also contain more than one active compound as necessary for the particular indication being treated, preferably those with complementary activities that do not adversely affect each other.

In some embodiments in which the engineered EVs are formulated for use in or with a vaccine, the vaccine composition can be formulated with the engineered EVs as an adjuvant. In other embodiments the vaccine composition can be formulated with the engineered EVs and an additional adjuvant, e.g., as known in the art.

As used herein in the context of immunization, immune response and vaccination, the term "adjuvant" refers to any substance than when used in combination with a specific antigen produces a more robust immune response than the antigen alone. When incorporated into a vaccine formulation, an adjuvant acts generally to accelerate, prolong, or enhance the quality of specific immune responses to the vaccine antigen(s). Adjuvants typically promote the accumulation and/or activation of accessory cells or factors to enhance antigen-specific immune responses and thereby enhance the efficacy of vaccines, i.e., antigen-containing or encoding compositions used to induce protective immunity against the antigen.

Adjuvants, in general, include adjuvants that create a depot effect, immune-stimulating adjuvants, and adjuvants that create a depot effect and stimulate the immune system. An adjuvant that creates a depot effect is an adjuvant that causes the antigen to be slowly released in the body, thus prolonging the exposure of immune cells to the antigen. This class of adjuvants includes but is not limited to alum (e.g., aluminum hydroxide, aluminum phosphate); emulsion-based formulations including mineral oil, non-mineral oil, water-in-oil or oil-in-water-in oil emulsion, oil-in-water emulsions such as Seppic ISA series of Montanide adjuvants (e.g., Montanide ISA 720; AirLiquide, Paris, France); MF-59 (a squalene-in-water emulsion stabilized with Span 85 and Tween 80; Chiron Corporation, Emeryville, Calif.); and PROVAX™ (an oil-in-water emulsion containing a stabilizing detergent and a micelle-forming agent; IDEC Pharmaceuticals Corporation, San Diego, Calif.).

An immune-stimulating adjuvant is an adjuvant that causes activation of a cell of the immune system. It may, for instance, cause an immune cell to produce and secrete cytokines and interferons. This class of adjuvants includes but is not limited to saponins purified from the bark of the *Q. saponaria* tree, such as QS21 (a glycolipid that elutes in the 21st peak with HPLC fractionation; Aquila Biopharmaceuticals, Inc., Worcester, Mass.); poly[di(carboxylatophenoxy)phosphazene (PCPP polymer; Virus Research Institute, USA); derivatives of lipopolysaccharides such as monophosphoryl lipid A (MPL; Ribi ImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); and *Leishmania* elongation factor (a purified *Leishmania* protein; Corixa Corporation, Seattle, Wash.). This class of adjuvants also includes CpG DNA.

Adjuvants that create a depot effect and stimulate the immune system are those compounds which have both of the above-identified functions. This class of adjuvants includes but is not limited to ISCOMS (immunostimulating complexes which contain mixed saponins, lipids and form virus-sized particles with pores that can hold antigen; CSL, Melbourne, Australia); SB-AS2 (SmithKline Beecham adjuvant system #2 which is an oil-in-water emulsion containing MPL and QS21: SmithKline Beecham Biologicals [SBB], Rixensart, Belgium); SB-AS4 (SmithKline Beecham adjuvant system #4 which contains alum and MPL; SBB, Belgium); non-ionic block copolymers that form micelles such as CRL 1005 (these contain a linear chain of hydrophobic polyoxypropylene flanked by chains of polyoxyethylene; Vaxcel, Inc., Norcross, Ga.); and Syntex Adjuvant Formulation (SAF, an oil-in-water emulsion containing Tween 80 and a nonionic block copolymer; Syntex Chemicals, Inc., Boulder, Colo.).

The active ingredients of the pharmaceutical compositions described herein can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

In some embodiments, sustained-release preparations can be used. Suitable examples of sustained-release preparations include semipermeable matrices of solid hydrophobic polymers containing a composition described herein in which the matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated, the composition can remain in the body for a long time (e.g., up to about 1 hour, between 1-12 hours, 12-24 hours, 24 hours to 2 days, 2-3 days, 3-4 days, 4-5 days, 5-6 days, 6-7 days, 1-2 weeks, 3-4 weeks, 4 weeks to 2 months, 2-3 months, 3-4 months, 4-5 months, 5-6 months, or more than 6 months, or a variation thereof), denature, or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S— bond formation through thio-disulfide interchange, stabilization can be achieved by modifying sulfhydryl residues, lyophilizing from acidic solutions, controlling moisture content, using appropriate additives, and developing specific polymer matrix compositions.

Administration, Dosing, Efficacy

The engineered EV compositions, pharmaceutical compositions, or vaccine compositions described herein can be formulated, dosed, and administered in a fashion consistent with good medical practice. Factors for consideration in this context include the particular disorder being treated, the particular subject being treated, the clinical condition of the individual subject, the cause of the disorder, the site of delivery of the vaccine composition, the method of administration, the scheduling of administration, and other factors known to medical practitioners.

Generally, application of artificial synapses as therapy will take into account similar parameters as other therapeutic strategies, including concentration, timing of delivery, and sustained bioavailability at injury/disease site. Extracellular vesicle can be delivered via a number of routes: intravenous, intracoronary, and intramyocardial. Extracellular vesicles (e.g., exosomes), also allow for new delivery routes that were previously infeasible for cell therapy, such as inhalation or injection. These various approaches are described below, including injection, topical application, enteral administration, and pulmonary delivery.

The engineered EV compositions provided herein can be administered to a subject in need thereof by any appropriate route which results in an effective treatment in the subject. As used herein, the terms "administering," and "introducing" are used interchangeably and refer to the placement of a composition provided herein into a subject by a method or route which results in at least partial localization of such compositions at a desired site, such as a site of inflammation or a tumor, such that a desired effect(s) is produced. The compositions can be administered to a subject by any mode of administration that delivers the composition systemically or to a desired surface or target, and can include, but is not limited to, injection, infusion, instillation, and inhalation administration. To the extent that the composition can be protected from inactivation in the gut, oral administration forms are also contemplated. "Injection" includes, without limitation, intravenous, intramuscular, intra-arterial, intrathecal, intraventricular, intracapsular, intraorbital, retro-orbital, intravitreal, intraocular, intracardiac, intradermal, intraperitoneal, transtracheal, subcutaneous, subcuticular, intraarticular, sub capsular, subarachnoid, intraspinal, intracerebral, intratarsal, and intrasternal, intratumoral injection, and infusion or the like as known in the art.

A therapeutic does of the present invention may be delivered to a patient by means of controlled release, for example but not limited to, implantable pump and implantable cannulas to provide continuous access to the venous or arterial system.

Topical application refers to applying or spreading a composition of the present invention onto surfaces on or in the body, both internally and/or externally, in a therapeutically effective amount for local and/or systemic treatment. Topical application may be epicutaneuos wherein a composition of the present invention may be directly applied onto a localized surface of the skin or mucous membranes. Topical application may include transdermal application wherein a composition of the present invention may be absorbed into the body to obtain systemic delivery and systemic distribution. Topical application formulations may include, but are not limited to, creams, foams, gels, lotions, solutions, ointments, dermal patch, transdermal patches, powder, solid, sponge, tape, vapor, paste, film, liposomes, balm, shampoo, spray, or tincture or the like or a combination thereof. A therapeutic dose of a composition of the present invention may be delivered vaginally (for example a vaginal suppository, vaginal ring, douche, intrauterine device, intravesical infusion, and the like) or urethra or the like or a combination thereof.

Enteral administration refers to a composition of the present invention administered via the gastrointestinal tract in a therapeutically effective amount for local or systemic treatment. Enteral administration may include, but is not limited to, delivery of a composition of the present invention via the mouth, sublingual, esophagus, gastric (for example the stomach), small intestines, large intestines or rectum. Oral delivery of the present invention may include, but is not limited to, the use of a capsule, pastille, pill, tablet, solution, gel, suspension, emulsion, syrup, elixir, tincture, mouthwash, lozenges, chewing gum, lollipop, cream, foam, solution, powder, solid, vapor, liposomes, spray, or tincture osmotic-controlled release oral delivery system, or the like. Gastric delivery may involve the use of a tube or nasal passage that leads directly to the stomach, for example, a percutaneous endoscopic gastrostomy tube. Gastric delivery may involve direct injection made through the abdominal wall. Rectal delivery may involve, but is not limited to, the use of a suppository, ointment, enema, murphy drip, or the like. A therapeutic does of the present invention may be delivered to a patient by means of controlled release, for example but not limited to, controlled release drug delivery pellet or pill.

Inhalation (i.e., pulmonary delivery, pulmonary administration refers to delivery to the respiratory system through the respiratory route, including but not limited to, intranasal administration, oral administration, and oral inhalative administration (e.g., intratracheal instillation and intratracheal inhalation) of a therapeutically effective amount for local or systemic treatment. Pulmonary delivery of a therapeutically effective amount of a composition of the present invention may be achieved by dispersion, for example by using a syringe. Pulmonary delivery of a composition of the present invention may be achieved by aerosol administration, wherein aerosol administration may deposit a therapeutically effective amount of the present invention by gravitational sedimentation, inertial impaction, or diffusion.

Intravenous delivery technique can occur through a peripheral or central venous catheter. As the simplest delivery mode, this technique avoids the risk of an invasive procedure. However, intravenous may be regarded as a comparatively inefficient and less localized delivery method, as a high percentage of infused cell exosomes may become sequestered in organs such as the lung, liver, or spleen. Such sequestration may result in few or no cellular exosomes reaching broader circulation or have unintended systemic effects following their distribution.

In certain embodiments, administration can include delivery to a tissue or organ site that is the same as the site of diseased and/or dysfunctional tissue. In certain embodiments, administration can include delivery to a tissue or organ site that is different from the site or diseased and/or dysfunctional tissue. In certain embodiments, the delivery is via inhalation or oral administration. In various embodiments, administration of artificial synapses can include combinations of multiple delivery techniques.

In some embodiments, the compositions described herein are administered by aerosol administration, nebulizer administration, or tracheal lavage administration.

The term "effective amount" as used herein refers to the amount of an engineered EV composition needed to alleviate or prevent at least one or more symptom of a disease or disorder (e.g., autoimmune disease or cancer), and relates to a sufficient amount of pharmacological composition to provide the desired effect, e.g., reduce the pathology, or any symptom associated with or caused by a disease. The term "therapeutically effective amount" therefore refers to an amount of an engineered EV composition or vaccine composition described herein using the methods as disclosed herein, that is sufficient to affect a particular disease state when administered to a typical subject. An effective amount as used herein would also include an amount sufficient to delay the development of a symptom of the disease, alter the course of a symptom disease (for example, but not limited to, slow the progression of a symptom of the disease), or reverse a symptom of the disease. Thus, it is not possible to specify the exact "effective amount." However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of the engineered EVs or fusion polypeptides provided herein), which achieves a half-maximal inhibition of symptoms) as determined in cell culture, or in an appropriate animal model. Levels of therapeutic engineered Evs in plasma can be measured, for example, by high performance liquid chromatography, enzyme linked immunosorbent assay (ELISA), flow cytometry, FACS sorting, western blot, mass spectroscopy, tunable resistive pulse sensing, EXOVIEW®, qRT-PCR, next generation sequencing (NGS), or by any analysis technique known by one of ordinary skill in the art. The effects of any particular dosage can be monitored by a suitable bioassay. The dosage can be determined by a physician and adjusted, as necessary, to suit observed effects of the treatment.

The engineered EV compositions, pharmaceutical compositions, or vaccine compositions described herein can be formulated, in some embodiments, with one or more additional therapeutic agents currently used to prevent or treat the infection, for example. The effective amount of such other agents depends on the amount of an engineered EV in the formulation, the type of disorder or treatment, and other factors discussed above. These are generally used in the same dosages and with administration routes as used herein before or about from 1 to 99% of the heretofore employed dosages.

The dosage ranges for the pharmaceutical compositions described herein depend upon the potency and encompass amounts large enough to produce the desired effect. The dosage should not be so large as to cause unacceptable adverse side effects. Generally, the dosage will vary with the age, condition, health, and sex of the patient and can be determined by one of skill in the art. The dosage can also be adjusted by the individual physician in the event of any complication. In some embodiments, the dosage ranges from 0.001 mg/kg body weight to 100 mg/kg body weight. In some embodiments, the dose range is from 5 μg/kg body weight to 100 μg/kg body weight. Alternatively, the dose range can be titrated to maintain serum levels between 0.1 μg/mL and 1000 μg/mL. For systemic administration, subjects can be administered a therapeutic amount, such as, e.g., 0.1 mg/kg, 0.5 mg/kg, 1.0 mg/kg, 2.0 mg/kg, 2.5 mg/kg, 5 mg/kg, 7.5 mg/kg, 10 mg/kg, 15 mg/kg, 20 mg/kg, 25 mg/kg, 30 mg/kg, 40 mg/kg, 50 mg/kg, or more. These doses can be administered by one or more separate administrations, or by continuous infusion. For repeated administrations over several days or longer, depending on the condition, the treatment is sustained until, for example, the infection is treated, as measured by the methods described above or known in the art. However, other dosage regimens can be useful.

In various embodiments, the quantities of artificial synapses that are administered to achieve these effects range from $1\times10^6$ to $1\times10^7$, $1\times10^7$ to $1\times10^8$, $1\times10^8$ to $1\times10^9$, $1\times10^9$ to $1\times10^{10}$, $1\times10^{10}$ to $1\times10^{11}$, $1\times10^{11}$ to $1\times10^{12}$, $1\times10^{12}$ to $1\times10^{13}$, $1\times10^{13}$ to $1\times10^{14}$, $1\times10^{14}$ to $1\times10^{15}$, $1\times10^{15}$ or more Evs/artificial synapses. In other embodiments, the numbers of artificial synapses are relative to the number of cells used in a clinically relevant dose for a cell-therapy method. For example, defining an effective dose range, dosing regimen and route of administration, may be guided by studies using fluorescently labeled artificial synapses, and measuring target tissue retention, which can be >10×, >50×, or >100× background, as measured 5, 10, 15, 30, or 30 or more min as a screening criterion. In certain embodiments, >100× background measured at 30 mins is a baseline measurement for a low and high dose that is then assess for safety and bioactivity (e.g., using MRI endpoints: scar size, global and regional function of the target organ being treated). In various embodiments, single doses are compared to two, three, four, four or more sequentially-applied doses. In various embodiments, the repeated or sequentially-applied doses are provided for treatment of an acute disease and/or condition. In various embodiments, the repeated or sequentially-applied doses are provided for treatment of a chronic disease and/or condition. In other embodiments, administration of the plurality of artificial synapses is adjunctive to standard therapy.

In other embodiments, administering a composition includes $1\times10^{10}$ or more artificial synapses in a single dose. In various embodiments, exosome quantity may be defined by protein quantity, such as dosages including 1-10, 10-25, 25-50, 50-75, 75-100, or 100 or more mg exosome protein. In other embodiments, a single dose is administered multiple times to the subject. In other embodiments, administering a composition consists of one or more of: injection, topical administration, enteral, intravenous, intra-arterial, or inhalation.

In various embodiments, exosome quantity may be defined by protein quantity, such as dosages including 1-10, 10-25, 25-50, 50-75, 75-100, or 100 or more mg exosome protein. In various embodiments, administering a composition includes multiple dosages of the artificial synapses. In various embodiments, the repeated or sequentially-applied doses are provided for treatment of an acute disease and/or condition. In various embodiments, the repeated or sequentially-applied doses are provided for treatment of a chronic disease and/or condition.

In other embodiments, administering a composition including a plurality of artificial synapses to the subject is adjunctive to standard therapy.

The duration of a therapy using the methods described herein will continue for as long as medically indicated or until a desired therapeutic effect (e.g., those described herein) is achieved. In certain embodiments, the administration of the vaccine composition described herein is continued for 1 month, 2 months, 4 months, 6 months, 8 months, 10 months, 1 year, 2 years, 3 years, 4 years, 5 years, 10 years, 20 years, or for a period of years up to the lifetime of the subject.

As will be appreciated by one of skill in the art, appropriate dosing regimens for a given composition can comprise a single administration/immunization or multiple ones. Subsequent doses may be given repeatedly at time periods, for example, about two weeks or greater up through the entirety of a subject's life, e.g., to provide a sustained preventative effect. Subsequent doses can be spaced, for example, about two weeks, about three weeks, about four weeks, about one month, about two months, about three months, about four months, about five months, about six months, about seven months, about eight months, about nine months, about ten months, about eleven months, or about one year after a primary immunization.

The precise dose to be employed in the formulation will also depend on the route of administration and should be decided according to the judgment of the practitioner and each patient's circumstances. Ultimately, the practitioner or physician will decide the amount of the engineered EV or composition thereof to administer to particular subjects.

Methods of Modulating Inflammation and Treating Autoimmune Diseases

The artificial synapses/engineered Evs and compositions thereof provided herein can be deployed in a therapeutic strategy against virtually any injury/disease, as providing a platform for altering biological signaling. This includes, for example, inflammation and immune signaling, which plays a role in virtually all injuries and diseases in living organisms.

Thus, described herein is a method of modulating inflammation, including selecting a subject afflicted with an inflammatory related disease and/or condition; and administering to the subject a composition including a plurality of artificial synapses (engineered Evs) to the subject, wherein administration of the composition modulates inflammation.

As used herein, the term "inflammation" or "inflamed" refers to activation or recruitment of the immune system or immune cells (e.g., T cells, B cells, macrophages). A tissue that has inflammation can become reddened, white, swollen, hot, painful, sensitivity, exhibit a loss of function, or have a film or mucus. Methods of identifying inflammation are well known in the art. Inflammation typically occurs following injury, infection by a microorganism, exposure to a substance (e.g., a toxin, chemical, or dust) or autoimmune dysfunction. Onset of inflammation may be rapid (e.g., immediately following injury) or slow (e.g., repeated exposure to an irritant such as a chemical over time) with a duration of minutes, hours, days, months, years, or an individual's life.

Inflammation plays a vital role in alerting the immune system of potential danger and damage within a body. Inflammation is necessary to control and repair injury. For example, acute inflammation is a response to physical trauma, infection, and stress. Acute inflammation helps prevent further injury and triggers healing and recovery. Unfortunately, inflammation can become excessive and inappropriately active, lasting beyond the typical recovery time from an injury or infection. Wherein healthy inflammation helps a body respond to injury, chronic inflammation perpetuates injury and may lead to negative consequences to one's health. In particular, autoimmune diseases are chronic diseases from a host's immune system attacking itself, often due to aberrant biological signaling in the host. Restoring normal homeostatic signaling via application of artificial synapses, particularly targeting immune checkpoints, represents a highly promising avenue. For example, surface bound immune-checkpoint proteins or fragments thereof may modulate immune cell stimulation and affect suppression of immune cell function when delivered via artificial synapses. Injection, inhalation, ingestion or topical application of artificial synapses with surface bound immune-checkpoint proteins or fragments thereof may be used to treat immune, auto-immune, inflammatory, and auto-inflammatory conditions. Examples include chronic obstructive pulmonary disease (COPD) which is an inflammatory, progressive, life-threatening lung disease, psoriasis, a common chronic noncommunicable inflammatory skin disease, arthritis, a debilitating and painful degeneration of joints, among others well-understood to one of skill in the art.

In other embodiments, the inflammatory related disease and/or condition is acute, for example septicemia. In other embodiments, the inflammatory related disease and/or condition is chronic, for example chronic obstructive pulmonary disease. In other embodiments, the inflammatory condition is an autoimmune disease wherein the autoimmune disease and/or condition is one or more of: polymyositis, dermatomyositis, Graves' disease, Hashimoto's thyroiditis, myasthenia gravis, vasculitis, multiple sclerosis, psoriasis, rheumatoid arthritis, psoriatic arthritis, scleroderma, systemic lupus erythematosus, inflammatory bowel disease, Crohn's disease, hyperthyroidism, autoimmune adrenal insufficiency, Sjogren syndrome, type I diabetes mellitus, autoimmune hemolytic anemia, idiopathic thrombocytopeniarpura, myasthenia gravis, ulcerative colitis, uveitis, polyarteritis nodosa, relapsing polychondritis, Behcet's disease, reactive arthritis, ankylosing spondylitis, Guillain-Barre syndrome, or optic neuropathy. In other embodiments, the disease and/or condition is chronic obstructive pulmonary disease, rheumatoid arthritis, uveoretinitis, psoriasis, and eczema. In other embodiments, the disease and/or condition is irritable bowel disease, multiple sclerosis or lupus.

In other embodiments, the inflammatory related disease and/or condition is an ocular disease. As used herein, the terms "ocular disease", "eye disorder" and "eye disease" are used interchangeably and refer to a disease or disorder that affects the health and/or vision of either one or both eyes or the general area of the eye(s), eye lid(s), or area surrounding or in near proximity to the eye(s). Eye disease may include, but are not limited to, macular degeneration (e.g., age-related macular degeneration), cataracts, diabetic retinopathy, diabetic macular edema, eye floaters, eye flashes, glaucoma, amblyopia, strabismus, retinitis (e.g., CMV retinitis), color blindness, keratoconus, retinal detachment, eyelid twitching, ocular hypertension, blepharitis, uveitis, Bietti's crystalline dystrophy, blepharospasm, cornea and corneal diseases, dry eye, histoplasmosis, macular hole, macular pucker, conjunctivitis, presbyopia, retinoblastoma, retinitis pigmentosa, retinopathy, Stargardt disease, Usher syndrome, uveal Coloma, and vitreous detachment, or the like.

Described herein is a method for treatment including, selecting a subject in need of treatment, administering a composition including a plurality of artificial synapses to the individual, wherein administration of the composition treats the subject. In certain embodiments, the subject is in need to treatment for a disease and/or condition involving tissue damage or dysfunction.

Described herein is a method of treating an autoimmune disease, inflammation, inflammatory disease or condition, or cancer in a subject, the method comprising: administering to a subject an engineered EV or composition thereof as provided herein to the subject.

Measured or measurable parameters include clinically detectable markers of disease, for example, elevated or depressed levels of a clinical or biological marker, as well as parameters related to a clinically accepted scale of symptoms or markers for a disease or disorder. It will be understood, however, that the total usage of the compositions and formulations as disclosed herein will be decided by the attending physician within the scope of sound medical judgment. The exact amount required will vary depending on factors such as the type of disease being treated.

Non-limiting examples of clinical tests that can be used to assess autoimmune diseases, inflammatory conditions, or inflammation parameters include blood tests, skin biopsy, MRI, eye examination, ocular pressure tests, etc. Where necessary or desired, animal models of injury or disease can be used to gauge the effectiveness of a particular composition as described herein. For example, an EAU animal model, as demonstrated in the working examples can be used.

In various embodiments, administration of the plurality of artificial synapses alters gene expression in the damaged or dysfunctional tissue, improves viability of the damaged tissue, and/or enhances regeneration or production of new tissue in the individual. In various embodiments, administration of the plurality of artificial synapses alters gene expression in the damaged or dysfunctional tissue, improves viability of the damaged tissue, and/or enhances regeneration or production of new tissue in the individual.

In various embodiments, the damaged or dysfunctional tissue is in need of repair, regeneration, or improved function due to an acute event. Acute events include, but are not limited to, trauma such as laceration, crush or impact injury, shock, loss of blood or oxygen flow, infection, chemical or heat exposure, poison or venom exposure, drug overuse or overexposure, and the like. Other sources of damage also include, but are not limited to, injury, age-related degeneration, cancer, and infection. In several embodiments, the regenerative cells used to prepare the engineered EVs provided herein are from the same tissue type as is in need of repair or regeneration. In several other embodiments, the regenerative cells are from a tissue type other than the tissue in need of repair or regeneration. In some embodiments, the engineered EVs provided herein are derived from the subject being treated. In some embodiments, the engineered EVs are derived from a donor subject.

In other embodiments, the damaged or dysfunctional tissue is in need of repair, regeneration, or improved function due to damage from chronic disease.

Some Selected Definitions

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy 22$^{nd}$ ed.*, Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology 3$^{rd}$ ed., revised ed.*, J. Wiley & Sons (New York, NY 2006); Smith, *March's Advanced Organic Chemistry Reactions, Mechanisms and Structure 7$^{th}$ ed.*, J. Wiley & Sons (New York, NY 2013); Singleton, *Dictionary of DNA and Genome Technology 3$^{rd}$ ed.*, Wiley-Blackwell (Nov. 28, 2012); and Green and Sambrook, *Molecular Cloning: A Laboratory Manual 4th ed.*, Cold Spring Harbor Laboratory Press (Cold Spring Harbor, NY 2012), provide one skilled in the art with a general guide to many of the terms used in the present application. For references on the preparation and structure of antibodies and fusion polypeptides, see, e.g., Greenfield, *Antibodies A Laboratory Manual 2$^{nd}$ ed.*, Cold Spring Harbor Press (Cold Spring Harbor NY, 2013); Köhler and Milstein, *Derivation of specific antibody-producing tissue culture and tumor lines by cell fusion*, Eur. J. Immunol. 1976 Jul. 6 (7): 511-9; Queen and Selick, Humanized immunoglobulins, U.S. Pat. No. 5,585,089 (1996 December); and Riechmann et al., *Reshaping human antibodies for therapy*, Nature 1988 Mar. 24, 332 (6162): 323-7. See also, Kabat et al., Sequences of Proteins of Immunological Interest, 5th Ed. Public Health Service, National Institutes of Health, Bethesda, Md. (1991), Lanzavecchia et al., Eur. J. Immunol. 17, 105 (1987)), Huston et al., Proc. Natl. Acad. Sci. U.S.A., 85, 5879-5883 (1988), Bird et al., Science 242, 423-426 (1988), Brinkman et al. mAbs Vol 9, No. 2, 182-212 (2017), Chothia & Lesk, J. Mol. Biol, 196:901-917 (1987), Chothia et al., Nature 342:877-883 (1989)), Holliger et al. (1993) Proc. Natl. Acad. Sci. USA 90:6444-6448; Poljak (1994) Structure 2:1121-1123); Kontermann and Dubel eds., Antibody Engineering, Springer-Verlag, N.Y. (2001), p. 790 (ISBN 3-540-41354-5, Zapata et al. (1995) Protein Eng. 8 (10): 1057-1062; Morrison, et al., Proc. Natl. Acad. Sci. USA, 81:6851 (1984), U.S. Pat. Nos. 4,816,567, 5,693,780, which are incorporated herein by reference in their entireties.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

As used herein, the term "extracellular vesicle" and "vesicle" are used interchangeably and refer to a particle, wherein the particle comprises a phospholipid bilayer that encloses an internal space and an exterior surface and may or may not be derived from a cell. The size of extracellular vesicles can range between 20 nm to 3 μm in diameter but may be smaller than 20 nm or larger than 3 μm. Examples of extracellular vesicles include, but is not limited to, exosomes (for example small exosomes and large exosomes), ectosomes, macrovesicles, microparticles, apoptotic bodies, vesicular organelles, oncosomes (for examples large oncosomes), exospheres, exomeres, cell derived nanovesicles (CDN) (e.g., by genesis via grating or shearing cells), liposomes or the like known by one of ordinary skill in the art. Extracellular vesicles may originate naturally via known or unknown biosynthetic pathways. Extracellular vesicles may be promoted to originate by using mechanical methods such as cell grating or cell shearing wherein a cell is grated or sheared causing portions or parts of the cell membrane to from vesicles. For example, CDNs may be formed by using mechanical methods such as cell grating or cell shearing wherein a cell is grated or sheared causing portions or parts of the cell membrane to from vesicles. Additional non-limiting examples of mechanical methods that can be used to form cell derived nanovesicles are further described in detail, e.g., Goh, W. J., Zou, S., Ong, W. Y. et al. Bioinspired Cell-Derived Nanovesicles versus Exosomes as Drug Delivery Systems: a Cost-Effective Alternative. *Sci Rep* 7, 14322 (2017). doi: 10.1038/s41598-017-14725-x, the contents of which are incorporated herein by reference in their entireties.

Extracellular vesicles comprise cargo, wherein the term "cargo" refers to peptides, proteins, nucleic acids, lipids, metabolites, carbohydrates, biomolecules, small molecules, large molecules, vesicles, organelles, or fragments thereof. In some embodiments, cargo may refer to existing drugs or therapeutics known in the art. Extracellular vesicle cargo may be located within the internal space of the extracellular vesicle. Extracellular vesicle cargo may be membrane bound and span one or both layers of the extracellular vesicle phospholipid bilayer (for example a transmembrane protein). Extracellular vesicle cargo may be in contact with the external or internal surface of the extracellular vesicle, for example through a covalent bond or a non-covalent bond. The phospholipid bilayer of the extracellular vesicle may comprise one or more transmembrane proteins, wherein a portion of the one or more transmembrane membrane proteins is located within the internal space of the extracellular vesicle. The phospholipid bilayer of the extracellular vesicle may comprise one or more transmembrane proteins, wherein the one or more transmembrane membrane proteins comprises a domain on the exterior of the extracellular vesicle. The phospholipid bilayer of the extracellular vesicle may comprise one or more transmembrane proteins, wherein the one or more transmembrane membrane proteins comprises a domain on the interior of the extracellular vesicle. Cargo may refer to a protein on the luminal side (e.g., in the internal space) of the extracellular vesicle wherein said protein encodes a vesicle targeting domain that may be in contact with the interior phospholipid layer of the extracellular vesicle. Cargo may refer to a protein on the luminal side (e.g., in the internal space) of the extracellular vesicle wherein said protein encodes a vesicle targeting domain that may be in contact with the interior phospholipid layer of the extracellular vesicle and wherein said protein may be presented into the internal space of the extracellular vesicle.

As used herein, the terms "sticky binder" and "vesicle targeting domain" and "anchor protein" are used interchangeably and refer to a protein that is covalently or non-covalently attached to at least one lipid wherein the one or more lipid is embedded within a membrane (e.g., a cell membrane), and the lipid serves to anchor the protein to the membrane. The terms "sticky binder" and "vesicle targeting domain" and "anchor protein" can also mean a protein sequence that encodes for one or more transmembrane domains wherein the one or more transmembrane domains spans at least partly through a phospholipid bilayer, for example the phospholipid bilayer of an extracellular vesicle. The transmembrane domain can be of a Type I or Type II membrane protein. Transmembrane domains can be structurally identified using methods known to those of skill in the art, such as sequence analysis programs that identify hydrophobic and hydrophilic domains (for example TMHMM Server, v. 2.0-DTU, Erik L. L. Sonnhammer, Gunnar von Heijne, and Anders Krogh: *A hidden Markov model for predicting transmembrane helices in protein sequences. In Proc. of Sixth Int. Conf. on Intelligent Systems for Molecular Biology, p* 175-182 Ed J. Glasgow, T. Littlejohn, F. Major, R. Lathrop, D. Sankoff, and C. Sensen Menlo Park, CA: AAAI Press, 1998, which is incorporated herein by reference in its entirety.)

A vesicle targeting domain may include, but is not limited to, one or more prenylation site, fatty acylation site, and/or glycosylphosphatidylinositol (GPI) linked protein. One preferred embodiment of a vesicle targeting domain is the GPI sequence from CD55. Another preferred embodiment of a vesicle targeting domain is the GPI sequence from CD59. Another embodiment of a vesicle targeting domain is the C1C2 domain from MFGE8. Other embodiments of sequences for vesicle targeting domains include transmembrane regions of CD9 (for example transmembrane 2 or 3 of CD9, CD9tm2 or CD9tm3, respectively), K-Ras (for example K-Ras4A and K-Ras4B), transmembrane domain from A Disintegrin and Metalloproteinase Domain-containing protein 10 (ADAM10, also known as CDw156 or CD156c) or other ADAM proteins. Vesicle targeting domains may include one or more sequences from 4F2 (for example 4F2 encoded by the solute carrier family 3 member 2 (SLC3A2) gene which makes up the heavy subunit of CD98). Vesicle targeting domains can include a sequence for one or more myristoylation sites. For example, the protein sequence for a myristoylation site from myristoylated alanine-rich C-kinase substrate (MARCKS) protein. Vesicle targeting domains can include a sequence for one or more palmitoylation sites. For example, the myristoylation sequence from the MARCKS protein may be modified to encode for a palmitoylation site. All variants, isoforms, or fragments or the like known by one of ordinary skill in the art are encompassed by the present invention.

Vesicle targeting domains may include transmembrane sequences from *Homo sapiens* transferrin receptor 2 (TFR2), transcript variant 1 (transferrin receptor protein 2 isoform 1) or versions therefore. In a preferred embodiment, the vesicle targeting domain may be a transmembrane domain from CD298.

As used herein, the terms "proteins" and "peptides" and "polypeptides" are used interchangeably herein to designate a series of amino acid residues connected to the other by peptide bonds between the alpha-amino and carboxy groups of adjacent residues. Although "protein" is often used in reference to relatively large polypeptides, and "peptide" is often used in reference to small polypeptides, usage of these terms in the art overlaps and varies. The term "peptide" as used herein refers to peptides, polypeptides, proteins and fragments of proteins, unless otherwise noted. The terms "protein" and "peptide" are used interchangeably herein when referring to a gene product and fragments thereof. Thus, exemplary peptides or proteins include gene products, naturally occurring proteins, homologs, orthologs, paralogs, fragments and other equivalents, variants, fragments, and analogs of the foregoing.

As used herein, the term "linker" refers to a synthetic protein sequence of amino acids that is used to connect two polypeptide domains via peptide bonds.

As used herein, the term "fusion protein" refers to a single chimeric protein comprising a protein of interest (e.g., checkpoint protein) joined to an exogenous protein or protein fragment (e.g., an anchor protein), wherein the components of the fusion protein are linked to each other by peptide-bonds, either directly or through a peptide linker. The anchor protein of the fusion protein may enhance incorporation of the fusion protein onto and/or into the membrane of a vesicle, for example the internal and/or external leaflet of the phospholipid bilayer of an exosome membrane. The fusion protein may have at least a part of an amino acid sequence of an immune checkpoint protein or proteins involved in immune synapses. The fusion protein may have at least a part of an amino acid sequence of A2AR, VTCN1, Galectin 9, FGL-1, PECAM-1, TSG-6, STAB-1, NRP1, NRP2, SEMA3A, SEMA3F, RGMB, TIM-3, TIGIT, HLA class I, HLA class II, VISTA, HMGB1, phosphatidylserine, T-cell receptor (TCR), SHP-1, SHP-2, FBXO38, SH2D1A, B7RP1, IDO, NOX2, TNFRSF18, B7-H4, B7-H5, SISP1, B7-H6, B7-H7, APLNR, IFN y, PD-1, WNT5A, IL-6, IL-10, NKG2 family of C-type lectin receptors, ligands of NKG2 family, killer cell immunoglobulin-like receptors, CD2, CD4, CD8, CD27, CD27 ligand (CD70), CD28, CD28H, CD39, CD40, CD44, CD47, CD63, CD66a, CD80, B7-2, CD86, CD73, CD94, CD96, CD101, CD112, CD112R, CD122, CD134, CD137 (4-1BB), CD137 ligand (4-1BBL), CD152, CD154, CD155, CD158, CD158a, CD158g, CD158h, KIR2DL1, KIR2DS1, KIRDS3, KIR2DS5, CD160, CD172a, CD200, CD200R, CD223, CD226, CD252, CD270, CD272, CD273, CD274, CD275, CD276, CD278, CD279 (PD-1), CD279 ligand (PD-L1/PDL-2), CD328, CD329, and/or CD337. The fusion protein may have a polypeptide linker sequence (e.g., an Fc domain and/or a GSSG linker (SEQ ID NO: 319)), followed by an amino acid sequence coding for an anchor protein sequence (e.g., a prenylation site, fatty acylation site, or a GPI sequence) or any isoform, fragment, variation thereof, or a ligand to the aforementioned proteins thereof, or the like known by one of ordinary skill in the art. All variants are encompassed by the present invention.

As used herein, the term "immune synapse" and "cell synapse" are used interchangeably and refer to cell-to-cell interaction wherein said interaction results in activation, suppression, and/or adhesion of either one or more cells. Immune synapse or cell synapse are mediated by proteins that may be cytoplasmic, membrane bound, membrane associated, and/or secreted. Immune or cell synapses may be mediated by one or more "immune checkpoint proteins" which herein refers to any protein that is involved in maintaining immune homeostasis or plays a role in regulating immune activation or suppression. Immune checkpoint proteins may be cytoplasmic, membrane bound, membrane associated, and/or secreted.

As used herein, the term "fragment" or "active fragment" refers to a portion of a nucleic acid or polypeptide provided herein that retains the ability to be expressed by the engineered EVs provided herein. In some embodiments, the active fragment retains the ability to activate a target polypeptide, thereby increasing the activity of said target polypeptide (e.g., suppressing an immune response).

As used herein, the terms "specifically bind" and/or "specifically recognize" or "substantially binds" refers to the affinity of a binding molecule for a target molecule compared to the binding molecule's affinity for non-target molecules. A binding molecule (e.g., a POI domain) that specifically binds a target molecule (e.g., a target polypeptide provided herein) does not substantially recognize or bind non-target molecules. e.g., an antibody "specifically binds" and/or "specifically recognize" another molecule, meaning that this interaction is dependent on the presence of the binding specificity of the molecule structure, e.g., an antigenic epitope. As used herein, "non-specific binding" and "background binding" refers to the interaction that does not depend on the presence of specific structure (e.g., a specific antigenic epitopes). Methods of measuring binding of a polypeptide to a target are known in the art (e.g., differential scanning calorimetry, isothermal titration calorimetry, spectroscopy, crystallography, surface plasmon resonance, co-immunoprecipitation, pulldown assays, crosslinking, yeast two-hybrid system, tandem affinity purification-mass spectroscopy, protein microarrays, bio-layer interferometry, far-Western blots, computational prediction, analytical ultracentrifugation, light scattering, fluorescence spectroscopy, resonance energy transfer, ELISA or ELISPOT assays, or any other assays known in the art).

As used herein, the terms "treat," "treatment," "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a condition, disease or disorder associated with an infection or a cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation or at least slowing of progress or worsening of symptoms that would be expected in absence of treatment. Beneficial or desired clinical results include, but are not limited to, alleviation of one or more symptom(s), diminishment of extent of disease, stabilized (i.e., not worsening)

state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

As used herein "preventing" or "prevention" refers to any methodology where the disease state does not occur due to the actions of the methodology (such as, for example, administration of a composition or construct as described herein). In one aspect, it is understood that prevention can also mean that the disease is not established to the extent that occurs in untreated controls. Accordingly, prevention of a disease encompasses a reduction in the likelihood that a subject can develop the disease, relative to an untreated subject (e.g., a subject who is not treated with the methods or compositions described herein).

As used herein, the terms "autoimmune condition" and "autoimmune disease" are used interchangeably and refer to any disease characterized by abnormal functioning of the immune system and may include, but is not limited to, achalasia, Addison's disease, adult Still's disease, agammaglobulinemia, alopecia areata, amyloidosis, ankylosing spondylitis, anti-GBM/Anti-TBM nephritis, antiphospholipid syndrome, autoimmune angioedema, autoimmune dysautonomia, autoimmune encephalomyelitis, autoimmune hepatitis, autoimmune inner ear disease (AIED), autoimmune myocarditis, autoimmune oophoritis, autoimmune orchitis, autoimmune pancreatitis, autoimmune retinopathy, autoimmune urticaria, axonal & neuronal neuropathy (AMAN), Baló disease, Behcet's disease, benign mucosal pemphigoid, bullous pemphigoid, Castleman disease, celiac disease, Chagas disease, chronic inflammatory demyelinating polyneuropathy (CIDP), chronic recurrent multifocal osteomyelitis (CRMO), Churg-Strauss syndrome (CSS), eosinophilic granulomatosis (EGPA), cicatricial pemphigoid, Cogan's syndrome, cold agglutinin disease, congenital heart block, coxsackie myocarditis, CREST syndrome, Crohn's disease, dermatitis herpetiformis, dermatomyositis, Devic's disease (neuromyelitis optica), discoid lupus, Dressler's syndrome, endometriosis, eosinophilic esophagitis (EoE), eosinophilic fasciitis, erythema nodosum, essential mixed cryoglobulinemia, Evans syndrome, fibromyalgia, fibrosing alveolitis, giant cell arteritis (temporal arteritis), giant cell myocarditis, glomerulonephritis, Goodpasture's syndrome, granulomatosis with polyangiitis, Graves' disease, Guillain-Barre syndrome, Hashimoto's thyroiditis, hemolytic anemia, Henoch-Schonlein purpura (HSP), Herpes gestationis or pemphigoid gestationis (PG), hidradenitis suppurativa (HS) (acne inversa), hypogammalglobulinemia, IgA nephropathy, IgG4-related sclerosing disease, immune thrombocytopenia purpura (ITP), inclusion body myositis (IBM), interstitial cystitis (IC), juvenile arthritis, type 1 diabetes, juvenile myositis (JM), Kawasaki disease, Lambert-Eaton syndrome, leukocytoclastic vasculitis, lichen planus, lichen sclerosus, ligneous conjunctivitis, linear IgA disease (LAD), lupus, lyme disease chronic, Meniere's disease, microscopic polyangiitis (MPA), mixed connective tissue disease (MCTD), Mooren's ulcer, Mucha-Habermann disease, multifocal motor neuropathy (MMN) or MMNCB, multiple sclerosis, myasthenia gravis, myositis, narcolepsy, neonatal Lupus, neuromyelitis optica, neutropenia, ocular cicatricial pemphigoid, optic neuritis, palindromic rheumatism (PR), PANDA, paraneoplastic cerebellar degeneration (PCD), paroxysmal nocturnal hemoglobinuria (PNH), Parry Romberg syndrome, pars planitis (peripheral uveitis), Parsonage-Turner syndrome, pemphigus, peripheral neuropathy, perivenous encephalomyelitis, pernicious anemia (PA), POEMS syndrome, polyarteritis nodosa, polyglandular syndromes type I, II, III, polymyalgia rheumatica, polymyositis, postmyocardial infarction syndrome, postpericardiotomy syndrome, primary biliary cirrhosis, primary sclerosing cholangitis, progesterone dermatitis, psoriasis, psoriatic arthritis, pure red cell aplasia (PRCA), pyoderma gangrenosum, Raynaud's phenomenon, reactive arthritis, reflex sympathetic dystrophy, relapsing polychondritis, restless legs syndrome (RLS), retroperitoneal fibrosis, rheumatic fever, rheumatoid arthritis, sarcoidosis, Schmidt syndrome, scleritis, scleroderma, Sjögren's syndrome, sperm & testicular autoimmunity, stiff person syndrome (SPS), subacute bacterial endocarditis (SBE), Susac's syndrome, sympathetic ophthalmia (SO), takayasu's arteritis, temporal arteritis/Giant cell arteritis, thrombocytopenia purpura (TTP), Tolosa-Hunt syndrome (THS), transverse myelitis, type 1 diabetes, ulcerative colitis (UC), undifferentiated connective tissue disease (UCTD), uveitis, vasculitis, vitiligo, Vogt-Koyanagi-Harada disease. An autoimmune condition or autoimmune diseases may be caused by, but not limited to, a natural predisposition, an infection (e.g., bacteria or virus), drugs, vaccination, environmental triggers (e.g., toxins or chemicals such as dust, silica, oil, benzene, tri- or per-chloroethylene etc.), stress, cancer, blood or tissue or organ transplantation, or unknown etiology. Autoimmune disorders may result in but not limited to the destruction of body tissue, abnormal growth of an organ or tissue, changes in organ or tissue function (e.g., changes in blood vessels, connective tissue, function of endocrine glands, joints, muscles, blood cells, skin, etc.).

As used herein, the term "cancer" refers to a hyperproliferation of cells that exhibit a loss of normal cellular control that results in unregulated growth, lack of differentiation, local tissue invasion, and metastasis. The methods and compositions described herein can be used for the treatment of solid tumors (e.g., cancer) or non-solid tumors, such as leukemia, blood cell cancers, and the like. Solid tumors can be found in bones, muscles, the brain, or organs, and can be sarcomas or carcinomas. Where the methods and compositions described herein can overcome barriers of tumor treatment, including, but not limited to barriers to treatment or inhibition of metastases, it is contemplated that aspects of the technology described herein can be used to treat all types of solid and non-solid tumor cancers, including cancers not listed in the instant specification. The compositions and methods described herein, without limitation, include methods of treating cancer, methods of inhibiting metastases, and methods of inducing an anti-tumor immune response.

As used herein, the terms "subject", "individual", "host", and "patient" are used interchangeably and may refer to any animal, mammal, bird, fish, reptile, and amphibian, for example, human, monkey, dog, cat, horse, pig, cattle, ox, donkey, rabbit, sheep, goat, mouse, rat, guinea pig, llama, chicken, goose, duck, turkey, or the like receiving or registered to receive a therapeutic amount of a composition of the present invention for medical care or treatment.

As used herein, the term "injection" refers to any process or method which allows the person skilled in the art to administer any therapeutic to a target site by penetration. Examples of injection are, but not limited to, subcutaneous, subcuticular, subcapsular, subarachnoid, intradermal, intramuscular, intravenous, intra-arterial, intraventricular, intracapsular, intraorbital, intraocular, intrathoracic, intraperitoneal, intravitreal, retro-orbital, intranasal, intracerebral, intrathymic, intraspinal, intrasternal, intra-articular, intracavernous, intracardiac, intraosseous, intrathecal, transtracheal, epidural, or the like as known in the art. A therapeutic does of the present invention may be delivered to a patient by means of controlled release, for example but not limited to, implantable pump and implantable cannulas to provide continuous access to the venous or arterial system.

As used herein, the term "topical application" refers to applying or spreading a composition of the present invention onto surfaces on or in the body, both internally and/or externally, in a therapeutically effective amount for local and/or systemic treatment. Topical application may be epicutaneuos wherein a composition of the present invention may be directly applied onto a localized surface of the skin or mucous membranes. Topical application may include transdermal application wherein a composition of the present invention may be absorbed into the body to obtain systemic delivery and systemic distribution. For example, a transdermal patch may be applied onto the body to deliver a therapeutic dose of a composition of the invention presented herein. Topical application formulations may include, but are not limited to, creams, foams, gels, lotions, solutions, ointments, dermal patch, transdermal patches, powder, solid, sponge, tape, vapor, paste, film, liposomes, balm, shampoo, spray, or tincture. A therapeutic dose of a composition of the present invention may be delivered vaginally (for example a vaginal suppository, vaginal ring, douche, intrauterine device, intravesical infusion, and the like) or urethra.

As used herein, the term "enteral administration" refers to a composition of the present invention administered via the gastrointestinal tract in a therapeutically effective amount for local or systemic treatment. Enteral administration may include, but is not limited to, delivery of a composition of the present invention via the mouth, sublingual, esophagus, gastric (for example the stomach), small intestines, large intestines or rectum. Oral delivery of the present invention may include, but is not limited to, the use of a capsule, pastille, pill, tablet, solution, gel, suspension, emulsion, syrup, elixir, tincture, mouthwash, lozenges, chewing gum, lollipop, osmotic-controlled release oral delivery system, or the like. Gastric delivery may involve the use of a tube or nasal passage that leads directly to the stomach, for example, a percutaneous endoscopic gastrostomy tube. Gastric delivery may involve direct injection made through the abdominal wall. Rectal delivery may involve, but is not limited to, the use of a suppository, ointment, enema, murphy drip, or the like. A therapeutic does of the present invention may be delivered to a patient by means of controlled release, for example but not limited to, controlled release drug delivery pellet or pill.

As used herein, the terms "pulmonary system" or "respiratory system" are used interchangeably and refer, but are not limited, to the respiratory region, conducting airways, nasal cavity, sinuses, nasopharynx, oropharynx, larynx, trachea, bronchi, bronchioles, respiratory bronchioles, alveolar ducts, alveolar sacs, respiratory epithelium (e.g., alveolar epithelial cells), endothelial cells, or the like.

As used herein, the terms "pulmonary delivery" and "pulmonary administration" are used interchangeably and refer to delivering a composition of the present invention to the respiratory system through the respiratory route, including but not limited to, intranasal administration, oral administration, and oral inhalative administration (e.g., intratracheal instillation and intratracheal inhalation) of a therapeutically effective amount for local or systemic treatment. Pulmonary delivery of a therapeutically effective amount of a composition of the present invention may be achieved by dispersion, for example by using a syringe. Pulmonary delivery of a composition of the present invention may be achieved by aerosol administration, wherein aerosol administration may deposit a therapeutically effective amount of the present invention by gravitational sedimentation, inertial impaction, or diffusion.

Pulmonary delivery of a therapeutically effective amount of a composition of the present invention may be deposited on any mucus layer of the respiratory system, for example, but not limited to, the mucus layer which coats the walls of conducting airways, the smaller airway, and/or alveolar space.

As used herein, an "appropriate control" refers to an untreated, otherwise identical cell or population (e.g., a subject who was not administered the composition described herein, or was administered by only a subset of agents provided herein, as compared to a non-control cell).

As used herein, a "reference level" can refer to one or more parameters or markers as measured for a normal, otherwise unaffected cell population or tissue (e.g., a biological sample obtained from a healthy subject, or a biological sample obtained from the subject at a prior time point, or a biological sample that has not yet been contacted with a pathogen as described herein). For measuring or monitoring therapeutic efficacy, a level determined prior to treatment or earlier in treatment can also provide a reference level for a given parameter or value.

As used herein, the term "modulates" refers to an effect including increasing or decreasing a given parameter as those terms are defined herein.

The terms "increased," "increase," "increases," or "enhance" or "activate" are all used herein to generally mean an increase of a property, level, or other parameter by a statistically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level. For example, increasing activity can refer to activating a receptor or a signaling pathway (e.g., antibody production or inflammation).

The terms "decrease", "reduced", "reduction", or "inhibit" are all used herein to mean a decrease or lessening of a property, level, or other parameter by a statistically significant amount. In some embodiments of any of the aspects, "reduce," "reduction" or "decrease" or "inhibit" typically means a decrease by at least 10% as compared to a reference level (e.g., the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

As used herein the term "comprising" or "comprises" is used in reference to compositions, methods, and respective component(s) thereof, that are essential to the method or composition, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. Similarly, the word "or" is intended to include "and" unless the context clearly indicates otherwise. Although methods and materials similar or equivalent to those described herein can be used in the practice or testing of this disclosure, suitable methods and materials are described below.

The abbreviation, "e.g." is derived from the Latin exempli gratia, and is used herein to indicate a non-limiting example. Thus, the abbreviation "e.g." is synonymous with the term "for example."

The abbreviation, "etc." is derived from the Latin et cetera, and is used herein to indicate a non-limiting list. Thus, the abbreviation "etc.," is synonymous with the term "and other similar things", or "and so forth".

Other than in the operating examples, or where otherwise indicated, all numbers expressing quantities of ingredients or reaction conditions used herein should be understood as modified in all instances by the term "about." The term "about" when used in connection with percentages can mean±1%.

The term "statistically significant" or "significantly" refers to statistical significance and generally means a two-standard deviation (2SD) difference, above or below a reference value. Additional definitions are provided in the text of individual sections below.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. The term "or" is inclusive unless modified, for example, by "either." Other than in the operating examples, or where otherwise indicated, all numbers expressing quantities of ingredients or reaction conditions used herein should be understood as modified in all instances by the term "about."

Unless otherwise explained, all technical and scientific terms used herein have the same meaning as commonly understood by one of ordinary skill in the art to which this disclosure belongs.

It is to be understood that the foregoing description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

All patents and other publications identified are expressly incorporated herein by reference for the purpose of describing and disclosing, for example, the methodologies described in such publications that could be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Some embodiments of the technology described herein can be defined according to any of the following numbered paragraphs:

1. An engineered extracellular vesicle comprising:
   at least one fusion polypeptide comprising:
      (i) at least one protein of interest (POI) domain or a fragment thereof; and
      (ii) at least one vesicle targeting domain,
   wherein the POI domain is in an extracellular position relative to a lipid membrane of the extracellular vesicle.
2. The engineered extracellular vesicle of paragraph 1, wherein the extracellular vesicle is an exosome.
3. The engineered extracellular vesicle of paragraph 1 or paragraph 2, wherein the protein of interest (POI) domain or a fragment thereof is a N-terminal domain of the fusion polypeptide.
4. The engineered extracellular vesicle of any one of paragraphs 1-3, wherein the vesicle targeting domain is a C-terminal domain of the fusion polypeptide.
5. The engineered extracellular vesicle of any one of paragraphs 1-4, wherein the fusion polypeptide comprises at least two POI domains and/or at least two exosome targeting domains.
6. The engineered extracellular vesicle of any one of paragraphs 1-5, wherein the fusion polypeptide further comprises a peptide linker.
7. The engineered extracellular vesicle of any one of paragraphs 1-6, wherein the fusion polypeptide further comprises a fragment crystallizable region (Fc) domain.
8. The engineered extracellular vesicle of any one of paragraphs 1-7, wherein the vesicle targeting domain is in a luminal position relative to the lipid membrane of the extracellular vesicle.

9. The engineered extracellular vesicle of any one of paragraphs 1-7, wherein the vesicle targeting domain in an exterior position relative to the lipid membrane of the extracellular vesicle.
10. The engineered extracellular vesicle of any one of paragraphs 1-9, wherein the POI domain is selected from the group consisting of: Table 1.
11. The engineered extracellular vesicle of any one of paragraphs 1-10, wherein the POI domain is PD-L1 or a fragment thereof.
12. The engineered extracellular vesicle of any one of paragraphs 1-11, wherein the POI domain is PD-L2 or a fragment thereof.
13. The engineered extracellular vesicle of any one of paragraphs 1-12, wherein the POI domain is FGL1 or a fragment thereof.
14. The engineered extracellular vesicle of any one of paragraphs 1-13, wherein the POI domain is 4-1BBL or a fragment thereof.
15. The engineered extracellular vesicle of any one of paragraphs 1-14, wherein the POI domain is CTLA-4 or a fragment thereof.
16. The engineered extracellular vesicle of any one of paragraphs 1-15, wherein the POI domain substantially binds to one or more of a target polypeptide.
17. The engineered extracellular vesicle of paragraph 16, wherein the target polypeptide is selected from the group consisting of: Table 2.
18. The engineered extracellular vesicle of any one of paragraphs 1-17, wherein the vesicle targeting domain is selected from the group consisting of: Table 3.
19. The engineered extracellular vesicle of any one of paragraphs 1-18, wherein the linker is in an exterior position relative to the lipid membrane of the extracellular vesicle.
20. The engineered extracellular vesicle of any one of paragraphs 1-18, wherein the linker is a transmembrane linker.
21. The engineered extracellular vesicle of any one of paragraphs 1-18, wherein the linker is in a luminal position relative to the lipid membrane of the extracellular vesicle.
22. The engineered extracellular vesicle of any one of paragraphs 1-21, wherein the extracellular vesicle does not comprise an endogenous POI polypeptide.
23. A composition comprising a plurality of the engineered extracellular vesicles of any one of paragraphs 1-22.
24. The composition of paragraph 23, further comprising a pharmaceutically acceptable carrier.
25. An engineered extracellular vesicle comprising:
   (a) a first fusion polypeptide comprising:
      (i) at least one protein of interest (POI) domain or a fragment thereof; and
      (ii) at least one vesicle targeting domain,
   wherein the at least one POI domain is in an extracellular position relative to a lipid membrane of the extracellular vesicle,
   (b) a second fusion polypeptide comprising:
      (i) at least one protein of interest (POI) domain or a fragment thereof; and
      (ii) at least one vesicle targeting domain,
   wherein the POI domain is in an extracellular position relative to a lipid membrane of the extracellular vesicle,
   and wherein the at least one vesicle targeting domain is within a lipid membrane of the extracellular vesicle.
26. A composition comprising two or more of the engineered extracellular vesicles selected from any one of paragraphs 1-25.
27. An extracellular vesicle composition comprising:
   a plurality of artificial synapses,
   wherein each artificial synapse comprises (i) an extracellular vesicle; (ii) one or more sticky binders; and (iii) one or more signaling domains.
   The composition of paragraph 27, wherein the extracellular vesicle comprises an exosome.
28. The composition of paragraph 27, wherein the one or more sticky binders is selected from the group consisting of: a GPI anchor, a fatty acylation site, and a prenylation site.
30. The composition of paragraph 27, wherein the signaling domain comprises one or more of: PD-L1, PD-L2, CTLA-4 (CD152), 4-1BBL (CD137L), HVEM (CD270), FGL1, OX-2 (CD200), Galectin-9, PVR (CD155), Nectin-2 (CD112) isoform alpha, Nectin-2 (CD112) isoform beta, Nectin-2 (CD112) isoform delta, IL-10, TSG-6, B7-H3 (CD276), B7-H4 (VTCN1), B7-H5 (VISTA), B7-H7 (HHLA2), BTNL1, VSIG8, VSIG3 (IGSF11), VSIG4, TIM-3 (HAVCR2), TIM-4 (TIMD4), CEACAM1, BTN3A1, BTN3A2, BTN2A1, BTNL8, BTN2A2, BTN1A1, TIGIT, CD27L (CD70), CD30L (CD153), GITRL, CD40L (CD154), LIGHT (CD258), TL1, CD80, CD86, LFA-3 (CD58), SLAM (CD150), CD40, CD28, CD28H, CD2, LFA-3 (CD58), CD48, CD226, DR3, DcR3, FasL, TIM-1 (CD365), PD-1, or active fragment thereof.
29. A method of producing the engineered extracellular vesicle or the composition of any one of paragraphs 1-30, comprising:
   (a) providing a population of cells expressing a vector construct encoding one or more sticky binder and one or more signaling domains; and
   (b) isolating a plurality of artificial synapses from the population of cells.
30. A method of producing the engineered extracellular vesicle or the composition of any one of paragraphs 1-30, comprising:
   (a) providing a population of cells expressing a vector construct encoding one or more sticky binder and one or more signaling domains; and
   (b) isolating a plurality of artificial synapses from the population of cells; and
   (c) purifying the plurality of artificial synapses from the population of cells.
33. The method of paragraph 31 or paragraph 32, the isolating is via size exclusion chromatography.
34. The method of paragraph 32, wherein the purifying is via multimodal chromatography.
35. The method of any of paragraphs 31-34, further comprising performing an assay for POI binding to a target polypeptide.
36. The method of paragraph 35, wherein the vector construct further encodes a promoter.
37. The method of paragraph 36, wherein the promoter is a tissue-specific promoter or an inducible promotor.
38. A method of modulating inflammation in a subject, the method comprising:
   administering a composition comprising a plurality of engineered extracellular vesicles to a subject in need thereof, wherein the engineered extracellular vesicles comprise at least one fusion polypeptide comprising:
(i) at least one protein of interest (POI) domain or a fragment thereof; and
(ii) at least one vesicle targeting domain.

39. The method of paragraph 38, wherein the extracellular vesicle comprises an exosome.

40. The method of any one of paragraphs 38-39, further comprising selecting a subject that has or is suspected of having an autoimmune disease or an inflammatory disease or condition.

41. The method of any one of paragraphs 38-40, wherein the vesicle targeting domain is selected from the group consisting of: a Glycosylphosphatidylinositol (GPI) anchor, a fatty acylation site, and a prenylation site.

42. The method of any one of paragraphs 38-41, wherein the vesicle targeting domain is a GPI anchor.

43. The method of any one of paragraphs 38-41, wherein the vesicle targeting domain is C1C2.

44. The method of any one of paragraphs 38-43, wherein the protein of interest (POI) domain comprises one or more of: PD-L1, PD-L2, CTLA-4 (CD152), 4-1BBL (CD137L), HVEM (CD270), FGL1, OX-2 (CD200), Galectin-9, PVR (CD155), Nectin-2 (CD112) isoform alpha, Nectin-2 (CD112) isoform beta, Nectin-2 (CD112) isoform delta, IL-10, TSG-6, B7-H3 (CD276), B7-H4 (VTCN1), B7-H5 (VISTA), B7-H7 (HHLA2), BTNL1, VSIG8, VSIG3 (IGSF11), VSIG4, TIM-3 (HAVCR2), TIM-4 (TIMD4), CEACAM1, BTN3A1, BTN3A2, BTN2A1, BTNL8, BTN2A2, BTN1A1, TIGIT, CD27L (CD70), CD30L (CD153), GITRL, CD40L (CD154), LIGHT (CD258), TL1, CD80, CD86, LFA-3 (CD58), SLAM (CD150), CD40, CD28, CD28H, CD2, LFA-3 (CD58), CD48, CD226, DR3, DcR3, FasL, TIM-1 (CD365), PD-1, or active fragment thereof. 45. The method of any one of paragraphs 38-44, wherein the protein of interest (POI) domain is PD-L1 or a fragment thereof.

46. The method of any one of paragraphs 38-44, wherein the protein of interest (POI) domain is PD-L2 or a fragment thereof.

47. The method of any one of paragraphs 38-44, wherein the protein of interest (POI) domain is CTLA-4 or a fragment thereof.

48. The method of any one of paragraphs 38-44, wherein the protein of interest (POI) domain is HVEM or a fragment thereof.

49. The method of paragraph 40, wherein the inflammatory disease and/or condition is acute.

50. The method of paragraph 40, wherein the inflammatory related disease and/or condition is chronic.

51. The method of paragraph 38, wherein administering the composition comprises injection, topical administration, or inhalation.

52. Use of a composition comprising a plurality of engineered extracellular vesicles, the engineered extracellular vesicles each comprising:
at least one fusion polypeptide comprising:
(i) at least one protein of interest (POI) domain or a fragment thereof; and
(ii) at least one vesicle targeting domain
for the treatment of an inflammatory disease or condition.

53. Use of a composition comprising a plurality of engineered extracellular vesicles, the engineered extracellular vesicles each comprising:
at least one fusion polypeptide comprising:
(i) at least one protein of interest (POI) domain or a fragment thereof; and
(ii) at least one vesicle targeting domain
for the treatment of an autoimmune disease or condition.

54. Use of a composition comprising a plurality of engineered extracellular vesicles, the engineered extracellular vesicles each comprising:
at least one fusion polypeptide comprising:
(i) at least one protein of interest (POI) domain or a fragment thereof; and
(ii) at least one vesicle targeting domain
for the treatment of cancer.

EXAMPLES

The following examples are provided by way of illustration, not limitation.

Example 1

Design of Artificial Synapse

Figure 1:
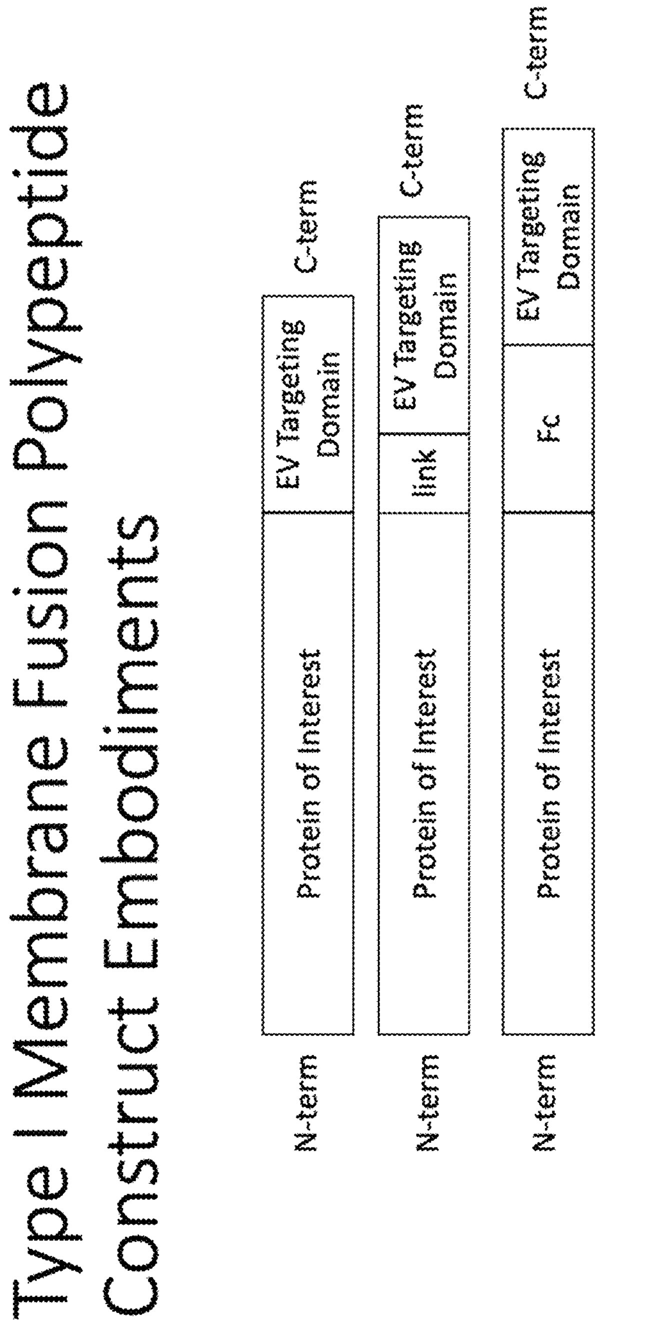

As described, artificial synapses are engineered to induce and propagate biological signaling, including for example, antagonist and agonist signaling. Artificial synapses are designed to include hallmark biophysical and biochemical features of extracellular vesicles, further including vesicle targeting domains and signaling domains. Vesicle targeting domains capable of attaching to extracellular vesicles such as exosomes, signaling domains, optionally including a linker (e.g., Fc linker), can be organized in genetic vector constructs. Designs are shown in FIG. 1.

Sticky binders are extracellular vesicle targeting sequences. Preliminary extracellular vesicle targeting sequences of interest are from, but not limited to, 4F2 (CD98), ADAM10, CD298, TFR2, transmembrane domains of CD9, MARCKS, KRAS, etc. or the like as appreciate by one of ordinary skill in the art. The Inventors discovered high efficiency when proteins are engineered with a GPI domain. Optionally, linker regions such as an Fc linker between the vesicle targeting domains and signaling domains can be added.

A variety of signaling domains are of interest with proof-of-concept examples including PD-L1, PD-L2 and CTLA-4 (CD152). Artificial synapses including these three signaling domains are shown in FIGS. 2-5.

Each of these elements are described in the following non-limiting examples.

Example 2

Genetic Constructs

Examples of constructs including these variable elements (e.g., sticky binders GPI or C1C2, or signaling domains including PD-L1, PD-L2 and CTLA-4 (CD152) were engineered into vectors shown in FIGS. 2-5.

Example 3

Figure 6:
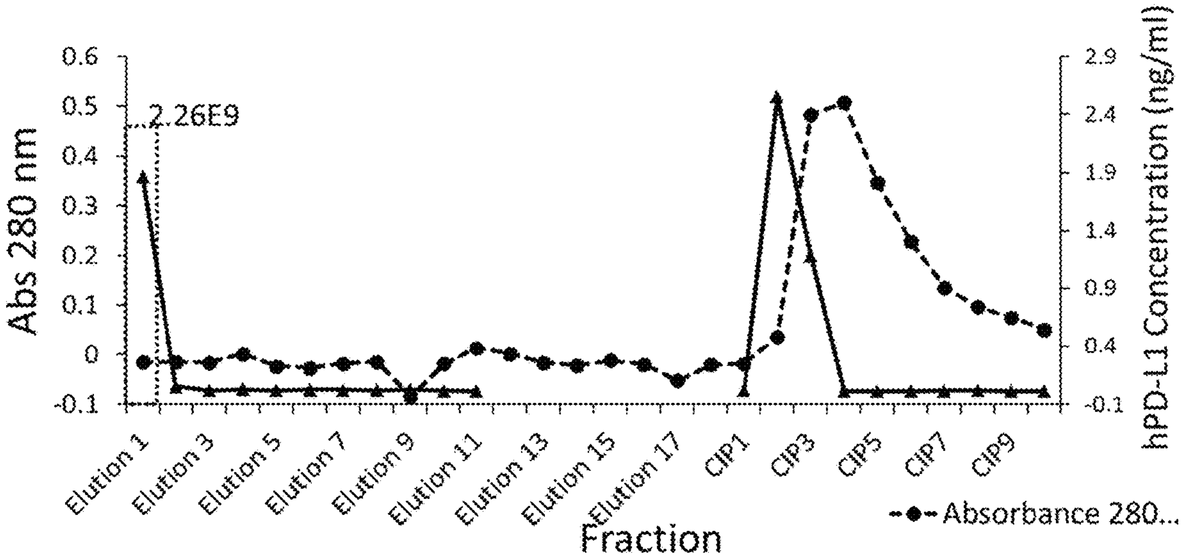

Purification of hPD-L1 Tagged Artificial Synapses by a Multimodal Resin Marketed for Exosome Purification Upon expression of hPD-L1-Fc-GPI in mammalian cells, artificial synapses were further purified using a size exclusion resin marketed for exosome purification. Large MW artificial synapses elute in the first fraction as shown by the high hPD-L1 concentration and exosome quantity (2.26E9 artificial synapses/ml) in elution 1. Clean in place (CIP) fractions show bound and eliminated proteins from the Inventors' exosome elution. Results are shown in FIG. 6.

Example 4 hPDL1-Fc-GPI Exosome Purification-Size Exclusion Chromatography Column

Figure 7:
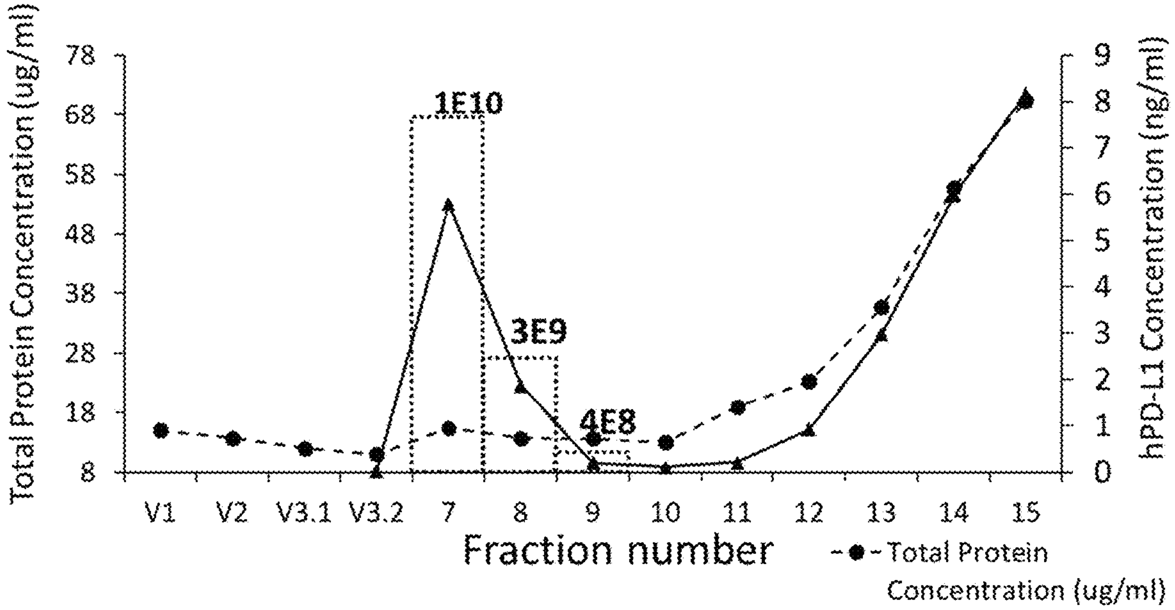

Artificial synapses engineered from exosomes such as hPDL1-Fc-GPI after elution from size exclusion resin marketed for exosome purification can be further purified via a size exclusion column as shown here. Using a size exclusion chromatography (SEC), artificial synapses elute in fractions 7-9. Total protein (determined by Qubit™) and hPD-L1 ng/ml (determined by ELISA) of each fraction is shown in the graph. Bars show exosome number per ml (i.e., 1E10 artificial synapses/ml etc.). Fractions 7-9 contain >99% purified artificial synapses. Fractions 7-9 are pooled and may be concentrated using a filtration device, for example a 10K MWCO Amicon® Centrifugal Filter. Final purified product is filtered through a low protein binding 0.2 μm or 0.45 μm filter, for example a PES filter. Results are shown in FIG. 7.

Example 5 hPD-L1 Expression on Artificial Synapses

Figure 8:
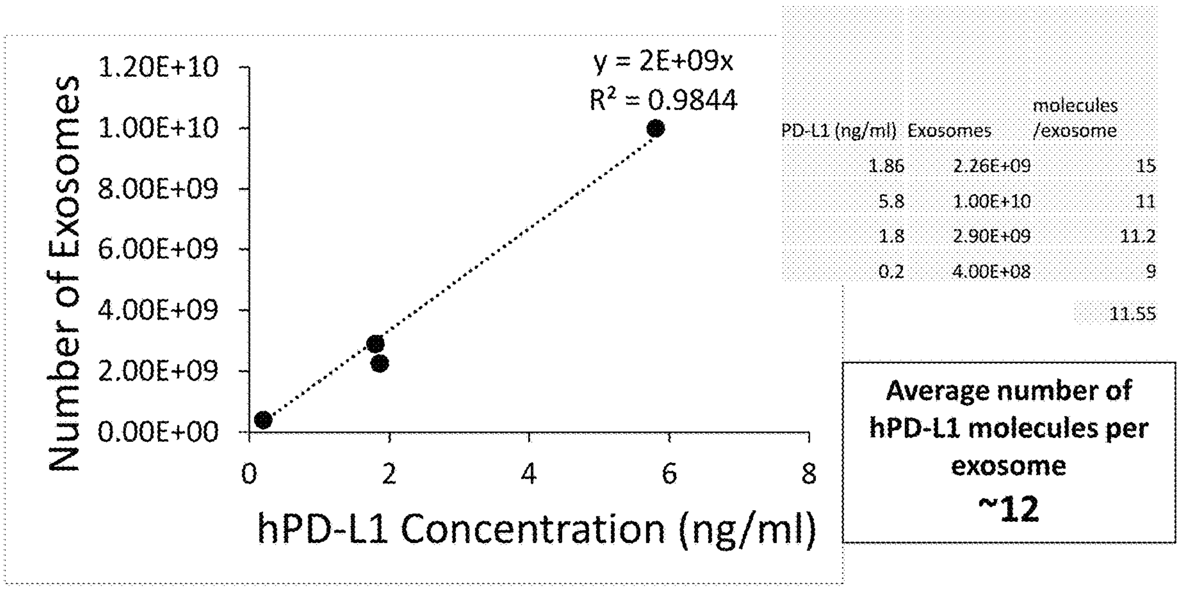

Exosome quantity and hPD-L1 concentration was determined in SEC fractions 7-9. Knowing the molecular weight of engineered hPD-L1, the Inventors can determine the number of hPD-L1 molecules per exosome to be approximately between 12 to 40 PD-L1/exosome. This value is consistent between different purification runs and constructs. Results are shown in FIG. 8.

Example 6

Purification of hPD-L2-Fc-GPI Artificial Synapses Via Multimodal Resin Chromatography Marketed for Exosome Purification This graph shows Abs 280 of multimodal resin chromatography fractions and quantity of hPDL2 in indicated fractions. Artificial synapses eluted in Elution 1.

Figure 9:
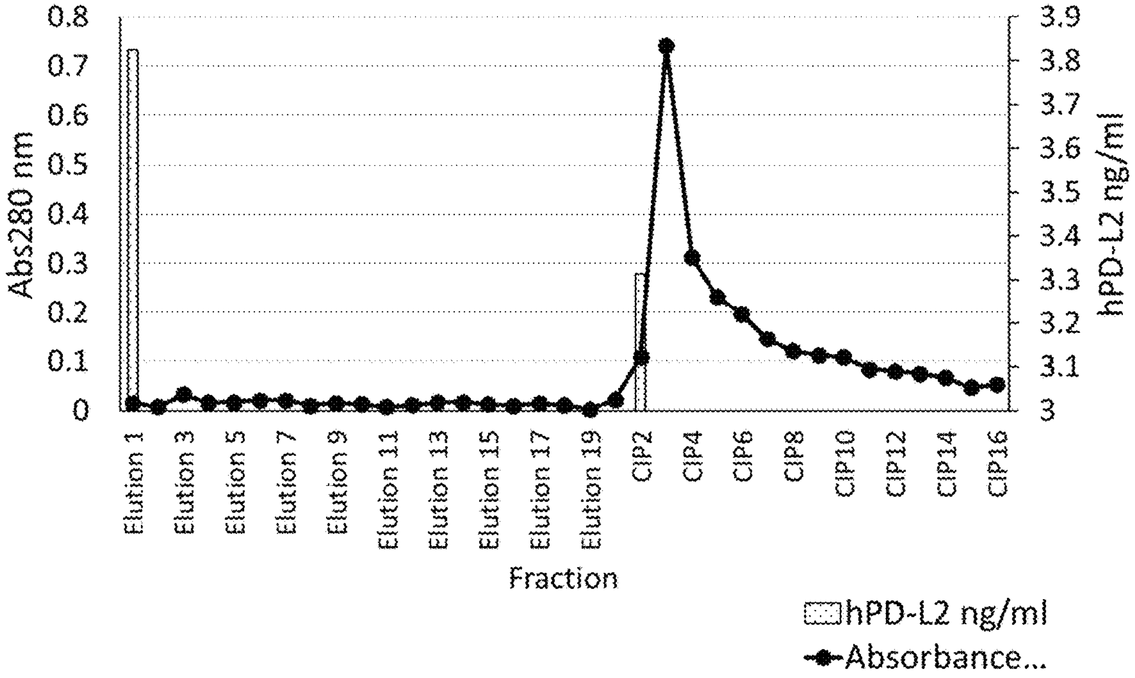

Clean in place (CIP) fractions show bound and eliminated proteins from the Inventors' exosome elution. Results are shown in FIG. 9.

Example 7

PD-L2 Purification Via Size Exclusion Chromatography

Figure 10:
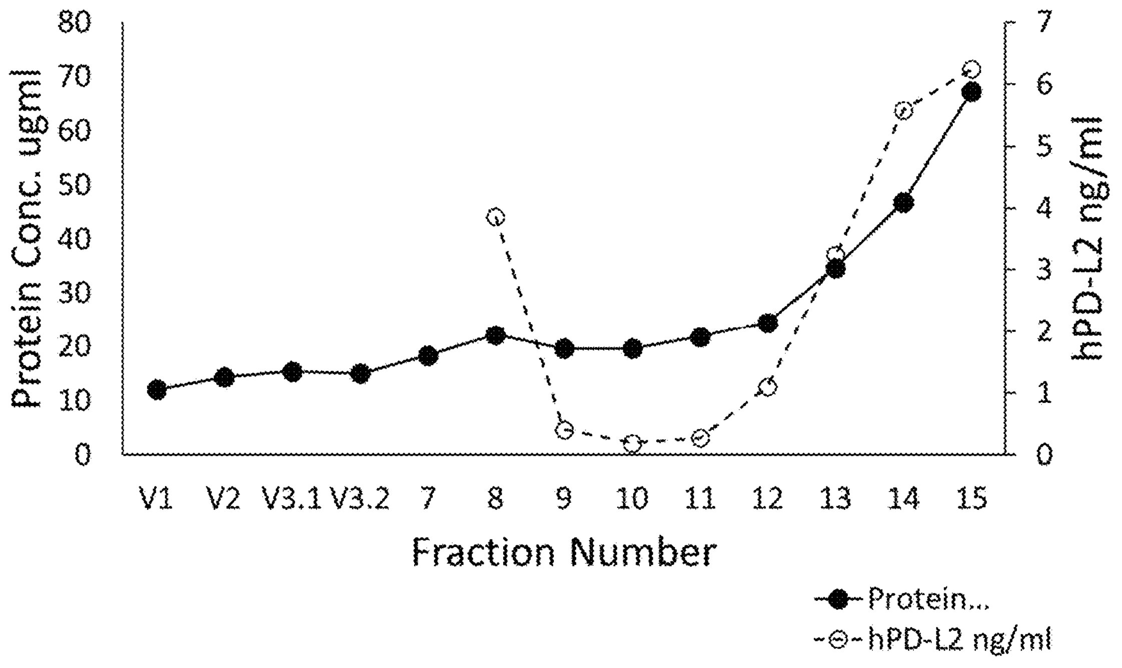

Artificial synapses engineered from artificial synapses such as hPDL2-GPI after elution from size exclusion resin size exclusion resin marketed for exosome purification are further purified via size exclusion chromatography as shown. Results are shown in FIG. 10.

Example 8 hCTLA4-Fc-GPI Exosome Purification Via Size Exclusion Chromatography

Figure 11:
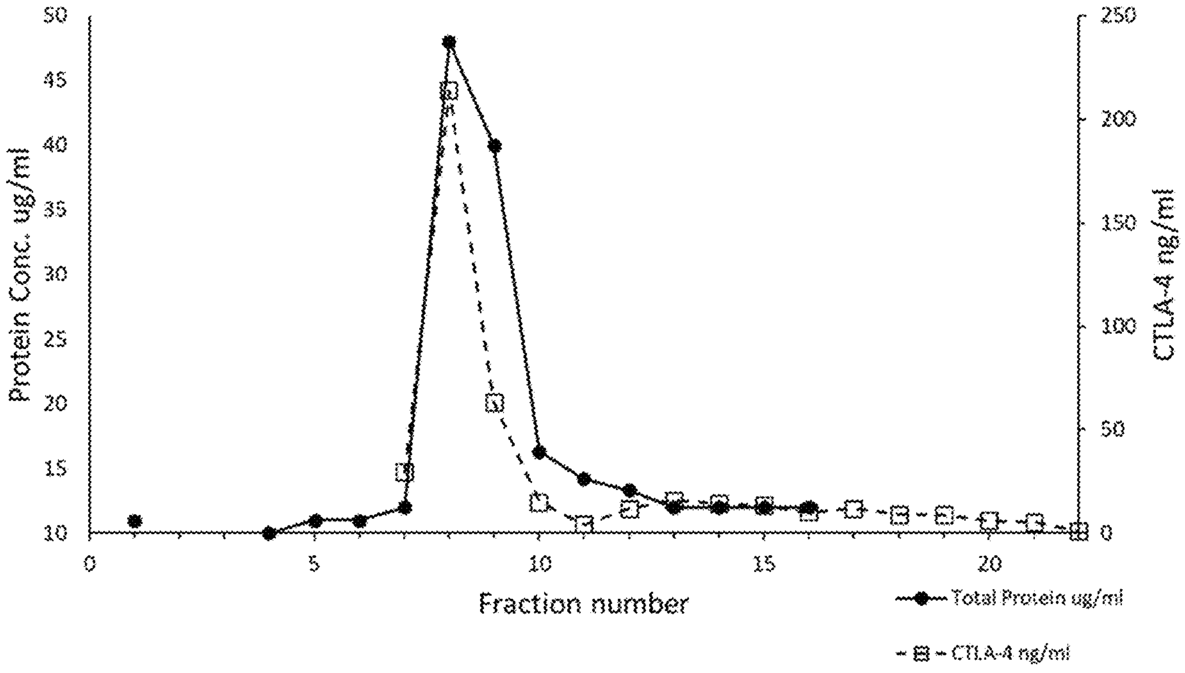

Using size exclusion chromatography marketed for exosome purification, artificial synapses elute in fractions 7-9. Total protein (determined by Qubit™) and hPD-L1 ng/ml (determined by ELISA) of each fraction is shown in the graph. Fractions 7-9 are pooled and contain >99% purified artificial synapses. Pooled artificial synapses engineered from artificial synapses fractions may then be concentrated using a filtration device, for example a 10K MWCO Amicon®. Final purified product is filtered through a low protein binding filter, for example a 0.2 μm or 0.45 μm PES filter. Results are shown in FIG. 11.

Example 9

PD-L1 and PD-L2 In Vitro Assay from DISCOVERX®

To perform this validation method, the Inventors modified the PathHunter® PD-1 Signaling Bioassay from DISCOVERX® Briefly, the PathHunter® PD-1 Signaling Bioassay relies on the well-established PathHunter® Enzyme Fragment Complementation (EFC) technology to interrogate receptor activity. EFC consists of a split β-galactosidase (β-gal) enzyme: the Enzyme Donor (ED) and Enzyme Acceptor (EA) fragments which independently have no β-gal activity. However, when forced to complement they form an active β-gal enzyme that will hydrolyze substrate to produce a chemiluminescent signal. The PathHunter® PD-1 Signaling Bioassay consists of human cells engineered to stably express an ED-tagged PD-1 receptor, while EA is fused to the phosphotyrosine-binding SH2 domain of the intracellular signaling protein, SHP1. Ligand or antibody-induced activation of the receptor results in phosphorylation of the receptor's cytosolic tail. The SH2-domain fused to EA binds the phosphorylated receptor, forcing complementation of ED and EA, resulting in formation of an active β-gal enzyme, which hydrolyzes the substrate to produce a chemiluminescent signal. Full-length PD-1 receptor was engineered with a small β-gal fragment (ED in red) fused to its C-terminus, and the SH2-domain of SHP1 was engineered with the complementing β-gal fragment (EA). These constructs were stably expressed in Jurkat cells (produced by DISCOVERX®), while PD-L1 and PD-L2 was stably expressed on artificial synapses produced by Diadem Biotherapeutics. Artificial synapses were engineered to have surface expressed human PD-L1 or PD-L2. Briefly, the gene sequence coding for the extracellular domain of human PD-L1 or PD-L2 was linked to the exosome via a glycosylphosphatidylinositol (GPI) linker with an Fc domain between the linker and PD-L1 or PD-L2 (PD-L1-Fc-GPI and PD-L2-Fc-GPI). Additional variations of the Inventors' PD-L1 and PD-L2 artificial synapses include cloning a C1C2 linker (from MFGE8) in place of the GPI linker, and with or without the Fc domain. The Inventors also cloned murine versions of PD-L1 and PD-L2 extracellular domains in place of the human PD-L1 and PD-L2 all variations. Ligand engagement, through addition of ligand-presenting artificial synapses, results in phosphorylation of PD-1, leading to the recruitment of SHP1-EA The Inventors obtained approximately 1000× higher increase in Relative Light Units (RLU) in Jurkat signaling cells treated with PD-L1 or PD-L2 labeled artificial synapses when compared to soluble PD-L1-Fc or PD-L2-Fc ligand, respectively. Meaning, it took 1000× less μg/ml of PD-L1 or PD-L2 on artificial synapses than solubilized PD-L1-Fc or PD-L2 ligand to achieve the same RLU signaling. Results are shown in FIG. 12.

Example 10

Figure 13B:
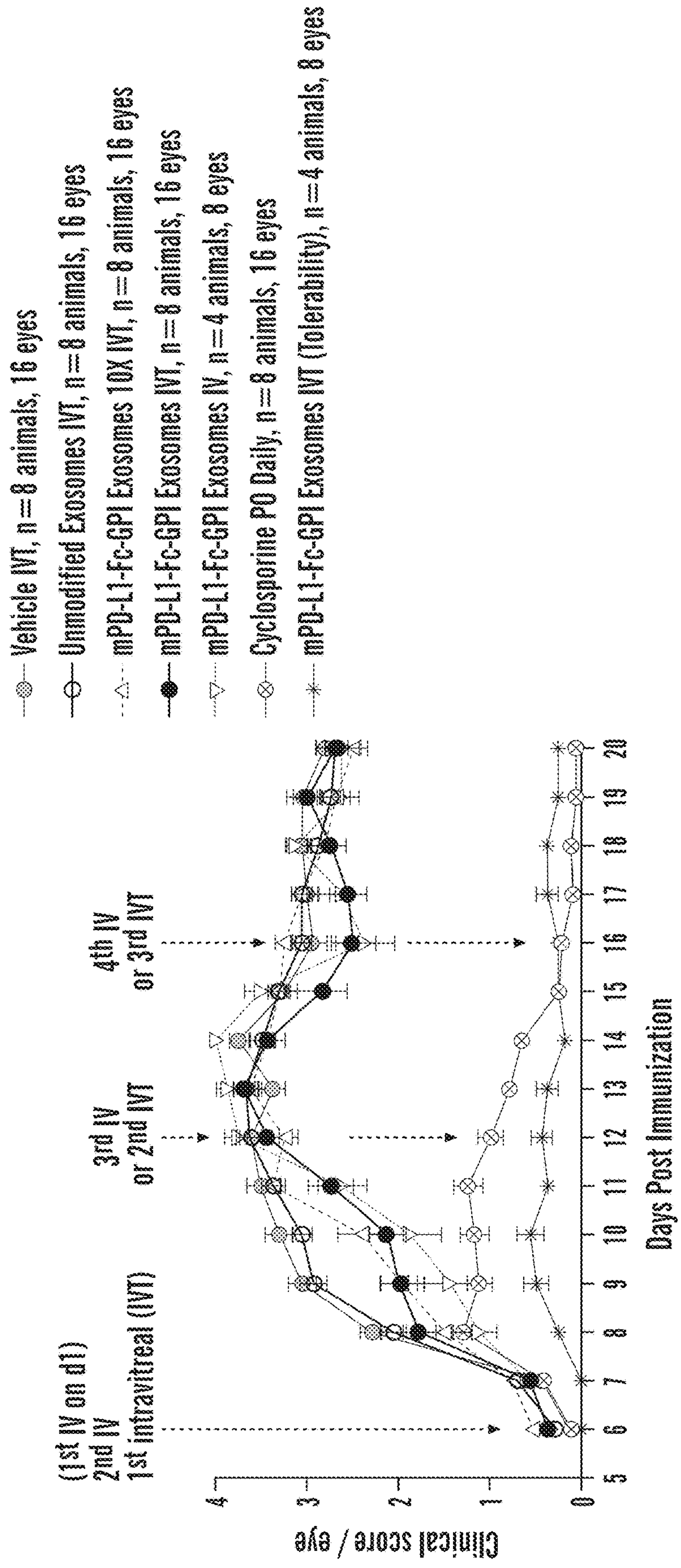

PD-L1 In Vivo Assay-Experimental Autoimmune Uveoretinitis (EAU) in Lewis Rats Bioassay Experimental autoimmune uveoretinitis (EAU) is an organ-specific, T lymphocyte-mediated autoimmune disease, which serves as a model for several human ocular inflammations of an apparently autoimmune nature. There is a statistically significant initial reduction in EAU in mPDL1 artificial synapse treated rats via either the intravitreal and intravenous delivery modes. 2nd intravitreal and 3rd intravenous injections are performed on Day 12. There appears to be a more rapid rate of resolution in the 1× intravitreal and intravenous groups. (C) Simplified view of aforementioned results. (D) Weight of rats was monitored throughout the study. 3rd intravitreal and 4th intravenous injections are performed on Day 16. There does not appear to be any significant change in EAU in any of the test groups. The aforementioned results provide proof of principle of successfully immunizing the rats with human cell derived artificial synapses with mouse PDL1 injected into rats. Results are shown in FIG. 13.

Example 11

Engineered Exosome Multivalent Display

The inventors have developed the following 3 types of protein display on or within exosomes:

- Type I membrane proteins wherein the N-Terminus is on the luminal (interior) side of the exosome membrane and the C-Terminus is on the exterior of the exosome.
- Type II membrane proteins wherein the N-Terminus is on the exterior while the C-Terminus is on the interior.
- Luminal internally loaded proteins which are linked to the exosome by a Myristoylation/Palmitoylation site which attaches proteins to the interior of the exosome membrane.

FIGS. 14-21 demonstrate the various embodiments of the engineered extracellular vesicles.

Additional embodiments or ligands displayed on the exosome surface (Type I and Type II membrane proteins) and internal luminal display can include the following:

- Type I: PD-L1, PD-L2, FGL1, OX40L.
- Type II: 4-1BBL, GITRL, CD27L, CD30L
- Luminal: NanoLuc® luciferase; Green fluorescent protein (GFP) (e.g., eGFP, etc.); Red fluorescent protein (RFP) (e.g., mScarlet, mCherry, mRuby, tdTomato, etc.); Cyan fluorescent protein (CFP); Yellow fluorescent protein (YFP); A therapeutic protein; and CRISPR/CAS-9

FIG. 20 shows an exemplary multiple protein display construct. Sequences such as P2A, E2A, F2A, and T2A induce ribosomal slippage which prevent peptide bond formation, meaning that a single mRNA transcript with a 2A sequence will result in two separate peptides after translation. This allows the expression of two separate proteins from one promoter region and thus loading of two proteins on an exosome. Any combination of the proteins of interest domains provided herein can be engineered. Furthermore, a cell line with multiple transgene inserts under separate promoter control. Either method can be used to label Type I, Type II, and luminal display proteins.

Example 12a

Designed and Engineered Human Fusion Polypeptide Constructs

Figure 5A:
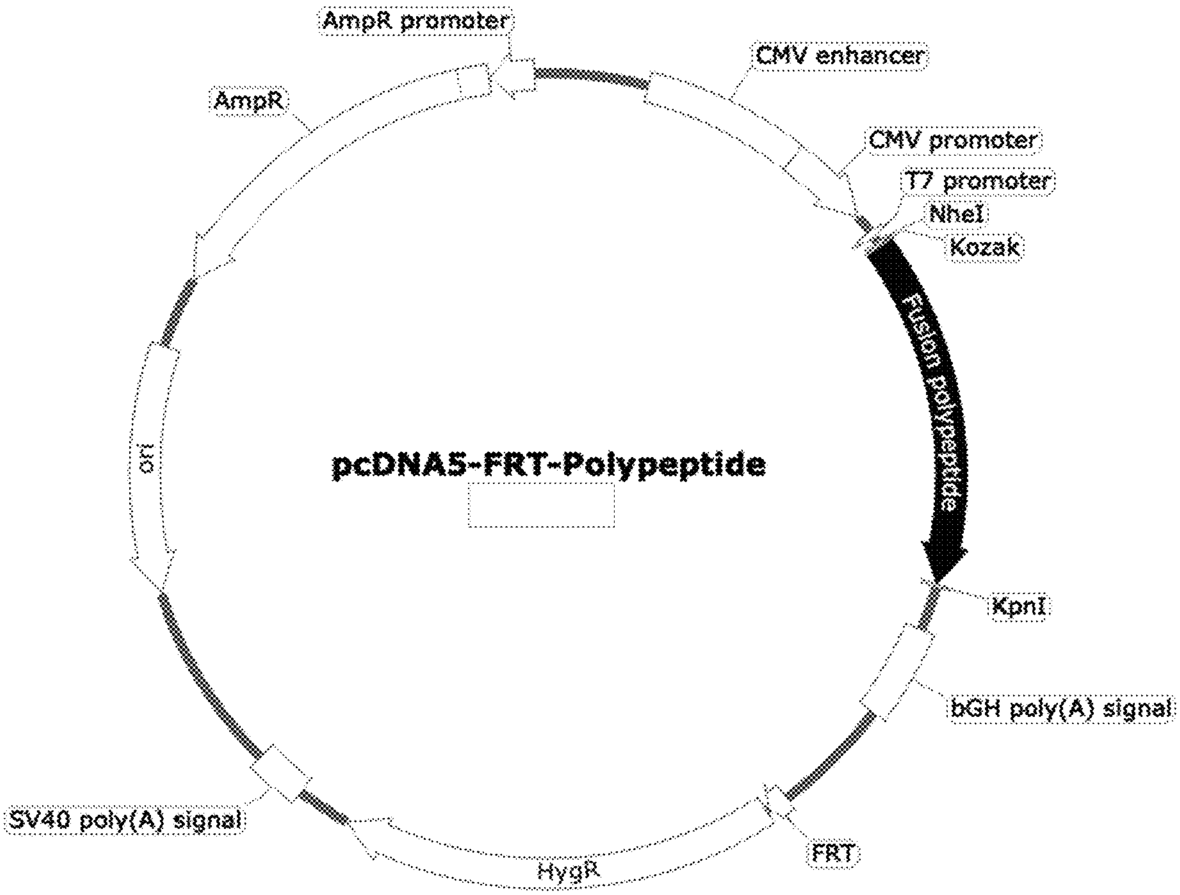
Figure 5B:
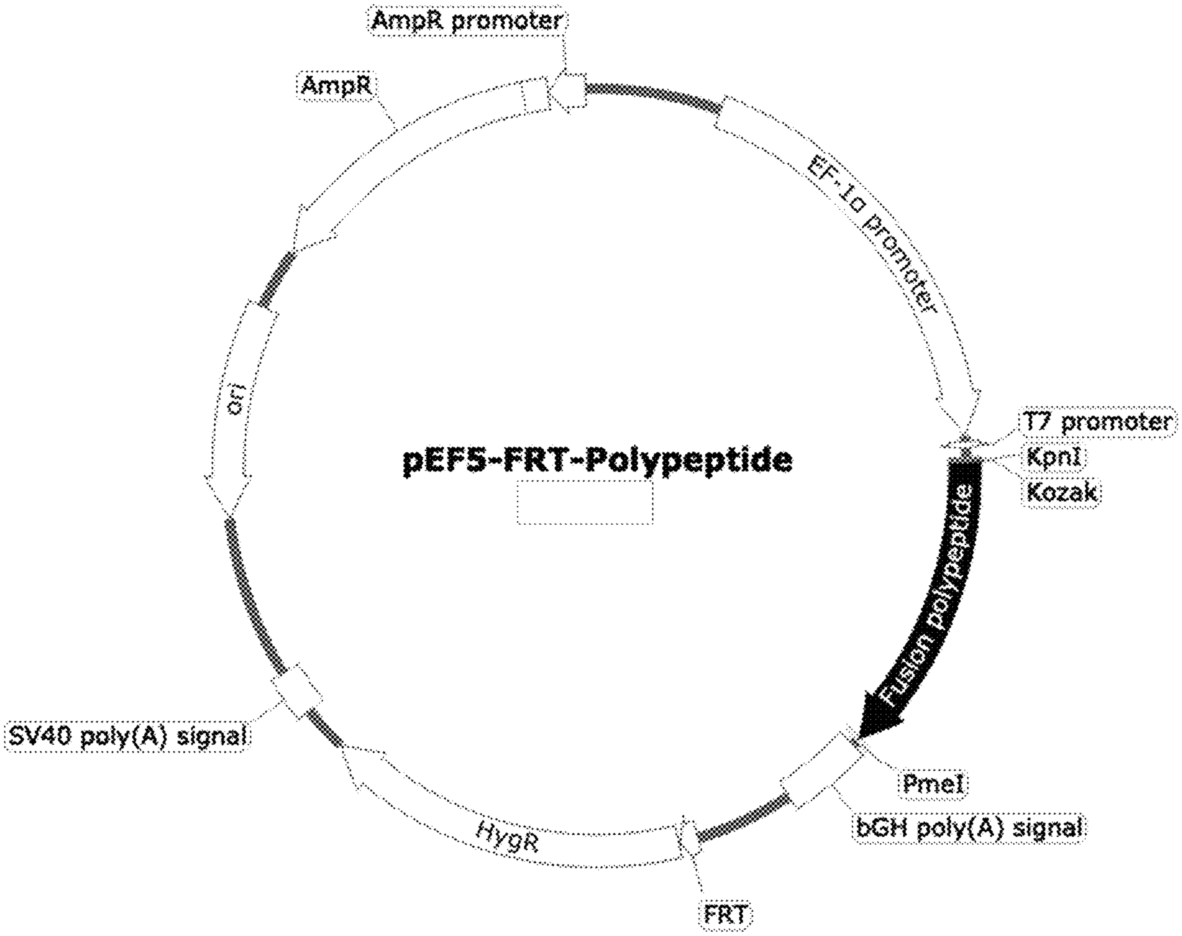

The inventors have designed, engineered, and purified the following human fusion polypeptide constructs for therapeutic use (FIG. 5A-FIG. 5WW):

- pEF5-FRT-hPDL1-C1C2 (FIG. 5I)
- pEF5-FRT-hPDL2-C1C2 (FIG. 5J)
- pEF5-FRT-hPDL1-GPI-P2A-hFGL1-GPI (FIG. 5E)
- pEF5-FRT-hCTLA4-Fc-GPI (FIG. 5C)
- pEF5-FRT-hPDL2-Fc-GPI (FIG. 5H)
- pEF5-FRT-hPD-L1-GPI-P2A-hHVEM-GPI (FIG. 5D)
- pEF5-FRT-hPDL1-GPI (FIG. 5F)
- pcDNA5-FRT-hSecPDL1-GPI (FIG. 5O)
- pcDNA5-FRT-hPDL1-GPI (FIG. 5F)
- pcDNA5-FRT-hPDL1-Link-GPI (FIG. 5T)
- pcDNA5-FRT-4F2-h41BBL (FIG. 5K)
- pcDNA5-FRT-Tfr2-h41BBL (FIG. 5P)
- pEF5-FRT-hPDL1-Fc-GPI (FIG. 5G)
- pcDNA5-FRT-CD9tm3-h41BBL (FIG. 5Q)
- pcDNA5-FRT-hPDL1-Fc-GPI (FIG. 5G)
- pcDNA5-FRT-hPDL1-4Fc-CD9tm2 (FIG. 5RR)
- pcDNA5-FRT-hPDL1-Fc-CD9tm2KRAS (FIG. 5UU)
- pcDNA5-FRT-hPDL1-4Fc-CD9tm2KRAS (FIG. 5SS)
- pcDNA5-FRT-hPDL1-4Fc-GPI (FIG. 5L)
- pcDNA5-FRT-hPDL1-ADAM10 (FIG. 5QQ)
- pcDNA5-FRT-MyrPalm-4F2-h41BBL (FIG. 5R)
- pcDNA5-FRT-MyrPalm-h41BBL (FIG. 5S)
- pcDNA5-FRT-hPDL1-Fc-CD9tm2 (FIG. 5TT)
- pcDNA5-FRT-hSecPDL1-CD9tm4 (FIG. 5W)
- pcDNA5-FRT-hSecPDL1-CD9tm2KRas (FIG. 5V)
- pcDNA5-FRT-hSecPDL1-CD9tm2 (FIG. 5U)
- pcDNA5-FRT-hSecPDL1-CD81 (FIG. 5X)
- pEF5-FRT-hCD200-Fc-GPI (FIG. 5Y)
- pEF5-FRT-hCD200-GPI (FIG. 5BB)
- pEF5-FRT-hTSG6-GPI (FIG. 5FF)
- pEF5-FRT-hPDL2-GPI (FIG. 5EE)
- pEF5-FRT-hFGL-1-GPI (FIG. 5Z)
- pEF5-FRT-hHVEM-GPI (FIG. 5DD)
- pEF5-FRT-hGal9-GPI (FIG. 5CC)
- pEF5-FRT-hHVEM-Fc-GPI (FIG. 5GG); and
- pEF5-FRT-hGal9-Fc-GPI (FIG. 5AA)

Example 12b

Designed and Engineered Fusion Polypeptide Constructs

The inventors have designed, engineered, and purified the following mouse fusion polypeptide constructs for therapeutic use (FIG. 5A-FIG. 5WW):

- pcDNA5-FRT-mPDL1-mFc-CD9tm2KRAS (FIG. 5WW)
- pcDNA5-FRT-mPDL1-mFc-CD9tm2 (FIG. 5VV)
- pcDNA5-FRT-mPDL1-mFc-GPI (FIG. 5NN)
- pcDNA5-FRT-mPDL1-GPI (FIG. 5KK)
- pEF5-FRT-mPDL2-GPI (FIG. 5OO)
- pEF5-FRT-mPDL1-GPI-P2A-mHVEM-GPI (FIG. 5PP)
- pEF5-FRT-mPDL1-GPI (FIG. 5KK)
- pEF5-FRT-mPDL2-Fc-GPI (FIG. 5 MM)
- pEF5-FRT-mPDL1-Fc-GPI (FIG. 5JJ)

pEF5-FRT-mCTLA4-Fc-GPI (FIG. 5HH)
pEF5-FRT-mPDL1-C1C2 (FIG. 5II); and
pEF5-FRT-mPDL2-C1C2 (FIG. 5LL).

Example 12c

Designed and Engineered Luminal Loaded Fusion Polypeptide Constructs

The inventors have designed, engineered, and purified the following fusion polypeptide constructs for internal luminal loading of the fusion polypeptide:
pcDNA5-FRT-Myr-NanoLuc (FIG. 5M)
pcDNA5-FRT-Myr-mScarlet (FIG. 5N)

Example 13

Purification of Exosomes Labeled with Type I Membrane Fusion Polypeptides

The inventors have purified engineered EVs, including hPD-L1-GPI; hPDL1-Fc-GPI; hPDL2-Fc-GPI; hCTLA4-Fc-GPI; mPDL1-GPI; and mPD-L1-Fc-GPI. The process for purification and analytical processing of the engineered EVs are shown in the flow chart provided in FIG. 21.

Size exclusion chromatography was performed to purify hPD-L1-GPI (no Fc) exosomes (FIG. 24). Protein, RNA and DNA measurements in SEC fractions. Invitrogen Qubit™ fluorometric assays were used to measure biomolecules from unmodified concentrated cell media SEC fractions or hPD-L1-Exo-Tag concentrated cell media SEC fractions. PD-L1 was measured using an R&D systems PD-L1 ELISA kit. Dot-blot immunoblot analysis of SEC fractions. A 96-well dot blot apparatus was used to immobilize 50 μl of each SEC fraction onto PVDF. Exosome size and concentration was measured in fraction 7 by tunable resistive pulse sensing (TRPS). It was confirmed that GPI anchors the hPD-L1 fusion protein onto the exosomes (FIG. 25).

Furthermore, a commercially available multimodal exosome purification resin was also used to purify and isolate PD-L1-GPI exosomes and PD-L1-Fc-GPI exosomes. Fraction 7 was further analyzed by dot blots (FIG. 28A-28B). In particular, FIG. 28B shows SEC purification results of various embodiments of human PD-L1 displayed on the surface of extracellular vesicles. One embodiment is the hPD-L1-4Fc-GPI (CMV) construct as seen in the top dot blot (stained with rabbit monoclonal anti-PD-L1 antibody). Another embodiment is the hPD-L1-4Fc-GPI (EF1a) as seen in the top dot blot (stained with rabbit monoclonal anti-PD-L1 antibody).

Large MW exosomes elute in the first fraction as shown by the high hPD-L1 concentration and exosome quantity (2.26E9 exosomes/ml) in elution 1. Clean in place (CIP) fractions show bound and eliminated proteins from our exosome elution. Exosome quantity and hPD-L1 concentration was determined in SEC fractions 7-9. Knowing the molecular weight of engineered hPD-L1, we can determine the number of hPD-L1 molecules per exosome to be approximately 12 PD-L1/exosome. This value is consistent between different purification runs and constructs (FIG. 8).

Human hPD-L2 and hCTLA-4-Fc-GPI SEC fractions were purified. In addition, purification of the mouse PD-L1-FcGPI exosomes was performed (FIG. 29). The mouse Fc-PD-L1 expressing exosomes have a higher valency than those that do not comprise the Fc linker.

Example 14

Comparative Proteomics Analysis of the Engineered EVs

Fc-GPI enables high density display and has a higher abundance than endogenous PTGFRN or CD81. Therefore, comparison proteomics of transprotein expression and surface labeling on the engineered exosomes, hPD-L1-Fc-GPI; hPD-L2-Fc-GPI; and hCTLA-Fc-GPI, was performed to determine the effects on endogenous protein expression in engineered exosomes. It was confirmed that the fusion polypeptide expression does not affect the relative expression of native and associated exosome proteins. However, the trans protein may crowd out abundant proteins like CD81 (data not shown).

Example 15

Scale-Up Production and Purification of mPD-L1-Fc-GPI Exosomes Using Microcarriers in a Stirred Tank Single-Use Bioreactor (STR)

1E7 HEK 293 cells were utilized for the production of mPDL1-Fc-GPI exosomes. Cells were passaged on Solo-Hill® Microcarriers up to Passage 4, at which point cells were expanded in a 2.5 L Stirred Tank Single-Use Bioreactor. Passage 4 cells were cultured for an additional 5 days and media was harvested on Day 5 and used for exosome purification. The general aim and process is provided below AIM: Utilize SoloHill®'s Xeno-free microcarrier technology to scale up cells for engineering EVs and evaluate Microcarrier-stir tank bioreactor technology for production of therapeutic exosomes in the Xeno-free medium conditions.

Passage 1:

Thaw vial (1.00E+07) of cells and seed Corning® T-150 & CellSTACK®2 tissue culture treated flask at 1.00E+04 cells per $cm^2$ seed density.

Perform 100% medium exchange from both flasks on day 3.

Harvest Corning® T-150 & CellSTACK®2 flasks on day 4 post seeding and seed spinner microcarrier culture.

Passage 2:

Expand cells in 2×200 mL spinner flasks at 10 $cm^2$/mL microcarrier density using SoloHill®'s Xeno-free prototype microcarrier.

Seed microcarrier cultures at 1.00E+04 cells per $cm^2$ seed density and T-25 as flatware control flask.

Perform 80% batch volume medium exchange from spinners and T-25 flasks on day 3.

Harvest both microcarrier and T-25 flasks on day 4 post seeding and seed spinner microcarrier culture.

Passage 3:

Expand cells in 3×300 mL spinner flasks at 10 $cm^2$/mL microcarrier density using SoloHill®'s Xeno-free prototype microcarrier.

Seed microcarrier cultures at 1.00E+04 cells per $cm^2$ seed density and T-25 as flatware control flask.

Perform 80% batch volume medium exchange from spinners and T-25 flasks on day 3.

Harvest both microcarrier and T-25 flasks on day 4 post seeding.

Seed microcarrier-stir tank bioreactor for exosome production.

Passage 4:

Expand cells into a 2.5 L microcarrier-stir tank at 10 $cm^2$/mL surface area to medium ratio.

Seed cultures at 1.00E+04 cells per $cm^2$ seed density and T-25 as flatware control flask.

Perform 80% batch volume medium exchange on day 2.

On day 3 rinse all cultures with 2×cell culture volumes of DPBS containing Ca and Mg.

Add exosome production medium (DMEM-1% GlutaMAX™) to all cultures at 10 $cm^2$/mL surface area to medium volume ratio.

On day 5 collect harvest spent medium from all cultures, filter using 0.45 μm Nalgene rapid flow system and freeze at −20° C.

Procedures:

Medium Composition

DMEM 1× (Corning ref #10-013-CV)

1% GlutaMAX™ (Thermo ref #35050061)

3% Human platelet lysate (Stemulate from Cook Reagentec PG-NH-500)

Cell Harvest Protocol for Planar Culture

Settle microcarriers and remove maximum volume of spent medium without removing microcarriers.

Wash microcarrier culture with DPBS 2× time at 0.1 mL/$cm^2$ volume to surface area ratio.

Add 37° C. warmed TrypLE™ 5× enzyme at 0.012 mL/$cm^2$ and incubate flask at room temperature for ~15 minutes.

Add complete medium at 0.024 mL/$cm^2$ to quench TrypLE™ 5× activity.

Perform viable cell count using NC200 cell count instrument.

Nuclei Count Protocol for Microcarrier Culture

Obtain 4-5 mL of microcarrier culture from bioreactor or spinner flask

Settle microcarriers and remove maximum volume of spent medium without removing microcarriers.

Add 1.5 mL NucleoCounter® Reagent A to macrocarrier sample tube and vortex at high speed for a minute.

Add 1.5 mL NucleoCounter® Reagent B to macrocarrier sample tube and vortex at high speed for a minute.

Perform nuclei count using NC200 nuclei count instrument.

Medium Collection from STR Bioreactor

Stop all controls and settle microcarriers in the bioreactor vessel.

Pump out medium through screen bag into collection bottle at 200 mL/minute flowrate using peristaltic pump.

Inside BSC pour medium into 0.45 μm Nalgene™ Rapid-Flow™ filter system and remove free floating cells.

Freeze medium bottles in minus 20° C. freezer.

Medium Collection from Spinner Flasks

Inside BSC pour microcarrier culture into 0.45 μm Nalgene™ Rapid-Flow™ system and remove free floating cells as well as microcarriers.

Freeze medium bottles in minus 20° C. freezer.

Cell culture set points

| | Temperature ° C. | Agitation rpm | Dissolved (DO) % | Oxygen pH | Incubator $CO_2$ setting % |
|---|---|---|---|---|---|
| T-Flask | 37 | n/a | n/a | n/a | 5 ± 1 |
| CellSTACK 2 | 37 | n/a | n/a | n/a | 5 ± 1 |

-continued

Cell culture set points

| | Temperature ° C. | Agitation rpm | Dissolved (DO) % | Oxygen pH | Incubator $CO_2$ setting % |
|---|---|---|---|---|---|
| Spinner flask | 37 | 35 | n/a | n/a | 5 ± 1 |
| STR bioreactor | 37 | 35 | 50 | 7.35 | n/a |

FIG. 31 shows mPDL1-Fc-GPI production, growth parameters, and analyte concentrations from a 2.6-L culture in a Stirred Tank Single-Use (STR) bioreactor. Day 2: 80% batch volume medium was exchanged (1st increase in glucose and decreased in lactate) Day 3: rinse culture with 2× cell culture volumes of DPBS containing Ca and Mg. (2nd increase in glucose and decreased in lactate). Add exosome production medium (DMEM-1% GlutaMAX™) to culture at 10 $cm^2$/mL surface area to medium volume ratio.

mPDL1 was purified using the purification process outlined above (FIGS. 32-33).

Example 16

PD-L1-Fc-GPI and PDL2-Fc-GPI Exosomes Increase PD-1 Signaling

Figure 12A:
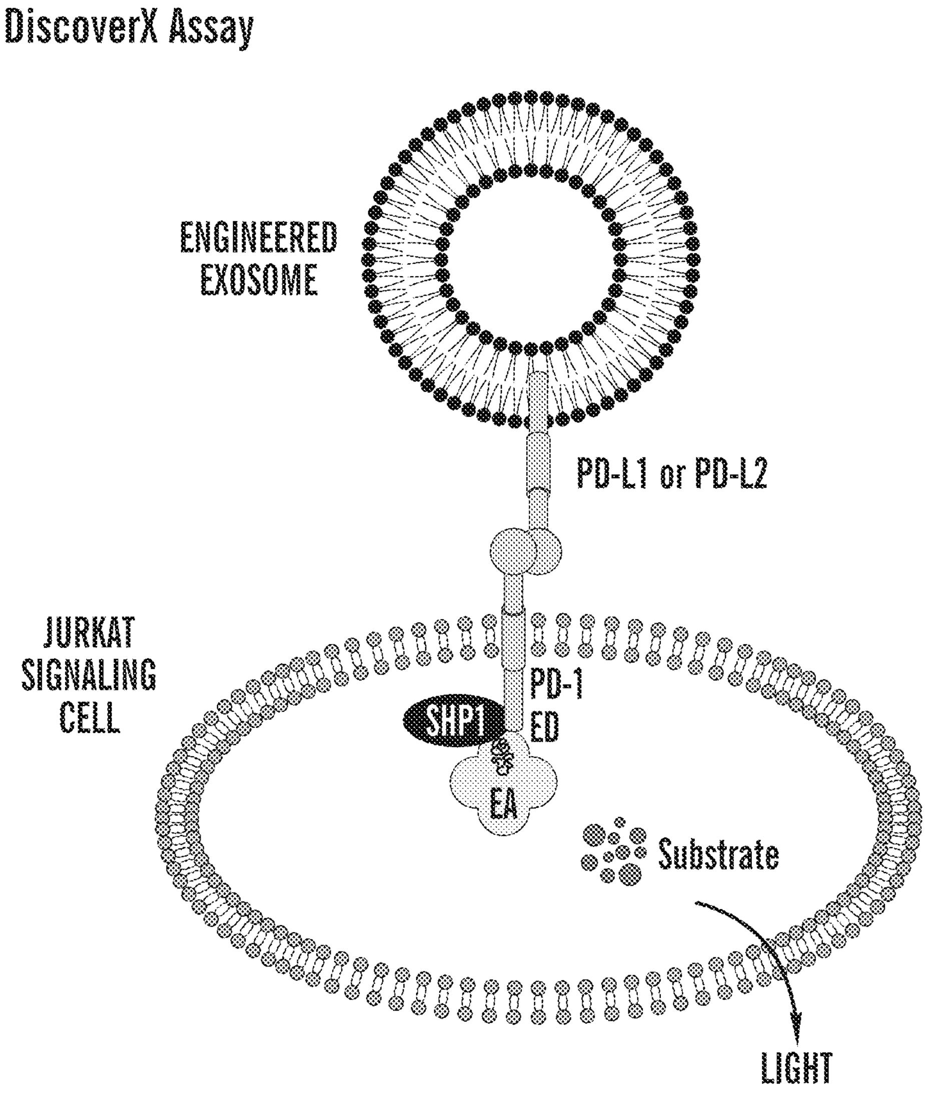
Figure 12B:
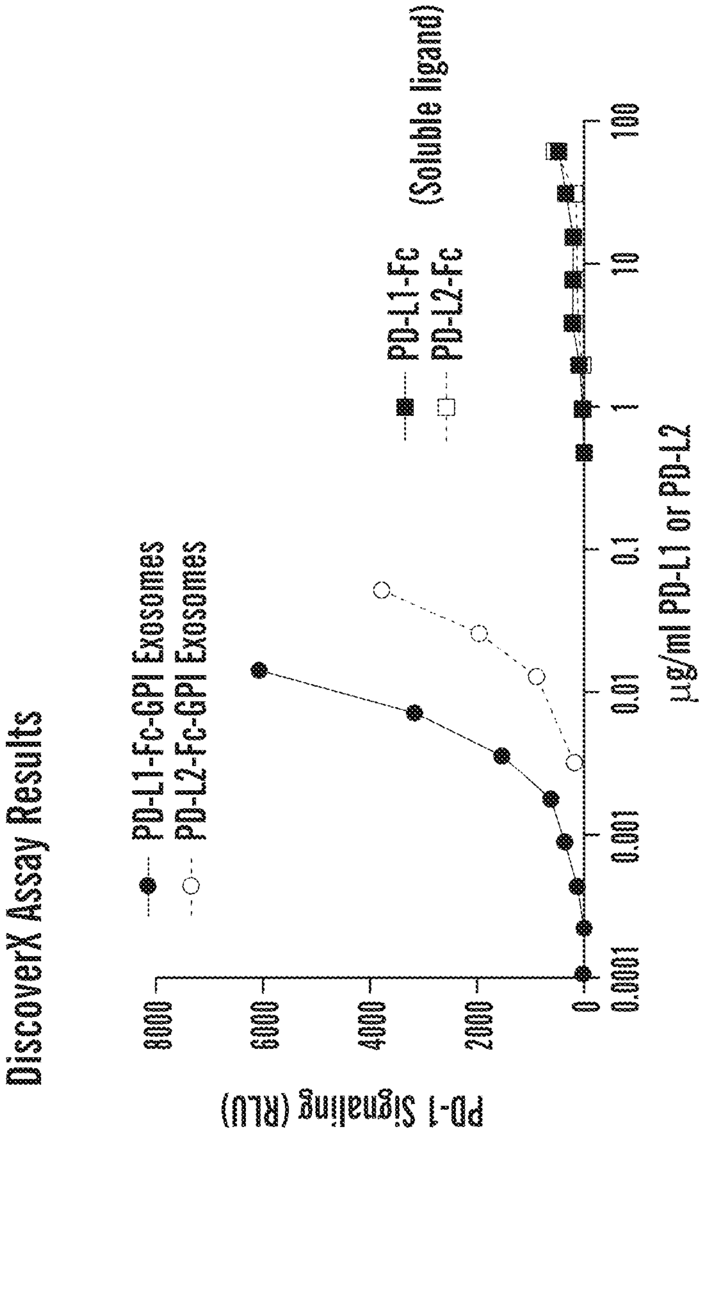

The purified exosomes were tested using the modified DISCOVERX® Assay in FIG. 12A. Approximately a 1000× increase in Relative Light Units (RLU) was achieved for Jurkat signaling cells treated with PD-L1 or PD-L2 labeled exosomes when compared to soluble PD-L1-Fc or PD-L2-Fc ligands alone, respectively. Therefore, it takes 1000× less μg/ml of PD-L1 or PD-L2 on the engineered exosomes to activate PD-1 over solubilized ligands, PD-L1-Fc or PD-L2, achieve the same RLU signaling. FIG. 12B show a dose-response curves for the PD-L1 and PD-L2 exosomes vs soluble PD-L1 and PD-L2 signaling bioassay. FIG. 12B shows dose-response curves for the PD-L1 and PD-L2 exosomes comprising an Fc linker and GPI sticky binder vs. soluble ligands with an Fc domain linker. These results show that the PD-L1 and PD-L2 polypeptides fused with the Fc and GPI domains on EVs have a more potent effect on PD-1 signaling than the soluble ligands alone.

Example 17

In Vivo Assay—Therapeutic Effect of mPD-L1 Exosomes in an Experimental Autoimmune Uveoretinitis (EAU) Model in Lewis Rats Lewis rats were challenged with retinal antigen interphotoreceptor retinoid-binding protein (IRBP) peptide. This model can be used to study anterior and posterior chamber dependent EAU. Rats were immunized on Day 1 with EAU presenting typically at Day 6. Clinical scores in the rat were determined. The EAU dosing schedule is shown in FIG. 13A. EAU dosing test article are shown in the following table.

| EAU dosing test articles | | | | |
|---|---|---|---|---|
| | Unmodified Exosomes (IVT) | mPD-Ll-Fc-GPI Exosomes 1X (IVT) | mPD-L1-Fc-GPI Exosomes 10X (IVT) | mPD-L1 Exosomes (IV) |
| Dose | 2 ul | 2 ul | 2 ul | 5 ml/kg |
| Total protein concentration | 40 ug/ml | 40 ug/ml | 400 ug/ml | 40 ug/ml |
| Total protein administered | 80 ng/eye | 80 ng/eye | 800 ng/eye | 50 ug/animal |
| Exosome concentration | $5.7 \times 10^{10}$/ml | $2.34 \times 10^{10}$/ml | $2.34 \times 10^{11}$/ml | $2.34 \times 10^{10}$/ml |
| Total exosomes administered | $4.7 \times 10^{7}$ | $4.7 \times 10^{7}$ | $4.7 \times 10^{8}$ | $2.93 \times 10^{10}$ |

*IVT-intravitreal, IV-intravenous

The study design is outlined below:

| Group | Test Article | N | Route | Concentration | Dosage | Regimen |
|---|---|---|---|---|---|---|
| 1 | Cyclosporine | 8 | p.o. | 1 mg/mL | 10 mg/kg | BID from day 0 to Day 20 |
| 2 | Negative control (PBS vehicle) | 8 | Intravitreal both eyes | 1× | 2-3 μL | Day 6, Day 12, and Day 16 |
| 3 | Unmodified exosomes (Control exosomes) | 8 | Intravitreal both eyes | 1× (~40 ug/ml) | 2-3 μL | Day 6 and Day 12 |
| 4 | mPD-L1-Fc-GPI (40 ug/ml) | 8 | Intravitreal both eyes | 1× (~40 ug/ml) | 2-3 μL | Day 6, Day 12, and Day 16 |
| 5 | mPD-Ll-Fc-GPI (40 ug/ml) | 4 | Intravenous Injection | 1× (~40 ug/ml) | 5 mL/kg | Day 1, Day 6, Day 12, and Day 16 |
| 6 | No IRBP peptide but treated with Test Agent B (for tolerability) | 4 | Intravitreal both eyes | 1× (~40 ug/ml) | 2-3 μL | Day 6, Day 12, and Day 16 |
| 7 | mPD-L1-Fc-GPI (400 ug/ml) | 8 | Intravitreal both eyes | 1× (400 ug/ml) | 2-3 μL | Day 6, Day 12, and Day 16 |

Clinical Scores were determined as follows:

| EAU Clinical Scores in Rats | |
|---|---|
| Score | Clinical Criteria |
| 0 | No disease; eye is translucent and reflects light(red reflex) |
| 0.5 (trace) | Dilated blood vessels in the iris |
| 1 | Engorged blood vessels in the iris; abnormal pupil contraction |
| 2 | Hazy anterior chamber;decreased red reflex |
| 3 | Moderately opaque anterior chamber,but pupil still visible; dull red reflex |
| 4 | Opaque anterior chamber and obscured pupil; red reflex absent; proptosis |

Each higher grade includes the criteria of the preceding one.

Figure 13C:
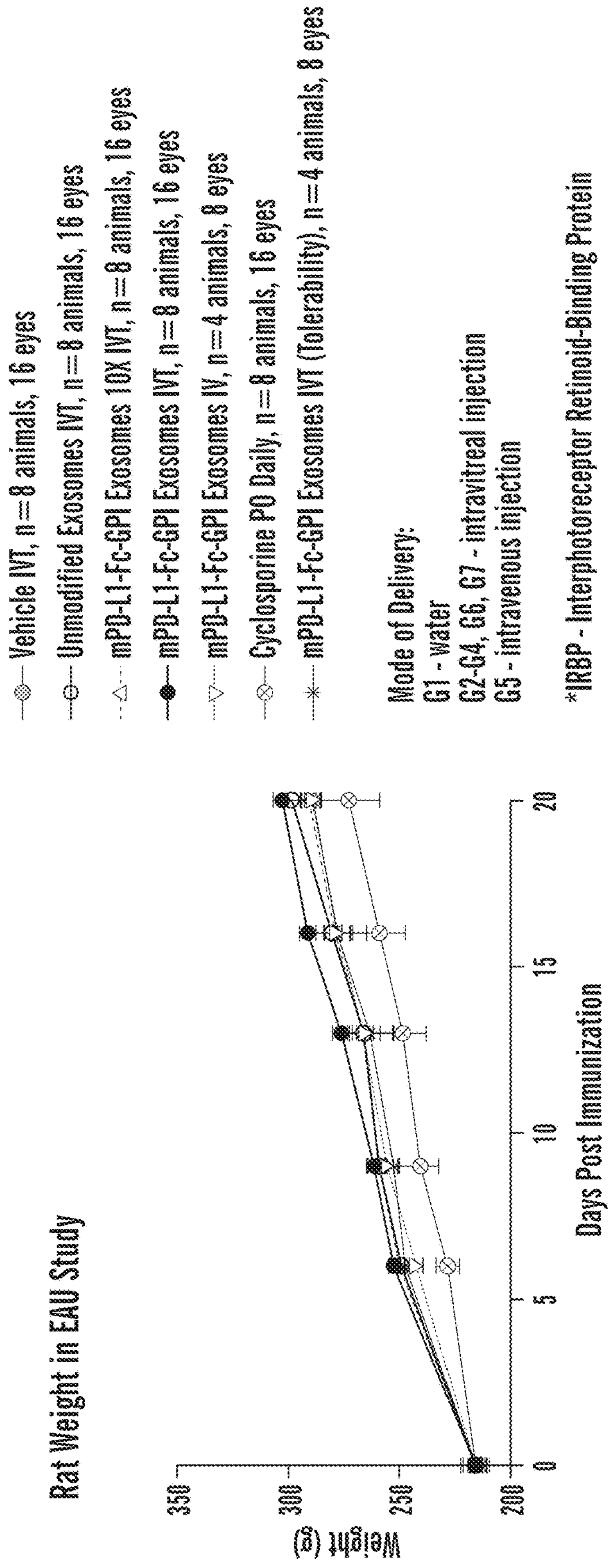
Figure 14:
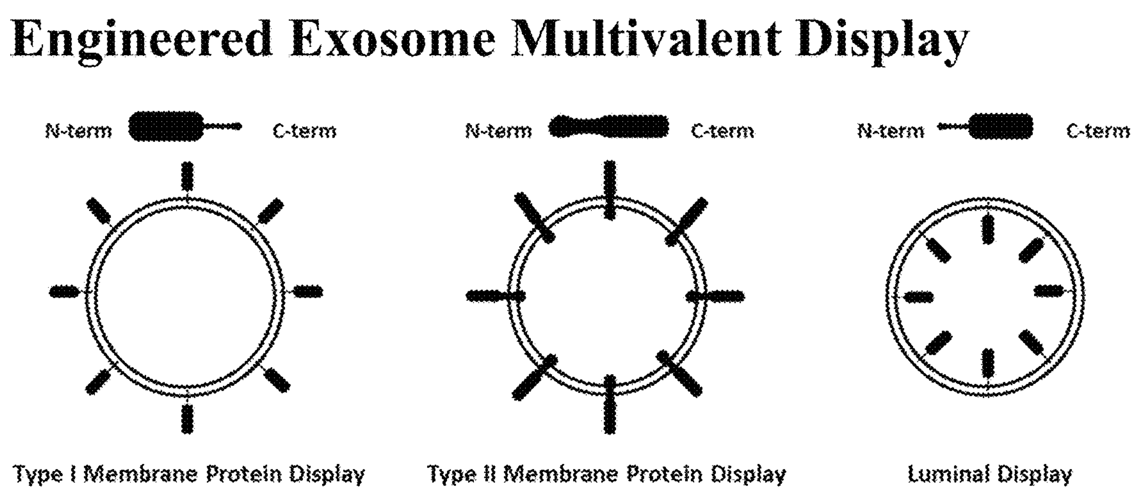
Figure 15:
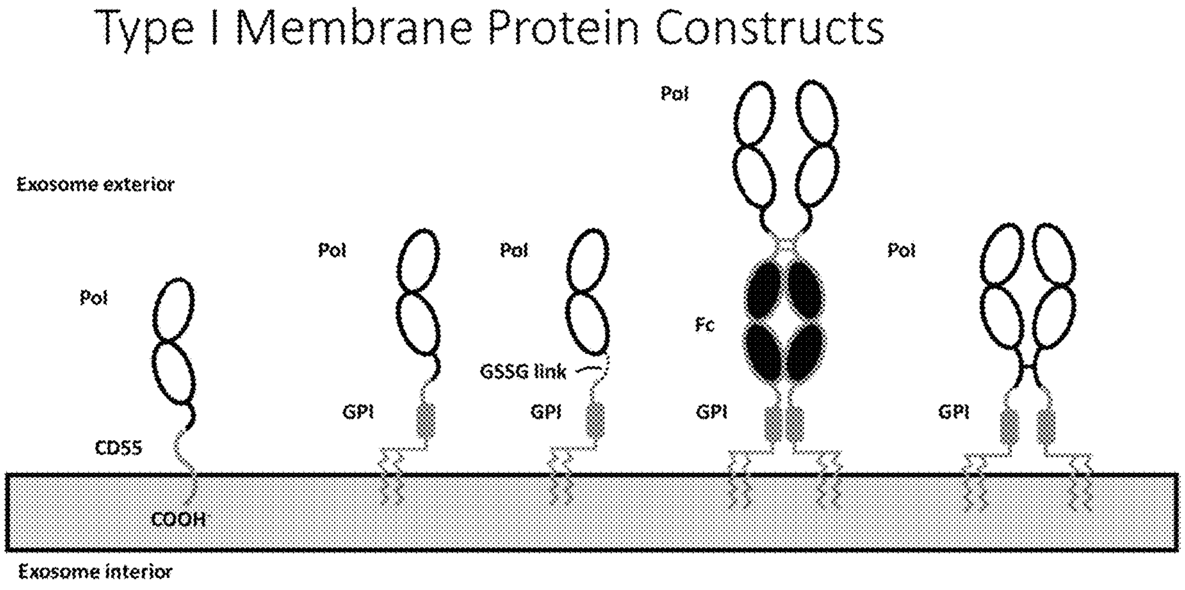
Figure 16:
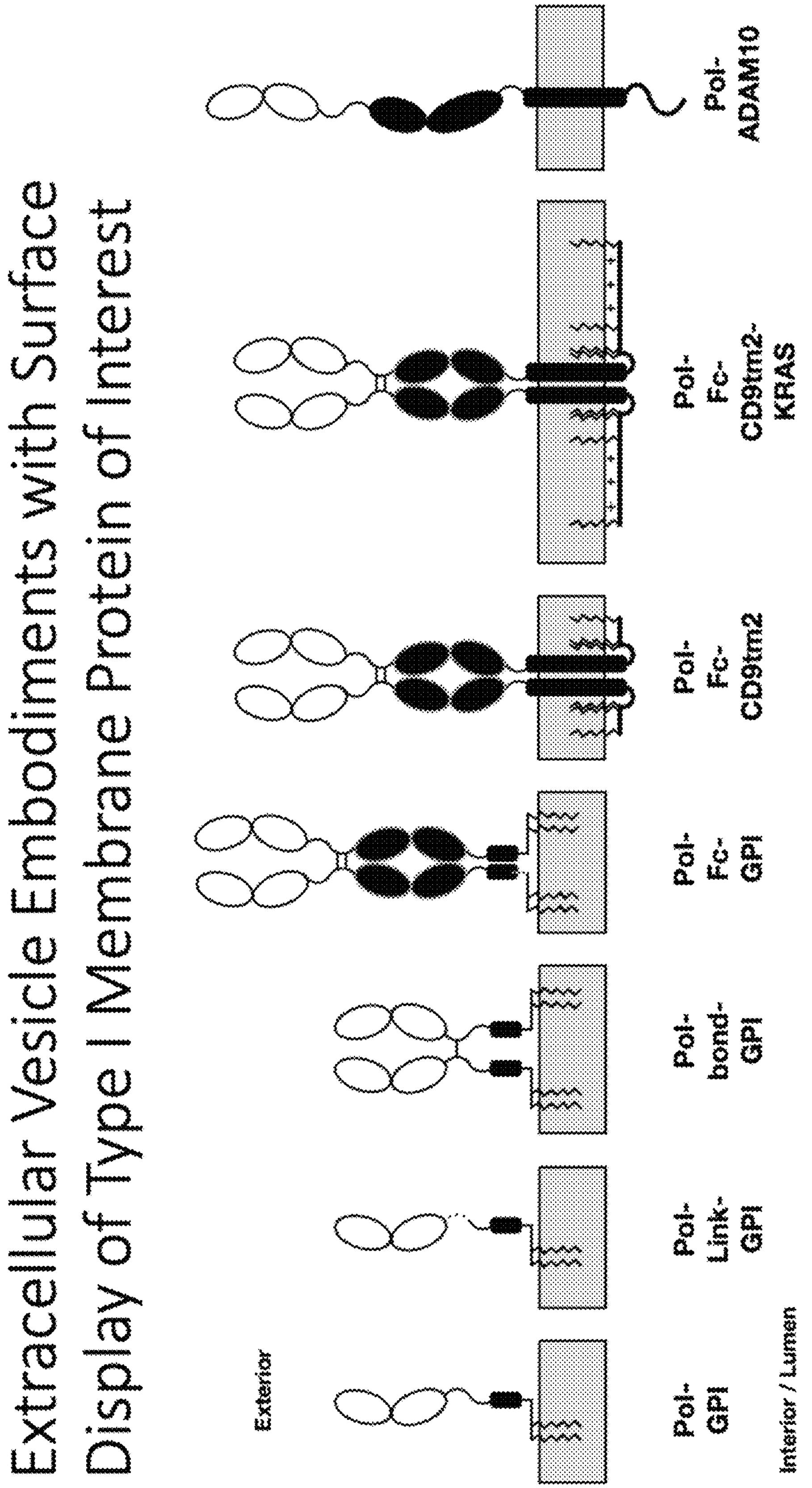
Figure 17:
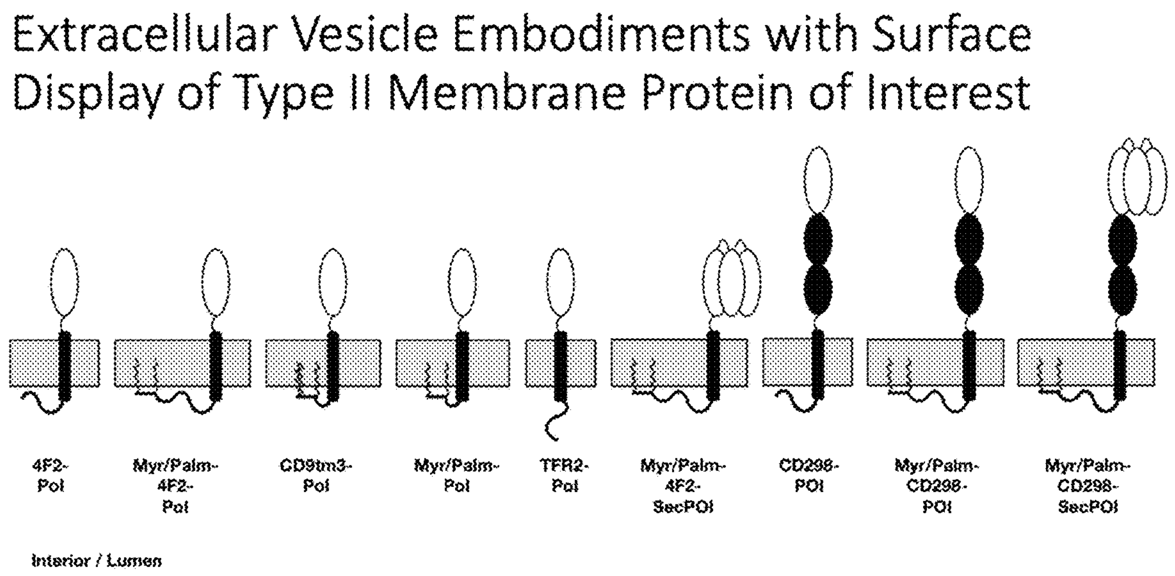
FIG. 17 shows a schematic representation of the surface of an exosome engineered with an extracellular portion of the Type II membrane protein of interest (POI) with transmembrane/exosome targeting domains.
Figure 18:
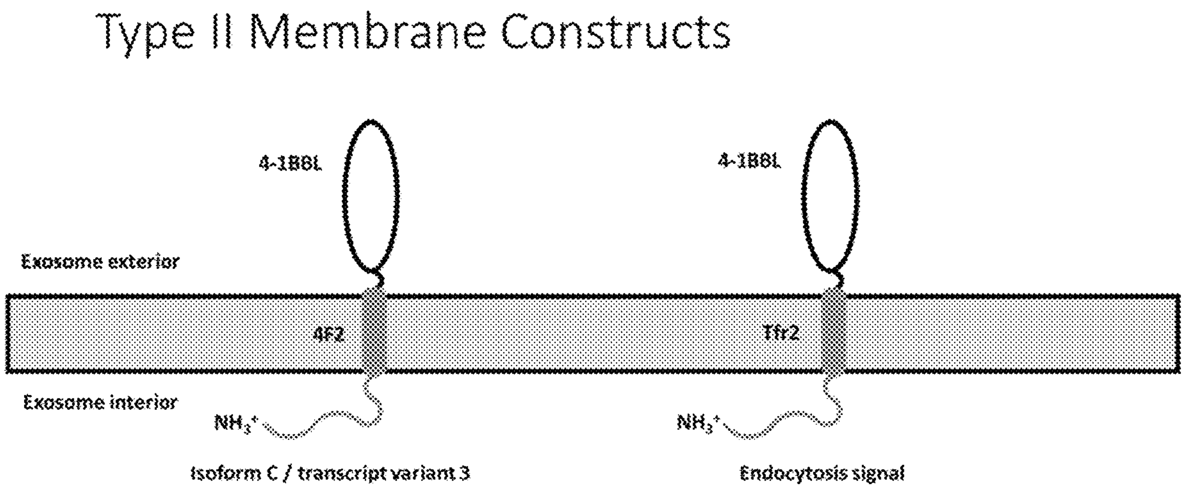
FIG. 18 shows a schematic representation of an exosome engineered with an extracellular portion of the Type II membrane protein 4-1BB.

It was discovered that there is a statistically significant initial reduction in EAU in mPDL1 exosome treated rats via either the intravitreal and intravenous delivery modes as compared with untreated animals (FIG. 13A). Rat weight did not change post immunization (FIG. 13C).

Example 18

Purification of Exosomes Labeled with Type II Membrane Proteins

The inventors designed, engineered, and purified pcDNA5-FRT-4F2-4-1BBL exosomes by the methods provided herein (FIG. 34). Several embodiments of the 4-1BBL labeled exosomes are shown in FIG. 35. Cell expression of the 4F2-4-1BBL was confirmed (data not shown). FIGS. 92A-92B shows the purification of 4F2-4-1BBL exosomes.

Example 19

Purification of Luminal Labeled Exosomes (Internal Loading)

In addition to Type I and Type II display fusion proteins on the surface of an EV, exosomes can be loaded with fusion proteins that are localized to the lumen of the phospholipid bilayer of the exosome (FIG. 37). The Myr/Palm sequence used herein when fused to mScarlet the fusion protein into the luminal interior of extracellular vesicles. Fluorescence at an excitation wavelength 470 nm and emission wavelength of 665-720 nm peaks in SEC fractions 7, 8, and 9. SEC fractions 7, 8, and 9 contain exosomes as demonstrated by the dot blot. Fraction 8 was further analyzed for exosome quantification using an EXOVIEW® system (FIG. 38). Unmodified exosomes do not show fluorescence. Exosomes show near 80% loading with Myr/Palm-mScarlet. The remaining 20% were out of the detection limit. Thus, nearly 100% internal loading was achieved using the specific Myr/Palm sequence.

NanoLuc® luciferase expressing exosomes were also purified with the Myr/Palm sequence incorporated into the vector encoding the fusion polypeptide. A Qubit™ fluorometer was used to measure total protein and PROMEGA® Nano-Glo® substrate and plate luminometer to measure luminescence (FIG. 39A). Tetraspanin characterization of exosomes was performed and determined that the NanoLuc® luciferase exosomes were internally loaded and purified in fraction 8 (FIG. 39B).

SEQUENCE LISTING

```
Sequence total quantity: 320
SEQ ID NO: 1            moltype = DNA  length = 3634
FEATURE                 Location/Qualifiers
source                  1..3634
                        mol_type = genomic DNA
                        organism = Homo sapiens
SEQUENCE: 1
agttctgcgc agcttcccga ggctccgcac cagccgcgct tctgtccgcc tgcagggcat  60
tccagaaaga tgaggatatt tgctgtcttt atattcatga cctactggca tttgctgaac  120
gcatttactg tcacggttcc caaggaccta tatgtggtag agtatggtag caatatgaca  180
attgaatgca aattcccagt agaaaaacaa ttagacctgg ctgcactaat tgtctattgg  240
gaaatggagg ataagaacat tattcaattt gtgcatggag aggaagacct gaaggttcag  300
catagtagct acagacagag ggcccggctg ttgaaggacc agctctccct gggaaatgct  360
gcacttcaga tcacagatgt gaaattgcag gatgcagggg tgtaccgctg catgatcagc  420
tatggtggtg ccgactacaa gcgaattact gtgaaagtca atgccccata caacaaaatc  480
aaccaaagaa ttttggttgt ggatccagtc acctctgaac atgaactgac atgtcaggct  540
gagggctacc ccaaggccga agtcatctgg acaagcagtg accatcaagt cctgagtggt  600
aagaccacca ccaccaattc caagagagag gagaagcttt tcaatgtgac cagcacactg  660
agaatcaaca caacaactaa tgagattttc tactgcactt ttaggagatt agatcctgag  720
gaaaaccata cagctgaatt ggtcatccca gaactacctc tggcacatcc tccaaatgaa  780
aggactcact tggtaattct gggagccatc ttattatgcc ttggtgtagc actgacattc  840
atcttccgtt taagaaaagg gagaatgatg gatgtgaaaa aatgtggcat ccaagataca  900
aactcaaaga agcaaagtga tacacatttg gaggagacgt aatccagcat tggaacttct  960
gatcttcaag cagggattct caacctgtgg tttaggggtt catcggggct gagcgtgaca  1020
agaggaagga atgggcccgt gggatgcagg caatgtggga cttaaaaggc ccaagcactg  1080
aaaatggaac ctggcgaaag cagaggagga gaatgaagaa agatggagtc aaacagggag  1140
cctggaggga gaccttgata ctttcaaatg cctgaggggc tcatcgacgc ctgtgacagg  1200
gagaaaggat acttctgaac aaggagcctc caagcaaatc atccattgct catcctagga  1260
agacgggttg agaatcccta atttgagggt cagttcctgc agaagtgccc tttgcctcca  1320
ctcaatgcct caatttgttt tctgcatgac tgagagtctc agtgttggaa cgggacagta  1380
tttatgtatg agtttttcct atttattttg agtctgtgag gtcttcttgt catgtgagtg  1440
tggttgtgaa tgatttcttt tgaagatata ttgtagtaga tgttacaatt ttgtcgccaa  1500
actaaacttg ctgcttaatg atttgctcac atctagtaaa acatggagta tttgtaaggt  1560
gcttggtctc ctctataact acaagtatac attggaagca taaagatcaa accgttggtt  1620
gcataggatg tcacctttat ttaacccatt aatactctgg ttgacctaat cttattctca  1680
gacctcaagt gtctgtgcag tatctgttcc atttaaatat cagctttaca attatgtggt  1740
agcctacaca cataatctca tttcatcgct gtaaccaccc tgttgtgata accactatta  1800
ttttacccat cgtacagctg aggaagcaaa cagattaagt aacttgccca aaccagtaaa  1860
tagcagacct cagactgcca cccactgtcc ttttataata caatttacag ctatatttta  1920
ctttaagcaa ttcttttatt caaaaaccat ttattaagtg cccttgcaat atcaatcgct  1980
gtgccaggca ttgaatctac agatgtgagc aagacaaagt acctgtcctc aaggagctca  2040
tagtataatg aggagattaa caagaaaatg tattattaca atttagtcca gtgtcatagc  2100
ataaggatga tgcgagggga aaacccgagc agtgttgcca agaggaggaa ataggccaat  2160
gtggtctggg acggttggat atacttaaac atcttaataa tcagagtaat ttcatttac  2220
aaagagaggt cggtacttaa aataaccctg aaaaataaca ctggaattcc ttttctagca  2280
ttatatttat tcctgatttg cctttgccat ataatctaat gcttgtttat atagtgtctg  2340
gtattgttta acagttctgt cttttctatt taaatgccac taaattttaa attcatacct  2400
ttccatgatt caaaattcaa aagatcccat gggagatggt tggaaaatct ccacttcatc  2460
ctccaagcca ttcaagtttc ctttccagaa gcaactgcta ctgcctttca ttcatatgtt  2520
cttctaaaga tagtctacat ttggaaatgt atgttaaaag cacgtatttt taaaattttt  2580
ttcctaaata gtaacacatt gtatgtctgc tgtgtacttt gctattttta tttattttag  2640
tgtttcttat atagcagatg gaatgaattt gaagttccca gggctgagga tccatgcctt  2700
ctttgtttct aagttatctt tcccatagct tttcattatc tttcatatga tccagtatat  2760
gttaaatatg tcctacatat acatttagac aaccaccatt tgttaagtat ttgctctagg  2820
acagagtttg gatttgttta tgtttgctca aaaggagacc catgggctct ccagggtgca  2880
ctgagtcaat ctagtcctaa aaagcaatct tattattaac tctgtatgac agaatcatgt  2940
ctggaacttt tgttttctgc tttctgtcaa gtataaactt cactttgatg ctgtacttgc  3000
aaaatcacat tttctttctg gaaattccgg cagtgtacct tgactgctag ctaccctgtg  3060
ccagaaaagc ctcattcgtt gtgcttgaac ccttgaatgc caccagctgt catcactaca  3120
cagccctcct aagaggcttc ctggaggttt cgagattcag atgccctggg agatcccaga  3180
gtttcctttc cctcttggcc atattctggt gtcaatgaca aggagtacct tggctttgcc  3240
acatgtcaag gctgaagaaa cagtgtctcc aacagagctc cttgtgttat ctgtttgtac  3300
atgtgcattt gtacagtaat tggtgtgaca gtgttctttg tgtgaattac aggcaagaat  3360
tgtggctgag caaggcacat agtctactca gtctattcct aagtcctaac tcctccttgt  3420
ggtgttggat ttgtaaggca ctttatccct tttgtctcat gtttcatcgt aaatggcata  3480
ggcagagatg atacctaatt ctgcatttga ttgtcacttt ttgtacctgc attaatttaa  3540
taaaatattc ttatttattt tgttacttgg tacaccagca tgtccatttt cttgtttatt  3600
ttgtgtttaa taaaatgttc agtttaacat ccca                              3634

SEQ ID NO: 2            moltype = AA  length = 290
FEATURE                 Location/Qualifiers
source                  1..290
                        mol_type = protein
                        organism = Homo sapiens
SEQUENCE: 2
MRIFAVFIFM TYWHLLNAFT VTVPKDLYVV EYGSNMTIEC KFPVEKQLDL AALIVYWEME  60
DKNIIQFVHG EEDLKVQHSS YRQRARLLKD QLSLGNAALQ ITDVKLQDAG VYRCMISYGG  120
ADYKRITVKV NAPYNKINQR ILVVDPVTSE HELTCQAEGY PKAEVIWTSS DHQVLSGKTT  180
```

-continued

```
TTNSKREEKL FNVTSTLRIN TTTNEIFYCT FRRLDPEENH TAELVIPELP LAHPPNERTH  240
LVILGAILLC LGVALTFIFR LRKGRMMDVK KCGIQDTNSK KQSDTHLEET             290

SEQ ID NO: 3           moltype = DNA  length = 3653
FEATURE                Location/Qualifiers
source                 1..3653
                       mol_type = genomic DNA
                       organism = Mus musculus
SEQUENCE: 3
gaaatcgtgg tccccaagcc tcatgccagg ctgcacttgc acgtcgcggg ccagtctcct  60
cgcctgcaga tagttcccaa aacatgagga tatttgctgg cattatattc acagcctgct  120
gtcacttgct acgggcgttt actatcacgg ctccaaagga cttgtacgtg gtggagtatg  180
gcagcaacgt cacgatggag tgcagattcc ctgtagaacg ggagctggac ctgcttgcgt  240
tagtggtgta ctgggaaaag gaagatgagc aagtgattca gtttgtggca ggagaggagg  300
accttaagcc tcagcacagc aacttcaggg ggagagcctc gctgccaaag gaccagcttt  360
tgaagggaaa tgctgccctt cagatcacag acgtcaagct gcaggacgca ggcgtttact  420
gctgcataat cagctacggt ggtgcggact acaagcgaat cacgctgaaa gtcaatgccc  480
cataccgcaa aatcaaccag agaatttccg tggatccagc cacttctgag catgaactaa  540
tatgtcaggc cgagggttat ccagaagctg aggtaatctg gacaaacagt gaccaccaac  600
ccgtgagtgg gaagagaagt gtcaccactt cccggacaga ggggatgctt ctcaatgtga  660
ccagcagtct gagggtcaac gccacagcga atgatgtttt ctactgtacg ttttggagat  720
cacagccagg gcaaaaccac acagcggagc tgatcatccc agaactgcct gcaacacatc  780
ctccacagaa caggactcac tgggtgcttc tgggatccat cctgttgttc ctcattgtag  840
tgtccacggt cctcctcttc ttgagaaaac aagtgagaat gctagatgtg gagaaatgtg  900
gcgttgaaga tacaagctca aaaaaccgaa atgatacaca attcgaggag acgtaagcag  960
tgttgaaccc tctgatcgtc gattggcagc ttgtggtctg tgaaagaaag ggcccatggg  1020
acatgagtcc aaagactcaa gatggaacct gagggagaga accaagaaag tgttgggaga  1080
ggagcctgga acaacggaca ttttttccag ggagacactg ctaagcaagt tgcccatcag  1140
tcgtcttggg aaatggattg agggttcctg gcttagcagc tggtccttgc acagtgacct  1200
tttcctctgc tcagtgccgg gatgagagat ggagtcatga gtgttgaaga ataagtgcct  1260
tctatttatt ttgagtctgt gtgttctcac tttgggcatg taattatgac tggtgaattc  1320
tgacgacatg atagatctta agatgtagtc accaaactca actgctgctt agcatcctcc  1380
gtaactactg atacaagcag ggaacacaga ggtcacctgc ttggtttgac aggctcttgc  1440
tgtctgactc aaataatctt tatttttcag tcctcaaggc tcttcgatag cagttgttct  1500
gtatcagcct tataggtgtc aggtatagca ctcaacatct catctcatta caatagcaac  1560
cctcatcacc atagcaacag ctaacctctg ttatcctcac ttcatagcca ggaagctgag  1620
cgactaagtc acttgcccac agagtatcag ctctcagatt tctgttcttc agccactgtc  1680
ctttcaggat agaatttgtc gttaagaaat taatttaaaa actgattatt gagtagcatt  1740
gtatatcaat cacaacatgc cttgtgcact gtgctggcct ctgagcataa agatgtacgc  1800
cggagtaccg gtcggacatg tttatgtgtg ttaaatactc agagaaatgt tcattaacaa  1860
ggagcttgca ttttagagac actggaaagt aactccagtt cattgtctag cattacattt  1920
acctcatttg ctatccttgc catacagtct cttgttctcc atgaagtgtc atgaatcttg  1980
ttgaatagtt cttttatttt ttaaatgttt ctatttaaat gatattgaca tctgaggcga  2040
tagctcagtt ggtaaaaccc tttcctcaca agtgtgaaac cctgagtctt atccctagaa  2100
cccacataaa aaacagttgc gtatgtttgt gcatgctttt gatcccagca ctagggaggc  2160
agaggcaggc agatcctgag ctctcattga ccacccagcc tagcctacat ggttagctcc  2220
aggcctacag gagctggcag agcctgaaaa acgatgccta gacacacaca cacacacaca  2280
cacacacaca cacacacaca cacaccatgt actcatagac ctaagtgcac cctcctacac  2340
atgcacacac atacaattca aacacaaatc aacagggaat tgtctcagaa tggtccccaa  2400
gacaaagaag aagaaaaaca ccaaaccagc tctattccct cagcctatcc tctctactcc  2460
ttcctagaag caactactat tgtttttgta tataaattta cccaacgaca gttaatatgt  2520
agaatatata ttaaagtgtc tgtcaatata tattatctct ttctttcttt cttcctttct  2580
ttctttcttt ctttctttct ttctttcttt ctttctttct ttcttccttc cttccttcct  2640
tccttccttc cttccttcct ttctttcttt ctttcttttt ttctgtctat ctgtacctaa  2700
atggttgctc actatgcatt ttctgtgctc ttcgcccttt ttatttaatg tatggatatt  2760
tatgctgctt ccagaatgga tctaaagctc tttgtttcta ggttttctcc cccatccttc  2820
taggcatctc tcacactgtc taggccagac accatgtctg ctgcctgaat ctgtagacac  2880
catttataaa gcacgtactc accgagtttg tatttggctt gttctgtgtc tgattaaagg  2940
gagaccatga gtccccaggg tacactgagt taccccagta ccaaggggga gccttgtttg  3000
tgtctccatg gcagaagcag gcctggagcc attttggttt cttccttgac ttctctcaaa  3060
cacagacgcc tcacttgctc attacaggtt ctcctttggg aatgtcagca ttgctccttg  3120
actgctggct gccctggaag gagcccatta gctctgtgtg agcccttgac agctactgcc  3180
tctccttacc acaggggcct ctaagatact gttacctaga ggtcttgagg atctgtgttc  3240
tctgggggga ggaaaggagg aggaacccag aactttctta cagttttcct tgttctgtca  3300
catgtcaaga ctgaaggaac aggctgggct acgtagtgag atcctgtctc aaaggaaaga  3360
cgagcatagc cgaacccccg gtggaacccc ctctgttacc tgttcacaca agcttattga  3420
tgagtctcat gttaatgtct tgtttgtatg aagtttaaga aaatatcggg ttgggcaaca  3480
cattctattt attcatttta tttgaaatct taatgccatc tcatggtgtt ggattggtgt  3540
ggcactttat tcttttgtgt tgtgtataac cataaatttt attttgcatc agattgtcaa  3600
tgtattgcat taatttaata aatattttta tttattaaaa aaaaaaaaaa aaa         3653

SEQ ID NO: 4           moltype = AA  length = 290
FEATURE                Location/Qualifiers
source                 1..290
                       mol_type = protein
                       organism = Mus musculus
SEQUENCE: 4
MRIFAGIIFT ACCHLLRAFT ITAPKDLYVV EYGSNVTMEC RFPVERELDL LALVVYWEKE  60
DEQVIQFVAG EEDLKPQHSN FRGRASLPKD QLLKGNAALQ ITDVKLQDAG VYCCIISYGG  120
```

```
ADYKRITLKV NAPYRKINQR ISVDPATSEH ELICQAEGYP EAEVIWTNSD HQPVSGKRSV  180
TTSRTEGMLL NVTSSLRVNA TANDVFYCTF WRSQPGQNHT AELIIPELPA THPPQNRTHW  240
VLLGSILLFL IVVSTVLLFL RKQVRMLDVE KCGVEDTSSK NRNDTQFEET             290

SEQ ID NO: 5            moltype = DNA  length = 2432
FEATURE                 Location/Qualifiers
source                  1..2432
                        mol_type = genomic DNA
                        organism = Homo sapiens
SEQUENCE: 5
actctcatgt tacggcaaac cttaagctga atgaacaact tttcttctct tgaatatatc  60
ttaacgccaa attttgagtg cttttttgtt acccatcctc atatgtccca gctagaaaga  120
atcctgggtt ggagctactg catgttgatt gttttgtttt tccttttggc tgttcatttt  180
ggtggctact ataaggaaat ctaacacaaa cagcaactgt tttttgttgt ttacttttgc  240
atctttactt gtggagctgt ggcaagtcct catatcaaat acagaacatg atcttcctcc  300
tgctaatgtt gagcctggaa ttgcagcttc accagatagc agctttattc acagtgacag  360
tccctaagga actgtacata atagagcatg gcagcaatgt gaccctggaa tgcaactttg  420
acactggaag tcatgtgaac cttggagcaa taacagccag tttgcaaaag gtggaaaatg  480
atacatcccc acaccgtgaa agagccactt tgctggagga gcagctgccc ctagggaagg  540
cctcgttcca catacctcaa gtccaagtga gggacgaagg acagtaccaa tgcataatca  600
tctatggggt cgcctgggac tacaagtacc tgactctgaa agtcaaagct tcctacagga  660
aaataaacac tcacatccta aaggttccag aaacagatga ggtagagctc acctgccagg  720
ctacaggtta tcctctggca gaagtatcct ggccaaacgt cagcgttcct gccaacacca  780
gccactccag gaccccctgaa ggcctctacc aggtcaccag tgttctgcgc ctaaagccac  840
cccctggcag aaacttcagc tgtgtgttct ggaatactca cgtgagggaa cttactttgg  900
ccagcattga ccttcaaagt cagatggaac ccaggaccca tccaacttgg ctgcttcaca  960
ttttcatccc cttctgcatc attgctttca ttttcatagc cacagtgata gccctaagaa  1020
aacaactctg tcaaaagctg tattcttcaa aagacacaac aaaaagacct gtcaccacaa  1080
caaagaggga agtgaacagt gctatctgaa cctgtggtct tgggagccag ggtgacctga  1140
tatgacatct aaagaagctt ctggactctg aacaagaatt cggtggcctg cagagcttgc  1200
catttgcact tttcaaatgc ctttggatga cccagcactt taatctgaaa cctgcaacaa  1260
gactagccaa cacctggcca tgaaacttgc cccttcactg atctggactc acctctggag  1320
cctatggctt taagcaagca ctactgcact ttacagaatt accccactgg atcctggacc  1380
cacagaattc cttcaggatc cttcttgctg ccagactgaa agcaaaagga attatttccc  1440
ctcaagtttt ctaagtgatt tccaaaagca gaggtgtgtg gaaatttcca gtaacagaaa  1500
cagatgggtt gccaatagag ttatttttta tctatagctt cctctgggta ctagaagagg  1560
ctattgagac tatgagctca cagacagggc ttcgcacaaa ctcaaatcat aattgacatg  1620
ttttatggat tactggaatc ttgatagcat aatgaagttg ttctaattaa cagagagcat  1680
ttaaatatac actaagtgca caaattgtgg agtaaagtca tcaagctctg tttttgaggt  1740
ctaagtcaca aagcatttgt tttaacctgt aatggcacca tgtttaatgg tggttttttt  1800
tttgaactac atctttcctt taaaaattat tggtttcttt ttatttgttt ttaccttaga  1860
aatcaattat atacagtcaa aaatatttga tatgctcata cgttgtatct gcagcaattt  1920
cagataagta gctaaaatgg ccaaagcccc aaactaagcc tccttttctg gccctcaata  1980
tgactttaaa tttgactttt cagtgcctca gtttgcacat ctgtaataca gcaatgctaa  2040
gtagtcaagg cctttgataa ttggcactat ggaaatcctg caagatccca ctacatatgt  2100
gtggagcaga agggtaactc ggctacagta acagcttaat tttgttaaat ttgttcttta  2160
tactggagcc atgaagctca gagcattagc tgacccttga actattcaaa tgggcacatt  2220
agctagtata acagacttac ataggtgggc ctaaagcaag ctccttaact gagcaaaatt  2280
tggggcttat gagaatgaaa gggtgtgaaa ttgactaaca gacaaatcat acatctcagt  2340
ttctcaattc tcatgtaaat cagagaatgc ctttaaagaa taaaactcaa ttgttattct  2400
tcaacgttct ttatatattc tacttttggg ta                                2432

SEQ ID NO: 6            moltype = AA  length = 273
FEATURE                 Location/Qualifiers
source                  1..273
                        mol_type = protein
                        organism = Homo sapiens
SEQUENCE: 6
MIFLLLMLSL ELQLHQIAAL FTVTVPKELY IIEHGSNVTL ECNFDTGSHV NLGAITASLQ  60
KVENDTSPHR ERATLLEEQL PLGKASFHIP QVQVRDEGQY QCIIIYGVAW DYKYLTLKVK  120
ASYRKINTHI LKVPETDEVE LTCQATGYPL AEVSWPNVSV PANTSHSRTP EGLYQVTSVL  180
RLKPPPGRNF SCVFWNTHVR ELTLASIDLQ SQMEPRTHPT WLLHIFIPFC IIAFIFIATV  240
IALRKQLCQK LYSSKDTTKR PVTTTKREVN SAI                                273

SEQ ID NO: 7            moltype = DNA  length = 3415
FEATURE                 Location/Qualifiers
source                  1..3415
                        mol_type = genomic DNA
                        organism = Mus musculus
SEQUENCE: 7
gaccacatca tttttgttcc ctttgttgga tatatcctaa tgtcaaatgt ggcatatctt  60
tgttgtctcc ttctgtctcc caactagaga gaacacactt acggctcctg tcccgggcag  120
gtttggttgt cggtgtgatt ggcttccagg gaacctgata caaggagcaa ctgtgtgctg  180
ccttttctgt gtctttgctt gaggagctgt gctgggtgct gatattgaca cagaccatgc  240
tgctcctgct gccgatactg aacctgagct tacaacttca tcctgtagca gctttattca  300
ccgtgacagc ccctaaagaa gtgtacaccg tagacgtcgg cagcagtgtg agcctggagt  360
gcgattttga ccgcagagaa tgcactgaac tggaagggat aagagccagt ttgcagaagg  420
tagaaaatga tacgtctctg caaagtgaaa gagccaccct gctggaggag cagctgcccc  480
tgggaaaggc tttgttccac atccctagtg tccaagtgag agattccggg cagtaccgtt  540
```

```
gcctggtcat ctgcggggcc gcctgggact acaagtacct gacggtgaaa gtcaaagctt  600
cttacatgag gatagacact aggatcctgg aggttccagg tacaggggag gtgcagctta  660
cctgccaggc tagaggttat cccctagcag aagtgtcctg gcaaaatgtc agtgttcctg  720
ccaacaccag ccacatcagg acccccgaag gcctctacca ggtcaccagt gttctgcgcc  780
tcaagcctca gcctagcaga aacttcagct gcatgttctg gaatgctcac atgaaggagc  840
tgacttcagc catcattgac cctctgagtc ggatggaacc caaagtcccc agaacgtggc  900
cacttcatgt tttcatcccg gcctgcacca tcgctttgat cttcctggcc atagtgataa  960
tccagagaaa gaggatctag gggaagctgt attacggaag aagatctgga cctgcggtct  1020
tgggagttgg aaggatctga tgggaaaccc tcaagagact tctggactca aagtgagaat  1080
cttgcaggac ctgccatttg cacttttgaa ccctttggac ggtgacccag ggctccgaag  1140
aggagcttgt aagactgaca atcttccctc tgtctcaaga ctctctgaac agcaagaccc  1200
caatggcact ttagacttac ccctgggatc ctggacccca gtgagggcct aaggctccta  1260
atgactttca gggtgagaac aaaaggaatt gctctccgcc ccacccccac ctcctgcttt  1320
ccgcagggag acatggaaat tcccagttac taaaatagat tgtcaataga gttatttata  1380
gccctcattt cctccgggga cttggaagct tcagacaggg tttttcataa acaaagtcat  1440
aactgatgtg ttttacagca tcctagaatc ctggcagcct ctgaagttct aattaactgg  1500
aagcatttaa gcaacacgtt aagtaccccc actgtggtat ttgtttctac ttttctgttt  1560
ttaaagtgtg agtcacaagg taattgttgt aacctgtgat atcactgttt cttgtgtctc  1620
ttctttcaac tacatctttt aaaacaaaac ggtgtggggt ttggttgttt tggtggtagt  1680
ggtagtgttt ctcagtggta tctccttaag aaaaaaaatc atcatgccag tgaattgttt  1740
cttcagccat ttcagatggg aagctggaat agcctgtccc ccaagctaag ccttcttccc  1800
tagctttctg cgtgatttta cattgagcat tcctgttgct ttgtttctat aactgtaatg  1860
tggtgatgtc attgttaggg cacttgaggg tgggcgttct ggaagtcctt tcaggttagt  1920
gtttggggc agggttgctc agaatacata aaggtgctaa cttaaactgc agccatggag  1980
ctcagtgaat tcactaacct tcgggctgtc caaatgtgca cattagctac tgtgacccct  2040
gtaggttagg gagcctgaag ccagctcttt acctggtgtt tagactcagc agaatttgga  2100
gtcaatggga ccaaatggtt gtgaaattaa gatttgaagt gtgcatctta ttttatcacc  2160
atctgcccaa caaaacttca gaaaatgcct ttgaagcaca aaaatgtaat cgtttatgtg  2220
aaatctctga gttgcattta gatgcccatt gcagcaaggt ggctctctca cagattccac  2280
accttagcct aagataccag acagcaggac agagagaaaa gtccttcctg gtgtgcaaac  2340
ttccttacac tggacctcgc ctctcaggtg tgtgattggt aggccaaatc ccgatagcca  2400
atcggtgttg ggtgctttgt ctgctctact gggagtccag tggtacaatg gattctggca  2460
aaatgctgcc atcttggccc tcgctgggct gctttctagg atattcatag agaaagggcc  2520
gtccagatcc agtatcctaa aatcctgaga ggagaatata agttagtgtg tctcactata  2580
actatctcta tgatcggtca cattactatc taacagttac caaatactat atgcctaata  2640
ctggtaagca ttttatacac accattggat tgaatcctct caaaatcctc aaaaaggaag  2700
ttattaatac ctccataggc aaggagccca gaacccagag aggtcaggca gtctagttat  2760
agatgcctgc tttgtttaga agtgaacaag agcatcaaat tattaatgtg ccctggttat  2820
taatgcgccc tggttacctg ctggatggaa catcaaggtg gacttttggc agttgcatac  2880
acccagaggt attttggcta ttcacggatt aatttcacac gaagtgtttc agagacatgt  2940
gtaggggaag tccgggttca gggggcctaa gattcaaact ctagcttagc tacgtctgac  3000
ctccctaagc actaacttac tatcaaaaga atgagcagta aaagaatggt gtttactgcc  3060
tgcctttatc aggcagtgaa cgtgcagcgg gcaacgaatg cttgataagt gtgtgtcagt  3120
gtgaagtccc atgtaccagc cgctgtcccc actgcaaaag cagcagagcg ctcagacatc  3180
atcagctgat ttaccagcag cagatttctt cttctagtcc catccctgaa gaagcttcca  3240
gcctaggtac attgcatggg ctttgtgctc caggagttcc tacacagccc tcaacttcaa  3300
cacaggcaaa gtgcttactg atcctcatgt atcttacagg gtcccctcta cccacaatac  3360
ctcattgctg gaacttcaaa tcttcctgaa taaaagcttg cccgtggttt aatta       3415

SEQ ID NO: 8            moltype = AA  length = 247
FEATURE                 Location/Qualifiers
source                  1..247
                        mol_type = protein
                        organism = Mus musculus
SEQUENCE: 8
MLLLLPILNL SLQLHPVAAL FTVTAPKEVY TVDVGSSVSL ECDFDRRECT ELEGIRASLQ  60
KVENDTSLQS ERATLLEEQL PLGKALFHIP SVQVRDSGQY RCLVICGAAW DYKYLTVKVK  120
ASYMRIDTRI LEVPGTGEVQ LTCQARGYPL AEVSWQNVSV PANTSHIRTP EGLYQVTSVL  180
RLKPQPSRNF SCMFWNAHMK ELTSAIIDPL SRMEPKVPRT WPLHVFIPAC TIALIFLAIV  240
IIQRKRI                                                            247

SEQ ID NO: 9            moltype = DNA  length = 1997
FEATURE                 Location/Qualifiers
source                  1..1997
                        mol_type = genomic DNA
                        organism = Homo sapiens
SEQUENCE: 9
gctttctatt caagtgcctt ctgtgtgtgc acatgtgtaa tacatatctg ggatcaaagc  60
tatctatata aagtccttga ttctgtgtgg gttcaaacac atttcaaagc ttcaggatcc  120
tgaaaggttt tgctctactt cctgaagacc tgaacaccgc tcccataaag ccatggcttg  180
ccttggattt cagcggcaca aggctcagct gaacctggct accaggacct ggccctgcac  240
tctcctgttt tttcttctct tcatccctgt cttctgcaaa gcaatgcacg tggcccagcc  300
tgctgtggta ctggccagca gccgaggcat cgccagcttt gtgtgtgagt atgcatctcc  360
aggcaaagcc actgaggtcc gggtgacagt gcttcggcag gctgacagcc aggtgactga  420
agtctgtgcg gcaacctaca tgatggggaa tgagttgacc ttcctagatg attccatctg  480
cacgggcacc tccagtggaa atcaagtgaa cctcactatc caaggactga gggccatgga  540
cacgggactc tacatctgca aggtggagct catgtaccca ccgccatact acctgggcat  600
aggcaacgga acccagattt atgtaattga tccagaaccg tgcccagatt ctgacttcct  660
cctctggatc cttgcagcag ttagttcggg gttgtttttt tatagctttc tcctcacagc  720
```

-continued

```
tgtttctttg agcaaaatgc taaagaaaag aagccctctt acaacagggg tctatgtgaa  780
aatgcccccca acagagccag aatgtgaaaa gcaatttcag ccttatttta ttcccatcaa  840
ttgagaaacc attatgaaga agagagtcca tatttcaatt tccaagagct gaggcaattc  900
taactttttt gctatccagc tatttttatt tgtttgtgca tttgggggga attcatctct  960
ctttaatata aagttggatg cggaacccaa attacgtgta ctacaattta aagcaaagga  1020
gtagaaagac agagctggga tgtttctgtc acatcagctc cactttcagt gaaagcatca  1080
cttgggatta atatggggat gcagcattat gatgtgggtc aaggaattaa gttagggaat  1140
ggcacagccc aaagaaggaa aaggcaggga gcgagggaga agactatatt gtacacacct  1200
tatatttacg tatgagacgt ttatagccga aatgatcttt tcaagttaaa ttttatgcct  1260
tttatttctt aaacaaatgt atgattacat caaggcttca aaaatactca catggctatg  1320
ttttagccag tgatgctaaa ggttgtattg catatataca tatatatata tatatatata  1380
tatatatata tatatatata tatatatata tatattttaa tttgatagta ttgtgcatag  1440
agccacgtat gtttttgtgt atttgttaat ggtttgaata taaacactat atggcagtgt  1500
ctttccacct tgggtcccag ggaagttttg tggaggagct caggacacta atacaccagg  1560
tagaacacaa ggtcatttgc taactagctt ggaaactgga tgaggtcata gcagtgcttg  1620
attgcgtgga attgtgctga gttggtgttg acatgtgctt tggggctttt acaccagttc  1680
ctttcaatgg tttgcaagga agccacagct ggtggtatct gagttgactt gacagaacac  1740
tgtcttgaag acaatggctt actccaggag acccacaggt atgaccttct aggaagctcc  1800
agttcgatgg gcccaattct tacaaacatg tggttaatgc catggacaga agaaggcagc  1860
aggtggcaga atggggtgca tgaaggtttc tgaaaattaa cactgcttgt gtttttaact  1920
caatattttc catgaaaatg caacaacatg tataaatatt ttaattaaat aaaaatctgt  1980
ggtggtcgtt ttccgga                                                  1997

SEQ ID NO: 10           moltype = AA  length = 223
FEATURE                 Location/Qualifiers
source                  1..223
                        mol_type = protein
                        organism = Homo sapiens
SEQUENCE: 10
MACLGFQRHK AQLNLATRTW PCTLLFFLLF IPVFCKAMHV AQPAVVLASS RGIASFVCEY  60
ASPGKATEVR VTVLRQADSQ VTEVCAATYM MGNELTFLDD SICTGTSSGN QVNLTIQGLR  120
AMDTGLYICK VELMYPPPYY LGIGNGTQIY VIDPEPCPDS DFLLWILAAV SSGLFFYSFL  180
LTAVSLSKML KKRSPLTTGV YVKMPPTEPE CEKQFQPYFI PIN                     223

SEQ ID NO: 11           moltype = DNA  length = 1933
FEATURE                 Location/Qualifiers
source                  1..1933
                        mol_type = genomic DNA
                        organism = Mus musculus
SEQUENCE: 11
ctacacatat gtagcacgta ccttggatca aagctgtcta tataaagtcc ccgagtctgt  60
gtgggttcaa acacatctca aggcttctgg atcctgttgg gttttactct gctccctgag  120
gacctcagca catttgcccc ccagccatgg cttgtcttgg actccggagg tacaaagctc  180
aactgcagct gccttctagg acttggcctt ttgtagccct gctcactctt cttttcatcc  240
cagtcttctc tgaagccata caggtgaccc aaccttcagt ggtgttggct agcagccatg  300
gtgtcgccag ctttccatgt gaatattcac catcacacaa cactgatgag gtccgggtga  360
ctgtgctgcg gcagacaaat gaccaaatga ctgaggtctg tgccacgaca ttcacagaga  420
agaatacagt gggcttccta gattacccct tctgcagtgg tacctttaat gaaagcagag  480
tgaacctcac catccaagga ctgagagctg ttgacacggg actgtacctc tgcaaggtgg  540
aactcatgta cccaccgcca tactttgtgg gcatgggcaa cgggacgcag atttatgtca  600
ttgatccaga accatgcccg gattctgact tcctcctttg gatccttgtc gcagttagct  660
tggggttgtt tttttacagt ttcctggtca ctgctgtttc tttgagcaag atgctaaaga  720
aaagaagtcc tcttacaaca ggggtctatg tgaaaatgcc cccaacagag ccagaatgtg  780
aaaagcaatt tcagccttat tttattccca tcaactgaaa ggccgtttat gaagaagaag  840
gagcatactt cagtctctaa aagctgaggc aatttcaact ttccttttct ctccagctat  900
ttttacctgt ttgtatattt taaggagagt atgcctctct ttaatagaaa gctggatgca  960
aaattccaat taagcatact acaatttaaa gctaaggagc atgaacagag agctgggata  1020
tttctgttgt gtcagaacca ttttactaaa agcatcactt ggaagcagca taaggatata  1080
gcattatggt gtggggtcaa gggaacatta gggaatggca cagcccaaag aaaggaaggg  1140
ggtgaaggaa gagattatat tgtacacatc ttgtatttac ctgagagatg tttatgactt  1200
aaataatttt taaatttttc atgctgttat tttctttaac aatgtataat tacacgaagg  1260
tttaaacatt tattcacaga gctatgtgac atagccagtg gttccaaagg ttgtagtgtt  1320
ccaagatgta tttttaagta atattgtaca tgggtgtttc atgtgctgtt gtgtatttgc  1380
tggtggtttg aatataaaca ctatgtatca gtgtcgtccc acagtgggtc ctggggaggt  1440
ttggctgggg agcttaggac actaatccat caggttggac tcgaggtcct gcaccaactg  1500
gcttggaaac tagatgaggc tgtcacaggg ctcagttgca taaaccgatg gtgatggagt  1560
gtaaactggg tctttacact cattttattt tttgtttctg cttttgtttt cttcaatgat  1620
ttgcaaggaa accaaaagct ggcagtgttt gtatgaacct gacagaacac tgtcttcaag  1680
gaaatgcctc attcctgaga ccagtaggtt tgtttttttta ggaagttcca atactaggac  1740
cccctacaag tactatggct cctcgaaaac acaaagttaa tgccacagga agcagcagat  1800
ggtaggatgg gatgcacaag agttcctgaa aactaacact gttagtgttt tttttttaac  1860
tcaatatttt ccatgaaaat gcaaccacat gtataatatt tttaattaaa taaaagtttc  1920
ttgtgattgt ttt                                                      1933

SEQ ID NO: 12           moltype = AA  length = 223
FEATURE                 Location/Qualifiers
source                  1..223
                        mol_type = protein
                        organism = Mus musculus
```

-continued

```
SEQUENCE: 12
MACLGLRRYK AQLQLPSRTW PFVALLTLLF IPVFSEAIQV TQPSVVLASS HGVASFPCEY  60
SPSHNTDEVR VTVLRQTNDQ MTEVCATTFT EKNTVGFLDY PFCSGTFNES RVNLTIQGLR  120
AVDTGLYLCK VELMYPPPYF VGMGNGTQIY VIDPEPCPDS DFLLWILVAV SLGLFFYSFL  180
VTAVSLSKML KKRSPLTTGV YVKMPPTEPE CEKQFQPYFI PIN                    223

SEQ ID NO: 13          moltype = DNA  length = 1634
FEATURE                Location/Qualifiers
source                 1..1634
                       mol_type = genomic DNA
                       organism = Homo sapiens
SEQUENCE: 13
agtctctcgt catggaatac gcctctgacg cttcactgga ccccgaagcc ccgtggcctc  60
ccgcgccccg cgctcgcgcc tgccgcgtac tgccttgggc cctggtcgcg gggctgctgc  120
tgctgctgct gctcgctgcc gcctgcgccg tcttcctcgc ctgcccctgg gccgtgtccg  180
gggctcgcgc ctcgcccggc tccgcggcca gcccgagact ccgcgagggt cccgagcttt  240
cgccccgacga tcccgccggc ctcttggacc tgcggcaggg catgtttgcg cagctggtgg  300
cccaaaatgt tctgctgatc gatgggcccc tgagctggta cagtgaccca ggcctggcag  360
gcgtgtccct gacgggggc ctgagctaca aagaggacac gaaggagctg gtggtggcca  420
aggctggagt ctactatgtc ttctttcaac tagagctgcg gcgcgtggtg gccggcgagg  480
gctcaggctc cgtttcactt gcgctgcacc tgcagccact gcgctctgct gctggggccg  540
ccgccctggc tttgaccgtg gacctgccac ccgcctcctc cgaggctcgg aactcggcct  600
tcggtttcca gggccgcttg ctgcacctga gtgccggcca gcgcctgggc gtccatcttc  660
acactgaggc cagggcacgc catgcctggc agcttaccca gggcgccaca gtcttgggac  720
tcttccgggt gacccccgaa atcccagccg gactcccttc accgaggtcg gaataacgtc  780
cagcctgggt gcagcccacc tggacagagt ccgaatccta ctccatcctt catggagacc  840
cctggtgctg ggtccctgct gctttctcta cctcaagggg cttggcaggg gtccctgctg  900
ctgacctccc cttgaggacc ctcctcaccc actccttccc caagttggac cttgatattt  960
attctgagcc tgagctcaga taatatatta tatatattat atatatatat atatttctat  1020
ttaaagagga tcctgagttt gtgaatggac ttttttagag gagttgtttt gggggggggg  1080
gggtcttcga cattgccgag gctggtcttg aactcctgga cttagacgat cctcctgcct  1140
cagcctccca agcaactggg attcatcctt tctattaatt cattgtactt atttgcttat  1200
ttgtgtgtat tgagcatctg taatgtgcca gcattgtgcc caggctaggg ggctatagaa  1260
acatctagaa atagactgaa agaaaatctg agttatggta atacgtgagg aatttaaaga  1320
ctcatcccca gcctccacct cctgtgtgat acttgggggc tagcttttt ctttctttct  1380
ttttttgag atggtcttgt tctgtcaacc aggctagaat gcagcggtgc aatcatgagt  1440
caatgcagcc tccagcctcg acctcccgag gctcaggtga tcctcccatc tcagcctctc  1500
gagtagctgg gaccacagtt gtgtgccacc acacttggct aactttttaa tttttttgcg  1560
gagacggtat tgctatgttg ccaaggttgt ttacatgcca gtacaattta taataaacac  1620
tcatttttcc tccc                                                    1634

SEQ ID NO: 14          moltype = AA  length = 254
FEATURE                Location/Qualifiers
source                 1..254
                       mol_type = protein
                       organism = Homo sapiens
SEQUENCE: 14
MEYASDASLD PEAPWPPAPR ARACRVLPWA LVAGLLLLLL LAAACAVFLA CPWAVSGARA  60
SPGSAASPRL REGPELSPDD PAGLLDLRQG MFAQLVAQNV LLIDGPLSWY SDPGLAGVSL  120
TGGLSYKEDT KELVVAKAGV YYVFFQLELR RVVAGEGSGS VSLALHLQPL RSAAGAAALA  180
LTVDLPPASS EARNSAFGFQ GRLLHLSAGQ RLGVHLHTEA RARHAWQLTQ GATVLGLFRV  240
TPEIPAGLPS PRSE                                                    254

SEQ ID NO: 15          moltype = DNA  length = 1230
FEATURE                Location/Qualifiers
source                 1..1230
                       mol_type = genomic DNA
                       organism = Mus musculus
SEQUENCE: 15
ataaagcacg ggcactggcg ggagacgtgc actgaccgac cgtggtaatg gaccagcaca  60
cacttgatgt ggaggatacc gcggatgcca gacatccagc aggtacttcg tgcccctcgg  120
atgcggcgct cctcagagat accgggctcc tcgcggacgc tgcgctcctc tcagatactg  180
tgcgccccac aaatgccgcg ctccccacgg atgctgccta ccctgcggtt aatgttcggg  240
atcgcgaggc cgcgtggccg cctgcactga acttctgttc ccgccaccca aagctctatg  300
gcctagtcgc tttggttttg ctgcttctga tcgccgcctg tgttcctatc ttcacccgca  360
ccgagcctcg gccagcgctc acaatcacca cctcgcccaa cctgggtacc cgagagaata  420
atgcagacca ggtcacccct gtttcccaca ttggctgccc caacactaca caacagggct  480
ctcctgtgtt cgccaagcta ctggctaaaa accaagcatc gttgtgcaat acaactctga  540
actggcacag ccaagatgga gctgggagct catacctatc tcaaggtctg aggtacgaag  600
aagacaaaaa ggagttggtg gtagacagtc ccgggctcta ctacgtattt ttggaactga  660
agctcagtcc aacattcaca aacacaggcc acaaggtgca gggctgggtc tctcttgttt  720
tgcaagcaaa gcctcaggta gatgactttg acaacttggc cctgacagtg gaactgttcc  780
cttgctccat ggagaacaag ttagtggacc gttcctggag tcaactgttg ctcctgaagg  840
ctggccaccg cctcagtgtg ggtctgaggg cttatctgca tggagcccag gatgcataca  900
gagactggga gctgtcttat cccaacacca ccagctttgg actctttctt gtgaaacccg  960
acaacccatg ggaatgagaa ctatccttct tgtgactcct agttgctaag tcctcaagct  1020
gctatgtttt atggggtctg agcaggggtc ccttccatga ctttctcttg tctttaactg  1080
gacttggtat ttattctgag catagctcag acaagacttt atataattca ctagatagca  1140
ttagtaaact gctgggcagc tgctagataa aaaaaaattt ctaaatcaaa gtttatattt  1200
```

```
atattaatat ataaaaataa atgtgtttgt                                   1230

SEQ ID NO: 16          moltype = AA  length = 309
FEATURE                Location/Qualifiers
source                 1..309
                       mol_type = protein
                       organism = Mus musculus
SEQUENCE: 16
MDQHTLDVED TADARHPAGT SCPSDAALLR DTGLLADAAL LSDTVRPTNA ALPTDAAYPA  60
VNVRDREAAW PPALNFCSRH PKLYGLVALV LLLLIAACVP IFTRTEPRPA LTITTSPNLG  120
TRENNADQVT PVSHIGCPNT TQQGSPVFAK LLAKNQASLC NTTLNWHSQD GAGSSYLSQG  180
LRYEEDKKEL VVDSPGLYYV FLELKLSPTF TNTGHKVQGW VSLVLQAKPQ VDDFDNLALT  240
VELFPCSMEN KLVDRSWSQL LLLKAGHRLS VGLRAYLHGA QDAYRDWELS YPNTTSFGLF  300
LVKPDNPWE                                                          309

SEQ ID NO: 17          moltype = DNA  length = 1702
FEATURE                Location/Qualifiers
source                 1..1702
                       mol_type = genomic DNA
                       organism = Homo sapiens
SEQUENCE: 17
ataccggccc ttcccctcgg ctttgcctgg acagctcctg cctcccgcag ggcccacctg  60
tgtcccccag cgccgctcca cccagcaggc ctgagcccct ctctgctgcc agacacccc   120
tgctgcccac tctcctgctg ctcgggttct gaggcacagc ttgtcacacc gaggcggatt  180
ctctttctct ttctctttct cttctggccc acagccgcag caatggcgct gagttcctct  240
gctggagttc atcctgctag ctgggttccc gagctgccgg tctgagcctg aggcatggag  300
cctcctggag actgggggcc tcctccctgg agatccaccc ccaaaaccga cgtcttgagg  360
ctggtgctgt atctcacctt cctgggagcc ccctgctacg ccccagctct gccgtcctgc  420
aaggaggacg agtacccagt gggctccgag tgctgcccca agtgcagtcc aggttatcgt  480
gtgaaggagg cctgcgggga gctgacgggc acagtgtgtg aaccctgccc tccaggcacc  540
tacattgccc acctcaatgg cctaagcaag tgtctgcagt gccaaatgtg tgacccagcc  600
atgggcctgc gcgcgagccg gaactgctcc aggacagaga acgccgtgtg tggctgcagc  660
ccaggccact tctgcatcgt ccaggacggg gaccactgcg ccgcgtgccg cgcttacgcc  720
acctccagcc cgggccagag ggtgcagaag ggaggcaccg agagtcagga caccctgtgt  780
cagaactgcc ccccggggac cttctctccc aatgggaccc tggaggaatg tcagcaccag  840
accaagtgca gctggctggt gacgaaggcc ggagctggga ccagcagctc ccactgggta  900
tggtggtttc tctcagggag cctcgtcatc gtcattgttt gctccacagt tggcctaatc  960
atatgtgtga aaagaagaaa gccaaggggt gatgtagtca aggtgatcgt ctccgtccag  1020
cggaaaagac aggaggcaga aggtgaggcc acagtcattg aggccctgca ggcccctccg  1080
gacgtcacca cggtggccgt ggaggagaca ataccctcat tcacggggag gagcccaaac  1140
cactgaccca cagactctgc accccgacgc cagagatacc tggagcgacg gctgctgaaa  1200
gaggctgtcc acctggcgga accaccggag cccggaggct tgggggctcc gccctgggct  1260
ggcttccgtc tcctccagtg gagggagagg tggggcccct gctggggtag agctggggac  1320
gccacgtgcc attcccatgg gccagtgagg gcctggggcc tctgttctgc tgtggcctga  1380
gctccccaga gtcctgagga ggagcgccag ttgcccctcg ctcacagacc acacacccag  1440
ccctcctggg ccagcccaga gggcccttca gaccccagct gtctgcgcgt ctgactcttg  1500
tggcctcagc aggacaggcc ccgggcactg cctcacagcc aaggctggac tgggttggct  1560
gcagtgtggt gtttagtgga taccacatcg gaagtgattt tctaaattgg atttgaattc  1620
ggctcctgtt ttctatttgt catgaaacag tgtatttggg gagatgctgt gggaggatgt  1680
aaatatcttg tttctcctca aa                                           1702

SEQ ID NO: 18          moltype = AA  length = 283
FEATURE                Location/Qualifiers
source                 1..283
                       mol_type = protein
                       organism = Homo sapiens
SEQUENCE: 18
MEPPGDWGPP PWRSTPKTDV LRLVLYLTFL GAPCYAPALP SCKEDEYPVG SECCPKCSPG  60
YRVKEACGEL TGTVCEPCPP GTYIAHLNGL SKCLQCQMCD PAMGLRASRN CSRTENAVCG  120
CSPGHFCIVQ DGDHCAACRA YATSSPGQRV QKGGTESQDT LCQNCPPGTF SPNGTLEECQ  180
HQTKCSWLVT KAGAGTSSSH WVWWFLSGSL VIVIVCSTVG LIICVKRRKP RGDVVKVIVS  240
VQRKRQEAEG EATVIEALQA PPDVTTVAVE ETIPSFTGRS PNH                    283

SEQ ID NO: 19          moltype = DNA  length = 893
FEATURE                Location/Qualifiers
source                 1..893
                       mol_type = genomic DNA
                       organism = Mus musculus
SEQUENCE: 19
gctcttggcc tgaagtttct tgatcaagaa aatggaacct ctcccaggat gggggtcggc  60
accctggagc caggccccta cagacaacac cttcaggctg gtgccttgtg tcttcctttt  120
gaacttgctg cagcgcatct ctgcccagcc ctcatgcaga caggaggagt tccttgtggg  180
agacgagtgc tgccccatgt gcaacccagg ttaccatgtg aagcaggtct gcagtgagca  240
tacaggcaca gtgtgtgccc cctgtccccc acagacatat accgcccatg caaatggcct  300
gagcaagtgt ctgccctgcg gagtctgtga tccagacatg ggcctgctga cctggcagga  360
gtgctccagc tggaaggaca ctgtgtgcag atgcatccca ggctacttct gtgagaacca  420
ggatgggagc cactgttcca catgcttgca gcacaccacc tgccctccag ggcagagggt  480
agagaagaga gggactcacg accaggacac tgtatgtgct gactgcctaa cagggacctt  540
ctcacttgga gggactcagg aggaatgcct gccctggacc aactgcagtg catttcaaca  600
```

-continued

```
ggaagtaaga cgtgggacca acagcacaga caccacctgc tcctcccagg tcgtctacta  660
cgttgtgtcc atccttttgc cacttgtgat agtgggagct gggatagctg gattcctcat  720
ctgcacgcga agacacctgc acaccagctc agtggccaag gagctggagc ctttccagga  780
acaacaggag aacaccatca ggtttccagt caccgaggtt gggtttgctg agaccgagga  840
ggagacagcc tccaactgaa caaattctgg gtgacaagac accgaggaga cgt         893

SEQ ID NO: 20           moltype = AA  length = 275
FEATURE                 Location/Qualifiers
source                  1..275
                        mol_type = protein
                        organism = Mus musculus
SEQUENCE: 20
MEPLPGWGSA PWSQAPTDNT FRLVPCVFLL NLLQRISAQP SCRQEEFLVG DECCPMCNPG  60
YHVKQVCSEH TGTVCAPCPP QTYTAHANGL SKCLPCGVCD PDMGLLTWQE CSSWKDTVCR  120
CIPGYFCENQ DGSHCSTCLQ HTTCPPGQRV EKRGTHDQDT VCADCLTGTF SLGGTQEECL  180
PWTNCSAFQQ EVRRGTNSTD TTCSSQVVYY VVSILLPLVI VGAGIAGFLI CTRRHLHTSS  240
VAKELEPFQE QQENTIRFPV TEVGFAETEE ETASN                            275

SEQ ID NO: 21           moltype = DNA  length = 1237
FEATURE                 Location/Qualifiers
source                  1..1237
                        mol_type = genomic DNA
                        organism = Homo sapiens
SEQUENCE: 21
aatgcagtta caggatcctg ggaagcagag tgtctggatg gaacctgagc tgggtctctg  60
actcacttct gactttagtt ttttcaaggg ggaacatggc aaaggtgttc agtttcatcc  120
ttgttaccac cgctctgaca atgggcaggg aaatttcggc gctcgaggac tgtgcccagg  180
agcagatgcg gctcagagcc caggtgcgcc tgcttgagac ccgggtcaaa cagcaacagg  240
tcaagatcaa gcagcttttg caggagaatg aagtccagtt ccttgataaa ggagatgaga  300
atactgtcat tgatcttgga agcaagaggc agtatgcaga ttgttcagag attttcaatg  360
atgggtataa gctcagtgga ttttacaaaa tcaaacctct ccagagccca gcagaatttt  420
ctgtttattg tgacatgtcc gatggaggag gatggactgt aattcagaga cgatctgatg  480
gcagtgaaaa ctttaacaga ggatggaaag actatgaaaa tggctttgga aattttgtcc  540
aaaaacatgg tgaatattgg ctgggcaata aaaatcttca cttcttgacc actcaagaag  600
actacacttt aaaaatcgac cttgcagatt ttgaaaaaaa tagccgttat gcacaatata  660
agaatttcaa agttggagat gaaaagaatt tctacgagtt gaatattggg gaatattctg  720
gaacagctgg agattccctt gcggggaatt ttcatcctga ggtgcagtgg tgggctagtc  780
accaaagaat gaaattcagc acgtgggaca gagatcatga caactatgaa gggaactgcg  840
cagaagaaga tcagtctggc tggtggttta acaggtgtca ctctgcaaac ctgaatggtg  900
tatactacag cggcccctac acggctaaaa cagacaatgg gattgtctgg tacacctggc  960
atgggtggtg gtattctctg aaatctgtgg ttatgaaaat taggccaaat gattttattc  1020
caaatgtaat ttaattgctg ctgttgggct ttcgtttctg caattcagct ttgtttaaag  1080
tgatttgaaa aatactcatt ctgaacatat ccatgcgcaa tcatgataac tgttgtgagt  1140
agtgcttttc attcttctca cttgcctttg ttacttaatg tgctttcagt acagcagata  1200
tgcaatattc accaaataaa tgtagactgt gttaata                          1237

SEQ ID NO: 22           moltype = AA  length = 312
FEATURE                 Location/Qualifiers
source                  1..312
                        mol_type = protein
                        organism = Homo sapiens
SEQUENCE: 22
MAKVFSFILV TTALTMGREI SALEDCAQEQ MRLRAQVRLL ETRVKQQQVK IKQLLQENEV  60
QFLDKGDENT VIDLGSKRQY ADCSEIFNDG YKLSGFYKIK PLQSPAEFSV YCDMSDGGGW  120
TVIQRRSDGS ENFNRGWKDY ENGFGNFVQK HGEYWLGNKN LHFLTTQEDY TLKIDLADFE  180
KNSRYAQYKN FKVGDEKNFY ELNIGEYSGT AGDSLAGNFH PEVQWWASHQ RMKFSTWDRD  240
HDNYEGNCAE EDQSGWWFNR CHSANLNGVY YSGPYTAKTD NGIVWYTWHG WWYSLKSVVM  300
KIRPNDFIPN VI                                                     312

SEQ ID NO: 23           moltype = DNA  length = 1120
FEATURE                 Location/Qualifiers
source                  1..1120
                        mol_type = genomic DNA
                        organism = Mus musculus
SEQUENCE: 23
gttagaagtt cctgggaggc tctgtgtgga tggactgagc ctagctaagt cctgattcat  60
tttgacttga gttctctcag tgggaagaat gggaaagatt tacagcttcg tcctggtcgc  120
cattgctctg atgatgggaa gggaaggttg ggccctcgag agtgagaact gcttgcggga  180
gcaggtgagg ctcagggctc aggtgcacca gcttgagacc cgggtcaaac aacaacagac  240
catgattgca cagctcttgc atgagaagga agtccagttt ctggataaag gatcggagaa  300
cagtttcatt gaccttggag gcaagaagca gtatgcagat tgttcagaga tttacaatga  360
cggatttaag cagagtggat tttacaaaat caaacctctt cagagcctgg cagaattctc  420
tgtttattgt gacatgtctg atggaggggg atggactgta attcagagac gatctgatgg  480
cagtgagaac tttaacaggg gttggaatga ctatgaaaat ggctttggaa actttgtcca  540
aaacaatggc gaatactggc tgggtaacaa aaacattaac ttgctaacta ttcaaggaga  600
ctacacttta aaaatcgacc tgacagattt tgagaaaaac agcagcttcg cacaatacca  660
aagttttaaa gttggtgata aaaagtcttt ttatgaacta aatattggag aatattctgg  720
cacagctgga gattccctgt caggaacttt tcatcctgaa gtacagtggt gggctagtca  780
ccaaaggatg aagttcagca cgtgggacag agataacgac aattaccaag gaaactgtgc  840
```

```
tgaggaagag cagtctggct ggtggtttaa caggtgtcac tctgcaaacc tgaacggtgt  900
ttactaccgt ggttcctaca gggcagaaac ggataatggt gttgtgtggt acacctggca  960
tgggtggtgg tattccttga aatctgtggt tatgaaaatt aggccaagtg attttattcc  1020
aaatattatt tagttgccct cattgggatc tcctttctgt aattcatctt ggtttacttg  1080
aaaataaata tttgaaaaag atataattct gaataacaca                        1120

SEQ ID NO: 24          moltype = AA  length = 314
FEATURE                Location/Qualifiers
source                 1..314
                       mol_type = protein
                       organism = Mus musculus
SEQUENCE: 24
MGKIYSFVLV AIALMMGREG WALESENCLR EQVRLRAQVH QLETRVKQQQ TMIAQLLHEK  60
EVQFLDKGSE NSFIDLGGKK QYADCSEIYN DGFKQSGFYK IKPLQSLAEF SVYCDMSDGG  120
GWTVIQRRSD GSENFNRGWN DYENGFGNFV QNNGEYWLGN KNINLLTIQG DYTLKIDLTD  180
FEKNSSFAQY QSFKVGDKKS FYELNIGEYS GTAGDSLSGT FHPEVQWWAS HQRMKFSTWD  240
RDNDNYQGNC AEEEQSGWWF NRCHSANLNG VYYRGSYRAE TDNGVVWYTW HGWWYSLKSV  300
VMKIRPSDFI PNII                                                    314

SEQ ID NO: 25          moltype = DNA  length = 2129
FEATURE                Location/Qualifiers
source                 1..2129
                       mol_type = genomic DNA
                       organism = Homo sapiens
SEQUENCE: 25
agagctccag gcgcacatcc gcagtcagcc acctcgcgcg cgcctccagg agcaaggatg  60
gagaggctgg tgatcaggat gcccttctct catctgtcta cctacagcct ggtttgggtc  120
atggcagcag tggtgctgtg cacagcacaa gtgcaagtgg tgacccagga tgaaagagag  180
cagctgtaca cacctgcttc cttaaaatgc tctctgcaaa atgcccagga agccctcatt  240
gtgacatggc agaaaaagaa agctgtaagc ccagaaaaca tggtcacctt cagcgagaac  300
catggggtgg tgatccagcc tgcctataag gacaagataa acattaccca gctgggactc  360
caaaactcaa ccatcacctt ctggaatatc accctggagg atgaagggtg ttacatgtgt  420
ctcttcaata cctttggttt tgggaagatc tcaggaacgg cctgcctcac cgtctatgta  480
cagcccatag tatcccttca ctacaaattc tctgaagacc acctaaatat cacttgctct  540
gccactgccc gcccagcccc catggtcttc tggaaggtcc ctcggtcagg gattgaaaat  600
agtacagtga ctctgtctca cccaaatggg accacgtctg ttaccagcat cctccatatc  660
aaagacccta agaatcaggt ggggaaggag gtgatctgcc aggtgctgca cctggggact  720
gtgaccgact ttaagcaaac cgtcaacaaa ggctattggt tttcagttcc gctattgcta  780
agcattgttt ccctggtaat tcttctcgtc ctaatctcaa tcttactgta ctggaaacgt  840
caccggaatc aggaccgaga gccctaaata agtcacacag caccctgaaa gtgattccct  900
ggtctacttg aatttgacac aagagaaaag caggaggaaa aggggccatt ctccaaagga  960
cctgaaagag caaaagaggt gggagcgaaa gccttaagga tcccacgact ttttactgcc  1020
atctgagcta ctcagtgttt gaatcccaag aggaagtcag tttacctctc aggtctgttg  1080
taggacttga ttttgtaaag caatgccatg ttatgtggtt gaaagggcac tggacttagt  1140
tagtatcagg agcactgagc tcacagactg acttgggctc ctactggtgg ggacctctgt  1200
tagtcacttt acctcatcca aagtataaag gaattggacc aaataattta ccacatagct  1260
ctaaaactta atttaaaatg taattccaga aaaaaaaagg gaataagcaa agggggaaga  1320
attgaaagag agagagaaga aagaatacag agagcttacc ttttgccttt ctgttgatgt  1380
tacatctctt cttcctatgt tcttaggtct atgagtctgt ttccccatca tttggtatct  1440
agtccagttc ctgcttactg ctttgctaat agctggcctt gctagaatcc ttggtttcac  1500
tgctgttctt catgtgcttc tatgagattt actccaacac aaataggact gaatttattg  1560
tgaagtaaca ttggcaatct taacttattc atttaactta tttttatagc tagataaata  1620
ttgttagtct tagacaatag ctcacatttt ttgagaagca tgccctccct gtccatttgt  1680
cttataacat gacccagccc tattttacgt cattctaaat tcagcctcat ataatgaaaa  1740
tacattatga aaacagatgt ttaggagatt tcctgtatag cagtcagcca attcatatgc  1800
tttgtctctg ctggcttctt tttccatgcg ttaacttttc ccaatagcag aggaggcaaa  1860
tatgagcata caatcccttt gttctaaaga tattgttcca gctagtggaa tgatgttgaa  1920
tctttaataa ccataattag ttgctttttc agtatcttct gctttgtctg tgtctatcca  1980
gtggcctagg aattaaagtg taagttgttt tcgctgttaa attggatatt tatatatata  2040
tatagcaaga ttttcatgtg ttatttaatt ctgtattgtt tcttatattt gtagtaaaat  2100
attgaacaat taaaagtgtt gactccaaa                                    2129

SEQ ID NO: 26          moltype = AA  length = 269
FEATURE                Location/Qualifiers
source                 1..269
                       mol_type = protein
                       organism = Homo sapiens
SEQUENCE: 26
MERLVIRMPF SHLSTYSLVW VMAAVVLCTA QVQVVTQDER EQLYTPASLK CSLQNAQEAL  60
IVTWQKKKAV SPENMVTFSE NHGVVIQPAY KDKINITQLG LQNSTITFWN ITLEDEGCYM  120
CLFNTFGFGK ISGTACLTVY VQPIVSLHYK FSEDHLNITC SATARPAPMV FWKVPRSGIE  180
NSTVTLSHPN GTTSVTSILH IKDPKNQVGK EVICQVLHLG TVTDFKQTVN KGYWFSVPLL  240
LSIVSLVILL VLISILLYWK RHRNQDREP                                    269

SEQ ID NO: 27          moltype = DNA  length = 2363
FEATURE                Location/Qualifiers
source                 1..2363
                       mol_type = genomic DNA
                       organism = Mus musculus
```

SEQUENCE: 27
gggcgtggtt ggttggtcgt ctcttcctcc acactagagg agctgtagag tctgcctgtg 60
cagtggaggg ggctctctct acggcgaata gtagtgtccc tgctcacagg tgttgcggag 120
atatcctcca tcgtggaaga gctcagaccc cgagaagctg gtgtctagct gcggcccaga 180
gcaaggatgg gcagtctggt attcaggaga cctttctgcc atctctccac ctacagcctg 240
atttggggca tggcagcagt agcgctgagc acagctcaag tggaagtggt gacccaggat 300
gaaagaaagg cgctgcacac aactgcatcc ttacgatgtt ctctaaaaac atcccaggaa 360
cccttgattg tgacatggca gaaaaagaaa gccgtgagcc cagaaaacat ggtcacctac 420
agcaaaaccc atggggttgt aatccagcct gcctacaaag acaggataaa tgtcacagag 480
ctgggactct ggaactcaag catcaccttc tggaacacaa cattggaaga tgagggctgc 540
tacatgtgtc tcttcaacac gtttggttct cagaaggtct caggaacagc ttgccttacc 600
ctctatgtac agcccatagt acaccttcac tacaactatt ttgaagacca cctaaacatc 660
acttgctctg cgactgcccg tccagcccct gccatctcct ggaagggtac tgggacagga 720
attgagaata gtaccgagag tcacttccat tcaaatggga ctacatctgt caccagcatc 780
ctccgggtca aagaccccaa aactcaagtt gggaaggaag tgatctgcca ggttttatac 840
ctggggaatg tgattgacta caagcagagt ctggacaaag gattttggtt ttcagttcca 900
ctgttgctaa gcattgtttc tctggtaatt cttctgatct tgatctccat cttactatac 960
tggaaacgtc accgaaatca ggagcggggt gaatcatcac aggggatgca aagaatgaaa 1020
taagagctct aaagaaatta tacagaaccc tgaacgtgtt tccctggtct acttgaatct 1080
gatgtgaaag aaaagcagga gggaaaaggc cattctccat aggacctaag gagagcaaaa 1140
gaccagacac gagcctgtga gggatttgac tttttgctgt tgtcccaggt cctcggtgtt 1200
tgcattccaa gaggaagtcg agtgcctcgg gtctgttgta ggacttgatt tttttttttt 1260
ttgtagagca atgcagtgcc atgctgttag aaaggctcca gacttagaac caccagtgcc 1320
aagccagctc tcagaccgac tagggctccc atcggaggaa caaatcgtag tcaacttacc 1380
tcacagagct ctctggtcct tacacaaagt agaaaggagt gggaccagaa aattggccat 1440
gtctgaaatc tgatggaatt tttaggaaga aaactgaaga ataagcaaaa gaagaaagaa 1500
cacagaaggg tccaaagagc ttctgagagt accttttgcc tttctgttgg tgtcccagct 1560
ctggttttgt tcttaggtcc gccagtgtgt ttccctgttg tttgagtatc tagttgacta 1620
cctgctactg ttctgctgat ggttggcctt gctagaatcc ctgactcccc tgccgttctc 1680
tatgtgcttc tatgagggtt actatgatga aaatagagca gaagatagtg tgaagtaaca 1740
ttggcaactg taatgtgtcc atttaactta tttttatagc acttaggcaa tattgttagt 1800
cttagtgagt agttcacatc tttacaaaag catgctctcc ctatccattg ggcccacaat 1860
aacactctct ttgaggccat tctgaatcct gtctcgtgta atgataatat attatgaaaa 1920
cagatacttt aagaatttcc tgtacagcag tcagttgttt attctctctc tctctctctc 1980
tctctctctc cctcccccac cccagcttct ttttctgtga ctttgttttt cataaagaga 2040
aggcatctcc tgaatacaat cgctttgttc tgaagacatc gtgaactatt aattcttaac 2100
cctttgacaa aactagtgaa gttgttttct gtatcttttg cttcatctgt ctttatagag 2160
tgacctagga attcaagtgt aagttgtttc cattgttgaa ctggatattt atatacttgg 2220
tatgcttttc acgtgttatt taattctgta taatttccta tatttgtatt aaaatattga 2280
gcaattaaaa gtgtcaacta aatatttgat gtggcattcc cttgagaaat atagaaataa 2340
agaataaaaa aaaaaaaaaa aaa 2363

SEQ ID NO: 28 moltype = AA length = 278
FEATURE Location/Qualifiers
source 1..278
mol_type = protein
organism = Mus musculus
SEQUENCE: 28
MGSLVFRRPF CHLSTYSLIW GMAAVALSTA QVEVVTQDER KALHTTASLR CSLKTSQEPL 60
IVTWQKKKAV SPENMVTYSK THGVVIQPAY KDRINVTELG LWNSSITFWN TTLEDEGCYM 120
CLFNTFGSQK VSGTACLTLY VQPIVHLHYN YFEDHLNITC SATARPAPAI SWKGTGTGIE 180
NSTESHFHSN GTTSVTSILR VKDPKTQVGK EVICQVLYLG NVIDYKQSLD KGFWFSVPLL 240
LSIVSLVILL ILISILLYWK RHRNQERGES SQGMQRMK 278

SEQ ID NO: 29 moltype = DNA length = 1724
FEATURE Location/Qualifiers
source 1..1724
mol_type = genomic DNA
organism = Homo sapiens
SEQUENCE: 29
ctttgttaag tcgttccctc tacaaaggac ttcctagtgg gtgtgaaagg cagcggtggc 60
cacagaggcg gcggagagat ggccttcagc ggttcccagg ctccctacct gagtccagct 120
gtccccttt ctgggactat tcaaggaggt ctccaggacg gacttcagat cactgtcaat 180
gggaccgttc tcagctccag tggaaccagg tttgctgtga actttcagac tggcttcagt 240
ggaaatgaca ttgccttcca cttcaaccct cggtttgaag atggagggta cgtggtgtgc 300
aacacgaggc agaacggaag ctgggggccc gaggagagga agacacacat gcctttccag 360
aaggggatgc cctttgacct ctgcttcctg gtgcagagct cagatttcaa ggtgatggtg 420
aacgggatcc tcttcgtgca gtacttccac cgcgtgccct tccaccgtgt ggacaccatc 480
tccgtcaatg gctctgtgca gctgtcctac atcagcttcc agaacccccg cacagtccct 540
gttcagcctg ccttctccac ggtgccgttc tcccagcctg tctgtttccc acccaggccc 600
agggggcgca gacaaaaacc tcccggcgtg tggcctgcca acccggctcc cattacccag 660
acagtcatcc acacagtgca gagcgcccct ggacagatgt tctctactcc cgccatccca 720
cctatgatgt acccccaccc cgcctatccg atgcctttca tcaccaccat tctgggaggg 780
ctgtacccat ccaagtccat cctcctgtca ggcactgtcc tgcccagtgc tcagaggttc 840
cacatcaacc tgtgctctgg gaaccacatc gccttccacc tgaacccccg ttttgatgag 900
aatgctgtgg tccgcaacac ccagatcgac aactcctggg ggtctgagga gcgaagtctg 960
ccccgaaaaa tgcccttcgt ccgtggccag agcttctcag tgtggatctt gtgtgaagct 1020
cactgcctca aggtggccgt ggatggtcag cacctgtttg aatactacca tcgcctgagg 1080
aacctgccca ccatcaacag actggaagtg gggggcgaca tccagctgac ccatgtgcag 1140

```
acataggcgg cttcctggcc ctggggccgg gggctggggt gtggggcagt ctgggtcctc  1200
tcatcatccc cacttcccag gcccagcctt tccaaccctg cctgggatct gggctttaat  1260
gcagaggcca tgtccttgtc tggtcctgct tctggctaca gccaccctgg aacggagaag  1320
gcagctgacg gggattgcct tcctcagccg cagcagcacc tggggctcca gctgctggaa  1380
tcctaccatc ccaggaggca ggcacagcca gggagagggg aggagtgggc agtgaagatg  1440
aagccccatg ctcagtcccc tcccatcccc cacgcagctc caccccagtc ccaagccacc  1500
agctgtctgc tcctggtggg aggtggcctc ctcagcccct cctctctgac ctttaacctc  1560
actctcacct tgcaccgtgc accaaccctt caccccctcct ggaaagcagg cctgatggct  1620
tcccactggc ctccaccacc tgaccagagt gttctcttca gaggactggc tcctttccca  1680
gtgtccttaa aataaagaaa tgaaaatgct tgttggcaca ttca                   1724

SEQ ID NO: 30           moltype = AA  length = 355
FEATURE                 Location/Qualifiers
source                  1..355
                        mol_type = protein
                        organism = Homo sapiens
SEQUENCE: 30
MAFSGSQAPY LSPAVPFSGT IQGGLQDGLQ ITVNGTVLSS SGTRFAVNFQ TGFSGNDIAF  60
HFNPRFEDGG YVVCNTRQNG SWGPEERKTH MPFQKGMPFD LCFLVQSSDF KVMVNGILFV  120
QYFHRVPFHR VDTISVNGSV QLSYISFQNP RTVPVQPAFS TVPFSQPVCF PPRPRGRRQK  180
PPGVWPANPA PITQTVIHTV QSAPGQMFST PAIPPMMYPH PAYPMPFITT ILGGLYPSKS  240
ILLSGTVLPS AQRFHINLCS GNHIAFHLNP RFDENAVVRN TQIDNSWGSE ERSLPRKMPF  300
VRGQSFSVWI LCEAHCLKVA VDGQHLFEYY HRLRNLPTIN RLEVGGDIQL THVQT       355

SEQ ID NO: 31           moltype = DNA  length = 1586
FEATURE                 Location/Qualifiers
source                  1..1586
                        mol_type = genomic DNA
                        organism = Mus musculus
SEQUENCE: 31
gccaaatagc tgtggtttct gtttcctagc tcagccctgc cctgcgcaga gttctgtcgt  60
ccaccatcga gtgaggaaga gagcattggt tcccctgaga tagaagagat ggctctcttc  120
agtgcccagt ctccatacat taacccgatc atccccttta ctggaccaat ccaaggaggg  180
ctgcaggagg gacttcaggt gaccctccag gggactacca agagttttgc acaaaggttt  240
gtggtgaact ttcagaacag cttcaatgga aatgacattg ccttccactt caacccccgg  300
tttgaggaag gagggtatgt ggtttgcaac acgaagcaga acggacagtg gggtcctgag  360
gagagaaaga tgcagatgcc cttccagaag ggcatgccct ttgagctttg cttcctggtg  420
cagaggtcag agttcaaggt gatggtgaac aagaaattct ttgtgcagta ccaacaccgc  480
gtaccctacc acctcgtgga caccatcgct gtctccggct gcttgaagct gtcctttatc  540
accttccaga actctgcagc ccctgtccag catgtcttct ccacagtgca gttctctcag  600
ccagtccagt tcccacggac ccctaagggg cgcaaacaga aaactcagaa ctttcgtcct  660
gcccaccagg cacccatggc tcaaactacc atccatatgg ttcacagcac ccctggacag  720
atgttctcta ctcctggaat ccctcctgtg gtgtacccca ccccagccta taccatacct  780
ttctacaccc ccattccaaa tgggctttac ccgtccaagt ccatcatgat atcaggcaat  840
gtcttgccag atgctacgag gttccatatc aaccttcgct gtggaggtga cattgctttc  900
cacctgaacc cccgtttcaa tgagaatgct gttgtccgaa acactcagat caacaactcc  960
tgggggcagg aagagcgaag tctgcttggg aggatgccct tcagtcgagg ccagagcttc  1020
tcggtgtgga tcatatgtga aggtcactgc ttcaaggtag ctgtgaatgg tcaacacatg  1080
tgtgaatatt accaccgcct gaagaacttg caggatatca acactctaga agtggcgggt  1140
gatatccagc tgacccacgt gcagacatag gcaaggtctc tggcctaggg ataagggctg  1200
gagcactctg cctgtgtctt atctttcccc tgtctcagcc ctggcaccat cagaagagat  1260
catcacttat aggaattcca ggaaggtgaa attcccaatt gactccctcc acaaaggggg  1320
ttttctaggc tgtgtggcac atggctgtca gcccatagtc tgagccattg cccccaagct  1380
agctatatac tgagggaagt gaccctcctg ggtttgctca gatctctgat cgttcccccc  1440
tctgtggccc ttttctttca cccctccagg agagccaccc tgatatcatc ccactggcct  1500
ccaactgacc cacaatgtcc acagtaactt tcccccattc tcacccagta tccataaaat  1560
aaagaaataa tattgcttgt ctacac                                        1586

SEQ ID NO: 32           moltype = AA  length = 353
FEATURE                 Location/Qualifiers
source                  1..353
                        mol_type = protein
                        organism = Mus musculus
SEQUENCE: 32
MALFSAQSPY INPIIPFTGP IQGGLQEGLQ VTLQGTTKSF AQRFVVNFQN SFNGNDIAFH  60
FNPRFEEGGY VVCNTKQNGQ WGPEERKMQM PFQKGMPFEL CFLVQRSEFK VMVNKKFFVQ  120
YQHRVPYHLV DTIAVSGCLK LSFITFQNSA APVQHVFSTV QFSQPVQFPR TPKGRKQKTQ  180
NFRPAHQAPM AQTTIHMVHS TPGQMFSTPG IPPVVYPTPA YTIPFYTPIP NGLYPSKSIM  240
ISGNVLPDAT RFHINLRCGG DIAFHLNPRF NENAVVRNTQ INNSWGQEER SLLGRMPFSR  300
GQSFSVWIIC EGHCFKVAVN GQHMCEYYHR LKNLQDINTL EVAGDIQLTH VQT          353

SEQ ID NO: 33           moltype = DNA  length = 5792
FEATURE                 Location/Qualifiers
source                  1..5792
                        mol_type = genomic DNA
                        organism = Homo sapiens
SEQUENCE: 33
agtcacttgt ctggagcttg aagaagtggg tattcccctt cccaccccag gcactggagg  60
agcggccccc cggggattcc aggacctgag ctccgggagc tggactcgca gcgaccgcgg  120
```

-continued

```
cagagcgagc gggcgccggg aagcgaggag acgcccgcgg gaggcccagc tgctcggagc  180
aactggcatg gcccgagcca tggccgccgc gtggccgctg ctgctggtgg cgctactggt  240
gctgtcctgg ccaccccag gaaccgggga cgtcgtcgtg caggcgccca cccaggtgcc  300
cggcttcttg ggcgactccg tgacgctgcc ctgctaccta caggtgccca acatggaggt  360
gacgcatgtg tcacagctga cttgggcgcg gcatggtgaa tctggcagca tggccgtctt  420
ccaccaaacg cagggcccca gctattcgga gtccaaacgg ctggaattcg tggcagccag  480
actgggcgcg gagctgcgga atgcctcgct gaggatgttc gggttgcgcg tagaggatga  540
aggcaactac acctgcctgt tcgtcacgtt cccgcagggc agcaggagcg tggatatctg  600
gctccgagtg cttgccaagc cccagaacac agctgaggtt cagaaggtcc agctcactgg  660
agagccagtg cccatggccc gctgcgtctc cacagggggt cgcccgccag cccaaatcac  720
ctggcactca gacctgggcg ggatgcccaa tacgagccag gtgccagggt tcctgtctgg  780
cacagtcact gtcaccagcc tctggatatt ggtgccctca agccaggtgg acggcaagaa  840
tgtgacctgc aaggtggagc acgagagctt tgagaagcct cagctgctga ctgtgaacct  900
caccgtgtac taccccccag aggtatccat ctctggctat gataacaact ggtaccttgg  960
ccagaatgag gccaccctga cctgcgatgc tcgcagcaac ccagagccca caggctataa  1020
ttggagcacg accatgggtc ccctgccacc ctttgctgtg gcccagggcg cccagctcct  1080
gatccgtcct gtggacaaac caatcaacac aactttaatc tgcaacgtca ccaatgccct  1140
aggagctcgc caggcagaac tgaccgtcca ggtcaaagag ggacctccca gtgagcactc  1200
aggcatgtcc cgtaacgcca tcatcttcct ggttctggga atcctggttt ttctgatcct  1260
gctgggggatc gggatttatt tctattggtc caaatgttcc cgtgaggtcc tttggcactg  1320
tcatctgtgt ccctcgagta cagagcatgc cagcgcctca gctaatgggc atgtctccta  1380
ttcagctgtg agcagagaga acagctcttc ccaggatcca cagacagagg gcacaaggtg  1440
acagcgtcgg gactgagagg ggagagagac tggagctggc aaggacgtgg gcctccagag  1500
ttggacccga ccccaatgga tgaagacccc ctccaaagag accagcctcc ctccctgtgc  1560
cagacctcaa aacgacgggg gcaggtgcaa gttcataggt ctccaagacc accctccttt  1620
catttgctag aaggactcac tagactcagg aaagctgtta ggctcacagt tacagtttat  1680
tacagtaaaa ggacagagat taagatcagc aaagggagga ggtgcacagc acacgttcca  1740
cgacagatga ggcgacggct tccatctgcc ctctcccagt ggagccatat aggcagcacc  1800
tgattctcac agcaacatgt gacaacatgc aagaagtact gccaatactg ccaaccagag  1860
cagctcactc gagatctttg tgtccagagt tttttgtttg tcttgagaca gggtctggct  1920
ctgttggcag actagagtac agtggtgaga tcacagttca ttgcagcctt gacttctcaa  1980
cgccaagtca tcctcccacc tcagcctcct gagtagctat gactacaggt atgtgccacc  2040
acgtctggct aatcttttta ttatttgtaa agtcgaggtt tccctgtgtt gcccaggctg  2100
gtcttgaact cttggctcca agtgatactt ctgccttggc ctcccaaagt gctgaattaa  2160
gcagctcacc atccacacgg ctgacctcat acatcaagcc aataccgtgt ggcccaagac  2220
ccccaccata aatcacatca ttagcatgaa ccacccagag tggcccaaga ctccaagatc  2280
agctaccagg caggatattc caagggctta gagatgaatg cccaggagct gaggataaag  2340
ggcccgatct ttctttgggc aaggttaagc ctttactgca tagcagacca cacagaaggg  2400
tgtgggccac cagagaattt tggtaaaaat ttggcctctg gccttgagct tctaaatctc  2460
tgtatccgtc agatctctgt ggttacaaga aacagccact gaccctggtc accagaggct  2520
gcaattcagg ccgcaagcag ctgcctgggg ggtgtccaag gagcagagaa aactactaga  2580
tgtgaacttg aagaaggttg tcagctgcag ccactttctg ccagcatctg cagccacttt  2640
ctgccagcat ctgcagccag caagctggga ctggcaggaa ataacccaca aaagaagcaa  2700
atgcaatttc caacacaagg gggaagggat gcaggggggag gcagcgctgc agttgctcag  2760
gacacgctcc tataggacca agatggatgc gacccaagac ccaggaggcc cagctgctca  2820
gtgcaactga caagttaaaa aggtctatga tcttgagggc agacagcaga attcctctta  2880
taaagaaaac tgtttgggaa aatacgttga gggagagaag accttgggcc aagatgctaa  2940
atgggaatgc aaagcttgag ctgctctgca agagaaaata agcaggacag aggatttgct  3000
ctggacagag atggaagagc cgggaacaga gaagtgtggg gaagagatag gaaccagcag  3060
gatggcaggg gcaaagggct caagggtgag gaggccagtg ggaccccaca gagttgggga  3120
gataaaggaa cattggttgc tttggtggca cgtaagctcc ttgtctgtct ccagcaccca  3180
gaatctcatt aaagcttatt tattgtacct ccagcggctg tgtgcaatgg ggtcttttgt  3240
ggaaatcaag gagcagacag gtttcatgtg tactgtcacc acgtgggatg gaaccagagg  3300
catggaagca agacgctaaa tgaagagggc cataagggct gggattccca ggcaccttag  3360
gaacagcttg tcttttttttt tttcctctcc aaaaaaaatg tttaagggac ggtgtctcct  3420
gtcacccagg ctggagtgca atggcacgat catagctcat tgcagcctct aactccgggg  3480
ctcaagcaat cctcccacct cagcctacca agtagctgtg accacagctg cccctcacca  3540
tgctaagcta attttttttaa ttagatagta cataaacgtc ccaaaattag aagataaaaa  3600
gacatgaggg atccattcta atttgtgttt ggagtgtaat ggtccagctc cattcttctg  3660
cacatggata tccagtttta cacaacactg tgaatgtaat gaatgccact gaatcataca  3720
ctcaaaaata gctaaaatgg caaattgtct gttatctctt tttaaccacc atttttgaaa  3780
attaattata ccaaaaaacc attgaatagt gcactttatt tatttattta tttgtttatt  3840
tatttattta ttttagaaat aagagtctca ctttgttgcc caggctggag tgcagtggcg  3900
tgatcatggc tcattgcagc ctcgacctgc tgggctcggg ctatccttcc atctcagcct  3960
cccgagtagc tgggactata ggtgggcgcc accccacctg gctaaatctc tttttaactt  4020
ttgtagagat aggcatctcg ctatgttgcc taggctgggc tggaactcct gggctcaagt  4080
gctcctcctg ccttggcctc ccaaagcgct aggattacag atgtgagcca ccgcgcccac  4140
cctgaacctt actttttttg ctcagtttct ggtaattcag agaatgcctc ctgagttgtt  4200
ctacacccac ctcatattcc atgggaggc tgtacagggc tttttttaacg aggcctctaa  4260
ggacaggcat ttgtatcctt tccagccttt cactattaca atgttgtagt gaataacttt  4320
acacactgtc atttatttta ctttttttttt tttttatttt agagaaagga atcttgccat  4380
cttgcccagg ctggtctcaa attcctgggc ccaaacaatc ctcccgcctt ggcctcctaa  4440
agtactggga tttataggca taagccaccg tgcctggcca atgcacactg tcatttagct  4500
catgttaaca cctgagtgta ggacacactc ctggaggtgg aattgctggg ccaaagagta  4560
tgtttcttgt cattgtgata gatattgaca aatgaaccct cacagaagtt gtgctgagtt  4620
ctgttcccac cagcgacgta ggcgatgacc tttttctgga gggaggggggc atccttggag  4680
tccacagagc caggaatgga gagtgggccc agaattttgg tataggtgtt gtataaactt  4740
atagtaaggt taagaaaacc gcaactatcc ttatcagaga cttggcgggg ggcagggtat  4800
gatggagatc ataaggaggc taaaacactc cacaccctcc ctctgcattg ctcctgcacg  4860
```

```
ggagtcggga atcttttcag gttgatacga tctcaccttg aggagctgtg aggtcccaga  4920
agcctctggg ttgcagattg cttggggtga aaatgtctgt gctactgaaa tctaactttt  4980
tacaaaaaat tacgggctgg gcgcagtggc tcacgcctgt aatcccagca ctttgggagg  5040
ctgcagcggg tggatcactt gaggtaagga gttcaagacc agaccatagt gaaaccgtgt  5100
ctctacaaaa aaaattagcc aggtgtggtg gtgcatgctt gtaatcccag ctactcagaa  5160
ggctgaggtg ggagaatccc ttgaacccgg gaagtggagg ctggagtaaa ccatgatcga  5220
gttactgcac tccagcctgg gtgacaagag tgagactctg tctccaaaaa aaaaaaaaaa  5280
aaaaaaaaaa ctggattgcc tggctctact ccgggcacag catgcaggcc cagttctgct  5340
gctctgctgt ttgttctgct ttcctccaca tattggcatc accctctggt gccaagatgg  5400
ctgctgcatt ccaggcatca catccagact cagacccaga gaagctgccc atccctacct  5460
gggtgagcct ttgtaggaac gagaaaccgc atccagcagc agaaacctca cccagcagcg  5520
tcttttccgg tctcattcac cagcgccgcc caccgctcaa ccaatccctg gccaaaagaa  5580
tgggaccgcc tggaaggctg gaccaaacag gacctgccct ctggggctgg ggagaggccc  5640
agatgaaggc tgcaggacag gatggactcc tagacctctg ttaccagcag tgactacctc  5700
tgtctgggtg gttggaacat gtttgaattt tattctaagt actgtctaca agttctgcaa  5760
taaaccttga ctcttctttt aataatgcaa aa                               5792

SEQ ID NO: 34          moltype = AA  length = 417
FEATURE                Location/Qualifiers
source                 1..417
                       mol_type = protein
                       organism = Homo sapiens
SEQUENCE: 34
MARAMAAAWP LLLVALLVLS WPPPGTGDVV VQAPTQVPGF LGDSVTLPCY LQVPNMEVTH  60
VSQLTWARHG ESGSMAVFHQ TQGPSYSESK RLEFVAARLG AELRNASLRM FGLRVEDEGN  120
YTCLFVTFPQ GSRSVDIWLR VLAKPQNTAE VQKVQLTGEP VPMARCVSTG GRPPAQITWH  180
SDLGGMPNTS QVPGFLSGTV TVTSLWILVP SSQVDGKNVT CKVEHESFEK PQLLTVNLTV  240
YYPPEVSISG YDNNWYLGQN EATLTCDARS NPEPTGYNWS TTMGPLPPFA VAQGAQLLIR  300
PVDKPINTTL ICNVTNALGA RQAELTVQVK EGPPSEHSGM SRNAIIFLVL GILVFLILLG  360
IGIYFYWSKC SREVLWHCHL CPSSTEHASA SANGHVSYSA VSRENSSSQD PQTEGTR     417

SEQ ID NO: 35          moltype = DNA  length = 2902
FEATURE                Location/Qualifiers
source                 1..2902
                       mol_type = genomic DNA
                       organism = Mus musculus
SEQUENCE: 35
aggcggcacc cgcttagctg agattccagc acttgacttc agggtttcgg agagataagg  60
cgcttggccg ttactaactg gactacaaag agctggatcg gaccggaacc acatggctca  120
actcgcccga gccacccgct ccccgctgtc atggctgctg ctgctgttct gctatgcact  180
ccggaaagcg ggtggggata tacgtgtgct ggtgccctac aattcgacag gcgtcttggg  240
agggtcgacc accttgcact gtagtctgac ttctaatgag aatgtgacta tcactcaaat  300
aacctggatg aagaaggatt caggtggatc ccacgctctt gtggctgtct tccaccccaa  360
gaaggggccc aacatcaaag agccagagag ggtgaaattc ttggctgccc aacaggatct  420
gaggaacgca tctctggcca tctcgaactt aagtgtagaa gacgaaggca tctatgaatg  480
tcagattgcc acattcccca gaggcagtag aagcaccaat gcctggctga aggtgcaagc  540
ccgacctaag aacactgcag aggccctgga gccctctccc accttgatac tgcaggatgt  600
ggctaaatgc atctctgcca atggtcaccc tcctggacga atctcttggc cctcgaatgt  660
gaatggaagt caccgtgaaa tgaaggaacc agggtcccag ccgggcacca ccacagttac  720
cagctacctc tccatggtac cttctcgcca ggcagacggc aagaacatca cctgcacggt  780
ggagcatgaa agcttacagg agctggacca gctgctggtg accctttccc aaccctatcc  840
acctgaaaac gtgtccatct ctggctatga cggcaactgg tatgttggcc tcactaactt  900
gaccctgacc tgtgaagctc acagcaaacc agcgcctgac atggctggat ataactggag  960
cacgaacacg ggtgactttc ccaactctgt taagcgccag ggcaatatgc ttctaatctc  1020
caccgtagag gatggtctca ataacacggt cattgtgtgc gaagtcacca atgccctagg  1080
gtctgggcag ggccaagtgc acatcattgt taaagagaaa cctgagaata tgcagcaaaa  1140
tacaagatta cacctaggct acatctttct tatcgtcttt gtcctcgctg tagtcatcat  1200
catcgcagca ctatacacta tacgaagatg caggcatggt cgtgctctgc agtccaatcc  1260
ctcagagagg gagaacgtcc agtattcatc tgtgaacggc gactgtagac tgaacatgga  1320
gccaaacagc acaaggtgac ggtgctgggt agacagaact aaggaacttg aaggcatagc  1380
aactggaacc ctactctcat aaatgaagaa gcctccagag agactggctg ctcagtgtga  1440
tgagcatagc aagtttgggg ggtctcccag gatgctgccg aattccacgt tgtcaaaagg  1500
acccatggag gccagtgtgt tggctcactc ttgacatctc agcaagctgg gggggggggg  1560
gggagcataa agcaaggttg agtctagctt gggctataga gcaaagccct gtccatacac  1620
aaacaagcta aggggctttg agacggtcag aaactgaagt cttgctttgg gtaaggtaaa  1680
tcctctaccg catgtatgtg ctagacttga aagacttcca cacagacctc tttataagtt  1740
gactccattg gggctatccc ctcctctctg gacaaggtct ctgtatgtag ccaaggctag  1800
gctcaaactc acagagatat gtctgcttct acctccccag tgctagagtt gaaagtattt  1860
gtgccactgc acttttctag gtcttctttt aatgaagtaa agtatatatt tataaaaagc  1920
tatttagtta tatatatata tatttttgag actatttcat agagcccaag ctaacctcaa  1980
acttactatg tagccaagag tgatggtaaa ctaatttatt ttaatttatt tgtcttcaat  2040
tttaaccatc acccaacccc tgctcccttc catatcttct ttcaatccat ttcattgtct  2100
ttttcttccc agacactatt ctgacttacg tctccattac aaacatttta ttgaactaca  2160
taaaaatgtg tgaaccacaa aaaaaaaatg tatttgtcaa aattgtagtt gtctttctga  2220
ggctgacctg agttctctga taccattctc tccagttgta tccagtttcc tgtaaacaat  2280
gtgactttgt ttttctcagt agctaaaaca tcccaattat gtgagtgtac actttcttta  2340
ctcattcctc tgtgggccac cagctgggtt ggttccatat ctgagctatt gtgcatggaa  2400
ttgtctctgt ggtgggttta gtaaactccc aggaatgcct gtacatgttt gtagaggcca  2460
gaagaaggca caaaatcttg agccaggctt acatgcactt gtgagtagcc ccacataggt  2520
```

```
gctaagaacc cagttcaggt cctctgctgt gggatggtgg gctgtgcaca gaaagcctgg  2580
tcccggtcta gcaaaggtct ggaactccgg agccggtggg ctgtgattta caccagcatg  2640
ggatggaagg agttggacct cgcctcctgg gcacctggct cctgtcacat agctacagcc  2700
tcccacagcc cccctatagg gaggtatgca gcatcaatca catagtagct gcactaagcc  2760
ctcccacatg caaataaggt ttccccaaac tctcagtcca agccaatgaa aagtacctgc  2820
tgtcaaaccc taaatcatcc ccaaaactct gtaagtccta tcagggaata aaatgtgtgt  2880
gaaaactaaa aaaaaaaaaa aa                                          2902

SEQ ID NO: 36          moltype = AA  length = 408
FEATURE                Location/Qualifiers
source                 1..408
                       mol_type = protein
                       organism = Mus musculus
SEQUENCE: 36
MAQLARATRS PLSWLLLLFC YALRKAGGDI RVLVPYNSTG VLGGSTTLHC SLTSNENVTI  60
TQITWMKKDS GGSHALVAVF HPKKGPNIKE PERVKFLAAQ QDLRNASLAI SNLSVEDEGI  120
YECQIATFPR GSRSTNAWLK VQARPKNTAE ALEPSPTLIL QDVAKCISAN GHPPGRISWP  180
SNVNGSHREM KEPGSQPGTT TVTSYLSMVP SRQADGKNIT CTVEHESLQE LDQLLVTLSQ  240
PYPPENVSIS GYDGNWYVGL TNLTLTCEAH SKPAPDMAGY NWSTNTGDFP NSVKRQGNML  300
LISTVEDGLN NTVIVCEVTN ALGSGQGQVH IIVKEKPENM QQNTRLHLGY IFLIVFVLAV  360
VIIIAALYTI RRCRHGRALQ SNPSERENVQ YSSVNGDCRL NMEPNSTR                408

SEQ ID NO: 37          moltype = DNA  length = 1987
FEATURE                Location/Qualifiers
source                 1..1987
                       mol_type = genomic DNA
                       organism = Homo sapiens
SEQUENCE: 37
gtgacgtcag cgggttcgaa ccgccggagc tgagcgagag gccgggggtg ccgagccggg  60
cggggagagc tgggccggga gagcagaaca gggaggctag agcgcagcgg gaaccggccc  120
ggagccggag ccggagcccc acaggcacct actaaaccgc ccagccgatc ggcccccaca  180
gagtggcccg cgggcctccg gccgggccca gtcccctccc gggccctcca tggcccgggc  240
cgctgccctc ctgccgtcga gatcgccgcc gacgccgctg ctgtggccgc tgctgctgct  300
gctgctcctg gaaaccggag cccaggatgt gcgagttcaa gtgctacccg aggtgcgagg  360
ccagctcggg ggcaccgtgg agctgccgtg ccacctgctg ccacctgttc ctggactgta  420
catctccctg gtgacctggc agcgcccaga tgcacctgcg aaccaccaga atgtggccgc  480
cttccaccct aagatgggtc ccagcttccc cagcccgaag cctggcagcg agcggctgtc  540
cttcgtctct gccaagcaga gcactgggca agacacagag gcagagctcc aggacgccac  600
gctggccctc cacgggctca cggtggagga cgagggcaac tacacttgcg agtttgccac  660
cttccccaag ggtccgtcc gagggatgac ctggctcaga gtcatagcca agcccaagaa  720
ccaagctgag gcccagaagg tcacgttcag ccaggaccct acgacagtgg ccctctgcat  780
ctccaaagag ggccgcccac ctgcccggat ctcctggctc tcatccctgg actgggaagc  840
caaagagact caggtgtcag ggaccctggc cggaactgtc actgtcacca gccgcttcac  900
cttggtgccc tcgggccgag cagatggtgt cacggtcacc tgcaaagtgg agcatgagag  960
cttcgaggaa ccagccctga tacctgtgac cctctctgta cgctaccctc ctgaagtgtc  1020
catctccggc tatgatgaca actggtacct cggccgtact gatgccaccc tgagctgtga  1080
cgtccgcagc aacccagagc ccacgggcta tgactggagc acgacctcag gcaccttccc  1140
gacctccgca gtggcccagg gctcccagct ggtcatccac gcagtggaca gtctgttcaa  1200
taccaccttc gtctgcacag tcaccaatgc cgtgggcatg ggccgcgctg agcaggtcat  1260
ctttgtccga gaaaccccca gggcctcgcc ccgagatgtg ggcccgctgg tgtgggggc  1320
cgtggggggg acactgctgg tgctgctgct tctggctggg gggtccttgg ccttcatcct  1380
gctgagggtg aggaggagga ggaagagccc tggaggagca ggaggaggag ccagtggcga  1440
cgggggattc tacgatccga aagctcaggt gttgggaaat ggggacccccg tcttctggac  1500
accagtagtc cctggtccca tggaaccaga tggcaaggat gaggaggagg aggaggagga  1560
agagaaggca gagaaaggcc tcatgttgcc tccaccccca gcactcgagg atgacatgga  1620
gtcccagctg gacggctccc tcatctcacg gcgggcagtt tatgtgtgac ctggacacag  1680
acagagacag agccaggccc ggccctcccg cccccgacct gaccacgccg gcctagggtt  1740
ccagactggt tggacttgtt cgtctggacg acactggagt ggaacactgc ctcccacttt  1800
cttgggactt ggagggaggt ggaacagcac actggacttc tcccgtctct agggctgcat  1860
ggggagcccg gggagctgag tagtggggat ccagagagga cccccgcccc cagagacttg  1920
gttttggctc cagccttccc ctggccccgt gacactcagg agttaataaa tgccttggag  1980
gaaaaca                                                           1987

SEQ ID NO: 38          moltype = AA  length = 479
FEATURE                Location/Qualifiers
source                 1..479
                       mol_type = protein
                       organism = Homo sapiens
SEQUENCE: 38
MARAAALLPS RSPPTPLLWP LLLLLLLETG AQDVRVQVLP EVRGQLGGTV ELPCHLLPPV  60
PGLYISLVTW QRPDAPANHQ NVAAFHPKMG PSFPSPKPGS ERLSFVSAKQ STGQDTEAEL  120
QDATLALHGL TVEDEGNYTC EFATFPKGSV RGMTWLRVIA KPKNQAEAQK VTFSQDPTTV  180
ALCISKEGRP PARISWLSSL DWEAKETQVS GTLAGTVTVT SRFTLVPSGR ADGVTVTCKV  240
EHESFEEPAL IPVTLSVRYP PEVSISGYDD NWYLGRTDAT LSCDVRSNPE PTGYDWSTTS  300
GTFPTSAVAQ GSQLVIHAVD SLFNTTFVCT VTNAVGMGRA EQVIFVRETP RASPRDVGPL  360
VWGAVGGTLL VLLLLAGGSL AFILLRVRRR RKSPGGAGGG ASGDGGFYDP KAQVLGNGDP  420
VFWTPVVPGP MEPDGKDEEE EEEEKAEKG LMLPPPPALE DDMESQLDGS LISRRAVYV   479

SEQ ID NO: 39          moltype = DNA  length = 2009
```

-continued

```
FEATURE                 Location/Qualifiers
source                  1..2009
                        mol_type = genomic DNA
                        organism = Mus musculus
SEQUENCE: 39
gagccctagg atcggcttgg cgaagagggg cggggcctgt gacgtcatga gtccggcccg  60
ctggagctaa gcgaggggcc ggggggcgcg gatcctgaga gccaggcgag ggaaagctgg  120
gccgaacgaa ctgatccggg gagccgtgag cggcggaagc cggcctggag ccggacactt  180
cagacccctg actgccctcc cagccgatcg gtacacgaag agtggtccct aggcaccccc  240
tgcccgggcc cagtccctcc ccgggccccc catggcccgg gccgcagtcc tcccgccgtc  300
cagattgtca ccgacgctgc cgttgttgcc gctgctactg ctcctgcttc aggaaacagg  360
agcccaagat gtgcgggtac gagtgcttcc cgaggtccgg ggccgcttgg gaggcaccgt  420
ggagttaccg tgccacctgc tcccacccac gacggagcgc gtctctcagg tgacctggca  480
gcgcctggat ggcacagttg tggctgcttt ccacccatcc ttcggagtgg atttccccaa  540
ctctcagttc agcaaggacc gtctgtcctt tgtcagagcg agaccagaaa caaacgcaga  600
cctgcgggat gccacactgg ccttccgggg actgagggta gaggacgagg gcaattacac  660
ctgcgagttt gccacgtttc ccaacggtac ccgcaggggg gtgacctggc tcagagtcat  720
agcccagcct gagaaccacg ctgaagccca ggaggtcaca attggccccc agtcggtggc  780
tgtagcccgc tgtgtctcca ctgggggccg ccccccctgcc cgaatcacct ggatctcatc  840
tctgggtgga gaggccaaag atactcagga gccagggata caggctggca ccgtcactat  900
catcagccga tactccttgg tgcccgtggg ccgagcggat ggcgtcaagg tcacgtgtag  960
agtggaacac gagagcttcg aagagccgat cctgctgcca gtgaccctct ctgtgcgcta  1020
ccctccagaa gtatccatct ccggctatga tgacaactgg taccttggcc gcagtgaggc  1080
catactgacc tgtgatgtac gaagcaaccc agagcccaca gactatgact ggagcacgac  1140
ctcgggcgtc ttcccagcct ctgcagtggc ccagggctct cagctgcttg tccactctgt  1200
ggatcgaatg gtcaacacta ccttcatctg tacagccacc aacgctgtgg ggacaggccg  1260
tgctgagcag gtcatcctgg tgcgagacac cccccaggcc tcccgagatg tgggtccgct  1320
ggtgtggggg gccgtggggg gaacattgct ggtgctactc ctggctgggg ggttcctggc  1380
cttgatcctg ctgagggggga ggaggaggcg gaagagccct ggaggaggag gaaatgatgg  1440
cgacagagga tcctacgatc caaagactca ggtgtttggg aacgggggtc ctgtcttctg  1500
gaggtcagca tcccctgagc ccatgaggcc agatggcagg gaggaagatg aggaggagga  1560
ggaagaaatg aaggcagagg aaggtctcat gctacctcca cacgagtcac ctaaggacga  1620
catggagtcc catctggatg gctccctcat ctctcggcgg gcagtttacg tgtgaccct a  1680
cgatatagac actggacaca tggaaacacc aagttccacc ctcactgcca accacaccaa  1740
tgccagccag caacgatggc tagggaccgg ttggactggt tcttctgggg cacactggag  1800
ttggaagggc accgcccctg ctttcaggat agaggacaag tggaaccaca cagactccta  1860
tctttagggc ctcatggagt aggggacccc aggagcgcca tggtgcacac tcaggactcc  1920
tcagagcttg ctttcggccc cagcctagcc ctggccccga aacactcagg agctaataaa  1980
tgccttgtcg gaaaaaaaaa aaaaaaaaa                                   2009

SEQ ID NO: 40           moltype = AA  length = 467
FEATURE                 Location/Qualifiers
source                  1..467
                        mol_type = protein
                        organism = Mus musculus
SEQUENCE: 40
MARAAVLPPS RLSPTLPLLP LLLLLLQETG AQDVRVRVLP EVRGRLGGTV ELPCHLLPPT  60
TERVSQVTWQ RLDGTVVAAF HPSFGVDFPN SQFSKDRLSF VRARPETNAD LRDATLAFRG  120
LRVEDEGNYT CEFATFPNGT RRGVTWLRVI AQPENHAEAQ EVTIGPQSVA VARCVSTGGR  180
PPARITWISS LGGEAKDTQE PGIQAGTVTI ISRYSLVPVG RADGVKVTCR VEHESFEEPI  240
LLPVTLSVRY PPEVSISGYD DNWYLGRSEA ILTCDVRSNP EPTDYDWSTT SGVFPASAVA  300
QGSQLLVHSV DRMVNTTFIC TATNAVGTGR AEQVILVRDT PQASRDVGPL VWGAVGGTLL  360
VLLLAGGFLA LILLRGRRRR KSPGGGGNDG DRGSYDPKTQ VFGNGGPVFW RSASPEPMRP  420
DGREEDEEEE EEMKAEEGLM LPPHESPKDD MESHLDGSLI SRRAVYV                467

SEQ ID NO: 41           moltype = DNA  length = 2690
FEATURE                 Location/Qualifiers
source                  1..2690
                        mol_type = genomic DNA
                        organism = Homo sapiens
SEQUENCE: 41
gtgacgtcag cgggttcgaa ccgccggagc tgagcgagag gccgggggtg ccgagccggg  60
cggggagagc tgggccggga gagcagaaca gggaggctag agcgcagcgg gaaccggccc  120
ggagccggag ccggagcccc acaggcacct actaaaccgc ccagccgatc ggcccccaca  180
gagtggcccg cgggcctccg gccgggccca gtcccctccc gggccctcca tggcccgggc  240
cgctgccctc ctgccgtcga gatcgccgcc gacgccgctg ctgtggccgc tgctgctgct  300
gctgctcctg gaaaccggag cccaggatgt gcgagttcaa gtgctacccg aggtgcgagg  360
ccagctcggg ggcaccgtgg agctgccgtg ccacctgctg ccacctgttc ctggactgta  420
catctccctg gtgacctggc agcgcccaga tgcacctgcg aaccaccaga atgtggccgc  480
cttccaccct aagatgggtc ccagcttccc cagcccgaag cctggcagcg agcggctgtc  540
cttcgtctct gccaagcaga gcactgggca agacacagag gcagagctcc aggacgccac  600
gctggccctc cacgggctca cggtggagga cgagggcaac tacacttgcg agtttgccac  660
cttccccaag gggtccgtcc gagggatgac ctggctcaga gtcatagcca agcccaagaa  720
ccaagctgag gcccagaagg tcacgttcag ccaggaccct acgacagtgg ccctctgcat  780
ctccaaagag ggccgcccac ctgcccggat ctcctggctc tcatccctgg actgggaagc  840
caaagagact caggtgtcag ggaccctggc cggaactgtc actgtcacca gccgcttcac  900
cttggtgccc tcgggccgag cagatggtgt cacggtcacc tgcaaagtgg agcatgagag  960
cttcgaggaa ccagccctga tacctgtgac cctctctgta cgctaccctc ctgaagtgtc  1020
catctccggc tatgatgaca actggtacct cggccgtact gatgccaccc tgagctgtga  1080
```

```
cgtccgcagc aacccagagc ccacgggcta tgactggagc acgacctcag gcaccttccc  1140
gacctccgca gtggcccagg gctcccagct ggtcatccac gcagtggaca gtctgttcaa  1200
taccaccttc gtctgcacag tcaccaatgc cgtgggcatg ggccgcgctg agcaggtcat  1260
ctttgtccga gagaccccca acacagcagg cgcaggggcc acaggcggca tcatcggggg  1320
catcatcgcc gccatcattg ctactgctgt ggctgccacg ggcatcctta tctgccggca  1380
gcagcggaag gagcagacgc tgcagggggc agaggaggac gaagacctgg agggacctcc  1440
ctcctacaag ccaccgaccc caaaagcgaa gctggaggca caggagatgc cctcccagct  1500
cttcactctg ggggcctcgg agcacagccc actcaagacc ccctactttg atgctggcgc  1560
ctcatgcact gagcaggaaa tgcctcgata ccatgagctg cccacccttgg aagaacggtc  1620
aggacccttg caccctggag ccacaagcct ggggtccccc atcccggtgc ctccagggcc  1680
acctgctgtg gaagacgttt ccctggatct agaggatgag gagggggagg aggaggaaga  1740
gtatctggac aagatcaacc ccatctatga tgctctgtcc tatagcagcc cctctgattc  1800
ctaccagggc aaaggctttg tcatgtcccg ggccatgtat gtgtgagctg ccatgcgcct  1860
ggcgtctcac atctcacctg ttgatccctt agctttcttg ccaaggatct agtgcccccct  1920
gacctctggc caggccactg tcagttaaca catatgcatt ccatttgtga tgtctacctt  1980
ggtggctcca ctatgacccc taacccatga gcccagagaa attcaccgtg ataatggaat  2040
cctggcaacc ttatctcatg aggcaggagg tggggaaggt gcttctgcac aacctctgat  2100
cccaaggact cctctcccag actgtgacct tagaccatac ctctcacccc ccaatgcctc  2160
gactccccca aaatcacaaa gaagacccta gacctataat ttgtcttcag gtagtaaatt  2220
cccaataggt ctgctggagt gggcgctgag ggctccctgc tgctcagacc tgagccctcc  2280
aggcagcagg gtcccactta ccccctcccc accctgttcc ccaaaggtgg gaaagagggg  2340
attccccagc ccaaggcagg gttttcccag caccctcctg taagcagaag tctcagggtc  2400
cagacccttc cctgagcccc cacccccacc ccaattcctg cctaccaagc aagcagcccc  2460
agcctagggt cagacagggt gagcctcata cagactgtgc cttgatggcc ccagccttgg  2520
gagaagaatt tactgttaac ctggaagact actgaatcat tttacccttg cccagtggaa  2580
taggacctaa acatcccccct tccggggaaa gtgggtcatc tgaattgggg gtagcaattg  2640
atactgtttt gtaaactaca tttcctacaa aatatgaatt tatactttga              2690

SEQ ID NO: 42           moltype = AA  length = 538
FEATURE                 Location/Qualifiers
source                  1..538
                        mol_type = protein
                        organism = Homo sapiens
SEQUENCE: 42
MARAAALLPS RSPPTPLLWP LLLLLLLETG AQDVRVQVLP EVRGQLGGTV ELPCHLLPPV  60
PGLYISLVTW QRPDAPANHQ NVAAFHPKMG PSFPSPKPGS ERLSFVSAKQ STGQDTEAEL  120
QDATLALHGL TVEDEGNYTC EFATFPKGSV RGMTWLRVIA KPKNQAEAQK VTFSQDPTTV  180
ALCISKEGRP PARISWLSSL DWEAKETQVS GTLAGTVTVT SRFTLVPSGR ADGVTVTCKV  240
EHESFEEPAL IPVTLSVRYP PEVSISGYDD NWYLGRTDAT LSCDVRSNPE PTGYDWSTTS  300
GTFPTSAVAQ GSQLVIHAVD SLFNTTFVCT VTNAVGMGRA EQVIFVRETP NTAGAGATGG  360
IIGGIIAAII ATAVAATGIL ICRQQRKEQT LQGAEEDEDL EGPPSYKPPT PKAKLEAQEM  420
PSQLFTLGAS EHSPLKTPYF DAGASCTEQE MPRYHELPTL EERSGPLHPG ATSLGSPIPV  480
PPGPPAVEDV SLDLEDEEGE EEEEYLDKIN PIYDALSYSS PSDSYQGKGF VMSRAMYV    538

SEQ ID NO: 43           moltype = DNA  length = 2735
FEATURE                 Location/Qualifiers
source                  1..2735
                        mol_type = genomic DNA
                        organism = Mus musculus
SEQUENCE: 43
gagccctagg atcggcttgg cgaagagggg cggggcctgt gacgtcatga gtccggcccg  60
ctggagctaa gcgaggggcc gggggggcgcg gatcctgaga gccaggcgag ggaaagctgg  120
gccgaacgaa ctgatccggg gagccgtgag cggcggaagc cggcctggag ccggacactt  180
cagacccctg actgccctcc cagccgatcg gtacacgaag agtggtccct aggcaccccc  240
tgcccgggcc cagtccctcc ccgggccccc catggcccgg gccgcagtcc tcccgccgtc  300
cagattgtca ccgacgctgc cgttgttgcc gctgctactg ctcctgcttc aggaaacagg  360
agcccaagat gtgcgggtac gagtgcttcc cgaggtccgg ggccgcttgg gaggcaccgt  420
ggagttaccg tgccacctgc tcccacccac gacggagcgc gtctctcagg tgacctggca  480
gcgcctggat ggcacagttg tggctgcttt ccacccatcc ttcggagtgg atttccccaa  540
ctctcagttc agcaaggacc gtctgtcctt tgtcagagcg agaccagaaa caaacgcaga  600
cctgcgggat gccacactgg ccttccgggg actgagggta gaggacgagg gcaattacac  660
ctgcgagttt gccacgtttc ccaacggtac ccgcaggggg gtgacctggc tcagagtcat  720
agcccagcct gagaaccacg ctgaagccca ggaggtcaca attggccccc agtcggtggc  780
tgtagcccgc tgtgtctcca ctgggggccg ccccccctgcc cgaatcacct ggatctcatc  840
tctgggtgga gaggccaaag atactcagga gccagggata caggctggca ccgtcactat  900
catcagccga tactccttgg tgcccgtggg ccgagcggat ggcgtcaagg tcacgtgtag  960
agtggaacac gagagcttcg aagagccgat cctgctgcca gtgaccctct ctgtgcgcta  1020
ccctccagaa gtatccatct ccggctatga tgacaactgg taccttggcc gcagtgaggc  1080
catactgacc tgtgatgtac gaagcaaccc agagcccaca gactatgact ggagcacgac  1140
ctcgggcgtc ttcccagcct ctgcagtggc ccagggctct cagctgcttg tccactctgt  1200
ggatcgaatg gtcaacacta ccttcatctg tacagccacc aacgctgtgg ggacaggccg  1260
tgctgagcag gtcatcctgg tgcgagagtc acccagcaca gcaggagcag gggccactgg  1320
tggcatcatt ggaggtatta tcgctgccat catcgccacc gcagtggctg gcacaggcat  1380
cctcatctgc cgacaacagc ggaaggagca gaggcttcaa gctgcggatg aggaagaaga  1440
actggaagga cctccctcct ataaaccacc caccccgaag gccaagctgg aggaaccaga  1500
gatgccctct caactcttca ccttgggggc ctcagagcac agcccagtga agacgccata  1560
ctttgatgct ggtgtctctt gtgctgatca ggagatgcct cggtatcacg agctgcccac  1620
tctggaagag cggtcagggc ccctgctgtt gggggctaca ggcctgggac cttctcttct  1680
ggtgcctcca ggacccaatg ttgtggaggg ggtttccctg agtctcgaag atgaggagga  1740
```

```
agatgatgag gaggaagact tcctggataa aatcaaccct atttatgatg ccctgtccta  1800
ccccagcccc tctgactcct accagagcaa agactttttt gtgtcacggg ccatgtatgt  1860
gtgagggagg cacaggggct ctgacgtctc acctttcacc cttgacccat gagctttcca  1920
ccagtaatct aggacactct gacttccagg cagaccaggg acaactatca cccattgcaa  1980
tccacctgtg acttcttagt gactccacca tgacgtccaa tctatgatgt ctgaggcagg  2040
caaacctgca caactggaaa cctggagatt tttatctccc ttggcaggga gctcaccata  2100
tccttctgca ccacctgtga cccccccccc ccccccaagg actcctaaga ctacgaccct  2160
ttgaccatgc cactcagtat ctcaagaacc cttaaagtcc caaaggaatc ggaccttgca  2220
cttgtcctca ggcaatagag tccaacagat atgcaagaac gggatcaggg gctccctgtt  2280
gctcagacct gagccctcca ggcagcagaa gctcacctga tccctcccca ccctgctccc  2340
caaaggtgaa aaggagagga ttccccaatg taaggtagga cctccccatc tccacctact  2400
cctgcaggca ggaatctcag gtttctcaca ccctctcctc agcacccagg ttcctgtctc  2460
cagagcatga attccaggtc caatgctaga ggggagaacc taatgcaagt gtgccttgcc  2520
accccaagtt tgggagactc tgctcttatc ctgaggacta ctgaattctt ttaacccta  2580
cccagtgaga tgagaactac atatccctct ttaggggatg gtgtgtgtat gtgtgtgtga  2640
tggagaatct gggcatctgg gttgggaatt ttattttgta agcatttcct acataatatg  2700
agtttctact ttgataaagt cttgtgtttt ctgtg                            2735

SEQ ID NO: 44          moltype = AA  length = 530
FEATURE                Location/Qualifiers
source                 1..530
                       mol_type = protein
                       organism = Mus musculus
SEQUENCE: 44
MARAAVLPPS RLSPTLPLLP LLLLLLQETG AQDVRVRVLP EVRGRLGGTV ELPCHLLPPT  60
TERVSQVTWQ RLDGTVVAAF HPSFGVDFPN SQFSKDRLSF VRARPETNAD LRDATLAFRG  120
LRVEDEGNYT CEFATFPNGT RRGVTWLRVI AQPENHAEAQ EVTIGPQSVA VARCVSTGGR  180
PPARITWISS LGGEAKDTQE PGIQAGTVTI ISRYSLVPVG RADGVKVTCR VEHESFEEPI  240
LLPVTLSVRY PPEVSISGYD DNWYLGRSEA ILTCDVRSNP EPTDYDWSTT SGVFPASAVA  300
QGSQLLVHSV DRMVNTTFIC TATNAVGTGR AEQVILVRES PSTAGAGATG GIIGGIIAAI  360
IATAVAGTGI LICRQQRKEQ RLQAADEEEE LEGPPSYKPP TPKAKLEEPE MPSQLFTLGA  420
SEHSPVKTPY FDAGVSCADQ EMPRYHELPT LEERSGPLLL GATGLGPSLL VPPGPNVVEG  480
VSLSLEDEEE DDEEEDFLDK INPIYDALSY PSPSDSYQSK DFFVSRAMYV            530

SEQ ID NO: 45          moltype = DNA  length = 1630
FEATURE                Location/Qualifiers
source                 1..1630
                       mol_type = genomic DNA
                       organism = Homo sapiens
SEQUENCE: 45
acacatcagg ggcttgctct tgcaaaacca aaccacaaga cagacttgca aaagaaggca  60
tgcacagctc agcactgctc tgttgcctgg tcctcctgac tggggtgagg gccagcccag  120
gccagggcac ccagtctgag aacagctgca cccacttccc aggcaacctg cctaacatgc  180
ttcgagatct ccgagatgcc ttcagcagag tgaagacttt ctttcaaatg aaggatcagc  240
tggacaactt gttgttaaag gagtccttgc tggaggactt taagggttac ctgggttgcc  300
aagccttgtc tgagatgatc cagttttacc tggaggaggt gatgccccaa gctgagaacc  360
aagacccaga catcaaggcg catgtgaact ccctggggga gaacctgaag accctcaggc  420
tgaggctacg gcgctgtcat cgatttcttc cctgtgaaaa caagagcaag gccgtggagc  480
aggtgaagaa tgcctttaat aagctccaag agaaaggcat ctacaaagcc atgagtgagt  540
ttgacatctt catcaactac atagaagcct acatgacaat gaagatacga aactgagaca  600
tcagggtggc gactctatag actctaggac ataaattaga ggtctccaaa atcggatctg  660
gggctctggg atagctgacc cagccccttg agaaacctta ttgtacctct cttatagaat  720
atttattacc tctgatacct caacccccat ttctatttat ttactgagct tctctgtgaa  780
cgatttagaa agaagcccaa tattatatt tttttcaata tttattattt tcacctgttt  840
ttaagctgtt tccatagggt gacacactat ggtatttgag tgttttaaga taaattataa  900
gttacataag ggaggaaaaa aaatgttctt tggggagcca acagaagctt ccattccaag  960
cctgaccacg ctttctagct gttgagctgt tttccctgac ctccctctaa tttatcttgt  1020
ctctgggctt ggggcttcct aactgctaca aatactctta ggaagagaaa ccagggagcc  1080
cctttgatga ttaattcacc ttccagtgtc tcggagggat tcccctaacc tcattcccca  1140
accacttcat tcttgaaagc tgtggccagc ttgttattta taacaaccta aatttggttc  1200
taggccgggc gcggtggctc acgcctgtaa tcccagcact ttgggaggct gaggcgggtg  1260
gatcacttga ggtcaggagt tcctaaccag cctggtcaac atggtgaaac cccgtctcta  1320
ctaaaaatac aaaaattagc cggcatggt ggcgcgcacc tgtaatccca gctacttggg  1380
aggctgaggc aagagaattg cttgaaccca ggagatggaa gttgcagtga gctgatatca  1440
tgcccctgta ctccagcctg ggtgacagag caagactctg tctcaaaaaa taaaaataaa  1500
aataaatttg gttctaatag aactcagttt taactagaat ttattcaatt cctctgggaa  1560
tgttacattg tttgtctgtc ttcatagcag attttaattt tgaataaata aatgtatctt  1620
attcacatca                                                        1630

SEQ ID NO: 46          moltype = AA  length = 178
FEATURE                Location/Qualifiers
source                 1..178
                       mol_type = protein
                       organism = Homo sapiens
SEQUENCE: 46
MHSSALLCCL VLLTGVRASP GQGTQSENSC THFPGNLPNM LRDLRDAFSR VKTFFQMKDQ  60
LDNLLLKESL LEDFKGYLGC QALSEMIQFY LEEVMPQAEN QDPDIKAHVN SLGENLKTLR  120
LRLRRCHRFL PCENKSKAVE QVKNAFNKLQ EKGIYKAMSE FDIFINYIEA YMTMKIRN    178
```

```
SEQ ID NO: 47          moltype = DNA  length = 1306
FEATURE                Location/Qualifiers
source                 1..1306
                       mol_type = genomic DNA
                       organism = Mus musculus
SEQUENCE: 47
acatttagag acttgctctt gcactaccaa agccacaagg cagccttgca gaaaagagag  60
ctccatcatg cctggctcag cactgctatg ctgcctgctc ttactgactg gcatgaggat  120
cagcaggggc cagtacagcc gggaagacaa taactgcacc cacttcccag tcggccagag  180
ccacatgctc ctagagctgc ggactgcctt cagccaggtg aagactttct ttcaaacaaa  240
ggaccagctg gacaacatac tgctaaccga ctccttaatg caggacttta agggttactt  300
gggttgccaa gccttatcgg aaatgatcca gttttacctg gtagaagtga tgccccaggc  360
agagaagcat ggcccagaaa tcaaggagca tttgaattcc ctgggtgaga agctgaagac  420
cctcaggatg cggctgaggc gctgtcatcg atttctcccc tgtgaaaata agagcaaggc  480
agtggagcag gtgaagagtg attttaataa gctccaagac caaggtgtct acaaggccat  540
gaatgaattt gacatcttca tcaactgcat agaagcatac atgatgatca aaatgaaaag  600
ctaaaacacc tgcagtgtgt attgagtctg ctggactcca ggacctagac agagctctct  660
aaatctgatc cagggatctt agctaacgga aacaactcct tggaaaacct cgtttgtacc  720
tctctccgaa atatttatta cctctgatac ctcagttccc attctattta ttcactgagc  780
ttctctgtga actatttaga aagaagccca atattataat tttacagtat ttattatttt  840
taacctgtgt ttaagctgtt tccattgggg acactttata gtatttaaag ggagattata  900
ttatatgatg ggaggggttc ttccttggga agcaattgaa gcttctattc taaggctggc  960
cacacttgag agctgcaggg ccctttgcta tggtgtcctt tcaattgctc tcatccctga  1020
gttcagagct cctaagagag ttgtgaagaa actcatgggt cttgggaaga gaaaccaggg  1080
agatcctttg atgatcattc ctgcagcagc tcagagggtt cccctactgt catccccccag  1140
ccgcttcatc cctgaaaact gtggccagtt tgttatttat aaccacctaa aattagttct  1200
aatagaactc atttttaact agaagtaatg caattcctct gggaatggtg tattgtttgt  1260
ctgcctttgt agcagactct aattttgaat aaatggatct tattcg                  1306

SEQ ID NO: 48          moltype = AA  length = 178
FEATURE                Location/Qualifiers
source                 1..178
                       mol_type = protein
                       organism = Mus musculus
SEQUENCE: 48
MPGSALLCCL LLLTGMRISR GQYSREDNNC THFPVGQSHM LLELRTAFSQ VKTFFQTKDQ  60
LDNILLTDSL MQDFKGYLGC QALSEMIQFY LVEVMPQAEK HGPEIKEHLN SLGEKLKTLR  120
MRLRRCHRFL PCENKSKAVE QVKSDFNKLQ DQGVYKAMNE FDIFINCIEA YMMIKMKS    178

SEQ ID NO: 49          moltype = DNA  length = 1439
FEATURE                Location/Qualifiers
source                 1..1439
                       mol_type = genomic DNA
                       organism = Homo sapiens
SEQUENCE: 49
agtcacattt cagccactgc tctgagaatt tgtgagcagc ccctaacagg ctgttacttc  60
actacaactg acgatatgat catcttaatt tacttatttc tcttgctatg ggaagacact  120
caaggatggg gattcaagga tggaattttt cataactcca tatggcttga acgagcagcc  180
ggtgtgtacc acagagaagc acggtctggc aaatacaagc tcacctacgc agaagctaag  240
gcggtgtgtg aatttgaagg cggccatctc gcaacttaca agcagctaga ggcagccaga  300
aaaattggat ttcatgtctg tgctgctgga tggatggcta agggcagagt tggataccccc  360
attgtgaagc cagggcccaa ctgtggattt ggaaaaactg gcattattga ttatggaatc  420
cgtctcaata ggagtgaaag atgggatgcc tattgctaca acccacacgc aaaggagtgt  480
ggtggcgtct ttacagatcc aaagcaaatt tttaaatctc caggcttccc aaatgagtac  540
gaagataacc aaatctgcta ctggcacatt agactcaagt atggtcagcg tattcacctg  600
agtttttag attttgacct tgaagatgac ccaggttgct tggctgatta tgttgaaata  660
tatgacagtt acgatgatgt ccatggcttt gtgggaagat actgtggaga tgagcttcca  720
gatgacatca tcagtacagg aaatgtcatg accttgaagt ttctaagtga tgcttcagtg  780
acagctggag gtttccaaat caaatatgtt gcaatggatc ctgtatccaa atccagtcaa  840
ggaaaaaata caagtactac ttctactgga aataaaaact ttttagctgg aagatttagc  900
cacttataaa aaaaaaaaaa aggatgatca aaacacacag tgtttatgtt ggaatctttt  960
ggaactcctt tgatctcact gttattatta acatttattt attatttttc taaatgtgaa  1020
agcaatacat aatttaggga aaattggaaa atataggaaa ctttaaacga gaaaatgaaa  1080
cctctcataa tcccactgca tagaaataac aagcgttaac attttcatat tttttctttt  1140
cagtcatttt tctatttgtg gtatatgtat atatgtacct atatgtattt gcatttgaaa  1200
ttttggaatc ctgctctatg tacagttttg tattatactt tttaaatctt gaactttata  1260
aacattttct gaaatcattg attattctac aaaaacatga ttttaaacag ctgtaaaata  1320
ttctatgata tgaatgtttt atgcattatt taagcctgtc tctattgttg gaatttcagg  1380
tcattttcat aaatattgtt gcaataaata tccttgaaca cacaaaaaaa aaaaaaaaa   1439

SEQ ID NO: 50          moltype = AA  length = 277
FEATURE                Location/Qualifiers
source                 1..277
                       mol_type = protein
                       organism = Homo sapiens
SEQUENCE: 50
MIILIYLFLL LWEDTQGWGF KDGIFHNSIW LERAAGVYHR EARSGKYKLT YAEAKAVCEF  60
EGGHLATYKQ LEAARKIGFH VCAAGWMAKG RVGYPIVKPG PNCGFGKTGI IDYGIRLNRS  120
ERWDAYCYNP HAKECGGVFT DPKQIFKSPG FPNEYEDNQI CYWHIRLKYG QRIHLSFLDF  180
```

-continued

```
DLEDDPGCLA DYVEIYDSYD DVHGFVGRYC GDELPDDIIS TGNVMTLKFL SDASVTAGGF  240
QIKYVAMDPV SKSSQGKNTS TTSTGNKNFL AGRFSHL                           277

SEQ ID NO: 51          moltype = DNA  length = 1601
FEATURE                Location/Qualifiers
source                 1..1601
                       mol_type = genomic DNA
                       organism = Mus musculus
SEQUENCE: 51
ccgctgctct gagaatttcg tgtgggcagc cccgacattg taaccggctc tgcaaccgaa  60
gagatggtcg tcctcctttg cttatgcgtc ttgctgtggg aagaggctca cggatgggga  120
ttcaagaacg ggatctttca taactccata tggcttgaac aagcagcggg cgtataccac  180
agagaagctc gggctggcag atacaagctc acctacgccg aagccaaggc cgtatgtgaa  240
tttgaaggtg gtcgtctcgc aacctacaag cagctagagg cagccagaaa aattggattc  300
catgtctgtg ctgctggatg gatggccaag ggtagagtcg gataccccat tgtgaaacct  360
gggcccaact gtggatttgg gaaaacgggt atcatcgatt atggaatccg gctcaacagg  420
agtgagcgat gggatgccta ttgctacaac ccacatgcaa aggagtgtgg tggtgtcttc  480
acagatccga agcgaatttt taaatccccg ggcttcccaa atgagtacga tgacaaccag  540
gtctgctact ggcacattcg gctcaagtac ggtcagcgaa ttcacctgag ctttttggac  600
tttgaccttg aacatgatcc aggctgcttg gctgactatg tagaaatcta tgacagttat  660
gatgacgtcc acggctttgt aggaagatac tgtggtgatg aacttccaga agacatcatt  720
agcacaggaa atgtcatgac cttgaagttt ctgagtgatg catccgtcac ggctggaggc  780
ttccagatta aatacgtcac agtggatcct gcatctaaat ccagtcaagc caaaaataca  840
agtactactg gaaataagaa gttcttacct ggaaggttta gccatctata aaaaattttt  900
tttaaaaatg ttcaaaacat ccagtacaat atttatattt gtttttgttg ttgttgttgg  960
ttttttttt tttattttgt tttgttttgt tttttgaga cggggtttct ctgtatagcc  1020
ttggctgtcc tggaactcac tttgaagacc aggctggcct cgaactcaga aatccacctg  1080
cctccgccta ccaagtgctg ggattaaagg cgtccaccac caccgcccgg cttcaatatt  1140
tatatttgta gctcttggac ctcgtttgtt ctcttttgta tttttattat taacatgtat  1200
ttattatttt tccaaatgtg aaagccatat gtaattatgt ggaaaattga caaataaata  1260
cagagaactt caaatgagtt tttttttaa atctcataat tgtactacac agaaataact  1320
aatgttaaag tttttaaatg tttgtctttc attcattttt ctacttgtag tatatgtaca  1380
tatgtaactc tatgatttgc gtttgaattt tggcattctg ccttttgtaa cctgatattt  1440
ttaaccttga cattgtatag ctcaagcact tcccaagatc tctgagtttt ctacaaaatg  1500
ggactttgta aatatgattg ttccctgctt tatttaagct gaatttatat taggatttaa  1560
ggttgttttc ataaatattg ctgtaataaa tacttttgga t                     1601

SEQ ID NO: 52          moltype = AA  length = 275
FEATURE                Location/Qualifiers
source                 1..275
                       mol_type = protein
                       organism = Mus musculus
SEQUENCE: 52
MVVLLCLCVL LWEEAHGWGF KNGIFHNSIW LEQAAGVYHR EARAGRYKLT YAEAKAVCEF  60
EGGRLATYKQ LEAARKIGFH VCAAGWMAKG RVGYPIVKPG PNCGFGKTGI IDYGIRLNRS  120
ERWDAYCYNP HAKECGGVFT DPKRIFKSPG FPNEYDDNQV CYWHIRLKYG QRIHLSFLDF  180
DLEHDPGCLA DYVEIYDSYD DVHGFVGRYC GDELPEDIIS TGNVMTLKFL SDASVTAGGF  240
QIKYVTVDPA SKSSQAKNTS TTGNKKFLPG RFSHL                             275

SEQ ID NO: 53          moltype = DNA  length = 3295
FEATURE                Location/Qualifiers
source                 1..3295
                       mol_type = genomic DNA
                       organism = Homo sapiens
SEQUENCE: 53
attcgggccg ggcctcgctg cggcggcgac tgagccaggc tgggccgcgt ccctgagtcc  60
cagagtcggc gcggcgcggc aggggcagcc ttccaccacg gggagcccag ctgtcagccg  120
cctcacagga agatgctgcg tcggcggggc agccctggca tgggtgtgca tgtgggtgca  180
gccctgggag cactgtggtt ctgcctcaca ggagccctgg aggtccaggt ccctgaagac  240
ccagtggtgg cactggtggg caccgatgcc accctgtgct gctccttctc ccctgagcct  300
ggcttcagcc tggcacagct caacctcatc tggcagctga cagataccaa acagctggtg  360
cacagctttg ctgagggcca ggaccagggc agcgcctatg ccaaccgcac ggccctcttc  420
ccggacctgc tggcacaggg caacgcatcc ctgaggctgc agcgcgtgcg tgtggcggac  480
gagggcagct tcacctgctt cgtgagcatc cgggatttcg gcagcgctgc cgtcagcctg  540
caggtggccg ctccctactc gaagcccagc atgaccctgg agcccaacaa ggacctgcgg  600
ccaggggaca cggtgaccat cacgtgctcc agctaccagg gctaccctga ggctgaggtg  660
ttctggcagg atgggcaggg tgtgccccctg actggcaacg tgaccacgtc gcagatggcc  720
aacgagcagg gcttgtttga tgtgcacagc atcctgcggg tggtgctggg tgcaaatggc  780
acctacagct gcctggtgcg caaccccgtg ctgcagcagg atgcgcacag ctctgtcacc  840
atcacacccc agagaagccc cacaggagcc gtggaggtcc aggtccctga ggacccggtg  900
gtggccctag tgggcaccga tgccaccctg cgctgctcct tctcccccga gcctggcttc  960
agcctggcac agctcaacct catctggcag ctgacagaca ccaaacagct ggtgcacagt  1020
ttcaccgaag gccgggacca gggcagcgcc tatgccaacc gcacggccct cttcccggac  1080
ctgctggcac aaggcaatgc atccctgagg ctgcagcgcg tgcgtgtggc ggacgagggc  1140
agcttcacct gcttcgtgag catccgggat ttcggcagcg ctgccgtcag cctgcaggtg  1200
gccgctccct actcgaagcc cagcatgacc ctggagccca acaaggacct gcggccaggg  1260
gacacggtga ccatcacgtg ctccagctac cggggctacc ctgaggctga ggtgttctgg  1320
caggatgggc agggtgtgcc cctgactggc aacgtgacca cgtcgcagat ggccaacgag  1380
cagggcttgt ttgatgtgca cagcgtcctg cgggtggtgc tgggtgcgaa tggcacctac  1440
```

```
agctgcctgg tgcgcaaccc cgtgctgcag caggatgcgc acggctctgt caccatcaca  1500
gggcagccta tgacattccc cccagaggcc ctgtgggtga ccgtggggct gtctgtctgt  1560
ctcattgcac tgctggtggc cctggctttc gtgtgctgga gaaagatcaa acagagctgt  1620
gaggaggaga atgcaggagc tgaggaccag gatggggagg gagaaggctc caagacagcc  1680
ctgcagcctc tgaaacactc tgacagcaaa gaagatgatg gacaagaaat agcctgacca  1740
tgaggaccag ggagctgcta cccctcccta cagctcctac cctctggctg caatggggct  1800
gcactgtgag ccctgccccc aacagatgca tcctgctctg acaggtgggc tccttctcca  1860
aaggatgcga tacacagacc actgtgcagc cttatttctc caatggacat gattcccaag  1920
tcatcctgct gcctttttttc ttatagacac aatgaacaga ccacccacaa ccttagttct  1980
ctaagtcatc ctgcctgctg ccttatttca cagtacatac atttcttagg gacacagtac  2040
actgaccaca tcaccaccct cttcttccag tgctgcgtgg accatctggc tgcctttttt  2100
ctccaaaaga tgcaatattc agactgactg accccctgcc ttatttcacc aaagacacga  2160
tgcatagtca ccccggcctt gtttctccaa tggccgtgat acactagtga tcatgttcag  2220
ccctgcttcc acctgcatag aatcttttct tctcagacag ggacagtgcg gcctcaacat  2280
ctcctggagt ctagaagctg tttcctttcc cctccttcct cctcttgctc tagccttaat  2340
actggccttt tccctccctg ccccaagtga agacagggca ctctgcgccc accacatgca  2400
cagctgtgca tggagacctg caggtgcacg tgctggaaca cgtgtggttc cccccctggcc  2460
cagcctcctc tgcagtgccc ctctcccctg cccatcctcc ccacggaagc atgtgctggt  2520
cacactggtt ctccaggggt ctgtgatggg gcccctgggg gtcagcttct gtccctctgc  2580
cttctcacct ctttgttcct ttcttttcat gtatccattc agttgatgtt tattgagcaa  2640
ctacagatgt cagcactgtg ttaggtgctg ggggccctgc gtgggaagat aaagttcctc  2700
cctcaaggac tccccatcca gctgggagac agacaactaa ctacactgca ccctgcggtt  2760
tgcagggggc tcctgcctgg ctccctgctc cacacctcct ctgtggctca aggcttcctg  2820
gatacctcac ccccatccca cccataattc ttacccagag catggggttg gggcggaaac  2880
ctggagagag ggacatagcc cctcgccacg gctagagaat ctggtggtgt ccaaaatgtc  2940
tgtccaggtg tgggcaggtg ggcaggcacc aaggccctct ggacctttca tagcagcaga  3000
aaaggcagag cctggggcag ggcagggcca ggaatgcttt ggggacaccg aggggactgc  3060
cccccacccc caccatggtg ctattctggg gctggggcag tcttttcctg gcttgcctct  3120
ggccagctcc tggcctctgg tagagtgaga cttcagacgt tctgatgcct tccggatgtc  3180
atctctccct gccccaggaa tggaagatgt gaggacttct aatttaaatg tgggactcgg  3240
agggattttg taaactgggg gtatattttg gggaaaataa atgtctttgt aaaaa       3295

SEQ ID NO: 54           moltype = AA  length = 534
FEATURE                 Location/Qualifiers
source                  1..534
                        mol_type = protein
                        organism = Homo sapiens
SEQUENCE: 54
MLRRRGSPGM GVHVGAALGA LWFCLTGALE VQVPEDPVVA LVGTDATLCC SFSPEPGFSL  60
AQLNLIWQLT DTKQLVHSFA EGQDQGSAYA NRTALFPDLL AQGNASLRLQ RVRVADEGSF  120
TCFVSIRDFG SAAVSLQVAA PYSKPSMTLE PNKDLRPGDT VTITCSSYQG YPEAEVFWQD  180
GQGVPLTGNV TTSQMANEQG LFDVHSILRV VLGANGTYSC LVRNPVLQQD AHSSVTITPQ  240
RSPTGAVEVQ VPEDPVVALV GTDATLRCSF SPEPGFSLAQ LNLIWQLTDT KQLVHSFTEG  300
RDQGSAYANR TALFPDLLAQ GNASLRLQRV RVADEGSFTC FVSIRDFGSA AVSLQVAAPY  360
SKPSMTLEPN KDLRPGDTVT ITCSSYRGYP EAEVFWQDGQ GVPLTGNVTT SQMANEQGLF  420
DVHSVLRVVL GANGTYSCLV RNPVLQQDAH GSVTITGQPM TFPPEALWVT VGLSVCLIAL  480
LVALAFVCWR KIKQSCEEEN AGAEDQDGEG EGSKTALQPL KHSDSKEDDG QEIA        534

SEQ ID NO: 55           moltype = DNA  length = 3197
FEATURE                 Location/Qualifiers
source                  1..3197
                        mol_type = genomic DNA
                        organism = Mus musculus
SEQUENCE: 55
cggcgcggcg cgccaaagtg acctggtaca gcctggaccc caagctcatc ggctttgtct  60
ggctggccgc ctggcctctt cccacttgga tttggatgat cctgaggcct ttggaggaac  120
ttcgagacaa aggcccctct tcctcttcca cgggcaggag cagccattcg ccacggagag  180
cccagctgtc agctgtctca caggaagatg cttcgaggat ggggtggccc cagtgtgggt  240
gtgtgtgtgc gcacagcact gggggtgctg tgcctctgcc tcacaggagc tgtggaagtc  300
caggtctctg aagaccccgt ggtggccctg gtggacacgg atgccaccct acgctgctcc  360
ttttccccag agcctggctt cagtctggca cagctcaacc tcatctggca gctgacagac  420
accaaacagc tggtgcacag cttcacggag ggccgggacc aaggcagtgc ctactccaac  480
cgcacagcgc tcttccctga cctgttggtg caaggcaatg cgtccttgag gctgcagcgc  540
gtccgagtaa ccgacgaggg cagctacacc tgctttgtga gcatccagga ctttgacagc  600
gctgctgtta gcctgcaggt ggccgccccc tactcgaagc ccagcatgac cctggagccc  660
aacaaggacc tacgtccagg gaacatggtg accatcacgt gctctagcta ccagggctat  720
ccggaggccg aggtgttctg gaaggatgga cagggagtgc ccttgactgg caatgtgacc  780
acatcccaga tggccaacga gcggggcttg ttcgatgttc acagcgtgct gagggtggtg  840
ctgggtgcta acggcaccta cagctgcctg gtacgcaacc cggtgttgca gcaagatgct  900
cacggctcag tcaccatcac agggcagccc ctgacattcc cccctgaggc tctgtgggta  960
accgtggggc tctctgtctg tcttgtggta ctactggtgg ccctggcttt cgtgtgctgg  1020
agaaagatca agcagagctg cgaggaggag aatgcaggtg ccgaggacca ggatggagat  1080
ggagaaggat ccaagacagc tctacggcct ctgaaaccct ctgaaaacaa agaagatgac  1140
ggacaagaaa ttgcttgatt gggagctgct gcccttccca ggtgggggc ccaccctctg  1200
gcagtgttga gcttcaatgc gagcccttcc cccaacgaat gggtttgtcc cacagatcta  1260
cccgttcgtc aaaggacgtg gtccatagac cacccacagc cttacttttc caatggactt  1320
aattcccatc atcctgcagc ctcatttctc cagtgacacg atacacgaac catcctgcgg  1380
ccttatttcc cacggacacg acacaaagat gtccctcctc ggtgttcctc cagagtcgtc  1440
tggtggcctt gtgatacggc gtgaaccttc ttccttctgc cttacgtcta atggacacac  1500
```

```
acgcaccacc cccacaccct tgctcctcca aagccatgca gactgtgtaa ctgctattat  1560
tctccaaggg gcatcctgtg cagatgaaac cctgctttat ttccctgaag acagctgcac  1620
agtgacctct tagttcttgc tcccatggcc ctgatgtatc ctagttacca gccctcaacc  1680
tcagttctga gggtgggatc ccatcgctca gcaaggcttc atcctgacct ccctgccctg  1740
atctgatctg gccctggctt ttgttgtctc gctccctgac taagtgagat ggggcactct  1800
cccgcccccg cccccccag gtcacagata cctacctgca gctgtgcgtg ctggatcacg  1860
cacatacttg ccttgcatgg tctcctggct gccctgggct gtgcctgttc ttccatagga  1920
agcaagttct tgtctccctg gttctcaggg cccctcaggg gctcagcctt cagccctgtg  1980
cttccccatg ttgggaatct ttgttacctt tttcttcttt gtaaattaac atctgataac  2040
aaccacaggg tccaatggga ctttcacaga cctgccagct agataaataa tgacaacaga  2100
agtttattaa tattttaaga cttaggcctt ttgctgggca gcctcccaac tattctatcc  2160
tgactaatcc tggcactatg tcccaccaca tggccaggtc tacctctctg ctccactctc  2220
catccacctc catgtctgcc agcaaatctc ccgtgattca gttcttctcc cagagtccct  2280
atctctgccc agaagtacca tcttcgactt cctgcccaac tattggccgt cagctcttca  2340
ttaaagccga tcagatgtaa ttctagattg ccttaggcag gtgaggaaga aacaagtatt  2400
tgtaaaatat gagaccagca atgggccata gaaataacag caccagatcc tgccagcatt  2460
tagccctctg ttggtacaaa attaacaatt gaatatacag agacctactt ccagagtgta  2520
ccccaacaac aggcgtgagc atggtgctgg gtactagggt cctgctggaa aatcagagac  2580
cttacctaca gctgggacat gaccttgctt ccgacttacc caccacttct ggatacctca  2640
ccctcagccc acactatccc tggcctaggg cccagggtag agccagaaac atggagaaag  2700
catggcccct tgccgtacct ggagaactgg gtattttcca gagtctttat agatgtggac  2760
tggaaggcag gtggccacag ccgtgcagac ctgggtcagg tcagaaacct atgccatgct  2820
gggacctact caacagcaga agcatgaaga gggcctgagg acaagaaagg ccttcttacc  2880
atggtgctat tctggagctg ggatatatac ctggcttgtc tctgactgcc ctggcttctg  2940
gcagaacttc tgatgtcctc ctgaaggcct ctctcccacc ccagtacctg agaacctgag  3000
gataatttaa acatgggact ctggccagca cctgggagag acaggtagat ctctgatttt  3060
tgactcagcc tggtctatcg agtgagttcc aggacatctg gggctacaca gagaaaccat  3120
cttaaagact aaaaataata aacatgagac tgtaaactgg gtgtattttg ggagaaataa  3180
atgtcttttt ctttcaa                                                 3197

SEQ ID NO: 56          moltype = AA  length = 316
FEATURE                Location/Qualifiers
source                 1..316
                       mol_type = protein
                       organism = Mus musculus
SEQUENCE: 56
MLRGWGGPSV GVCVRTALGV LCLCLTGAVE VQVSEDPVVA LVDTDATLRC SFSPEPGFSL  60
AQLNLIWQLT DTKQLVHSFT EGRDQGSAYS NRTALFPDLL VQGNASLRLQ RVRVTDEGSY  120
TCFVSIQDFD SAAVSLQVAA PYSKPSMTLE PNKDLRPGNM VTITCSSYQG YPEAEVFWKD  180
GQGVPLTGNV TTSQMANERG LFDVHSVLRV VLGANGTYSC LVRNPVLQQD AHGSVTITGQ  240
PLTFPPEALW VTVGLSVCLV VLLVALAFVC WRKIKQSCEE ENAGAEDQDG DGEGSKTALR  300
PLKPSENKED DGQEIA                                                  316

SEQ ID NO: 57          moltype = DNA  length = 2605
FEATURE                Location/Qualifiers
source                 1..2605
                       mol_type = genomic DNA
                       organism = Homo sapiens
SEQUENCE: 57
gtgagtcacc aaggaaggca gcggcagctc cactcagcca gtacccagat acgctgggaa  60
ccttccccag ccatggcttc cctggggcag atcctcttct ggagcataat tagcatcatc  120
attattctgg ctggagcaat tgcactcatc attggctttg gtatttcagg gagacactcc  180
atcacagtca ctactgtcgc ctcagctggg aacattgggg aggatggaat cctgagctgc  240
acttttgaac ctgacatcaa actttctgat atcgtgatac aatggctgaa ggaaggtgtt  300
ttaggcttgg tccatgagtt caaagaaggc aaagatgagc tgtcggagca ggatgaaatg  360
ttcagaggcc ggacagcagt gtttgctgat caagtgatag ttggcaatgc ctctttgcgg  420
ctgaaaaacg tgcaactcac agatgctggc acctacaaat gttatatcat cacttctaaa  480
ggcaagggga atgctaacct tgagtataaa actggagcct tcagcatgcc ggaagtgaat  540
gtggactata atgccagctc agagaccttg cggtgtgagg ctccccgatg gttcccccag  600
cccacagtgg tctgggcatc ccaagttgac cagggagcca acttctcgga agtctccaat  660
accagctttg agctgaactc tgagaatgtg accatgaagg ttgtgtctgt gctctacaat  720
gttacgatca acaacacata ctcctgtatg attgaaaatg acattgccaa agcaacaggg  780
gatatcaaag tgacagaatc ggagatcaaa aggcggagtc acctacagct gctaaactca  840
aaggcttctc tgtgtgtctc ttctttcttt gccatcagct gggcacttct gcctctcagc  900
ccttacctga tgctaaaata atgtgcctcg gccacaaaaa agcatgcaaa gtcattgtta  960
caacagggat ctacagaact atttcaccac cagatatgac ctagttttat atttctggga  1020
ggaaatgaat tcatatctag aagtctggag tgagcaaaca agagcaagaa acaaaaagaa  1080
gccaaaagca gaaggctcca atatgaacaa gataaatcta tcttcaaaga catattagaa  1140
gttgggaaaa taattcatgt gaactagaca agtgtgttaa gagtgataag taaaatgcac  1200
gtggagacaa gtgcatcccc agatctcagg gacctccccc tgcctgtcac ctggggagtg  1260
agaggacagg atagtgcatg ttctttgtct ctgaattttt agttatatgt gctgtaatgt  1320
tgctctgagg aagcccctgg aaagtctatc ccaacatatc cacatcttat attccacaaa  1380
ttaagctgta gtatgtaccc taagacgctg ctaattgact gccacttcgc aactcagggg  1440
cggctgcatt ttagtaatgg gtcaaatgat tcactttttta tgatgcttcc aaaggtgcct  1500
tggcttctct tcccaactga caaatgccaa agttgagaaa aatgatcata attttagcat  1560
aaacagagca gtcggcgaca ccgattttat aaataaactg agcaccttct ttttaaacaa  1620
acaaatgcgg gtttatttct cagatgatgt tcatccgtga atggtccagg gaaggacctt  1680
tcaccttgtc tatatggcat tatgtcatca caagctctga ggcttctcct ttccatcctg  1740
cgtggacagc taagacctca gttttcaata gcatctagag cagtgggact cagctggggt  1800
```

```
gatttcgccc cccatctccg ggggaatgtc tgaagacaat tttggttacc tcaatgaggg  1860
agtggaggag gatacagtgc tactaccaac tagtggatag aggccaggga tgctgctcaa  1920
cctcctacca tgtacaggac gtctccccat tacaactacc caatccgaag tgtcaactgt  1980
gtcagggcta agaaaccctg gttttgagta gaaaagggcc tggaaagagg ggagccaaca  2040
aatctgtctg cttcctcaca ttagtcattg gcaaataagc attctgtctc tttggctgct  2100
gcctcagcac agagagccag aactctatcg ggcaccagga taacatctct cagtgaacag  2160
agttgacaag gcctatggga aatgccttgat gggattatct tcagcttgtt gagcttctaa  2220
gtttctttcc cttcattcta ccctgcaagc caagttctgt aagagaaatg cctgagttct  2280
agctcaggtt ttcttactct gaatttagat ctccagaccc tgcctggcca caattcaaat  2340
taaggcaaca aacatatacc ttccatgaag cacacacaga cttttgaaag caaggacaat  2400
gactgcttga attgaggcct tgaggaatga agctttgaag gaaaagaata ctttgtttcc  2460
agcccccttc ccacactctt catgtgttaa ccactgcctt cctggacctt ggagccacgg  2520
tgactgtatt acatgttgtt atagaaaact gattttagag ttctgatcgt tcaagagaat  2580
gattaaatat acatttccta cacca                                        2605

SEQ ID NO: 58          moltype = AA  length = 282
FEATURE                Location/Qualifiers
source                 1..282
                       mol_type = protein
                       organism = Homo sapiens
SEQUENCE: 58
MASLGQILFW SIISIIIILA GAIALIIGFG ISGRHSITVT TVASAGNIGE DGILSCTFEP  60
DIKLSDIVIQ WLKEGVLGLV HEFKEGKDEL SEQDEMFRGR TAVFADQVIV GNASLRLKNV  120
QLTDAGTYKC YIITSKGKGN ANLEYKTGAF SMPEVNVDYN ASSETLRCEA PRWFPQPTVV  180
WASQVDQGAN FSEVSNTSFE LNSENVTMKV VSVLYNVTIN NTYSCMIEND IAKATGDIKV  240
TESEIKRRSH LQLLNSKASL CVSSFFAISW ALLPLSPYLM LK                     282

SEQ ID NO: 59          moltype = DNA  length = 2622
FEATURE                Location/Qualifiers
source                 1..2622
                       mol_type = genomic DNA
                       organism = Mus musculus
SEQUENCE: 59
gtgagtcaca acacccagga gggcagcagc aggcaggcag ctccactcac caaaatctgg  60
ccccacacac agcaggactg tgggaaggaa ctccctctcc atggcttcct tggggcagat  120
catcttttgg agtattatta acatcatcat catcctggct ggggccatcg cactcatcat  180
tggctttggc atttcaggca agcacttcat cacggtcacg accttcacct cagctggaaa  240
cattggagag gacgggaccc tgagctgcac ttttgaacct gacatcaaac tcaacggcat  300
cgtcatccag tggctgaaag aaggcatcaa aggtttggtc cacgagttca aagaaggcaa  360
agacgacctc tcacagcagc atgagatgtt cagaggccgc acagcagtgt ttgctgatca  420
ggtggtagtt ggcaatgctt ccctgagact gaaaaacgtg cagctcacgg atgctggcac  480
ctacacatgt tacatccgca cctcaaaagg caaagggaat gcaaaccttg agtataagac  540
cggagccttc agtatgccag agataaatgt ggactataat gccagttcag agagtttacg  600
ctgcgaggct cctcggtggt tcccccagcc cacagtggcc tgggcatctc aagtcgacca  660
aggagccaat ttctcagaag tctccaacac cagctttgag ttgaactctg agaatgtgac  720
catgaaggtc gtatctgtgc tctacaatgt cacaatcaac aacacatact cctgtatgat  780
tgaaaacgac attgccaaag ccaccgggga catcaaagtg acagattcag aggtcaaaag  840
gcgaagtcag ctgcagttgc tgaactctgg gccttccccg tgtgtttttt cttctgcctt  900
tgtggctggc tgggcactcc tatctctctc ctgttgcctg atgctaagat gaggggccct  960
ggctacacaa aagcatgcaa cgttgctggt ccaacagaat cccggagaac tacagaaata  1020
ttttcctcaa gacatgacct agttttatat ttctagaaga agatgaaatc atgtctagaa  1080
gtctggagag agcagacagg aacaagatgt ggaaggaaaa caaaagtaac ccacagacac  1140
ccccgatcgg aacaagatgg acctagaaaa taattcaacc aaactagagt atactaagtg  1200
tgctgttaca atgtgtgtag ggtaggtgtc ctcccacatc tcaggggcct cccctggtcc  1260
accagctcct gagttaggat gggctgttat gatgtcactc tgaaggttcc tggatggttc  1320
ctactgccat atactcattt tatattcagc acattaaacc atagtgaatg ctatgaaaag  1380
ctgctaatca gctgccactc cgagattcgg aggtggcaac gtctgagtga caggtccagt  1440
gattcgcttc tccttaggat gcttttacaa gctctttggc gtctcctccc acctggcaaa  1500
tgccaaatgc ataggggagg gtgatcatca ttctagggca aacaaaatag ttgagggatg  1560
ctgatttccc aaatcatccg aatcacttct cccttgagca aacaagcgcc ctgttatttc  1620
tcaaatgctg ctttgtgaat cagtccaggg caaggcgctc tcctcatccc gctatgtggc  1680
cttaagtcat cgtaaggttt gaagtttcta ctttcgatcc tgcatggaga gctataatct  1740
cagctccccc gcccccccca cacacacctc tgcacacaca cccccccca acactgggag  1800
taaaccagga tgatgtccgt cttctcattc cccatgtgac cgttggcagt gtagagagac  1860
tgattgtcac agctaaagga agagggacaa cagggtcact ggtgtctaca gagattatat  1920
tctacgtgtc tcactgaatt tacacaactc caagtgccaa ccacatcaag gtcaggaaat  1980
cctgaactgg aataagaaag acccagaaga tgaatgtgaa cagatccatt tgcttcccga  2040
cagtgggcac agacttcagt ctctggctac tgttccaaga cccagggctc tgcaattgtg  2100
tgacatcctt cagtgaaccc acatgggaaa ttctccatgg aattatcttc agcccactgt  2160
acttctgaat ccctcttcct tccttctgtg ccacacagca agtctggctt aaatgctgcc  2220
tgatctccat ttcaagtttt ctgcctctgg atttttagat ctcaagacca tggacgaaac  2280
atcagttaca gcaacaaaag tgaattttcc gtgcagagac ttctaggggt tctgtttgtt  2340
ttcagggtgc tagagatcac actcagatgc tcatatatgt taggtaaatg ttctcccact  2400
gagttacagc ccagctcaca cagagacttc taaaagaaaa tacggccatg ctctttgaaa  2460
tggagcattg agggatgaag tttggatggc gaagaaaact tctcaccagc tctctcccca  2520
cattcgtgcc aagcactgcc tccctagact tcgggtcacc atatctgtac tacgttttga  2580
tacagaaggc tcgagaccat tcaagagaat tatttagtac ac                     2622

SEQ ID NO: 60          moltype = AA  length = 283
```

```
FEATURE                 Location/Qualifiers
source                  1..283
                        mol_type = protein
                        organism = Mus musculus
SEQUENCE: 60
MASLGQIIFW SIINIIIILA GAIALIIGFG ISGKHFITVT TFTSAGNIGE DGTLSCTFEP  60
DIKLNGIVIQ WLKEGIKGLV HEFKEGKDDL SQQHEMFRGR TAVFADQVVV GNASLRLKNV  120
QLTDAGTYTC YIRTSKGKGN ANLEYKTGAF SMPEINVDYN ASSESLRCEA PRWFPQPTVA  180
WASQVDQGAN FSEVSNTSFE LNSENVTMKV VSVLYNVTIN NTYSCMIEND IAKATGDIKV  240
TDSEVKRRSQ LQLLNSGPSP CVFSSAFVAG WALLSLSCCL MLR                  283

SEQ ID NO: 61           moltype = DNA  length = 4714
FEATURE                 Location/Qualifiers
source                  1..4714
                        mol_type = genomic DNA
                        organism = Homo sapiens
SEQUENCE: 61
agtcgcggga ggcttccccg cgccggccgc gtcccgcccg ctccccggca ccagaagttc  60
ctctgcgcgt ccgacggcga catgggcgtc cccacggccc tggaggccgg cagctggcgc  120
tggggatccc tgctcttcgc tctcttcctg gctgcgtccc taggtccggt ggcagccttc  180
aaggtcgcca cgccgtattc cctgtatgtc tgtcccgagg ggcagaacgt caccctcacc  240
tgcaggctct tgggccctgt ggacaaaggg cacgatgtga ccttctacaa gacgtggtac  300
cgcagctcga ggggcgaggt gcagacctgc tcagagcgcc ggcccatccg caacctcacg  360
ttccaggacc ttcacctgca ccatggaggc caccaggctg ccaacaccag ccacgacctg  420
gctcagcgcc acgggctgga gtcggcctcc gaccaccatg gcaacttctc catcaccatg  480
cgcaacctga ccctgctgga tagcggcctc tactgctgcc tggtggtgga gatcaggcac  540
caccactcgg agcacagggt ccatggtgcc atggagctgc aggtgcagac aggcaaagat  600
gcaccatcca actgtgtggt gtacccatcc tcctcccagg atagtgaaaa catcacggct  660
gcagccctgg ctacgggtgc ctgcatcgta ggaatcctct gcctcccccct catcctgctc  720
ctggtctaca agcaaaggca ggcagcctcc aaccgccgtg cccaggagct ggtgcggatg  780
gacagcaaca ttcaagggat tgaaaacccc ggctttgaag cctcaccacc tgcccagggg  840
atacccgagg ccaaagtcag gcacccccctg tcctatgtgg cccagcggca gccttctgag  900
tctgggcggc atctgctttc ggagcccagc accccccctgt ctcctccagg ccccggagac  960
gtcttcttcc catccctgga ccctgtccct gactctccaa actttgaggt catctagccc  1020
agctggggga cagtgggctg ttgtggctgg gtctggggca ggtgcatttg agccagggct  1080
ggctctgtga gtggcctcct tggcctcggc cctggttccc tccctcctgc tctgggctca  1140
gatactgtga catcccagaa gcccagcccc tcaacccctc tggatgctac atggggatgc  1200
tggacggctc agcccctgtt ccaaggattt tggggtgctg agattctccc ctagagacct  1260
gaaattcacc agctacagat gccaaatgac ttacatctta agaagtctca gaacgtccag  1320
cccttcagca gctctcgttc tgagacatga gccttgggat gtggcagcat cagtgggaca  1380
agatggacac tgggccaccc tcccaggcac cagacacagg gcacggtgga gagacttctc  1440
ccccgtggcc gccttggctc ccccgttttg cccgaggctg ctcttctgtc agacttcctc  1500
tttgtaccac agtggctctg gggccaggcc tgcctgccca ctggccatcg ccaccttccc  1560
cagctgcctc ctaccagcag tttctctgaa gatctgtcaa caggttaagt caatctgggg  1620
cttccactgc ctgcattcca gtccccagag cttggtggtc ccgaaacggg aagtacatat  1680
tggggcatgg tggcctccgt gagcaaatgg tgtcttgggc aatctgaggc caggacagat  1740
gttgccccac ccactggaga tggtgctgag ggaggtgggt ggggccttct gggaaggtga  1800
gtggagaggg gcacctgccc cccgccctcc ccatccccta ctcccactgc tcagcgcggg  1860
ccattgcaag ggtgccacac aatgtcttgt ccaccctggg acacttctga gtatgaagcg  1920
ggatgctatt aaaaactaca tggggaaaca ggtgcaaacc ctggagatgg attgtaagag  1980
ccagtttaaa tctgcactct gctgctcctc ccccaccccc accttccact ccatacaatc  2040
tgggcctggt ggagtcttcg cttcagagcc attcggccag gtgcgggtga tgttcccatc  2100
tcctgcttgt gggcatgccc tggctttgtt tttatacaca taggcaaggt gagtcctctg  2160
tggaattgtg attgaaggat tttaaagcag gggaggagag taggggggcat ctctgtacac  2220
tctgggggta aaacagggaa ggcagtgcct gagcatgggg acaggtgagg tggggctggg  2280
cagacccccct gtagcgttta gcaggatggg ggccccaggt actgtggaga gcatagtcca  2340
gcctgggcat ttgtctccta gcagcctaca ctggctctgc tgagctgggc ctgggtgctg  2400
aaagccagga tttggggcta ggcgggaaga tgttcgccca attgcttggg gggttggggg  2460
gatggaaaag gggagcacct ctaggctgcc tggcagcagt gagccctggg cctgtggcta  2520
cagccaggga accccacctg gacacatggc cctgcttcta agcccccccag ttaggcccaa  2580
aggaatggtc cactgagggc ctcctgctct gcctgggctg ggccaggggc tttgaggaga  2640
gggtaaacat aggcccggag atggggctga cacctcgagt ggccagaata tgcccaaacc  2700
ccggcttctc ccttgtccct aggcagaggg gggtcccttc ttttgttccc tctggtcacc  2760
acaatgcttg atgccagctg ccataggaag agggtgctgg ctggccatgg tggcacacac  2820
ctgtcctccc agcactttgc agggctgagg tggaaggacc gcttaagccc aggtgttcaa  2880
ggctgctgtg agctgtgttc gagccactac actccagcct ggggacggag caaaactttg  2940
cctcaaaaca aattttaaaa agaaagaaag aaggaaagag ggtatgtttt tcacaattca  3000
tgggggcctg catggcagga gtggggacag gacacctgct gttcctggag tcgaaggaca  3060
agcccacagc ccagattccg gttctcccaa ctcaggaaga gcatgccctg ccctctgggg  3120
aggctggcct ggccccagcc ctcagctgct gaccttgagg cagagacaac ttctaagaat  3180
ttggctgcca gaccccaggc ctggctgctg ctgtgtggag agggaggcgg cccgcagcag  3240
aacagccacc gcacttcctc ctcagcttcc tctggtgcgg ccctgccctc tcttctctgg  3300
acccttttac aactgaacgc atctgggctt cgtggtttcc tgttttcagc gaaatttact  3360
ctgagctccc agttccatct tcatccatgg ccacaggccc tgcctacaac gcactaggga  3420
cgtccctccc tgctgctgct ggggaggggc aggctgctgg agccgccctc tgagttgccc  3480
gggatggtag tgcctctgat gccagccctg gtggctgtgg gctggggtgc atgggagagc  3540
tgggtgcgag aacatggcgc ctccaggggg cgggaggagc actaggggct ggggcaggag  3600
gctcctggag cgctggattc gtggcacagt ctgaggccct gagagggaaa tccatgcttt  3660
taagaactaa ttcattgtta ggagatcaat caggaattag gggccatctt acctatctcc  3720
```

```
tgacattcac agtttaatag agacttcctg cctttattcc ctcccaggga gaggctgaag  3780
gaatggaatt gaaagcacca tttggagggt tttgctgaca cagcggggac tgctcagcac  3840
tccctaaaaa cacaccatgg aggccactgg tgactgctgg tgggcaggct ggccctgcct  3900
gggggagtcc gtggcgatgg gcgctggggt ggaggtgcag gagccccagg acctgctttt  3960
caaaagactt ctgcctgacc agagctccca ctacatgcag tggcccaggg cagaggggct  4020
gatacatggc ctttttcagg gggtgctcct cgcggggtgg acttgggagt gtgcagtggg  4080
acagggggct gcaggggtcc tgccaccacc gagcaccaac ttggcccctg gggtcctgcc  4140
tcatgaatga ggccttcccc agggctggcc tgactgtgct gggggctggg ttaacgtttt  4200
ctcagggaac cacaatgcac gaaagaggaa ctggggttgc taaccaggat gctgggaaca  4260
aaggcctctt gaagcccagc cacagcccag ctgagcatga ggcccagccc atagacggca  4320
caggccacct ggcccattcc ctgggcattc cctgctttgc attgctgctt ctcttcaccc  4380
catggaggct atgtcaccct aactatcctg gaatgtgttg agagggattc tgaatgatca  4440
atatagcttg gtgagacagt gccgagatag atagccatgt ctgccttggg cacgggagag  4500
ggaagtggca gcatgcatgc tgtttcttgg ccttttctgt tagaatactt ggtgctttcc  4560
aacacacttt cacatgtgtt gtaacttgtt tgatccaccc ccttccctga aaatcctggg  4620
aggttttatt gctgccattt aacacagagg gcaatagagg ttctgaaagg tctgtgtctt  4680
gtcaaaacaa gtaaacggtg gaactacgac taaa                              4714

SEQ ID NO: 62          moltype = AA  length = 311
FEATURE                Location/Qualifiers
source                 1..311
                       mol_type = protein
                       organism = Homo sapiens
SEQUENCE: 62
MGVPTALEAG SWRWGSLLFA LFLAASLGPV AAFKVATPYS LYVCPEGQNV TLTCRLLGPV  60
DKGHDVTFYK TWYRSSRGEV QTCSERRPIR NLTFQDLHLH HGGHQAANTS HDLAQRHGLE  120
SASDHHGNFS ITMRNLTLLD SGLYCCLVVE IRHHHSEHRV HGAMELQVQT GKDAPSNCVV  180
YPSSSQDSEN ITAAALATGA CIVGILCLPL ILLLVYKQRQ AASNRRAQEL VRMDSNIQGI  240
ENPGFEASPP AQGIPEAKVR HPLSYVAQRQ PSESGRHLLS EPSTPLSPPG PGDVFFPSLD  300
PVPDSPNFEV I                                                     311

SEQ ID NO: 63          moltype = DNA  length = 4846
FEATURE                Location/Qualifiers
source                 1..4846
                       mol_type = genomic DNA
                       organism = Mus musculus
SEQUENCE: 63
gggggcgctg ctgggcgggg agcttgctcg gccgcctgcc tcgccttggg ctcagcattc  60
actctagcga gcgagcggcg tgtacagccg gctccctggg ctcctggagt cccgcttgct  120
ccaagcgcac tccagcagtc tctttctgct cttgcccggc tcgacggcga catgggtgtc  180
cccgcggtcc cagaggccag cagcccgcgc tggggaaccc tgctccttgc tattttcctg  240
gctgcatcca gaggtctggt agcagccttc aaggtcacca ctccatattc tctctatgtg  300
tgtcccgagg gacagaatgc caccctcacc tgcaggattc tgggccccgt gtccaaaggg  360
cacgatgtga ccatctacaa gacgtggtac ctcagctcac gaggcgaggt ccagatgtgc  420
aaagaacacc ggcccatacg caacttcaca ttgcagcacc ttcagcacca cggaagccac  480
ctgaaagcca acgccagcca tgaccagccc cagaagcatg ggctagagct agcttctgac  540
caccacggta acttctctat caccctgcgc aatgtgaccc caagggacag cggcctctac  600
tgctgtctag tgatagaatt aaaaaaccac cacccagaac aacggttcta cgggtccatg  660
gagctacagg tacaggcagg caaaggctcg gggtccacat gcatggcgtc taatgagcag  720
gacagtgaca gcatcacggc tgcggccctg gccaccggcg cctgcatcgt gggaatcctc  780
tgcctccccc ttatcctgct gctggtctat aagcagagac aggtggcctc tcaccgccgt  840
gcccaggagt tggtgaggat ggacagcagc aacacccaag gaatcgaaaa cccaggcttc  900
gagaccactc cacccttcca ggggatgcct gaggccaaga ccaggccgcc actgtcctat  960
gtggcccagc ggcaaccttc ggagtcagga cggtacctgc tctctgaccc cagcacacct  1020
ctgtcgcctc caggccctgg ggacgtcttt ttcccatccc tagatccagt ccctgactcc  1080
cctaactctg aagccatcta aaccagctgg ggaaccatga accatggtac ctgggtcagg  1140
gatatgtgca cttgatctat ggctggccct tggacagtct tttaggcact gactccagct  1200
tccttgctcc tgctctgagc ctagactctg cttttacaag atgcacagac cctcccctat  1260
ctctttcaga cgctacttgg ggggcaggga gaagatgttg gattgctcat tgctgttctc  1320
aagatcttgg gatgctgagt tctccctaga gacttgactt cgacagccac agatgtcaga  1380
tgacctgcat cctatgaacg tccggcttgg caagagcctt tcttcatgga aaccagtagc  1440
ccggagggga tgaggtaggc accttgccac cctcccggga gagagacaca agatgtgaga  1500
gactcctgct cactgtgggg gtgtggctgg cctgcttgtt tgcctgagga tgctcctctg  1560
ttggactgac tctatccccc tggattctgg agcttggctg gcctatgtcc caccagagga  1620
gcatctcagc agccttccac cagcaacctg agggcctgcc agcttcgtgg ctctgggctc  1680
tcattacctg tatggccgtc cacagagctc agtggccaga ggctttgaaa caggaagtac  1740
atgtcaggtt caggaaccac tgtgagctca ttagtgtctt gagcaatgtg aggcctggac  1800
cagtggacac ggagggaggg tggcgagagg atgatgggga tgatgagggg aacacgctcc  1860
cttcctgtcc ttgtcatcca ccactaccac tattcagtgt ggagcagtgg caaaggtgac  1920
cgacctccac aatgtcctag tgatgctgga ccatttctaa gtgtgaaaga gatgctatta  1980
aaaacagtat gtggcaatgg ctgccaacag ctgagtggac tggaggcact ggctttaagg  2040
ccctggaggt gcagggcccg gtatggggat agggatggga gtttcagtga gggcctaggg  2100
atcactccgc ttctgaccac tcttcttctg agcctcacct cagggtgacc ttcaggcaca  2160
cagaagagct tgcccctggt ccgatactac tcttggctct catctccagg gtttggcatg  2220
acctgggcac acagggggag tcttcagaaa ggattttaaa gcatgaaaag aaagggtagt  2280
tcttgtgagg tagggatggg cagctgatgt ttgagagtga ggagggatac ggctgggcag  2340
atcactctcc agtctctaga gggaaagtag ctctaagtct gggagagcag cagcccagtg  2400
gtaccatatg tcttcttgca gcttccactg gctgggctga actgggcatg ggtaggaaag  2460
ctcctgttct gggcctgcag ccagggagaa ccccattcat tccctgagga cagatgggtg  2520
```

```
gggagagaag agagagtttc aggccgggaa gcagcaataa gctatctgct ggggacccag  2580
acaagttgtc tgatgaggtc caagatgtgg gatgccagtt atacctgggg cttggggatc  2640
cttagaggct ttgtatcatc atcataggag tgtcggggtg gccagggcat caaagccatg  2700
acccctgttt tatcctcagg gtccactctt ctgcaccatc cattgctcta gatctatgca  2760
gttactatag acagaatgtg ttgttctgtt tggctttggg gataatggcc tggcgaactg  2820
ccagctgttc agtggcaggg ctgtgaggcc agtcaaagac tagaacccac agaccagctg  2880
aacgatgagt atagcctgtc ccctggggga gcctgacctg tctccagccc taagcttcag  2940
acctcaccac tcagatgact tctaagaatt tgcctgtggg gacccctgca tggctgcagc  3000
tccgtggaaa ggagaggagg cccccagcag aagaaccact cgcttcctgc ccagcttcct  3060
cctgtagggc tctaagtctc ttcttcttgg gaccctgcaa gcaaaggcat gtcagcttgg  3120
tggtttcctg ttttgggtga agttttgtgt ggtccgggtt ctgtctacat ccatgaactt  3180
gggtgctacc accttgctgc tgctgtagag acagctgcag gatcttaggg tggaaaatgg  3240
aggtgccctg aggtgctagc ccttggggca aaagatgggg tggcaatgag acacagtggg  3300
gaactgagtt ccccaagagg agggaggagc cctgtagcct caagggccat attgggttcc  3360
tggtaccagc aaaagcctag agagcgaagt ctgtattttg aggaggtaat tgatccttac  3420
ggaatccatc agaaatttgg agcgggtgct ttatctatct ctggagggtc tctacctatc  3480
tccgatgaag ctctccctgg gcctgggatg ggagaaacca ggaggaaagg tgtctgataa  3540
agcaggggct tcttgacaag ccaaagggcc actggtagct gttgtggacc gagctgaccc  3600
tgctgaagta ttgtagtgtg ccttggacca acttctcaaa agagcaaccc cggggctacc  3660
ctacttctgc caggaagagg cggagaaggg gctgagaggc ctggaagggg ctagctcctt  3720
ctttgagaac tgctccccgg aggacttgga ggaggcggct aggctacggg ctgctgaggg  3780
ccctttgtct ttcctaacct gggcactgtt aggatgctcc ctcctggaaa aggctttcct  3840
gggtgtgagc tagagcagtg tccatgccag cgctgaacct gccatggtgg gagctgaact  3900
aaaaatttct cagggaacta aaataggcaa aagaggaact gggggaggag ggtgccaggc  3960
aggatggggg gaagggaggg cagtgcaaaa gtctcttgaa acacagacag cccagctgag  4020
tgccagtccc agatcacaga gaatacggct catctggctc atgttctgca tgcttgctgc  4080
tttaccctgg cactttcctt ctccaccatg agtgcgagtc ctgggagtcc tgggagggtg  4140
aggattaatg ccagcctggg gagcagatag ctgacagagt ccttgggtaa ctggcttgaa  4200
ccaggacctc aggattccac tctggggatc tagctttgtc tgggccagtg aagatctcta  4260
taatggcatt attgccaggg gataaacatt tcactgggtt ctgatctgtt gggtgtggct  4320
tcctggaaaa tatggtgaga ggaattctgc taaggataca gttgataaga aagttctgag  4380
attgattagt aatgcctgcc ttggactcag gaagggaagt ggcagtatga atgccatgtc  4440
ttaatcattt tggttaaaat atgcttccca aaagatttcc acgtgtgttc ttgtttattt  4500
gacatctgtc tccatatcag tcttgaaagc ctttctgtgt gtatatatat gatgtttgcg  4560
tgtatatatg tttttgtgtg tgcatatgga agtcagaaat cactgggtgt cttcctccat  4620
tcctttgcaa tgtatgtttt tttttttttt acgatttatt tactatatga atgttttgcc  4680
tgaatacatg cataggtgtc acgtacatgc ctgctggaac gcttggaact ggagttacag  4740
gtggctatga gctacagtgt gagcactggg aatcaaacct gggtcttctg caagagcaac  4800
aaattaaaag tcagctctta actacttgag ctatttttcc aactcc                 4846
```

```
SEQ ID NO: 64          moltype = AA  length = 309
FEATURE                Location/Qualifiers
source                 1..309
                       mol_type = protein
                       organism = Mus musculus
SEQUENCE: 64
MGVPAVPEAS SPRWGTLLLA IFLAASRGLV AAFKVTTPYS LYVCPEGQNA TLTCRILGPV  60
SKGHDVTIYK TWYLSSRGEV QMCKEHRPIR NFTLQHLQHH GSHLKANASH DQPQKHGLEL  120
ASDHHGNFSI TLRNVTPRDS GLYCCLVIEL KNHHPEQRFY GSMELQVQAG KGSGSTCMAS  180
NEQDSDSITA AALATGACIV GILCLPLILL LVYKQRQVAS HRRAQELVRM DSSNTQGIEN  240
PGFETTPPFQ GMPEAKTRPP LSYVAQRQPS ESGRYLLSDP STPLSPPGPG DVFFPSLDPV  300
PDSPNSEAI                                                         309
```

```
SEQ ID NO: 65          moltype = DNA  length = 2666
FEATURE                Location/Qualifiers
source                 1..2666
                       mol_type = genomic DNA
                       organism = Homo sapiens
SEQUENCE: 65
agttctcttc aagtcatgta atcgactttt ttgaattagt tttcagtttc attttgtttt  60
ccctaattca agttgggaac acttcatttt ccccaattca agttgggaac acttccttgg  120
tatttccttg ctacatggac tttagcaaat gctactttac tctccttcca gctactcagg  180
aggctgaggc aggagaatcg cttgaacccg ggaggcggag gttacagtga gccttttcct  240
agttttactg ttggaagcct aactcacagg agagattatg caatacagtc ctgaagtcaa  300
gggaggagag catgtaggag aatactaacc ctgcacagat tgtgatggtg atgtggaata  360
tactaaagcc tagaacgcac ctcctctgca tgactaatat gttctgcaca agacatgaag  420
gcacagacag cactgtcttt cttcctcatt ctcataacat ctctgagtgg atctcaaggc  480
atattccctt tggctttctt catttatgtt cctatgaatg aacaaatcgt cattggaaga  540
cttgatgaag atataattct cccttcttca tttgagaggg gatccgaagt cgtaatacac  600
tggaagtatc aagatagcta taaggttcac agttactaca aaggcagtga ccatttggaa  660
agccaagatc ccagatatgc aaacaggaca tcccttttct ataatgagat tcaaaatggg  720
aatgcgtcgc tatttttcag aagagtaagc cttctggacg aaggaattta cacctgctat  780
gtaggaacag caattcaagt gattacaaac aaagtggtgc taaaggtggg agtttttctc  840
acacccgtga tgaagtatga aaagaggaac acaaacagct tcttaatatg cagcgtgtta  900
agtgtttatc ctcgtccaat tatcacgtgg aaaatggaca acacacctat ctctgaaaac  960
aacatggaag aaacagggtc tttggattct ttttctatta acagcccact gaatattaca  1020
ggatcaaatt catcttatga atgtacaatt gaaaattcac tgctgaagca aacatggaca  1080
gggcgctgga cgatgaaaga tggccttcat aaaatgcaaa gtgaacacgt ttcactctca  1140
tgtcaacctg taaatgatta tttttcacca aaccaagact tcaaagttac ttggtccaga  1200
```

```
atgaaaagtg ggactttctc tgtcctggct tactatctga gctcctcaca aaatacaatt  1260
atcaatgaat cccgattctc atggaacaaa gagctgataa accagagtga cttctctatg  1320
aatttgatgg atcttaatct ttcagacagt ggggaatatt tatgcaatat ttcttcggat  1380
gaatatactt tacttaccat ccacacagtg catgtagaac cgagccaaga aacagcttcc  1440
cataacaaag gcttatggat tttggtgccc tctgcgattt tggcagcttt tctgctgatt  1500
tggagcgtaa aatgttgcag agcccagcta gaagccagga ggagcagaca ccctgctgat  1560
ggagcccaac aagaaagatg ttgtgtccct cctggtgagc gctgtcccag tgcaccccgat  1620
aatggcgaag aaaatgtgcc tctttcagga aaagtatagg aaatgagaga agactgtgac  1680
aactcatgac ctgcatcctt aatatccagt gacttcatct cccctttctt caccacaatt  1740
ccaggcaatg gcctgtcgga gcagacaatt ctaccactgc aaagagttgt aaccattttc  1800
tggtatcaca tttatttttc aagacatact tttcaagaca tcattcactg acccactacc  1860
tgcattgagt ataaatgcct ggatgttaag gattccaatt taactttgaa aagaactgtc  1920
tcattcattt acatttctgt tacagtcagc ccaggaggtt acagtgagct ctccactaag  1980
aatctggaag aaatgcatca ctaggggttg attcccaatc tgatcaactg ataatgggtg  2040
agagagcagg taagagccaa agtcacctta gtggaaaggt taaaaaccag agcctggaaa  2100
ccaagatgat tgatttgaca aggtatttta gtctagtttt atatgaacgg ttgtatcagg  2160
gtaaccaact cgatttggga tgaatcttag ggcaccaaag actaagacag tatctttaag  2220
attgctaggg aaaagggccc tatgtgtcag gcctctgagc ccaagccaag catcgcatcc  2280
cctgtgattt gcacgtatac atccagatgg cctaaagtaa ctgaagatcc acaaaagaag  2340
taaaaatagc cttaactgat gacattccac cattgtgatt tgttcctgcc ccaccctaac  2400
tgatcaatgt actttgtaat ctcccccacc cttaagaagg tactttgtaa tcttccccac  2460
ccttaagaag gttctttgta attctcccca cccttgagaa tgtactttgt gagatccacc  2520
ctgcccacaa aacattgctc ttaacttcac cgcctaaccc aaaacctata agaactaatg  2580
ataatccatc acccttcgct gactctcttt tcggactcag cccacctgca cccaggtgaa  2640
ataaacagct ttattgctca cacaaa                                      2666

SEQ ID NO: 66          moltype = AA  length = 414
FEATURE                Location/Qualifiers
source                 1..414
                       mol_type = protein
                       organism = Homo sapiens
SEQUENCE: 66
MKAQTALSFF LILITSLSGS QGIFPLAFFI YVPMNEQIVI GRLDEDIILP SSFERGSEVV  60
IHWKYQDSYK VHSYYKGSDH LESQDPRYAN RTSLFYNEIQ NGNASLFFRR VSLLDEGIYT  120
CYVGTAIQVI TNKVVLKVGV FLTPVMKYEK RNTNSFLICS VLSVYPRPII TWKMDNTPIS  180
ENNMEETGSL DSFSINSPLN ITGSNSSYEC TIENSLLKQT WTGRWTMKDG LHKMQSEHVS  240
LSCQPVNDYF SPNQDFKVTW SRMKSGTFSV LAYYLSSSQN TIINESRFSW NKELINQSDF  300
SMNLMDLNLS DSGEYLCNIS SDEYTLLTIH TVHVEPSQET ASHNKGLWIL VPSAILAAFL  360
LIWSVKCCRA QLEARRSRHP ADGAQQERCC VPPGERCPSA PDNGEENVPL SGKV        414

SEQ ID NO: 67          moltype = DNA  length = 2113
FEATURE                Location/Qualifiers
source                 1..2113
                       mol_type = genomic DNA
                       organism = Mus musculus
SEQUENCE: 67
acccttaaat aagagctgaa gatggctgca gctttctcct agactcctcc aggagaaact  60
ctaaagccag agcctggggg cagcattgtg tgtccacctt gccactgaga acatctacgg  120
aaattggaca ctctggcccc agcatccaca cgcttgactg ttggccacag taacacaggt  180
gtggatggtc cccagagcca gggtccagga gtgcactgag gatccctggg gcttcaagga  240
acccacagct ctgtccagac gggaattttt ttcctgagaa ctttcacctg ttgccctcct  300
atggtgaacc tggacttgac cttccactct gatgatgaag ggctccccct ccgtccctcc  360
agctggttgt ctcctccctc tgctcctcct gctgtttacc ggagtctctg gagaagtgtc  420
ttggtttcct gtgaagggac cagctgagcc catcactgtc ctgctgggga ctgaagccac  480
cctgccctgc cagctgtctc ctgaacagag tgcagctcgc atgcacatcc gatggtaccg  540
tgcccagccc acccctgctg tgctggtgtt ccacaacgga caggagcagg gagaggtgca  600
gatgccggaa tacaggggca ggacccagat ggtgagacaa gccattgaca tgggaagtgt  660
ggctctgcag atacagcagg tccaggcctc tgatgatggc ctgtaccact gtcagtttac  720
agatggcttc acctcccaag aggtctccat ggagcttcga gtcataggtt taggctctgc  780
ccctcttgtt cacatgacag gacctgagaa tgatgggatc cgagtgttgt gctcctcaag  840
tggctggttc ccaaaaccca aagtgcaatg gagagacacc tccgggaaca tgctactgtc  900
ctcctctgag ttgcagaccc aagacagaga agggctcttc caggtggaag tgtctctttt  960
ggtcacagat agagctattg gcaatgtgat ctgctccatc caaaatccca tgtatgacca  1020
ggagaaatcg aaggccatcc tcctcccaga gcccttcttc cccaagacgt gtccatggaa  1080
agtagccctg gtttgttctg tcctcatact attggtcctg ctcggtggga tcagccttgg  1140
aatctggaaa gaacatcaag tcaaaaggag agaaattaaa aaatggtcaa aggaacatga  1200
agaaatgctt ctgttgaaga aggggacaaa atctgtactg aagatcagag atgacctcca  1260
ggccgaccta gatcggagga aggcgctgta caaagaagac tggaagaagg ccttgctgta  1320
ccctgactgg aggaaggagc tgttccagag ggctcctgtg aggataaatt atgaaatgcc  1380
tgaccaggac aagacagact caaggacaga agagaacaga ggtgaggaga ctgtcagcag  1440
ctcacaagta gaccacaacc tcatcacact ctcccaggaa ggcttcatgt tgggaagata  1500
ctactgggag gtggatgtca aggacacaga ggagtggaca ctaggagttt atgagctgtg  1560
cactcaggat gcatcactta cagacccctt gaggaaattc agagtcctgg aaaagaatgg  1620
agatggatac agggctcttg acttctgttc ccaaaacatt aattcggaag aacctctgca  1680
actgaagaca cgtccgctga agatcgccat cttcttggat caggaagaca atgacctctc  1740
tttctacaac atgaccgatg agacacacat cttttccttt gcccaggtcc ctttcttggg  1800
atcaccctat ccttacttca cacgtaattc catggggctc tctgcaacag cacagcccta  1860
agtgatgtgc acagggaatt caatgggtgg gtgctgcagc gtgctacccg taaggccctc  1920
ttaggcaggc acagggggcc tctgaccaag aggcctctta acctgagact ccatgagcct  1980
```

```
cggggatcag atcctggaca agattctcgg accatctgtg tcgtgcatgg tgttatagtt  2040
attaatagcc ttccttcttt tgacaaaaat gtgtttaatc attcctaaga taaatgaatc  2100
catggctttc tga                                                     2113

SEQ ID NO: 68          moltype = AA  length = 509
FEATURE                Location/Qualifiers
source                 1..509
                       mol_type = protein
                       organism = Mus musculus
SEQUENCE: 68
MMKGSPSVPP AGCLLPLLLL LFTGVSGEVS WFSVKGPAEP ITVLLGTEAT LPCQLSPEQS  60
AARMHIRWYR AQPTPAVLVF HNGQEQGEVQ MPEYRGRTQM VRQAIDMGSV ALQIQQVQAS  120
DDGLYHCQFT DGFTSQEVSM ELRVIGLGSA PLVHMTGPEN DGIRVLCSSS GWFPKPKVQW  180
RDTSGNMLLS SSELQTQDRE GLFQVEVSLL VTDRAIGNVI CSIQNPMYDQ EKSKAILLPE  240
PFFPKTCPWK VALVCSVLIL LVLLGGISLG IWKEHQVKRR EIKKWSKEHE EMLLLKKGTK  300
SVLKIRDDLQ ADLDRRKALY KEDWKKALLY PDWRKELFQE APVRINYEMP DQDKTDSRTE  360
ENRGEETVSS SQVDHNLITL SQEGFMLGRY YWEVDVKDTE EWTLGVYELC TQDASLTDPL  420
RKFRVLEKNG DGYRALDFCS QNINSEEPLQ LKTRPLKIAI FLDQEDNDLS FYNMTDETHI  480
FSFAQVPFLG SPYPYFTRNS MGLSATAQP                                    509

SEQ ID NO: 69          moltype = DNA  length = 1818
FEATURE                Location/Qualifiers
source                 1..1818
                       mol_type = genomic DNA
                       organism = Homo sapiens
SEQUENCE: 69
actcattgca ccttcctgcc accccaggca gtgtctgggc cctcagctcc ccctccctcc  60
acctaccccc tcacacccac cactacgacc ccacgggata cccagcccag acggaggaaa  120
caccgagcct agagacatga gagttggagg agcattccac cttctactcg tgtgcctgag  180
cccagcactg ctgtctgctg tgcggatcaa cggggatgga caggaggtcc tgtacctggc  240
agaaggtgat aatgtgaggc tgggctgccc ctacgtcctg gaccctgagg actatggtcc  300
caatgggctg gacatcgagt ggatgcaggt caactcagac cccgcccacc accgagagaa  360
cgtgttcctt agttaccagg acaagaggat caaccatggc agccttcccc atctgcagca  420
gagggtccgc tttgcagcct cagacccaag ccagtacgat gcctccatca acctcatgaa  480
cctgcaggta tctgatacag ccacttatga gtgccgggtg aagaagacca ccatggccac  540
ccggaaggtc attgtcactg tccaagcacg acctgcagtg cccatgtgct ggacagaggg  600
ccacatgaca tatggcaacg atgtggtgct gaagtgctat gccagtgggg gctcccagcc  660
cctctcctac aagtgggcca agatcagtgg gcaccattac ccctatcgag ctgggtctta  720
cacctcccag cacagctacc actcagagct gtcctaccag gagtccttcc acagctccat  780
aaaccaaggc ctgaacaatg gggacctggt gttgaaggat atctccagag cagatgatgg  840
gctgtatcag tgcacagtgg ccaacaacgt gggctacagt gtttgtgtgg tggaggtgaa  900
ggtctcagac tcccggcgta taggcgtgat catcggcatc gtcctgggct ctctgctcgc  960
gctgggctgc ctggccgtag gcatctgggg gctcgtctgc tgctgctgcg ggggctccgg  1020
ggctggcggc gcccgcggtg ccttcggcta cggcaacggc ggcggggtcg gcggaggggc  1080
ctgcggcgac ttggctagtg agatcagaga ggacgccgtg gcgcccgggt gcaaggccag  1140
cgggcgcggc agccgcgtca cccacctcct ggggtacccg acgcagaacg tcagccgctc  1200
cctgcgccgc aagtacgcgc ctcccccctg cggcggcccc gaggacgtgg ccctggcgcc  1260
ctgcaccgcc gccgccgcct gcgaagcggg cccctccccg gtctacgtca aggtcaagag  1320
cgcggagccg gctgactgcg ccgaggggcc ggtgcagtgc aagaacggcc tcttggtgtg  1380
agcgcgcgcg ccgggccggg ctgcgcccca gccaggagga gggcgcgggg ctctctgtct  1440
gcagctgggg acacgtcggg gctggggacg acctcgctcg ccccaggctg ccaggcggct  1500
gggggtgaag gcatttccct aaggaaatgc gtagggaggc agagcctcct ccccaaaagt  1560
gggaaggggc gggcgagggc ggaggaaggc gatcctgagc cttctccgca cccccgggac  1620
cgaaggcttg gggagaggg agggaggagg aggctgagtg tcctagagcg gctgaggccg  1680
gaggcctggt gtccccagcc taagcagagg gccccggggg ccgggtgggt gggggtctgt  1740
ctggacgaat tgttctgtgt gtgaggtctg agctctgagg cagcagtgtt agcacaataa  1800
agaaacattg agacgtga                                                1818

SEQ ID NO: 70          moltype = AA  length = 414
FEATURE                Location/Qualifiers
source                 1..414
                       mol_type = protein
                       organism = Homo sapiens
SEQUENCE: 70
MRVGGAFHLL LVCLSPALLS AVRINGDGQE VLYLAEGDNV RLGCPYVLDP EDYGPNGLDI  60
EWMQVNSDPA HHRENVFLSY QDKRINHGSL PHLQQRVRFA ASDPSQYDAS INLMNLQVSD  120
TATYECRVKK TTMATRKVIV TVQARPAVPM CWTEGHMTYG NDVVLKCYAS GGSQPLSYKW  180
AKISGHHYPY RAGSYTSQHS YHSELSYQES FHSSINQGLN NGDLVLKDIS RADDGLYQCT  240
VANNVGYSVC VVEVKVSDSR RIGVIIGIVL GSLLALGCLA VGIWGLVCCC CGGSGAGGAR  300
GAFGYGNGGG VGGGACGDLA SEIREDAVAP GCKASGRGSR VTHLLGYPTQ NVSRSLRRKY  360
APPPCGGPED VALAPCTAAA ACEAGPSPVY VKVKSAEPAD CAEGPVQCKN GLLV        414

SEQ ID NO: 71          moltype = DNA  length = 1814
FEATURE                Location/Qualifiers
source                 1..1814
                       mol_type = genomic DNA
                       organism = Mus musculus
SEQUENCE: 71
actcattgca tcttcctgcc accccgggca gtgtctgggc cctccgctcc ccctccctcc  60
```

-continued

```
acctgcccct tccacccacc accaccagcc cactggagcc cagctcaggc ggaggaaaga  120
ccaagcctag agacatggga gttcgaggag cactccatct tctacttgtg tgcctgagcc  180
cagcactgtt gtctgctgta aggatcaacg gggatggcca ggaggtcatg tacctggcag  240
aaggtgacaa tgtgaggcta ggctgtccct acctcctgga tcctgaggat ttgggtacca  300
acagtctgga cattgagtgg atgcaagtca actcagagcc ctcacacagg gagaatgttt  360
ttcttactta tcaagacaag aggataggtc atggcaacct cccccatctg cagcagaggg  420
tccgctttgc agcctcagac cccagccagt acgatgcctc catcaacctc atgaacctgc  480
aggtatctga cacagcaacc tatgagtgcc gggtgaagaa gaccaccatg gccaccagga  540
aggtcattgt cactgtccaa gcacgtcctg cggtgcccat gtgttggacg gaaggccaca  600
tgtcaaaggg caacgatgtg gtgctgaagt gctttgccaa cggaggctct cagcccctct  660
cctacaagtg ggccaagatc agtgggcaca gtcacccccta ccgagctggg gcttaccact  720
cacagcacag cttccactct gagctttctt accaagagtc attccacagc accatcaacc  780
aaggcctggg caacggagac ctgctgttga agggcatcaa cgcagacgac gatgggctgt  840
atcagtgcac agtggccaac catgtgggct acagcgtctg tgtggtagag gtgaaagtct  900
cagactccca gcgagtaggc atgatcgttg gagcagtgct gggctctttg ctcatgctgg  960
cctgcctggc actaggcatc tgggggctca tctgctgctg ctgcggaggc ggcggggccg  1020
gtggtgcccg aggtgccttc ggctacgggg tcggcggcgg ggtcggcgga ggggcctgcg  1080
gcgacttggc tagtgagatc agagtggacg ccgaggcgcc cgggtgtaag gccagcgggc  1140
gcggcagccg cgtcacccac ctcctggggt acccgacgca gaacgtcagc cgctccctgc  1200
gccgcaagta cgcgcctccg ccctgcggcg gccccgagga cgtggcccta gtgccccgca  1260
ccgcctccgc ctcctgcgaa gcgggtccct cccccgtcta catcaaggtc aagagcgcgg  1320
agccggccga ctgcgccgac tgtgcccagg tcgagcagcg ctcgtgcaag gacggcctct  1380
tagtgtgagc gcacagcacc gggctgcgcc ccggctggga ggtggttcgg gggctctctg  1440
cccgcagctg ggacaggtt cggccagca gacctggctc tctcattggc cacctagcgg  1500
tggtaaggaa atttccctct gagaagccaa gccgggcaga ccctcctccc ctgtagtggg  1560
aggagaggcg ggggagacag aaaacagttc agagctctcc ctcacccctg gtttccaggg  1620
agaggaaggg agaggagagc tgtcggtatc ccagaaccgc agaggtacaa cccagatgtc  1680
cccagccaag gcgagggccc cccagccctg ggtaggtgga tgtcagggct gaattgctct  1740
gtgtgtgaga tctgagctcc aaggcaacag tgttagcaca ataaagaaac ttaaagactg  1800
aaaaaaaaaa aaaa                                                    1814
```

```
SEQ ID NO: 72          moltype = AA  length = 417
FEATURE                Location/Qualifiers
source                 1..417
                       mol_type = protein
                       organism = Mus musculus
SEQUENCE: 72
MGVRGALHLL LVCLSPALLS AVRINGDGQE VMYLAEGDNV RLGCPYLLDP EDLGTNSLDI  60
EWMQVNSEPS HRENVFLTYQ DKRIGHGNLP HLQQRVRFAA SDPSQYDASI NLMNLQVSDT  120
ATYECRVKKT TMATRKVIVT VQARPAVPMC WTEGHMSKGN DVVLKCFANG GSQPLSYKWA  180
KISGHSHPYR AGAYHSQHSF HSELSYQESF HSTINQGLGN GDLLLKGINA DDDGLYQCTV  240
ANHVGYSVCV VEVKVSDSQR VGMIVGAVLG SLLMLACLAL GIWGLICCCC GGGGAGGARG  300
AFGYGVGGGV GGGACGDLAS EIRVDAEAPG CKASGRGSRV THLLGYPTQN VSRSLRRKYA  360
PPPCGGPEDV ALVPRTASAS CEAGPSPVYI KVKSAEPADC ADCAQVEQRS CKDGLLV     417
```

```
SEQ ID NO: 73          moltype = DNA  length = 3523
FEATURE                Location/Qualifiers
source                 1..3523
                       mol_type = genomic DNA
                       organism = Homo sapiens
SEQUENCE: 73
agtcctgggg cagggctggg tggcacggct ggcgagcccg gaacgcctct ggtcacagct  60
cagcgtccgc ggagccgggc ggcgctgcag ctgcacttgg ctcgtctgtg ggtctgacag  120
tcccagctct gcgcggggaa cagcggcccg gcgctgggtg tgggaggacc aggctgcccc  180
aagagcgcgg agactcacgc ccgctcctct cctgttgcga ccgggagccg ggtaggaggc  240
aggcgcgctc cctgcggccc cggatgact tctcagcgtt cccctctggc gcctttgctg  300
ctcctctctc tgcacggtgt tgcagcatcc ctggaagtgt cagagagccc tgggagtatc  360
caggtggccc ggggtcagcc agcagtcctg ccctgcactt tcactaccag cgctgccctc  420
attaacctca atgtcatttg gatggtcact cctctctcca atgccaacca acctgaacag  480
gtcatcctgt atcagggtgg acagatgttt gatggtgccc cccggttcca cggtagggta  540
ggatttacag gcaccatgcc agctaccaat gtctctatct tcattaataa cactcagtta  600
tcagacactg gcacctacca gtgcctggtc aacaaccttc cagacatagg gggcaggaac  660
attggggtca ccggtctcac agtgttagtt ccccctctg ccccacactg ccaaatccaa  720
ggatcccagg atattggcag cgatgtcatc ctgctctgta gctcagagga aggcattcct  780
cgaccaactt acctttggga gaagttagac aataccctca aactacctcc aacagctact  840
caggaccagg tccagggaac agtcaccatc cggaacatca gtgccctgtc ttcaggtttg  900
taccagtgcg tggcttctaa tgctattgga accagcacct gtcttctgga tctccaggtt  960
atttcacccc agcccaggaa cattggacta atagctggag ccattggcac tggtgcagtt  1020
attatcattt tttgcattgc actaatttta ggggcattct tttactggag aagcaaaaat  1080
aaagaggagg aagaagaaga aattcctaat gaaataagag aggatgatct tccacccaag  1140
tgttcttctg ccaaagcatt tcacactgag atttcctcct cggacaacaa cacactaacc  1200
tcttccaatg cctacaacag tcgatactgg agcaacaatc caaaagttca tagaaacaca  1260
gagtcagtca gccacttcag tgacttgggc caatctttct ctttccactc aggcaatgcc  1320
aacataccat ccatttatgc taatgggacc catctggtcc cgggtcaaca taagactctg  1380
gtagtgacag ccaacagagg gtcatcacca caggtgatgt ccaggagcaa tggctcagtc  1440
agtaggaagc ctcggcctcc acacactcat tcctacacca tcagccacgc aacactggaa  1500
cgaattggtg cagtacctgt catggtacca gcccagagtc gggccgggtc cttggtatag  1560
gacatgagga aatgttgtgt tcagaaatga ataaatggaa tgccctcata caagggggag  1620
ggtggggtgg ggagtgctgg gaaagaaaca cttccttata attatattag taaaatgcac  1680
```

```
aaagaagaag gcagtgctgt tacttggcca ctaagatgtg taaaatggac tgaaatgctc  1740
catcatgaag acttgcttcc ccaccaaaga tgtcctggga ttctgctgga tctcaaagat  1800
gtgccaagcc aaggaaaaag atacaagagc agaatagtac ttaaaatcca aactgccgcc  1860
cagatgggct tgttcttcat gcctaactta ataattttta agagattaaa gtgccagatg  1920
gagtttaaat attgaaatta ttttaaaagg taggtgtctt taagaaaata acaagcaacc  1980
ctgtgatatg ttccgtctct cccaattccc tcgttatata gagggcttaa tggtataaat  2040
ggttaatatt ggtcccaaca gggctgactc ttctatcata taatcaaaac tttttacatg  2100
agcaaaattc agtaagaaat gggggaagac aaaggaaacg tctttgagaa gccccttcat  2160
atttatttat ttatctcttc ctgaaccatg aatttcatat gtggaatatt gctatattga  2220
cagattcttg cctgtctgtg ttattctagg atctgttaca ggtccatggc aattactgtt  2280
tatttttcc tggaaaaata tttttttata aaaggctttt tttttttttt aaatacatga  2340
gaggcattgg gctaagaaag aaaagactgt tgtataatac cttgttcaat ggttgtattt  2400
agtgagctca tagaggtcca tcatatcatg accgagctag gttgtgtggg caggaaggta  2460
gggctaaggg gttgtagcct tgctgggcag cctctcagag caaggttgtt cagatctccc  2520
ttgctattac agtaggttac tattaatgag ggcagcacct gatgcctttt gtactgaggt  2580
atgtaacttt ctccttattt gacaagtaga agttaactta cttgtcaggg agggcagacg  2640
ttttttgtt ctgtttcgtt tttcaaaata atgctttttg caaaagaggt aagactgaga  2700
ctaaaggtgt tatcttctgg tgtgctcctg gaagtgtcta ccctacattt gtgtcagctc  2760
agggttgcag tgttgcccag atgcatttta catcactgta aagagattac ttttgtggtt  2820
actacctggc ttggctggcc ttgcggttca ccagattaat ttacaaactc ccccacttta  2880
ttttgtgcta tgtagatctg gccatacttg cattagtgac tgtcttgcct taaccacact  2940
taagcaaccc acaaatttct tctcagattt gtttcctaga ttacttatga tactcatccc  3000
atgtctcaat aagagtgtct tttctttctg gatgtgttct cttactccct cttaccacca  3060
tactttttgc tctcttctcc tgcaagcgta gtcttcacag ggagtggctt cctgacattt  3120
ttttcagtta tgtgaatgaa tggaaaccaa cagctgctgc aaacactgtt tttccaagaa  3180
ggctacactc agaacctaac cattgccaac catttcagta ttgataaaaa gctgaattta  3240
ctttagcatt acttattttt ttttccattt gatggttctt actttgtaaa aatttaaata  3300
aatgaatgtc tatacttttt ataaagaaaa gtgaaaatac catgacactg aaaagatgat  3360
gctatcagat gctgtttaga aagcatttat cttgcatttc tttattcttt ctaattatct  3420
aaaattcaat aaaattttat tcatataaaa taagttgtca ttaattatca atactaacga  3480
gtatgtcatt ttaaaactta gtattctctt taatgttaca aga                    3523

SEQ ID NO: 74          moltype = AA  length = 431
FEATURE                Location/Qualifiers
source                 1..431
                       mol_type = protein
                       organism = Homo sapiens
SEQUENCE: 74
MTSQRSPLAP LLLLSLHGVA ASLEVSESPG SIQVARGQPA VLPCTFTTSA ALINLNVIWM  60
VTPLSNANQP EQVILYQGGQ MFDGAPRFHG RVGFTGTMPA TNVSIFINNT QLSDTGTYQC  120
LVNNLPDIGG RNIGVTGLTV LVPPSAPHCQ IQGSQDIGSD VILLCSSEEG IPRPTYLWEK  180
LDNTLKLPPT ATQDQVQGTV TIRNISALSS GLYQCVASNA IGTSTCLLDL QVISPQPRNI  240
GLIAGAIGTG AVIIIFCIAL ILGAFFYWRS KNKEEEEEEI PNEIREDDLP PKCSSAKAFH  300
TEISSSDNNT LTSSNAYNSR YWSNNPKVHR NTESVSHFSD LGQSFSFHSG NANIPSIYAN  360
GTHLVPGQHK TLVVTANRGS SPQVMSRSNG SVSRKPRPPH THSYTISHAT LERIGAVPVM  420
VPAQSRAGSL V                                                       431

SEQ ID NO: 75          moltype = DNA  length = 3430
FEATURE                Location/Qualifiers
source                 1..3430
                       mol_type = genomic DNA
                       organism = Mus musculus
SEQUENCE: 75
cggctggtgg tggccgcggc ggccggcgag cccgggacgc ccgagcctgc cccgagcctc  60
ggcggagcgg agtggcctcg gcgctcccgt gtcccgcttg gtcccacgct gcaccccgcc  120
gcccaggagc ccggcggacg gcggctcccc cggcggctcc ggcatgactc ggcggcgctc  180
cgctccggcg tcctggctgc tcgtgtcgct gctcggtgtc gcaacatccc tggaagtgtc  240
cgagagccca ggcagtgtcc aggtggcccg gggccagaca gcagtcctgc cctgcgcctt  300
ctccaccagt gctgccctcc tgaacctcaa tgtcatttgg atggtcattc ccctctccaa  360
tgcaaaccag cccgaacagg tcattcttta tcagggtgga caaatgtttg acggcgccct  420
ccggttccac gggagggtag gatttaccgg caccatgcct gctaccaatg tctcgatctt  480
catcaataac acacagctgt cagatacggg cacgtaccag tgcttggtga ataaccttcc  540
agacagaggg ggcagaaaca tcggggtcac tggcctcaca gtgttagtcc cccctctgc  600
tccacaatgc caaatccaag gatcccagga cctcggcagt gacgtcatcc ttctgtgtag  660
ttcagaggaa ggcatccctc ggcccacgta cctttgggag aagttagata atacgctcaa  720
gctacctcca acagccactc aggaccaggt ccagggaaca gtcaccatcc ggaatatcag  780
tgccctctct tccggtctgt accagtgtgt ggcttctaat gccatcggga ccagcacctg  840
tctgctggac ctccaggtta tctcacccca gccccggagc gttggagtaa tagccggagc  900
ggttggcacc ggtgctgttc ttatcgtcat ctgccttgca ctaatttcag gggcgttctt  960
ttactggaga agcaaaaaca aagaggagga ggaggaagaa attcctaatg aaatcagaga  1020
ggatgatctt ccccctaaat gctcttctgc caaagccttc cacacggaga tatcctcctc  1080
agaaaataac acgctgacct cttccaatac ctacaacagt cgatactgga acaacaatcc  1140
aaaaccccat agaaacacag agtctttcaa ccacttcagt gacttacgcc agtctttctc  1200
tggcaatgca gttatcccat caatctatgc aaatgggaac catctggttt tgggtccaca  1260
taagactctg gtagttacag ccaacagagg gtcatcacct caggtcttgc ccaggaacaa  1320
tggttcagtc agcaggaagc cttggcctca acacactcat tcctacacag taagccaaat  1380
gaccctggag cgcatcggtg cagtgcctgt catggtgcct gcccagagtc gagcagggtc  1440
cctggtatag gatgactgag gaaaccatgt tcagaagaga ataaatggac cgccttcagg  1500
caagggggga gcactgcctt caggcaaggg gggagcactg ccttcaggca agagggagag  1560
```

-continued

```
tgggatgggt gagtgctgaa aaataaactt ttgttacgat tccattagca aaaagcacaa  1620
agaggaggcg tgtgtgaagt ggcctggggt tgttccataa tgaagactca agaagactgt  1680
ttccccacca cagatgtcct gagattcagt taaaacgaaa catgctgcat ctccagagat  1740
gtgccaagcc aaggagaatg ctagaagcag agtaaagctt acccccccaaa ctgtggtcca  1800
gctggacccc ttctttaatt cttgcctaac ttaattattt tcaggaccct tcaagtgcca  1860
ggtggaattt acataatgaa attatttttt aaaaataggt gtccttaggg agagaaaaca  1920
ggagcaagct catggtctgg cctagtctcc ctctcccact ccttctgatg acactagcaa  1980
tgcattccat ctgacctgac tttatcatag aggcaaaatt gttcagaaca ctggctggag  2040
atggggagaa ataaggaaac ttcttgtgaa caccctacac acacacacac acacacacac  2100
acacacacac acacacacac acacacacac acacacacat ttatttacct cctcctgaac  2160
catgaatcgt attggtgatt ttgctatatt gacagattct catctgttac actctaggat  2220
ctctcacagg tctgtggcaa ttactgttca tgatttcctg aaaaaatatt tttttaaaag  2280
aaaactattt tttttaaata ctagagagac agtggactag gaaagcgaga acttgccgcc  2340
ttgtctagtg actgtattca atgactgaac agaggccccc cccaccatac aagagtttta  2400
ggtgattgag tgggtggaac cagctggagc caggtgggag gggcctttac attgccagca  2460
gggcccccaaa gaattgagat tgtgtatggc aaccgttaat gaggacagcg cctgatgcct  2520
tttgtaccga ggaagataat tgcctcttgt ttgacaagta gagtttagta ggttattaca  2580
aaaagggcaa gagttgtttt ggttttgttt ctttcaaaat aatttttttt caaaagaata  2640
acaagggtta ggcaaatggg ggaccttcct gtgtgctctt ggggtctgc tcagcatctg  2700
gaaatttggg tgtgcgattt tccctgaaca cattgcatac cagtgtaaaa agactctgcc  2760
tcccccccttt ttggcttttt tactgggctt ggctggcctt gcagtttacc agattcattt  2820
acagactctc tgctctgtat ggcgccgcct gccatgtctg tcttggtgac tatcctgcct  2880
taatcacttt gctttagggc aactcatggt gatctcttcc aagatctgtt tttaaattgt  2940
ttggactact tgagccacaa ctctcagagg acattccttt tttttttttt tttttttct  3000
cctttcttcc attgctttgt ccctcttccc ctgtgcttcc tgccttcttt ccctgtccca  3060
tgggcacagt cctcacaggg agtggcctcc tctctccagt gatgtaagtg aatggaagcc  3120
atcactggct gcacatacct ttttcaaaag ggacactcgg gaagtcactg ctgtgaccgt  3180
ttcgatgttg ataagaaggt gaatttactg tagtgttacc accttctccc cacttgatgg  3240
ttcttgactt tgtaaaaatt taaataaatg aatgtctata ctttttaagg aaaagagaaa  3300
ataccatgtc acagaaaagg tgaaactatt agatgctgtt tagaaagcat ttatcttgca  3360
tttctttatt ctttctaatt acctaaaatt caataaaagt ttattcatat aaaaaaaaaa  3420
aaaaaaaaaa                                                         3430

SEQ ID NO: 76           moltype = AA  length = 428
FEATURE                 Location/Qualifiers
source                  1..428
                        mol_type = protein
                        organism = Mus musculus
SEQUENCE: 76
MTRRRSAPAS WLLVSLLGVA TSLEVSESPG SVQVARGQTA VLPCAFSTSA ALLNLNVIWM  60
VIPLSNANQP EQVILYQGGQ MFDGALRFHG RVGFTGTMPA TNVSIFINNT QLSDTGTYQC  120
LVNNLPDRGG RNIGVTGLTV LVPPSAPQCQ IQGSQDLGSD VILLCSSEEG IPRPTYLWEK  180
LDNTLKLPPT ATQDQVQGTV TIRNISALSS GLYQCVASNA IGTSTCLLDL QVISPQPRSV  240
GVIAGAVGTG AVLIVICLAL ISGAFFYWRS KNKEEEEEEI PNEIREDDLP PKCSSAKAFH  300
TEISSSENNT LTSSNTYNSR YWNNNPKPHR NTESFNHFSD LRQSFSGNAV IPSIYANGNH  360
LVLGPHKTLV VTANRGSSPQ VLPRNNGSVS RKPWPQHTHS YTVSQMTLER IGAVPVMVPA  420
QSRAGSLV                                                           428

SEQ ID NO: 77           moltype = DNA  length = 1807
FEATURE                 Location/Qualifiers
source                  1..1807
                        mol_type = genomic DNA
                        organism = Homo sapiens
SEQUENCE: 77
acagacgctg gcggccacca gaagtttgag cctctttggt agcaggaggc tggaagaaag  60
gacagaagta gctctggctg tgatggggat cttactgggc ctgctactcc tggggcacct  120
aacagtggac acttatggcc gtcccatcct ggaagtgcca gagagtgtaa caggaccttg  180
gaaaggggat gtgaatcttc cctgcaccta tgaccccctg caaggctaca cccaagtctt  240
ggtgaagtgg ctggtacaac gtggctcaga ccctgtcacc atctttctac gtgactcttc  300
tggagaccat atccagcagg caaagtacca gggccgcctg catgtgagcc acaaggttcc  360
aggagatgta tccctccaat tgagcaccct ggagatggat gaccggagcc actacacgtg  420
tgaagtcacc tggcagactc ctgatggcaa ccaagtcgtg agagataaga ttactgagct  480
ccgtgtccag aaactctctg tctccaagcc cacagtgaca actggcagcg gttatggctt  540
cacggtgccc cagggaatga ggattagcct tcaatgccag gctcggggtt ctcctcccat  600
cagttatatt tggtataagc aacagactaa taaccaggaa cccatcaaag tagcaaccct  660
aagtacctta ctcttcaagc ctgcggtgat agccgactca ggctcctatt tctgcactgc  720
caagggccag gttggctctg agcagcacag cgacattgtg aagtttgtgg tcaaagactc  780
ctcaaagcta ctcaagacca agactgaggc acctacaacc atgacatacc ccttgaaagc  840
aacatctaca gtgaagcagt cctgggactg gaccactgac atggatggct accttggaga  900
gaccagtgct gggccaggaa agagcctgcc tgtctttgcc atcatcctca tcatctcctt  960
gtgctgtatg gtggttttta ccatggccta tatcatgctc tgtcggaaga catcccaaca  1020
agagcatgtc tacgaagcag ccagggcaca tgccagagag gccaacgact ctggagaaac  1080
catgagggtg gccatcttcg caagtggctg ctccagtgat gagccaactt cccagaatct  1140
gggcaacaac tactctgatg agccctgcat aggacaggag taccagatca tcgcccagat  1200
caatggcaac tacgcccgcc tgctggacac agttcctctg gattatgagt ttctggccac  1260
tgagggcaaa agtgtctgtt aaaaatgccc cattaggcca ggatctgctg acataattgc  1320
ctagtcagtc cttgccttct gcatggcctt cttccctgct acctctcttc ctggatagcc  1380
caaagtgtcc gcctaccaac actggagccg ctgggagtca ctggctttgc cctggaattt  1440
gccagatgca tctcaagtaa gccagctgct ggatttggct ctgggccctt ctagtatctc  1500
```

```
tgccgggggc ttctggtact cctctctaaa taccagaggg aagatgccca tagcactagg  1560
acttggtcat catgcctaca gacactattc aactttggca tcttgccacc agaagacccg  1620
agggaggctc agctctgcca gctcagagga ccagctatat ccaggatcat ttctctttct  1680
tcagggccag acagctttta attgaaattg ttatttcaca ggccagggtt cagttctgct  1740
cctccactat aagtctaatg ttctgactct ctcctggtgc tcaataaata tctaatcata  1800
acagcaa                                                            1807

SEQ ID NO: 78          moltype = AA  length = 399
FEATURE                Location/Qualifiers
source                 1..399
                       mol_type = protein
                       organism = Homo sapiens
SEQUENCE: 78
MGILLGLLLL GHLTVDTYGR PILEVPESVT GPWKGDVNLP CTYDPLQGYT QVLVKWLVQR  60
GSDPVTIFLR DSSGDHIQQA KYQGRLHVSH KVPGDVSLQL STLEMDDRSH YTCEVTWQTP  120
DGNQVVRDKI TELRVQKLSV SKPTVTTGSG YGFTVPQGMR ISLQCQARGS PPISYIWYKQ  180
QTNNQEPIKV ATLSTLLFKP AVIADSGSYF CTAKGQVGSE QHSDIVKFVV KDSSKLLKTK  240
TEAPTTMTYP LKATSTVKQS WDWTTDMDGY LGETSAGPGK SLPVFAIILI ISLCCMVVFT  300
MAYIMLCRKT SQQEHVYEAA RAHAREANDS GETMRVAIFA SGCSSDEPTS QNLGNNYSDE  360
PCIGQEYQII AQINGNYARL LDTVPLDYEF LATEGKSVC                         399

SEQ ID NO: 79          moltype = DNA  length = 1434
FEATURE                Location/Qualifiers
source                 1..1434
                       mol_type = genomic DNA
                       organism = Mus musculus
SEQUENCE: 79
agctaccagc acttccaggt tcttcagcag caagaggatg gaaggatgaa tagaagtagc  60
ttcaaatagg atggagatct catcaggctt gctgttcctg ggccacctaa tagtgctcac  120
ctatggccac cccaccctaa aaacacctga gagtgtgaca gggacctgga aaggagatgt  180
gaagattcag tgcatctatg atcccctgag aggctacagg caagttttgg tgaaatggct  240
ggtaagacac ggctctgact ccgtcaccat cttcctacgt gactccactg gagaccatat  300
ccagcaggca aagtacagag gccgcctgaa agtgagccac aaagttccag gagatgtgtc  360
cctccaaata aataccctgc agatggatga caggaatcac tatacatgtg aggtcacctg  420
gcagactcct gatggaaacc aagtaataag agataagatc attgagctcc gtgttcggaa  480
atataatcca cctagaatca atactgaagc acctacaacc ctgcactcct ctttggaagc  540
aacaactata atgagttcaa cctctgactt gaccactaat gggactggaa aacttgagga  600
gaccattgct ggttcaggga ggaacctgcc aatctttgcc ataatcttca tcatctccct  660
ttgctgcata gtagctgtca ccatacctta tatcttgttc cgctgcagga cattccaaca  720
agagtatgtc tatggagtga gcagggtgtt tgccaggaag acaagcaact ctgaagaaac  780
cacaagggtg actaccatcg caactgatga accagattcc caggctctga ttagtgacta  840
ctctgatgat ccttgcctca gccaggagta ccaaataacc atcagatcaa caatgtctat  900
tcctgcctgc tgaacacagt ttccagaaac taagaagttc ttgctactga agaaaataac  960
atctgctaaa atgcccctac taagtcaagg tctactggcg taattacctg ttacttattt  1020
actacttgcc ttcaacatag ctttctccct ggcttccttt cttcttagac aacctaaagt  1080
atctatctag tctgccaatt ctggggccat tgagaaatcc tgggtttggc taagaatata  1140
ctacatgcac ctcaagaaat ctagcttctg ggcttcaccc agaacaattt tcttcctagg  1200
gccttcacaa ctcttctcca aacagcagag aaattccata gcagtagagg ttctttatca  1260
tgcctccaga cagcgtgagt ctcagtccta caaactcaga caagcacatg ggtctaggat  1320
tactcctctt tctctagggc cagatgactt ttaattgata ttactattgc tacattatga  1380
atctaatgca catgtattct tttgttgtta ataaatgttt aatcatgaca tcaa        1434

SEQ ID NO: 80          moltype = AA  length = 280
FEATURE                Location/Qualifiers
source                 1..280
                       mol_type = protein
                       organism = Mus musculus
SEQUENCE: 80
MEISSGLLFL GHLIVLTYGH PTLKTPESVT GTWKGDVKIQ CIYDPLRGYR QVLVKWLVRH  60
GSDSVTIFLR DSTGDHIQQA KYRGRLKVSH KVPGDVSLQI NTLQMDDRNH YTCEVTWQTP  120
DGNQVIRDKI IELRVRKYNP PRINTEAPTT LHSSLEATTI MSSTSDLTTN GTGKLEETIA  180
GSGRNLPIFA IIFIISLCCI VAVTIPYILF RCRTFQQEYV YGVSRVFARK TSNSEETTRV  240
TTIATDEPDS QALISDYSDD PCLSQEYQIT IRSTMSIPAC                         280

SEQ ID NO: 81          moltype = DNA  length = 2237
FEATURE                Location/Qualifiers
source                 1..2237
                       mol_type = genomic DNA
                       organism = Homo sapiens
SEQUENCE: 81
atttggagag ttaaaactgt gcctaacaga ggtgtcctct gacttttctt ctgcaagctc  60
catgttttca catcttccct ttgactgtgt cctgctgctg ctgctgctac tacttacaag  120
gtcctcagaa gtggaataca gagcggaggt cggtcagaat gcctatctgc cctgcttcta  180
caccccagcc gccccaggga acctcgtgcc cgtctgctgg ggcaaaggag cctgtcctgt  240
gtttgaatgt ggcaacgtgg tgctcaggac tgatgaaagg gatgtgaatt attggacatc  300
cagatactgg ctaaatgggg atttccgcaa aggagatgtg tccctgacca tagagaatgt  360
gactctagca gacagtggga tctactgctg ccggatccaa atcccaggca taatgaatga  420
tgaaaaattt aacctgaagt tggtcatcaa accagccaag gtcacccctg caccgactcg  480
gcagagagac ttcactgcag cctttccaag gatgcttacc accaggggac atggcccagc  540
```

```
agagacacag acactgggga gcctccctga tataaatcta acacaaatat ccacattggc  600
caatgagtta cgggactcta gattggccaa tgacttacgg gactctggag caaccatcag  660
aataggcatc tacatcggag cagggatctg tgctgggctg gctctggctc ttatcttcgg  720
cgctttaatt ttcaaatggt attctcatag caaagagaag atacagaatt taagcctcat  780
ctctttggcc aacctccctc cctcaggatt ggcaaatgca gtagcagagg gaattcgctc  840
agaagaaaac atctatacca ttgaagagaa cgtatatgaa gtggaggagc ccaatgagta  900
ttattgctat gtcagcagca ggcagcaacc ctcacaacct ttgggttgtc gctttgcaat  960
gccatagatc caaccacctt atttttgagc ttggtgtttt gtctttttca gaaactatga  1020
gctgtgtcac ctgactggtt ttggaggttc tgtccactgc tatggagcag agttttccca  1080
ttttcagaag ataatgactc acatgggaat tgaactggga cctgcactga acttaaacag  1140
gcatgtcatt gcctctgtat ttaagccaac agagttaccc aacccagaga ctgttaatca  1200
tggatgttag agctcaaacg ggcttttata tacactagga attcttgacg tggggtctct  1260
ggagctccag gaaattcggg cacatcatat gtccatgaaa cttcagataa actagggaaa  1320
actgggtgct gaggtgaaag cataactttt ttggcacaga aagtctaaag ggccactga  1380
ttttcaaaga gatctgtgat ccctttttgt tttttgtttt tgagatggag tcttgctctg  1440
ttgcccaggc tggagtgcaa tggcacaatc tcggctcact gcaagctccg cctcctgggt  1500
tcaagcgatt ctcctgcctc agcctcctga gtggctggga ttacaggcat gcaccaccat  1560
gcccagctaa tttgttgtat ttttagtaga gacagggttt caccatgttg gccagtgtgg  1620
tctcaaactc ctgacctcat gatttgcctg cctcggcctc ccaaagcact gggattacag  1680
gcgtgagcca ccacatccag ccagtgatcc ttaaaagatt aagagatgac tggaccaggt  1740
ctaccttgat cttgaagatt cccttggaat gttgagattt aggcttattt gagcactgcc  1800
tgcccaactg tcagtgccag tgcatagccc ttcttttgtc tcccttatga agactgccct  1860
gcagggctga gatgtggcag gagctcccag ggaaaaacga agtgcatttg attggtgtgt  1920
attggccaag ttttgcttgt tgtgtgcttg aaagaaaata tctctgacca acttctgtat  1980
tcgtggacca aactgaagct atatttttca cagaagaaga agcagtgacg gggacacaaa  2040
ttctgttgcc tggtggaaag aaggcaaagg ccttcagcaa tctatattac cagcgctgga  2100
tcctttgaca gagagtggtc cctaaactta aatttcaaga cggtataggc ttgatctgtc  2160
ttgcttattg ttgccccctg cgcctagcac aattctgaca cacaattgga acttactaaa  2220
aatttttttt tactgtt                                                 2237

SEQ ID NO: 82          moltype = AA  length = 301
FEATURE                Location/Qualifiers
source                 1..301
                       mol_type = protein
                       organism = Homo sapiens
SEQUENCE: 82
MFSHLPFDCV LLLLLLLLTR SSEVEYRAEV GQNAYLPCFY TPAAPGNLVP VCWGKGACPV  60
FECGNVVLRT DERDVNYWTS RYWLNGDFRK GDVSLTIENV TLADSGIYCC RIQIPGIMND  120
EKFNLKLVIK PAKVTPAPTR QRDFTAAFPR MLTTRGHGPA ETQTLGSLPD INLTQISTLA  180
NELRDSRLAN DLRDSGATIR IGIYIGAGIC AGLALALIFG ALIFKWYSHS KEKIQNLSLI  240
SLANLPPSGL ANAVAEGIRS EENIYTIEEN VYEVEEPNEY YCYVSSRQQP SQPLGCRFAM  300
P                                                                  301

SEQ ID NO: 83          moltype = DNA  length = 2725
FEATURE                Location/Qualifiers
source                 1..2725
                       mol_type = genomic DNA
                       organism = Mus musculus
SEQUENCE: 83
accattttaa ccgaggagct aaagctatcc ctacacagag ctgtccttgg atttcccctg  60
ccaagtactc atgttttcag gtcttaccct caactgtgtc ctgctgctgc tgcaactact  120
acttgcaagg tcattggaaa atgcttatgt gtttgaggtt ggtaagaatg cctatctgcc  180
ctgcagttac actctatcta cacctggggc acttgtgcct atgtgctggg gcaagggatt  240
ctgtccttgg tcacagtgta ccaacgagtt gctcagaact gatgaaagaa atgtgacata  300
tcagaaatcc agcagatacc agctaaaggg cgatctcaac aaaggagacg tgtctctgat  360
cataaagaat gtgactctgg atgaccatgg gacctactgc tgcaggatac agttccctgg  420
tcttatgaat gataaaaaat tagaactgaa attagacatc aaagcagcca aggtcactcc  480
agctcagact gcccatgggg actctactac agcttctcca agaaccctaa ccacggagag  540
aaatggttca gagacacaga cactggtgac cctccataat aacaatggaa caaaaatttc  600
cacatgggct gatgaaatta aggactctgg agaaacgatc agaactgcta tccacattgg  660
agtgggagtc tctgctgggt tgaccctggc acttatcatt ggtgtcttaa tccttaaatg  720
gtattcctgt aagaaaaaga agttatcgag tttgagcctt attacactgg ccaacttgcc  780
tccaggaggg ttggcaaatg caggagcagt caggattcgc tctgaggaaa atatctacac  840
catcgaggag aacgtatatg aagtggagaa ttcaaatgag tactactgct acgtcaacag  900
ccagcagcca tcctgaccgc ctctggactg ccactttttaa aggctcgcct tcatttctga  960
ctttggtatt tccctttttg aaaactatgt gatatgtcac ttggcaacct cattggaggt  1020
tctgaccaca gccactgaga aaagagttcc agttttctgg ggataattaa ctcacaaggg  1080
gattcgactg taactcatgc tacattgaaa tgctccattt tatccctgag tttcagggat  1140
cggatctccc actccagaga cttcaatcat gcgtgttgaa gctcactcgt gctttcatac  1200
attaggaatg gttagtgtga tgtctttgag acatagaggt ttgtggtata tctgcaaagc  1260
tcctgaacag gtagggggaa taaagggcta agataggaag gtgaggttct ttgttgatgt  1320
tgaaaatcta aagaagttgg tagcttttct agagatttct gaccttgaaa gattaagaaa  1380
aagccaggtg gcatatgctt aacactatat aacttgggaa ccttaggcag gagggtgata  1440
agttcaaggt cagccagggc tatgctggta agactgtctc aaaatccaaa gacgaaaata  1500
aacatagaga cagcaggagg ctggagatga ggctcggaca gtgaggtgca ttttgtacaa  1560
gcacgaggaa tctatatttg atcgtagacc ccacatgaaa aagctaggcc tggtagagca  1620
tgcttgtaga ctcaagagat ggagaggtaa aggcacaaca gatccccggg gcttgcgtgc  1680
agtcagctta gcctaggtgc tgagttccaa gtccacaaga gtccctgtct caaagtaaga  1740
tggactgagt atctggcgaa tgtccatggg ggttgtcctc tgctctcaga agagacatgc  1800
```

```
acatgaacct gcacacacac acacacacac acacacacac acacacacac acacacacac  1860
acacacatga aatgaaggtt ctctctgtgc ctgctacctc tctataacat gtatctctac  1920
aggactctcc tctgcctctg ttaagacatg agtgggagca tggcagagca gtccagtaat  1980
taattccagc actcagaagg ctggagcaga agcgtggaga gttcaggagc actgtgccca  2040
acactgccag actcttctta cagaagaaaa aggttacccg caagcagcct gctgtctgta  2100
aaaggaaacc ctgcgaaagg caaactttga ctgttgtgtg ctcaagggga actgactcag  2160
acaacttctc cattcctgga ggaaactgga gctgtttctg acagaagaac aaccggtgac  2220
tgggacatac gaaggcagag ctcttgcagc aatctatata gtcagcaaaa tattctttgg  2280
gaggacagtc gtcaccaaat tgatttccaa gccggtggac ctcagtttca tctggcttac  2340
agctgcctgc ccagtgccct tgatctgtgc tggctcccat ctataacaga atcaaattaa  2400
atagaccccg agtgaaaata ttaagtgagc agaaaggtag ctttgttcaa agattttttt  2460
gcattgggga gcaactgtgt acatcagagg acatctgtta gtgaggacac caaaacctgt  2520
ggtaccgttt tttcatgtat gaattttgtt gtttaggttg cttctagcta gctgtggagg  2580
tcctggcttt cttaggtggg tatggaaggg agaccatcta acaaaatcca ttagagataa  2640
cagctctcat gcagaaggga aaactaatct caaatgtttt aaagtaataa aactgtactg  2700
gcaaagtact ttgagcatat ttaaa                                        2725

SEQ ID NO: 84          moltype = AA  length = 281
FEATURE                Location/Qualifiers
source                 1..281
                       mol_type = protein
                       organism = Mus musculus
SEQUENCE: 84
MFSGLTLNCV LLLLQLLLAR SLENAYVFEV GKNAYLPCSY TLSTPGALVP MCWGKGFCPW  60
SQCTNELLRT DERNVTYQKS SRYQLKGDLN KGDVSLIIKN VTLDDHGTYC CRIQFPGLMN  120
DKKLELKLDI KAAKVTPAQT AHGDSTTASP RTLTTERNGS ETQTLVTLHN NNGTKISTWA  180
DEIKDSGETI RTAIHIGVGV SAGLTLALII GVLILKWYSC KKKKLSSLSL ITLANLPPGG  240
LANAGAVRIR SEENIYTIEE NVYEVENSNE YYCYVNSQQP S                     281

SEQ ID NO: 85          moltype = DNA  length = 1330
FEATURE                Location/Qualifiers
source                 1..1330
                       mol_type = genomic DNA
                       organism = Homo sapiens
SEQUENCE: 85
agactcctgg gtccggtcaa ccgtcaaaat gtccaaagaa cctctcattc tctggctgat  60
gattgagttt tggtggcttt acctgacacc agtcacttca gagactgttg tgacggaggt  120
tttgggtcac cgggtgactt tgccctgtct gtactcatcc tggtctcaca acagcaacag  180
catgtgctgg gggaaagacc agtgccccta ctccggttgc aaggaggcgc tcatccgcac  240
tgatggaatg agggtgacct caagaaagtc agcaaaatat agacttcagg ggactatccc  300
gagaggtgat gtctccttga ccatcttaaa ccccagtgaa agtgacagcg gtgtgtactg  360
ctgccgcata gaagtgcctg gctggttcaa cgatgtaaag ataaacgtgc gcctgaatct  420
acagagagcc tcaacaacca cgcacagaac agcaaccacc accacacgca gaacaacaac  480
aacaagcccc accaccaccc gacaaatgac aacaacccca gctgcacttc caacaacagt  540
cgtgaccaca cccgatctca caaccggaac accactccag atgacaacca ttgccgtctt  600
cacaacagca aacacgtgcc tttcactaac cccaagcacc cttccggagg aagccacagg  660
tcttctgact cccgagcctt ctaaggaagg gcccatcctc actgcagaat cagaaactgt  720
cctccccagt gattcctgga gtagtgttga gtctacttct gctgacactg tcctgctgac  780
atccaaagag tccaaagttt gggatctccc atcaacatcc cacgtgtcaa tgtggaaaac  840
gagtgattct gtgtcttctc ctcagcctgg agcatctgat acagcagttc ctgagcagaa  900
caaaacaaca aaaacaggac agatggatgg aatacccatg tcaatgaaga atgaaatgcc  960
catctcccaa ctactgatga tcatcgcccc ctccttggga tttgtgctct tcgcattgtt  1020
tgtggcgttt ctcctgagag ggaaactcat ggaaacctat tgttcgcaga aacacacaag  1080
gctagactac attggagata gtaaaaatgt cctcaatgac gtgcagcatg gaagggaaga  1140
cgaagacggc ctttttaccc tctaacaacg cagtagcatg ttagattgag gatgggggca  1200
tgacactcca gtgtcaaaat aagtcttagt agatttcctt gtttcataaa aaagactcac  1260
ttattccatg gatgtcattg atccaggctt gctttagttt catgaatgaa gggtacttta  1320
gagaccacaa                                                         1330

SEQ ID NO: 86          moltype = AA  length = 378
FEATURE                Location/Qualifiers
source                 1..378
                       mol_type = protein
                       organism = Homo sapiens
SEQUENCE: 86
MSKEPLILWL MIEFWWLYLT PVTSETVVTE VLGHRVTLPC LYSSWSHNSN SMCWGKDQCP  60
YSGCKEALIR TDGMRVTSRK SAKYRLQGTI PRGDVSLTIL NPSESDSGVY CCRIEVPGWF  120
NDVKINVRLN LQRASTTTHR TATTTTRRTT TTSPTTTRQM TTTPAALPTT VVTTPDLTTG  180
TPLQMTTIAV FTTANTCLSL TPSTLPEEAT GLLTPEPSKE GPILTAESET VLPSDSWSSV  240
ESTSADTVLL TSKESKVWDL PSTSHVSMWK TSDSVSSPQP GASDTAVPEQ NKTTKTGQMD  300
GIPMSMKNEM PISQLLMIIA PSLGFVLFAL FVAFLLRGKL METYCSQKHT RLDYIGDSKN  360
VLNDVQHGRE DEDGLFTL                                                378

SEQ ID NO: 87          moltype = DNA  length = 2175
FEATURE                Location/Qualifiers
source                 1..2175
                       mol_type = genomic DNA
                       organism = Mus musculus
SEQUENCE: 87
```

```
agatcctatc aaaatgtcca aggggcttct cctcctctgg ctggtgacgg agctctggtg  60
gctttatctg acaccagctg cctcagagga tacaataata gggtttttgg gccagccggt  120
gactttgcct tgtcattacc tctcgtggtc ccagagccgc aacagtatgt gctggggcaa  180
aggttcatgt cccaattcca agtgcaatgc agagcttctc cgtacagatg gaacaagaat  240
catctccagg aagtcaacaa aatatacact tttggggaag gtccagtttg gtgaagtgtc  300
cttgaccatc tcaaacacca atcgaggtga cagtggggtg tactgctgcc gtatagaggt  360
gcctggctgg ttcaatgatg tcaagaagaa tgtgcgcttg gagctgagga gagccacaac  420
aaccaaaaaa ccaacaacaa ccacccggcc aaccaccacc ccttatgtga ccaccaccac  480
cccagagctg cttccaacaa cagtcatgac cacatctgtt ctcccaacca ccacaccacc  540
ccagacacta gccaccactg ccttcagtac agcagtgacc acgtgcccct caacaacacc  600
tggctccttc tcacaagaaa ccacaaaagg gtccgccttc actacagaat cagaaactct  660
gcctgcatcc aatcactctc aaagaagcat gatgaccata tctacagaca tagccgtact  720
caggcccaca ggctctaacc ctgggattct cccatccact tcacagctga cgacacagaa  780
aacaacatta acaacaagtg agtctttgca gaagacaact aaatcacatc agatcaacag  840
cagacagacc atcttgatca ttgcctgctg tgtgggattt gtgctaatgg tgttattgtt  900
tctggcgttt ctccttcgag ggaaagtcac aggagccaac tgtttgcaga gacacaagag  960
gccagacaac actgaagata gtgacagcgt cctcaatgac atgtcacacg ggagggatga  1020
tgaagacggg atcttcactc tctgactcac catctttatt taggattaag gatagggaat  1080
ggcacttgaa ttgtcaaaat aagtttgggg acattgtaat ttccgtttaa agtctcactc  1140
tgtttactga tgctgtgggt cctgtctggt tgtatcttcc cacatgaagg tgctttagag  1200
acacattttc cctgcctcgt gccttagtcc tctttgttgt tttgtggcta ggtgactttt  1260
cacactgggc ttgaacactg tcagtgatgg tgaaatcctt gccacagctt tgggagtctc  1320
ttgcagtctc ccagcagtag agggagttag aaatatccag aggggaaaaa aaaatctctc  1380
ttttcagaca gtatctgctt tattggtggt agctgaactt catttataca gagctccttt  1440
aacctgtctg tcttcttctt ggtatctaag ctgccttttg tttttgtttt tgtttttgtt  1500
tttatgatat taacttcttt tcacattcaa gtttctttaa agttgactat agtgccttct  1560
gaactcttgc agagagtttg gattttggaa gctgccaggt acccatcaca gcaggggtgc  1620
cagtgacaag gatggtgtac aaatgaaaca ctgaagctat ccaaataaat tcctctaagt  1680
gtaattcatt ttactgcagc acaggaagaa caaatttgtc ttacaacttt aataattagt  1740
accattatga accctaggag agaaataaga gcaaatacct gttgaataaa tgaatgtaag  1800
aaaatgtgtg tctgagcaag aatactctgt ctggctacta tgggaagcta gctagatctg  1860
aaagacattc tcagactatc ctcatgttca aggcattaaa ggaataagcc tccagcccct  1920
aaccttagga gaattctgca gtcaagtgag gagtttttaa aacaggaatc tctaggttcc  1980
agtcctctag ctattctttt atgcttagtc caggtaatga gttgaacatc caagtatttt  2040
ttaaggaccc aaagaaatgc aaccagagct attaccagaa ttttggagtg gtcctcctag  2100
agttgccgca tgttgctggg aaaattgggg tcttagagtt cttagtctac ttaataaaag  2160
aattttaaaa aatgg                                                  2175
```

```
SEQ ID NO: 88           moltype = AA  length = 343
FEATURE                 Location/Qualifiers
source                  1..343
                        mol_type = protein
                        organism = Mus musculus
SEQUENCE: 88
MSKGLLLLWL VTELWWLYLT PAASEDTIIG FLGQPVTLPC HYLSWSQSRN SMCWGKGSCP  60
NSKCNAELLR TDGTRIISRK STKYTLLGKV QFGEVSLTIS NTNRGDSGVY CCRIEVPGWF  120
NDVKKNVRLE LRRATTTKKP TTTTRPTTTP YVTTTTPELL PTTVMTTSVL PTTTPPQTLA  180
TTAFSTAVTT CPSTTPGSFS QETTKGSAFT TESETLPASN HSQRSMMTIS TDIAVLRPTG  240
SNPGILPSTS QLTTQKTTLT TSESLQKTTK SHQINSRQTI LIIACCVGFV LMVLLFLAFL  300
LRGKVTGANC LQRHKRPDNT EDSDSVLNDM SHGRDDEDGI FTL                   343
```

```
SEQ ID NO: 89           moltype = DNA  length = 3491
FEATURE                 Location/Qualifiers
source                  1..3491
                        mol_type = genomic DNA
                        organism = Homo sapiens
SEQUENCE: 89
agcacagaga gtggaaaaca gcagaggtga cagagcagcc gtgctcgaag cgttcctgga  60
gcccaagctc tcctccacag gtgaagacag ggccagcagg agacaccatg gggcacctct  120
cagccccact tcacagagtg cgtgtaccct ggcaggggct tctgctcaca gcctcacttc  180
taaccttctg gaacccgccc accactgccc agctcactac tgaatccatg ccattcaatg  240
ttgcagaggg gaaggaggtt cttctccttg tccacaatct gccccagcaa ctttttggct  300
acagctggta caaaggggaa agagtggatg gcaaccgtca aattgtagga tatgcaatag  360
gaactcaaca agctacccca gggcccgcaa acagcggtcg agagacaata taccccaatg  420
catccctgct gatccagaac gtcacccaga atgacacagg attctacacc ctacaagtca  480
taaagtcaga tcttgtgaat gaagaagcaa ctggacagtt ccatgtatac ccggagctgc  540
ccaagccctc catctccagc aacaactcca accctgtgga ggacaaggat gctgtggcct  600
tcacctgtga acctgagact caggacacaa cctacctgtg gtggataaac aatcagagcc  660
tcccggtcag tcccaggctg cagctgtcca atggcaacag gaccctcact ctactcagtg  720
tcacaaggaa tgacacagga ccctatgagt gtgaaataca gaacccagtg agtgcgaacc  780
gcagtgaccc agtcaccttg aatgtcacct atggcccgga cacccccacc atttcccctt  840
cagacaccta ttaccgtcca ggggcaaacc tcagcctctc ctgctatgca gcctctaacc  900
cacctgcaca gtactcctgg cttatcaatg gaacattcca gcaaagcaca caagagctct  960
ttatccctaa catcactgtg aataatagtg gatcctatac ctgccacgcc aataactcag  1020
tcactggctg caacaggacc acagtcaaga cgatcatagt cactgagcta agtccagtag  1080
tagcaaagcc ccaaatcaaa gccagcaaga ccacagtcac aggagataag gactctgtga  1140
acctgacctg ctccacaaat gacactggaa tctccatccg ttggttcttc aaaaaccaga  1200
gtctcccgtc ctcggagagg atgaagctgt cccagggcaa caccaccctc agcataaacc  1260
ctgtcaagag ggaggatgct gggacgtatt ggtgtgaggt cttcaaccca atcagtaaga  1320
```

-continued

```
accaaagcga ccccatcatg ctgaacgtaa actataatgc tctaccacaa gaaaatggcc  1380
tctcacctgg ggccattgct ggcattgtga ttggagtagt ggccctggtt gctctgatag  1440
cagtagccct ggcatgtttt ctgcatttcg ggaagaccgg cagggcaagc gaccagcgtg  1500
atctcacaga gcacaaaccc tcagtctcca accacactca ggaccactcc aatgacccac  1560
ctaacaagat gaatgaagtt acttattcta ccctgaactt tgaagcccag caacccacac  1620
aaccaacttc agcctcccca tccctaacag ccacagaaat aatttattca gaagtaaaaa  1680
agcagtaatg aaacctgtcc tgctcactgc agtgctgatg tatttcaagt ctctcaccct  1740
catcactagg agattccttt cccctgtagg ggtagagggg tggggacaga aacaactttc  1800
tcctactctt ccttcctaat aggcatctcc aggctgcctg gtcactgccc ctctctcagt  1860
gtcaatagat gaaagtacat tgggagtctg taggaaaccc aaccttcttg tcattgaaat  1920
ttggcaaagc tgactttggg aaagagggac cagaacttcc cctcccttcc cctttttccca  1980
acctggactt gttttaaact tgcctgttca gagcactcat tccttcccac ccccagtcct  2040
gtcctatcac tctaattcgg atttgccata gccttgaggt tatgtccttt tccattaagt  2100
acatgtgcca ggaaacaaga gagagagaaa gtaaaggcag taatgccttc tcctatttct  2160
ccaaagcctt gtgtgaactc accaaacaca agaaaatcaa atatataacc aatagtgaaa  2220
tgccacacct ttgtccactg tcagggttgt ctacctgtag gatcagggtc taagcacctt  2280
ggtgcttagc tagaatacca cctaatcctt ctggcaagcc tgtcttcaga gaacccacta  2340
gaagcaacta ggaaaatcac ttgccaaaat ccaaggcaat tcctgatgga aaatgcaaaa  2400
gcacatatat gttttaatat ctttatgggc tctgttcaag gcagtgctga gagggagggg  2460
ttatagcttc aggagggaac cagcttctga taaacacaat ctgctaggaa cttgggaaag  2520
gaatcagaga gctgcccttc agcgattatt taaattattg ttaaagaata cacaatttgg  2580
ggtattggga tttttctcct tttctctgag acattccacc attttaattt ttgtaactgc  2640
ttatttatgt gaaaagggtt atttttactt agcttagcta tgtcagccaa tccgattgcc  2700
ttaggtgaaa gaaaccaccg aaatccctca ggtcccttgg tcaggagcct ctcaagattt  2760
tttttgtcag aggctccaaa tagaaaataa gaaaaggttt tcttcattca tggctagagc  2820
tagatttaac tcagtttcta ggcacctcag accaatcatc aactaccatt ctattccatg  2880
tttgcacctg tgcatttttct gtttgccccc attcactttg tcaggaaacc ttggcctctg  2940
ctaaggtgta tttggtcctt gagaagtggg agcaccctac agggacacta tcactcatgc  3000
tggtggcatt gtttacagct agaaagctgc actggtgcta atgccccttg gggaaatggg  3060
gctgtgagga ggaggattat aacttaggcc tagcctcttt taacagcctc tgaaatttat  3120
cttttcttct atggggtcta taaatgtatc ttataataaa aaggaaggac aggaggaaga  3180
caggcaaatg tacttctcac ccagtcttct acacagatgg aatctctttg gggctaagag  3240
aaaggtttta ttctatattg cttacctgat ctcatgttag gcctaagagg ctttctccag  3300
gaggattagc ttggagttct ctatactcag gtacctcttt cagggttttc taaccctgac  3360
acggactgtg catactttcc ctcatccatg ctgtgctgtg ttatttaatt tttcctggct  3420
aagatcatgt ctgaattatg tatgaaaatt attctatgtt tttataataa aaataatata  3480
tcagacatcg a                                                        3491

SEQ ID NO: 90          moltype = AA  length = 526
FEATURE                Location/Qualifiers
source                 1..526
                       mol_type = protein
                       organism = Homo sapiens
SEQUENCE: 90
MGHLSAPLHR VRVPWQGLLL TASLLTFWNP PTTAQLTTES MPFNVAEGKE VLLLVHNLPQ  60
QLFGYSWYKG ERVDGNRQIV GYAIGTQQAT PGPANSGRET IYPNASLLIQ NVTQNDTGFY  120
TLQVIKSDLV NEEATGQFHV YPELPKPSIS SNNSNPVEDK DAVAFTCEPE TQDTTYLWWI  180
NNQSLPVSPR LQLSNGNRTL TLLSVTRNDT GPYECEIQNP VSANRSDPVT LNVTYGPDTP  240
TISPSDTYYR PGANLSLSCY AASNPPAQYS WLINGTFQQS TQELFIPNIT VNNSGSYTCH  300
ANNSVTGCNR TTVKTIIVTE LSPVVAKPQI KASKTTVTGD KDSVNLTCST NDTGISIRWF  360
FKNQSLPSSE RMKLSQGNTT LSINPVKRED AGTYWCEVFN PISKNQSDPI MLNVNYNALP  420
QENGLSPGAI AGIVIGVVAL VALIAVALAC FLHFGKTGRA SDQRDLTEHK PSVSNHTQDH  480
SNDPPNKMNE VTYSTLNFEA QQPTQPTSAS PSLTATEIIY SEVKKQ                  526

SEQ ID NO: 91          moltype = DNA  length = 3736
FEATURE                Location/Qualifiers
source                 1..3736
                       mol_type = genomic DNA
                       organism = Mus musculus
SEQUENCE: 91
aaagctcctt taagaaaagc agggcagata tcagggcagc ctggcttagc agtagtgttg  60
gagaagaagc tagcaggcag gcagcagaga catggagctg gcctcagcac atctccacaa  120
agggcaggtt ccctggggag gactactgct cacagcctca cttttagcct cctggagccc  180
tgccaccact gctgaagtca ccattgaggc tgtgccgccc caggttgctg aagacaacaa  240
tgttcttcta cttgttcaca atctgcccct ggcgcttgga gcctttgcct ggtacaaggg  300
aaacactacg gctatagaca aagaaattgc acgatttgta ccaaatagta atatgaattt  360
cacggggcaa gcatacagcg gcagagagat aatatacagc aatggatccc tgctcttcca  420
aatgatcacc atgaaggata tgggagtcta cacactagat atgacagatg aaaactatcg  480
tcgtactcag gcgactgtgc gatttcatgt acaccccata ttattaaagc ccaacatcac  540
aagcaacaac tccaatcccg tggagggtga cgactccgta tcattaacct gtgactctta  600
cactgaccct gataatataa actacctgtg gagcagaaat ggtgaaagcc tttcagaagg  660
tgacaggctg aagctgtctg agggcaacag gactctcact ttactcaatg tcacgaggaa  720
tgacacagga ccctatgtgt gtgaaacccg gaatccagtg agtgtcaacc gaagtgaccc  780
attcagcctg aacattatct atggtccgga cacccccgatt atatccccct cagatattta  840
tttgcatcca gggtcaaacc tcaacctctc ctgccatgca gcctctaacc cacctgcaca  900
gtacttttgg cttatcaatg agaagcccca tgcatcctcc caagagctct ttatccccaa  960
catcactact aataatagcg gaacctatac ctgcttcgtc aataactctg tcactggcct  1020
cagtaggacc acagtcaaga acattacagt ccttgagcca gtgactcagc ccttcctcca  1080
agtcaccaac accacagtca aagaactaga ctctgtgacc ctgacctgct tgtcgaatga  1140
```

```
cattggagcc aacatccagt ggctcttcaa tagccagagt cttcagctca cagagagaat  1200
gacactctcc cagaacaaca gcatcctcag aatagaccct attaagaggg aagatgccgg  1260
cgagtatcag tgtgaaatct cgaatccagt cagcgtcagg aggagcaact caatcaagct  1320
ggacataata tttgacccaa cacaaggagg cctctcagat ggcgccattg ctggcatcgt  1380
gattggagtt gtggctgggg tggctctaat agcagggctg gcatatttcc tctattccag  1440
gaagtctggc gggggaagtg accagcgaga tctcacagag cacaaaccct cagcctccaa  1500
ccacaatctg gctccttctg acaactctcc taacaaggtg gatgacgtcg catacactgt  1560
cctgaacttc aattcccagc aacccaaccg gccaacttca gccccttctt ctccaagagc  1620
cacagaaaca gtttattcag aagtaaaaaa gaagtgagca taatctgtcc gtctgtcctg  1680
ctggctgcac cagtgatgca ttcccggatt ctgttcctca ctggagggtc tcagcacaca  1740
cacacacgta cacatgcgcg cgcgcacaca cacacacaca cacacacaca cacacttaca  1800
cacacactca tgcattcact ctattgactc cttcagtgtc tatagaagaa aaggtggatc  1860
ctggagccta cagaaaactc aacccttcta ggctttcaaa tttggctgag agtgaggtat  1920
caaaatttct cacccttca ctttcctgac ccagattgtt gaaaattgac ctattcagag  1980
caccttcatt cccctcccaa ctccaagtcc tgccctatca gagtctgact tgaatttcca  2040
taaaccttgg aggtcaccta agtgcttacg ccaaacaaaa caaaacaaaa caaaacaaaa  2100
caaaacaaaa caaaacaaaa caaaccagaa gcaggaaatg gccagtccca tatctttaaa  2160
ggctgattgg aagccaccat acatgagaag atcaaacctc catgggcaat ctacacaccc  2220
gacaactgtc atgcttaccc atctgggaca ttcgagtctc tgaaccttgt gccctcacgc  2280
ctgagccctt ctctgagcct ttctccagaa aatccactca cagcaactag agaggctctt  2340
tgtcagcaac tccaagcaaa ctgctaggca ggattcagaa gaaaagacag catctctaac  2400
atccaccagg aaggtgccca gaaaagcaga gctggtgact ttggactgac agacatctgg  2460
agtgtgaaaa agcagcacag agctaacctt cggagagtgt tgaaattatt tgaaaagaag  2520
ccatatttgg aggtattgga gtttcctct ttctgagaca atccactatt tgaaaattgt  2580
agctactgaa ttgcctctca gtatgcgagc tgatcacttt gccttagggc cactagattt  2640
ctgtctccct tagcccctca agccctttg atcatgagtt ccaaaccaaa aataaataaa  2700
tgaacagtga ggcagtccct tgcagtacca ctgtcatggg tcaggctaag cctcctgctt  2760
ttctgaatta gtcaagaaaa gccttggttt ccctttttcc atctctttat cttgtctttc  2820
agatactggc cagagcctgg acactcttcc tctgagatct ccagcttctc tgccttcttg  2880
tgtttctttt aaactctaac aaaaactgtt ctcaccttca aaaaataaaa taataacaag  2940
ctttccacat ccccaccaaa gagggaccca gctaggtttc tggaaaccca gcaccagcct  3000
ccagctgccc ttctgcagtg tttctgcctc tgtttccctt tcgttttgac ttttttcctt  3060
cttttgagac agagttccag catggagcct gtgcaggttt caatcccaca gtaacacctt  3120
ctgcagcacc ccacctgctc agactgcagc cctggccacc aggcctggct acctggacat  3180
tctgtctgcc ctgcactctc aggaaacctt ggcctctgct actgtctgtt tggctcattc  3240
aaagtgtgtc cttaaaggaa tgcagtcacc catgccagag gcagtgttta cagcctggaa  3300
tgctctgcac ttccagtgga ccagtgctcc accggaagtg ggctgttagc agggtcctct  3360
cacctggccc tggcctttct gtagccttga atcctgcctt ccccaccagg gcaccaggga  3420
tgagtgcagc agcaggagga gaggcaaaca gtcacctcag gaaccttctg agctaaggca  3480
caccctctgt gcctgtcaag caaaggttgt attggatatc aagtgtttgg tctcacgcca  3540
agccaacagg ctttggagag aattaattag ttctcctact cagggatttc tttcagtcct  3600
aacacagcct gtgtatattt tgcttcaccc acgcaatgct ggattattta attttgcccg  3660
gcttaagaca aatctgagtt acttgtaaat ttgctctatg ttcataataa aaatgtatta  3720
tatatcactg atagca                                                  3736
```

```
SEQ ID NO: 92          moltype = AA  length = 521
FEATURE                Location/Qualifiers
source                 1..521
                       mol_type = protein
                       organism = Mus musculus
SEQUENCE: 92
MELASAHLHK GQVPWGGLLL TASLLASWSP ATTAEVTIEA VPPQVAEDNN VLLLVHNLPL  60
ALGAFAWYKG NTTAIDKEIA RFVPNSNMNF TGQAYSGREI IYSNGSLLFQ MITMKDMGVY  120
TLDMTDENYR RTQATVRFHV HPILLKPNIT SNNSNPVEGD DSVSLTCDSY TDPDNINYLW  180
SRNGESLSEG DRLKLSEGNR TLTLLNVTRN DTGPYVCETR NPVSVNRSDP FSLNIIYGPD  240
TPIISPSDIY LHPGSNLNLS CHAASNPPAQ YFWLINEKPH ASSQELFIPN ITTNNSGTYT  300
CFVNNSVTGL SRTTVKNITV LEPVTQPFLQ VTNTTVKELD SVTLTCLSND IGANIQWLFN  360
SQSLQLTERM TLSQNNSILR IDPIKREDAG EYQCEISNPV SVRRSNSIKL DIIFDPTQGG  420
LSDGAIAGIV IGVVAGVALI AGLAYFLYSR KSGGGSDQRD LTEHKPSASN HNLAPSDNSP  480
NKVDDVAYTV LNFNSQQPNR PTSAPSSPRA TETVYSEVKK K                      521
```

```
SEQ ID NO: 93          moltype = DNA  length = 3388
FEATURE                Location/Qualifiers
source                 1..3388
                       mol_type = genomic DNA
                       organism = Homo sapiens
SEQUENCE: 93
attcctcacg atgacccgac agtctctgct ttctttttcc tttcttccag aaggagattt  60
aaccatagta gaaagaatgg agaactatta actgcctttc ttctgtgggc tgtgattttc  120
agaggggaat gctaagaggt gattttcaat gttgggactc aaaggtgaag acactgaagg  180
acagaatttt tggcagagga aagatcttct tcggtcacca tacttgagtt agctctaggg  240
aagtggaggt ttccatttgg aattctatag cttcttccag gtcatagtgt ctgcccccca  300
ccttccagta tctcctgata tgcagcatga atgaaaatgg caagtttcct ggccttcctt  360
ctgctcaact ttcgtgtctg cctccttttg cttcagctgc tcatgcctca ctcagctcag  420
ttttctgtgc ttggaccctc tgggcccatc ctggccatgg tgggtgaaga cgctgatctg  480
ccctgtcacc tgttcccgac catgagtgca gagaccatgg agctgaagtg ggtgagttcc  540
agcctaaggc aggtggtgaa cgtgtatgca gatggaaagg aagtggaaga caggcagagt  600
gcaccgtatc gagggagaac ttcgattctg cgggatggca tcactgcagg gaaggctgct  660
ctccgaatac acaacgtcac agcctctgac agtggaaagt acttgtgtta tttccaagat  720
```

```
ggtgacttct atgaaaaagc cctggtggag ctgaaggttg cagcactggg ttctgatctt  780
cacgttgatg tgaagggtta caaggatgga gggatccatc tggagtgcag gtccactggc  840
tggtacccc aaccccaaat acagtggagc aacaacaagg gagagaacat cccgactgtg  900
gaagcacctg tggttgcaga cggagtgggc ctgtatgcag tagcagcatc tgtgatcatg  960
agaggcagct ctggggaggg tgtatcctgt accatcagaa gttccctcct cggcctggaa  1020
aagacagcca gcatttccat cgcagacccc ttcttcagga gcgcccagag gtggatcgcc  1080
gccctggcag ggaccctgcc tgtcttgctg ctgcttcttg ggggagccgg ttacttcctg  1140
tggcaacagc aggaggaaaa aaagactcag ttcagaaaga aaaagagaga gcaagagttg  1200
agagaaatgg catggagcac aatgaagcaa gaacaaagca caagagtgaa gctcctggag  1260
gaactcagat ggagaagtat ccagtatgca tctcggggag agagacattc agcctataat  1320
gaatggaaaa aggccctctt caagcctgcg gatgtgattc tggatccaaa aacagcaaac  1380
cccatcctcc ttgtttctga ggaccagagg agtgtgcagc gtgccaagga gccccaggat  1440
ctgccagaca accctgagag atttaattgg cattattgtg ttctcggctg tgagagcttc  1500
atatcaggga gacattactg ggaggtggag gtaggggaca ggaaagagtg gcatataggg  1560
gtgtgcagta agaatgtgca gagaaaaggc tgggtcaaaa tgacacctga gaatggattc  1620
tggactatgg ggctgactga tgggaataag tatcggactc taactgagcc cagaaccaac  1680
ctgaaacttc ctaagccccc taagaaagtg ggggtcttcc tggactatga gactggagat  1740
atctcattct acaatgctgt ggatggatcg catattcata ctttcctgga cgtctccttc  1800
tctgaggctc tatatcctgt tttcagaatt ttgaccttgg agcccacggc cctgactatt  1860
tgtccagcgt gaaaagaaga agagagttcc tccaattctg accgagtgct gatcattccc  1920
tagagacacc agtaaccccg ggcttagcta acgaaagtgg ggagcctcag gctgaagtaa  1980
cttttctctg cttctccctg cccagctcag agctgagggc ctccccctcc acagcaacca  2040
atcacaacca taaagctaca agcacgcact gaagcacttt actgatactc attcaattat  2100
tcatatgaca gttgtttgag tttggtacca tcttatttc ccttataca gataaggaaa  2160
ctggggtgca gaaaagtgaa ttgactacaa agtagacatg actagttaac aacacagctg  2220
ggatctaaac agcaataact aacattaatg gagaacttaa aatgctctga gtgctgtgtt  2280
atgagctttg gtggatgtca ctcctttaat cctcgcaaca ccctgtcggg tagtctcatt  2340
tagcaagtat ggaagttgag gcagggcaac attaagcaac ttacataact catgcagtaa  2400
tttctgcagt tgggagatgt tcagcttcag tccccggccc tatggccgtt cttttccacc  2460
ctgtttcttc ccccatagga agaacccacc tgtagccctg aggttctttt cccaggatgg  2520
ctccaggata aggatcactg taggtggttg tggagttgac acccctgttg actccttccc  2580
agctgattgt cagagcctta gacccagcac gccttggatt agctctgcag agtgtcttgg  2640
ttgagagaat aacctcaccg tacccacatg acacgtgatt tggaaagaga ctagaggcca  2700
cacttgataa atcatgggga acagatgtgt tccacccaac aaatgtgata agtgatcatg  2760
cagccagagc cagccttcct tcaatcaagg tttccaggca gagcaaatac cctagagatt  2820
ctctgtgata taggaaattt ggatgaaggg agctagaaga aatacaggga tttttttttt  2880
tttttaagat ggagtcttac tctgttgcta ggctggagtg cagtggtgcg atctcagctc  2940
cctgcaacct ccacctcctg ggttcaaaca attctcctgc ctcagcctcc cgagtactgg  3000
gaatataggt gcacgccacc acacccaaca aatttttgta cttttagtac agatgagggt  3060
tcactatgtt ggccaggatg gtctcgatct cttgacctca tgatccaccc acctcggtct  3120
cccaaagtgc tgggattaca ggcttgagcc accgggtgac cggcttacag ggatattttt  3180
aatcccgtta tggactctgt ctccaggaga ggggtctatc caccccctgct cattggtgga  3240
tgttaaacca atattccttt caactgctgc ctgctaggga aaaactactc ctcattatca  3300
tcattattat tgctctccac tgtatcccct ctacctggca tgtgcttgtc aagttctagt  3360
tgttcaataa atttgttaat aatgctga                                    3388
```

```
SEQ ID NO: 94          moltype = AA  length = 513
FEATURE                Location/Qualifiers
source                 1..513
                       mol_type = protein
                       organism = Homo sapiens
SEQUENCE: 94
MKMASFLAFL LLNFRVCLLL LQLLMPHSAQ FSVLGPSGPI LAMVGEDADL PCHLFPTMSA  60
ETMELKWVSS SLRQVVNVYA DGKEVEDRQS APYRGRTSIL RDGITAGKAA LRIHNVTASD  120
SGKYLCYFQD GDFYEKALVE LKVAALGSDL HVDVKGYKDG GIHLECRSTG WYPQPQIQWS  180
NNKGENIPTV EAPVVADGVG LYAVAASVIM RGSSGEGVSC TIRSSLLGLE KTASISIADP  240
FFRSAQRWIA ALAGTLPVLL LLLGGAGYFL WQQQEEKKTQ FRKKKREQEL REMAWSTMKQ  300
EQSTRVKLLE ELRWRSIQYA SRGERHSAYN EWKKALFKPA DVILDPKTAN PILLVSEDQR  360
SVQRAKEPQD LPDNPERFNW HYCVLGCESF ISGRHYWEVE VGDRKEWHIG VCSKNVQRKG  420
WVKMTPENGF WTMGLTDGNK YRTLTEPRTN LKLPKPPKKV GVFLDYETGD ISFYNAVDGS  480
HIHTFLDVSF SEALYPVFRI LTLEPTALTI CPA                              513
```

```
SEQ ID NO: 95          moltype = DNA  length = 3776
FEATURE                Location/Qualifiers
source                 1..3776
                       mol_type = genomic DNA
                       organism = Homo sapiens
SEQUENCE: 95
gactcttact gtttctcatg gtgagaagac aatatttgct ttctcttttt cctttcttcc  60
ggatgagagg ctaagccata atagaaagaa tggagaatta ttgattgacc gtctttattc  120
tgtgggctct gattctccaa tgggaatacc aagggatggt tttccatact ggaacccaaa  180
ggtaaagaca ctcaaggaca gacatttttg gcagagcata gatgaaaatg gcaagttccc  240
tggctttcct tctgctcaac tttcatgtct ccctcctctt ggtccagctg ctcactcctt  300
gctcagctca gttttctgtg cttggaccct ctgggcccat cctggccatg gtgggtgaag  360
acgctgatct gccctgtcac ctgttcccga ccatgagtgc agagaccatg gagctgaagt  420
gggtaagttc cagcctaagg caggtggtga acgtgtatgc agatggaaag gaagtggaag  480
acaggcagag tgcaccgtat cgagggagaa cttcgattct gcgggatggc atcactgcag  540
ggaaggctgc tctccgaata cacaacgtca cagcctctga cagtggaaag tacttgtgtt  600
atttccaaga tggtgacttc tatgaaaaag ccctggtgga gctgaaggtt gcagcactgg  660
```

-continued

```
gttctaatct tcacgtcgaa gtgaagggtt atgaggatgg agggatccat ctggagtgca  720
ggtccaccgg ctggtacccc caaccccaaa tacagtggag caacgccaag ggagagaaca  780
tcccagctgt ggaagcacct gtggttgcag atggagtggg cctatatgaa gtagcagcat  840
ctgtgatcat gagaggcggc tccggggagg gtgtatcctg catcatcaga aattccctcc  900
tcggcctgga aaagacagcc agcatttcca tcgcagaccc cttcttcagg agcgcccagc  960
cctggatcgc agccctggca gggaccctgc ctatcttgct gctgcttctc gccggagcca  1020
gttacttctt gtggagacaa cagaaggaaa taactgctct gtccagtgag atagaaagtg  1080
agcaagagat gaaagaaatg ggatatgctg caacagagcg ggaaataagc ctaagagaga  1140
gcctccagga ggaactcaag aggaaaaaaa tccagtactt gactcgtgga gaggagtctt  1200
cgtccgatac caataagtca gcctgatgct ctaatggaaa aatggccctc ttcaagcctg  1260
gtgaggaaat gcttcagatg aggctccacc ttgttaaata aattggatgt atggaaaaat  1320
agactgcaga aaaggggaac tcatttagct cacgagtggt cgagtgaaga ttgaaaatta  1380
acctctgagg gccagcacag cagctcatgc ctgtaatcct agcactttgg aaggctgagg  1440
agggcggatc acaaggtcag gagatcaaga ccatcctggc taacacggtg aaaccccgtc  1500
tctactaaaa atacaaaaaa taaaaaatta gccgggcatg gtgacgggca cctgtagtcc  1560
cagctactcg ggaggctgag gcaggagaat ggcatgaacc cggaaggcag agcttgcagt  1620
gagccgagat cacgccactg cactccagcc tgggagacag agcgagactc tgtctcaaga  1680
aaaaaaaaaa aaaaaaaaaa gaaaagaaaa ttaacctctg agtataaagc atcagtgggc  1740
agaatcaatg tggggaggga aacaacaaaa atgtagaaag aggatccttg ttgcttcttg  1800
gggccgcatc agggtattgg gttaggcaga tactgacctt actttcattt cccctctggt  1860
cactagaccc ctggggcttt caccaatgac attgatgaga gaatcacatt cagggcaggc  1920
tagggacacg gggttctgga aggacctcct cagcatggcc caagccttgc atgctgtggc  1980
tcttaaatcc aggaaaaatg gctgacccca tggacacctc ctcaaactct ctgcagcaga  2040
tgtaattctg tatccagaca tggcaaatgc catcctcctt gtttctgagg accagaggag  2100
tgtacagcgt gctgaggagc cccatgacct accagacaac cctgagagat ttgaatggcg  2160
ttactgtgtg cttggctgtg aaagcttcat gtcagagaga cactactggg aggtggaagt  2220
gggggacaga aaagagtggc atattggggt atgtagtaag aacgtggaga ggaaaaaagt  2280
ttgggtcaaa atgacaccgg agaacggata ctggactatg ggcctgactg atgggaataa  2340
gtatcgggct ctcactgagc ccagaaccaa cctgaaactt cctgagcctc ctaggaaagt  2400
gggggtcatc ctggactatg agactggaca tatctcgttc tacaatgcca cggatggatc  2460
tcatatctac acatttctgc acgcctcttc ctctgagcct ctgtatcctg tattcagaat  2520
tttgaccttg gagcccactg ccctgaccgt ttgcccaata ccaaaagtag agagttcccc  2580
cgatcccgac ctagtgcctg atcattccct ggagatacca ctgaccccag gcttagctaa  2640
tgaaagtggg gagcctcagg ctgaagtaac atctctgctt ctccctgccc agcctggagc  2700
taagggtctc accctccaca acagccagtc agaaccataa agctacaggc acacactgaa  2760
gcactttact gatattcatt caattattcc ataggacagt tgtttgagtt tggtgccacc  2820
ttattggccc ctttatacag ataaggaaac tggggtgtag aaaagtgtat tgactttaca  2880
aagcagacag gaatagtgaa caacagagct gggatctgaa caacaatgac taacattaat  2940
ggagaattta aaacgttctg agtgctgtgt tatgagcttt ggtgggtgtc actcctttaa  3000
tcctcacaac accctgtcag gtagtctcat ttggcaagta tggaagcaga ggcagggcaa  3060
cattaagtag cttacataac tcacacggta atttgtgcag ttgggagatg ttcagcttca  3120
gtccctggcc aattgcccgt tcttttccag cctgattttt cctgcatggg aagagcccac  3180
atgtagccct gaggttccct tcccaggaca gctccaggat cgagatcact gtgagtggtt  3240
gtggagttaa gacccctatg gactccttcc cagctgatta tcagagcctt agacccagca  3300
ctccttggat tggctctgca gagtgtcttg gttgagagaa taacgttgca gttcccacag  3360
ggcatgtgac tttgaaagag actagaggcc acactcagtt aataatgggg cacagatgtg  3420
ttcccaccca acaaatgtga taagtgatcg tgcagccaga gccagccttc cttcagtcaa  3480
ggtttccagg cagagcaaat accctagaga ttctctgtaa tattggtaat ttggatgaag  3540
gaagctagaa gaattacagg gatgttttta atcccactat ggactcagtc tcctggaaaa  3600
ggatctgtcc actcctggtc attggtggat gttaaaccca tattcctttc aactgctgcc  3660
tgctagggaa aactgctcct cattatcatc actattattg ctcaccactg tatcccctct  3720
actgggcaag tgcttgtcaa gttctagttg ttcaataaat ttgttaataa tgctga      3776

SEQ ID NO: 96          moltype = AA  length = 334
FEATURE                Location/Qualifiers
source                 1..334
                       mol_type = protein
                       organism = Homo sapiens
SEQUENCE: 96
MKMASSLAFL LLNFHVSLLL VQLLTPCSAQ FSVLGPSGPI LAMVGEDADL PCHLFPTMSA  60
ETMELKWVSS SLRQVVNVYA DGKEVEDRQS APYRGRTSIL RDGITAGKAA LRIHNVTASD  120
SGKYLCYFQD GDFYEKALVE LKVAALGSNL HVEVKGYEDG GIHLECRSTG WYPQPQIQWS  180
NAKGENIPAV EAPVVADGVG LYEVAASVIM RGGSGEGVSC IIRNSLLGLE KTASISIADP  240
FFRSAQPWIA ALAGTLPILL LLLAGASYFL WRQQKEITAL SSEIESEQEM KEMGYAATER  300
EISLRESLQE ELKRKKIQYL TRGEESSSDT NKSA                              334

SEQ ID NO: 97          moltype = DNA  length = 2890
FEATURE                Location/Qualifiers
source                 1..2890
                       mol_type = genomic DNA
                       organism = Homo sapiens
SEQUENCE: 97
agatttcgtt tcctgcatct ccaaacatgg cgacctagga gaaggggaag aacaattttt  60
tctcctcttt tgggaaggtt tgtgtctagt agtgcctgtg cccctgggca gattggagag  120
aagagggacg actggagaat cgtcgagaac cagcggagaa aagaaaaagc aacgtttaat  180
tctagaaggc ctcctgtccc tgcctgctct gggtgctcat ggaatcagct gctgccctgc  240
acttctcccg gccagcctcc ctcctcctcc tcctcctcag cctgtgtgca ctggtctcag  300
cccagtttat tgtcgtgggg cccactgatc ccatcttggc cacggttgga gaaaacacta  360
cgttacgctg ccatctgtca cccgagaaaa atgctgagga catggaggtg cggtggttcc  420
```

```
ggtctcagtt ctccccgca gtgtttgtgt ataaaggtgg cagagagaga acagaggagc  480
agatggagga gtaccgagga agaaccacct ttgtgagcaa agacatcagc aggggcagcg  540
tggccctggt catacacaac atcacagccc aggaaaacgg cacctaccgc tgttacttcc  600
aagaaggcag gtcctacgat gaggccatcc tgcacctcgt agtggcagga ctaggctcta  660
agcccctcat ttcaatgagg ggccatgaag acgggggcat ccggctggag tgcatatcta  720
gagggtggta cccaaagccc ctcacagtgt ggagggaccc ctacggtggg gttgcgcctg  780
ccctgaaaga ggtctccatg cctgatgcag acggcctctt catggtcacc acggctgtga  840
tcatcagaga caagtctgtg aggaacatgt cctgctctat caacaacacc ctgctcggcc  900
agaagaaaga aagtgtcatt tttattccag aatcctttat gcccagtgtg tctccctgtg  960
cagtggccct gcctatcatt gtggttattc tgatgatacc cattgccgta tgcatctatt  1020
ggatcaacaa actccaaaag gaaaaaaaga ttctgtcagg ggaaaaggag tttgaacggg  1080
aaacaagaga aattgctcta aaggaactgg agaaagaacg tgtgcaaaaa gaggaagaac  1140
ttcaagtaaa agagaaactt caagaagaat tgcgatggag aagaacattc ttacatgctg  1200
ttgatgtggt cctggatcca gacaccgctc atcccgatct cttcctgtca gaggaccgga  1260
gaagtgtgag aaggtgcccc ttcaggcacc taggggagag cgtgcctgac aacccagaga  1320
gattcgacag tcagccttgt gtcctaggcc gggagagctt cgcttcaggg aaacattact  1380
gggaggtgga ggtggaaaac gtgattgagt ggactgtggg ggtctgtaga gacagtgttg  1440
agaggaaagg ggaggtcctg ctgattcctc agaatggctt ctggaccttg gagatgcata  1500
aagggcaata ccgggccgtg tcctcccctg ataggattct ccctttgaag gagtcccttt  1560
gccgggtggg cgtcttcctg gactatgaag ctggagatgt ctccttctac aacatgaggg  1620
acagatcgca catctacaca tgtccccgtt cagccttttc cgtgcctgtg aggccccttct  1680
tcaggttggg gtgtgaggac agccccatct tcatctgccc tgcactcaca ggagccaatg  1740
gggtcacggt gcctgaagag ggcctgacac ttcacagagt ggggacccac cagagcctat  1800
agaatcaatt ccttggtctc acagccatgt agacaagccc tggtcatctc agcagccacc  1860
gcacaacacc cctggtggaa gacacgccct cctcccctct ggtcacacaa gagaacatct  1920
tccagctgcc tctttcacac ccactacaga cctcagcccc agttttctcc tcctcactag  1980
gctgtgtttt tagtagttcc tttgcttgta actatgggat gggatccagg catagggaac  2040
tagttgttac acagctccca gccaagaaga aagtgtgaga agttgatggg cagcaaacct  2100
gctgtttaac atcagggtga ccacattaag cccagtattc cagttggcac cagaagatat  2160
ggacttggaa tgaggcctac agggttcacc aggatgtaag aggagagagg aatccacagg  2220
accaccagag aggagaggga accagatatg cagatcagag atagaggaag tggaaccaga  2280
gagctgggag ggaccaaggt tgtaagggtg gctaagtccc accataacag ctaaggggac  2340
ctgggagatg atggctcatt tccacccagc cccaggattt ccagagcgca catccacagg  2400
cctggacctg ggatgaagat gaatgaagaa catggatgca cgtggatgta gtttggctca  2460
ggtgtccctg cagttggcaa ggagtcagta ctcagtccct gagtgtggct gaaatttgag  2520
gtcctggctg agccaaggag taatggacca gatctacctc agtattcaag ttcagtgggg  2580
acaccagtgg cttcaaactt cctggtttca tgatatcttg agacgcctta caaatgatgg  2640
aggattccaa agagtttttg tttatttggg ttaatatttg ttggtattta tggcatttga  2700
gattgaaact aagaaatgtt ttaatttatt acctttacaa catttattta cattacatac  2760
atacatttac aacatttatt aatttatatt aaaatagcat gaataagcca attataggtt  2820
aatataagta gaatgtttgt gaaaaataag tatggtatcc aaagcaaaat aaattttatt  2880
gtgaagtgtg                                                        2890
```

```
SEQ ID NO: 98          moltype = AA  length = 527
FEATURE                Location/Qualifiers
source                 1..527
                       mol_type = protein
                       organism = Homo sapiens
SEQUENCE: 98
MESAAALHFS RPASLLLLLL SLCALVSAQF IVVGPTDPIL ATVGENTTLR CHLSPEKNAE  60
DMEVRWFRSQ FSPAVFVYKG GRERTEEQME EYRGRTTFVS KDISRGSVAL VIHNITAQEN  120
GTYRCYFQEG RSYDEAILHL VVAGLGSKPL ISMRGHEDGG IRLECISRGW YPKPLTVWRD  180
PYGGVAPALK EVSMPDADGL FMVTTAVIIR DKSVRNMSCS INNTLLGQKK ESVIFIPESF  240
MPSVSPCAVA LPIIVVILMI PIAVCIYWIN KLQKEKKILS GEKEFERETR EIALKELEKE  300
RVQKEEELQV KEKLQEELRW RRTFLHAVDV VLDPDTAHPD LFLSEDRRSV RRCPFRHLGE  360
SVPDNPERFD SQPCVLGRES FASGKHYWEV EVENVIEWTV GVCRDSVERK GEVLLIPQNG  420
FWTLEMHKGQ YRAVSSPDRI LPLKESLCRV GVFLDYEAGD VSFYNMRDRS HIYTCPRSAF  480
SVPVRPFFRL GCEDSPIFIC PALTGANGVT VPEEGLTLHR VGTHQSL               527
```

```
SEQ ID NO: 99          moltype = DNA  length = 2017
FEATURE                Location/Qualifiers
source                 1..2017
                       mol_type = genomic DNA
                       organism = Homo sapiens
SEQUENCE: 99
agaacagcgc agtttgccct ccgctcacgc agagcctctc cgtggcttcc gcaccttgag  60
cattaggcca gttctcctct tctctctaat ccatccgtca cctctcctgt catccgtttc  120
catgccgtga ggtccattca cagaacacat ccatggctct catgctcagt ttggttctga  180
gtctcctcaa gctgggatca gggcagtggc aggtgtttgg gccagacaag cctgtccagg  240
ccttggtggg ggaggacgca gcattctcct gtttcctgtc tcctaagacc aatgcagagg  300
ccatggaagt gcggttcttc aggggccagt tctctagcgt ggtccacctc tacagggacg  360
ggaaggacca gccatttatg cagatgccac agtatcaagg caggacaaaa ctggtgaagg  420
attctattgc ggaggggcgc atctctctga ggctggaaaa cattactgtg ttggatgctg  480
gcctctatgg gtgcaggatt agttcccagt cttactacca gaaggccatc tgggagctac  540
aggtgtcagc actgggctca gttcctctca tttccatcac gggatatgtt gatagagaca  600
tccagctact ctgtcagtcc tcgggctggt tcccccggcc cacagcgaag tggaaaggtc  660
cacaaggaca ggatttgtcc acagactcca ggacaaacag agacatgcat ggcctgtttg  720
atgtggagat ctctctgacc gtccaagaga acgccgggag catatcctgt tccatgcggc  780
atgctcatct gagccgagag gtggaatcca gggtacagat aggagatacc tttttcgagc  840
```

```
ctatatcgtg gcacctggct accaaagtac tgggaatact ctgctgtggc ctatttttg  900
gcattgttgg actgaagatt ttcttctcca aattccagtg gaaaatccag gcggaactgg  960
actggagaag aaagcacgga caggcagaat tgagagacgc ccggaaacac gcagtggagg  1020
tgactctgga tccagagacg gctcacccga agctctgcgt ttctgatctg aaaactgtaa  1080
cccatagaaa agctccccag gaggtgcctc actctgagaa gagatttaca aggaagagtg  1140
tggtggcttc tcagagtttc caagcaggga aacattactg ggaggtggac ggaggacaca  1200
ataaaaggtg gcgcgtggga gtgtgccggg atgatgtgga caggaggaag gagtacgtga  1260
ctttgtctcc cgatcatggg tactgggtcc tcagactgaa tggagaacat ttgtatttca  1320
cattaaatcc ccgttttatc agcgtcttcc ccaggacccc acctacaaaa atagggtct  1380
tcctggacta tgagtgtggg accatctcct tcttcaacat aaatgaccag tcccttattt  1440
ataccctgac atgtcggttt gaaggcttat tgaggcccta cattgagtat ccgtcctata  1500
atgagcaaaa tggaactccc atagtcatct gcccagtcac ccaggaatca gagaaagagg  1560
cctcttggca aagggcctct gcaatcccag agacaagcaa cagtgagtcc tcctcacagg  1620
caaccacgcc cttcctcccc aggggtgaaa tgtaggatga atcacatccc acattcttct  1680
ttagggatat taaggtctct ctcccagatc caaagtcccg cagcagccgg ccaaggtggc  1740
ttccagatga agggggactg gcctgtccac atgggagtca ggtgtcatgg ctgccctgag  1800
ctgggaggga agaaggctga cattacattt agtttgctct cactccatct ggctaagtga  1860
tcttgaaata ccacctctca ggtgaagaac cgtcaggaat tcccatctca caggctgtgg  1920
tgtagattaa gtagacaagg aatgtgaata atgcttagat cttattgatg acagagtgta  1980
tcctaatggt ttgttcatta tattacactt tcagtaa                          2017
```

```
SEQ ID NO: 100          moltype = AA  length = 500
FEATURE                 Location/Qualifiers
source                  1..500
                        mol_type = protein
                        organism = Homo sapiens
SEQUENCE: 100
MALMLSLVLS LLKLGSGQWQ VFGPDKPVQA LVGEDAAFSC FLSPKTNAEA MEVRFFRGQF  60
SSVVHLYRDG KDQPFMQMPQ YQGRTKLVKD SIAEGRISLR LENITVLDAG LYGCRISSQS  120
YYQKAIWELQ VSALGSVPLI SITGYVDRDI QLLCQSSGWF PRPTAKWKGP QGQDLSTDSR  180
TNRDMHGLFD VEISLTVQEN AGSISCSMRH AHLSREVESR VQIGDTFFEP ISWHLATKVL  240
GILCCGLFFG IVGLKIFFSK FQWKIQAELD WRRKHGQAEL RDARKHAVEV TLDPETAHPK  300
LCVSDLKTVT HRKAPQEVPH SEKRFTRKSV VASQSFQAGK HYWEVDGGHN KRWRVGVCRD  360
DVDRRKEYVT LSPDHGYWVL RLNGEHLYFT LNPRFISVFP RTPPTKIGVF LDYECGTISF  420
FNINDQSLIY TLTCRFEGLL RPYIEYPSYN EQNGTPIVIC PVTQESEKEA SWQRASAIPE  480
TSNSESSSQA TTPFLPRGEM                                              500
```

```
SEQ ID NO: 101          moltype = DNA  length = 3583
FEATURE                 Location/Qualifiers
source                  1..3583
                        mol_type = genomic DNA
                        organism = Homo sapiens
SEQUENCE: 101
gggacttttt ggacacccag agaacaggtc ccagataccg agtccgcaac tccaaacatc  60
gcgattaata ggaggcctct ggtctctgcc tgccctgggt gctcatggaa ccagctgctg  120
ctctgcactt ctccctgcca gcctccctcc tcctcctcct gctcctcctc cttctcagcc  180
tgtgtgcact ggtctcagcc cagtttactg tcgtggggcc agctaatccc atcctggcca  240
tggtgggaga aaacactaca ttacgctgcc atctgtcacc cgagaaaaat gctgaggaca  300
tggaggtgcg gtggttccgg tctcagttct cccccgcagt gtttgtgtat aagggtggga  360
gagagagaac agaggagcag atggaggagt accggggaag aatcaccttt gtgagcaaag  420
acatcaacag gggcagcgtg gccctggtca tacataacgt cacagcccag gagaatggga  480
tctaccgctg ttacttccaa gaaggcaggt cctacgatga ggccatccta cgcctcgtgg  540
tggcaggcct tgggtctaag cccctcattg aaatcaaggc ccaagaggat gggagcatct  600
ggctggagtg catatctgga gggtggtacc cagagcccct cacagtgtgg agggacccct  660
acggtgaggt tgtgcccgcc ctgaaggagg tttccatcgc tgatgctgac ggcctcttca  720
tggtcaccac agctgtgatc atcagagaca agtatgtgag gaatgtgtcc tgctctgtca  780
acaacaccct gctcggccag gagaaggaaa ctgtcatttt tattccagaa tcctttatgc  840
ccagcgcatc tccctggatg gtggccctag ctgtcatcct gaccgcatct ccctggatgg  900
tgtccatgac tgtcatcctg gctgttttca tcatcttcat ggctgtcagc atctgttgca  960
tcaagaaact tcaaagggaa aaaaagattc tgtcagggga aaagaaagtt gaacaagagg  1020
aaaaagaaat tgcacagcaa cttcaagaag aattgcgatg gagaagaaca ttcttacatg  1080
ctgctgatgt ggtcctggat ccagacaccg ctcatcccga gctcttcctg tcagaggacc  1140
ggagaagtgt gaggcggggc ccctacaggc agagagtgcc tgacaaccca gagagattcg  1200
acagtcagcc ttgtgtcctg ggatgggaga gcttcgcctc agggaaacat tactgggagg  1260
tggaggtgga aaacgtgatg gtgtggactg tgggggtctg cagacacagt gttgagagga  1320
aaggggaggt cctgctgatt cctcagaatg gcttctggac cctggagatg tttggaaacc  1380
aataccgggc cctgtcctcc cctgagagga ttctcccttt gaaggagtcc ctttgccggg  1440
tgggcgtctt cctggactat gaagctggag atgtctcctt ctacaacatg agggacagat  1500
cgcacatcta cacatgtccc cgttcagcct ttactgtgcc tgtgaggccc ttcttcaggt  1560
tagggtctga tgacagcccc atcttcatct gccctgcact cacaggagcc agtggggtca  1620
tggtgcctga agagggcctg aaacttcaca gagtggggac ccaccagagc ctatagaatc  1680
aattccttgg actcacagcc atgcagataa gccctggcca tctcagcagc caccgcacaa  1740
ccccccctaat gaaagacacg ccctcctccc ctctggtcac gtaagagaac atcttccagc  1800
tgcctttttc acacccactc cagccctctg ccccagtttt ctcctcctca ctagtctgtg  1860
gctttagtag ttcctttgct tgtaattatg ggatgggatc caggcatagg gaactagttg  1920
tttcatagct cccagtcaaa aagaaagtga gagaagctgt tgggcagcga acctactgtt  1980
taaaatcagg ataaccacat taagcccaat atgccagttg gcaccagatg ctgtggactt  2040
ggaatgaggc caacagggtt caccaggatg agagaggaga gaggaatcca caggaccacc  2100
agaagggaga gggaaccaga tatgcagatc agagatagag gaagtggaac cagagagctg  2160
```

```
ggagggacca aggttgtaag gatggctaag tcccaccata agagctaaag ggtcctggga  2220
gatgatggct catttccacc caaccccagg atttccacag cacacaccca caggcctgga  2280
cctgggatga agatgaatga agaacatgga ctcatgtgga tgtggtttgg ctcagatgtc  2340
cctgcaataa acaaggggtc agtacttagt ccctgagtgt ggttgaggtt tgaggtcctg  2400
gtcgagcagg gcagtactgg accaggtcta cgtcagcatt caggttcaat ggggacacca  2460
gtggcttcaa acttcctgat ctaattatgt ttttagacac ttagaagtta ttgaggactt  2520
taaagagctt ttgtttattt gggttaatat ttatgacatt tgacattgaa acaaaaattt  2580
aaaatgttat cttttaattt atgttaaaat agcattaata aatcagttat aggttaatgt  2640
agataggatg ttttgtgaaa aagcaatcta ttgtgtccaa ataaaaaaac aaaaagtgtg  2700
acactggtta actttttcca gatctcatgt ctggcttaat aagagatatt tgtattatca  2760
tatctgcctt tgtattaaac ctattggtat atcataggtc atgttagctc aaaaaaactt  2820
tactgcacac tactgagaga atgagatgaa aaacgattaa tgtttcatta ttattattgt  2880
gaaaatatta ttaacactgg ggactcctta agagtacatc agagttctct ctaggaatcc  2940
caaaaccaca ttttgaaact agaatagtgg atcctggaag ttaatccatg tgctggttaa  3000
ttttagatgt caacctgact ggattaagga atacctagac agctggtaca acattatttc  3060
tgggtgtgtc tgtgagtgtg tttccagaag agattggcaa gtgagtcagt gggaaattct  3120
ctccttctgt tggctgggtg cccaatacaa caaaaaggca gaggaaaggc aaattcttct  3180
ctcctctgga gctgagacac tcttcttctt ctgcccttgg acatcagaac tcctggctct  3240
ccggcctttg aacttcagga cttgtaccag gaggccctgg gttctcaggc ctttggcttt  3300
ggactgagag ttacacaatc agcttccctg gttctgaggc tttcagactt aaactgagcc  3360
atgctaccag catcccaggg tctccagcct acagatgagc tgttgtgcga tttcttagcc  3420
tccataatca catgagccaa tctccttaat aaatgcctgc tcatagatct gtatctacat  3480
ctatatctgt atgtgcatct atatctatgc ctatatctat atctatatca tattgatttt  3540
gtctctctgg agaaccctga ctaataaaat gaggcatcta aaa                   3583

SEQ ID NO: 102          moltype = AA  length = 523
FEATURE                 Location/Qualifiers
source                  1..523
                        mol_type = protein
                        organism = Homo sapiens
SEQUENCE: 102
MEPAAALHFS LPASLLLLLL LLLLSLCALV SAQFTVVGPA NPILAMVGEN TTLRCHLSPE  60
KNAEDMEVRW FRSQFSPAVF VYKGGRERTE EQMEEYRGRI TFVSKDINRG SVALVIHNVT  120
AQENGIYRCY FQEGRSYDEA ILRLVVAGLG SKPLIEIKAQ EDGSIWLECI SGGWYPEPLT  180
VWRDPYGEVV PALKEVSIAD ADGLFMVTTA VIIRDKYVRN VSCSVNNTLL GQEKETVIFI  240
PESFMPSASP WMVALAVILT ASPWMVSMTV ILAVFIIFMA VSICCIKKLQ REKKILSGEK  300
KVEQEEKEIA QQLQEELRWR RTFLHAADVV LDPDTAHPEL FLSEDRRSVR RGPYRQRVPD  360
NPERFDSQPC VLGWESFASG KHYWEVEVEN VMVWTVGVCR HSVERKGEVL LIPQNGFWTL  420
EMFGNQYRAL SSPERILPLK ESLCRVGVFL DYEAGDVSFY NMRDRSHIYT CPRSAFTVPV  480
RPFFRLGSDD SPIFICPALT GASGVMVPEE GLKLHRVGTH QSL                   523

SEQ ID NO: 103          moltype = DNA  length = 2983
FEATURE                 Location/Qualifiers
source                  1..2983
                        mol_type = genomic DNA
                        organism = Mus musculus
SEQUENCE: 103
gaaattgtga gacttgcacg cggaatgggt cctccgaggt ctgctgtcgc gagtcccagc  60
actttgcaag taatggagaa cagaaaattc tttcctctct actgtagcag tttgttctct  120
ggtggcgact gtgctcagcg acaagttgga gagtagagaa aaggcaagat aatcagcatt  180
tgagggtcag agaagaaaag aaaacgcagt taattctaga aggttttctg tccacacgtg  240
acctaggtga ctctgtcctg aagacctatg gagcctacaa cttccctgcg ttcttgcccg  300
atagcctccc ttctcttctt cttggtcctc agcctgtttg tgctggtctc agcccagttt  360
actgtcatag gaccagctga gcccatcctg gccatggtag gagagaatac cacactacac  420
tgccacctgt caccagagag aaatgccgaa gagatggagg tgcggtggtt ccggtggcgt  480
ttcttccctg cagtgctggt gtacagaggc catcaagaga gaccagagga gcagatggtg  540
gcataccgag gaagaaccac cttcatgcgc acagacatca gcaagggaag agttgcgctc  600
attatccaca atgtcacagc ctatgacaat ggcatctact gctgttactt ccaggaaggc  660
aggtcctatg accaggcaac catgaagctt atggtggcaa gccttggctc tgagccactt  720
attaaaatga agacacttga ggatgggagc atcttgctag agtgcacatc tgaagggtgg  780
tacccagagc cccgagctgt gtggagagac ccctatgatg aagttgtacc tgccctggag  840
gaggagtata cagctgacag agaaggcctc ttcacagtca ccatgactat aatcatcagg  900
gactgctctg tgaggaacat gacctgctct gtcaataaca ctctgctcag ccaggaggtg  960
gaaagtgtga ttctcattcc agaatccttc gtgcccagcc ttcctctgtg gatggtggct  1020
gtggctgtca ctctgcctgt agtaatgctg attctcctca catctggaag catctgcctt  1080
gtcaagaaac accgcaggaa gaaatctatt ctgtcagctg aaaaagaagc cgaatatgaa  1140
gagaaggaag ctgcacggca acttcaagag gaactgcgat ggagacgaac cctcttacat  1200
gctgctgacg tggtcctgga cccagataca gctcatcctg agctcttcct gtcagatgac  1260
cagagaagtg taatacgagg ctcttcgagg cagagtgtgc ctgacaaccc tgagagattt  1320
gactgccgtc catgtgtcct gggcagggaa agcttctcct cagggaagca ttactgggag  1380
gtggaggtgg aaaatgtaat ggtgtgggcc attggtgttt gtagagacag cgtggaaagg  1440
aaaggggagg ccctgttggt tcctcagaat ggcttctgga ccctggagat gtttggaagc  1500
cagtatcgag ccctgtcctc cccagaaaag atcatacctc tgaaagagcg tcttcaccgt  1560
atagctgtct tcctggactg tgagggtgga gatatttctt tctacaacat gagagacaga  1620
tcacacattt acacatgtcc tcctgtgact ttcactgggc ccctgagacc cttctttagg  1680
cttggttctg atgacagtcc cctgttcatc tgtccagcat tcacaggggc acagggagtt  1740
acaatacctg agggtggctt attcctatat aagacaagac caatttctca gagccttgta  1800
aggaagccat agctctctac acagtaccat ctgttggaga ctagacccca tgtccttcag  1860
atcacatgga gcatcttcca gctgccacct tcacacatac ttcaggccca gtcctcagat  1920
```

```
tactacatca tttcttctaa ctatgggcct aggtagagcc agtcttaggg gactattgct  1980
gtaatacagc tctctcctga gaagaaagtg tgagaagggc agaaaacttg gagtttcaac  2040
atgctgctct ggtcacagtg gatatcaggc aagagcaaca gggtggatca ggatgtaaga  2100
agtgagaact acagaggaag gagacagata aagatgaatt gaggccgaag atggaggaaa  2160
tggactgaag agctctgggg taagccctat gtgacagctg tggataggta ggagctaatg  2220
gtccattgat atccaaagcc aaagatttaa atatcacata gtgtgtctgg agtgtatatc  2280
tgtagaccta cacatgagag gaaacaatca tagtgatgaa ctggatgtaa gctggctcag  2340
acgtccctac aataaacact tctgagttcc atgtctgtgc tcagtaagaa tggcttgagg  2400
cttgcggtcc atgctgagca gccaggtcca catgaatcgg atttactaga gtaggtagca  2460
gttcaagttc cttaggctca ggatgtcttc ctttccccca agcccttccc ccttcaagat  2520
aggtctcact atgtagacca ggccagcctc cacctccaga gttctgggat taaagacaag  2580
cacaaccatg tccagtttat gagcttgtga tatatacaga agattaagtt ctgtgttctt  2640
gggttagtaa ctgttgagat ttgttttgag tcatgctctc actggctagc actgctcttg  2700
actttctctc cccatctttt tgttattgct tttcaagaca tggtttcact gtgtatttct  2760
ggctgataag ctgattttga attcacagag atctgcctct gcctcctgag tgctgggatt  2820
aaaggtgtgt tacactacgc ctggcttcac tctatctctt cagtgtgggg attataggtt  2880
tatactatca tgcctaacta atgtctgttg ctgcatatga catttgaact ttagaacaga  2940
aaaacaacta tacatattaa tatatattaa actaataata agc                    2983

SEQ ID NO: 104         moltype = AA  length = 514
FEATURE                Location/Qualifiers
source                 1..514
                       mol_type = protein
                       organism = Mus musculus
SEQUENCE: 104
MEPTTSLRSC PIASLLFFLV LSLFVLVSAQ FTVIGPAEPI LAMVGENTTL HCHLSPERNA  60
EEMEVRWFRW RFFPAVLVYR GHQERPEEQM VAYRGRTTFM RTDISKGRVA LIIHNVTAYD  120
NGIYCCYFQE GRSYDQATMK LMVASLGSEP LIKMKTLEDG SILLECTSEG WYPEPRAVWR  180
DPYDEVVPAL EEEYTADREG LFTVTMTIII RDCSVRNMTC SVNNTLLSQE VESVILIPES  240
FVPSLPLWMV AVAVTLPVVM LILLTSGSIC LVKKHRRKKS ILSAEKEAEY EEKEAARQLQ  300
EELRWRRTLL HAADVVLDPD TAHPELFLSD DQRSVIRGSS RQSVPDNPER FDCRPCVLGR  360
ESFSSGKHYW EVEVENVMVW AIGVCRDSVE RKGEALLVPQ NGFWTLEMFG SQYRALSSPE  420
KIIPLKERLH RIAVFLDCEG GDISFYNMRD RSHIYTCPPV TFTGPLRPFF RLGSDDSPLF  480
ICPAFTGAQG VTIPEGGLFL YKTRPISQSL VRKP                              514

SEQ ID NO: 105         moltype = DNA  length = 2945
FEATURE                Location/Qualifiers
source                 1..2945
                       mol_type = genomic DNA
                       organism = Homo sapiens
SEQUENCE: 105
agctttctca cttggtagca gtggcctctt gtgccttttt ctccaagatc acccaggctg  60
aagctcctga ggggactcac atcagttatc ttgctgctcc agaagggtgg gagatggcag  120
ttttcccaag ctccggtctc cccagatgtc tgctcaccct cattctcctc cagctgccca  180
aactggattc agctcccttt gacgtgattg gacccccgga gcccatcctg gccgttgtgg  240
gtgaggacgc cgagctgccc tgtcgcctgt ctccgaacgc gagcgccgag cacttggagc  300
tacgctggtt ccgaaagaag gtttcgccgg ccgtgctggt gcataggacg gggcgcgagc  360
aggaagccga gcagatgccc gagtaccgcg ggcgggcgac gctggtccag gacggcatcg  420
ccaaggggcg cgtggccttg aggatccgtg gcgtcagagt ctctgacgac ggggagtaca  480
cgtgcttttt cagggaggat ggaagctacg aagaagccct ggtgcatctg aaggtggctg  540
ctctgggctc tgaccctcac atcagtatgc aagttcaaga gaatggagaa atctgtctgg  600
agtgcacctc agtgggatgg tacccagagc cccaggtgca gtggagaact tccaagggag  660
agaagtttcc atctacatca gagtccagga atcctgatga agaaggtttg ttcactgtgg  720
ctgcttcagt gatcatcaga gacacttctg cgaaaaatgt gtcctgctac atccagaatc  780
tccttcttgg ccaggagaag aaagtagaaa tatccatacc agcttcctcc ctccccaggc  840
tgactccctg gatagtggct gtggctgtca tcctgatggt tctaggactt ctcaccattg  900
ggtccatatt tttcacttgg agactataca acgaaagacc cagagagagg aggaatgaat  960
tcagctctaa agagagactc ctggaagaac tcaaatggaa aaaggctacc ttgcatgcag  1020
ttgatgtgac tctggaccca gacacagctc atccccacct ctttctttat gaggattcaa  1080
aatctgttcg actggaagat tcacgtcaga aactgcctga gaaaacagag agatttgact  1140
cctggccctg tgtgttgggc cgtgagacct tcacctcagg aaggcattac tgggaggtgg  1200
aggtgggaga caggactgac tgggcaatcg gcgtgtgtag ggagaatgtg atgaagaaag  1260
gatttgaccc catgactcct gagaatgggt tctgggctgt agagttgtat ggaaatgggt  1320
actgggccct cactccctc cggacccctc tcccattggc agggcccccca cgccgggttg  1380
ggattttcct agactatgaa tcaggagaca tctccttcta caacatgaat gatggatctg  1440
atatctatac tttctccaat gtcactttct ctggcccccct ccggcccttc ttttgcctat  1500
ggtctagcgg taaaaagccc ctgaccatct gcccaattgc tgatgggcct gagagggtca  1560
cagtcattgc taatgcccag gacctttcta aggagatccc attgtccccc atgggggagg  1620
actctgcccc tagggatgca gacactctcc attctaagct aatccctacc caacccagcc  1680
aaggggcacc ttaaggaata tctcagctca tctgttttcc tttcctctaa cccctctcct  1740
ccatagcctt ctgaggcttc acctgctagc tttacccagt ctgtttcttc ctgttgggtg  1800
gcaattaatt aatcctgtga aggttacatt gctgctgcta gagagggtgg ggattgcacc  1860
ttccaaatct gtttctgtac caatatttgg gggatggagg ggtgactcaa actgcttcta  1920
gtgttctcct aatcccttaa gactagaacc tataggaaac tacttggagc aaactcaaag  1980
gacagattag ggatcgagat tgggtcaggt tagcatgggg ttgtggttga aatatcttgg  2040
tatccaggat aagggtatgt ggaaaaacag gctttaggca agtggaaaat tcaaaatgtg  2100
ctgtgaaagg acaatctcag gctgaaatcc cataaaggaa cttggaggga atattatgat  2160
ggagggaagt gaggtgaatc caggcacatg atgaacacct ggctcatcca tagagttttc  2220
acagcctata tcgcaaattt tctaagccac gtcctatagg acagaggaga ctggccccac  2280
```

```
ttctatgggt ctgagctgtg gaaaagggag agcagagagg aactgagatg agcagggatg  2340
aagggtcagg cagaaagcgt gatagaggag agaatttttg acaaaactca aaagttgttt  2400
gcacagctgt tctttgtacc ctgttccttt ctctgcgccc tcctgtttct cccttgcctg  2460
gaagtcattc caccctcaat ttgttgatcc acaagtttcc agttgtcctc ttctttttgt  2520
tatagcatct ctctatttca aagacattcc tagaagtcat ccttcagtga tatcaccact  2580
tgctcagtca ccatctcaac cttatgtcac ctcagccctc atctcaatgc ccaaacccct  2640
tacacacacc ttcagttagc ttcaactgcc tccgtttcca cactgtgcac ctttcacttt  2700
ccctacccag ctttcctaca tgctgcctct cctcagggtc ccctgaatgc tgcatcattg  2760
tgttcagtgc agctggactg attgcacctg tgtatttgcc cctgagcact ttcctttaca  2820
catgtggctt gtcttgccaa tagactccag gcttatacct tccatttcca tcgtattctc  2880
cagtttccag gatagacgtt gctcatcgtc tttacctaat aaataagttt gtctgattgc  2940
tgaaa                                                              2945

SEQ ID NO: 106          moltype = AA  length = 526
FEATURE                 Location/Qualifiers
source                  1..526
                        mol_type = protein
                        organism = Homo sapiens
SEQUENCE: 106
MAVFPSSGLP RCLLTLILLQ LPKLDSAPFD VIGPPEPILA VVGEDAELPC RLSPNASAEH  60
LELRWFRKKV SPAVLVHRDG REQEAEQMPE YRGRATLVQD GIAKGRVALR IRGVRVSDDG  120
EYTCFFREDG SYEEALVHLK VAALGSDPHI SMQVQENGEI CLECTSVGWY PEPQVQWRTS  180
KGEKFPSTSE SRNPDEEGLF TVAASVIIRD TSAKNVSCYI QNLLLGQEKK VEISIPASSL  240
PRLTPWIVAV AVILMVLGLL TIGSIFFTWR LYNERPRERR NEFSSKERLL EELKWKKATL  300
HAVDVTLDPD TAHPHLFLYE DSKSVRLEDS RQKLPEKTER FDSWPCVLGR ETFTSGRHYW  360
EVEVGDRTDW AIGVCRENVM KKGFDPMTPE NGFWAVELYG NGYWALTPLR TPLPLAGPPR  420
RVGIFLDYES GDISFYNMND GSDIYTFSNV TFSGPLRPFF CLWSSGKKPL TICPIADGPE  480
RVTVIANAQD LSKEIPLSPM GEDSAPRDAD TLHSKLIPTQ PSQGAP                  526

SEQ ID NO: 107          moltype = DNA  length = 3454
FEATURE                 Location/Qualifiers
source                  1..3454
                        mol_type = genomic DNA
                        organism = Mus musculus
SEQUENCE: 107
aacagcacac agccttcttc cttctgaaga gctctctctt tggccccggg gtgacaagca  60
gcccttttca cttgatcact gtggctctgg ctccctttc ctctgggtct gtcgaaatcg  120
cctgaagctc ttggcgggct tcattgcccc agttagctca gagatggcag ttcccaccaa  180
ctcctgcctc ctggtctgtc tgctcaccct cactgtccta cagctgccca cgctggattc  240
ggcagctccc ttcgatgtga ccgcacctca ggagccagtg ttggccctag tgggctcaga  300
tgccgagctg acctgtggct tttccccaaa cgcgagctca gaatacatgg agctgctgtg  360
gtttcgacag acgaggtcga cagcggtact tctataccgg gatggccagg agcaggaggg  420
ccagcagatg acggagtacc gcgggagggc gacgctggcg acagccgggc ttctagacgg  480
ccgcgctact ctgctgatcc gagatgtcag ggtctcagac caggggggagt accggtgcct  540
tttcaaagac aacgacgact tcgaggaggc cgccgtatac ctcaaagtgg ctgctgtggg  600
ttcagatcct caaatcagta tgacggttca agagaatgga gaaatggagc tggagtgcac  660
ctcctctgga tggtacccag agcctcaggt gcagtggaga acaggcaaca gagagatgct  720
accatccacg tcagagtcca agaagcataa tgaggaaggc ctgttcactg tggcagtttc  780
aatgatgatc agagacagct ccataaagaa catgtcctgc tgcatccaga atatcctcct  840
tggccagggg aaggaagtag agatctcctt accagctccc ttcgtgccaa ggctgactcc  900
ctggatagta gctgtggcta tcatcttact ggccttagga tttctcacca ttgggtccat  960
atttttcact tggaaactat acaaggaaag atccagtctg cggaagaagg aatttggctc  1020
taaagagaga cttctggaag aactcagatg caaaaagact gtactgcatg aagttgacgt  1080
gactctggat ccagacacag cccaccccca cctcttcctg tatgaagatt caaagtcagt  1140
tcgattggaa gattcacgtc agatcctgcc tgatagacca gagagatttg actcctggcc  1200
ctgtgtgttg ggccgtgaga cctttacttc agggagacat tactgggagg tggaggtggg  1260
agatagaact gactgggcca ttggtgtgtg tagggagaat gtggtgaaga aagggtttga  1320
ccccatgact cctgataatg ggttctgggc tgtggagttg tatggaaatg ggtactgggc  1380
cctcacccca ctcaggacct ctctccgatt agcagggccc cctcgcagag ttggggtttt  1440
tctggactat gacgcaggag acatttcctt ctacaacatg agtaacggat ctcttatcta  1500
tactttccct agcatctctt tctctggccc cctccgtccc ttctttttgtc tgtggtcctg  1560
tggtaaaaag cccctgacca tctgttcaac tgccaatggg cctgagaaag tcacagtcat  1620
tgctaatgtc caggacgaca ttcccttgtc cccgctgggg gaaggctgta cttctggaga  1680
caaagacact ctccattcta aactgatccc gttctcacct agccaagcgg caccataaca  1740
aatattccag cttcacgact ttgccttcct ttgactaatc cctcatgccc cgaagcttca  1800
gctgttggct tcttgcagcc ctgcttcttc ctggtggatg gagattaatt cacattggga  1860
aggttaggta tgttgctgcc agacaaggca ggaagaaagg ccatcctagt ttgtttctgt  1920
actaacagtg gggaggaaga gagctgaatc ctaaactatt tccagtgctc atattccttc  1980
aggccagagc ctatagagaa ggatttggta caatcactcg agggatcaag aggcaattag  2040
gttggcatgg aattatggca gaaacatctg gaataggggt atgtggaatg acaggtttta  2100
ggtaagggag aacaaaacca aaccatagga tgctgagaaa gaaagatctt ggactaaact  2160
cctaaaaaag cacttagaga agatatgaca ggcaaatgaa gtgaatttgg tctaatttga  2220
tacacttgcc ctgtccctag ggtttttcag ttatatctca atttttttgt tgttaattac  2280
atttttgaca gcttcataca tgtatataat gcattctaat tactctcact ctcctctatt  2340
ctgtcttatt tccctcccct cccctcatac cttccttctt gcttcaaacc tggcacactg  2400
agtttaatgg gctatcatgg gaacatggat ttagagcttt cctctgagct caagagagca  2460
ggtgtgactg aatacagtga tttcccctct cctacaatca atcagcagtc aatagctcag  2520
ctgggagggg tagggcctca tgagacttcc cctatcaagg ctaaatgttg aaagggccag  2580
tttttagcac ctgtgagatc atgattgcaa gagcccagaa gacagcattg ctcggtcatt  2640
```

```
ctccctaccc tttggctttt ctggtctttt gtcctctctt tcaggatgtg tctgaactct  2700
gtatcttaag ttttctatgt catgttctat aagatagagg agactggccc tgcttgtttg  2760
agagcaatgt gagcaagcta gcaagagaca gaaaggagcg gagatgaata ggggtagaga  2820
aaatttttaa acaaaccctc caggtgtgtg tgtgtgtgtg tgtgtcttcc tctttttga  2880
cctccctaaa ggtcaatcca acctcacatt attgactcca ctaggtgggg gttctgtgtg  2940
tgtgtgtgtg tgtgtgtgtg tgtgtgtgtg tgttttaaga tagaggttta ctatgtagct  3000
taggctggct ttgaattcct gatcctcctg cctctacctt ccaagtgctg gaaacatagc  3060
cacatccacc acccctatcc agtccacctg gtttgattca gcaacgctca ggtagcatcg  3120
ctgtttgatc tggagctgcc agctccctcg gcccccactg caatgcttaa ccccctcaca  3180
ggcaccttcc cttgcctaac actgccatcc ttttccacac tgagccattt gctcaatgta  3240
gcctacccag gtatcctgct ttctggtccc caaagttaca ccatgatgct cagcacagct  3300
ggacagtttg tcccaatttg tgtgtgtcct cctgtttgta tgggacttct ttttgtcaat  3360
ggcctgtgtg tgtatccaag ctcttccact tctattgtat ttttccggct tctaaaacag  3420
atgttaccaa ataaagaaag agaaagaaaa aaaa                               3454

SEQ ID NO: 108          moltype = AA  length = 524
FEATURE                 Location/Qualifiers
source                  1..524
                        mol_type = protein
                        organism = Mus musculus
SEQUENCE: 108
MAVPTNSCLL VCLLTLTVLQ LPTLDSAAPF DVTAPQEPVL ALVGSDAELT CGFSPNASSE  60
YMELLWFRQT RSTAVLLYRD GQEQEGQQMT EYRGRATLAT AGLLDGRATL LIRDVRVSDQ  120
GEYRCLFKDN DDFEEAAVYL KVAAVGSDPQ ISMTVQENGE MELECTSSGW YPEPQVQWRT  180
GNREMLPSTS ESKKHNEEGL FTVAVSMMIR DSSIKNMSCC IQNILLGQGK EVEISLPAPF  240
VPRLTPWIVA VAIILLALGF LTIGSIFFTW KLYKERSSLR KKEFGSKERL LEELRCKKTV  300
LHEVDVTLDP DTAHPHLFLY EDSKSVRLED SRQILPDRPE RFDSWPCVLG RETFTSGRHY  360
WEVEVGDRTD WAIGVCRENV VKKGFDPMTP DNGFWAVELY GNGYWALTPL RTSLRLAGPP  420
RRVGVFLDYD AGDISFYNMS NGSLIYTFPS ISFSGPLRPF FCLWSCGKKP LTICSTANGP  480
EKVTVIANVQ DDIPLSPLGE GCTSGDKDTL HSKLIPFSPS QAAP                    524

SEQ ID NO: 109          moltype = DNA  length = 2926
FEATURE                 Location/Qualifiers
source                  1..2926
                        mol_type = genomic DNA
                        organism = Homo sapiens
SEQUENCE: 109
acatctgctt cctgtaggcc ctctgggcag aagcatgcgc tggtgtctcc tcctgatctg  60
ggcccagggg ctgaggcagg ctcccctcgc ctcaggaatg atgacaggca caatagaaac  120
aacggggaac atttctgcag agaaaggtgg ctctatcatc ttacaatgtc acctctcctc  180
caccacggca caagtgaccc aggtcaactg ggagcagcag gaccagcttc tggccatttg  240
taatgctgac ttggggtggc acatctcccc atccttcaag gatcgagtgg ccccaggtcc  300
cggcctgggc ctcaccctcc agtcgctgac cgtgaacgat acaggggagt acttctgcat  360
ctatcacacc taccctgatg ggacgtacac tgggagaatc ttcctggagg tcctagaaag  420
ctcagtggct gagcacggtg ccaggttcca gattccattg cttggagcca tggccgcgac  480
gctggtggtc atctgcacag cagtcatcgt ggtggtcgcg ttgactagaa agaagaaagc  540
cctcagaatc cattctgtgg aaggtgacct caggagaaaa tcagctggac aggaggaatg  600
gagccccagt gctccctcac ccccaggaag ctgtgtccag gcagaagctg cacctgctgg  660
gctctgtgga gagcagcggg gagaggactg tgccgagctg catgactact tcaatgtcct  720
gagttacaga agcctgggta actgcagctt cttcacagag actggttagc aaccagaggc  780
atcttctgga agatacactt ttgtctttgc tattatagat gaatatataa gcagctgtac  840
tctccatcag tgctgcgtgt gtgtgtgtgt gtgtatgtgt gtgtgtgttc agttgagtga  900
ataaatgtca tcctcttctc catcttcatt tccttggcct tttcgttcta ttccattttg  960
cattatggca ggcctagggt gagtaacgtg gatcttgatc ataaatgcaa aattaaaaaa  1020
tatcttgacc tggttttaaa tctggcagtt tgagcagatc ctatgtctct gagagacaca  1080
ttcctcataa tggccagcat tttgggctac aaggttttgt ggttgatgat gaggatggca  1140
tgactgcaga gccatcctca tctcattttt tcacgtcatt ttcagtaact ttcactcatt  1200
caaaggcagg ttataagtaa gtcctggtag cagcctctat ggggagattt gagagtgact  1260
aaatcttggt atctgccctc aagaacttac agttaaatgg ggagacaatg ttgtcatgaa  1320
aaggtattat agtaaggaga gaaggagaca tacacaggcc ttcaggaaga gacgacagtt  1380
tggggtgagg tagttggcat aggcttatct gtgatgaagt ggcctgggag caccaagggg  1440
atgttgaggc tagtctggga ggagcaggag ttttgtctag ggaacttgta ggaaattctt  1500
ggagctgaaa gtcccacaaa gaaggccctg gcaccaaggg agtcagcaaa cttcagattt  1560
tattctctgg gcaggcattt caagtttcct tttgctgtga catactcatc cattagacag  1620
cctgatacag gcctgtagcc tcttccggcc gtgtgtgctg gggaagcccc aggaaacgca  1680
catgcccaca cagggagcca agtcgtagca tttgggcctt gatctacctt ttctgcatca  1740
atacactctt gagcctttga aaaaagaacg tttcccacta aaaagaaaat gtggattttt  1800
aaaataggga ctcttcctag gggaaaaagg ggggctggga gtgatagagg gtttaaaaaa  1860
taaacacctt caaactaact tcttcgaacc cttttattca ctccctgacg actttgtgct  1920
ggggttgggg taactgaacc gcttatttct gtttaattgc attcaggctg gatcttagaa  1980
gacttttatc cttccaccat ctctctcaga ggaatgagcg gggaggttgg atttactggt  2040
gactgatttt ctttcatggg ccaaggaact gaaagagaat gtgaagcaag gttgtgtctt  2100
gcgcatggtt aaaaataaag cattgtcctg cttcctaaga cttagactgg ggttgacaat  2160
tgttttagca acaagacaat tcaactattt ctcctaggat ttttattatt attattttt  2220
cacttttcta ccaaatgggt tacataggaa gaatgaactg aaatctgtcc agagctccaa  2280
gtcctttgga agaaagatta gatgaacgta aaaatgttgt tgtttgctgt ggcagtttac  2340
agcatttttc ttgcaaaatt agtgcaaatc tgttggaaat agaacacaat tcacaaattg  2400
gaagtgaact aaaatgtaat gacgaaaagg gagtagtgtt ttgatttgga ggaggtgtat  2460
attcggcaga ggttggactg agagttgggt gttatttaac ataattatgg taattgggaa  2520
```

```
acatttataa acactattgg gatggtgata aaatacaaaa gggcctatag atgttagaaa  2580
tgggtcaggt tactgaaatg ggattcaatt tgaaaaaaat ttttttaaat agaactcact  2640
gaactagatt ctcctctgag aaccagagaa gaccatttca tagttggatt cctggagaca  2700
tgcgctatcc accacgtagc cactttccac atgtggccat caaccactta agatggggtt  2760
agtttaaatc aagatgtgct gttataattg gtataagcat aaaatcacac tagattctgg  2820
agatttaata tgaataataa gaatactatt tcagtagttt tggtatattg tgtgtcaaaa  2880
atgataatat tttggatgta ttgggtgaaa taaaatatta acatta                 2926

SEQ ID NO: 110         moltype = AA  length = 244
FEATURE                Location/Qualifiers
source                 1..244
                       mol_type = protein
                       organism = Homo sapiens
SEQUENCE: 110
MRWCLLLIWA QGLRQAPLAS GMMTGTIETT GNISAEKGGS IILQCHLSST TAQVTQVNWE  60
QQDQLLAICN ADLGWHISPS FKDRVAPGPG LGLTLQSLTV NDTGEYFCIY HTYPDGTYTG  120
RIFLEVLESS VAEHGARFQI PLLGAMAATL VVICTAVIVV VALTRKKKAL RIHSVEGDLR  180
RKSAGQEEWS PSAPSPPGSC VQAEAAPAGL CGEQRGEDCA ELHDYFNVLS YRSLGNCSFF  240
TETG                                                               244

SEQ ID NO: 111         moltype = DNA  length = 726
FEATURE                Location/Qualifiers
source                 1..726
                       mol_type = genomic DNA
                       organism = Mus musculus
SEQUENCE: 111
atgcatggct ggctgctcct ggtctgggtc caggggctga tacaggctgc cttcctcgct  60
acaggagcca cagcaggcac gatagataca aagaggaaca tctctgcaga ggaaggtggc  120
tctgtcatct tacagtgtca cttctcctct gacacagctg aagtgaccca agtcgactgg  180
aagcagcagg accagcttct ggccatttat agtgttgacc tggggtggca tgtcgcttca  240
gtcttcagtg atcgggtggt cccaggcccc agcctaggcc tcaccttcca gtctctgaca  300
atgaatgaca cgggagagta cttctgtacc tatcatacgt atcctggtgg gatttacaag  360
gggagaatat tcctgaaggt ccaagaaagc tcagtggctc agttccagac tgccccgctt  420
ggaggaacca tggctgctgt gctgggactc atttgcttaa tggtcacagg agtgactgta  480
ctggctagaa agaagtctat tagaatgcat tctatagaaa gtggccttgg gagaacagaa  540
gcggagccac aggaatggaa cctgaggagt ctctcatccc ctggaagccc tgtccagaca  600
caaactgccc ctgctggtcc ctgtggagag caggcagaag atgactatgc tgacccacag  660
gaatacttta atgtcctgag ctacagaagc ctagagagct tcattgctgt atcgaagact  720
ggctaa                                                             726

SEQ ID NO: 112         moltype = AA  length = 241
FEATURE                Location/Qualifiers
source                 1..241
                       mol_type = protein
                       organism = Mus musculus
SEQUENCE: 112
MHGWLLLVWV QGLIQAAFLA TGATAGTIDT KRNISAEEGG SVILQCHFSS DTAEVTQVDW  60
KQQDQLLAIY SVDLGWHVAS VFSDRVVPGP SLGLTFQSLT MNDTGEYFCT YHTYPGGIYK  120
GRIFLKVQES SVAQFQTAPL GGTMAAVLGL ICLMVTGVTV LARKKSIRMH SIESGLGRTE  180
AEPQEWNLRS LSSPGSPVQT QTAPAGPCGE QAEDDYADPQ EYFNVLSYRS LESFIAVSKT  240
G                                                                  241

SEQ ID NO: 113         moltype = DNA  length = 911
FEATURE                Location/Qualifiers
source                 1..911
                       mol_type = genomic DNA
                       organism = Homo sapiens
SEQUENCE: 113
agagaggggc aggctggtcc cctgacaggt tgaagcaagt agacgcccag gagccccggg  60
agggggctgc agtttccttc cttccttctc ggcagcgctc cgcgccccca tcgcccctcc  120
tgcgctagcg gaggtgatcg ccgcggcgat gccggaggag ggttcgggct gctcggtgcg  180
gcgcaggccc tatgggtgcg tcctgcgggc tgctttggtc ccattggtcg cgggcttggt  240
gatctgcctc gtggtgtgca tccagcgctt cgcacaggct cagcagcagc tgccgctcga  300
gtcacttggg tgggacgtag ctgagctgca gctgaatcac acaggacctc agcaggaccc  360
caggctatac tggcaggggg gcccagcact gggccgctcc ttcctgcatg gaccagagct  420
ggacaagggg cagctacgta tccatcgtga tggcatctac atggtacaca tccaggtgac  480
gctggccatc tgctcctcca cgacggcctc caggcaccac cccaccaccc tggccgtggg  540
aatctgctct cccgcctccc gtagcatcag cctgctgcgt ctcagcttcc accaaggttg  600
taccattgcc tcccagcgcc tgacgcccct ggcccgaggg gacacactct gcaccaacct  660
cactgggaca cttttgcctt cccgaaacac tgatgagacc ttctttggag tgcagtgggt  720
gcgcccctga ccactgctgc tgattagggt tttttaaatt ttattttatt ttatttaagt  780
tcaagagaaa aagtgtacac acaggggcca cccggggttg gggtgggagt gtggtggggg  840
gtagtggtgg caggacaaga gaaggcattg agctttttct ttcattttcc tattaaaaaa  900
tacaaaaatc a                                                       911

SEQ ID NO: 114         moltype = AA  length = 193
FEATURE                Location/Qualifiers
source                 1..193
                       mol_type = protein
```

```
                         organism = Homo sapiens
SEQUENCE: 114
MPEEGSGCSV RRRPYGCVLR AALVPLVAGL VICLVVCIQR FAQAQQQLPL ESLGWDVAEL  60
QLNHTGPQQD PRLYWQGGPA LGRSFLHGPE LDKGQLRIHR DGIYMVHIQV TLAICSSTTA  120
SRHHPTTLAV GICSPASRSI SLLRLSFHQG CTIASQRLTP LARGDTLCTN LTGTLLPSRN  180
TDETFFGVQW VRP                                                    193

SEQ ID NO: 115           moltype = DNA  length = 842
FEATURE                  Location/Qualifiers
source                   1..842
                         mol_type = genomic DNA
                         organism = Mus musculus
SEQUENCE: 115
gaaggtgcca aaagctccag gggatttccc tgccctccga gaagaggccc agttcttccc  60
ctgcatcgga catccccgag gttctaaggg caggtcaagg caggcagaag cttcaaaagc  120
tcggctgagg aggctacagc ttcccgctgc cttcaggccg ctgcttccgt gcagggatgc  180
cggaggaagg tcgcccttgc ccctgggttc gctggagcgg gaccgcgttc cagcgccaat  240
ggccatggct gctgctggtg gtgtttatta ctgtgttttg ctgttggttt cattgtagcg  300
gactactcag taagcagcaa cagaggctgc tggagcaccc tgagccgcac acagctgagt  360
tacagctgaa tctcacagtt cctcggaagg accccacact gcgctgggga gcaggcccag  420
ccttgggaag gtccttcaca cacggaccag agctggagga gggccatctg cgtatccatc  480
aagatggcct ctacaggctg catatccagg tgacactggc caactgctct tccccaggca  540
gcaccctgca gcacagggcc accctggctg tgggcatctg ctccccccgct gcgcacggca  600
tcagcttgct gcgtgggcgc tttggacagg actgtacagt ggcattacag cgcctgacat  660
acctggtcca cggagatgtc ctctgtacca acctcaccct gcctctgctg ccgtcccgca  720
acgctgatga gaccttcttt ggagttcagt ggatatgccc ttgaccacaa ctccaggatg  780
acttgtgaat atttttttc ttttcaagtt ctacgtattt ataaatgtat atagtacaca  840
ta                                                                842

SEQ ID NO: 116           moltype = AA  length = 195
FEATURE                  Location/Qualifiers
source                   1..195
                         mol_type = protein
                         organism = Mus musculus
SEQUENCE: 116
MPEEGRPCPW VRWSGTAFQR QWPWLLLVVF ITVFCCWFHC SGLLSKQQQR LLEHPEPHTA  60
ELQLNLTVPR KDPTLRWGAG PALGRSFTHG PELEEGHLRI HQDGLYRLHI QVTLANCSSP  120
GSTLQHRATL AVGICSPAAH GISLLRGRFG QDCTVALQRL TYLVHGDVLC TNLTLPLLPS  180
RNADETFFGV QWICP                                                  195

SEQ ID NO: 117           moltype = DNA  length = 3779
FEATURE                  Location/Qualifiers
source                   1..3779
                         mol_type = genomic DNA
                         organism = Homo sapiens
SEQUENCE: 117
gtcattttcc tacgcgccct ctgacatcag ccaccttctc tgtagctagt ttctctgcac  60
acaacttaat ccctggcaat gaaaaatgaa cctctccccc acccttgctg ccgcctctcg  120
cctcacgccc ccagagaaga gtttctccac caggcagcag gtgaaggttt ttttccaagt  180
cacatgattc aggattcagg gggagaatcc ttcttggaac agagatgggc ccagaactga  240
atcagatgaa gagagataag gtgtgatgtg gggaagacta tataaagaat ggacccaggg  300
ctgcagcaag cactcaacgg aatggcccct cctggagaca cagccatgca tgtgccggcg  360
ggctccgtgg ccagccacct ggggaccacg agccgcagct atttctattt gaccacagcc  420
actctggctc tgtgccttgt cttcacggtg gccactatta tggtgttggt cgttcagagg  480
acggactcca ttcccaactc acctgacaac gtccccctca aaggaggaaa ttgctcagaa  540
gacctcttat gtatcctgaa aagggctcca ttcaagaagt catgggccta cctccaagtg  600
gcaaagcatc taaacaaaac caagttgtct tggaacaaag atggcattct ccatggagtc  660
agatatcagg atgggaatct ggtgatccaa ttccctggtt tgtacttcat catttgccaa  720
ctgcagtttc ttgtacaatg cccaaataat tctgtcgatc tgaagttgga gcttctcatc  780
aacaagcata tcaaaaaaca ggccctggtg acagtgtgtg agtctggaat gcaaacgaaa  840
cacgtatacc agaatctctc tcaattcttg ctggattacc tgcaggtcaa caccaccata  900
tcagtcaatg tggatacatt ccagtacata gatacaagca cctttcctct tgagaatgtg  960
ttgtccatct tcttatacag taattcagac tgaacagttt ctcttggcct tcaggaagaa  1020
agcgcctctc taccatacag tatttcatcc ctccaaacac ttgggcaaaa agaaaacttt  1080
agaccaagac aaactacaca gggtattaaa tagtatactt ctccttctgt ctcttggaaa  1140
gatacagctc cagggttaaa aagagagttt ttagtgaagt atctttcaga tagcaggcag  1200
ggaagcaatg tagtgtggtg ggcagagccc cacacagaat cagaagggat gaatggatgt  1260
cccagcccaa cctctaattc actgtatggt cttgatctat ttcttctgtt ttgagagcct  1320
ccagttaaaa tggggctcca gtaccagagc agctagcaac tctgccctaa tgggaaatga  1380
aggggagctg ggtgtgagtg tttacactgt gcccttcacg ggatacttct tttatctgca  1440
gatggcctaa tacttagttg tccaagtcgc gatcaaggac tctctcacac aggaaacttc  1500
cctatactgg cagatacact tgtgactgaa ccatgcccag tttatgcctg tctgactgtc  1560
actctggcac taggaggctg atcttgtact ccatatgacc ccacccctag gaaccccccag  1620
ggaaaaccag gctgggacag ccccctgttc ctgagatgga aagcacaaat ttaatacacc  1680
accacaatgg aaaacaagtt caaagacttt tacttacaga tcctggacag aaagggcata  1740
atgagtctga agggcagtcc tccttctcta ggttacatga ggcaggaata agaagtcaga  1800
cagagacagc aagacagtta acaatgtagg taaagaaata gggtgtggtc actctcaatt  1860
cactggcaaa tgcctgaatg gtctgtctga aggaagcaac agagaagtgg ggaatccagt  1920
ctgctaggca ggaaagatgc ctctaagttc ttgtctctgg ccagaggtgt ggtatagaac  1980
```

```
cagaaaccca tatcaagggt gactaagccc ggcttctggt atgagaaatt aaacttgtat  2040
acaaaatggt tgccaaggca acataaaatt ataagaattc actatacctt cccctccctg  2100
gaactcagga tccaagtcta gaaaatgaaa ggactgggtt tgaattgctt caaaacctct  2160
tccatctcag aagaccagac cctgggaact gagattccag acacaatttt ggaagctctc  2220
caaccaaaat aaggcccccc taccccagta tataattgaa gacactagta acacctgact  2280
gcatctcatc tcagcagagc cagaatatgg ggacaaggtt cagggtgccc tgctgaatgg  2340
tgtgaacagc aggatctcaa ggatgtaatg gaaagaacta ccacactgac catccagaat  2400
ctaagagacc atctgggtgt ttgggaaacc atctgacgag gcctgactct attccagtta  2460
gattgacaat aattgagcag caggcatttt tcatttctgg tcaggaaagc attgtgcctt  2520
tagcaaacaa tcagtgtgca acagtgatgt ggtcatctag ccagggaatg gctgctccat  2580
cccctgcata atatattcct gcttcaaaca cctctcagaa aaccagttcc gcgagggttt  2640
ttatatcccc acaaagttgt tgagagacaa tgatgaccct ggaagtgggg aggaggactt  2700
ctgagaaaca gcaacctctc tcctgattgg ggtagccatg agatttctct agctatatcc  2760
aacttggcat ctgtacatca tctttggagg aacatcttat ttgtggaagg accttgacaa  2820
gccgtttgag atggaatgta ggccctgatg ttatgcttca gtaaaaaaag atggaagctt  2880
ccctgctata ccaaaacatg gagcaaaatt tgcatttttc tcaagaagga gagaaaagga  2940
gtaggactcc agcaaagttt gtcagaagga aagctagaaa agatttaaaa gaaaaaaaga  3000
aagaacaaat cagcagtggt ggtatggatg aaagggactt gagagaacaa aaatggctaa  3060
gggaaaattt taagtcatct gctgagcagt gtgctgtgtc aacctcctcc taggtctcct  3120
ctatgaaata tttagtaaag tctacatttc tctttaactc tttctgtgag tagattcttt  3180
gggagaagca ggcattggaa gaggtgttga attcagcaag ccaaatggtc tgtggtaaaa  3240
aacaaaacag actttgagac tcaaggctaa aaaaacaggg aaatggctgg catttgagtc  3300
acacactaac tgcataggac aaatgaatct tgcttaaacc aactcatgca ttcttgaaaa  3360
ggtatatgca acccaactgt gtgttaacta agcaattttt ttgccatctc acattctaac  3420
tcgagaaaga ttccattttc atttttcacc aactgttctc tgagcagagg tacctgactt  3480
ttgcactgtg agtggtttct aatctcagtc tctgtcaagc aatgctaaga aagccaacac  3540
ctaaagacac aaggggtaca tcatttaaat gaataatgta accaaacaaa caaaaaaaga  3600
gaataatcat taataactca actgatagat atgtagggag taggcaaccc aggaagttta  3660
aaactaaatt ctgttactct tgagggttaa ccagcccctg ggaatgttat gagcaaatga  3720
tactccatga gtaaaatgat atctatgcaa gtaaaataaa taatttatct aactgggaa   3779

SEQ ID NO: 118          moltype = AA  length = 234
FEATURE                 Location/Qualifiers
source                  1..234
                        mol_type = protein
                        organism = Homo sapiens
SEQUENCE: 118
MDPGLQQALN GMAPPGDTAM HVPAGSVASH LGTTSRSYFY LTTATLALCL VFTVATIMVL  60
VVQRTDSIPN SPDNVPLKGG NCSEDLLCIL KRAPFKKSWA YLQVAKHLNK TKLSWNKDGI  120
LHGVRYQDGN LVIQFPGLYF IICQLQFLVQ CPNNSVDLKL ELLINKHIKK QALVTVCESG  180
MQTKHVYQNL SQFLLDYLQV NTTISVNVDT FQYIDTSTFP LENVLSIFLY SNSD        234

SEQ ID NO: 119          moltype = DNA  length = 2228
FEATURE                 Location/Qualifiers
source                  1..2228
                        mol_type = genomic DNA
                        organism = Mus musculus
SEQUENCE: 119
agattaatcc caggcgatga aaaatgaacc tctcccccac ccttgcagcc acccttcgcc  60
tcacgccccc agagaagagt ttctccatcc ggcaactggt gaaggctttt ttccaagtca  120
catgatccag gatgcagggg aaaatccttc ttggaacaga gctgggtaca gaaccgaatc  180
agatgaggag agataaggtg tgatgtggga cagactatat aaagcatgga gccagggctg  240
caacaagcag gcagctgtgg ggctccttcc cctgacccag ccatgcaggt gcagcccggc  300
tcggtagcca gcccctggag aagcacgagg ccctggagaa gcacaagtcg cagctacttc  360
tacctcagca ccaccgcact ggtgtgcctt gttgtggcag tggcgatcat tctggtactg  420
gtagtccaga aaaaggactc cactccaaat acaactgaga aggcccccct taaaggagga  480
aattgctcag aggatctctt ctgtaccctg aaaagtactc catccaagaa gtcatgggcc  540
tacctccaag tgtcaaagca tctcaacaat accaaactgt catggaacga agatggcacc  600
atccacggac tcatatacca ggacgggaac ctgatagtcc aattccctgg cttgtacttc  660
atcgtttgcc aactgcagtt cctcgtgcag tgctcaaatc attctgtgga cctgacattg  720
cagctcctca tcaattccaa gatcaaaaag cagacgttgg taacagtgtg tgagtctgga  780
gttcagagta agaacatcta ccagaatctc tctcagtttt tgctgcatta cttacaggtc  840
aactctacca tatcagtcag ggtggataat ttccagtatg tggatacaaa cactttccct  900
cttgataatg tgctatccgt cttcttatat agtagctcag actgaatagt tgttcttaac  960
ctttatgaaa atgctgtcta ccatacagta cttcatctgt ccaaacatgg gccaaagaaa  1020
atattaggac aactcaaact aagcatgtga gttagtgcac ttctctttct gtcctttgga  1080
aaaatacaaa cccaggattt agaaagtgga gtctccttca gatgcacaaa caggaaagaa  1140
tgtgatatgt gcacagagac ctacttgggc actagaaggg gttgagttgt cccagtataa  1200
ccactaattc actgaccttg agccattttt ccttcccctg gaacttgggg tctgaatctg  1260
gaaaagtagg agatgagatt tacatttccc caatattttc ttcaactcag aagacgagac  1320
tgtggagctg agctccctac acagatgaag gcctcccatg gcatgaggaa aatgatggta  1380
ccagtaatgt ctgtctgact gtcatctcag caagtcctaa ggacttccat gctgccttgt  1440
tgaaagatac tctaacctct tgtaatgggc aaagtgatcc tgtctctcac tgaggggagt  1500
agctgctgcc atctcctgag acatacatgg agacattttc tgcccaaatt ccattctgtg  1560
tgcagttttt aagtattccc ccaaaagttc ttgacaatga gaactttgaa tgtgggaaga  1620
gcttctggac agcaaacatt aacagcttct cctgaccaga gagaccatgc aagcttggtc  1680
ttagacccat caagcttgag gtttctacat tgtgggagac agacttttga caaaccattt  1740
gagttgatgt ctgggcccct gggagttctc cttcagtaag gagagcaagc cgttctagtg  1800
ctgtgtcaga ggatggagta aaatagacac ttttctgaag gaaaggagaa caaagttcca  1860
```

```
gaaaaaggct agaaaatgtt taaaaggaaa agaaaaaact cagcttttct catatgagag  1920
gaacccagaa aaacaacact gaaaaagaag agtggctctg tcaacctcct cttaggtctc  1980
ctcctctcta gttattggga aaggagttgc atggtacagg acaagttctg gtgtgtggtc  2040
aaatagaatc agatgtggag aacaccatgc agagaataag gagacctgtc atatttgtgt  2100
tgtactcaaa tgaggggcaa atgaatctta ggctaaatca aataacagtc tctgtcaagc  2160
tgtgctcaga aagtcaacca ctgaagatgg agggtgaggc acgtcattta aaaaaagtga  2220
aatgtagc                                                           2228

SEQ ID NO: 120         moltype = AA  length = 239
FEATURE                Location/Qualifiers
source                 1..239
                       mol_type = protein
                       organism = Mus musculus
SEQUENCE: 120
MEPGLQQAGS CGAPSPDPAM QVQPGSVASP WRSTRPWRST SRSYFYLSTT ALVCLVVAVA  60
IILVLVVQKK DSTPNTTEKA PLKGGNCSED LFCTLKSTPS KKSWAYLQVS KHLNNTKLSW  120
NEDGTIHGLI YQDGNLIVQF PGLYFIVCQL QFLVQCSNHS VDLTLQLLIN SKIKKQTLVT  180
VCESGVQSKN IYQNLSQFLL HYLQVNSTIS VRVDNFQYVD TNTFPLDNVL SVFLYSSSD   239

SEQ ID NO: 121         moltype = DNA  length = 2744
FEATURE                Location/Qualifiers
source                 1..2744
                       mol_type = genomic DNA
                       organism = Homo sapiens
SEQUENCE: 121
atcacttgtg aatttttgtt ttccacagct ctcatttctc caaaaatgtg tttgagccac  60
ttggaaaata tgcctttaag ccattcaaga actcaaggag ctcagagatc atcctggaag  120
ctgtggctct tttgctcaat agttatgttg ctatttcttt gctccttcag ttggctaatc  180
tttatttttc tccaattaga gactgctaag gagccctgta tggctaagtt tggaccatta  240
ccctcaaaat ggcaaatggc atcttctgaa cctccttgcg tgaataaggt gtctgactgg  300
aagctggaga tacttcagaa tggcttatat ttaatttatg gccaagtggc tcccaatgca  360
aactacaatg atgtagctcc ttttgaggtg cggctgtata aaaacaaaga catgatacaa  420
actctaacaa acaaatctaa aatccaaaat gtaggaggga cttatgaatt gcatgttggg  480
gacaccatag acttgatatt caactctgag catcaggttc taaaaaataa tacatactgg  540
ggtatcattt tactagcaaa tccccaattc atctcctaga gacttgattt gatctcctca  600
ttcccttcag cacatgtaga ggtgccagtg ggtggattgg agggagaaga tattcaattt  660
ctagagtttg tctgtctaca aaaatcaaca caaacagaac tcctctgcac gtgaattttc  720
atctatcatg cctatctgaa agagactcag gggaagagcc aaagactttt ggttggatct  780
gcagagatac ttcattaatc catgataaaa caaatatgga tgacagagga catgtgcttt  840
tcaaagaatc tttatctaat tcttgaattc atgagtggaa aaatggagtt ctattcccat  900
ggaagattta cctggtatgc aaaaaggatc tggggcagta gcctggcttt gttctcatat  960
tcttgggctg ctgtaattca ttcttctcat actcccatct tctgagaccc tcccaataaa  1020
aagtagactg ataggatggc cacagatatg cctaccatac cctactttag atatggtggt  1080
gttagaagat aaagaacaat ctgagaacta ttggaataga ggtacaagtg gcataaaatg  1140
gaatgtacgc tatctggaaa tttctcttgg ttttatcttc ctcaggatgc agggtgcttt  1200
aaaaagcctt atcaaaggag tcattccgaa ccctcacgta gagctttgtg agaccttact  1260
gttggtgtgt gtgtctaaac attgctaatt gtaaagaaag agtaaccatt agtaatcatt  1320
aggtttaacc ccagaatggt attatcatta ctggattatg tcatgtaatg atttagtatt  1380
tttagctagc tttccacagt ttgcaaagtg ctttcgtaaa acagttagca attctatgaa  1440
gttaattggg caggcatttg gggaaaaatt ttagtgatga gaatgtgata gcatagcata  1500
gccaactttc ctcaactcat aggacaagtg actacaagag gcaatgggta gtcccctgca  1560
ttgcactgtc tcagctttag aattgttatt tctgctatcg tgttataaga ctctaaaact  1620
tagcgaattc acttttcagg aagcatattc ccctttagcc caaggtgagc agagtgaagc  1680
tacaacagat ctttccttta ccagcacact tttttttttt ttcctgcctg aatcagggag  1740
atccaggatg ctgttcaggc cttatcccaa ccaaattccc ctcttcactt tgcagggccc  1800
atcttagtca aatgtgctaa cttctaaaat aataaatagc actaattcaa aatttttgga  1860
ctcttaaatt agctacttgc aggttcttgt tgaaaggtat ataatattac attgtaaaca  1920
aatttaaaat atttatggat atttgtgaaa agctgcatta tgttaaataa tattacatgt  1980
aaagctattt aaaagaggtt ttttttgtat tttgtttaac aaaaattgct caggagcatg  2040
ctaagcctga ggccaagttg tttcttagta tgacttttta aaaaaacatc tgctgagtag  2100
ctacagggcc aaagacttgg agagcttgtt tctgttgcat ttgcatatct tctcaggaaa  2160
ttaaagtgtg tcatacatat gtgtgtgtgt gtgtgtgtgt gtgtgtatat gtgtgtgtgt  2220
atatatatgt atacttataa aatcttggtg ttcttgatct ttgttgtgtt ataagcaatg  2280
tgtgctggag tgggctggtg ctagcttata agcacatatt attaaatttt caggaatgtt  2340
gcactttagt tattaactat aggcattctt gaaattggct atggtgggag tatttatacc  2400
atgtaaattg gcaaacacta cacattttcc ttttggacag ctagttcacc agcacaccac  2460
tgtgaaactc tccttaatga ctcctctctg cccccgcttc attcctggga taatcatagc  2520
agactaaggg agaaaatgaa attgtaaaaa tttggcatac tggtgatttc tcagggcaag  2580
cagaggttac tacagctgca gctagaggga tgactaccaa caggtgacct ttacattttc  2640
ctgatgttat aattttagct tttgttttca atgtatactg ttttcctgtt tctccacata  2700
gtagtctgca ttttaaatct ataataaaac atgctgataa ctgg                   2744

SEQ ID NO: 122         moltype = AA  length = 177
FEATURE                Location/Qualifiers
source                 1..177
                       mol_type = protein
                       organism = Homo sapiens
SEQUENCE: 122
MCLSHLENMP LSHSRTQGAQ RSSWKLWLFC SIVMLLFLCS FSWLIFIFLQ LETAKEPCMA  60
```

-continued

```
KFGPLPSKWQ MASSEPPCVN KVSDWKLEIL QNGLYLIYGQ VAPNANYNDV APFEVRLYKN  120
KDMIQTLTNK SKIQNVGGTY ELHVGDTIDL IFNSEHQVLK NNTYWGIILL ANPQFIS     177

SEQ ID NO: 123          moltype = DNA  length = 2064
FEATURE                 Location/Qualifiers
source                  1..2064
                        mol_type = genomic DNA
                        organism = Mus musculus
SEQUENCE: 123
ttgtgggtat ctgctttccc cagttctcat tccatcagag aacgagttct agcctcatgg  60
aggaaatgcc tttgagagaa tcaagtcctc aaagggcaga gaggtgcaag aagtcatggc  120
tcttgtgcat agtggctctg ttactgatgt tgctctgttc tttgggtaca ctgatctata  180
cttcactcaa gccaactgcc atcgagtcct gcatggttaa gtttgaacta tcatcctcaa  240
aatggcacat gacatctccc aaacctcact gtgtgaatac gacatctgat gggaagctga  300
agatactgca gagtggcaca tatttaatct acggccaagt gattcctgtg gataagaaat  360
acataaaaga caatgccccc ttcgtagtac agatatataa aaagaatgat gtcctacaaa  420
ctctaatgaa tgattttcaa atcttgccta taggaggggt ttatgaactg catgctggag  480
ataacatata tctgaagttc aactctaaag accatattca gaaaactaac acatactggg  540
ggatcatctt aatgcctgat ctaccattca tctcttagag attgggtttg gtctcctcat  600
cttcttcttt gtatcccgag atgctggtgg gtgggttgga gggggatgat tgatggcaat  660
gcacacagtt tgtgagggct tacaaattga cacaatcaga gcctcttggc atataaaatt  720
ttagccctca tatctgtctg aagaggactc agcaaatggg ccaatcccta atgttgggtc  780
tgcaaatgga cttgtacaat ccatgataaa aaggagtatg ggccacagaa gacagaaact  840
cttccaaaga atgtctttct aaccttgatc cctgggtaga atgagatcct gtttccatgg  900
gagtcttact tggcttgcaa aaaagggtgt agggcagtag cttggccttt tttccatcat  960
aatttccttg agctgtttta ccttaatccc tccaaactct caccttctga gagcctccta  1020
atgaaacatt gttagactgg tggggtggcc aagacatgcc aacaacaccc ttctttagag  1080
gtggtgtttt tagaggacag agaacattat gaagcctaga gcagcagagg tcaagatgcc  1140
acgaaatgga attgatctgg gaattttttt ttttttcat tctcaggatg caggttcatt  1200
ctgaactttc ccctaggcct tcattgcttt tgtgtgtatg tgtgcataaa ttctgcaaat  1260
agaaaaatga gagtttgcac cagtactcac tagatttaac accagaaagt ggtacttttc  1320
tggctgtatt atgccatgat agcacatttt ctgttggtgt tccctaactg acaagtataa  1380
cagttttcct aaaccacaca acaatgctat gatgttaatg gggtagatat ttttggaaaa  1440
aaattgcaca gtgagaacat gggtagatga accctaagac tcttacctca attcagaact  1500
cgcaaggagt taagtgagtg gggtcttcat tagaccattc acatggtctc tgctttgaaa  1560
ctggcgttgc tactgtctca ttatacatca ctaaaatgga attaactcaa ctttgaaatg  1620
gatgcatcga ctttacccca aggtgtccag aatgaagcta caagactttt accagcagtc  1680
atttcctttt tgcctggagc aagaagatcc aggatactgt tggaagagtt catctcactc  1740
aaccatgctg actttccaaa gtaataatga acatttgtgt tcaaattttg gattctgtta  1800
aatttagcca gcttgtgagt tcttgtcgaa aagtatttta aaccaattta cactatttat  1860
gggtatttgt gaaaagctat atagtgatat tttatatata actaatttaa aatattttta  1920
ttttatgtaa caaaaatact ataggctaag ctatttcttc ttattttttt atgaatactt  1980
gctgaattgc catagggcac aaagactctt ctgtttgcat atcttctcag gaaattaaaa  2040
ttgtatcaca tgtatttata agaa                                        2064

SEQ ID NO: 124          moltype = AA  length = 173
FEATURE                 Location/Qualifiers
source                  1..173
                        mol_type = protein
                        organism = Mus musculus
SEQUENCE: 124
MEEMPLRESS PQRAERCKKS WLLCIVALLL MLLCSLGTLI YTSLKPTAIE SCMVKFELSS  60
SKWHMTSPKP HCVNTTSDGK LKILQSGTYL IYGQVIPVDK KYIKDNAPFV VQIYKKNDVL  120
QTLMNDFQIL PIGGVYELHA GDNIYLKFNS KDHIQKTNTY WGIILMPDLP FIS         173

SEQ ID NO: 125          moltype = DNA  length = 1852
FEATURE                 Location/Qualifiers
source                  1..1852
                        mol_type = genomic DNA
                        organism = Homo sapiens
SEQUENCE: 125
aatcctgagt aaggtggcca ctttgacagt cttctcatgc tgcctctgcc accttctctg  60
ccagaagata ccatttcaac tttaacacag catgatcgaa acatacaacc aaacttctcc  120
ccgatctgcg gccactggac tgcccatcag catgaaaatt tttatgtatt tacttactgt  180
ttttcttatc acccagatga ttgggtcagc actttttgct gtgtatcttc atagaaggtt  240
ggacaagata gaagatgaaa ggaatcttca tgaagatttt gtattcatga aaacgataca  300
gagatgcaac acaggagaaa gatccttatc cttactgaac tgtgaggaga ttaaaagcca  360
gtttgaaggc tttgtgaagg atataatgtt aaacaaagag gagacgaaga aagaaaacag  420
ctttgaaatg caaaaaggtg atcagaatcc tcaaattgcg gcacatgtca taagtgaggc  480
cagcagtaaa acaacatctg tgttacagtg ggctgaaaaa ggatactaca ccatgagcaa  540
caacttggta accctggaaa atgggaaaca gctgaccgtt aaaagacaag gactctatta  600
tatctatgcc caagtcacct tctgttccaa tcgggaagct tcgagtcaag ctccatttat  660
agccagcctc tgcctaaagt cccccggtag attcgagaga atcttactca gagctgcaaa  720
tacccacagt tccgccaaac cttgcgggca acaatccatt cacttgggag gagtatttga  780
attgcaacca ggtgcttcgg tgtttgtcaa tgtgactgat ccaagccaag tgagccatgg  840
cactggcttc acgtcctttg gcttactcaa actctgaaca gtgtcacctt gcaggctgtg  900
gtggagctga cgctgggagt cttcataata cagcacagcg gttaagccca ccccctgtta  960
actgcctatt tataaccota ggatcctcct tatggagaac tatttattat acactccaag  1020
gcatgtagaa ctgtaataag tgaattacag gtcacatgaa accaaaacgg gccctgctcc  1080
```

```
ataagagctt atatatctga agcagcaacc ccactgatgc agacatccag agagtcctat  1140
gaaaagacaa ggccattatg cacaggttga attctgagta aacagcagat aacttgccaa  1200
gttcagtttt gtttctttgc gtgcagtgtc tttccatgga taatgcattt gatttatcag  1260
tgaagatgca gaagggaaat ggggagcctc agctcacatt cagttatggt tgactctggg  1320
ttcctatggc cttgttggag ggggccaggc tctagaacgt ctaacacagt ggagaaccga  1380
aacccccccc cccccccgc caccctctcg gacagttatt cattctcttt caatctctct  1440
ctctccatct ctctctttca gtctctctct ctcaacctct ttcttccaat ctctctttct  1500
caatctctct gtttcccttt gtcagtctct tccctccccc agtctctctt ctcaatcccc  1560
ctttctaaca cacacacaca cacacacaca cacacacaca cacacacaca cacacacaca  1620
gagtcaggcc gttgctagtc agttctcttc tttccaccct gtccctatct ctaccactat  1680
agatgagggt gaggagtagg gagtgcagcc ctgagcctgc ccactcctca ttacgaaatg  1740
actgtattta aaggaaatct attgtatcta cctgcagtct ccattgtttc cagagtgaac  1800
ttgtaattat cttgttattt attttttgaa taataaagac ctcttaacat ta          1852

SEQ ID NO: 126          moltype = AA  length = 261
FEATURE                 Location/Qualifiers
source                  1..261
                        mol_type = protein
                        organism = Homo sapiens
SEQUENCE: 126
MIETYNQTSP RSAATGLPIS MKIFMYLLTV FLITQMIGSA LFAVYLHRRL DKIEDERNLH  60
EDFVFMKTIQ RCNTGERSLS LLNCEEIKSQ FEGFVKDIML NKEETKKENS FEMQKGDQNP  120
QIAAHVISEA SSKTTSVLQW AEKGYYTMSN NLVTLENGKQ LTVKRQGLYY IYAQVTFCSN  180
REASSQAPFI ASLCLKSPGR FERILLRAAN THSSAKPCGQ QSIHLGGVFE LQPGASVFVN  240
VTDPSQVSHG TGFTSFGLLK L                                             261

SEQ ID NO: 127          moltype = DNA  length = 1250
FEATURE                 Location/Qualifiers
source                  1..1250
                        mol_type = genomic DNA
                        organism = Mus musculus
SEQUENCE: 127
ctttcagtca gcatgataga aacatacagc caaccttccc ccagatccgt ggcaactgga  60
cttccagcga gcatgaagat ttttatgtat ttacttactg ttttccttat cacccaaatg  120
attggatctg tgctttttgc tgtgtatctt catagaagat tggataaggt cgaagaggaa  180
gtaaaccttc atgaagattt tgtattcata aaaaagctaa agagatgcaa caaaggagaa  240
ggatctttat ccttgctgaa ctgtgaggag atgagaaggc aatttgaaga ccttgtcaag  300
gatataacgt taaacaaaga agagaaaaaa gaaaacagct ttgaaatgca aagaggtgat  360
gaggatcctc aaattgcagc acacgttgta agcgaagcca acagtaatgc agcatccgtt  420
ctacagtggg ccaagaaagg atattatacc atgaaaagca acttggtaat gcttgaaaat  480
gggaaacagc tgacggttaa aagagaagga ctctattatg tctacactca agtcaccttc  540
tgctctaatc gggagccttc gagtcaacgc ccattcatcg tcggcctctg gctgaagccc  600
agcagtggat ctgagagaat cttactcaag gcggcaaata cccacagttc ctcccagctt  660
tgcgagcagc agtctgttca cttgggcgga gtgtttgaat tacaagctgg tgcttctgtg  720
tttgtcaacg tgactgaagc aagccaagtg atccacagag ttggcttctc atcttttggc  780
ttactcaaac tctgaacagt gcgctgtcct aggctgcagc agggctgatg ctggcagtct  840
tccctataca gcaagtcagt taggacctgc cctgtgttga actgcctatt tataaccccta  900
ggatcctcct catggagaac tatttattat gtacccccaa ggcacataga gctggaataa  960
gagaattaca gggcaggcaa aaatcccaag ggaccctgct ccctaagaac ttacaatctg  1020
aaacagcaac cccactgatt cagacaacca gaaaagacaa agccataata cacagatgac  1080
agagctctga tgaaacaaca gataactaat gagcacagtt ttgttgtttt atgggtgtgt  1140
cgttcaatgg acagtgtact tgacttacca gggaagatgc agaagggcaa ctgtgagcct  1200
cagctcacaa tctgttatgg ttgacctggg ctccctgcgg ccctagtagg            1250

SEQ ID NO: 128          moltype = AA  length = 260
FEATURE                 Location/Qualifiers
source                  1..260
                        mol_type = protein
                        organism = Mus musculus
SEQUENCE: 128
MIETYSQPSP RSVATGLPAS MKIFMYLLTV FLITQMIGSV LFAVYLHRRL DKVEEEVNLH  60
EDFVFIKKLK RCNKGEGSLS LLNCEEMRRQ FEDLVKDITL NKEEKKENSF EMQRGDEDPQ  120
IAAHVVSEAN SNAASVLQWA KKGYYTMKSN LVMLENGKQL TVKREGLYYV YTQVTFCSNR  180
EPSSQRPFIV GLWLKPSSGS ERILLKAANT HSSSQLCEQQ SVHLGGVFEL QAGASVFVNV  240
TEASQVIHRV GFSSFGLLKL                                               260

SEQ ID NO: 129          moltype = DNA  length = 4778
FEATURE                 Location/Qualifiers
source                  1..4778
                        mol_type = genomic DNA
                        organism = Homo sapiens
SEQUENCE: 129
cgagactcca tctcaaaaac aaaacaaata aacgaacaaa aaaacccaca acgtattatt  60
ttcttgttta cgaggtttct tgtctctctg gctccaccag aagaggagca gggacccttc  120
ttgctgttgt tcattgctgc atcccccaca ccgagagcag agcctggcat gggcagaaag  180
tcctcagtcg atatttggtg gccccaagcg aatgaagcat ccaagaaggg aaagctgggg  240
gctccccact gcacttgcca cctgagtcac attttcagaa gcctctggaa agtcgtgcac  300
agcccaggag tgttgagcaa tttcggtttc ctctgaggtt gaaggaccca ggcgtgtcag  360
ccctgctcca gacaccttgg gcatggagga gagtgtcgta cggccctcag tgtttgtggt  420
```

-continued

```
ggatggacag accgacatcc cattcacgag gctgggacga agccaccgga gacagtcgtg  480
cagtgtggcc cgggtgggtc tgggtctctt gctgttgctg atgggggccg ggctggccgt  540
ccaaggctgg ttcctcctgc agctgcactg gcgtctagga gagatggtca cccgcctgcc  600
tgacggacct gcaggctcct gggagcagct gatacaagag cgaaggtctc acgaggtcaa  660
cccagcagcg catctcacag gggccaactc cagcttgacc ggcagcgggg ggccgctgtt  720
atgggagact cagctgggcc tggccttcct gaggggcctc agctaccacg atggggccct  780
tgtggtcacc aaagctggct actactacat ctactccaag gtgcagctgg gcggtgtggg  840
ctgcccgctg ggcctggcca gcaccatcac ccacggcctc tacaagcgca caccccgcta  900
ccccgaggag ctggagctgt tggtcagcca gcagtcaccc tgcggacggg ccaccagcag  960
ctcccgggtc tggtgggaca gcagcttcct gggtggtgtg gtacacctgg aggctgggga  1020
gaaggtggtc gtccgtgtgc tggatgaacg cctggttcga ctgcgtgatg gtacccggtc  1080
ttacttcggg gctttcatgg tgtgaaggaa ggagcgtggt gcattggaca tgggtctgac  1140
acgtggagaa ctcagagggt gcctcagggg aaagaaaact cacgaagcag aggctgggcg  1200
tggtggctct cgcctgtaat cccagcactt tgggaggcca aggcaggcgg atcacctgag  1260
gtcaggagtt cgagaccagc ctggctaaca tggcaaaacc ccatctctac taaaaataca  1320
aaaattagcc ggacgtggtg gtgcctgcct gtaatccagc tactcaggag gctgaggcag  1380
gataattttg cttaaacccg ggaggcggag gttgcagtga gccgagatca caccactgca  1440
ctccaacctg ggaaacgcag tgagactgtg cctcaaaaaa aagaaaggaa gaaaaaagaa  1500
aactcaggaa acagatcttg gggacactc cagggaaccc aaaactcaaa ggcggagagc  1560
tcagtgggca ccaccaaggc gagatgaagc cccagcaggc accttcagaa gacccacgta  1620
gactgcagac cctgccacgg acaatactaa ggacaaaaac ccagagactt ggggtctgtg  1680
ggcccccaaa catggggtaa agttgatttg cctgatattc aggaagaagg ggtgaggggt  1740
gggtatttat gcttttgatt cagaagaaag tggggcttgg gattccaggg acttggctgg  1800
gggtgggaaa cttcatccac ttccctactc tcatcatgag tacggacagg gtgggcggga  1860
gactgatcat cgggactcat catgaagagc ccagccccac cccacatact cagatcccac  1920
ccacagactg gtggccacac ctcagcctgg tcacaaagag ttacactcag atacatgagc  1980
acggcagcgt gctcataact gtttaacaac cagctgtcct gggaggggga cagctttgta  2040
atgtttgcca atttccatgg tgtaaatgct accaccatgg ctgatttcat cactgccaag  2100
catagacatc cctaatagga caccacggat ctgtccccgg catccggccc agggcctggc  2160
acaaagcatg ctctagggaa atgcttgctg attgaaagga aggaagaatg actctacagt  2220
cacacctatg gcatcccaca aaatctgtca catggctgca taatctcagc cactctttca  2280
caactataga ctcatacacg cgaagtgcca gattcatgca caaccacaca atcacatgga  2340
agtcacagac ggcatcacag acagtcacag cactgtgtgt atgttataac acaagcacac  2400
aaaactcaga cagcatccca gctacacagc cactcccaga ggtgtcaccg tcacacttgg  2460
taattaatac tcattacatt agacacagac agaccaagtt atagtcagac ctggttacac  2520
acatacacac acacaatatc accatgacaa atacacatta cacacacaca acatcacaat  2580
gacaaacaca cattacacac acaacatcac gatgacaaac acacattaca cacacaacat  2640
cacgatgaca aacacacatt acacacacat cacaatgaca aacacaacat tacacacaca  2700
caacatcaca atgacacaca catcacacac acatcacaat gacaaacaca caacattaca  2760
cacatataca cacagcctga gggccctccc cagcccagac taacacatct cggggtgagg  2820
accagacctt gttcataacc ctgggcctct taaccactga tctttgaaat aaatggcaaa  2880
tagttgtacc tggatctgtc tagttcttag gggaacaaac tgaagaaggg tggagaggaa  2940
ttgtcaggcc taaagagccc cacagggaaa gggaggagtc ggatgggggg caaccatcag  3000
caacaagtgg tggctcctag aggcagaggg atggaggtaa tgacccatgg aggtcattct  3060
acagatgagg aacctggacc cagttggctc aagtccatgc aggaaatgtg ggggaaacca  3120
gagacctcac gtctggatct ggcttcctct ccaatccaca attcctgagg aagtagaggc  3180
tacatcccgc aagacgccct tattagacac atccaggaca gaatgacaat ccgccaagcc  3240
agctggaagc ataaaacaca gggagctggt gggttgggtg ggggcagata atgatatgca  3300
tacaaattag agggtctatg caaatgagca ttgctgcagt gtggctggag ggaatcctta  3360
gttcctagga ttctaggata tgggtttcga ccccagaggt gaatgtattg ttattattgt  3420
tttgttgttg ttgtgaatga caagtcaaaa tttgtgggtt attgttgtta tcgccaatag  3480
tattcttgtc attgttgcac agtacagaga tgaaggaaac agattttgca atcagatgat  3540
cctgggttct gagtccactc tgccactcac cagctatatg acctccagca atttccatca  3600
cctctcaatg cttcagtttc cccatcggca agatggttgt ggggggagag gaacaacagt  3660
acagattcac catcccaaat tcaaaatgct ccaaaatcta ggccgggcgt ggtggctcat  3720
acctgtaatc ccagcacttt gggaggtcaa agtggacgga taacctgagg tcaggagctc  3780
cagaccagcc tggccaacat ggcgaaaccc catctctact aaaaatacaa aaaattacct  3840
gggtgtggtg gggggcacct gtaaccccag ctactcggga ggctgaggca ggaaccctgg  3900
aggttgaggt tgcagtgagc tgagatcaca ccactgcact ccagcctggg tgacagagca  3960
aggctcccat ctcaaaaaac aaaaaaacat gctccaaaat ctgaaactct ttgagcccca  4020
gtgtgatgcc acaagtggga aattccacaa ctcatcacat gtgatagatt gcagtggaaa  4080
tgcaggcaca caccacgaag tttactcagc atcctcaaag gaaatccccg tcagtagcta  4140
tatatcattt tctcacatgc cagataggta tctctcatct tttactgtta ggtacttctg  4200
tgttgaatag gtggaggaaa atgattgctg gttagtagta tataaattca gagtcaggaa  4260
ggatggtgat gtcggctggg tgcagtggct catgcctgta attccaatgt gataccctac  4320
cttgtgttta acgtgattga ctctccctta gctgagaggg ccaggcagac tctattttgg  4380
cttcttcgct tgcagtctct cacccacccc ccttcctcaa ggacttaagc tgactcccag  4440
cacatccaag aatgcgatta ctgataagat actgtgacaa gctatatcca caattcccag  4500
gaattcgtcc ggttgatagc acccaaagcc cccgcgtcta tcaccttgtg atagatttaa  4560
agcccctgca cctggaactg tttgtttttc tgttaccatt tatctttttc actttcttgc  4620
ctgttttgct tctgtaaaat tgcttcagct cggctccctc ttccccttct aaaccaaggt  4680
ataaaaagaa acctagcccc ttctttgggg tggagagaat tttgagcgct agccgtctct  4740
cagtcgccgg ctaataaagg actcctgaat tagtctaa                          4778
```

```
SEQ ID NO: 130          moltype = AA  length = 240
FEATURE                 Location/Qualifiers
source                  1..240
                        mol_type = protein
                        organism = Homo sapiens
```

```
SEQUENCE: 130
MEESVVRPSV FVVDGQTDIP FTRLGRSHRR QSCSVARVGL GLLLLLMGAG LAVQGWFLLQ  60
LHWRLGEMVT RLPDGPAGSW EQLIQERRSH EVNPAAHLTG ANSSLTGSGG PLLWETQLGL  120
AFLRGLSYHD GALVVTKAGY YYIYSKVQLG GVGCPLGLAS TITHGLYKRT PRYPEELELL  180
VSQQSPCGRA TSSSRVWWDS SFLGGVVHLE AGEKVVVRVL DERLVRLRDG TRSYFGAFMV  240

SEQ ID NO: 131          moltype = DNA  length = 1869
FEATURE                 Location/Qualifiers
source                  1..1869
                        mol_type = genomic DNA
                        organism = Mus musculus
SEQUENCE: 131
ttttgcagtt tgcacagccc gagcgtgttg ggcaattgtg gtttcctccg gagaggagga  60
actcaggctt gccaaccctt tccctgggct tcggagcctc agctgctctg gcatggagag  120
tgtggtacag ccttcagtgt ttgtggtgga tggacagacg gacatcccat tcaggcggct  180
ggaacagaac caccggagac ggcgctgtgg cactgtccag gtcagcctgg ccctggtgct  240
gctgctaggt gctgggctgg ccactcaggg ctggtttctc ctgagactgc atcaacgtct  300
tggagacata gtagctcatc tgccagatgg aggcaaaggc tcctgggaga agctgataca  360
agatcaacga tctcaccagg ccaacccagc agcacatctt acaggagcca acgccagctt  420
gataggtatt ggtggacctc tgttatggga gacacgactt ggcctggcct tcttgagggg  480
cttgacgtat catgatgggg ccctggtgac catggagccc ggttactact atgtgtactc  540
caaagtgcag ctgagcggcg tgggctgccc ccaggggctg gccaatggcc tccccatcac  600
ccatggacta tacaagcgca catcccgcta cccgaaggag ttagaactgc tggtcagtcg  660
gcggtcaccc tgtggccggg ccaacagctc ccgagtctgg tgggacagca gcttcctggg  720
cggcgtggta catctggagg ctggggaaga ggtggtggtc cgcgtgcctg gaaaccgcct  780
ggtcagacca cgtgacggca ccaggtccta tttcggagct ttcatggtct gaaggctgcg  840
gtgacaatgt attttgtgga gggacctctc caggactcac ctcaaaccca gcaatagggt  900
ttgaagtcct ccctttaagg agccctgaac tctgcagtgc tcggggcggt gtagactgct  960
gacctgcttt gggcaatctt caaatcagag acctggagac ttggggcgtg gagcccagga  1020
gcgaggggtc agctcatttg cctgatattc aggaagaaag aatcaagctg gggtatttat  1080
gcttctgatg caaacactga gatttcggct ttctgggttt tgagctggag gcaagaaacc  1140
ttcccagagt gtcatcagga ccatgttggc aggacttggg gctccagact tgccaccaca  1200
ctctggcctc tcccatccat ccgctgcatt ggtttccagc caccaaaaca gcactggccc  1260
cctggctgca actggccagg tacgagcttc tgagcaccta cattcctcag ggacatcttg  1320
atgagatctc agtactcagt ccaatgcgca gcagcgacag acatgccagg aatggttggt  1380
cagaagggaa gggaggaaag ggaggaaaga agggaatgca gaagagaagg ggggaaaaca  1440
agaccaaaac aaaacagcaa caacaaagcg gcagggagga ggtgacaccc ttggggatac  1500
tttagtcaac acacttagaa cagattgtgc caggcctgtt ggattcctgg agttgatggg  1560
atcgtgggaa ggcacaatgg ggagcaagtg ggcttgggtt atggctcagt gggtaaagtg  1620
caattatggg gatctgagtt tgaatccctg gtacccatat aaagacacag atgcggtgat  1680
gggcacttgt gacaatgaga tcatcaatag ggaatggaga caggagggac ctctggggtt  1740
cactggccag gcagtctagc tgaatcaaag agctccaagt tcagtcgata gctcctgaag  1800
atgacaactg aggctattct ccaaacccca cacgcaggac acatgcgtaa taaataaaat  1860
tttaaaaat                                                          1869

SEQ ID NO: 132          moltype = AA  length = 239
FEATURE                 Location/Qualifiers
source                  1..239
                        mol_type = protein
                        organism = Mus musculus
SEQUENCE: 132
MESVVQPSVF VVDGQTDIPF RRLEQNHRRR RCGTVQVSLA LVLLLGAGLA TQGWFLLRLH  60
QRLGDIVAHL PDGGKGSWEK LIQDQRSHQA NPAAHLTGAN ASLIGIGGPL LWETRLGLAF  120
LRGLTYHDGA LVTMEPGYYY VYSKVQLSGV GCPQGLANGL PITHGLYKRT SRYPKELELL  180
VSRRSPCGRA NSSRVWWDSS FLGGVVHLEA GEEVVVRVPG NRLVRPRDGT RSYFGAFMV   239

SEQ ID NO: 133          moltype = DNA  length = 6583
FEATURE                 Location/Qualifiers
source                  1..6583
                        mol_type = genomic DNA
                        organism = Homo sapiens
SEQUENCE: 133
agaggtgcct ccaggagcag caggagcatg gccgaggatc tgggactgag ctttggggaa  60
acagccagtg tggaaatgct gccagagcac ggcagctgca ggcccaaggc caggagcagc  120
agcgcacgct gggctctcac ctgctgcctg gtgttgctcc ccttccttgc aggactcacc  180
acatacctgc ttgtcagcca gctccgggcc cagggagagg cctgtgtgca gttccaggct  240
ctaaaaggac aggagtttgc accttcacat cagcaagttt atgcacctct tagagcagac  300
ggagataagc caagggcaca cctgacagtt gtgagacaaa ctcccacaca gcactttaaa  360
aatcagttcc cagctctgca ctgggaacat gaactaggcc tggccttcac caagaaccga  420
atgaactata ccaacaaatt cctgctgatc ccagagtcgg gagactactt catttactcc  480
caggtcacat tccgtgggat gacctctgag tgcagtgaaa tcagacaagc aggccgacca  540
aacaagccag actccatcac tgtggtcatc accaaggtaa cagacagcta ccctgagcca  600
acccagctcc tcatggggac caagtctgta tgcgaagtag gtagcaactg gttccagccc  660
atctacctcg gagccatgtt ctccttgcaa gaaggggaca agctaatggt gaacgtcagt  720
gacatctctt tggtggatta cacaaaagaa gataaaacct tctttggagc cttcttacta  780
taggaggaga gcaaatatca ttatatgaaa gtcctctgcc accgagttcc taattttctt  840
tgttcaaatg taattataac caggggtttt cttggggccg ggagtagggg gcattccaca  900
gggacaacgg tttagctatg aaatttgggg cccaaaattt cacacttcat gtgccttact  960
gatgagagta ctaactggaa aaaggctgaa gagagcaaat atattattaa gatgggttgg  1020
```

-continued

```
aggattggcg agtttctaaa tattaagaca ctgatcacta aatgaatgga tgatctactc  1080
gggtcaggat tgaaagagaa atatttcaac accttcctgc tatacaatgg tcaccagtgg  1140
tccagttatt gttcaatttg atcataaatt tgcttcaatt caggagcttt gaaggaagtc  1200
caaggaaagc tctagaaaac agtataaact ttcagaggca aaatccttca ccaatttttc  1260
cacatacttt catgccttgc ctaaaaaaaa tgaaaagaga gttggtatgt ctcatgaatg  1320
ttcacacaga aggagttggt tttcatgtca tctacagcat atgagaaaag ctacctttct  1380
tttgattatg tacacagata tctaaataag gaagtatgag tttcacatgt atatcaaaaa  1440
tacaacagtt gcttgtattc agtagagttt tcttgcccac ctattttgtg ctgggttcta  1500
ccttaaccca gaagacacta tgaaaaacaa gacagactcc actcaaaatt tatatgaaca  1560
ccactagata cttcctgatc aaacatcagt caacatactc taaagaataa ctccaagtct  1620
tggccaggcg cagtggctca cacctgtaat cccaacactt tgggaggcca aggtgggtgg  1680
atcatctaag gccgggagtt caagaccagc ctgaccaacg tggagaaacc ccatctctac  1740
taaaaataca aaattagccg ggcgtggtag cgcatggctg taatcctggc tactcaggag  1800
gccgaggcag aagaattgct tgaactgggg aggcagaggt tgcggtgagc ccagatcgcg  1860
ccattgcact ccagcctggg taacaagagc aaaactctgt ccaaaaaaaa aaaaataaaa  1920
taataactcc aagcctttaa aaaatatcat ctgaaactgt tacatcagat ttctggcact  1980
ctactgactg tggaagatag ccagctgact ggaagatagc cagctgatta gttccctgaa  2040
gaaacctgaa gacagatacc tggttaacta gatcaactac actgccaact tgtttgatgc  2100
tgagagacaa tggacttatt ccatggggga agggaaaaaa gaagtcaatc accaaatctg  2160
aagaagttaa cctagatctt tgaggtttga tttgcaactt tatatgcaga gtattatgtg  2220
ggtattttcc cttaaaatat tcaaagggat ttacatatgg gattagctaa tgagcctagc  2280
caagaccttc cctggaggac aggctggtca ttgcggaggt cccttctgtg cttcagtggg  2340
ttcatatcct ctagtccgta tgattttcct acgctaatat gtcaagggca ggagaggcag  2400
ctctgttctc ctagcctttg ttgacttgtc tgcaaagcag gaatctgccc atttgtttcc  2460
aaggagcaaa tgagctcatg agaatgaaag atgttaactt catgcattct gtgccatctg  2520
agcatttcgg tattatatga ctggtgaccc ttggcccgta ttataaatgc ttcctatcct  2580
gggagacctc atggatgagt ctgagaggaa atttggcacc aaaatcactc tcactctggt  2640
ttccagtaga ctatagaggc agagaggcat ttgagaggct cctgagcaaa gtgtccagtg  2700
tagcaggagc acttcattaa tatttattga gttataatta aataaaaatt aatttctgat  2760
ttctcagttt ggaggttaag gctctaaata tattttctaa cctctgctag gctaacttaa  2820
gccaggcctt tttcttgcct tccctttctc aaaacagtca gcacagactc agtgggagca  2880
cagaggagtg tggtcacctc cacctggctc accagagtct tcatagagga agtgaagcct  2940
ggaagaaact gggcgggccc cagatgacca cagggaaagg gcatctcaga tggaggaatt  3000
acccttgact taaagcagaa aagaaagatt tctcagtaac tccaaaactt gcttgatagg  3060
agaatattcc ctcaaccaat tcctaggaca atatttattg gtagatcaag aatgtttcct  3120
caataactct agtctagctc catgatcaga actaacaccc attaaaaaca taaaatgttc  3180
tttctgaacc ggtcttcatg gtgcgtgaga gcaccaagca gctttggtat gcaggaggag  3240
ttttgcacag aagagtggcc tgctcaaacc tgcccactgt tctgtaggtg atctggtgga  3300
tctggaaatt tatcccaaga caggaatttc ctaatattcg aagacatttg aggctttggg  3360
aaattctctg ctgtgcattt atttggctcc tgtcataagc ttgtttttta aagaatgtat  3420
catagctcaa gtttttactg ctgattttgt taaattctgt atagtatatt ttttacggaa  3480
aggcacagtc agacattcct aatagggctc atgtcagaac ttctgttccc aaggcattat  3540
ctccatagca aaaattagtg cactgttttc aaaagtgagg tgggaaaatg cttttaagat  3600
catgtgatgt tcccctaaaa ggggttaatg gggtgtattc agggtttggg agggaggaag  3660
aagcatgctt tagaaaacag taaatttagg gagaaaatgc tttgttggtt aaatgtcact  3720
caaaaggctg aattcaaatc aattccacaa acatttactg agtacctact gcccctgggg  3780
acacagagat aaattattta gtctcagaca cactcattct aacttcccag cacctctact  3840
gtctgcagat tctttaattt attttggttg tattagctaa ttaattcgta aactttaggc  3900
acatggatct attctcatta tgaaaatgga tgccatttga ttaaggctga tgactaacaa  3960
aatgatttgt gtttactcga agtgtttttt taaaaatagc tactcaagga tagtttttcca  4020
taaatcaaga aggtaaaaaa gttcccattt tttattgtag aatccattat ttaaactaca  4080
tgtagagaca ggttattatt tgctatattc aagtttggtc atcaataccc ttaaaaaatat  4140
tagaatttta tggatgaccc agaaatgctt tgaaaatctg tgttcctcag caaatacaga  4200
gaccatgatc aaaatgcaca gaatcactaa cattttgatg ctagcatggt ttcagtctat  4260
ttggcagaac agaattgatt atgctactaa aatttctttt tctttttttt tttttttttt  4320
tttgagacag agtcttgctt tgtcacccag gctgaagtgc agtggcagga tctcagttca  4380
ctgcaacctc tgcctcccag gttcacgcca ttctcctgct tcagcctccc gagtagctgg  4440
gactacaggc tcccaccacc atgcccggct aattttttgc atttttagta gagacggggt  4500
ttcaccgtgt tagccaggat ggtctcgatc tcctgacctc gtgatccgcc cgcctcagcc  4560
ttccaaagtg ctgggattac aggcgtgagc cactgtgccc ggactctgat ttttttttta  4620
ctaaggtaca gtaagaaaag ggaaaagtgt acgttttcac ttcctgaaat atgtcaggtt  4680
gaatcaataa tagagcacac cagaactctt ggctccattt caacctaaac tattcagttc  4740
tcatcacccc agaggaaatt ccgcctctgt gctggtcagt aatccccctg gattataaaa  4800
gtttaactaa ctcactgtgc acaaggcacg gccattgcca acattctctt gcaaggtatt  4860
ttcccaagcc cttacccaat tctgtttcca tgattgtgac attggggatt aattctgcaa  4920
gacagaactg tttatattct gtaccttaaa aacacatgca aacatctctt gccttaagat  4980
ttctggcttt cctatggccc agagtcctag aagtgttttg atatttgtag cagaattttc  5040
aagtgtacat ccttatcctg gatattaaca tttttgcatc atattggcag ctggacctac  5100
agagaattta gtagactgtt aacctaataa gccttgaatc cttttgcacc agtggtgaga  5160
gaatgtggat cagagccatc acctccatgc cccgtcaccc tctaacaacc acatttacaa  5220
cttccccagc tctgagacac acttgcctcc accccttcca tcaccccatt ttaagatgaa  5280
aataccacac cagcctggaa ggaagaagtt acttgcccag ggccacatag tgagttaagg  5340
gctgatctag agctaggaag ctgtcttcct gaaccataat cctggactct tctaacctct  5400
ctactcatcg caaatagagt tcattttagt gatttgaagg aagatgggac aagtattttc  5460
aaacacctgt aggacaacat ggaagtggga ggagacttct actgtagctc cccagagaag  5520
agagctaggg ctacagagtt gcagttacaa ggttgccctc tctggcttga tccccaaagg  5580
aattttctac tccaaaatag aatttttcta ggatgctatt tctcagtccc tggagatact  5640
caaacaaagg gcttgtcaca agggtttttg tagaagctat tcttcacaga ggttggggga  5700
gagattaagc caaaggatct ctgaggtctt tttcaaatct ataattatgt ggccttttgt  5760
```

```
tcattgactt ccatgtgttc tagttgatca ttacaaacct ggcaggcctt ctcaagggtt  5820
cagtaattag ctgtcatttc ccatttgtcc agagagtgtc caacacaaaa taccccctaag  5880
atcttggcca atagagaaat gtcatggaat tttagaaatg acagtatctg cggagtttat  5940
tccaagttat atcatttcaa agatgaagaa acccaggctc agagggagcc atcacatcca  6000
caccctgtca cccttcgtgg ccagtgccag acagtagcta gttggatgct aaaagtagaa  6060
tttagatatc ttaacaataa gcccagcagt ctttcaactt cattcgtaaa tcatttttgt  6120
tttgagcatc tgtcacgtgg cagcacttgc ctggatactg gagagctgag aaggaatgcg  6180
acaggcaagt cctactctca cagtgtatac attcaggagg aacaagacac acagtgccaa  6240
gtaaataaag tagctgaact tcatcaaatg attttattct taaagtcatt aaagcatgta  6300
atgttcccct ttttttgttt caggggtgta cagattgaag aagtgtaggt gtttatgtgg  6360
ttttagtgac aaaccccatg tgctttcatt gattttatgt tttatgttaa aacatcaacc  6420
gcaaggtaaa atgcatattg tatgttgttg gatacgtact taactggtat gcatcccatg  6480
tctttgggta ctagtgtatg aattctaatc tctgtaaatg aaatgttgta tgtgttaata  6540
tatttaatag atgtaactta ataaactggc attgaagact gaa                    6583

SEQ ID NO: 134         moltype = AA  length = 251
FEATURE                Location/Qualifiers
source                 1..251
                       mol_type = protein
                       organism = Homo sapiens
SEQUENCE: 134
MAEDLGLSFG ETASVEMLPE HGSCRPKARS SSARWALTCC LVLLPFLAGL TTYLLVSQLR  60
AQGEACVQFQ ALKGQEFAPS HQQVYAPLRA DGDKPRAHLT VVRQTPTQHF KNQFPALHWE  120
HELGLAFTKN RMNYTNKFLL IPESGDYFIY SQVTFRGMTS ECSEIRQAGR PNKPDSITVV  180
ITKVTDSYPE PTQLLMGTKS VCEVGSNWFQ PIYLGAMFSL QEGDKLMVNV SDISLVDYTK  240
EDKTFFGAFL L                                                       251

SEQ ID NO: 135         moltype = DNA  length = 5777
FEATURE                Location/Qualifiers
source                 1..5777
                       mol_type = genomic DNA
                       organism = Mus musculus
SEQUENCE: 135
atcagaagtc tctccaagac agcagaagga tggcagagga gctggggttg ggcttcggag  60
aaggagtccc agtggaagtg ctgccggaag gctgtagaca caggccagag gccagggccg  120
ggctagctgc caggagcaaa gcctgcctgg ctctcacctg ctgcctgttg tcatttccca  180
tcctcgcagg acttagcacc ctcctaatgg ctggccagct ccgggtcccc ggaaaagact  240
gtatgcttcg ggccataaca gaagagagat ctgagccttc accacagcaa gtttactcac  300
ctcccagagg caagccgaga gcacacctga caattaagaa acaaacccca gcaccacatc  360
tgaaaaatca gctctctgct ctacactggg aacatgacct agggatggcc ttcaccaaga  420
acgggatgaa gtacatcaac aaatccctgg tgatcccaga gtcaggagac tatttcatct  480
actcccagat cacattccga gggaccacat ctgtgtgtgg tgacatcagt cgggggagac  540
gaccaaacaa gccagactcc atcaccatgg ttatcaccaa ggtagcagac agctaccctg  600
agcctgcccg cctactaaca gggtccaagt ctgtgtgtga aataagcaac aactggttcc  660
agtccctcta ccttggggcc acgttctcct tggaagaagg agacagacta atggtaaacg  720
tcagtgacat ctccttggtg gattacacaa aagaagataa aactttcttt ggagctttct  780
tgctataagg aggagaaaac catcattcca aggggctccc ctgcctccta ctttccaatt  840
tccttttctc atatggatct ataaacaggg gctttagagg gatcagggaa ggggacagtg  900
gtttagctat ataatttagg aacccaatat tgatccgtat atgccttatg gactaaaata  960
gtaaatggaa aacccagtac agctcatgtt tgatagagac ctgctgggtt ttaaaaattg  1020
aaacacgcct catccaatgg cacaatctac tgatttcagg acagaacctt tccacagtgc  1080
cctctgtcca agtcctttct gaattcagca gttcagttag agctgaattc gacaatgaac  1140
ttactccaga tcaagagcta aagacagaat ccaaagaaag actgagaaaa tgatgttatt  1200
tctccaagag gcaatgcatt tccacattct tttgtgccta acctaaaaaa taagaaagaa  1260
gaaaggaagg aaggaaggaa ggaaggaagg aaggaaggaa ggaaggaagg aaggaaggaa  1320
ggaaggaagg aagggacaag aaaagacaag acaagacaag aaaaaagaaa aaatggtatt  1380
tctcgtgaat attccctaaa aggaattggt tttctgctgt gaaggagaaa cctcaccttt  1440
cttctgattg catcctttag tatccaaaca tacaagtggg aattccaaat gcacatggaa  1500
catagaacac ttttattatt gtgagaacat gtttattgag tacctactat gctctgggca  1560
ctcagcccac aggaccatga agagaaagtc aaattttctt aaaaactaaa tgaatcctca  1620
atacatactt cctgatcaac taccactcaa aatgtataac ttccaaagta taacttcaag  1680
tcagccatct aggtggtttc ttgggtaaag gtgcttgtca ttaagcctga cacctgggtt  1740
tgacctccca gaacccaaaa gctggaagga gagaattggt tcccacaaat tatcctcaaa  1800
cccccataca aatgatgtgg catgcacaca tgtaactaaa taaataagtg taaaacaaaa  1860
acaaaaacaa aattttaaag aaaaatttca agtcctgaaa gacagcattc ctgagaatgt  1920
tgtctccatc gttgtccagt ataggctaac cagctgatag agacactgaa ggaatttaaa  1980
gacagacatc aagtgaaatg gagcactgta gaaacacttg attcatgcca ggagtcaatg  2040
tactatgaag accaacaaca aagtgtcagt catcaaatcc agaggtgttt atctagatct  2100
gctttcaagt ttggtttgca gcctttatat agtctctatt acaaatgctc gtgtcatggt  2160
agatgccaca aggagtcaga gggtaaactt agccccaaac cactgctgag ccatcttcta  2220
ggaaaccttc gaagcagagc tgggcagcgt gactcccaca caatgactgg gaaagtagta  2280
gctgatcaaa atttgttgag taataatttg ttagaaaatt catctccact gcctactaaa  2340
cctaagttgt atactatcta gcttctgcta agccaactta cattggccac tttttctgtc  2400
ttcaacttct tgaagtatca caggtctcag tgagaacaca gggaaaggtg aggtcgcctt  2460
cccctggttc ttcatagggg aaaccacacc tgaaagaaga tgagcagcct gaggtgacct  2520
ggaggaaggg cctgtctcaga agaaggactt attttttggc ttaggtctaa aaccttgaga  2580
gtaatgctca ctggtcaatt gaggatgctt tatcaatgac tccagtctga ctccaaggtc  2640
agaaaggaga gtgagatgct ctctctgcct gcatatatct tcatggaaca tgagaatatt  2700
gagcaacata gacttatagg aaaacacttg cccaaaagta gccagagtga cctggtcatc  2760
```

-continued

```
ccctctacta aacccaagct ttgtgtcaag ggccttcaaa gctgcccaga agtgatctgg  2820
atggcttggg aatttatcca agacaggaat ttcctgacag ccaaagatgc ttgagtcctt  2880
gtgcctgaca tgcatttatt ttgcccctgt ttattgaaga ctgtaactgt tgatttgtgg  2940
gtatacatac atacatacat acatacatac atacatacat acatatgctg tcatgaaggc  3000
agcatcaaac attactaatt ggactcaaac cagcatttct gtttccaaga tactaagtat  3060
tcccatgcaa acaggagcat gctatttttc taaagcaaaa tgaaaaaaat agttttgaaa  3120
gtatatatat gatggagtca agtgtaatgg catacatctg taaacccagc acatgggatg  3180
ctgagccagg aggattgccg tgagtttgag gagaacaggg gctaaatagt aattttcagg  3240
aaagccttgc ctatataaca agaccttgtc tcaaatgaaa aaaaaaaaaa aaatagaccc  3300
caggctggtc cttggagata aggtaatata ttcattgggt gagggggtgt gtgttttgga  3360
aaatagttaa tttagtgaga aatgcttttc ggtcaaatgc atctcaaagg ctgctgaatt  3420
caaatcgggt ctgtaaatgc ttacctagtg cttgcttgcc ctggggacag agacataaat  3480
tactttagtc tcagatccac tcgttctaac agattggcat ctccatcgtc tgtggagctt  3540
ttaatcactc tgtttgtatt agctaattaa ttagctaact tgagacacac tgatattttc  3600
ttattataaa catgggtgcc atttgataaa agacaatcat taacaaaatg gttcgaattt  3660
ccgcttaagt gatcttcttt tttccttttc attttttta actagctaat caaaggtagt  3720
ttcccaaaaa taaatgcaaa gggagtataa agaaaaaatt ccctgtggtg ggagctagta  3780
ttgaaacaac agtatcaaag aggctgttac ctactggcct caaattttgg caggaacgcc  3840
tttgaaaatg ttagaacttt acggacagcc tagaggtgct ttgaaaagtc tctgttgcca  3900
acaaaagcca ttaatcagca tgcggcacag gttactcaaa ttttgacctt gactgttttt  3960
tagatctgtt acacagaaca caacttctgg gctgtaatct ctgatgtgga tttggtgatt  4020
tactaaggta ccgtgggaaa caaggaaagt gtacttgtac cacatcgttt ctcagtgcat  4080
gtcagagtct actcaacagc agggcatgcc agagccttgg atacattccg ggacaaacta  4140
tgtcactcct aaggaaattc caagtgtgtg cctgtcaagc actctggatc atagaagccc  4200
acgagttcac tgtgcacaag gcacagccat ggccagcact ctcttgcatg gtatttctct  4260
taagctctta ctcaatcacg gtcccatgat tgtgacattg gggattaatt gcttgagcag  4320
gtttatttac agtctgttcc ttgcaaaata catgcagata tgtctggcct caaaatcccc  4380
tgattgtttt agggcttaga gaatactggg gatgttttttg ctgttttcag atgtacttta  4440
tttaagcttg cagaattacc ctgaatatta acagtgttct aagatattgc ctgctagctt  4500
ctggctaatt tactagtggt gacagtatca gatcagagta tctatattta tgtcttgcta  4560
ttatagttaa aacttcctga tctctgtaac acactcaccc ctacctcatc tatctaccca  4620
tcttgtggat gtagctgtga gaagactcac aagcccgagt tgcagttact tttctgaagc  4680
aacatagtat gttaatggaa tggccagaac tctactcttg gcacatggca ctgaatttga  4740
tgccactaaa agaaaaattg aaggcagaaa tattttttac tatgcatggg acaacgtaga  4800
agagcaagga gactgcttac acatggtggt cacatctctg gcttcatccc taaaccaatt  4860
ttctgacccc aagtcgattt tttttcatgt agttattgtt cattttctgg aaagagtcaa  4920
gcaaaaagag agttttatag aaaccattgc atcatggagg tcaggggagg gattaagcca  4980
aagaattcct tctccaaatc tatagccata tggccaccct ttggtgtact tctatttgat  5040
catgacaaac ctgagagccc tgcccagagt tcagtggatc ctaatgaact ccaagagtaa  5100
ttcattccct caccaactct aggggcttgg ccagtgcaga aaatgtcatg ggattttaaa  5160
gttaacatga gctgctatcc aaacttatgt ctctttaaga atggagagac acaggccagg  5220
agaggtaaca tatgaagcct ggtattgggc agtagcttga tggagtattg aggctaaaag  5280
tagacttcct gcccctgacc atacacaaca ccctttcagt ttgatccatg gtggtcttat  5340
tctactttat tttgagcacc tgtcacacct agttactgtc atgccaagaa ggtccataac  5400
aggcaaatcc tactctgctg tgtgcacaca agaggaagga ggctcacagt agcaagtaaa  5460
cagataagca aacgtacacg attttcgtct taaagtcatt aagacacacg cgtacccctc  5520
ttttgtttca gagggtatac aggctgaaca gatgtcagtg ttcacctatt cttattgata  5580
agccccatgt gctttcattg gttgaatgtt ttatgttaaa acgtcatatt gccatcgtaa  5640
aatgcatatt gtatgttgtt gggtatataa ttaactaata tgcatcgcat gtatgaattc  5700
taatctctgt aaatgaaaac ttatatatgt taacatatgt aatagttata atttaataaa  5760
ctgacactgg agactac                                                 5777
```

```
SEQ ID NO: 136          moltype = AA  length = 252
FEATURE                 Location/Qualifiers
source                  1..252
                        mol_type = protein
                        organism = Mus musculus
SEQUENCE: 136
MAEELGLGFG EGVPVEVLPE GCRHRPEARA GLAARSKACL ALTCCLLSFP ILAGLSTLLM  60
AGQLRVPGKD CMLRAITEER SEPSPQQVYS PPRGKPRAHL TIKKQTPAPH LKNQLSALHW  120
EHDLGMAFTK NGMKYINKSL VIPESGDYFI YSQITFRGTT SVCGDISRGR RPNKPDSITM  180
VITKVADSYP EPARLLTGSK SVCEISNNWF QSLYLGATFS LEEGDRLMVN VSDISLVDYT  240
KEDKTFFGAF LL                                                      252
```

```
SEQ ID NO: 137          moltype = DNA  length = 2737
FEATURE                 Location/Qualifiers
source                  1..2737
                        mol_type = genomic DNA
                        organism = Homo sapiens
SEQUENCE: 137
aaaccctctg taaagtaaca gaagttagaa ggggaaatgt cgcctctctg aagattaccc  60
aaagaaaaag tgatttgtca ttgctttata gactgtaaga agagaacatc tcagaagtgg  120
agtcttaccc tgaaatcaaa ggatttaaag aaaaagtgga atttttcttc agcaagctgt  180
gaaactaaat ccacaacctt tggagaccca ggaacaccct ccaatctctg tgtgttttgt  240
aaacatcact ggagggtctt ctacgtgagc aattggattg tcatcagccc tgcctgtttt  300
gcacctggga agtgccctgg tcttacttgg gtccaaattg ttggctttca cttttgaccc  360
taagcatctg aagccatggg ccacacacgg aggcagggaa catcaccatc caagtgtcca  420
tacctcaatt tctttcagct cttggtgctg gctggtcttt ctcacttctg ttcaggtgtt  480
atccacgtga ccaaggaagt gaaagaagtg gcaacgctgt cctgtggtca caatgtttct  540
```

```
gttgaagagc tggcacaaac tcgcatctac tggcaaaagg agaagaaaat ggtgctgact  600
atgatgtctg gggacatgaa tatatggccc gagtacaaga accggaccat ctttgatatc  660
actaataacc tctccattgt gatcctggct ctgcgcccat ctgacgaggg cacatacgag  720
tgtgttgttc tgaagtatga aaaagacgct ttcaagcggg aacacctggc tgaagtgacg  780
ttatcagtca aagctgactt ccctacacct agtatatctg actttgaaat tccaacttct  840
aatattagaa ggataatttg ctcaacctct ggaggttttc cagagcctca cctctcctgg  900
ttggaaaatg gagaagaatt aaatgccatc aacacaacag tttcccaaga tcctgaaact  960
gagctctatg ctgttagcag caaactggat ttcaatatga caaccaacca cagcttcatg  1020
tgtctcatca agtatggaca tttaagagtg aatcagacct tcaactggaa tacaaccaag  1080
caagagcatt ttcctgataa cctgctccca tcctgggcca ttaccttaat ctcagtaaat  1140
ggaatttttg tgatatgctg cctgacctac tgctttgccc caagatgcag agagagaagg  1200
aggaatgaga gattgagaag ggaaagtgta cgccctgtat aacagtgtcc gcagaagcaa  1260
ggggctgaaa agatctgaag gtcccacctc catttgcaat tgacctcttc tgggaacttc  1320
ctcagatgga caagattacc ccaccttgcc ctttacgtat ctgctcttag gtgcttcttc  1380
acttcagttg ctttgcagga agtgtctaga ggaatatggt gggcacagaa gtagctctgg  1440
tgaccttgat caaggtgttt tgaaatgcag aattcttgag ttctggaagg gactttagag  1500
aataccagtg ttattaatga caaaggcact gaggcccagg gaggtgaccc gaattataaa  1560
ggccagcgcc agaacccaga tttcctaact ctggtgctct ttccctttat cagtttgact  1620
gtggcctgtt aactggtata tacatatata tgtcaggcaa agtgctgctg gaagtagaat  1680
ttgtccaata acaggtcaac ttcagagact atctgatttc ctaatgtcag agtagaagat  1740
tttatgctgc tgtttacaaa agcccaatgt aatgcatagg aagtatggca tgaacatctt  1800
taggagacta atggaaatat tattggtgtt tacccagtat tccatttttt tcattgtgtt  1860
ctctattgct gctctctcac tcccccatga ggtacagcag aaaggagaac tatccaaaac  1920
taatttcctc tgacatgtaa gacgaatgat ttaggtacgt caaagcagta gtcaaggagg  1980
aaagggatag tccaaagact taactggttc atattggact gataatctct ttaaatggct  2040
ttatgctagt ttgacctcat ttgtaaaata tttatgagaa agttctcatt taaaatgaga  2100
tcgttgttta cagtgtatgt actaagcagt aagctatctt caaatgtcta aggtagtaac  2160
tttccatagg gcctccttag atccctaaga tggctttttc tccttggtat ttctgggtct  2220
ttctgacatc agcagagaac tggaaagaca tagccaactg ctgttcatgt tactcatgac  2280
tcctttctct aaaactgcct tccacaattc actagaccag aagtggacgc aacttaagct  2340
gggataatca cattatcatc tgaaaatctg gagttgaaca gcaaaagaag acaacatttc  2400
tcaaatgcac atctcatggc agctaagcca catggctggg atttaaagcc tttagagcca  2460
gcccatggct ttagctacct cactatgctg cttcacaaac cttgctcctg tgtaaaacta  2520
tattctcagt gtagggcaga gaggtctaac accaacataa ggtactagca gtgtttcccg  2580
tattgacagg aatacttaac tcaataattc ttttctttc catttagtaa cagttgtgat  2640
gactatgttt ctattctaag taattcctgt attctacagc agatactttg tcagcaatac  2700
taagggaaga aacaaagttg aaccgtttct ttaataa                          2737

SEQ ID NO: 138         moltype = AA  length = 288
FEATURE                Location/Qualifiers
source                 1..288
                       mol_type = protein
                       organism = Homo sapiens
SEQUENCE: 138
MGHTRRQGTS PSKCPYLNFF QLLVLAGLSH FCSGVIHVTK EVKEVATLSC GHNVSVEELA  60
QTRIYWQKEK KMVLTMMSGD MNIWPEYKNR TIFDITNNLS IVILALRPSD EGTYECVVLK  120
YEKDAFKREH LAEVTLSVKA DFPTPSISDF EIPTSNIRRI ICSTSGGFPE PHLSWLENGE  180
ELNAINTTVS QDPETELYAV SSKLDFNMTT NHSFMCLIKY GHLRVNQTFN WNTTKQEHFP  240
DNLLPSWAIT LISVNGIFVI CCLTYCFAPR CRERRRNERL RRESVRPV              288

SEQ ID NO: 139         moltype = DNA  length = 1701
FEATURE                Location/Qualifiers
source                 1..1701
                       mol_type = genomic DNA
                       organism = Mus musculus
SEQUENCE: 139
gagttttata cctcaataga ctcttactag tttctctttt tcaggttgtg aaactcaacc  60
ttcaaagaca ctctgttcca tttctgtgga ctaataggat catctttagc atctgccggg  120
tggatgccat ccaggcttct ttttctacat ctctgtttct cgatttttgt gagcctagga  180
ggtgcctaag ctccattggc tctagattcc tggctttccc catcatgttc tccaaagcat  240
ctgaagctat ggcttgcaat tgtcagttga tgcaggatac accactcctc aagtttccat  300
gtccaaggct cattcttctc tttgtgctgc tgattcgtct ttcacaagtg tcttcagatg  360
ttgatgaaca actgtccaag tcagtgaaag ataaggtatt gctgccttgc cgttacaact  420
ctcctcatga agatgagtct gaagaccgaa tctactggca aaaacatgac aaagtggtgc  480
tgtctgtcat tgctgggaaa ctaaaagtgt ggcccgagta taagaaccgg actttatatg  540
acaacactac ctactctctt atcatcctgg gcctggtcct ttcagaccgg ggcacataca  600
gctgtgtcgt tcaaaagaag gaaagaggaa cgtatgaagt taaacacttg gctttagtaa  660
agttgtccat caaagctgac ttctctaccc ccaacataac tgagtctgga aacccatctg  720
cagacactaa aaggattacc tgctttgctt ccgggggttt cccaaagcct cgcttctctt  780
ggttggaaaa tggaagagaa ttacctggca tcaatacgac aatttcccag gatcctgaat  840
ctgaattgta caccattagt agccaactag atttcaatac gactcgcaac cacaccatta  900
agtgtctcat taaatatgga gatgctcacg tgtcagagga cttcacctgg gaaaaacccc  960
cagaagaccc tcctgatagc aagaacacac ttgtgctctt tggggcagga ttcggcgcag  1020
taataacagt cgtcgtcatc gttgtcatca tcaaatgctt ctgtaagcac agaagctgtt  1080
tcagaagaaa tgaggcaagc agagaaacaa acaacagcct taccttcggg cctgaagaag  1140
cattagctga acagaccgtc ttcctttagt tcttctctgt ccatgtggga tacatggtat  1200
tatgtggctc atgaggtaca atctttcttt cagcaccgtg ctagctgatc tttcggacaa  1260
cttgacacaa gatagagtta actgggaaga gaaagccttg aatgaggatt tctttccatc  1320
aggaagccta cgggcaagtt tgctgggcct ttgattgctt gatgactgaa gtggaaaggc  1380
```

```
tgagcccact gtgggtggtg ctagccctgg gcaggggcag gtgaccctgg gtggtataag  1440
aaaaagagct gtcactaaaa ggagaggtgc ctagtcttac tgcaacttga tatgtcatgt  1500
ttggttggtg tctgtgggag gcctgccctt ttctgaagag aagtggtggg agagtggatg  1560
gggtgggggc agaggaaaag tgggggagag ggcctgggag gagaggaggg agggggacgg  1620
ggtgggggtg gggaaaacta tggttgggat gtaaaaacga taataatata aatattaaat  1680
aaaaagagag tattgagcaa a                                             1701

SEQ ID NO: 140         moltype = AA  length = 306
FEATURE                Location/Qualifiers
source                 1..306
                       mol_type = protein
                       organism = Mus musculus
SEQUENCE: 140
MACNCQLMQD TPLLKFPCPR LILLFVLLIR LSQVSSDVDE QLSKSVKDKV LLPCRYNSPH  60
EDESEDRIYW QKHDKVVLSV IAGKLKVWPE YKNRTLYDNT TYSLIILGLV LSDRGTYSCV  120
VQKKERGTYE VKHLALVKLS IKADFSTPNI TESGNPSADT KRITCFASGG FPKPRFSWLE  180
NGRELPGINT TISQDPESEL YTISSQLDFN TTRNHTIKCL IKYGDAHVSE DFTWEKPPED  240
PPDSKNTLVL FGAGFGAVIT VVVIVVIIKC FCKHRSCFRR NEASRETNNS LTFGPEEALA  300
EQTVFL                                                              306

SEQ ID NO: 141         moltype = DNA  length = 2720
FEATURE                Location/Qualifiers
source                 1..2720
                       mol_type = genomic DNA
                       organism = Homo sapiens
SEQUENCE: 141
agtcattgcc gaggaaggct tgcacagggt gaaagctttg cttctctgct gctgtaacag  60
ggactagcac agacacacgg atgagtgggg tcatttccag atattaggtc acagcagaag  120
cagccaaaat ggatccccag tgcactatgg gactgagtaa cattctcttt gtgatggcct  180
tcctgctctc tggtgctgct cctctgaaga ttcaagctta tttcaatgag actgcagacc  240
tgccatgcca atttgcaaac tctcaaaacc aaagcctgag tgagctagta gtattttggc  300
aggaccagga aaacttggtt ctgaatgagg tatacttagg caaagagaaa tttgacagtg  360
ttcattccaa gtatatgggc cgcacaagtt ttgattcgga cagttggacc ctgagacttc  420
acaatcttca gatcaaggac aagggcttgt atcaatgtat catccatcac aaaaagccca  480
caggaatgat tcgcatccac cagatgaatt ctgaactgtc agtgcttgct aacttcagtc  540
aacctgaaat agtaccaatt tctaatataa cagaaaatgt gtacataaat ttgacctgct  600
catctataca cggttaccca gaacctaaga agatgagtgt tttgctaaga accaagaatt  660
caactatcga gtatgatggt gttatgcaga aatctcaaga taatgtcaca gaactgtacg  720
acgtttccat cagcttgtct gtttcattcc ctgatgttac gagcaatatg accatcttct  780
gtattctgga aactgacaag acgcggcttt tatcttcacc tttctctata gagcttgagg  840
accctcagcc tcccccagac cacattcctt ggattacagc tgtacttcca acagttatta  900
tatgtgtgat ggttttctgt ctaattctat ggaaatggaa gaagaagaag cggcctcgca  960
actcttataa atgtggaacc aacacaatgg agagggaaga gagtgaacag accaagaaaa  1020
gagaaaaaat ccatatacct gaaagatctg atgaagccca gcgtgttttt aaaagttcga  1080
agacatcttc atgcgacaaa agtgatacat gtttttaatt aaagagtaaa gcccatacaa  1140
gtattcattt tttctaccct ttcctttgta agttcctggg caaccttttt gatttcttcc  1200
agaaggcaaa aagacattac catgagtaat aagggggctc caggactccc tctaagtgga  1260
atagcctccc tgtaactcca gctctgctcc gtatgccaag aggagacttt aattctctta  1320
ctgcttcttt tcacttcaga gcacacttat gggccaagcc cagcttaatg gctcatgacc  1380
tggaaataaa atttaggacc aatacctcct ccagatcaga ttcttctctt aatttcatag  1440
attgtgtttt tttttaaat agacctctca atttctggaa aactgccttt tatctgccca  1500
gaattctaag ctggtgcccc actgaatttt gtgtgtacct gtgactaaac aactacctcc  1560
tcagtctggg tgggacttat gtatttatga ccttatagtg ttaatatctt gaaacataga  1620
gatctatgta ctgtaatagt gtgattacta tgctctagag aaaagtctac ccctgctaag  1680
gagttctcat ccctctgtca gggtcagtaa ggaaaacggt ggcctagggt acaggcaaca  1740
atgagcagac caacctaaat ttggggaaat taggagaggc agagatagaa cctggagcca  1800
cttctatctg ggctgttgct aatattgagg aggcttgccc cacccaacaa gccatagtgg  1860
agagaactga ataaacagga aaatgccaga gcttgtgaac cctgtttctc ttgaagaact  1920
gactagtgag atggcctggg gaagctgtga aagaaccaaa agagatcaca atactcaaaa  1980
gagagagaga gagaaaaaag agagatcttg atccacagaa atacatgaaa tgtctggtct  2040
gtccacccca tcaacaagtc ttgaaacaag caacagatgg atagtctgtc caaatggaca  2100
taagacagac agcagtttcc ctggtggtca gggaggggtt ttggtgatac ccaagttatt  2160
gggatgtcat cttcctggaa gcagagctgg ggagggagag ccatcacctt gataatggga  2220
tgaatggaag gaggcttagg actttccact cctggctgag agaggaagag ctgcaacgga  2280
attaggaaga ccaagacaca gatcacccgg ggcttactta gcctacagat gtcctacggg  2340
aacgtgggct ggcccagcat aggctagca aatttgagtt ggatgattgt ttttgctcaa  2400
ggcaaccaga ggaaacttgc atacagagac agatatactg ggagaaatga ctttgaaaac  2460
ctggctctaa ggtgggatca ctaagggatg gggcagtctc tgcccaaaca taaagagaac  2520
tctggggagc ctgagccaca aaaatgttcc tttattttat gtaaaccctc aagggttata  2580
gactgccatg ctagacaagc ttgtccatgt aatattccca tgtttttacc ctgcccctgc  2640
cttgattaga ctcctagcac ctggctagtt tctaacatgt tttgtgcagc acagttttta  2700
ataaatgctt gttacattca                                              2720

SEQ ID NO: 142         moltype = AA  length = 329
FEATURE                Location/Qualifiers
source                 1..329
                       mol_type = protein
                       organism = Homo sapiens
SEQUENCE: 142
```

```
MDPQCTMGLS NILFVMAFLL SGAAPLKIQA YFNETADLPC QFANSQNQSL SELVVFWQDQ  60
ENLVLNEVYL GKEKFDSVHS KYMGRTSFDS DSWTLRLHNL QIKDKGLYQC IIHHKKPTGM  120
IRIHQMNSEL SVLANFSQPE IVPISNITEN VYINLTCSSI HGYPEPKKMS VLLRTKNSTI  180
EYDGVMQKSQ DNVTELYDVS ISLSVSFPDV TSNMTIFCIL ETDKTRLLSS PFSIELEDPQ  240
PPPDHIPWIT AVLPTVIICV MVFCLILWKW KKKKRPRNSY KCGTNTMERE ESEQTKKREK  300
IHIPERSDEA QRVFKSSKTS SCDKSDTCF                                   329

SEQ ID NO: 143         moltype = DNA  length = 2539
FEATURE                Location/Qualifiers
source                 1..2539
                       mol_type = genomic DNA
                       organism = Mus musculus
SEQUENCE: 143
attgctgagg aagaaagagg agcaagcaga cgcgtaagag tggctcctgt aggcagcacg  60
gacttgaaca accagactcc tgtagacgtg ttccagaact tacggaagca cccacgatgg  120
accccagatg caccatgggc ttggcaatcc ttatctttgt gacagtcttg ctgatctcag  180
atgctgtttc cgtggagacg caagcttatt tcaatgggac tgcatatctg ccgtgcccat  240
ttacaaaggc tcaaaacata agcctgagtg agctggtagt attttggcag gaccagcaaa  300
agttggttct gtacgagcac tatttgggca cagagaaact tgatagtgtg aatgccaagt  360
acctgggccg cacgagcttt gacaggaaca actggactct acgacttcac aatgttcaga  420
tcaaggacat gggctcgtat gattgtttta tacaaaaaaa gccacccaca ggatcaatta  480
tcctccaaca gacattaaca gaactgtcag tgatcgccaa cttcagtgaa cctgaaataa  540
aactggctca gaatgtaaca ggaaattctg gcataaattt gacctgcacg tctaagcaag  600
gtcacccgaa acctaagaag atgtattttc tgataactaa ttcaactaat gagtatggtg  660
ataacatgca gatatcacaa gataatgtca cagaactgtt cagtatctcc aacagcctct  720
ctctttcatt cccggatggt gtgtggcata tgaccgttgt gtgtgttctg gaaacggagt  780
caatgaagat ttcctccaaa cctctcaatt tcactcaaga gtttccatct cctcaaacgt  840
attggaagga gattacagct tcagttactg tggccctcct ccttgtgatg ctgctcatca  900
ttgtatgtca caagaagccg aatcagccta gcaggcccag caacacagcc tctaagttag  960
agcgggatag taacgctgac agagagacta tcaacctgaa ggaacttgaa ccccaaattg  1020
cttcagcaaa accaaatgca gagtgaaggc agtgagagcc tgaggaaaga gttaaaaatt  1080
gctttgcctg aaataagaag tgcagagttt ctcagaattc aaaaatgttc tcagctgatt  1140
ggaattctac agttgaataa ttaaagaaca aaatacacaa cagtgtccat attttatcct  1200
gtttcctttc caagttttg ggcaatgtca attgtgtccc ctatgccagg agcagacatc  1260
tattttgtct tgctttgttt aactcagtgc acactcatag gccaagagca ctgaaatggc  1320
ttctttccca ggaataacat tttggatcaa tctctcctac ttgagatcag attcttcttc  1380
taattttgca tagtgtgttt ttatatggaa ctccttgttg taggaatact ggcttttatc  1440
tgtcttgcac acttgcatac ttatatactt atacctggac agctacctct tcagtcagga  1500
tgggagtggt atatttggtg atgttatttg atgtgttcgt gttgctatct taaaacagca  1560
aagagcatat actatagtag ctcaactaca atgatctaga gaaagaccca gcacttataa  1620
gaaacactgt ccctccatca gggtcaataa tgaatacaat gacctaagta atatacaggt  1680
gacagcaaca gcacagagtt ctcagtgctg gcaaatcaag aaacacaaat atggaaccat  1740
ctctagatcc aagagccact cctacctggg ctgccacaga tactggaaga atccacctgc  1800
ctggccagca agtcacaact tagcaggcag cactgaagaa agcaagatgt actgtatgcc  1860
cttttaagaa aatgcctgga aaggtctgga gaatgctgtg caaggataag acagccaagc  1920
actcaaaacc aggagacatc actagaatcc aaccaacaaa tgtttatgga aggactgatc  1980
tgcccagtcc attgaaaagt caagaggtca gagatagacc agtgtgtgtc tcaatggatg  2040
tagatatcag ccacctcggt gctcaacagg tattttatga tctccttgtt tcaaattcat  2100
ctagatgtag aactagggag agagcagtca cattgatgaa aggctaggac tctttcagct  2160
catggcttgt gtggaaggag ggaaagcaga aatcacaaca ctctgagact actgtagtct  2220
gcagatacct gagtgggtgt ggcttggcct ttcaaaggac aaagagcaac taatgctgaa  2280
agcacatagt gtatctatac ggcatggaat agtcatcacc cagacttaaa gagaactttg  2340
gcaggtctga gcagcaaaat attgttgttt ccattttaca taaagggccc tggagggcta  2400
tagactattc cgctggcagg gctcatgctt gtaatgtgtc catcttgatt caccctgtgc  2460
agactcttaa gatctggcca gttaccaaca tgttctgtac agagtggatt tcaataaagt  2520
tttcttgaat tttttcaag                                              2539

SEQ ID NO: 144         moltype = AA  length = 309
FEATURE                Location/Qualifiers
source                 1..309
                       mol_type = protein
                       organism = Mus musculus
SEQUENCE: 144
MDPRCTMGLA ILIFVTVLLI SDAVSVETQA YFNGTAYLPC PFTKAQNISL SELVVFWQDQ  60
QKLVLYEHYL GTEKLDSVNA KYLGRTSFDR NNWTLRLHNV QIKDMGSYDC FIQKKPPTGS  120
IILQQTLTEL SVIANFSEPE IKLAQNVTGN SGINLTCTSK QGHPKPKKMY FLITNSTNEY  180
GDNMQISQDN VTELFSISNS LSLSFPDGVW HMTVVCVLET ESMKISSKPL NFTQEFPSPQ  240
TYWKEITASV TVALLLVMLL IIVCHKKPNQ PSRPSNTASK LERDSNADRE TINLKELEPQ  300
IASAKPNAE                                                         309

SEQ ID NO: 145         moltype = DNA  length = 1086
FEATURE                Location/Qualifiers
source                 1..1086
                       mol_type = genomic DNA
                       organism = Homo sapiens
SEQUENCE: 145
gaacttaggg ctgcttgtgg ctgggcactc gcgcagaggc cggcccgacg agccatggtt  60
gctgggagcg acgcggggcg ggccctgggg gtcctcagcg tggtctgcct gctgcactgc  120
tttggtttca tcagctgttt ttcccaacaa atatatggtg ttgtgtatgg gaatgtaact  180
```

-continued

```
ttccatgtac caagcaatgt gcctttaaaa gaggtcctat ggaaaaaaca aaaggataaa  240
gttgcagaac tggaaaattc tgaattcaga gctttctcat cttttaaaaa tagggtttat  300
ttagacactg tgtcaggtag cctcactatc tacaacttaa catcatcaga tgaagatgag  360
tatgaaatgg aatcgccaaa tattactgat accatgaagt tctttcttta tgtgcttgag  420
tctcttccat ctcccacact aacttgtgca ttgactaatg gaagcattga agtccaatgc  480
atgataccag agcattacaa cagccatcga ggacttataa tgtactcatg ggattgtcct  540
atggagcaat gtaaacgtaa ctcaaccagt atatatttta agatggaaaa tgatcttcca  600
caaaaaatac agtgtactct tagcaatcca ttatttaata caacatcatc aatcattttg  660
acaacctgta tcccaagcag cggtcattca agacacagat atgcacttat acccatacca  720
ttagcagtaa ttacaacatg tattgtgctg tatatgaatg gtattctgaa atgtgacaga  780
aaaccagaca gaaccaactc caattgattg gtaacagaag atgaagacaa cagcataact  840
aaattatttt aaaaactaaa aagccatctg atttctcatt tgagtattac aattttttgaa  900
caactgttgg aaatgtaact tgaagcagct gctttaagaa gaaataccca ctaacaaaga  960
acaagcatta gttttggctg tcatcaactt attatatgac taggtgcttg cttttttttgt  1020
cagtaaattg tttttactga tgatgtagat acttttgtaa ataaatgtaa atatgtacac  1080
aagtga                                                              1086

SEQ ID NO: 146          moltype = AA  length = 250
FEATURE                 Location/Qualifiers
source                  1..250
                        mol_type = protein
                        organism = Homo sapiens
SEQUENCE: 146
MVAGSDAGRA LGVLSVVCLL HCFGFISCFS QQIYGVVYGN VTFHVPSNVP LKEVLWKKQK  60
DKVAELENSE FRAFSSFKNR VYLDTVSGSL TIYNLTSSDE DEYEMESPNI TDTMKFFLYV  120
LESLPSPTLT CALTNGSIEV QCMIPEHYNS HRGLIMYSWD CPMEQCKRNS TSIYFKMEND  180
LPQKIQCTLS NPLFNTTSSI ILTTCIPSSG HSRHRYALIP IPLAVITTCI VLYMNGILKC  240
DRKPDRTNSN                                                          250

SEQ ID NO: 147          moltype = DNA  length = 3749
FEATURE                 Location/Qualifiers
source                  1..3749
                        mol_type = genomic DNA
                        organism = Homo sapiens
SEQUENCE: 147
agacagcctc tgctgcatga cacgaagctt gcttctgcct ggcatctgtg agcagctgcc  60
aggctccggc caggatccct tccttctcct cattggctga tggatcccaa ggggctcctc  120
tccttgacct tcgtgctgtt tctctccctg gcttttgggg caagctacgg aacaggtggg  180
cgcatgatga actgcccaaa gattctccgg cagttgggaa gcaaagtgct gctgcccctg  240
acatatgaaa ggataaataa gagcatgaac aaaagcatcc acattgtcgt cacaatggca  300
aaatcactgg agaacagtgt cgagaacaaa atagtgtctc ttgatccatc cgaagcaggc  360
cctccacgtt atctaggaga tcgctacaag ttttatctgg agaatctcac cctgggggata  420
cgggaaagca ggaaggagga tgagggatgg taccttatga ccctggagaa aaatgtttca  480
gttcagcgct tttgcctgca gttgaggctt tatgagcagg tctccactcc agaaattaaa  540
gttttaaaca agacccagga gaacgggacc tgcaccttga tactgggctg cacagtggag  600
aagggggacc atgtggctta cagctggagt gaaaaggcgg gcacccaccc actgaaccca  660
gccaacagct cccacctcct gtccctcacc ctcggccccc agcatgctga caatatctac  720
atctgcaccg tgagcaaccc tatcagcaac aattcccaga ccttcagccc gtggcccgga  780
tgcaggacag acccctcaga aacaaaacca tgggcagtgt atgctgggct gttagggggt  840
gtcatcatga ttctcatcat ggtggtaata ctacagttga gaagaagagg taaaacgaac  900
cattaccaga caacagtgga aaaaaaaagc cttacgatct atgcccaagt ccagaaacca  960
ggtcctcttc agaagaaact tgactccttc ccagctcagg acccttgcac caccatatat  1020
gttgctgcca cagagcctgt cccagagtct gtccaggaaa caaattccat cacagtctat  1080
gctagtgtga cacttccaga gagctgacac cagagaccaa caaagggact ttctgaagga  1140
aaatggaaaa accaaaatga acactgaact tggccacagg ccccaagttt cctctggcag  1200
acatgctgca cgtctgtacc cttctcagat caactccctg gtgatgtttc ttccacatac  1260
atctgtgaaa tgaacaagga agtgaggctt cccaagaatt tagcttgctg tgcagtggct  1320
gcaggcgcag aacagagcgt tacttgataa cagcgttcca tctttgtgtt gtagcagatg  1380
aaatggacag taatgtgagt tcagactttg ggcatcttgc tcttggctgg aactggataa  1440
taaaaatcag actgaaagcc aggacatctg agtacctatc tcacacactg gaccaccagt  1500
cacaaagtct ggaaaagttt acattttggc tatctttact ttgttctggg agctgatcat  1560
gataacctgc agacctgatc aagcctctgt gcctcagttt ctctctcagg ataaagagtg  1620
aatagaggct gaagggtgaa tttcttatta tacataaaac actctgatat tattgtataa  1680
aggaagctaa gaatattatt ttatttgcaa aacccagaag ctaaaaagtc aataaacaga  1740
aagaatgatt ttgagatctc tgagttttga acagtggact ggaaaccatg taagagcctt  1800
aaaagtacag ttctgtgcaa atggcattca gttttaaaga aaaacgtagc aaatgtttga  1860
tggtgctgtt acaaaggagc ttggaatact cagaggaact tgtcccatgg tgatttttca  1920
cttctcaaaa tgatgtttaa atcccagttc tctgttgatt cccttgaaca acaaacctgg  1980
aacctcagct aagactctct gtgaccagat tctgaacctc ttatatccag ggcttcaagg  2040
ggtattgcag gtcaaggtct ttcctaggca ctttctactc cctgcatacc tctcctcaca  2100
ctaaatttat cctctagtag aaaattaagt tattttggtc taacagcttc aaatctttga  2160
atgctcaata acttattttg caagctgcag gcagaaagag actttttaag taaagtcctt  2220
tgttttttcc tattctctgc ttttagacag gctgtcctca atttaagccc tgctttttct  2280
tattgtttct tatataaact tggtaagtac tgtaagaaac agccactatc ataccattgc  2340
ataataagga gcaccaactt cccagctcaa aactcaggtc cttattgcct tgtatcttac  2400
ctcctctatg aggtcaattc acattgtaag cctgttgctt agtgcatctc gtttcctggt  2460
accagcttct ttaatagagt tcttagttgc aatcaacaga agctggcttt ggcttttttta  2520
tgtagaaaag gaacctattg aaaagatact gattggttcc aataactgct agaagtttct  2580
gcaaaaccat gctttgaaag tgagcaggaa aagaagagac taggctgtgg ctgggagcac  2640
```

```
agccaaaatt acaaaaccag cccagggatg atgatcctgt tcatgcacag ccactgtccc  2700
cagcactagg cacagactct accactgcct cactgtctct gctggacttg gaaacttgat  2760
attactgtta ctgctgcact gtctgccatg aaaatgaatt ctccagggtc ccttcttcat  2820
cctttcatct ctagcttata attcaaagtc tgggattgag tggccaatcc taggtcacat  2880
gtccatgtcc tatctccaag gggggctggg aattgaatat ctggcatttt ccactttcac  2940
ttcttatgaa ttaaggaatt ctacaaataa tagaagtggg attcaggtgg taggcagaca  3000
aaaaagcctc acaattatcc actacgccac ccttgtataa ccttaccctc attcactgtc  3060
tactctcaaa actgtggagc tactaatgaa gatttgtaaa cccgggctta tgagcaccca  3120
ttcctttact acaactcaga ttgctctaga agctcagttc ccagcacttg gatttttcca  3180
gtagctgaat tctacctgaa ggaagggcag aaacaaaggg tgaagaagag gctatcactt  3240
ccaagtatcc tgcacccctg ggctcaagac ctcactgggg agggagtctt ttgggccacc  3300
caccaaacag cactggcatt atgcctctca ccctagacca tggttacacg tggtaaaaca  3360
accccttctg gtgatacatt cacaactctc tagtttcccc caaatggcac tatgggggagc  3420
gggagcttgc cttttcctca gacttaaaac aataagtttt ccccgtgttt cccctctaat  3480
gctgttttct tttgaccaag catgtctgaa ttctagagaa gtcaggagga acacacccat  3540
tctcggtttg aagggactga tgttctgaag tacaactggg cacagtccca ggctcttcag  3600
gacgcttcct ccattcacac agcggggatg tgattgttac agcgggtggt gtgtgctggc  3660
tgagaagcca ctgtgaattg attcttcttc tgaagtttat gtttctactt tttggaaatg  3720
aataaattac agccagtcca tcaaggaaa                                     3749

SEQ ID NO: 148         moltype = AA  length = 335
FEATURE                Location/Qualifiers
source                 1..335
                       mol_type = protein
                       organism = Homo sapiens
SEQUENCE: 148
MDPKGLLSLT FVLFLSLAFG ASYGTGGRMM NCPKILRQLG SKVLLPLTYE RINKSMNKSI  60
HIVVTMAKSL ENSVENKIVS LDPSEAGPPR YLGDRYKFYL ENLTLGIRES RKEDEGWYLM  120
TLEKNVSVQR FCLQLRLYEQ VSTPEIKVLN KTQENGTCTL ILGCTVEKGD HVAYSWSEKA  180
GTHPLNPANS SHLLSLTLGP QHADNIYICT VSNPISNNSQ TFSPWPGCRT DPSETKPWAV  240
YAGLLGGVIM ILIMVVILQL RRRGKTNHYQ TTVEKKSLTI YAQVQKPGPL QKKLDSFPAQ  300
DPCTTIYVAA TEPVPESVQE TNSITVYASV TLPES                             335

SEQ ID NO: 149         moltype = DNA  length = 2688
FEATURE                Location/Qualifiers
source                 1..2688
                       mol_type = genomic DNA
                       organism = Mus musculus
SEQUENCE: 149
gagcttcttc cttgggggta acagtaagca gctgtcctgc cgagctgagc tgagctgagc  60
tcacagctgg ggaccctgtc tgcgattgct ggctaatgga tcccaaagga tccctttcct  120
ggagaatact tctgtttctc tccctggctt ttgagttgag ctacggaaca ggtggaggtg  180
tgatggattg cccagtgatt ctccagaagc tgggacagga cacgtggctg cccctgacga  240
atgaacatca gataaataag agcgtgaaca aaagtgtccg catcctcgtc accatggcga  300
cgtccccagg aagcaaatcc aacaagaaaa ttgtgtcttt tgatctctct aaagggagct  360
atccagatca cctggaggat ggctaccact ttcaatcaaa aaacctgagc ctgaagatcc  420
tcgggaacag gcgggagagt gaaggatggt acttggtgag cgtggaggag aacgtttctg  480
ttcagcaatt ctgcaagcag ctgaagcttt atgaacaggt ctcccctcca gagattaaag  540
tgctaaacaa aacccaggag aacgagaatg ggacctgcag cttgctgttg gcctgcacag  600
tgaagaaagg ggaccatgtg acttacagct ggagtgatga ggcaggcacc cacctgctga  660
gccgagccaa ccgctcccac ctcctgcaca tcactcttag caaccagcat caagacagca  720
tctacaactg caccgcaagc aaccctgtca gcagtatctc taggaccttc aacctatcat  780
cgcaagcatg caagcaggaa tcctcctcag aatcgagtcc atggatgcaa tatactcttg  840
taccactggg ggtcgttata atcttcatcc tggttttcac ggcaataata atgatgaaaa  900
gacaaggtaa atcaaatcac tgccagccac cagtggaaga aaaaagcctt actatttatg  960
cccaagtaca gaaatcaggg cctcaagaga agaaacttca tgatgcccta acagatcagg  1020
acccctgcac aaccatttat gtggctgcca cagagcctgc cccagagtct gtccaggaac  1080
caaaccccac cacagtttat gccagtgtga cactgccaga gagctgaccc atatacccag  1140
tgaaaggact ttttgaagga ggatagaaga accaaaatcc acactgaact ggacccccggg  1200
tcccaagttc tctgtgacag aaactgcaca tctgtaacct tctccaatca gttccctggt  1260
gacggatctg cacaggcgtg cttatgaagt agatgagaag tgaggcttcc tgggcatgca  1320
acctgctctg ctgctgacac agatatgaag cagagatccc gtggtacagt gtaccatctt  1380
tgctgtagca gataatgtgg gtttaggcat ctcactcttt gctggactgg ataacagaac  1440
tcaaaaaaaa accaacaagc caaagacata gactccatct cagatggctg agcacaaagt  1500
ataaaagcca ttttggctct ctggacttta ttctggaagc tgatcctgat cacctcaagg  1560
ccaagggctc catgcctcag tttctctctc accctctaga tgaagaggga acaaagcata  1620
aagagtgaaa tccttgttgt ctgagatcat tctataaacg aactgacatt ttatttgcaa  1680
aactcaagct agtaattcag tagacttgaa gatgatttta gagcctctta tgcttcaaac  1740
aacagaatga aatccatcca atgttcttca aagtgtggtt ctctgattaa gtcaaagcaa  1800
cactgtttgg caatgctgct gtaaagttgc ctggaatact cagaggaact tgtcccaggg  1860
aggttttttt cacttcttca aagaactttt gaatttaagt tctctgttta ttcccttgag  1920
caaaactctg gaacctcaag agtctctctc cgttggttct gaggccattt tatagcctag  1980
gcctcctgtg gatctacatg tgtatcaccc acttcctatc tcactgcata cctctgtgta  2040
gtagtaaatt taacctcaag tagaaaatta aattatttg gatgatcagt tccaaatgat  2100
tagatgttta gtctcttata ataggatgta ggtagagtct atataaagtc ctatattctt  2160
cacgttgtct gtcctcagag agaccatctt tcaacctatc ttccttcttg cacaactttg  2220
gcaaatactt taaaaataac cattgtggag atggggagag gtctaaatgg ataatagtac  2280
ttgctttgca aacatgaaga tctgggttca aactcccagt gtccatgtaa aaagataagt  2340
gtggttgagt gtgccagtaa catagacaca gataggtcct gagactttgc tccctagcct  2400
```

-continued

```
tcccagccag gcataaatgt caagtcccct gagagtgaca gaggaagata ctccccccac  2460
acacacacac atacacgcac agtgatacac atatacatgc atacaaaaaa aaaacttatt  2520
gtaacaaaga acaccaactg cctggctcaa aactctcatg tcccattact ctgtaccttt  2580
ctgtatttag ataatttaca gtgtgagttc tgctgttcca tgtatcctat ttgtgttact  2640
aacttatgtc aaagtatttc taattataat caacaaaagc taactttg               2688

SEQ ID NO: 150         moltype = AA  length = 343
FEATURE                Location/Qualifiers
source                 1..343
                       mol_type = protein
                       organism = Mus musculus
SEQUENCE: 150
MDPKGSLSWR ILLFLSLAFE LSYGTGGGVM DCPVILQKLG QDTWLPLTNE HQINKSVNKS  60
VRILVTMATS PGSKSNKKIV SFDLSKGSYP DHLEDGYHFQ SKNLSLKILG NRRESEGWYL  120
VSVEENVSVQ QFCKQLKLYE QVSPPEIKVL NKTQENENGT CSLLLACTVK KGDHVTYSWS  180
DEAGTHLLSR ANRSHLLHIT LSNQHQDSIY NCTASNPVSS ISRTFNLSSQ ACKQESSSES  240
SPWMQYTLVP LGVVIIFILV FTAIIMMKRQ GKSNHCQPPV EEKSLTIYAQ VQKSGPQEKK  300
LHDALTDQDP CTTIYVAATE PAPESVQEPN PTTVYASVTL PES                    343

SEQ ID NO: 151         moltype = DNA  length = 1682
FEATURE                Location/Qualifiers
source                 1..1682
                       mol_type = genomic DNA
                       organism = Homo sapiens
SEQUENCE: 151
agtggtcctg ccgcctggtc tcacctcgct atggttcgtc tgcctctgca gtgcgtcctc  60
tggggctgct tgctgaccgc tgtccatcca gaaccaccca ctgcatgcag agaaaaacag  120
tacctaataa acagtcagtg ctgttctttg tgccagccag gacagaaact ggtgagtgac  180
tgcacagagt tcactgaaac ggaatgcctt ccttgcggtg aaagcgaatt cctagacacc  240
tggaacagag agacacactg ccaccagcac aaatactgcg accccaacct agggcttcgg  300
gtccagcaga agggcacctc agaaacagac accatctgca cctgtgaaga aggctggcac  360
tgtacgagtg aggcctgtga gagctgtgtc ctgcaccgct catgctcgcc cggctttggg  420
gtcaagcaga ttgctacagg ggtttctgat accatctgcg agccctgccc agtcggcttc  480
ttctccaatg tgtcatctgc tttcgaaaaa tgtcaccctt ggacaagctg tgagaccaaa  540
gacctggttg tgcaacaggc aggcacaaac aagactgatg ttgtctgtgg tccccaggat  600
cggctgagag ccctggtggt gatccccatc atcttcggga tcctgtttgc catcctcttg  660
gtgctggtct ttatcaaaaa ggtggccaag aagccaacca ataaggcccc ccaccccaag  720
caggaacccc aggagatcaa ttttcccgac gatcttcctg gctccaacac tgctgctcca  780
gtgcaggaga ctttacatgg atgccaaccg gtcacccagg aggatggcaa agagagtcgc  840
atctcagtgc aggagagaca gtgaggctgc acccacccag gagtgtggcc acgtgggcaa  900
acaggcagtt ggccagagag cctggtgctg ctgctgctgt ggcgtgaggg tgaggggctg  960
gcactgactg ggcatagctc cccgcttctg cctgcacccc tgcagtttga gacaggagac  1020
ctggcactgg atgcagaaac agttcacctt gaagaacctc tcacttcacc ctggagccca  1080
tccagtctcc caacttgtat taaagacaga ggcagaagtt tggtggtggt ggtgttgggg  1140
tatggtttag taatatccac cagaccttcc gatccagcag tttggtgccc agagaggcat  1200
catggtggct tccctgcgcc caggaagcca tatacacaga tgcccattgc agcattgttt  1260
gtgatagtga acaactggaa gctgcttaac tgtccatcag caggagactg gctaaataaa  1320
attagaatat atttatacaa cagaatctca aaaacactgt tgagtaagga aaaaaaggca  1380
tgctgctgaa tgatgggtat ggaacttttt aaaaaagtac atgcttttat gtatgtatat  1440
tgcctatgga tatatgtata aatacaatat gcatcatata ttgatataac aagggttctg  1500
gaagggtaca cagaaaaccc acagctcgaa gagtggtgac gtctggggtg gggaagaagg  1560
gtctggggga gggttggtta aagggagatt tggctttccc ataatgcttc atcatttttc  1620
ccaaaaggag agtgaattca cataatgctt atgtaattaa aaaatcatca aacatgtaaa  1680
aa                                                                 1682

SEQ ID NO: 152         moltype = AA  length = 277
FEATURE                Location/Qualifiers
source                 1..277
                       mol_type = protein
                       organism = Homo sapiens
SEQUENCE: 152
MVRLPLQCVL WGCLLTAVHP EPPTACREKQ YLINSQCCSL CQPGQKLVSD CTEFTETECL  60
PCGESEFLDT WNRETHCHQH KYCDPNLGLR VQQKGTSETD TICTCEEGWH CTSEACESCV  120
LHRSCSPGFG VKQIATGVSD TICEPCPVGF FSNVSSAFEK CHPWTSCETK DLVVQQAGTN  180
KTDVVCGPQD RLRALVVIPI IFGILFAILL VLVFIKKVAK KPTNKAPHPK QEPQEINFPD  240
DLPGSNTAAP VQETLHGCQP VTQEDGKESR ISVQERQ                           277

SEQ ID NO: 153         moltype = DNA  length = 1621
FEATURE                Location/Qualifiers
source                 1..1621
                       mol_type = genomic DNA
                       organism = Mus musculus
SEQUENCE: 153
agcagggact ttggagtgac ttgtggcttc agcaggagcc ctgtgatttg gctcttctga  60
tctcgccctg cgatggtgtc tttgcctcgg ctgtgcgcgc tatggggctg cttgttgaca  120
gcggtccatc tagggcagtg tgttacgtgc agtgacaaac agtacctcca cgatggccag  180
tgctgtgatt tgtgccagcc aggaagccga ctgacaagcc actgcacagc tcttgagaag  240
acccaatgcc acccatgtga ctcaggcgaa ttctcagccc agtggaacag ggagattcgc  300
tgtcaccagc acagacactg tgaacccaat caagggcttc gggttaagaa ggagggcacc  360
```

```
gcagaatcag acactgtctg tacctgtaag gaaggacaac actgcaccag caaggattgc  420
gaggcatgtg ctcagcacac gccctgtatc cctggctttg gagttatgga gatggccact  480
gagaccactg ataccgtctg tcatccctgc ccagtcggct tcttctccaa tcagtcatca  540
cttttcgaaa agtgttatcc ctggacaagg tttaaagtcc cggatgcgag ccctgctggt  600
cattcctgtc gtgatgggca tcctcatcac catttcgggg gtgtttctct atatcaaaaa  660
ggtggtcaag aaaccaaagg ataatgagat cttacccccct gcggctcgac ggcaagatcc  720
ccaggagatg gaagattatc ccggtcataa caccgctgct ccagtgcagg agacgctgca  780
cgggtgtcag cctgtcacac aggaggatgg taaagagagt cgcatctcag tgcaggagcg  840
gcaggtgaca gacagcatag ccttgaggcc ccctggtctga accctggaac tgctttggag  900
gcgatggctc ggctcgggag caggggcctg gctctgagga ctgcttgctg acctttgaag  960
tttgagatga gccaagacag agcccagtgc agctaactct catgcctgcc ccctatcatt  1020
tctcaacttg ctttttaagg atggagggag agctcgggca tcgggggtcc acagtgatac  1080
ctaccaagtg cagcagtgca ggacccagag tcgtcttgct gcggcgttca ctgtaaggag  1140
tcatggacac aggagtccgt ggcccacagc ttgtgctgct agagggcacc tggttgccca  1200
tcagcagggt actggctaaa taaatctgta attatttata caatgacatc tcagaaactc  1260
tagcaggtgg ggcagaaaac aggtagtaga atgatgggta gagaaatagc ttttaaaaca  1320
cattccaagg caggtaagat ggcttttgtg agtaaaggag cttgctgccc aaacccggtt  1380
acctgatttt gatccctggg acttcatggt aaaagggaga gaaccaaatc cagagggttg  1440
tcatttgacc tccatgtgtg ctctgtggta atgtaccccg tgtgtgcaca tgtgcacata  1500
tcctaaaatg gatgtggtgg tgtattgtag aaattattta atcccgccct ggggtttcta  1560
cctgtgtgtt accatttagt tcttgaataa aagacacact caacctttat atttacaata  1620
a                                                                 1621
```

```
SEQ ID NO: 154         moltype = AA  length = 203
FEATURE                Location/Qualifiers
source                 1..203
                       mol_type = protein
                       organism = Mus musculus
SEQUENCE: 154
MVSLPRLCAL WGCLLTAVHL GQCVTCSDKQ YLHDGQCCDL CQPGSRLTSH CTALEKTQCH  60
PCDSGEFSAQ WNREIRCHQH RHCEPNQGLR VKKEGTAESD TVCTCKEGQH CTSKDCEACA  120
QHTPCIPGFG VMEMATETTD TVCHPCPVGF FSNQSSLFEK CYPWTRFKVP DASPAGHSCR  180
DGHPHHHFRG VSLYQKGGQE TKG                                          203
```

```
SEQ ID NO: 155         moltype = DNA  length = 4721
FEATURE                Location/Qualifiers
source                 1..4721
                       mol_type = genomic DNA
                       organism = Homo sapiens
SEQUENCE: 155
acacttcggg ttcctcgggg aggaggggct ggaaccctag cccatcgtca ggacaaagat  60
gctcaggctg ctcttggctc tcaacttatt cccttcaatt caagtaacag gaaacaagat  120
tttggtgaag cagtcgccca tgcttgtagc gtacgacaat gcggtcaacc ttagctgcaa  180
gtattcctac aatctcttct caagggagtt ccgggcatcc cttcacaaag gactggatag  240
tgctgtggaa gtctgtgttg tatatgggaa ttactcccag cagcttcagg tttactcaaa  300
aacggggttc aactgtgatg ggaaattggg caatgaatca gtgacattct acctccagaa  360
tttgtatgtt aaccaaacag atatttactt ctgcaaaatt gaagttatgt atcctcctcc  420
ttacctagac aatgagaaga gcaatggaac cattatccat gtgaaaggga aacacctttg  480
tccaagtccc ctatttcccg gaccttctaa gccctttttgg gtgctggtgg tggttggtgg  540
agtcctggct tgctatagct tgctagtaac agtggccttt attattttct gggtgaggag  600
taagaggagc aggctcctgc acagtgacta catgaacatg actccccgcc gccccgggcc  660
cacccgcaag cattaccagc cctatgcccc accacgcgac ttcgcagcct atcgctcctg  720
acacggacgc ctatccagaa gccagccggc tggcagcccc catctgctca atatcactgc  780
tctggatagg aaatgaccgc catctccagc cggccacctc aggcccctgt tgggccacca  840
atgccaattt ttctcgagtg actagaccaa atatcaagat cattttgaga ctctgaaatg  900
aagtaaaaga gatttcctgt gacaggccaa gtcttacagt gccatggccc acattccaac  960
ttaccatgta cttagtgact tgactgagaa gttagggtag aaaacaaaaa gggagtggat  1020
tctgggagcc tcttcccttt ctcactcacc tgcacatctc agtcaagcaa agtgtggtat  1080
ccacagacat tttagttgca gaagaaaggc taggaaatca ttccttttgg ttaaatgggt  1140
gtttaatctt ttggttagtg ggttaaacgg ggtaagttag agtagggggga gggataggaa  1200
gacatattta aaaaccatta aaacactgtc tcccactcat gaaatgagcc acgtagttcc  1260
tatttaatgc tgttttcctt tagtttagaa atacatagac attgtctttt atgaattctg  1320
atcatattta gtcattttga ccaaatgagg gatttggtca aatgagggat tccctcaaag  1380
caatatcagg taaaccaagt tgctttcctc actccctgtc atgagacttc agtgttaatg  1440
ttcacaatat actttcgaaa gaataaaata gttctcctac atgaagaaag aatatgtcag  1500
gaaataaggt cactttatgt caaaattatt tgagtactat gggacctggc gcagtggctc  1560
atgcttgtaa tcccagcact ttgggaggcc gaggtgggca gatcacttga gatcaggacc  1620
agcctggtca agatggtgaa actccgtctg tactaaaaat acaaaattta gcttggcctg  1680
gtggcaggca cctgtaatcc cagctgccca agaggctgag gcatgagaat cgcttgaacc  1740
tggcaggcgg aggttgcagt gagccgagat agtgccacag ctctccagcc tgggcgacag  1800
agtgagactc catctcaaac aacaacaaca acaacaacaa caacaacaaa ccacaaaatt  1860
atttgagtac tgtgaaggat tatttgtcta acagttcatt ccaatcagac caggtaggag  1920
ctttcctgtt tcatatgttt cagggttgca cagttggtct ctttaatgtc ggtgtggaga  1980
tccaaagtgg gttgtggaaa gagcgtccat aggagaagtg agaatactgt gaaaaaggga  2040
tgttagcatt cattagagta tgaggatgag tcccaagaag gttctttgga aggaggacga  2100
atagaatgga gtaatgaaat tcttgccatg tgctgaggag atagccagca ttaggtgaca  2160
atcttccaga agtggtcagg cagaaggtgc cctggtgaga gctcctttac agggacttta  2220
tgtggtttag ggctcagagc tccaaaactc tgggctcagc tgctcctgta ccttggaggt  2280
ccattcacat gggaaagtat tttggaatgt gtcttttgaa gagagcatca gagttcttaa  2340
```

```
gggactgggt aaggcctgac cctgaaatga ccatggatat ttttctacct acagtttgag  2400
tcaactagaa tatgcctggg gaccttgaag aatggccctt cagtggccct caccatttgt  2460
tcatgcttca gttaattcag gtgttgaagg agcttaggtt ttagaggcac gtagacttgg  2520
ttcaagtctc gttagtagtt gaatagcctc aggcaagtca ctgcccacct aagatgatgg  2580
ttcttcaact ataaaatgga gataatggtt acaaatgtct cttcctatag tataatctcc  2640
ataagggcat ggcccaagtc tgtctttgac tctgcctatc cctgacattt agtagcatgc  2700
ccgacataca atgttagcta ttggtattat tgccatatag ataaattatg tataaaaatt  2760
aaactgggca atagcctaag aagggggaa tattgtaaca caaatttaaa cccactacgc  2820
agggatgagg tgctataata tgaggacctt ttaacttcca tcattttcct gtttcttgaa  2880
atagtttatc ttgtaatgaa atataaggca cctcccactt ttatgtatag aaagaggtct  2940
tttaattttt ttttaatgtg agaaggaagg gaggagtagg aatcttgaga ttccagatcg  3000
aaaatactgt actttggttg atttttaagt gggcttccat tccatggatt taatcagtcc  3060
caagaagatc aaactcagca gtacttgggt gctgaagaac tgttggattt accctggcac  3120
gtgtgccact tgccagcttc ttgggcacac agagttcttc aatccaagtt atcagattgt  3180
atttgaaaat gacagagctg gagagttttt tgaaatggca gtggcaaata aataaatact  3240
ttttttaaa tggaaagact tgatctatgg taataaatga ttttgttttc tgactggaaa  3300
aataggccta ctaaagatga atcacacttg agatgtttct tactcactct gcacagaaac  3360
aaagaagaaa tgttatacag ggaagtccgt tttcactatt agtatgaacc aagaaatggt  3420
tcaaaaacag tggtaggagc aatgctttca tagtttcaga tatggtagtt atgaagaaaa  3480
caatgtcatt tgctgctatt attgtaagag tcttataatt aatggtactc ctataatttt  3540
tgattgtgag ctcacctatt tgggttaagc atgccaattt aaagagacca agtgtatgta  3600
cattatgttc tacatattca gtgataaaat tactaaacta ctatatgtct gctttaaatt  3660
tgtactttaa tattgtcttt tggtattaag aaagatatgc tttcagaata gatatgcttc  3720
gctttggcaa ggaatttgga tagaacttgc tatttaaaag aggtgtgggg taaatccttg  3780
tataaatctc cagtttagcc ttttttgaaa aagctagact ttcaaatact aatttcactt  3840
caagcagggt acgtttctgg tttgtttgct tgacttcagt cacaatttct tatcagacca  3900
atggctgacc tctttgagat gtcaggctag gcttacctat gtgttctgtg tcatgtgaat  3960
gctgagaagt ttgacagaga tccaacttca gccttgaccc catcagtccc tcgggttaac  4020
taactgagcc accggtcctc atggctattt taatgagggt attgatggtt aaatgcatgt  4080
ctgatccctt atcccagcca tttgcactgc cagctgggaa ctataccaga cctggatact  4140
gatcccaaag tgttaaattc aactacatgc tggagattag agatggtgcc aataaaggac  4200
ccagaaccag gatcttgatt gctatagact tattaataat ccaggtcaaa gagagtgaca  4260
cacactctct caagacctgg ggtgagggag tctgtgttat ctgcaaggcc atttgaggct  4320
cagaaagtct ctctttccta tagatatatg catactttct gacatatagg aatgtatcag  4380
gaatactcaa ccatcacagg catgttccta cctcagggcc tttacatgtc ctgtttactc  4440
tgtctagaat gtccttctgt agatgacctg gcttgcctcg tcacccttca ggtccttgct  4500
caagtgtcat cttctcccct agttaaacta ccccacaccc tgtctgcttt ccttgcttat  4560
ttttctccat agcattttac catctcttac attagacatt tttcttattt atttgtagtt  4620
tataagcttc atgaggcaag taactttgct ttgtttcttg ctgtatctcc agtgcccaga  4680
gcagtgcctg gtatataata aatatttatt gactgagtga a                      4721
```

```
SEQ ID NO: 156         moltype = AA  length = 220
FEATURE                Location/Qualifiers
source                 1..220
                       mol_type = protein
                       organism = Homo sapiens
SEQUENCE: 156
MLRLLLALNL FPSIQVTGNK ILVKQSPMLV AYDNAVNLSC KYSYNLFSRE FRASLHKGLD  60
SAVEVCVVYG NYSQQLQVYS KTGFNCDGKL GNESVTFYLQ NLYVNQTDIY FCKIEVMYPP  120
PYLDNEKSNG TIIHVKGKHL CPSPLFPGPS KPFWVLVVVG GVLACYSLLV TVAFIIFWVR  180
SKRSRLLHSD YMNMTPRRPG PTRKHYQPYA PPRDFAAYRS                      220
```

```
SEQ ID NO: 157         moltype = DNA  length = 4317
FEATURE                Location/Qualifiers
source                 1..4317
                       mol_type = genomic DNA
                       organism = Mus musculus
SEQUENCE: 157
agaccttggc agatgtgact tcagttcaca ccacactctg ccttgctcac agaggagggg  60
ctgcagccct ggccctcatc agaacaatga cactcaggct gctgttcttg gctctcaact  120
tcttctcagt tcaagtaaca gaaaacaaga ttttggtaaa gcagtcgccc ctgcttgtgg  180
tagatagcaa cgaggtcagc ctcagctgca ggtattccta caaccttctc gcaaaggaat  240
tccgggcatc cctgtacaag ggcgtgaaca gcgacgtgga agtctgtgtc gggaatggga  300
attttaccta tcagccccag tttcgctcga atgccgagtt caactgcgac ggggatttcg  360
acaacgaaac agtgacgttc cgtctctgga atctgcacgt caatcacaca gatatttact  420
tctgcaaaat tgagttcatg taccctccgc cttacctaga caacgagagg agcaatggaa  480
ctattattca cataaaagag aaacatcttt gtcatactca gtcatctcct aagctgtttt  540
gggcactggt cgtggttgct ggagtcctgt tttgttatgg cttgctagtg acagtggctc  600
tttgtgttat ctggacaaat agtagaagga acagactcct tcaaagtgac tacatgaaca  660
tgactccccg gaggcctggg ctcactcgaa agccttacca gccctacgcc cctgccagag  720
actttgcagc gtaccgcccc tgacagggac ccctatccag aagcccgccg gctggtaccc  780
gtctacctgc tcatcatcac tgctctggat aggaaaggac agcctcatct tcagccggcc  840
actttggacc tctactgggc caccaatgcc aactatttta gagtgtctag atctaacatc  900
atgatcatct tgagactctg gaatgaatga cagaagcttc tatggcagga taaagtctgt  960
gtggcttgac ccaaactcaa gcttaataca tttattgact tgattgggga agttagagta  1020
gagcaatcaa aaagatcatt cattcagcct tgggaagtca atttgcaggc tcctggatga  1080
gccctgcccc gttttcactt gccagcacat ttcagtcatg tggtgtgata gccaaagatg  1140
ttttggacag agaagaaagg atagaaaaac cttctctttg gctaagttgg tgtttggggt  1200
ggggataggt tagagtatag tacttaacta tttgaaaaat aatgaaaaca ctttttcac  1260
```

-continued

```
tcatgaaatg agccacttag ctcctaaata gtgttttcct gttagtttag aaagttgtgg  1320
acatattttt ttaatgattt ctgaccattt ttaatcacat tgactcatgg aatggcctca  1380
aagcaccccc cagtgcttct ttcctcattc ccggtcatgg gaactcagta ttattaatag  1440
tcacaacatg atttcagaac tagatagccc tcccacacca agaagaatgt gagaggaagt  1500
aaggtcactt tatgtaaaaa aaaaaaaaaa caaacgcgta cacatatgta tgtatacata  1560
catacctatg tgcacacaca cacacatata catacacaca aaatgctatg aagagttatc  1620
tgtttagtag cctgttatag tcaaatcatt ttaagtttca acttcttaca gttgggccac  1680
ttgttgtcct ttgtggatgg atatctgaaa ttgtgtctat atattgctag tcatgatact  1740
gtgaacaaaa agggtagtgt tagtatttgt cagggtggta aggatgcatt ccaggaagct  1800
tcctctgagg aagggaatga ggtcattctt gccatgtatg aaagacatag atgttttcca  1860
gaaggcacca ttgggagccc cagtataagt tcctttagac tctacagttt agagggattt  1920
tatatgtcct aggactcagg actccagaac tttgtgggct cagctgcttc ataccatggg  1980
gatacattga catgaacaat tattttggaa tgtgtcttta gggacgacat caaagttctc  2040
aagtacctac aagacctgat actggaatga aggtggactt tctttttgc ttccagttcg  2100
gatcaactgg aatgtatctg gggaccttga agaacggctg tccagctgtc ttcaccattt  2160
gtatagtgct ttgaattatt cagaggtttt aaagtcagga agacctggtt taaaaaacat  2220
ttcattatga gttaaatggc ctcaggcaag tcactgttca tccaagtcta tgactcctca  2280
actgtaagat ggccacactg aaacttgcta agatcctctg gcctctgcct cccaagagtt  2340
gggatttcag gagtgcacaa tcatgaccca aactcgtgat aatctctcag cttcaataac  2400
tttccagcta attggaatat cctgtaatca aacatgaggc atttcccctc cccccactgt  2460
ttttgtgtat aaagagatct ttaaactttt tttttaatat gaggggtaag aaaagatagg  2520
aatcttttaa ttctagacag aagatattgt gctttggttt tttttttttt taatggcttc  2580
tattctgtgc ttttaattaa accagagaag gccaagatta gccctacttg tgtgataaaa  2640
gaatgctggc ccttgtgatt gcagtcagcc tcttgacaca tagagttctt gaatctaagt  2700
tataaaatta tatttgaaaa tgacagagct ggagaattta tagaaagggt catagcaaat  2760
aacaaaccat tttttttaa acggaaagat ttggtctttg gcaatcaata actttgtttt  2820
ctaactggaa aaggaggttt actggagatg aatcacacct gaaagttttc atacctcctc  2880
tgaacacaac cgaaacatag gtgtccaaag cctttcgctc tcggtatgaa ccaacaggcg  2940
ggttaaaaac actgggtcag agtaaagctt ttgcagtttc agatgtagtg tgtatgaaga  3000
aaactatgtc acttgctgct attattgtaa gagtctaaga actaaaggtg tgcctgtaat  3060
ttctaattat gagctcacct atttggtacc gagcatgcca attttaaaga gacccggtgt  3120
accttatagc tacatccaat gataaaatta ccacactagc acatgcctgt gtttaaactc  3180
gtgctttaat gtttttctta gggcaggtat gcacccccct tgcagtgagt tgggagagat  3240
tttgaaaaag tgtatgacaa acatttttaa cacctttggt ttcctctctc tgtgtctctt  3300
tgtctctgtc tctctctttc tctcctgtgc atatgtctcc cctccctcac ttctctgtct  3360
cttcctctct ccctctctct gtctttctct gtgtgtctct ctgtctctgt gtatctctct  3420
gtctgtctct ttctctgcag attttcaaaa cgttgttttt ctatggaaga aatacaagct  3480
gtggttggtt tgctacgagt cagtagcagt ttatcagtag gccaatgttt tatctcttgg  3540
agatttcagt ctgggtttac ccaatgtatt ctctgtaatg tgactgctgg ggacagatat  3600
aacttgattg agccttcaaa tcatttaggt cttcaatcat ttagtcaacg gagtgagcca  3660
ctaatctgca atggctattt taatatgcat actgatggtc aaatggatgt ctgatctctc  3720
atcccagctt tctgtactac catatgggaa ctatatgtaa cttgtatact tacctgaata  3780
tgttaaattc aactacatgg taagatggac cagaaattgc aatgttcatg tccatatagc  3840
caccattaac ccaagttaag cacagtagtg tgggttctct caggacttgt gaatgagttt  3900
atgctctcta caaagacagg tgaagcttaa atctctcttg cactgctatg tttatgcaaa  3960
tatcaagatt gtttctgtac cagggactta acacattcta ttcatactat tttccctgtc  4020
tacaatgtta tttcatagat atctacttgg tttgctctta cttccttgac atatttgccc  4080
aaatgccacc ttcaactgta gttaattacc tgtacaacct gtctccatgc cttgttttat  4140
tttctctata actctactaa taggtatttt tcttatttat tggtttattg cctgtttttt  4200
ttcctaaatc tacaccggat ctccaaaggg aaagaactcc atttgctttg attttattgc  4260
tgtatcccca gtgcctagaa taatgcttag cctgcaataa atatttattc attgact     4317
```

```
SEQ ID NO: 158          moltype = AA  length = 218
FEATURE                 Location/Qualifiers
source                  1..218
                        mol_type = protein
                        organism = Mus musculus
SEQUENCE: 158
MTLRLLFLAL NFFSVQVTEN KILVKQSPLL VVDSNEVSLS CRYSYNLLAK EFRASLYKGV  60
NSDVEVCVGN GNFTYQPQFR SNAEFNCDGD FDNETVTFRL WNLHVNHTDI YFCKIEFMYP  120
PPYLDNERSN GTIIHIKEKH LCHTQSSPKL FWALVVVAGV LFCYGLLVTV ALCVIWTNSR  180
RNRLLQSDYM NMTPRRPGLT RKPYQPYAPA RDFAAYRP                        218

SEQ ID NO: 159          moltype = DNA  length = 1282
FEATURE                 Location/Qualifiers
source                  1..1282
                        mol_type = genomic DNA
                        organism = Homo sapiens
SEQUENCE: 159
ggaagtctgt caactgggag ggggagaggg gggtgatggg ccaggaatgg ggtccccggg  60
catggtgctg ggcctcctgg tgcagatctg ggccctgcaa gaagcctcaa gcctgagcgt  120
gcagcagggg cccaacttgc tgcaggtgag gcagggcagt caggcgaccc tggtctgcca  180
ggtggaccag gccacagcct gggaacggct ccgtgttaag tggacaaagg atggggccat  240
cctgtgtcaa ccgtacatca ccaacggcag cctcagcctg ggggtctgcg ggccccaggg  300
acggctctcc tggcaggcac ccagccatct caccctgcag ctggaccctg tgagcctcaa  360
ccacagcggg gcgtacgtgt gctgggcggc cgtagagatt cctgagttgg aggaggctga  420
gggcaacata acaaggctct ttgtggaccc agatgacccc acacagaaca gaaaccggat  480
cgcaagcttc ccaggattcc tcttcgtgct gctgggggtg ggaagcatgg gtgtggctgc  540
gatcgtgtgg ggtgcctggt tctggggccg ccgcagctgc cagcaaaggg actcaggtaa  600
```

-continued

```
cagcccagga aatgcattct acagcaacgt cctataccgg ccccgggggg ccccaaagaa  660
gagtgaggac tgctctggag aggggaagga ccagaggggc cagagcattt attcaacctc  720
cttcccgcaa ccggcccccc gccagccgca cctggcgtca agaccctgcc ccagcccgag  780
accctgcccc agccccaggc ccggccaccc cgtctctatg gtcagggtct ctcctagacc  840
aagccccacc cagcagccga ggccaaaagg gttccccaaa gtgggagagg agtgagagat  900
cccaggagac ctcaacagga ccccacccat aggtacacac aaaaaagggg ggatcgaggc  960
cagacacggt ggctcacgcc tgtaatccca gcagtttggg aagccgaggc gggtggaaca  1020
cttgaggtca ggggtttgag accagcctgg cttgaacctg ggaggcggag gttgcagtga  1080
gccgagattg cgccactgca ctccagcctg ggcgacagag tgagactccg tctcaaaaaa  1140
aacaaaaagc aggaggattg ggagcctgtc agccccatcc tgagaccccg tcctcatttc  1200
tgtaatgatg gatctcgctc ccactttccc ccaagaacct aataaaggct tgtgaagaaa  1260
aagcaaaaaa aaaaaaaaaa aa                                           1282

SEQ ID NO: 160         moltype = AA  length = 282
FEATURE                Location/Qualifiers
source                 1..282
                       mol_type = protein
                       organism = Homo sapiens
SEQUENCE: 160
MGSPGMVLGL LVQIWALQEA SSLSVQQGPN LLQVRQGSQA TLVCQVDQAT AWERLRVKWT  60
KDGAILCQPY ITNGSLSLGV CGPQGRLSWQ APSHLTLQLD PVSLNHSGAY VCWAAVEIPE  120
LEEAEGNITR LFVDPDDPTQ NRNRIASFPG FLFVLLGVGS MGVAAIVWGA WFWGRRSCQQ  180
RDSGNSPGNA FYSNVLYRPR GAPKKSEDCS GEGKDQRGQS IYSTSFPQPA PRQPHLASRP  240
CPSPRPCPSP RPGHPVSMVR VSPRPSPTQQ PRPKGFPKVG EE                    282

SEQ ID NO: 161         moltype = DNA  length = 1643
FEATURE                Location/Qualifiers
source                 1..1643
                       mol_type = genomic DNA
                       organism = Homo sapiens
SEQUENCE: 161
agtctcactt cagttccttt tgcatgaaga gctcagaatc aaaagaggaa accaacccct  60
aagatgagct ttccatgtaa atttgtagcc agcttccttc tgattttcaa tgtttcttcc  120
aaaggtgcag tctccaaaga gattacgaat gccttggaaa cctggggtgc cttgggtcag  180
gacatcaact tggacattcc tagttttcaa atgagtgatg atattgacga tataaaatgg  240
gaaaaaactt cagacaagaa aaagattgca caattcagaa aagagaaaga gactttcaag  300
gaaaaagata catataagct atttaaaaat ggaactctga aaattaagca tctgaagacc  360
gatgatcagg atatctacaa ggtatcaata tatgatacaa aaggaaaaaa tgtgttggaa  420
aaaatatttg atttgaagat tcaagagagg gtctcaaaac caaagatctc ctggacttgt  480
atcaacacaa ccctgacctg tgaggtaatg aatggaactg accccgaatt aaacctgtat  540
caagatggga aacatctaaa actttctcag agggtcatca cacacaagtg gaccaccagc  600
ctgagtgcaa aattcaagtg cacagcaggg aacaaagtca gcaaggaatc cagtgtcgag  660
cctgtcagct gtccaggagg cagcatcctt ggccagagta atgggctctc tgcctggacc  720
cctcccagcc atcccacttc tcttcctttt gcagagaaag gtctggacat ctatctcatc  780
attggcatat gtggaggagg cagcctcttg atggtctttg tggcactgct cgttttctat  840
atcaccaaaa ggaaaaaaca gaggagtcgg agaaatgatg aggagctgga gacaagagcc  900
cacagagtag ctactgaaga aaggggccgg aagccccacc aaattccagc ttcaacccct  960
cagaatccag caacttccca acatcctcct ccaccacctg gtcatcgttc ccaggcacct  1020
agtcatcgtc ccccgcctcc tggacaccgt gttcagcacc agcctcagaa gaggcctcct  1080
gctccgtcgg gcacacaagt tcaccagcag aaaggcccgc ccctccccag acctcgagtt  1140
cagccaaaac ctccccatgg ggcagcagaa aactcattgt ccccttcctc taattaaaaa  1200
agatagaaac tgtctttttc aataaaaagc actgtggatt tctgccctcc tgatgtgcat  1260
atccgtactt ccatgaggtg ttttctgtgt gcagaacatt gtcacctcct gaggctgtgg  1320
gccacagcca cctctgcatc ttcgaactca gccatgtggt caacatctgg agtttttggt  1380
ctcctcagag agctccatca caccagtaag gagaagcaat ataagtgtga ttgcaagaat  1440
ggtagaggac cgagcacaga aatcttagag atttcttgtc cctctcaggg tcatgtgtag  1500
atgcgataaa tcaagtgatt ggtgtgcctg ggtctcacta caagcagcct atctgcttaa  1560
gagactctgg agtttcttat gtgccctggt ggacacttgc ccaccatcct gtgagtaaaa  1620
gtgaaataaa agctttgact aga                                          1643

SEQ ID NO: 162         moltype = AA  length = 377
FEATURE                Location/Qualifiers
source                 1..377
                       mol_type = protein
                       organism = Homo sapiens
SEQUENCE: 162
MSFPCKFVAS FLLIFNVSSK GAVSKEITNA LETWGALGQD INLDIPSFQM SDDIDDIKWE  60
KTSDKKKIAQ FRKEKETFKE KDTYKLFKNG TLKIKHLKTD DQDIYKVSIY DTKGKNVLEK  120
IFDLKIQERV SKPKISWTCI NTTLTCEVMN GTDPELNLYQ DGKHLKLSQR VITHKWTTSL  180
SAKFKCTAGN KVSKESSVEP VSCPGGSILG QSNGLSAWTP PSHPTSLPFA EKGLDIYLII  240
GICGGGSLLM VFVALLVFYI TKRKKQRSRR NDEELETRAH RVATEERGRK PHQIPASTPQ  300
NPATSQHPPP PPGHRSQAPS HRPPPPGHRV QHQPQKRPPA PSGTQVHQQK GPPLPRPRVQ  360
PKPPHGAAEN SLSPSSN                                                 377

SEQ ID NO: 163         moltype = DNA  length = 1144
FEATURE                Location/Qualifiers
source                 1..1144
                       mol_type = genomic DNA
                       organism = Mus musculus
```

```
SEQUENCE: 163
gcctcaccac agtcctgaca gaaagaactc agagtcaccc ctgggaaaag aactctaaag  60
atgaaatgta aattcctggg tagcttcttt ctgctcttca gcctttccgg caaaggggcg  120
gactgcagag acaatgagac catctggggt gtcttgggtc atggcatcac cctgaacatc  180
cccaactttc aaatgactga tgatattgat gaggtgcgat gggtaaggag gggcaccctg  240
gtcgcagagt ttaaaaggaa gaagccacct tttttgatat cagaaacgta tgaggtctta  300
gcaaacggat ccctgaagat aaagaagccg atgatgagaa acgacagtgg cacctataat  360
gtaatggtgt atggcacaaa tgggatgact aggctggaga aggacctgga cgtgaggatt  420
ctggagaggg tctcaaagcc catgatccac tgggaatgcc ccaacacaac cctgacctgt  480
gcggtcttgc aagggacaga ttttgaactg aagctgtatc aaggggaaac actactcaat  540
agtctccccc agaagaacat gagttaccag tggaccaacc tgaacgcacc attcaagtgt  600
gaggcgataa acccggtcag caaggagtct aagatggaag ttgttaactg tccagagaaa  660
ggtctgtcct tctatgtcac agtgggggtc ggtgcaggag gactcctctt ggtgctcttg  720
gtggcgcttt ttattttctg tatctgcaag aggagaaaac ggaacaggag gagaaaagat  780
gaagagctgg aaataaaagc ttccagaaca agcactgtgg aaaggggccc caagccgcac  840
tcaaccccag ccgcagcagc gcagaattca gtggcgctcc aagctcctcc tccacctggc  900
catcacctcc agacacctgg ccatcgtccc ttgcctccag gccaccgtac ccgtgagcac  960
cagcagaaga agagacctcc tccatcaggc acacagattc accagcagaa aggccctcct  1020
ttacccagac cccgagttca gccaaaacct ccctgtggga gtggagatgg tgtttcactg  1080
ccgccccccta attaagaagg cagagttcgt catttccaat aaaaagctgt gtggatttat  1140
cttc                                                              1144

SEQ ID NO: 164         moltype = AA  length = 344
FEATURE                Location/Qualifiers
source                 1..344
                       mol_type = protein
                       organism = Mus musculus
SEQUENCE: 164
MKCKFLGSFF LLFSLSGKGA DCRDNETIWG VLGHGITLNI PNFQMTDDID EVRWVRRGTL  60
VAEFKRKKPP FLISETYEVL ANGSLKIKKP MMRNDSGTYN VMVYGTNGMT RLEKDLDVRI  120
LERVSKPMIH WECPNTTLTC AVLQGTDFEL KLYQGETLLN SLPQKNMSYQ WTNLNAPFKC  180
EAINPVSKES KMEVVNCPEK GLSFYVTVGV GAGGLLLVLL VALFIFCICK RRKRNRRRKD  240
EELEIKASRT STVERGPKPH STPAAAAQNS VALQAPPPPG HHLQTPGHRP LPPGHRTREH  300
QQKKRPPPSG TQIHQQKGPP LPRPRVQPKP PCGSGDGVSL PPPN                  344

SEQ ID NO: 165         moltype = DNA  length = 1086
FEATURE                Location/Qualifiers
source                 1..1086
                       mol_type = genomic DNA
                       organism = Homo sapiens
SEQUENCE: 165
gaacttaggg ctgcttgtgg ctgggcactc gcgcagaggc cggcccgacg agccatggtt  60
gctgggagcg acgcggggcg ggccctgggg gtcctcagcg tggtctgcct gctgcactgc  120
tttggtttca tcagctgttt ttcccaacaa atatatggtg ttgtgtatgg gaatgtaact  180
ttccatgtac caagcaatgt gcctttaaaa gaggtcctat ggaaaaaaca aaaggataaa  240
gttgcagaac tggaaaattc tgaattcaga gctttctcat cttttaaaaa tagggtttat  300
ttagacactg tgtcaggtag cctcactatc tacaacttaa catcatcaga tgaagatgag  360
tatgaaatgg aatcgccaaa tattactgat accatgaagt tctttcttta tgtgcttgag  420
tctcttccat ctcccacact aacttgtgca ttgactaatg gaagcattga agtccaatgc  480
atgataccag agcattacaa cagccatcga ggacttataa tgtactcatg ggattgtcct  540
atggagcaat gtaaacgtaa ctcaaccagt atatatttta agatggaaaa tgatcttcca  600
caaaaaatac agtgtactct tagcaatcca ttatttaata caacatcatc aatcattttg  660
acaacctgta tcccaagcag cggtcattca agacacagat atgcacttat acccatacca  720
ttagcagtaa ttacaacatg tattgtgctg tatatgaatg gtattctgaa atgtgacaga  780
aaaccagaca gaaccaactc caattgattg gtaacagaag atgaagacaa cagcataact  840
aaattatttt aaaaactaaa aagccatctg atttctcatt tgagtattac aatttttgaa  900
caactgttgg aaatgtaact tgaagcagct gctttaagaa gaaataccca ctaacaaaga  960
acaagcatta gttttggctg tcatcaactt attatatgac taggtgcttg cttttttttgt  1020
cagtaaattg tttttactga tgatgtagat actttttgtaa ataaatgtaa atatgtacac  1080
aagtga                                                            1086

SEQ ID NO: 166         moltype = AA  length = 250
FEATURE                Location/Qualifiers
source                 1..250
                       mol_type = protein
                       organism = Homo sapiens
SEQUENCE: 166
MVAGSDAGRA LGVLSVVCLL HCFGFISCFS QQIYGVVYGN VTFHVPSNVP LKEVLWKKQK  60
DKVAELENSE FRAFSSFKNR VYLDTVSGSL TIYNLTSSDE DEYEMESPNI TDTMKFFLYV  120
LESLPSPTLT CALTNGSIEV QCMIPEHYNS HRGLIMYSWD CPMEQCKRNS TSIYFKMEND  180
LPQKIQCTLS NPLFNTTSSI ILTTCIPSSG HSRHRYALIP IPLAVITTCI VLYMNGILKC  240
DRKPDRTNSN                                                        250

SEQ ID NO: 167         moltype = DNA  length = 1097
FEATURE                Location/Qualifiers
source                 1..1097
                       mol_type = genomic DNA
                       organism = Homo sapiens
SEQUENCE: 167
```

-continued

```
cttttctag ccaggctctc aactgtctcc tgcgttgctg ggaagttctg gaaggaagca  60
tgtgctccag aggttgggat tcgtgtctgg ctctggaatt gctactgctg cctctgtcac  120
tcctggtgac cagcattcaa ggtcacttgg tacatatgac cgtggtctcc ggcagcaacg  180
tgactctgaa catctctgag agcctgcctg agaactacaa acaactaacc tggttttata  240
ctttcgacca gaagattgta gaatgggatt ccagaaaatc taagtacttt gaatccaaat  300
ttaaaggcag ggtcagactt gatcctcaga gtggcgcact gtacatctct aaggtccaga  360
aagaggacaa cagcacctac atcatgaggg tgttgaaaaa gactgggaat gagcaagaat  420
ggaagatcaa gctgcaagtg cttgaccctg tacccaagcc tgtcatcaaa attgagaaga  480
tagaagacat ggatgacaac tgttatctga aactgtcatg tgtgatacct ggcgagtctg  540
taaactacac ctggtatggg gacaaaaggc ccttcccaaa ggagctccag aacagtgtgc  600
ttgaaaccac ccttatgcca cataattact ccaggtgtta tacttgccaa gtcagcaatt  660
ctgtgagcag caagaatggc acggtctgcc tcagtccacc ctgtaccctg gcccggtcct  720
ttggagtaga atggattgca agttggctag tggtcacggt gcccaccatt cttggcctgt  780
tacttacctg agatgagctc ttttaactca agcgaaactt caaggccaga agatcttgcc  840
tgttggtgat catgctcctc accaggacag agactgtata ggctgaccag aagcatgctg  900
ctgaattatc aacgaggatt ttcaagttaa cttttaaata ctggttatta tttaatttta  960
tatccctttg ttgttttcta gtacacagag atatagagat acacatgctt ttttcccacc  1020
caaaattgtg acaacattat gtgaatgttt tattattttt taaaataaac atttgatata  1080
attgtcaatt aactgaa                                                1097

SEQ ID NO: 168         moltype = AA  length = 243
FEATURE                Location/Qualifiers
source                 1..243
                       mol_type = protein
                       organism = Homo sapiens
SEQUENCE: 168
MCSRGWDSCL ALELLLLPLS LLVTSIQGHL VHMTVVSGSN VTLNISESLP ENYKQLTWFY  60
TFDQKIVEWD SRKSKYFESK FKGRVRLDPQ SGALYISKVQ KEDNSTYIMR VLKKTGNEQE  120
WKIKLQVLDP VPKPVIKIEK IEDMDDNCYL KLSCVIPGES VNYTWYGDKR PFPKELQNSV  180
LETTLMPHNY SRCYTCQVSN SVSSKNGTVC LSPPCTLARS FGVEWIASWL VVTVPTILGL  240
LLT                                                               243

SEQ ID NO: 169         moltype = DNA  length = 1205
FEATURE                Location/Qualifiers
source                 1..1205
                       mol_type = genomic DNA
                       organism = Mus musculus
SEQUENCE: 169
atacgacttc cggttttggg ttttgcttcc tgattgaagg gcaggcgccc tgacttctct  60
tacagttgtc tccagtgttc tggggaagct tctctaagta ttatgtgctt cataaaacag  120
ggatggtgtc tggtcctgga actgctactg ctgcccttgg gaactggatt tcaaggtcat  180
tcaataccag atataaatgc caccaccggc agcaatgtaa ccctgaaaat ccataaggac  240
ccacttggac catataaacg tatcacctgg cttcatacta aaatcagaa gattttagag  300
tacaactata atagtacaaa gacaatcttc gagtctgaat ttaaaggcag ggtttatctt  360
gaagaaaaca atggtgcact tcatatctct aatgtccgga aagaggacaa aggtacctac  420
tacatgagag tgctgcgtga aactgagaac gagttgaaga taaccctgga agtatttgat  480
cctgtgccca agccttccat agaaatcaat aagactgaag cgtcgactga ttcctgtcac  540
ctgaggctat cgtgtgaggt aaaggaccag catgttgact atacttggta tgagagctcg  600
ggaccctttcc ccaaaaagag tccaggatat gtgctcgatc tcatcgtcac accacagaac  660
aagtctacat tttacacctg ccaagtcagc aatcctgtaa gcagcaagaa cgacacagtg  720
tacttcactc taccttgtga tctagccaga tcttctggag tatgttggac tgcaacttgg  780
ctagtggtca caacactcat cattcacagg atcctgttaa cctgacaaga actcttctca  840
cccaagaagg caacttggaa gcacagagtc ttgccttcat ccctagcagt gttcctagcc  900
agcgaagcaa ctctggctct attggacaaa ggaaaatgtg ttactgaacg tctgcgagag  960
tttgcatgca tgctctatga aacaagcaca ggaccttgta cagtgctcca ccactgacct  1020
gtgtgcccag tcctttacaa agatttcaaa tcaacctttt aaaaactgtg cataatatct  1080
aattttatat accctagttg tttcccaaca tatattaaag ataaatgcat tctttttacc  1140
aaaatgtgac tatattattt tcatgttttc atatctcttt ttaaaataaa ttcttttaaa  1200
aaact                                                             1205

SEQ ID NO: 170         moltype = AA  length = 240
FEATURE                Location/Qualifiers
source                 1..240
                       mol_type = protein
                       organism = Mus musculus
SEQUENCE: 170
MCFIKQGWCL VLELLLLPLG TGFQGHSIPD INATTGSNVT LKIHKDPLGP YKRITWLHTK  60
NQKILEYNYN STKTIFESEF KGRVYLEENN GALHISNVRK EDKGTYYMRV LRETENELKI  120
TLEVFDPVPK PSIEINKTEA STDSCHLRLS CEVKDQHVDY TWYESSGPFP KKSPGYVLDL  180
IVTPQNKSTF YTCQVSNPVS SKNDTVYFTL PCDLARSSGV CWTATWLVVT TLIIHRILLT  240

SEQ ID NO: 171         moltype = DNA  length = 12123
FEATURE                Location/Qualifiers
source                 1..12123
                       mol_type = genomic DNA
                       organism = Homo sapiens
SEQUENCE: 171
gcagatggga agaagcgtta gagcgagcag cactcacatc tcaagaacca gcctttcaaa  60
cagtttccag agatggatta tcctacttta cttttggctc ttcttcatgt atacagagct  120
```

-continued ctatgtgaag aggtgctttg gcatacatca gttccctttg ccgagaacat gtctctagaa 180
tgtgtgtatc catcaatggg catcttaaca caggtggagt ggttcaagat cgggacccag 240
caggattcca tagccatttt cagccctact catggcatgg tcataaggaa gccctatgct 300
gagagggttt actttttgaa ttcaacgatg gcttccaata acatgactct tttctttcgg 360
aatgcctctg aagatgatgt tggctactat tcctgctctc tttacactta cccacaggga 420
acttggcaga aggtgataca ggtggttcag tcagatagtt ttgaggcagc tgtgccatca 480
aatagccaca ttgtttcgga acctggaaag aatgtcacac tcacttgtca gcctcagatg 540
acgtggcctg tgcaggcagt gaggtgggaa aagatccagc cccgtcagat cgacctctta 600
acttactgca acttggtcca tggcagaaat ttcacctcca agttcccaag acaaatagtg 660
agcaactgca gccacggaag gtggagcgtc atcgtcatcc ccgatgtcac agtctcagac 720
tcggggcttt accgctgcta cttgcaggcc agcgcaggag aaaacgaaac cttcgtgatg 780
agattgactg tagccgaggg taaaaccgat aaccaatata ccctctttgt ggctggaggg 840
acagttttat tgttgttgtt tgttatctca attaccacca tcattgtcat tttccttaac 900
agaaggagaa ggagagagag aagagatcta tttacagagt cctgggatac acagaaggca 960
cccaataact atagaagtcc catctctacc agtcaaccta ccaatcaatc catggatgat 1020
acaagagagg atatttatgt caactatcca accttctctc gcagaccaaa gactagagtt 1080
taagcttatt cttgacatga gtgcattagt aatgactctt atgtactcat gcatggatct 1140
ttatgcaatt tttttccact acccaaggtc taccttagat actagttgtc tgaattgagt 1200
tactttgata ggaaaaatac ttcattacct aaaatcattt ttcatagaac tgtttcagaa 1260
aacctgactc taactggttt atatacaaaa gaaaacttac tgtatcatat aacagaatga 1320
tccaggggag attaagcttt gggcaagggc tatttaccag ggcttaaatg ttgtgtctag 1380
aattaagtat gggcataaac tggcttctga atccctttcc agagtgttgg atccatttcc 1440
ctggtcttgg cctcactctc atgcaggctt tcctcttgtg ttggcaagat ggctgccaac 1500
tcttggcaat tcatacatcc ttgtttctgt ctggtagaga gtttgcttct caaatggagc 1560
aaacaaattt gattattttt tcattgttaa ataggcaaca tgaccagaaa ggatggaatg 1620
gcttaagtaa actaagggtt cacttctaga gctgagaagc agggtcaaag cacaatactg 1680
ggcaattcag agcatggtta gaagaggaaa ggggagtctc aaagctggag agtttaccaa 1740
caaatattga ctgcagtgat taaccaagac atttttgtta actaaaaagt gaaatatggg 1800
atggattcta gaaatggggt atctctgtcc atacttctag aatccactct atcagcatag 1860
tccagaagaa tacctggcag tagaagaaat gaatattcaa gaggaagata aatgcgagag 1920
ggcaatcctt tactattctc atatttattt atctctcatt ctgtatagaa ttcttgccgc 1980
catcccaggt ctagccttag gagcaaatgt agtagatagt cgaataataa ataacttaat 2040
gttttggaca tattttgtct acttttgaga attattttta atatgtaaat tctctcaaaa 2100
gggtcaggca cctagttatt attttttaat gattatgtga aagttgaata taatatacca 2160
ctaaaagtga cagttgaaag tggtggcata ggacggtagg gtagaaattt gggagggaaa 2220
aaagaaattg ggagggtaca ggcaacagga gaaaggaatc aaaccacaga aaaatacaaa 2280
gggaaacttc tgcttcacta ttcagacaaa gacagcccta atgacatcac caacagtcaa 2340
agcaattaga gaccatacct aatattgttt aaattctaga tgtaggctaa caatgaaaag 2400
tatttgccaa actgaataaa actgtcatgg ttaccttgaa aggacaatgg ttattgttaa 2460
atatagtgat cattcatgtc taaaagattc attatttatc tctaaagatt tctaaagacc 2520
accatctaga aaagattcat tatgaaggct gtatttaaat atcaaagttg tggacttcat 2580
gataatctta aataaagcaa atccaaattc tcctgttgcc tagacagatt ctaagatgta 2640
atttacactt ttaagctaat tagtgagtat tttatgattt tagccttaaa caccatgtat 2700
gccaaataat gcacttgttt tgtgaattac agaaatggta agtgcccaca tttctgtgaa 2760
ttataaaatt tgtgagtttc ttttaaccct tttcaggagt gaaaaaataa aaacgaccat 2820
ttcctggttg tgcttaagta tatgcaagaa gggtaaactc tcatttttat tatgtttgct 2880
taaagatctt tttatacctg gattcatgaa atgtttccac aaatatatta gtgtaacaaa 2940
cttgaaaggc agtttacaag aaagcactct actatcagat caatcaaaga ttctgtgagt 3000
gaatttattg gtttgcatgg tgaagcaagc ttagcatcaa ttaaaaggta aataatttct 3060
tttctgaatg gtaaagacaa tcaaaatatt actttctgga aaactccaat aaccaaattc 3120
tcaatgatta gtgtatgtga gcaggaaaac atttttacag ttgtagtatg gggaaatata 3180
aatccaattt taagagagaa aattatgact gggtgtggaa gggacagtat agtcagatac 3240
cattgtcatg gtggttttta ctgggaactt catgaaagac ttttgtagca aaccactgca 3300
gtattgcaaa gcctccagaa catttggaac ttgtctcttt ttccttgtgt gtgtttgtgt 3360
ttttggtctc tcattcaaaa tattgatgag aactatttac tctgtccttt cttctctata 3420
tattcttcct ctacagagtg tagggttttt tcaggaattt ggagccatct gaagtcctcc 3480
caaaaattct ctgacgtctt ctgatgctcc tgttataccc tcaggggtaa tgcttgtgaa 3540
attccattca ttcattttct ttctctggac atctttactt accaaagcac tttcattgtc 3600
atctttttaa catcattctt aattcgtgat agttttggga ctctccctag tgtatgtttc 3660
tccccctcta ctcttttgca cctatgattc tgattgttac taagaaagca gatgaaaaac 3720
agatccacag aataaacgat cagaattcca gtaaattcta ttttaaatac agatactttt 3780
tacaagttgc tgctttggaa gcaaaatgct tcttaagttt tacatatata tatatatata 3840
tacatatata tatacacata taatttatat cgatggataa tacattaaga atctatgctt 3900
cctttgaatg ccattaatat ttatgttaaa gtaaccaatg aaaggaaatt actttgttat 3960
aataagatag gaagacttgt taatggagta cacagttttg tcagggaaag aacacatctt 4020
attgaactat gatgactatg cattgactat attattataa gagatacctt caaactttat 4080
ttaaagaact ttaggtataa tatgttgaga aaataaaata gaaatttcat ttacttgtaa 4140
tcatgcttaa aatgggaggc aggtaggtga agatataatt tttagtaaaa actccaattt 4200
atgttttaag taattcagtg tattactaaa atactatata tataaactta aaatacatgg 4260
gttatcaatt taaaagacaa agtaagtaaa aatactttta gtaggcattc gtggattgtg 4320
aacatccaag ttatattggt ttgtatagaa tggcattaag taaaaattac agctgtataa 4380
cagtagtttt ctaaattgag agagtccaca ttgtaattag agatcactgt gaccaaaatg 4440
cttctccttg atttataatg atgtactgta ttttgtactg cttatatgaa atttcagcaa 4500
gattgacgat attataaaga tgcttataaa gtgtaagtgg agacgctaaa ttgtgagtac 4560
aaagtttctt tttcacaaca gtgataagaa aatatcttta aaaaatataa gacaatataa 4620
acatgtcatc attagtttag ctactattaa aatgtaacat ctagaaagta ctgatctcca 4680
ccttcagact tctgtataag tatatttttt cactgatctg ttcattagag ttcttccagc 4740
caagactctg ggctcttaaa acatgtatct gaaaactaaa aacaagttaa ttttttttaaa 4800
agcttctcta tttctagtga ttcaataggt agaaaaatag cttctagaat taactgcaat 4860

-continued

```
gctttctaag gaaattttat aaatcctcaa ggtcggttta cacatatttt tccagattca  4920
gagcactaac tatcttgtaa gatgtaagaa aaggtccatt tggaagtatg agtaataaat  4980
gtctgggata attctggttt atttcgtatt atccttgtta gaataagtta tatggtcaac  5040
ctgttcagaa cactttttct agtgttagtg tgtacttttg gatttttggt tcttgtaggg  5100
tatagaaata ttttcctttg tcttgtattc tgttgttttg aatgaataaa acacaatgtt  5160
tcacgatcac tactttcatt tgccatggag aaatagcagg gaaaaatttc tacagaataa  5220
aattaactga tgaattacat gcagaaaaaa ttcaaatcaa tgatacattg taatttttat  5280
ctcaatgcaa tgttctttgt attttatttt attattattt ttttgagacg gagtttcact  5340
tttgttgccc gggctggagt gcaatggcac aatctcggct caccacaacc tctgcctccc  5400
ggattcaagt gattctcctg cctcagcctc ctgaatagct gggattacag gcatatgcca  5460
acatgcctgg ctaattttgt atttttagtg gagacggggt ttctccacgt tggtcagact  5520
tgtcttgaac tctggacctc aggtgatcca cctgcctcag cctcctaaat tgctgggatt  5580
acaggcatga gcgaccactc ctggccttgt tctttgtatt ttataagtgc atgtagtgca  5640
aagggtcaaa gggctttaca ggttttttgt ttgtttgttt ttgtttttcc cgaaacatag  5700
tagtcccttg cccttcctca tttttgttac cttgagacaa caaattttac tacttctaac  5760
tcattatttt atttatgttc acttttctga atagcatgct tatgacacta atactttttt  5820
tttcaatttt agacattcat tattcattta gatgtctttc tctccccaaa ctcaccacat  5880
aaaatactct tctcatgtct ctttcagaaa tatttgtatt aaaatatgat tatatcaata  5940
tttggcattt atttcttatg accttgccag tactcttagt taaactacat ggtaaaaatg  6000
attttgcttt ccctcctaca taactttttt tccacctaga gctaataatt gtcattctgg  6060
ggactgactt tttctgtatt taccataaat tgacctgaaa ctcccctgtg atgcagcagg  6120
aattctacca acgtcaactt ccttagaaag actccattag aagcttgact tggggctaga  6180
aggagaggca cacaactgcc atcctggtgt ctcccttcat ccagaaaaag ggggaggaat  6240
acatgaaacc tagaatccac tctaaaacat tttccagaac aaaaggacat gtgtttccgt  6300
gttgtaaatg tttaacgagt gcccataaca aggaataata agtctattat gtttgctttt  6360
gtgtctgtaa aagttggggg tattggttgt aagcacgaaa acagatactg actgttgaag  6420
aaaaaaaaaa atacgaggtc aggagtttga gaccaacttg gccaatatgg tgaaaccctg  6480
tcttagtaaa aatagaaaaa ttagccaggc ctggtggcac gcacctgtag tcccagctac  6540
ttgggaggct gaggcagaag aatcgcttga acccgggagg cagaggttgc agtgagccaa  6600
gatcgcacca ctgcactcca ccctgggcaa cagagcgaga ctccgtctca aaaaaaaaaa  6660
aaaaaaaaaa aaaaaaaagt taagtatttg aacataggggg tggctcatag aattcccagg  6720
acacccgatg gagtaggctt gcaaaacaca acatgtggca actccagtgg gaaacgaggc  6780
aggaaacact cgtttcctgc agaaagcaac aatttgggct tcgataccct ccctagaaca  6840
cagggcagtg aatctgagca gcatcagtac cccacgttcg gatgagtcct gagcccctat  6900
ttttattcac tgacttattc caaaatcagt gtctcttaaa tatatctgga aggcagcagc  6960
ttgtatctcc cccttcagct tccatagtgg cagtcagggt acaacttact ttccaaacag  7020
aacacactgc gacattccct ccaggctcgt tgaagaactt caactgacaa atgtccctcc  7080
tcgaccagat gatagtttc ttaaaggcag ggtttaatat accctttat aaatgtttca  7140
aggccctgtg taatacctga gtttattcca gatgtaacta aatatatcca agattgtttt  7200
aaaataaatt gctgaaaaaa caaataaata cagttagtat ctatatcaat attctcagtt  7260
ggcagttttg caataatggc cgatagttca tttttagtaa cactattgac attgcatttg  7320
gatattaggg tttactaatc atccgcatgt atacattgca tatttttcta gactttaact  7380
ttattcaaat ctattgattt ttaaacctgc aacttatgtc tagacacagg tatacctta  7440
caagaactac catttttttt ggtaacatac tacctccaaa atttcaagta agaagttgat  7500
ttttgtccat ttttaaatgg aaaacttgta atcaaaatgc cacaaaatta tactgtgtat  7560
catttgacct atagaaacca atattattac aggaagaaag cagagccaat cttctacctg  7620
tggtcaaata agtggaggcc ctttctagac taagttctca tgagtttaaa ataccaagca  7680
taagttctcc aaattcctga aaaggaagcc ttgtgttgta ttgcccagcc atatttgtaa  7740
gacataaaaa taaaacttga gaagaagcta tgataactta ctttcttcat tcttcaaaat  7800
ttacataatc tcaactgatt ttatgttttt atgaaaatgc attcttaaga tatatcctta  7860
ttcaatcatg tattcattac atcctttatg ccaggtatcc aaaagtactt acagtgacta  7920
agaccattat tctttgatca gctgcctgag taagactttg agctctccaa tatactctca  7980
gtgatactaa gttttctgag taacagcttt ggatgtggct tcagttgagc tgatttatcc  8040
cacactttat ttttatcgta taatggtcct cagaagcaaa ttttgatttt agctcacata  8100
aaaaatgtac aaagaaatgt aatggctcag tagcttctag agatagagat tactcttcta  8160
acctttctgt aattttgtat gtctatttta taattctttc aatgtctaat gaatagctat  8220
ctttttttga gacggagtct cgctctgtcg cccaggctgg agtgcagtgg tgcgacctcg  8280
gctcaccgca agctgcgtct tccaggttca cgccattctc ctgcctcagc ctcccgagta  8340
gctgggactt caggcgccca ccaccatgcc cagctaattt ttttgtattt ttagtagaga  8400
cggggtttca ccgtgttagc cagggtggtc tcgatctcct gacctcgtga tccgcccgcc  8460
tcggcctccc aacgtgctgg gattacagga gtgagccacc gcgcccggcc tccttagttt  8520
cttaaggtgg aagcctagat tattgatttt atatgttgtt ttcttttcca atagtggcac  8580
ttaatgctat aaatttcact ttgttccaca agttttggta agctctattt ttattttcat  8640
ttagtccaaa atattttaaa atttcttttg atatttcttc tttgagccat gaattattta  8700
caatgtgttg tttaatctct atatattttg ggatttttct actttatatc tcttacagat  8760
ttctaactta atttcatcat gttttaaaaa cattctttgt ataatttcta ttcttttaaa  8820
tttttcaggt gtattttatg gcccagaata tggtctatct tgtagaatgt ttcatgtgat  8880
cttaagaaga atgttcattc tgctgttgag tgtaatattc tacaaatgtc cattagatta  8940
aactgattga taccaccgtt cagattatct atatccttc tgattttccc tcttcttgat  9000
ctatcacata ctgacagatc aagtgatcaa gtctcgttaa agactgcaag taaaatagtg  9060
gatttttcta tttctccttg cagttttgtt agtttttgtc tcatgtatct tgatactctt  9120
gttagtacat atactttcag aatcgttagg ttttcttgga gaattgaccc ctttaccaca  9180
tgtaatgtcc cttttattct tgataatctt tcttgttctg tctgcttttt ctgatattaa  9240
cataactttc agttttttaa aaaattaaca ttagcatctc acatctttat ccttttaatt  9300
ttaaattatc taaatattta tatttaatgt gcctttctta tagacaatgt atagttgcgt  9360
ctatttgtaa tttccccact tttcttactt aaaaatgttg tagatatata ggagttgtat  9420
atatttgggg ggtacatgtg atgttttgat acctgtatac aatatgtaat gatcatattg  9480
ggtaatcgtg atatctgtca cctctaacat tcatcttttt tgtgtgttta aacccaccac  9540
ttctaattgg tacatttaga ttattcaaat ttaagtgatt attgatatag ttggattaat  9600
```

-continued

```
atctactatg tttgtaactt ttctatcctt gcactcgttc tttctttttt atcctccttt  9660
ttctgtgttc tctgatttta actggggttt ttacatgatt taattttctc tcgtggcata  9720
tctttcattg atcaacctag gtttttctcc ttttcccctc ttttttttgg tatttattct  9780
atttagtgtt atctgagcta cctgagttgg tgtctatcac taattttggc aagttcccag  9840
acgttattac ttctaacatt cttttgctcc attctttctt cttcttcaat tattccatag  9900
tcttgaatat tctgggtttt tcccactctt tgaattttag tttgaaaagt ttctattggc  9960
ctagcttcaa agtcattcat tcttccttcg gggttccaag tcaactgata attgcatcaa  10020
agatatcctt cctttctatt actatgtttt ttattgctac catttctttt ttattccttc  10080
ttagtgtttc catctttctt cttacattat ccatctgttg tctatttttt tcatgagagc  10140
tcttaacata ttaatgataa gttccatgtc tgataattct gacacgtgtc atgtctctat  10200
ctggttccaa tgattgcttt atctcttcag accatgactt ttcttgcctt ttgacgttct  10260
ttgacatttt ttttgaattt tttgttgcaa gccagatctg gtgtgtttatg taataggaac  10320
aggtaaataa gtctttagct tgcagactta tcttaatctg actaactatt agactgtgtt  10380
taaagtctgt tataaccata ggtgctaaat ttcttcaaat tcctctagtg tctttgtttt  10440
gtttgttcat gtgtttttcc ccttcttgag ttcaggcttc cctaagtgct cctcttcaga  10500
gagactttct gtctttcagc tctttcctct gcaattcact gttactatac tggagccctg  10560
ttggtgtagt actaagctgt gggaaaggag agtgctctgt aatcttacag tgaaatctca  10620
gtcttttagt gggtctgtgt ctgggacatt cacagagctt ctccagtggt attgcttcct  10680
catcctcaac tctctttcct ggctgcagca ttcccaatgt atttctttga aggcctgccc  10740
cctgttgact gttattttcc ctctttcctt aagtgggaca gggagacttc aggggctggg  10800
atgaggtttg ggaattgtgc ttggcagagt cctttccatc tttgttacca agaaggttca  10860
tggcttattt ctcaatggat gtccctctct atctgttgcc agagccacga ggaaattttt  10920
cttggatcct cataatgaga accttggagt ttcctactgg aaaagccctt gaatgtgtgg  10980
agtgcctcaa gagcacagcc cccatgggtt tcttgctcac accagtccac aaacagatgc  11040
cagcaattca cccaacttac catataaagg ctcatactag tttatggctc cagtgctttg  11100
actccagata aatggctatt ggttgcgtat ctctctggat gtatctgtat ctccagattt  11160
tggggtggca gtttgctcag gaccttggtt ctctaatagg tctaataaga aaagtcattg  11220
attttcagct ttccaacttt ccagctttgt cttgttataa gcatggcagc aacatcttcc  11280
atgccttaac atgatgacac taaaggcaga agtcgatctc catgtataaa cattttaaca  11340
catatgtttt ttgttatcgt ggtttctgac ctgtctcttt gccctgactt tctgatactg  11400
cactagggtt cctgttgctg gactccattc catatgactt gctctcgtct aggctgctct  11460
ttggctcatc tttataaatc atgatccaaa atgaagcaca tatttatttt ttaaataaat  11520
atgaaatgaa gtatagacat caaactgaag atgagtagat catactgagt ttcactgtct  11580
gtgcttggat caacatcagg ccttatacaa atattcaagt ccagaggcaa aaggtaataa  11640
ggaaaatttg tagcacaagc cacaaggaga taacatgtca agtctatgcg attggaaata  11700
aactaaagat gaactgctgg ggatgctcac tcatcacaga gctcagtcta aagcaccaga  11760
tttcacaagc atttttggg ggaaattctg ttaaaatgaa atatgagtca catggtggtg  11820
tttcactcat catatgtgtt caatattaat tcattttaag gtttagttgc acaaaaggta  11880
aatgagaatt agaagactcc atgggtaaga ggagccacag aagtaaagca ttgtcaaggg  11940
ttctatgtct atatatttag atattaggct tctgagaaaa aaacacaata ggaaggaaga  12000
tgaacacaac agagggcaga aggtctatac gtcctgaggc cttttatgca acgtttgttt  12060
gtggaatgtt ttttaagaat gtgtgagagt cattttaatg tgaaataaag acctacgtct  12120
aca                                                                12123
```

```
SEQ ID NO: 172         moltype = AA  length = 336
FEATURE                Location/Qualifiers
source                 1..336
                       mol_type = protein
                       organism = Homo sapiens
SEQUENCE: 172
MDYPTLLLAL LHVYRALCEE VLWHTSVPFA ENMSLECVYP SMGILTQVEW FKIGTQQDSI  60
AIFSPTHGMV IRKPYAERVY FLNSTMASNN MTLFFRNASE DDVGYYSCSL YTYPQGTWQK  120
VIQVVQSDSF EAAVPSNSHI VSEPGKNVTL TCQPQMTWPV QAVRWEKIQP RQIDLLTYCN  180
LVHGRNFTSK FPRQIVSNCS HGRWSVIVIP DVTVSDSGLY RCYLQASAGE NETFVMRLTV  240
AEGKTDNQYT LFVAGGTVLL LLFVISITTI IVIFLNRRRR RERRDLFTES WDTQKAPNNY  300
RSPISTSQPT NQSMDDTRED IYVNYPTFSR RPKTRV                           336
```

```
SEQ ID NO: 173         moltype = DNA  length = 2487
FEATURE                Location/Qualifiers
source                 1..2487
                       mol_type = genomic DNA
                       organism = Mus musculus
SEQUENCE: 173
acacagaaga cttcttgact tcaggagaca ctgctgtatg aaacagtgct tgctatcagt  60
ggctgctgga agaggctgtg gtggaaagaa aacctcaact gcaggccaga gttggttccc  120
caaaagaggc aaactcccag tgctagccag aggctaggaa gctctaagca acccacttat  180
ctgcaaggag agttacgccc aaagagcatc aagtccaacc tcctgaactg tttccagaga  240
tggcttatgt tacttggctt ttggctattc ttcatgtgca caaagcactg tgtgaagaga  300
cattgtggga cacaacagtt cggctttctg agactatgac tctggaatgt gtatatccat  360
tgacgcataa cttaacccag gtggagtgga ccaagaacac tggcacaaag acagtgagca  420
tagcagttta caaccctaac cataatatgc atatagaatc taactacctc catagagtac  480
acttcctaaa ctcaacagtg gggttccgca acatgagcct ttccttttac aatgcctcag  540
aagcagacat tggcatctac tcctgcttgt ttcatgcttt cccaaatgga ccttgggaaa  600
agaagataaa agtagtctgg tcagatagtt ttgagatagc agcaccctcg gatagctacc  660
tgtctgcaga acctggacaa gatgtcacac tcacttgcca gcttccaagg acttggccag  720
tgcaacaagt catatgggaa aaagtccagc cccatcaggt agacatctta gcttcctgta  780
acctatctca agagacaaga tacacttcaa agtacctaag acaaacaagg agcaactgta  840
gccaggggag catgaagagc atcctcatca ttccaaatgc catggccgct gactcaggac  900
tttacagatg tcgctcagag gccattacag gaaaaaacaa gtcctttgtc ataaggctga  960
```

```
tcataactga tggtggaacc aataaacatt ttatccttcc catcgttgga gggttagttt  1020
cactgttact tgtcatccta attatcatca ttttcatttt atataacagg aagagacgga  1080
gacaggtgag aattccactt aaagagccca gggataaaca gagtaaggta gccaccaact  1140
gcagaagtcc tacttctccc atccagtcta cagatgatga aaaagaggac atttatgtaa  1200
actatccaac tttctctcga agaccaaaac caagactcta agctgctctt ttggcctgaa  1260
cacattagtg atgacttcta tggcatggaa ttttacccat gatttcctta ccactaggat  1320
ctacattgat aaaaaaaatt gattaaattt atttcatctc atatatagaa gtactttatt  1380
acctggaaac attcttaata gagattcatt agaaaaccca aatctaatgt tcatgtgttc  1440
aaggaacctt cttccattat gtaacagaac agtctagaga agattaagga ccacatggct  1500
ttcttgctct acttgaaatt aattgtgagc ataagcttgt ttctggagtc ttcttacatt  1560
gttggttcta cttacatact actggtccaa ctctcatgct gtttctctca gatgttccca  1620
tgatggttgc caaggacact tgatagaaag actactggtt aaacacaata aacaaagttc  1680
attattcact tattagcaag aaggtagcat tatcataaag gattagatga cttaagttag  1740
ctataggttc aagacctgga ctaaagtatt acttggaaat tctgagtatt gctaaaaagg  1800
aggatgaaag ggacctagaa gttgagttat tactaaaaac tttgagtgcg aagatattac  1860
tcattaacca gataacaagt gaatatgctg tagcatcaac ataattcaaa agagtaaaga  1920
aatggctagg aatgaggtag ttgtgtaatt atttcttctc ttactagttt caaataaatt  1980
catctctaat tctatagaga attcttgcct cccattcagg actggccttc tatacagtga  2040
gatggtccag taagaaataa tttttattag tgttttttct attttgagaa ttattttaat  2100
atatatttta atatataaac ttgtgagtta aatttttttt ttgcaaaatt agcacatgaa  2160
aagagattga tggttttaag tagtagaaca cagtagtgta ggaatctgag agcagagagt  2220
ttgggagggg gtgaagagaa aacaacatca ccaaatagtg atatataaga gaaaatctgt  2280
gcttcagagt ttgatcaggg ccatctctcc caactctgct ggaactgaga gaatgcacct  2340
gatgttgtct ccattttaga tagagaaaaa aaaaacccga atatttataa aactaaataa  2400
aactatagtt acctcaaaac tatggggatc actataacat agaatagaat agaatagaat  2460
agaatagaat agaatagaat agaatag                                      2487

SEQ ID NO: 174          moltype = AA  length = 333
FEATURE                 Location/Qualifiers
source                  1..333
                        mol_type = protein
                        organism = Mus musculus
SEQUENCE: 174
MAYVTWLLAI LHVHKALCEE TLWDTTVRLS ETMTLECVYP LTHNLTQVEW TKNTGTKTVS  60
IAVYNPNHNM HIESNYLHRV HFLNSTVGFR NMSLSFYNAS EADIGIYSCL FHAFPNGPWE  120
KKIKVVWSDS FEIAAPSDSY LSAEPGQDVT LTCQLPRTWP VQQVIWEKVQ PHQVDILASC  180
NLSQETRYTS KYLRQTRSNC SQGSMKSILI IPNAMAADSG LYRCRSEAIT GKNKSFVIRL  240
IITDGGTNKH FILPIVGGLV SLLLVILIII IFILYNRKRR RQVRIPLKEP RDKQSKVATN  300
CRSPTSPIQS TDDEKEDIYV NYPTFSRRPK PRL                              333

SEQ ID NO: 175          moltype = DNA  length = 1968
FEATURE                 Location/Qualifiers
source                  1..1968
                        mol_type = genomic DNA
                        organism = Homo sapiens
SEQUENCE: 175
gaaggcggaa ccacgacggg cagagagcac ggagccggga agcccctggg cgcccgtcgg  60
agggctatgg agcagcggcc gcggggctgc gcggcggtgg cggcggcgct cctcctggtg  120
ctgctggggg cccgggccca gggcggcact cgtagcccca ggtgtgactg tgccggtgac  180
ttccacaaga agattggtct gttttgttgc agaggctgcc cagcggggca ctacctgaag  240
gccccttgca cggagccctg cggcaactcc acctgccttg tgtgtcccca agacaccttc  300
ttggcctggg agaaccacca taattctgaa tgtgcccgct gccaggcctg tgatgagcag  360
gcctcccagg tggcgctgga gaactgttca gcagtggccg acacccgctg tggctgtaag  420
ccaggctggt ttgtggagtg ccaggtcagc caatgtgtca gcagttcacc cttctactgc  480
caaccatgcc tagactgcgg ggccctgcac cgccacacac ggctactctg ttcccgcaga  540
gatactgact gtgggacctg cctgcctggc ttctatgaac atggcgatgg ctgcgtgtcc  600
tgccccacga gcaccctggg gagctgtcca gagcgctgtg ccgctgtctg tggctggagg  660
cagatgttct gggtccaggt gctcctggct ggccttgtgg tcccccctcct gcttggggcc  720
accctgacct acacatacccg ccactgctgg cctcacaagc ccctggttac tgcagatgaa  780
gctgggatgg aggctctgac cccaccaccg gccacccatc tgtcaccctt ggacagcgcc  840
cacacccttc tagcacctcc tgacagcagt gagaagatct gcaccgtcca gttggtgggt  900
aacagctgga cccctggcta ccccgagacc caggaggcgc tctgcccgca ggtgacatgg  960
tcctgggacc agttgcccag cagagctctt ggccccgctg ctgcgcccac actctcgcca  1020
gagtccccag ccggctcgcc agccatgatg ctgcagccgg gcccgcagct ctacgacgtg  1080
atggacgcgg tcccagcgcg gcgctggaag gagttcgtgc gcacgctggg gctgcgcgag  1140
gcagagatcg aagccgtgga ggtggagatc ggccgcttcc gagaccagca gtacgagatg  1200
ctcaagcgct ggcgccagca gcagcccgcg ggcctcggag ccgtttacgc ggccctggag  1260
cgcatggggc tggacggctg cgtggaagac ttgcgcagcc gcctgcagcg cggcccgtga  1320
cacggcgccc acttgccacc taggcgctct ggtggccctt gcagaagccc taagtacggt  1380
tacttatgcg tgtagacatt ttatgtcact tattaagccg ctggcacggc cctgcgtagc  1440
agcaccagcc ggccccaccc ctgctcgccc ctatcgctcc agccaaggcg aagaagcacg  1500
aacgaatgtc gagagggggt gaagacattt ctcaacttct cggccggagt ttggctgaga  1560
tcgcggtatt aaatctgtga aagaaaacaa aacaaaacaa aaacggcttc ttggcgtttc  1620
tgcggggctg gggtgttaag tggactggac ttttctcgag ggattcgaag gggacgggaa  1680
tcttgtcacc ccgggatctg gcacccatgg tggagtccag tgtggcctta gctcccaagc  1740
ctgcccctcc cgagtccact ctggctcaat taccccgaga aggagagagc aagtcgcggc  1800
cacagcgagt gagtgaaccg gagcccagat gagagcgctt taatggggct gcgaggtggc  1860
ggagacaggg tcgggatggg gtgcagcagt tggagacaca gggtcagggc ccctcatcct  1920
ctattcactc caccggggca gtgaaagggt cccggcagcg agtgggtc              1968
```

```
SEQ ID NO: 176         moltype = AA  length = 417
FEATURE                Location/Qualifiers
source                 1..417
                       mol_type = protein
                       organism = Homo sapiens
SEQUENCE: 176
MEQRPRGCAA VAAALLLVLL GARAQGGTRS PRCDCAGDFH KKIGLFCCRG CPAGHYLKAP  60
CTEPCGNSTC LVCPQDTFLA WENHHNSECA RCQACDEQAS QVALENCSAV ADTRCGCKPG  120
WFVECQVSQC VSSSPFYCQP CLDCGALHRH TRLLCSRRDT DCGTCLPGFY EHGDGCVSCP  180
TSTLGSCPER CAAVCGWRQM FWVQVLLAGL VVPLLLGATL TYTYRHCWPH KPLVTADEAG  240
MEALTPPPAT HLSPLDSAHT LLAPPDSSEK ICTVQLVGNS WTPGYPETQE ALCPQVTWSW  300
DQLPSRALGP AAAPTLSPES PAGSPAMMLQ PGPQLYDVMD AVPARRWKEF VRTLGLREAE  360
IEAVEVEIGR FRDQQYEMLK RWRQQQPAGL GAVYAALERM GLDGCVEDLR SRLQRGP     417

SEQ ID NO: 177         moltype = DNA  length = 1611
FEATURE                Location/Qualifiers
source                 1..1611
                       mol_type = genomic DNA
                       organism = Mus musculus
SEQUENCE: 177
ctgcgtggag gggaaatggg ccagaggctg ctggcagggg gcctcctctg ctgtacacaa  60
gctggttttg tagacagtga gagggaagct gatcccagtc ccctaaccct gttctgccca  120
ggagcctgag aactgagctt actcgggcaa atgctagggc ttcagaaatg gaggagctgc  180
ctaggaggga gaggtcacct cctggggcag ccacaccagg gtcaactgca cgtgttctcc  240
agcctctgtt cctaccactg ctgctgctgc tgctgctgct gcttggtggc cagggccagg  300
gcggcatgtc tggcaggtgt gactgtgcca gtgagtccca gaagaggtat ggcccgtttt  360
gttgcagggg ctgcccaaag ggacactaca tgaaggcccc ctgcgcagaa ccctgtggca  420
actccacctg ccttccctgt ccctcggaca ccttcttgac cagagacaac cactttaaga  480
ctgactgtac ccgctgccaa gtctgtgatg aagaggccct tcaagtgacc cttgagaact  540
gctcggcaaa gtcggacacc cactgtggct gccagtcagg ctggtgtgtt gactgctcca  600
ccgagccatg tgggaaaagc tcacctttct cttgtgtccc atgcggggct acaacaccag  660
tccatgaggc tccaaccccc ctgttttggg tccaggtgct tctaggagtc gcgttccttt  720
ttggggctat cctgatctgt gcatattgtc gatggcagcc ttgtaaggcc gtggtcactg  780
cagacacagc tgggacggag accctggcct caccacagac tgcccatctc tcagcctcag  840
acagcgccca caccctcctg gcacctccaa gcagtactgg gaaaatctgt accactgtcc  900
agttggtagg caacaactgg acccctggct tatcccagac tcaggaggtg gtctgcggac  960
aggcctcaca accctgggat cagctgccaa acagaactct tggaactcct ctggcatctc  1020
cgctctcgcc agcgcccccct gcgggctctc cggctgctgt gctccagcct ggcccgcagc  1080
tctacgatgt gatggatgcg gtcccagcac gaaggtggaa ggagttcgtg cgcacgctgg  1140
ggctgcggga agcggaaatt gaagccgtgg aggtggaaat ctgccgcttc cgagaccagc  1200
agtatgagat gctcaagcgc tggcgtcagc agcagcctgc aggcctcggt gccatctatg  1260
cggctctgga gcgcatgggt ctggaaggct gtgccgagga cctgcgcagc cgcctgcagc  1320
gtggcccgtg atggaaggtc catcagccac tttgacaccc tagtgaccct tgaaggagcc  1380
ttaagtattg ttacttatgc gtgtagacat tttatgtcaa ttactaaccc cctgccgtgg  1440
tcctgcgtag cagggctggc tgcctcactt ttgcttatct gcagcacgga gctcctgcta  1500
agggaagcgt catggagaaa taccagaagg ggccaagtga ttggttgctc agctgttaat  1560
tagcccgagt ttggacttgg tattaaattt cgtaagaaaa gcagctgctt g          1611

SEQ ID NO: 178         moltype = AA  length = 387
FEATURE                Location/Qualifiers
source                 1..387
                       mol_type = protein
                       organism = Mus musculus
SEQUENCE: 178
MEELPRRERS PPGAATPGST ARVLQPLFLP LLLLLLLLLG GQGQGGMSGR CDCASESQKR  60
YGPFCCRGCP KGHYMKAPCA EPCGNSTCLP CPSDTFLTRD NHFKTDCTRC QVCDEEALQV  120
TLENCSAKSD THCGCQSGWC VDCSTEPCGK SSPFSCVPCG ATTPVHEAPT PLFWVQVLLG  180
VAFLFGAILI CAYCRWQPCK AVVTADTAGT ETLASPQTAH LSASDSAHTL LAPPSSTGKI  240
CTTVQLVGNN WTPGLSQTQE VVCGQASQPW DQLPNRTLGT PLASPLSPAP PAGSPAAVLQ  300
PGPQLYDVMD AVPARRWKEF VRTLGLREAE IEAVEVEICR FRDQQYEMLK RWRQQQPAGL  360
GAIYAALERM GLEGCAEDLR SRLQRGP                                     387

SEQ ID NO: 179         moltype = DNA  length = 1140
FEATURE                Location/Qualifiers
source                 1..1140
                       mol_type = genomic DNA
                       organism = Homo sapiens
SEQUENCE: 179
ggacttgggc ggcccctccg caggcggacc gggggcaaag gaggtggcat gtcggtcagg  60
cacagcaggg tcctgtgtcc gcgctgagcc gcgctctccc tgctccagca aggaccatga  120
gggcgctgga ggggccaggc ctgtcgctgc tgtgcctggt gttggcgctg cctgccctgc  180
tgccggtgcc ggctgtacgc ggagtggcag aaacacccac ctacccctgg cgggacgcag  240
agacagggga gcggctggtg tgcgcccagt gccccccagg cacctttgtg cagcggccgt  300
gccgccgaga cagccccacg acgtgtggcc cgtgtccacc gcgccactac acgcagttct  360
ggaactacct agagcgctgc cgctactgca acgtcctctg cggggagcgt gaggaggagg  420
cacgggcttg ccacgccacc cacaaccgtg cctgccgctg ccgcaccggc ttcttcgcgc  480
acgctggttt ctgcttggag cacgcatcgt gtccacctgg tgccggcgtg attgccccgg  540
gcacccccag ccagaacacg cagtgccagc cgtgcccccc aggcaccttc tcagccagca  600
```

```
gctccagctc agagcagtgc cagccccacc gcaactgcac ggccctgggc ctggccctca  660
atgtgccagg ctcttcctcc catgacaccc tgtgcaccag ctgcactggc ttccccctca  720
gcaccagggt accaggagct gaggagtgtg agcgtgccgt catcgacttt gtggctttcc  780
aggacatctc catcaagagg ctgcagcggc tgctgcaggc cctcgaggcc ccggagggct  840
ggggtccgac accaagggcg ggccgcgcgg ccttgcagct gaagctgcgt cggcggctca  900
cggagctcct gggggcgcag gacggggcgc tgctggtgcg gctgctgcag gcgctgcgcg  960
tggccaggat gcccgggctg gagcggagcg tccgtgagcg cttcctccct gtgcactgat  1020
cctggccccc tcttatttat tctacatcct tggcacccca cttgcactga aagaggcttt  1080
tttttaaata gaagaaatga ggtttcttaa agcttatttt tataaagctt tttcataaaa  1140

SEQ ID NO: 180         moltype = AA  length = 300
FEATURE                Location/Qualifiers
source                 1..300
                       mol_type = protein
                       organism = Homo sapiens
SEQUENCE: 180
MRALEGPGLS LLCLVLALPA LLPVPAVRGV AETPTYPWRD AETGERLVCA QCPPGTFVQR  60
PCRRDSPTTC GPCPPRHYTQ FWNYLERCRY CNVLCGEREE EARACHATHN RACRCRTGFF  120
AHAGFCLEHA SCPPGAGVIA PGTPSQNTQC QPCPPGTFSA SSSSSEQCQP HRNCTALGLA  180
LNVPGSSSHD TLCTSCTGFP LSTRVPGAEE CERAVIDFVA FQDISIKRLQ RLLQALEAPE  240
GWGPTPRAGR AALQLKLRRR LTELLGAQDG ALLVRLLQAL RVARMPGLER SVRERFLPVH  300

SEQ ID NO: 181         moltype = DNA  length = 1805
FEATURE                Location/Qualifiers
source                 1..1805
                       mol_type = genomic DNA
                       organism = Homo sapiens
SEQUENCE: 181
agcagtcagc aacagggtcc cgtccttgac acctcagcct ctacaggact gagaagaagt  60
aaaaccgttt gctggggctg gcctgactca ccagctgcca tgcagcagcc cttcaattac  120
ccatatcccc agatctactg ggtggacagc agtgccagct ctccctgggc ccctccaggc  180
acagttcttc cctgtccaac ctctgtgccc agaaggcctg gtcaaaggag gccaccacca  240
ccaccgccac cgccaccact accacctccg ccgccgccgc caccactgcc tccactaccg  300
ctgccacccc tgaagaagag agggaaccac agcacaggcc tgtgtctcct tgtgatgttt  360
ttcatggttc tggttgcctt ggtaggattg ggcctgggga tgtttcagct cttccaccta  420
cagaaggagc tggcagaact ccgagagtct accagccaga tgcacacagc atcatctttg  480
gagaagcaaa taggccaccc cagtccaccc cctgaaaaaa aggagctgag gaaagtggcc  540
catttaacag gcaagtccaa ctcaaggtcc atgcctctgg aatgggaaga cacctatgga  600
attgtcctgc tttctggagt gaagtataag aagggtggcc ttgtgatcaa tgaaactggg  660
ctgtactttg tatattccaa agtatacttc cggggtcaat cttgcaacaa cctgcccctg  720
agccacaagg tctacatgag gaactctaag tatccccagg atctggtgat gatggagggg  780
aagatgatga gctactgcac tactgggcag atgtgggccc gcagcagcta cctgggggca  840
gtgttcaatc ttaccagtgc tgatcattta tatgtcaacg tatctgagct ctctctggtc  900
aattttgagg aatctcagac gtttttcggc ttatataagc tctaagagaa gcactttggg  960
attctttcca ttatgattct ttgttacagg caccgagaat gttgtattca gtgagggtct  1020
tcttacatgc atttgaggtc aagtaagaag acatgaacca agtggacctt gagaccacag  1080
ggttcaaaat gtctgtagct cctcaactca cctaatgttt atgagccaga caaatggagg  1140
aatatgacgg aagaacatag aactctgggc tgccatgtga agagggagaa gcatgaaaaa  1200
gcagctacca ggtgttctac actcatctta gtgcctgaga gtatttaggc agattgaaaa  1260
ggacaccttt taactcacct ctcaaggtgg gccttgctac ctcaaggggg actgtctttc  1320
agatacatgg ttgtgacctg aggatttaag ggatggaaaa ggaagactag aggcttgcat  1380
aataagctaa agaggctgaa agaggccaat gccccactgg cagcatcttc acttctaaat  1440
gcatatcctg agccatcggt gaaactaaca gataagcaag agagatgttt tggggactca  1500
tttcattcct aacacagcat gtgtatttcc agtgcaattg taggggtgtg tgtgtgtgtg  1560
tgtgtgtgtg tgtgtgtatg actaaagaga gaatgtagat attgtgaagt acatattagg  1620
aaaatatggg ttgcatttgg tcaagatttt gaatgcttcc tgacaatcaa ctctaatagt  1680
gcttaaaaat cattgattgt cagctactaa tgatgttttc ctataatata ataaatattt  1740
atgtagatgt gcatttttgt gaaatgaaaa catgtaataa aaagtatatg ttaggataca  1800
aataa                                                              1805

SEQ ID NO: 182         moltype = AA  length = 281
FEATURE                Location/Qualifiers
source                 1..281
                       mol_type = protein
                       organism = Homo sapiens
SEQUENCE: 182
MQQPFNYPYP QIYWVDSSAS SPWAPPGTVL PCPTSVPRRP GQRRPPPPPP PPPLPPPPPP  60
PPLPPLPLPP LKKRGNHSTG LCLLVMFFMV LVALVGLGLG MFQLFHLQKE LAELRESTSQ  120
MHTASSLEKQ IGHPSPPPEK KELRKVAHLT GKSNSRSMPL EWEDTYGIVL LSGVKYKKGG  180
LVINETGLYF VYSKVYFRGQ SCNNLPLSHK VYMRNSKYPQ DLVMMEGKMM SYCTTGQMWA  240
RSSYLGAVFN LTSADHLYVN VSELSLVNFE ESQTFFGLYK L                      281

SEQ ID NO: 183         moltype = DNA  length = 1935
FEATURE                Location/Qualifiers
source                 1..1935
                       mol_type = genomic DNA
                       organism = Mus musculus
SEQUENCE: 183
tgaggcttct cagcttcaga tgcaagtgag tgggtgtctc acagagaagc aaagagaaga  60
```

-continued

```
gaacaggaga aaggtgtttc ccttgactgc ggaaacttta taaagaaaac ttagcttctc  120
tggagcagtc agcgtcagag ttctgtcctt gacacctgag tctcctccac aaggctgtga  180
gaaggaaacc ctttcctggg gctgggtgcc atgcagcagc ccatgaatta cccatgtccc  240
cagatcttct gggtagacag cagtgccact tcatcttggg ctcctccagg gtcagttttt  300
ccctgtccat cttgtgggcc tagagggccg gaccaaagga gaccgccacc tccaccacca  360
cctgtgtcac cactaccacc gccatcacaa ccactcccac tgccgccact gacccctcta  420
aagaagaagg accacaacac aaatctgtgg ctaccggtgg tatttttcat ggttctggtg  480
gctctggttg gaatgggatt aggaatgtat cagctcttcc acctgcagaa ggaactggca  540
gaactccgtg agttcaccaa ccaaagcctt aaagtatcat cttttgaaaa gcaaatagcc  600
aaccccagta caccctctga aaaaaaagag ccgaggagtg tggcccattt aacagggaac  660
ccccactcaa ggtccatccc tctggaatgg gaagacacat atggaaccgc tctgatctct  720
ggagtgaagt ataagaaagg tggccttgtg atcaacgaaa ctgggttgta cttcgtgtat  780
tccaaagtat acttccgggg tcagtcttgc aacaaccagc cctaaacca caaggtctat  840
atgaggaact ctaagtatcc tgaggatctg gtgctaatgg aggagaagag gttgaactac  900
tgcactactg gacagatatg ggcccacagc agctacctgg gggcagtatt caatcttacc  960
agtgctgacc atttatatgt caacatatct caactctctc tgatcaattt tgaggaatct  1020
aagacctttt tcggcttgta taagctttaa aagaaaaagc attttaaaat gatctactat  1080
tctttatcat gggcaccagg aatattgtct tgaatgagag tcttcttaag acctattgag  1140
attaattaag actacatgag ccacaaagac ctcatgaccg caaggtccaa caggtcagct  1200
atccttcatt ttctcgaggt ccatggagtg gtccttaatg cctgcatcat gagccagatg  1260
gaaggaggtc tgtgactgag ggacataaag ctttgggctg ctgtgtgaca atgcagaggc  1320
acagagaaag aactgtctga tgttaaatgg ccaagagaat tttaaccatt gaagaagaca  1380
cctttacact cacttccagg gtgggtctac ttactacctc acagaggccg tttttgagac  1440
atagttgtgg tatgaatata caagggtgag aaaggaggct catttgactg ataagctaga  1500
gactgaaaaa aagacagtgt ctcattggca ccatctttac tgttacctaa tgtttctga  1560
gccgaccttt gatcctaacg gagaagtaag agggatgttt gaggcacaaa tcattctcta  1620
catagcatgc atacctccag tgcaatgatg tctgtgtgtt tgtatgtatg agagcaaaca  1680
gattctaagg agtcatataa ataaaatatg tacattatgg agtacatatt agaaacctgt  1740
tacatttgat gctagatatc tgaatgtttc ttggcaataa actctaatag tcttcaaaat  1800
cttttattat cagctactga tgctgttttt ctttaataca actagtattt atgctctgaa  1860
catcctaatg aggaaaagac aaataaaatt atgttataga atacagaaat gccttaagga  1920
catagacttt ggaaa                                                  1935

SEQ ID NO: 184         moltype = AA  length = 279
FEATURE                Location/Qualifiers
source                 1..279
                       mol_type = protein
                       organism = Mus musculus
SEQUENCE: 184
MQQPMNYPCP QIFWVDSSAT SSWAPPGSVF PCPSCGPRGP DQRRPPPPPP PVSPLPPPSQ  60
PLPLPPLTPL KKKDHNTNLW LPVVFFMVLV ALVGMGLGMY QLFHLQKELA ELREFTNQSL  120
KVSSFEKQIA NPSTPSEKKE PRSVAHLTGN PHSRSIPLEW EDTYGTALIS GVKYKKGGLV  180
INETGLYFVY SKVYFRGQSC NNQPLNHKVY MRNSKYPEDL VLMEEKRLNY CTTGQIWAHS  240
SYLGAVFNLT SADHLYVNIS QLSLINFEES KTFFGLYKL                        279

SEQ ID NO: 185         moltype = DNA  length = 1713
FEATURE                Location/Qualifiers
source                 1..1713
                       mol_type = genomic DNA
                       organism = Homo sapiens
SEQUENCE: 185
gaccaggagt cagtttggcg gttatgtgtg gggaagaagc tgggaagtca ggggctgttt  60
ctgtggacag ctttccctgt cctttggaag gcacagagct ctcagctgca gggaactaac  120
agagctctga agccgttata tgtggtcttc tctcatttcc agcagagcag gctcatatga  180
atcaaccaac tgggtgaaaa gataagttgc aatctgagat ttaagacttg atcagatacc  240
atctggtgga gggtaccaac cagcctgtct gctcattttc cttcaggctg atcccataat  300
gcatcctcaa gtggtcatct taagcctcat cctacatctg gcagattctg tagctggttc  360
tgtaaaggtt ggtggagagg caggtccatc tgtcacacta ccctgccact acagtggagc  420
tgtcacatcc atgtgctgga atagaggctc atgttctcta ttcacatgcc aaaatggcat  480
tgtctggacc aatggaaccc acgtcaccta tcggaaggac acacgctata agctattggg  540
ggacctttca agaagggatg tctctttgac catagaaaat acagctgtgt ctgacagtgg  600
cgtatattgt tgccgtgttg agcaccgtgg gtggttcaat gacatgaaaa tcaccgtatc  660
attggagatt gtgccaccca aggtcacgac tactccaatt gtcacaactg ttccaaccgt  720
cacgactgtt cgaacgagca ccactgttcc aacgacaacg actgttccaa tgacgactgt  780
tccaacgaca actgttccaa caacaatgag cattccaacg acaacgactg ttctgacgac  840
aatgactgtt tcaacgacaa cgagcgttcc aacgacaacg agcattccaa caacaacaag  900
tgttccagtg acaacaactg tctctacctt tgttcctcca atgcctttgc ccaggcagaa  960
ccatgaacca gtagccactt caccatcttc acctcagcca gcagaaaccc accctacgac  1020
actgcaggga gcaataagga gagaacccac cagctcacca ttgtactctt acacaacaga  1080
tgggaatgac accgtgacag agtcttcaga tggcctttgg aataacaatc aaactcaact  1140
gttcctagaa catagtctac tgacggccaa taccactaaa ggaatctatg ctggagtctg  1200
tatttctgtc ttggtgcttc ttgctctttt gggtgtcatc attgccaaaa agtatttctt  1260
caaaaaggag gttcaacaac taagtgtttc atttagcagc cttcaaatta aagctttgca  1320
aaatgcagtt gaaaaggaag tccaagcaga agacaatatc tacattgaga atagtcttta  1380
tgccacggac taagacccag tggtgctctt tgagagttta cgcccatgag tgcagaagac  1440
tgaacagaca tcagcacatc agacgtcttt tagaccccaa gacaattttt ctgtttcagt  1500
ttcatctggc attccaacat gtcagtgata ctgggtagag taactctctc actccaaact  1560
gtgtatagtc aacctcatca ttaatgtagt cctaattttt tatgctaaaa ctggctcaat  1620
ccttctgatc attgcagttt tctctcaaat atgaacactt tataattgta tgttcttttt  1680
```

```
agaccccata aatcctgtat acatcaaaga gaa                             1713

SEQ ID NO: 186          moltype = AA  length = 364
FEATURE                 Location/Qualifiers
source                  1..364
                        mol_type = protein
                        organism = Homo sapiens
SEQUENCE: 186
MHPQVVILSL ILHLADSVAG SVKVGGEAGP SVTLPCHYSG AVTSMCWNRG SCSLFTCQNG  60
IVWTNGTHVT YRKDTRYKLL GDLSRRDVSL TIENTAVSDS GVYCCRVEHR GWFNDMKITV  120
SLEIVPPKVT TTPIVTTVPT VTTVRTSTTV PTTTTVPMTT VPTTTVPTTM SIPTTTTVLT  180
TMTVSTTTSV PTTTSIPTTT SVPVTTTVST FVPPMPLPRQ NHEPVATSPS SPQPAETHPT  240
TLQGAIRREP TSSPLYSYTT DGNDTVTESS DGLWNNNQTQ LFLEHSLLTA NTTKGIYAGV  300
CISVLVLLAL LGVIIAKKYF FKKEVQQLSV SFSSLQIKAL QNAVEKEVQA EDNIYIENSL  360
YATD                                                             364

SEQ ID NO: 187          moltype = DNA  length = 1909
FEATURE                 Location/Qualifiers
source                  1..1909
                        mol_type = genomic DNA
                        organism = Mus musculus
SEQUENCE: 187
gtcagtacca tgaatcagat tcaagtcttc atttcaggcc tcatactgct tctcccaggc  60
gctgtggatt cttatgtgga agtaaagggg gtggtgggtc accctgtcac acttccatgt  120
acttactcaa catatcgtgg aatcacaacg acatgttggg gccgagggca atgcccatct  180
tctgcttgtc aaaatacact tatttggacc aatggacatc gtgtcaccta tcagaagagc  240
agtcggtaca acttaaaggg gcatatttca gaaggagatg tgtccttgac gatagagaac  300
tctgttgaga gtgacagtgg tctgtattgt tgtcgagtgg agattcctgg atggtttaat  360
gatcagaaag tgaccttttc attgcaagtt aaaccagaga ttcccacacg tcctccaaga  420
agacccacaa ctacaaggcc cacagctaca ggaagaccca cgactatttc aacaagatcc  480
acacatgtac caacatcaac cagagtctct acctccactc ctccaacatc tacacacaca  540
tggactcaca aaccagaacc cactacattt tgtccccatg agacaacagc tgaggtgaca  600
ggaatcccat cccatactcc tacagactgg aatggcactg tgacatcctc aggagatacc  660
tggagtaatc acactgaagc aatccctcca gggaagccgc agaaaaaccc tactaagggc  720
ttctatgttg gcatctgcat cgcagccctg ctgctactgc tccttgtgag caccgtggct  780
atcaccaggt acatacttat gaaaaggaag tcagcatctc taagcgtggt tgccttccgt  840
gtctctaaga ttgaagcttt gcagaacgca gcggttgtgc attcccgagc tgaagacaac  900
atctacattg ttgaagatag accttgaggg gcagaatgag taccagtggc cctctgaggg  960
accttctgcc tgagatttat agagactgtc actgatgtca tagagtcaca cccattacag  1020
cgccaaggcg attttctgtg ttggttcttc cagctgcagc agagagggta accctctact  1080
gtgtatactc aaaactcaga ttaacatcat cctaattttg gtatctgcac cacctccgtg  1140
tctctgctca ctacagagat tctctcaaac atgaacgttt tagaagtttg tgtttccctt  1200
agtcaatgta atcattggta atactattct attcttggtt actaaaacca ttactaagag  1260
agggatagga attaaaagtt ggtgtgaggg gcctcctgaa tttagaagca cttgattctg  1320
ttttatctac tttcttgaaa tgttacttct acccttccca atgggtaaaa tcatgggagc  1380
atggtgccct catagataaa tagaagagag tctattgctg ccaatataga tggttatgct  1440
ttctcatagc tctgaaaata tgacacattt attatgaggt tgatcttagg ataaggatag  1500
gtgttttatg tcaggagagg ttatcatggt gaatatggac cagcagacag cagtggagga  1560
aaataatgaa ccaagggatt gagttcatta gtgctaattc tactccactc ctgtctttat  1620
gctcctaaac ttactgactg agctctgaat taggtgctag gaggagacaa tgcagacatg  1680
aaaggggaag gagcgccttc aggacacagg ctctctgctg agagaagtcc tatttgcagg  1740
tgtgatagag gttgggacaa tctctgagtt gtaaatttct aattgtcttc aggccatatt  1800
tatagttaaa ttcatttccg aaagacatag catcttcccc aatgggtcag tttgtcaaaa  1860
tcaataaaat attttgtttt gctaagaatt aaaaaaaaaa aaaaaaaaa            1909

SEQ ID NO: 188          moltype = AA  length = 305
FEATURE                 Location/Qualifiers
source                  1..305
                        mol_type = protein
                        organism = Mus musculus
SEQUENCE: 188
MNQIQVFISG LILLLPGAVD SYVEVKGVVG HPVTLPCTYS TYRGITTTCW GRGQCPSSAC  60
QNTLIWTNGH RVTYQKSSRY NLKGHISEGD VSLTIENSVE SDSGLYCCRV EIPGWFNDQK  120
VTFSLQVKPE IPTRPPRRPT TTRPTATGRP TTISTRSTHV PTSTRVSTST PPTSTHTWTH  180
KPEPTTFCPH ETTAEVTGIP SHTPTDWNGT VTSSGDTWSN HTEAIPPGKP QKNPTKGFYV  240
GICIAALLLL LLVSTVAITR YILMKRKSAS LSVVAFRVSK IEALQNAAVV HSRAEDNIYI  300
VEDRP                                                            305

SEQ ID NO: 189          moltype = DNA  length = 2097
FEATURE                 Location/Qualifiers
source                  1..2097
                        mol_type = genomic DNA
                        organism = Homo sapiens
SEQUENCE: 189
gctcacctcc gcctgagcag tggagaaggc ggcactctgg tggggctgct ccaggcatgc  60
agatcccaca ggcgccctgg ccagtcgtct gggcggtgct acaactgggc tggcggccag  120
gatggttctt agactcccca gacaggccct ggaacccccc caccttctcc ccagccctgc  180
tcgtggtgac cgaaggggac aacgccacct tcacctgcag cttctccaac acatcggaga  240
gcttcgtgct aaactggtac cgcatgagcc ccagcaacca gacggacaag ctggccgcct  300
```

```
tccccgagga ccgcagccag cccggccagg actgccgctt ccgtgtcaca caactgccca  360
acgggcgtga cttccacatg agcgtggtca gggcccggcg caatgacagc ggcacctacc  420
tctgtggggc catctccctg gcccccaagg cgcagatcaa agagagcctg cgggcagagc  480
tcagggtgac agagagaagg gcagaagtgc ccacagccca ccccagcccc tcacccaggc  540
cagccggcca gttccaaacc ctggtggttg gtgtcgtggg cggcctgctg ggcagcctgg  600
tgctgctagt ctgggtcctg gccgtcatct gctcccgggc cgcacgaggg acaataggag  660
ccaggcgcac cggccagccc ctgaaggagg acccctcagc cgtgcctgtg ttctctgtgg  720
actatgggga gctggatttc cagtggcgag agaagacccc ggagcccccc gtgccctgtg  780
tccctgagca gacggagtat gccaccattg tctttcctag cggaatgggc acctcatccc  840
ccgcccgcag gggctcagct gacggccctc ggagtgccca gccactgagg cctgaggatg  900
gacactgctc ttggcccctc tgaccggctt ccttggccac cagtgttctg cagaccctcc  960
accatgagcc cgggtcagcg catttcctca ggagaagcag gcagggtgca ggccattgca  1020
ggccgtccag ggctgagct gcctgggggc gaccggggct ccagcctgca cctgcaccag  1080
gcacagcccc accacaggac tcatgtctca atgcccacag tgagcccagg cagcaggtgt  1140
caccgtcccc tacagggagg gccagatgca gtcactgctt caggtcctgc cagcacagag  1200
ctgcctgcgt ccagctccct gaatctctgc tgctgctgct gctgctgctg ctgctgcctg  1260
cggcccgggg ctgaaggcgc cgtggccctg cctgacgccc cggagcctcc tgcctgaact  1320
tgggggctgg ttggagatgg ccttggagca gccaaggtgc ccctggcagt ggcatcccga  1380
aacgccctgg acgcagggcc caagactggg cacaggagtg ggaggtacat ggggctgggg  1440
actccccagg agttatctgc tccctgcagg cctagagaag tttcagggaa ggtcagaaga  1500
gctcctggct gtggtgggca gggcaggaaa cccctccacc tttacacatg cccaggcagc  1560
acctcaggcc ctttgtgggg cagggaagct gaggcagtaa gcgggcaggc agagctggag  1620
gcctttcagg cccagccagc actctggcct cctgccgccg cattccaccc cagcccctca  1680
caccactcgg gagagggaca tcctacggtc ccaaggtcag gagggcaggg ctggggttga  1740
ctcaggcccc tcccagctgt ggccacctgg gtgttgggag ggcagaagtg caggcaccta  1800
gggcccccca tgtgcccacc ctgggagctc tccttggaac ccattcctga aattatttaa  1860
aggggttggc cgggctccca ccagggcctg ggtgggaagg tacaggcgtt cccccggggc  1920
ctagtacccc cgccgtggcc tatccactcc tcacatccac acactgcacc cccactcctg  1980
gggcagggcc accagcatcc aggcggccag caggcacctg agtggctggg acaagggatc  2040
ccccttccct gtggttctat tatattataa ttataattaa atatgagagc atgctaa     2097

SEQ ID NO: 190          moltype = AA  length = 288
FEATURE                 Location/Qualifiers
source                  1..288
                        mol_type = protein
                        organism = Homo sapiens
SEQUENCE: 190
MQIPQAPWPV VWAVLQLGWR PGWFLDSPDR PWNPPTFSPA LLVVTEGDNA TFTCSFSNTS  60
ESFVLNWYRM SPSNQTDKLA AFPEDRSQPG QDCRFRVTQL PNGRDFHMSV VRARRNDSGT  120
YLCGAISLAP KAQIKESLRA ELRVTERRAE VPTAHPSPSP RPAGQFQTLV VGVVGGLLGS  180
LVLLVWVLAV ICSRAARGTI GARRTGQPLK EDPSAVPVFS VDYGELDFQW REKTPEPPVP  240
CVPEQTEYAT IVFPSGMGTS SPARRGSADG PRSAQPLRPE DGHCSWPL                288

SEQ ID NO: 191          moltype = DNA  length = 1933
FEATURE                 Location/Qualifiers
source                  1..1933
                        mol_type = genomic DNA
                        organism = Mus musculus
SEQUENCE: 191
tgagcagcgg ggaggaggaa gaggagactg ctactgaagg cgacactgcc aggggctctg  60
ggcatgtggg tccggcaggt accctggtca ttcacttggg ctgtgctgca gttgagctgg  120
caatcagggt ggcttctaga ggtccccaat gggccctgga ggtccctcac cttctaccca  180
gcctggctca cagtgtcaga gggagcaaat gccaccttca cctgcagctt gtccaactgg  240
tcggaggatc ttatgctgaa ctggaaccgc ctgagtccca gcaaccagac tgaaaaacag  300
gccgccttct gtaatggttt gagccaaccc gtccaggatg cccgcttcca gatcatacag  360
ctgcccaaca ggcatgactt ccacatgaac atccttgaca cacggcgcaa tgacagtggc  420
atctacctct gtggggccat ctccctgcac cccaaggcaa aaatcgagga gagccctgga  480
gcagagctcg tggtaacaga gagaatcctg gagacctcaa caagatatcc cagcccctcg  540
cccaaaccag aaggccggtt tcaaggcatg gtcattggta tcatgagtgc cctagtgggt  600
atccctgtat tgctgctgct ggcctgggcc ctagctgtct tctgctcaac aagtatgtca  660
gaggccagag gagctggaag caaggacgac actctgaagg aggagccttc agcagcacct  720
gtccctagtg tggcctatga ggagctggac ttccagggac gagagaagac accagagctc  780
cctaccgcct gtgtgcacac agaatatgcc accattgtct tcactgaagg gctgggtgcc  840
tcggccatgg gacgtagggg ctcagctgat ggcctgcagg gtcctcggcc tccaagacat  900
gaggatggac attgttcttg gcctctttga ccagattctt cagccattag catgctgcag  960
accctccaca gagagcaccg gtccgtccct cagtcaagag gagcatgcag gctacagttc  1020
agccaaggct cccagggtct gagctagctg gagtgacagc ccagcgcctg caccaattcc  1080
agcacatgca ctgttgagtg agagctcact tcaggtttac cacaagctgg gagcagcagg  1140
cttcccggtt tcctattgtc acaaggtgca gagctggggc ctaagcctat gtctcctgaa  1200
tcctactgtt gggcacttct agggacttga gacactatag ccaatggcct ctgtgggttc  1260
tgtgcctgga aatggagaga tctgagtaca gcctgctttg aatggccctg tgaggcaacc  1320
ccaaagcaag gggtccagg tatactatgg gcccagcacc taaagccacc cttgggagat  1380
gatactcagg tgggaaattc gtagactggg ggactgaacc aatcccaaga tctggaaaag  1440
ttttgatgaa gacttgaaaa gctcctagct tcgggggtct gggaagcatg agcacttacc  1500
aggcaaaagc tccgtgagcg tatctgctgt ccttctgcat gcccaggtac ctcagttttt  1560
ttcaacagca aggaaactag ggcaataaag ggaaccagca gagctagagc cacccacaca  1620
tccagggggg cacttgactc tccctactcc tcctaggaac caaaaggaca aagtccatgt  1680
tgacagcagg gaaggaaagg gggatataac cttgacgcaa accaacactg ggtgttaga   1740
atctcctcat tcactctgtc ctggagttgg gttctggctc tccttcacac ctaggactct  1800
```

```
gaaatgagca agcacttcag acagtcaggg tagcaagagt ctagctgtct ggtgggcacc  1860
caaaatgacc agggcttaag tccctttcct ttggtttaag cccgttataa ttaaatggta  1920
ccaaaagctt taa                                                     1933

SEQ ID NO: 192         moltype = DNA  length = 696
FEATURE                Location/Qualifiers
misc_feature           1..696
                       note = Description of Artificial Sequence: Synthetic
                        polynucleotide
source                 1..696
                       mol_type = other DNA
                       organism = synthetic construct
SEQUENCE: 192
atggtgagca agggcgaggc agtgatcaag gagttcatgc ggttcaaggt gcacatggag  60
ggctccatga acggccacga gttcgagatc gagggcgagg gcgagggccg cccctacgag  120
ggcacccaga ccgccaagct gaaggtgacc aagggtggcc ccctgccctt ctcctgggac  180
atcctgtccc ctcagttcat gtacggctcc agggccttca ccaagcaccc cgccgacatc  240
cccgactact ataagcagtc cttccccgag ggcttcaagt gggagcgcgt gatgaacttc  300
gaggacggcg gcgccgtgac cgtgacccag gacacctccc tggaggacgg caccctgatc  360
tacaaggtga agctccgcgg caccaacttc cctcctgacg gccccgtaat gcagaagaag  420
acaatgggct gggaagcgtc caccgagcgg ttgtaccccg aggacggcgt gctgaagggc  480
gacattaaga tggccctgcg cctgaaggac ggcggccgct acctggcgga cttcaagacc  540
acctacaagg ccaagaagcc cgtgcagatg cccggcgcct acaacgtcga ccgcaagttg  600
gacatcacct cccacaacga ggactacacc gtggtggaac agtacgaacg ctccgagggc  660
cgccactcca ccggcggcat ggacgagctg tacaag                            696

SEQ ID NO: 193         moltype = AA  length = 232
FEATURE                Location/Qualifiers
REGION                 1..232
                       note = Description of Artificial Sequence: Synthetic
                        polypeptide
source                 1..232
                       mol_type = protein
                       organism = synthetic construct
SEQUENCE: 193
MVSKGEAVIK EFMRFKVHME GSMNGHEFEI EGEGEGRPYE GTQTAKLKVT KGGPLPFSWD  60
ILSPQFMYGS RAFTKHPADI PDYYKQSFPE GFKWERVMNF EDGGAVTVTQ DTSLEDGTLI  120
YKVKLRGTNF PPDGPVMQKK TMGWEASTER LYPEDGVLKG DIKMALRLKD GGRYLADFKT  180
TYKAKKPVQM PGAYNVDRKL DITSHNEDYT VVEQYERSEG RHSTGGMDEL YK          232

SEQ ID NO: 194         moltype = DNA  length = 3861
FEATURE                Location/Qualifiers
misc_feature           1..3861
                       note = Description of Artificial Sequence: Synthetic
                        polynucleotide
source                 1..3861
                       mol_type = other DNA
                       organism = synthetic construct
SEQUENCE: 194
ggcctaactg gcctcaatat tggccattag ccatattatt cattggttat atagcataaa  60
tcaatattgg ctattggcca ttgcatacgt tgtatctata tcataatatg tacatttata  120
ttggctcatg tccaatatga ccgccatgtt ggcattgatt attgactagt tattaatagt  180
aatcaattac ggggtcatta gttcatagcc catatatgga gttccgcgtt acataactta  240
cggtaaatgg cccgcctggc tgaccgccca acgacccccg cccattgacg tcaataatga  300
cgtatgttcc catagtaacg ccaataggga ctttccattg acgtcaatgg gtggagtatt  360
tacggtaaac tgcccacttg gcagtacatc aagtgtatca tatgccaagt ccgcccccta  420
ttgacgtcaa tgacggtaaa tggcccgcct ggcattatgc ccagtacatg accttacggg  480
actttcctac ttggcagtac atctacgtat tagtcatcgc tattaccatg gtgatgcggt  540
tttggcagta caccaatggg cgtggatagc ggtttgactc acggggattt ccaagtctcc  600
accccattga cgtcaatggg agtttgtttt ggcaccaaaa tcaacgggac tttccaaaat  660
gtcgtaataa ccccgccccg ttgacgcaaa tgggcggtag gcgtgtacgg tgggaggtct  720
atataagcag agctcgttta gtgaaccgtc agatcactag aagctttatt gcggtagttt  780
atcacagtta aattgctaac gcagtcagtg ggcctcggcg gccaagcttg gcaatccggt  840
actgttggta aagccaccat ggtcttcaca ctcgaagatt tcgttgggga ctggcgacag  900
acagccggct acaacctgga ccaagtcctt gaacagggag gtgtgtccag tttgtttcag  960
aatctcgggg tgtccgtaac tccgatccaa aggattgtcc tgagcggtga aaatgggctg  1020
aagatcgaca tccatgtcat catcccgtat gaaggtctga gcggcgacca aatgggccag  1080
atcgaaaaaa tttttaaggt ggtgtaccct gtggatgatc atcactttaa ggtgatcctg  1140
cactatggca cactggtaat cgacggggtt acgccgaaca tgatcgacta tttcggacgg  1200
ccgtatgaag gcatcgccgt gttcgacggc aaaaagatca ctgtaacagg gaccctgtgg  1260
aacggcaaca aaattatcga cgagcgcctg atcaaccccg acggctccct gctgttccga  1320
gtaaccatca acggagtgac cggctggcgg ctgtgcgaac gcattctggc gtaattctag  1380
agtcggggcg gccggccgct tcgagcagac atgataagat acattgatga gtttggacaa  1440
accacaacta gaatgcagtg aaaaaaatgc tttatttgtg aaatttgtga tgctattgct  1500
ttatttgtaa ccattataag ctgcaataaa caagttaaca acaacaattg cattcatttt  1560
atgtttcagg ttcaggggga ggtgtgggag gtttttaaa gcaagtaaaa cctctacaaa   1620
tgtggtaaaa tcgataagga tccgtcgacc gatgcccttg agagccttca acccagtcag  1680
ctccttccgg tgggcgcggg gcatgactat cgtcgccgca cttatgactg tcttctttat  1740
catgcaactc gtaggacagg tgccggcagc gctcttccgc ttcctcgctc actgactcgc  1800
```

```
tgcgctcggt cgttcggctg cggcgagcgg tatcagctca ctcaaaggcg gtaatacggt  1860
tatccacaga atcaggggat aacgcaggaa agaacatgtg agcaaaaggc cagcaaaagg  1920
ccaggaaccg taaaaaggcc gcgttgctgg cgtttttcca taggctccgc ccccctgacg  1980
agcatcacaa aaatcgacgc tcaagtcaga ggtggcgaaa cccgacagga ctataaagat  2040
accaggcgtt tccccctgga agctccctcg tgcgctctcc tgttccgacc ctgccgctta  2100
ccggatacct gtccgccttt ctcccttcgg gaagcgtggc gctttctcat agctcacgct  2160
gtaggtatct cagttcggtg taggtcgttc gctccaagct gggctgtgtg cacgaacccc  2220
ccgttcagcc cgaccgctgc gccttatccg gtaactatcg tcttgagtcc aacccggtaa  2280
gacacgactt atcgccactg gcagcagcca ctggtaacag gattagcaga gcgaggtatg  2340
taggcggtgc tacagagttc ttgaagtggt ggcctaacta cggctacact agaagaacag  2400
tatttggtat ctgcgctctg ctgaagccag ttaccttcgg aaaaagagtt ggtagctctt  2460
gatccggcaa acaaaccacc gctggtagcg gtggtttttt tgtttgcaag cagcagatta  2520
cgcgcagaaa aaaaggatct caagaagatc ctttgatctt ttctacgggg tctgacgctc  2580
agtggaacga aaactcacgt taagggattt tggtcatgag attatcaaaa aggatcttca  2640
cctagatcct tttaaattaa aaatgaagtt ttaaatcaat ctaaagtata tatgagtaaa  2700
cttggtctga cagcggccgc aaatgctaaa ccactgcagt ggttaccagt gcttgatcag  2760
tgaggcaccg atctcagcga tctgcctatt tcgttcgtcc atagtggcct gactccccgt  2820
cgtgtagatc actacgattc gtgagggctt accatcaggc cccagcgcag caatgatgcc  2880
gcgagagccg cgttcaccgg cccccgattt gtcagcaatg aaccagccag cagggagggc  2940
cgagcgaaga agtggtcctg ctactttgtc cgcctccatc cagtctatga gctgctgtcg  3000
tgatgctaga gtaagaagtt cgccagtgag tagtttccga agagttgtgg ccattgctac  3060
tggcatcgtg gtatcacgct cgtcgttcgg tatggcttcg ttcaactctg gttcccagcg  3120
gtcaagccgg gtcacatgat cacccatatt atgaagaaat gcagtcagct ccttagggcc  3180
tccgatcgtt gtcagaagta agttggccgc ggtgttgtcg ctcatggtaa tggcagcact  3240
acacaattct cttaccgtca tgccatccgt aagatgcttt tccgtgaccg gcgagtactc  3300
aaccaagtcg ttttgtgagt agtgtatacg gcgaccaagc tgctcttgcc cggcgtctat  3360
acgggacaac accgcgccac atagcagtac tttgaaagtg ctcatcatcg ggaatcgttc  3420
ttcggggcgg aaagactcaa ggatcttgcc gctattgaga tccagttcga tatagcccac  3480
tcttgcaccc agttgatctt cagcatcttt tactttcacc agcgtttcgg ggtgtgcaaa  3540
aacaggcaag caaaatgccg caaagaaggg aatgagtgcg acacgaaaat gttggatgct  3600
catactcgtc ctttttcaat attattgaag catttatcag ggttactagt acgtctctca  3660
aggataagta agtaatatta aggtacggga ggtattggac aggccgcaat aaaatatctt  3720
tattttcatt acatctgtgt gttggttttt tgtgtgaatc gatagtacta acatacgctc  3780
tccatcaaaa caaaacgaaa caaaacaaac tagcaaaata ggctgtcccc agtgcaagtg  3840
caggtgccag aacatttctc t                                            3861
```

```
SEQ ID NO: 195          moltype = AA  length = 171
FEATURE                 Location/Qualifiers
REGION                  1..171
                        note = Description of Artificial Sequence: Synthetic
                         polypeptide
source                  1..171
                        mol_type = protein
                        organism = synthetic construct
SEQUENCE: 195
MVFTLEDFVG DWRQTAGYNL DQVLEQGGVS SLFQNLGVSV TPIQRIVLSG ENGLKIDIHV  60
IIPYEGLSGD QMGQIEKIFK VVYPVDDHHF KVILHYGTLV IDGVTPNMID YFGRPYEGIA  120
VFDGKKITVT GTLWNGNKII DERLINPDGS LLFRVTINGV TGWRLCERIL A           171
```

```
SEQ ID NO: 196          moltype = DNA  length = 2590
FEATURE                 Location/Qualifiers
source                  1..2590
                        mol_type = genomic DNA
                        organism = Homo sapiens
SEQUENCE: 196
ctgcttactg caactcgctc cggccgctgg gcgtagctgc gactcggcgg agtcccggcg  60
gcgcgtcctt gttctaaccc ggcgcgccat gaccgtcgcg cggccgagcg tgcccgcggc  120
gctgcccctc ctcggggagc tgccccggct gctgctgctg gtgctgttgt gcctgccggc  180
cgtgtggggt gactgtggcc ttcccccaga tgtacctaat gcccagccag ctttggaagg  240
ccgtacaagt ttttcccgagg atactgtaat aacgtacaaa tgtgaagaaa gctttgtgaa  300
aattcctggc gagaaggact cagtgatctg ccttaagggc agtcaatggt cagatattga  360
agagttctgc aatcgtagct gcgaggtgcc aacaaggcta aattctgcat ccctcaaaca  420
gccttatatc actcagaatt attttccagt cggtactgtt gtggaatatg agtgccgtcc  480
aggttacaga agagaacctt ctctatcacc aaaactaact tgccttcaga atttaaaatg  540
gtccacagca gtcgaatttt gtaaaaagaa atcatgccct aatccgggag aaatacgaaa  600
tggtcagatt gatgtaccag gtggcatatt atttggtgca accatctcct tctcatgtaa  660
cacagggtac aaattatttg gctcgacttc tagtttttgt cttatttcag gcagctctgt  720
ccagtggagt gacccgttgc cagagtgcag agaaatttat tgtccagcac caccacaaat  780
tgacaatgga ataattcaag gggaacgtga ccattatgga tatagacagt ctgtaacgta  840
tgcatgtaat aaaggattca ccatgattgg agagcactct atttattgta ctgtgaataa  900
tgatgaagga gagtggagtg gcccaccacc tgaatgcaga ggaaaatctc taacttccaa  960
ggtcccacca acagttcaga aacctaccac agtaaatgtt ccaactacag aagtctcacc  1020
aacttctcag aaaaccacca caaaaaccac cacaccaaat gctcaagcaa cacggagtac  1080
acctgtttcc aggacaacca agcattttca tgaaacaacc ccaaataaag gaagtggaac  1140
cacttcaggt actacccgtc ttctatctgg gcacacgtgt ttcacgttga caggtttgct  1200
tgggacgcta gtaaccatgg gcttgctgac ttagccaaag aagagttaag aagaaaatac  1260
acacaagtat acagactgtt cctagtttct tagacttatc tgcatattgg ataaaataaa  1320
tgcaattgtg ctcttcattt aggatgcttt cattgtcttt aagatgtgtt aggaatgtca  1380
acagagcaag gagaaaaaag gcagtcctgg aatcacattc ttagcacacc tacacctctt  1440
```

```
gaaaatagaa caacttgcag aattgagagt gattcctttc ctaaaagtgt aagaaagcat  1500
agagatttgt tcgtatttag aatgggatca cgaggaaaag agaaggaaag tgattttttt  1560
ccacaagatc tgtaatgtta tttccactta taaaggaaat aaaaaatgaa aaacattatt  1620
tggatatcaa aagcaaataa aaacccaatt cagtctcttc taagcaaaat tgctaaagag  1680
agatgaacca cattataaag taatctttgg ctgtaaggca ttttcatctt tccttcgggt  1740
tggcaaaata ttttaaaggt aaaacatgct ggtgaaccag gggtgttgat ggtgataagg  1800
gaggaatata gaatgaaaga ctgaatcttc ctttgttgca caaatagagt ttggaaaaag  1860
cctgtgaaag gtgtcttctt tgacttaatg tctttaaaag tatccagaga tactacaata  1920
ttaacataag aaaagattat atattatttc tgaatcgaga tgtccatagt caaatttgta  1980
aatcttattc ttttgtaata tttatttata tttatttatg acagtgaaca ttctgatttt  2040
acatgtaaaa caagaaaagt tgaagaagat atgtgaagaa aaatgtattt ttcctaaata  2100
gaaataaatg atcccatttt ttggtatcat gtagtatgtg aaatttattc ttaaacgtga  2160
ctactttatt tctaaataag aaattcccta cctgcttcct acaagcagtt cagaatgcca  2220
tgccttggtt gtcctagtgt gaataatttt cagctacttt aaaattatat tgtactttct  2280
caagcatgtc atatcctttc ctattagagt atctatatta cttgttactg atttacctga  2340
aggcaatctg attaatttct aggtttttac catattcttg tcatcttgcc aattacattt  2400
taagtgttag actagactaa gatgtactag ttgtatagaa tataactaga tttattatgg  2460
caatgtttat tttgtcattt tgcttcatct gttttgttgt tgaagtactt taaatttcat  2520
acgttcatgg catttcactg taaagacttt aatgtgtatt tcttaaaata aaactttttt  2580
tcctccttaa                                                          2590

SEQ ID NO: 197         moltype = AA  length = 381
FEATURE                Location/Qualifiers
source                 1..381
                       mol_type = protein
                       organism = Homo sapiens
SEQUENCE: 197
MTVARPSVPA ALPLLGELPR LLLLVLLCLP AVWGDCGLPP DVPNAQPALE GRTSFPEDTV  60
ITYKCEESFV KIPGEKDSVI CLKGSQWSDI EEFCNRSCEV PTRLNSASLK QPYITQNYFP  120
VGTVVEYECR PGYRREPSLS PKLTCLQNLK WSTAVEFCKK KSCPNPGEIR NGQIDVPGGI  180
LFGATISFSC NTGYKLFGST SSFCLISGSS VQWSDPLPEC REIYCPAPPQ IDNGIIQGER  240
DHYGYRQSVT YACNKGFTMI GEHSIYCTVN NDEGEWSGPP PECRGKSLTS KVPPTVQKPT  300
TVNVPTTEVS PTSQKTTTKT TTPNAQATRS TPVSRTTKHF HETTPNKGSG TTSGTTRLLS  360
GHTCFTLTGL LGTLVTMGLL T                                             381

SEQ ID NO: 198         moltype = AA  length = 128
FEATURE                Location/Qualifiers
source                 1..128
                       mol_type = protein
                       organism = Homo sapiens
SEQUENCE: 198
MGIQGGSVLF GLLLVLAVFC HSGHSLQCYN CPNPTADCKT AVNCSSDFDA CLITKAGLQV  60
YNKCWKFEHC NFNDVTTRLR ENELTYYCCK KDLCNFNEQL ENGGTSLSEK TVLLLVTPFL  120
AAAWSLHP                                                            128

SEQ ID NO: 199         moltype = DNA  length = 1936
FEATURE                Location/Qualifiers
source                 1..1936
                       mol_type = genomic DNA
                       organism = Homo sapiens
SEQUENCE: 199
agaaccccgc ggggtctgag cagcccagcg tgcccattcc agcgcccgcg tccccgcagc  60
atgccgcgcc cccgcctgct ggccgcgctg tgcggcgcgc tgctctgcgc ccccagcctc  120
ctcgtcgccc tggatatctg ttccaaaaac ccctgccaca acggtggttt atgcgaggag  180
atttcccaag aagtgcgagg agatgtcttc ccctcgtaca cctgcacgtg ccttaagggc  240
tacgcgggca accactgtga gacgaaatgt gtcgagccac tgggcctgga gaatgggaac  300
attgccaact cacagatcgc cgcctcgtct gtgcgtgtga ccttcttggg tttgcagcat  360
tgggtcccgg agctggcccg cctgaaccgc gcaggcatgg tcaatgcctg gacacccagc  420
agcaatgacg ataacccctg gatccaggtg aacctgctgc ggaggatgtg ggtaacaggt  480
gtggtgacgc agggtgccag ccgcttggcc agtcatgagt acctgaaggc cttcaaggtg  540
gcctacagcc ttaatggaca cgaattcgat ttcatccatg atgttaataa aaaacacaag  600
gagtttgtgg gtaactggaa caaaaacgcg gtgcatgtca acctgtttga gacccctgtg  660
gaggctcagt acgtgagatt gtaccccacg agctgccaca cggcctgcac tctgcgcttt  720
gagctactgg gctgtgagct gaacggatgc gccaatcccc tgggcctgaa gaataacagc  780
atccctgaca agcagatcac ggcctccagc agctacaaga cctggggctt gcatctcttc  840
agctggaacc cctcctatgc acggctggac aagcagggca acttcaacgc ctgggttgcg  900
gggagctacg gtaacgatca gtggctgcag gtggacctgg gctcctcgaa ggaggtgaca  960
ggcatcatca cccagggggc ccgtaacttt ggctctgtcc agtttgtggc atcctacaag  1020
gttgcctaca gtaatgacag tgcgaactgg actgagtacc aggaccccag gactggcagc  1080
agtaagatct tccctggcaa ctgggacaac cactccccaca agaagaactt gtttgagacg  1140
cccatcctgg ctcgctatgt gcgcatcctg cctgtagcct ggcacaaccg catcgccctg  1200
cgcctggagc tgctgggctg ttagtggcca cctgccaccc ccaggtcttc ctgctttcca  1260
tgggcccgct gcctcttggc ttctcagccc ctttaaatca ccatagggct ggggactggg  1320
gaaggggagg gtgttcagag gcagcaccac cacacagtca cccctccctc cctctttccc  1380
accctccacc tctcacgggc cctgccccag cccctaagcc ccgtccccta acccccagtc  1440
ctcactgtcc tgttttctta ggcactgagg gatctgagta ggtctgggat ggacaggaaa  1500
gggcaaagta gggcgtgtgg tttccctgcc cctgtccgga ccgccgatcc caggtgcgtg  1560
tgtctctgtc tctcctagcc cctctctcac acatcacatt cccatggtgg cctcaagaaa  1620
ggcccggaag cgccaggctg gagataacag cctcttgccc gtcggccctg cgtcggccct  1680
```

-continued

```
ggggtaccat gtggccacaa ctgctgtggc cccctgtccc caagacactt ccccttgtct  1740
ccctggttgc ctctcttgcc ccttgtcctg aagcccagcg acacagaagg gggtggggcg  1800
ggtctatggg gagaaaggga gcgaggtcag aggagggcat gggttggcag ggtgggcgtt  1860
tggggccctc tatgctggct tttcacccca gaggacacag gcagcttcca aaatatattt  1920
atcttcttca cgggaa                                                   1936

SEQ ID NO: 200          moltype = AA  length = 387
FEATURE                 Location/Qualifiers
source                  1..387
                        mol_type = protein
                        organism = Homo sapiens
SEQUENCE: 200
MPRPRLLAAL CGALLCAPSL LVALDICSKN PCHNGGLCEE ISQEVRGDVF PSYTCTCLKG  60
YAGNHCETKC VEPLGLENGN IANSQIAASS VRVTFLGLQH WVPELARLNR AGMVNAWTPS  120
SNDDNPWIQV NLLRRMWVTG VVTQGASRLA SHEYLKAFKV AYSLNGHEFD FIHDVNKKHK  180
EFVGNWNKNA VHVNLFETPV EAQYVRLYPT SCHTACTLRF ELLGCELNGC ANPLGLKNNS  240
IPDKQITASS SYKTWGLHLF SWNPSYARLD KQGNFNAWVA GSYGNDQWLQ VDLGSSKEVT  300
GIITQGARNF GSVQFVASYK VAYSNDSANW TEYQDPRTGS SKIFPGNWDN HSHKKNLFET  360
PILARYVRIL PVAWHNRIAL RLELLGC                                       387

SEQ ID NO: 201          moltype = DNA  length = 2221
FEATURE                 Location/Qualifiers
source                  1..2221
                        mol_type = genomic DNA
                        organism = Homo sapiens
SEQUENCE: 201
gcattgcggc ttggtttct cacccagtgc atgtggcagg agcggtgaga tcactgcctc  60
acggcgatcc tggactgacg gtcacgactg cctaccctct aaccctgttc tgagctgccc  120
cttgcccaca caccccaaac ctgtgtgcag gatccgcctc catggagcta cagcctcctg  180
aagcctcgat cgccgtcgtg tcgattccgc gccagttgcc tggctcacat tcggaggctg  240
gtgtccaggg tctcagcgcg ggggacgact cagagttggg gtctcactgt gttgcccaga  300
ctggtctcga actcttggcc tcaggtgatc ctcttccctc agcttcccag aatgccgaga  360
tgatagagac ggggtctgac tgtgttaccc aggctggtct tcaactcttg gcctcaagtg  420
atcctcctgc cttagcttcc aagaatgctg aggttacagg caccatgagc caggacaccg  480
aggtggatat gaaggaggtg gagctgaatg agttagagcc cgagaagcag ccgatgaacg  540
cggcgtctgg ggcggccatg tccctggcgg gagccgagaa gaatggtctg gtgaagatca  600
aggtggcgga agacgaggcg gaggcggcag ccgcggctaa gttcacgggc ctgtccaagg  660
aggagctgct gaaggtggca ggcagccccg gctgggtacg cacccgctgg gcactgctgc  720
tgctcttctg gctcggctgg ctcggcatgc ttgctggtgc cgtggtcata atcgtgcgag  780
cgccgcgttg tcgcgagcta ccggcgcaga agtggtggca cacgggcgcc ctctaccgca  840
tcggcgacct tcaggccttc cagggccacg gcgcgggcaa cctggcgggt ctgaaggggc  900
gtctcgatta cctgagctct ctgaaggtga agggccttgt gctgggtcca attcacaaga  960
accagaagga tgatgtcgct cagactgact tgctgcagat cgaccccaat tttggctcca  1020
aggaagattt tgacagtctc ttgcaatcgg ctaaaaaaaa gagcatccgt gtcattctgg  1080
accttactcc caactaccgg ggtgagaact cgtggttctc cactcaggtt gacactgtgg  1140
ccaccaaggt gaaggatgct ctggagtttt ggctgcaagc tggcgtggat gggttccagg  1200
ttcgggacat agagaatctg aaggatgcat cctcattctt ggctgagtgg caaaatatca  1260
ccaagggctt cagtgaagac aggctcttga ttgcggggac taactcctcc gaccttcagc  1320
agatcctgag cctactcgaa tccaacaaag acttgctgtt gactagctca tacctgtctg  1380
attctggttc tactggggag catacaaaat ccctagtcac acagtatttg aatgccactg  1440
gcaatcgctg gtgcagctgg agtttgtctc aggcaaggct cctgacttcc ttcttgccgg  1500
ctcaacttct ccgactctac cagctgatgc tcttcaccct gccagggacc cctgttttca  1560
gctacgggga tgagattggc ctggatgcag ctgcccttcc tggacagcct atggaggctc  1620
cagtcatgct gtgggatgag tccagcttcc ctgacatccc aggggctgta agtgccaaca  1680
tgactgtgaa gggccagagt gaagaccctg gctccctcct ttccttgttc cggcggctga  1740
gtgaccagcg gagtaaggag cgctccctac tgcatgggga cttccacgcg ttctccgctg  1800
ggcctggact cttctcctat atccgccact gggaccagaa tgagcgtttt ctggtagtgc  1860
ttaactttgg ggatgtgggc ctctcggctg gactgcaggc ctccgacctg cctgccagcg  1920
ccagcctgcc agccaaggct gacctcctgc tcagcaccca gccaggccgt gaggagggct  1980
cccctcttga gctggaacgc ctgaaactgg agcctcacga agggctgctg ctccgcttcc  2040
cctacgcggc ctgacttcag cctgacatgg acccactacc cttctccttt ccttcccagg  2100
ccctttggct tctgattttt ctcttttta aaaacaaaca aacaaactgt tgcagattat  2160
gagtgaaccc ccaaataggg tgttttctgc cttcaaataa aagtcacccc tgcatggtga  2220
a                                                                   2221

SEQ ID NO: 202          moltype = AA  length = 630
FEATURE                 Location/Qualifiers
source                  1..630
                        mol_type = protein
                        organism = Homo sapiens
SEQUENCE: 202
MELQPPEASI AVVSIPRQLP GSHSEAGVQG LSAGDDSELG SHCVAQTGLE LLASGDPLPS  60
ASQNAEMIET GSDCVTQAGL QLLASSDPPA LASKNAEVTG TMSQDTEVDM KEVELNELEP  120
EKQPMNAASG AAMSLAGAEK NGLVKIKVAE DEAEAAAAAK FTGLSKEELL KVAGSPGWVR  180
TRWALLLLFW LGWLGMLAGA VVIIVRAPRC RELPAQKWWH TGALYRIGDL QAFQGHGAGN  240
LAGLKGRLDY LSSLKVKGLV LGPIHKNQKD DVAQTDLLQI DPNFGSKEDF DSLLQSAKKK  300
SIRVILDLTP NYRGENSWFS TQVDTVATKV KDALEFWLQA GVDGFQVRDI ENLKDASSFL  360
AEWQNITKGF SEDRLLIAGT NSSDLQQILS LLESNKDLLL TSSYLSDSGS TGEHTKSLVT  420
QYLNATGNRW CSWSLSQARL LTSFLPAQLL RLYQLMLFTL PGTPVFSYGD EIGLDAAALP  480
```

```
GQPMEAPVML WDESSFPDIP GAVSANMTVK GQSEDPGSLL SLFRRLSDQR SKERSLLHGD  540
FHAFSAGPGL FSYIRHWDQN ERFLVVLNFG DVGLSAGLQA SDLPASASLP AKADLLLSTQ  600
PGREEGSPLE LERLKLEPHE GLLLRFPYAA                                  630

SEQ ID NO: 203         moltype = DNA  length = 2886
FEATURE                Location/Qualifiers
source                 1..2886
                       mol_type = genomic DNA
                       organism = Homo sapiens
SEQUENCE: 203
atcgctgggg gacagcctgc aggcttcagg aggggacaca agcatggagc ggctttgggg  60
tctattccag agagcgcaac aactgtcccc aagatcctct cagaccgtct accagcgtgt  120
ggaaggcccc cggaaagggc acctggagga ggaagaggaa gacggggagg agggggcgga  180
gacattggcc cacttctgcc ccatggagct gaggggccct gagcccctgg gctctagacc  240
caggcagcca aacctcattc cctgggcggc agcaggacgg agggctgccc cctacctggt  300
cctgacggcc ctgctgatct tcactggggc cttcctactg ggctacgtcg ccttccgagg  360
gtcctgccag gcgtgcggag actctgtgtt ggtggtcagt gaggatgtca actatgagcc  420
tgacctggat ttccaccagg gcagactcta ctggagcgac ctccaggcca tgttcctgca  480
gttcctgggg gaggggcgcc tggaggacac catcaggcaa accagccttc gggaacgggt  540
ggcaggctcg gccgggatgg ccgctctgac tcaggacatt cgcgcggcgc tctcccgcca  600
gaagctggac cacgtgtgga ccgacacgca ctacgtgggg ctgcaattcc cggatccggc  660
tcaccccaac accctgcact gggtcgatga ggccgggaag gtcggagagc agctgccgct  720
ggaggaccct gacgtctact gcccctacag cgccatcggc aacgtcacgg gagagctggt  780
gtacgcccac tacgggcggc ccgaagacct gcaggacctg cgggccaggg gcgtggatcc  840
agtgggccgc ctgctgctgg tgcgcgtggg ggtgatcagc ttcgcccaga aggtgaccaa  900
tgctcaggac ttcggggctc aaggagtgct catataccca gagccagcgg acttctccca  960
ggacccaccc aagccaagcc tgtccagcca gcaggcagtg tatggacatg tgcacctggg  1020
aactggagac ccctacacac ctggcttccc ttccttcaat caaacccagt tccctccagt  1080
tgcatcatca ggccttccca gcatcccagc ccagcccatc agtgcagaca ttgcctcccg  1140
cctgctgagg aagctcaaag gccctgtggc cccccaagaa tggcagggga gcctcctagg  1200
ctccccttat cacctgggcc ccgggccacg actgcggcta gtggtcaaca atcacaggac  1260
ctccaccccc atcaacaaca tcttcggctg catcgaaggc cgctcagagc cagatcacta  1320
cgttgtcatc ggggcccaga gggatgcatg gggcccagga gcagctaaat ccgctgtggg  1380
gacggctata ctcctggagc tggtgcggac cttttcctcc atggtgagca acggcttccg  1440
gccccgcaga agtctcctct tcatcagctg ggacggtggt gactttggaa gcgtgggctc  1500
cacggagtgg ctagagggct acctcagcgt gctgcacctc aaagccgtag tgtacgtgag  1560
cctggacaac gcagtgctgg gggatgacaa gtttcatgcc aagaccagcc cccttctgac  1620
aagtctcatt gagagtgtcc tgaagcaggt ggattctccc aaccacagtg ggcagactct  1680
ctatgaacag gtggtgttca ccaatcccag ctgggatgct gaggtgatcc ggcccctacc  1740
catggacagc agtgcctatt ccttcacggc ctttgtggga gtccctgccg tcgagttctc  1800
ctttatggag gacgaccagg cctacccatt cctgcacaca aaggaggaca cttatgagaa  1860
cctgcataag gtgctgcaag gccgcctgcc cgccgtggcc caggccgtgg cccagctcgc  1920
agggcagctc ctcatccggc tcagccacga tcgcctgctg cccctcgact tcggccgcta  1980
cggggacgtc gtcctcaggc acatcgggaa cctcaacgag ttctctgggg acctcaaggc  2040
ccgcgggctg accctgcagt gggtgtactc ggcgcggggg gactacatcc gggcggcgga  2100
aaagctgcgg caggagatct acagctcgga ggagagagac gagcgactga cacgcatgta  2160
caacgtgcgc ataatgcggg tggagttcta cttcctttcc cagtacgtgt cgccagccga  2220
ctccccgttc cgccacatct tcatgggccg tggagaccac acgctgggcg ccctgctgga  2280
ccacctgcgg ctgctgcgct ccaacagctc cgggaccccc ggggccacct cctccactgg  2340
cttccaggag agccgtttcc ggcgtcagct agccctgctc acctggacgc tgcaaggggc  2400
agccaatgcg cttagcgggg atgtctggaa cattgataac aacttctgag gccctgggga  2460
tcctcacatc cccgtccccc agtcaagagc tcctctgctc ctcgcttgaa tgattcaggg  2520
tcagggaggt ggctcagagt ccacctctca ttgctgatca atttctcatt accccctacac  2580
atctctccac ggagcccaga ccccagcaca gatatccaca caccccagcc ctgcagtgta  2640
gctgacccta atgtgacggt catactgtcg gttaatcaga gagtagcatc ccttcaatca  2700
cagccccttc ccctttctgg ggtcctccat acctagagac cactctggga ggtttgctag  2760
gccctgggac ctggccagct ctgttagtgg gagagatcgc tggcaccata gccttatggc  2820
caacaggtgg tctgtggtga aaggggcgtg gagtttcaat atcaataaac cacctgatat  2880
caataa                                                            2886

SEQ ID NO: 204         moltype = AA  length = 801
FEATURE                Location/Qualifiers
source                 1..801
                       mol_type = protein
                       organism = Homo sapiens
SEQUENCE: 204
MERLWGLFQR AQQLSPRSSQ TVYQRVEGPR KGHLEEEEED GEEGAETLAH FCPMELRGPE  60
PLGSRPRQPN LIPWAAAGRR AAPYLVLTAL LIFTGAFLLG YVAFRGSCQA CGDSVLVVSE  120
DVNYEPDLDF HQGRLYWSDL QAMFLQFLGE GRLEDTIRQT SLRERVAGSA GMAALTQDIR  180
AALSRQKLDH VWTDTHYVGL QFPDPAHPNT LHWVDEAGKV GEQLPLEDPD VYCPYSAIGN  240
VTGELVYAHY GRPEDLQDLR ARGVDPVGRL LLVRVGVISF AQKVTNAQDF GAQGVLIYPE  300
PADFSQDPPK PSLSSQQAVY GHVHLGTGDP YTPGFPSFNQ TQFPPVASSG LPSIPAQPIS  360
ADIASRLLRK LKGPVAPQEW QGSLLGSPYH LGPGPRLRLV VNNHRTSTPI NNIFGCIEGR  420
SEPDHYVVIG AQRDAWGPGA AKSAVGTAIL LELVRTFSSM VSNGFRPRRS LLFISWDGGD  480
FGSVGSTEWL EGYLSVLHLK AVVYVSLDNA VLGDDKFHAK TSPLLTSLIE SVLKQVDSPN  540
HSGQTLYEQV VFTNPSWDAE VIRPLPMDSS AYSFTAFVGV PAVEFSFMED DQAYPFLHTK  600
EDTYENLHKV LQGRLPAVAQ AVAQLAGQLL IRLSHDRLLP LDFGRYGDVV LRHIGNLNEF  660
SGDLKARGLT LQWVYSARGD YIRAAEKLRQ EIYSSEERDE RLTRMYNVRI MRVEFYFLSQ  720
YVSPADSPFR HIFMGRGDHT LGALLDHLRL LRSNSSGTPG ATSSTGFQES RFRRQLALLT  780
```

-continued

```
WTLQGAANAL SGDVWNIDNN F                                        801

SEQ ID NO: 205         moltype = DNA  length = 11158
FEATURE                Location/Qualifiers
source                 1..11158
                       mol_type = genomic DNA
                       organism = Homo sapiens
SEQUENCE: 205
gttgccggcc cctgaagtgg agcgagaggg aggtgcttcg ccgtttctcc tgccagggga  60
ggtcccggct tcccgtggag gctccggacc aagccccttc agcttctccc tccggatcga  120
tgtgctgctg ttaacccgtg aggaggcggc ggcggcggca gcggcagcgg aagatggtgt  180
tgctgagagt gttaattctg ctcctctcct gggcggcggg gatgggaggt cagtatggga  240
atcctttaaa taaatatatc agacattatg aaggattatc ttacaatgtg gattcattac  300
accaaaaaca ccagcgtgcc aaaagagcag tctcacatga agaccaattt ttacgtctag  360
atttccatgc ccatggaaga catttcaacc tacgaatgaa gagggacact tccctttca  420
gtgatgaatt taaagtagaa acatcaaata aagtacttga ttatgatacc tctcatattt  480
acactggaca tatttatggt gaagaaggaa gttttagcca tgggtctgtt attgatggaa  540
gatttgaagg attcatccag actcgtggtg gcacatttta tgttgagcca gcagagagat  600
atattaaaga ccgaactctg ccatttcact ctgtcattta tcatgaagat gatattaact  660
atccccataa atacggtcct caggggggct gtgcagatca ttcagtattt gaaagaatga  720
ggaaatacca gatgactggt gtagaggaag taacacagat acctcaagaa gaacatgctg  780
ctaatggtcc agaacttctg aggaaaaaac gtacaacttc agctgaaaaa aatacttgtc  840
agctttatat tcagactgat catttgttct ttaaatatta cggaacacga gaagctgtga  900
ttgcccagat atccagtcat gttaaagcga ttgatacaat ttaccagacc acagacttct  960
ccggaatccg taacatcagt ttcatggtga aacgcataag aatcaataca actgctgatg  1020
agaaggaccc tacaaatcct ttccgtttcc caaatattgg tgtggagaag tttctggaat  1080
tgaattctga gcagaatcat gatgactact gtttggccta tgtcttcaca gaccgagatt  1140
ttgatgatgg cgtacttggt ctggcttggg ttggagcacc ttcaggaagc tctggaggaa  1200
tatgtgaaaa aagtaaactc tattcagatg gtaagaagaa gtccttaaac actggaatta  1260
ttactgttca gaactatggg tctcatgtac ctcccaaagt ctctcacatt actttgctc  1320
acgaagttgg acataacttt ggatccccac atgattctgg aacagagtgc acaccaggag  1380
aatctaagaa tttgggtcaa aaagaaaatg gcaattacat catgtatgca agagcaacat  1440
ctggggacaa acttaacaac aataaattct cactctgtag tattagaaat ataagccaag  1500
ttcttgagaa gaagagaaac aactgttttg ttgaatctgg ccaacctatt tgtggaaatg  1560
gaatggtaga acaaggtgaa gaatgtgatt gtggctatag tgaccagtgt aaagatgaat  1620
gctgcttcga tgcaaatcaa ccagagggaa gaaaatgcaa actgaaacct gggaaacagt  1680
gcagtccaag tcaaggtcct tgttgtacag cacagtgtgc attcaagtca aagtctgaga  1740
agtgtcggga tgattcagac tgtgcaaggg aaggaatatg taatggcttc acagctctct  1800
gcccagcatc tgaccctaaa ccaaacttca cagactgtaa taggcataca caagtgtgca  1860
ttaatgggca atgtgcaggt tctatctgtg agaaatatgg cttagaggag tgtacgtgtg  1920
ccagttctga tggcaaagat gataaagaat tatgccatgt atgctgtatg aagaaaatgg  1980
acccatcaac ttgtgccagt acagggtctg tgcagtggag taggcacttc agtggtcgaa  2040
ccatcaccct gcaacctgga tccccttgca acgattttag aggttactgt gatgttttca  2100
tgcggtgcag attagtagat gctgatggtc ctctagctag gcttaaaaaa gcaattttta  2160
gtccagagct ctatgaaaac attgctgaat ggattgtggc tcattggtgg gcagtattac  2220
ttatgggaat tgctctgatc atgctaatgg ctggatttat taagatatgc agtgttcata  2280
ctccaagtag taatccaaag ttgcctcctc ctaaaccact tccaggcact ttaaagagga  2340
ggagacctcc acagcccatt cagcaacccc agcgtcagcg gccccgagag agttatcaaa  2400
tgggacacat gagacgctaa ctgcagcttt tgccttggtt cttcctagtg cctacaatgg  2460
gaaaacttca ctccaaagag aaacctatta agtcatcatc tccaaactaa accctcacaa  2520
gtaacagttg aagaaaaaat ggcaagagat catatcctca gaccaggtgg aattacttaa  2580
attttaaagc ctgaaaattc caatttgggg gtgggaggtg gaaaaggaac ccaattttct  2640
tatgaacaga tattttttaac ttaatggcac aaagtcttag aatattatta tgtgccccgt  2700
gttccctgtt cttcgttgct gcattttctt cacttgcagg caaacttggc tctcaataaa  2760
cttttaccac aaattgaaat aaatatattt ttttcaactg ccaatcaagg ctaggaggct  2820
cgaccacctc aacattggag acatcacttg ccaatgtaca taccttgtta tatgcagaca  2880
tgtatttctt acgtacactg tacttctgtg tgcaattgta aacagaaatt gcaatatgga  2940
tgtttctttg tattataaaa tttttccgct cttaattaaa aattactgtt taattgacat  3000
actcaggata acagagaatg gtggtattca gtggtccagg attctgtaat gctttacaca  3060
ggcagttttg aaatgaaaat caatttacct ttctgttacg atggagttgg ttttgatact  3120
cattttttct ttatcacatg gctgctacgg gcacaagtga ctatactgaa gaacacagtt  3180
aagtgttgtg caaactggac atagcagcac atactacttc agagttcatg atgtagatgt  3240
ctggtttctg cttacgtctt ttaaactttc taattcaatt ccatttttca attaataggt  3300
gaaattttat tcatgctttg atagaaatta tgtcaatgaa atgattcttt ttatttgtag  3360
cctacttatt tgtgtttttc atatatctga aatatgctaa ttatgtttttc tgtctgatat  3420
ggaaaagaaa agctgtgtct ttatcaaaat atttaaacgg ttttttcagc atatcatcac  3480
tgatcattgg taaccactaa agatgagtaa tttgcttaag tagtagttaa aattgtagat  3540
aggccttctg acattttttt tcctaaaatt tttaacagca ttgaaggtga aacagcacaa  3600
tgtcccattc caaatttatt tttgaaacag atgtaaataa ttggcatttt aaagagaaag  3660
caaaaacatt taatgtatta acaggcttat tgctatgcag gaaatagaag gggcattaca  3720
aaaattgaag cttgtgacat atttattgct tctgttttcc aactacatca cttcaactag  3780
aagtaaagct atgattttcc tgacttcaca taggaggcaa atttagagaa agttgtaaag  3840
atttctatgt tttgggtttt ttttttttcct ttttttttt aagagtataa ggtttacaca  3900
atcattctca taatgtgacg caagccagca aggccaaaaa tgctagagaa aataacggga  3960
tctcttcctt gtaaacttgt acagtatgtg gtgacttttt caaaatacag ctttttgtac  4020
atgatttaga gacaaatttt gtacatgaaa ccccagatag actataaata attctaaaca  4080
aacaagtagg tagatatgta tgtaattgct tttaaatcat ttaaatgcct ttgtttttgg  4140
actgtgcaaa ggttggaagt gggtttgcat ttctaaaatg gtgactttta ttctgcaaga  4200
gttcttagta acttcttgag tgtggtagac tttggaacat gtaaattttt tgcttgtaat  4260
```

-continued

```
gttatcctgt ggtaggattt tggcaggtac acacactgcc ctattttatt ttgagtctaa  4320
gttaaatgtt ttctgaaaag agatacatgc actgaactct ttccactgcg aatcaagatg  4380
tggtaatata aaaggatcaa gacaaatgag atctaatact actgtcagtt ttaatgtcca  4440
ctgtgtttta tacagtatct ttttttgttc actttggaaa tttttactaa aaattgcaaa  4500
aaataaagta ttgtgcaaag atgtaaggtt ttttgaaact tgaaatgcat taataaatag  4560
acgattaaat caacttgaag gttctatact ctttgaactc tgagaactat cacaagaagc  4620
ttcccacaag gcagtgtttt cttacagttg tctcttccta caaaagtata gattatcttt  4680
attcttaata ctttggaatc catgtagaaa atttccagtt agatactctg cgtacacaca  4740
ataaaccttt ttaaaacacc caactaatct caactgcatt acattgtttc taatcaatat  4800
tcagtgcttg tcttggtgga agaggtgagt cattttgaaa acttatggtc ttgtttttat  4860
gtgtttttca aagttttgaa tgctaagtac ctcatttatt ttaaaaagcc tagtttaatg  4920
ataagtttgt ttaaaatttt gagccatcat ttttctcttc atagcaaata aggagagaat  4980
tgacatttca gtgttaccta gaaaaggaat tgtaagccca gaataattcc ctgcatgagg  5040
taatctgctt caaattcttt ttttagtcaa ggttagctat aagtaatact tgttaaatga  5100
gtaaatatgt aatactttgt gaattacttt gttaatttag gagcatcaaa tgtatattat  5160
gtttagttat ttatgaaact ctcaatattg attgatttgg gtaattataa attagttatt  5220
tttacttgta attgaatgct taaattctgt ttacagtccg tcctctctcc ctccatccct  5280
ccctccccag ttttataaat tcaggtacca attcacaaac aaaatcagaa ataaaataaa  5340
tttattgact gcttctggat ttagcattcc ctgtagtgtc aagcaatgtc atgcagtttg  5400
gggaagcatt tatttaagga aatgacaact ttctctgatc agtcttgttt tgtgaggtgt  5460
cttcaacact ttatgctttg ggtacttcgt gtttgtcaca gtcttaggat agtgaaatct  5520
gatttgtcca agcggagcaa actactcgac cctcagtcct tgtatttgtc cctgtagtaa  5580
gacctaatta ttattatttc ttaaagatgg gattggtgtc cttggcaact atgaaatttc  5640
ggggcttgtg catgagaagg catttcttat taagtatttc taattgaagg tatcagagtg  5700
tcaagcatta caaacctgga cagttcacct ggaggagtac aagaagagat attcattatc  5760
catatttaaa gggtcaaggt ttcccaaaac cagggtgcaa gccagatgta gttttaaagc  5820
agctgccagg gacagttcat ctttagagaa gtcactaaag ttgtaagaaa ttttagtttc  5880
cccaaaacca ctttcaactt cttagaaact agaaagacaa ttggtttgcc ccacagagga  5940
caacttcagt ttcagcatct ctcatgttgt gttcttgatt aaaaacaact tccatttgat  6000
atacttttcc gtttattacc agtttagttt tttcactatt gtttctgtat tcaactcttt  6060
atatgattag gatagaaatt tagcccttct gttttatatt actatattgt ttgtgtgtct  6120
tagatatata catgtatgta ctattttcag tagaaattca tgtattttat aattggtaag  6180
ttcttcagag catctcttct ataaaaagca acaggatgct aggtaaaacg gagcattgag  6240
caaaatactg attagttttt gctttttcct gaaatctaca ctaaagtgat agggtgtggg  6300
gtaatccaac aaggacaagg tgaattgaac aagaacgaaa tctggaagca gatgaaggag  6360
tactattgat tgggcagacc cagggaagtc aaatcctaaa ccagcagtgg gaacacaaca  6420
gaatggtgta gtttgcactg gtaagatttg ggtacctggc agggctgggt gcggtggctc  6480
acacctgtaa tcccagcact ttgggaggcc aaggcgggtg gatcacttga ggtcaggagt  6540
tcgagaccac cctggccaac atggtgaaac cccgtctcta ctaaaaatac agctgggcgt  6600
ggtggcacat gcttgtaatc ccagctactc gggaggcaga ggcaggagat ttgcttgaac  6660
ccgggaggca gaggcaggag atttgcttga acccaggagg cagaggctgc agtgagccgc  6720
gattgcgcca ttgcactcca gcctgggtga cagagcgaga ctctgtctca aaaaaaaaaa  6780
aaaaaaaaaa aaaaaaaaaa aaaaaaaaaa aaaaaaattt gagtacctgg cctttgttac  6840
tttttttcta tgtgtgtgac aaaaacataa tatgcacact tttgtaaccc acctttctca  6900
tttaatggta cattgataat gtatatcaca ttaactactc taaatatttc tgtggatgta  6960
tgtttttttt tttcttaacc aatttcccat tgtttggaca tgtaggttcc acattgttta  7020
ttattttaaa caattctaaa gaattttaaa caattcttag gaaaatcctc agcctaataa  7080
tgaaattaat tcctaaaagt ggaattgttg gggtaaaggt tttttgaggg acattgataa  7140
aaattatggt actgtctccc agatagatgt accaagttat actaccacga tttaatatat  7200
atatatatat atattaaatc agagtcccat ccttagaaat ccacatatat gcagccacat  7260
gaatgtatta gaaacaataa tagaagactc atgcttaatt cagttgatta gctttagaca  7320
taattcaaat gcaagtcaaa ttgagtgccc taattgtggt ctcttaagta ccatttttct  7380
tcaagggaac cagactcctt tggataaatc actaattcca cctgtaagaa agaaatgtac  7440
aagaagaacc taggaaacat tgttttgtac cagatcagaa agattcagga ggcaccttag  7500
aagttaccac tggccaaggc tgagataact ttagcatcag caaggataat atctgcaaga  7560
gattgaaact catagtattg tatttaactc tgtgagttaa tgatggtagt ggacagaatt  7620
atagttacct ttgggatacg cttttaaaga aattccaggt aataagagaa atgatagaat  7680
taggatatca ccattttacc cccccaacaa tttatggatc tagacaataa tcgccagtga  7740
ctgctaacct cacaaagtga gagcaatcag attttgtgcc tcctaatgga agtacatata  7800
ccacctatga agcagttctg ccaaaagtca catctcatca tgatgaagcc tcctgatcta  7860
actacccctt cattagaaat acaggggaca gagggacaaa taatatacaa gggactcaat  7920
cagcaaaatc cagactctgg aaaactacaa gacatatggt cctgcttcaa caacagaaat  7980
gcaaagagaa aagacaacga tgggttaaag gagacttaag agctacatct atcaagacaa  8040
tttatggact tatttggata ctgatttgaa caaactgttg agaccattgg aaaaatgtga  8100
aaagtggata tttgatatta aggtttttaa ttatttttag gtgtgataat ggtattgtta  8160
catttttaa aggacccctt ttagagatgc aaattgaaac acttaaaaaa tgaaatgata  8220
cgatgtataa gtttttgctt aaaaataagg attgaagttg gctggtgtgt gtggatatag  8280
ttgaaacaag attggctgtg agttgataat tattgaagct gggtgatggg cacttgggga  8340
tttattatac tattttctct acctgtgttt atatttgaaa tttttcatag aagttttaaa  8400
atgtggccag ttgtgatggc tcatacctgt aatcccaaca ctttgggagg ccaaggtggg  8460
aggatcactt gagctcagga gttagagacc agcctgggca aaatagtgag actccatctc  8520
aaagaaaaaa aaaaagtgtt ttaaatgtga atcaaattcc tatagaagct gattcattac  8580
tgtttttatt ttagcagtaa ttcatgataa tgacctgtat tcataatgat tttcataatg  8640
attgttttag tggaattaaa cttgaaccag tcaagctaac ataattatat tctgctccag  8700
ttacaatgaa taattaattg atttcaactg ctagggtgaa ctcttgaagc tatcagtcat  8760
ccagcaatct tagcaagcag gccattgggt ccctgtttgc tctgtctctc tctctctctc  8820
tcactgttga agggcttagc taactactta agtaaaatat ttgttctctg ttaaacatgt  8880
caaggagtat ggtcagctta tccacattaa gcctgtgtgt cccacgttgg agtaaatgtt  8940
aagtagctca ctacaataaa ctagattctt ctgccctctc ttgtttaaat gatcatgttc  9000
```

```
cctggaggtg gaaatagatc tttaaaaaga tattctgtag ttgtttgttc tcagtgtaaa  9060
aaaatgagaa taatttgata agagtgtagg ttgtcttata taaaaagtgg ttccatttgc  9120
atgaatttta gaaaaatcat tttggaaaaa tgaaggctat gtggttatac tgaacacatt  9180
aagcaatttt attctttatt ttaaatgaat attttattat cgttttcttc ccttgccctt  9240
tgggtatggg agttagcctt tgtgtttcta aatacaacag gccggttttt ataaattaag  9300
gtgtcaatat attcttcatt atttagtttt gtgattgtgg ttagttttca tttttcttaa  9360
gtatctgcta gtagcatctg taattaagtg aagtgacctg ttaaccattt tcctctttct  9420
cctcctttcc tcctccttga aacatatcag agcatgtttg aaattctttg gcttttatgg  9480
tatgcatttg ctgatatgca ttgaccagtt accttactca cagatacttc ttaggcactt  9540
gattgtgcca gggccttggc tagatgataa gaatacagta gtgaacttaa cagtttccct  9600
gccctggtga agcgtatggt cttgtaggtg agatagatat cagataatca tgtgaataaa  9660
tgtacaattc cagctgtgat acatgctgag gaggaggttt ttggtgatcc aagagctgat  9720
catgcagaga taggactgag aaaggagggt gggacgttgt cacagctgat aatgcagaga  9780
taggactgag aaaggagggt gggacatcag gaaggtcaga gaattcctta tgaaagtgat  9840
gcttgagtca aaatatgatg gatgaagaga gtttaaatag attacataga atttttaata  9900
atgtcgattg gttatatact gggcactgat agctgatttt tctttgggga aaggtatgtc  9960
agcctagtca ttcagattcc tttatttttt taaatgtttt ttcatttttt gctttgcatt  10020
gcattcattt gctgaagagc tggcttgtac tttggcaggt gtcatacttg gttattctcc  10080
ttaggatatt ggcccaacaa tctgggagtt gtgaaaggcg cttcgctttt cagacctggg  10140
cgtctgtatc atgactatca taaatttagg attaagacac ctagcctcct accaggatga  10200
atgaggtgtc catgtgacct gctgtgccct ggaattttat acatctttct ctcatagcac  10260
acaccatatt acaatataat cctgcctcat ctaagccaaa ctttcgagag aatcatttac  10320
actcagtggc tacttcagct cccattcact tatcaacctg ctgcaatttt tcacagcccc  10380
caaaggactg cagtctgtgc cttcagggag ctgagggtct agcggaagga aagaaaccag  10440
cagttacagt acagaggggt ttgtgttgga aactctacaa acacaggatg ccctggtagc  10500
tcagaggaag tgcatatcga gcatggtagg taggtagtgg gaagagccaa gatgacttcc  10560
cagaggagaa aagctggacc tgagttttgg agtttcggta aaagtttgct ctaactagtc  10620
caagctgctg tcacaagctt ttagaaatga tgtaaccatg gggcagttga ctgtcgtcat  10680
gttctttgct attttcatga ctctggatgt gcttttccta ttccctggat tgccctttcc  10740
ctcgattcct ctgcaggact gggctttatt aatctccatt tccttgagct tggctatagt  10800
aggtgttcaa taaacatttg ttttgttgtg tgctttgtaa ataggcaatg aagctgattt  10860
cacaagatag gcacaaaagt tagtttcatt acaacacatt accaacagct gtatttttaa  10920
cttttaacat atctcattct aaatcctgtg gcagcacaac ctccttccgt catacctgga  10980
gataaatttt ctttcaaaat ctaatatgca ctgtatttat agaatatgaa acataccgac  11040
catgttttgc aaaaatggga aaggcataac ttagctttgg ggcatgtaag taacaactcc  11100
tgataggaga agaaatgtat tcagaaagct caaattagaa ataaaatggg agactcta    11158
```

```
SEQ ID NO: 206          moltype = AA  length = 748
FEATURE                 Location/Qualifiers
source                  1..748
                        mol_type = protein
                        organism = Homo sapiens
SEQUENCE: 206
MVLLRVLILL LSWAAGMGGQ YGNPLNKYIR HYEGLSYNVD SLHQKHQRAK RAVSHEDQFL  60
RLDFHAHGRH FNLRMKRDTS LFSDEFKVET SNKVLDYDTS HIYTGHIYGE EGSFSHGSVI  120
DGRFEGFIQT RGGTFYVEPA ERYIKDRTLP FHSVIYHEDD INYPHKYGPQ GGCADHSVFE  180
RMRKYQMTGV EEVTQIPQEE HAANGPELLR KKRTTSAEKN TCQLYIQTDH LFFKYYGTRE  240
AVIAQISSHV KAIDTIYQTT DFSGIRNISF MVKRIRINTT ADEKDPTNPF RFPNIGVEKF  300
LELNSEQNHD DYCLAYVFTD RDFDDGVLGL AWVGAPSGSS GGICEKSKLY SDGKKKSLNT  360
GIITVQNYGS HVPPKVSHIT FAHEVGHNFG SPHDSGTECT PGESKNLGQK ENGNYIMYAR  420
ATSGDKLNNN KFSLCSIRNI SQVLEKKRNN CFVESGQPIC GNGMVEQGEE CDCGYSDQCK  480
DECCFDANQP EGRKCKLKPG KQCSPSQGPC CTAQCAFKSK SEKCRDDSDC AREGICNGFT  540
ALCPASDPKP NFTDCNRHTQ VCINGQCAGS ICEKYGLEEC TCASSDGKDD KELCHVCCMK  600
KMDPSTCAST GSVQWSRHFS GRTITLQPGS PCNDFRGYCD VFMRCRLVDA DGPLARLKKA  660
IFSPELYENI AEWIVAHWWA VLLMGIALIM LMAGFIKICS VHTPSSNPKL PPPKPLPGTL  720
KRRRPPQPIQ QPQRQRPRES YQMGHMRR                                    748
```

```
SEQ ID NO: 207          moltype = DNA  length = 1225
FEATURE                 Location/Qualifiers
source                  1..1225
                        mol_type = genomic DNA
                        organism = Homo sapiens
SEQUENCE: 207
agccgcctgc atctgtatcc agcgccaggt cccgccagtc ccagctgcgc gcgcccccca  60
gtcccgcacc cgttcggccc aggctaagtt agccctcacc atgccggtca aaggaggcac  120
caagtgcatc aaatacctgc tgttcggatt taacttcatc ttctggcttg ccgggattgc  180
tgtccttgcc attggactat ggctccgatt cgactctcag accaagagca tcttcgagca  240
agaaactaat aataataatt ccagcttcta cacaggagtc tatattctga tcggagccgg  300
cgccctcatg atgctggtgg gcttcctggg ctgctgcggg gctgtgcagg agtcccagtg  360
catgctggga ctgttcttcg gcttcctctt ggtgatattc gccattgaaa tagctgcggc  420
catctgggga tattcccaca aggatgaggt gattaaggaa gtccaggagt tttacaagga  480
cacctacaac aagctgaaaa ccaaggatga gccccagcgg gaaacgctga aagccatcca  540
ctatgcgttg aactgctgtg gtttggctgg gggcgtggaa cagtttatct cagacatctg  600
ccccaagaag gacgtactcg aaaccttcac cgtgaagtcc tgtcctgatg ccatcaaaga  660
ggtcttcgac aataaattcc acatcatcgg cgcagtgggc atcggcattg ccgtggtcat  720
gatatttggc atgatcttca gtatgatctt gtgctgtgct atccgcagga accgcgagat  780
ggtctagagt cagcttacat ccctgagcag gaaagtttac ccatgaagat tggtgggatt  840
ttttgtttgt ttgttttgtt ttgtttgttg tttgttgttt gttttttgc cactaatttt  900
agtattcatt ctgcattgct agataaaagc tgaagttact ttatgtttgt cttttaatgc  960
```

-continued

```
ttcattcaat attgacattt gtagttgagc ggggggtttg gtttgctttg gtttatattt  1020
tttcagttgt ttgtttttgc ttgttatatt aagcagaaat cctgcaatga aaggtactat  1080
atttgctaga ctctagacaa gatattgtac ataaaagaat tttttgtct ttaaatagat  1140
acaaatgtct atcaacttta atcaagttgt aacttatatt gaagacaatt tgatacataa  1200
taaaaaatta tgacaatgtc ctgga                                        1225

SEQ ID NO: 208          moltype = AA  length = 228
FEATURE                 Location/Qualifiers
source                  1..228
                        mol_type = protein
                        organism = Homo sapiens
SEQUENCE: 208
MPVKGGTKCI KYLLFGFNFI FWLAGIAVLA IGLWLRFDSQ TKSIFEQETN NNNSSFYTGV  60
YILIGAGALM MLVGFLGCCG AVQESQCMLG LFFGFLLVIF AIEIAAAIWG YSHKDEVIKE  120
VQEFYKDTYN KLKTKDEPQR ETLKAIHYAL NCCGLAGGVE QFISDICPKK DVLETFTVKS  180
CPDAIKEVFD NKFHIIGAVG IGIAVVMIFG MIFSMILCCA IRRNREMV               228

SEQ ID NO: 209          moltype = DNA  length = 1847
FEATURE                 Location/Qualifiers
source                  1..1847
                        mol_type = genomic DNA
                        organism = Homo sapiens
SEQUENCE: 209
agtcggctcg agtactcccc gtaacgagga ggtgttctcg gccgtcccac ccttcactgc  60
cgtctccggg ctgcgccgcc ggagccggga cgcgcctccg cagccctcgc cgcctccatc  120
cccgcggccg cagctcctct cgccgtccgc gcgcacacca tgacgaagaa cgagaagaag  180
tccctcaacc agagcctggc cgagtggaag ctcttcatct acaacccgac caccggagaa  240
ttcctggggc gcaccgccaa gagctggggt ttgatcttgc tcttctacct agtttttat   300
gggttcctgg ctgcactctt ctcattcacg atgtgggtta tgcttcagac tctcaacgat  360
gaggttccaa aataccgtga ccagattcct agcccaggac tcatggtttt tccaaaacca  420
gtgaccgcat tggaatatac attcagtagg tctgatccaa cttcgtatgc agggtacatt  480
gaagacctta agaagtttct aaaaccatat actttagaag aacagaagaa cctcacagtc  540
tgtcctgatg gagcactttt tgaacagaag ggtccagttt atgttgcatg tcagtttcct  600
atttcattac ttcaagcatg cagtggtatg aatgatcctg attttggcta ttctcaagga  660
aacccttgta ttcttgtgaa aatgaacaga ataattggat taaagcctga aggagtgcca  720
aggatagatt gtgtttcaaa gaatgaagat ataccaaatg tagcagttta tcctcataat  780
ggaatgatag acttaaaata tttcccatat tatgggaaaa aactgcatgt tgggtatcta  840
cagccattgg ttgctgttca ggtcagcttt gctcctaaca acactgggaa agaagtaaca  900
gttgagtgca agattgatgg atcagccaac ctaaaaagtc aggatgatcg tgacaagttt  960
ttgggacgag ttatgttcaa aatcacagca cgtgcatagt atgagtagga tatctccaca  1020
gagtaaatgt tgtgttgtct gtcttcattt tgtaacagct ggaccttcca ttctagaatt  1080
atgagaccac cttggagaaa ggtgtgtggt acatgacatt gggttacatc ataacgtgct  1140
tccagatcat agtgttcagt gtcctctgaa gtaactgcct gttgcctctg ctgccctttg  1200
aaccagtgta cagtcgccag atagggaccg gtgaacacct gattccaaac atgtaggatg  1260
ggggtcttgt cctcttttta tgtggtttaa ttgccaagtg tctaaagctt aatatgccgt  1320
gctatgtaaa tattttatgg atataacaac tgtcatattt tgatgtcaac agagttttag  1380
ggataaaatg gtacccggcc aacatcaagt gactttatag ctgcaagaaa tgtggtatgt  1440
ggagaagttc tgtatgtgag gaaggaaaaa aagaaaataa aagtgtgttt gaaaaatatt  1500
atcttgggtt ctttgtaaaa tttatttttt acatgctgaa ttagcctcga tctttttgat  1560
taagagcaca aacttttttt tgtaaaacat gtaaaaaaaa aaactgggat taatttttag  1620
tgttggaact gcctcttatt ttaggctgta gataaaatag catttttagg ttagccagtg  1680
tgactatgca cctaattttt tatgagatta aattcataag acttaatttg tacaatagtt  1740
tgtgaaatat cttgttactg cttttattta gcagactgtg gactgtaata aagtatataa  1800
attgtgaaat ataaaaactt ggaacttatt caaagcttca aagcaaa               1847

SEQ ID NO: 210          moltype = AA  length = 279
FEATURE                 Location/Qualifiers
source                  1..279
                        mol_type = protein
                        organism = Homo sapiens
SEQUENCE: 210
MTKNEKKSLN QSLAEWKLFI YNPTTGEFLG RTAKSWGLIL LFYLVFYGFL AALFSFTMWV  60
MLQTLNDEVP KYRDQIPSPG LMVFPKPVTA LEYTFSRSDP TSYAGYIEDL KKFLKPYTLE  120
EQKNLTVCPD GALFEQKGPV YVACQFPISL LQACSGMNDP DFGYSQGNPC ILVKMNRIIG  180
LKPEGVPRID CVSKNEDIPN VAVYPHNGMI DLKYFPYYGK KLHVGYLQPL VAVQVSFAPN  240
NTGKEVTVEC KIDGSANLKS QDDRDKFLGR VMFKITARA                        279

SEQ ID NO: 211          moltype = DNA  length = 5306
FEATURE                 Location/Qualifiers
source                  1..5306
                        mol_type = genomic DNA
                        organism = Homo sapiens
SEQUENCE: 211
ctaggcggcg gccgcggcgg cggaggcagc agcggcggcg gcagtggcgg cggcgaaggt  60
ggcggcggct cggccagtac tcccggcccc cgccatttcg gactgggagc gagcgcggcg  120
caggcactga aggcggcggc ggggccagag gctcagcggc tcccaggtgc gggagagagg  180
cctgctgaaa atgactgaat ataaacttgt ggtagttgga gctggtggcg taggcaagag  240
tgccttgacg atacagctaa ttcagaatca ttttgtggac gaatatgatc caacaataga  300
ggattcctac aggaagcaag tagtaattga tggagaaacc tgtctcttgg atattctcga  360
```

-continued cacagcaggt caagaggagt acagtgcaat gagggaccag tacatgagga ctggggaggg 420
ctttctttgt gtatttgcca taaataatac taaatcattt gaagatattc accattatag 480
agaacaaatt aaaagagtta aggactctga agatgtacct atggtcctag taggaaataa 540
atgtgatttg ccttctagaa cagtagacac aaaacaggct caggacttag caagaagtta 600
tggaattcct tttattgaaa catcagcaaa gacaagacag ggtgttgatg atgccttcta 660
tacattagtt cgagaaattc gaaaacataa agaaaaagatg agcaaagatg gtaaaaagaa 720
gaaaaagaag tcaaagacaa agtgtgtaat tatgtaaata caatttgtac tttttcttta 780
aggcatacta gtacaagtgg taatttttgt acattacact aaattattag catttgtttt 840
agcattacct aatttttttc ctgctccatg cagactgtta gcttttacct taaatgctta 900
ttttaaaatg acagtggaag ttttttttc ctctaagtgc cagtattccc agagttttgg 960
tttttgaact agcaatgcct gtgaaaaaga aactgaatac ctaagatttc tgtcttgggg 1020
cttttggtgc atgcagttga ttacttctta tttttcttac caattgtgaa tgttggtgtg 1080
aaacaaatta atgaagcttt tgaatcatcc ctattctgtg ttttatctag tcacataaat 1140
ggattaatta ctaatttcag ttgagacctt ctaattggtt tttactgaaa cattgaggga 1200
acacaaattt atgggcttcc tgatgatgat tcttctaggc atcatgtcct atagtttgtc 1260
atccctgatg aatgtaaagt tacactgttc acaaaggttt tgtctccttt ccactgctat 1320
tagtcatggt cactctcccc aaaatattat atttttcta taaaaagaaa aaaatggaaa 1380
aaaattacaa ggcaatggaa actattataa ggccatttcc ttttcacatt agataaatta 1440
ctataaagac tcctaatagc ttttcctgtt aaggcagacc cagtatgaaa tggggattat 1500
tatagcaacc attttggggc tatatttaca tgctactaaa tttttataat aattgaaaag 1560
attttaacaa gtataaaaaa ttctcatagg aattaaatgt agtctccctg tgtcagactg 1620
ctctttcata gtataacttt aaatcttttc ttcaacttga gtctttgaag atagttttaa 1680
ttctgcttgt gacattaaaa gattatttgg gccagttata gcttattagg tgttgaagag 1740
accaaggttg caaggccagg ccctgtgtga acctttgagc tttcatagag agtttcacag 1800
catggactgt gtccccacgg tcatccagtg ttgtcatgca ttggttagtc aaaatgggga 1860
gggactaggg cagtttggat agctcaacaa gatacaatct cactctgtgg tggtcctgct 1920
gacaaatcaa gagcattgct tttgtttctt aagaaaacaa actctttttt aaaaattact 1980
tttaaatatt aactcaaaag ttgagatttt ggggtggtgg tgtgccaaga cattaatttt 2040
ttttttaaac aatgaagtga aaaagtttta caatctctag gtttggctag ttctcttaac 2100
actggttaaa ttaacattgc ataaacactt ttcaagtctg atccatattt aataatgctt 2160
taaaataaaa ataaaaacaa tccttttgat aaatttaaaa tgttacttat tttaaaataa 2220
atgaagtgag atggcatggt gaggtgaaag tatcactgga ctaggaagaa ggtgacttag 2280
gttctagata ggtgtctttt aggactctga ttttgaggac atcacttact atccatttct 2340
tcatgttaaa agaagtcatc tcaaactctt agtttttttt ttttacaact atgtaattta 2400
tattccattt acataaggat acacttattt gtcaagctca gcacaatctg taaattttta 2460
acctatgtta caccatcttc agtgccagtc ttgggcaaaa ttgtgcaaga ggtgaagttt 2520
atatttgaat atccattctc gttttaggac tcttcttcca tattagtgtc atcttgcctc 2580
cctaccttcc acatgcccca tgacttgatg cagttttaat acttgtaatt cccctaacca 2640
taagatttac tgctgctgtg gatatctcca tgaagttttc ccactgagtc acatcagaaa 2700
tgccctacat cttatttcct cagggctcaa gagaatctga cagataccat aaagggattt 2760
gacctaatca ctaattttca ggtggtggct gatgctttga acatctcttt gctgcccaat 2820
ccattagcga cagtaggatt tttcaaacct ggtatgaata gacagaaccc tatccagtgg 2880
aaggagaatt taataaagat agtgctgaaa gaattcctta ggtaatctat aactaggact 2940
actcctggta acagtaatac attccattgt tttagtaacc agaaatcttc atgcaatgaa 3000
aaatacttta attcatgaag cttacttttt tttttggtg tcagagtctc gctcttgtca 3060
cccaggctgg aatgcagtgg cgccatctca gctcactgca acctccatct cccaggttca 3120
agcgattctc gtgcctcggc ctcctgagta gctgggatta caggcgtgtg ccactacact 3180
caactaattt ttgtattttt aggagagacg gggtttcacc ctgttggcca ggctggtctc 3240
gaactcctga cctcaagtga ttcacccacc ttggcctcat aaacctgttt tgcagaactc 3300
atttattcag caaatattta ttgagtgcct accagatgcc agtcaccaca caaggcactg 3360
ggtatatggt atccccaaac aagagacata atcccggtcc ttaggtagtg ctagtgtggt 3420
ctgtaatatc ttactaaggc ctttggtata cgacccagag ataacacgat gcgtatttta 3480
gttttgcaaa gaaggggttt ggtctctgtg ccagctctat aattgttttg ctacgattcc 3540
actgaaactc ttcgatcaag ctactttatg taaatcactt cattgtttta aaggaataaa 3600
cttgattata ttgttttttt atttggcata actgtgattc ttttaggaca attactgtac 3660
acattaaggt gtatgtcaga tattcatatt gacccaaatg tgtaatattc cagttttctc 3720
tgcataagta attaaaatat acttaaaaat taatagtttt atctgggtac aaataaacag 3780
gtgcctgaac tagttcacag acaaggaaac ttctatgtaa aaatcactat gatttctgaa 3840
ttgctatgtg aaactacaga tctttggaac actgtttagg tagggtgtta agacttacac 3900
agtacctcgt ttctacacag agaaagaaat ggccatactt caggaactgc agtgcttatg 3960
aggggatatt taggcctctt gaatttttga tgtagatggg cattttttta aggtagtggt 4020
taattacctt tatgtgaact ttgaatggtt taacaaaaga tttgtttttg tagagatttt 4080
aaagggggag aattctagaa ataaatgtta cctaattatt acagccttaa agacaaaaat 4140
ccttgttgaa gttttttaa aaaaagctaa attacataga cttaggcatt aacatgtttg 4200
tggaagaata tagcagacgt atattgtatc atttgagtga atgttcccaa gtaggcattc 4260
taggctctat ttaactgagt cacactgcat aggaatttag aacctaactt ttataggtta 4320
tcaaaactgt tgtcaccatt gcacaatttt gtcctaatat atacatagaa actttgtggg 4380
gcatgttaag ttacagtttg cacaagttca tctcatttgt attccattga ttttttttt 4440
cttctaaaca tttttcttc aaacagtata taactttttt taggggattt ttttttagac 4500
agcaaaaact atctgaagat ttccatttgt caaaaagtaa tgatttcttg ataattgtgt 4560
agtaatgttt tttagaaccc agcagttacc ttaaagctga atttatattt agtaacttct 4620
gtgttaatac tggatagcat gaattctgca ttgagaaact gaatagctgt cataaaatga 4680
aactttcttt ctaaagaaag atactcacat gagttcttga agaatagtca taactagatt 4740
aagatctgtg ttttagttta atagtttgaa gtgcctgttt gggataatga taggtaattt 4800
agatgaattt aggggaaaaa aaagttatct gcagatatgt tgagggccca tctctccccc 4860
cacaccccca cagagctaac tgggttacag tgttttatcc gaaagtttcc aattccactg 4920
tcttgtgttt tcatgttgaa aatactttg catttttcct ttgagtgcca atttcttact 4980
agtactattt cttaatgtaa catgtttacc tggaatgtat tttaactatt tttgtatagt 5040
gtaaactgaa acatgcacat tttgtacatt gtgctttctt ttgtgggaca tatgcagtgt 5100

```
gatccagttg ttttccatca tttggttgcg ctgacctagg aatgttggtc atatcaaaca  5160
ttaaaaatga ccactctttt aattgaaatt aacttttaaa tgtttatagg agtatgtgct  5220
gtgaagtgat ctaaaatttg taatattttt gtcatgaact gtactactcc taattattgt  5280
aatgtaataa aaatagttac agtgac                                      5306

SEQ ID NO: 212         moltype = AA  length = 188
FEATURE                Location/Qualifiers
source                 1..188
                       mol_type = protein
                       organism = Homo sapiens
SEQUENCE: 212
MTEYKLVVVG AGGVGKSALT IQLIQNHFVD EYDPTIEDSY RKQVVIDGET CLLDILDTAG  60
QEEYSAMRDQ YMRTGEGFLC VFAINNTKSF EDIHHYREQI KRVKDSEDVP MVLVGNKCDL  120
PSRTVDTKQA QDLARSYGIP FIETSAKTRQ GVDDAFYTLV REIRKHKEKM SKDGKKKKKK  180
SKTKCVIM                                                          188

SEQ ID NO: 213         moltype = DNA  length = 42
FEATURE                Location/Qualifiers
misc_feature           1..42
                       note = Description of Artificial Sequence: Synthetic
                        oligonucleotide
source                 1..42
                       mol_type = other DNA
                       organism = synthetic construct
SEQUENCE: 213
aaaaagaaga aaaagaagaa gaagacaaag tgtgtaatta tg                    42

SEQ ID NO: 214         moltype = AA  length = 14
FEATURE                Location/Qualifiers
REGION                 1..14
                       note = Description of Artificial Sequence: Synthetic peptide
source                 1..14
                       mol_type = protein
                       organism = synthetic construct
SEQUENCE: 214
KKKKKKKKTK CVIM                                                   14

SEQ ID NO: 215         moltype = DNA  length = 4296
FEATURE                Location/Qualifiers
source                 1..4296
                       mol_type = genomic DNA
                       organism = Homo sapiens
SEQUENCE: 215
gcacttgggc gttggacccc gcatcttatt agcaaccagg gagatttctc cattttcctc  60
ttgtctacag tgcggctaca aatctgggat ttttttatta cttctttttt tttcgaacta  120
cacttgggct cctttttttg tgctcgactt ttccaccctt tttccctccc tcctgtgctg  180
ctgctttttg atctcttcga ctaaaatttt tttatccgga gtgtatttaa tcggttctgt  240
tctgtcctct ccaccacccc cacccccctc cctccggtgt gtgtgccgct gccgctgttg  300
ccgccgccgc tgctgctgct gctcgccccg tcgttacacc aacccgaggc tctttgtttc  360
ccctcttgga tctgttgagt ttctttgttg aagaagccag catgggtgcc cagttctcca  420
agaccgcagc gaagggagaa gccgccgcgg agaggcctgg ggaggcggct gtggcctcgt  480
cgccttccaa agcgaacgga caggagaatg gccacgtgaa ggtaaacggc gacgcttcgc  540
ccgcggccgc cgagtcgggc gccaaggagg agctgcaggc caacggcagc gccccggccg  600
ccgacaagga ggagcccgcg gccgccggga gcggggcggc gtcgccctcc gcggccgaga  660
aaggtgagcc ggccgccgcc gctgcccccg aggccggggc cagcccggta gagaaggagg  720
cccccgcgga aggcgaggct gccgagcccg gctcgcccac ggccgcggag ggagaggccg  780
cgtcggccgc ctcctcgact tcttcgccca aggccgagga cggggccacg ccctcgccca  840
gcaacgagac cccgaaaaaa aaaaagaagc gcttttcctt caagaagtct ttcaagctga  900
gcggcttctc cttcaagaag aacaagaagg aggctggaga aggcggtgag gctgaggcgc  960
ccgctgccga aggcggcaag gacgaggccg ccgggggcgc agctgcggcc gccgccgagg  1020
cgggcgcggc ctccggggag caggcagcgg cgccgggcga ggaggcggca gcgggcgagg  1080
agggggcggc gggtggcgac ccgcaggagg ccaagcccca ggaggccgct gtcgcgccag  1140
agaagccgcc cgccagcgac gagaccaagg ccgccgagga gcccagcaag gtggaggaga  1200
aaaaggccga ggaggccggg gccagcgccg ccgcctgcga ggccccctcc gccgccgggc  1260
ccggcgcgcc cccggagcag gaggcagccc ccgcggagga gcccgcggcc gccgcagcct  1320
cgtcagcctg cgcagccccc tcacaggagg cccagcccga gtgcagtcca gaagcccccc  1380
cagcggaggc ggcagagtaa aagagcaagc ttttgtgaga taatcgaaga actttctcc   1440
cccgtttgtt tgttggagtg gtgccaggta ctggttttgg agaacttgtc tacaaccagg  1500
gattgatttt aaagatgtct ttttttattt tacttttttt taagcaccaa attttgttgt  1560
tttttttttt tctcccctcc ccacagatcc catctcaaat cattctgtta accaccattc  1620
caacaggtcg aggagagctt aaacaccttc ttcctctgcc ttgtttctct tttatttttt  1680
attttttcgc atcagtatta atgtttttgc atactttgca tctttattca aaagtgtaaa  1740
ctttctttgt caatctatgg acatgcccat atatgaagga gatgggtggg tcaaaaaggg  1800
atatcaaatg aagtgatggg gtcacaatgg ggaaattgaa gtggtgcata acattgccaa  1860
aatagtgtgc cactagaaat ggtgtaaagg ctgtcttttt ttttttttta aaagaaaagt  1920
tattaccatg tattttgtga ggcaggttta caacactaca agtcttgagt taagaaggaa  1980
agaggaaaaa agaaaaaaca ccaataccca gatttaaaaa aaaaaaaacg atcatagtct  2040
taggagttca tttaaaccat aggaactttt cacttatctc atgttagctg taccagtcag  2100
tgattaagta gaactacaag ttgtataggc tttattgttt attgctggtt tatgacctta  2160
```

-continued

```
ataaagtgta attatgtatt accagcaggg tgtttttaac tgtgactatt gtataaaaac  2220
aaatcttgat atccagaagc acatgaagtt tgcaactttc caccctgccc atttttgtaa  2280
aactgcagtc atcttggacc ttttaaaaca caaattttaa actcaaccaa gctgtgataa  2340
gtggaatggt tactgtttat actgtggtat gtttttgatt acagcagata atgctttctt  2400
ttccagtcgt ctttgagaat aaaggaaaaa aaatcttcag atgcaatggt tttgtgtagc  2460
atcttgtcta tcatgttttg taaatactgg agaagctttg accaatttga cttagagatg  2520
gaatgtaact ttgcttacaa aaattgctat taaactcctg cttaaggtgt tctaattttc  2580
tgtgagcaca ctaaaagcga aaaataaatg tgaataaaat gtacaaattt gttgtgtttt  2640
tttatgttct aataaatactg agacttctag gtcttaggtt aatttttagg aagatcttgc  2700
atgccatcag gagtaaattt tattgtggtt cttaatctga agttttcaag ctctgaaatt  2760
cataatccgc agtgtcagat tacgtagagg aagatcttac aacatttcca tgtcaaatct  2820
gttaccattt attggcattt agttttcatt taagaattga acataattat ttttattgta  2880
gctatatagc atgtcagatt aaatcattta caacaaaagg ggtgtgaacc taagactatt  2940
taaatgtctt atgagaaaat ttcataaagc cattctcttg tcattcaggt ccagaaacaa  3000
attttaaact gagtgagagt ctatagaatc catactgcag atgggtcatg aaatgtgacc  3060
aaatgtgttt caaaaattga tggtgtatta cctgctattg taattgctta gtgcttggct  3120
aatttccaaa ttattgcata atatgttcta ccttaagaaa acaggttat gtaacaaagt  3180
aatggtgttg aatggatgat gtcagttcat gggcctttag catagtttta agcatccttt  3240
ttttttttt tttttgaaag tgtgttagca tcttgttact caaaggataa gacagacaat  3300
aatacttcac tgaatcttaa taatctttac tagtttacct cctctgctct ttgccacccg  3360
ataactggat atcttttcct tcaaaggacc ctaaactgat tgaaatttaa gatatgtatc  3420
aaaaacatta tttcatttaa tgcacatctg ttttgctgtt tttgagcagt gtgcagttta  3480
gggttcatga taaatcattg aaccacatgt gtaacaactg aatgccaaat cttaaactca  3540
ttagaaaaat aacaaattag gtttgacac gcattcttaa ttggaataat ggatcaaaaa  3600
tagtggttca tgaccttacc aaacaccctt gctactaata aaatcaaata acacttagaa  3660
gggtatgtat ttttagttag ggtttcttga tcttggagga tgtttgaaag ttaaaaattg  3720
aatttggtaa ccaaaggact gatttatggg tctttcctat cttaaccaac gttttcttag  3780
ttacctagat ggccaagtac agtgcctggt atgtagtaag actcagtaaa aaagtggatt  3840
tttaaaaata actcccaaag tgaatagtca aaaatcctgt tagcaaactg ttatatattg  3900
ctaagtttgt tcttttaaca gctggaattt attaagatgc attattttga ttttattcac  3960
tgcctaaaac actttgggtg gtattgatgg agttggtgga ttttcctcca agtgattaaa  4020
tgaaatttga cgtatctttt catccaaagt tttgtacatc atgttttcta acggaaaaaa  4080
atgttaatat ggctttttg tattactaaa aatagctttg agattaagga aaaataaata  4140
actcttgtac agttcagtat tgtctattaa atctgtattg gcagtatgta taatggcatt  4200
tgctgtggtt acaaaatact tcctctgggt tataataatc atttgatcca attcctattg  4260
cttgtaaaat aaagttttac cagttgatat aatcaa                           4296
```

```
SEQ ID NO: 216         moltype = AA  length = 332
FEATURE                Location/Qualifiers
source                 1..332
                       mol_type = protein
                       organism = Homo sapiens
SEQUENCE: 216
MGAQFSKTAA KGEAAAERPG EAAVASSPSK ANGQENGHVK VNGDASPAAA ESGAKEELQA  60
NGSAPAADKE EPAAAGSGAA SPSAAEKGEP AAAAAPEAGA SPVEKEAPAE GEAAEPGSPT  120
AAEGEAASAA SSTSSPKAED GATPSPSNET PKKKKKRFSF KKSFKLSGFS FKKNKKEAGE  180
GGEAEAPAAE GGKDEAAGGA AAAAAEAGAA SGEQAAAPGE EAAAGEEGAA GGDPQEAKPQ  240
EAAVAPEKPP ASDETKAAEE PSKVEEKKAE EAGASAAACE APSAAGPGAP PEQEAAPAEE  300
PAAAAASSAC AAPSQEAQPE CSPEAPPAEA AE                              332
```

```
SEQ ID NO: 217         moltype = DNA  length = 24
FEATURE                Location/Qualifiers
misc_feature           1..24
                       note = Description of Artificial Sequence: Synthetic
                        oligonucleotide
source                 1..24
                       mol_type = other DNA
                       organism = synthetic construct
SEQUENCE: 217
atgggttgct gtttctccaa gacc                                       24
```

```
SEQ ID NO: 218         moltype = AA  length = 8
FEATURE                Location/Qualifiers
REGION                 1..8
                       note = Description of Artificial Sequence: Synthetic peptide
source                 1..8
                       mol_type = protein
                       organism = synthetic construct
SEQUENCE: 218
MGCCFSKT                                                         8
```

```
SEQ ID NO: 219         moltype = DNA  length = 2079
FEATURE                Location/Qualifiers
misc_feature           1..2079
                       note = Description of Artificial Sequence: Synthetic
                        polynucleotide
source                 1..2079
                       mol_type = other DNA
                       organism = synthetic construct
```

```
SEQUENCE: 219
atgtacagga tgcaactcct gtcttgcatt gcactaagtc ttgcacttgt cacgaactcg  60
atatcggcca tggttagatc tgacaaaact cacacatgcc caccgtgccc agcacctgaa  120
ctcctggggg gaccgtcagt cttcctcttc cccccaaaac ccaaggacac cctcatgatc  180
tcccggaccc ctgaggtcac atgcgtggtg gtggacgtga gccacgaaga ccctgaggtc  240
aagttcaact ggtacgtgga cggcgtggag gtgcataatg ccaagacaaa gccgcgggag  300
gagcagtaca acagcacgta ccgtgtggtc agcgtcctca ccgtcctgca ccaggactgg  360
ctgaatggca aggagtacaa gtgcaaggtc tccaacaaag ccctcccagc ccccatcgag  420
aaaaccatct ccaaagccaa agggcagccc cgagaaccac aggtgtacac cctgccccca  480
tcccgggagg agatgaccaa gaaccaggtc agcctgacct gcctggtcaa aggcttctat  540
cccagcgaca tcgccgtgga gtgggagagc aatgggcagc cggagaacaa ctacaagacc  600
acgcctcccg tgctggactc cgacggctcc ttcttcctct acagcaagct caccgtggac  660
aagagcaggt ggcagcaggg gaacgtcttc tcatgctccg tgatgcacga ggctctgcac  720
aaccactaca cgcagaagag cctctccctg tctccgggta aagccagcgg aagtggcgga  780
ggaggcggtc ctggagaagg tgcctatgta taccgctcag cattcagtgt gggattggag  840
acttacgtta ctatccccaa catgcccatt cgctttacca agatcttcta caatcagcaa  900
aaccactatg atggctccac tggtaaattc cactgcaaca ttcctgggct gtactacttt  960
gcctaccaca tcacagtcta tatgaaggat gtgaaggtca gcctcttcaa gaaggacaag  1020
gctatgctct tcacctatga tcagtaccag gaaaataatg tggaccaggc ctccggctct  1080
gtgctcctgc atctggaggt gggcgaccaa gtctggctcc aggtgtatgg ggaaggagag  1140
cgtaatggac tctatgctga taatgacaat gactccacct tcacaggctt tcttctctac  1200
catgacacca actctagaaa gcttcctgga gaaggtgcct atgtataccg ctcagcattc  1260
agtgtgggat tggagactta cgttactatc cccaacatgc ccattcgctt taccaagatc  1320
ttctacaatc agcaaaacca ctatgatggc tccactggta aattccactg caacattcct  1380
gggctgtact actttgccta ccacatcaca gtctatatga aggatgtgaa ggtcagcctc  1440
ttcaagaagg acaaggctat gctcttcacc tatgatcagt accaggaaaa taatgtggac  1500
caggcctccg gctctgtgct cctgcatctg gaggtgggcg accaagtctg gctccaggtg  1560
tatggggaag gagagcgtaa tggactctat gctgataatg acaatgactc caccttcaca  1620
ggctttcttc tctaccatga caccaacact agtcctggag aaggtgccta tgtataccgc  1680
tcagcattca gtgtgggatt ggagacttac gttactatcc ccaacatgcc cattcgcttt  1740
accaagatct tctacaatca gcaaaaccac tatgatggct ccactggtaa attccactgc  1800
aacattcctg ggctgtacta ctttgcctac cacatcacag tctatatgaa ggatgtgaag  1860
gtcagcctct tcaagaagga caaggctatg ctcttcacct atgatcagta ccaggaaaat  1920
aatgtggacc aggcctccgg ctctgtgctc ctgcatctgg aggtgggcga ccaagtctgg  1980
ctccaggtgt atggggaagg agagcgtaat ggactctatg ctgataatga caatgactcc  2040
accttcacag gctttcttct ctaccatgac accaactaa                        2079

SEQ ID NO: 220         moltype = AA  length = 227
FEATURE                Location/Qualifiers
REGION                 1..227
                       note = Description of Artificial Sequence: Synthetic
                        polypeptide
source                 1..227
                       mol_type = protein
                       organism = synthetic construct
SEQUENCE: 220
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 221         moltype = DNA  length = 27
FEATURE                Location/Qualifiers
misc_feature           1..27
                       note = Description of Artificial Sequence: Synthetic
                        oligonucleotide
source                 1..27
                       mol_type = other DNA
                       organism = synthetic construct
SEQUENCE: 221
gctactaact tcagcctgct gaagcag                                      27

SEQ ID NO: 222         moltype = AA  length = 17
FEATURE                Location/Qualifiers
REGION                 1..17
                       note = Description of Artificial Sequence: Synthetic peptide
source                 1..17
                       mol_type = protein
                       organism = synthetic construct
SEQUENCE: 222
ATNFSLKQAG DVENPGP                                                 17

SEQ ID NO: 223         moltype = DNA  length = 1290
FEATURE                Location/Qualifiers
misc_feature           1..1290
                       note = Description of Artificial Sequence: Synthetic
                        polynucleotide
source                 1..1290
                       mol_type = other DNA
```

```
                         organism = synthetic construct
SEQUENCE: 223
atggcttgcc ttggatttca gcggcacaag gctcagctga acctggctac caggacctgg  60
ccctgcactc tcctgttttt tcttctcttc atccctgtct tctgcaaagc aatgcacgtg  120
gcccagcctg ctgtggtact ggccagcagc cgaggcatcg ccagctttgt gtgtgagtat  180
gcatctccag gcaaagccac tgaggtccgg gtgacagtgc ttcggcaggc tgacagccag  240
gtgactgaag tctgtgcggc aacctacatg atggggaatg agttgacctt cctagatgat  300
tccatctgca cgggcacctc cagtggaaat caagtgaacc tcactatcca aggactgagg  360
gccatggaca cgggactcta catctgcaag gtggagctca tgtacccacc gccatactac  420
ctgggcatag gcaacggaac ccagatttat gtaattgatc cagaaccgtg cccagattct  480
gacatcgatg acaaaactca cacatgccca ccgtgcccag cacctgaact cctgggggga  540
ccgtcagtct tcctcttccc cccaaaaccc aaggacaccc tcatgatctc ccggacccct  600
gaggtcacat gcgtggtggt ggacgtgagc cacgaagacc ctgaggtcaa gttcaactgg  660
tacgtggacg gcgtggaggt gcataatgcc aagacaaagc cgcgggagga gcagtacaac  720
agcacgtacc gtgtggtcag cgtcctcacc gtcctgcacc aggactggct gaatggcaag  780
gagtacaagt gcaaggtctc caacaaagcc ctcccagccc ccatcgagaa aaccatctcc  840
aaagccaaag ggcagccccg agaaccacag gtgtacaccc tgcccccatc ccgggaggag  900
atgaccaaga accaggtcag cctgacctgc ctggtcaaag gcttctatcc cagcgacatc  960
gccgtggagt gggagagcaa tgggcagccg gagaacaact acaagaccac gcctcccgtg  1020
ctggactccg acggctcctt cttcctctac agcaagctca ccgtggacaa gagcaggtgg  1080
cagcagggga acgtcttctc atgctccgtg atgcacgagg ctctgcacaa ccactacacg  1140
cagaagagcc tctccctgtc tccgggtaaa atcgatccaa ataaaggaag tggaaccact  1200
tcaggtacta cccgtcttct atctgggcac acgtgtttca cgttgacagg tttgcttggg  1260
acgctagtaa ccatgggctt gctgacttag                                 1290

SEQ ID NO: 224           moltype = AA  length = 429
FEATURE                  Location/Qualifiers
REGION                   1..429
                         note = Description of Artificial Sequence: Synthetic
                          polypeptide
source                   1..429
                         mol_type = protein
                         organism = synthetic construct
SEQUENCE: 224
MACLGFQRHK AQLNLATRTW PCTLLFFLLF IPVFCKAMHV AQPAVVLASS RGIASFVCEY  60
ASPGKATEVR VTVLRQADSQ VTEVCAATYM MGNELTFLDD SICTGTSSGN QVNLTIQGLR  120
AMDTGLYICK VELMYPPPYY LGIGNGTQIY VIDPEPCPDS DIDDKTHTCP PCPAPELLGG  180
PSVFLFPPKP KDTLMISRTP EVTCVVVDVS HEDPEVKFNW YVDGVEVHNA KTKPREEQYN  240
STYRVVSVLT VLHQDWLNGK EYKCKVSNKA LPAPIEKTIS KAKGQPREPQ VYTLPPSREE  300
MTKNQVSLTC LVKGFYPSDI AVEWESNGQP ENNYKTTPPV LDSDGSFFLY SKLTVDKSRW  360
QQGNVFSCSV MHEALHNHYT QKSLSLSPGK IDPNKGSGTT SGTTRLLSGH TCFTLTGLLG  420
TLVTMGLLT                                                        429

SEQ ID NO: 225           moltype = DNA  length = 828
FEATURE                  Location/Qualifiers
misc_feature             1..828
                         note = Description of Artificial Sequence: Synthetic
                          polynucleotide
source                   1..828
                         mol_type = other DNA
                         organism = synthetic construct
SEQUENCE: 225
atgaggatat ttgctgtctt tatattcatg acctactggc atttgctgaa cgcatttact  60
gtcacggttc ccaaggacct atatgtggta gagtatggta gcaatatgac aattgaatgc  120
aaattcccag tagaaaaaca attagacctg gctgcactaa ttgtctattg ggaaatggag  180
gataagaaca ttattcaatt tgtgcatgga gaggaagacc tgaaggttca gcatagtagc  240
tacagacaga gggcccggct gttgaaggac cagctctccc tgggaaatgc tgcacttcag  300
atcacagatg tgaaattgca ggatgcaggg gtgtaccgct gcatgatcag ctatggtggt  360
gccgactaca agcgaattac tgtgaaagtc aatgccccat acaacaaaat caaccaaaga  420
attttggttg tggatccagt cacctctgaa catgaactga catgtcaggc tgagggctac  480
cccaaggccg aagtcatctg gacaagcagt gaccatcaag tcctgagtgg taagaccacc  540
accaccaatt ccaagagaga ggagaagctt ttcaatgtga ccagcacact gagaatcaac  600
acaacaacta atgagatttt ctactgcact tttaggagat tagatcctga ggaaaaccat  660
acagctgaat tggtcatccc agaactacct ctggcacatc ctccaaatga aaggccaaat  720
aaaggaagtg gaaccacttc aggtactacc cgtcttctat ctgggcacac gtgtttcacg  780
ttgacaggtt tgcttgggac gctagtaacc atggcttgc tgacttag               828

SEQ ID NO: 226           moltype = AA  length = 275
FEATURE                  Location/Qualifiers
REGION                   1..275
                         note = Description of Artificial Sequence: Synthetic
                          polypeptide
source                   1..275
                         mol_type = protein
                         organism = synthetic construct
SEQUENCE: 226
MRIFAVFIFM TYWHLLNAFT VTVPKDLYVV EYGSNMTIEC KFPVEKQLDL AALIVYWEME  60
DKNIIQFVHG EEDLKVQHSS YRQRARLLKD QLSLGNAALQ ITDVKLQDAG VYRCMISYGG  120
ADYKRITVKV NAPYNKINQR ILVVDPVTSE HELTCQAEGY PKAEVIWTSS DHQVLSGKTT  180
```

```
TTNSKREEKL FNVTSTLRIN TTTNEIFYCT FRRLDPEENH TAELVIPELP LAHPPNERPN  240
KGSGTTSGTT RLLSGHTCFT LTGLLGTLVT MGLLT                             275

SEQ ID NO: 227          moltype = DNA  length = 1518
FEATURE                 Location/Qualifiers
misc_feature            1..1518
                        note = Description of Artificial Sequence: Synthetic
                         polynucleotide
source                  1..1518
                        mol_type = other DNA
                        organism = synthetic construct
SEQUENCE: 227
atgaggatat ttgctgtctt tatattcatg acctactggc atttgctgaa cgcatttact  60
gtcacggttc ccaaggacct atatgtggta gagtatggta gcaatatgac aattgaatgc  120
aaattcccag tagaaaaaca attagacctg gctgcactaa ttgtctattg ggaaatggag  180
gataagaaca ttattcaatt tgtgcatgga gaggaagacc tgaaggttca gcatagtagc  240
tacagacaga gggcccggct gttgaaggac cagctctccc tgggaaatgc tgcacttcag  300
atcacagatg tgaaattgca ggatgcaggg gtgtaccgct gcatgatcag ctatggtggt  360
gccgactaca agcgaattac tgtgaaagtc aatgccccat acaacaaaat caaccaaaga  420
attttggttg tggatccagt cacctctgaa catgaactga catgtcaggc tgagggctac  480
cccaaggccg aagtcatctg gacaagcagt gaccatcaag tcctgagtgg taagaccacc  540
accaccaatt ccaagagaga ggagaagctt ttcaatgtga ccagcacact gagaatcaac  600
acaacaacta atgagatttt ctactgcact tttaggagat tagatcctga ggaaaaccat  660
acagctgaat tggtcatccc agaactacct ctggcacatc ctccaaatga aaggatcgat  720
gtcgagccac tgggcatgga gaatgggaac attgccaact cacagatcgc cgcctcatct  780
gtgcgtgtga ccttcttggg tttgcagcat tgggtcccgg agctggcccg cctgaaccgc  840
gcaggcatgg tcaatgcctg gacacccagc agcaatgacg ataacccctg gatccaggtg  900
aacctgctgc ggaggatgtg ggtaacaggt gtggtgacgc agggtgccag ccgcttggcc  960
agtcatgagt acctgaaggc cttcaaggtg gcctacagcc ttaatggaca cgaattcgat  1020
ttcatccatg atgttaataa aaaacacaag gagtttgtgg gtaactggaa caaaaacgcg  1080
gtgcatgtca acctgtttga gacccctgtg gaggctcagt acgtgagatt gtaccccacg  1140
agctgccaca cggcctgcac tctgcgcttt gagctactgg gctgtgagct gaacggatgc  1200
gccaatcccc tgggcctgaa gaataacagc atccctgaca agcagatcac ggcctccagc  1260
agctacaaga cctggggctt gcatctcttc agctggaacc cctcctatgc acggctggac  1320
aagcagggca acttcaacgc ctgggttgcg gggagctacg gtaacgatca gtggctgcag  1380
atcttccctg gcaactggga caaccactcc cacaagaaga acttgtttga gacgcccatc  1440
ctggctcgct atgtgcgcat cctgcctgta gcctggcaca accgcatcgc cctgcgcctg  1500
gagctgctgg gctgttag                                                1518

SEQ ID NO: 228          moltype = AA  length = 505
FEATURE                 Location/Qualifiers
REGION                  1..505
                        note = Description of Artificial Sequence: Synthetic
                         polypeptide
source                  1..505
                        mol_type = protein
                        organism = synthetic construct
SEQUENCE: 228
MRIFAVFIFM TYWHLLNAFT VTVPKDLYVV EYGSNMTIEC KFPVEKQLDL AALIVYWEME  60
DKNIIQFVHG EEDLKVQHSS YRQRARLLKD QLSLGNAALQ ITDVKLQDAG VYRCMISYGG  120
ADYKRITVKV NAPYNKINQR ILVVDPVTSE HELTCQAEGY PKAEVIWTSS DHQVLSGKTT  180
TTNSKREEKL FNVTSTLRIN TTTNEIFYCT FRRLDPEENH TAELVIPELP LAHPPNERID  240
VEPLGMENGN IANSQIAASS VRVTFLGLQH WVPELARLNR AGMVNAWTPS SNDDNPWIQV  300
NLLRRMWVTG VVTQGASRLA SHEYLKAFKV AYSLNGHEFD FIHDVNKKHK EFVGNWNKNA  360
VHVNLFETPV EAQYVRLYPT SCHTACTLRF ELLGCELNGC ANPLGLKNNS IPDKQITASS  420
SYKTWGLHLF SWNPSYARLD KQGNFNAWVA GSYGNDQWLQ IFPGNWDNHS HKKNLFETPI  480
LARYVRILPV AWHNRIALRL ELLGC                                        505

SEQ ID NO: 229          moltype = DNA  length = 1521
FEATURE                 Location/Qualifiers
misc_feature            1..1521
                        note = Description of Artificial Sequence: Synthetic
                         polynucleotide
source                  1..1521
                        mol_type = other DNA
                        organism = synthetic construct
SEQUENCE: 229
atgaggatat ttgctgtctt tatattcatg acctactggc atttgctgaa cgcatttact  60
gtcacggttc ccaaggacct atatgtggta gagtatggta gcaatatgac aattgaatgc  120
aaattcccag tagaaaaaca attagacctg gctgcactaa ttgtctattg ggaaatggag  180
gataagaaca ttattcaatt tgtgcatgga gaggaagacc tgaaggttca gcatagtagc  240
tacagacaga gggcccggct gttgaaggac cagctctccc tgggaaatgc tgcacttcag  300
atcacagatg tgaaattgca ggatgcaggg gtgtaccgct gcatgatcag ctatggtggt  360
gccgactaca agcgaattac tgtgaaagtc aatgccccat acaacaaaat caaccaaaga  420
attttggttg tggatccagt cacctctgaa catgaactga catgtcaggc tgagggctac  480
cccaaggccg aagtcatctg gacaagcagt gaccatcaag tcctgagtgg taagaccacc  540
accaccaatt ccaagagaga ggagaagctt ttcaatgtga ccagcacact gagaatcaac  600
acaacaacta atgagatttt ctactgcact tttaggagat tagatcctga ggaaaaccat  660
acagctgaat tggtcatccc agaactacct ctggcacatc ctccaaatga aaggatcgat  720
```

```
gacaaaactc acacatgccc accgtgccca gcacctgaac tcctgggggg accgtcagtc  780
ttcctcttcc ccccaaaacc caaggacacc ctcatgatct cccggacccc tgaggtcaca  840
tgcgtggtgg tggacgtgag ccacgaagac cctgaggtca agttcaactg gtacgtggac  900
ggcgtggagg tgcataatgc caagacaaag ccgcgggagg agcagtacaa cagcacgtac  960
cgtgtggtca gcgtcctcac cgtcctgcac caggactggc tgaatggcaa ggagtacaag  1020
tgcaaggtct ccaacaaagc cctcccagcc cccatcgaga aaaccatctc caaagccaaa  1080
gggcagcccc gagaaccaca ggtgtacacc ctgcccccat cccgggagga gatgaccaag  1140
aaccaggtca gcctgacctg cctggtcaaa ggcttctatc ccagcgacat cgccgtggag  1200
tgggagagca atgggcagcc ggagaacaac tacaagacca cgcctcccgt gctggactcc  1260
gacggctcct tcttcctcta cagcaagctc accgtggaca agagcaggtg gcagcagggg  1320
aacgtcttct catgctccgt gatgcacgag gctctgcaca accactacac gcagaagagc  1380
ctctccctgt ctccgggtaa aatcgatcca aataaaggaa gtggaaccac ttcaggtact  1440
acccgtcttc tatctgggca cacgtgtttc acgttgacag gtttgcttgg gacgctagta  1500
accatgggct tgctgactta g                                            1521

SEQ ID NO: 230          moltype = AA  length = 506
FEATURE                 Location/Qualifiers
REGION                  1..506
                        note = Description of Artificial Sequence: Synthetic
                         polypeptide
source                  1..506
                        mol_type = protein
                        organism = synthetic construct
SEQUENCE: 230
MRIFAVFIFM TYWHLLNAFT VTVPKDLYVV EYGSNMTIEC KFPVEKQLDL AALIVYWEME  60
DKNIIQFVHG EEDLKVQHSS YRQRARLLKD QLSLGNAALQ ITDVKLQDAG VYRCMISYGG  120
ADYKRITVKV NAPYNKINQR ILVVDPVTSE HELTCQAEGY PKAEVIWTSS DHQVLSGKTT  180
TTNSKREEKL FNVTSTLRIN TTTNEIFYCT FRRLDPEENH TAELVIPELP LAHPPNERID  240
DKTHTCPPCP APELLGGPSV FLFPPKPKDT LMISRTPEVT CVVVDVSHED PEVKFNWYVD  300
GVEVHNAKTK PREEQYNSTY RVVSVLTVLH QDWLNGKEYK CKVSNKALPA PIEKTISKAK  360
GQPREPQVYT LPPSREEMTK NQVSLTCLVK GFYPSDIAVE WESNGQPENN YKTTPPVLDS  420
DGSFFLYSKL TVDKSRWQQG NVFSCSVMHE ALHNHYTQKS LSLSPGKIDP NKGSGTTSGT  480
TRLLSGHTCF TLTGLLGTLV TMGLLT                                       506

SEQ ID NO: 231          moltype = DNA  length = 1464
FEATURE                 Location/Qualifiers
misc_feature            1..1464
                        note = Description of Artificial Sequence: Synthetic
                         polynucleotide
source                  1..1464
                        mol_type = other DNA
                        organism = synthetic construct
SEQUENCE: 231
atgatcttcc tcctgctaat gttgagcctg gaattgcagc ttcaccagat agcagcttta  60
ttcacagtga cagtccctaa ggaactgtac ataatagagc atggcagcaa tgtgaccctg  120
gaatgcaact ttgacactgg aagtcatgtg aaccttggag caataacagc cagtttgcaa  180
aaggtggaaa atgatacatc cccacaccgt gaaagagcca ctttgctgga ggagcagctg  240
cccctaggga aggcctcgtt ccacatacct caagtccaag tgagggacga aggacagtac  300
caatgcataa tcatctatgg ggtcgcctgg gactacaagt acctgactct gaaagtcaaa  360
gcttcctaca ggaaaataaa cactcacatc ctaaaggttc cagaaacaga tgaggtagag  420
ctcacctgcc aggctacagg ttatcctctg gcagaagtat cctggccaaa cgtcagcgtt  480
cctgccaaca ccagccactc caggacccct gaaggcctct accaggtcac cagtgttctg  540
cgcctaaagc cacccccctgg cagaaacttc agctgtgtgt tctggaatac tcacgtgagg  600
gaacttactt tggccagcat tgaccttcaa agtcagatgg aacccaggac ccatccaact  660
atcgatgtcg agccactggg catggagaat gggaacattg ccaactcaca gatcgccgcc  720
tcatctgtgc gtgtgacctt cttgggtttg cagcattggg tcccggagct ggcccgcctg  780
aaccgcgcag gcatggtcaa tgcctggaca cccagcagca atgacgataa cccctggatc  840
caggtgaacc tgctgcggag gatgtgggta acaggtgtgg tgacgcaggg tgccagccgc  900
ttggccagtc atgagtacct gaaggccttc aaggtggcct acagccttaa tggacacgaa  960
ttcgatttca tccatgatgt taataaaaaa cacaaggagt ttgtgggtaa ctggaacaaa  1020
aacgcggtgc atgtcaacct gtttgagacc cctgtggagg ctcagtacgt gagattgtac  1080
cccacgagct gccacacggc ctgcactctg cgctttgagc tactgggctg tgagctgaac  1140
ggatgcgcca atcccctggg cctgaagaat aacagcatcc ctgacaagca gatcacggcc  1200
tccagcagct acaagacctg gggcttgcat ctcttcagct ggaacccctc ctatgcacgg  1260
ctggacaagc agggcaactt caacgcctgg gttgcgggga gctacggtaa cgatcagtgg  1320
ctgcagatct tccctggcaa ctgggacaac cactcccaca agaagaactt gtttgagacg  1380
cccatcctgg ctcgctatgt gcgcatcctg cctgtagcct ggcacaaccg catcgccctg  1440
cgcctggagc tgctgggctg ttag                                         1464

SEQ ID NO: 232          moltype = AA  length = 487
FEATURE                 Location/Qualifiers
REGION                  1..487
                        note = Description of Artificial Sequence: Synthetic
                         polypeptide
source                  1..487
                        mol_type = protein
                        organism = synthetic construct
SEQUENCE: 232
MIFLLLMLSL ELQLHQIAAL FTVTVPKELY IIEHGSNVTL ECNFDTGSHV NLGAITASLQ  60
```

```
KVENDTSPHR ERATLLEEQL PLGKASFHIP QVQVRDEGQY QCIIIYGVAW DYKYLTLKVK  120
ASYRKINTHI LKVPETDEVE LTCQATGYPL AEVSWPNVSV PANTSHSRTP EGLYQVTSVL  180
RLKPPPGRNF SCVFWNTHVR ELTLASIDLQ SQMEPRTHPT IDVEPLGMEN GNIANSQIAA  240
SSVRVTFLGL QHWVPELARL NRAGMVNAWT PSSNDDNPWI QVNLLRRMWV TGVVTQGASR  300
LASHEYLKAF KVAYSLNGHE FDFIHDVNKK HKEFVGNWNK NAVHVNLFET PVEAQYVRLY  360
PTSCHTACTL RFELLGCELN GCANPLGLKN NSIPDKQITA SSSYKTWGLH LFSWNPSYAR  420
LDKQGNFNAW VAGSYGNDQW LQIFPGNWDN HSHKKNLFET PILARYVRIL PVAWHNRIAL  480
RLELLGC                                                            487

SEQ ID NO: 233         moltype = DNA  length = 1467
FEATURE                Location/Qualifiers
misc_feature           1..1467
                       note = Description of Artificial Sequence: Synthetic
                        polynucleotide
source                 1..1467
                       mol_type = other DNA
                       organism = synthetic construct
SEQUENCE: 233
atgatcttcc tcctgctaat gttgagcctg gaattgcagc ttcaccagat agcagcttta  60
ttcacagtga cagtccctaa ggaactgtac ataatagagc atggcagcaa tgtgaccctg  120
gaatgcaact ttgacactgg aagtcatgtg aaccttggag caataacagc cagtttgcaa  180
aaggtggaaa atgatacatc ccccaccgt gaaagagcca ctttgctgga ggagcagctg  240
cccctaggga aggcctcgtt ccacatacct caagtccaag tgagggacga aggacagtac  300
caatgcataa tcatctatgg ggtcgcctgg gactacaagt acctgactct gaaagtcaaa  360
gcttcctaca ggaaaataaa cactcacatc ctaaaggttc cagaaacaga tgaggtagag  420
ctcacctgcc aggctacagg ttatcctctg gcagaagtat cctggccaaa cgtcagcgtt  480
cctgccaaca ccagccactc caggacccct gaaggcctct accaggtcac cagtgttctg  540
cgcctaaagc cacccctgg cagaaacttc agctgtgtgt tctggaatac tcacgtgagg  600
gaacttactt tggccagcat tgaccttcaa agtcagatgg aacccaggac ccatccaact  660
atcgatgaca aaactcacac atgcccaccg tgcccagcac ctgaactcct ggggggaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgca aggtctccaa caaagccctc ccagcccca tcgagaaaac catctccaaa  1020
gccaaagggc agccccgaga accacaggtg tacaccctgc ccccatcccg ggaggagatg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctacagc aagctcaccg tggacaagag caggtggcag  1260
caggggaacg tcttctcatg ctccgtgatg cacgaggctc tgcacaacca ctacacgcag  1320
aagagcctct ccctgtctcc gggtaaaatc gatccaaata aaggaagtgg aaccacttca  1380
ggtactaccc gtcttctatc tggcacacg tgtttcacgt tgacaggttt gcttgggacg  1440
ctagtaacca tgggcttgct gacttag                                      1467

SEQ ID NO: 234         moltype = AA  length = 488
FEATURE                Location/Qualifiers
REGION                 1..488
                       note = Description of Artificial Sequence: Synthetic
                        polypeptide
source                 1..488
                       mol_type = protein
                       organism = synthetic construct
SEQUENCE: 234
MIFLLLMLSL ELQLHQIAAL FTVTVPKELY IIEHGSNVTL ECNFDTGSHV NLGAITASLQ  60
KVENDTSPHR ERATLLEEQL PLGKASFHIP QVQVRDEGQY QCIIIYGVAW DYKYLTLKVK  120
ASYRKINTHI LKVPETDEVE LTCQATGYPL AEVSWPNVSV PANTSHSRTP EGLYQVTSVL  180
RLKPPPGRNF SCVFWNTHVR ELTLASIDLQ SQMEPRTHPT IDDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGKI DPNKGSGTTS GTTRLLSGHT CFTLTGLLGT  480
LVTMGLLT                                                           488

SEQ ID NO: 235         moltype = DNA  length = 930
FEATURE                Location/Qualifiers
misc_feature           1..930
                       note = Description of Artificial Sequence: Synthetic
                        polynucleotide
source                 1..930
                       mol_type = other DNA
                       organism = synthetic construct
SEQUENCE: 235
atgagccagg acaccgaggt ggatatgaag gaggtggagc tgaatgagtt agagcccgag  60
aagcagccga tgaacgcggc gtctggggcg gccatgtccc tggcgggagc cgagaagaat  120
ggtctggtga agatcaaggt ggcggaagac gaggcggagg cggcagccgc ggctaagttc  180
acgggcctgt ccaaggagga gctgctgaag gtggcaggca gccccggctg ggtacgcacc  240
cgctgggcac tgctgctgct cttctggctc ggctggctcg gcatgcttgc tggtgccgtg  300
gtcataatcg tggcctgccc ctgggccgtg tccggggctc gcgcctcgcc cggctccgcg  360
gccagcccga gactccgcga gggtcccgag ctttcgcccg acgatcccgc cggcctcttg  420
```

```
gacctgcggc agggcatgtt tgcgcagctg gtggcccaaa atgttctgct gatcgatggg  480
cccctgagct ggtacagtga cccaggcctg gcaggcgtgt ccctgacggg gggcctgagc  540
tacaaagagg acacgaagga gctggtggtg gccaaggctg gagtctacta tgtcttcttt  600
caactagagc tgcggcgcgt ggtggccggc gagggctcag gctccgtttc acttgcgctg  660
cacctgcagc cactgcgctc tgctgctggg gccgccgccc tggctttgac cgtggacctg  720
ccacccgcct cctccgaggc tcggaactcg gccttcggtt tccagggccg cttgctgcac  780
ctgagtgccg gccagcgcct gggcgtccat cttcacactg aggccagggc acgccatgcc  840
tggcagctta cccagggcgc cacagtcttg ggactcttcc gggtgacccc cgaaatccca  900
gccggactcc cttcaccgag gtcggaataa                                   930

SEQ ID NO: 236          moltype = AA  length = 309
FEATURE                 Location/Qualifiers
REGION                  1..309
                        note = Description of Artificial Sequence: Synthetic
                         polypeptide
source                  1..309
                        mol_type = protein
                        organism = synthetic construct
SEQUENCE: 236
MSQDTEVDMK EVELNELEPE KQPMNAASGA AMSLAGAEKN GLVKIKVAED EAEAAAAAKF  60
TGLSKEELLK VAGSPGWVRT RWALLLLFWL GWLGMLAGAV VIIVACPWAV SGARASPGSA  120
ASPRLREGPE LSPDDPAGLL DLRQGMFAQL VAQNVLLIDG PLSWYSDPGL AGVSLTGGLS  180
YKEDTKELVV AKAGVYYVFF QLELRRVVAG EGSGSVSLAL HLQPLRSAAG AAALALTVDL  240
PPASSEARNS AFGFQGRLLH LSAGQRLGVH LHTEARARHA WQLTQGATVL GLFRVTPEIP  300
AGLPSPRSE                                                          309

SEQ ID NO: 237          moltype = DNA  length = 1515
FEATURE                 Location/Qualifiers
misc_feature            1..1515
                        note = Description of Artificial Sequence: Synthetic
                         polynucleotide
source                  1..1515
                        mol_type = other DNA
                        organism = synthetic construct
SEQUENCE: 237
atgaggatat ttgctgtctt tatattcatg acctactggc atttgctgaa cgcatttact  60
gtcacggttc ccaaggacct atatgtggta gagtatggta gcaatatgac aattgaatgc  120
aaattcccag tagaaaaaca attagacctg gctgcactaa ttgtctattg ggaaatggag  180
gataagaaca ttattcaatt tgtgcatgga gaggaagacc tgaaggttca gcatagtagc  240
tacagacaga gggcccggct gttgaaggac cagctctccc tgggaaatgc tgcacttcag  300
atcacagatg tgaaattgca ggatgcaggg gtgtaccgct gcatgatcag ctatggtggt  360
gccgactaca agcgaattac tgtgaaagtc aatgccccat acaacaaaat caaccaaaga  420
attttggttg tggatccagt cacctctgaa catgaactga catgtcaggc tgagggctac  480
cccaaggccg aagtcatctg gacaagcagt gaccatcaag tcctgagtgg taagaccacc  540
accaccaatt ccaagagaga ggagaagctt ttcaatgtga ccagcacact gagaatcaac  600
acaacaacta atgagatttt ctactgcact tttaggagat tagatcctga ggaaaaccat  660
acagctgaat tggtcatccc agaactacct ctggcacatc ctccaaatga aagggagtcc  720
aaatatggtc ccccatgccc atcatgccca gcacctgagt tcctgggggg accatcagtc  780
ttcctgttcc ccccaaaacc caaggacact ctcatgatct cccggacccc tgaggtcacg  840
tgcgtggtgg tggacgtgag ccaggaagac cccgaggtcc agttcaactg gtacgtggat  900
ggcgtggagg tgcataatgc caagacaaag ccgcgggagg agcagttcaa cagcacgtac  960
cgtgtggtca gggtcctcac cgtcctgcac caggactggc tgaacggtaa ggagtacaag  1020
tgcaaggtct ccaacaaagg cctcccgtcc tccatcgaga aaaccatctc caaagccaaa  1080
gggcagcccc gagagccaca ggtgtacacc ctgcccccat cccaggagga gatgaccaag  1140
aaccaggtca gcctgacctg cctggtcaaa ggcttctacc ccagcgacat cgccgtggag  1200
tgggagagca atgggcagcc ggaggacaac tacaagacca cgcctcccgt gctggactcc  1260
gacggctcct tcttcctcta cagcaggcta accgtggaca agagcaggtg gcaggagggg  1320
aatgtcttct catgctccgt gatgcatgag gctctgcaca accactacac acagaagagc  1380
ctctccctgt ctccgggtaa accaaataaa ggaagtggaa ccacttcagg tactacccgt  1440
cttctatctg ggcacacgtg tttcacgttg acaggtttgc ttgggacgct agtaaccatg  1500
ggcttgctga cttag                                                   1515

SEQ ID NO: 238          moltype = AA  length = 504
FEATURE                 Location/Qualifiers
REGION                  1..504
                        note = Description of Artificial Sequence: Synthetic
                         polypeptide
source                  1..504
                        mol_type = protein
                        organism = synthetic construct
SEQUENCE: 238
MRIFAVFIFM TYWHLLNAFT VTVPKDLYVV EYGSNMTIEC KFPVEKQLDL AALIVYWEME  60
DKNIIQFVHG EEDLKVQHSS YRQRARLLKD QLSLGNAALQ ITDVKLQDAG VYRCMISYGG  120
ADYKRITVKV NAPYNKINQR ILVVDPVTSE HELTCQAEGY PKAEVIWTSS DHQVLSGKTT  180
TTNSKREEKL FNVTSTLRIN TTTNEIFYCT FRRLDPEENH TAELVIPELP LAHPPNERES  240
KYGPPCPSCP APEFLGGPSV FLFPPKPKDT LMISRTPEVT CVVVDVSQED PEVQFNWYVD  300
GVEVHNAKTK PREEQFNSTY RVVRVLTVLH QDWLNGKEYK CKVSNKGLPS SIEKTISKAK  360
GQPREPQVYT LPPSQEEMTK NQVSLTCLVK GFYPSDIAVE WESNGQPEDN YKTTPPVLDS  420
DGSFFLYSRL TVDKSRWQEG NVFSCSVMHE ALHNHYTQKS LSLSPGKPNK GSGTTSGTTR  480
```

```
LLSGHTCFTL TGLLGTLVTM GLLT                                   504

SEQ ID NO: 239         moltype = DNA  length = 1941
FEATURE                Location/Qualifiers
misc_feature           1..1941
                       note = Description of Artificial Sequence: Synthetic
                        polynucleotide
source                 1..1941
                       mol_type = other DNA
                       organism = synthetic construct
SEQUENCE: 239
atgaggatat ttgctgtctt tatattcatg acctactggc atttgctgaa cgcatttact  60
gtcacggttc ccaaggacct atatgtggta gagtatggta gcaatatgac aattgaatgc  120
aaattcccag tagaaaaaca attagacctg gctgcactaa ttgtctattg ggaaatggag  180
gataagaaca ttattcaatt tgtgcatgga gaggaagacc tgaaggttca gcatagtagc  240
tacagacaga gggcccggct gttgaaggac cagctctccc tgggaaatgc tgcacttcag  300
atcacagatg tgaaattgca ggatgcaggg gtgtaccgct gcatgatcag ctatggtggt  360
gccgactaca agcgaattac tgtgaaagtc aatgccccat acaacaaaat caaccaaaga  420
attttggttg tggatccagt cacctctgaa catgaactga catgtcaggc tgagggctac  480
cccaaggccg aagtcatctg gacaagcagt gaccatcaag tcctgagtgg taagaccacc  540
accaccaatt ccaagagaga ggagaagctt ttcaatgtga ccagcacact gagaatcaac  600
acaacaacta atgagatttt ctactgcact tttaggagat tagatcctga ggaaaaccat  660
acagctgaat tggtcatccc agaactacct ctggcacatc ctccaaatga aaggccaaat  720
aaaggaagtg gaaccacttc aggtactacc cgtcttctat ctgggcacac gtgtttcacg  780
ttgacaggtt tgcttgggac gctagtaacc atgggcttgc tgactggaag cggagctact  840
aacttcagcc tgctgaagca ggctggcgac gtggaggaga accctggacc tatggcaaag  900
gtgttcagtt tcatccttgt taccaccgct ctgacaatgg gcagggaaat ttcggcgctc  960
gaggactgtg cccaggagca gatgcggctc agagcccagg tgcgcctgct tgagacccgg  1020
gtcaaacagc aacaggtcaa gatcaagcag cttttgcagg agaatgaagt ccagttcctt  1080
gataaaggag atgagaatac tgtcattgat cttggaagca agaggcagta tgcagattgt  1140
tcagagattt tcaatgatgg gtataagctc agtggatttt acaaaatcaa acctctccag  1200
agcccagcag aattttctgt ttattgtgac atgtccgatg gaggaggatg gactgtaatt  1260
cagagacgat ctgatggcag tgaaaacttt aacagaggat ggaaagacta tgaaaatggc  1320
tttggaaatt ttgtccaaaa acatggtgaa tattggctgg gcaataaaaa tcttcacttc  1380
ttgaccactc aagaagacta cactttaaaa atcgaccttg cagattttga aaaaaatagc  1440
cgttatgcac aatataagaa tttcaaagtt ggagatgaaa agaatttcta cgagttgaat  1500
attggggaat attctggaac agctggagat tcccttgcgg ggaattttca tcctgaggtg  1560
cagtggtggg ctagtcacca aagaatgaaa ttcagcacgt gggacagaga tcatgacaac  1620
tatgaaggga actgcgcaga agaagatcag tctggctggt ggtttaacag gtgtcactct  1680
gcaaacctga atggtgtata ctacagcggc ccctacacgg ctaaaacaga caatgggatt  1740
gtctggtaca cctggcatgg gtggtggtat tctctgaaat ctgtggttat gaaaattagg  1800
ccaaatgatt ttattccaaa tgtaattcca aataaaggaa gtggaaccac ttcaggtact  1860
acccgtcttc tatctgggca cacgtgtttc acgttgacag gtttgcttgg gacgctagta  1920
accatgggct tgctgactta g                                      1941

SEQ ID NO: 240         moltype = AA  length = 646
FEATURE                Location/Qualifiers
REGION                 1..646
                       note = Description of Artificial Sequence: Synthetic
                        polypeptide
source                 1..646
                       mol_type = protein
                       organism = synthetic construct
SEQUENCE: 240
MRIFAVFIFM TYWHLLNAFT VTVPKDLYVV EYGSNMTIEC KFPVEKQLDL AALIVYWEME  60
DKNIIQFVHG EEDLKVQHSS YRQRARLLKD QLSLGNAALQ ITDVKLQDAG VYRCMISYGG  120
ADYKRITVKV NAPYNKINQR ILVVDPVTSE HELTCQAEGY PKAEVIWTSS DHQVLSGKTT  180
TTNSKREEKL FNVTSTLRIN TTTNEIFYCT FRRLDPEENH TAELVIPELP LAHPPNERPN  240
KGSGTTSGTT RLLSGHTCFT LTGLLGTLVT MGLLTGSGAT NFSLLKQAGD VEENPGPMAK  300
VFSFILVTTA LTMGREISAL EDCAQEQMRL RAQVRLLETR VKQQQVKIKQ LLQENEVQFL  360
DKGDENTVID LGSKRQYADC SEIFNDGYKL SGFYKIKPLQ SPAEFSVYCD MSDGGGWTVI  420
QRRSDGSENF NRGWKDYENG FGNFVQKHGE YWLGNKNLHF LTTQEDYTLK IDLADFEKNS  480
RYAQYKNFKV GDEKNFYELN IGEYSGTAGD SLAGNFHPEV QWWASHQRMK FSTWDRDHDN  540
YEGNCAEEDQ SGWWFNRCHS ANLNGVYYSG PYTAKTDNGI VWYTWHGWWY SLKSVVMKIR  600
PNDFIPNVIP NKGSGTTSGT TRLLSGHTCF TLTGLLGTLV TMGLLT           646

SEQ ID NO: 241         moltype = DNA  length = 729
FEATURE                Location/Qualifiers
misc_feature           1..729
                       note = Description of Artificial Sequence: Synthetic
                        polynucleotide
source                 1..729
                       mol_type = other DNA
                       organism = synthetic construct
SEQUENCE: 241
atgggttgct gtttctccaa gaccggctcg agcggcgtga gcaagggcga ggcagtgatc  60
aaggagttca tgcggttcaa ggtgcacatg gagggctcca tgaacggcca cgagttcgag  120
atcgagggcg agggcgaggg ccgcccctac gagggcaccc agaccgccaa gctgaaggtg  180
accaagggtg gcccccctgcc cttctcctgg gacatcctgt cccctcagtt catgtacggc  240
```

```
tccagggcct tcaccaagca ccccgccgac atccccgact actataagca gtccttcccc  300
gagggcttca agtgggagcg cgtgatgaac ttcgaggacg gcggcgccgt gaccgtgacc  360
caggacacct ccctggagga cggcaccctg atctacaagg tgaagctccg cggcaccaac  420
ttccctcctg acggccccgt aatgcagaag aagacaatgg gctgggaagc gtccaccgag  480
cggttgtacc ccgaggacgg cgtgctgaag ggcgacatta agatggccct gcgcctgaag  540
gacggcggcc gctacctggc ggacttcaag accacctaca aggccaagaa gcccgtgcag  600
atgcccggcg cctacaacgt cgaccgcaag ttggacatca cctcccacaa cgaggactac  660
accgtggtgg aacagtacga acgctccgag ggccgccact ccaccggcgg catggacgag  720
ctgtacaag                                                          729

SEQ ID NO: 242          moltype = AA  length = 243
FEATURE                 Location/Qualifiers
REGION                  1..243
                        note = Description of Artificial Sequence: Synthetic
                         polypeptide
source                  1..243
                        mol_type = protein
                        organism = synthetic construct
SEQUENCE: 242
MGCCFSKTGS SGVSKGEAVI KEFMRFKVHM EGSMNGHEFE IEGEGEGRPY EGTQTAKLKV  60
TKGGPLPFSW DILSPQFMYG SRAFTKHPAD IPDYYKQSFP EGFKWERVMN FEDGGAVTVT  120
QDTSLEDGTL IYKVKLRGTN FPPDGPVMQK KTMGWEASTE RLYPEDGVLK GDIKMALRLK  180
DGGRYLADFK TTYKAKKPVQ MPGAYNVDRK LDITSHNEDY TVVEQYERSE GRHSTGGMDE  240
LYK                                                                243

SEQ ID NO: 243          moltype = DNA  length = 549
FEATURE                 Location/Qualifiers
misc_feature            1..549
                        note = Description of Artificial Sequence: Synthetic
                         polynucleotide
source                  1..549
                        mol_type = other DNA
                        organism = synthetic construct
SEQUENCE: 243
atgggttgct gtttctccaa gaccggctcg agcggcgtct tcacactcga agatttcgtt  60
ggggactggc gacagacagc cggctacaac ctggaccaag tccttgaaca gggaggtgtg  120
tccagtttgt ttcagaatct cggggtgtcc gtaactccga tccaaaggat tgtcctgagc  180
ggtgaaaatg ggctgaagat cgacatccat gtcatcatcc cgtatgaagg tctgagcggc  240
gaccaaatgg gccagatcga aaaaattttt aaggtggtgt accctgtgga tgatcatcac  300
tttaaggtga tcctgcacta tggcacactg gtaatcgacg gggttacgcc gaacatgatc  360
gactatttcg gacggccgta tgaaggcatc gccgtgttcg acggcaaaaa gatcactgta  420
acagggaccc tgtggaacgg caacaaaatt atcgacgagc gcctgatcaa ccccgacggc  480
tccctgctgt tccgagtaac catcaacgga gtgaccggct ggcggctgtg cgaacgcatt  540
ctggcgtaa                                                          549

SEQ ID NO: 244          moltype = AA  length = 182
FEATURE                 Location/Qualifiers
REGION                  1..182
                        note = Description of Artificial Sequence: Synthetic
                         polypeptide
source                  1..182
                        mol_type = protein
                        organism = synthetic construct
SEQUENCE: 244
MGCCFSKTGS SGVFTLEDFV GDWRQTAGYN LDQVLEQGGV SSLFQNLGVS VTPIQRIVLS  60
GENGLKIDIH VIIPYEGLSG DQMGQIEKIF KVVYPVDDHH FKVILHYGTL VIDGVTPNMI  120
DYFGRPYEGI AVFDGKKITV TGTLWNGNKI IDERLINPDG SLLFRVTING VTGWRLCERI  180
LA                                                                 182

SEQ ID NO: 245          moltype = DNA  length = 849
FEATURE                 Location/Qualifiers
misc_feature            1..849
                        note = Description of Artificial Sequence: Synthetic
                         polynucleotide
source                  1..849
                        mol_type = other DNA
                        organism = synthetic construct
SEQUENCE: 245
atgaggatat ttgctgtctt tatattcatg acctactggc atttgctgaa cgcatttact  60
gtcacggttc ccaaggacct atatgtggta gagtatggta gcaatatgac aattgaatgc  120
aaattcccag tagaaaaaca attagacctg gctgcactaa ttgtctattg ggaaatggag  180
gataagaaca ttattcaatt tgtgcatgga gaggaagacc tgaaggttca gcatagtagc  240
tacagacaga gggcccggct gttgaaggac cagctctccc tgggaaatgc tgcacttcag  300
atcacagatg tgaaattgca ggatgcaggg gtgtaccgct gcatgatcag ctatggtggt  360
gccgactaca agcgaattac tgtgaaagtc aatgccccat acaacaaaat caaccaaaga  420
attttggttg tggatccagt cacctctgaa catgaactga catgtcaggc tgagggctac  480
cccaaggccg aagtcatctg gacaagcagt gaccatcaag tcctgagtgg taagaccacc  540
accaccaatt ccaagagaga ggagaagctt ttcaatgtga ccagcacact gagaatcaac  600
acaacaacta atgagatttt ctactgcact tttaggagat tagatcctga ggaaaaccat  660
```

```
acagctgaat tggtcatccc aggtaatatt ctgaatgtgt ccattaaaat atgtctaaca  720
ctgtccccta gcaccccaaa taaaggaagt ggaaccactt caggtactac ccgtcttcta  780
tctgggcaca cgtgtttcac gttgacaggt ttgcttggga cgctagtaac catgggcttg  840
ctgacttag                                                          849

SEQ ID NO: 246         moltype = AA  length = 282
FEATURE                Location/Qualifiers
REGION                 1..282
                       note = Description of Artificial Sequence: Synthetic
                        polypeptide
source                 1..282
                       mol_type = protein
                       organism = synthetic construct
SEQUENCE: 246
MRIFAVFIFM TYWHLLNAFT VTVPKDLYVV EYGSNMTIEC KFPVEKQLDL AALIVYWEME  60
DKNIIQFVHG EEDLKVQHSS YRQRARLLKD QLSLGNAALQ ITDVKLQDAG VYRCMISYGG  120
ADYKRITVKV NAPYNKINQR ILVVDPVTSE HELTCQAEGY PKAEVIWTSS DHQVLSGKTT  180
TTNSKREEKL FNVTSTLRIN TTTNEIFYCT FRRLDPEENH TAELVIPGNI LNVSIKICLT  240
LSPSTPNKGS GTTSGTTRLL SGHTCFTLTG LLGTLVTMGL LT                     282

SEQ ID NO: 247         moltype = DNA  length = 939
FEATURE                Location/Qualifiers
misc_feature           1..939
                       note = Description of Artificial Sequence: Synthetic
                        polynucleotide
source                 1..939
                       mol_type = other DNA
                       organism = synthetic construct
SEQUENCE: 247
atggagcggc tttggggtct attccagaga gcgcaacaac tgtccccaag atcctctcag  60
accgtctacc agcgtgtgga aggcccccgg aaagggcacc tggaggagga agaggaagac  120
ggggaggagg gggcggagac attggcccac ttctgcccca tggagctgag gggccctgag  180
cccctgggct ctagacccag gcagccaaac ctcattccct gggcggcagc aggacggagg  240
gctgcccccct acctggtcct gacggccctg ctgatcttca ctggggcctt cctactgggc  300
tacgtcgcct tccgagggtc cgcctgcccc tgggccgtgt ccggggctcg cgcctcgccc  360
ggctccgcgg ccagcccgag actccgcgag ggtcccgagc tttcgcccga cgatcccgcc  420
ggcctcttgg acctgcggca gggcatgttt gcgcagctgg tggcccaaaa tgttctgctg  480
atcgatgggc ccctgagctg gtacagtgac ccaggcctgg caggcgtgtc cctgacgggg  540
ggcctgagct acaaagagga cacgaaggag ctggtggtgg ccaaggctgg agtctactat  600
gtcttctttc aactagagct gcggcgcgtg gtggccggcg agggctcagg ctccgtttca  660
cttgcgctgc acctgcagcc actgcgctct gctgctgggg ccgccgccct ggctttgacc  720
gtggacctgc cacccgcctc ctccgaggct cggaactcgg ccttcggttt ccagggccgc  780
ttgctgcacc tgagtgccgg ccagcgcctg ggcgtccatc ttcacactga ggccagggca  840
cgccatgcct ggcagcttac ccagggcgcc acagtcttgg gactcttccg ggtgaccccc  900
gaaatcccag ccggactccc ttcaccgagg tcggaataa                         939

SEQ ID NO: 248         moltype = AA  length = 311
FEATURE                Location/Qualifiers
REGION                 1..311
                       note = Description of Artificial Sequence: Synthetic
                        polypeptide
source                 1..311
                       mol_type = protein
                       organism = synthetic construct
SEQUENCE: 248
MERLWGLFQR AQQLSPRSSQ TVYQRVEGPR KGHLEEEEED GEEGAETLAH FCPMELRGPE  60
PLGSRPRQPN LIPWAAAGRR AAPYLVLTAL LIFTGAFLLG YVAFRGSACP WAVSGARASP  120
GSAASPRLRG PELSPDDPAG LLDLRQGMFA QLVAQNVLLI DGPLSWYSDP GLAGVSLTGG  180
LSYKEDTKEL VVAKAGVYYV FFQLELRRVV AGEGSGSVSL ALHLQPLRSA AGAAALALTV  240
DLPPASSEAR NSAFGFQGRL LHLSAGQRLG VHLHTEARAR HAWQLTQGAT VLGLFRVTPE  300
IPAGLPSPRS E                                                       311

SEQ ID NO: 249         moltype = DNA  length = 741
FEATURE                Location/Qualifiers
misc_feature           1..741
                       note = Description of Artificial Sequence: Synthetic
                        polynucleotide
source                 1..741
                       mol_type = other DNA
                       organism = synthetic construct
SEQUENCE: 249
atgggctgct gcggggctgt gcaggagtcc cagtgcatgc tgggactgtt cttcggcttc  60
ctcttggtga tattcgccat tgaaatagct gcggccatct ggggatattc ccacaaggat  120
gaggcctgcc cctgggccgt gtccggggct cgcgcctcgc ccggctccgc ggccagcccg  180
agactccgcg agggtcccga gctttcgccc gacgatcccg ccggcctctt ggacctgcgg  240
cagggcatgt ttgcgcagct ggtggcccaa aatgttctgc tgatcgatgg gcccctgagc  300
tggtacagtg acccaggcct ggcaggcgtg tccctgacgg ggggcctgag ctacaaagag  360
gacacgaagg agctggtggt ggccaaggct ggagtctact atgtcttctt tcaactagag  420
ctgcggcgcg tggtggccgg cgagggctca ggctccgttt cacttgcgct gcacctgcag  480
```

```
ccactgcgct ctgctgctgg ggccgccgcc ctggctttga ccgtggacct gccacccgcc  540
tcctccgagg ctcggaactc ggccttcggt ttccagggcc gcttgctgca cctgagtgcc  600
ggccagcgcc tgggcgtcca tcttcacact gaggccaggg cacgccatgc ctggcagctt  660
acccagggcg ccacagtctt gggactcttc cgggtgaccc ccgaaatccc agccggactc  720
ccttcaccga ggtcggaata a                                            741

SEQ ID NO: 250         moltype = AA  length = 246
FEATURE                Location/Qualifiers
REGION                 1..246
                       note = Description of Artificial Sequence: Synthetic
                        polypeptide
source                 1..246
                       mol_type = protein
                       organism = synthetic construct
SEQUENCE: 250
MGCCGAVQES QCMLGLFFGF LLVIFAIEIA AAIWGYSHKD EACPWAVSGA RASPGSAASP  60
RLREGPELSP DDPAGLLDLR QGMFAQLVAQ NVLLIDGPLS WYSDPGLAGV SLTGGLSYKE  120
DTKELVVAKA GVYYVFFQLE LRRVVAGEGS GSVSLALHLQ PLRSAAGAAA LALTVDLPPA  180
SSEARNSAFG FQGRLLHLSA GQRLGVHLHT EARARHAWQL TQGATVLGLF RVTPEIPAGL  240
PSPRSE                                                             246

SEQ ID NO: 251         moltype = DNA  length = 963
FEATURE                Location/Qualifiers
misc_feature           1..963
                       note = Description of Artificial Sequence: Synthetic
                        polynucleotide
source                 1..963
                       mol_type = other DNA
                       organism = synthetic construct
SEQUENCE: 251
atgggttgct gtttctccaa gaccggctcg agcggcagcc aggacaccga ggtggatatg  60
aaggaggtgg agctgaatga gttagagccc gagaagcagc cgatgaacgc ggcgtctggg  120
gcggccatgt ccctggcggg agccgagaag aatggtctgg tgaagatcaa ggtggcggaa  180
gacgaggcgg aggcggcagc cgcggctaag ttcacgggcc tgtccaagga ggagctgctg  240
aaggtggcag gcagccccgg ctgggtacgc acccgctggg cactgctgct gctcttctgg  300
ctcggctggc tcggcatgct tgctggtgcc gtggtcataa tcgtggcctg cccctgggcc  360
gtgtccgggg ctcgcgcctc gcccggctcc gcggccagcc cgagactccg cgagggtccc  420
gagctttcgc ccgacgatcc cgccggcctc ttggacctgc ggcagggcat gtttgcgcag  480
ctggtggccc aaaatgttct gctgatcgat gggcccctga gctggtacag tgacccaggc  540
ctggcaggcg tgtccctgac gggggggctg agctacaaag aggacacgaa ggagctggtg  600
gtggccaagg ctggagtcta ctatgtcttc tttcaactag agctgcggcg cgtggtggcc  660
ggcgagggct caggctccgt ttcacttgcg ctgcacctgc agccactgcg ctctgctgct  720
ggggccgccg ccctggcttt gaccgtggac ctgccacccg cctcctccga ggctcggaac  780
tcggccttcg gtttccaggg ccgcttgctg cacctgagtg ccggccagcg cctgggcgtc  840
catcttcaca ctgaggccag ggcacgccat gcctggcagc ttacccaggg cgccacagtc  900
ttgggactct tccgggtgac ccccgaaatc ccagccggac tcccttcacc gaggtcggaa  960
taa                                                                963

SEQ ID NO: 252         moltype = AA  length = 320
FEATURE                Location/Qualifiers
REGION                 1..320
                       note = Description of Artificial Sequence: Synthetic
                        polypeptide
source                 1..320
                       mol_type = protein
                       organism = synthetic construct
SEQUENCE: 252
MGCCFSKTGS SGSQDTEVDM KEVELNELEP EKQPMNAASG AAMSLAGAEK NGLVKIKVAE  60
DEAEAAAAAK FTGLSKEELL KVAGSPGWVR TRWALLLLFW LGWLGMLAGA VVIIVACPWA  120
VSGARASPGS AASPRLREGP ELSPDDPAGL LDLRQGMFAQ LVAQNVLLID GPLSWYSDPG  180
LAGVSLTGGL SYKEDTKELV VAKAGVYYVF FQLELRRVVA GEGSGSVSLA LHLQPLRSAA  240
GAAALALTVD LPPASSEARN SAFGFQGRLL HLSAGQRLGV HLHTEARARH AWQLTQGATV  300
LGLFRVTPEI PAGLPSPRSE                                              320

SEQ ID NO: 253         moltype = DNA  length = 717
FEATURE                Location/Qualifiers
misc_feature           1..717
                       note = Description of Artificial Sequence: Synthetic
                        polynucleotide
source                 1..717
                       mol_type = other DNA
                       organism = synthetic construct
SEQUENCE: 253
atgggttgct gtttctccaa gaccggctcg agcggctggg ccctggtcgc ggggctgctg  60
ctgctgctgc tgctcgctgc cgcctgcgcc gtcttcctcg cctgcccctg ggccgtgtcc  120
ggggctcgcg cctcgcccgg ctccgcggcc agcccgagac tccgcgaggg tcccgagctt  180
tcgcccgacg atcccgccgg cctcttggac ctgcggcagg gcatgtttgc gcagctggtg  240
gcccaaaatg ttctgctgat cgatgggccc ctgagctggt acagtgaccc aggcctggca  300
ggcgtgtccc tgacgggggg cctgagctac aaagaggaca cgaaggagct ggtggtggcc  360
```

```
aaggctggag tctactatgt cttctttcaa ctagagctgc ggcgcgtggt ggccggcgag  420
ggctcaggct ccgtttcact tgcgctgcac ctgcagccac tgcgctctgc tgctggggcc  480
gccgccctgg ctttgaccgt ggacctgcca cccgcctcct ccgaggctcg gaactcggcc  540
ttcggtttcc agggccgctt gctgcacctg agtgccggcc agcgcctggg cgtccatctt  600
cacactgagg ccagggcacg ccatgcctgg cagcttaccc agggcgccac agtcttggga  660
ctcttccggg tgacccccga aatcccagcc ggactccctt caccgaggtc ggaataa     717

SEQ ID NO: 254          moltype = AA  length = 238
FEATURE                 Location/Qualifiers
REGION                  1..238
                        note = Description of Artificial Sequence: Synthetic
                         polypeptide
source                  1..238
                        mol_type = protein
                        organism = synthetic construct
SEQUENCE: 254
MGCCFSKTGS SGWALVAGLL LLLLLAAACA VFLACPWAVS GARASPGSAA SPRLREGPEL  60
SPDDPAGLLD LRQGMFAQLV AQNVLLLIDGP LSWYSDPGLA GVSLTGGLSY KEDTKELVVA  120
KAGVYYVFFQ LELRRVVAGE GSGSVSLALH LQPLRSAAGA AALALTVDLP PASSEARNSA  180
FGFQGRLLHL SAGQRLGVHL HTEARARHAW QLTQGATVLG LFRVTPEIPA GLPSPRSE    238

SEQ ID NO: 255          moltype = DNA  length = 798
FEATURE                 Location/Qualifiers
misc_feature            1..798
                        note = Description of Artificial Sequence: Synthetic
                         polynucleotide
source                  1..798
                        mol_type = other DNA
                        organism = synthetic construct
SEQUENCE: 255
atgaggatat ttgctgtctt tatattcatg acctactggc atttgctgaa cgcatttact  60
gtcacggttc ccaaggacct atatgtggta gagtatggta gcaatatgac aattgaatgc  120
aaattcccag tagaaaaaca attagacctg gctgcactaa ttgtctattg ggaaatggag  180
gataagaaca ttattcaatt tgtgcatgga gaggaagacc tgaaggttca gcatagtagc  240
tacagacaga gggcccggct gttgaaggac cagctctccc tgggaaatgc tgcacttcag  300
atcacagatg tgaaattgca ggatgcaggg gtgtaccgct gcatgatcag ctatggtggt  360
gccgactaca agcgaattac tgtgaaagtc aatgccccat acaacaaaat caaccaaaga  420
attttggttg tggatccagt cacctctgaa catgaactga catgtcaggc tgagggctac  480
cccaaggccg aagtcatctg gacaagcagt gaccatcaag tcctgagtgg taagaccacc  540
accaccaatt ccaagagaga ggagaagctt ttcaatgtga ccagcacact gagaatcaac  600
acaacaacta atgagatttt ctactgcact tttaggagat tagatcctga ggaaaaccat  660
acagctgaat tgggctcgag cggcccaaat aaaggaagtg gaaccacttc aggtactacc  720
cgtcttctat ctgggcacac gtgtttcacg ttgacaggtt tgcttgggac gctagtaacc  780
atgggcttgc tgacttag                                                 798

SEQ ID NO: 256          moltype = AA  length = 265
FEATURE                 Location/Qualifiers
REGION                  1..265
                        note = Description of Artificial Sequence: Synthetic
                         polypeptide
source                  1..265
                        mol_type = protein
                        organism = synthetic construct
SEQUENCE: 256
MRIFAVFIFM TYWHLLNAFT VTVPKDLYVV EYGSNMTIEC KFPVEKQLDL AALIVYWEME  60
DKNIIQFVHG EEDLKVQHSS YRQRARLLKD QLSLGNAALQ ITDVKLQDAG VYRCMISYGG  120
ADYKRITVKV NAPYNKINQR ILVVDPVTSE HELTCQAEGY PKAEVIWTSS DHQVLSGKTT  180
TTNSKREEKL FNVTSTLRIN TTTNEIFYCT FRRLDPEENH TAELGSSGPN KGSGTTSGTT  240
RLLSGHTCFT LTGLLGTLVT MGLLT                                          265

SEQ ID NO: 257          moltype = DNA  length = 834
FEATURE                 Location/Qualifiers
misc_feature            1..834
                        note = Description of Artificial Sequence: Synthetic
                         polynucleotide
source                  1..834
                        mol_type = other DNA
                        organism = synthetic construct
SEQUENCE: 257
atgaggatat ttgctgtctt tatattcatg acctactggc atttgctgaa cgcatttact  60
gtcacggttc ccaaggacct atatgtggta gagtatggta gcaatatgac aattgaatgc  120
aaattcccag tagaaaaaca attagacctg gctgcactaa ttgtctattg ggaaatggag  180
gataagaaca ttattcaatt tgtgcatgga gaggaagacc tgaaggttca gcatagtagc  240
tacagacaga gggcccggct gttgaaggac cagctctccc tgggaaatgc tgcacttcag  300
atcacagatg tgaaattgca ggatgcaggg gtgtaccgct gcatgatcag ctatggtggt  360
gccgactaca agcgaattac tgtgaaagtc aatgccccat acaacaaaat caaccaaaga  420
attttggttg tggatccagt cacctctgaa catgaactga catgtcaggc tgagggctac  480
cccaaggccg aagtcatctg gacaagcagt gaccatcaag tcctgagtgg taagaccacc  540
accaccaatt ccaagagaga ggagaagctt ttcaatgtga ccagcacact gagaatcaac  600
```

-continued

```
acaacaacta atgagatttt ctactgcact tttaggagat tagatcctga ggaaaaccat  660
acagctgaat tggtcatccc aggtaatatt ctgaatgtgt ccattaaaat atgtctaaca  720
ctgtccccta gcaccttcta cacaggagtc tatattctga tcggagccgg cgccctcatg  780
atgctggtgg gcttcctggg ctgctgcggg gctgtgcagg agtcccagtg ctag        834

SEQ ID NO: 258         moltype = AA  length = 277
FEATURE                Location/Qualifiers
REGION                 1..277
                       note = Description of Artificial Sequence: Synthetic
                        polypeptide
source                 1..277
                       mol_type = protein
                       organism = synthetic construct
SEQUENCE: 258
MRIFAVFIFM TYWHLLNAFT VTVPKDLYVV EYGSNMTIEC KFPVEKQLDL AALIVYWEME  60
DKNIIQFVHG EEDLKVQHSS YRQRARLLKD QLSLGNAALQ ITDVKLQDAG VYRCMISYGG  120
ADYKRITVKV NAPYNKINQR ILVVDPVTSE HELTCQAEGY PKAEVIWTSS DHQVLSGKTT  180
TTNSKREEKL FNVTSTLRIN TTTNEIFYCT FRRLDPEENH TAELVIPGNI LNVSIKICLT  240
LSPSTFYTGV YILIGAGALM MLVGFLGCCG AVQESQC                          277

SEQ ID NO: 259         moltype = DNA  length = 876
FEATURE                Location/Qualifiers
misc_feature           1..876
                       note = Description of Artificial Sequence: Synthetic
                        polynucleotide
source                 1..876
                       mol_type = other DNA
                       organism = synthetic construct
SEQUENCE: 259
atgaggatat ttgctgtctt tatattcatg acctactggc atttgctgaa cgcatttact  60
gtcacggttc ccaaggacct atatgtggta gagtatggta gcaatatgac aattgaatgc  120
aaattcccag tagaaaaaca attagacctg gctgcactaa ttgtctattg ggaaatggag  180
gataagaaca ttattcaatt tgtgcatgga gaggaagacc tgaaggttca gcatagtagc  240
tacagacaga gggcccggct gttgaaggac cagctctccc tgggaaatgc tgcacttcag  300
atcacagatg tgaaattgca ggatgcaggg gtgtaccgct gcatgatcag ctatggtggt  360
gccgactaca agcgaattac tgtgaaagtc aatgccccat acaacaaaat caaccaaaga  420
attttggttg tggatccagt cacctctgaa catgaactga catgtcaggc tgagggctac  480
cccaaggccg aagtcatctg gacaagcagt gaccatcaag tcctgagtgg taagaccacc  540
accaccaatt ccaagagaga ggagaagctt ttcaatgtga ccagcacact gagaatcaac  600
acaacaacta atgagatttt ctactgcact tttaggagat tagatcctga ggaaaaccat  660
acagctgaat tggtcatccc aggtaatatt ctgaatgtgt ccattaaaat atgtctaaca  720
ctgtccccta gcaccttcta cacaggagtc tatattctga tcggagccgg cgccctcatg  780
atgctggtgg gcttcctggg ctgctgcggg gctgtgcagg agtcccagtg caaaaagaag  840
aaaaagaagt caaagacaaa gtgtgtaatt atgtaa                           876

SEQ ID NO: 260         moltype = AA  length = 291
FEATURE                Location/Qualifiers
REGION                 1..291
                       note = Description of Artificial Sequence: Synthetic
                        polypeptide
source                 1..291
                       mol_type = protein
                       organism = synthetic construct
SEQUENCE: 260
MRIFAVFIFM TYWHLLNAFT VTVPKDLYVV EYGSNMTIEC KFPVEKQLDL AALIVYWEME  60
DKNIIQFVHG EEDLKVQHSS YRQRARLLKD QLSLGNAALQ ITDVKLQDAG VYRCMISYGG  120
ADYKRITVKV NAPYNKINQR ILVVDPVTSE HELTCQAEGY PKAEVIWTSS DHQVLSGKTT  180
TTNSKREEKL FNVTSTLRIN TTTNEIFYCT FRRLDPEENH TAELVIPGNI LNVSIKICLT  240
LSPSTFYTGV YILIGAGALM MLVGFLGCCG AVQESQCKKK KKKSKTKCVI M           291

SEQ ID NO: 261         moltype = DNA  length = 837
FEATURE                Location/Qualifiers
misc_feature           1..837
                       note = Description of Artificial Sequence: Synthetic
                        polynucleotide
source                 1..837
                       mol_type = other DNA
                       organism = synthetic construct
SEQUENCE: 261
atgaggatat ttgctgtctt tatattcatg acctactggc atttgctgaa cgcatttact  60
gtcacggttc ccaaggacct atatgtggta gagtatggta gcaatatgac aattgaatgc  120
aaattcccag tagaaaaaca attagacctg gctgcactaa ttgtctattg ggaaatggag  180
gataagaaca ttattcaatt tgtgcatgga gaggaagacc tgaaggttca gcatagtagc  240
tacagacaga gggcccggct gttgaaggac cagctctccc tgggaaatgc tgcacttcag  300
atcacagatg tgaaattgca ggatgcaggg gtgtaccgct gcatgatcag ctatggtggt  360
gccgactaca agcgaattac tgtgaaagtc aatgccccat acaacaaaat caaccaaaga  420
attttggttg tggatccagt cacctctgaa catgaactga catgtcaggc tgagggctac  480
cccaaggccg aagtcatctg gacaagcagt gaccatcaag tcctgagtgg taagaccacc  540
accaccaatt ccaagagaga ggagaagctt ttcaatgtga ccagcacact gagaatcaac  600
```

```
acaacaacta atgagatttt ctactgcact tttaggagat tagatcctga ggaaaaccat  660
acagctgaat tggtcatccc aggtaatatt ctgaatgtgt ccattaaaat atgtctaaca  720
ctgtccccta gcaccatcgg cgcagtgggc atcggcattg ccgtggtcat gatatttggc  780
atgatcttca gtatgatctt gtgctgtgct atccgcagga accgcgagat ggtctag     837

SEQ ID NO: 262          moltype = AA  length = 278
FEATURE                 Location/Qualifiers
REGION                  1..278
                        note = Description of Artificial Sequence: Synthetic
                         polypeptide
source                  1..278
                        mol_type = protein
                        organism = synthetic construct
SEQUENCE: 262
MRIFAVFIFM TYWHLLNAFT VTVPKDLYVV EYGSNMTIEC KFPVEKQLDL AALIVYWEME  60
DKNIIQFVHG EEDLKVQHSS YRQRARLLKD QLSLGNAALQ ITDVKLQDAG VYRCMISYGG  120
ADYKRITVKV NAPYNKINQR ILVVDPVTSE HELTCQAEGY PKAEVIWTSS DHQVLSGKTT  180
TTNSKREEKL FNVTSTLRIN TTTNEIFYCT FRRLDPEENH TAELVIPGNI LNVSIKICLT  240
LSPSTIGAVG IGIAVVMIFG MIFSMILCCA IRRNREMV                         278

SEQ ID NO: 263          moltype = DNA  length = 843
FEATURE                 Location/Qualifiers
misc_feature            1..843
                        note = Description of Artificial Sequence: Synthetic
                         polynucleotide
source                  1..843
                        mol_type = other DNA
                        organism = synthetic construct
SEQUENCE: 263
atgaggatat ttgctgtctt tatattcatg acctactggc atttgctgaa cgcatttact  60
gtcacggttc ccaaggacct atatgtggta gagtatggta gcaatatgac aattgaatgc  120
aaattcccag tagaaaaaca attagacctg gctgcactaa ttgtctattg ggaaatggag  180
gataagaaca ttattcaatt tgtgcatgga gaggaagacc tgaaggttca gcatagtagc  240
tacagacaga gggcccggct gttgaaggac cagctctccc tgggaaatgc tgcacttcag  300
atcacagatg tgaaattgca ggatgcaggg gtgtaccgct gcatgatcag ctatggtggt  360
gccgactaca agcgaattac tgtgaaagtc aatgccccat acaacaaaat caaccaaaga  420
attttggttg tggatccagt cacctctgaa catgaactga catgtcaggc tgagggctac  480
cccaaggccg aagtcatctg gacaagcagt gaccatcaag tcctgagtgg taagaccacc  540
accaccaatt ccaagagaga ggagaagctt ttcaatgtga ccagcacact gagaatcaac  600
acaacaacta atgagatttt ctactgcact tttaggagat tagatcctga ggaaaaccat  660
acagctgaat tggtcatccc aggtaatatt ctgaatgtgt ccattaaaat atgtctaaca  720
ctgtccccta gcaccctgta cctcatcggc attgctgcca tcgtggtcgc tgtgatcatg  780
atcttcgaga tgatcctgag catggtgctg tgctgtggca tccggaacag ctccgtgtac  840
tga                                                                843

SEQ ID NO: 264          moltype = AA  length = 280
FEATURE                 Location/Qualifiers
REGION                  1..280
                        note = Description of Artificial Sequence: Synthetic
                         polypeptide
source                  1..280
                        mol_type = protein
                        organism = synthetic construct
SEQUENCE: 264
MRIFAVFIFM TYWHLLNAFT VTVPKDLYVV EYGSNMTIEC KFPVEKQLDL AALIVYWEME  60
DKNIIQFVHG EEDLKVQHSS YRQRARLLKD QLSLGNAALQ ITDVKLQDAG VYRCMISYGG  120
ADYKRITVKV NAPYNKINQR ILVVDPVTSE HELTCQAEGY PKAEVIWTSS DHQVLSGKTT  180
TTNSKREEKL FNVTSTLRIN TTTNEIFYCT FRRLDPEENH TAELVIPGNI LNVSIKICLT  240
LSPSTLYLIG IAAIVVAVIM IFEMILSMVL CCGIRNSSVY                       280

SEQ ID NO: 265          moltype = DNA  length = 1503
FEATURE                 Location/Qualifiers
misc_feature            1..1503
                        note = Description of Artificial Sequence: Synthetic
                         polynucleotide
source                  1..1503
                        mol_type = other DNA
                        organism = synthetic construct
SEQUENCE: 265
atggagaggc tggtgatcag gatgcccttc tctcatctgt ctacctacag cctggtttgg  60
gtcatggcag cagtggtgct gtgcacagca caagtgcaag tggtgaccca ggatgaaaga  120
gagcagctgt acacacctgc ttccttaaaa tgctctctgc aaaatgccca ggaagccctc  180
attgtgacat ggcagaaaaa gaaagctgta agcccagaaa acatggtcac cttcagcgag  240
aaccatgggg tggtgatcca gcctgcctat aaggacaaga taaacattac ccagctggga  300
ctccaaaact caaccatcac cttctggaat atcaccctgg aggatgaagg gtgttacatg  360
tgtctcttca ataccttttgg ttttgggaag atctcaggaa cggcctgcct caccgtctat  420
gtacagccca tagtatccct tcactacaaa ttctctgaag accacctaaa tatcacttgc  480
tctgccactg cccgcccagc cccatggtc ttctggaagg tccctcggtc agggattgaa  540
aatagtacag tgactctgtc tcacccaaat gggaccacgt ctgttaccag catcctccat  600
```

```
atcaaagacc ctaagaatca ggtggggaag gaggtgatct gccaggtgct gcacctgggg  660
actgtgaccg actttaagca aaccgtcaac aaaggcatcg atgacaaaac tcacacatgc  720
ccaccgtgcc cagcacctga actcctgggg ggaccgtcag tcttcctctt ccccccaaaa  780
cccaaggaca ccctcatgat ctcccggacc cctgaggtca catgcgtggt ggtggacgtg  840
agccacgaag accctgaggt caagttcaac tggtacgtgg acggcgtgga ggtgcataat  900
gccaagacaa agccgcggga ggagcagtac aacagcacgt accgtgtggt cagcgtcctc  960
accgtcctgc accaggactg gctgaatggc aaggagtaca agtgcaaggt ctccaacaaa  1020
gccctcccag cccccatcga gaaaaccatc tccaaagcca aagggcagcc ccgagaacca  1080
caggtgtaca ccctgccccc atcccgggag gagatgacca agaaccaggt cagcctgacc  1140
tgcctggtca aaggcttcta tcccagcgac atcgccgtgg agtgggagag caatgggcag  1200
ccggagaaca actacaagac cacgcctccc gtgctggact ccgacggctc cttcttcctc  1260
tacagcaagc tcaccgtgga caagagcagg tggcagcagg ggaacgtctt ctcatgctcc  1320
gtgatgcacg aggctctgca caaccactac acgcagaaga gcctctccct gtctccgggt  1380
aaaatcgatc caaataaagg aagtggaacc acttcaggta ctacccgtct tctatctggg  1440
cacacgtgtt tcacgttgac aggtttgctt gggacgctag taaccatggg cttgctgact  1500
tag                                                                1503

SEQ ID NO: 266         moltype = AA  length = 500
FEATURE                Location/Qualifiers
REGION                 1..500
                       note = Description of Artificial Sequence: Synthetic
                        polypeptide
source                 1..500
                       mol_type = protein
                       organism = synthetic construct
SEQUENCE: 266
MERLVIRMPF SHLSTYSLVW VMAAVVLCTA QVQVVTQDER EQLYTPASLK CSLQNAQEAL  60
IVTWQKKKAV SPENMVTFSE NHGVVIQPAY KDKINITQLG LQNSTITFWN ITLEDEGCYM  120
CLFNTFGFGK ISGTACLTVY VQPIVSLHYK FSEDHLNITC SATARPAPMV FWKVPRSGIE  180
NSTVTLSHPN GTTSVTSILH IKDPKNQVGK EVICQVLHLG TVTDFKQTVN KGIDDKTHTC  240
PPCPAPELLG GPSVFLFPPK PKDTLMISRT PEVTCVVVDV SHEDPEVKFN WYVDGVEVHN  300
AKTKPREEQY NSTYRVVSVL TVLHQDWLNG KEYKCKVSNK ALPAPIEKTI SKAKGQPREP  360
QVYTLPPSRE EMTKNQVSLT CLVKGFYPSD IAVEWESNGQ PENNYKTTPP VLDSDGSFFL  420
YSKLTVDKSR WQQGNVFSCS VMHEALHNHY TQKSLSLSPG KIDPNKGSGT TSGTTRLLSG  480
HTCFTLTGLL GTLVTMGLLT                                              500

SEQ ID NO: 267         moltype = DNA  length = 1050
FEATURE                Location/Qualifiers
misc_feature           1..1050
                       note = Description of Artificial Sequence: Synthetic
                        polynucleotide
source                 1..1050
                       mol_type = other DNA
                       organism = synthetic construct
SEQUENCE: 267
atggcaaagg tgttcagttt catccttgtt accaccgctc tgacaatggg cagggaaatt  60
tcggcgctcg aggactgtgc ccaggagcag atgcggctca gagcccaggt gcgcctgctt  120
gagacccggg tcaaacagca acaggtcaag atcaagcagc ttttgcagga gaatgaagtc  180
cagttccttg ataaaggaga tgagaatact gtcattgatc ttggaagcaa gaggcagtat  240
gcagattgtt cagagatttt caatgatggg tataagctca gtggatttta caaaatcaaa  300
cctctccaga gcccagcaga attttctgtt tattgtgaca tgtccgatgg aggaggatgg  360
actgtaattc agagacgatc tgatggcagt gaaaacttta acagaggatg gaaagactat  420
gaaaatggct ttggaaattt tgtccaaaaa catggtgaat attggctggg caataaaaat  480
cttcacttct tgaccactca agaagactac actttaaaaa tcgaccttgc agattttgaa  540
aaaaatagcc gttatgcaca atataagaat ttcaaagttg gagatgaaaa gaatttctac  600
gagttgaata ttggggaata ttctggaaca gctggagatt cccttgcggg gaattttcat  660
cctgaggtgc agtggtgggc tagtcaccaa agaatgaaat tcagcacgtg ggacagagat  720
catgacaact atgaagggaa ctgcgcagaa gaagatcagt ctggctggtg gtttaacagg  780
tgtcactctg caaacctgaa tggtgtatac tacagcggcc cctacacggc taaaacagac  840
aatgggattg tctggtacac ctggcatggg tggtggtatt ctctgaaatc tgtggttatg  900
aaaattaggc caaatgattt tattccaaat gtaattccaa ataaaggaag tggaaccact  960
tcaggtacta cccgtcttct atctgggcac acgtgtttca cgttgacagg tttgcttggg  1020
acgctagtaa ccatgggctt gctgacttag                                   1050

SEQ ID NO: 268         moltype = AA  length = 349
FEATURE                Location/Qualifiers
REGION                 1..349
                       note = Description of Artificial Sequence: Synthetic
                        polypeptide
source                 1..349
                       mol_type = protein
                       organism = synthetic construct
SEQUENCE: 268
MAKVFSFILV TTALTMGREI SALEDCAQEQ MRLRAQVRLL ETRVKQQQVK IKQLLQENEV  60
QFLDKGDENT VIDLGSKRQY ADCSEIFNDG YKLSGFYKIK PLQSPAEFSV YCDMSDGGGW  120
TVIQRRSDGS ENFNRGWKDY ENGFGNFVQK HGEYWLGNKN LHFLTTQEDY TLKIDLADFE  180
KNSRYAQYKN FKVGDEKNFY ELNIGEYSGT AGDSLAGNFH PEVQWWASHQ RMKFSTWDRD  240
HDNYEGNCAE EDQSGWWFNR CHSANLNGVY YSGPYTAKTD NGIVWYTWHG WWYSLKSVVM  300
KIRPNDFIPN VIPNKGSGTT SGTTRLLSGH TCFTLTGLLG TLVTMGLLT              349
```

```
SEQ ID NO: 269          moltype = DNA  length = 1872
FEATURE                 Location/Qualifiers
misc_feature            1..1872
                        note = Description of Artificial Sequence: Synthetic
                         polynucleotide
source                  1..1872
                        mol_type = other DNA
                        organism = synthetic construct
SEQUENCE: 269
atggccttca gcggttccca ggctccctac ctgagtccag ctgtcccctt ttctgggact  60
attcaaggag gtctccagga cggacttcag atcactgtca atgggaccgt tctcagctcc  120
agtggaacca ggtttgctgt gaactttcag actggcttca gtggaaatga cattgccttc  180
cacttcaacc ctcggtttga agatggaggg tacgtggtgt gcaacacgag gcagaacgga  240
agctgggggc ccgaggagag gaagacacac atgcctttcc agaaggggat gccctttgac  300
ctctgcttcc tggtgcagag ctcagatttc aaggtgatgg tgaacgggat cctcttcgtg  360
cagtacttcc accgcgtgcc cttccaccgt gtggacacca tctccgtcaa tggctctgtg  420
cagctgtcct acatcagctt ccagaacccc cgcacagtcc ctgttcagcc tgccttctcc  480
acggtgccgt tctcccagcc tgtctgtttc ccacccaggc ccaggggggcg cagacaaaaa  540
cctcccggcg tgtggcctgc caacccggct cccattaccc agacagtcat ccacacagtg  600
cagagcgccc ctggacagat gttctctact cccgccatcc cacctatgat gtacccccac  660
cccgcctatc cgatgccttt catcaccacc attctgggag ggctgtaccc atccaagtcc  720
atcctcctgt caggcactgt cctgcccagt gctcagaggt tccacatcaa cctgtgctct  780
gggaaccaca tcgccttcca cctgaacccc cgttttgatg agaatgctgt ggtccgcaac  840
acccagatcg acaactcctg ggggtctgag gagcgaagtc tgccccgaaa aatgcccttc  900
gtccgtggcc agagcttctc agtgtggatc ttgtgtgaag ctcactgcct caaggtggcc  960
gtggatggtc agcacctgtt tgaatactac catcgcctga ggaacctgcc caccatcaac  1020
agactggaag tgggggggcga catccagctg acccatgtgc agacaatcga tgacaaaact  1080
cacacatgcc caccgtgccc agcacctgaa ctcctggggg gaccgtcagt cttcctcttc  1140
cccccaaaac ccaaggacac cctcatgatc tcccggaccc ctgaggtcac atgcgtggtg  1200
gtggacgtga gccacgaaga ccctgaggtc aagttcaact ggtacgtgga cggcgtggag  1260
gtgcataatg ccaagacaaa gccgcgggag gagcagtaca acagcacgta ccgtgtggtc  1320
agcgtcctca ccgtcctgca ccaggactgg ctgaatggca aggagtacaa gtgcaaggtc  1380
tccaacaaag ccctcccagc ccccatcgag aaaaccatct ccaaagccaa agggcagccc  1440
cgagaaccac aggtgtacac cctgccccca tcccgggagg agatgaccaa gaaccaggtc  1500
agcctgacct gcctggtcaa aggcttctat cccagcgaca tcgccgtgga gtgggagagc  1560
aatgggcagc cggagaacaa ctacaagacc acgcctcccg tgctggactc cgacggctcc  1620
ttcttcctct acagcaagct caccgtggac aagagcaggt ggcagcaggg gaacgtcttc  1680
tcatgctccg tgatgcacga ggctctgcac aaccactaca cgcagaagag cctctccctg  1740
tctccgggta aaatcgatcc aaataaagga agtggaacca cttcaggtac tacccgtctt  1800
ctatctgggc acacgtgttt cacgttgaca ggtttgcttg ggacgctagt aaccatgggc  1860
ttgctgactt ag                                                   1872

SEQ ID NO: 270          moltype = AA  length = 623
FEATURE                 Location/Qualifiers
REGION                  1..623
                        note = Description of Artificial Sequence: Synthetic
                         polypeptide
source                  1..623
                        mol_type = protein
                        organism = synthetic construct
SEQUENCE: 270
MAFSGSQAPY LSPAVPFSGT IQGGLQDGLQ ITVNGTVLSS SGTRFAVNFQ TGFSGNDIAF  60
HFNPRFEDGG YVVCNTRQNG SWGPEERKTH MPFQKGMPFD LCFLVQSSDF KVMVNGILFV  120
QYFHRVPFHR VDTISVNGSV QLSYISFQNP RTVPVQPAFS TVPFSQPVCF PPRPRGRRQK  180
PPGVWPANPA PITQTVIHTV QSAPGQMFST PAIPPMMYPH PAYPMPFITT ILGGLYPSKS  240
ILLSGTVLPS AQRFHINLCS GNHIAFHLNP RFDENAVVRN TQIDNSWGSE ERSLPRKMPF  300
VRGQSFSVWI LCEAHCLKVA VDGQHLFEYY HRLRNLPTIN RLEVGGDIQL THVQTIDDKT  360
HTCPPCPAPE LLGGPSVFLF PPKPKDTLMI SRTPEVTCVV VDVSHEDPEV KFNWYVDGVE  420
VHNAKTKPRE EQYNSTYRVV SVLTVLHQDW LNGKEYKCKV SNKALPAPIE KTISKAKGQP  480
REPQVYTLPP SREEMTKNQV SLTCLVKGFY PSDIAVEWES NGQPENNYKT TPPVLDSDGS  540
FFLYSKLTVD KSRWQQGNVF SCSVMHEALH NHYTQKSLSL SPGKIDPNKG SGTTSGTTRL  600
LSGHTCFTLT GLLGTLVTMG LLT                                        623

SEQ ID NO: 271          moltype = DNA  length = 810
FEATURE                 Location/Qualifiers
misc_feature            1..810
                        note = Description of Artificial Sequence: Synthetic
                         polynucleotide
source                  1..810
                        mol_type = other DNA
                        organism = synthetic construct
SEQUENCE: 271
atggagaggc tggtgatcag gatgcccttc tctcatctgt ctacctacag cctggtttgg  60
gtcatggcag cagtggtgct gtgcacagca caagtgcaag tggtgaccca ggatgaaaga  120
gagcagctgt acacacctgc ttccttaaaa tgctctctgc aaaatgccca ggaagccctc  180
attgtgacat ggcagaaaaa gaaagctgta agcccagaaa acatggtcac cttcagcgag  240
aaccatgggg tggtgatcca gcctgcctat aaggacaaga taaacattac ccagctggga  300
ctccaaaact caaccatcac cttctggaat atcaccctgg aggatgaagg gtgttacatg  360
```

-continued

```
tgtctcttca ataccttttgg ttttgggaag atctcaggaa cggcctgcct caccgtctat  420
gtacagccca tagtatccct tcactacaaa ttctctgaag accacctaaa tatcacttgc  480
tctgccactg cccgcccagc ccccatggtc ttctggaagg tccctcggtc agggattgaa  540
aatagtacag tgactctgtc tcacccaaat gggaccacgt ctgttaccag catcctccat  600
atcaaagacc ctaagaatca ggtggggaag gaggtgatct gccaggtgct gcacctgggg  660
actgtgaccg actttaagca aaccgtcaac aaaggcccaa ataaaggaag tggaaccact  720
tcaggtacta cccgtcttct atctgggcac acgtgtttca cgttgacagg tttgcttggg  780
acgctagtaa ccatgggctt gctgacttag                                   810

SEQ ID NO: 272         moltype = AA  length = 269
FEATURE                Location/Qualifiers
REGION                 1..269
                       note = Description of Artificial Sequence: Synthetic
                        polypeptide
source                 1..269
                       mol_type = protein
                       organism = synthetic construct
SEQUENCE: 272
MERLVIRMPF SHLSTYSLVW VMAAVVLCTA QVQVVTQDER EQLYTPASLK CSLQNAQEAL  60
IVTWQKKKAV SPENMVTFSE NHGVVIQPAY KDKINITQLG LQNSTITFWN ITLEDEGCYM  120
CLFNTFGFGK ISGTACLTVY VQPIVSLHYK FSEDHLNITC SATARPAPMV FWKVPRSGIE  180
NSTVTLSHPN GTTSVTSILH IKDPKNQVGK EVICQVLHLG TVTDFKQTVN KGPNKGSGTT  240
SGTTRLLSGH TCFTLTGLLG TLVTMGLLT                                   269

SEQ ID NO: 273         moltype = DNA  length = 1179
FEATURE                Location/Qualifiers
misc_feature           1..1179
                       note = Description of Artificial Sequence: Synthetic
                        polynucleotide
source                 1..1179
                       mol_type = other DNA
                       organism = synthetic construct
SEQUENCE: 273
atggccttca gcggttccca ggctccctac ctgagtccag ctgtcccctt ttctgggact  60
attcaaggag gtctccagga cggacttcag atcactgtca atgggaccgt tctcagctcc  120
agtggaacca ggtttgctgt gaactttcag actggcttca gtggaaatga cattgccttc  180
cacttcaacc ctcggtttga agatggaggg tacgtggtgt gcaacacgag gcagaacgga  240
agctgggggc ccgaggagag gaagacacac atgcctttcc agaaggggat gccctttgac  300
ctctgcttcc tggtgcagag ctcagatttc aaggtgatgg tgaacgggat cctcttcgtg  360
cagtacttcc accgcgtgcc cttccaccgt gtggacacca tctccgtcaa tggctctgtg  420
cagctgtcct acatcagctt ccagaacccc cgcacagtcc ctgttcagcc tgccttctcc  480
acggtgccgt tctcccagcc tgtctgtttc ccacccaggc ccagggggcg cagacaaaaa  540
cctcccggcg tgtggcctgc caacccggct cccattaccc agacagtcat ccacacagtg  600
cagagcgccc ctggacagat gttctctact cccgccatcc cacctatgat gtacccccac  660
cccgcctatc cgatgccttt catcaccacc attctgggag ggctgtaccc atccaagtcc  720
atcctcctgt caggcactgt cctgcccagt gctcagaggt tccacatcaa cctgtgctct  780
gggaaccaca tcgccttcca cctgaacccc cgttttgatg agaatgctgt ggtccgcaac  840
acccagatcg acaactcctg gggtctgag gagcgaagtc tgccccgaaa aatgcccttc  900
gtccgtggcc agagcttctc agtgtggatc ttgtgtgaag ctcactgcct caaggtggcc  960
gtggatggtc agcacctgtt tgaatactac catcgcctga ggaacctgcc caccatcaac  1020
agactggaag tgggggcga catccagctg acccatgtgc agacaccaaa taaaggaagt  1080
ggaaccactt caggtactac ccgtcttcta tctgggcaca cgtgtttcac gttgacaggt  1140
ttgcttggga cgctagtaac catgggcttg ctgacttag                        1179

SEQ ID NO: 274         moltype = AA  length = 392
FEATURE                Location/Qualifiers
REGION                 1..392
                       note = Description of Artificial Sequence: Synthetic
                        polypeptide
source                 1..392
                       mol_type = protein
                       organism = synthetic construct
SEQUENCE: 274
MAFSGSQAPY LSPAVPFSGT IQGGLQDGLQ ITVNGTVLSS SGTRFAVNFQ TGFSGNDIAF  60
HFNPRFEDGG YVVCNTRQNG SWGPEERKTH MPFQKGMPFD LCFLVQSSDF KVMVNGILFV  120
QYFHRVPFHR VDTISVNGSV QLSYISFQNP RTVPVQPAFS TVPFSQPVCF PPRPRGRRQK  180
PPGVWPANPA PITQTVIHTV QSAPGQMFST PAIPPMMYPH PAYPMPFITT ILGGLYPSKS  240
ILLSGTVLPS AQRFHINLCS GNHIAFHLNP RFDENAVVRN TQIDNSWGSE ERSLPRKMPF  300
VRGQSFSVWI LCEAHCLKVA VDGQHLFEYY HRLRNLPTIN RLEVGGDIQL THVQTPNKGS  360
GTTSGTTRLL SGHTCFTLTG LLGTLVTMGL LT                                392

SEQ ID NO: 275         moltype = DNA  length = 720
FEATURE                Location/Qualifiers
misc_feature           1..720
                       note = Description of Artificial Sequence: Synthetic
                        polynucleotide
source                 1..720
                       mol_type = other DNA
                       organism = synthetic construct
```

```
SEQUENCE: 275
atggagcctc ctggagactg ggggcctcct ccctggagat ccacccccaa aaccgacgtc  60
ttgaggctgg tgctgtatct caccttcctg ggagcccccct gctacgcccc agctctgccg  120
tcctgcaagg aggacgagta cccagtgggc tccgagtgct gccccaagtg cagtccaggt  180
tatcgtgtga aggaggcctg cggggagctg acgggcacag tgtgtgaacc ctgccctcca  240
ggcacctaca ttgcccacct caatggccta agcaagtgtc tgcagtgcca aatgtgtgac  300
ccagccatgg gcctgcgcgc gagccggaac tgctccagga cagagaacgc cgtgtgtggc  360
tgcagcccag gccacttctg catcgtccag gacggggacc actgcgccgc gtgccgcgct  420
tacgccacct ccagcccggg ccagagggtg cagaagggag gcaccgagag tcaggacacc  480
ctgtgtcaga actgcccccc ggggaccttc tctcccaatg ggaccctgga ggaatgtcag  540
caccagacca agtgcagctg gctggtgacg aaggccggag ctgggaccag cagctcccac  600
tgggtaccaa ataaaggaag tggaaccact tcaggtacta cccgtcttct atctgggcac  660
acgtgtttca cgttgacagg tttgcttggg acgctagtaa ccatgggctt gctgacttag  720

SEQ ID NO: 276         moltype = AA  length = 239
FEATURE                Location/Qualifiers
REGION                 1..239
                       note = Description of Artificial Sequence: Synthetic
                        polypeptide
source                 1..239
                       mol_type = protein
                       organism = synthetic construct
SEQUENCE: 276
MEPPGDWGPP PWRSTPKTDV LRLVLYLTFL GAPCYAPALP SCKEDEYPVG SECCPKCSPG  60
YRVKEACGEL TGTVCEPCPP GTYIAHLNGL SKCLQCQMCD PAMGLRASRN CSRTENAVCG  120
CSPGHFCIVQ DGDHCAACRA YATSSPGQRV QKGGTESQDT LCQNCPPGTF SPNGTLEECQ  180
HQTKCSWLVT KAGAGTSSSH WVPNKGSGTT SGTTRLLSGH TCFTLTGLLG TLVTMGLLT   239

SEQ ID NO: 277         moltype = DNA  length = 774
FEATURE                Location/Qualifiers
misc_feature           1..774
                       note = Description of Artificial Sequence: Synthetic
                        polynucleotide
source                 1..774
                       mol_type = other DNA
                       organism = synthetic construct
SEQUENCE: 277
atgatcttcc tcctgctaat gttgagcctg gaattgcagc ttcaccagat agcagcttta  60
ttcacagtga cagtccctaa ggaactgtac ataatagagc atggcagcaa tgtgaccctg  120
gaatgcaact ttgacactgg aagtcatgtg aaccttggag caataacagc cagtttgcaa  180
aaggtggaaa atgatacatc cccacaccgt gaaagagcca ctttgctgga ggagcagctg  240
cccctaggga aggcctcgtt ccacatacct caagtccaag tgagggacga aggacagtac  300
caatgcataa tcatctatgg ggtcgcctgg gactacaagt acctgactct gaaagtcaaa  360
gcttcctaca ggaaaataaa cactcacatc ctaaaggttc cagaaacaga tgaggtagag  420
ctcacctgcc aggctacagg ttatcctctg gcagaagtat cctggccaaa cgtcagcgtt  480
cctgccaaca ccagccactc caggacccct gaaggcctct accaggtcac cagtgttctg  540
cgcctaaagc cacccccctgg cagaaacttc agctgtgtgt tctggaatac tcacgtgagg  600
gaacttactt tggccagcat tgaccttcaa agtcagatgg aacccaggac ccatccaact  660
ccaaataaag gaagtggaac cacttcaggt actacccgtc ttctatctgg gcacacgtgt  720
ttcacgttga caggtttgct tgggacgcta gtaaccatgg gcttgctgac ttag        774

SEQ ID NO: 278         moltype = AA  length = 257
FEATURE                Location/Qualifiers
REGION                 1..257
                       note = Description of Artificial Sequence: Synthetic
                        polypeptide
source                 1..257
                       mol_type = protein
                       organism = synthetic construct
SEQUENCE: 278
MIFLLLMLSL ELQLHQIAAL FTVTVPKELY IIEHGSNVTL ECNFDTGSHV NLGAITASLQ  60
KVENDTSPHR ERATLLEEQL PLGKASFHIP QVQVRDEGQY QCIIIYGVAW DYKYLTLKVK  120
ASYRKINTHI LKVPETDEVE LTCQATGYPL AEVSWPNVSV PANTSHSRTP EGLYQVTSVL  180
RLKPPPGRNF SCVFWNTHVR ELTLASIDLQ SQMEPRTHPT PNKGSGTTSG TTRLLSGHTC  240
FTLTGLLGTL VTMGLLT                                                257

SEQ ID NO: 279         moltype = DNA  length = 951
FEATURE                Location/Qualifiers
misc_feature           1..951
                       note = Description of Artificial Sequence: Synthetic
                        polynucleotide
source                 1..951
                       mol_type = other DNA
                       organism = synthetic construct
SEQUENCE: 279
atgatcatct taatttactt atttctcttg ctatgggaag acactcaagg atggggattc  60
aaggatggaa tttttcataa ctccatatgg cttgaacgag cagccggtgt gtaccacaga  120
gaagcacggt ctggcaaata caagctcacc tacgcagaag ctaaggcggt gtgtgaattt  180
gaaggcggcc atctcgcaac ttacaagcag ctagaggcag ccagaaaaat tggatttcat  240
```

```
gtctgtgctg ctggatggat ggctaagggc agagttggat accccattgt gaagccaggg  300
cccaactgtg gatttggaaa aactggcatt attgattatg gaatccgtct caataggagt  360
gaaagatggg atgcctattg ctacaaccca cacgcaaagg agtgtggtgg cgtctttaca  420
gatccaaagc aaatttttaa atctccaggc ttcccaaatg agtacgaaga taaccaaatc  480
tgctactggc acattagact caagtatggt cagcgtattc acctgagttt tttagatttt  540
gaccttgaag atgacccagg ttgcttggct gattatgttg aaatatatga cagttacgat  600
gatgtccatg gctttgtggg aagatactgt ggagatgagc ttccagatga catcatcagt  660
acaggaaatg tcatgacctt gaagtttcta agtgatgctt cagtgacagc tggaggtttc  720
caaatcaaat atgttgcaat ggatcctgta tccaaatcca gtcaaggaaa aaatacaagt  780
actacttcta ctggaaataa aaacttttta gctggaagat ttagccactt aatcgatcca  840
aataaaggaa gtggaaccac ttcaggtact acccgtcttc tatctgggca cacgtgtttc  900
acgttgacag gtttgcttgg gacgctagta accatgggct tgctgactta g           951

SEQ ID NO: 280          moltype = AA  length = 316
FEATURE                 Location/Qualifiers
REGION                  1..316
                        note = Description of Artificial Sequence: Synthetic
                         polypeptide
source                  1..316
                        mol_type = protein
                        organism = synthetic construct
SEQUENCE: 280
MIILIYLFLL LWEDTQGWGF KDGIFHNSIW LERAAGVYHR EARSGKYKLT YAEAKAVCEF  60
EGGHLATYKQ LEAARKIGFH VCAAGWMAKG RVGYPIVKPG PNCGFGKTGI IDYGIRLNRS  120
ERWDAYCYNP HAKECGGVFT DPKQIFKSPG FPNEYEDNQI CYWHIRLKYG QRIHLSFLDF  180
DLEDDPGCLA DYVEIYDSYD DVHGFVGRYC GDELPDDIIS TGNVMTLKFL SDASVTAGGF  240
QIKYVAMDPV SKSSQGKNTS TTSTGNKNFL AGRFSHLIDP NKGSGTTSGT TRLLSGHTCF  300
TLTGLLGTLV TMGLLT                                                  316

SEQ ID NO: 281          moltype = DNA  length = 1413
FEATURE                 Location/Qualifiers
misc_feature            1..1413
                        note = Description of Artificial Sequence: Synthetic
                         polynucleotide
source                  1..1413
                        mol_type = other DNA
                        organism = synthetic construct
SEQUENCE: 281
atggagcctc ctggagactg ggggcctcct ccctggagat ccacccccaa aaccgacgtc  60
ttgaggctgg tgctgtatct caccttcctg ggagccccct gctacgcccc agctctgccg  120
tcctgcaagg aggacgagta cccagtgggc tccgagtgct gccccaagtg cagtccaggt  180
tatcgtgtga aggaggcctg cggggagctg acgggcacag tgtgtgaacc ctgccctcca  240
ggcacctaca ttgcccacct caatggccta agcaagtgtc tgcagtgcca aatgtgtgac  300
ccagccatgg gcctgcgcgc gagccggaac tgctccagga cagagaacgc cgtgtgtggc  360
tgcagcccag gccacttctg catcgtccag gacggggacc actgcgccgc gtgccgcgct  420
tacgccacct ccagcccggg ccagagggtg cagaagggag gcaccgagag tcaggacacc  480
ctgtgtcaga actgcccccc ggggaccttc tctcccaatg ggaccctgga ggaatgtcag  540
caccagacca agtgcagctg gctggtgacg aaggccggag ctgggaccag cagctcccac  600
tgggtaatcg atgacaaaac tcacacatgc ccaccgtgcc cagcacctga actcctgggg  660
ggaccgtcag tcttcctctt ccccccaaaa cccaaggaca ccctcatgat ctcccggacc  720
cctgaggtca catgcgtggt ggtggacgtg agccacgaag accctgaggt caagttcaac  780
tggtacgtgg acggcgtgga ggtgcataat gccaagacaa agccgcggga ggagcagtac  840
aacagcacgt accgtgtggt cagcgtcctc accgtcctgc accaggactg gctgaatggc  900
aaggagtaca agtgcaaggt ctccaacaaa gccctcccag cccccatcga gaaaaccatc  960
tccaaagcca aagggcagcc ccgagaacca caggtgtaca ccctgccccc atcccgggag  1020
gagatgacca agaaccaggt cagcctgacc tgcctggtca aaggcttcta tcccagcgac  1080
atcgccgtgg agtgggagag caatgggcag ccggagaaca actacaagac cacgcctccc  1140
gtgctggact ccgacggctc cttcttcctc tacagcaagc tcaccgtgga caagagcagg  1200
tggcagcagg ggaacgtctt ctcatgctcc gtgatgcacg aggctctgca caaccactac  1260
acgcagaaga gcctctccct gtctccgggt aaaatcgatc caaataaagg aagtggaacc  1320
acttcaggta ctacccgtct tctatctggg cacacgtgtt tcacgttgac aggtttgctt  1380
gggacgctag taaccatggg cttgctgact tag                               1413

SEQ ID NO: 282          moltype = AA  length = 470
FEATURE                 Location/Qualifiers
REGION                  1..470
                        note = Description of Artificial Sequence: Synthetic
                         polypeptide
source                  1..470
                        mol_type = protein
                        organism = synthetic construct
SEQUENCE: 282
MEPPGDWGPP PWRSTPKTDV LRLVLYLTFL GAPCYAPALP SCKEDEYPVG SECCPKCSPG  60
YRVKEACGEL TGTVCEPCPP GTYIAHLNGL SKCLQCQMCD PAMGLRASRN CSRTENAVCG  120
CSPGHFCIVQ DGDHCAACRA YATSSPGQRV QKGGTESQDT LCQNCPPGTF SPNGTLEECQ  180
HQTKCSWLVT KAGAGTSSSH WVIDDKTHTC PPCPAPELLG GPSVFLFPPK PKDTLMISRT  240
PEVTCVVVDV SHEDPEVKFN WYVDGVEVHN AKTKPREEQY NSTYRVVSVL TVLHQDWLNG  300
KEYKCKVSNK ALPAPIEKTI SKAKGQPREP QVYTLPPSRE EMTKNQVSLT CLVKGFYPSD  360
IAVEWESNGQ PENNYKTTPP VLDSDGSFFL YSKLTVDKSR WQQGNVFSCS VMHEALHNHY  420
```

-continued

```
TQKSLSLSPG KIDPNKGSGT TSGTTRLLSG HTCFTLTGLL GTLVTMGLLT          470

SEQ ID NO: 283          moltype = DNA  length = 1611
FEATURE                 Location/Qualifiers
misc_feature            1..1611
                        note = Description of Artificial Sequence: Synthetic
                         polynucleotide
source                  1..1611
                        mol_type = other DNA
                        organism = synthetic construct
SEQUENCE: 283
atgaggatat ttgctgtctt tatattcatg acctactggc atttgctgaa cgcatttact  60
gtcacggttc ccaaggacct atatgtggta gagtatggta gcaatatgac aattgaatgc  120
aaattcccag tagaaaaaca attagacctg gctgcactaa ttgtctattg ggaaatggag  180
gataagaaca ttattcaatt tgtgcatgga gaggaagacc tgaaggttca gcatagtagc  240
tacagacaga gggcccggct gttgaaggac cagctctccc tgggaaatgc tgcacttcag  300
atcacagatg tgaaattgca ggatgcaggg gtgtaccgct gcatgatcag ctatggtggt  360
gccgactaca agcgaattac tgtgaaagtc aatgccccat acaacaaaat caaccaaaga  420
attttggttg tggatccagt cacctctgaa catgaactga catgtcaggc tgagggctac  480
cccaaggccg aagtcatctg gacaagcagt gaccatcaag tcctgagtgg taagaccacc  540
accaccaatt ccaagagaga ggagaagctt ttcaatgtga ccagcacact gagaatcaac  600
acaacaacta atgagatttt ctactgcact tttaggagat tagatcctga ggaaaaccat  660
acagctgaat tggtcatccc agaactacct ctggcacatc ctccaaatga aaggccaaat  720
aaaggaagtg gaaccacttc aggtactacc cgtcttctat ctgggcacac gtgtttcacg  780
ttgacaggtt tgcttgggac gctagtaacc atgggcttgc tgactggaag cggagctact  840
aacttcagcc tgctgaagca ggctggcgac gtggaggaga accctggacc tatggagcct  900
cctggagact gggggcctcc tccctggaga tccacccccca aaaccgacgt cttgaggctg  960
gtgctgtatc tcaccttcct gggagccccc tgctacgccc cagctctgcc gtcctgcaag  1020
gaggacgagt acccagtggg ctccgagtgc tgccccaagt gcagtccagg ttatcgtgtg  1080
aaggaggcct gcggggagct gacgggcaca gtgtgtgaac cctgccctcc aggcacctac  1140
attgcccacc tcaatggcct aagcaagtgt ctgcagtgcc aaatgtgtga cccagccatg  1200
ggcctgcgcg cgagccggaa ctgctccagg acagagaacg ccgtgtgtgg ctgcagccca  1260
ggccacttct gcatcgtcca ggacggggac cactgcgccg cgtgccgcgc ttacgccacc  1320
tccagcccgg gccagagggt gcagaaggga ggcaccgaga gtcaggacac cctgtgtcag  1380
aactgccccc cggggacctt ctctcccaat gggaccctgg aggaatgtca gcaccagacc  1440
aagtgcagct ggctggtgac gaaggccgga gctgggacca gcagctccca ctgggtacca  1500
aataaaggaa gtggaaccac ttcaggtact acccgtcttc tatctgggca cacgtgtttc  1560
acgttgacag gtttgcttgg gacgctagta accatgggct tgctgactta g          1611

SEQ ID NO: 284          moltype = AA  length = 536
FEATURE                 Location/Qualifiers
REGION                  1..536
                        note = Description of Artificial Sequence: Synthetic
                         polypeptide
source                  1..536
                        mol_type = protein
                        organism = synthetic construct
SEQUENCE: 284
MRIFAVFIFM TYWHLLNAFT VTVPKDLYVV EYGSNMTIEC KFPVEKQLDL AALIVYWEME  60
DKNIIQFVHG EEDLKVQHSS YRQRARLLKD QLSLGNAALQ ITDVKLQDAG VYRCMISYGG  120
ADYKRITVKV NAPYNKINQR ILVVDPVTSE HELTCQAEGY PKAEVIWTSS DHQVLSGKTT  180
TTNSKREEKL FNVTSTLRIN TTTNEIFYCT FRRLDPEENH TAELVIPELP LAHPPNERPN  240
KGSGTTSGTT RLLSGHTCFT LTGLLGTLVT MGLLTGSGAT NFSLLKQAGD VEENPGPMEP  300
PGDWGPPPWR STPKTDVLRL VLYLTFLGAP CYAPALPSCK EDEYPVGSEC CPKCSPGYRV  360
KEACGELTGT VCEPCPPGTY IAHLNGLSKC LQCQMCDPAM GLRASRNCSR TENAVCGCSP  420
GHFCIVQDGD HCAACRAYAT SSPGQRVQKG GTESQDTLCQ NCPPGTFSPN GTLEECQHQT  480
KCSWLVTKAG AGTSSSHWVP NKGSGTTSGT TRLLSGHTCF TLTGLLGTLV TMGLLT      536

SEQ ID NO: 285          moltype = DNA  length = 1289
FEATURE                 Location/Qualifiers
misc_feature            1..1289
                        note = Description of Artificial Sequence: Synthetic
                         polynucleotide
source                  1..1289
                        mol_type = other DNA
                        organism = synthetic construct
SEQUENCE: 285
atggcttgtc ttggactccg gaggtacaaa gctcaactgc agctgccttc taggacttgg  60
ccttttgtag ccctgctcac tcttcttttc atcccagtct tctctgaagc catacaggtg  120
acccaacctt cagtggtgtt ggctagcagc catggtgtcg ccagctttcc atgtgaatat  180
tcaccatcac acaacactga tgaggtccgg gtgactgtgc tgcggcagac aaatgaccaa  240
atgactgagg tctgtgccac gacattcaca gagaagaata cagtgggctt cctagattac  300
cccttctgca gtggtacctt taatgaaagc agagtgaacc tcaccatcca aggactgaga  360
gctgttgaca cgggactgta cctctgcaag gtggaactca tgtacccacc gccatacttt  420
gtgggcatgg gcaacgggac gcagatttat gtcattgatc cagaaccatg cccggattct  480
gaatcgatga caaaactcac acatgcccac cgtgcccagc acctgaactc ctgggggac  540
cgtcagtctt cctcttcccc ccaaaaccca aggacaccct catgatctcc cggacccctg  600
aggtcacatg cgtggtggtg gacgtgagcc acgaagaccc tgaggtcaag ttcaactggt  660
acgtggacgg cgtggaggtg cataatgcca agacaaagcc gcgggaggag cagtacaaca  720
```

-continued

```
gcacgtaccg tgtggtcagc gtcctcaccg tcctgcacca ggactggctg aatggcaagg  780
agtacaagtg caaggtctcc aacaaagccc tcccagcccc catcgagaaa accatctcca  840
aagccaaagg gcagccccga gaaccacagg tgtacaccct gcccccatcc cgggaggaga  900
tgaccaagaa ccaggtcagc ctgacctgcc tggtcaaagg cttctatccc agcgacatcg  960
ccgtggagtg ggagagcaat gggcagccgg agaacaacta caagaccacg cctcccgtgc  1020
tggactccga cggctccttc ttcctctaca gcaagctcac cgtggacaag agcaggtggc  1080
agcaggggaa cgtcttctca tgctccgtga tgcacgaggc tctgcacaac cactacacgc  1140
agaagagcct ctccctgtct ccgggtaaaa tcgatccaaa taaaggaagt ggaaccactt  1200
caggtactac ccgtcttcta tctgggcaca cgtgtttcac gttgacaggt ttgcttggga  1260
cgctagtaac catgggcttg ctgacttag                                    1289
```

```
SEQ ID NO: 286         moltype = AA  length = 429
FEATURE                Location/Qualifiers
REGION                 1..429
                       note = Description of Artificial Sequence: Synthetic
                        polypeptide
source                 1..429
                       mol_type = protein
                       organism = synthetic construct
SEQUENCE: 286
MACLGLRRYK AQLQLPSRTW PFVALLTLLF IPVFSEAIQV TQPSVVLASS HGVASFPCEY  60
SPSHNTDEVR VTVLRQTNDQ MTEVCATTFT EKNTVGFLDY PFCSGTFNES RVNLTIQGLR  120
AVDTGLYLCK VELMYPPPYF VGMGNGTQIY VIDPEPCPDS DIDDKTHTCP PCPAPELLGG  180
PSVFLFPPKP KDTLMISRTP EVTCVVVDVS HEDPEVKFNW YVDGVEVHNA KTKPREEQYN  240
STYRVVSVLT VLHQDWLNGK EYKCKVSNKA LPAPIEKTIS KAKGQPREPQ VYTLPPSREE  300
MTKNQVSLTC LVKGFYPSDI AVEWESNGQP ENNYKTTPPV LDSDGSFFLY SKLTVDKSRW  360
QQGNVFSCSV MHEALHNHYT QKSLSLSPGK IDPNKGSGTT SGTTRLLSGH TCFTLTGLLG  420
TLVTMGLLT                                                          429
```

```
SEQ ID NO: 287         moltype = DNA  length = 1518
FEATURE                Location/Qualifiers
misc_feature           1..1518
                       note = Description of Artificial Sequence: Synthetic
                        polynucleotide
source                 1..1518
                       mol_type = other DNA
                       organism = synthetic construct
SEQUENCE: 287
atgaggatat ttgctggcat tatattcaca gcctgctgtc acttgctacg ggcgtttact  60
atcacggctc caaaggactt gtacgtggtg gagtatggca gcaacgtcac gatggagtgc  120
agattccctg tagaacggga gctggacctg cttgcgttag tggtgtactg ggaaaaggaa  180
gatgagcaag tgattcagtt tgtggcagga gaggaggacc ttaagcctca gcacagcaac  240
ttcaggggga gagcctcgct gccaaaggac cagcttttga agggaaatgc tgcccttcag  300
atcacagacg tcaagctgca ggacgcaggc gtttactgct gcataatcag ctacggtggt  360
gcggactaca agcgaatcac gctgaaagtc aatgccccat accgcaaaat caaccagaga  420
atttccgtgg atccagccac ttctgagcat gaactaatat gtcaggccga gggttatcca  480
gaagctgagg taatctggac aaacagtgac caccaacccg tgagtgggaa gagaagtgtc  540
accacttccc ggacagaggg gatgcttctc aatgtgacca gcagtctgag ggtcaacgcc  600
acagcgaatg atgttttcta ctgtacgttt tggagatcac agccagggca aaaccacaca  660
gcggagctga tcatcccaga actgcctgca acacatcctc cacagaacag gactatcgat  720
gtcgagccac tgggcatgga gaatgggaac attgccaact cacagatcgc cgcctcatct  780
gtgcgtgtga ccttcttggg tttgcagcat tgggtcccgg agctggcccg cctgaaccgc  840
gcaggcatgg tcaatgcctg gacacccagc agcaatgacg ataacccctg gatccaggtg  900
aacctgctgc ggaggatgtg ggtaacaggt gtggtgacgc agggtgccag ccgcttggcc  960
agtcatgagt acctgaaggc cttcaaggtg gcctacagcc ttaatggaca cgaattcgat  1020
ttcatccatg atgttaataa aaaacacaag gagtttgtgg gtaactggaa caaaaacgcg  1080
gtgcatgtca acctgtttga gacccctgtg gaggctcagt acgtgagatt gtaccccacg  1140
agctgccaca cggcctgcac tctgcgcttt gagctactgg gctgtgagct gaacggatgc  1200
gccaatcccc tgggcctgaa gaataacagc atccctgaca agcagatcac ggcctccagc  1260
agctacaaga cctggggctt gcatctcttc agctggaacc cctcctatgc acggctggac  1320
aagcagggca acttcaacgc ctgggttgcg ggagctacgg gtaacgatca gtggctgcag  1380
atcttccctg gcaactggga caaccactcc cacaagaaga acttgtttga gacgcccatc  1440
ctggctcgct atgtgcgcat cctgcctgta gcctggcaca accgcatcgc cctgcgcctg  1500
gagctgctgg gctgttag                                                1518
```

```
SEQ ID NO: 288         moltype = AA  length = 505
FEATURE                Location/Qualifiers
REGION                 1..505
                       note = Description of Artificial Sequence: Synthetic
                        polypeptide
source                 1..505
                       mol_type = protein
                       organism = synthetic construct
SEQUENCE: 288
MRIFAGIIFT ACCHLLRAFT ITAPKDLYVV EYGSNVTMEC RFPVERELDL LALVVYWEKE  60
DEQVIQFVAG EEDLKPQHSN FRGRASLPKD QLLKGNAALQ ITDVKLQDAG VYCCIISYGG  120
ADYKRITLKV NAPYRKINQR ISVDPATSEH ELICQAEGYP EAEVIWTNSD HQPVSGKRSV  180
TTSRTEGMLL NVTSSLRVNA TANDVFYCTF WRSQPGQNHT AELIIPELPA THPPQNRTID  240
VEPLGMENGN IANSQIAASS VRVTFLGLQH WVPELARLNR AGMVNAWTPS SNDDNPWIQV  300
```

```
NLLRRMWVTG VVTQGASRLA SHEYLKAFKV AYSLNGHEFD FIHDVNKKHK EFVGNWNKNA  360
VHVNLFETPV EAQYVRLYPT SCHTACTLRF ELLGCELNGC ANPLGLKNNS IPDKQITASS  420
SYKTWGLHLF SWNPSYARLD KQGNFNAWVA GSYGNDQWLQ IFPGNWDNHS HKKNLFETPI  480
LARYVRILPV AWHNRIALRL ELLGC                                        505

SEQ ID NO: 289         moltype = DNA  length = 1521
FEATURE                Location/Qualifiers
misc_feature           1..1521
                       note = Description of Artificial Sequence: Synthetic
                        polynucleotide
source                 1..1521
                       mol_type = other DNA
                       organism = synthetic construct
SEQUENCE: 289
atgaggatat ttgctggcat tatattcaca gcctgctgtc acttgctacg ggcgtttact  60
atcacggctc caaaggactt gtacgtggtg gagtatggca gcaacgtcac gatggagtgc  120
agattccctg tagaacggga gctggacctg cttgcgttag tggtgtactg ggaaaaggaa  180
gatgagcaag tgattcagtt tgtggcagga gaggaggacc ttaagcctca gcacagcaac  240
ttcaggggga gagcctcgct gccaaaggac cagcttttga agggaaatgc tgcccttcag  300
atcacagacg tcaagctgca ggacgcaggc gtttactgct gcataatcag ctacggtggt  360
gcggactaca agcgaatcac gctgaaagtc aatgccccat accgcaaaat caaccagaga  420
atttccgtgg atccagccac ttctgagcat gaactaatat gtcaggccga gggttatcca  480
gaagctgagg taatctggac aaacagtgac caccaacccg tgagtgggaa gagaagtgtc  540
accacttccc ggacagaggg gatgcttctc aatgtgacca gcagtctgag ggtcaacgcc  600
acagcgaatg atgttttcta ctgtacgttt tggagatcac agccagggca aaaccacaca  660
gcggagctga tcatcccaga actgcctgca acacatcctc cacagaacag gactatcgat  720
gacaaaactc acacatgccc accgtgccca gcacctgaac tcctgggggg accgtcagtc  780
ttcctcttcc ccccaaaacc caaggacacc ctcatgatct cccggacccc tgaggtcaca  840
tgcgtggtgg tggacgtgag ccacgaagac cctgaggtca agttcaactg gtacgtggac  900
ggcgtggagg tgcataatgc caagacaaag ccgcgggagg agcagtacaa cagcacgtac  960
cgtgtggtca gcgtcctcac cgtcctgcac caggactggc tgaatggcaa ggagtacaag  1020
tgcaaggtct ccaacaaagc cctcccagcc cccatcgaga aaaccatctc caaagccaaa  1080
gggcagcccc gagaaccaca ggtgtacacc ctgcccccat cccgggagga gatgaccaag  1140
aaccaggtca gcctgacctg cctggtcaaa ggcttctatc ccagcgacat cgccgtggag  1200
tgggagagca atgggcagcc ggagaacaac tacaagacca cgcctcccgt gctggactcc  1260
gacggctcct tcttcctcta cagcaagctc accgtggaca agagcaggtg gcagcagggg  1320
aacgtcttct catgctccgt gatgcacgag gctctgcaca accactacac gcagaagagc  1380
ctctccctgt ctccgggtaa aatcgatcca aataaaggaa gtggaaccac ttcaggtact  1440
acccgtcttc tatctgggca cacgtgtttc acgttgacag gtttgcttgg gacgctagta  1500
accatgggct tgctgactta g                                            1521

SEQ ID NO: 290         moltype = AA  length = 506
FEATURE                Location/Qualifiers
REGION                 1..506
                       note = Description of Artificial Sequence: Synthetic
                        polypeptide
source                 1..506
                       mol_type = protein
                       organism = synthetic construct
SEQUENCE: 290
MRIFAGIIFT ACCHLLRAFT ITAPKDLYVV EYGSNVTMEC RFPVERELDL LALVVYWEKE  60
DEQVIQFVAG EEDLKPQHSN FRGRASLPKD QLLKGNAALQ ITDVKLQDAG VYCCIISYGG  120
ADYKRITLKV NAPYRKINQR ISVDPATSEH ELICQAEGYP EAEVIWTNSD HQPVSGKRSV  180
TTSRTEGMLL NVTSSLRVNA TANDVFYCTF WRSQPGQNHT AELIIPELPA THPPQNRTID  240
DKTHTCPPCP APELLGGPSV FLFPPKPKDT LMISRTPEVT CVVVDVSHED PEVKFNWYVD  300
GVEVHNAKTK PREEQYNSTY RVVSVLTVLH QDWLNGKEYK CKVSNKALPA PIEKTISKAK  360
GQPREPQVYT LPPSREEMTK NQVSLTCLVK GFYPSDIAVE WESNGQPENN YKTTPPVLDS  420
DGSFFLYSKL TVDKSRWQQG NVFSCSVMHE ALHNHYTQKS LSLSPGKIDP NKGSGTTSGT  480
TRLLSGHTCF TLTGLLGTLV TMGLLT                                       506

SEQ ID NO: 291         moltype = DNA  length = 828
FEATURE                Location/Qualifiers
misc_feature           1..828
                       note = Description of Artificial Sequence: Synthetic
                        polynucleotide
source                 1..828
                       mol_type = other DNA
                       organism = synthetic construct
SEQUENCE: 291
atgaggatat ttgctggcat tatattcaca gcctgctgtc acttgctacg ggcgtttact  60
atcacggctc caaaggactt gtacgtggtg gagtatggca gcaacgtcac gatggagtgc  120
agattccctg tagaacggga gctggacctg cttgcgttag tggtgtactg ggaaaaggaa  180
gatgagcaag tgattcagtt tgtggcagga gaggaggacc ttaagcctca gcacagcaac  240
ttcaggggga gagcctcgct gccaaaggac cagcttttga agggaaatgc tgcccttcag  300
atcacagacg tcaagctgca ggacgcaggc gtttactgct gcataatcag ctacggtggt  360
gcggactaca agcgaatcac gctgaaagtc aatgccccat accgcaaaat caaccagaga  420
atttccgtgg atccagccac ttctgagcat gaactaatat gtcaggccga gggttatcca  480
gaagctgagg taatctggac aaacagtgac caccaacccg tgagtgggaa gagaagtgtc  540
accacttccc ggacagaggg gatgcttctc aatgtgacca gcagtctgag ggtcaacgcc  600
```

```
acagcgaatg atgttttcta ctgtacgttt tggagatcac agccagggca aaaccacaca  660
gcggagctga tcatcccaga actgcctgca acacatcctc cacagaacag gactccaaat  720
aaaggaagtg gaaccacttc aggtactacc cgtcttctat ctgggcacac gtgtttcacg  780
ttgacaggtt tgcttgggac gctagtaacc atgggcttgc tgacttag               828

SEQ ID NO: 292         moltype = AA  length = 275
FEATURE                Location/Qualifiers
REGION                 1..275
                       note = Description of Artificial Sequence: Synthetic
                        polypeptide
source                 1..275
                       mol_type = protein
                       organism = synthetic construct
SEQUENCE: 292
MRIFAGIIFT ACCHLLRAFT ITAPKDLYVV EYGSNVTMEC RFPVERELDL LALVVYWEKE  60
DEQVIQFVAG EEDLKPQHSN FRGRASLPKD QLLKGNAALQ ITDVKLQDAG VYCCIISYGG  120
ADYKRITLKV NAPYRKINQR ISVDPATSEH ELICQAEGYP EAEVIWTNSD HQPVSGKRSV  180
TTSRTEGMLL NVTSSLRVNA TANDVFYCTF WRSQPGQNHT AELIIPELPA THPPQNRTPN  240
KGSGTTSGTT RLLSGHTCFT LTGLLGTLVT MGLLT                             275

SEQ ID NO: 293         moltype = DNA  length = 1464
FEATURE                Location/Qualifiers
misc_feature           1..1464
                       note = Description of Artificial Sequence: Synthetic
                        polynucleotide
source                 1..1464
                       mol_type = other DNA
                       organism = synthetic construct
SEQUENCE: 293
atgctgctcc tgctgccgat actgaacctg agcttacaac ttcatcctgt agcagcttta  60
ttcaccgtga cagcccctaa agaagtgtac accgtagacg tcggcagcag tgtgagcctg  120
gagtgcgatt ttgaccgcag agaatgcact gaactggaag ggataagagc cagtttgcag  180
aaggtagaaa atgatacgtc tctgcaaagt gaaagagcca ccctgctgga ggagcagctg  240
cccctgggaa aggctttgtt ccacatccct agtgtccaag tgagagattc cgggcagtac  300
cgttgcctgg tcatctgcgg ggccgcctgg gactacaagt acctgacggt gaaagtcaaa  360
gcttcttaca tgaggataga cactaggatc ctggaggttc caggtacagg ggaggtgcag  420
cttacctgcc aggctagagg ttatccccta gcagaagtgt cctggcaaaa tgtcagtgtt  480
cctgccaaca ccagccacat caggaccccc gaaggcctct accaggtcac cagtgttctg  540
cgcctcaagc ctcagcctag cagaaacttc agctgcatgt tctggaatgc tcacatgaag  600
gagctgactt cagccatcat tgaccctctg agtcggatgg aacccaaagt ccccagaacg  660
atcgatgtcg agccactggg catggagaat gggaacattg ccaactcaca gatcgccgcc  720
tcatctgtgc gtgtgacctt cttgggtttg cagcattggg tcccggagct ggcccgcctg  780
aaccgcgcag gcatggtcaa tgcctggaca cccagcagca atgacgataa cccctggatc  840
caggtgaacc tgctgcggag gatgtgggta acaggtgtgg tgacgcaggg tgccagccgc  900
ttggccagtc atgagtacct gaaggccttc aaggtggcct acagccttaa tggacacgaa  960
ttcgatttca tccatgatgt taataaaaaa cacaaggagt ttgtgggtaa ctggaacaaa  1020
aacgcggtgc atgtcaacct gtttgagacc cctgtggagg ctcagtacgt gagattgtac  1080
cccacgagct gccacacggc ctgcactctg cgctttgagc tactgggctg tgagctgaac  1140
ggatgcgcca atcccctggg cctgaagaat aacagcatcc ctgacaagca gatcacggcc  1200
tccagcagct acaagacctg ggcttgcat ctcttcagct ggaacccctc ctatgcacgg  1260
ctggacaagc agggcaactt caacgcctgg gttgcgggga gctacggtaa cgatcagtgg  1320
ctgcagatct tccctggcaa ctgggacaac cactcccaca agaagaactt gtttgagacg  1380
cccatcctgg ctcgctatgt gcgcatcctg cctgtagcct ggcacaaccg catcgccctg  1440
cgcctggagc tgctgggctg ttag                                         1464

SEQ ID NO: 294         moltype = AA  length = 487
FEATURE                Location/Qualifiers
REGION                 1..487
                       note = Description of Artificial Sequence: Synthetic
                        polypeptide
source                 1..487
                       mol_type = protein
                       organism = synthetic construct
SEQUENCE: 294
MLLLLPILNL SLQLHPVAAL FTVTAPKEVY TVDVGSSVSL ECDFDRRECT ELEGIRASLQ  60
KVENDTSLQS ERATLLEEQL PLGKALFHIP SVQVRDSGQY RCLVICGAAW DYKYLTVKVK  120
ASYMRIDTRI LEVPGTGEVQ LTCQARGYPL AEVSWQNVSV PANTSHIRTP EGLYQVTSVL  180
RLKPQPSRNF SCMFWNAHMK ELTSAIIDPL SRMEPKVPRT IDVEPLGMEN GNIANSQIAA  240
SSVRVTFLGL QHWVPELARL NRAGMVNAWT PSSNDDNPWI QVNLLRRMWV TGVVTQGASR  300
LASHEYLKAF KVAYSLNGHE FDFIHDVNKK HKEFVGNWNK NAVHVNLFET PVEAQYVRLY  360
PTSCHTACTL RFELLGCELN GCANPLGLKN NSIPDKQITA SSSYKTWGLH LFSWNPSYAR  420
LDKQGNFNAW VAGSYGNDQW LQIFPGNWDN HSHKKNLFET PILARYVRIL PVAWHNRIAL  480
RLELLGC                                                            487

SEQ ID NO: 295         moltype = DNA  length = 1467
FEATURE                Location/Qualifiers
misc_feature           1..1467
                       note = Description of Artificial Sequence: Synthetic
                        polynucleotide
```

```
source                 1..1467
                       mol_type = other DNA
                       organism = synthetic construct
SEQUENCE: 295
atgctgctcc tgctgccgat actgaacctg agcttacaac ttcatcctgt agcagcttta  60
ttcaccgtga cagcccctaa agaagtgtac accgtagacg tcggcagcag tgtgagcctg  120
gagtgcgatt ttgaccgcag agaatgcact gaactggaag ggataagagc cagtttgcag  180
aaggtagaaa atgatacgtc tctgcaaagt gaaagagcca ccctgctgga ggagcagctg  240
cccctgggaa aggctttgtt ccacatccct agtgtccaag tgagagattc cgggcagtac  300
cgttgcctgg tcatctgcgg ggccgcctgg gactacaagt acctgacggt gaaagtcaaa  360
gcttcttaca tgaggataga cactaggatc ctggaggttc caggtacagg ggaggtgcag  420
cttacctgcc aggctagagg ttatccccta gcagaagtgt cctggcaaaa tgtcagtgtt  480
cctgccaaca ccagccacat caggaccccc gaaggcctct accaggtcac cagtgttctg  540
cgcctcaagc ctcagcctag cagaaacttc agctgcatgt tctggaatgc tcacatgaag  600
gagctgactt cagccatcat tgaccctctg agtcggatgg aacccaaagt ccccagaacg  660
atcgatgaca aaactcacac atgcccaccg tgcccagcac ctgaactcct ggggggaccg  720
tcagtcttcc tcttcccccc aaaacccaag gacaccctca tgatctcccg gacccctgag  780
gtcacatgcg tggtggtgga cgtgagccac gaagaccctg aggtcaagtt caactggtac  840
gtggacggcg tggaggtgca taatgccaag acaaagccgc gggaggagca gtacaacagc  900
acgtaccgtg tggtcagcgt cctcaccgtc ctgcaccagg actggctgaa tggcaaggag  960
tacaagtgca aggtctccaa caaagccctc ccagccccca tcgagaaaac catctccaaa  1020
gccaaagggc agccccgaga accacaggtg tacaccctgc ccccatcccg ggaggagatg  1080
accaagaacc aggtcagcct gacctgcctg gtcaaaggct tctatcccag cgacatcgcc  1140
gtggagtggg agagcaatgg gcagccggag aacaactaca agaccacgcc tcccgtgctg  1200
gactccgacg gctccttctt cctctacagc aagctcaccg tggacaagag caggtggcag  1260
caggggaacg tcttctcatg ctccgtgatg cacgaggctc tgcacaacca ctacacgcag  1320
aagagcctct ccctgtctcc gggtaaaatc gatccaaata aaggaagtgg aaccacttca  1380
ggtactaccc gtcttctatc tggcacacg tgtttcacgt tgacaggttt gcttgggacg  1440
ctagtaacca tgggcttgct gacttag                                     1467

SEQ ID NO: 296         moltype = AA  length = 488
FEATURE                Location/Qualifiers
REGION                 1..488
                       note = Description of Artificial Sequence: Synthetic
                        polypeptide
source                 1..488
                       mol_type = protein
                       organism = synthetic construct
SEQUENCE: 296
MLLLLPILNL SLQLHPVAAL FTVTAPKEVY TVDVGSSVSL ECDFDRRECT ELEGIRASLQ  60
KVENDTSLQS ERATLLEEQL PLGKALFHIP SVQVRDSGQY RCLVICGAAW DYKYLTVKVK  120
ASYMRIDTRI LEVPGTGEVQ LTCQARGYPL AEVSWQNVSV PANTSHIRTP EGLYQVTSVL  180
RLKPQPSRNF SCMFWNAHMK ELTSAIIDPL SRMEPKVPRT IDDKTHTCPP CPAPELLGGP  240
SVFLFPPKPK DTLMISRTPE VTCVVVDVSH EDPEVKFNWY VDGVEVHNAK TKPREEQYNS  300
TYRVVSVLTV LHQDWLNGKE YKCKVSNKAL PAPIEKTISK AKGQPREPQV YTLPPSREEM  360
TKNQVSLTCL VKGFYPSDIA VEWESNGQPE NNYKTTPPVL DSDGSFFLYS KLTVDKSRWQ  420
QGNVFSCSVM HEALHNHYTQ KSLSLSPGKI DPNKGSGTTS GTTRLLSGHT CFTLTGLLGT  480
LVTMGLLT                                                          488

SEQ ID NO: 297         moltype = DNA  length = 1494
FEATURE                Location/Qualifiers
misc_feature           1..1494
                       note = Description of Artificial Sequence: Synthetic
                        polynucleotide
source                 1..1494
                       mol_type = other DNA
                       organism = synthetic construct
SEQUENCE: 297
atgaggatat ttgctggcat tatattcaca gcctgctgtc acttgctacg ggcgtttact  60
atcacggctc caaaggactt gtacgtggtg gagtatggca gcaacgtcac gatggagtgc  120
agattccctg tagaacggga gctggacctg cttgcgttag tggtgtactg ggaaaaggaa  180
gatgagcaag tgattcagtt tgtggcagga gaggaggacc ttaagcctca gcacagcaac  240
ttcaggggga gagcctcgct gccaaaggac cagcttttga agggaaatgc tgcccttcag  300
atcacagacg tcaagctgca ggacgcaggc gtttactgct gcataatcag ctacggtggt  360
gcggactaca agcgaatcac gctgaaagtc aatgccccat accgcaaaat caaccagaga  420
atttccgtgg atccagccac ttctgagcat gaactaatat gtcaggccga gggttatcca  480
gaagctgagg taatctggac aaacagtgac caccaacccg tgagtgggaa gagaagtgtc  540
accacttccc ggacagaggg gatgcttctc aatgtgacca gcagtctgag ggtcaacgcc  600
acagcgaatg atgttttcta ctgtacgttt tggagatcac agccagggca aaaccacaca  660
gcggagctga tcatcccaga actgcctgca acacatcctc cacagaacag gactggttgt  720
aagccttgca tatgtacagt cccagaagta tcatctgtct tcatcttccc cccaaagccc  780
aaggatgtgc tcaccattac tctgactcct aaggtcacgt gtgttgtggt agacatcagc  840
aaggatgatc ccgaggtcca gttcagctgg tttgtagatg atgtggaggt gcacacagct  900
cagacgcaac cccgggagga gcagttcaac agcactttcc gctcagtcag tgaacttccc  960
atcatgcacc aggactggct caatggcaag gagttcaaat gcagggtcaa cagtgcagct  1020
ttccctgccc ccatcgagaa aaccatctcc aaaaccaaag gcagaccgaa ggctccacag  1080
gtgtacacca ttccacctcc caaggagcag atggccaagg ataaagtcag tctgacctgc  1140
atgataacag acttcttccc tgaagacatt actgtggagt ggcagtggaa tgggcagcca  1200
gcggagaact acaagaacac tcagcccatc atggacacag atggctctta cttcgtctac  1260
```

```
agcaagctca atgtgcagaa gagcaactgg gaggcaggaa atactttcac ctgctctgtg  1320
ttacatgagg gcctgcacaa ccaccatact gagaagagcc tctcccactc tcctggtaaa  1380
ccaaataaag gaagtggaac cacttcaggt actacccgtc ttctatctgg gcacacgtgt  1440
ttcacgttga caggtttgct tgggacgcta gtaaccatgg gcttgctgac ttag        1494

SEQ ID NO: 298         moltype = AA  length = 497
FEATURE                Location/Qualifiers
REGION                 1..497
                       note = Description of Artificial Sequence: Synthetic
                        polypeptide
source                 1..497
                       mol_type = protein
                       organism = synthetic construct
SEQUENCE: 298
MRIFAGIIFT ACCHLLRAFT ITAPKDLYVV EYGSNVTMEC RFPVERELDL LALVVYWEKE  60
DEQVIQFVAG EEDLKPQHSN FRGRASLPKD QLLKGNAALQ ITDVKLQDAG VYCCIISYGG  120
ADYKRITLKV NAPYRKINQR ISVDPATSEH ELICQAEGYP EAEVIWTNSD HQPVSGKRSV  180
TTSRTEGMLL NVTSSLRVNA TANDVFYCTF WRSQPGQNHT AELIIPELPA THPPQNRTGC  240
KPCICTVPEV SSVFIFPPKP KDVLTITLTP KVTCVVVDIS KDDPEVQFSW FVDDVEVHTA  300
QTQPREEQFN STFRSVSELP IMHQDWLNGK EFKCRVNSAA FPAPIEKTIS KTKGRPKAPQ  360
VYTIPPPKEQ MAKDKVSLTC MITDFFPEDI TVEWQWNGQP AENYKNTQPI MDTDGSYFVY  420
SKLNVQKSNW EAGNTFTCSV LHEGLHNHHT EKSLSHSPGK PNKGSGTTSG TTRLLSGHTC  480
FTLTGLLGTL VTMGLLT                                                 497

SEQ ID NO: 299         moltype = DNA  length = 774
FEATURE                Location/Qualifiers
misc_feature           1..774
                       note = Description of Artificial Sequence: Synthetic
                        polynucleotide
source                 1..774
                       mol_type = other DNA
                       organism = synthetic construct
SEQUENCE: 299
atgctgctcc tgctgccgat actgaacctg agcttacaac ttcatcctgt agcagcttta  60
ttcaccgtga cagcccctaa agaagtgtac accgtagacg tcggcagcag tgtgagcctg  120
gagtgcgatt ttgaccgcag agaatgcact gaactggaag ggataagagc cagtttgcag  180
aaggtagaaa atgatacgtc tctgcaaagt gaaagagcca ccctgctgga ggagcagctg  240
cccctgggaa aggctttgtt ccacatccct agtgtccaag tgagagattc cgggcagtac  300
cgttgcctgg tcatctgcgg ggccgcctgg gactacaagt acctgacggt gaaagtcaaa  360
gcttcttaca tgaggataga cactaggatc ctggaggttc caggtacagg ggaggtgcag  420
cttacctgcc aggctagagg ttatccccta gcagaagtgt cctggcaaaa tgtcagtgtt  480
cctgccaaca ccagccacat caggaccccc gaaggcctct accaggtcac cagtgttctg  540
cgcctcaagc ctcagcctag cagaaacttc agctgcatgt tctggaatgc tcacatgaag  600
gagctgactt cagccatcat tgaccctctg agtcggatgg aacccaaagt ccccagaacg  660
ccaaataaag gaagtggaac cacttcaggt actacccgtc ttctatctgg gcacacgtgt  720
ttcacgttga caggtttgct tgggacgcta gtaaccatgg gcttgctgac ttag        774

SEQ ID NO: 300         moltype = AA  length = 257
FEATURE                Location/Qualifiers
REGION                 1..257
                       note = Description of Artificial Sequence: Synthetic
                        polypeptide
source                 1..257
                       mol_type = protein
                       organism = synthetic construct
SEQUENCE: 300
MLLLLPILNL SLQLHPVAAL FTVTAPKEVY TVDVGSSVSL ECDFDRRECT ELEGIRASLQ  60
KVENDTSLQS ERATLLEEQL PLGKALFHIP SVQVRDSGQY RCLVICGAAW DYKYLTVKVK  120
ASYMRIDTRI LEVPGTGEVQ LTCQARGYPL AEVSWQNVSV PANTSHIRTP EGLYQVTSVL  180
RLKPQPSRNF SCMFWNAHMK ELTSAIIDPL SRMEPKVPRT PNKGSGTTSG TTRLLSGHTC  240
FTLTGLLGTL VTMGLLT                                                 257

SEQ ID NO: 301         moltype = DNA  length = 1623
FEATURE                Location/Qualifiers
misc_feature           1..1623
                       note = Description of Artificial Sequence: Synthetic
                        polynucleotide
source                 1..1623
                       mol_type = other DNA
                       organism = synthetic construct
SEQUENCE: 301
atgaggatat ttgctggcat tatattcaca gcctgctgtc acttgctacg ggcgtttact  60
atcacggctc caaaggactt gtacgtggtg gagtatggca gcaacgtcac gatggagtgc  120
agattccctg tagaacggga gctggacctg cttgcgttag tggtgtactg ggaaaaggaa  180
gatgagcaag tgattcagtt tgtggcagga gaggaggacc ttaagcctca gcacagcaac  240
ttcaggggga gagcctcgct gccaaaggac cagcttttga agggaaatgc tgcccttcag  300
atcacagacg tcaagctgca ggacgcaggc gtttactgct gcataatcag ctacggtggt  360
gcggactaca agcgaatcac gctgaaagtc aatgccccat accgcaaaat caaccagaga  420
atttccgtgg atccagccac ttctgagcat gaactaatat gtcaggccga gggttatcca  480
```

-continued

```
gaagctgagg taatctggac aaacagtgac caccaacccg tgagtgggaa gagaagtgtc  540
accacttccc ggacagaggg gatgcttctc aatgtgacca gcagtctgag ggtcaacgcc  600
acagcgaatg atgttttcta ctgtacgttt tggagatcac agccagggca aaaccacaca  660
gcggagctga tcatcccaga actgcctgca acacatcctc cacagaacag gactccaaat  720
aaaggaagtg gaaccacttc aggtactacc cgtcttctat ctgggcacac gtgtttcacg  780
ttgacaggtt tgcttgggac gctagtaacc atgggcttgc tgactggaag cggagctact  840
aacttcagcc tgctgaagca ggctggcgac gtggaggaga accctggacc tatggaacct  900
ctcccaggat gggggtcggc accctggagc caggccccta cagacaacac cttcaggctg  960
gtgccttgtg tcttcctttt gaacttgctg cagcgcatct ctgcccagcc ctcatgcaga  1020
caggaggagt tccttgtggg agacgagtgc tgccccatgt gcaacccagg ttaccatgtg  1080
aagcaggtct gcagtgagca tacaggcaca gtgtgtgccc cctgtccccc acagacatat  1140
accgcccatg caaatggcct gagcaagtgt ctgccctgcg gagtctgtga tccagacatg  1200
ggcctgctga cctggcagga gtgctccagc tggaaggaca ctgtgtgcag atgcatccca  1260
ggctacttct gtgagaacca ggatgggagc cactgttcca catgcttgca gcacaccacc  1320
tgccctccag ggcagagggt agagaagaga gggactcacg accaggacac tgtatgtgct  1380
gactgcctaa cagggacctt ctcacttgga gggactcagg aggaatgcct gccctggacc  1440
aactgcagtg catttcaaca ggaagtaaga cgtgggacca acagcacaga caccacctgc  1500
tcctcccagc caaataaagg aagtggaacc acttcaggta ctacccgtct tctatctggg  1560
cacacgtgtt tcacgttgac aggtttgctt gggacgctag taaccatggg cttgctgact  1620
tag                                                                1623
```

```
SEQ ID NO: 302          moltype = AA  length = 540
FEATURE                 Location/Qualifiers
REGION                  1..540
                        note = Description of Artificial Sequence: Synthetic
                         polypeptide
source                  1..540
                        mol_type = protein
                        organism = synthetic construct
SEQUENCE: 302
MRIFAGIIFT ACCHLLRAFT ITAPKDLYVV EYGSNVTMEC RFPVERELDL LALVVYWEKE  60
DEQVIQFVAG EEDLKPQHSN FRGRASLPKD QLLKGNAALQ ITDVKLQDAG VYCCIISYGG  120
ADYKRITLKV NAPYRKINQR ISVDPATSEH ELICQAEGYP EAEVIWTNSD HQPVSGKRSV  180
TTSRTEGMLL NVTSSLRVNA TANDVFYCTF WRSQPGQNHT AELIIPELPA THPPQNRTPN  240
KGSGTTSGTT RLLSGHTCFT LTGLLGTLVT MGLLTGSGAT NFSLLKQAGD VEENPGPMEP  300
LPGWGSAPWS QAPTDNTFRL VPCVFLLNLL QRISAQPSCR QEEFLVGDEC CPMCNPGYHV  360
KQVCSEHTGT VCAPCPPQTY TAHANGLSKC LPCGVCDPDM GLLTWQECSS WKDTVCRCIP  420
GYFCENQDGS HCSTCLQHTT CPPGQRVEKR GTHDQDTVCA DCLTGTFSLG GTQEECLPWT  480
NCSAFQQEVR RGTNSTDTTC SSQPNKGSGT TSGTTRLLSG HTCFTLTGLL GTLVTMGLLT  540
```

```
SEQ ID NO: 303          moltype = DNA  length = 1584
FEATURE                 Location/Qualifiers
misc_feature            1..1584
                        note = Description of Artificial Sequence: Synthetic
                         polynucleotide
source                  1..1584
                        mol_type = other DNA
                        organism = synthetic construct
SEQUENCE: 303
atgaggatat ttgctgtctt tatattcatg acctactggc atttgctgaa cgcatttact  60
gtcacggttc ccaaggacct atatgtggta gagtatggta gcaatatgac aattgaatgc  120
aaattcccag tagaaaaaca attagacctg gctgcactaa ttgtctattg ggaaatggag  180
gataagaaca ttattcaatt tgtgcatgga gaggaagacc tgaaggttca gcatagtagc  240
tacagacaga gggcccggct gttgaaggac cagctctccc tgggaaatgc tgcacttcag  300
atcacagatg tgaaattgca ggatgcaggg gtgtaccgct gcatgatcag ctatggtggt  360
gccgactaca agcgaattac tgtgaaagtc aatgccccat acaacaaaat caaccaaaga  420
attttggttg tggatccagt cacctctgaa catgaactga catgtcaggc tgagggctac  480
cccaaggccg aagtcatctg gacaagcagt gaccatcaag tcctgagtgg taagaccacc  540
accaccaatt ccaagagaga ggagaagctt ttcaatgtga ccagcacact gagaatcaac  600
acaacaacta atgagatttt ctactgcact tttaggagat tagatcctga ggaaaaccat  660
acagctgaat tggtcatccc agaactacct ctggcacatc ctccaaatga aaggtgtgga  720
aatggaatgg tagaacaagg tgaagaatgt gattgtggct atagtgacca gtgtaaagat  780
gaatgctgct tcgatgcaaa tcaaccagag ggaagaaaat gcaaactgaa acctgggaaa  840
cagtgcagtc caagtcaagg tccttgttgt acagcacagt gtgcattcaa gtcaaagtct  900
gagaagtgtc gggatgattc agactgtgca agggaaggaa tatgtaatgg cttcacagct  960
ctctgcccag catctgaccc taaaccaaac ttcacagact gtaataggca tacacaagtg  1020
tgcattaatg ggcaatgtgc aggttctatc tgtgagaaat atggcttaga ggagtgtacg  1080
tgtgccagtt ctgatggcaa agatgataaa gaattatgcc atgtatgctg tatgaagaaa  1140
atggacccat caacttgtgc cagtacaggg tctgtgcagt ggagtaggca cttcagtggt  1200
cgaaccatca ccctgcaacc tggatcccct tgcaacgatt ttagaggtta ctgtgatgtt  1260
ttcatgcggt gcagattagt agatgctgat ggtcctctag ctaggcttaa aaaagcaatt  1320
tttagtccag agctctatga aaacattgct gaatggattg tggctcattg gtgggcagta  1380
ttacttatgg gaattgctct gatcatgcta atggctggat ttattaagat atgcagtgtt  1440
catactccaa gtagtaatcc aaagttgcct cctcctaaac cacttccagg cactttaaag  1500
aggaggagac ctccacagcc cattcagcaa ccccagcgtc agcggccccg agagagttat  1560
caaatgggac acatgagacg ctaa                                         1584
```

```
SEQ ID NO: 304          moltype = AA  length = 527
FEATURE                 Location/Qualifiers
```

```
REGION                1..527
                      note = Description of Artificial Sequence: Synthetic
                       polypeptide
source                1..527
                      mol_type = protein
                      organism = synthetic construct
SEQUENCE: 304
MRIFAVFIFM TYWHLLNAFT VTVPKDLYVV EYGSNMTIEC KFPVEKQLDL AALIVYWEME  60
DKNIIQFVHG EEDLKVQHSS YRQRARLLKD QLSLGNAALQ ITDVKLQDAG VYRCMISYGG  120
ADYKRITVKV NAPYNKINQR ILVVDPVTSE HELTCQAEGY PKAEVIWTSS DHQVLSGKTT  180
TTNSKREEKL FNVTSTLRIN TTTNEIFYCT FRRLDPEENH TAELVIPELP LAHPPNERCG  240
NGMVEQGEEC DCGYSDQCKD ECCFDANQPE GRKCKLKPGK QCSPSQGPCC TAQCAFKSKS  300
EKCRDDSDCA REGICNGFTA LCPASDPKPN FTDCNRHTQV CINGQCAGSI CEKYGLEECT  360
CASSDGKDDK ELCHVCCMKK MDPSTCASTG SVQWSRHFSG RTITLQPGSP CNDFRGYCDV  420
FMRCRLVDAD GPLARLKKAI FSPELYENIA EWIVAHWWAV LLMGIALIML MAGFIKICSV  480
HTPSSNPKLP PPKPLPGTLK RRRPPQPIQQ PQRQRPRESY QMGHMRR                527

SEQ ID NO: 305        moltype = DNA  length = 1497
FEATURE               Location/Qualifiers
misc_feature          1..1497
                      note = Description of Artificial Sequence: Synthetic
                       polynucleotide
source                1..1497
                      mol_type = other DNA
                      organism = synthetic construct
SEQUENCE: 305
atgaggatat ttgctgtctt tatattcatg acctactggc atttgctgaa cgcatttact  60
gtcacggttc ccaaggacct atatgtggta gagtatggta gcaatatgac aattgaatgc  120
aaattcccag tagaaaaaca attagacctg gctgcactaa ttgtctattg ggaaatggag  180
gataagaaca ttattcaatt tgtgcatgga gaggaagacc tgaaggttca gcatagtagc  240
tacagacaga gggcccggct gttgaaggac cagctctccc tgggaaatgc tgcacttcag  300
atcacagatg tgaaattgca ggatgcaggg gtgtaccgct gcatgatcag ctatggtggt  360
gccgactaca agcgaattac tgtgaaagtc aatgccccat acaacaaaat caaccaaaga  420
attttggttg tggatccagt cacctctgaa catgaactga catgtcaggc tgagggctac  480
cccaaggccg aagtcatctg gacaagcagt gaccatcaag tcctgagtgg taagaccacc  540
accaccaatt ccaagagaga ggagaagctt ttcaatgtga ccagcacact gagaatcaac  600
acaacaacta atgagatttt ctactgcact tttaggagat tagatcctga ggaaaaccat  660
acagctgaat tggtcatccc agaactacct ctggcacatc ctccaaatga aagggagtcc  720
aaatatggtc ccccatgccc atcatgccca gcacctgagt tcctgggggg accatcagtc  780
ttcctgttcc ccccaaaacc caaggacact ctcatgatct cccggacccc tgaggtcacg  840
tgcgtggtgg tggacgtgag ccaggaagac cccgaggtcc agttcaactg gtacgtggat  900
ggcgtggagg tgcataatgc caagacaaag ccgcgggagg agcagttcaa cagcacgtac  960
cgtgtggtca gggtcctcac cgtcctgcac caggactggc tgaacggtaa ggagtacaag  1020
tgcaaggtct ccaacaaagg cctcccgtcc tccatcgaga aaaccatctc caaagccaaa  1080
gggcagcccc gagagccaca ggtgtacacc ctgcccccat cccaggagga gatgaccaag  1140
aaccaggtca gcctgacctg cctggtcaaa ggcttctacc ccagcgacat cgccgtggag  1200
tgggagagca atgggcagcc ggaggacaac tacaagacca cgcctcccgt gctggactcc  1260
gacggctcct tcttcctcta cagcaggcta accgtggaca agagcaggtg gcaggagggg  1320
aatgtcttct catgctccgt gatgcatgag gctctgcaca accactacac acagaagagc  1380
ctctccctgt ctccgggtaa attctacaca ggagtctata ttctgatcgg agccggcgcc  1440
ctcatgatgc tggtgggctt cctgggctgc tgcggggctg tgcaggagtc ccagtgc     1497

SEQ ID NO: 306        moltype = AA  length = 502
FEATURE               Location/Qualifiers
REGION                1..502
                      note = Description of Artificial Sequence: Synthetic
                       polypeptide
source                1..502
                      mol_type = protein
                      organism = synthetic construct
SEQUENCE: 306
MRIFAVFIFM TYWHLLNAFT VTVPKDLYVV EYGSNMTIEC KFPVEKQLDL AALIVYWEME  60
DKNIIQFVHG EEDLKVQHSS YRQRARLLKD QLSLGNAALQ ITDVKLQDAG VYRCMISYGG  120
ADYKRITVKV NAPYNKINQR ILVVDPVTSE HELTCQAEGY PKAEVIWTSS DHQVLSGKTT  180
TTNSKREEKL FNVTSTLRIN TTTNEIFYCT FRRLDPEENH TAELVIPELP LAHPPNERES  240
KYGPPCPSCP APEFLGGPSV FLFPPKPKDT LMISRTPEVT CVVVDVSQED PEVQFNWYVD  300
GVEVHNAKTK PREEQFNSTY RVVRVLTVLH QDWLNGKEYK CKVSNKGLPS SIEKTISKAK  360
GQPREPQVYT LPPSQEEMTK NQVSLTCLVK GFYPSDIAVE WESNGQPEDN YKTTPPVLDS  420
DGSFFLYSRL TVDKSRWQEG NVFSCSVMHE ALHNHYTQKS LSLSPGKFYT GVYILIGAGA  480
LMMLVGFLGC CGAVQESQCV IM                                           502

SEQ ID NO: 307        moltype = DNA  length = 1542
FEATURE               Location/Qualifiers
misc_feature          1..1542
                      note = Description of Artificial Sequence: Synthetic
                       polynucleotide
source                1..1542
                      mol_type = other DNA
                      organism = synthetic construct
```

SEQUENCE: 307
atgaggatat ttgctgtctt tatattcatg acctactggc atttgctgaa cgcatttact 60
gtcacggttc ccaaggacct atatgtggta gagtatggta gcaatatgac aattgaatgc 120
aaattcccag tagaaaaaca attagacctg gctgcactaa ttgtctattg ggaaatggag 180
gataagaaca ttattcaatt tgtgcatgga gaggaagacc tgaaggttca gcatagtagc 240
tacagacaga gggcccggct gttgaaggac cagctctccc tgggaaatgc tgcacttcag 300
atcacagatg tgaaattgca ggatgcaggg gtgtaccgct gcatgatcag ctatggtggt 360
gccgactaca agcgaattac tgtgaaagtc aatgccccat acaacaaaat caaccaaaga 420
attttggttg tggatccagt cacctctgaa catgaactga catgtcaggc tgagggctac 480
cccaaggccg aagtcatctg gacaagcagt gaccatcaag tcctgagtgg taagaccacc 540
accaccaatt ccaagagaga ggagaagctt ttcaatgtga ccagcacact gagaatcaac 600
acaacaacta atgagatttt ctactgcact tttaggagat tagatcctga ggaaaaccat 660
acagctgaat tggtcatccc agaactacct ctggcacatc ctccaaatga aagggagtcc 720
aaatatggtc ccccatgccc atcatgccca gcacctgagt tcctgggggg accatcagtc 780
ttcctgttcc ccccaaaacc caaggacact ctcatgatct cccggacccc tgaggtcacg 840
tgcgtggtgg tggacgtgag ccaggaagac cccgaggtcc agttcaactg gtacgtggat 900
ggcgtggagg tgcataatgc caagacaaag ccgcgggagg agcagttcaa cagcacgtac 960
cgtgtggtca gggtcctcac cgtcctgcac caggactggc tgaacggtaa ggagtacaag 1020
tgcaaggtct ccaacaaagg cctcccgtcc tccatcgaga aaaccatctc caaagccaaa 1080
gggcagcccc gagagccaca ggtgtacacc ctgcccccat cccaggagga gatgaccaag 1140
aaccaggtca gcctgacctg cctggtcaaa ggcttctacc ccagcgacat cgccgtggag 1200
tgggagagca atgggcagcc ggaggacaac tacaagacca cgcctcccgt gctggactcc 1260
gacggctcct tcttcctcta cagcaggcta accgtggaca agagcaggtg gcaggagggg 1320
aatgtcttct catgctccgt gatgcatgag gctctgcaca accactacac acagaagagc 1380
ctctccctgt ctccgggtaa attctacaca ggagtctata ttctgatcgg agccggcgcc 1440
ctcatgatgc tggtgggctt cctgggctgc tgcggggctg tgcaggagtc ccagtgcaaa 1500
aagaagaaaa agaagaagaa gacaaagtgt gtaattatgt aa 1542

SEQ ID NO: 308 moltype = AA length = 513
FEATURE Location/Qualifiers
REGION 1..513
note = Description of Artificial Sequence: Synthetic polypeptide
source 1..513
mol_type = protein
organism = synthetic construct
SEQUENCE: 308
MRIFAVFIFM TYWHLLNAFT VTVPKDLYVV EYGSNMTIEC KFPVEKQLDL AALIVYWEME 60
DKNIIQFVHG EEDLKVQHSS YRQRARLLKD QLSLGNAALQ ITDVKLQDAG VYRCMISYGG 120
ADYKRITVKV NAPYNKINQR ILVVDPVTSE HELTCQAEGY PKAEVIWTSS DHQVLSGKTT 180
TTNSKREEKL FNVTSTLRIN TTTNEIFYCT FRRLDPEENH TAELVIPELP LAHPPNERES 240
KYGPPCPSCP APEFLGGPSV FLFPPKPKDT LMISRTPEVT CVVVDVSQED PEVQFNWYVD 300
GVEVHNAKTK PREEQFNSTY RVVRVLTVLH QDWLNGKEYK CKVSNKGLPS SIEKTISKAK 360
GQPREPQVYT LPPSQEEMTK NQVSLTCLVK GFYPSDIAVE WESNGQPEDN YKTTPPVLDS 420
DGSFFLYSRL TVDKSRWQEG NVFSCSVMHE ALHNHYTQKS LSLSPGKFYT GVYILIGAGA 480
LMMLVGFLGC CGAVQESQCK KKKKKKTKC VIM 513

SEQ ID NO: 309 moltype = DNA length = 1515
FEATURE Location/Qualifiers
misc_feature 1..1515
note = Description of Artificial Sequence: Synthetic polynucleotide
source 1..1515
mol_type = other DNA
organism = synthetic construct
SEQUENCE: 309
atgaggatat ttgctgtctt tatattcatg acctactggc atttgctgaa cgcatttact 60
gtcacggttc ccaaggacct atatgtggta gagtatggta gcaatatgac aattgaatgc 120
aaattcccag tagaaaaaca attagacctg gctgcactaa ttgtctattg ggaaatggag 180
gataagaaca ttattcaatt tgtgcatgga gaggaagacc tgaaggttca gcatagtagc 240
tacagacaga gggcccggct gttgaaggac cagctctccc tgggaaatgc tgcacttcag 300
atcacagatg tgaaattgca ggatgcaggg gtgtaccgct gcatgatcag ctatggtggt 360
gccgactaca agcgaattac tgtgaaagtc aatgccccat acaacaaaat caaccaaaga 420
attttggttg tggatccagt cacctctgaa catgaactga catgtcaggc tgagggctac 480
cccaaggccg aagtcatctg gacaagcagt gaccatcaag tcctgagtgg taagaccacc 540
accaccaatt ccaagagaga ggagaagctt ttcaatgtga ccagcacact gagaatcaac 600
acaacaacta atgagatttt ctactgcact tttaggagat tagatcctga ggaaaaccat 660
acagctgaat tggtcatccc agaactacct ctggcacatc ctccaaatga aaggatcgat 720
gacaaaactc acacatgccc accgtgccca gcacctgaac tcctgggggg accgtcagtc 780
ttcctcttcc ccccaaaacc caaggacacc ctcatgatct cccggacccc tgaggtcaca 840
tgcgtggtgg tggacgtgag ccacgaagac cctgaggtca agttcaactg gtacgtggac 900
ggcgtggagg tgcataatgc caagacaaag ccgcgggagg agcagtacaa cagcacgtac 960
cgtgtggtca gcgtcctcac cgtcctgcac caggactggc tgaatggcaa ggagtacaag 1020
tgcaaggtct ccaacaaagc cctcccagcc cccatcgaga aaaccatctc caaagccaaa 1080
gggcagcccc gagaaccaca ggtgtacacc ctgcccccat cccgggagga gatgaccaag 1140
aaccaggtca gcctgacctg cctggtcaaa ggcttctatc ccagcgacat cgccgtggag 1200
tgggagagca atgggcagcc ggagaacaac tacaagacca cgcctcccgt gctggactcc 1260
gacggctcct tcttcctcta cagcaagctc accgtggaca agagcaggtg gcagcagggg 1320
aacgtcttct catgctccgt gatgcacgag gctctgcaca accactacac gcagaagagc 1380

```
ctctccctgt ctccgggtaa aatcgatttc tacacaggag tctatattct gatcggagcc  1440
ggcgccctca tgatgctggt gggcttcctg ggctgctgcg ggctgtgca ggagtcccag  1500
tgcgtaatta tgtaa                                                   1515

SEQ ID NO: 310         moltype = AA  length = 504
FEATURE                Location/Qualifiers
REGION                 1..504
                       note = Description of Artificial Sequence: Synthetic
                        polypeptide
source                 1..504
                       mol_type = protein
                       organism = synthetic construct
SEQUENCE: 310
MRIFAVFIFM TYWHLLNAFT VTVPKDLYVV EYGSNMTIEC KFPVEKQLDL AALIVYWEME  60
DKNIIQFVHG EEDLKVQHSS YRQRARLLKD QLSLGNAALQ ITDVKLQDAG VYRCMISYGG  120
ADYKRITVKV NAPYNKINQR ILVVDPVTSE HELTCQAEGY PKAEVIWTSS DHQVLSGKTT  180
TTNSKREEKL FNVTSTLRIN TTTNEIFYCT FRRLDPEENH TAELVIPELP LAHPPNERID  240
DKTHTCPPCP APELLGGPSV FLFPPKPKDT LMISRTPEVT CVVVDVSHED PEVKFNWYVD  300
GVEVHNAKTK PREEQYNSTY RVVSVLTVLH QDWLNGKEYK CKVSNKALPA PIEKTISKAK  360
GQPREPQVYT LPPSREEMTK NQVSLTCLVK GFYPSDIAVE WESNGQPENN YKTTPPVLDS  420
DGSFFLYSKL TVDKSRWQQG NVFSCSVMHE ALHNHYTQKS LSLSPGKIDF YTGVYILIGA  480
GALMMLVGFL GCCGAVQESQ CVIM                                         504

SEQ ID NO: 311         moltype = DNA  length = 1548
FEATURE                Location/Qualifiers
misc_feature           1..1548
                       note = Description of Artificial Sequence: Synthetic
                        polynucleotide
source                 1..1548
                       mol_type = other DNA
                       organism = synthetic construct
SEQUENCE: 311
atgaggatat ttgctgtctt tatattcatg acctactggc atttgctgaa cgcatttact  60
gtcacggttc ccaaggacct atatgtggta gagtatggta gcaatatgac aattgaatgc  120
aaattcccag tagaaaaaca attagacctg gctgcactaa ttgtctattg ggaaatggag  180
gataagaaca ttattcaatt tgtgcatgga gaggaagacc tgaaggttca gcatagtagc  240
tacagacaga gggcccggct gttgaaggac cagctctccc tgggaaatgc tgcacttcag  300
atcacagatg tgaaattgca ggatgcaggg gtgtaccgct gcatgatcag ctatggtggt  360
gccgactaca agcgaattac tgtgaaagtc aatgccccat acaacaaaat caaccaaaga  420
attttggttg tggatccagt cacctctgaa catgaactga catgtcaggc tgagggctac  480
cccaaggccg aagtcatctg gacaagcagt gaccatcaag tcctgagtgg taagaccacc  540
accaccaatt ccaagagaga ggagaagctt ttcaatgtga ccagcacact gagaatcaac  600
acaacaacta atgagatttt ctactgcact tttaggagat tagatcctga ggaaaaccat  660
acagctgaat tggtcatccc agaactacct ctggcacatc ctccaaatga aaggatcgat  720
gacaaaactc acacatgccc accgtgccca gcacctgaac tcctgggggg accgtcagtc  780
ttcctcttcc ccccaaaacc caaggacacc ctcatgatct cccggacccc tgaggtcaca  840
tgcgtggtgg tggacgtgag ccacgaagac cctgaggtca agttcaactg gtacgtggac  900
ggcgtggagg tgcataatgc caagacaaag ccgcgggagg agcagtacaa cagcacgtac  960
cgtgtggtca gcgtcctcac cgtcctgcac caggactggc tgaatggcaa ggagtacaag  1020
tgcaaggtct ccaacaaagc cctcccagcc cccatcgaga aaaccatctc caaagccaaa  1080
gggcagcccc gagaaccaca ggtgtacacc ctgcccccat cccgggagga gatgaccaag  1140
aaccaggtca gcctgacctg cctggtcaaa ggcttctatc ccagcgacat cgccgtggag  1200
tgggagagca atgggcagcc ggagaacaac tacaagacca cgcctcccgt gctggactcc  1260
gacggctcct tcttcctcta cagcaagctc accgtggaca agagcaggtg gcagcagggg  1320
aacgtcttct catgctccgt gatgcacgag gctctgcaca accactacac gcagaagagc  1380
ctctccctgt ctccgggtaa aatcgatttc tacacaggag tctatattct gatcggagcc  1440
ggcgccctca tgatgctggt gggcttcctg ggctgctgcg ggctgtgca ggagtcccag  1500
tgcaaaaaga agaaaaagaa gaagaagaca aagtgtgtaa ttatgtaa               1548

SEQ ID NO: 312         moltype = AA  length = 515
FEATURE                Location/Qualifiers
REGION                 1..515
                       note = Description of Artificial Sequence: Synthetic
                        polypeptide
source                 1..515
                       mol_type = protein
                       organism = synthetic construct
SEQUENCE: 312
MRIFAVFIFM TYWHLLNAFT VTVPKDLYVV EYGSNMTIEC KFPVEKQLDL AALIVYWEME  60
DKNIIQFVHG EEDLKVQHSS YRQRARLLKD QLSLGNAALQ ITDVKLQDAG VYRCMISYGG  120
ADYKRITVKV NAPYNKINQR ILVVDPVTSE HELTCQAEGY PKAEVIWTSS DHQVLSGKTT  180
TTNSKREEKL FNVTSTLRIN TTTNEIFYCT FRRLDPEENH TAELVIPELP LAHPPNERID  240
DKTHTCPPCP APELLGGPSV FLFPPKPKDT LMISRTPEVT CVVVDVSHED PEVKFNWYVD  300
GVEVHNAKTK PREEQYNSTY RVVSVLTVLH QDWLNGKEYK CKVSNKALPA PIEKTISKAK  360
GQPREPQVYT LPPSREEMTK NQVSLTCLVK GFYPSDIAVE WESNGQPENN YKTTPPVLDS  420
DGSFFLYSKL TVDKSRWQQG NVFSCSVMHE ALHNHYTQKS LSLSPGKIDF YTGVYILIGA  480
GALMMLVGFL GCCGAVQESQ CKKKKKKKT KCVIM                              515

SEQ ID NO: 313         moltype = DNA  length = 1488
```

-continued

```
FEATURE                 Location/Qualifiers
misc_feature            1..1488
                        note = Description of Artificial Sequence: Synthetic
                         polynucleotide
source                  1..1488
                        mol_type = other DNA
                        organism = synthetic construct
SEQUENCE: 313
atgaggatat ttgctggcat tatattcaca gcctgctgtc acttgctacg ggcgtttact  60
atcacggctc caaaggactt gtacgtggtg gagtatggca gcaacgtcac gatggagtgc  120
agattccctg tagaacggga gctggacctg cttgcgttag tggtgtactg ggaaaaggaa  180
gatgagcaag tgattcagtt tgtggcagga gaggaggacc ttaagcctca gcacagcaac  240
ttcaggggga gagcctcgct gccaaaggac cagcttttga agggaaatgc tgcccttcag  300
atcacagacg tcaagctgca ggacgcaggc gtttactgct gcataatcag ctacggtggt  360
gcggactaca agcgaatcac gctgaaagtc aatgccccat accgcaaaat caaccagaga  420
atttccgtgg atccagccac ttctgagcat gaactaatat gtcaggccga gggttatcca  480
gaagctgagg taatctggac aaacagtgac caccaacccg tgagtgggaa gagaagtgtc  540
accacttccc ggacagaggg gatgcttctc aatgtgacca gcagtctgag ggtcaacgcc  600
acagcgaatg atgttttcta ctgtacgttt tggagatcac agccagggca aaaccacaca  660
gcggagctga tcatcccaga actgcctgca acacatcctc cacagaacag gactggttgt  720
aagccttgca tatgtacagt cccagaagta tcatctgtct tcatcttccc cccaaagccc  780
aaggatgtgc tcaccattac tctgactcct aaggtcacgt gtgttgtggt agacatcagc  840
aaggatgatc ccgaggtcca gttcagctgg tttgtagatg atgtggaggt gcacacagct  900
cagacgcaac cccgggagga gcagttcaac agcactttcc gctcagtcag tgaacttccc  960
atcatgcacc aggactggct caatggcaag gagttcaaat gcagggtcaa cagtgcagct  1020
ttccctgccc ccatcgagaa aaccatctcc aaaaccaaag gcagaccgaa ggctccacag  1080
gtgtacacca ttccacctcc caaggagcag atggccaagg ataaagtcag tctgacctgc  1140
atgataacag acttcttccc tgaagacatt actgtggagt ggcagtggaa tgggcagcca  1200
gcggagaact acaagaacac tcagcccatc atggacacag atggctctta cttcgtctac  1260
agcaagctca atgtgcagaa gagcaactgg gaggcaggaa atactttcac ctgctctgtg  1320
ttacatgagg gcctgcacaa ccaccatact gagaagagcc tctcccactc tcctggtaaa  1380
ttctacacag gagtctatat tctgatcgga gccggcgccc tcatgatgct ggtgggcttc  1440
ctgggctgct gcggggctgt gcaggagtcc cagtgcgtaa ttatgtaa              1488

SEQ ID NO: 314          moltype = AA  length = 495
FEATURE                 Location/Qualifiers
REGION                  1..495
                        note = Description of Artificial Sequence: Synthetic
                         polypeptide
source                  1..495
                        mol_type = protein
                        organism = synthetic construct
SEQUENCE: 314
MRIFAGIIFT ACCHLLRAFT ITAPKDLYVV EYGSNVTMEC RFPVERELDL LALVVYWEKE  60
DEQVIQFVAG EEDLKPQHSN FRGRASLPKD QLLKGNAALQ ITDVKLQDAG VYCCIISYGG  120
ADYKRITLKV NAPYRKINQR ISVDPATSEH ELICQAEGYP EAEVIWTNSD HQPVSGKRSV  180
TTSRTEGMLL NVTSSLRVNA TANDVFYCTF WRSQPGQNHT AELIIPELPA THPPQNRTGC  240
KPCICTVPEV SSVFIFPPKP KDVLTITLTP KVTCVVVDIS KDDPEVQFSW FVDDVEVHTA  300
QTQPREEQFN STFRSVSELP IMHQDWLNGK EFKCRVNSAA FPAPIEKTIS KTKGRPKAPQ  360
VYTIPPPKEQ MAKDKVSLTC MITDFFPEDI TVEWQWNGQP AENYKNTQPI MDTDGSYFVY  420
SKLNVQKSNW EAGNTFTCSV LHEGLHNHHT EKSLSHSPGK FYTGVYILIG AGALMMLVGF  480
LGCCGAVQES QCVIM                                                  495

SEQ ID NO: 315          moltype = DNA  length = 1521
FEATURE                 Location/Qualifiers
misc_feature            1..1521
                        note = Description of Artificial Sequence: Synthetic
                         polynucleotide
source                  1..1521
                        mol_type = other DNA
                        organism = synthetic construct
SEQUENCE: 315
atgaggatat ttgctggcat tatattcaca gcctgctgtc acttgctacg ggcgtttact  60
atcacggctc caaaggactt gtacgtggtg gagtatggca gcaacgtcac gatggagtgc  120
agattccctg tagaacggga gctggacctg cttgcgttag tggtgtactg ggaaaaggaa  180
gatgagcaag tgattcagtt tgtggcagga gaggaggacc ttaagcctca gcacagcaac  240
ttcaggggga gagcctcgct gccaaaggac cagcttttga agggaaatgc tgcccttcag  300
atcacagacg tcaagctgca ggacgcaggc gtttactgct gcataatcag ctacggtggt  360
gcggactaca agcgaatcac gctgaaagtc aatgccccat accgcaaaat caaccagaga  420
atttccgtgg atccagccac ttctgagcat gaactaatat gtcaggccga gggttatcca  480
gaagctgagg taatctggac aaacagtgac caccaacccg tgagtgggaa gagaagtgtc  540
accacttccc ggacagaggg gatgcttctc aatgtgacca gcagtctgag ggtcaacgcc  600
acagcgaatg atgttttcta ctgtacgttt tggagatcac agccagggca aaaccacaca  660
gcggagctga tcatcccaga actgcctgca acacatcctc cacagaacag gactggttgt  720
aagccttgca tatgtacagt cccagaagta tcatctgtct tcatcttccc cccaaagccc  780
aaggatgtgc tcaccattac tctgactcct aaggtcacgt gtgttgtggt agacatcagc  840
aaggatgatc ccgaggtcca gttcagctgg tttgtagatg atgtggaggt gcacacagct  900
cagacgcaac cccgggagga gcagttcaac agcactttcc gctcagtcag tgaacttccc  960
atcatgcacc aggactggct caatggcaag gagttcaaat gcagggtcaa cagtgcagct  1020
```

```
ttccctgccc ccatcgagaa aaccatctcc aaaaccaaag gcagaccgaa ggctccacag  1080
gtgtacacca ttccacctcc caaggagcag atggccaagg ataaagtcag tctgacctgc  1140
atgataacag acttcttccc tgaagacatt actgtggagt ggcagtggaa tgggcagcca  1200
gcggagaact acaagaacac tcagcccatc atggacacag atggctctta cttcgtctac  1260
agcaagctca atgtgcagaa gagcaactgg gaggcaggaa atactttcac ctgctctgtg  1320
ttacatgagg gcctgcacaa ccaccatact gagaagagcc tctcccactc tcctggtaaa  1380
ttctacacag gagtctatat tctgatcgga gccggcgccc tcatgatgct ggtgggcttc  1440
ctgggctgct gcggggctgt gcaggagtcc cagtgcaaaa agaagaaaaa gaagaagaag  1500
acaaagtgtg taattatgta a                                            1521

SEQ ID NO: 316         moltype = AA  length = 506
FEATURE                Location/Qualifiers
REGION                 1..506
                       note = Description of Artificial Sequence: Synthetic
                        polypeptide
source                 1..506
                       mol_type = protein
                       organism = synthetic construct
SEQUENCE: 316
MRIFAGIIFT ACCHLLRAFT ITAPKDLYVV EYGSNVTMEC RFPVERELDL LALVVYWEKE  60
DEQVIQFVAG EEDLKPQHSN FRGRASLPKD QLLKGNAALQ ITDVKLQDAG VYCCIISYGG  120
ADYKRITLKV NAPYRKINQR ISVDPATSEH ELICQAEGYP EAEVIWTNSD HQPVSGKRSV  180
TTSRTEGMLL NVTSSLRVNA TANDVFYCTF WRSQPGQNHT AELIIPELPA THPPQNRTGC  240
KPCICTVPEV SSVFIFPPKP KDVLTITLTP KVTCVVVDIS KDDPEVQFSW FVDDVEVHTA  300
QTQPREEQFN STFRSVSELP IMHQDWLNGK EFKCRVNSAA FPAPIEKTIS KTKGRPKAPQ  360
VYTIPPPKEQ MAKDKVSLTC MITDFFPEDI TVEWQWNGQP AENYKNTQPI MDTDGSYFVY  420
SKLNVQKSNW EAGNTFTCSV LHEGLHNHHT EKSLSHSPGK FYTGVYILIG AGALMMLVGF  480
LGCCGAVQES QCKKKKKKKK TKCVIM                                       506

SEQ ID NO: 317         moltype = AA  length = 288
FEATURE                Location/Qualifiers
source                 1..288
                       mol_type = protein
                       organism = Mus musculus
SEQUENCE: 317
MWVRQVPWSF TWAVLQLSWQ SGWLLEVPNG PWRSLTFYPA WLTVSEGANA TFTCSLSNWS  60
EDLMLNWNRL SPSNQTEKQA AFCNGLSQPV QDARFQIIQL PNRHDFHMNI LDTRRNDSGI  120
YLCGAISLHP KAKIEESPGA ELVVTERILE TSTRYPSPSP KPEGRFQGMV IGIMSALVGI  180
PVLLLLAWAL AVFCSTSMSE ARGAGSKDDT LKEEPSAAPV PSVAYEELDF QGREKTPELP  240
TACVHTEYAT IVFTEGLGAS AMGRRGSADG LQGPRPPRHE DGHCSWPL                288

SEQ ID NO: 318         moltype = DNA  length = 7796
FEATURE                Location/Qualifiers
source                 1..7796
                       mol_type = genomic DNA
                       organism = Homo sapiens
SEQUENCE: 318
ggggccgggg ggcggagcct tgcgggctgg agcgaaagaa tgcgggggct gagcgcagaa  60
gcggctcgag gctggaagag gatcttgggc gccgccagtc tctctctgtt gcccaagctg  120
gagtgcagtg gcacagtctt ggctcactgc aacctccacc tcctgggtgc aagcgattct  180
cgtgtctcag cctctcaagt agctgggatt acagtcttta gcaccagttg gtgtaggagt  240
tgagacctac ttcacagtag ttctgtggac aatcacaatg ggaatccaag gagggtctgt  300
cctgttcggg ctgctgctcg tcctggctgt cttctgccat tcaggtcata gcctgcagtg  360
ctacaactgt cctaacccaa ctgctgactg caaaacagcc gtcaattgtt catctgattt  420
tgatgcgtgt ctcattacca aagctgggtt acaagtgtat aacaagtgtt ggaagtttga  480
gcattgcaat ttcaacgacg tcacaacccg cttgagggaa aatgagctaa cgtactactg  540
ctgcaagaag gacctgtgta actttaacga acagcttgaa aatggtggga catccttatc  600
agagaaaaca gttcttctgc tggtgactcc atttctggca gcagcctgga gccttcatcc  660
ctaagtcaac accaggagag cttctcccaa actccccgtt cctgcgtagt ccgctttctc  720
ttgctgccac attctaaagg cttgatattt tccaaatgga tcctgttggg aaagaataaa  780
attagcttga gcaacctggc taagatagag gggctctggg agactttgaa gaccagtcct  840
gtttgcaggg aagccccact tgaaggaaga agtctaagag tgaagtaggt gtgacttgaa  900
ctagattgca tgcttcctcc tttgctcttg ggaagaccag ctttgcagtg acagcttgag  960
tgggttctct gcagccctca gattattttt cctctggctc cttggatgta gtcagttagc  1020
atcattagta catctttgga gggtggggca ggagtatatg agcatcctct ctcacatgga  1080
acgctttcat aaacttcagg gatcccgtgt tgccatggag gcatgccaaa tgttccatat  1140
gtgggtgtca gtcagggaca acaagatcct taatgcagag ctagaggact tctggcaggg  1200
aagtggggaa gtgttccaga tagcagggca tgaaaactta gagaggtaca agtggctgaa  1260
aatcgagttt ttcctctgtc tttaaatttt atatgggctt tgttatcttc cactggaaaa  1320
gtgtaatagc atacatcaat ggtgtgttaa agctatttcc ttgccttttt tttattggaa  1380
tggtaggata tcttggcttt gccacacaca gttacagagt gaacactcta ctacatgtga  1440
ctggcagtat taagtgtgct tattttaaat gttactggta gaaaggcagt tcaggtatgt  1500
gtgtatatag tatgaatgca gtggggacac cctttgtggt tacagtttga gacttccaaa  1560
ggtcatcctt aataacaaca gatctgcagg ggtatgtttt accatctgca tccagcctcc  1620
tgctaactcc tagctgactc agcatagatt gtataaaata cctttgtaac ggctcttagc  1680
acactcacag atgtttgagg ctttcagaag ctcttctaaa aaatgataca cacctttcac  1740
aagggcaaac tttttccttt tccctgtgta ttctagtgaa tgaatctcaa gattcagtag  1800
acctaatgac atttgtattt tatgatcttg gctgtattta atggcatagg ctgacttttg  1860
cagatggagg aatttcttga ttaatgttga aaaaaaaccc ttgattatac tctgttggac  1920
```

-continued

```
aaaccgagtg caatgaatga tgcttttctg aaaatgaaat ataacaagtg ggtgaatgtg  1980
gttatggccg aaaaggatat gcagtatgct taatggtagc aactgaaaga agacatcctg  2040
agcagtgcca gctttcttct gttgatgccg ttccctgaac ataggaaaat agaaacttgc  2100
ttatcaaaac ttagcattac cttggtgctc tgtgttctct gttagctcag tgtctttcct  2160
tacatcaata ggtttttttt tttttttttg gcctgaggaa gtactgacca tgcccacagc  2220
caccggctga gcaaagaagc tcatttcatg tgagttctaa ggaatgagaa acaattttga  2280
tgaatttaag cagaaaatga atttctggga actttttttgg gggcgggggg gtggggaatt  2340
cagccacact ccagaaagcc aggagtcgac agttttggaa gcctctctca ggattgagat  2400
tctaggatga gattggctta ctgctatctt gtgtcatgta cccacttttt ggccagacta  2460
cactgggaag aaggtagtcc tctaaagcaa aatctgagtg ccactaaatg gggagatggg  2520
gctgttaagc tgtccaaatc aacaagggtc atataaatgg ccttaaactt tggggttgct  2580
ttctgcaaaa agttgctgtg actcatgcca tagacaaggt tgagtgcctg gacccaaagg  2640
caatactgta atgtaaagac atttatagta ctaggcaaac agcaccccag gtactccagg  2700
ccctcctggc tggagagggc tgtggcaata gaaaattagt gccaactgca gtgagtcagc  2760
ctaggttaaa tagagagtgt aagagtgctg gacaggaacc tccaccctca tgtcacattt  2820
cttcaatgtg acccttctgg cccctctcct cctgacagcg gaacaatgac tgccccgata  2880
ggtgaggctg gaggaagaat cagtcctgtc cttggcaagc tcttcactat gacagtaaag  2940
gctctctgcc tgctgccaag gcctgtgact ttctaacctg gcctcacgct gggtaagctt  3000
aaggtagagg tgcaggatta gcaagcccac ctggctacca ggccgacagc tacatcctcc  3060
aactgaccct gatcaacgaa gagggattca tgtgtctgtc tcagttggtt ccaaatgaaa  3120
ccagggagca ggggagttag gaatcgaaca ccagtcatgc ctactggctc tctgctcgag  3180
agccaatacc ctgtgccctc cactcatctg gatttacagg aactgtcata gtgttcagta  3240
ttgggtggtg ataagcccat tggattgtcc ccttgggggg atgagctagg ggtgcaagga  3300
acacctgatg agtagataag tggagctcat ggtatttcct gaaagatgct aatctatttg  3360
ccaaacttgg tcttgaatgt actgggggct tcaaggtatg ggtatatttt tcttgtgtcc  3420
ttgcagttag cccccatgtc ttatgtgtgt cctgaaaaaa taagagcctg cccaagactt  3480
tgggcctctt gacagaatta accactttta tacatctgag ttctcttggt aagttcttta  3540
gcagtgttca aagtctacta gctcgcatta gtttctgttg ctgccaacag atctgaacta  3600
atgctaacag atcccccctga gggattcttg atgggctgag cagctggctg gagctagtac  3660
tgactgacat tcattgtgat gagggcagct ttctggtaca ggattctaag ctctatgttt  3720
tatatacatt ttcatctgta cttgcacctc actttacaca agaggaaact atgcaaagtt  3780
agctggatcg ctcaaggtca cttaggtaag ttggcaagtc catgcttccc actcagctcc  3840
tcaggtcagc aagtctactt ctctgcctat tttgtatact ctctttaata tgtgcctagc  3900
tttggaaagt ctagaatggg tccctggtgc ctttttactt tgaagaaatc agtttctgcc  3960
tctttttgga aaagaaaaca aagtgcaatt gtttttttact ggaaagttac ccaatagcat  4020
gaggtgaaca ggacgtagtt aggccttcct gtaaacagaa aatcatatca aaacactatc  4080
ttcccatctg tttctcaatg cctgctactt cttgtagata tttcatttca ggagagcagc  4140
agttaaaccc gtggattttg tagttaggaa cctgggttca aaccctcttc cactaattgg  4200
ctatgtctct ggacaagttt tttttttttt tttttttaa accctttctg aactttcact  4260
ttctatgtct acctcaaaga attgttgtga ggcttgagat aatgcatttg taaagggtct  4320
gccagatagg aagatgctag ttatggattt acaaggttgt taaggctgta agagtctaaa  4380
acctacagtg aatcacaatg catttacccc cactgacttg gacataagtg aaaactagcc  4440
agaagtctct ttttcaaatt acttacaggt tattcaatat aaaatttttg taatggataa  4500
tcttatttat ctaaactaaa gcttcctgtt tatacacact cctgttattc tgggataaga  4560
taaatgacca cagtacctta atttctaggt gggtgcctgt gatggttcat tgtaggtaag  4620
gacattttct ctttttcagc agctgtgtag gtccagagcc tctgggagag gagggggggta  4680
gcatgcaccc agcaggggac tgaactggga aactcaaggt tctttttact gtggggtagt  4740
gagctgcctt tctgtgatcg gtttccctag ggatgttgct gttcccctcc ttgctattcg  4800
cagctacata caacgtggcc aaccccagta ggctgatcct atatatgatc agtgctggtg  4860
ctgactctca atagccccac ccaagctggc tataggttta cagatacatt aattaggcaa  4920
cctaaaatat tgatgctggt gttggtgtga cataatgcta tggccagaac tgaaacttag  4980
agttataatt catgtattag ggttctccag agggacagaa ttagtaggat atatgtatat  5040
atgaaaggga ggttattagg gagaactggc tcccacagtt agaaggcgaa gtcgcacaat  5100
aggccgtctg caagctgggt tagagagaag ccagtagtgg ctcagcctga gttcaaaaac  5160
ctcaaaactg gggaagctga cagtgcagcc agccttcagt ctgtggccaa aggcccaaga  5220
gcccctggca accaacccac tggtgcaagt cctagattcc aaaggctgaa gaacctggag  5280
tctgatgtcc aagagcagga agagtggaag aaagccagaa gactcagcaa acaaggtaga  5340
cagtgtctac caccatagtg gccataccaa agaggctacc gattccttcc tgctacctgg  5400
atccctgaag ttgccctggt ctctgcacct tctaaaccta gttcttaaga gctttccatt  5460
acatgagctg tctcaaagcc ctccaataaa ttctcagtgt aagcttctgt tgcttgtgga  5520
cagaaaattc tgacagacct accctataag tgttactgtc aggataacat gagaacgcac  5580
aacagtaagt ggtcactaag tgttagctac ggttattttg cccaaggtag catggctagt  5640
tgatgccggt tgatggggct taaacccagc tccctcatct tccaggcctc tgtactccct  5700
attccactaa actacctctc aggtttattt ttttaaattc ttactctgca agtacatagg  5760
accacattta cctgggaaaa caagaataaa ggctgctctg catttttttag aaactttttt  5820
gaaagggaga tgggaatgcc tgcaccccca agtccagacc aacacaatgg ttaattgaga  5880
tgaataataa aggaaagact gttctgggct tcccagaata gcttggtcct taaattgtgg  5940
cacaaacaac ctcctgtcag agccagcctc ctgccaggaa gaggggtagg agactagagg  6000
ccgtgtgtgc agccttgccc tgaaggctag ggtgacaatt tggaggctgt ccaaacaccc  6060
tggcctctag agctggcctg tctatttgaa atgccggctc tgatgctaat cggcgaccct  6120
caggcaagtt acttaacctt acatgcctca gttttctcat ctggaaaatg agaaccctag  6180
gtttagggtt gttagaaaag ttaaatgagt taagacaagt gcctgggaca cagtagcctc  6240
ttgtgtgtgt ttatcattat gtcctcagca ggtcgtagaa gcagcttctc aggtgtgagg  6300
ctggcgcgat tatctggagt gggttgggtt ttctaggatg gacccccctgc tgcattttcc  6360
tcattcatcc accagggctt aatggggaat caaggaatcc atgtgtaact gtataataac  6420
tgtagccaca ctccaatgac cacctactag ttgtccctgg cactgcttat acatatgtcc  6480
atcaaatcaa tcctatgaag tagatactgt cttcatttta tagatcagag acaattgggg  6540
ttcagagagc tgatgtgatt ttcccagggt cacagagagt cccagattca ggcacaactc  6600
ttgtattcca agacacaacc actacatgtc caaaggctgc ccagagccac cgggcacggc  6660
```

-continued

```
aaattgtgac atatccctaa agaggctgag cacctggtca ggatctgatg gctgacagtg  6720
tgtccagatg cagagctgga gtgggggagg ggaaggggggg ctccttggga cagagaaggc  6780
tttctgtgct ttctctgaag ggagcagtct gaggaccaag ggaacccggc aaacagcacc  6840
tcaggtactc caggccctcc tggctggaga gggctgtggc aatggaaaat tagtgccaac  6900
tgcaatgagt cagcctcggt taaatagaga gtgaagaatg ctggacagga acctccaccc  6960
tcatgtcaca tttcttcagt gtgacccttc tggcccctct cctcctgaca gcggaacaat  7020
gactgccccg ataggtgagg ctggaggaag aatcagtcct gtccttggca agctcttcac  7080
tatgacagta aaggctctct gcctgctgcc aaggcctgtg actttctaac ctggcctcac  7140
gctgggtaag cttaaggtag aggtgcagga ttagcaagcc cacctggcta ccaggccgac  7200
agctacatct ttcaactgac cctgatcaac gaagagggac ttgtgtctct cagttggttc  7260
caaatgaaac cagggagcag gggcgttagg aagctccaac aggatggtac ttaatggggc  7320
atttgagtgg agaggtaggt gacatagtgc tttggagccc agggagggaa aggttctgct  7380
gaagttgaat tcaagactgt tctttcatca caaacttgag tttcctggac atttgtttgc  7440
agaaacaacc gtagggtttt gccttaacct cgtgggttta ttattacctc atagggactt  7500
tgcctcctga cagcagttta tgggtgttca ttgtggcact tgagttttct tgcatacttg  7560
ttagagaaac caagtttgtc atcaacttct tatttaaccc cctggctata acttcatgga  7620
ttatgttata attaagccat ccagagtaaa atctgtttag attatcttgg agtaaggggg  7680
aaaaaatctg taattttttc tcctcaacta gatatataca taaaaaatga ttgtattgct  7740
tcatttaaaa aatataacgc aaaatctctt ttccttctaa aaaaaaaaaa aaaaaa      7796

SEQ ID NO: 319         moltype = AA  length = 4
FEATURE                Location/Qualifiers
REGION                 1..4
                       note = Description of Artificial Sequence: Synthetic peptide
source                 1..4
                       mol_type = protein
                       organism = synthetic construct
SEQUENCE: 319
GSSG                                                                   4

SEQ ID NO: 320         moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 320
GGGGS                                                                  5
```

What is claimed is:

1. An engineered extracellular vesicle comprising a fusion protein, the fusion protein comprising:

at least two signaling domains, each of the at least two signaling domains being a same signaling domain and selected from the group consisting of either full length or active fragments of 4-1BBL (CDI37L), CD27L (CD70), CD30L (CD153), mCD30L, GITRL, CD40L (CD154), mCD140L, LIGHT (CD258), TL1, mTL1, FasL, NKG2 family, CD94, CD98, OX40L (CD252), and 4-1BB/TNFRSF4/CD137;

at least one linker, and at least one vesicle targeting domain linked to the at least two signaling domains;

wherein the at least one linker comprises a fragment crystallizable region (Fc) domain, wherein the at least one vesicle targeting domain comprises a Type II transmembrane domain, and wherein the at least two signaling domains are in an extracellular position relative to a lipid membrane of the extracellular vesicle.

2. The engineered extracellular vesicle of claim 1, wherein the at least one vesicle targeting domain comprises a fatty acylation site or a prenylation site, whereby the at least one vesicle targeting domain is embedded in a phospholipid bilayer of the engineered extracellular vesicle through covalent lipid attachment to the fatty acylation site or the prenylation site.

3. The engineered extracellular vesicle of claim 1, wherein the at least one vesicle targeting domain is selected from the group consisting of sequences encoding peptides or protein domains from ADAM10, TFR2, and MARCKS comprising modified myristoylation and palmitoylation tags; sequences encoding prenylation sites and fatty acylation sites; and sequences encoding lipid affinity tags derived from KRAS, CD81, CD63, ALIX, TSG101, CD98, CD298, GPI, CD9, and CD105.

4. The engineered extracellular vesicle of claim 1, wherein the at least one vesicle targeting domain comprises at least two exosome targeting domains.

5. The engineered extracellular vesicle of claim 1, further comprising a tetraspanin selected from the group consisting of CD9, CD63, CD81, CD82, CD53, and CD37.

6. The engineered extracellular vesicle of claim 5, wherein the at least two signaling domains comprise three identical signaling domains.

7. The engineered extracellular vesicle of claim 1, comprising a plurality of the fusion protein, and wherein the density of the plurality of fusion protein is configured to support receptor clustering on a target cell.

8. The engineered extracellular vesicle of claim 1, wherein the at least two signaling domains substantially bind to one or more of a target polypeptide.

9. The engineered extracellular vesicle of claim 1, further comprising one or more secondary fusion proteins, each comprising a secondary signaling domain different from the at least two signaling domains of the fusion protein.

10. The engineered extracellular vesicle of claim 9, wherein the secondary signaling domains are each independently selected from the group consisting of either full-length or active fragments of PD-L1 (CD274), PD-L2 (CD273), CTLA-4 (CD152), 4-1BBL (CD137L), HVEM (CD270), FGL1, OX-2 (CD200), Galectin-9, PVR (CD155), Nectin-2 (CD112) isophorm alpha, Nectin-2 (CD112) isophorm delta, mNectin-2 beta, IL-10, TSG-6, B7-H3 (CD276), B7-H4 (VTCN1), B7-H5 (VISTA), B7-H7 (HHLA2), VSIG8, VSIG3 (IGSF11), VSIG4, Tim-3 (HAVCR2), Tim-4, CEACAM1 (CD66a), BTN3A1, BTN3A2, BTN2A1, BTNLR, BTN2A2, mBTN2A2, BTN1A1, TIGIT, CD27L (CD70), CD30L (CD153), mCD30L, GITRL, CD40L (CD154), mCD140L, LIGHT (CD258), TL1, mTL1, B7-1 (CD80), B7-2 (CD86), LFA-3 (CD58), SLAM (CD150), mSLAM, CD40, CD28, mCD28, CD28H/TMIGD2/IGPR1, CD2, CD48, CD226, DR3, DcR3, FasL, Tim-1 (CD365), PD-1 (CD279), mScarlet, Nanoluciferase, A2AR, PECAM-1, STAB-1, Clever-I, NRP1, NRP2, SEMA3A, SEMA3F, RGMB/DRG11, HLA DII, HMGB1, TCR, SHP-1, SHP-2, FBOX38, SH2DIA, B7RP1, IDO, NOX2, TNFRSF18/GITR/CD357, SISP1, B7-H6/NCR3LG1, APLNR, IFNg receptor, WNTSA, PAK4, IL-6, NKG2 family, NKG2 family ligands, Killer cell Ig-like receptors, CD4, CD5, CD27, CD39, CD44, CD47, CD73, CD94, CD96, CD98, 1GSF2/CD101, PVIRG/CD112R, IL5RB/CD122, OX40L (CD252), 4-1BB/TNFRSF4/CD137, KIRs/CD158 family, CD160, SIRP alpha/CD172a, CD200R, LAG-3/CD223, CD244, BTLA/CD272, B7H2/ICOSLG/B7RP1/CD275, ICOS/CD278, LIAR-1/CD305, Collagen family members, SIGLEC7/CD328, SIGLEC9/CD329, NKp30/CD337, TNFR superfamily, Nectin-like binding receptors, Nectin, IL10RA, IL10RB, TNFRSF25, TNFRSF6B, CDI13, CD30, TRAF family members, and TIM family members.

11. The engineered extracellular vesicle of claim 9, wherein the one or more secondary fusion proteins each comprises a secondary vesicle targeting domain linked to its secondary signaling domain.

12. The engineered extracellular vesicle of claim 11, wherein the one or more secondary vesicle targeting domains are each independently selected from the group consisting of sequence prides or protein domains from ADAM10, TFR2, and MARCKS comprising modified myristoylation and palmitoylation tags; sequences encoding prenylation sites and fatty acylation sites; and sequences encoding lipid affinity tags derived from KRAS, CD81, CD63, ALIX, TSG101, CD98, CD298, GPL CD9, and CD105.

13. An engineered extracellular vesicle comprising a fusion protein, the fusion protein comprising:

at least two signaling domains, each of the at least two signaling domains being a same signaling domain and selected from the group consisting of either full-length of active fragments of 4-1BBL (CD137L), CD27L (CD70), CD30L (CD153), mCD30L, GITRL, CD40L (CD154), mCD140L, LIGHT (CD258), TL1, mTL1 FasL, NKG2 family, CD94, CD98, OX40L (CD252), and 4-1BB/TNFRSF4/CD137;

at least one linker, and at least one vesicle targeting domain linked to the at least two signaling domains;

wherein the at least one linker comprises a fragment crystallizable region (Fc) domain and is between the at lea st two signaling domains and the at least one vesicle targeting domain, wherein the at least one vesicle targeting domain comprises a Type II transmembrane domain, and wherein the at least two signaling domains are in an extracellular position relative to a lipid membrane of the extracellular vesicle.

14. The engineered extracellular vesicle of claim 13, wherein the linker is an Fc from IgG1, Fc from IgG2, Fc from IgG3, or Fc from IgG4, or wherein the linker further comprises Gly-Ser-Ser-Gly (SEQ ID NO: 319), a cleavable 2A sequence, P2A, E2A, F2A, T2A, or (GGGGS (SEQ ID NO: 320)) n.

15. The engineered extracellular vesicle of claim 13, wherein the at least one vesicle targeting domain comprises a sequence encoding a fatty acylation site or a prenylation site, whereby the at least one vesicle targeting domain is embedded in a phospholipid bilayer of the engineered extracellular vesicle through covalent lipid attachment to the fatty acylation site or the prenylation site.

16. The engineered extracellular vesicle of claim 13, wherein the at least one vesicle targeting domain is selected from the group consisting of sequences encoding peptides or protein domains from ADAM10, TFR2, and MARCKS comprising modified myristoylation and palmitoylation tags; sequences encoding prenylation sites and fatty acylation sites; and sequences encoding lipid affinity tags derived from KRAS, CD81, CD63, ALIX, TSG101, CD98, CD298, GPI, CD9, and CD105.

17. The engineered extracellular vesicle of claim 13, further comprising a tetraspanin selected from the group consisting of CD9, CD63, CD81, CD82, CD53, and CD37.

18. The engineered extracellular vesicle of claim 17, wherein the at least two signaling domains comprise three identical signaling domains.

19. The engineered extracellular vesicle of claim 13, comprising a plurality of the fusion protein, and wherein the density of the plurality of fusion protein is configured to support receptor clustering on a target cell.

20. The engineered extracellular vesicle of claim 13, further comprising one or more secondary fusion proteins, each comprising a secondary signaling domain different from the signaling domain of the fusion protein.

21. The engineered extracellular vesicle of claim 20, wherein the secondary signaling domains are each independently selected from the group consisting of either full-length or active fragments of PD-L1, PD-L2, CTLA-4 (CD152), 4-1BBL (CD137L), HVEM (CD270), FOL1, OX-2 (CD200), Galectin-9, PVR (CD155), Nectin-2 (CD112) isophorm alpha, Nectin-2 (CD112) isophorm delta, mNectin-2 beta, IL-10, TSG-6, B7-H3 (CD276), B7-H4 (VTCN1), B7-H5 (VISTA), B7-H7 (HHLA2), VSIG8, VSIG3 (IGSF11), VSIG4, Tim-3 (HAVCR2), Tim-4, CEACAM1 (CD66a), BTN3A1, BTN3A2, BTN2A1, BTNL8, BTN2A2, mBTN2A2, BTN1A1, TIGIT, CD27L (CD70), CD30L (CD153), mCD30L, GITRL, CD40L (CD154), mCD140L, LIGHT (CD258), TL1, mTL1, B7-1 (CD80), B7-2 (CD86), LFA-3 (CD58), SLAM (CD150), mSLAM, CD40, CD28, mCD28, CD28H/TMIGD2/IGPR1, CD2, CD48, CD226, DR3, DcR3, FasL, Tim-1 (CD365), PD-1 (CD279), mScarlet, Nanoluciferase, AZAR, PECAM-I, STAB-1, Clever-1, NRP1, NRP2, SEMA3A, SEMA3F, RGMB/DRG11, HLA I/II, HMGB1, TCR, SHP-1, SHP-2, FBOX38, SH2D1A, B7RP1, IDO, NOX2, TNERSF18/GITR/CD357, SISP1, B7-H6/NCR3LG1, APLNR, IFNg receptor, WNTSA, PAK4, IL-6, NKG2 family, NKG2 family ligands, Killer cell Ig-like receptors, CD4, CD8, CD27, CD39, CD44, CD47, CD73, CD94, CD96, CD98, IGSF2/CD101, NECTIN2/CD112, PVIRO/CD112R, ILSRB/CD122, OX40L (CD252), 4-1BB/TNFRSF4/CD137, CTLA-4/CD152, KIRs/CD158 family, CD160, SIRP alpha/CD172a, CD200R, LAG-3/CD223, CD244, BTLA/CD272, B7H2/ICOSLG/B7RP1/CD275, ICOS/CD278, LIAR-1/CD305, Collagen family members, SIGLEC7/CD328, SIGLEC9/CD329, NKp30/CD337, TNER superfamily, Nectin-like binding receptors, Nectin, IL10RA, IL10RB, TNERSF25, TNFRSF6B, CD113, CD30, TRAF family members, and TIM family members.

22. The engineered extracellular vesicle of claim 20, wherein the one or more secondary fusion proteins each comprises a secondary vesicle targeting domain linked to its secondary signaling domain.

23. The engineered extracellular vesicle of claim 22, wherein the one or more secondary vesicle targeting domains are each independently selected from the group consisting of sequences encoding peptides or protein domains from ADAM10, TFR2, and MARCKS comprising modified myristoylation and palmitoylation tags; sequences encoding prenylation sites and fatty acylation sites; and sequences encoding lipid affinity s derived from KRAS, CD81, CD63, ALIX, TSG101, CD98, CD298, GPI, CD9, and CD105.

* * * * *